(12) United States Patent
Wilson et al.

(10) Patent No.: US 10,669,277 B2
(45) Date of Patent: Jun. 2, 2020

(54) INHIBITORS OF ACTIVIN RECEPTOR-LIKE KINASE

(71) Applicant: Blueprint Medicines Corporation, Cambridge, MA (US)

(72) Inventors: Kevin J. Wilson, Boston, MA (US); Josh Waetzig, Waltham, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/293,317

(22) Filed: Mar. 5, 2019

(65) Prior Publication Data

US 2020/0031830 A1 Jan. 30, 2020

Related U.S. Application Data

(63) Continuation of application No. 15/488,257, filed on Apr. 14, 2017, now Pat. No. 10,233,186.

(60) Provisional application No. 62/322,948, filed on Apr. 15, 2016, provisional application No. 62/411,172, filed on Oct. 21, 2016.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................... C07D 487/04; C07D 5129/00
See application file for complete search history.

(56) References Cited

U.S. PATENT DOCUMENTS

| | | | |
|---|---|---|---|
| 8,415,336 B2 | 4/2013 | Steinhagen et al. | |
| 8,802,697 B2 | 8/2014 | Bifulco, Jr. et al. | |
| 8,980,878 B2 | 3/2015 | Siegel et al. | |
| 9,126,951 B2 | 9/2015 | Bifulco, Jr. et al. | |
| 9,200,002 B2 | 12/2015 | Hodous et al. | |
| 9,334,263 B2 | 5/2016 | Hodous et al. | |
| 9,340,514 B2 | 5/2016 | Bifulco, Jr. et al. | |
| 9,434,700 B2 | 9/2016 | Bifulco, Jr. et al. | |
| 9,499,522 B2 | 11/2016 | DiPietro, et al. | |
| 9,688,680 B2 | 6/2017 | Hodous | |
| 9,695,165 B2 | 7/2017 | Bifulco, Jr. et al. | |
| 9,884,861 B2 | 2/2018 | Hodous et al. | |
| 9,944,651 B2 | 4/2018 | Hodous et al. | |
| 9,994,552 B2 | 6/2018 | DiPietro et al. | |
| 9,994,575 B2 | 6/2018 | Hodous et al. | |
| 10,000,490 B2 | 6/2018 | Bifulco, Jr. et al. | |
| 10,000,496 B2 | 6/2018 | Hodous et al. | |
| 10,017,512 B2 | 7/2018 | Wenglowsky et al. | |
| 10,030,005 B2 | 7/2018 | Brubaker et al. | |
| 10,035,789 B2 | 7/2018 | Brubaker et al. | |
| 10,233,186 B2 * | 3/2019 | Brooijmans | C07D 519/00 |
| 2007/0027093 A1 | 2/2007 | Ogawa et al. | |
| 2009/0176778 A1 | 7/2009 | Schmitz et al. | |
| 2009/0181941 A1 | 7/2009 | Leblanc et al. | |
| 2013/0273037 A1 | 10/2013 | Siegel et al. | |
| 2014/0187559 A1 | 7/2014 | Miduturu | |
| 2014/0275009 A1 | 9/2014 | Brenchley et al. | |
| 2015/0064196 A1 | 3/2015 | Thakkar et al. | |
| 2016/0045528 A1 | 2/2016 | Blatt et al. | |
| 2017/0066812 A1 | 3/2017 | Bifulco, Jr. et al. | |
| 2017/0145018 A1 | 5/2017 | Wenglowsky et al. | |
| 2017/0174652 A1 | 6/2017 | Bifulco, Jr. et al. | |
| 2017/0267661 A1 | 9/2017 | Kim et al. | |
| 2017/0298069 A1 | 10/2017 | Brooijmans et al. | |
| 2018/0022731 A1 | 1/2018 | Brooijmans et al. | |
| 2018/0022732 A1 | 1/2018 | Brubaker et al. | |

FOREIGN PATENT DOCUMENTS

| | | |
|---|---|---|
| WO | WO 2009/087225 A2 | 7/2009 |
| WO | WO 2014/138088 A1 | 9/2014 |
| WO | WO 2014/151444 A1 | 9/2014 |
| WO | WO 2015/187684 A1 | 12/2015 |
| WO | WO 2016/165808 A1 | 10/2016 |
| WO | WO 2017/181117 A1 | 10/2017 |
| WO | WO 2018/049233 A9 | 7/2018 |

OTHER PUBLICATIONS

Bocciardi, R. et al. (2009) "Mutational analysis of the ACVR1 gene in Italian patients affected with fibrodysplasia ossificans progressiva: confirmations and advancements" *Eur J Hum Genetics*, 17:311-318.

Chakkalakal, S.A. et al. (Aug. 2012) "An Acyr1 R206H Knock-in Mouse Has Fibrodysplasia Ossificans Progressiva" *J Bone Miner Res*, 27(8):1746-1756.

Crofford, L.J. et al. (1990) "Failure of Surgery and Isotrentinoin to Relieve Jaw Immobilization in Fibrodysplasia Ossificans Progressiva: Report of Two Cases" *J Oral Maxillofac Surg*, 48:204-208.

Eekhoff, E. et al. (2018) "Flare-Up After Maxillofacial Surgery in a Patient with Fibrodysplasia Ossificans Progressiva: An [$^{18}$F]-NaF PET/CT Study and a Systematic Review" *JBMR Plus*, 2(1):55-58.

Fukuda, T. et al. (2006) "Generation of a Mouse With Conditionally Activated Signaling Through the BMP Receptor, ALK2" *Genesis*, 44:159-167.

Garner, A. (Apr. 16, 2016) "Generation of Highly Selective ALK2 Inhibitors for the Treatment of FOP" Slides presented at the 2016 Annual F.O.P. Italia Meeting (17 pages).

Garner, A. (Oct. 24, 2016) "Characterization of Highly Selective ALK2 Inhibitors for the Treatment of FOP" Slides presented at the 2016 FOP Drug Development Forum in Boston, MA (17 pages).

Gregson, C.L. et al. (2011) "A novel ACVR1 mutation in the glycine/serine-rich domain found in the most benign case of a fibrodysplasia ossificans progressiva variant reported to date" *Bone*, 48:654-658.

(Continued)

*Primary Examiner* — Alexander R Pagano
*Assistant Examiner* — Ebenezer O Sackey
(74) *Attorney, Agent, or Firm* — McCarter & English, LLP; Steven G. Davis; Wei Song

(57) ABSTRACT

Described herein are compounds that inhibit ALK2 and its mutants, pharmaceutical compositions including such compounds, and methods of using such compounds and compositions.

17 Claims, No Drawings

(56) References Cited

OTHER PUBLICATIONS

International Search Report and Written Opinion dated Jul. 21, 2017, in International Patent Application No. PCT/US2017/027775, filed Apr. 14, 2017, by Blueprint Medicines Corp. (9 pages).

Jones, C. and S.J. Baker (2014) "Unique genetic and epigenetic mechanisms driving paediatric diffuse high-grade glioma" *Nat Rev Cancer*, 14:651-661.

Kaplan, F.S. et al. (May 2008) "Early Diagnosis of Fibrodysplasia Ossificans Progressiva" *Pediatrics*, 121(5):e1295-e1300. NIH Public Access Author Manuscript; available in PMC Nov. 20, 2012 (12 pages).

Kaplan, F.S. et al. (2009) "Classic and Atypical Fibrodysplasia Ossificans Progressiva (FOP) Phenotypes Are Caused by Mutations in the Bone Morphogenetic Protein (BMP) Type I Receptor ACVR1" *Hum Mutat*, 30(3):379-390.

Kaplan, F.S. et al. (2015) "Multi-System Involvement in a Severe Variant of Fibrodysplasia Ossificans Progressiva (ACVR1c. 772G>A; R258G): A Report of Two Patients" *Am J Med Genet*, 167:2265-2271.

Kaplan, F.S. et al. (2017) "Hard targets for a second skeleton: therapeutic horizons for fibrodysplasia ossificans progressiva (FOP)" *Exp Opin Orphan Drugs*, 5(4):291-294.

Mohedas, A.H. et al. (Jun. 2013) "Development of an ALK2-biased BMP type I receptor kinase inhibitor" *ACS Chem Biol*, 8(6):1291-1302. NIH Public Access Author Manuscript; available in PMC Jun. 21, 2014 (20 pages).

Notice of Allowance dated Aug. 6, 2018, in U.S. Appl. No. 15/462,255, filed Mar. 17, 2017, by Blueprint Medicines Corp.

Notice of Allowance dated Sep. 21, 2018, in U.S. Appl. No. 15/548,925, filed Aug. 4, 2017, by Blueprint Medicines Corp.

Notice of Allowance dated Sep. 26, 2018, in U.S. Appl. No. 15/867,637, filed Jan. 10, 2018, by Blueprint Medicines Corp.

Notice of Allowance dated Oct. 11, 2018, in U.S. Appl. No. 15/222,523, filed Jul. 28, 2016, by Blueprint Medicines Corp.

Notice of Allowance dated Oct. 19, 2018, in U.S. Appl. No. 15/657,057, filed Jul. 21, 2017, by Blueprint Medicines Corp.

Pacifici, M. and E.M. Shore (Feb. 2016) "Common mutations in ALK2/ACVR1, a multi-faceted receptor, have roles in distinct pediatric musculoskeletal and neural orphan disorders" *Cytokine Growth Factor Rev.*, 27:93-104. HHS Public Access Author Manuscript; available in PMC Feb. 1, 2017 (27 pages).

Petrie, K.A. et al. (Mar. 30, 2009) "Novel Mutations in ACVR1 Result in Atypical Features in Two Fibrodysplasia Ossificans Progressiva Patients" *PLoS One*, 4(3):e5005 (4 pages).

Shore, E.M. et al. (2006) "A recurrent mutation in the BMP type I receptor ACVR1 causes inherited and sporadic fibrodysplasia ossificans progressiva" *Nat Genet*, 38(5):525-527, including Corrigendum (1 page).

U.S. Appl. No. 15/867,637, filed Jan. 10, 2018, by Blueprint Medicines Corp.

U.S. Appl. No. 15/973,340, filed May 7, 2018, by Blueprint Medicines Corp.

U.S. Appl. No. 15/973,378, filed May 7, 2018, by Blueprint Medicines Corp.

U.S. Appl. No. 16/002,587, filed Jun. 7, 2018, by Blueprint Medicines Corp.

U.S. Appl. No. 16/027,166, filed Jul. 3, 2018, by Blueprint Medicines Corp.

U.S. Appl. No. 16/041,719, filed Jul. 20, 2018, by Blueprint Medicines Corp.

Yu, P.B. et al. (Dec. 2008) "BMP type I receptor inhibition reduces heterotopic ossification" *Nat Med*, 14(12):1363-1369, including Erratum (1 page).

\* cited by examiner

INHIBITORS OF ACTIVIN RECEPTOR-LIKE KINASE

CLAIM OF PRIORITY

This application is a continuation of U.S. patent application Ser. No. 15/488,257, filed Apr. 14, 2017, which claims priority from U.S. Provisional Application No. 62/332,948, filed Apr. 15, 2016, and U.S. Provisional Application No. 62/411,172, filed Oct. 21, 2016, each of which is incorporated herein in its entirety.

The disclosure relates to inhibitors of Activin receptor-like kinase-2 (ALK2).

BACKGROUND

Activin receptor-like kinase-2 (ALK2) is encoded by the Activin A receptor, type I gene (ACVR1). ALK2 is a serine/threonine kinase in the bone morphogenetic protein (BMP) pathway (Shore et al., *Nature Genetics* 2006, 38: 525-27). It binds to complexes comprising bone morphogenetic proteins (BMPs) and is responsible for transducing BMP signals. Certain mutations in ALK2 cause the kinase to be constitutively active and are associated with various diseases. Fibrodysplasia ossificans progressiva (FOP) is a rare, severely debilitating heritable disorder characterized by progressive heterotopic ossification in extraskeletal sites. Individuals with this disease experience significantly reduced mobility and shortened lifespan. Current therapy is limited to ameliorating swellings (flare-ups) that characterize the disease.

All FOP patients carry heterozygous, activating mutations in the ACVR1 gene. Further, the vast majority of FOP patients harbor the same ALK2 mutation, R206H. Transgenic mice that express ALK2-R206H recapitulate the key features of the human disease, including malformation of the first digit in the hind limbs and inflammatory infiltration and muscle cell apoptosis followed by formation of heterotopic bone through an endochondral pathway (Chakkalakal et al., *J Bone Miner Res.* 2012, 27(8): 1746-1756). A second engineered mouse strain has been developed that expresses the activated ALK2-Q207D variant in muscle and phenocopies key features of human FOP. Treatment of these mice with an inhibitor of BMP receptor type 1 kinases resulted in inhibition of SMAD signaling and reduction in ectopic ossification and associated functional impairment (Fukuda et al., *Genesis* 2006, 44, 159-167). Other mutations in ALK2 that have been associated with FOP include but are not limited to L196P, PF197-8L, R202I, R258S, R258G, G328A, G328W, G328E, G328R, G356D, and R375P (Kaplan et al., *Hum Mutat.* 2009, 30(3): 379-390; Gregson et al., *Bone* 2011, 48:654-658; Kaplan et al., *Am J Med Genet* 2015, 167: 2265-2271; Petrie et al., *PLoS One* 2009, 4(3): e5005; Bocciardi et al., *Eur J Hum Genetics* 2009, 17:311-318; Pacifici and Shore, *Cytokine & Growth Factor Reviews* 2016, 27:93-104).

In certain circumstances, heterotopic ossification (HO) can also be induced in people who are wild-type ALK2. These circumstances can include major surgical interventions, trauma (such as head or blast injuries), protracted immobilization, or severe burns. An ALK2 inhibitor could potentially be an effective therapy for the treatment of FOP and other conditions caused by HO.

Diffuse intrinsic pontine glioma (DIPG) is a rare, aggressive and typically fatal pediatric brain stem cancer with no effective treatment options. Due to its anatomical location and diffuse nature, DIPG cannot be treated by surgery. DIPG arises exclusively in young children and the two year survival rate is approximately less than 10%. Because of their location in the brainstem, DIPGs cause pressure on cranial nerves leading to double vision, difficulty in controlling eye movement, difficulty chewing/swallowing, weakness in the arms/legs leading to loss of movement and difficulty speaking. As the tumor progresses there is increasing pressure inside the skull causing severe headaches, nausea/vomiting and fatigue. Unlike many other pediatric cancers, there has been virtually no progress in improving treatments for DIPG over the last few decades. Historically, the lack of understanding regarding the drivers of DIPG has hindered the identification of potential new treatment options. Consequently, the medical need for DIPG treatments is exceedingly high. Recent genomic characterization has demonstrated that ~25% of DIPG tumors possess somatic, heterozygous ALK2 activating mutations. Mutations in ALK2 associated with DIPG include, but are not limited to R206H, G328V, G328W, G328E, and G356D (Jones and Baker, *Nature Rev Cancer* 2014, 14:651-661).

Notably, the ALK2 mutations found in DIPG overlap with those found in FOP, suggesting a potential synergy between inhibitor development efforts for the two diseases (e.g., via overlapping screening funnels and chemistry efforts). The finding that a significant proportion of DIPG contain activating ALK2 mutations suggests that ALK2 inhibitors may be of clinical benefit for DIPG patients.

Anemia of chronic disease, inflammation or cancer can develop in settings of chronic inflammatory, infectious, or neoplastic disease. In this form of anemia, inflammatory cytokines, induce hepatic expression of hepcidin, which negatively regulates iron bioavailability by inactivating ferroportin. Hepcidin is transcriptionally regulated by amongst other things bone morphogenetic protein (BMP) signaling. Inhibition of BMP phosphorylation through inhibition of ALK2 can modulate BMP-mediated signaling, thus reducing hepcidin expression. Reduced hepcidin expression may be an effective strategy for the treatment of anemia of chronic disease, inflammation, or cancer.

SUMMARY

The present disclosure provides inhibitors of ALK2 and ALK2 mutants, e.g., ALK2 mutants as defined herein, for example, inhibitors of structural formula (I) and formula (Ia) and pharmaceutically acceptable salts and compositions thereof. The present disclosure further provides methods of using the compounds of the disclosure, and pharmaceutically acceptable salts and compositions thereof, to inhibit the activity of ALK2 or ALK2 mutants in a cell or in a patient. The present disclosure further provides methods for using the compounds of the disclosure and pharmaceutically acceptable salts and compositions thereof, to treat a subject or patient suffering from a condition mediated by aberrant ALK2 activity, e.g., at least one of fibrodysplasia ossificans progressiva (FOP) or heterotopic ossification or diffuse intrinsic pontine glioma (DIPG) or anemia of chronic disease or anemia of inflammation or anemia of cancer.

In one aspect, the disclosure features a compound of structural formula (I) or at least one of pharmaceutically acceptable salt thereof:

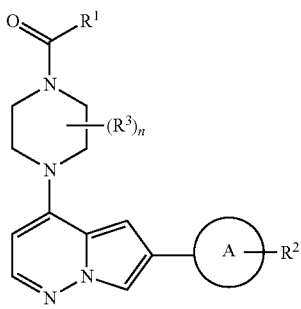

(I)

wherein each of ring A, $R^1$, $R^2$, $R^3$, and n is defined as described herein.

In another aspect, the present disclosure provides pharmaceutical compositions comprising a compound of structural formula (I) or a pharmaceutically acceptable salt thereof and a pharmaceutically acceptable carrier.

In another aspect, the present disclosure provides a method for treating or ameliorating fibrodysplasia ossificans progressiva in a subject. In an embodiment, said method comprises administering to the subject a therapeutically effective amount of a compound of structural formula (I) or a pharmaceutically acceptable salt or composition thereof. In an embodiment, the subject has a mutation in an ALK2 gene that results in the expression of an ALK2 enzyme having an amino acid modification selected from one or more of L196P, PF197-8L, R202I, R206H, Q207E, R258S, R258G, G328A, G328W, G328E, G328R, G356D, and R375P.

In another aspect, the present disclosure provides a method of treating or ameliorating diffuse intrinsic pontine glioma in a subject. In an embodiment, said method comprises administering to the subject a therapeutically effective amount of a compound of structural formula (I) or a pharmaceutically acceptable salt or composition thereof. In an embodiment, the subject has a mutation in an ALK2 gene that results in the expression of an ALK2 enzyme having an amino acid modification selected from one or more of R206H, G328V, G328W, G328E, and G356D.

In another aspect, the present disclosure provides a method of inhibiting aberrant ALK2 activity in a subject. In an embodiment, said method comprises administering to the subject a therapeutically effective amount of a compound of structural formula (I) or a pharmaceutically acceptable salt or composition thereof. In an embodiment, the subject has a mutation in an ALK2 gene that results in the expression of an ALK2 enzyme having an amino acid modification selected from one or more of L196P, PF197-8L, R202I, R206H, Q207E, R258S, R258G, G328A, G328V, G328W, G328E, G328R, G356D, and R375P.

The methods described herein can additionally comprise various evaluation steps prior to, during, and/or following treatment with a compound of the disclosure. In an embodiment, prior to, during and/or following treatment with a compound of the disclosure, the method further comprises the step of evaluating, e.g., visualizing, heterotopic ossification in the subject. This may be achieved by spectroscopic analysis, e.g., magnetic resonance-based analysis, e.g., MRI, positron emission tomography (PET), micro computed tomography (μCT), or by histology.

In an embodiment, the methods comprise evaluating a pre-treatment or baseline level of the heterotopic ossification in a subject, e.g., using spectroscopic analysis, e.g., magnetic resonance-based analysis, e.g., MRI, positron emission tomography (PET), micro computed tomography (μCT), or by histology. In an embodiment, the methods further comprise administering to the subject a compound of the disclosure; evaluating the post-treatment level of heterotopic ossification, e.g., using spectroscopic analysis, e.g., magnetic resonance-based analysis, e.g., MRI, positron emission tomography (PET), micro computed tomography (μCT), or by histology; comparing the post-treatment level of heterotopic ossification in the subject with the pre-treatment or baseline level of heterotopic ossification; and determining whether to continue treatment, e.g., using spectroscopic analysis, e.g., magnetic resonance-based analysis, e.g., MRI, positron emission tomography (PET), micro computed tomography (μCT), or by histology.

In an embodiment, the heterotopic ossification is preceded by edema, e.g., sustained edema.

EMBODIMENTS OF THE DISCLOSURE

Definitions

As used herein, the terms a "patient," "subject," "individual," and "host" refer to either a human or a non-human animal suffering from or suspected of suffering from a disease or disorder associated with aberrant ALK2 activity (i.e., aberrant ALK2 activity due to a mutation in an ALK2 gene that results in the expression of an ALK2 enzyme having an amino acid modification) or aberrant ALK2 biological activity.

"Treat", "treatment" and "treating" such a disease or disorder refers to ameliorating at least one symptom of the disease or disorder described herein. These terms, when used in connection with a condition such as fibrodysplasia ossificans progressiva, refer to one or more of: controlling the rate of heterotropic bone growth; relieving pain and inflammation associated with development of new bone; extending the expected survival time of the patient; reducing the size or the number of heterotopic bone growth lesions; maintaining or improving mobility; preventing or treating new flare ups; inhibiting the development of new heterotopic bone lesions; enabling surgery to remove existing heterotopic ossifications to restore limb function and/or mobility; prolonging survival; prolonging progression-free survival; prolonging time to progression; inhibiting FOP related injury induced edema, and/or enhancing quality of life. When used in connection with a condition such as diffuse intrinsic pontine glioma, these terms refer to one or more of: impeding growth of the glioma, causing the glioma to shrink by weight or volume, extending the expected survival time of the patient, inhibiting glial tissue growth, reducing glial tumor mass, reducing size or number of metastatic lesions, inhibiting the development of new metastatic lesions, prolonging survival, prolonging progression-free survival, prolonging time to progression, and/or enhancing quality of life.

The term "therapeutic effect" refers to a beneficial local or systemic effect in animals, particularly mammals, and more particularly humans, caused by administration of a compound or composition of the disclosure. The phrase "therapeutically effective amount" means that amount of a compound or composition of the disclosure that is effective to treat a disease or condition associated with aberrant ALK2 activity at a reasonable benefit/risk ratio. The therapeutically effective amount of such substance will vary, for example, depending upon the subject and disease condition being treated, the weight and age of the subject, the severity of the disease condition, the manner of administration, etc., which can readily be determined by one of skill in the art.

"Alkylene" refers to a divalent radical of an alkyl group, e.g., —CH$_2$—, —CH$_2$CH$_2$—, and —CH$_2$CH$_2$CH$_2$—.

"Alkyl" or "alkyl group" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Aromatic" when referring to a ring is art-recognized, and refers to a fully conjugated, unsaturated ring that has 4n+2π electrons and is often characterized by structural formulae showing alternating double and single bonds. Aromatic rings include both benzene and rings containing one or more heteroatoms selected from N, O and S.

"Aryl" refers to a ring system is art-recognized and refers to a monocyclic, bicyclic or polycyclic hydrocarbon ring system wherein at least one ring is aromatic.

"Halo" refers to a radical of any halogen, e.g., —F, —Cl, —Br, or —I.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom may be substituted (e.g., by one or more substituents). The cycloalkyl groups can contain fused or spiro rings. Fused rings are rings that share at least two common (carbon) atoms. Examples of cycloalkyl moieties include, but are not limited to, cyclopropyl, cyclohexyl, methylcyclohexyl, adamantyl, and norbornyl.

"Heteroalkyl" refers to a monovalent, straight or branched alkyl chain where one methylene unit other than the methylene unit bound to the rest of the molecule is replaced with —O—, —S—, or —N(R$^d$), wherein R$^d$ is defined below. For the sake of clarity, the moiety —CH$_2$—NH—CH$_3$ would be a heteroalkyl, but —NH—CH$_2$—CH$_3$ would not because the —NH group is bound to the rest of the molecule.

"Heteroalkylene" refers to a divalent radical of a heteroalkyl group.

"Heteroaromatic ring system" is art-recognized and refers to a monocyclic, bicyclic or polycyclic ring system wherein at least one ring is both aromatic and comprises at least one heteroatom (e.g., N, O, or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl, pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and that ring comprises at least one heteroatom. A heterocyclic ring system can be attached to its pendant group at any heteroatom or carbon atom that results in a stable structure and any of the ring atoms can be optionally substituted. Heterocyclic ring systems may be fused rings.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Cyano" refers to a —CN radical.

"Hydroxy" or "hydroxyl" refers to —OH.

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure. Thus, when a disclosed compound is named or depicted by a structure without specifying the stereochemistry and has one or more chiral centers, it is understood to represent all possible stereoisomers of the compound, as well as enantiomeric mixtures thereof. When a disclosed compound is named or depicted by a structure specifying stereochemistry at each chiral center, it is understood to represent only the compound having the designated stereochemistry at such chiral centers. However, when a disclosed compound specifies stereochemistry at some, but not all chiral centers, it is understood to represent all possible stereoisomers at the non-specified chiral centers of the compound, as well as enantiomeric mixtures thereof.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

ee=(90−10)/100=80%.

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present disclosure. In addition, all tautomeric forms of the compounds described herein are intended to be within the scope of the claimed disclosure.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthalate, mesylate, glucoheptonate, lactobionate, and laurylsulfonate salts and the like. (See, for example, Berge et al. (1977) "Pharmaceutical Salts", *J. Pharm. Sci.* 66:1-19.)

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable substituents for an optionally substituted alkyl, alkylene, carbocyclyl, heterocyclyl, aryl group and heteroaryl group include halogen, =O, —CN, —OR$^e$, —NR$^d$R$^e$, —S(O)$_k$R$^e$, —NR$^c$S(O)$_2$R$^e$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S)NR$^d$R$^e$, —C(=S)R$^c$, —C(=O)R$^c$, $C_1$-$C_6$ alkyl, $C_1$-$C_6$ haloalkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, wherein each of said alkyl, alkylene, heteroalkyl, heteroalkylene, carbocyclyl, heterocyclyl, aryl, and heteroaryl are optionally substituted with one or more of halogen, OR$^e$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, $C_1$-$C_6$ alkyl, $C_1$-$C_6$ haloalkyl, or $C_1$-$C_6$ heteroalkyl, and wherein R$^c$ is hydrogen, hydroxy, $C_1$-$C_6$ alkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, each of which is optionally substituted with one or more of halogen, hydroxy, $C_1$-$C_6$ alkyl, $C_1$-$C_6$ haloalkyl, $C_1$-$C_6$ heteroalkyl, carbocyclyl, heterocyclyl, aryl, or heteroaryl; R$^d$ and R$^e$ are each independently selected from hydrogen, $C_1$-$C_6$ alkyl, or $C_1$-$C_6$ heteroalkyl; and k is 0, 1, or 2. The claimed disclosure is not intended to be limited in any manner by the above exemplary listing of substituents.

Compounds

In one aspect, the present disclosure features a compound having the structural formula (I):

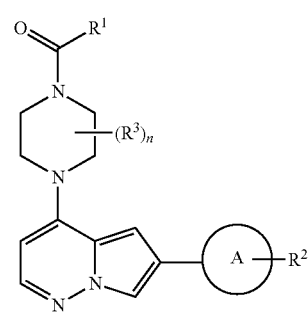

(I)

or a pharmaceutically acceptable salt thereof, wherein:

ring A is phenyl or heteroaryl, wherein ring A is substituted with 0, 1, 2, or 3 independently selected substituents in addition to R$^2$;

R$^1$ is selected from NH($C_1$-$C_6$ alkyl), N($C_1$-$C_6$ alkyl)$_2$, $C_1$-$C_6$ alkyl, —O—$C_1$-$C_6$ alkyl, —C(O)—$C_1$-$C_4$ alkyl, carbocyclyl, heterocyclyl, —O—($C_0$-$C_4$ alkylene)-carbocyclyl, —O—($C_0$-$C_4$ alkylene)-heterocyclyl, —NH—($C_0$-$C_4$ alkylene)-carbocyclyl, and —NH—($C_0$-$C_4$ alkylene)-heterocyclyl, wherein each alkyl, alkylene, carbocyclyl, and heterocyclyl portion of R$^1$ is unsubstituted or is independently substituted with 1, 2, 3, or 4 independently selected substituents; or R$^1$ is taken together with one R$^3$ to form a saturated ring fused to the piperazine ring in formula (I), and wherein the ring formed by R$^1$ and R$^3$ is unsubstituted, or is substituted with 1, 2, or 3 independently selected substituents;

R$^2$ is selected from halo, $C_1$-$C_6$ alkyl, heterocyclyl, cycloalkyl, —NH—($C_0$-$C_4$ alkylene)-heterocyclyl, alkylene)-heterocyclyl, and —O—($C_0$-$C_4$ alkylene)-heterocyclyl, wherein any heterocyclyl, cycloalkyl, alkyl, or alkylene portion of $R^2$ is unsubstituted or is substituted with 1, 2, 3, or 4 independently selected substituents; or $R^2$ is taken together with any ring atom in ring A to form a cycloalkyl or saturated heterocyclyl ring that is fused, spirofused, or bridged to ring A, and wherein the ring formed by $R^2$ and the ring atom in ring A is unsubstituted, or is substituted with 1, 2, or 3 independently selected substituents;

each $R^3$, if present, is independently selected from $C_1$-$C_4$ alkyl and $C_1$-$C_4$ haloalkyl; and n is 0, 1, 2, or 3.

In certain embodiments of Formula I, $R^1$ may additionally be selected from —NH-aryl, —NH—O—($C_1$-$C_4$ alkyl), and —S-heterocyclyl.

In certain embodiments of Formula I, $R^2$ may additionally be selected from —($C_1$-$C_4$ alkylene)-NH-heterocyclyl.

In an embodiment, the compound is a compound of Formula (I) or a pharmaceutically acceptable salt thereof, wherein:

ring A is phenyl or heteroaryl, wherein ring A is substituted with 0, 1, 2, or 3 independently selected substituents in addition to $R^2$;

$R^1$ is selected from NH($C_1$-$C_6$ alkyl), N($C_1$-$C_6$ alkyl)$_2$, $C_1$-$C_6$ alkyl, —O—$C_1$-$C_6$ alkyl, —C(O)—$C_1$-$C_4$ alkyl, carbocyclyl, heterocyclyl, —O—($C_0$-$C_4$ alkylene)-carbocyclyl, —O—($C_0$-$C_4$ alkylene)-heterocyclyl, —NH—($C_0$-$C_4$ alkylene)-carbocyclyl, and —NH—($C_0$-$C_4$ alkylene)-heterocyclyl, wherein each alkyl, alkylene, carbocyclyl, and heterocyclyl portion of $R^1$ is unsubstituted or is independently substituted with 1, 2, 3, or 4 independently selected substituents; or $R^1$ is taken together with one $R^3$ to form a saturated ring fused to the piperazine ring in formula (I), and wherein the ring formed by $R^1$ and $R^3$ is unsubstituted, or is substituted with 1, 2, or 3 independently selected substituents;

$R^2$ is selected from halo, $C_1$-$C_6$ alkyl, heterocyclyl, cycloalkyl, —NH—($C_0$-$C_4$ alkylene)-heterocyclyl, and —O—($C_0$-$C_4$ alkylene)-heterocyclyl, wherein any heterocyclyl, cycloalkyl, alkyl, or alkylene portion of $R^2$ is unsubstituted or is substituted with 1, 2, 3, or 4 independently selected substituents; or $R^2$ is taken together with any ring atom in ring A to form a cycloalkyl or saturated heterocyclyl ring that is fused, spirofused, or bridged to ring A, and wherein the ring formed by $R^2$ and the ring atom in ring A is unsubstituted, or is substituted with 1, 2, or 3 independently selected substituents;

each $R^3$, if present, is independently selected from $C_1$-$C_1$ alkyl and $C_1$-$C_4$ haloalkyl; and n is 0, 1, 2, or 3.

In an embodiment, n is 0 or 1; and $R^3$, if present, is selected from methyl, ethyl, and —CHF$_2$.

In an embodiment, ring A is selected from:

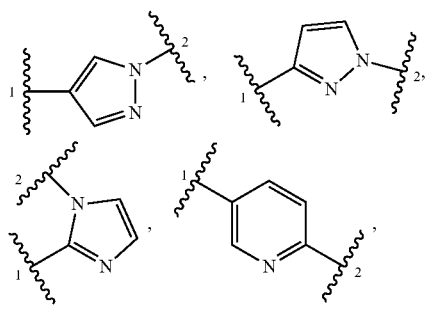

-continued

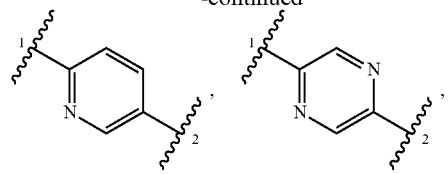

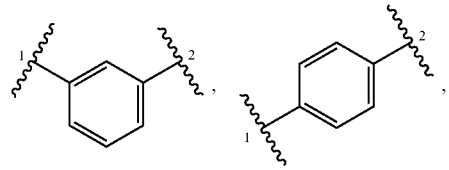

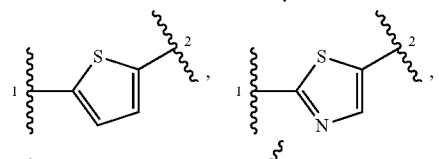

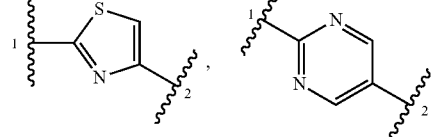

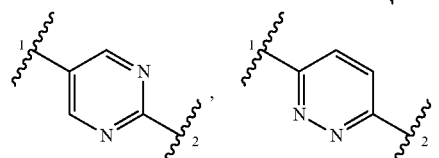 and

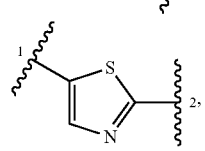

wherein:

"1" represents a portion of ring A bound to a pyrrolo[1,2-b]pyridazine moiety;

"2" represents a portion of ring A bound to $R^2$; and ring A is substituted with 0, 1, 2, or 3 independently selected substituents in addition to $R^2$.

In an embodiment, ring A is selected from:

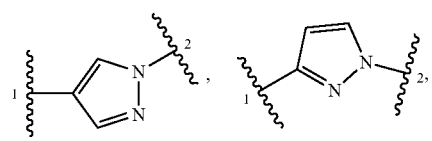

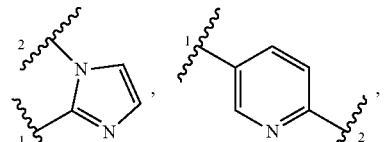

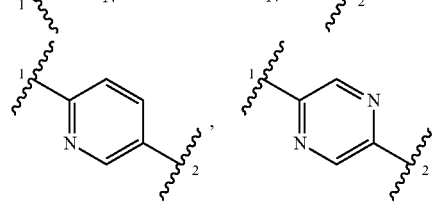

-continued

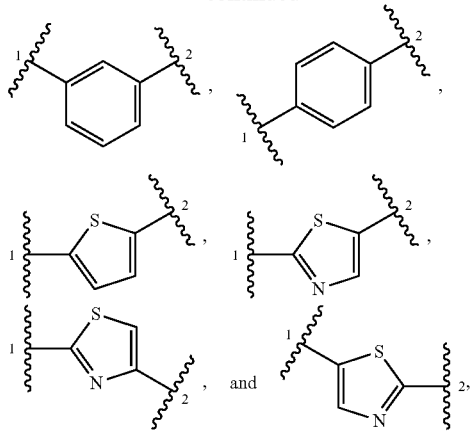

wherein:
"1" represents a portion of ring A bound to a pyrrolo[1,2-b]pyridazine moiety;
"2" represents a portion of ring A bound to $R^2$; and
ring A is substituted with 0, 1, 2, or 3 independently selected substituents in addition to $R^2$.

In an embodiment, ring A is selected from phenyl and pyridinyl. In one aspect of this embodiment, ring A is selected from phenyl and pyridin-2-yl.

In an embodiment, ring A is substituted with 0, 1, or 2 substituents in addition to $R^2$, wherein each of the substituents is independently selected from halo, methyl, and —$OCHF_2$.

In an embodiment, ring A is substituted with 0, 1, or 2 substituents in addition to $R^2$, wherein each of the substituents is independently selected from halo, methyl, —CN, and —$OCHF_2$.

In an embodiment, $R^1$ is selected from —C(O)—($C_1$-$C_3$ alkyl), $C_1$-$C_3$ alkyl, —O—($C_1$-$C_5$ alkyl), —NH($C_1$-$C_5$ alkyl), —N($C_1$-$C_4$ alkyl)$_2$, —NH—($C_3$-$C_6$ cycloalkyl), $C_3$-$C_6$ cycloalkyl, —O—($C_3$-$C_6$ cycloalkyl), —O—($C_1$-$C_3$ alkyl)-($C_3$-$C_6$ cycloalkyl), —($C_1$-$C_3$ alkylene)-($C_3$-$C_6$ cycloalkyl), —O—($C_0$-$C_3$ alkylene)-(O-containing heterocyclyl), —NH—($C_0$-$C_3$ alkylene)-(O-containing heterocyclyl), an O-containing heterocyclyl, and an N-containing heterocyclyl, wherein any alkyl, alkylene, cycloalkyl, or heterocyclyl portion of $R^1$ is unsubstituted, or is substituted with 1, 2, or 3 substituents independently selected from halo, cyano, acetyl, $C_1$-$C_4$ alkyl, $C_1$-$C_4$ haloalkyl, —O—$C_1$-$C_4$ alkyl, —$C_1$-$C_4$ alkylene-O—$C_1$-$C_4$ alkyl, optionally substituted heteroaryl, optionally substituted phenyl, optionally substituted cycloalkyl, and —OH; or $R^1$ is taken together with any ring atom in the piperazine moiety of formula (I) to form a carbocyclyl or heterocyclyl ring fused to the piperazine moiety.

In some embodiments, any alkyl, alkylene, cycloalkyl, or heterocyclyl portion of $R^1$ is substituted with 1, 2, or 3 substituents independently selected from deuterium, halo, cyano, acetyl, $C_1$-$C_4$ alkyl, $C_1$-$C_4$ haloalkyl, —O—$C_1$-$C_4$ alkyl, —$C_1$-$C_4$ alkylene-O—$C_1$-$C_4$ alkyl, optionally substituted heteroaryl, optionally substituted phenyl, optionally substituted cycloalkyl, —COOH, and —OH.

In some embodiments, $R^1$ is selected from —O—($C_0$-$C_3$ alkylene)-(N-containing heterocyclyl), —S—($C_0$-$C_3$ alkylene)-(O-containing heterocyclyl), —NH—O—($C_1$-$C_3$ alkyl), and —NH-phenyl, wherein any alkyl, alkylene, phenyl, or heterocyclyl portion of $R^1$ is unsubstituted, or is substituted with 1, 2, or 3 substituents independently selected from deuterium, halo, cyano, acetyl, $C_1$-$C_4$ alkyl, $C_1$-$C_4$ haloalkyl, —O—$C_1$-$C_4$ alkyl, —$C_1$-$C_4$ alkylene-O—$C_1$-$C_4$ alkyl, optionally substituted heteroaryl, optionally substituted phenyl, optionally substituted cycloalkyl, —COOH, and —OH.

In an embodiment, $R^1$ is selected from —C(O)—($C_1$-$C_3$ alkyl), $C_1$-$C_3$ alkyl, —O—($C_1$-$C_3$ alkyl), —NH($C_1$-$C_3$ alkyl), —N($C_1$-$C_4$ alkyl)$_2$, —NH—($C_3$-$C_6$ cycloalkyl), $C_3$-$C_6$ cycloalkyl, —O—($C_3$-$C_6$ cycloalkyl), —O—($C_1$-$C_3$ alkyl)-($C_3$-$C_6$ cycloalkyl), —($C_1$-$C_3$ alkylene)-($C_3$-$C_6$ cycloalkyl), and an N-containing heterocyclyl, wherein any alkyl, cycloalkyl, or heterocyclyl portion of $R^1$ is unsubstituted, or is substituted with 1, 2, or 3 substituents independently selected from halo, cyano, acetyl, $C_1$-$C_4$ alkyl, $C_1$-$C_4$ haloalkyl, —O—$C_1$-$C_4$ alkyl, —$C_1$-$C_4$ alkylene-O—$C_1$-$C_4$ alkyl, optionally substituted heteroaryl, optionally substituted phenyl, optionally substituted cycloalkyl, and —OH; or $R^1$ is taken together with any ring atom in the piperazine moiety of formula (I) to form a carbocyclyl or heterocyclyl ring fused to the piperazine moiety.

In an embodiment, $R^1$ is selected from 1-(3-chlorophenyl)cyclopropyl, 1-(3-fluorophenyl)cyclopropyl, 1-acetylcyclopropyl, 1-cyclopropylcyclopropyl, 1-difluoromethylcyclopropyl, 1-fluorocyclopropyl, 1-methylpropylamino, 1-pyridin-3-ylcyclopropyl, 1-thiazol-2-ylcyclopropyl, 1-thien-2-ylcyclopropyl, 1-trifluoromethylcyclopropyl, 2-(4-chlorophenyl)cyclopropyl, 2,2,2-trifluoroethoxy, 2,2-difluorocyclopropyl, 2,2-dimethylcyclopropyl, 2-cyanocyclopropyl, 2-cyanoethyl, 2-cyanoethylamino, 2-cyclobutylcyclopropyl, 2-fluorocyclopropyl, 2-fluoroethoxy, 2-hydroxyethylamino, 2-methoxyethoxy, 2-methylcyclopropyl, 2-oxa-6-azaspiro[3.3]heptan-6-yl, 3,3-difluorocyclobutyl, 3-cyanoazetidin-1-yl, 3-cyanocyclobutyl, 3-fluorocyclobutyl, 3-hydroxy-3-methylcyclobutyl, 3-hydroxy-3-trifluoromethylcyclobutyl, 3-hydroxyazetidin-1-yl, 3-hydroxycyclobutyl, 3-methoxyazetidin-1-yl, 3-methoxymethylazetidin-1-yl, 3-phenyl-3-hydroxycyclobutyl, 4-cyanocyclohexyl, 4-cyanopiperidin-1-yl, 4-hydroxy-4-methylcyclohexyl, 4-hydroxycyclohexyl, 4-hydroxypiperidin-1-yl, 4-methylcyclohexyl, acetyl, azetidin-1-yl, cyclobutoxy, cyclobutyl, cyclobutylamino, cyclopentylamino, cyclopropyl, cyclopropylmethyl, diethylamino, ethoxy, ethyl, ethylamino, isobutoxy, isopropoxy, isopropyl, isopropylamino, methoxymethyl, N-ethyl-N-methylamino, pentylamino, piperidin-1-yl, propylamino, propyloxypyrrolidin-1-yl, t-butylamino, t-butoxy, 2,2-dimethylpropoxy, 2,2-difluoroethoxy, N-(2,2-dimethylpropyl)amino, N-(1,2-dimethylpropyl)amino, 2,2,2-trifluoroethylamino, N-(methoxymethyl)amino, oxetan-3-yloxy, oxetan-3-yl, oxetan-3-ylamino, oxetan-3-ylmethoxy, N-(oxetan-3-ylmethyl)amino, tetrahydrofuran-3-yloxy, tetrahydropyran-4-yloxy, and 3-cyanocyclobutoxy, or $R^1$ is taken together with a ring atom in the piperazine moiety to form a 6-oxohexahydropyrrolo[1,2-a]pyrazin-2-yl, or 2-ethyl-3-oxohexahydroimidazo[1,5-a]pyrazin-7-yl.

In an embodiment, $R^1$ is selected from 1,3-dihydroxypropan-2-yloxy, 1-acetylazetidin-3-yloxy, 1-hydroxy-2-hydroxycarbonylethan-2-yloxy, 1-methyl-2-fluoroethoxy, 2,2-difluoroethylamino, 2-cyanoethan-1-yloxy, 2-fluoroethylamino, 2-fluorophenylamino, 2-fluoropropoxy, 2-methyloxetan-3-yloxy, 3-cyano-oxetan-3-yloxy, 3-deutero-oxetan-3-yloxy, 6-oxa-1-azaspiro[3.3]heptan-1-yl, cyclopropoxy, ethoxyamino, oxetan-3-ylthio, perdeuteroethoxy, phenylamino, tetrahydrofuran-2-yloxy, and tetrahydrofuran-3-yl. In an embodiment, $R^1$ is selected from 1-(3-chlorophenyl)cyclopropyl, 1-(3-fluorophenyl)cyclopropyl, 1-acetylcyclopropyl, 1-cyclopropylcyclopropyl, 1-difluoromethylcyclopropyl, 1-fluorocyclopropyl, 1-methylpropylamino1-pyridin-3-ylcyclopropyl, 1-thiazol-2-ylcyclopropyl, 1-thien-2-ylcyclopropyl, 1-trifluoromethylcyclopropyl, 2-(4-chlorophenyl)cyclopropyl, 2,2,2-trifluoroethoxy, 2,2-difluorocyclopropyl, 2,2-dimethylcyclopropyl, 2-cyanocyclopropyl, 2-cyanoethyl, 2-cyanoethylamino, 2-cyclobutylcyclopropyl, 2-fluorocyclopropyl, 2-fluoroethoxy, 2-hydroxyethylamino, 2-methoxyethoxy, 2-methylcyclopropyl, 2-oxa-6-azaspiro[3.3]heptan-6-yl, 3,3-difluorocyclobutyl, 3-cyanoazetidin-1-yl, 3-cyanocyclobutyl, 3-fluorocyclobutyl, 3-hydroxy-3-methylcyclobutyl, 3-hydroxy-3-trifluoromethylcyclobutyl, 3-hydroxyazetidin-1-yl, 3-hydroxycyclobutyl, 3-methoxyazetidin-1-yl, 3-methoxymethylazetidin-1-yl, 3-phenyl-3-hydroxycyclobutyl, 4-cyanocyclohexyl, 4-cyanoypiperidin-1-yl, 4-hydroxy-4-methylcyclohexyl, 4-hydroxycyclohexyl, 4-hydroxypiperidin-1-yl, 4-methylcyclohexyl, acetyl, azetidin-1-yl, cyclobutoxy, cyclobutyl, cyclobutylamino, cyclopentylamino, cyclopropyl, cyclopropylmethyl, diethylamino, ethoxy, ethyl, ethylamino, isobutoxy, isopropoxy, isopropyl, isopropylamino, methoxymethyl, N-ethyl-N-methylamino, pentylamino, piperidin-1-yl, propylamino, propyloxypyrrolidin-1-yl, and t-butylamino, or $R^1$ is taken together with a ring atom in the piperazine moiety to form a 6-oxohexahydropyrrolo[1,2-a]pyrazin-2-yl, or 2-ethyl-3-oxohexahydroimidazo[1,5-a]pyrazin-7-yl.

In an embodiment, $R^2$ is selected from halo, cycloalkyl, heterocyclyl, —O—($C_0$-$C_4$ alkylene)-(heterocyclyl), —($C_1$-$C_3$ alkylene)-heterocyclyl, —($C_1$-$C_3$ alkylene)-NH—($C_1$-$C_3$ alkyl), -(hydroxy-substituted $C_1$-$C_3$ alkylene)-NH—($C_1$-$C_3$ alkyl), $C_1$-$C_3$ alkyl substituted with both hydroxy and amino, and cyano-substituted $C_1$-$C_4$ alkyl, or $R^2$ is taken together with a ring atom in ring A to form a heterocyclyl or a carbocyclyl that is fused to ring A, wherein any heterocyclyl, cycloalkyl, or carbocyclyl is optionally substituted with up to 3 substituents independently selected from halo, cyano, —NH_2, —NH($C_1$-$C_4$ alkyl), —NH—C(O)—O—($C_1$-$C_4$ alkyl), =O, —OH, —C(O)—$C_1$-$C_4$ alkyl, —$C_1$-$C_4$ alkyl, deuterated $C_1$-$C_4$ alkyl, —$C_1$-$C_4$ haloalkyl, hydroxy-substituted —$C_1$-$C_4$ alkyl, —O—$C_1$-$C_4$ alkyl, —($C_1$-$C_4$ alkylene)-O—($C_1$-$C_4$ alkyl), —($C_1$-$C_4$ alkylene)-O—($C_1$-$C_4$ haloalkyl), —C(O)—O—$C_1$-$C_4$ alkyl, $C_3$-$C_6$ cycloalkyl, an optionally substituted second heterocyclyl, or —NH-(optionally substituted second heterocyclyl).

In an embodiment $R^2$ is selected from —OH, —S(O)_2—$C_1$-$C_4$ alkyl, -(amino substituted $C_1$-$C_3$ alkylene)-heterocyclyl, $C_4$ alkyl, $C_1$-$C_3$ alkyl substituted with both hydroxy and either $C_1$-$C_4$ alkylamino or di-$C_1$-$C_4$ alkylamino.

In an embodiment, any heterocyclyl, cycloalkyl, or carbocyclyl is optionally substituted with up to 3 substituents independently selected from halo, cyano, —OH, —NH($C_1$-$C_4$ alkyl), —NH—C(O)—O—($C_1$-$C_4$ alkyl), =O, —OH, —C(O)—$C_1$-$C_4$ alkyl, —$C_1$-$C_4$ alkyl, deuterated $C_1$-$C_4$ alkyl, —$C_1$-$C_4$ haloalkyl, hydroxy-substituted —$C_1$-$C_4$ alkyl, —O—$C_1$-$C_4$ alkyl, —O—$C_1$-$C_4$ haloalkyl, —($C_1$-$C_4$ alkylene)-O—($C_1$-$C_4$ alkyl), -(amino substituted $C_1$-$C_4$ alkylene)-O—($C_1$-$C_4$ alkyl), —($C_1$-$C_4$ alkylene)-O—($C_1$-$C_4$ haloalkyl), —C(O)—O—$C_1$-$C_4$ alkyl, —COOH, $C_3$-$C_6$ cycloalkyl, an optionally substituted second heterocyclyl, or —NH-(optionally substituted second heterocyclyl).

In an embodiment, $R^2$ is selected from halo, cycloalkyl, heterocyclyl, —O—($C_0$-$C_4$ alkylene)-(heterocyclyl), and cyano-substituted $C_1$-$C_4$ alkyl, or $R^2$ is taken together with a ring atom in ring A to form a heterocyclyl that is fused to ring A, wherein any heterocyclyl is optionally substituted with up to 3 substituents independently selected from halo, —NH_2, =O, —OH, —C(O)—$C_1$-$C_4$ alkyl, —$C_1$-$C_4$ alkyl, deuterated $C_1$-$C_4$ alkyl, —$C_1$-$C_4$ haloalkyl, hydroxy-substituted —$C_1$-$C_4$ alkyl, —O—$C_1$-$C_4$ alkyl, —($C_1$-$C_4$ alkyl)-O—($C_1$-$C_4$ alkyl), $C_3$-$C_6$ cycloalkyl, an optionally substituted second heterocyclyl, or —NH-(optionally substituted second heterocyclyl).

In an embodiment, $R^2$ is selected from 1-(1-hydroxypropan-2-yl)-4-methoxypiperidin-4-yl, 1-(3-difluoromethoxy)propan-2-yl-4-methoxypiperidin-4-yl, 1-(3-methoxy)propan-2-yl-4-methoxypiperidin-4-yl, 1-(oxetan-3-yl)-4-methoxypiperidin-4-yl, 1-(oxetan-3-yl)piperidin-4-yl, 1-(propan-2-yl)piperidin-3-yl, 1-(propan-2-yl)piperidin-4-yl, 1-(pyrrolidin-1-yl)ethan-1-yl, 1,2,3,6-tetrahydropyridin-4-yl, 1,4-diazabicyclo[4.2.0]octan-4-yl, 1-acetylpiperdin-4-yl, 1-cyclobutylpiperidin-3-yl, 1-ethyl-3,3-difluoropiperidin-4-yl, 1-ethyl-3-fluoropiperidin-4-yl, 1-ethyl-3-hydroxyazetidin-3-yl, 1-ethyl-4-fluoropyrrolidin-3-yl, 1-ethylazetidin-3-yl, 1-ethylazetidin-3-yloxy, 1-ethylpiperidin-3-yl, 1-ethylpiperidin-3-yloxy, 1-ethylpiperidin-4-yl, 1-ethylpiperidin-4-yloxy, 1-ethylpyrrolidin-3-yl, 1-ethylpyrrolidin-3-ylmethoxy, 1-ethylpyrrolidin-3-yloxy, 1H-pyrrolidin-2-yl, 1-hydroxy-2-aminoprop-2-yl, 1-isopropyl-1,2,3,6-tetrahydropyridin-4-yl, 1-isopropyl-2-methylpyrrolidin-2-yl, 1-isopropyl-3,4-dimethylpiperazin-3-yl, 1-isopropyl-3-ethoxypiperidin-3-yl, 1-isopropyl-3-fluoropiperidin-3-yl, 1-isopropyl-3-hydroxyazetidin-3-yl, 1-isopropyl-3-hydroxypiperidin-3-yl, 1-isopropyl-3-hydroxypyrrolidin-3-yl, 1-isopropyl-3-methoxyazetidin-3-yl, 1-isopropyl-3-methoxypiperidin-3-yl, 1-isopropyl-3-methoxypyrrolidin-3-yl, 1-isopropyl-3-methylpiperazin-3-yl, 1-isopropyl-4-cyanopiperidin-4-yl, 1-isopropyl-4-ethoxypiperidin-4-yl, 1-isopropyl-4-fluoropiperidin-4-yl, 1-isopropyl-4-fluoropyrrolidin-3-yl, 1-isopropyl-4-hydroxypiperidin-3-yl, 1-isopropyl-4-hydroxypiperidin-4-yl, 1-isopropyl-4-methoxypiperidin-4-yl, 1-isopropyl-4-methylpiperazin-3-yl, 1-isopropyl-4-methylpiperidin-4-yl, 1-isopropyl-4-trifluoromethylpiperidin-4-yl, 1-isopropyl-5-methylpyrrolidin-3-yl, 1-isopropylazetidin-2-ylmethoxy, 1-isopropylazetidin-3-yl, 1-isopropylazetidin-3-ylmethoxy, 1-isopropylazetidin-3-yloxy, 1-isopropylpiperazin-3-yl, 1-isopropylpiperazin-4-yl, 1-isopropylpiperidin-2-yl, 1-isopropylpiperidin-3-yl, 1-isopropylpiperidin-4-yl, 1-isopropylpyrrolidin-2-yl, 1-isopropylpyrrolidin-3-yl, 1-methyl-1-cyanoethyl, 1-sec-butylpiperidin-4-yl, 1-t-butoxycarbonyl-4-aminopiperidin-4-yl, 2-(isopropylamino)-3-hydroxypropan-2-yl, 2-(isopropylamino)-propan-2-yl, 2,3,5,6-tetrahydroimidazo[2,1-b]thiazol-6-yl, 2,6-diazaspiro[3.3]heptan-2-yl, 2,6-diazaspiro[3.4]octan-2-yl, 2,6-diazaspiro[3.4]octan-6-yl, 2,7-diazaspiro[4.4]nonan-2-yl, 2-difluoromethylpiperazin-1-yl, 2-isopropyl-2,6-diazaspiro[3.3]heptan-6-yl, 2-methyl-1H-pyrrolidin-2-yl, 2-oxa-5,8-diazaspiro[3.5]nonan-8-yl, 2-oxo-4-ethylpiperazin-1-yl, 2-oxopiperazin-1-yl, 2-trifluoromethylpiperazin-1-yl, 3,3-difluoropiperidin-4-yl, 3,3-dimethyl-4-ethylpiperazin-1-yl, 3-aminopyrrolidin-1-yl, 3-fluoropiperidin-3-yl, 3-fluoropiperidin-4-yl, 3-hydroxyazetidin-3-yl, 3-hydroxyquinuclidin-3-yl, 3-methyl-4-ethylpiperazin-1-yl, 3-methylpiperazin-1-yl, 3-trifluoromethylpiperazin-1-yl, 4-(1,1,2,2,2-pentadeuteroethyl)piperazin-1-yl, 4-(2,2-difluoroethyl)piperazin-1-yl, 4-(2-hydroxyethyl)piperazin-1-yl, 4-(2-methoxyethyl)piperazin-1-yl, 4-(methoxycarbonylamino)piperidin-4-yl, 4-(oxetan-3-yl)piperazin-1-yl, 4,5-dihydro-1H-imidazol-2-yl, 4,5-dihydro-1H-imidazol-2-ylamino, 4-aminopiperidin-1-yl, 4-cyanopiperidin-4-yl, 4-ethoxypiperidin-4-yl, 4-ethylmorpholin-2-yl, 4-ethylpiperazin-1-yl, 4-ethylpiperazin-1-ylethoxy, 4-fluoropiperidin-4-yl, 4-fluoropyrrolidin-3-yl, 4-hydroxy-tetrahydro-2H-pyran-4-yl, 4-isopropylmorpholin-3-yl, 4-isopropylpiperazin-1-yl, 4-methoxypiperidin-4-yl, 4-methylpiperazin-1-yl, 4-methylpiperidin-4-yl, 5,5-difluoropiperidin-3-yl, 5-ethyl-2,5-diazabicyclo[2.2.1]heptan-2-yl, 6-ethyl-2,6-diazaspiro[3.3]heptan-2-yl, 6-isopropyl-2,6-diazaspiro[3.3]heptan-2-yl, 6-methylmorpholin-2-yl, azetidin-2-ylmethoxy, azetidin-3-yl, bromo, cyclopentyl, hexahydropyrazino[2,1-c][1,4]oxazin-8(1H)-yl, hexahydropyrrolo[1,2-a]pyrazin-2(1H)-yl, morpholin-2-yl, morpholin-3-yl, octahydro-2H-pyrido[1,2-a]pyrazin-2-yl, piperazin-1-yl, piperazin-1-ylethoxy, piperdin-4-yl, piperidin-2-yl, piperidin-3-yl, piperidin-3-yloxy, piperidin-4-yloxy, pyrrolidin-2-yl, pyrrolidin-3-yl, pyrrolidin-3-ylmethoxy, pyrrolidin-3-yloxy, quinuclidin-4-yl, tetrahydro-2H-pyran-4-yl, or $R^2$ is taken together with ring A to form 3'H-spiro[azetidine-3,1'-isobenzofuran]-5'-yl, 6-isopropyl-4,5,6,7-tetrahydrothieno[2,3-c]pyridin-2-yl, 4,5,6,7-tetrahydrothiazolo[4,5-c]pyridin-2-yl, 4,5,6,7-tetrahydrothiazolo[5,4-c]pyridin-2-yl, 5,6,7,8-tetrahydroimidazo[1,5-a]pyrazin-3-yl, 7-methyl-5,6,7,8-tetrahydroimidazo[1,5-a]pyrazin-3-yl, 4,5,6,7-tetrahydrothieno[2,3-c]pyridin-2-yl, or 5-isopropyl-4,5,6,7-tetrahydrothiazolo[5,4-c]pyridin-2-yl, 1-amino-2,3-dihydro-1H-inden-5-yl, or 1-(isopropylamino)-2,3-dihydro-1H-inden-5-yl.

In an embodiment, $R^2$ is selected from 1-(1-fluoropropan-2-yl)-4-ethoxypiperidin-4-yl, 1-(1-fluoropropan-2-yl)-4-methoxypiperidin-4-yl, 1-(2-fluoropropyl)-4-ethoxypiperidin-4-yl, 1-(2-fluoropropyl)-4-ethoxypiperidin-4-yl, 1-(3-(difluoromethoxy)propan-2-yl)-4-methoxypiperidin-4-yl, 1-(oxetan-3-yl)-4-ethoxypiperidin-4-yl, 1-(tetrahydrofuran-2-yl)-1-aminomethyl, 1-amino-2-hydroxy-2-methylpropyl, 1-amino-2-methoxyethyl, 1-azabicyclo[2.2.1]heptan-4-yl, 1-cyclopropyl-4-ethoxypiperidin-4-yl, 1-diethylamino-2-hydroxyethyl, 1-ethylamino-2-hydroxyethyl, 1-isopropyl-4-difluoromethoxypiperidin-3-yl, 1-isopropyl-4-difluoromethoxypiperidin-4-yl, 1-isopropyl-4-hydroxymethylpiperidin-4-yl, 1-isopropyl-4-methoxycarbonylpiperidin-4-yl, 1-isopropyl-4-(methoxymethyl)piperidin-4-yl, 1-isopropyl-4-methoxypiperidin-4-yl, 1-methyl-1-isopropylamino-2-hydroxyethyl, 2,2,5,5-tetramethyl-4-hydroxypiperidin-4-yl, 2,2-dimethyl-4-methoxypiperidin-4-yl, 2-amino-1-hydroxyethyl, 2-amino-3-hydroxypropyl, 2-azaspiro[3.3]heptan-6-yl, 2-hydroxy-1-aminoethyl, 2-hydroxy-1-isopropylaminoethyl, 2-hydroxyethylaminomethyl, 3-amino-oxetan-3-yl, 3-ethoxypiperidin-3-yl, 3-methoxypiperidin-3-yl, 4-aminotetrahydropyran-4-yl, 4-ethoxytetrahydropyran-4-yl, 4-hydroxycarbonylpiperidin-4-yl, 4-hydroxymethylpiperidin-4-yl, 4-methoxycarbonylpiperidin-4-yl, 4-methoxytetrahydropyran-4-yl, 4-trifluoromethylpiperidin-4-yl, ethylsulfonyl, and oxetan-3-ylaminomethyl.

In an embodiment, $R^2$ is selected from 1-(oxetan-3-yl)piperidin-4-yl, 1-acetylpiperdin-4-yl, 1-cyclobutylpiperidin-3-yl, 1-ethyl-3-fluoropiperidin-4-yl, 1-ethyl-3-hydroxyazetidin-3-yl, 1-ethyl-4-fluoropyrrolidin-3-yl, 1-ethylazetidin-3-yl, 1-ethylpiperidin-3-yl, 1-ethylpiperidin-4-yl, 1-ethylpyrrolidin-3-yl, 1-isopropyl-3-hydroxyazetidin-3-yl, 1-isopropyl-3-hydroxypiperidin-3-yl, 1-isopropylazetidin-3-yl, 1-isopropylpiperidin-3-yl, 1-isopropylpiperidin-4-yl, 1-isopropylpyrrolidin-2-yl, 1-isopropylpyrrolidin-3-yl, 1-methyl-1-cyanoethyl, 2-difluoromethylpiperazin-1-yl, 2-oxo-4-ethylpiperazin-1-yl, 2-oxopiperazin-1-yl, 2-trifluoromethylpiperazin-1-yl, 3-fluoropiperidin-3-yl, 3-fluoropiperidin-4-yl, 3-hydroxyazetidin-3-yl, 3-methyl-4-ethylpiperazin-1-yl, 3-methylpiperazin-1-yl, 3-trifluoromethylpiperazin-1-yl, 4-(2-hydroxyethyl)-piperazin-1-yl, 4-(oxetan-3-yl)piperazin-1-yl, 4-aminopiperidin-1-yl, 4-ethylmorpholin-2-yl, 4-ethylpiperazin-1-yl, 4-fluoropyrrolidin-3-yl, 4-hydroxy-tetrahydro-2H-pyran-4-yl, 4-isopropylpiperazin-1-yl, 4-(2-methoxyethyl)piperazin-1-yl, 4-methylpiperazin-1-yl, 6-methylmorpholin-2-yl, azetidin-3-yl, morpholin-2-yl, piperazin-1-yl, piperdin-4-yl, piperidin-3-yl, pyrrolidin-2-yl, pyrrolidin-3-yl, tetrahydro-2H-pyran-4-yl, azetidin-2-ylmethoxy, pyrrolidin-3-yloxy, piperidin-2-yl, piperidin-3-yloxy, piperidin-4-yloxy, pyrrolidin-3-ylmethoxy, 1-ethylazetidin-3-yloxy, 1-isopropylazetidin-3-yloxy, 1-ethylpyrrolidin-3-yloxy, 1-isopropylazetidin-3-ylmethoxy, 1-isopropylazetidin-2-ylmethoxy, piperazin-1-ylethoxy, 4-(2-hydroxyethyl)piperazin-1-yl, 1-isopropyl-4-fluoropyrrolidin-3-yl, 1-ethylpiperidin-4-yloxy, 1-ethylpiperidin-3-yloxy, 1-ethylpyrrolidin-3-ylmethoxy, 1-isopropyl-3-hydroxypyrrolidin-3-yl, 1-isopropylpiperidin-2-yl, 1-isopropyl-4-hydroxypiperidin-4-yl, 4-ethylpiperazin-1-ylethoxy, 1-sec-butylpiperidin-4-yl, 1-isopropyl-4-methoxypiperidin-4-yl, 1-isopropyl-3-methoxypiperidin-3-yl, bromo, cyclopentyl, 1,4-diazabicyclo[4.2.0]octan-4-yl, 5-ethyl-2,5-diazabicyclo[2.2.1]heptan-2-yl, 4-(1,1,2,2,2-pentadeuteroethyl)piperazin-1-yl, 1-ethyl-3,3-difluoropiperidin-4-yl, hexahydropyrrolo[1,2-a]pyrazin-2(1H)-yl, octahydro-2H-pyrido[1,2-a]pyrazin-2-yl, hexahydropyrazino[2,1-c][1,4]oxazin-8(1H)-yl, 4-(2,2-difluoroethyl)piperazin-1-yl, 2,6-diazaspiro[3.3]heptan-2-yl, 3,3-difluoropiperidin-4-yl, 3,3-dimethyl-4-ethylpiperazin-1-yl, 6-ethyl-2,6-diazaspiro[3.3]heptan-2-yl, 6-isopropyl-2,6-diazaspiro[3.3]heptan-2-yl, 2,6-diazaspiro[3.4]octan-6-yl, 2,6-diazaspiro[3.4]octan-2-yl, 2-oxa-5,8-diazaspiro[3.5]nonan-8-yl, 2,7-diazaspiro[4.4]nonan-2-yl, 4,5-dihydro-1H-imidazol-2-yl, 4,5-dihydro-1H-imidazol-2-ylamino, and 5,5-difluoropiperidin-3-yl, or $R^2$ is taken together with ring A to form 3'H-spiro[azetidine-3,1'-isobenzofuran]-5'-yl, 6-isopropyl-4,5,6,7-tetrahydrothieno[2,3-c]pyridin-2-yl, 4,5,6,7-tetrahydrothiazolo[4,5-c]pyridin-2-yl, 4,5,6,7-tetrahydrothiazolo[5,4-c]pyridin-2-yl, 5,6,7,8-tetrahydroimidazo[1,5-a]pyrazin-3-yl, 7-methyl-5,6,7,8-tetrahydroimidazo[1,5-a]pyrazin-3-yl, 4,5,6,7-tetrahydrothieno[2,3-c]pyridin-2-yl, or 5-isopropyl-4,5,6,7-tetrahydrothiazolo[5,4-c]pyridin-2-yl.

In another aspect, the compound has formula (Ia):

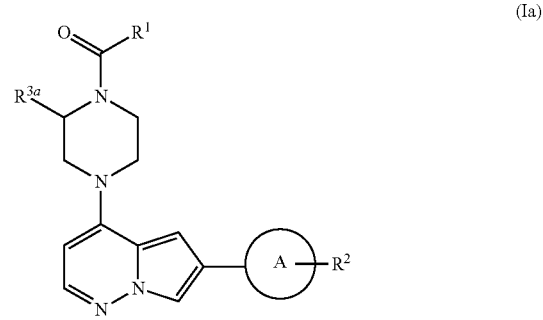

or a pharmaceutically acceptable salt thereof, wherein ring A, $R^1$ and $R^2$ are as defined as for Formula (I).

In an embodiment, ring A is selected from:

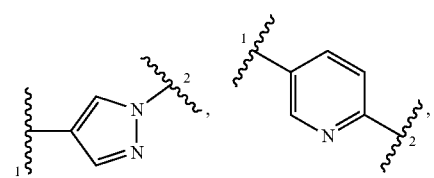

-continued

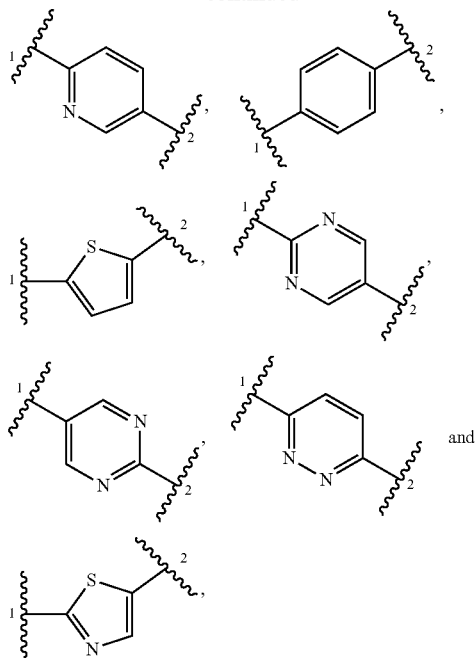

wherein:
"1" represents a portion of ring A bound to a pyrrolo[1,2-b]pyridazine moiety;
"2" represents a portion of ring A bound to $R^2$; and
ring A is substituted with 0, 1, 2, or 3 independently selected substituents in addition to $R^2$;

$R^1$ is selected from $C_1$-$C_3$ alkyl, —O—($C_1$-$C_5$ alkyl), —NH($C_1$-$C_5$ alkyl), —NH—($C_3$-$C_6$ cycloalkyl), $C_3$-$C_6$ cycloalkyl, —O—($C_3$-$C_6$ cycloalkyl), an N-containing heterocyclyl, —O—($C_0$-$C_3$ alkylene)-(O-containing heterocyclyl), —NH—($C_0$-$C_3$ alkylene)-(O-containing heterocyclyl), and an O-containing heterocyclyl, wherein any alkyl, cycloalkyl, or heterocyclyl portion of $R^1$ is unsubstituted, or is substituted with 1, 2, or 3 substituents independently selected from halo, cyano, $C_1$-$C_4$ alkyl, $C_1$-$C_4$ haloalkyl, —O—$C_1$-$C_4$ alkyl, and —OH;

$R^2$ is selected from heterocyclyl, —O—($C_0$-$C_4$ alkylene)-(heterocyclyl), —($C_1$-$C_3$ alkylene)-heterocyclyl, —($C_1$-$C_3$ alkylene)-NH—($C_1$-$C_3$ alkyl), -(hydroxy-substituted $C_1$-$C_3$ alkylene)-NH—($C_1$-$C_3$ alkyl), and $C_1$-$C_3$ alkyl substituted with both hydroxy and amino, or $R^2$ is taken together with a ring atom in ring A to form a heterocyclyl or a carbocyclyl that is fused to ring A, wherein any heterocyclyl is unsubstituted, or is substituted with 1, 2, or 3 substituents independently selected from halo, cyano, —$NH_2$, —OH, —$C_1$-$C_4$ alkyl, deuterated $C_1$-$C_4$ alkyl, —$C_1$-$C_4$ haloalkyl, hydroxy-substituted —$C_1$-$C_4$ alkyl, —O—$C_1$-$C_4$ alkyl, $C_3$-$C_6$ cycloalkyl, —NH($C_1$-$C_4$ alkyl), —NH—C(O)—O—($C_1$-$C_4$ alkyl), —($C_1$-$C_4$ alkylene)-O—($C_1$-$C_4$ alkyl), —($C_1$-$C_4$ alkylene)-O—($C_1$-$C_4$ haloalkyl), —C(O)—O—$C_1$-$C_4$ alkyl, and an optionally substituted second heterocyclyl; and $R^{1a}$ is selected from hydrogen and $C_1$-$C_4$ alkyl.

In an embodiment of Formula Ia, ring A is selected from:

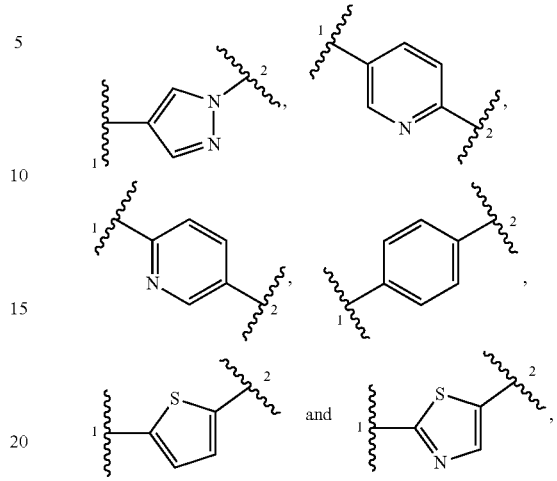

wherein:
"1" represents a portion of ring A bound to a pyrrolo[1,2-b]pyridazine moiety;
"2" represents a portion of ring A bound to $R^2$; and
ring A is substituted with 0, 1, 2, or 3 independently selected substituents in addition to $R^2$;

$R^1$ is selected from $C_1$-$C_3$ alkyl, —O—($C_1$-$C_3$ alkyl), —NH($C_1$-$C_3$ alkyl), —NH—($C_3$-$C_6$ cycloalkyl), $C_3$-$C_6$ cycloalkyl, —O—($C_3$-$C_6$ cycloalkyl), and an N-containing heterocyclyl, wherein any alkyl, cycloalkyl, or heterocyclyl portion of $R^1$ is unsubstituted, or is substituted with 1, 2, or 3 substituents independently selected from halo, cyano, $C_1$-$C_4$ alkyl, $C_1$-$C_4$ haloalkyl, and —OH;

$R^2$ is selected from heterocyclyl, and —O—($C_0$-$C_4$ alkylene)-(heterocyclyl), or $R^2$ is taken together with a ring atom in ring A to form a heterocyclyl that is fused to ring A, wherein any heterocyclyl is unsubstituted, or is substituted with 1, 2, or 3 substituents independently selected from halo, —OH, —$C_1$-$C_4$ alkyl, deuterated $C_1$-$C_4$ alkyl, —$C_1$-$C_4$ haloalkyl, —O—$C_1$-$C_4$ alkyl, and $C_3$-$C_6$ cycloalkyl; and $R^{1a}$ is selected from hydrogen and $C_1$-$C_4$ alkyl.

In another embodiment of Formula Ia, ring A is selected from:

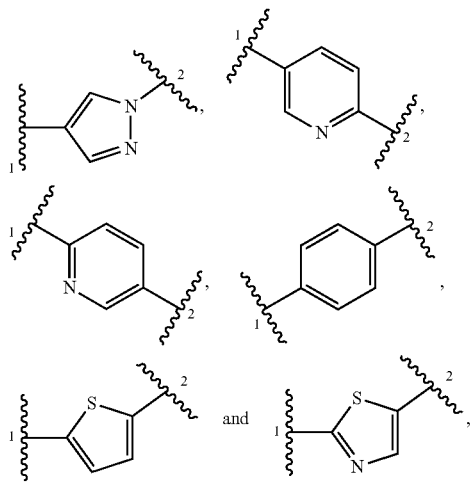

wherein:

"1" represents a portion of ring A bound to a pyrrolo[1,2-b]pyridazine moiety;

"2" represents a portion of ring A bound to $R^2$; and ring A is substituted with 0, 1, 2, or 3 independently selected substituents in addition to $R^2$;

$R^1$ is selected from $C_1$-$C_3$ alkyl, —O—($C_1$-$C_3$ alkyl), —NH($C_1$-$C_3$ alkyl), —NH—($C_3$-$C_6$ cycloalkyl), $C_3$-$C_6$ cycloalkyl, —O—($C_3$-$C_6$ cycloalkyl), an N-containing heterocyclyl, —O—(O-containing heterocycle), and —O—(N-containing heterocycle), wherein any alkyl, cycloalkyl, or heterocyclyl portion of $R^1$ is unsubstituted, or is substituted with 1, 2, or 3 substituents independently selected from deuterium, halo, cyano, $C_1$-$C_4$ alkyl, $C_1$-$C_1$ haloalkyl, and —OH;

$R^2$ is selected from heterocyclyl, and —O—($C_0$-$C_4$ alkylene)-(heterocyclyl), or $R^2$ is taken together with a ring atom in ring A to form a heterocyclyl that is fused to ring A, wherein any heterocyclyl portion of $R^2$ is unsubstituted, or is substituted with 1, 2, or 3 substituents independently selected from halo, —CN, —OH, —$C_1$-$C_5$ alkyl optionally substituted with one or more —OH and/or one or more —$NH_2$, deuterated $C_1$-$C_5$ alkyl, —$C_1$-$C_5$ haloalkyl, —O—$C_1$-$C_4$ alkyl, and $C_3$-$C_6$ cycloalkyl; and $R^{31a}$ is selected from hydrogen and $C_1$-$C_4$ alkyl.

In an embodiment, ring A is optionally substituted with up to 1 substituent in addition to $R^2$, wherein the substituent, if present, is halo or methyl. In an embodiment, ring A is optionally substituted with up to 1 substituent in addition to $R^2$, wherein the substituent, if present, is halo.

In an embodiment, $R^1$ is selected from 2,2,2-trifluoroethoxy, 2,2,2-trifluoroethylamino, 2,2-difluoroethoxy, 2,2-dimethylcyclopropyl, 2,2-dimethylpropoxy, 2-cyanocyclopropyl, 2-cyanoethyl, 2-cyanoethylamino, 2-fluorocyclopropyl, 2-methylcyclopropyl, 3-cyanoazetidin-1-yl, 3-cyanocyclobutoxy, 3-cyanocyclobutyl, 3-fluorocyclobutyl, 3-hydroxy-3-methylcyclobutyl, 3-hydroxy-3-trifluoromethylcyclobutyl, 3-hydroxyazetidin-1-yl, 3-hydroxycyclobutyl, 4-cyanocyclohexyl, 4-hydroxycyclohexyl, 4-methylcyclohexyl, cyclobutoxy, cyclobutyl, cyclobutylamino, cyclopropyl, ethoxy, ethylamino, isopropoxy, isopropylamino, N-(1,2-dimethylpropyl)amino, N-(2,2-dimethylpropyl)amino, N-(methoxymethyl)amino, N-(oxetan-3-ylmethyl)amino, oxetan-3-yl, oxetan-3-ylamino, oxetan-3-ylmethoxy, oxetan-3-yloxy, propylamino, t-butoxy, tetrahydrofuran-3-yloxy, and tetrahydropyran-4-yloxy.

In an embodiment, $R^1$ is selected from 2,2,2-trifluoroethoxy, 2,2-dimethylcyclopropyl, 2-cyanocyclopropyl, 2-cyanoethyl, 2-fluorocyclopropyl, 2-methylcyclopropyl, 3-cyanoazetidin-1-yl, 3-cyanocyclobutyl, 3-fluorocyclobutyl, 3-hydroxy-3-methylcyclobutyl, 3-hydroxy-3-trifluoromethylcyclobutyl, 3-hydroxyazetidin-1-yl, 3-hydroxycyclobutyl, 4-cyanocyclohexyl, 4-hydroxycyclohexyl, 4-methylcyclohexyl, cyclobutoxy, cyclobutyl, cyclobutylamino, cyclopropyl, ethoxy, ethyl amino, isopropoxy, isopropylamino, and propylamino.

In an embodiment, $R^2$ is selected from 1-(1-hydroxypropan-2-yl)-4-methoxypiperidin-4-yl, 1-(3-difluoromethoxy)propan-2-yl-4-methoxypiperidin-4-yl, 1-(3-methoxy)propan-2-yl-4-methoxypiperidin-4-yl, 1-(oxetan-3-yl)-4-methoxypiperidin-4-yl, 1-(propan-2-yl)piperidin-3-yl, 1-(propan-2-yl)piperidin-4-yl, 1-(pyrrolidin-1-yl)ethan-1-yl, 1,2,3,6-tetrahydropyridin-4-yl, 1-cyclobutylpiperidin-3-yl, 1-ethyl-3-fluoropiperidin-4-yl, 1-ethyl-3-hydroxyazetidin-3-yl, 1-ethyl-4-fluoropyrrolidin-3-yl, 1-ethylazetidin-3-yl, 1-ethylazetidin-3-yloxy, 1-ethylpiperidin-3-yl, 1-ethylpiperidin-3-yloxy, 1-ethylpiperidin-4-yl, 1-ethylpyrrolidin-3-yl, 1-ethylpyrrolidin-3-ylmethoxy, 1-ethylpyrrolidin-3-yloxy, 1H-pyrrolidin-2-yl, 1-hydroxy-2-aminoprop-2-yl, 1-isopropyl-1,2,3,6-tetrahydropyridin-4-yl, 1-isopropyl-2-methylpyrrolidin-2-yl, 1-isopropyl-3,4-dimethylpiperazin-3-yl, 1-isopropyl-3-ethoxypiperidin-3-yl, 1-isopropyl-3-fluoropiperidin-3-yl, 1-isopropyl-3-hydroxyazetidin-3-yl, 1-isopropyl-3-hydroxypiperidin-3-yl, 1-isopropyl-3-hydroxypyrrolidin-3-yl, 1-isopropyl-3-methoxyazetidin-3-yl, 1-isopropyl-3-methoxypiperidin-3-yl, 1-isopropyl-3-methoxypyrrolidin-3-yl, 1-isopropyl-3-methylpiperazin-3-yl, 1-isopropyl-4-cyanopiperidin-4-yl, 1-isopropyl-4-ethoxypiperidin-4-yl, 1-isopropyl-4-fluoropiperidin-4-yl, 1-isopropyl-4-fluoropyrrolidin-3-yl, 1-isopropyl-4-hydroxypiperidin-3-yl, 1-isopropyl-4-hydroxypiperidin-4-yl, 1-isopropyl-4-methoxypiperidin-4-yl, 1-isopropyl-4-methylpiperazin-3-yl, 1-isopropyl-4-methylpiperidin-4-yl, 1-isopropyl-4-trifluoromethylpiperidin-4-yl, 1-isopropyl-5-methylpyrrolidin-3-yl, 1-isopropylazetidin-3-yl, 1-isopropylpiperazin-3-yl, 1-isopropylpiperazin-4-yl, 1-isopropylpiperidin-2-yl, 1-isopropylpiperidin-3-yl, 1-isopropylpiperidin-4-yl, 1-isopropylpyrrolidin-2-yl, 1-isopropylpyrrolidin-3-yl, 1-sec-butylpiperidin-4-yl, 1-t-butoxycarbonyl-4-aminopiperidin-4-yl, 2-(isopropylamino)-3-hydroxypropan-2-yl, 2-(isopropylamino)-propan-2-yl, 2,3,5,6-tetrahydroimidazo[2,1-b]thiazol-6-yl, 2-difluoromethylpiperazin-1-yl, 2-isopropyl-2,6-diazaspiro[3.3]heptan-6-yl, 2-methyl-1H-pyrrolidin-2-yl, 3-aminopyrrolidin-1-yl, 3-fluoropiperidin-3-yl, 3-hydroxyquinuclidin-3-yl, 3-methyl-4-ethylpiperazin-1-yl, 3-methylpiperazin-1-yl, 4-(1,1,2,2,2-pentadeuteroethyl)piperazin-1-yl, 4-(methoxycarbonylamino)piperidin-4-yl, 4-cyanopiperidin-4-yl, 4-ethoxypiperidin-4-yl, 4-ethylpiperazin-1-yl, 4-fluoropiperidin-4-yl, 4-fluoropyrrolidin-3-yl, 4-isopropylmorpholin-3-yl, 4-isopropylpiperazin-1-yl, 4-methoxypiperidin-4-yl, 4-methylpiperidin-4-yl, 6-ethyl-2,6-diazaspiro[3.3]heptan-2-yl, 6-isopropyl-2,6-diazaspiro[3.3]heptan-2-yl, azetidin-2-ylmethoxy, hexahydropyrrolo[1,2-a]pyrazin-2(1H)-yl, morpholin-2-yl, morpholin-3-yl, piperazin-1-yl, piperdin-4-yl, piperidin-2-yl, piperidin-3-yl, piperidin-3-yloxy, pyrrolidin-2-yl, pyrrolidin-3-yloxy, and quinuclidin-4-yl, or $R^2$ is taken together with ring A to form 6-isopropyl-4,5,6,7-tetrahydrothieno[2,3-c]pyridin-2-yl, 4,5,6,7-tetrahydrothiazolo[5,4-c]pyridin-2-yl, 4,5,6,7-tetrahydrothieno[2,3-c]pyridin-2-yl, 5-isopropyl-4,5,6,7-tetrahydrothiazolo[5,4-c]pyridin-2-yl, 1-amino-2,3-dihydro-1H-inden-5-yl, or 1-(isopropylamino)-2,3-dihydro-1H-inden-5-yl.

In an embodiment, $R^2$ is selected from 1-cyclobutylpiperidin-3-yl, 1-ethyl-3-fluoropiperidin-4-yl, 1-ethyl-3-hydroxyazetidin-3-yl, 1-ethyl-4-fluoropyrrolidin-3-yl, 1-ethylazetidin-3-yl, 1-ethylazetidin-3-yloxy, 1-ethylpiperidin-3-yl, 1-ethylpiperidin-3-yloxy, 1-ethylpiperidin-4-yl, 1-ethylpyrrolidin-3-yl, 1-ethylpyrrolidin-3-ylmethoxy, 1-ethylpyrrolidin-3-yloxy, 1-isopropyl-3-hydroxyazetidin-3-yl, 1-isopropyl-3-hydroxypiperidin-3-yl, 1-isopropyl-3-methoxypiperidin-3-yl, 1-isopropyl-4-fluoropyrrolidin-3-yl, 1-isopropyl-4-hydroxypiperidin-4-yl, 1-isopropyl-4-methoxypiperidin-4-yl, 1-isopropylazetidin-3-yl, 1-isopropylpiperidin-2-yl, 1-isopropylpiperidin-3-yl, 1-isopropylpiperidin-4-yl, 1-isopropylpyrrolidin-2-yl, 1-isopropylpyrrolidin-3-yl, 1-sec-butylpiperidin-4-yl, 2-difluoromethylpiperazin-1-yl, 3-fluoropiperidin-3-yl, 3-methyl-4-ethylpiperazin-1-yl, 3-methylpiperazin-1-yl, 4-(1,1,2,2,2-pentadeuteroethyl)piperazin-1-yl, 4-ethylpiperazin-1-yl, 4-fluoropyrrolidin-3-yl, 4-isopropylpiperazin-1-yl, 6-ethyl-2,6-diazaspiro[3.3]heptan-2-yl, 6-isopropyl-2,6-diazaspiro[3.3]heptan-2-yl, azetidin-2-ylmethoxy, hexahydropyrrolo[1,2-a]pyrazin-2(1H)-yl, morpholin-2-yl, piperazin-1-yl, piperdin-4-yl, piperidin-2-yl, piperidin-3-yl, piperidin-3-yloxy, pyrrolidin-2-yl, and pyrrolidin-3-yloxy, or R² is taken together with ring A to form 6-isopropyl-4,5,6,7-tetrahydrothieno[2,3-c]pyridin-2-yl, 4,5,6,7-tetrahydrothiazolo[5,4-c]pyridin-2-yl, 4,5,6,7-tetrahydrothieno[2,3-c]pyridin-2-yl, or 5-isopropyl-4,5,6,7-tetrahydrothiazolo[5,4-c]pyridin-2-yl.

In an embodiment, $R^{3a}$ is selected from hydrogen and methyl.

In an embodiment, ring A is substituted with 0 or 1 substituent in addition to $R^2$, wherein the substituent, if present, is halo.

In an alternate embodiment, ring A is substituted with 0 or 1 substituent in addition to $R^2$, wherein the substituent, if present, is selected from chloro, fluoro, and methyl.

In yet another embodiment, the compound is a compound of formula (II):

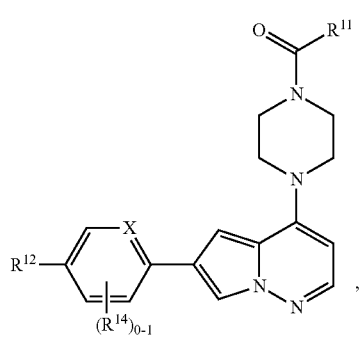
(II)

or a pharmaceutically acceptable salt thereof, wherein:

X is $C(R^{13})$ or N;

$R^{11}$ is selected from —NH—($C_3$-$C_4$ cycloalkyl); —NH—$C_1$-$C_3$ alkyl; —O—$C_3$-$C_4$ cycloalkyl; —O—$C_1$-$C_3$ alkyl optionally substituted with one or more substituents selected from fluoro, hydroxy, —CN, and deuterium; and —O—(O-containing heterocycle);

$R^{12}$ is selected from piperidin-3-yl optionally 3-substituted with $C_1$-$C_3$ alkoxy, fluoro, $C_1$-$C_3$ alkyl, or —CN; and piperidin-4-yl optionally 4-substituted with $C_1$-$C_3$ alkoxy, fluoro, $C_1$-$C_3$ alkyl, —CN, wherein $R^{12}$ is additionally optionally 1-substituted with $C_1$-$C_5$ alkyl optionally substituted with one or more —OH and/or one or more —NH₂;

$R^{13}$ is selected from hydrogen, —CN and fluoro; and $R^{14}$, if present, is fluoro.

In certain embodiments of Formula II, the compound is a compound of Formula IIa:

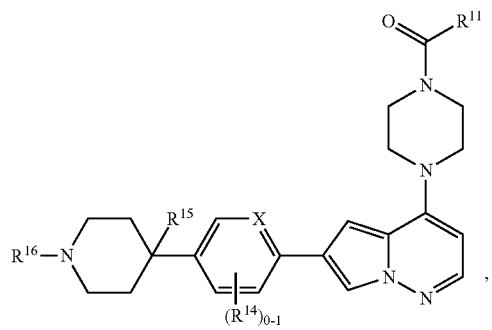
(IIa)

or a pharmaceutically acceptable salt thereof, wherein:

X, $R^{11}$, $R^{14}$, and subvariables thereof are as defined in Formula II;

The term "subvariables" as used herein means the variables that are used to define a variable. For example, X is $C(R^{13})$; $R_{13}$ is a subvariable of X.

$R^{15}$ is selected from hydrogen, $C_1$-$C_3$ alkoxy, fluoro, $C_1$-$C_3$ alkyl, and —CN; and $R^{16}$ is $C_1$-$C_5$ alkyl optionally substituted with one or more —OH and/or one or more —NH₂.

In certain embodiments of Formula II, the compound is a compound of Formula IIb:

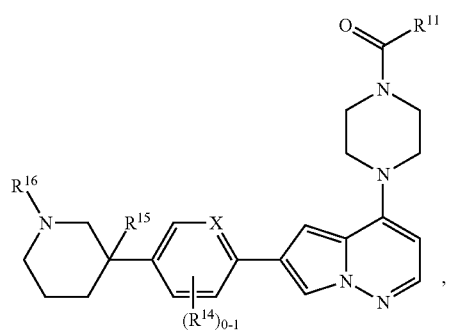
(IIb)

or a pharmaceutically acceptable salt thereof, wherein:

X, $R^{11}$, $R^{14}$, and subvariables thereof are as defined in Formula II;

$R^{15}$ is selected from hydrogen, $C_1$-$C_3$ alkoxy, fluoro, $C_1$-$C_3$ alkyl, and —CN; and $R^{16}$ is $C_1$-$C_5$ alkyl optionally substituted with one or more —OH and/or one or more —NH₂.

In certain embodiments of a compound of Formula IIb, the compound is a compound of Formula IIb-1:

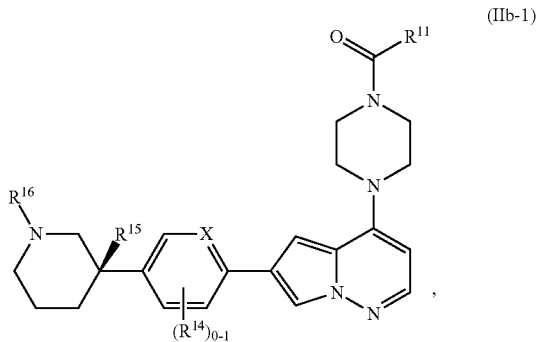

(IIb-1)

or a pharmaceutically acceptable salt thereof, wherein X, $R^{11}$, $R^{12}$, $R^{14}$, $R^{15}$ $R^{16}$, and subvariables thereof are as defined in Formula IIb.

In certain embodiments of a compound of Formula IIb, the compound is a compound of Formula IIb-2:

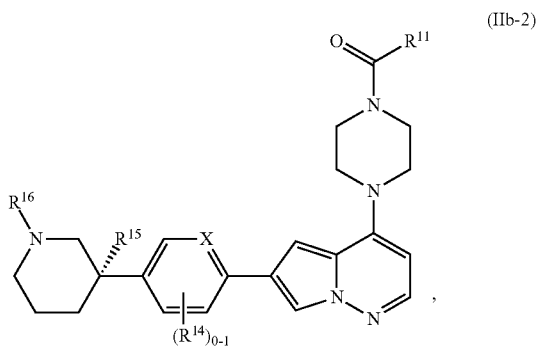

(IIb-2)

or a pharmaceutically acceptable salt thereof, wherein X, $R^{11}$, $R^{12}$, $R^{14}$, $R^{15}$ $R^{16}$, and subvariables thereof are as defined in Formula IIb.

In certain embodiments of Formula II, IIa, IIb, IIb-1 and IIb-2, $R^{14}$ is absent.

In certain embodiments of Formula II, IIa, IIb, IIb-1 and IIb-2, $R^{13}$ is hydrogen.

In certain embodiments of Formula II, IIa, IIb, IIb-1 and IIb-2, $R^{11}$ is selected from —NH—$C_1$-$C_3$ alkyl; —O—$C_1$-$C_3$ alkyl optionally substituted with one or more substituents selected from fluoro, hydroxy, —CN, and deuterium; oxetan-3-yl and tetrahydrofuran-3-yl. In some aspects of these embodiments, $R^{11}$ is selected from —OCH$_2$CH$_3$, —NHCH(CH$_3$)$_2$, oxetan-3-yl and tetrahydrofuran-3-yl.

In certain embodiments the compound is a compound of Formula I or Formula Ia that is not a compound of any of Formula II, IIa, IIb, IIb-1 or IIb-2.

In an embodiment, the compound is a compound of any of Formulae I, Ia, II, II, IIb, IIb-1, or IIb-2 selected from a compound in Table 1.

In another aspect, the present disclosure features a pharmaceutical composition comprising a compound of any of Formulae I, Ia, II, II, IIb, IIb-1, or IIb-2 described herein (e.g., a compound in Table 1) or a pharmaceutically acceptable salt thereof, and a pharmaceutically acceptable carrier.

Table 1 below shows the structures of compounds described herein.

TABLE 1

| # | Structure | LCMS (M + 1) | NMR |
|---|-----------|--------------|-----|
| 100 | 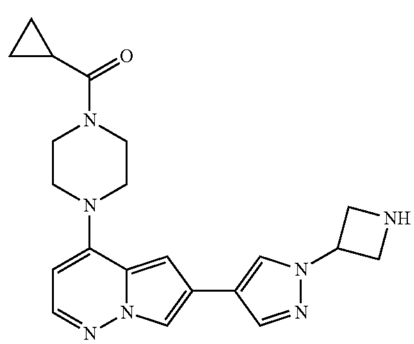 [SMILES: O=C(C1CC1)N1CCN(c2ccnn3cc(-c4cnn(C5CNC5)c4)cc23)CC1] | 392 | 1H-NMR (400 MHz, 6d-DMSO) δ ppm 8.23 (s, 1H), 7.94 (s, 1H), 7.88 (s, 1H), 7.86 (d, 1H, J = 5.2 Hz), 6.85 (s, 1H), 5.96 (d, 1H, J = 5.2 Hz), 5.18-5.13 (m, 1H), 3.92-3.88 (m, 4H), 3.74 (t, 2H, J = 8.0 Hz), 3.70-3.68 (m, 2H), 3.55-3.45 (m, 5H), 2.02-2.00 (m, 1H), 0.77-0.73 (m, 4H). |
| 101 | 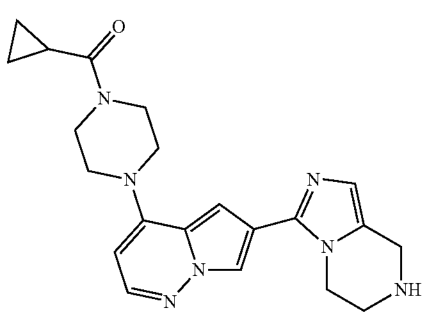 [SMILES: O=C(C1CC1)N1CCN(c2ccnn3cc(-c4ncc5n4CCNC5)cc23)CC1] | 392 | 1H-NMR (400 MHz, 6d-DMSO) δ ppm 8.04 (d, 1H, J = 1.6 Hz), 7.95 (d, 1H, J = 5.2 Hz), 6.92 (d, 1H, J = 1.6 Hz), 6.70 (s, 1H), 6.01 (d, 1H, J = 5.2 Hz), 4.09 (t, 2H, J = 5.2 Hz), 3.93-3.90 (m, 4H), 3.72-3.68 (m, 2H), 3.57-3.55 (m, 2H), 3.52-3.47 (m, 2H), 3.06 (t, 2H, J = 5.2 Hz), 2.04-1.99 (m, 1H), 0.78-0.72 (m, 4H). |

TABLE 1-continued

| # | Structure | LCMS (M + 1) | NMR |
|---|---|---|---|
| 102 | 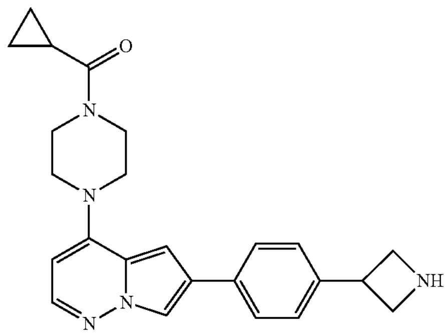 [SMILES: O=C(C1CC1)N1CCN(c2ccnn3cc(-c4ccc(C5CNC5)cc4)cc23)CC1] | 402 | 1H-NMR (400 MHz, CDCl3) δ ppm 7.93 (s, 1H), 7.85 (d, 1H, J = 5.2 Hz), 7.63 (d, 2H, J = 8.4 Hz), 7.36 (d, 2H, J = 8.4 Hz), .6.72 (s, 1H) 5.85 (d, 1H, J = 5.2 Hz), 4.00-3.90 (m, 4H), 3.90-3.80 (m, 4H), 3.57-3.50 (m, 2H), 3.50-3.40 (m, 2H), 1.85-1.80 (m, 1H), 1.79-1.73 (m, 1H), 1.06-1.04 (m, 2H), 0.85-0.81 (m, 2H). |
| 103 | 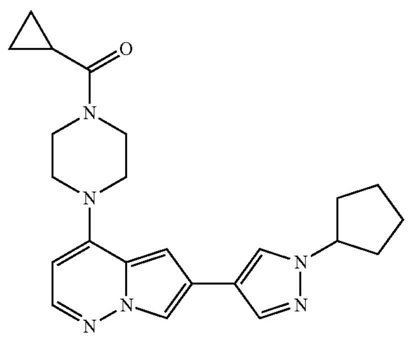 [SMILES: O=C(C1CC1)N1CCN(c2ccnn3cc(-c4cnn(C5CCCC5)c4)cc23)CC1] | 405 | 1H-NMR (400 MHz, DMSO-d6) δ ppm 8.12 (s, 1H), 7.94 (s, 1H), 7.86 (d, 1H, J = 5.2 Hz), 7.80 (s, 1H), 6.83 (s, 1H), 5.96 (d, 1H, J = 5.2 Hz), 4.68 (quintet, 1H, J = 9.0 Hz), 3.92-3.43 (m, 8H), 2.11-2.06 (m, 2H), 2.04-2.02 (m, 1H), 1.97-1.93 (m, 2H), 1.83-1.78 (m, 2H), 1.68-1.64 (m, 2H), 0.79-0.73 (m, 4H). |
| 104 | 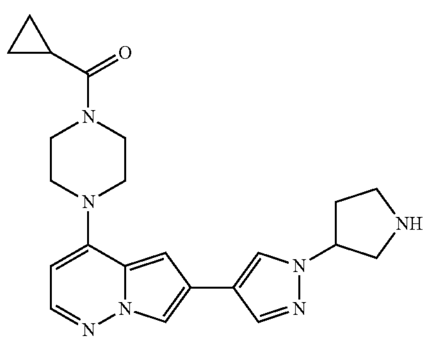 [SMILES: O=C(C1CC1)N1CCN(c2ccnn3cc(-c4cnn(C5CCNC5)c4)cc23)CC1] | 406 | 1H-NMR (400 MHz, 6d-DMSO) δ ppm 8.24 (s, 1H), 7.95 (s, 1H), 7.91 (s, 1H), 7.86 (d, 1H, J = 5.2 Hz), 6.83 (s, 1H), 5.96 (d, 1H, J = 5.2 Hz), 5.09-5.05 (br. s, 1H), 3.94-3.86 (m, 2H), 3.72-3.66 (m, 2H), 3.55-3.42 (m, 6H), 3.27-3.20 (m, 2H), 2.38-2.32 (m, 1H), 2.25-2.21 (m, 1H), 2.10-2.00 (m, 1H), 0.77-0.73 (m, 4H). |
| 105 | 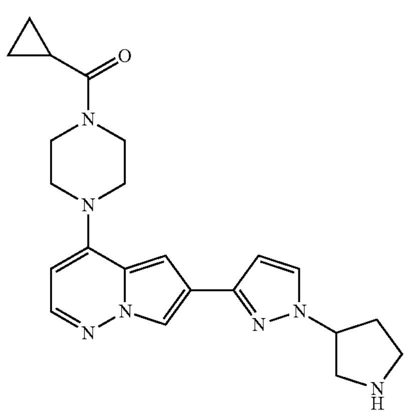 [SMILES: O=C(C1CC1)N1CCN(c2ccnn3cc(-c4ccn(C5CCNC5)n4)cc23)CC1] | 406 | 1H-NMR (400 MHz, 6d-DMSO) δ ppm 7.98 (s, 1H), 7.89 (d, 1H, J = 5.2 Hz), 7.78 (s, 1H), 6.86 (s, 1H), 6.61 (s, 1H), 5.97 (d, 1H, J = 5.2 Hz), 4.91-4.77 (m, 1H), 3.96-3.90 (m, 2H), 3.74-3.68 (m, 2H), 3.57-3.53 (m, 2H), 3.47-3.43 (m., 2H), 3.18-3.11 (m, 1H), 3.10-3.02 (m, 1H), 3.01-2.94 (m, 1H), 2.90-2.80 (m, 1H), 2.34-2.23 (m, 1H), 2.22-2.14 (m, 1H), 2.08-1.95 (m, 2H), 0.83-0.68 (m, 4H). |

TABLE 1-continued

| # | Structure | LCMS (M + 1) | NMR |
|---|---|---|---|
| 106 | 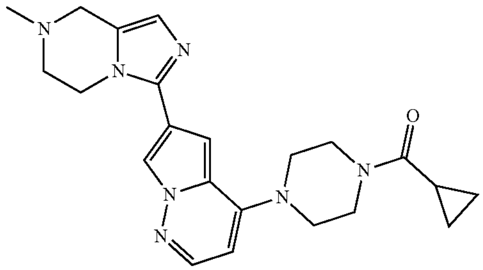 [SMILES: CN1CCn2c(cnc2-c2cc3c(N4CCN(C(=O)C5CC5)CC4)ccnn3c2)C1] | 406 | 1H-NMR (400 MHz, 6d-DMSO) δ ppm 8.06 (d, 1H, J = 2.0 Hz), 7.95 (d, 1H, J = 5.6 Hz), 6.93 (d, 1H, J = 2.0 Hz), 6.72 (s, 1H), 6.02 (d, 1H, J = 5.6 Hz), 4.21 (t, 2H, J = 5.6 Hz), 3.93-3.90 (m, 2H), 3.72-3.68 (m, 2H), 3.60-3.52 (m, 4H), 3.49-3.45 (m, 2H), 2.76 (t, 2H, J = 5.6 Hz), 2.38 (s, 3H), 2.04-1.99 (m, 1H), 0.79-0.74 (m, 4H). |
| 107 | 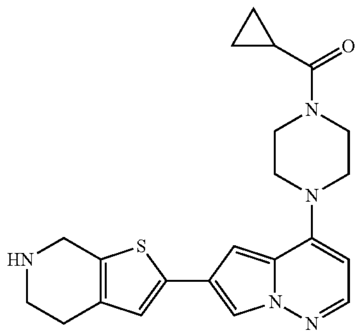 [SMILES: O=C(C1CC1)N1CCN(c2ccnn3cc(-c4cc5c(s4)CNCC5)cc23)CC1] | 408 | 1H-NMR (400 MHz, MeOD) δ ppm 7.86 (d, 1H, J = 5.6 Hz), 7.83 (d, 1H, J = 1.6 Hz), 7.09 (s, 1H), 6.77 (d, 1H, J = 1.6 Hz), 6.02 (d, 1H, J = 5.6 Hz), 4.24 (s, 2H), 4.05-3.92 (m, 2H), 3.90-3.77 (m, 2H), 3.70-3.60 (m, 2H), 3.59-3.49 (m, 2H), 3.35 (t, 2H, J = 6.0 Hz), 2.89 (t, 2H, J = 6.0 Hz), 2.05-1.97 (m, 1H), 0.95-0.91 (m, 2H), 0.89-0.85 (m, 2H). |
| 108 | 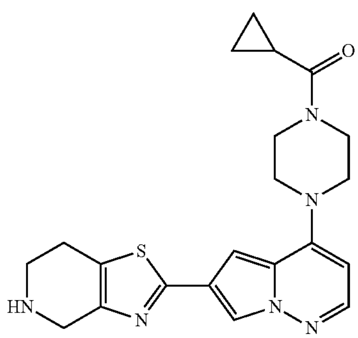 [SMILES: O=C(C1CC1)N1CCN(c2ccnn3cc(-c4nc5c(s4)CCNC5)cc23)CC1] | 409 | 1H-NMR (400 MHz, 6d-DMSO) δ ppm 8.32 (s, 1H), 7.98 (d, 1H, J = 5.6 Hz), 7.18 (s, 1H), 6.03 (d, 1H, J = 5.6 Hz), 4.05-3.80 (m, 2H), 3.75-3.65 (m, 2H), 3.65-3.55 (m, 2H), 3.50-3.40 (m, 2H), 3.27-3.24 (m, 2H), 2.81-2.76 (m, 2H), 2.05-1.97 (m, 1H), 1.97-1.8 (m, 2H), 0.79-0.74 (m, 4H). |
| 109 | 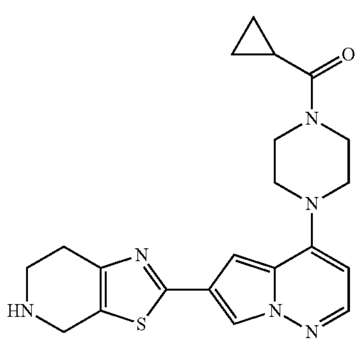 [SMILES: O=C(C1CC1)N1CCN(c2ccnn3cc(-c4nc5c(s4)CNCC5)cc23)CC1] | 409 | 1H-NMR (400 MHz, MeOD) δ ppm 8.10 (d, 1H, J = 1.6 Hz), 7.91 (d, 1H, J = 5.2 Hz), 7.04 (d, 1H, J = 1.6 Hz), 6.04 (d, 1H, J = 6.0 Hz), 4.10-3.95 (m, 4H), 3.95-3.75 (m, 2H), 3.70-3.60 (m, 2H), 3.60-3.50 (m, 2H), 3.19 (t, 2H, J = 6.0 Hz), 2.89 (t, 2H, J = 6.0 Hz), 2.05-1.97 (m, 1H), 0.99-0.85 (m, 2H), 0.85-0.80 (m, 2H). |

TABLE 1-continued

| # | Structure | LCMS (M + 1) | NMR |
|---|---|---|---|
| 110 | 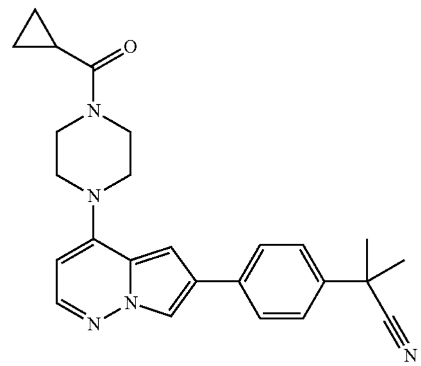 [SMILES: CC(C)(C#N)c1ccc(-c2cc3c(N4CCN(C(=O)C5CC5)CC4)ccnn3c2)cc1] | 414 | |
| 111 | 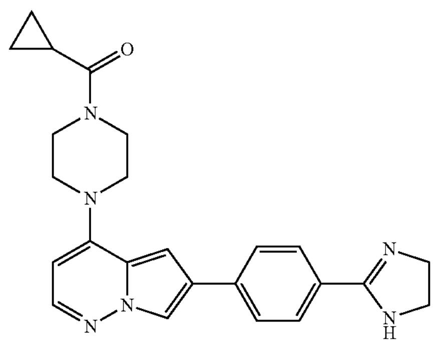 [SMILES: O=C(C1CC1)N1CCN(c2ccnn3cc(-c4ccc(C5=NCCN5)cc4)cc23)CC1] | 415 | 1H-NMR (400 MHz, 6d-DMSO) δ ppm 8.32 (d, 1H, J = 1.2 Hz), 7.97 (d, 2H, J = 8.0 Hz), 7.92 (d, 1H, J = 5.6 Hz), 7.88 (d, 2H, J = 8.0 Hz), 7.18 (d, 1H, J = 1.2 Hz), 5.98 (d, 1H, J = 5.6 Hz), 3.93-3.92 (m, 2H), 3.73-3.67 (m, 2H), 3.57-3.53 (m, 2H), 3.51-3.47 (m, 2H), 3.49-3.33 (m, 4H), 2.04-1.99 (m, 1H), 0.78-0.72 (m, 4H). |
| 112 | 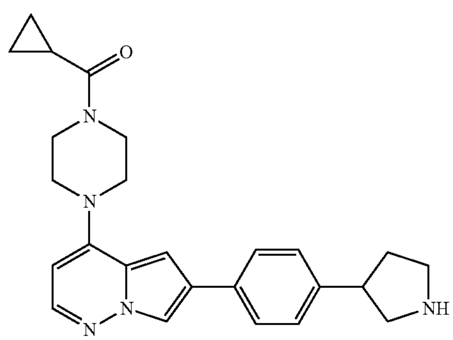 [SMILES: O=C(C1CC1)N1CCN(c2ccnn3cc(-c4ccc(C5CCNC5)cc4)cc23)CC1] | 416 | 1H-NMR (400 MHz, 6d-DMSO) δ ppm 8.17 (s, 1H), 7.89 (d, 1H, J = 6.0 Hz), 7.76 (d, 2H, J = 8.0 Hz), 7.31 (d, 2H, J = 7.6 Hz), 7.04 (s, 1H), 5.97 (d, 1H, J = 5.2 Hz), 3.92-3.91 (m, 2H), 3.69-3.68 (m, 2H), 3.53-3.47 (m, 4H), 3.43-3.41 (m, 1H), 3.41-3.38 (m, 1H), 3.30-3.28 (m, 1H), 3.09-3.06 (m, 1H), 2.89-2.84 (m, 1H, J = 10.0 Hz), 2.25-2.22 (m, 1H), 2.03-2.00 (m, 1H), 1.83-1.82 (m, 1H), 0.78-0.74 (m, 4H). |
| 113 | 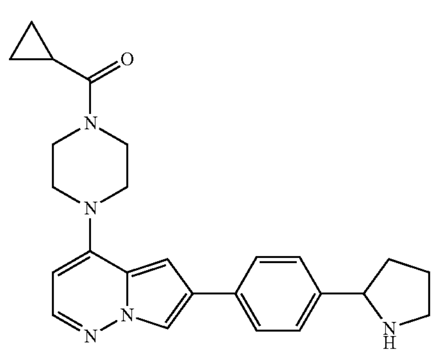 [SMILES: O=C(C1CC1)N1CCN(c2ccnn3cc(-c4ccc(C5CCCN5)cc4)cc23)CC1] | 417 | |

TABLE 1-continued

| # | Structure | LCMS (M + 1) | NMR |
|---|---|---|---|
| 114 | 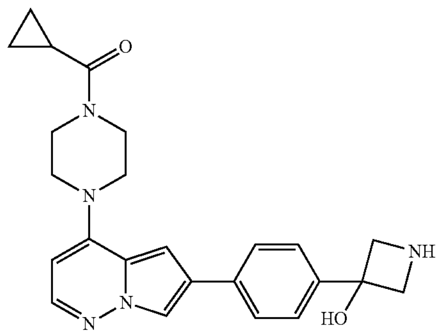 [SMILES: O=C(C1CC1)N1CCN(c2ccnn3cc(-c4ccc(C5(O)CNC5)cc4)cc23)CC1] | 420 | 1H-NMR (400 MHz, 6d-DMSO) δ ppm 8.25 (d, 1H, J = 2.0 Hz), 7.92 (d, 1H, J = 5.6 Hz), 7.88 (d, 2H, J = 8.4 Hz), 7.57 (d, 2H, J = 8.4 Hz), 7.10 (d, 1H, J = 1.6 Hz) 6.58 (br s, 1H), 5.99 (d, 1H, J = 5.6 Hz), 4.25 (d, 2H, J = 10.8 Hz), 4.02 (d, 2H, J = 10.4 Hz), 3.95-3.90 (m, 2H), 3.73-3.68 (m, 1H), 3.60-3.50 (m, 2H), 3.50-3.40 (m, 2H), 2.06-2.00 (m, 1H), 0.79-0.75 (m, 4H). |
| 115 | 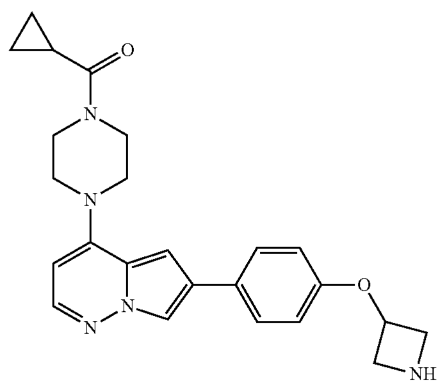 [SMILES: O=C(C1CC1)N1CCN(c2ccnn3cc(-c4ccc(OC5CNC5)cc4)cc23)CC1] | 418 | 1H-NMR (400 MHz, 6d-DMSO) δ ppm 8.11 (s, 1H), 7.89 (d, 1H, J = 5.6 Hz), 7.73 (d, 2H, J = 8.4 Hz), 6.98 (s, 1H), 6.84 (d, 2H, J = 8.4 Hz), 5.97 (d, 1H, J = 5.6 Hz), 5.05-4.98 (m, 1H), 3.97-3.92 (m, 3H), 3.75-3.70 (m, 2H), 3.68-3.61 (m, 2H), 3.53-3.49 (m, 2H), 3.45-3.41 (m, 2H), 2.04-1.98 (m, 1H), 0.78-0.74 (m, 4H). |
| 116 | 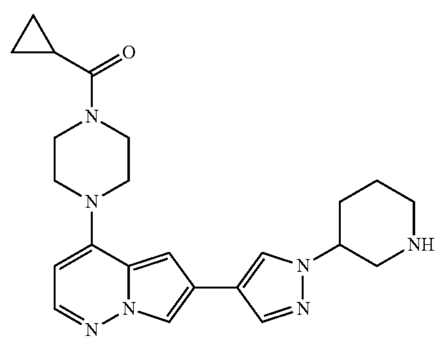 [SMILES: O=C(C1CC1)N1CCN(c2ccnn3cc(-c4cnn(C5CCCNC5)c4)cc23)CC1] | 420 | 1H-NMR (400 MHz, CDCl3) δ ppm 7.83 (d, 1H, J = 5.6 Hz), 7.76 (d, 1H, J = 1.6 Hz, ), 7.74 (s, 1H), 7.68 (s, 1H), 6.53 (d, 1H, J = 1.6 Hz, ), 5.84 (d, 1H, J = 5.6 Hz), 4.33-4.23 (m, 1H), 4.00-3.83 (m, 4H), 3.60-3.40 (m, 5H), 3.13-3.03 (m, 2H), 2.80-2.70 (m, 1H), 2.33-2.23 (m, 1H), 2.10-1.98 (m, 1H), 1.82-1.76 (m, 2H), 1.72-1.64 (m, 1H), 1.09-1.03 (m, 2H), 0.88-0.80 (m, 2H). |
| 117 | 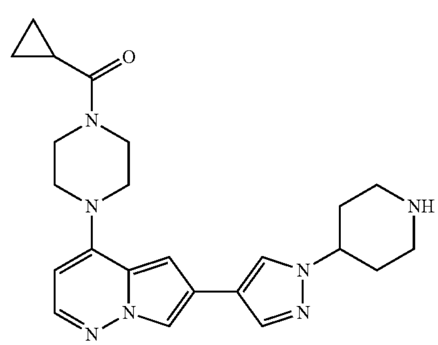 [SMILES: O=C(C1CC1)N1CCN(c2ccnn3cc(-c4cnn(C5CCNCC5)c4)cc23)CC1] | 420 | 1H-NMR (400 MHz, 6d-DMSO) δ ppm 8.11 (s, 1H), 7.92 (d, 1H, J = 1.6 Hz), 7.85 (d, 2H, J = 5.2 Hz), 7.80 (s, 1H), 6.82 (d, 1H, J = 1.6 Hz), 5.95 (d, 1H, J = 5.2 Hz), 4.18-4.13 (m, 1H), 3.91-3.90 (m, 2H), 3.69-3.68 (m, 2H), 3.50-3.43 (m, 3H), 3.05-3.02 (m, 2H), 2.61-2.55 (m, 2H), 2.04-1.96 (m, 3H), 1.81-1.73 (m, 2H), 0.78-0.72 (m, 4H). |

TABLE 1-continued

| # | Structure | LCMS (M + 1) | NMR |
|---|---|---|---|
| 118 | 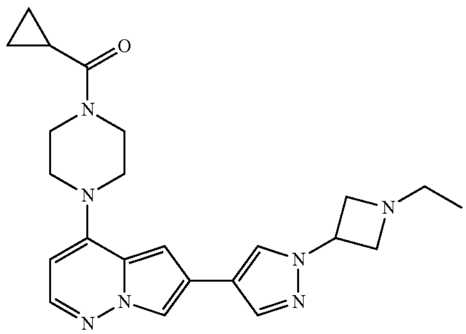 [SMILES: CCN1CC(n2cc(-c3cc4c(N5CCN(C(=O)C6CC6)CC5)ccnn4c3)cn2)C1] | 420 | 1H-NMR (400 MHz, 6d-DMSO) δ ppm 8.26-8.24 (m, 2H), 7.96 (s, 1H), 7.91 (s, 1H), 7.88 (d, 1H, J = 5.2 Hz), 6.86 (s, 1H), 5.97 (d, 1H, J = 4.8 Hz), 5.00 (br. s., 1H), 4.30-3.80 (m, 4H), 3.97-3.91 (m, 2H), 3.85-3.75 (m, 2H), 3.70-3.65 (m, 2H), 3.52-3.50 (m, 2H), 2.59 (q, 2H, J = 6.4 Hz), 2.03-2.01 (m, 1H), 0.95 (t, 3H, J = 6.4 Hz), 0.77-0.74 (m, 4H). |
| 119 | 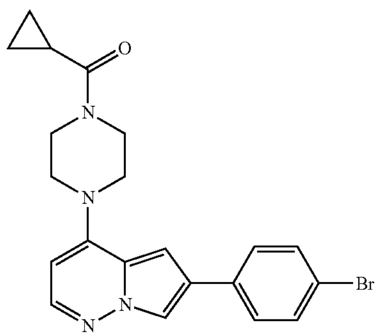 [SMILES: O=C(C1CC1)N1CCN(c2ccnn3cc(-c4ccc(Br)cc4)cc23)CC1] | 425 | 1H-NMR (400 MHz, CDCl3) δ ppm 7.92 (d, 1H, J = 1.6 Hz), 7.86 (d, 1H, J = 5.6 Hz), 7.53-7.51 (m, 4H), 6.69 (d, 1H, J = 1.6 Hz), 5.85 (d, 1H, J = 5.6 Hz), 3.94-3.90 (m, 4H), 3.56-3.49 (m, 4H), 1.81-1.74 (m, 1H), 1.06-1.03 (m, 2H), 0.86-0.82 (m, 2H). |
| 120 | 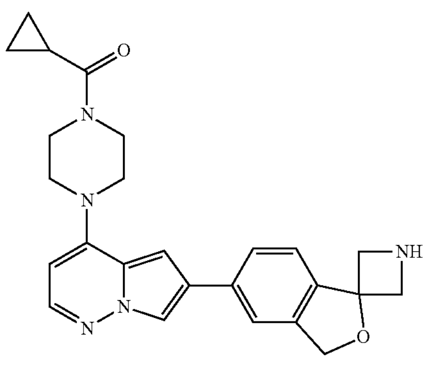 [SMILES: O=C(C1CC1)N1CCN(c2ccnn3cc(-c4ccc5c(c4)COC54CNC4)cc23)CC1] | 430 | 1H-NMR (400 MHz, MeOD) δ ppm 8.01 (d, 1H, J = 1.6 Hz), 7.85 (d, 1H, J = 5.2 Hz), 7.83 (d, 1H, J = 8.0 Hz), 7.72 (d, 1H, J = 8.0 Hz), 7.67 (s, 1H), 6.96 (d, 1H, J = 1.6 Hz), 6.00 (d, 1H, J = 5.2 Hz), 5.17 (s, 2H), 4.40-4.30 (m, 4H), 4.10-3.95 (m, 2H), 3.85-3.75 (m, 2H), 3.66-3.57 (m, 2H), 3.55-3.50 (m, 2H), 2.05-1.97 (m, 1H), 0.95-0.87 (m, 2H), 0.85-0.80 (m, 2H). |
| 121 | 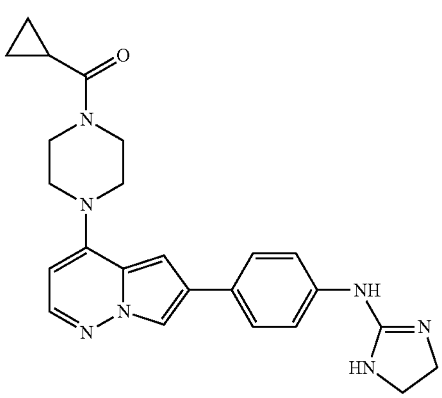 [SMILES: O=C(C1CC1)N1CCN(c2ccnn3cc(-c4ccc(NC5=NCCN5)cc4)cc23)CC1] | 430 | 1H NMR (400 MHz, 6d-DMSO) δ ppm 8.06 (s, 1H), 7.88 (d, 1H, J = 4.8 Hz), 7.62 (d, 2H, J = 8.4 Hz), 7.05-6.95 (m, 2H), 6.94 (s, 1H), 5.96 (d, 1H, J = 5.6 Hz), 3.95-3.90 (m, 2H), 3.75-3.65 (m, 2H), 3.58-3.50 (m, 2H), 3.50-3.40 (m, 2H), 3.45-3.20 (m, 4H), 2.05-11.95 (m, 1H), 0.78-0.74 (m, 4H). |

TABLE 1-continued

| # | Structure | LCMS (M + 1) | NMR |
|---|---|---|---|
| 122 | 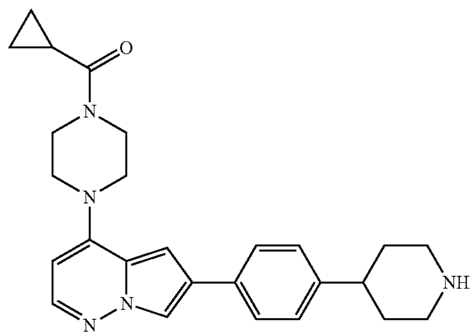 [SMILES: O=C(C1CC1)N1CCN(c2ccnn3cc(-c4ccc(C5CCNCC5)cc4)cc23)CC1] | 430 | 1H-NMR (400 MHz, DMSO-d6) δ ppm 8.14 (d, 1H, J = 1.6 Hz), 7.89 (d, 1H, J = 5.2 Hz), 7.72 (d, 2H, J = 8.0 Hz), 7.23 (d, 2H, J = 8.0 Hz), 7.01 (d, 1H, J = 1.6 Hz), 5.96 (d, 1H, J = 5.2 Hz), 3.91 (br. s., 2H), 3.70 (br. s., 2H), 3.53-3.46 (m, 4H), 3.05-3.02 (m, 2H), 2.62-2.49 (m, 3H), 2.05-1.99 (m, 1H), 1.76-1.70 (m, 2H), 1.58-1.48 (m, 2H), 0.80-0.70 (m, 4H). |
| 123 | 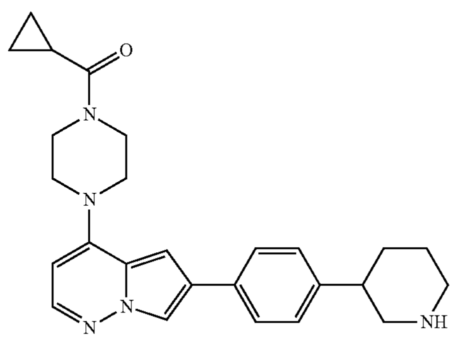 [SMILES: O=C(C1CC1)N1CCN(c2ccnn3cc(-c4ccc(C5CCCNC5)cc4)cc23)CC1] | 430 | 1H-NMR (400 MHz, 6d-DMSO) δ ppm 8.13 (d, 1H, J = 1.6 Hz), 7.89 (d, 1H, J = 5.6 Hz), 7.71 (d, 2H, J = 8.0 Hz), 7.23 (d, 2H, J = 8.0 Hz), 7.01 (d, 1H, J = 1.6 Hz), 5.96 (d, 1H, J = 5.6 Hz), 4.00-3.80 (m, 2H), 3.78-3.62 (m, 2H), 3.60-3.42 (m, 4H), 3.40-3.20 (m, 2H), 3.00-2.90 (m, 2H), 2.60-2.54 (m, 2H), 2.10-1.93 (m, 1H), 1.90-1.80 (m, 1H), 1.70-1.40 (m, 3H), 1.80-0.60 (m, 4H). |
| 124 | 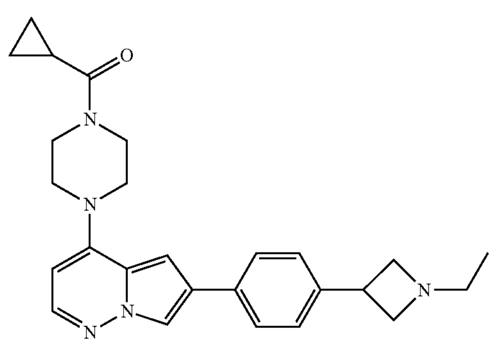 [SMILES: CCN1CC(c2ccc(-c3cc4c(N5CCN(C(=O)C6CC6)CC5)ccnn4c3)cc2)C1] | 430 | 1H-NMR (400 MHz, 6d-DMSO) δ ppm 8.61 (s, 1H), 7.94 (s, 1H), 7.87 (d, 1H, J = 4.8 Hz), 7.66 (d, 2H, J = 8.0 Hz), 7.31 (d, 2H, J = 8.0 Hz), 6.71 (s, 1H), 5.86 (d, 1H, J = 4.8 Hz), 4.41-4.39 (m, 2H), 4.21-4.17 (m, 1H), 3.96-3.90 (m, 2H), 3.85-3.90 (m, 2H), 3.76-3.75 (m, 2H), 3.57-3.54 (m, 2H), 3.51-3.48 (m, 2H), 3.07 (q, 2H, J = 6.4 Hz), 1.79-1.78 (m, 1H), 1.25 (t, 3H, J = 6.4 Hz), 1.11-1.05 (m, 2H), 0.85-0.83 (m, 2H). |
| 125 | 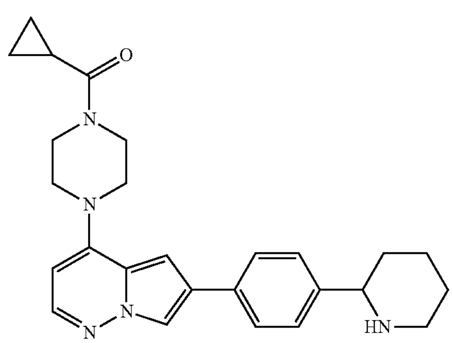 [SMILES: O=C(C1CC1)N1CCN(c2ccnn3cc(-c4ccc(C5CCCCN5)cc4)cc23)CC1] | 431 | 1H NMR (400 MHz, Chloroform-d) δ 7.92 (d, J = 1.8 Hz, 1H), 7.84 (d, J = 5.3 Hz, 1H), 7.61 (d, J = 8.1 Hz, 2H), 7.41 (d, J = 8.0 Hz, 2H), 6.71 (d, J = 1.9 Hz, 1H), 5.84 (d, J = 5.4 Hz, 1H), 3.91 (d, J = 19.0 Hz, 5H), 3.68-3.42 (m, 7H), 3.21 (d, J = 11.7 Hz, 2H), 2.82 (t, J = 11.1 Hz, 1H), 1.94-1.75 (m, 3H), 1.04 (dt, J = 6.5, 3.2 Hz, 2H), 0.82 (dq, J = 7.1, 3.8 Hz, 2H). |

TABLE 1-continued

| # | Structure | LCMS (M + 1) | NMR |
|---|---|---|---|
| 126 | 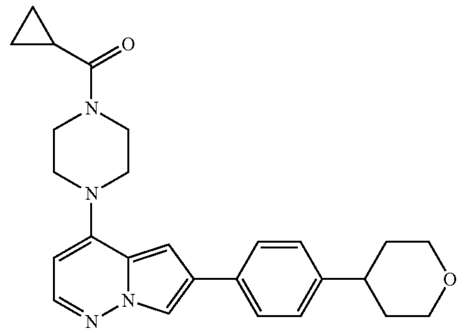 [SMILES: O=C(C1CC1)N1CCN(c2ccnn3cc(-c4ccc(C5CCOCC5)cc4)cc23)CC1] | 431 | 1H-NMR (400 MHz, 6d-DMSO) δ ppm 8.14 (d, 1H, J = 1.6 Hz), 7.90 (d, 1H, J = 5.2 Hz), 7.75 (d, 2H, J = 8.0 Hz), 7.27 (d, 2H, J = 7.6 Hz), 7.03 (d, 1H, J = 1.2 Hz), 5.98 (d, 1H, J = 5.6 Hz), 3.97-3.95 (m, 4H), 3.71-3.70 (m, 2H), 3.55-3.52 (m, 2H), 3.48-3.41 (m, 4H), 2.78-2.77 (m, 1H), 2.04-2.00 (m, 1H), 1.73-1.70 (m, 4H), 0.79-0.75 (m, 4H). |
| 127 | 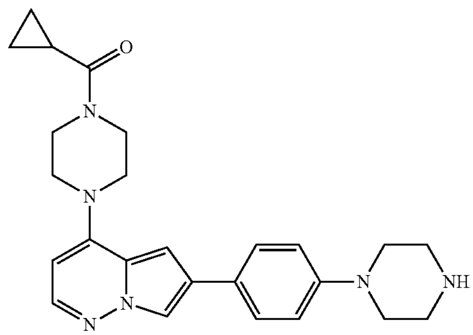 | 431 | 1H-NMR (400 MHz, DMSO-d6) δ ppm 8.06 (d, 1H, J = 1.2 Hz), 7.86 (d, 1H, J = 5.6 Hz), 7.64 (d, 2H, J = 8.4 Hz), 7.00-6.85 (m, 3H), 5.95 (d, 1H, J = 5.6 Hz), 3.91 (br. s. 2H), 3.69 (br. s. 2H), 3.52 (br. s. 2H), 3.44 (br. s. 2H), 3.06-3.04 (m, 4H), 2.82 (br. s. 4H), 2.05-1.95 (m, 1H), 0.80-0.65 (m, 4H). |
| 128 | 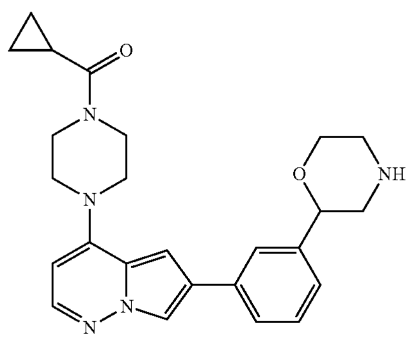 [SMILES: O=C(C1CC1)N1CCN(c2ccnn3cc(-c4cccc(C5CNCCO5)c4)cc23)CC1] | 432 | 1H-NMR (400 MHz, DMSO-d6) δ ppm 8.18 (d, 1H, J = 1.6 Hz), 7.90 (d, 1H, J = 5.6 Hz), 7.71-7.69 (m, 2H), 7.34 (t, 1H, J = 7.6 Hz), 7.21 (d, 1H, J = 7.6 Hz), 7.04 (d, 1H, J = 1.6 Hz), 5.97 (d, 1H, J = 5.6 Hz), 4.43-4.41 (m, 1H), 3.91-3.89 (m, 3H), 3.71 (br. s., 2H), 3.64-3.32 (m, 5H), 3.00-2.96 (m, 1H), 2.76-2.75 (m, 2H), 2.65-2.55 (m, 1H), 2.05-1.99 (m, 1H), 0.78-0.74 (m, 4H). |
| 129 | 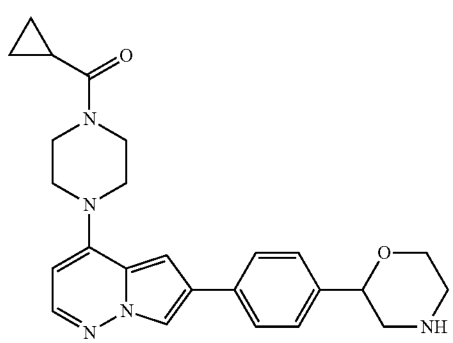 [SMILES: O=C(C1CC1)N1CCN(c2ccnn3cc(-c4ccc(C5CNCCO5)cc4)cc23)CC1] | 432 | 1H-NMR (400 MHz, DMSO-d6) δ ppm 8.16 (d, 1H, J = 1.6 Hz), 7.89 (d, 1H, J = 5.6 Hz), 7.76 (d, 2H, J = 8.0 Hz), 7.32 (d, 2H, J = 8.0 Hz), 7.04 (d, 1H, J = 1.6 Hz), 5.95 (d, 1H, J = 5.6 Hz), 4.40-4.36 (m, 1H), 3.89-3.87 (m, 3H), 3.69-3.46 (m, 8H), 2.94-2.90 (m, 1H), 2.75-2.73 (m, 2H), 2.55-2.49 (m, 1H), 2.05-1.97 (m, 1H), 0.77-0.71 (m, 4H). |

TABLE 1-continued

| # | Structure | LCMS (M + 1) | NMR |
|---|---|---|---|
| 130 | 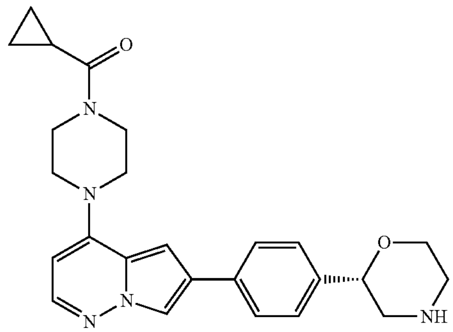 [SMILES: O=C(C1CC1)N1CCN(c2ccnn3cc(-c4ccc([C@H]5CNCCO5)cc4)cc23)CC1] | 432 | 1H-NMR (400 MHz, 6d-DMSO) δ ppm 8.16 (d, 1H, J = 1.6 Hz), 7.90 (d, 1H, J = 5.6 Hz), 7.76 (d, 2H, J = 8.4 Hz), 7.33 (d, 2H, J = 8.4 Hz), 7.04 (d, 1H, J = 1.6 Hz), 5.98 (d, 1H, J = 5.6 Hz), 4.38 (dd, 1H, J = 9.6, 1.6 Hz), 3.92-3.87 (m, 3H), 3.75-3.65 (m, 2H), 3.64-3.40 (m, 5H), 3.38-3.35 (m, 1H), 2.92 (dd, 1H, J = 12.0, 2.0 Hz), 2.76-2.70 (m, 2H), 2.52-2.50 (m, 1H), 2.05-1.99 (m, 1H), 0.80-0.72 (m, 4H). |
| 131 | 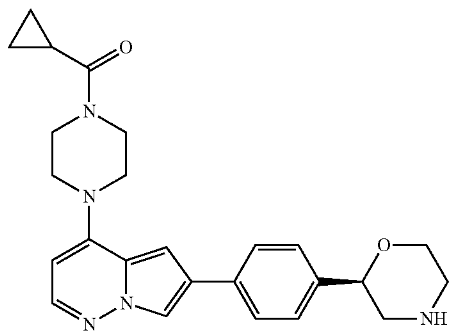 [SMILES: O=C(C1CC1)N1CCN(c2ccnn3cc(-c4ccc([C@@H]5CNCCO5)cc4)cc23)CC1] | 432 | 1H-NMR (400 MHz, 6d-DMSO) δ ppm 8.17 (d, 1H, J = 1.6 Hz), 7.89 (d, 1H, J = 5.6 Hz), 7.76 (d, 2H, J = 8.4 Hz), 7.33 (d, 2H, J = 8.4 Hz), 7.04 (d, 1H, J = 1.6 Hz), 5.97 (d, 1H, J = 5.6 Hz), 4.40-4.35 (m, 1H), 3.95-3.87 (m, 3H), 3.80-3.63 (m, 2H), 3.61-3.40 (m, 5H), 2.94-2.91 (m, 1H), 2.75-2.73 (m, 2H), 2.52-2.50 (m, 1H), 2.05-1.99 (m, 1H), 0.80-0.72 (m, 4H). |
| 132 | 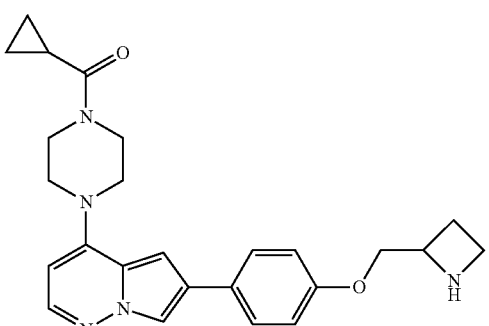 | 432 | 1H-NMR (400 MHz, 6d-DMSO) δ ppm 8.11 (s, 1H), 7.88 (d, 1H, J = 5.2 Hz), 7.73 (d, 2H, J = 8.4 Hz), 6.99 (s, 1H), 6.96 (d, 2H, J = 8.4 Hz), .5.96 (d, 1H, J = 5.2 Hz), 4.19-4.12 (m, 1H), 4.02-3.97 (m, 2H), 3.95-3.90 (m, 2H), 3.75-3.68 (m, 2H), 3.54-3.48 (m, 4H), 3.31-3.29 (m, 2H), 2.30-2.25 (m., 1H), 2.14-2.07 (m, 1H), 2.04-1.97 (m, 1H), 0.78-0.74 (m, 4H). |
| 133 | 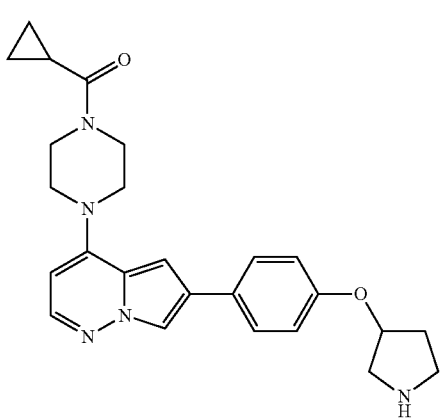 [SMILES: O=C(C1CC1)N1CCN(c2ccnn3cc(-c4ccc(OC5CCNC5)cc4)cc23)CC1] | 432 | 1H-NMR (400 MHz, 6d-DMSO) δ ppm 8.09 (s, 1H), 7.87 (d, 1H, J = 5.2 Hz), 7.71 (d, 2H, J = 8.4 Hz), 6.97 (s, 1H), 6.91 (d, 2H, J = 8.4 Hz), 5.96 (d, 1H, J = 6.0 Hz), 4.90-4.85 (m, 1H), 3.94-3.89 (m, 2H), 3.73-3.65 (m, 2H), 3.55-3.50 (m, 2H), 3.10-3.05 (m, 2H), 2.92-2.85 (m, 2H), 2.85-2.76 (m, 2H), 2.04-1.99 (m, 2H), 1.82-1.74 (m, 1H), 0.77-0.74 (m, 4H). |

TABLE 1-continued

| # | Structure | LCMS (M + 1) | NMR |
|---|---|---|---|
| 134 | 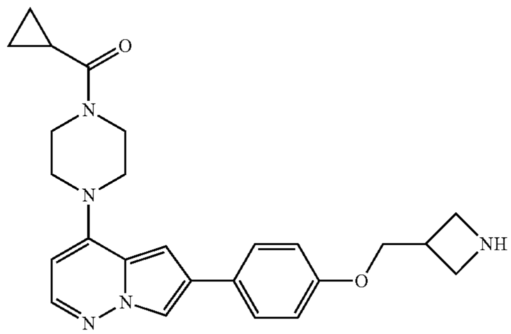 [SMILES: O=C(C1CC1)N1CCN(c2ccnn3cc(-c4ccc(OCC5CNC5)cc4)cc23)CC1] | 432 | 1H-NMR (400 MHz, 6d-DMSO) δ ppm 8.12 (d, 1H, J = 1.6 Hz), 7.89 (d, 1H, J = 5.6 Hz), 7.75 (d, 2H, J = 8.8 Hz), 6.98 (d, 3H, J = 8.8 Hz), 5.97 (d, 1H, J = 5.6 Hz), 4.14 (d, 2H, J = 6.8 Hz), 3.95-3.90 (m, 2H), 3.75-3.70 (m, 2H), 3.66 (d, 2H, J = 8.0 Hz), 3.55-3.50 (m, 2H), 3.49-3.45 (m, 2H), 3.44-3.40 (m, 2H), 3.09-2.99 (m, 1H), 2.05-2.01 (m, 1H), 0.78-0.75 (m, 4H). |
| 135 | 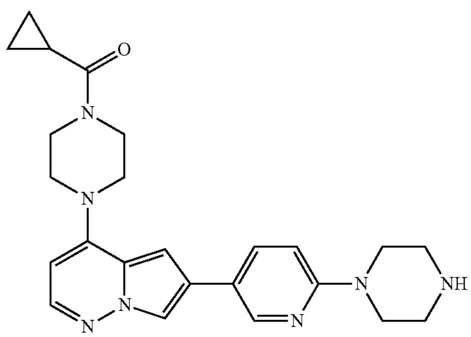 [SMILES: O=C(C1CC1)N1CCN(c2ccnn3cc(-c4ccc(N5CCNCC5)nc4)cc23)CC1] | 432 | 1H-NMR (400 MHz, CDCl3) δ ppm 8.52 (d, 1H, J = 2.4 Hz), 7.87-7.84 (m, 2H), 7.74 (dd, 1H, J = 2.4, 8.8 Hz), 6.71 (d, 1H, J = 8.8 Hz), 6.63 (d, 1H, J = 2.0 Hz), 5.85 (d, 1H, J = 5.6 Hz), 3.94-3.87 (m, 4H), 3.56-3.47 (m, 8H), 3.03-3.00 (m, 4H), 1.80-1.76 (m, 1H), 1.07-1.03 (m, 2H), 0.85-0.81 (m, 2H). |
| 136 | 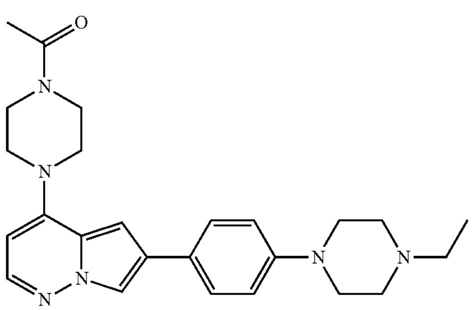 [SMILES: CCN1CCN(c2ccc(-c3cc4c(N5CCN(C(C)=O)CC5)ccnn4c3)cc2)CC1] | 433 | 1H-NMR (400 MHz, 6d-DMSO) δ ppm 8.05 (d, 1H, J = 1.2 Hz), 7.86 (d, 1H, J = 5.2 Hz), 7.64 (d, 2H, J = 8.8 Hz), 6.95 (d, 2H, J = 8.8 Hz), 6.91 (d, 1H, J = 1.2 Hz), 5.94 (d, 1H, J = 5.2 Hz), 3.66-3.65 (m, 4H), 3.49-3.48 (m, 2H), 3.42-3.41 (m, 4H), 3.15-3.14 (m, 4H), 2.52-2.51 (m, 2H), 2.38 (q, 2H, J = 7.2 Hz), 2.06 (s, 3H), 1.03 (t, 3H, J = 7.2 Hz). |
| 137 | 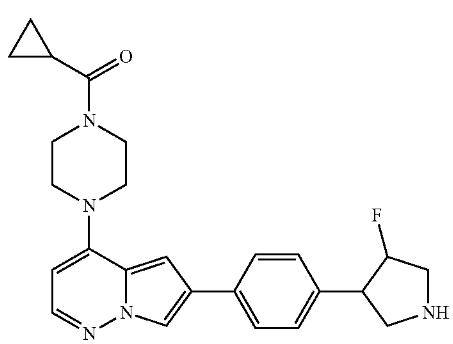 [SMILES: O=C(C1CC1)N1CCN(c2ccnn3cc(-c4ccc(C5CNCC5F)cc4)cc23)CC1] | 434 | 1H-NMR (400 MHz, 6d-DMSO) δ ppm 8.17 (d, 1H, J = 1.6 Hz), 7.90 (d, 1H, J = 5.2 Hz), 7.76 (d, 2H, J = 8.0 Hz), 7.27 (d, 2H, J = 8.8 Hz), 7.04 (d, 1H, J = 1.6 Hz), 5.97 (d, 1H, J = 5.6 Hz), 5.30-5.00 (m, 1H), 4.00-3.85 (m, 2H), 3.75-3.65 (m, 2H), 3.60-3.40 (m, 6H), 3.20-3.10 (m, 1H), 3.08-3.00 (m, 1H), 2.75-2.65 (m, 1H), 2.05-1.95 (m, 1H), 0.80-0.70 (m, 4H). |

TABLE 1-continued

| # | Structure | LCMS (M + 1) | NMR |
|---|---|---|---|
| 138 | 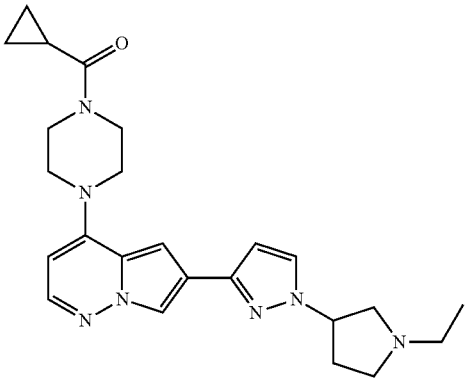 [SMILES: CCN1CCC(n2ccc(-c3cc4c(N5CCN(C(=O)C6CC6)CC5)ccnn4c3)n2)C1] | 434 | 1H-NMR (400 MHz, 6d-DMSO) δ ppm 7.97 (d, 1H, J = 1.6 Hz), 7.88 (d, 1H, J = 5.2 Hz), 7.78 (d, 1H, J = 2.4 Hz), 6.86 (d, 1H, J = 1.6 Hz), 7.96 (d, 1H, J = 5.2 Hz), 6.62 (d, 1H, J = 2.4 Hz), 5.96 (d, 1H, J = 5.2 Hz), 4.92-4.85 (m, 1H), 3.92 (br. s., 2H), 3.69 (br. s., 2H), 3.53-3.44 (m, 4H), 2.85 (q, 2H, J = 7.2 Hz), 2.807-2.77 (m, 1H), 2.48-2.42 (m, 3H), 2.39-2.30 (m, 1H), 2.13-2.06 (m, 1H), 2.04-1.97 (m, 1H), 1.04 (t, 3H, J = 7.2 Hz), 0.78-0.73 (m, 4H). |
| 139 | 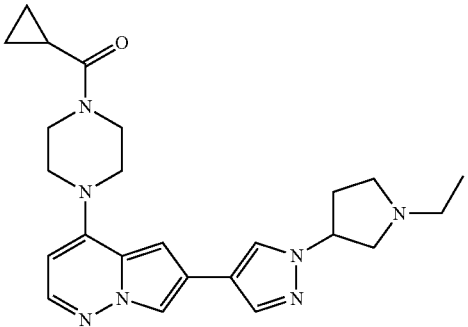 [SMILES: CCN1CCC(n2cc(-c3cc4c(N5CCN(C(=O)C6CC6)CC5)ccnn4c3)cn2)C1] | 434 | 1H-NMR (400 MHz, 6d-DMSO) δ ppm 8.13 (s, 1H), 7.93 (d, 1H, J = 1.2 Hz), 7.85 (d, 1H, J = 5.2 Hz), 7.81 (s, 1H), 6.83 (d, 1H, J = 1.2 Hz), 5.95 (d, 1H, J = 5.2 Hz), 4.87-4.85 (m, 1H), 3.91-3.90 (m, 2H), 3.68-3.67 (m, 2H), 3.50-3.49 (m, 4H), 3.43-3.34 (m, 4H), 2.91-2.90 (m, 1H), 2.76-2.74 (m, 2H), 2.08-2.07 (m, 1H), 2.02-1.98 (m, 1H). 1.04 (t, 3H, J = 7.2 Hz), 0.77-0.74 (m, 4H). |
| 140 | 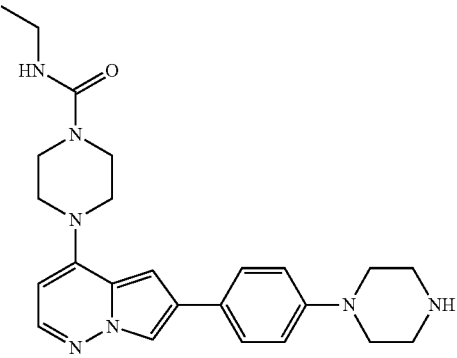 | 434 | 1H-NMR (400 MHz, 6d-DMSO) δ ppm 8.05 (d, 1H, J = 1.6 Hz), 7.86 (d, 1H, J = 5.6 Hz), 7.65 (d, 2H, J = 8.4 Hz), 6.94 (d, 2H, J = 8.4 Hz), 6.91 (d, 1H, J = 1.6 Hz), 6.60 (t, 1H, J = 5.6 Hz), 5.96 (d, 1H, J = 5.6 Hz), 3.52-3.51 (m, 4H), 3.43-3.41 (m, 4H), 3.12-3.09 (m, 2H), 3.10-3.05 (m, 4H), 2.86-2.83 (m, 4H), 1.04 (t, 3H, J = 6.8 Hz). |
| 141 | 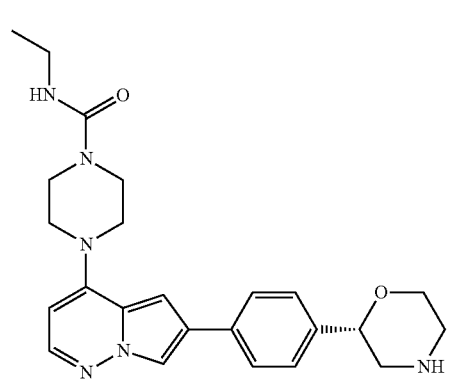 [SMILES: CCNC(=O)N1CCN(c2ccnn3cc(-c4ccc([C@H]5CNCCO5)cc4)cc23)CC1] | 435 | 1H-NMR (400 MHz, MeOD) δ ppm 7.99 (s, 1H), 7.86 (m, 1H), 7.78 (d, 2H, J = 8.0 Hz), 6.93 (s, 1H), 7.45 (d, 2H, J = 8.0 Hz), 6.96 (s, 1H), 6.00 (d, 1H, J = 5.6 Hz), 4.79-4.70 (m, 1H), 4.29-4.25 (m, 1H), 4.04-3.97 (m, 1H), 3.67-3.64 (m, 4H), 3.56-3.54 (m, 4H), 3.50-3.47 (m, 1H), 3.39-3.34 (m, 2H), 3.25-3.21 (m, 2H), 3.18-3.14 (m, 1H), 1.54 (t, 3H, J = 7.2 Hz). |

TABLE 1-continued

| # | Structure | LCMS (M + 1) | NMR |
|---|---|---|---|
| 142 | 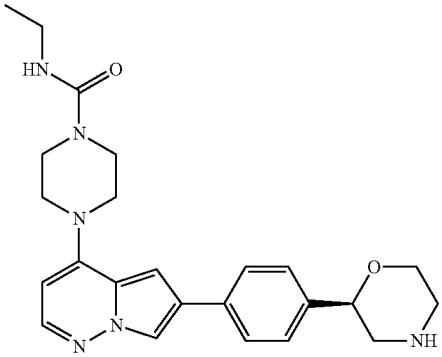 [SMILES: CCNC(=O)N1CCN(c2ccnn3cc(-c4ccc([C@@H]5CNCCO5)cc4)cc23)CC1] | 435 | 1H-NMR (400 MHz, MeOD) δ ppm 7.99 (s, 1H), 7.85 (m, 1 Hz), 7.77 (d, 2H, J = 8.4 Hz), 7.44 (d, 2H, J = 8.0 Hz), 6.93 (s, 1H), 6.00 (d, 1H, J = 5.2 Hz), 4.79-4.77 (m, 1H), 4.28-4.25 (m, 1H), 4.05-3.98 (m, 1H), 3.66-3.64 (m, 4H), 3.55-3.53 (m, 4H), 3.49-3.47 (m, 1H), 3.39-3.40 (m, 2H), 3.27-3.22 (m, 2H), 3.16-3.14 (m, 1H), 1.53 (t, 3H, J = 7.2 Hz). |
| 143 | 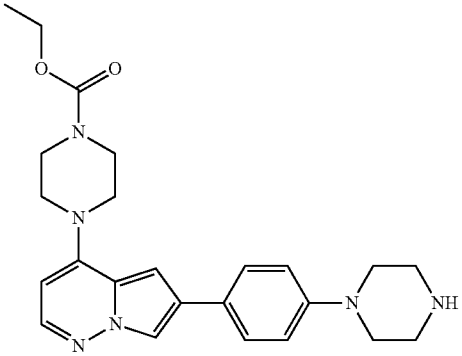 [SMILES: CCOC(=O)N1CCN(c2ccnn3cc(-c4ccc(N5CCNCC5)cc4)cc23)CC1] | 435 | 1H-NMR (400 MHz, 6d-DMSO) δ ppm 8.29 (br. s., 1H), 8.07 (d, 1H, J = 1.2 Hz), 7.87 (d, 1H, J = 5.6 Hz), 7.66 (d, 2H, J = 8.4 Hz), 6.96 (d, 2H, J = 8.4 Hz), 6.92 (d, 1H, J = 1.2 Hz), 5.96 (d, 1H, J = 5.6 Hz), 4.08 (q, 2H, J = 6.8 Hz), 3.65-3.55 (m, 4H), 3.50-3.40 (m, 4H), 3.20-3.10 (m, 4H), 3.05-2.90 (m, 4H), 1.21 (t, 3H, J = 6.8 Hz). |
| 144 | 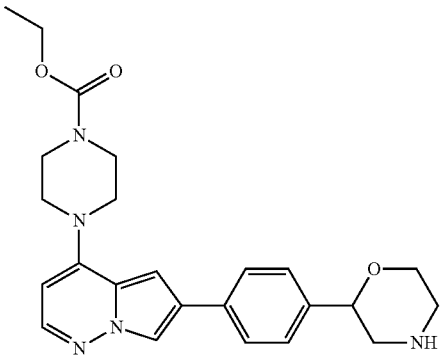 [SMILES: CCOC(=O)N1CCN(c2ccnn3cc(-c4ccc(C5CNCCO5)cc4)cc23)CC1] | 436 | 1H-NMR (400 MHz, 6d-DMSO) δ ppm 8.16 (d, 1H, J = 0.8 Hz), 7.89 (d, 1H, J = 5.6 Hz), 7.76 (d, 2H, J = 8.4 Hz), 7.32 (d, 2H, J = 8.4 Hz), 7.01 (d, 1H, J = 0.8 Hz), 5.97 (d, 1H, J = 5.6 Hz), 4.40-4.35 (m, 1H), 4.08 (q, 2H, J = 7.2 Hz), 3.90-3.80 (m, 1H), 3.65-3.60 (m, 1H), 3.61-3.56 (m, 4H), 3.48-3.40 (m, 4H), 3.00-2.90 (m, 1H), 2.80-2.70 (m, 2H), 2.60-2.40 (m, 1H), 1.21 (t, 3H, J = 7.2 Hz). |
| 145 | 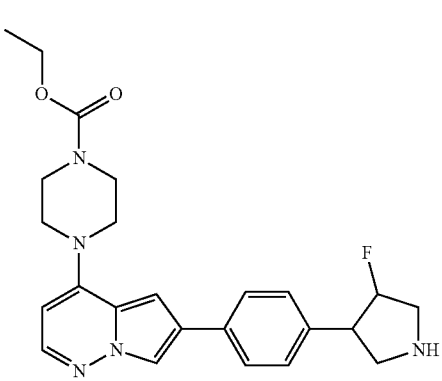 [SMILES: CCOC(=O)N1CCN(c2ccnn3cc(-c4ccc(C5CNCC5F)cc4)cc23)CC1] | 438 | 1H-NMR (400 MHz, 6d-DMSO) δ ppm 8.17 (d, 1H, J = 1.6 Hz), 7.89 (d, 1H, J = 5.6 Hz), 7.76 (d, 2H, J = 8.0 Hz), 7.29 (d, 2H, J = 8.0 Hz), 7.01 (d, 1H, J = 1.6 Hz), 5.97 (d, 1H, J = 5.6 Hz), 5.40-5.00 (m, 1H), 4.08 (q, 2H, J = 7.2 Hz), 3.70-3.50 (m, 4H), 3.50-3.47 (m, 2H), 3.45-3.40 (m, 4H), 3.20-3.15 (m, 1H), 3.12-3.05 (m, 1H), 2.85-2.75 (m, 1H), 1.21 (t, 3H, J = 7.2 Hz). |

TABLE 1-continued

| # | Structure | LCMS (M + 1) | NMR |
|---|---|---|---|
| 146 | 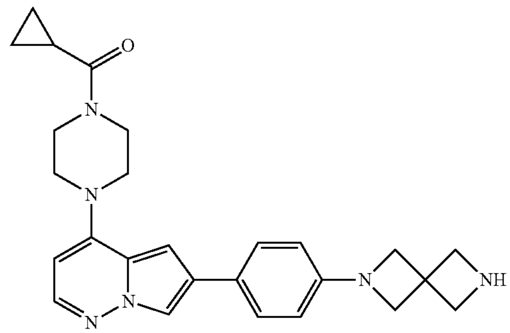 [SMILES: O=C(C1CC1)N1CCN(c2ccnn3cc(-c4ccc(N5CC6(CNC6)C5)cc4)cc23)CC1] | 443 | 1H-NMR (400 MHz, 6d-DMSO) δ ppm 8.31 (s, 1H), 8.04 (d, 1H, J = 1.2 Hz), 7.86 (d, 1H, J = 5.2 Hz), 7.62 (d, 2H, J = 8.4 Hz), 6.91 (d, 1H, J = 1.2 Hz), 6.47 (d, 2H, J = 8.4 Hz), 5.95 (d, 1H, J = 5.2 Hz), 4.17-407 (m, 4H), 4.01-3.95 (m, 4H), 3.95-3.90 (m, 2H), 3.73-3.65 (m, 2H), 3.52-3.51 (m, 2H), 3.46-3.44 (m, 2H), 2.05-1.99 (m, 1H), 0.80-0.72 (m, 4H). |
| 147 | 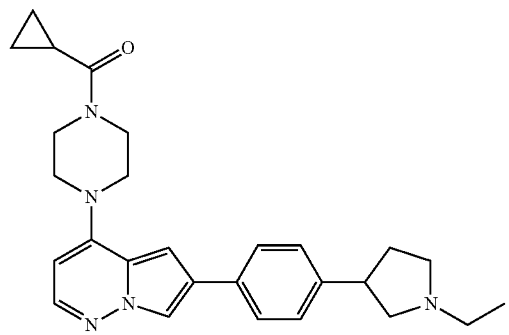 [SMILES: CCN1CCC(c2ccc(-c3cc4c(N5CCN(C(=O)C6CC6)CC5)ccnn4c3)cc2)C1] | 444 | 1H-NMR (400 MHz, 6d-DMSO) δ ppm 8.16 (s, 1H), 7.90 (d, 1H, J = 5.6 Hz), 7.74 (d, 2H, J = 8.0 Hz), 7.31 (d, 2H, J = 8.0 Hz), 7.03 (s, 1H), 5.97 (d, 1H, J = 5.6 Hz), 3.93-3.91 (m, 2H), 3.70-3.68 (m, 2H), 3.54-3.48 (m, 5H), 3.11-3.10 (m, 1H), 2.84-2.83 (m, 2H), 2.67-2.62 (m, 3H), 2.28-2.25 (m, 1H), 2.04-2.01 (m, 1H), 1.86-1.81 (m, 1H), 1.11 (t, 3H, J = 6.8 Hz), 0.79-0.73 (m, 4H). |
| 148 | 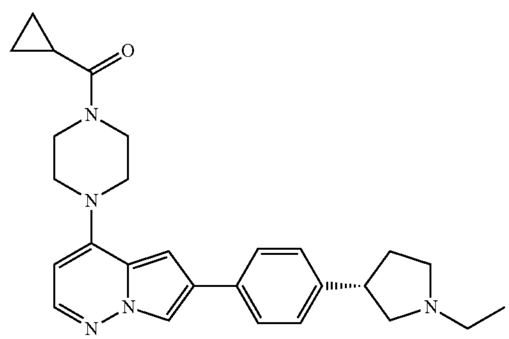 [SMILES: CCN1CC[C@@H](c2ccc(-c3cc4c(N5CCN(C(=O)C6CC6)CC5)ccnn4c3)cc2)C1] | 444 | 1H-NMR (400 MHz, 6d-DMSO) δ ppm 8.13 (d, 1H, J = 1.6 Hz), 7.89 (d, 1H, J = 5.6 Hz), 7.71 (d, 2H, J = 8.0 Hz), 7.29 (d, 2H, J = 8.4 Hz), 7.01 (d, 1H, J = 1.6 Hz), 5.97 (d, 1H, J = 5.6 Hz), 3.92-3.91 (m, 2H), 3.70-3.69 (m, 2H), 3.53-3.47 (m, 4H), 3.29-3.25 (m, 1H), 2.93-2.89 (m, 1H), 2.68-2.62 (m, 2H), 2.47-2.40 (m, 2H), 2.24-2.20 (m, 2H), 2.03-1.98 (m, 1H), 1.78-1.73 (m, 1H), 1.05 (t, 3H, J = 7.2 Hz), 0.78-0.72 (m, 4H). |
| 149 | 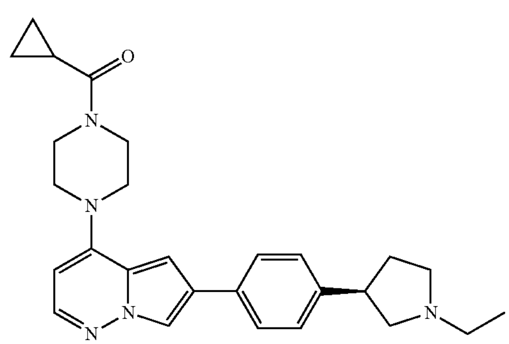 [SMILES: CCN1CC[C@H](c2ccc(-c3cc4c(N5CCN(C(=O)C6CC6)CC5)ccnn4c3)cc2)C1] | 444 | 1H-NMR (400 MHz, 6d-DMSO) δ ppm 8.13 (d, 1H, J = 1.6 Hz), 7.89 (d, 1H, J = 5.2 Hz), 7.71 (d, 2H, J = 8.4 Hz), 7.29 (d, 2H, J = 8.4 Hz), 7.01 (d, 1H, J = 1.2 Hz), 5.97 (d, 1H, J = 5.6 Hz), 3.92-3.91 (m, 2H), 3.70-3.69 (m, 2H), 3.53-3.47 (m, 5H), 2.95-2.91 (m, 1H), 2.70-2.63 (m, 2H), 2.47-2.40 (m, 2H), 2.24-2.20 (m, 2H), 2.03-1.98 (m, 1H), 1.77-1.75 (m, 1H), 1.05 (t, 3H, J = 7.6 Hz), 0.78-0.74 (m, 4H). |

TABLE 1-continued

| # | Structure | LCMS (M + 1) | NMR |
|---|---|---|---|
| 150 | 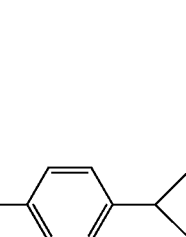 | 444 | 1H-NMR (400 MHz, MeOD) δ ppm 7.99 (d, 1H, J = 1.6 Hz), 7.85 (d, 1H, J = 5.6 Hz), 7.78 (d, 2H, J = 8.4 Hz), 7.41 (d, 2H, J = 8.4 Hz), 6.95 (d, 1H, J = 1.6 Hz), 6.00 (d, 1H, J = 5.6 Hz), 4.40-4.32 (m, 2H), 4.10-4.02 (m, 5H), 3.88-3.82 (m, 2H), 3.65-3.60 (m, 2H), 3.58-3.52 (m, 2H), 3.38-3.32 (m, 1H), 2.07-2.00 (m, 1H), 1.24 (d, 6H, J = 6.4 Hz), 0.96-0.92 (m, 2H), 0.92-0.84 (m, 2H). |
| 151 | 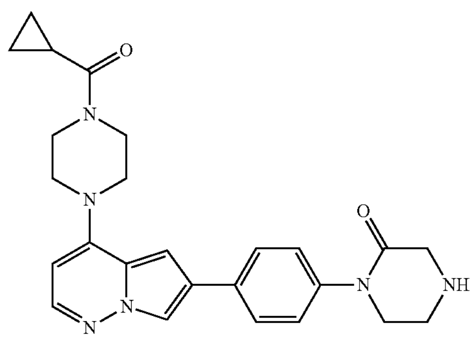 [SMILES: O=C(C1CC1)N1CCN(c2ccnn3cc(-c4ccc(N5CCNCC5=O)cc4)cc23)CC1] | 445 | 1H-NMR (400 MHz, 6d-DMSO) δ ppm 8.16 (d, 1H, J = 1.6 Hz), 7.89 (d, 1H, J = 5.6 Hz), 7.81 (d, 2H, J = 8.4 Hz), 7.31 (d, 2H, J = 8.4 Hz), 7.05 (d, 1H, J = 1.6 Hz), 5.98 (d, 1H, J = 5.6 Hz), 3.92 (br. s, 2H), 3.70-3.65 (m, 4H), 3.55-3.50 (m, 4H), 3.34 (s, 2H), 3.01 (t, 2H, J = 5.2 Hz), 2.00 (quintet, 1H, J = 5.2 Hz), 0.79-0.75 (m, 4H). |
| 152 | 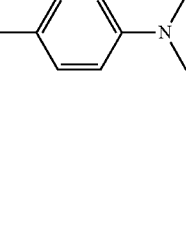 | 445 | 1H-NMR (400 MHz, DMSO-d6) δ ppm 8.06 (s, 1H), 7.85 (d, 1H, J = 5.2 Hz), 7.62 (d, 2H, J = 8.4 Hz), 6.93 (d, 2H, J = 8.4 Hz), 6.86 (s, 1H), 5.92 (d, 1H, J = 5.2 Hz), 4.65 (br. s., 1H), 4.25-4.10 (m, 1H), 4.00-3.80 (m, 2H), 3.40-3.20 (m, 4H), 3.10-3.00 (m, 4H), 2.90-2.70 (m, 4H), 2.05-1.90 (m, 1H), 1.45-1.20 (m, 3H), 0.75 (br. s., 4H). |
| 153 | 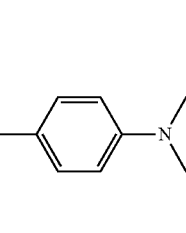 | 445 | 1H-NMR (400 MHz, CDCl3) δ ppm 7.87 (d, 1H, J = 1.6 Hz), 7.83 (d, 1H, J = 5.6 Hz), 7.57 (d, 2H, J = 8.8 Hz), 6.98 (d, 2H, J = 8.8 Hz), 6.66 (d, 1H, J = 0.8 Hz), 5.83 (d, 1H, J = 5.2 Hz), 3.95-3.89 (m, 4H), 3.56-3.47 (m, 4H), 3.29-3.27 (m, 4H), 2.66-2.23 (m, 4H), 2.40 (s, 3H), 1.82-1.75 (m, 1H), 1.06-1.04 (m, 2H), 0.84-0.82 (m, 2H). |

TABLE 1-continued

| # | Structure | LCMS (M + 1) | NMR |
|---|---|---|---|
| 154 | 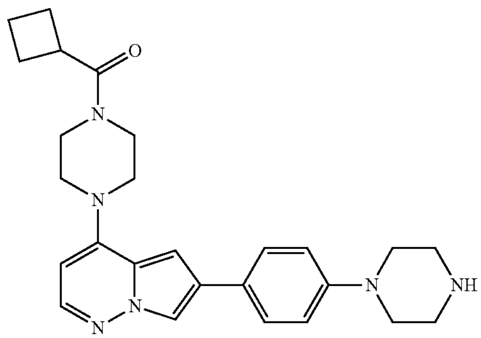 [SMILES: O=C(C1CCC1)N1CCN(c2ccnn3cc(-c4ccc(N5CCNCC5)cc4)cc23)CC1] | 445 | 1H-NMR (400 MHz, DMSO-d6) δ ppm 8.08 (s, 1H), 7.87 (d, 1H, J = 5.6 Hz), 7.67 (d, 2H, J = 8.4 Hz), 6.97 (d, 2H, J = 8.8 Hz), 6.94 (s, 1H), 5.96 (d, 1H, J = 5.2 Hz), 3.68-3.03 (m, 17H), 2.23-2.11 (m, 4H), 1.93-1.90 (m, 1H), 1.78-1.77 (m, 1H). |
| 155 | 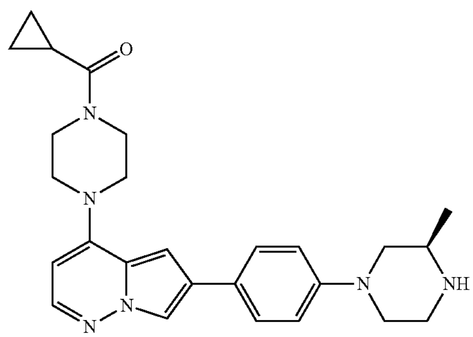 [SMILES: C[C@@H]1CN(c2ccc(-c3cc4c(N5CCN(C(=O)C6CC6)CC5)ccnn4c3)cc2)CCN1] | 445 | 1H-NMR (400 MHz, 6d-DMSO) δ ppm 8.06 (d, 1H, J = 1.6 Hz), 7.87 (d, 1H, J = 5.6 Hz), 7.65 (d, 2H, J = 8.4 Hz), 6.95 (d, 2H, J = 8.4 Hz), 6.94 (s, 1H), 5.96 (d, 1H, J = 5.6 Hz), 3.94-3.92 (m, 2H), 3.71-3.69 (m, 2H), 3.55-3.53 (m, 4H), 3.47-3.45 (m, 3H), 3.00-2.97 (m, 1H), 2.84-2.81 (m, 2H), 2.57-2.56 (m, 1H), 2.25-2.20 (m, 1H), 2.02-2.01 (m, 1H), 1.05 (d, 3H, J = 6.4 Hz), 0.78-0.75 (m, 4H). |
| 156 | 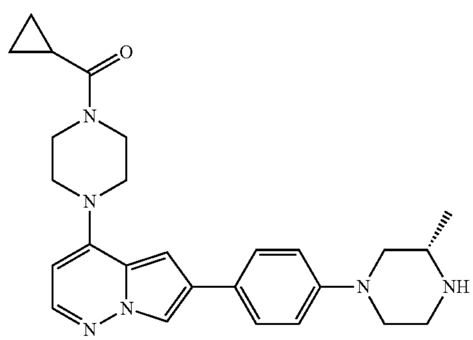 [SMILES: C[C@H]1CN(c2ccc(-c3cc4c(N5CCN(C(=O)C6CC6)CC5)ccnn4c3)cc2)CCN1] | 445 | 1H-NMR (400 MHz, 6d-DMSO) δ ppm 8.05 (d, 1H, J = 1.6 Hz), 7.86 (d, 1H, J = 5.6 Hz), 7.64 (d, 2H, J = 8.8 Hz), 6.94 (d, 2H, J = 8.8 Hz), 6.93 (s, 1H), 5.94 (d, 1H, J = 5.6 Hz), 3.92-3.91 (m, 2H), 3.71-3.70 (m, 2H), 3.58-3.45 (m, 7H), 3.01-2.98 (m, 1H), 2.86-2.85 (m, 2H), 2.58-2.57 (m, 1H), 2.27-2.21 (m, 1H), 2.01-1.99 (m, 1H), 1.05 (d, 3H, J = 6.4 Hz), 0.78-0.74 (m, 4H). |
| 157 | 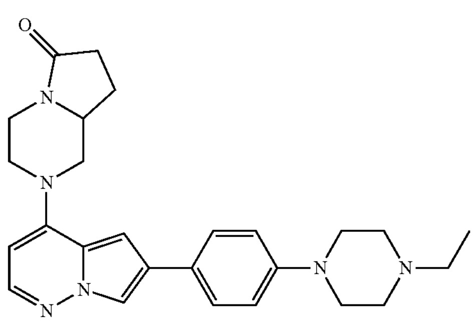 [SMILES: CCN1CCN(c2ccc(-c3cc4c(N5CCN6C(=O)CCC6C5)ccnn4c3)cc2)CC1] | 445 | 1H-NMR (400 MHz, 6d-DMSO) δ ppm 8.07 (d, 1H, J = 1.6 Hz), 7.88 (d, 1H, J = 5.6 Hz), 7.65 (d, 2H, J = 8.8 Hz), 6.95 (d, 2H, J = 8.8 Hz), 6.91 (d, 1H, J = 1.6 Hz), 6.03 (d, 1H, J = 5.6 Hz), 4.14-4.05 (m, 1H), 4.03-3.96 (m, 1H), 3.95-3.88 (m, 1H), 3.86-3.74 (m, 1H), 3.50-3.38 (m, 4H), 3.20-3.10 (m, 4H), 3.09-3.00 (m, 1H), 2.85-2.75 (m, 1H), 2.70-2.60 (m, 1H), 2.36 (q, 2H, J = 7.2 Hz), 2.33-2.25 (m, 2H), 2.20-2.10 (m, 1H), 1.70-1.55 (m, 1H), 1.03 (t, 3H, J = 7.2 Hz). |

TABLE 1-continued

| # | Structure | LCMS (M + 1) | NMR |
|---|---|---|---|
| 158 | 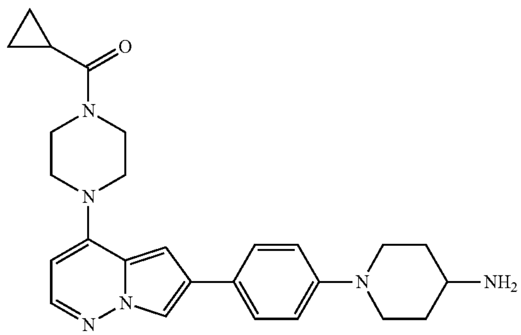 [SMILES: NC1CCN(c2ccc(-c3cc4c(N5CCN(C(=O)C6CC6)CC5)ccnn4c3)cc2)CC1] | 445 | 1H-NMR (400 MHz, 6d-DMSO) δ ppm 8.05 (d, 1H, J = 1.6 Hz), 7.86 (d, 1H, J = 5.6 Hz), 7.63 (d, 2H, J = 8.8 Hz), 6.95 (d, 2H, J = 8.8 Hz), 6.94-6.92 (m, 1H), 5.95 (d, 1H, J = 5.6 Hz), 3.92-3.91 (m, 2H), 3.67-3.64 (m, 4H), 3.54-3.40 (m, 4H), 3.40-3.35 (m, 1H), 2.75-2.69 (m, 4H), 2.02-2.01 (m, 1H), 1.80-1.77 (m, 2H), 1.35-1.22 (m, 2H), 0.77-0.73 (m, 4H). |
| 159 | 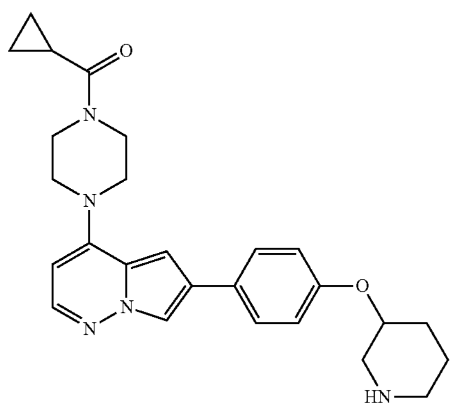 [SMILES: O=C(C1CC1)N1CCN(c2ccnn3cc(-c4ccc(OC5CCCNC5)cc4)cc23)CC1] | 446 | 1H-NMR (400 MHz, CDCl3) δ ppm 7.87 (d, 1H, J = 2.0 Hz), 7.84 (d, 1H, J = 5.2 Hz), 7.56 (d, 2H, J = 8.8 Hz), 6.97 (d, 2H, J = 8.8 Hz), 6.66 (d, 1H, J = 2.0 Hz), 5.84 (d, 1H, J = 5.2 Hz), 4.46 (heptet, 1H, J = 3.6 Hz), 3.99-3.90 (m, 2H), 3.90-3.81 (m, 2H), 3.61-3.50 (m, 2H), 3.50-3.39 (m, 2H), 3.23-3.18 (m, 1H), 2.92-2.85 (m, 2H), 2.82-.75 (m, 1H), 2.07-2.00 (m, 1H), 1.88-1.75 (m, 3H), 1.58-1.50 (m, 1H), 1.07-1.02 (m, 2H), 0.86-0.80 (m, 2H). |
| 160 | 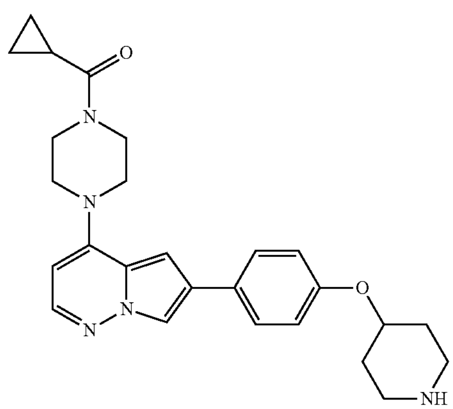 [SMILES: O=C(C1CC1)N1CCN(c2ccnn3cc(-c4ccc(OC5CCNCC5)cc4)cc23)CC1] | 446 | 1H-NMR (400 MHz, CDCl3) δ ppm 7.88 (d, 1H, J = 1.6 Hz), 7.84 (d, 1H, J = 5.2 Hz), 7.59 (d, 2H, J = 8.8 Hz), 6.96 (d, 2H, J = 8.8 Hz), 6.65 (d, 1H, J = 1.6 Hz), 5.85 (d, 1H, J = 5.2 Hz), 4.67-4.61 (m, 1H), 3.99-3.90 (m, 2H), 3.90-3.75 (m, 2H), 3.60-3.50 (m, 2H), 3.50-3.40 (m, 2H), 3.41-3.33 (m, 2H), 3.19-3.15 (m, 2H), 2.25-2.08 (m, 4H), 1.79-1.75 (m, 1H), 1.06-1.02 (m, 2H), 0.85-0.80 (m, 2H). |
| 161 | 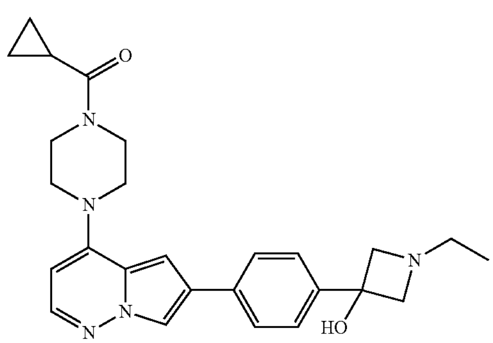 [SMILES: CCN1CC(O)(c2ccc(-c3cc4c(N5CCN(C(=O)C6CC6)CC5)ccnn4c3)cc2)C1] | 446 | 1H-NMR (400 MHz, 6d-DMSO) δ ppm 8.20 (d, 1H, J = 2.0 Hz), 8.17 (s, 1H), 7.91 (d, 1H, J = 5.2 Hz), 7.82 (d, 2H, J = 8.4 Hz), 7.61 (d, 2H, J = 8.4 Hz), 7.06 (d, 1H, J = 1.2 Hz), 6.09 (br s, 1H), 5.99 (d, 1H, J = 5.2 Hz), 3.96-3.92 (m, 2H), 3.79-3.77 (m, 2H), 3.73-3.68 (m, 2H), 3.57-3.52 (m, 2H), 3.47-3.45 (m, 4H), 2.72 (q, 2H, J = 6.8 Hz), 2.06-1.98 (m, 1H), 0.98 (t, 3H, J = 6.8 Hz), 0.79-0.74 (m, 4H). |

TABLE 1-continued

| # | Structure | LCMS (M + 1) | NMR |
|---|---|---|---|
| 162 | 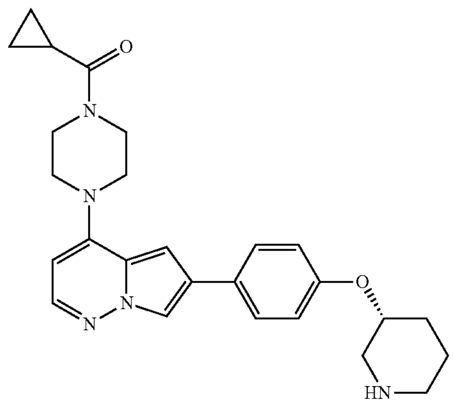 [SMILES: O=C(C1CC1)N1CCN(c2ccnn3cc(-c4ccc(O[C@@H]5CCCNC5)cc4)cc23)CC1] | 446 | 1H-NMR (400 MHz, CDCl3) δ ppm 7.87 (d, 1H, J = 2.0 Hz), 7.84 (d, 1H, J = 5.2 Hz), 7.56 (d, 2H, J = 8.8 Hz), 6.97 (d, 2H, J = 8.8 Hz), 6.66 (d, 1H, J = 2.0 Hz), 5.84 (d, 1H, J = 5.2 Hz), 4.46 (heptet, 1H, J = 3.6 Hz), 3.99-3.90 (m, 2H), 3.90-3.81 (m, 2H), 3.61-3.50 (m, 2H), 3.50-3.39 (m, 2H), 3.23-3.18 (m, 1H), 2.92-2.85 (m, 2H), 2.82-.75 (m, 1H), 2.07-2.00 (m, 1H), 1.88-1.75 (m, 3H), 1.58-1.50 (m, 1H), 1.07-1.02 (m, 2H), 0.86-0.80 (m, 2H). |
| 163 | 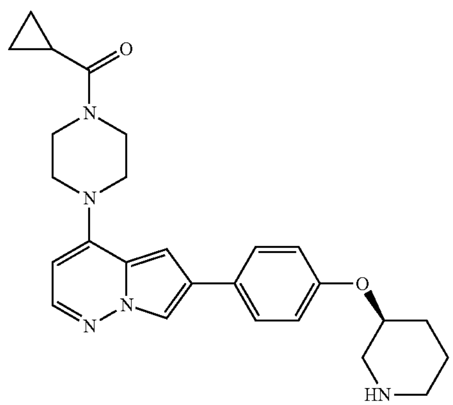 [SMILES: O=C(C1CC1)N1CCN(c2ccnn3cc(-c4ccc(O[C@H]5CCCNC5)cc4)cc23)CC1] | 446 | 1H-NMR (400 MHz, CDCl3) δ ppm 7.87 (d, 1H, J = 2.0 Hz), 7.84 (d, 1H, J = 5.2 Hz), 7.56 (d, 2H, J = 8.8 Hz), 6.97 (d, 2H, J = 8.8 Hz), 6.66 (d, 1H, J = 2.0 Hz), 5.84 (d, 1H, J = 5.2 Hz), 4.46 (heptet, 1H, J = 3.6 Hz), 3.99-3.90 (m, 2H), 3.90-3.81 (m, 2H), 3.61-3.50 (m, 2H), 3.50-3.39 (m, 2H), 3.23-3.18 (m, 1H), 2.92-2.85 (m, 2H), 2.82-.75 (m, 1H), 2.07-2.00 (m, 1H), 1.88-1.75 (m, 3H), 1.58-1.50 (m, 1H), 1.07-1.02 (m, 2H), 0.86-0.80 (m, 2H). |
| 164 | 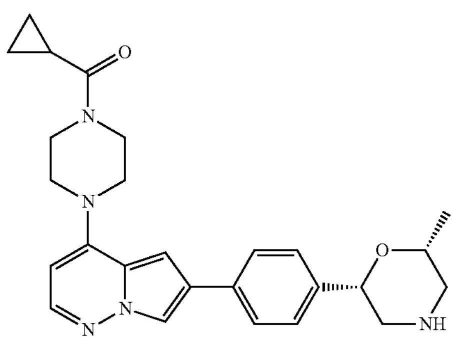 [SMILES: C[C@@H]1CNC[C@H](c2ccc(-c3cc4c(N5CCN(C(=O)C6CC6)CC5)ccnn4c3)cc2)O1] | 446 | 1H NMR (400 MHz, 6d-DMSO) δ ppm 8.18 (d, 1H, J = 1.6 Hz), 7.90 (d, 1H, J = 5.6 Hz), 7.77 (d, 1H, J = 8.0 Hz), 7.33 (d, 1H, J = 8.0 Hz), 7.05 (s, 1H), 5.98 (d, 1H, J = 5.6 Hz), 4.44 (d, 1H, J = 9.2 Hz), 3.95-3.90 (m, 2H), 3.73 = 3.69 (m, 2H), 3.69-3.68 (m, 1H), 3.57-3.54 (m, 2H), 3.49-3.46 (m, 2H), 2.90 (d, 1H, J = 14 Hz), 2.80 (d, 1H, J = 14 Hz), 2.50-2.45 (m, 1H), 2.35 (t, 1H, J = 14 Hz), 2.05-2.00 (m, 1H), 1.11 (d, 3H, J = 6.0 Hz), 0.78-0.74 (m, 4H). |
| 165 | 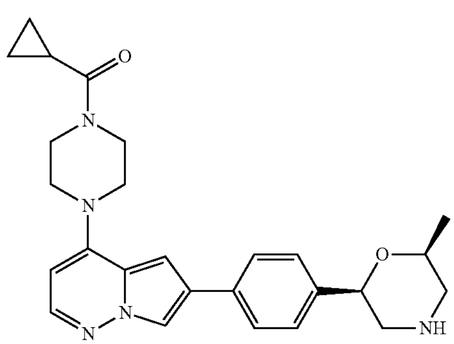 [SMILES: C[C@H]1CNC[C@@H](c2ccc(-c3cc4c(N5CCN(C(=O)C6CC6)CC5)ccnn4c3)cc2)O1] | 446 | 1H NMR (400 MHz, 6d-DMSO) δ ppm 8.18 (d, 1H, J = 1.6 Hz), 7.90 (d, 1H, J = 5.6 Hz), 7.77 (d, 1H, J = 8.0 Hz), 7.33 (d, 1H, J = 8.0 Hz), 7.05 (s, 1H), 5.98 (d, 1H, J = 5.6 Hz), 4.44 (d, 1H, J = 9.2 Hz), 3.95-3.90 (m, 2H), 3.73 = 3.69 (m, 2H), 3.69-3.68 (m, 1H), 3.57-3.54 (m, 2H), 3.49-3.46 (m, 2H), 2.90 (d, 1H, J = 14 Hz), 2.80 (d, 1H, J = 14 Hz), 2.50-2.45 (m, 1H), 2.35 (t, 1H, J = 14 Hz), 2.05-2.00 (m, 1H), 1.11 (d, 3H, J = 6.0 Hz), 0.78-0.74 (m, 4H). |

TABLE 1-continued

| # | Structure | LCMS (M + 1) | NMR |
|---|---|---|---|
| 166 | 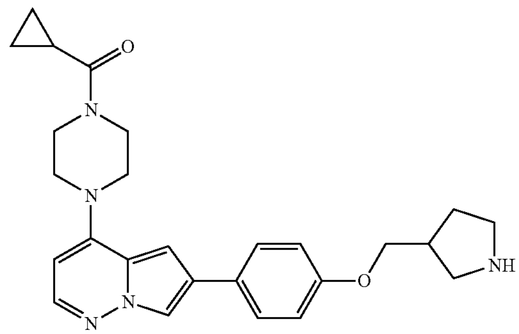 [SMILES: O=C(C1CC1)N1CCN(c2ccnn3cc(-c4ccc(OCC5CCNC5)cc4)cc23)CC1] | 446 | 1H-NMR (400 MHz, 6d-DMSO) δ ppm 8.34 (s, 1H), 8.12 (d, 1H, J = 1.6 Hz), 7.89 (d, 1H, J = 5.2 Hz), 7.75 (d, 2H, J = 8.4 Hz), 6.99 (s, 1H), 6.97 (d, 2H, J = 8.4 Hz), 5.97 (d, 1H, J = 5.2 Hz), 4.04-4.01 (m, 2H), 3.99-3.92 (m, 2H), 3.71-3.70 (m, 2H), 3.55-3.51 (m, 2H), 3.49-3.45 (m, 2H), 3.33-3.31 (m, 1H), 3.29-3.23 (m, 1H), 3.15-3.14 (m, 1H), 3.00-2.99 (m, 1H), 2.73-2.71 (m, 1H), 2.04-2.02 (m, 1H), 2.02-2.00 (m, 1H), 1.80-1.75 (m, 1H), 0.79-0.75 (m, 4H). |
| 167 | 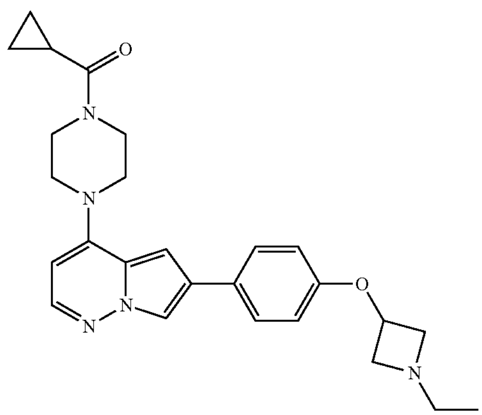 [SMILES: CCN1CC(Oc2ccc(-c3cc4c(N5CCN(C(=O)C6CC6)CC5)ccnn4c3)cc2)C1] | 446 | 1H-NMR (400 MHz, 6d-DMSO) δ ppm 8.16 (s, 1H), 8.12 (d, 1H, J = 1.6 Hz), 7.89 (d, 1H, J = 5.6 Hz), 7.74 (d, 2H, J = 8.8 Hz), 6.98 (d, 1H, J = 1.6 Hz), 6.87 (d, 2H, J = 8.8 Hz), 5.97 (d, 1H, J = 5.6 Hz), 4.89-3.86 (m, 1H), 3.94-3.92 (m, 4H), 3.56-3.51 (m, 4H), 3.47-3.45 (m, 2H), 3.22-3.20 (m, 2H), 2.64 (q, 2H, J = 7.2 Hz), 2.04-2.00 (m, 1H), 0.95 (t, 3H, J = 7.2 Hz), 0.79-0.73 (m, 4H). |
| 168 | 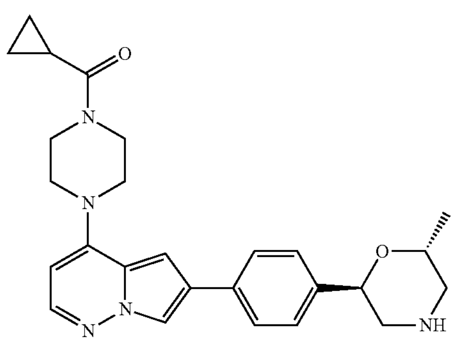 [SMILES: C[C@@H]1CNC[C@@H](c2ccc(-c3cc4c(N5CCN(C(=O)C6CC6)CC5)ccnn4c3)cc2)O1] | 446 | 1H NMR (400 MHz, 6d-DMSO) δ ppm 8.18 (s, 1H), 7.90 (d, 1H, J = 5.6 Hz), 7.77 (d, 2H, J = 8.4 Hz), 7.38 (d, 1H, J = 8.4 Hz), 7.05 (s, 1H), 5.98 (d, 1H, J = 5.6 Hz), 4.75-4.70 (m, 1H), 3.95-3.90 (m, 2H), 3.73-3.68 (m, 2H), 3.57-3.52 (m, 2H), 3.50-3.45 (m, 2H), 2.95-2.90 (m, 1H), 2.85-2.80 (m, 1H), 2.79-2.70 (m, 1H), 2.50-2.34 (m, 1H), 2.03-1.99 (m, 1H), 1.27 (d, 3H, J = 6.0 Hz), 0.78-0.74 (m, 4H). |
| 169 | 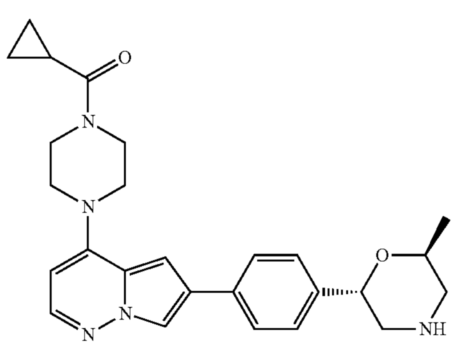 [SMILES: C[C@H]1CNC[C@H](c2ccc(-c3cc4c(N5CCN(C(=O)C6CC6)CC5)ccnn4c3)cc2)O1] | 446 | 1H NMR (400 MHz, 6d-DMSO) δ ppm 8.22 (d, 1H, J = 1.6 Hz), 7.92 (d, 1H, J = 5.6 Hz), 7.83 (d, 2H, J = 8.4 Hz), 7.40 (d, 2H, J = 8.4 Hz), 7.07 (d, 1H, J = 1.6 Hz), 5.98 (d, 1H, J = 5.6 Hz), 4.75-4.70 (m, 1H), 3.95-3.90 (m, 2H), 3.73-3.69 (m, 2H), 3.58-3.54 (m, 2H), 3.50-3.45 (m, 2H), 3.23-3.19 (m, 1H), 3.08-3.05 (m, 1H), 3.04-3.01 (m, 1H), 2.84-2.80 (m, 1H), 2.10-2.01 (m, 1H), 2.01-1.98 (m, 1H), 1.33 (d, 3H, J = 7.2 Hz), 0.78-0.74 (m, 4H). |

TABLE 1-continued

| # | Structure | LCMS (M + 1) | NMR |
|---|---|---|---|
| 170 | 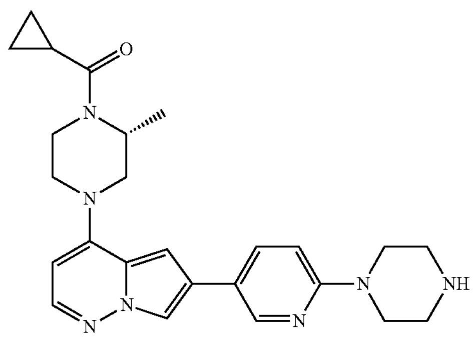 [SMILES: C[C@@H]1CN(c2ccnn3cc(-c4ccc(N5CCNCC5)nc4)cc23)CCN1C(=O)C1CC1] | 446 | 1H-NMR (400 MHz, DMSO-d6) δ ppm 8.63 (d, 1H, J = 2.0 Hz), 8.16 (d, 1H, J = 2.0 Hz), 8.01 (dd, 1H, J = 8.8, 2.4 Hz), 7.87 (d, 1H, J = 5.2 Hz), 7.00-6.90 (m, 2H), 5.95 (d, 1H, J = 5.2 Hz), 4.63 (br. s., 1H), 4.25-4.10 (m, 1H), 4.00-3.80 (m, 2H), 3.65 (br. s., 4H), 3.27 (br. s., 4H), 3.08 (br. s., 4H), 2.05-1.90 (m, 1H), 1.45-1.20 (m, 3H), 0.80-0.65 (m, 4H). |
| 171 | 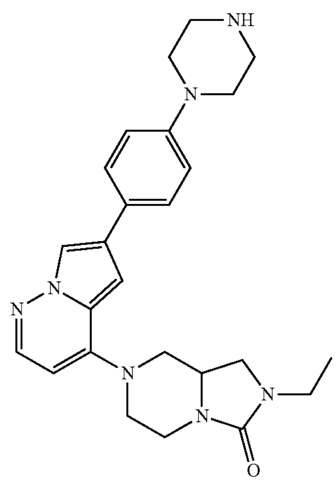 [SMILES: CCN1CC2CN(c3ccnn4cc(-c5ccc(N6CCNCC6)cc5)cc34)CCN2C1=O] | 447 | |
| 172 | 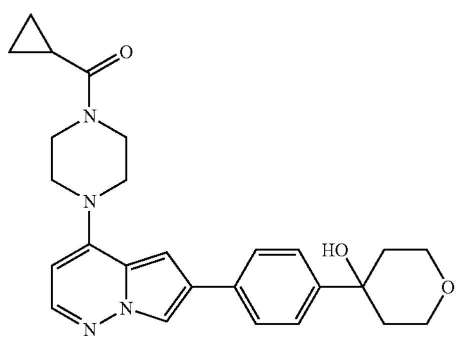 [SMILES: O=C(C1CC1)N1CCN(c2ccnn3cc(-c4ccc(C5(O)CCOCC5)cc4)cc23)CC1] | 447 | 1H-NMR (400 MHz, 6d-DMSO) δ ppm 8.17 (d, 1H, J = 1.6 Hz), 7.90 (d, 1H, J = 5.2 Hz), 7.77 (d, 2H, J = 8.0 Hz), 7.50 (d, 2H, J = 8.4 Hz), 7.05 (d, 1H, J = 1.2 Hz), 5.98 (d, 1H, J = 5.6 Hz), 5.02 (s, 1H), 3.92-3.93 (m, 2H), 3.80-3.70 (m, 6H), 3.55-3.48 (m, 4H), 2.03-1.94 (m, 3H), 1.57-1.54 (m, 2H), 0.79-0.75 (m, 4H). |
| 173 | 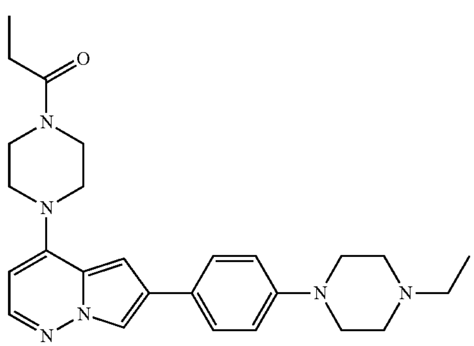 [SMILES: CCC(=O)N1CCN(c2ccnn3cc(-c4ccc(N5CCN(CC)CC5)cc4)cc23)CC1] | 447 | 1H-NMR (400 MHz, DMSO-d6) δ ppm 8.06 (br. s., 1H), 7.87 (br. s., 1H), 7.64-7.53 (m, 3H), 6.94 (br. s., 2H), 5.94 (br. s., 1H), 3.67 (br. s., 4H), 3.47-3.33 (m, 4H), 3.16 (br. s., 4H), 2.50-2.48 (m, 4H), 2.31 (br. s., 4H), 1.03 (d, 6H, J = 4.0 Hz). |

TABLE 1-continued

| # | Structure | LCMS (M + 1) | NMR |
|---|---|---|---|
| 174 | 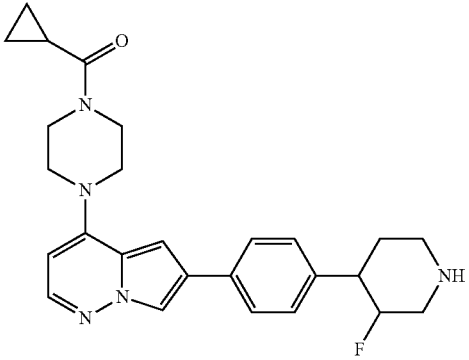 [SMILES: O=C(C1CC1)N1CCN(c2ccnn3cc(-c4ccc(C5CCNCC5F)cc4)cc23)CC1] | 448 | 1H-NMR (400 MHz, DMSO-d6) δ ppm 8.16 (d, 1H, J = 1.2 Hz), 7.89 (d, 1H, J = 5.2 Hz), 7.76 (d, 2H, J = 8.0 Hz), 7.30 (d, 2H, J = 8.0 Hz), 7.03 (d, 1H, J = 1.2 Hz), 5.96 (d, 1H, J = 5.2 Hz), 4.68-4.50 (m, 1H), 3.91 (br. s., 2H), 3.70 (br. s., 2H), 3.54 (br. s., 2H), 3.43 (br. s., 2H), 3.29-3.25 (m, 1H), 2.90-2.87 (m, 1H), 2.77-2.64 (m, 1H), 2.53-2.51 (m, 1H), 2.48-2.45 (m, 1H), 2.05-1.99 (m, 1H), 1.77-1.74 (m, 1H), 1.67-1.57 (m, 1H), 0.79-0.71 (m, 4H). |
| 175 | 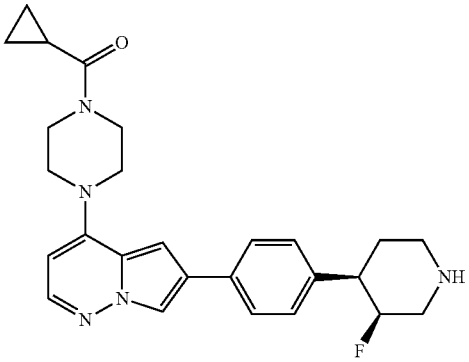 [SMILES: O=C(C1CC1)N1CCN(c2ccnn3cc(-c4ccc([C@H]5CCNC[C@H]5F)cc4)cc23)CC1] | 448 | 1H-NMR (400 MHz, 6d-DMSO) δ ppm 7.94 (d, 1H, J = 2.0 Hz), 7.86 (d, 1H, J = 5.2 Hz), 7.64 (d, 2H, J = 8.0 Hz), 7.33 (d, 2H, J = 8.0 Hz), 6.72 (d, 1H, J = 2.0 Hz), 5.85 (d, 1H, J = 5.6 Hz), 4.71-4.52 (m, 1H), 3.94-3.90 (m, 4H), 3.57-3.52 (m, 4H), 3.13-3.10 (m, 1H), 2.86-2.67 (m, 3H), 1.98-1.95 (m, 1H), 1.27 (s, 1H), 1.08-1.02 (m, 2H), 0.86-0.82 (m, 2H). |
| 176 | 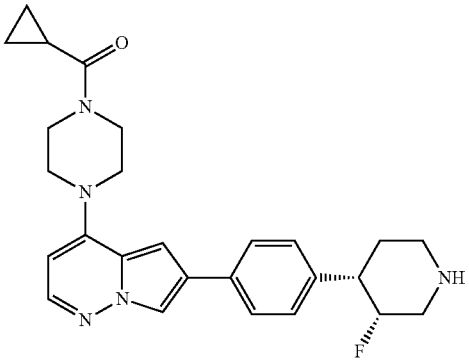 [SMILES: O=C(C1CC1)N1CCN(c2ccnn3cc(-c4ccc([C@@H]5CCNC[C@@H]5F)cc4)cc23)CC1] | 448 | 1H-NMR (400 MHz, 6d-DMSO) δ ppm 7.94 (d, 1H, J = 2.0 Hz), 7.86 (d, 1H, J = 5.2 Hz), 7.64 (d, 2H, J = 8.0 Hz), 7.33 (d, 2H, J = 8.0 Hz), 6.72 (d, 1H, J = 2.0 Hz), 5.85 (d, 1H, J = 5.2 Hz), 4.73-4.52 (m, 1H), 3.94-3.90 (m, 4H), 3.57-3.52 (m, 4H), 3.13-3.10 (m, 1H), 2.86-2.67 (m, 3H), 2.05-1.96 (m, 2H), 1.86-1.72 (m, 2H), 1.08-1.02 (m, 2H), 0.86-0.82 (m, 2H). |
| 177 | 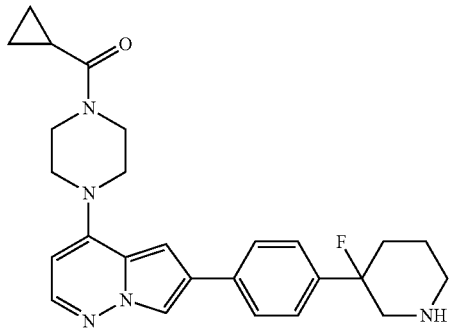 [SMILES: O=C(C1CC1)N1CCN(c2ccnn3cc(-c4ccc(C5(F)CCCNC5)cc4)cc23)CC1] | 448 | 1H-NMR (400 MHz, 6d-DMSO) δ ppm 8.20 (d, 1H, J = 2.0 Hz), 7.91 (d, 1H, J = 5.6 Hz), 7.82 (d, 2H, J = 8.4 Hz), 7.43 (d, 2H, J = 8.4 Hz), 7.07 (d, 1H, J = 2.0 Hz), 5.98 (d, 1H, J = 5.6 Hz), 3.95-3.90 (m, 2H), 3.73-3.68 (m, 2H), 3.58-3.50 (m, 2H), 3.49-3.40 (m, 2H), 2.99-2.78 (m, 3H), 2.65-2.60 (m, 1H), 2.22-2.15 (m, 1H), 2.10-1.95 (m, 2H), 1.82-1.67 (m, 1H), 1.60-1.49 (m, 1H), 0.80-0.73 (m, 4H). |

TABLE 1-continued

| # | Structure | LCMS (M + 1) | NMR |
|---|---|---|---|
| 178 | 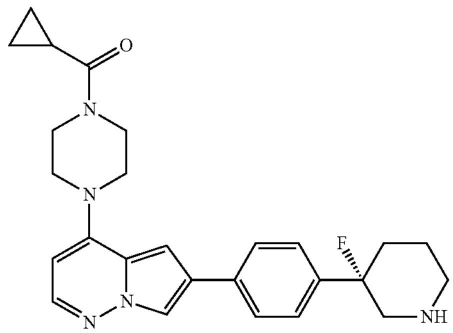 [SMILES: O=C(C1CC1)N1CCN(c2ccnn3cc(-c4ccc([C@@]5(F)CCCNC5)cc4)cc23)CC1] | 448 | 1H-NMR (400 MHz, 6d-DMSO) δ ppm 8.21 (d, 1H, J = 1.6 Hz), 7.91 (d, 1H, J = 5.6 Hz), 7.82 (d, 2H, J = 8.4 Hz), 7.43 (d, 2H, J = 8.4 Hz), 7.07 (d, 1H, J = 1.6 Hz), 5.98 (d, 1H, J = 5.6 Hz), 3.95-3.90 (m, 2H), 3.73-3.68 (m, 2H), 3.57-3.53 (m, 2H), 3.50-3.42 (m, 2H), 2.99-2.95 (m, 2H), 2.94-2.90 (m, 1H), 2.55-2.51 (m, 1H), 2.22-2.10 (m, 1H), 2.05-1.95 (m, 2H), 1.82-1.65 (m, 1H), 1.60-1.45 (m, 1H), 0.80-0.73 (m, 4H). |
| 179 | 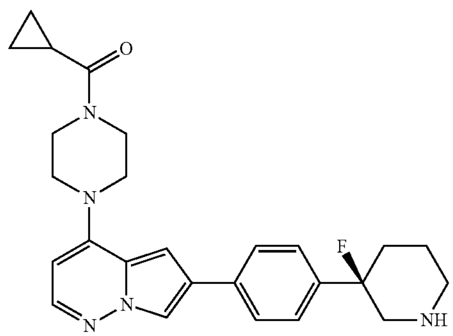 [SMILES: O=C(C1CC1)N1CCN(c2ccnn3cc(-c4ccc([C@]5(F)CCCNC5)cc4)cc23)CC1] | 448 | 1H-NMR (400 MHz, 6d-DMSO) δ ppm 8.21 (d, 1H, J = 1.6 Hz), 7.91 (d, 1H, J = 5.6 Hz), 7.82 (d, 2H, J = 8.4 Hz), 7.43 (d, 2H, J = 8.4 Hz), 7.07 (d, 1H, J = 1.6 Hz), 5.98 (d, 1H, J = 5.6 Hz), 3.95-3.90 (m, 2H), 3.73-3.68 (m, 2H), 3.57-3.53 (m, 2H), 3.50-3.42 (m, 2H), 2.99-2.95 (m, 2H), 2.94-2.90 (m, 1H), 2.55-2.51 (m, 1H), 2.22-2.10 (m, 1H), 2.05-1.95 (m, 2H), 1.82-1.65 (m, 1H), 1.60-1.45 (m, 1H), 0.80-0.73 (m, 4H). |
| 180 | 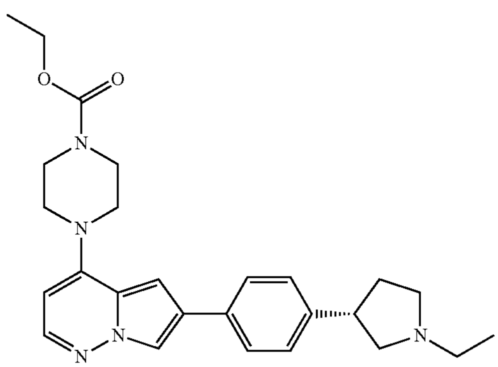 [SMILES: CCOC(=O)N1CCN(c2ccnn3cc(-c4ccc([C@@H]5CCN(CC)C5)cc4)cc23)CC1] | 464 | 1H-NMR (400 MHz, CDCl3) δ ppm 8.65 (s, 1H), 7.92 (d, 1H, J = 1.6 Hz), 7.85 (d, 1H, J = 5.6 Hz), 7.62 (d, 2H, J = 8.4 Hz), 7.31 (d, 2H, J = 8.4 Hz), 6.68 (d, 1H, J = 1.2 Hz), 5.85 (d, 1H, J = 4.8 Hz), 4.20 (q, 2H, J = 7.2 Hz), 3.81-3.70 (m, 4H), 3.67-3.55 (m, 2H), 3.49-3.40 (m, 4H), 3.39-3.35 (m, 1H), 3.26-3.14 (m, 1H), 3.10-3.00 (m, 2H), 2.99-2.95 (m, 1H), 2.51-2.42 (m, 1H), 2.21-2.08 (m, 1H), 1.34 (t, 3H, J = 7.2 Hz), 131 (t, 3H, J = 7.2 Hz). |
| 181 | 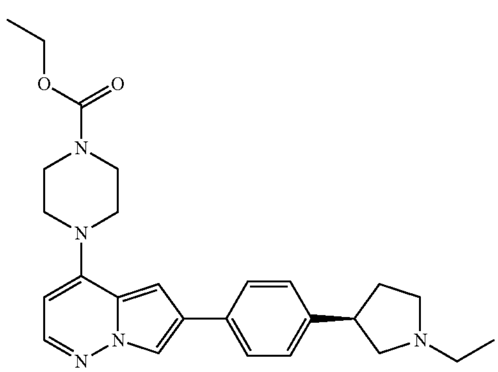 [SMILES: CCOC(=O)N1CCN(c2ccnn3cc(-c4ccc([C@H]5CCN(CC)C5)cc4)cc23)CC1] | 448 | 1H-NMR (400 MHz, 6d-DMSO) δ ppm 8.14 (s, 1H), 7.89 (d, 1H, J = 5.6 Hz), 7.71 (d, 2H, J = 8.0 Hz), 7.28 (d, 2H, J = 8.0 Hz), 6.98 (s, 1H), 5.97 (d, 1H, J = 5.6 Hz), 4.08 (q, 2H, J = 7.2 Hz), 3.70-3.55 (m, 4H), 3.50-3.40 (m, 4H), 3.30-3.20 (m, 1H), 2.91 (t, 1H, J = 8.4 Hz), 2.75-2.68 (m, 1H), 2.68-2.57 (m, 1H), 2.50-2.47 (m, 1H), 2.44 (q, 2H, J = 7.2 Hz), 2.25-2.10 (m, 1H), 1.80-1.65 (m, 1H), 1.21 (t, 3H, J = 7.2 Hz), 1.04 (t, 3H, J = 7.2 Hz). |

TABLE 1-continued

| # | Structure | LCMS (M + 1) | NMR |
|---|---|---|---|
| 182 | 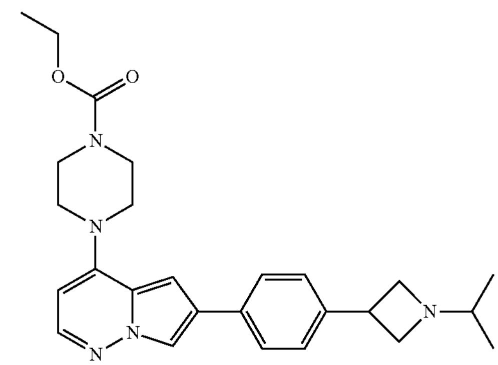 [SMILES: CCOC(=O)N1CCN(c2ccnn3cc(-c4ccc(C5CN(C(C)C)C5)cc4)cc23)CC1] | 448 | 1H-NMR (400 MHz, MeOD) δ ppm 7.97 (d, 1H, J = 1.6 Hz), 7.85 (d, 1H, J = 5.6 Hz), 7.72 (d, 2H, J = 8.0 Hz), 7.36 (d, 2H, J = 8.0 Hz), 6.90 (d, 1H, J = 1.6 Hz), 6.00 (d, 1H, J = 5.2 Hz), 4.18 (q, 2H, J = 7.2 Hz), 4.06-4.00 (m, 2H), 3.90-3.80 (m, 1H), 3.77-3.71 (m, 4H), 3.56-3.52 (m, 2H), 3.52-3.47 (m, 4H), 2.90-2.80 (m, 1H), 1.30 (t, 3H, J = 7.2 Hz), 1.10 (d, 6H, J = 6.0 Hz). |
| 183 | 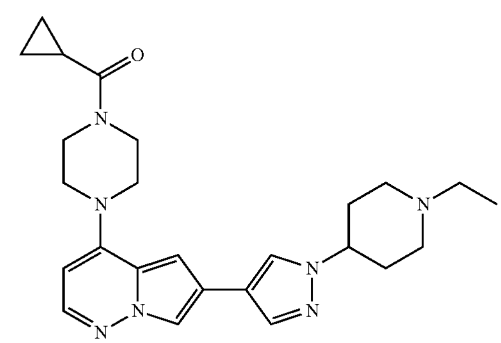 [SMILES: CCN1CCC(n2cc(-c3cc4c(N5CCN(C(=O)C6CC6)CC5)ccnn4c3)cn2)CC1] | 448 | 1H-NMR (400 MHz, 6d-DMSO) δ ppm 8.05 (s, 1H), 7.84-7.81 (m, 3H), 6.80 (d, 1H, J = 1.2 Hz), 6.00 (d, 1H, J = 4.0 Hz), 4.23-4.21 (m, 1H), 4.04-4.03 (m, 2H), 3.86-3.85 (m, 2H), 3.62-3.53 (m, 4H), 3.17-3.14 (m, 2H), 2.54 (q, 2H, J = 7.2 Hz), 2.25-2.12 (m, 2H), 2.12-2.04 (m, 7H), 1.17 (t, 3H, J = 7.2 Hz), 0.95-0.92 (m, 2H), 0.89-0.86 (m, 2H). |
| 184 | 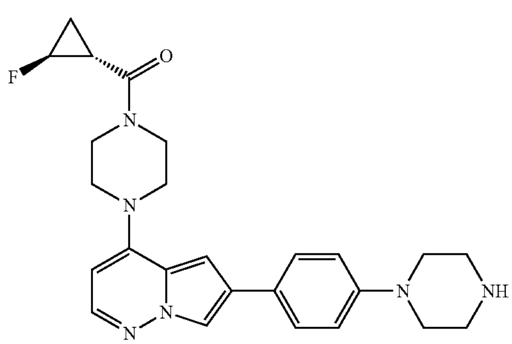 [SMILES: O=C([C@H]1C[C@@H]1F)N1CCN(c2ccnn3cc(-c4ccc(N5CCNCC5)cc4)cc23)CC1] | 449 | 1H-NMR (400 MHz, 6d-DMSO) δ ppm 8.07 (d, 1H, J = 1.6 Hz), 7.88 (d, 1H, J = 5.6 Hz), 7.65 (d, 2H, J = 8.8 Hz), 6.95 (s, 1H), 6.94 (d, 2H, J = 8.8 Hz), 5.97 (d, 1H, J = 5.6 Hz), 4.98-4.68 (m, 1H), 4.00-3.86 (m, 2H), 3.78-3.61 (m, 2H), 3.61-3.48 (m, 2H), 3.47-3.40 (m, 2H), 3.14-2.97 (m, 4H), 2.91-2.78 (m, 4H), 2.72-2.59 (m, 1H), 2.35-2.29 (m, 1H), 1.52-1.34 (m, 1H), 1.25-1.11 (m, 1H). |
| 185 | 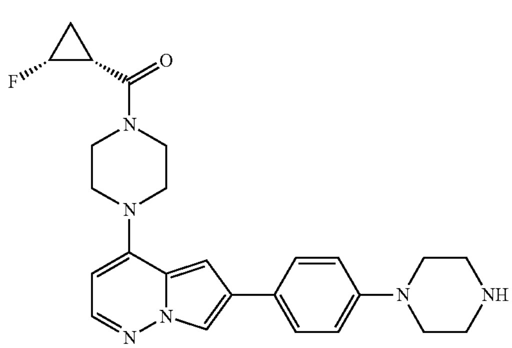 [SMILES: O=C([C@H]1C[C@H]1F)N1CCN(c2ccnn3cc(-c4ccc(N5CCNCC5)cc4)cc23)CC1] | 449 | 1H-NMR (400 MHz, 6d-DMSO) δ ppm 8.07 (d, 1H, J = 1.6 Hz), 7.88 (d, 1H, J = 5.6 Hz), 7.65 (d, 2H, J = 8.8 Hz), 6.96 (s, 1H), 6.94 (d, 2H, J = 8.8 Hz), 5.97 (d, 1H, J = 5.6 Hz), 5.08-4.83 (m, 1H), 4.00-3.82 (m, 2H), 3.80-3.66 (m, 2H), 3.63-3.54 (m, 2H), 3.53-3.45 (m, 2H), 3.16-3.04 (m, 4H), 2.93-2.80 (m, 4H), 2.27-2.16 (m, 1H), 1.62-1.48 (m, 1H), 1.12-0.98 (m, 1H). |

TABLE 1-continued

| # | Structure | LCMS (M + 1) | NMR |
|---|---|---|---|
| 186 | 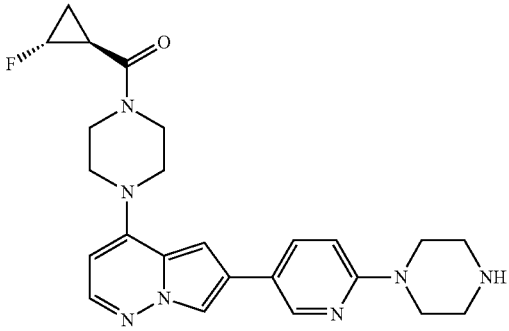 [SMILES: O=C([C@@H]1C[C@H]1F)N1CCN(c2ccnn3cc(-c4ccc(N5CCNCC5)nc4)cc23)CC1] | 450 | 1H-NMR (500 MHz, CD3OD) δ ppm 8.58 (d, 1H, J = 2.0 Hz), 8.01 (dd, 1H, J = 8.5 Hz, 2.5 Hz), 7.96 (d, 1H, J = 2.0 Hz), 7.87 (d, 1H, J = 5.5 Hz), 7.00 (d, 1H, J = 8.5 Hz), 6.91 (d, 1H, J = 2.0 Hz), 6.03 (d, 1H, J = 5.5 Hz), 4.07-4.01 (m, 2H), 3.89-3.79 (m, 6H), 3.70-3.60 (m, 3H), 3.57-3.51 (m, 2H), 3.39-3.35 (m, 4H), 2.61-2.52 (m, 1H), 1.55-1.45 (m, 1H), 1.35-1.28 (m, 1H). |
| 187 | 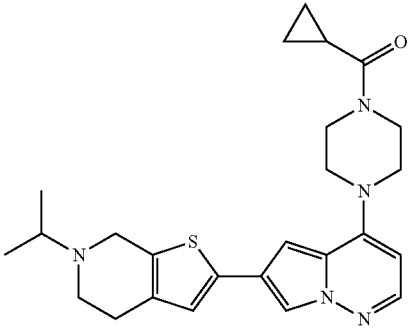 [SMILES: CC(C)N1CCc2cc(-c3cc4c(N5CCN(C(=O)C6CC6)CC5)ccnn4c3)sc2C1] | 450 | 1H-NMR (400 MHz, 6d-DMSO) δ ppm 7.92 (d, 1H, J = 1.6 Hz), 7.89 (d, 1H, J = 5.6 Hz), 7.11 (s, 1H), 6.80 (d, 1H, J = 1.6 Hz), 5.98 (d, 1H, J = 5.6 Hz), 3.90-3.89 (m, 2H), 3.69-3.68 (m, 2H), 3.51 (s, 2H), 3.45-3.40 (m, 2H), 3.35-3.30 (m, 2H), 2.90-2.85 (m, 1H), 2.73-2.71 (m, 2H), 2.62-2.61 (m, 2H), 2.02-2.00 (m, 1H), 1.05 (d, 6H, J = 6.4 Hz), 0.77-0.71 (m, 4H). |
| 188 | 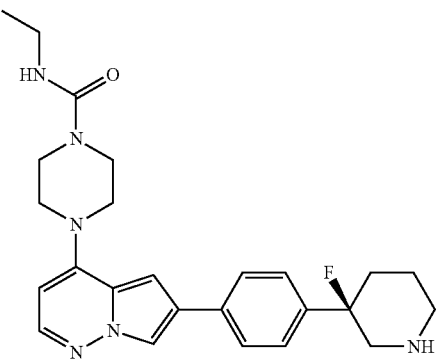 [SMILES: CCNC(=O)N1CCN(c2ccnn3cc(-c4ccc([C@]5(F)CCCNC5)cc4)cc23)CC1] | 451 | 1H-NMR (400 MHz, 6d-DMSO) δ ppm 8.20 (d, 1H, J = 1.2 Hz), 7.90 (d, 1H, J = 5.6 Hz), 7.83 (d, 2H, J = 8.4 Hz), 7.43 (d, 2H, J = 8.4 Hz), 7.05 (d, 1H, J = 1.6 Hz), 6.62 (t, 1H, J = 5.6 Hz), 5.99 (d, 1H, J = 5.6 Hz), 3.60-3.50 (m, 4H), 3.50-3.40 (m, 4H), 3.11-3.05 (m, 2H), 3.03-2.95 (m, 2H), 2.75-2.60 (m, 1H), 2.50-2.44 (m, 2H), 2.25-2.20 (m, 1H), 2.08-1.95 (m, 2H), 1.83-1.74 (m, 1H), 1.60-1.53 (m, 1H), 1.04 (t, 3H, J = 7.2 Hz). |
| 189 | 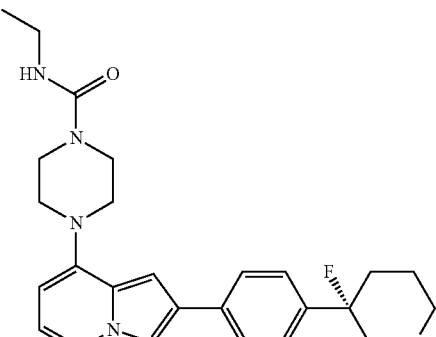 | 451 | 1H-NMR (400 MHz, 6d-DMSO) δ ppm 8.23 (d, 1H, J = 1.2 Hz), 7.91 (d, 1H, J = 5.6 Hz), 7.88 (d, 2H, J = 8.4 Hz), 7.47 (d, 2H, J = 8.4 Hz), 7.06 (d, 1H, J = 2.0 Hz), 6.62 (t, 1H, J = 5.6 Hz), 5.99 (d, 1H, J = 5.6 Hz), 3.60-3.52 (m, 4H), 3.48-3.42 (m, 4H), 3.42-3.38 (m, 1H), 3.23-3.18 (m, 1H), 3.12-3.05 (m, 2H), 2.98-2.90 (m, 2H), 2.30-2.20 (m, 1H), 2.15-2.00 (m, 2H), 1.98-1.85 (m, 1H), 1.83-1.75 (m, 1H), 1.04 (t, 3H, J = 7.6 Hz). |

TABLE 1-continued

| # | Structure | LCMS (M + 1) | NMR |
|---|---|---|---|
| 190 | 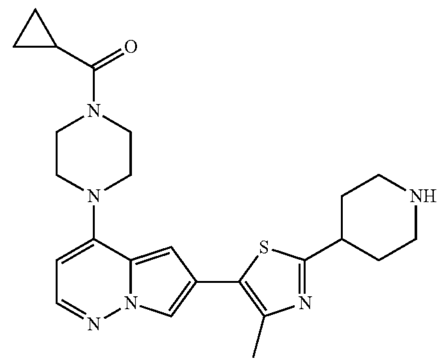 [SMILES: Cc1nc(C2CCNCC2)sc1-c1cc2c(N3CCN(C(=O)C4CC4)CC3)ccnn2c1] | 451 | 1H-NMR (400 MHz, 6d-DMSO) δ ppm 9.15-9.00 (m, 1H), 8.90-8.80 (m, 1H), 7.96 (d, 1H, J = 5.6 Hz), 7.95 (d, 1H, J = 1.2 Hz), 6.73 (d, 1H, J = 1.2 Hz), 6.03 (d, 1H, J = 5.6 Hz), 4.00-3.80 (m, 2H), 3.69-3.55 (m, 2H), 3.58-3.50 (m, 2H), 3.50-3.40 (m, 2H), 3.40-3.25 (m, 3H), 3.15-2.90 (m, 2H), 2.49 (s, 3H), 2.22-2.16 (m, 2H), 2.05-1.98 (m, 1H), 1.98-1.90 (m, 2H), 0.79-0.73 (m, 4H). |
| 191 | 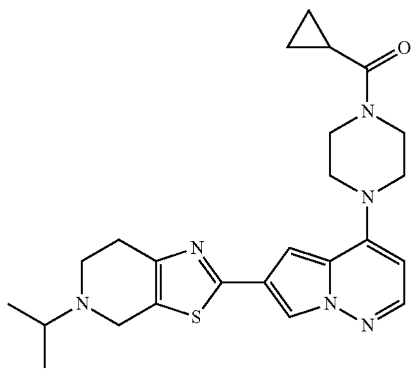 [SMILES: CC(C)N1CCc2nc(-c3cc4c(N5CCN(C(=O)C6CC6)CC5)ccnn4c3)sc2C1] | 451 | 1H-NMR (400 MHz, 6d-DMSO) δ ppm 8.16 (d, 1H, J = 1.6 Hz), 7.96 (d, 1H, J = 5.6 Hz), 6.97 (d, 1H, J = 1.6 Hz), 6.02 (d, 1H, J = 5.6 Hz), 3.95-3.92 (m, 2H), 3.73 (s, 2H), 3.73-3.68 (m, 2H), 3.58-3.54 (m, 2H), 3.50-3.45 (m, 2H), 2.97-2.92 (m, 1H), 2.81 (d, 2H, J = 4.4 Hz), 2.77 (d, 2H, J = 4.4 Hz), 2.02-1.98 (m, 1H), 1.07 (d, 6H, J = 6.8 Hz), 0.79-0.73 (m, 4H). |
| 192 | 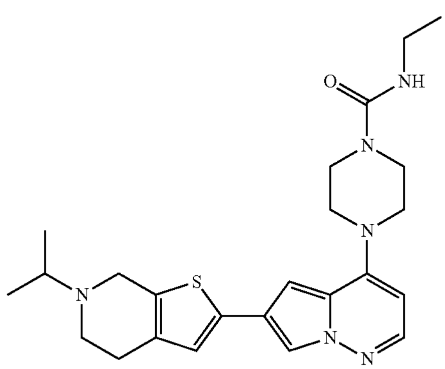 [SMILES: CCNC(=O)N1CCN(c2ccnn3cc(-c4cc5c(s4)CN(C(C)C)CC5)cc23)CC1] | 453 | 1H-NMR (400 MHz, 6d-DMSO) δ ppm 7.91 (d, 1H, J = 1.6 Hz), 7.88 (d, 1H, J = 5.6 Hz), 7.10 (s, 1H), 6.77 (d, 1H, J = 1.6 Hz), 6.59 (t, 1H, J = 5.2 Hz), 5.98 (d, 1H, J = 5.6 Hz), 3.64-3.62 (m, 2H), 3.51-3.48 (m, 4H), 3.40-3.38 (m, 4H), 3.08-3.05 (m, 2H), 2.90-2.88 (m, 1H), 2.61-2.58 (m, 2H), 2.50-2.48 (m, 2H), 1.05-1.00 (m, 9H). |
| 193 | 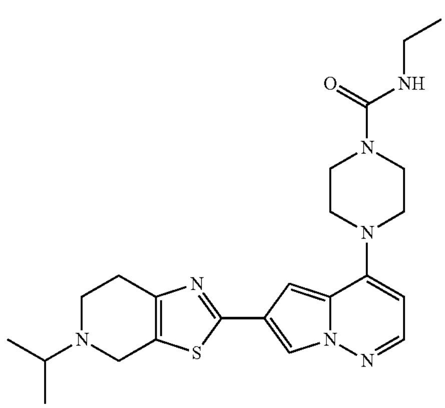 [SMILES: CCNC(=O)N1CCN(c2ccnn3cc(-c4nc5c(s4)CN(C(C)C)CC5)cc23)CC1] | 454 | 1H-NMR (400 MHz, 6d-DMSO) δ ppm 8.15 (s, 1H), 7.95 (d, 1H, J = 5.6 Hz), 6.94 (s, 1H), 6.59 (t, 1H, J = 5.6 Hz), 6.02 (d, 1H, J = 5.6 Hz), 3.73 (s, 2H), 3.53-3.50 (m, 4H), 3.46-3.44 (m, 4H), 3.10-3.06 (quintet, 2H, J = 6.4 Hz), 2.93 (heptet, 1H, J = 6.8 Hz), 2.82-2.79 (m, 2H), 2.77-2.72 (m, 2H), 1.07 (d, 6H, J = 6.8 Hz), 1.03 (t, 3H, J = 7.2 Hz). |

TABLE 1-continued

| # | Structure | LCMS (M + 1) | NMR |
|---|---|---|---|
| 194 | 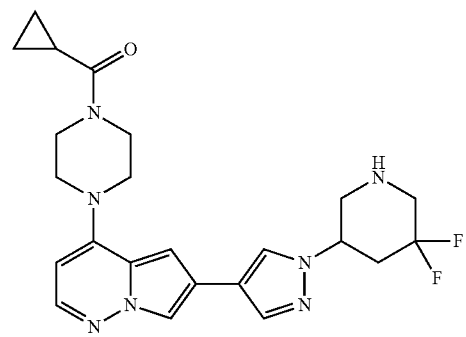 [SMILES: O=C(C1CC1)N1CCN(c2ccnn3cc(-c4cnn(C5CNCC(F)(F)C5)c4)cc23)CC1] | 456 | 1H-NMR (400 MHz, CDCl3) δ ppm 7.83 (d, 1H, J = 5.6 Hz), 7.75 (s, 2H), 7.63 (s, 1H), 6.52 (d, 1H, J = 1.6 Hz), 5.84 (d, 1H, J = 5.6 Hz), 4.49-4.40 (m, 1H), 3.93-3.88 (m, 4H), 3.53-3.45 (m, 4H), 3.41-3.22 (m, 2H), 3.10-2.89 (m, 2H), 2.70-2.45 (m, 2H), 1.80-1.75 (m, 1H), 1.06-1.03 (m, 2H), 0.89-0.80 (m, 2H). |
| 195 | 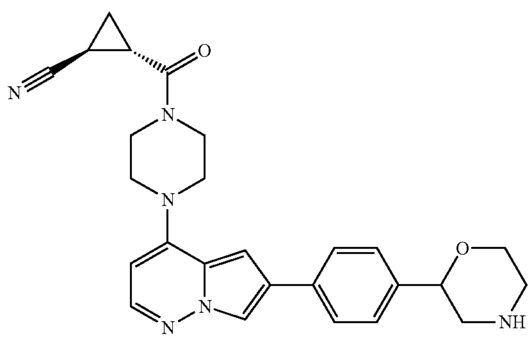 [SMILES: N#C[C@H]1C[C@@H]1C(=O)N1CCN(c2ccnn3cc(-c4ccc(C5CNCCO5)cc4)cc23)CC1] | 457 | 1H-NMR (400 MHz, 6d-DMSO) δ ppm 8.18 (d, 1H, J = 1.6 Hz), 7.90 (d, 1H, J = 5.6 Hz), 7.77 (d, 2H, J = 8.4 Hz), 7.33 (d, 2H, J = 8.4 Hz), 7.06 (d, 1H, J = 1.6 Hz), 5.98 (d, 1H, J = 5.6 Hz), 4.45-4.35 (m, 1H), 4.01-3.92 (m, 2H), 3.90-3.80 (m, 1H), 3.75-3.65 (m, 2H), 3.62-3.52 (m, 3H), 3.50-3.40 (m, 2H), 2.95-2.85 (m, 2H), 2.80-2.70 (m, 2H), 2.55-2.51 (m, 2H), 2.15-2.00 (m, 1H), 1.50-1.40 (m, 1H), 1.37-1.30 (m, 1H). |
| 196 | 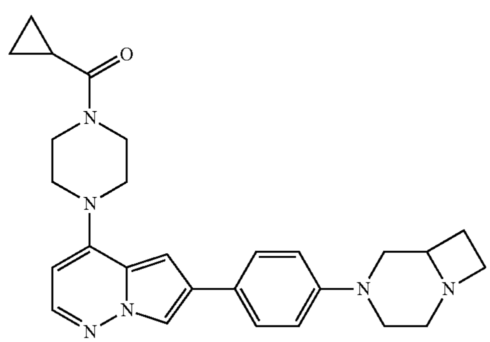 [SMILES: O=C(C1CC1)N1CCN(c2ccnn3cc(-c4ccc(N5CCN6CCC6C5)cc4)cc23)CC1] | 457 | 1H-NMR (400 MHz, 6d-DMSO) δ ppm 8.33-8.29 (br., 1H), 8.05 (d, 1H, J = 1.6 Hz), 7.86 (d, 1H, J = 5.6 Hz), 7.65 (d, 2H, J = 8.8 Hz), 6.93 (d, 1H, J = 1.6 Hz), 6.85 (d, 2H, J = 8.8 Hz), 5.96 (d, 1H, J = 5.6 Hz), 3.93-3.87 (m, 2H), 3.84-3.71 (m, 2H), 3.59-3.52 (m, 4H), 3.36-3.26 (m, 4H), 3.04-2.97 (m, 2H), 2.74-2.67 (m, 1H), 2.40-2.32 (m, 2H), 2.04-2.00 (m, 1H), 1.82-1.77 (m, 1H), 1.61-1.55 (m, 1H), 0.78-0.74 (m, 4H). |
| 197 | 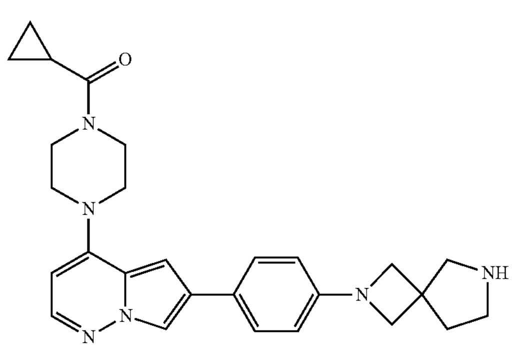 [SMILES: O=C(C1CC1)N1CCN(c2ccnn3cc(-c4ccc(N5CC6(CCNC6)C5)cc4)cc23)CC1] | 457 | 1H-NMR (400 MHz, 6d-DMSO) δ ppm 8.80-8.60 (br., 1H), 8.05 (d, 1H, J = 1.6 Hz), 7.87 (d, 1H, J = 5.6 Hz), 7.64 (d, 2H, J = 8.8 Hz), 6.92 (d, 1H, J = 1.6 Hz), 6.49 (d, 2H, J = 8.8 Hz), 5.97 (d, 1H, J = 5.6 Hz), 3.92-3.91 (m, 2H), 3.83 (dd, 4H, J = 12.8, 7.2 Hz), 3.71-3.70 (m, 2H), 3.52-3.50 (m, 2H), 3.48-3.44 (m, 2H), 3.39-3.37 (m, 2H), 3.22 (t, 2H, J = 7.2 Hz), 2.22 (t, 2H, J = 7.2 Hz), 2.03-2.02 (m, 1H), 0.79-0.75 (m, 4H). |

TABLE 1-continued

| # | Structure | LCMS (M + 1) | NMR |
|---|---|---|---|
| 198 | 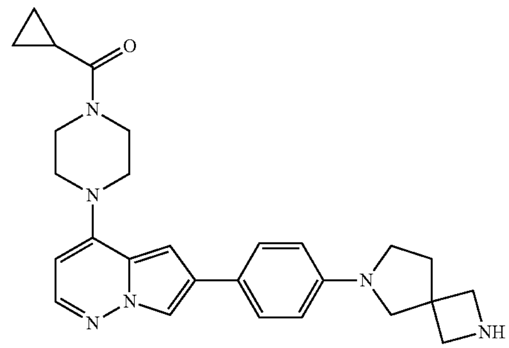 [SMILES: O=C(C1CC1)N1CCN(c2ccnn3cc(-c4ccc(N5CCC6(CNC6)C5)cc4)cc23)CC1] | 457 | 1H-NMR (400 MHz, CDCl3) δ ppm 7.86 (s, 1H), 7.82 (d, 1H, J = 5.2 Hz), 7.54 (d, 2H, J = 8.4 Hz), 6.64 (s, 1H), 6.60 (d, 2H, J = 8.4 Hz), 5.83 (d, 1H, J = 5.2 Hz), 3.95-3.90 (m, 2H), 3.90-3.85 (m, 2H), 3.60-3.53 (m, 4H), 3.53-3.42 (m, 2H), 3.41-3.37 (m, 2H), 2.62-2.40 (br., 4H), 2.30-2.25 (m, 2H), 1.80-1.77 (m, 1H), 1.05-1.03 (m, 2H), 0.84-0.81 (m, 2H). |
| 199 | 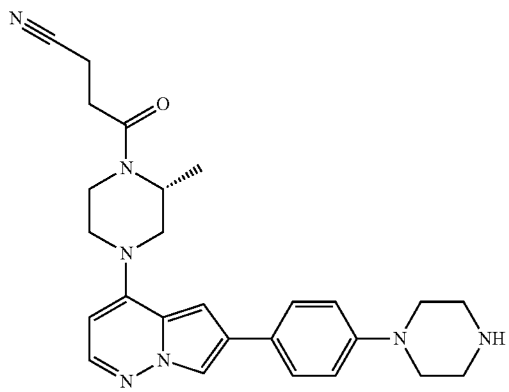 [SMILES: C[C@@H]1CN(c2ccnn3cc(-c4ccc(N5CCNCC5)cc4)cc23)CCN1C(=O)CCC#N] | 458 | 1H-NMR (400 MHz, DMSO-d6) δ ppm 8.06 (s, 1H), 7.90-7.80 (m, 1H), 7.63 (d, 2H, J = 8.0 Hz), 6.94 (d, 2H, J = 8.0 Hz), 6.85 (s, 1H), 6.00-5.88 (m, 1H), 4.66 (br. s., 1H), 4.40-4.20 (m, 1H), 4.00-3.40 (m, 4H), 3.26-3.12 (m, 2H), 3.10-3.02 (m, 4H), 2.98-2.76 (m, 5H), 2.74-2.60 (m, 3H), 1.40-1.20 (m, 3H). |
| 200 | 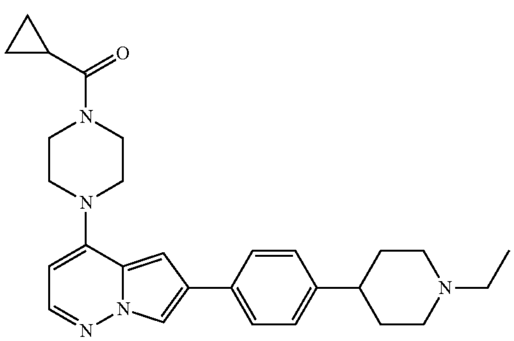 [SMILES: CCN1CCC(c2ccc(-c3cc4c(N5CCN(C(=O)C6CC6)CC5)ccnn4c3)cc2)CC1] | 458 | 1H-NMR (400 MHz, DMSO-d6) δ ppm 8.22 (s, 1H), 8.14 (d, 1H, J = 1.6 Hz), 7.89 (d, 1H, J = 5.2 Hz), 7.73 (d, 2H, J = 8.0 Hz), 7.25 (d, 2H, J = 8.0 Hz), 7.02 (d, 1H, J = 1.6 Hz), 5.97 (d, 1H, J = 5.2 Hz), 3.94-3.90 (m, 4H), 3.79-3.62 (m, 4H), 3.60-3.47 (m, 3H), 3.10-3.07 (m, 2H), 2.18-2.13 (m, 2H), 2.01-2.00 (m, 1H), 1.81-1.69 (m, 4H), 1.06 (t, 3H, J = 7.2 Hz), 0.80-0.73 (m, 4H). |
| 201 | 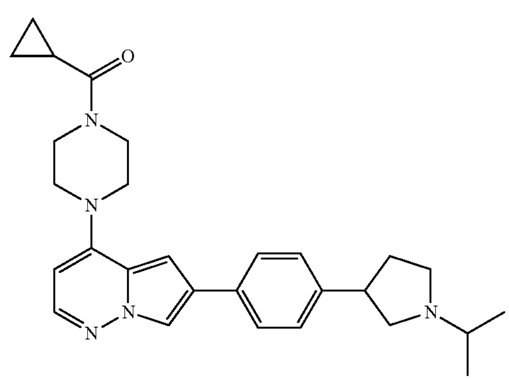 [SMILES: CC(C)N1CCC(c2ccc(-c3cc4c(N5CCN(C(=O)C6CC6)CC5)ccnn4c3)cc2)C1] | 458 | |

TABLE 1-continued
| # | Structure | LCMS (M + 1) | NMR |
|---|---|---|---|
| 202 | 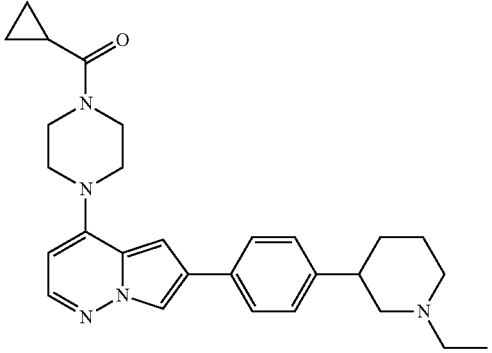 [SMILES: CCN1CCCC(c2ccc(-c3cc4c(N5CCN(C(=O)C6CC6)CC5)ccnn4c3)cc2)C1] | 458 | 1H-NMR (400 MHz, 6d-DMSO) δ ppm 8.15 (d, 1H, J = 1.6 Hz), 7.89 (d, 1H, J = 5.2 Hz), 7.74 (d, 2H, J = 8.0 Hz), 7.27 (d, 2H, J = 8.0 Hz), 7.02 (d, 1H, J = 1.6 Hz), 5.97 (d, 1H, J = 5.2 Hz), 4.00-3.80 (m, 2H), 3.78-3.62 (m, 2H), 3.60-3.42 (m, 4H), 3.30-3.20 (m, 2H), 3.10-2.90 (m, 2H), 2.85-2.70 (m, 1H), 2.48-2.45 (m, 1H), 2.10-1.95 (m, 2H), 1.90-1.70 (m, 2H), 1.68-1.40 (m, 2H), 1.15-0.90 (m, 3H), 0.80-0.60 (m, 4H). |
| 203 | 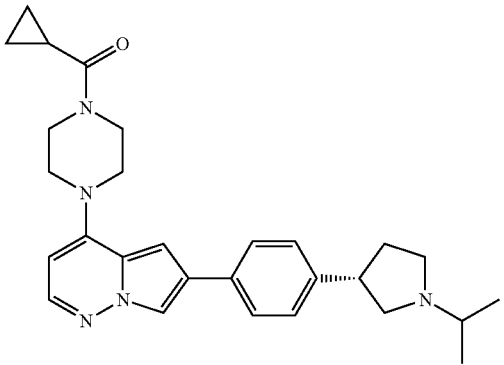 [SMILES: CC(C)N1CC[C@@H](c2ccc(-c3cc4c(N5CCN(C(=O)C6CC6)CC5)ccnn4c3)cc2)C1] | 458 | |
| 204 | 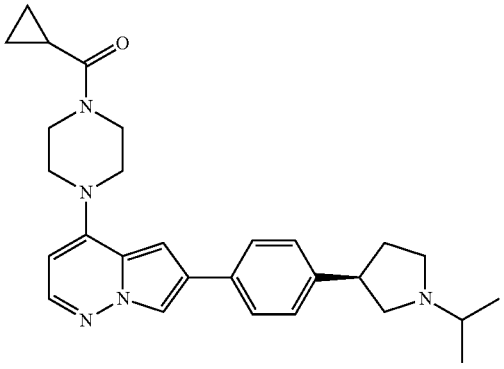 [SMILES: CC(C)N1CC[C@H](c2ccc(-c3cc4c(N5CCN(C(=O)C6CC6)CC5)ccnn4c3)cc2)C1] | 458 | 1H NMR (400 MHz, DMSO-d6) δ 8.14 (d, J = 1.8 Hz, 1H), 7.89 (d, J = 5.5 Hz, 1H), 7.76-7.67 (m, 2H), 7.35-7.22 (m, 2H), 7.01 (d, J = 1.9 Hz, 1H), 5.96 (d, J = 5.5 Hz, 1H), 3.91 (s, 2H), 3.70 (s, 2H), 3.50 (d, J = 27.8 Hz, 5H), 3.25 (dt, J = 9.4, 7.5 Hz, 1H), 2.98 (t, J = 8.4 Hz, 1H), 2.83-2.62 (m, 2H), 2.44-2.31 (m, 1H), 2.26-2.11 (m, 0H), 2.01 (tt, J = 7.7, 4.9 Hz, 1H), 1.81-1.68 (m, 1H), 1.05 (t, J = 6.3 Hz, 6H), 0.76 (ddt, J = 9.8, 5.0, 2.5 Hz, 4H). |
| 205 | 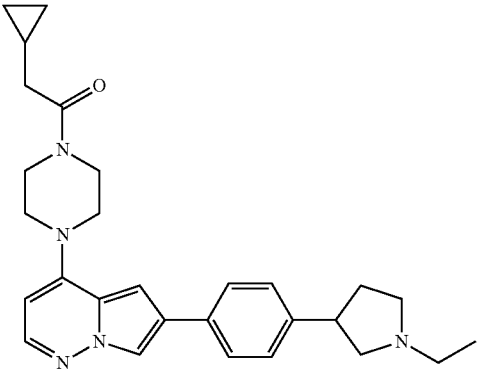 [SMILES: CCN1CCC(c2ccc(-c3cc4c(N5CCN(C(=O)CC6CC6)CC5)ccnn4c3)cc2)C1] | 458 | 1H-NMR (400 MHz, 6d-DMSO) δ ppm 8.22 (s, 1H), 7.92 (d, 1H, J = 5.6 Hz), 7.82 (d, 2H, J = 8.0 Hz), 7.40-7.35 (m, 2H), 7.05 (s, 1H), 5.98 (d, 1H, J = 5.6 Hz), 3.99-3.97 (m, 1H), 3.69-3.38 (m, 6H), 3.63-3.62 (m, 5H), 3.50-3.49 (m, 2H), 3.30-3.25 (m, 1H), 2.34-2.32 (m, 3H), 2.22-2.20 (m, 1H), 1.25 (t, 3H, J = 7.2 Hz), 1.01-0.99 (m, 1H), 0.48-0.45 (m, 2H), 0.15-0.14 (m, 2H). |

TABLE 1-continued
| # | Structure | LCMS (M + 1) | NMR |
|---|---|---|---|
| 206 | 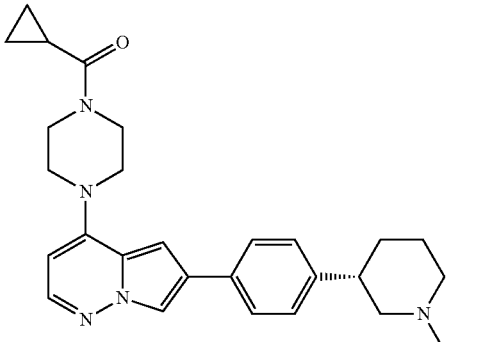 | 458 | 1H-NMR (400 MHz, 6d-DMSO) δ ppm 8.20 (d, 1H, J = 1.6 Hz), 7.90 (d, 1H, J = 5.6 Hz), 7.80 (d, 2H, J = 8.4 Hz), 7.30 (d, 2H, J = 8.0 Hz), 7.05 (d, 1H, J = 1.6 Hz), 5.98 (d, 1H, J = 5.6 Hz), 4.00-3.85 (m, 2H), 3.80-3.65 (m, 2H), 3.60-3.40 (m, 6H), 3.20-2.90 (m, 4H), 2.10-1.80 (m, 5H), 1.70-1.50 (m, 1H), 1.30-1.10 (m, 3H), 0.80-0.60 (m, 4H). |
| 207 | 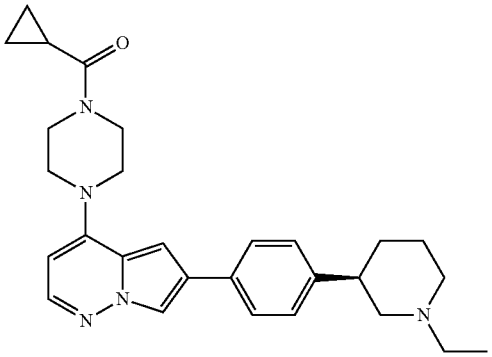 [SMILES: CCN1CCC[C@H](c2ccc(-c3cc4c(N5CCN(C(=O)C6CC6)CC5)ccnn4c3)cc2)C1] | 458 | 1H-NMR (400 MHz, 6d-DMSO) δ ppm 8.20 (d, 1H, J = 1.6 Hz), 7.90 (d, 1H, J = 5.6 Hz), 7.80 (d, 2H, J = 8.4 Hz), 7.30 (d, 2H, J = 8.0 Hz), 7.05 (d, 1H, J = 1.6 Hz), 5.98 (d, 1H, J = 5.6 Hz), 4.00-3.85 (m, 2H), 3.80-3.65 (m, 2H), 3.60-3.40 (m, 6H), 3.20-2.90 (m, 4H), 2.10-1.80 (m, 5H), 1.70-1.50 (m, 1H), 1.30-1.10 (m, 3H), 0.80-0.60 (m, 4H). |
| 208 | 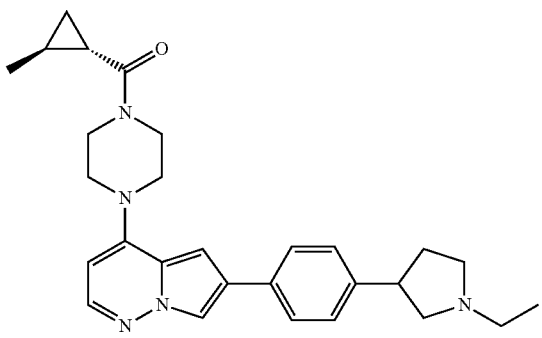 [SMILES: CCN1CCC(c2ccc(-c3cc4c(N5CCN(C(=O)[C@H]6C[C@@H]6C)CC5)ccnn4c3)cc2)C1] | 458 | 1H-NMR (400 MHz, 6d-DMSO) δ ppm 8.14 (s, 1H), 7.90 (d, 1H, J = 5.6 Hz), 7.72 (d, 2H, J = 8.0 Hz), 7.28 (d, 2H, J = 8.0 Hz), 7.01 (s, 1H), 5.97 (d, 1H, J = 5.6 Hz), 3.90-3.88 (m, 2H), 3.68-3.66 (m, 2H), 3.54-3.50 (m, 2H), 3.49-3.44 (m, 2H), 3.31-3.27 (m, 1H), 2.93-2.89 (m, 1H), 2.68-2.62 (m, 2H), 2.50-2.48 (m, 1H), 2.46-2.42 (m, 2H), 2.26-2.18 (m, 1H), 1.76-1.72 (m, 2H), 1.18-1.12 (m, 1H), 1.09-1.03 (m, 6H), 0.99-0.95 (m, 1H), 0.60-0.56 (m, 1H). |
| 209 | 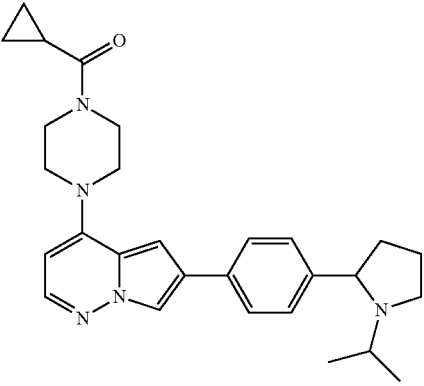 [SMILES: CC(C)N1CCCC1c1ccc(-c2cc3c(N4CCN(C(=O)C5CC5)CC4)ccnn3c2)cc1] | 459 | |

TABLE 1-continued

| # | Structure | LCMS (M + 1) | NMR |
|---|---|---|---|
| 210 | 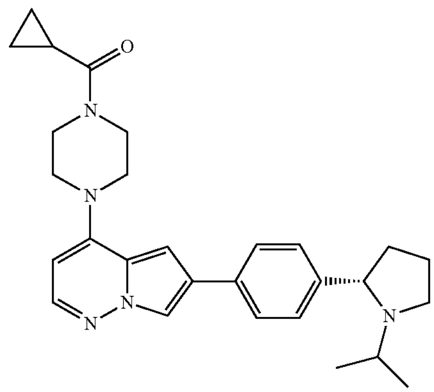 [SMILES: CC(C)N1CCC[C@H]1c1ccc(-c2cc3c(N4CCN(C(=O)C5CC5)CC4)ccnn3c2)cc1] | 459 | |
| 211 | 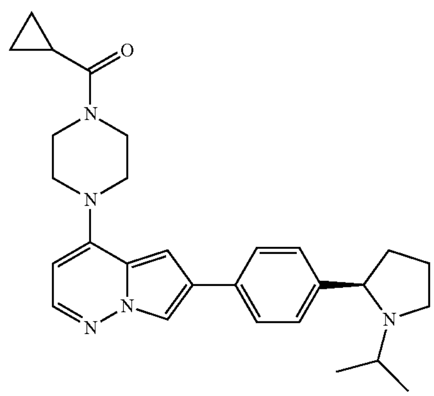 [SMILES: CC(C)N1CCC[C@@H]1c1ccc(-c2cc3c(N4CCN(C(=O)C5CC5)CC4)ccnn3c2)cc1] | 459 | |
| 212 | 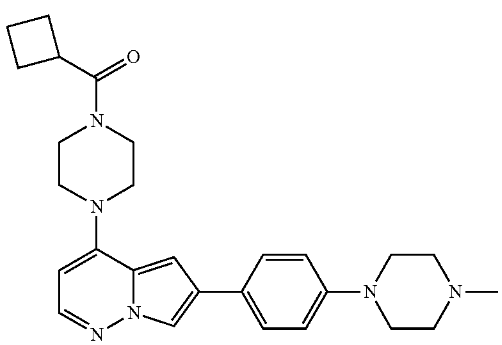 [SMILES: CN1CCN(c2ccc(-c3cc4c(N5CCN(C(=O)C6CCC6)CC5)ccnn4c3)cc2)CC1] | 459 | 1H-NMR (400 MHz, DMSO-d6) δ ppm 8.06 (s, 1H), 7.87 (d, 1H, J = 5.2 Hz), 7.65 (d, 2H, J = 8.4 Hz), 6.95 (d, 2H, J = 8.8 Hz), 6.93 (s, 1H), 5.95 (d, 1H, J = 5.6 Hz), 3.68-3.36 (m, 9H), 3.17-3.15 (m, 4H), 2.50-2.47 (m, 4H), 2.23-2.11 (m, 7H), 1.93-1.90 (m, 1H), 1.78-1.76 (m, 1H). |
| 213 | 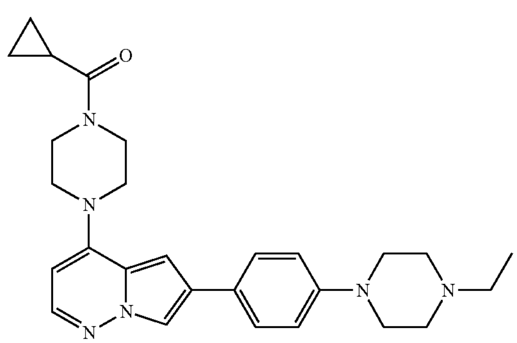 [SMILES: CCN1CCN(c2ccc(-c3cc4c(N5CCN(C(=O)C6CC6)CC5)ccnn4c3)cc2)CC1] | 459 | 1H-NMR (400 MHz, DMSO-d6) δ ppm 8.27 (br. s., 1H), 8.07 (d, 1H, J = 1.2 Hz), 7.88 (d, 1H, J = 5.2 Hz), 7.66 (d, 2H, J = 8.4 Hz), 6.97-6.95 (m, 3H), 5.96 (d, 1H, J = 5.6 Hz), 3.92-3.70 (m, 6H), 3.52-3.45 (m, 6H), 3.17-3.15 (m, 4H), 2.41-2.36 (q, 2H, J = 7.2 Hz), 2.03-2.00 (m, 1H), 1.06-1.02 (m, 3H) , 0.78-0.72 (m, 4H). |

| # | Structure | LCMS (M + 1) | NMR |
|---|---|---|---|
| 214 | 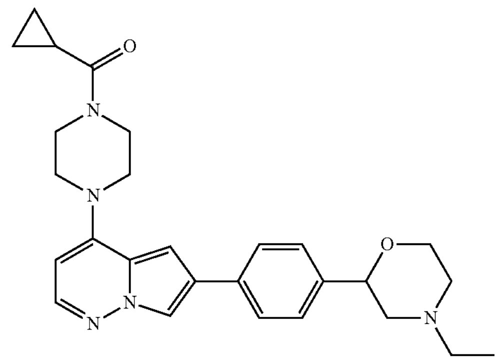 | 460 | 1H-NMR (400 MHz, DMSO-d6) δ ppm 8.18 (d, 1H, J = 1.6 Hz), 7.90 (d, 1H, J = 5.2 Hz), 7.77 (d, 2H, J = 8.0 Hz), 7.36 (d, 2H, J = 8.0 Hz), 7.05 (d, 1H, J = 1.6 Hz), 5.97 (d, 1H, J = 5.2 Hz), 4.49-4.47 (m, 1H), 3.96-3.93 (m, 3H), 3.70-3.64 (m, 3H), 3.54-3.47 (m, 4H), 2.94-2.91 (m, 1H), 2.80-2.77 (m, 1H), 2.50-2.35 (m, 2H), 2.08-2.00 (m, 2H), 1.91-1.88 (m, 1H), 1.02 (t, 3H, J = 7.2 Hz), 0.78-0.72 (m, 4H). |
| 215 | 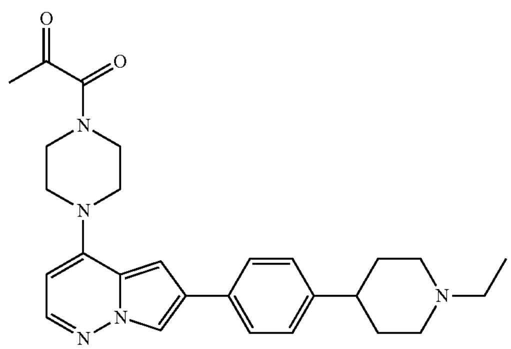 [SMILES: CCN1CCC(c2ccc(-c3cc4c(N5CCN(C(=O)C(C)=O)CC5)ccnn4c3)cc2)CC1] | 460 | 1H-NMR (400 MHz, 6d-DMSO) δ ppm 8.16 (d, 1H, J = 1.6 Hz), 7.91 (d, 1H, J = 5.2 Hz), 7.73 (d, 2H, J = 8.0 Hz), 7.26 (d, 2H, J = 8.0 Hz), 7.03 (s, 1H), 6.00 (d, 1H, J = 5.6 Hz), 3.77-3.68 (m, 2H), 3.66-3.58 (m, 2H), 3.56-3.44 (m, 4H), 3.06-2.94 (m, 2H), 2.42 (s, 3H), 2.40-2.29 (m, 1H), 2.36 (q, 2H, J = 7.2 Hz), 2.08-1.90 (m, 2H), 1.83-1.72 (m, 2H), 1.72-1.58 (m, 2H), 1.03 (t, 3H, J = 7.2 Hz). |
| 216 | 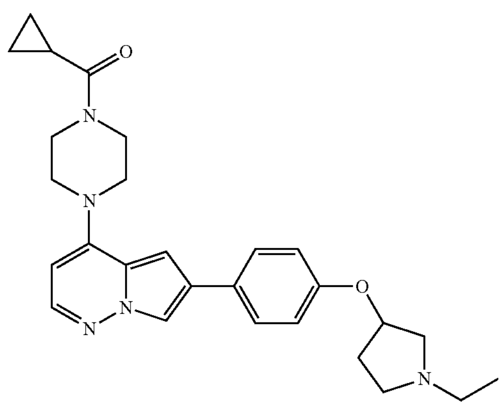 [SMILES: CCN1CCC(Oc2ccc(-c3cc4c(N5CCN(C(=O)C6CC6)CC5)ccnn4c3)cc2)C1] | 460 | 1H-NMR (400 MHz, 6d-DMSO) δ ppm 8.13 (d, 1H, J = 1.6 Hz), 7.89 (d, 1H, J = 5.6 Hz), 7.75 (d, 2H, J = 8.8 Hz), 6.99 (d, 1H, J = 1.6 Hz), 6.96 (d, 2H, J = 8.8 Hz), 5.97 (d, 1H, J = 5.6 Hz), 5.07-5.03 (m, 1H), 3.95-3.90 (m, 2H), 3.73-3.69 (m, 2H), 3.55-3.50 (m, 2H), 3.50-3.45 (m, 2H), 3.35-3.12 (m, 4H), 2.88-2.82 (m, 2H), 2.42-2.33 (m, 1H), 2.05-2.03 (m, 1H), 2.00-1.97 (m, 1H), 1.14 (t, 3H, J = 7.2 Hz), 0.79-0.75 (m, 4H). |
| 217 | 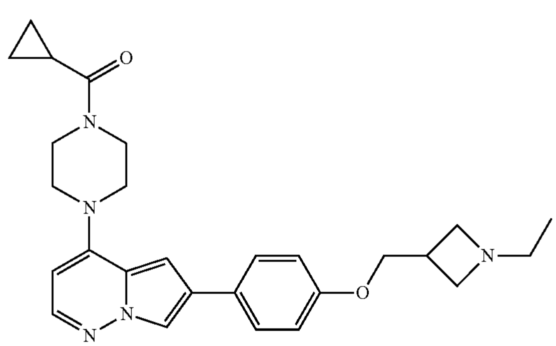 [SMILES: CCN1CC(COc2ccc(-c3cc4c(N5CCN(C(=O)C6CC6)CC5)ccnn4c3)cc2)C1] | 460 | 1H-NMR (400 MHz, 6d-DMSO) δ ppm 8.12 (d, 1H, J = 2.0 Hz), 7.89 (d, 1H, J = 5.2 Hz), 7.76 (d, 2H, J = 8.8 Hz), 7.01 (d, 2H, J = 8.8 Hz), 6.99 (s, 1H), 5.97 (d, 1H, J = 5.2 Hz), 4.17 (d, 2H, J = 5.2 Hz), 4.05-3.99 (m, 2H), 3.95-3.90 (m, 2H), 3.90-3.78 (m, 2H), 3.74-3.65 (m, 2H), 3.58-3.48 (m, 2H), 3.47-3.42 (m, 2H), 3.20-3.10 (m, 1H), 3.10-3.04 (m, 2H), 2.04-2.0 (m, 1H), 1.06 (t, 3H, J = 6.8 Hz), 0.78-0.74 (m, 4H). |

TABLE 1-continued

| # | Structure | LCMS (M + 1) | NMR |
|---|---|---|---|
| 218 | 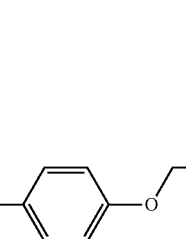 | 460 | 1H-NMR (400 MHz, 6d-DMSO) δ ppm 8.23 (s, 1H), 8.11 (d, 1H, J = 1.6 Hz), 7.89 (d, 1H, J = 5.6 Hz), 7.74 (d, 2H, J = 8.4 Hz), 6.99 (d, 1H, J = 1.6 Hz), 6.97 (d, 2H, J = 8.4 Hz), 5.98 (d, 1H, J = 5.6 Hz), 4.05-3.93 (m, 2H), 3.87-3.85 (m, 2H), 3.70-3.66 (m, 4H), 3.48-3.45 (m, 4H), 2.93-2.89 (m, 1H), 2.85-2.78 (m, 1H), 2.11-2.07 (m, 1H), 2.03-1.97 (m, 2H), 0.94 (t, 3H, J = 7.2 Hz), 0.78-0.75 (m, 4H). |
| 219 | 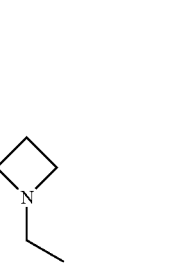 | 460 | 1H-NMR (400 MHz, 6d-DMSO) δ ppm 10.50-9.84 (m, 1H), 8.28 (d, 1H, J = 1.6 Hz), 7.92 (d, 1H, J = 5.6 Hz), 7.90 (d, 2H, J = 8.4 Hz), 7.53 (d, 2H, J = 8.4 Hz), 7.11 (d, 1H, J = 2.0 Hz), 6.76 (s, 1H), 5.99 (d, 1H, J = 5.6 Hz), 4.66-4.22 (m, 2H), 4.27-4.11 (m, 2H), 3.95-3.90 (m, 2H), 3.74-3.68 (m, 2H), 3.55-3.50 (m, 5H), 2.06-1.99 (m, 1H), 1.20-1.16 (m, 6H), 0.79-0.75 (m, 4H). |
| 220 | 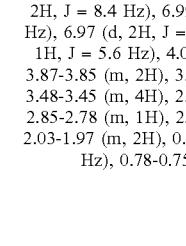 | 460 | 1H-NMR (400 MHz, 6d-DMSO) δ ppm 8.10 (d, 1H, J = 1.6 Hz), 7.88 (d, 1H, J = 5.6 Hz), 7.71 (d, 2H, J = 8.4 Hz), 6.97 (d, 1H, J = 1.6 Hz), 6.86 (d, 2H, J = 8.4 Hz), 5.96 (d, 1H, J = 5.6 Hz), 4.75-4.74 (m, 1H), 3.91-3.90 (m, 1H), 3.69 (dd, 4H, J = 7.6, 6.0 Hz), 3.53-3.48 (m, 2H), 3.46-3.41 (m, 2H), 2.93-2.89 (m, 2H), 2.32-2.29 (m, 2H), 2.02-2.01 (m, 1H), 0.87 (d, 6H, J = 6.0 Hz), 0.78-0.72 (m, 4H). |
| 221 | 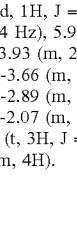 | 460 | 1H-NMR (400 MHz, DMSO-d6) δ ppm 8.61 (s, 1H), 8.13 (s, 1H), 7.98-7.96 (dd, 1H, J = 8.8, 1.6 Hz), 7.88 (d, 1H, J = 5.2 Hz), 7.01 (s, 1H), 6.88 (d, 1H, J = 5.2 Hz), 3.92 (br. s., 2H), 3.70 (br. s., 2H), 3.52-3.46 (m, 8H), 3.33 (br. s., 2H), 2.44-2.36 (m, 2H), 2.04-1.99 (m, 1H), 1.05 (t, 3H, J = 6.4 Hz), 0.78-0.74 (m, 4H). |

TABLE 1-continued

| # | Structure | LCMS (M + 1) | NMR |
|---|---|---|---|
| 222 | 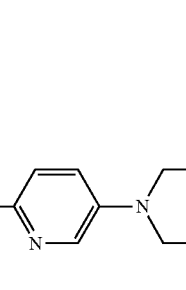 | 460 | 1H-NMR (400 MHz, 6d-DMSO) δ ppm 8.29 (s, 1H), 8.16 (s, 1H), 7.90 (d, 1H, J = 4.8 Hz), 7.76 (d, 1H, J = 8.8 Hz), 7.36 (d, 1H, J = 8.8 Hz), 7.08 (s, 1H), 5.97 (d, 1H, J = 4.8 Hz), 3.94-3.91 (m, 2H), 3.73-3.68 (m, 2H), 3.56-3.52 (m, 2H). 3.49-3.45 (m, 2H), 3.27-3.19 (m, 4H), 2.50-2.40 (m, 4H), 2.39 (q, 2H, J = 7.2 Hz), 2.03-1.97 (m, 1H), 1.04 (t, 3H, J = 7.2 Hz), 0.80-0.73 (m, 4H). |
| 223 | 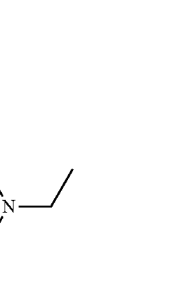 | 461 | 1H-NMR (400 MHz, 6d-DMSO) δ ppm 8.06 (d, 1H, J = 1.6 Hz), 7.87 (d, 1H, J = 5.6 Hz), 7.65 (d, 2H, J = 8.4 Hz), 6.97 (s, 1H), 6.95 (d, 2H, J = 8.4 Hz), 5.96 (d, 1H, J = 5.6 Hz), 3.74-3.69 (m, 4H), 3.59-3.57 (m, 8H), 3.17-3.15 (m, 4H), 2.90-2.80 (m, 1H), 2.37 (q, 2H, J = 7.2 Hz), 1.04 (d, 6H, , J = 7.2 Hz), 1.03 (t, 3H, J = 7.2 Hz). |
| 224 | 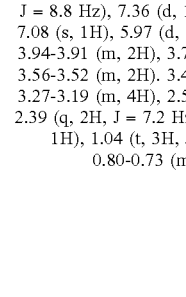 | 461 | 1H-NMR (400 MHz, 6d-DMSO) δ ppm 8.13 (d, 1H, J = 1.6 Hz), 7.88 (d, 1H, J = 5.6 Hz), 7.72 (d, 2H, J = 8.0 Hz), 7.29 (d, 2H, J = 8.0 Hz), 6.99 (d, 1H, J = 1.6 Hz), 6.61 (t, 1H, J = 5.6 Hz), 5.97 (d, 1H, J = 5.6 Hz), 3.60-3.47 (m, 4H), 3.46-3.38 (m, 4H), 3.30-3.20 (m, 1H), 3.12-3.03 (m, 2H), 3.02-2.94 (m, 1H), 2.80-2.64 (m, 2H), 2.49-2.44 (m, 1H), 2.43-2.35 (m, 1H), 2.26-2.15 (m, 1H), 1.80-1.70 (m, 1H), 1.10-1.00 (m, 9H). |
| 225 | 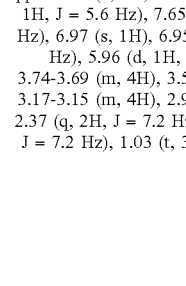 | 461 | 1H-NMR (400 MHz, 6d-DMSO) δ ppm 8.14 (d, 1H, J = 1.6 Hz), 7.89 (d, 1H, J = 5.6 Hz), 7.72 (d, 2H, J = 8.0 Hz), 7.29 (d, 2H, J = 8.0 Hz), 6.99 (d, 1H, J = 1.6 Hz), 6.61 (t, 1H, J = 5.6 Hz), 5.98 (d, 1H, J = 5.6 Hz), 3.52-3.51 (m, 4H), 3.44-3.43 (m, 4H), 3.31-3.25 (m, 1H), 3.12-3.05 (m, 2H), 3.01-2.97 (m, 1H), 2.74-2.68 (m, 2H), 2.47-2.38 (m, 2H), 2.23-2.19 (m, 1H), 1.78-1.73 (m, 1H), 1.07-1.01 (m, 9H). |

TABLE 1-continued

| # | Structure | LCMS (M + 1) | NMR |
|---|---|---|---|
| 226 | 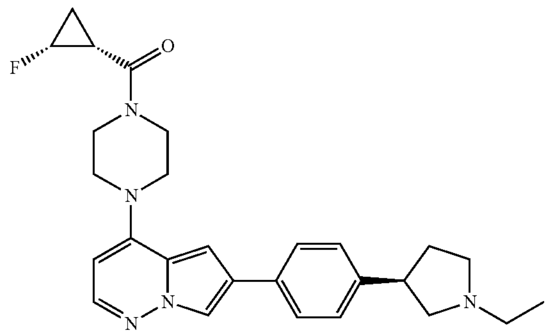 [SMILES: CCN1CC[C@H](c2ccc(-c3cc4c(N5CCN(C(=O)[C@H]6C[C@H]6F)CC5)ccnn4c3)cc2)C1] | 462 | 1H-NMR (400 MHz, 6d-DMSO) δ ppm 8.15 (d, 1H, J = 1.6 Hz), 7.90 (d, 1H, J = 5.6 Hz), 7.73 (d, 2H, J = 8.04 Hz), 7.30 (d, 2H, J = 8.4 Hz), 7.03 (d, 1H, J = 1.6 Hz), 5.99 (d, 1H, J = 5.2 Hz), 5.05-4.88 (m, 1H), 3.93-3.90 (m, 2H), 3.74-3.73 (m, 2H), 3.48-3.28 (m, 4H), 2.93-2.92 (m, 1H), 2.68-2.65 (m, 2H), 2.46-2.42 (m, 3H), 2.24-2.20 (m, 2H), 1.76-1.75 (m, 1H), 1.52-1.08 (m, 1H), 1.06 (t, 3H, J = 6.8 Hz). |
| 227 | 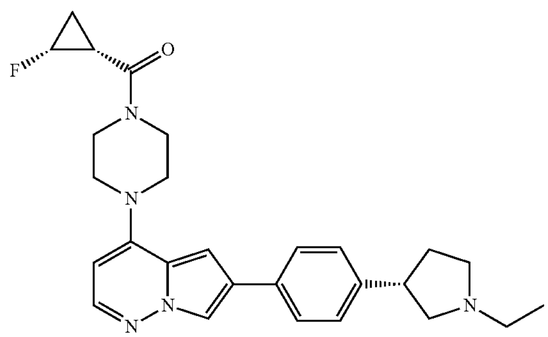 [SMILES: CCN1CC[C@@H](c2ccc(-c3cc4c(N5CCN(C(=O)[C@H]6C[C@H]6F)CC5)ccnn4c3)cc2)C1] | 462 | 1H-NMR (400 MHz, 6d-DMSO) δ ppm 8.24 (s, 1H), 8.17 (s, 1H), 7.91 (d, 1H, J = 5.2 Hz), 7.75 (d, 2H, J = 8.0 Hz), 7.32 (d, 2H, J = 8.0 Hz), 7.05 (s, 1H), 5.99 (d, 1H, J = 5.2 Hz), 5.09-4.83 (m, 1H), 4.01-3.82 (m, 3H), 3.79-3.68 (m, 3H), 3.62-3.58 (m, 1H), 3.53-3.41 (m, 3H), 3.12 (t, 1H, J = 8.4 Hz), 2.90-2.80 (m, 2H), 272-2.59 (m, 3H), 1.89-1.78 (m, 1H), 1.62-1.50 (m, 1H), 1.11 (t, 3H, J = 7.2 Hz). |
| 228 | 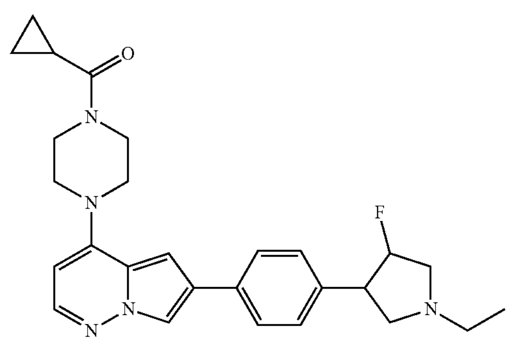 [SMILES: CCN1CC(F)C(c2ccc(-c3cc4c(N5CCN(C(=O)C6CC6)CC5)ccnn4c3)cc2)C1] | 462 | 1H-NMR (400 MHz, 6d-DMSO) δ ppm 8.18 (d, 1H, J = 2.0 Hz), 7.90 (d, 1H, J = 5.2 Hz), 7.77 (d, 2H, J = 8.4 Hz), 7.30 (d, 2H, J = 8.4 Hz), 7.04 (d, 1H, J = 2.0 Hz), 5.97 (d, 1H, J = 5.2 Hz), 5.30-5.00 (m, 1H), 4.00-3.83 (m, 2H), 3.80-3.62 (m, 2H), 3.57-3.50 (m, 2H), 3.49-3.42 (m, 2H), 3.40-3.35 (m, 2H), 3.30-3.20 (m, 2H), 3.18-3.00 (m, 1H), 2.80-2.60 (m, 1H), 2.35-2.20 (m, 1H), 2.10-1.95 (m, 1H), 1.06 (t, 3H, J = 7.2 Hz), 0.80-0.60 (m, 4H). |
| 229 | 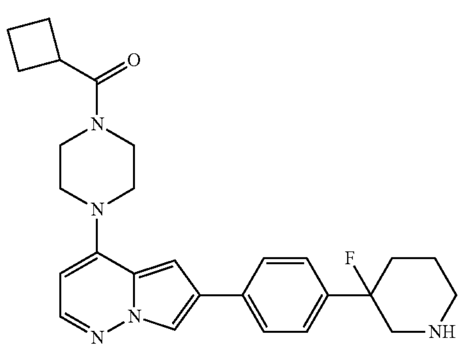 [SMILES: O=C(C1CCC1)N1CCN(c2ccnn3cc(-c4ccc(C5(F)CCCNC5)cc4)cc23)CC1] | 462 | 1H-NMR (400 MHz, 6d-DMSO) δ ppm 8.21 (d, 1H, J = 1.6 Hz), 7.91 (d, 1H, J = 5.6 Hz), 7.83 (d, 2H, J = 8.4 Hz), 7.44 (d, 2H, J = 8.4 Hz), 7.06 (d, 1H, J = 1.6 Hz), 5.98 (d, 1H, J = 5.6 Hz), 3.72-3.60 (m, 2H), 3.60-3.50 (m, 2H), 3.50-3.38 (m, 4H), 3.37-3.34 (m, 1H), 3.08-3.05 (m, 1H), 3.04-2.97 (m, 2H), 2.70-2.61 (m, 1H), 2.27-2.20 (m, 2H), 2.20-2.08 (m, 4H), 2.03-1.98 (m, 1H), 1.95-1.90 (m, 1H), 1.85-1.80 (m, 1H), 1.80-1.74 (m, 1H), 1.59-1.54 (m, 1H). |

TABLE 1-continued

| # | Structure | LCMS (M + 1) | NMR |
|---|---|---|---|
| 230 | 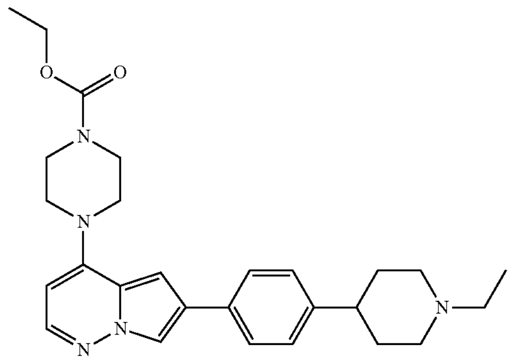 [SMILES: CCOC(=O)N1CCN(c2ccnn3cc(-c4ccc(C5CCN(CC)CC5)cc4)cc23)CC1] | 462 | 1H-NMR (400 MHz, 6d-DMSO) δ ppm 8.14 (d, 1H, J = 1.6 Hz), 7.90 (d, 1H, J = 5.6 Hz), 7.73 (d, 2H, J = 8.0 Hz), 7.26 (d, 2H, J = 8.0 Hz), 6.99 (d, 1H, J = 1.6 Hz), 5.98 (d, 1H, J = 5.6 Hz), 4.09 (q, 2H, J = 7.2 Hz), 3.66-3.55 (m, 4H), 3.49-3.41 (m, 4H), 3.03-2.93 (m, 2H), 2.35 (q, 2H, J = 7.2 Hz), 2.33-2.29 (m, 1H), 2.00-1.90 (m, 2H), 1.80-1.72 (m, 2H), 1.72-1.59 (m, 2H), 1.22 (t, 3H, J = 7.2 Hz), 1.02 (t, 3H, J = 7.2 Hz). |
| 231 | 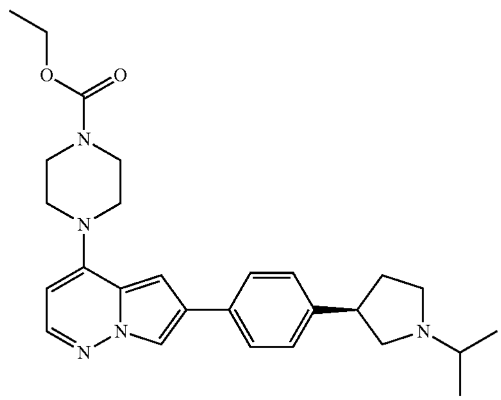 | 462 | 1H-NMR (400 MHz, 6d-DMSO) δ ppm 8.13 (d, 1H, J = 1.2 Hz), 7.88 (d, 1H, J = 5.2 Hz), 7.71 (d, 2H, J = 8.0 Hz), 7.28 (d, 2H, J = 8.0 Hz), 6.98 (d, 1H, J = 1.2 Hz), 5.95 (d, 1H, J = 5.2 Hz), 4.07 (q, 2H, J = 6.8 Hz), 3.65-3.55 (m, 4H), 3.50-3.42 (m, 4H), 3.30-3.20 (m, 1H), 2.98 (t, 1H, J = 8.4 Hz), 2.78-2.74 (m, 1H), 2.70-2.65 (m, 1H), 2.48 (t, 1H, J = 8.4 Hz), 2.45-2.37 (m, 1H), 2.25-2.10 (m, 1H), 1.80-1.65 (m, 1H), 1.20 (t, 3H, J = 6.8 Hz), 1.10-1.00 (m, 6H). |
| 232 | 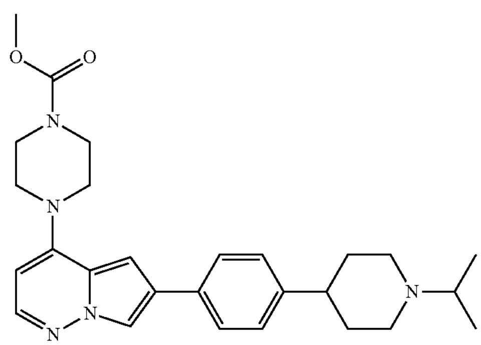 [SMILES: COC(=O)N1CCN(c2ccnn3cc(-c4ccc(C5CCN(C(C)C)CC5)cc4)cc23)CC1] | 463 | 1H NMR (400 MHz, DMSO-d6) δ 8.13 (d, J = 1.7 Hz, 1H), 7.89 (d, J = 5.4 Hz, 1H), 7.71 (d, J = 8.1 Hz, 2H), 7.24 (d, J = 8.1 Hz, 2H), 6.98 (d, J = 1.8 Hz, 1H), 5.97 (d, J = 5.5 Hz, 1H), 3.64 (s, 3H), 3.60 (t, J = 5.1 Hz, 4H), 3.45 (t, J = 5.1 Hz, 4H), 2.88 (d, J = 10.9 Hz, 3H), 2.70 (p, J = 6.6 Hz, 1H), 2.21 (t, J = 11.2 Hz, 2H), 1.76 (d, J = 12.4 Hz, 2H), 1.61 (tt, J = 12.2, 6.3 Hz, 2H), 0.99 (d, J = 6.5 Hz, 6H). |
| 233 | 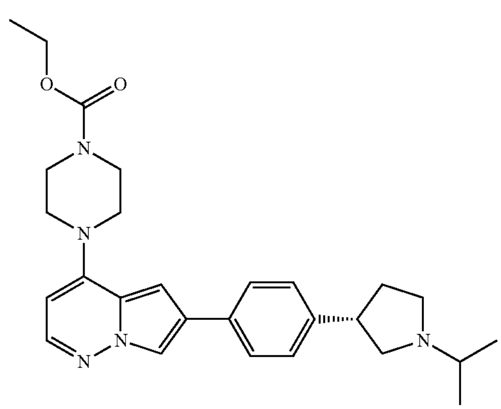 [SMILES: CCOC(=O)N1CCN(c2ccnn3cc(-c4ccc([C@@H]5CCN(C(C)C)C5)cc4)cc23)CC1] | 478 | 1H-NMR (400 MHz, CDCl3) δ ppm 8.68 (s, 1H), 7.92 (s, 1H), 7.85 (d, 1H, J = 5.6 Hz), 7.62 (d, 2H, J = 8.0 Hz), 7.32 (d, 2H, J = 8.0 Hz), 6.68 (s, 1H), 5.85 (d, 1H, J = 5.6 Hz), 4.20 (q, 2H, J = 7.2 Hz), 3.77-3.71 (m, 4H), 3.60-3.55 (m, 1H), 3.54-3.50 (m, 1H), 3.49-3.41 (m, 4H), 3.40-3.38 (m, 1H), 3.21-3.28 (m, 1H), 3.18-3.11 (m, 1H), 3.05-2.94 (m, 1H), 2.40-2.50 (m, 1H), 2.20-2.10 (m, 1H), 1.36 (d, 6H, J = 6.4 Hz), 1.31 (t, 3H, J = 7.2 Hz). |

TABLE 1-continued
| # | Structure | LCMS (M + 1) | NMR |
|---|---|---|---|
| 234 | 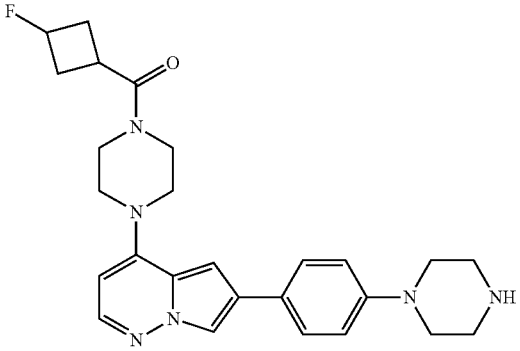 [SMILES: O=C(C1CC(F)C1)N1CCN(c2ccnn3cc(-c4ccc(N5CCNCC5)cc4)cc23)CC1] | 464 | |
| 235 | 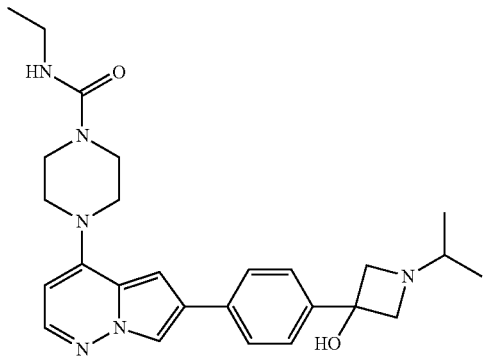 [SMILES: CCNC(=O)N1CCN(c2ccnn3cc(-c4ccc(C5(O)CN(C(C)C)C5)cc4)cc23)CC1] | 463 | 1H-NMR (400 MHz, 6d-DMSO) δ ppm 8.18 (d, 1H, J = 1.2 Hz), 8.15 (s, 1H), 7.89 (d, 1H, J = 5.2 Hz), 7.80 (d, 2H, J = 8.0 Hz), 7.61 (d, 2H, J = 8.0 Hz), 7.02 (d, 1H, J = 1.6 Hz), 6.60 (t, 1H, J = 5.6 Hz), 6.00-5.97 (m, 2H), 3.72-3.70 (m, 2H), 3.52-3.51 (m, 4H), 3.41-3.44 (m, 6H), 3.11-3.04 (m, 2H), 2.66-2.50 (m, 1H), 1.03 (t, 3H, J = 7.6 Hz), 0.96 (d, 6H, J = 6.0 Hz). |
| 236 | 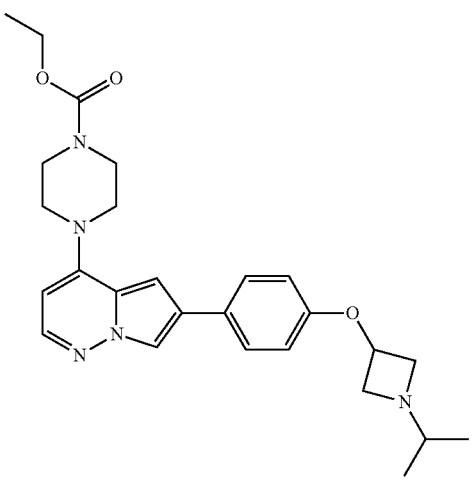 [SMILES: CCOC(=O)N1CCN(c2ccnn3cc(-c4ccc(OC5CN(C(C)C)C5)cc4)cc23)CC1] | 464 | 1H-NMR (400 MHz, 6d-DMSO) δ ppm 8.10 (d, 1H, J = 2.0 Hz), 7.88 (d, 1H, J = 5.6 Hz), 7.71 (d, 2H, J = 8.4 Hz), 6.97 (d, 1H, J = 2.0 Hz), 6.86 (d, 2H, J = 8.4 Hz), 5.96 (d, 1H, J = 5.6 Hz), 4.75-4.74 (m, 1H), 4.08 (q, 2H, J = 7.2 Hz), 3.71-3.68 (m, 2H), 3.59-3.58 (m, 4H), 3.43-3.40 (m, 4H), 3.35-3.30 (m, 1H), 2.95-2.90 (m, 2H), 1.21 (d, 3H, J = 7.2 Hz), 0.88 (d, 2H, J = 6.4 Hz). |
| 237 | 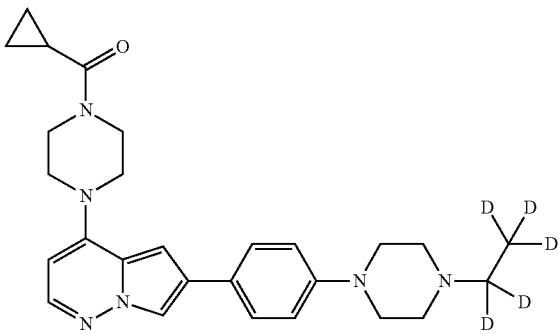 [SMILES: [2H]C([2H])([2H])C([2H])([2H])N1CCN(c2ccc(-c3cc4c(N5CCN(C(=O)C6CC6)CC5)ccnn4c3)cc2)CC1] | 464 | 1H-NMR (400 MHz, 6d-DMSO) δ ppm 8.06 (s, 1H), 7.87 (d, 1H, J = 5.6 Hz), 7.65 (d, 2H, J = 8.4 Hz), 7.00-6.90 (m, 3H), 5.95 (d, 1H, J = 5.6 Hz), 4.00-3.85 (m, 2H), 3.75-3.60 (m, 2H), 3.58-3.48 (m, 2H), 3.47-3.40 (m, 2H), 3.20-3.00 (m, 4H), 2.48-2.40 (m, 4H), 2.10-1.90 (m, 1H), 0.80-0.65 (m, 4H). |

TABLE 1-continued

| # | Structure | LCMS (M + 1) | NMR |
|---|-----------|--------------|-----|
| 238 | 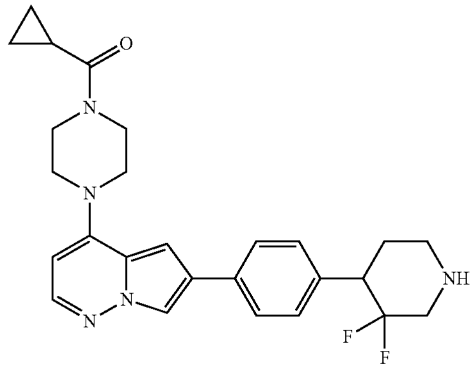 [SMILES: O=C(C1CC1)N1CCN(c2ccnn3cc(-c4ccc(C5CCNCC5(F)F)cc4)cc23)CC1] | 466 | 1H-NMR (400 MHz, DMSO-d6) δ ppm 8.17 (d, 1H, J = 1.6 Hz), 7.90 (d, 1H, J = 4.2 Hz), 7.76 (d, 2H, J = 8.4 Hz), 7.30 (d, 2H, J = 8.0 Hz), 7.05 (s, 1H), 5.96 (d, 1H, J = 4.2 Hz), 3.92 (br. s., 2H), 3.70 (br. s., 2H), 3.54 (br. s., 2H), 3.47 (br. s., 2H), 3.26-3.08 (m, 3H), 3.01-2.98 (m, 1H), 2.89-2.77 (m, 1H), 2.65-2.59 (m, 1H), 2.05-1.96 (m, 2H), 1.79-1.75 (m, 1H), 0.77-0.74 (m, 4H). |
| 239 | 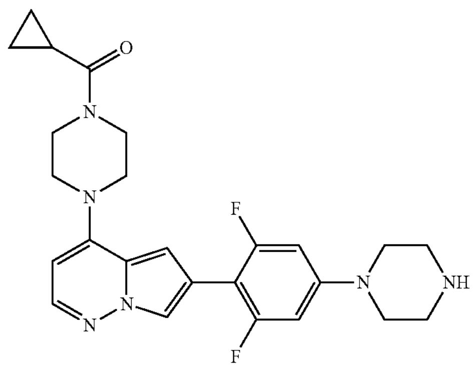 [SMILES: O=C(C1CC1)N1CCN(c2ccnn3cc(-c4c(F)cc(N5CCNCC5)cc4F)cc23)CC1] | 467 | 1H-NMR (400 MHz, 6d-DMSO) δ ppm 7.94 (d, 1H, J = 5.6 Hz), 7.89 (d, 1H, J = 1.2 Hz), 6.83 (d, 1H, J = 1.2 Hz), 6.73 (d, 2H, J = 12.8 Hz), 3.95-3.90 (m, 2H), 3.70-3.65 (m, 2H), 3.57-3.52 (m, 2H), 3.47-3.43 (m, 2H), 3.15-3.12 (m, 4H), 2.82-2.79 (m, 4H), 2.03-1.99 (m, 1H), 0.78-0.73 (m, 4H). |
| 240 | 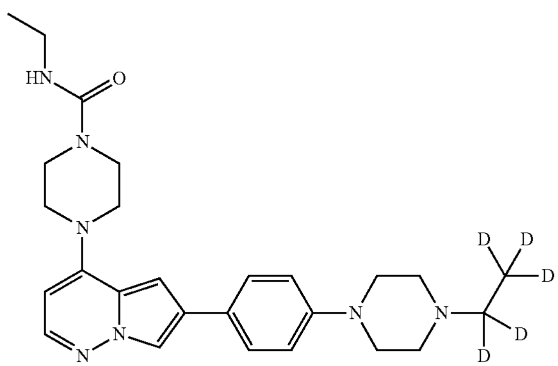 [SMILES: [2H]C([2H])([2H])C([2H])([2H])N1CCN(c2ccc(-c3cc4c(N5CCN(C(=O)NCC)CC5)ccnn4c3)cc2)CC1] | 467 | 1H-NMR (400 MHz, 6d-DMSO) δ ppm 8.05 (d, 1H, J = 1.6 Hz), 7.85 (d, 1H, J = 5.2 Hz), 7.64 (d, 2H, J = 8.4 Hz), 6.94 (d, 2H, J = 8.4 Hz), 6.91 (d, 1H, J = 1.6 Hz), 6.60 (t, 1H, J = 5.2 Hz), 5.96 (d, 1H, J = 5.2 Hz), 3.60-3.46 (m, 4H), 3.44-3.36 (m, 4H), 3.20-3.12 (m, 4H), 3.06 (quintet, 2H, J = 6.8 Hz), 2.48-2.40 (m, 4H), 1.02 (d, 3H, J = 7.2 Hz). |
| 241 | 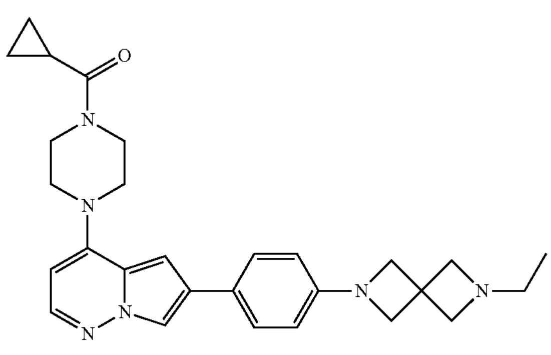 [SMILES: CCN1CC2(C1)CN(c1ccc(-c3cc4c(N5CCN(C(=O)C6CC6)CC5)ccnn4c3)cc1)C2] | 471 | 1H-NMR (400 MHz, CDCl3) δ ppm 7.85 (d, 1H, J = 2.0 Hz), 7.82 (d, 1H, J = 5.2 Hz), 7.52 (d, 2H, J = 8.4 Hz), 6.63 (d, 1H, J = 2.0 Hz), 6.50 (d, 2H, J = 8.8 Hz), 5.83 (d, 1H, J = 5.2 Hz), 4.07-4.02 (m, 4H), 3.95-3.92 (m, 2H), 3.90-3.85 (m, 2H), 3.80-3.75 (m, 4H), 3.56-3.52 (m, 2H), 3.48-3.44 (m, 2H), 2.79 (q, 2H, J = 7.2 Hz), 1.80-1.75 (m, 1H), 1.16 (t, 3H, J = 7.2 Hz), 1.06-1.03 (m, 2H), 0.84-0.81 (m, 2H). |

TABLE 1-continued

| # | Structure | LCMS (M + 1) | NMR |
|---|---|---|---|
| 242 | 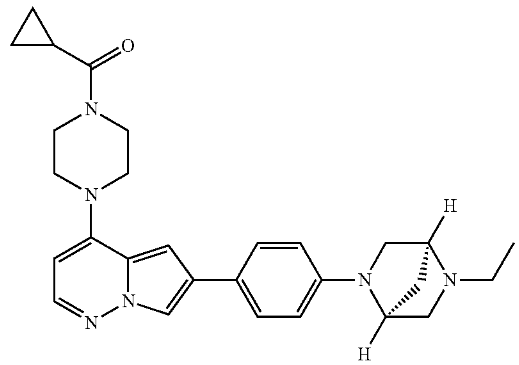 [SMILES: CCN1C[C@@H]2C[C@H]1CN2c1ccc(-c2cc3c(N4CCN(C(=O)C5CC5)CC4)ccnn3c2)cc1] | 471 | 1H-NMR (400 MHz, 6d-DMSO) δ ppm 8.01 (d, 1H, J = 1.6 Hz), 7.85 (d, 1H, J = 5.6 Hz), 7.57 (d, 2H, J = 8.8 Hz), 6.88 (d, 1H, J = 1.6 Hz), 6.59 (d, 2H, J = 8.8 Hz), 5.95 (d, 1H, J = 5.6 Hz), 4.35-4.30 (m, 1H), 3.95-3.85 (m, 2H), 3.75-3.65 (m, 2H), 3.60-.40 (m, 5H), 3.16-3.14 (m, 1H), 2.84-2.82 (m, 1H), 2.45-2.35 (m, 4H), 2.05-1.95 (m, 1H), 1.80 (q, 2H, J = 7.2 Hz), 0.93 (t, 3H, J = 7.2 Hz), 0.80-0.71 (m, 4H). |
| 243 | 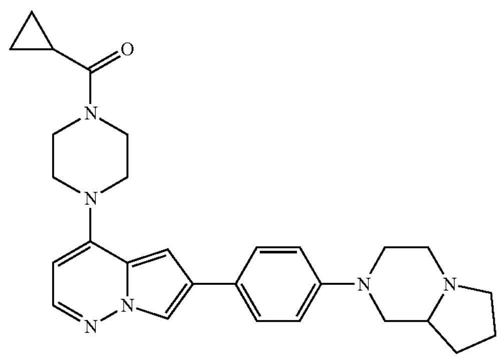 [SMILES: O=C(C1CC1)N1CCN(c2ccnn3cc(-c4ccc(N5CCN6CCCC6C5)cc4)cc23)CC1] | 471 | 1H-NMR (400 MHz, 6d-DMSO) δ ppm 8.24 (br s., 1H), 8.06 (d, 1H, J = 1.6 Hz), 7.87 (d, 1H, J = 5.2 Hz), 7.64 (d, 2H, J = 8.8 Hz), 6.97 (d, 2H, J = 8.8 Hz), 6.93 (d, 1H, J = 1.6 Hz), 5.95 (d, 1H, J = 5.2 Hz), 3.96-3.90 (m, 2H), 3.82-3.64 (m, 8H), 3.08-3.00 (m, 2H), 2.78-2.71 (m, 1H), 2.41 (t, 1H, J = 10.4 Hz), 2.27-2.21 (m, 1H), 2.11-2.00 (m, 3H), 1.86-1.80 (m, 1H), 1.76-1.66 (m, 2H), 1.43-1.32 (m, 1H), 0.78-0.74 (m, 4H). |
| 244 | 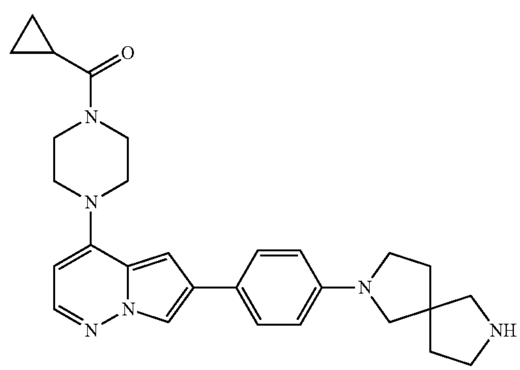 [SMILES: O=C(C1CC1)N1CCN(c2ccnn3cc(-c4ccc(N5CCC6(CCNC6)C5)cc4)cc23)CC1] | 471 | 1H-NMR (400 MHz, 6d-DMSO) δ ppm 8.37 (s, 1H), 8.02 (d, 1H, J = 2.0 Hz), 7.86 (d, 1H, J = .2 Hz), 7.63 (d, 2H, J = 8.8 Hz), 6.90 (d, 1H, J = 2.0 Hz), 6.54 (d, 2H, J = 8.8 Hz), 5.96 (d, 1H, J = 5.60 Hz), 3.92-3.91 (m, 2H), 3.71-3.70 (m, 2H), 3.52-3.49 (m, 2H), 3.47-3.44 (m, 2H), 3.35 (t, 2H, J = 7.2 Hz), 3.31-3.30 (m, 1H), 3.24-3.20 (m, 2H), 3.16 (t, 2H, J = 7.2 Hz), 3.01-3.00 (m, 2H), 205-1.97 (m, 3H), 1.88-1.85 (m, 2H), 0.78-0.74 (m, 4H). |
| 245 | 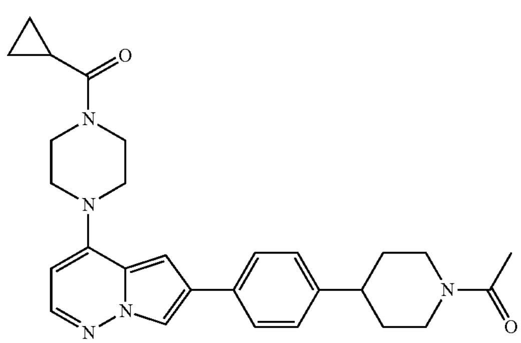 [SMILES: CC(=O)N1CCC(c2ccc(-c3cc4c(N5CCN(C(=O)C6CC6)CC5)ccnn4c3)cc2)CC1] | 472 | 1H-NMR (400 MHz, DMSO-d6) δ ppm 8.15 (d, 1H, J = 1.6 Hz), 7.89 (d, 1H, J = 5.6 Hz), 7.73 (d, 2H, J = 8.0 Hz), 7.26 (d, 2H, J = 8.0 Hz), 7.03 (d, 1H, J = 1.6 Hz), 5.97 (d, 1H, J = 5.6 Hz), 4.55-4.52 (m, 1H), 3.93-3.91 (m, 3H), 3.70 (br. s., 2H), 3.53-3.47 (m, 4H), 3.15-3.09 (m, 1H), 2.78-2.73 (m, 1H), 2.61-2.50 (m, 1H), 2.04-2.00 (m, 4H), 1.82-1.76 (m, 2H), 1.63-1.59 (m, 1H), 1.47-1.43 (m, 1H), 0.77-0.74 (m, 4H). |

TABLE 1-continued

| # | Structure | LCMS (M + 1) | NMR |
|---|---|---|---|
| 246 | 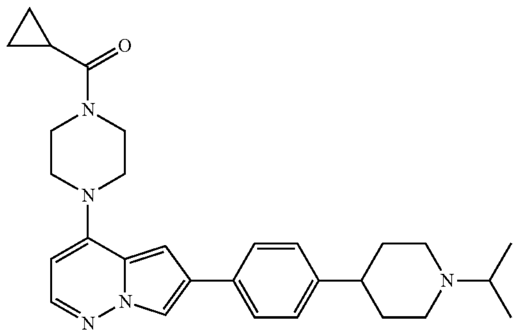 [SMILES: CC(C)N1CCC(c2ccc(-c3cc4c(N5CCN(C(=O)C6CC6)CC5)ccnn4c3)cc2)CC1] | 472 | 1H-NMR (400 MHz, 6d-DMSO) δ ppm 8.14 (d, 1H, J = 1.2 Hz), 7.89 (d, 1H, J = 5.6 Hz), 7.72 (d, 2H, J = 8.0 Hz), 7.25 (d, 2H, J = 8.0 Hz), 7.01 (d, 1H, J = 1.2 Hz), 5.96 (d, 1H, J = 5.6 Hz), 3.95-3.90 (m, 2H), 3.72-3.68 (m, 2H), 3.55-3.50 (m, 2H), 3.47-3.42 (m, 2H), 2.89-2.85 (m, 2H), 2.73-2.67 (m, 1H), 2.46-2.42 (m, 1H), 2.21 (t, 2H, J = 3.2 Hz), 2.05-1.98 (m, 1H), 1.77-1.74 (m, 2H), 1.67-1.55 (m, 2H), 0.98 (d, 6H, J = 6.8 Hz), 0.80-0.71 (m, 4H). |
| 247 | 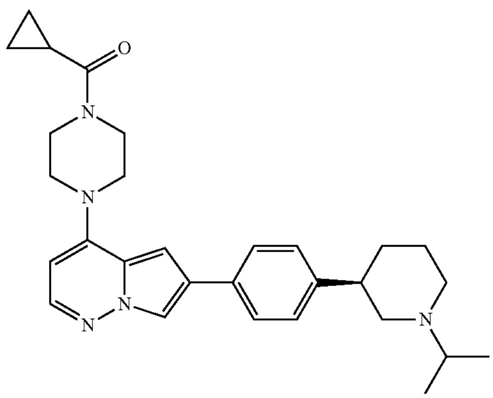 [SMILES: CC(C)N1CCC[C@H](c2ccc(-c3cc4c(N5CCN(C(=O)C6CC6)CC5)ccnn4c3)cc2)C1] | 472 | 1H-NMR (400 MHz, 6d-DMSO) δ ppm 8.15 (d, 1H, J = 1.6 Hz), 7.90 (d, 1H, J = 5.2 Hz), 7.72 (d, 2H, J = 8.0 Hz), 7.27 (d, 2H, J = 8.0 Hz), 7.02 (d, 1H, J = 1.6 Hz), 5.97 (d, 1H, J = 5.2 Hz), 3.93-3.92 (m, 2H), 3.71-3.70 (m, 2H), 3.54-3.50 (m, 2H), 3.49-3.43 (m, 2H), 2.81-2.79 (m, 2H), 2.74-2.10 (m, 1H), 2.67-2.63 (m, 1H), 2.19-2.14 (m, 2H), 2.04-2.00 (m, 1H), 1.81-1.80 (m, 1H), 1.71-170 (m, 1H), 1.59-1.50 (m, 1H), 1.45-1.30 (m, 1H), 0.98-0.92 (m, 6H), 0.79-0.74 (m, 4H). |
| 248 | 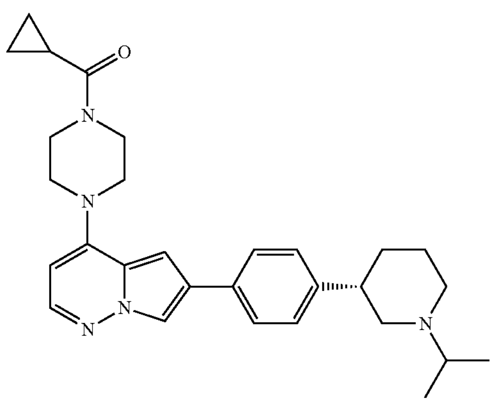 [SMILES: CC(C)N1CCC[C@@H](c2ccc(-c3cc4c(N5CCN(C(=O)C6CC6)CC5)ccnn4c3)cc2)C1] | 472 | 1H-NMR (400 MHz, 6d-DMSO) δ ppm 8.15 (d, 1H, J = 1.6 Hz), 7.90 (d, 1H, J = 5.2 Hz), 7.72 (d, 2H, J = 8.0 Hz), 7.27 (d, 2H, J = 8.0 Hz), 7.02 (d, 1H, J = 1.6 Hz), 5.97 (d, 1H, J = 5.2 Hz), 3.93-3.92 (m, 2H), 3.71-3.70 (m, 2H), 3.54-3.50 (m, 2H), 3.49-3.43 (m, 2H), 2.81-2.79 (m, 2H), 2.74-2.10 (m, 1H), 2.67-2.63 (m, 1H), 2.19-2.14 (m, 2H), 2.04-2.00 (m, 1H), 1.81-1.80 (m, 1H), 1.71-170 (m, 1H), 1.59-1.50 (m, 1H), 1.45-1.30 (m, 1H), 0.98-0.92 (m, 6H), 0.79-0.74 (m, 4H). |
| 249 | 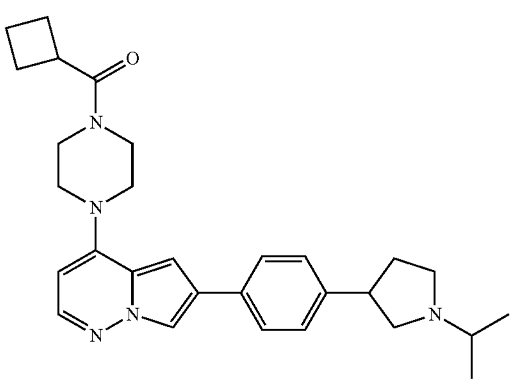 [SMILES: CC(C)N1CCC(c2ccc(-c3cc4c(N5CCN(C(=O)C6CCC6)CC5)ccnn4c3)cc2)C1] | 472 | 1H-NMR (400 MHz, 6d-DMSO) δ ppm 8.13 (d, 1H, J = 1.6 Hz), 7.89 (d, 1H, J = 5.6 Hz), 7.71 (d, 2H, J = 8.4 Hz), 7.28 (d, 2H, J = 8.4 Hz), 6.99 (d, 1H, J = 1.6 Hz), 5.96 (d, 1H, J = 5.6 Hz), 3.70-3.64 (m, 2H), 3.60-3.54 (m, 2H), 3.45-3.40 (m, 4H), 3.40-3.38 (m, 1H), 3.30-3.28 (m, 1H), 2.98 (t, 1H, J = 8.0 Hz), 2.75-2.71 (m, 1H), 2.70-2.67 (m, 1H), 2.50-2.45 (m, 1H), 2.44-2.38 (m, 1H), 2.25-2.20 (m, 3H), 2.19-2.11 (m, 2H), 1.90-1.92 (m, 1H), 1.74-1.77 (m, 2H), 1.05 (t, 6H, J = 6.4 Hz). |

TABLE 1-continued

| # | Structure | LCMS (M + 1) | NMR |
|---|---|---|---|
| 250 | 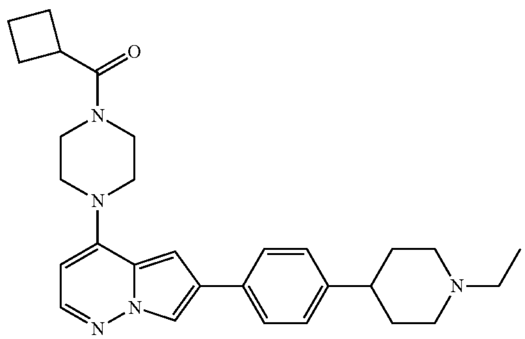 [SMILES: CCN1CCC(c2ccc(-c3cc4c(N5CCN(C(=O)C6CCC6)CC5)ccnn4c3)cc2)CC1] | 472 | 1H-NMR (400 MHz, 6d-DMSO) δ ppm 8.16 (d, 1H, J = 1.6 Hz), 7.90 (d, 1H, J = 5.6 Hz), 7.74 (d, 2H, J = 8.4 Hz), 7.26 (d, 2H, J = 8.4 Hz), 7.01 (d, 1H, J = 1.6 Hz), 5.97 (d, 1H, J = 5.6 Hz), 3.69-3.66 (m, 2H), 3.57-3.54 (m, 2H), 3.46-3.42 (m, 4H), 3.40-3.33 (m, 2H), 3.10-3.00 (m, 2H), 2.58-2.50 (m, 2H), 2.19 (q, 2H, J = 7.2 Hz), 2.20-2.11 (m, 4H), 1.98-1.86 (m, 1H), 1.83-1.73 (m, 4H), 1.72-1.69 (m, 1H), 1.08 (t, 3H, J = 7.2 Hz). |
| 251 | 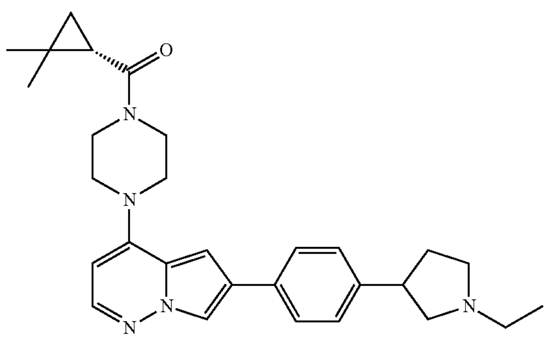 [SMILES: CCN1CCC(c2ccc(-c3cc4c(N5CCN(C(=O)[C@H]6CC6(C)C)CC5)ccnn4c3)cc2)C1] | 472 | 1H-NMR (400 MHz, 6d-DMSO) δ ppm 8.14 (s, 1H), 7.89 (d, 1H, J = 5.2 Hz), 7.72 (d, 2H, J = 8.4 Hz), 7.28 (d, 2H, J = 8.4 Hz), 7.02 (s, 1H), 5.97 (d, 1H, J = 5.2 Hz), 3.86-3.82 (m, 1H), 3.80-3.71 (m, 2H), 3.68-3.61 (m, 2H), 3.47-3.43 (m, 2H), 3.31-3.26 (m, 3H), 2.93-2.89 (m, 1H), 2.68-2.61 (m, 2H), 2.47-2.40 (m, 2H), 2.24-2.20 (m, 1H), 1.78-1.72 (m, 2H), 1.19 (s, 3H), 1.05 (t, 3H, J = 6.8 Hz), 0.97 (s, 3H), 0.96-0.93 (m, 1H), 0.68-0.65 (m, 1H). |
| 252 | 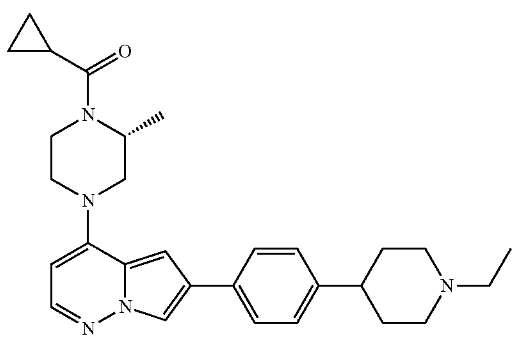 [SMILES: CCN1CCC(c2ccc(-c3cc4c(N5CCN(C(=O)C6CC6)[C@H](C)C5)ccnn4c3)cc2)CC1] | 472 | 1H-NMR (400 MHz, 6d-DMSO) δ ppm 8.31 (s, 1H), 8.14 (d, 1H, J = 1.6 Hz), 7.88 (d, 1H, J = 5.6 Hz), 7.71 (d, 2H, J = 8.0 Hz), 7.25 (d, 2H, J = 8.0 Hz), 6.94 (d, 1H, J = 1.6 Hz), 5.95 (d, 1H, J = 5.6 Hz), 4.65-4.64 (m, 1H), 4.20-4.16 (m, 1H), 3.94-3.87 (m, 2H), 3.75-3.63 (m, 1H), 3.25-3.23 (m, 2H), 3.01-2.98 (m, 2H), 2.54-2.49 (m, 1H), 2.38 (q, 2H, J = 7.2 Hz), 2.02-1.96 (m, 3H), 1.77-1.70 (m, 2H), 1.70-1.64 (m, 2H), 1.41-1.23 (m, 2H), 1.02 (t, 2H, J = 7.2 Hz), 0.81-0.71 (m, 4H). |
| 253 | 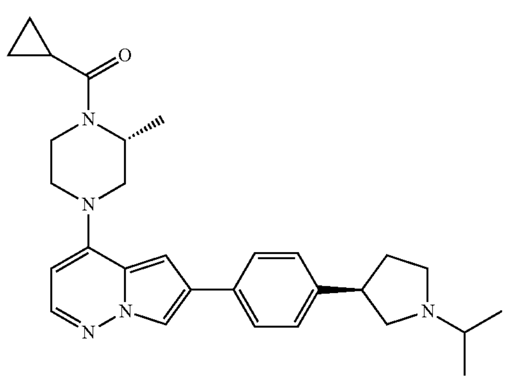 [SMILES: CC(C)N1CC[C@H](c2ccc(-c3cc4c(N5CCN(C(=O)C6CC6)[C@H](C)C5)ccnn4c3)cc2)C1] | 472 | 1H-NMR (400 MHz, 6d-DMSO) δ ppm 8.16 (s, 1H), 7.87 (d, 1H, J = 5.6 Hz), 7.73 (d, 2H, J = 7.2 Hz), 7.33 (d, 2H, J = 7.2 Hz), 6.95 (s, 1H), 5.94 (d, 1H, J = 5.2 Hz), 4.68-4.62 (m, 1H), 4.22-4.14 (m, 1H), 3.97-3.84 (m, 2H), 3.74-3.50 (m, 2H), 3.30-3.00 (m, 4H), 2.47-2.40 (m, 2H), 2.35-2.25 (m, 1H), 2.05-1.95 (m, 1H), 1.90-1.83 (m, 1H), 1.45-1.10 (m, 3H), 1.00 (m, 6H), 0.82-0.70 (m, 4H). |

TABLE 1-continued

| # | Structure | LCMS (M + 1) | NMR |
|---|---|---|---|
| 254 | 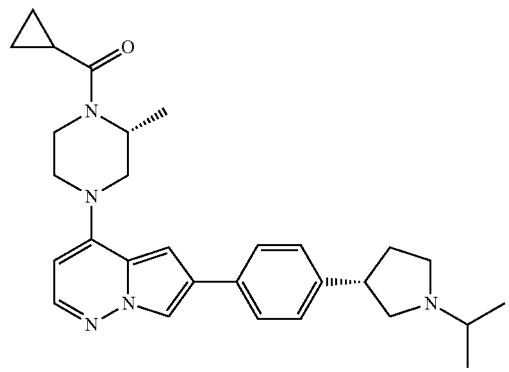 [SMILES: CC(C)N1CC[C@@H](c2ccc(-c3cc4c(N5CCN(C(=O)C6CC6)[C@H](C)C5)ccnn4c3)cc2)C1] | 472 | 1H NMR (400 MHz, 6d-DMSO) δ ppm 8.14 (d, 1H, J = 1.2 Hz), 7.87 (d, 1H, J = 5.6 Hz), 7.70 (d, 2H, J = 8.0 Hz), 7.30 (d, 2H, J = 8.0 Hz), 6.94 (d, 1H, J = 1.6 Hz), 5.94 (d, 1H, J = 5.6 Hz), 4.65-4.64 (m, 1H), 4.19-4.16 (m, 1H), 3.95-3.92 (m, 2H), 3.30-3.24 (m, 3H), 2.99-2.97 (m, 1H), 2.72-2.71 (m, 2H), 2.49-2.39 (m, 3H), 2.23-2.22 (m, 1H), 2.00-1.97 (m, 1H), 1.78-1.75 (m, 1H), 1.43-1.38 (m, 3H), 1.07-1.03 (m, 6H), 0.75-0.74 (m, 4H). |
| 255 | 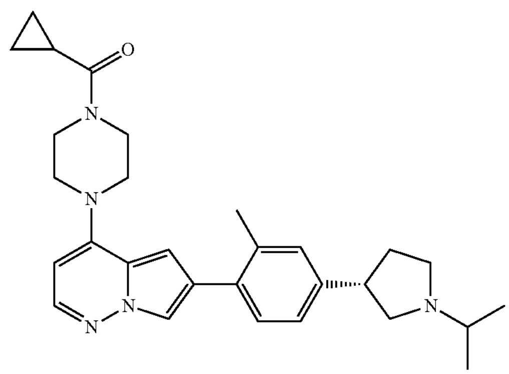 [SMILES: Cc1cc([C@@H]2CCN(C(C)C)C2)ccc1-c1cc2c(N3CCN(C(=O)C4CC4)CC3)ccnn2c1] | 472 | 1H-NMR (400 MHz, 6d-DMSO) δ ppm 7.93 (d, 1H, J = 5.6 Hz), 7.87 (s, 1H), 7.41 (d, 1H, J = 7.2 Hz), 7.20 (s, 1H), 7.17 (d, 1H, J = 7.2 Hz), 6.77 (d, 1H, J = 1.6 Hz), 6.00 (d, 1H, J = 5.6 Hz), 4.00-3.80 (m, 2H), 3.75-3.60 (m, 2H), 3.60-3.50 (m, 2H), 3.50-3.40 (m, 2H), 3.35-3.30 (m, 2H), 3.20-2.99 (m, 2H), 2.80-2.60 (m, 2H), 2.43 (s, 3H), 2.33-2.18 (m, 1H), 2.06-1.94 (m, 1H), 1.89-1.70 (m, 1H), 1.21-0.92 (m, 6H), 0.83-0.71 (m, 4H). |
| 256 | 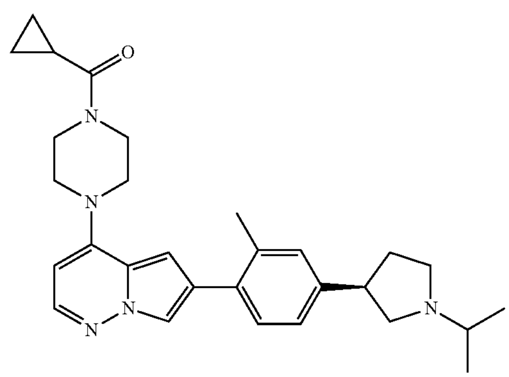 [SMILES: Cc1cc([C@H]2CCN(C(C)C)C2)ccc1-c1cc2c(N3CCN(C(=O)C4CC4)CC3)ccnn2c1] | 472 | 1H-NMR (400 MHz, 6d-DMSO) δ ppm 7.94 (d, 1H, J = 5.6 Hz), 7.89 (d, 1H, J = 1.6 Hz), 7.48 (d, 1H, J = 8.0 Hz), 7.28 (s, 1H), 7.23 (d, 1H, J = 8.0 Hz), 1H), J = 6.78 (d, = 1.6 Hz), 6.00 (d, 1H, J = 5.6 Hz), 3.95-3.90 (m, 2H), 3.75-3.70 (m, 2H), 3.60-3.53 (m, 2H), 3.50-3.40 (m, 2H), 3.35-3.30 (m, 4H), 3.30-3.00 (m, 1H), 2.45 (s, 3H), 2.45-2.25 (m, 2H), 2.20-1.91 (m, 2H), 1.30-0.14 (m, 6H), 0.83-0.71 (m, 4H). |
| 257 | 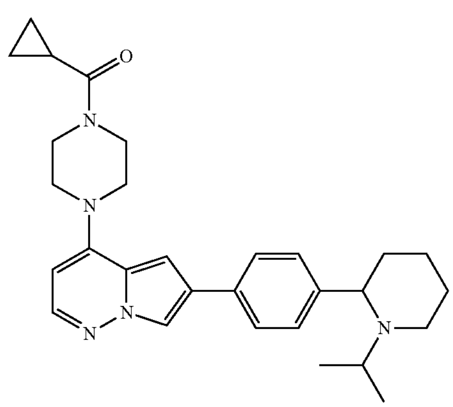 [SMILES: CC(C)N1CCCCC1c1ccc(-c2cc3c(N4CCN(C(=O)C5CC5)CC4)ccnn3c2)cc1] | 473 | 1H NMR (400 MHz, DMSO-d6) δ 8.13 (d, J = 1.8 Hz, 1H), 7.89 (d, J = 5.4 Hz, 1H), 7.72 (d, J = 7.8 Hz, 2H), 7.30 (t, J = 7.8 Hz, 2H), 7.02 (d, J = 1.8 Hz, 1H), 5.97 (d, J = 5.5 Hz, 1H), 3.92 (s, 1H), 3.70 (s, 2H), 3.60-3.43 (m, 6H), 2.91 (d, J = 11.4 Hz, 1H), 2.74 (q, J = 6.7 Hz, 1H), 2.20-2.06 (m, 1H), 2.01 (tt, J = 7.9, 3.8 Hz, 1H), 1.67 (dt, J = 25.8, 13.4 Hz, 3H), 1.47 (t, J = 11.7 Hz, 1H), 0.93 (d, J = 7.1 Hz, 4H), 0.83-0.66 (m, 8H). |

TABLE 1-continued

| # | Structure | LCMS (M + 1) | NMR |
|---|---|---|---|
| 258 | 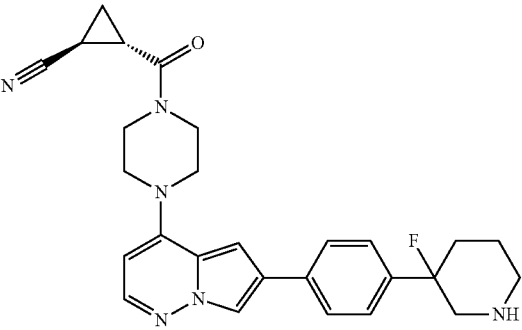 [SMILES: N#C[C@H]1C[C@@H]1C(=O)N1CCN(c2ccnn3cc(-c4ccc(C5(F)CCCNC5)cc4)cc23)CC1] | 473 | 1H-NMR (400 MHz, 6d-DMSO) δ ppm 8.24 (s, 1H), 7.92 (d, 1H, J = 5.2 Hz), 7.86 (d, 2H, J = 7.6 Hz), 7.46 (d, 2H, J = 7.6 Hz), 7.11 (s, 1H), 6.00 (d, 1H, J = 5.2 Hz), 4.10-3.90 (m, 2H), 3.80-3.57 (m, 2H), 3.70-3.57 (m, 2H), 3.55-3.48 (m, 2H), 3.40-3.35 (m, 2H), 3.25-3.20 (m, 1H), 3.10-3.00 (m, 1H), 2.95-2.90 (m, 1H), 2.81-2.74 (m, 1H), 2.20-2.08 (m, 2H), 2.05-1.97 (m, 2H), 1.93-1.78 (m, 1H), 1.74-1.62 (m, 1H), 1.50-1.43 (m, 1H), 1.40-1.28 (m, 1H). |
| 259 | 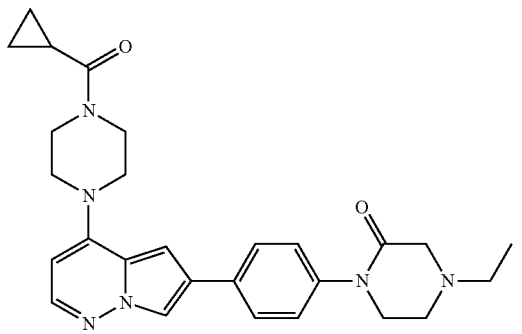 [SMILES: CCN1CCN(c2ccc(-c3cc4c(N5CCN(C(=O)C6CC6)CC5)ccnn4c3)cc2)C(=O)C1] | 473 | 1H-NMR (400 MHz, 6d-DMSO) δ ppm 8.17 (d, 1H, J = 1.6 Hz), 7.89 (d, 1H, J = 5.2 Hz), 7.81 (d, 2H, J = 8.0 Hz), 7.32 (d, 2H, J = 8.4 Hz), 7.05 (d, 1H, J = 1.6 Hz), 5.97 (d, 1H, J = 5.2 Hz), 3.91 (br. s, 2H), 3.70-3.65 (m, 2H), 3.55-3.50 (m, 4H), 3.48-3.45 (m, 2H), 3.14 (s, 2H), 2.76 (t, 2H, J = 5.2 Hz), 2.44 (q, 2H, J = 7.6 Hz), 1.99 (quintet, 1H, J = 5.2 Hz), 1.04 (t, 3H, J = 7.6 Hz), 0.77-0.72 (m, 4H). |
| 260 | 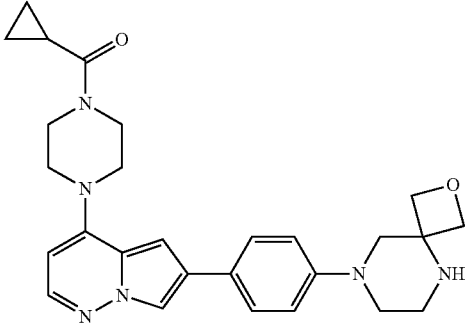 [SMILES: O=C(C1CC1)N1CCN(c2ccnn3cc(-c4ccc(N5CCNC6(COC6)C5)cc4)cc23)CC1] | 473 | 1H-NMR (400 MHz, 6d-DMSO) δ ppm 8.08 (d, 1H, J = 1.2 Hz), 7.87 (d, 1H, J = 5.2 Hz), 7.67 (d, 2H, J = 8.8 Hz), 7.01 (d, 2H, J = 8.8 Hz), 6.95 (d, 1H, J = 1.2 Hz), 5.95 (d, 1H, J = 5.2 Hz), 4.40-4.30 (m, 4H), 4.00-3.80 (m, 2H), 3.78-3.62 (m, 2H), 3.58-3.50 (m, 2H), 3.48-3.42 (m, 2H), 3.26-3.20 (m, 2H), 3.05-2.95 (m, 2H), 2.80-2.75 (m, 2H), 2.10-1.90 (m, 1H), 0.80-0.60 (m, 4H). |
| 261 | 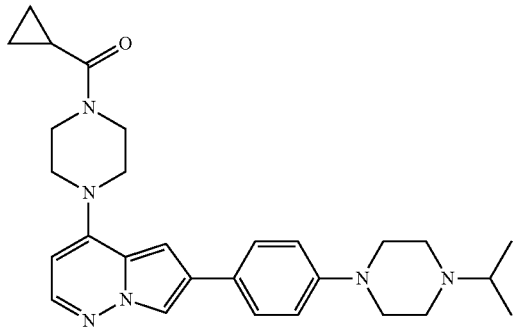 | 473 | 1H-NMR (400 MHz, CDCl3) δ ppm 7.88 (s, 1H), 7.83 (d, 1H, J = 5.2 Hz), 7.56 (d, 2H, J = 8.8 Hz), 6.98 (d, 2H, J = 8.4 Hz), 6.63 (s, 1H), 5.83 (d, 1H, J = 5.2 Hz), 3.94-3.89 (m, 4H), 3.55-3.47 (m, 4H), 3.31-3.28 (m, 4H), 2.80-2.74 (m, 5H), 1.82-1.75 (m, 1H), 1.15 (d, 6H, J = 5.2 Hz), 1.06-1.03 (m, 2H), 0.85-0.81 (m, 2H). |

TABLE 1-continued

| # | Structure | LCMS (M + 1) | NMR |
|---|---|---|---|
| 262 | 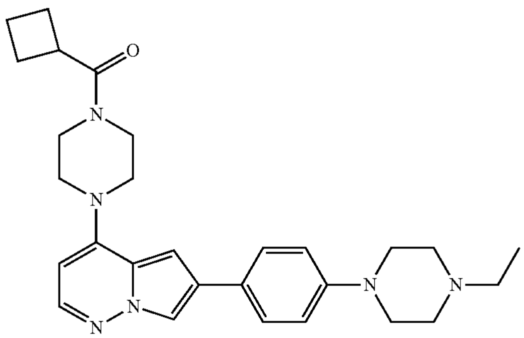 [SMILES: CCN1CCN(c2ccc(-c3cc4c(N5CCN(C(=O)C6CCC6)CC5)ccnn4c3)cc2)CC1] | 473 | 1H-NMR (500 MHz, DMSO-d6) δ ppm 8.06 (s, 1H), 7.86 (d, 1H, J = 5.5 Hz), 7.66-7.64 (m, 2H), 6.96-6.92 (m, 3H), 5.94 (d, 1H, J = 5.0 Hz), 3.68-3.66 (m, 2H), 3.56-3.54 (m, 2H), 3.45-3.39 (m, 6H), 3.32-3.30 (m, 2H), 3.18-3.14 (m, 4H), 2.43-2.34 (m, 2H), 2.24-2.11 (m, 5H), 1.94-1.89 (m, 1H), 1.79-1.75 (m, 1H), 1.04 (t, 3H, J = 7.0 Hz). |
| 263 | 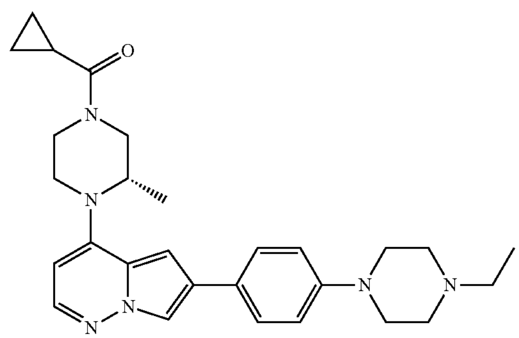 [SMILES: CCN1CCN(c2ccc(-c3cc4c(N5CCN(C(=O)C6CC6)C[C@@H]5C)ccnn4c3)cc2)CC1] | 473 | 1H-NMR (400 MHz, 6d-DMSO) δ ppm 8.04 (d, 1H, J = 1.2 Hz), 7.84 (d, 1H, J = 5.2 Hz), 7.64 (d, 2H, J = 8.8 Hz), 6.95 (d, 2H, J = 8.8 Hz), 6.94 (s, 1H), 5.93 (d, 1H-J = 5.2 Hz), 4.53-4.10 (m, 3H), 3.72-3.39 (m, 6H), 3.29-2.96 (m, 6H), 2.36 (q, 2H, J = 7.2 Hz), 2.07-1.97 (m, 1H), 1.08-0.98 (m, 3H), 1.03 (t, 3H, J = 7.2 Hz), 0.79-0.74 (m, 4H). |
| 264 | 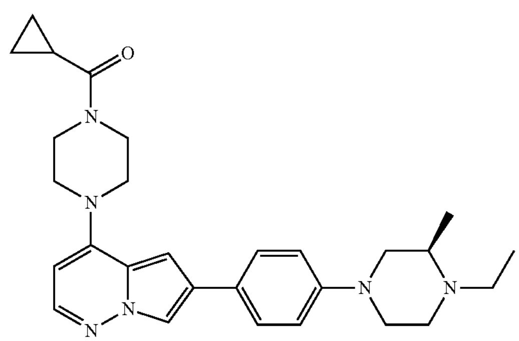 [SMILES: CCN1CCN(c2ccc(-c3cc4c(N5CCN(C(=O)C6CC6)CC5)ccnn4c3)cc2)C[C@H]1C] | 473 | 1H-NMR (400 MHz, 6d-DMSO) δ ppm 8.05 (d, 1H, J = 1.6 Hz), 7.86 (d, 1H, J = 5.6 Hz), 7.64 (d, 2H, J = 8.4 Hz), 6.94 (d, 2H, J = 8.4 Hz), 6.93 (s, 1H), 5.95 (d, 1H, J = 5.6 Hz), 3.92-3.91 (m, 2H), 3.70-3.69 (m, 2H), 3.51-3.45 (m, 6H), 2.88-2.80 (m, 1H), 2.80-2.72 (m, 2H), 2.47 (q, 2H, J = 7.2 Hz), 2.34-2.32 (m, 2H), 2.02-2.01 (m, 1H), 1.05 (d, 3H, J = 5.2 Hz), 0.98 (t, 3H, J = 7.2 Hz), 0.77-0.74 (m, 4H). |
| 265 | 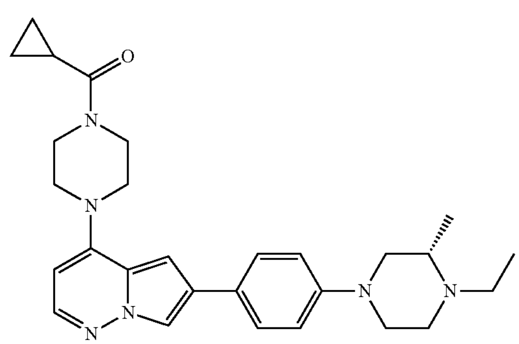 [SMILES: CCN1CCN(c2ccc(-c3cc4c(N5CCN(C(=O)C6CC6)CC5)ccnn4c3)cc2)C[C@@H]1C] | 473 | 1H-NMR (400 MHz, 6d-DMSO) δ ppm 8.05 (d, 1H, J = 1.2 Hz), 7.86 (d, 1H, J = 5.6 Hz), 7.63 (d, 2H, J = 8.8 Hz), 6.94 (d, 2H, J = 8.8 Hz), 6.93 (s, 1H), 5.94 (d, 1H, J = 6.0 Hz), 3.91-3.90 (m, 2H), 3.70-3.69 (m, 2H), 3.49-3.45 (m, 6H), 2.88-2.76 (m, 3H), 2.49-2.47 (m, 2H), 2.33-2.28 (m, 2H), 2.01-1.99 (m, 1H), 1.05 (d, 3H, J = 4.8 Hz), 0.98 (t, 3H, J = 7.2 Hz), 0.77-0.73 (m, 4H). |

TABLE 1-continued

| # | Structure | LCMS (M + 1) | NMR |
|---|---|---|---|
| 266 | 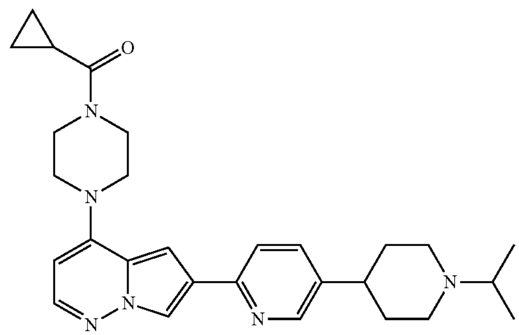 | 473 | 1H-NMR (400 MHz, 6d-DMSO) δ ppm 8.47 (d, 1H, J = 1.6 Hz), 8.27 (d, 1H, J = 1.2 Hz), 7.94-7.90 (m, 2H), 7.67 (d, 1H, J = 6.8 Hz), 7.18 (d, 1H, J = 1.6 Hz), 5.98 (d, 1H, J = 5.2 Hz), 3.97-3.94 (m, 2H), 3.73-3.69 (m, 2H), 3.60-3.55 (m, 2H), 3.54-3.49 (m, 2H), 3.34-3.28 (m, 2H), 3.01-2.90 (m, 2H), 2.88-2.81 (m, 2H), 2.06-2.00 (m, 2H), 1.99-1.91 (m, 2H), 1.23-1.15 (m, 7H), 0.79-0.73 (m, 4H). |
| 267 | 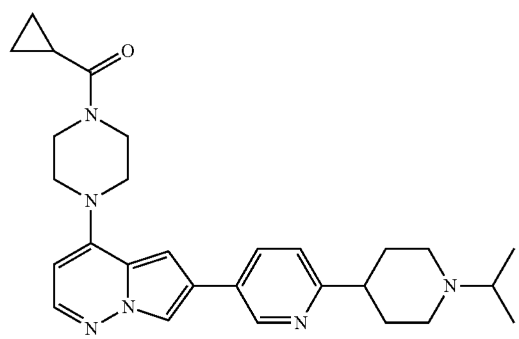 [SMILES: CC(C)N1CCC(c2ccc(-c3cc4c(N5CCN(C(=O)C6CC6)CC5)ccnn4c3)cn2)CC1] | 473 | 1H NMR (400 MHz, 6d-DMSO) δ ppm 8.97 (s, 1H), 8.27 (s, 1H), 8.11 (dd, 1H, J = 8.0, 2.0 Hz), 7.91 (d, 1H, J = 5.6 Hz), 7.29 (d, 1H, J = 8.0 Hz), 7.14 (d, 1H, J = 1.6 Hz), 5.98 (d, 1H, J = 5.6 Hz), 3.92-3.91 (m, 2H), 3.69-3.68 (m, 2H), 3.60-3.50 (m, 2H), 3.50-3.40 (m, 2H), 2.97-2.81 (m, 2H), 2.75-2.61 (m, 2H), 2.33-2.08 (m, 2H), 2.06-2.02 (m, 1H), 1.90-1.80 (m, 2H), 1.79-1.61 (m, 2H), 1.08-1.00 (m, 6H), 0.77-0.74 (m, 4H). |
| 268 | 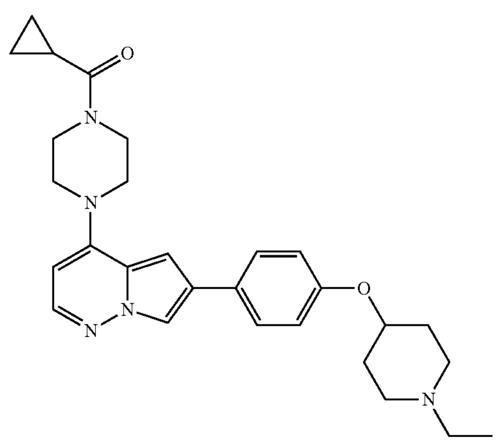 [SMILES: CCN1CCC(Oc2ccc(-c3cc4c(N5CCN(C(=O)C6CC6)CC5)ccnn4c3)cc2)CC1] | 474 | 1H-NMR (400 MHz, CDCl3) δ ppm 7.86 (d, 1H, J = 1.6 Hz), 7.82 (d, 1H, J = 5.2 Hz), 7.56 (d, 2H, J = 8.8 Hz), 6.95 (d, 2H, J = 8.8 Hz), 6.65 (d, 1H, J = 1.6 Hz), 5.82 (d, 1H, J = 5.2 Hz), 4.38 (quintet, 1H, J = 3.6 Hz), 3.99-3.90 (m, 2H), 3.90-3.75 (m, 2H), 3.60-3.50 (m, 2H), 3.50-3.40 (m, 2H), 2.83-2.72 (m, 2H), 2.50 (q, 2H, J = 7.2 Hz), 2.46-2.34 (m, 2H), 2.12-2.05 (m, 2H), 1.94-1.87 (m, 2H), 1.79-1.74 (m, 1H), 1.14 (t, 3H, J = 7.2 Hz), 1.06-1.01 (m, 2H), 0.84-0.78 (m, 2H). |
| 269 | 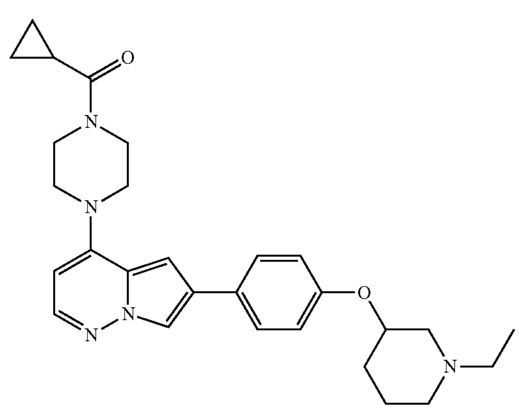 [SMILES: CCN1CCCC(Oc2ccc(-c3cc4c(N5CCN(C(=O)C6CC6)CC5)ccnn4c3)cc2)C1] | 474 | 1H-NMR (400 MHz, CDCl3) δ ppm 7.87 (d, 1H, J = 2.0 Hz), 7.83 (d, 1H, J = 5.2 Hz), 7.56 (d, 2H, J = 8.8 Hz), 6.98 (d, 2H, J = 8.8 Hz), 6.65 (d, 1H, J = 2.0 Hz), 5.83 (d, 1H, J = 5.2 Hz), 4.46 (heptet, 1H, J = 4.4 Hz), 3.97-3.90 (m, 2H), 3.90-3.85 (m, 2H), 3.60-3.50 (m, 2H), 3.50-3.38 (m, 2H), 2.88-2.78 (m, 1H), 2.52 (q, 2H, J = 7.2 Hz), 2.22-2.08 (m, 4H), 1.89-1.82 (m, 1H), 1.81-1.75 (m, 1H), 1.71-1.64 (m, 1H), 1.55-1.43 (m, 1H), 1.12 (t, 3H, J = 7.2 Hz), 1.07-1.01 (m, 2H), 0.85-0.78 (m, 2H). |

TABLE 1-continued

| # | Structure | LCMS (M + 1) | NMR |
|---|---|---|---|
| 270 | 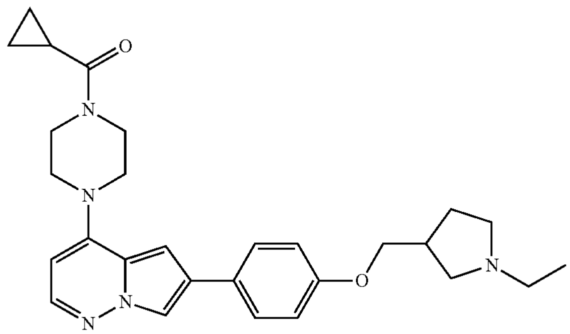 [SMILES: CCN1CCC(COc2ccc(-c3cc4c(N5CCN(C(=O)C6CC6)CC5)ccnn4c3)cc2)C1] | 474 | 1H-NMR (400 MHz, 6d-DMSO) δ ppm 8.29 (s, 1H), 8.10 (d, 1H, J = 1.6 Hz), 7.89 (d, 1H, J = 5.6 Hz), 7.73 (d, 2H, J = 8.8 Hz), 6.98 (d, 1H, J = 1.6 Hz), 6.95 (d, 2H, J = 8.8 Hz), 5.97 (d, 1H, J = 5.6 Hz), 3.92-3.89 (m, 4H), 3.71-3.70 (m, 2H), 3.54-3.50 (m, 2H), 3.48-3.43 (m, 2H), 2.76-2.73 (m, 1H), 2.70-2.65 (m, 1H), 2.65-2.62 (m, 2H), 2.60 (q, 2H, J = 7.2 Hz), 2.51-2.49 (m, 1H), 2.02-2.00 (m, 1H), 1.99-1.95 (m, 1H), 1.59-1.56 (m, 1H), 1.06 (t, 3H, J = 7.2 Hz), 0.78-0.74 (m, 4H). |
| 271 | 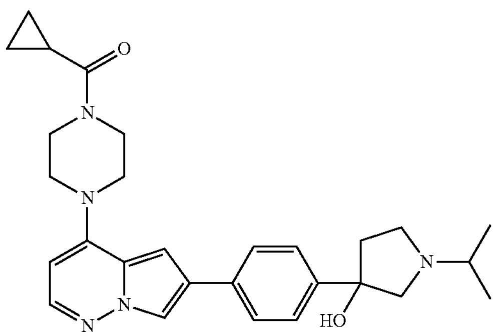 [SMILES: CC(C)N1CCC(O)(c2ccc(-c3cc4c(N5CCN(C(=O)C6CC6)CC5)ccnn4c3)cc2)C1] | 474 | 1H-NMR (400 MHz, MeOD) δ ppm 7.98 (d, 1H, J = 1.6 Hz), 7.84 (d, 1H, J = 5.2 Hz), 7.77 (d, 2H, J = 8.4 Hz), 7.56 (d, 2H, J = 8.4 Hz), 6.94 (d, 1H, J = 1.6 Hz), 6.00 (d, 1H, J = 5.2 Hz), 4.04-3.98 (m, 2H), 3.85-3.78 (m, 2H), 3.80-3.75 (m, 1H), 3.72-3.65 (m, 2H), 3.65-3.58 (m, 2H), 3.55-3.40 (m, 4H), 2.62-2.47 (m, 1H), 2.40-2.26 (m, 1H), 2.06-1.94 (m, 1H), 1.45-1.35 (m, 6H), 0.95-0.83 (m, 4H). |
| 272 | 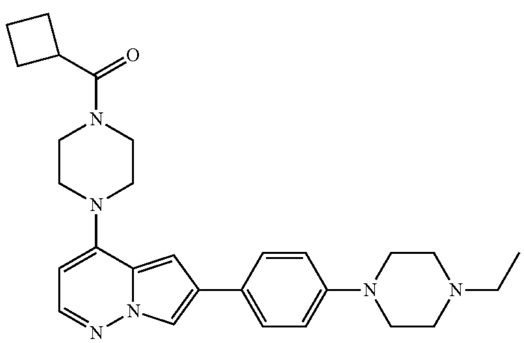 [SMILES: CCN1CCN(c2ccc(-c3cc4c(N5CCN(C(=O)C6CCC6)CC5)ccnn4c3)cc2)CC1] | 474 | 1H-NMR (400 MHz, 6d-DMSO) δ ppm 8.20 (s, 1H), 8.05 (d, 1H, J = 1.6 Hz), 7.86 (d, 1H, J = 4.8 Hz), 7.64 (d, 2H, J = 8.4 Hz), 6.95 (d, 2H, J = 8.4 Hz), 6.91 (d, 1H, J = 1.6 Hz), 5.94 (d, 1H, J = 5.2 Hz), 3.94 (t, 4H, J = 7.6 Hz), 3.45-3.38 (m, 10H), 3.17-3.15 (m, 6H), 2.38 (q, 2H, J = 7.2 Hz), 2.17 (quintet, 2H, J = 7.6 Hz), 1.04 (t, 3H, J = 7.2 Hz). |
| 273 | 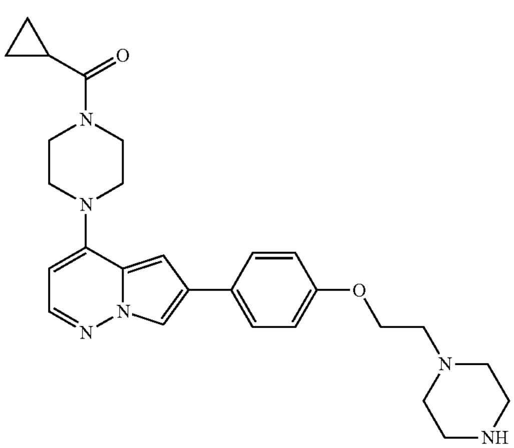 [SMILES: O=C(C1CC1)N1CCN(c2ccnn3cc(-c4ccc(OCCN5CCNCC5)cc4)cc23)CC1] | 475 | 1H-NMR (400 MHz, DMSO-d6) δ ppm 8.11 (d, 1H, J = 1.6 Hz), 7.89 (d, 1H, J = 5.2 Hz), 7.75-7.73 (m, 2H), 6.99-6.96 (m, 3H), 5.97 (d, 1H, J = 5.6 Hz), 4.11 (d, 1H, J = 5.6 Hz), 3.92 (br. s., 2H), 3.70 (br. s., 3H), 3.52-3.45 (m, 4H), 2.95 (br. s., 4H), 2.74 (t, 2H, J = 5.6 Hz), 2.61 (br. s., 4H), 2.06-1.99 (m, 1H), 0.78-0.75 (m, 4H). |

TABLE 1-continued

| # | Structure | LCMS (M + 1) | NMR |
|---|---|---|---|
| 274 | 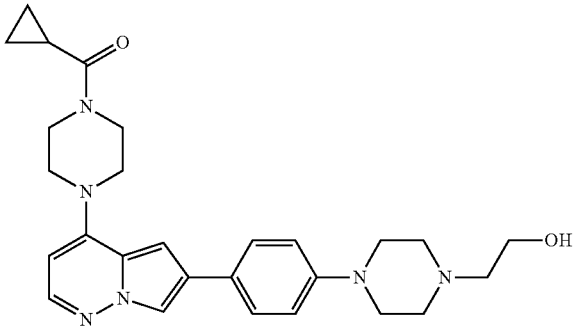 [SMILES: O=C(C1CC1)N1CCN(c2ccnn3cc(-c4ccc(N5CCN(CCO)CC5)cc4)cc23)CC1] | 475 | 1H-NMR (400 MHz, DMSO-d6) δ ppm 8.06 (d, 1H, J = 1.6 Hz), 7.87 (d, 1H, J = 4.8 Hz), 7.65 (d, 2H, J = 8.8 Hz), 6.95 (d, 2H, J = 8.8 Hz), 6.94 (s, 1H), 5.96 (d, 1H, J = 5.6 Hz), 4.44 (t, 1H, J = 5.2 Hz), 3.93-3.91 (m, 2H), 3.71-3.69 (m, 2H), 3.56-3.45 (m, 6H), 3.15 (t, 4H, J = 4.4 Hz), 2.56 (t, 4H, J = 4.4 Hz), 2.44 (t, 2H, J = 6.4 Hz), 2.04-2.00 (m, 1H), 0.78-0.72 (m, 4H). |
| 275 | 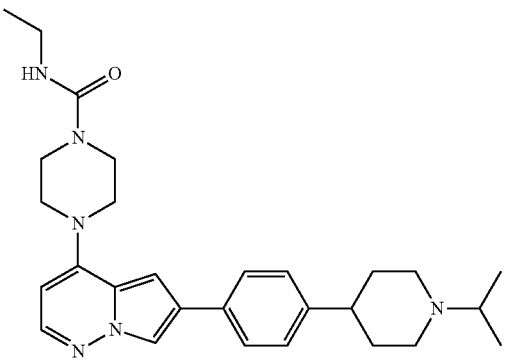 | 475 | 1H-NMR (400 MHz, 6d-DMSO) δ ppm 8.12 (s, 1H), 7.88 (d, 1H, J = 5.6 Hz), 7.71 (d, 2H, J = 8.0 Hz), 7.24 (d, 2H, J = 8.0 Hz), 6.98 (s, 1H), 6.59 (t, 1H, J = 1.6 Hz), 5.97 (d, 1H, J = 5.6 Hz), 3.54-3.48 (m, 4H), 3.45-3.40 (m, 4H), 3.09-3.05 (m, 2H), 2.89-2.85 (m, 2H), 2.73-2.68 (m, 1H), 2.45-2.40 (m, 1H), 2.23-2.17 (m, 2H), 1.78-1.72 (m, 2H), 1.63-1.57 (m, 2H), 1.03 (t, 3H, J = 7.2 Hz), 0.93 (d, 6H, J = 7.2 Hz). |
| 276 | 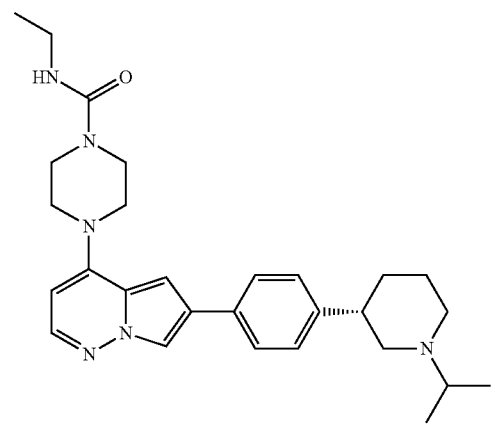 [SMILES: CCNC(=O)N1CCN(c2ccnn3cc(-c4ccc([C@@H]5CCCN(C(C)C)C5)cc4)cc23)CC1] | 475 | 1H-NMR (400 MHz, 6d-DMSO) δ ppm 8.13 (d, 1H, J = 1.6 Hz), 7.89 (d, 1H, J = 5.6 Hz), 7.72 (d, 2H, J = 8.0 Hz), 7.27 (d, 2H, J = 8.0 Hz), 6.99 (d, 1H, J = 1.6 Hz), 6.60 (t, 1H, J = 5.6 Hz), 5.98 (d, 1H, J = 5.6 Hz), 3.53-3.51 (m, 4H), 3.44-3.43 (m, 4H), 3.10-3.05 (m, 2H), 2.82-2.75 (m, 2H), 2.74-2.64 (m, 2H), 2.18-2.15 (m, 2H), 1.83-1.81 (m, 1H), 1.72-1.71 (m, 1H), 1.56-1.50 (m, 1H), 1.50-1.45 (m, 1H), 1.04 (t, 3H, J = 7.2 Hz), 0.99-0.97 (m, 6H). |
| 277 | 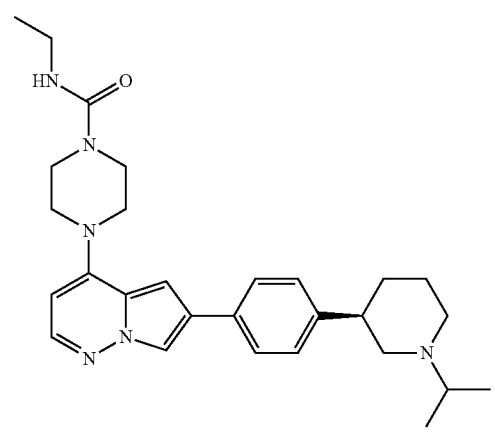 | 475 | 1H-NMR (400 MHz, 6d-DMSO) δ ppm 8.14 (d, 1H, J = 1.6 Hz), 7.89 (d, 1H, J = 5.2 Hz), 7.72 (d, 2H, J = 8.4 Hz), 7.27 (d, 2H, J = 8.4 Hz), 6.99 (d, 1H, J = 1.2 Hz), 6.62 (t, 1H, J = 5.2 Hz), 5.99 (d, 1H, J = 5.6 Hz), 3.52-3.51 (m, 4H), 3.44-3.43 (m, 4H), 3.10-3.05 (m, 2H), 2.82-2.75 (m, 2H), 2.73-2.67 (m, 2H), 2.19-2.16 (m, 2H), 1.83-1.81 (m, 1H), 1.75-1.72 (m, 1H), 1.54-1.50 (m, 1H), 1.49-1.44 (m, 1H), 1.04 (t, 3H, J = 7.2 Hz), 0.99-0.97 (m, 6H). |

TABLE 1-continued

| # | Structure | LCMS (M + 1) | NMR |
|---|---|---|---|
| 278 | 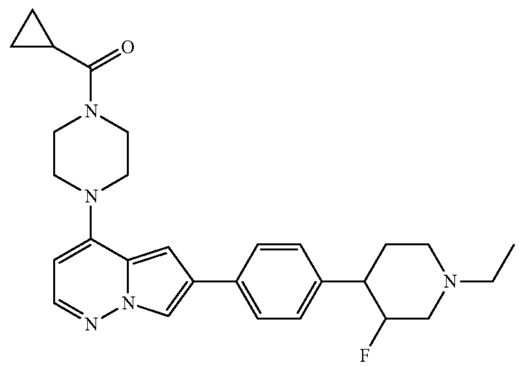 [SMILES: CCN1CCC(c2ccc(-c3cc4c(N5CCN(C(=O)C6CC6)CC5)ccnn4c3)cc2)C(F)C1] | 476 | 1H-NMR (400 MHz, DMSO-d6) δ ppm 8.17 (s, 1H), 7.89 (d, 1H, J = 4.8 Hz), 7.75 (d, 2H, J = 7.6 Hz), 7.32 (d, 2H, J = 7.2 Hz), 7.04 (s, 1H), 5.96 (d, 1H, J = 4.8 Hz), 4.78-4.62 (m, 1H), 3.92 (br. s., 2H), 3.70 (br. s., 2H), 3.54 (br. s., 2H), 3.47 (br. s., 2H), 2.89-2.87 (m, 1H), 2.66-2.64 (m, 1H), 2.45-2.42 (m, 2H), 2.00-1.93 (m, 3H), 1.78-1.65 (m, 2H), 1.22 (s, 1H), 1.03 (t, 3H, J = 6.4 Hz), 0.76-0.74 (m, 4H). |
| 279 | 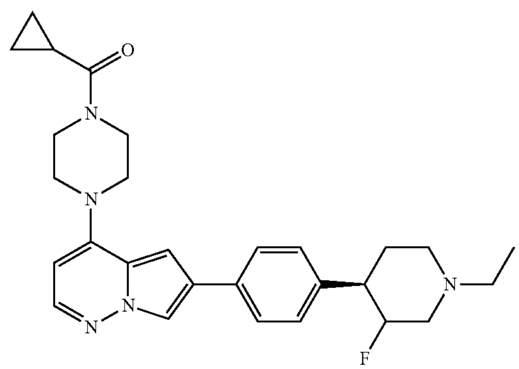 [SMILES: CCN1CC[C@H](c2ccc(-c3cc4c(N5CCN(C(=O)C6CC6)CC5)ccnn4c3)cc2)C(F)C1] | 476 | 1H-NMR (400 MHz, 6d-DMSO) δ ppm 8.17 (s, 1H), 7.89 (d, 1H, J = 4.8 Hz), 7.75 (d, 2H, J = 7.6 Hz), 7.32 (d, 2H, J = 7.2 Hz), 7.04 (d, 1H, J = 1.6 Hz), 5.96 (d, 1H, J = 4.8 Hz), 4.80-4.62 (m, 1H), 3.92 (br. s., 2H), 3.70 (br. s., 2H), 3.54 (br. s., 2H), 3.47 (br. s., 2H), 2.89-2.87 (m, 1H), 2.70-2.60 (m, 1H), 2.45-2.42 (m, 2H), 2.03-1.94 (m, 3H), 1.81-1.68 (m, 2H), 1.28 (s, 1H), 1.03 (t, 3H, J = 7.2 Hz), 0/7-0.74 (m, 4H). |
| 280 | 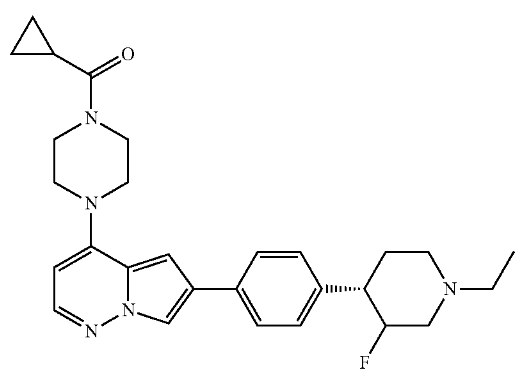 [SMILES: CCN1CC[C@@H](c2ccc(-c3cc4c(N5CCN(C(=O)C6CC6)CC5)ccnn4c3)cc2)C(F)C1] | 476 | 1H-NMR (400 MHz, 6d-DMSO) δ ppm 8.17 (s, 1H), 7.89 (d, 1H, J = 4.8 Hz), 7.75 (d, 2H, J = 7.6 Hz), 7.32 (d, 2H, J = 7.2 Hz), 7.04 (d, 1H, J = 1.6 Hz), 5.96 (d, 1H, J = 4.8 Hz), 4.80-4.62 (m, 1H), 3.92 (s, 2H), 3.70 (s, 2H), 3.54 (s, 2H), 3.47 (s, 2H), 2.89-2.87 (m, 1H), 2.70-2.60 (m, 1H), 2.45-2.42 (m, 2H), 2.03-1.94 (m, 3H), 1.81-1.68 (m, 2H), 1.28 (s, 1H), 1.03 (t, 3H, J = 7.2 Hz), 0.77-0.74 (m, 4H). |
| 281 | 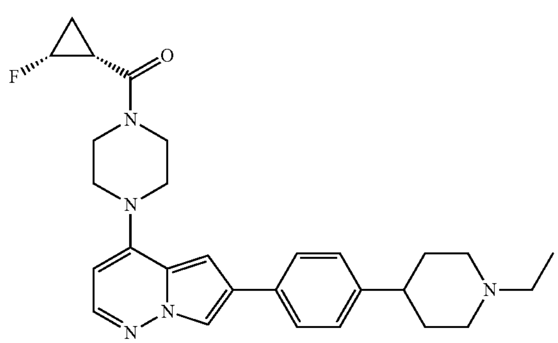 | 476 | 1H-NMR (400 MHz, 6d-DMSO) δ ppm 8.15 (s, 1H), 7.90 (d, 1H, J = 5.2 Hz), 7.73 (d, 2H, J = 8.0 Hz), 7.26 (d, 2H, J = 8.0 Hz), 7.04 (s, 1H), 5.99 (d, 1H, J = 5.2 Hz), 5.05-4.88 (m, 1H), 3.92-3.89 (m, 2H), 3.74-3.73 (m, 2H), 3.58-3.48 (m, 6H), 3.00-2.97 (m, 2H), 2.35 (q, 2H, J = 6.8 Hz), 2.22-2.20 (m, 1H), 1.99-1.96 (m, 2H), 1.74-1.65 (m, 4H), 1.03 (t, 3H, J = 6.8 Hz). |

TABLE 1-continued

| # | Structure | LCMS (M + 1) | NMR |
|---|---|---|---|
| 282 | 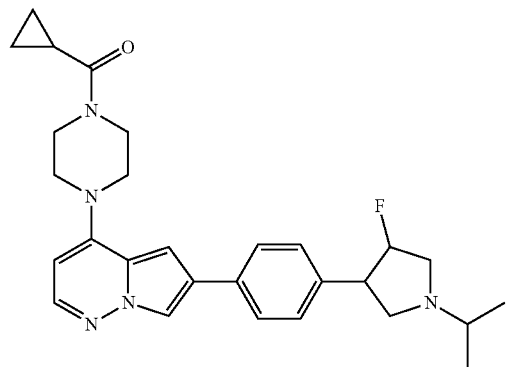 [SMILES: CC(C)N1CC(F)C(c2ccc(-c3cc4c(N5CCN(C(=O)C6CC6)CC5)ccnn4c3)cc2)C1] | 476 | 1H-NMR (400 MHz, 6d-DMSO) δ ppm 8.17 (d, 1H, J = 1.2 Hz), 7.90 (d, 1H, J = 5.2 Hz), 7.77 (d, 2H, J = 8.4 Hz), 7.31 (d, 2H, J = 8.4 Hz), 7.04 (s, 1H), 5.96 (d, 1H, J = 5.2 Hz), 5.26-5.00 (m, 1H), 4.00-3.86 (m, 2H), 3.76-3.64 (m, 2H), 3.54-3.50 (m, 2H), 3.45-3.40 (m, 2H), 3.32-3.26 (m, 2H), 3.16-3.00 (m, 1H), 2.86-2.70 (m, 1H), 2.46-2.36 (m, 1H), 2.34-2.26 (m, 1H), 2.06-1.96 (m, 1H), 1.10-1.00 (m, 6H), 0.80-0.70 (m, 4H). |
| 283 | 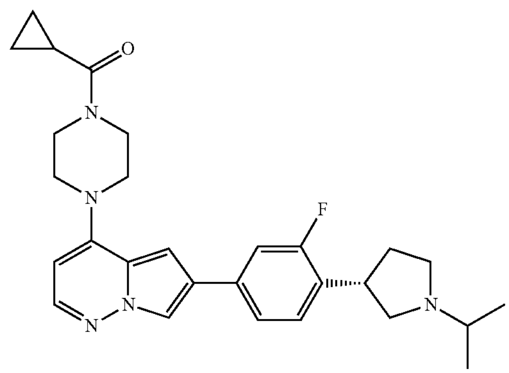 [SMILES: CC(C)N1CC[C@@H](c2ccc(-c3cc4c(N5CCN(C(=O)C6CC6)CC5)ccnn4c3)cc2F)C1] | 476 | 1H-NMR (400 MHz, 6d-DMSO) δ ppm 8.25 (s, 1H), 7.90 (d, 1H, J = 5.6 Hz), 7.71-7.62 (m, 2H), 7.49-7.40 (m, 1H), 7.11 (m, 1H), 5.97 (d, 1H, J = 5.6 Hz), 3.98-3.88 (m, 2H), 3.76-3.66 (m, 2H), 3.55-3.50 (m, 2H), 3.50-3.45 (m, 2H), 3.43-3.33 (m, 2H), 3.32-3.28 (m, 1H), 3.00-2.67 (m, 3H), 2.30-2.23 (m, 1H), 2.06-1.98 (m, 1H), 1.96-1.90 (m, 1H), 1.21-1.10 (m, 6H), 0.80-0.74 (m, 4H). |
| 284 | 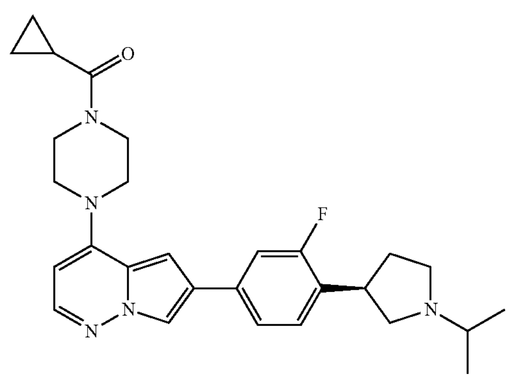 [SMILES: CC(C)N1CC[C@H](c2ccc(-c3cc4c(N5CCN(C(=O)C6CC6)CC5)ccnn4c3)cc2F)C1] | 476 | 1H-NMR (400 MHz, 6d-DMSO) δ ppm 8.23 (d, 1H, J = 1.6 Hz), 7.90 (d, 1H, J = 5.6 Hz), 7.68-7.64 (m, 1H), 7.61 (d, 1H, J = 8.0 Hz), 7.41 (t, 1H, J = 8.0 Hz), 7.10 (d, 1H, J = 1.6 Hz), 5.96 (d, 1H, J = 5.6 Hz), 3.95-3.91 (m, 2H), 3.73-3.65 (m, 2H), 3.60-3.50 (m, 2H), 3.49-3.41 (m, 2H), 3.32-3.27 (m, 1H), 3.10-2.92 (m, 1H), 2.82-2.74 (m, 2H), 2.64-2.57 (m, 1H), 2.28-2.19 (m, 1H), 2.04-1.98 (m, 1H), 1.86-1.78 (m, 1H), 1.12-1.04 (m, 6H), 0.79-0.74 (m, 4H). |
| 285 | 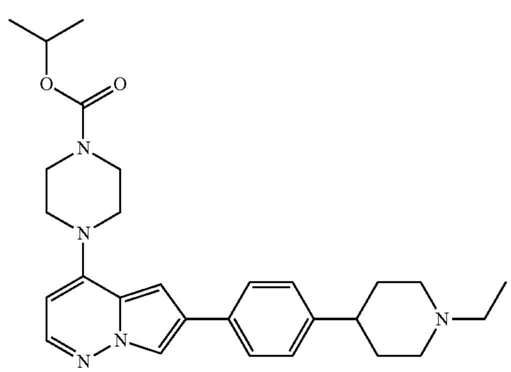 [SMILES: CCN1CCC(c2ccc(-c3cc4c(N5CCN(C(=O)OC(C)C)CC5)ccnn4c3)cc2)CC1] | 476 | 1H-NMR (400 MHz, 6d-DMSO) δ ppm 8.28-8.27 (m, 2H), 8.14 (d, 1H, J = 1.6 Hz), 7.89 (d, 1H, J = 5.6 Hz), 7.73 (d, 2H, J = 8.0 Hz), 7.25 (d, 2H, J = 8.0 Hz), 6.99 (d, 1H, J = 1.6 Hz), 5.97 (d, 1H, J = 5.6 Hz), 4.90-4.70 (m, 1H), 3.70-3.52 (m, 4H), 3.50-3.35 (m, 4H), 3.10-2.90 (m, 2H), 2.44 (q, 2H, J = 7.2 Hz), 2.15-2.00 (m, 2H), 1.82-1.70 (m, 4H), 1.70-1.60 (m, 1H), 1.30-1.12 (m, 6H), 1.04 (t, 3H, J = 7.2 Hz). |

TABLE 1-continued

| # | Structure | LCMS (M + 1) | NMR |
|---|---|---|---|
| 286 | 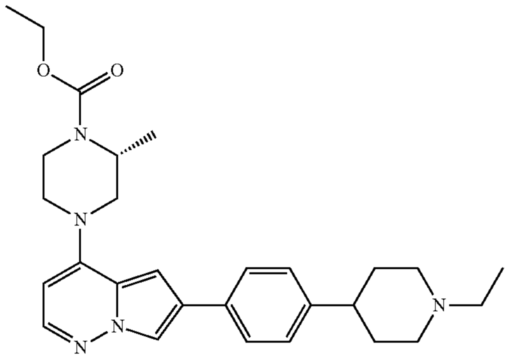 [SMILES: CCOC(=O)N1CCN(c2ccnn3cc(-c4ccc(C5CCN(CC)CC5)cc4)cc23)C[C@H]1C] | 476 | 1H-NMR (400 MHz, 6d-DMSO) δ ppm 8.12 (s, 1H), 7.87 (d, 1H, J = 5.6 Hz), 7.69 (d, 2H, J = 8.0 Hz), 7.25 (d, 2H, J = 8.0 Hz), 6.91 (s, 1H), 5.94 (d, 1H, J = 5.6 Hz), 4.31-4.30 (m, 1H), 4.09-4.07 (m, 2H), 3.89-3.85 (m, 2H), 3.85-3.83 (m, 1H), 3.22-3.21 (m, 2H), 3.03-3.00 (m, 1H), 3.00-2.97 (m, 2H), 3.50-2.45 (m, 1H), 2.35 (q, 2H, J = 7.2 Hz), 1.99-1.94 (m, 2H), 1.73-1.68 (m, 2H), 1.68-1.63 (m, 2H), 1.29-1.27 (d, 3H, J = 6.4 Hz), 1.20 (t, 3H, J = 7.2 Hz), 1.02 (t, 3H, J = 7.2 Hz). |
| 287 | 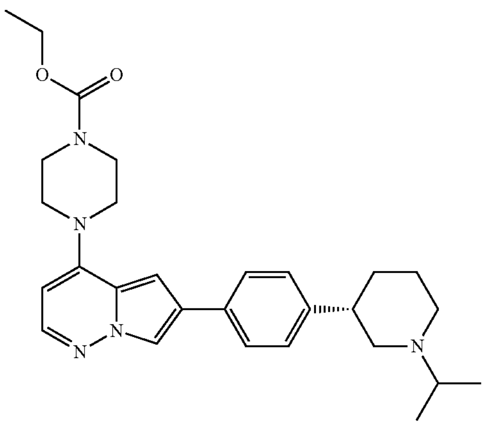 [SMILES: CCOC(=O)N1CCN(c2ccnn3cc(-c4ccc([C@@H]5CCCN(C(C)C)C5)cc4)cc23)CC1] | 476 | 1H-NMR (400 MHz, 6d-DMSO) δ ppm 8.13 (d, 1H, J = 1.6 Hz), 7.90 (d, 1H, J = 5.6 Hz), 7.75 (d, 2H, J = 8.4 Hz), 7.26 (d, 2H, J = 8.4 Hz), 6.97 (d, 1H, J = 1.6 Hz), 5.96 (d, 1H, J = 5.6 Hz), 4.08 (q, 2H, J = 7.2 Hz), 3.60-3.59 (m, 4H), 3.46-3.43 (m, 4H), 2.80-2.75 (m, 2H), 2.72-2.67 (m, 2H), 2.18-2.08 (m, 2H), 1.82-1.78 (m, 1H), 1.73-1.68 (m, 1H), 1.58-1.51 (m, 1H), 1.47-1.40 (m, 1H), 1.21 (t, 3H, J = 7.2 Hz), 1.11-1.10 (m, 6H). |
| 288 | 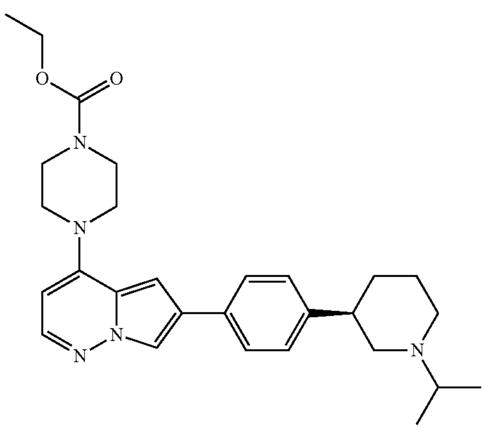 [SMILES: CCOC(=O)N1CCN(c2ccnn3cc(-c4ccc([C@H]5CCCN(C(C)C)C5)cc4)cc23)CC1] | 476 | 1H-NMR (400 MHz, 6d-DMSO) δ ppm 8.15 (d, 1H, J = 1.6 Hz), 7.90 (d, 1H, J = 5.6 Hz), 7.75 (d, 2H, J = 8.4 Hz), 7.26 (d, 2H, J = 8.4 Hz), 6.97 (d, 1H, J = 1.6 Hz), 5.96 (d, 1H, J = 5.6 Hz), 4.08 (q, 2H, J = 7.2 Hz), 3.60-3.59 (m, 4H), 3.46-3.43 (m, 4H), 2.80-2.75 (m, 2H), 2.72-2.67 (m, 2H), 2.18-2.08 (m, 2H), 1.82-1.78 (m, 1H), 1.73-1.68 (m, 1H), 1.58-1.51 (m, 1H), 1.47-1.40 (m, 1H), 1.21 (t, 3H, J = 7.2 Hz), 1.15-1.00 (m, 6H). |
| 289 | 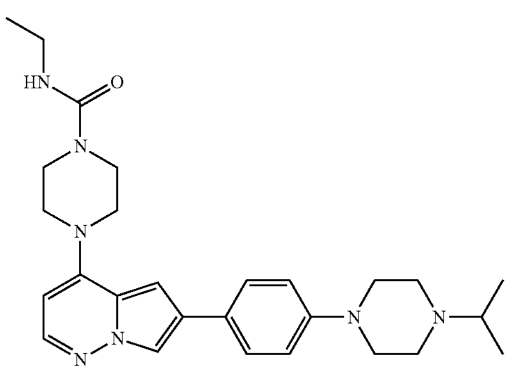 [SMILES: CCNC(=O)N1CCN(c2ccnn3cc(-c4ccc(N5CCN(C(C)C)CC5)cc4)cc23)CC1] | 476 | 1H-NMR (400 MHz, 6d-DMSO) δ ppm 8.06 (d, 1H, J = 1.6 Hz), 7.86 (d, 1H, J = 4.8 Hz), 7.65 (d, 2H, J = 8.8 Hz), 6.94 (d, 2H, J = 8.8 Hz), 6.91 (d, 1H, J = 1.6 Hz), 6.60 (t, 1H, J = 5.6 Hz), 5.96 (d, 1H, J = 5.6 Hz), 3.52-3.51 (m, 4H), 3.43-3.41 (m, 4H), 3.15-3.14 (m, 4H), 3.10-3.07 (m, 2H), 2.68-2.66 (m, 1H), 2.59-2.58 (m, 4H), 1.03 (t, 3H, J = 7.2 Hz), 1.00 (d, 2H, J = 6.8 Hz). |

TABLE 1-continued

| # | Structure | LCMS (M + 1) | NMR |
|---|---|---|---|
| 290 | 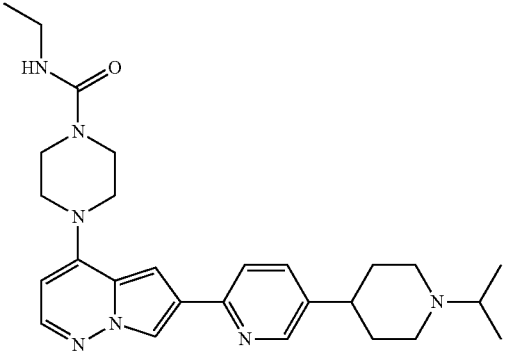 [SMILES: CCNC(=O)N1CCN(c2ccnn3cc(-c4ccc(C5CCN(C(C)C)CC5)cn4)cc23)CC1] | 476 | 1H-NMR (400 MHz, 6d-DMSO) δ ppm 8.44 (d, 1H, J = 2.0 Hz), 8.23 (d, 1H, J = 1.2 Hz), 7.90 (d, 1H, J = 5.6 Hz), 7.84 (d, 1H, J = 8.4 Hz), 7.67 (dd, 1H, J = 8.4, 2.0 Hz), 7.13 (d, 1H, J = 1.2 Hz), 6.60 (t, 1H, J = 5.6 Hz), 5.98 (d, 1H, J = 5.6 Hz), 3.53-3.50 (m, 4H), 3.45-3.42 (m, 4H), 3.33-3.31 (m, 1H), 3.11-3.04 (m, 2H), 2.90-2.87 (m, 2H), 2.73-2.69 (m, 1H), 2.24-2.19 (m, 2H), 1.78-1.75 (m, 2H), 1.70-1.63 (m, 2H), 1.03 (t, 3H, J = 7.2 Hz), 0.98 (d, 6H, J = 6.8 Hz). |
| 291 | 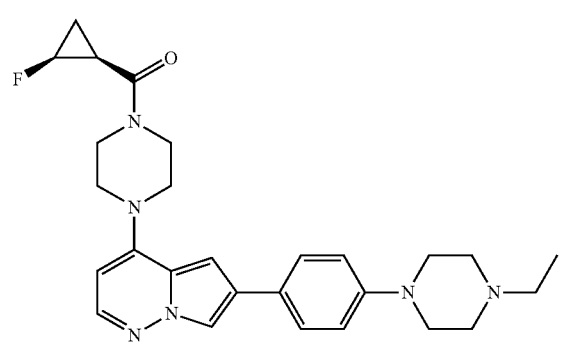 [SMILES: CCN1CCN(c2ccc(-c3cc4c(N5CCN(C(=O)[C@@H]6C[C@@H]6F)CC5)ccnn4c3)cc2)CC1] | 477 | 1H-NMR (400 MHz, 6d-DMSO) δ ppm 8.06 (d, 1H, J = 1.6 Hz), 7.87 (d, 1H, J = 5.6 Hz), 7.65 (d, 2H, J = 8.4 Hz), 6.95 (d, 2H, J = 8.4 Hz), 6.94 (d, 1H, J = 1.6 Hz), 5.97 (d, 1H, J = 5.6 Hz), 5.05-4.80 (m, 1H), 4.00-3.80 (m, 2H), 3.78-3.65 (m, 2H), 3.60-3.50 (m, 1H), 3.49-3.35 (m, 3H), 3.30-3.21 (m, 4H), 3.20-3.05 (m, 4H), 2.36 (q, 2H, J = 7.2 Hz), 2.30-2.10 (m, 1H), 1.60-1.40 (m, 1H), 1.10-1.00 (m, 1H), 1.03 (t, 3H, J = 7.2 Hz). |
| 292 | 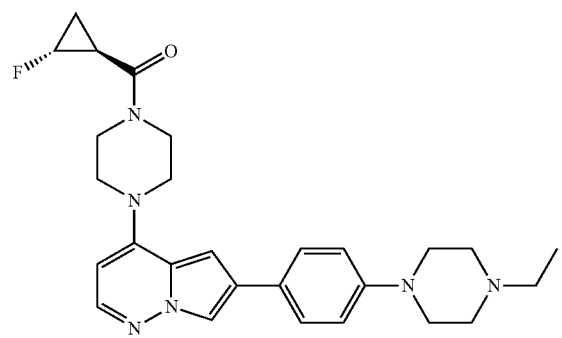 [SMILES: CCN1CCN(c2ccc(-c3cc4c(N5CCN(C(=O)[C@@H]6C[C@H]6F)CC5)ccnn4c3)cc2)CC1] | 478 | 1H-NMR (400 MHz, 6d-DMSO) δ ppm 8.06 (d, 1H, J = 1.2 Hz), 7.87 (d, 1H, J = 5.2 Hz), 7.65 (d, 2H, J = 8.4 Hz), 6.95 (d, 2H, J = 8.4 Hz), 6.95-6.93 (m, 1H), 5.96 (d, 1H, J = 5.2 Hz), 4.95-4.70 (m, 1H), 4.00-3.85 (m, 2H), 3.70-3.65 (m, 2H), 3.60-3.40 (m, 4H), 3.30-3.25 (m, 4H), 3.18-3.10 (m, 4H), 2.70-2.60 (m, 1H), 2.36 (q, 2H, J = 7.2 Hz), 1.50-1.30 (m, 1H), 1.25-1.10 (m, 1H), 1.03 (t, 3H, J = 7.2 Hz). |
| 293 | 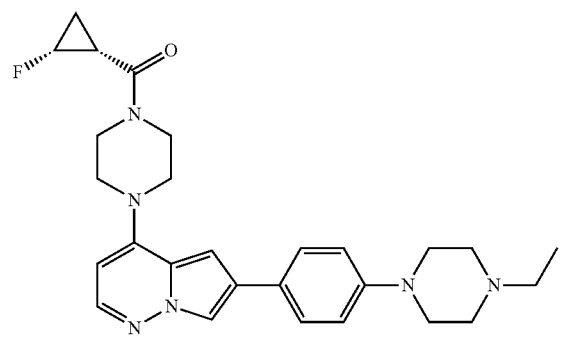 [SMILES: CCN1CCN(c2ccc(-c3cc4c(N5CCN(C(=O)[C@H]6C[C@H]6F)CC5)ccnn4c3)cc2)CC1] | 477 | 1H-NMR (400 MHz, 6d-DMSO) δ ppm 8.06 (d, 1H, J = 1.6 Hz), 7.87 (d, 1H, J = 5.6 Hz), 7.65 (d, 2H, J = 8.4 Hz), 6.95 (d, 2H, J = 8.4 Hz), 6.94 (d, 1H, J = 1.6 Hz), 5.97 (d, 1H, J = 5.6 Hz), 5.04-4.80 (m, 1H), 4.00-3.60 (m, 4H), 3.56-3.35 (m, 4H), 3.30-3.25 (m, 4H), 3.18-3.10 (m, 4H), 2.37 (q, 2H, J = 7.2 Hz), 2.23-2.17 (m, 1H), 1.60-1.50 (m, 1H), 1.10-1.00 (m, 1H), 1.03 (t, 3H, J = 7.2 Hz). |

TABLE 1-continued

| # | Structure | LCMS (M + 1) | NMR |
|---|---|---|---|
| 294 | 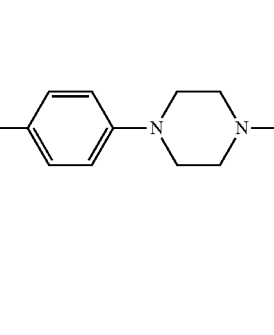 | 477 | 1H-NMR (400 MHz, 6d-DMSO) δ ppm 8.06 (d, 1H, J = 2.0 Hz), 7.87 (d, 1H, J = 5.6 Hz), 7.65 (d, 2H, J = 8.4 Hz), 6.96 (s, 1H), 6.94 (d, 2H, J = 8.4 Hz), 5.97 (d, 1H, J = 5.6 Hz), 4.00-3.70 (m, 4H), 3.60-3.45 (m, 4H), 3.30-3.25 (m, 4H), 3.18-3.10 (m, 4H), 2.37 (q, 2H, J = 7.2 Hz), 1.32-1.22 (m, 4H), 1.04 (t, 3H, J = 7.2 Hz). |
| 295 | 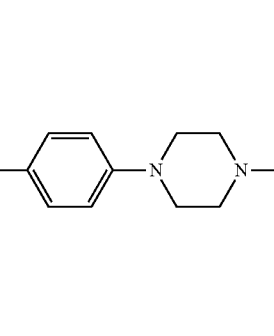 | 477 | 1H-NMR (400 MHz, 6d-DMSO) δ ppm 8.15 (s, 1H), 8.06 (d, 1H, J = 1.6 Hz), 7.86 (d, 1H, J = 5.6 Hz), 7.65 (d, 2H, J = 8.4 Hz), 6.95 (d, 2H, J = 8.4 Hz), 6.91 (d, 1H, J = 1.6 Hz), 5.96 (d, 1H, J = 5.6 Hz), 4.08 (q, 2H, J = 7.2 Hz), 3.80-3.70 (m, 8H), 3.25-3.05 (m, 4H), 2.85-2.75 (m, 1H), 2.72-2.60 (m, 4H), 1.21 (t, 3H, J = 7.2 Hz), 1.05 (d, 6H, J = 6.4 Hz). |
| 296 | 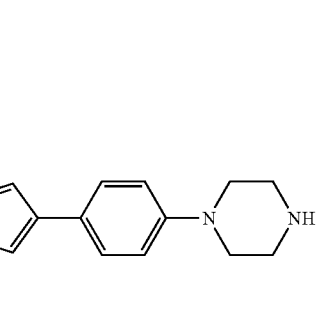 | 481 | 1H-NMR (500 MHz, CDCl3) δ ppm 7.88 (s, 1H), 7.83 (d, 1H, J = 5.5 Hz), 7.56 (d, 2H, J = 8.5 Hz), 6.97 (d, 2H, J = 8.5 Hz), 6.63 (s, 1H), 5.83 (d, 1H, J = 5.0 Hz), 3.90-3.88 (m, 2H), 3.66-3.64 (m, 2H), 3.48-3.44 (m, 4H), 3.23-3.21 (m, 4H), 3.15-3.13 (m, 1H), 3.11-3.08 (m, 4H), 3.02-2.92 (m, 2H), 2.82-2.73 (m, 2H). |
| 297 | 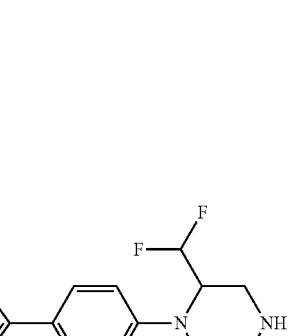 | 481 | 1H-NMR (500 MHz, CDCl3) δ ppm 7.88 (d, 1H, J = 1.5 Hz), 7.84 (d, 1H, J = 5.5 Hz), 7.57 (d, 2H, J = 9.0 Hz), 6.96 (d, 2H, J = 9.0 Hz), 6.66 (d, 1H, J = 1.5 Hz), 6.14 (td, 1H, J = 56.0, 4.5 Hz), 5.84 (d, 1H, J = 5.5 Hz), 4.00-3.84 (m, 5H), 3.60-3.44 (m, 4H), 3.43-3.34 (m, 2H), 3.32-3.24 (m, 1H), 3.19-3.09 (m, 2H), 3.01-2.93 (m, 1H), 1.83-1.75 (m, 1H), 1.08-1.02 (m, 2H), 0.86-0.79 (m, 2H). |

TABLE 1-continued

| # | Structure | LCMS (M + 1) | NMR |
|---|---|---|---|
| 298 | 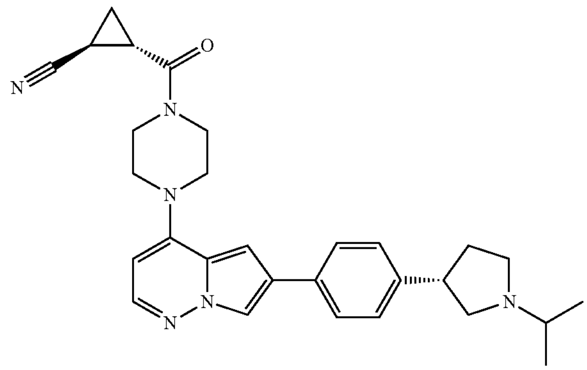 [SMILES: CC(C)N1CC[C@@H](c2ccc(-c3cc4c(N5CCN(C(=O)[C@H]6C[C@@H]6C#N)CC5)ccnn4c3)cc2)C1] | 483 | 1H-NMR (400 MHz, 6d-DMSO) δ ppm 8.15 (d, 1H, J = 1.6 Hz), 7.90 (d, 1H, J = 5.6 Hz), 7.72 (d, 2H, J = 8.4 Hz), 7.29 (d, 2H, J = 8.4 Hz), 7.03 (d, 1H, J = 1.6 Hz), 5.98 (d, 1H, J = 5.6 Hz), 4.00-3.90 (m, 2H), 3.75-3.65 (m, 2H), 3.60-3.55 (m, 2H), 3.54-3.50 (m, 2H), 3.30-3.20 (m, 1H), 3.05-2.97 (m, 1H), 2.95-2.90 (m, 1H), 2.80-2.60 (m, 2H), 2.45-2.35 (m, 2H), 2.25-2.15 (m, 1H), 2.13-2.05 (m, 1H), 1.80-1.70 (m, 1H), 1.50-1.40 (m, 1H), 1.38-1.30 (m, 1H), 1.10-1.00 (m, 6H). |
| 299 | 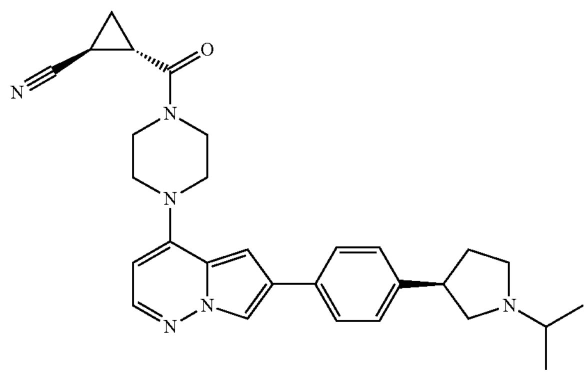 [SMILES: CC(C)N1CC[C@H](c2ccc(-c3cc4c(N5CCN(C(=O)[C@H]6C[C@@H]6C#N)CC5)ccnn4c3)cc2)C1] | 483 | 1H-NMR (400 MHz, 6d-DMSO) δ ppm 8.16 (d, 1H, J = 1.6 Hz), 7.91 (d, 1H, J = 5.6 Hz), 7.73 (d, 2H, J = 8.4 Hz), 7.30 (d, 2H, J = 8.4 Hz), 7.04 (d, 1H, J = 1.6 Hz), 5.99 (d, 1H, J = 5.6 Hz), 3.96-3.94 (m, 2H), 3.71-3.70 (m, 2H), 3.58-3.55 (m, 2H), 3.49-3.47 (m, 2H), 3.29-3.25 (m, 1H), 3.02-2.96 (m, 1H), 2.95-2.90 (m, 1H), 2.73-2.69 (m, 2H), 2.50-2.49 (m, 2H), 2.45-3.39 (m, 1H), 2.24-2.19 (m, 1H), 2.18-2.08 (m, 1H), 1.79-1.74 (m, 1H), 1.49-1.46 (m, 1H), 1.36-1.33 (m, 1H), 1.06 (t, 3H, J = 6.4 Hz). |
| 300 | 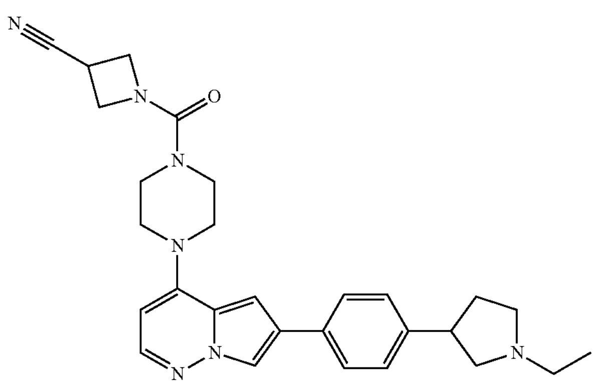 [SMILES: CCN1CCC(c2ccc(-c3cc4c(N5CCN(C(=O)N6CC(C#N)C6)CC5)ccnn4c3)cc2)C1] | 484 | 1H-NMR (400 MHz, 6d-DMSO) δ ppm 8.20 (d, 1H, J = 1.6 Hz), 7.90 (d, 1H, J = 5.2 Hz), 7.81 (d, 2H, J = 8.4 Hz), 7.38 (d, 2H, J = 8.4 Hz), 7.03 (d, 1H, J = 1.6 Hz), 5.96 (d, 1H, J = 5.6 Hz), 4.22 (t, 2H, J = 8.8 Hz), 4.11-4.08 (m, 2H), 3.80-3.73 (m, 4H), 3.55-3.30 (s, 9H), 3.25-3.20 (m, 2H), 3.10-3.04 (m, 1H), 2.40-2.42 (m, 1H), 2.10-2.00 (br, 1H), 1.27 (t, 3H, J = 7.2 Hz). |
| 301 | 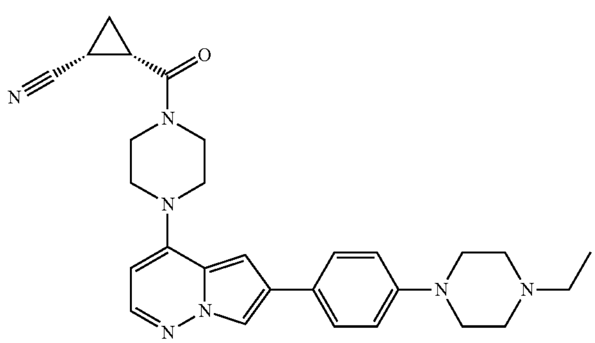 [SMILES: CCN1CCN(c2ccc(-c3cc4c(N5CCN(C(=O)[C@H]6C[C@H]6C#N)CC5)ccnn4c3)cc2)CC1] | 484 | 1H-NMR (400 MHz, 6d-DMSO) δ ppm 8.08 (d, 1H, J = 1.2 Hz), 7.89 (d, 1H, J = 5.6 Hz), 7.67 (d, 2H, J = 8.4 Hz), 6.99-6.95 (m, 3H), 5.99 (d, 1H, J = 5.6 Hz), 3.96-3.88 (m, 2H), 3.75-3.66 (m, 1H), 3.65-3.52 (m, 2H), 3.50-3.45 (m, 1H), 3.41-3.36 (m, 1H), 3.23-3.07 (m, 4H), 2.68-2.62 (m, 2H), 2.58-2.54 (m, 1H), 2.22-2.15 (m, 1H), 1.54-1.50 (m, 1H), 1.39-1.34 (m, 1H), 1.26-1.22 (m, 1H), 1.12-1.01 (m, 3H). |

TABLE 1-continued

| # | Structure | LCMS (M + 1) | NMR |
|---|---|---|---|
| 302 | 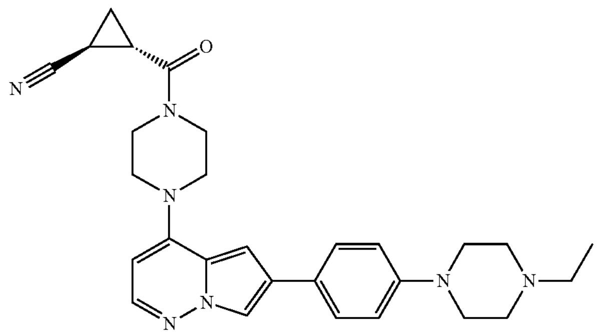 [SMILES: CCN1CCN(c2ccc(-c3cc4c(N5CCN(C(=O)[C@H]6C[C@@H]6C#N)CC5)ccnn4c3)cc2)CC1] | 484 | 1H-NMR (400 MHz, 6d-DMSO) δ ppm 8.09 (s, 1H), 7.88 (d, 1H, J = 5.2 Hz), 7.68 (d, 2H, J = 8.4 Hz), 6.98 (d, 2H, J = 8.4 Hz), 6.97 (s, 1H), 5.98 (d, 1H, J = 5.2 Hz), 4.00-3.91 (m, 2H), 3.75-3.66 (m, 2H), 3.61-3.51 (m, 3H), 3.50-3.43 (m, 2H), 3.21-3.08 (m, 4H), 2.96-2.91 (m, 1H), 2.13-2.08 (m, 1H), 1.50-1.44 (m, 1H), 1.38-1.32 (m, 1H), 1.27-1.21 (m, 1H), 1.17-1.02 (m, 3H). |
| 303 | 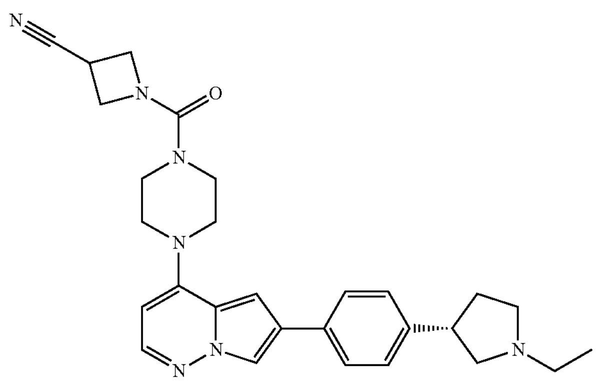 | 484 | 1H-NMR (400 MHz, 6d-DMSO) δ ppm 8.13 (d, 1H, J = 1.2 Hz), 7.88 (d, 1H, J = 5.6 Hz), 7.70 (d, 2H, J = 8.4 Hz), 7.28 (d, 2H, J = 8.4 Hz), 6.97 (d, 1H, J = 1.2 Hz), 5.94 (d, 1H, J = 5.6 Hz), 4.21 (t, 2H, J = 8.4 Hz), 4.08 (dd, 2H, J = 7.2, 6.0 Hz), 3.78-3,71 (m, 1H), 3.46-3.45 (m, 8H), 3.37-3.24 (m, 2H), 2.91 (t, 1H, J = 8.4 Hz), 2.71-2.59 (m, 2H), 2.49-2.40 (m, 2H), 2.27-2.18 (m, 1H), 1.79-1.71 (m, 1H), 1.05 (t, 3H, J = 7.2 Hz). |
| 304 | 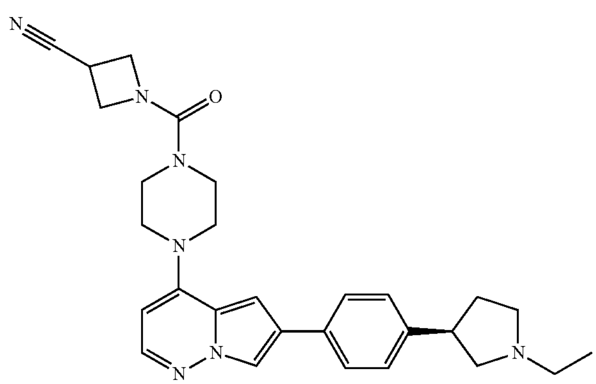 [SMILES: CCN1CC[C@H](c2ccc(-c3cc4c(N5CCN(C(=O)N6CC(C#N)C6)CC5)ccnn4c3)cc2)C1] | 484 | 1H-NMR (400 MHz, 6d-DMSO) δ ppm 8.13 (d, 1H, J = 1.2 Hz), 7.88 (d, 1H, J = 5.6 Hz), 7.71 (d, 2H, J = 8.4 Hz), 7.28 (d, 2H, J = 8.4 Hz), 6.98 (d, 1H, J = 1.2 Hz), 5.94 (d, 1H, J = 5.6 Hz), 4.21 (t, 2H, J = 8.4 Hz), 4.08 (dd, 2H, J = 7.2, 6.0 Hz), 3.78-3,71 (m, 1H), 3.46-3.45 (m, 8H), 3.32-3.26 (m, 2H), 2.96 (t, 1H, J = 8.4 Hz), 2.75-2.64 (m, 2H), 2.50-2.44 (m, 2H), 2.28-2.19 (m, 1H), 1.81-1.72 (m, 1H), 1.06 (t, 3H, J = 7.2 Hz). |
| 305 | 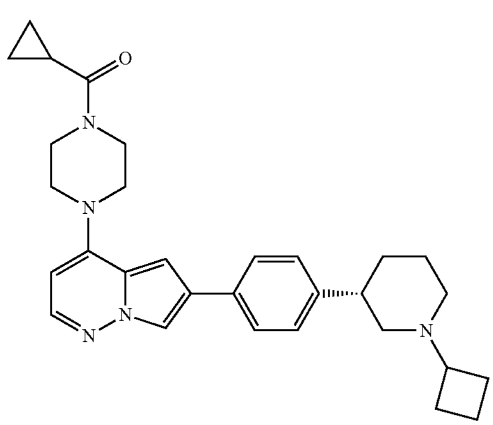 [SMILES: O=C(C1CC1)N1CCN(c2ccnn3cc(-c4ccc([C@@H]5CCCN(C6CCC6)C5)cc4)cc23)CC1] | 484 | 1H-NMR (400 MHz, 6d-DMSO) δ ppm 8.14 (d, 1H, J = 1.2 Hz), 7.89 (d, 1H, J = 5.2 Hz), 7.71 (d, 2H, J = 8.4 Hz), 7.25 (d, 2H, J = 8.4 Hz), 7.01 (d, 1H, J = 1.2 Hz), 5.96 (d, 1H, J = 5.2 Hz), 3.92-3.91 (m, 2H), 3.70-3.69 (m, 2H), 3.53-3.50 (m, 2H), 3.49-3.45 (m, 2H), 3.35-3.30 (m, 1H), 2.80-2.78 (m, 2H), 2.69-2.66 (m, 2H), 2.06-1.95 (m, 3H), 1.79-1.68 (m, 6H), 1.62-1.58 (m, 2H), 1.58-1.55 (m, 1H), 0.77-0.74 (m, 4H). |

TABLE 1-continued

| # | Structure | LCMS (M + 1) | NMR |
|---|---|---|---|
| 306 | 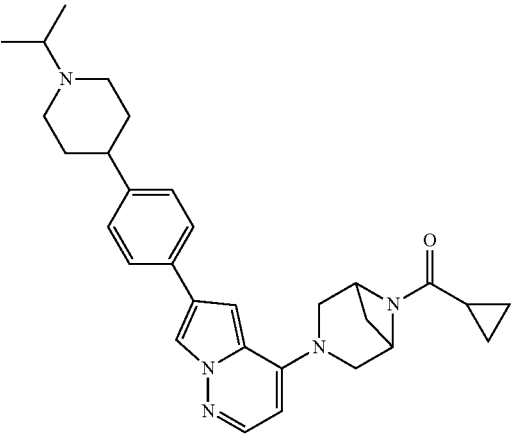 [SMILES: CC(C)N1CCC(c2ccc(-c3cc4c(N5CC6CC(C5)N6C(=O)C5CC5)ccnn4c3)cc2)CC1] | 485 | 1H NMR (400 MHz, DMSO-d6) δ 8.08 (d, J = 1.7 Hz, 1H), 7.74-7.62 (m, 3H), 7.32-7.18 (m, 3H), 5.60 (d, J = 5.9 Hz, 1H), 4.83 (s, 1H), 4.40 (s, 1H), 4.22 (d, J = 11.6 Hz, 2H), 3.98 (d, J = 11.5 Hz, 1H), 3.85 (d, J = 11.3 Hz, 1H), 2.87 (d, J = 10.9 Hz, 2H), 2.69 (q, J = 7.2 Hz, 2H), 2.4.38 (m, 1H), 2.20 (t, J = 11.3 Hz, 2H), 1.74 (q, J = 7.1, 4.5 Hz, 3H), 1.69-1.48 (m, 3H), 0.98 (d, J = 6.6 Hz, 6H), 0.91-0.72 (m, 2H), 0.71 (s, 1H), 0.51 (s, 1H). |
| 307 | 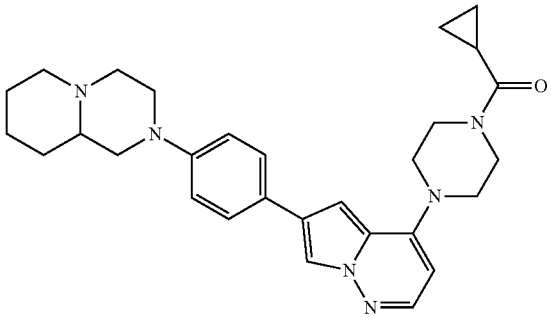 [SMILES: O=C(C1CC1)N1CCN(c2ccnn3cc(-c4ccc(N5CCN6CCCCC6C5)cc4)cc23)CC1] | 485 | 1H-NMR (400 MHz, 6d-DMSO) δ ppm 8.30 (br. s., 1H), 8.06 (s, 1H), 7.87 (d, 1H, J = 5.2 Hz), 7.64 (d, 2H, J = 8.0 Hz), 6.95 (d, 2H, J = 8.0 Hz), 6.93 (s, 1H), 5.96 (d, 1H, J = 5.2 Hz), 3.95-3.90 (br., 2H), 3.71-3.45 (m, 8H), 2.79-2.66 (m, 2H), 2.38-2.33 (m, 1H), 2.27-2.20 (m, 1H), 2.03-1.92 (m, 2H), 1.74-1.45 (m, 4H), 1.31-1.08 (m, 4H), 0.77-0.74 (m, 4H). |
| 308 | 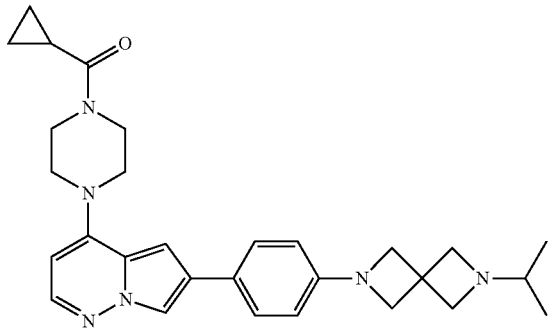 [SMILES: CC(C)N1CC2(CN(c3ccc(-c4cc5c(N6CCN(C(=O)C7CC7)CC6)ccnn5c4)cc3)C2)C1] | 485 | 1H-NMR (400 MHz, 6d-DMSO) δ ppm 8.17 (s, 1H), 8.03 (d, 1H, J = 1.6 Hz), 7.86 (d, 1H, J = 5.6 Hz), 7.62 (d, 2H, J = 8.8 Hz), 6.00 (d, 1H, J = 1.6 Hz), 6.45 (d, 2H, J = 8.8 Hz), 5.96 (d, 1H, J = 5.6 Hz), 3.96-3.89 (m, 6H), 3.72-3.68 (m, 2H), 3.45-3.45 (m, 9H), 2.04-2.00 (m, 1H), 0.91 (d, 6H, J = 6.0 Hz), 0.78-0.74 (m, 4H). |
| 309 | 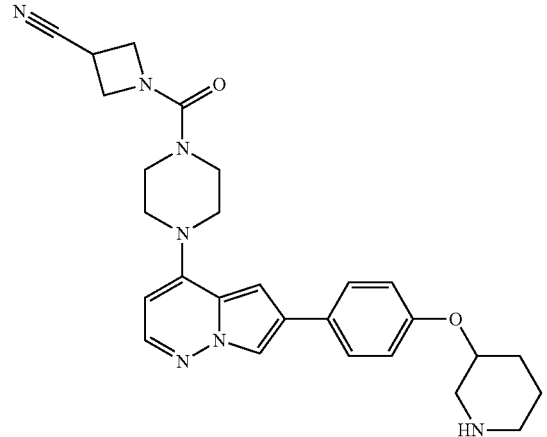 [SMILES: N#CC1CN(C(=O)N2CCN(c3ccnn4cc(-c5ccc(OC6CCCNC6)cc5)cc34)CC2)C1] | 486 | 1H-NMR (400 MHz, 6d-DMSO) δ ppm 8.11 (d, 1H, J = 1.6 Hz), 7.88 (d, 1H, J = 5.2 Hz), 7.73 (d, 2H, J = 8.4 Hz), 6.99 (d, 2H, J = 8.4 Hz), 6.94 (d, 1H, J = 1.6 Hz), 5.96 (d, 1H, J = 5.6 Hz), 4.48-4.41 (m, 1H), 4.22 (d, 2H, J = 8.4 Hz), 4.09 (dd, 2H, J = 8.4, 6.4 Hz), 3.80-3.72 (m, 1H), 3.47-3.45 (m, 8H), 3.21-3.18 (m, 1H), 2.92-2.86 (m, 1H), 2.82-2.67 (m, 2H), 2.01-1.96 (m, 1H), 1.80-1.72 (m, 1H), 1.68-1.60 (m, 1H), 1.57-1.43 (m, 2H). |

TABLE 1-continued

| # | Structure | LCMS (M + 1) | NMR |
|---|---|---|---|
| 310 | 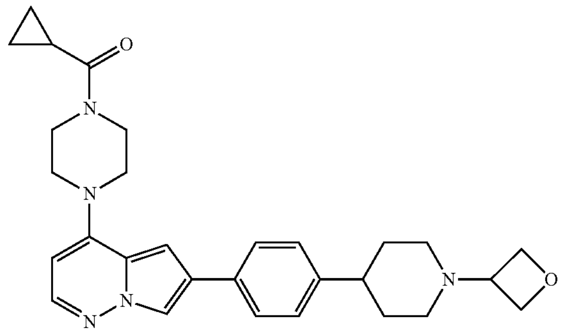 [SMILES: O=C(C1CC1)N1CCN(c2ccnn3cc(-c4ccc(C5CCN(C6COC6)CC5)cc4)cc23)CC1] | 486 | 1H-NMR (400 MHz, DMSO-d6) δ ppm 8.16 (s, 1H), 7.90 (d, 2H, J = 5.2 Hz), 7.73 (d, 2H, J = 8.0 Hz), 7.27 (d, 2H, J = 8.0 Hz), 7.03 (s, 1H), 5.97 (d, 1H, J = 5.6 Hz), 4.55 (t, 2H, J = 6.4 Hz), 4.45 (t, 2H, J = 6.4 Hz), 3.93 (br. s., 2H), 3.71 (br. s., 2H), 3.54-3.47 (m, 4H), 3.42-3.35 (m, 2H), 2.82-2.79 (m, 2H), 2.06-2.00 (m, 1H), 1.86-1.64 (m, 6H), 0.78-0.75 (m, 4H). |
| 311 | 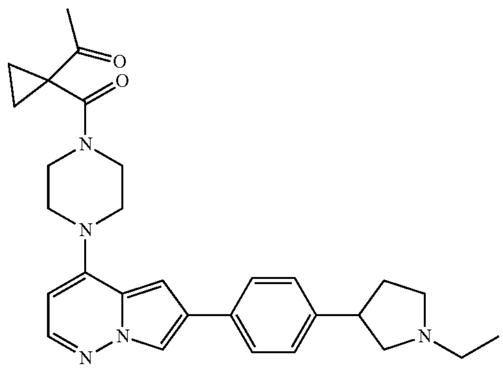 [SMILES: CCN1CCC(c2ccc(-c3cc4c(N5CCN(C(=O)C6(C(C)=O)CC6)CC5)ccnn4c3)cc2)C1] | 486 | 1H-NMR (400 MHz, 6d-DMSO) δ ppm 8.14 (d, 1H, J = 1.6 Hz), 7.89 (d, 1H, J = 5.6 Hz), 7.72 (d, 2H, J = 8.4 Hz), 7.28 (d, 2H, J = 8.4 Hz), 7.01 (d, 1H, J = 1.6 Hz), 5.97 (d, 1H, J = 5.6 Hz), 3.73-3.71 (m, 2H), 3.64-3.62 (m, 2H), 3.48-3.46 (m, 4H), 3.30-3.25 (m, 1H), 2.96-2.92 (m, 1H), 2.73-2.65 (m, 2H), 2.46-2.42 (m, 1H), 2.25-2.19 (m, 1H), 2.09 (s, 3H), 2.03-1.92 (m, 1H), 1.80-1.72 (m, 1H), 1.49-1.46 (m, 2H), 1.34-1.31 (m, 2H), 1.06 (t, 3H, J = 7.2 Hz). |
| 312 | 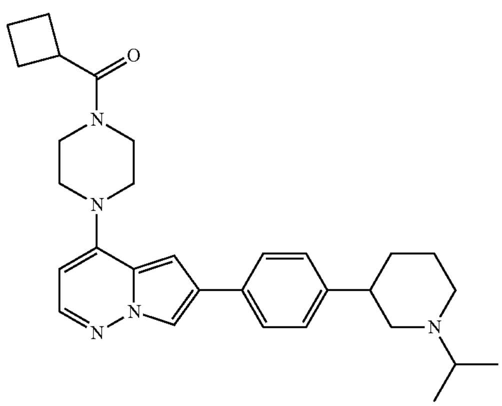 [SMILES: CC(C)N1CCCC(c2ccc(-c3cc4c(N5CCN(C(=O)C6CCC6)CC5)ccnn4c3)cc2)C1] | 486 | 1H-NMR (400 MHz, 6d-DMSO) δ ppm 8.14 (d, 1H, J = 1.2 Hz), 7.89 (d, 1H, J = 5.6 Hz), 7.71 (d, 2H, J = 8.4 Hz), 7.27 (d, 2H, J = 8.4 Hz), 6.99 (d, 1H, J = 1.2 Hz), 5.96 (d, 1H, J = 5.6 Hz), 3.65-3.66 (m, 2H), 3.55-3.52 (m, 2H), 3.46-3.43 (m, 4H), 3.42-3.39 (m, 1H), 2.85-2.75 (m, 2H), 2.73-2.65 (m, 2H), 2.22-2.17 (m, 2H), 2.16-2.09 (m, 4H), 1.95-1.87 (m, 1H), 1.85-1.78 (m, 1H), 1.77-1.69 (m, 2H), 1.60-1.50 (m, 1H), 1.50-1.39 (m, 1H), 0.95-0.98 (m, 6H). |
| 313 | 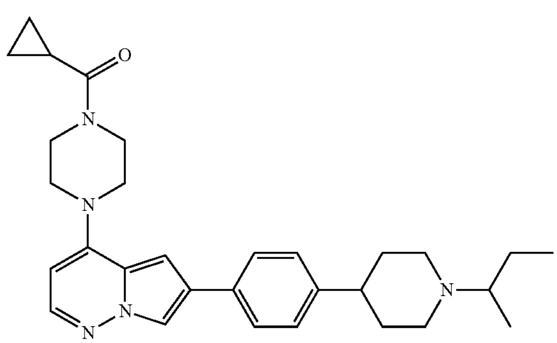 [SMILES: CCC(C)N1CCC(c2ccc(-c3cc4c(N5CCN(C(=O)C6CC6)CC5)ccnn4c3)cc2)CC1] | 486 | 1H-NMR (400 MHz, 6d-DMSO) δ ppm 8.13 (d, 1H, J = 1.6 Hz), 7.88 (d, 1H, J = 5.6 Hz), 7.71 (d, 2H, J = 8.0 Hz), 7.23 (d, 2H, J = 8.0 Hz), 7.01 (d, 1H, J = 1.6 Hz), 5.96 (d, 1H, J = 5.6 Hz), 3.92-3.91 (m, 2H), 3.70-3.68 (m, 2H), 3.55-3.50 (m, 2H), 3.50-3.45 (m, 2H), 2.82-2.78 (m, 2H), 2.50-2.45 (m, 2H), 2.40-2.35 (m, 1H), 2.22-2.17 (m, 1H), 2.03-1.98 (m, 1H), 1.78-1.72 (m, 2H), 1.67-1.60 (m, 2H), 1.57-1.49 (m, 1H), 1.30-1.22 (m, 1H), 0.92 (d, 3H, J = 6.8 Hz), 0.86 (t, 3H, J = 7.6 Hz), 0.78-0.71 (m, 4H). |

TABLE 1-continued

| # | Structure | LCMS (M + 1) | NMR |
|---|---|---|---|
| 314 | 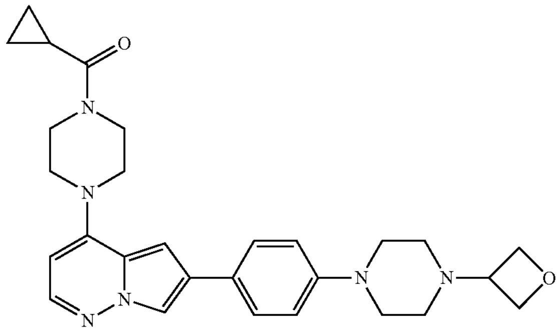 [SMILES: O=C(C1CC1)N1CCN(c2ccnn3cc(-c4ccc(N5CCN(C6COC6)CC5)cc4)cc23)CC1] | 487 | 1H-NMR (400 MHz, CDCl3) δ ppm 7.88 (d, 1H, J = 1.6 Hz), 7.83 (d, 1H, J = 5.2 Hz), 7.57 (d, 2H, J = 8.8 Hz), 6.98 (d, 2H, J = 8.8 Hz), 6.66 (d, 1H, J = 0.8 Hz), 5.83 (d, 1H, J = 5.2 Hz), 4.73-4.66 (m, 4H), 3.95-3.88 (m, 4H), 3.59-3.46 (m, 5H), 3.29-3.27 (m, 4H), 2.54-2.52 (m, 4H), 1.81-1.76 (m, 1H), 1.07-1.03 (m, 2H), 0.85-0.81 (m, 2H). |
| 315 | 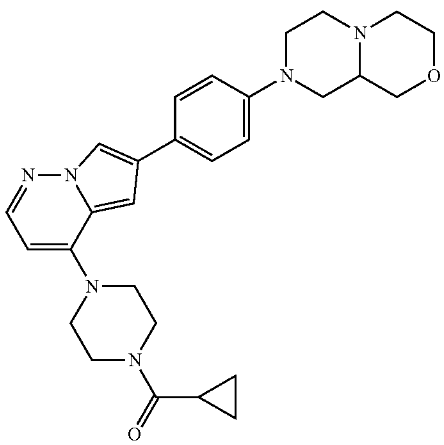 [SMILES: O=C(C1CC1)N1CCN(c2ccnn3cc(-c4ccc(N5CCN6CCOCC6C5)cc4)cc23)CC1] | 487 | 1H-NMR (400 MHz, 6d-DMSO) δ ppm 8.15 (s, 1H), 8.07 (d, 1H, J = 1.6 Hz), 7.87 (d, 1H, J = 4.8 Hz), 7.65 (d, 2H, J = 8.8 Hz), 6.96 (d, 2H, J = 8.8 Hz), 6.94 (s, 1H), 5.96 (d, 1H, J = 5.6 Hz), 3.95-3.90 (br., 2H), 3.79-3.65 (m, 5H), 3.57-3.46 (m, 6H), 3.20-3.15 (m, 1H), 2.84-2.67 (m, 3H), 2.33-2.20 (m, 4H), 2.04-2.00 (m, 1H), 0.79-0.74 (m, 4H). |
| 316 | 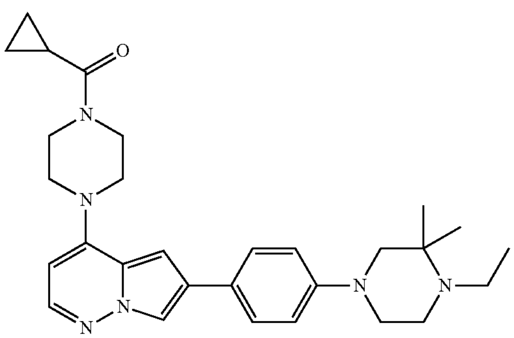 [SMILES: CCN1CCN(c2ccc(-c3cc4c(N5CCN(C(=O)C6CC6)CC5)ccnn4c3)cc2)CC1(C)C] | 487 | 1H-NMR (400 MHz, 6d-DMSO) δ ppm 8.05 (d, 1H, J = 1.6 Hz), 7.86 (d, 1H, J = 5.6 Hz), 7.63 (d, 2H, J = 8.8 Hz), 6.94-6.91 (m, 3H), 5.95 (d, 1H, J = 5.6 Hz), 3.95-3.85 (m, 2H), 3.75-3.65 (m, 2H), 3.60-3.40 (m, 4H), 3.14-3.10 (m, 2H), 2.88 (s, 2H), 2.63-2.59 (m, 2H), 2.39 (q, 2H, J = 7.2 Hz), 2.05-1.95 (m, 1H), 1.05 (s, 6H), 0.99 (t, 3H, J = 7.2 Hz), 0.80-0.70 (m, 4H). |
| 317 | 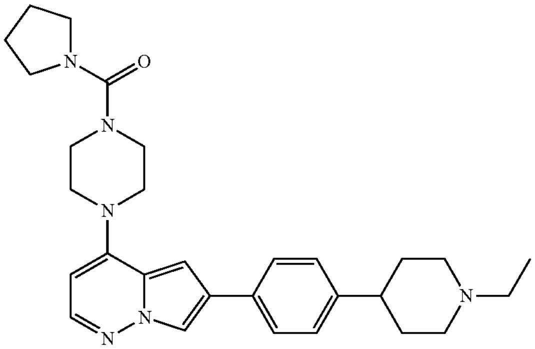 [SMILES: CCN1CCC(c2ccc(-c3cc4c(N5CCN(C(=O)N6CCCC6)CC5)ccnn4c3)cc2)CC1] | 487 | 1H-NMR (400 MHz, 6d-DMSO) δ ppm 8.13 (d, 1H, J = 1.6 Hz), 7.88 (d, 1H, J = 5.6 Hz), 7.72 (d, 2H, J = 8.4 Hz), 7.25 (d, 2H, J = 8.4 Hz), 6.99 (d, 1H, J = 1.6 Hz), 5.96 (d, 1H, J = 5.6 Hz), 3.46-3.45 (m, 4H), 3.41-3.40 (m, 4H), 3.34-3.31 (m, 4H), 3.01-2.98 (m, 2H), 2.36 (q, 2H, J = 7.2 Hz), 2.01-1.95 (m, 2H), 1.80-1.72 (m, 8H), 1.70-1.64 (m, 1H), 1.02 (t, 3H, J = 7.2 Hz). |

TABLE 1-continued

| # | Structure | LCMS (M + 1) | NMR |
|---|---|---|---|
| 318 | 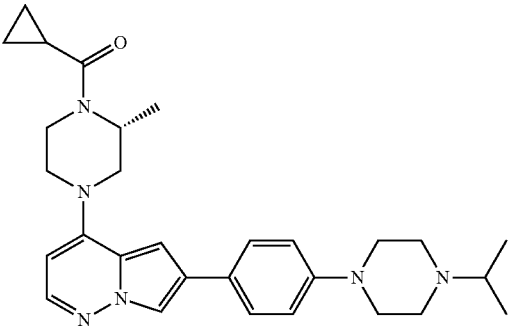 [SMILES: CC(C)N1CCN(c2ccc(-c3cc4c(N5CCN(C(=O)C6CC6)[C@H](C)C5)ccnn4c3)cc2)CC1] | 487 | 1H-NMR (500 MHz, 6d-DMSO) δ ppm 8.08 (d, 1H, J = 1.0 Hz), 7.86 (d, 1H, J = 5.5 Hz), 7.63 (d, 2H, J = 8.5 Hz), 6.96 (d, 1H, J = 8.5 Hz), 6.87 (d, 1H, J = 2.0 Hz), 5.95 (d, 1H, J = 5.5 Hz), 4.66-4.65 (m, 1H), 4.21-4.16 (m, 1H), 3.95-3.93 (m, 1H), 3.93-3.90 (m, 1H), 3.22-3.19 (m, 2H), 3.19-3.09 (m, 4H), 2.70-2.65 (m, 1H), 2.60-2.54 (m, 4H), 2.01-1.96 (m, 1H), 1.43-1.35 (m, 2H), 1.30-1.21 (m, 2H), 1.06-0.96 (m, 6H), 0.82-0.71 (m, 4H). |
| 319 | 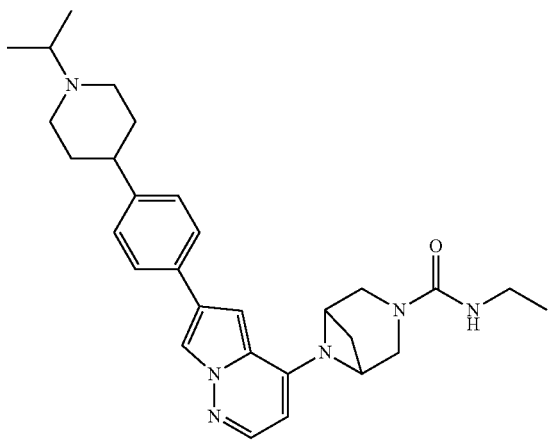 [SMILES: CCNC(=O)N1CC2CC(C1)N2c1ccnn2cc(-c3ccc(C4CCN(C(C)C)CC4)cc3)cc12] | 488 | 1H NMR (400 MHz, Methanol-d4) δ 7.90 (d, J = 1.8 Hz, 1H), 7.72 (d, J = 5.4 Hz, 1H), 7.67-7.59 (m, 2H), 7.30-7.20 (m, 2H), 6.82 (d, J = 1.8 Hz, 1H), 5.72 (d, J = 5.5 Hz, 1H), 4.73 (d, J = 33.7 Hz, 2H), 3.97 (d, J = 11.7 Hz, 2H), 3.44 (d, J = 11.8 Hz, 2H), 3.15-3.00 (m, 4H), 2.95 (q, J = 7.0 Hz, 1H), 2.79 (p, J = 6.5 Hz, 1H), 2.54 (tt, = 12.1, 4.3 Hz, 1H), 2.36 (td, J = 11.8, 2.8 Hz, 3H), 1.90-1.67 (m, 5H), 1.12 (dd, J = 6.7, 3.8 Hz, 7H), 1.02 (t, J = 7.2 Hz, 2H). |
| 320 | 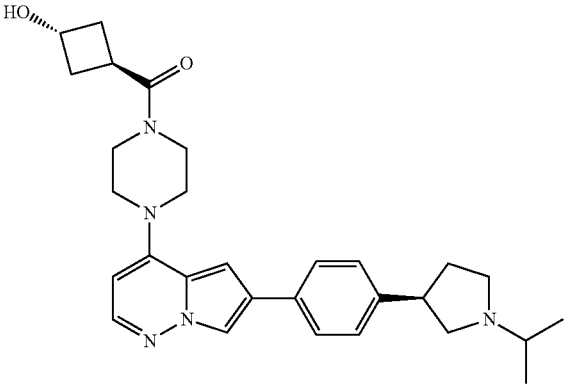 [SMILES: CC(C)N1CC[C@H](c2ccc(-c3cc4c(N5CCN(C(=O)[C@H]6C[C@H](O)C6)CC5)ccnn4c3)cc2)C1] | 488 | 1H-NMR (400 MHz, 6d-DMSO) δ ppm 8.14 (d, 1H, J = 1.6 Hz), 7.89 (d, 1H, J = 6.0 Hz), 7.72 (d, 2H, J = 8.4 Hz), 7.29 (d, 2H, J = 8.4 Hz), 7.00 (d, 1H, J = 1.2 Hz), 5.96 (d, 1H, J = 5.2 Hz), 5.10 (d, 1H, J = 6.0 Hz), 4.20-4.00 (m, 1H), 3.70-3.60 (m, 2H), 3.58-3.50 (m, 2H), 3.48-3.35 (m, 4H), 3.30-3.15 (m, 2H), 3.05-2.95 (m, 1H), 2.80-2.60 (m, 2H), 2.47-2.30 (m, 4H), 2.25-2.15 (m, 1H), 2.10-2.00 (m, 2H), 1.80-1.70 (m, 1H), 1.10-1.00 (m, 6H). |
| 321 | 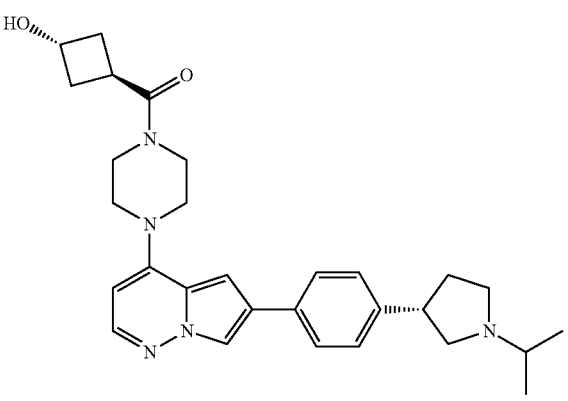 [SMILES: CC(C)N1CC[C@@H](c2ccc(-c3cc4c(N5CCN(C(=O)[C@H]6C[C@H](O)C6)CC5)ccnn4c3)cc2)C1] | 488 | 1H-NMR (400 MHz, CDCl3) δ ppm 7.92 (d, 1H, J = 1.6 Hz), 7.85 (d, 1H, J = 5.2 Hz), 7.59 (d, 2H, J = 8.0 Hz), 7.32 (d, 2H, J = 8.0 Hz), 6.68 (d, 1H, J = 1.6 Hz), 5.84 (d, 1H, J = 5.2 Hz), 4.54-4.48 (m, 1H), 3.92-3.83 (m, 2H), 3.65-3.57 (m, 2H), 3.50-3.42 (m, 4H), 3.41-3.37 (m, 1H), 3.35-3.25 (m, 2H), 3.11-3.00 (m, 1H), 2.81-2.72 (m, 1H), 2.69-2.63 (m, 2H), 2.59-2.51 (m, 2H), 2.40-2.32 (m, 1H), 2.28-2.21 (m, 2H), 1.99-1.94 (m, 2H), 1.20-1.16 (dd, 6H, J = 6.4, 1.2 Hz). |

TABLE 1-continued

| # | Structure | LCMS (M + 1) | NMR |
|---|---|---|---|
| 322 | 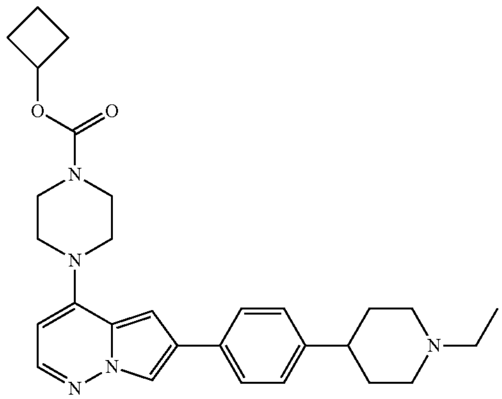 [SMILES: CCN1CCC(c2ccc(-c3cc4c(N5CCN(C(=O)OC6CCC6)CC5)ccnn4c3)cc2)CC1] | 488 | 1H-NMR (400 MHz, 6d-DMSO) δ ppm 8.36 (s, 1H), 8.14 (d, 1H, J = 1.6 Hz), 7.89 (d, 1H, J = 5.6 Hz), 7.72 (d, 2H, J = 8.0 Hz), 7.25 (d, 2H, J = 8.0 Hz), 6.99 (d, 1H, J = 1.6 Hz), 5.97 (d, 1H, J = 5.6 Hz), 4.86 (quintet, 1H, J = 7.2 Hz), 3.60-3.52 (m, 4H), 3.50-3.40 (m, 4H), 3.10-2.90 (m, 2H), 2.48-2.42 (m, 1H), 2.36 (q, 2H, J = 7.2 Hz), 2.30-2.20 (m, 2H), 2.10-1.90 (m, 4H), 1.80-1.62 (m, 4H), 1.60-1.50 (m, 2H), 1.02 (t, 3H, J = 7.2 Hz). |
| 323 | 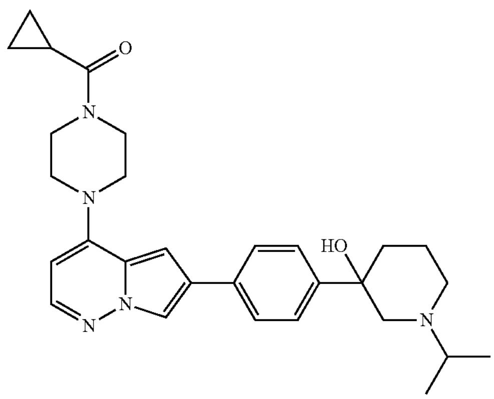 [SMILES: CC(C)N1CCCC(O)(c2ccc(-c3cc4c(N5CCN(C(=O)C6CC6)CC5)ccnn4c3)cc2)C1] | 488 | 1H-NMR (400 MHz, 6d-DMSO) δ ppm 8.26-8.17 (m, 1H), 7.92-7.88 (m, 1H), 7.77-7.72 (m, 2H), 7.57 (d, 2H, J = 7.6 Hz), 7.05 (s, 1H), 5.98 (d, 1H, J = 5.6 Hz), 4.56-4.44 (m, 1H), 4.00-3.80 (m, 2H), 3.80-3.60 (m, 2H), 3.60-3.50 (m, 2H), 3.50-3.40 (m, 2H), 3.31-3.00 (m, 1H), 2.90-2.75 (m, 1H), 2.70-2.51 (m, 1H), 2.45-2.38 (m, 1H), 2.05-1.98 (m, 2H), 1.90-1.79 (m, 2H), 1.58-1.50 (m, 1H), 1.50-1.41 (m, 1H), 1.03-0.98 (m, 6H), 0.79-0.73 (m, 4H). |
| 324 | 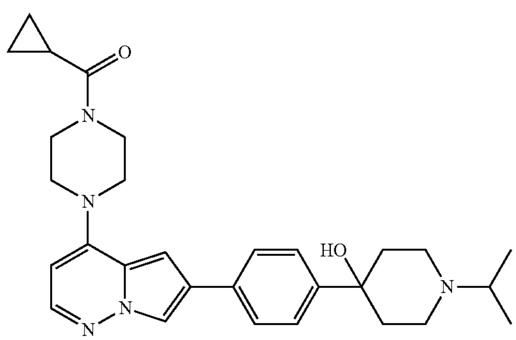 [SMILES: CC(C)N1CCC(O)(c2ccc(-c3cc4c(N5CCN(C(=O)C6CC6)CC5)ccnn4c3)cc2)CC1] | 488 | 1H-NMR (400 MHz, MeOD) δ ppm 7.89 (s, 1H), 7.75 (d, 1H, J = 5.6 Hz), 7.66 (d, 1H, J = 8.8 Hz), 7.44 (d, 1H, J = 8.8 Hz), 6.84 (s, 1H), 5.90 (d, 1H, J = 5.6 Hz), 3.93 (m, 2H), 3.75 (m, 2H), 3.53-3.33 (m, 9H), 2.28-2.19 (m, 2H), 1.99-1.94 (m, 2H), 1.91 (m, 1H), 1.33 (d, 6H, J = 6.4 Hz), 0.85-0.83 (m, 2H), 0.78-0.74 (m, 2H). |
| 325 | 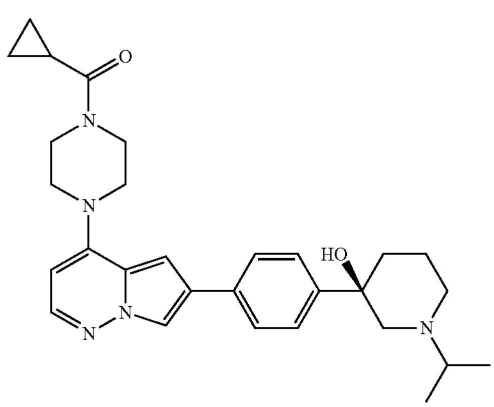 [SMILES: CC(C)N1CCC[C@@](O)(c2ccc(-c3cc4c(N5CCN(C(=O)C6CC6)CC5)ccnn4c3)cc2)C1] | 488 | 1H-NMR (400 MHz, 6d-DMSO) δ ppm 8.17 (s, 1H), 7.90 (d, 1H, J = 5.6 Hz), 7.75 (d, 2H, J = 8.0 Hz), 7.56 (d, 2H, J = 8.0 Hz), 7.05 (s, 1H), 5.98 (d, 1H, J = 5.6 Hz), 4.53-4.48 (m, 1H), 4.00-3.80 (m, 2H), 3.80-3.65 (m, 2H), 3.60-3.50 (m, 2H), 3.50-3.40 (m, 2H), 3.33-3.25 (m, 1H), 2.85-2.51 (m, 2H), 2.50-2.30 (m, 2H), 2.05-1.95 (m, 1H), 1.90-1.70 (m, 2H), 1.62-1.55 (m, 1H), 1.55-1.48 (m, 1H), 1.15-0.85 (m, 6H), 0.79-0.70 (m, 4H). |

TABLE 1-continued

| # | Structure | LCMS (M + 1) | NMR |
|---|---|---|---|
| 326 | 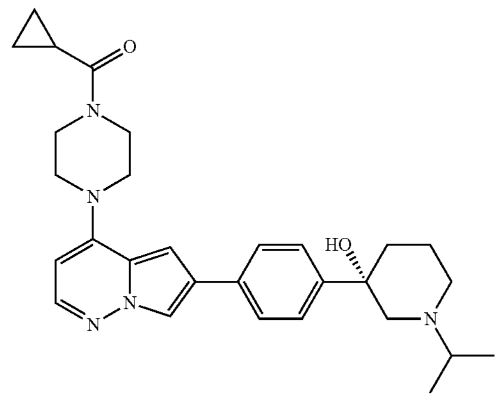 | 488 | 1H-NMR (400 MHz, 6d-DMSO) δ ppm 8.20 (s, 1H), 7.91 (d, 1H, J = 5.6 Hz), 7.89-7.65 (m, 2H), 7.57 (d, 2H, J = 8.0 Hz), 7.06 (s, 1H), 5.98 (d, 1H, J = 5.6 Hz), 4.00-3.85 (m, 2H), 3.80-3.65 (m, 2H), 3.60-3.50 (m, 2H), 3.50-3.40 (m, 2H), 3.33-3.25 (m, 1H), 2.50-2.10 (m, 4H), 2.05-1.40 (m, 5H), 1.30-0.80 (m, 6H), 0.79-0.70 (m, 4H). |
| 327 | 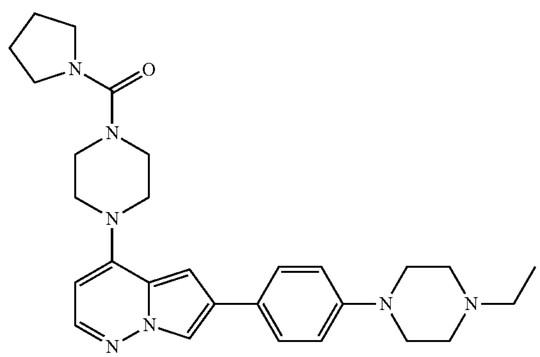 [SMILES: CCN1CCN(c2ccc(-c3cc4c(N5CCN(C(=O)N6CCCC6)CC5)ccnn4c3)cc2)CC1] | 488 | 1H-NMR (400 MHz, DMSO-d6) δ ppm 8.05 (d, 1H, J = 1.6 Hz), 7.86 (d, 1H, J = 5.6 Hz), 7.65-7.63 (m, 2H), 6.96-6.94 (m, 2H), 6.91 (d, 1H, J = 1.2 Hz), 5.95 (d, 1H, J = 5.6 Hz), 3.44-3.40 (m, 4H), 3.39-3.35 (m, 8H), 3.16 (br. s., 4H), 2.56 (br. s., 4H), 2.49 (br. s., 2H), 1.76 (br. s., 4H), 1.05 (d, 3H, J = 7.2 Hz). |
| 328 | 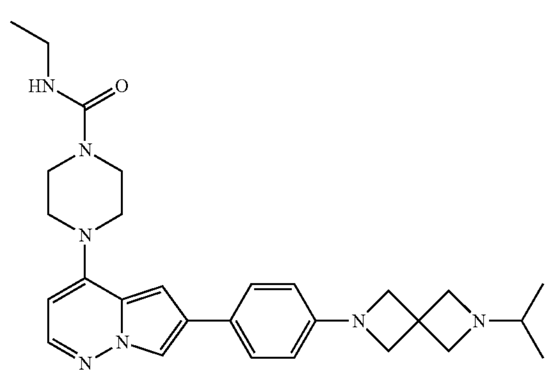 [SMILES: CCNC(=O)N1CCN(c2ccnn3cc(-c4ccc(N5CC6(C5)CN(C(C)C)C6)cc4)cc23)CC1] | 488 | 1H-NMR (400 MHz, 6d-DMSO) δ ppm 8.23 (s, 1H), 8.02 (d, 1H, J = 1.6 Hz), 7.85 (d, 1H, J = 5.6 Hz), 7.61 (d, 2H, J = 8.4 Hz), 6.88 (s, 1H), 6.61 (t, 1H, J = 5.6 Hz), 6.44 (d, 2H, J = 8.4 Hz), 5.96 (d, 1H, J = 5.6 Hz), 3.87 (s, 4H), 3.55-3.50 (m, 4H), 3.48-3.45 (m, 4H), 3.32 (s, 4H), 3.15-3.04 (m, 2H), 2.34-2.32 (m, 1H), 1.03 (t, 3H, J = 7.2 Hz), 0.87 (d, 6H, J = 6.4 Hz). |

TABLE 1-continued

| # | Structure | LCMS (M + 1) | NMR |
|---|---|---|---|
| 329 | 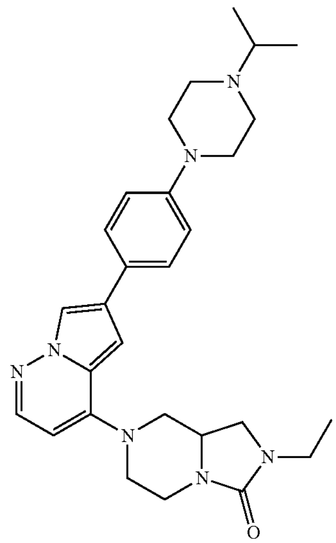 [SMILES: CCN1CC2CN(c3ccnn4cc(-c5ccc(N6CCN(C(C)C)CC6)cc5)cc34)CCN2C1=O] | 489 | |
| 330 | 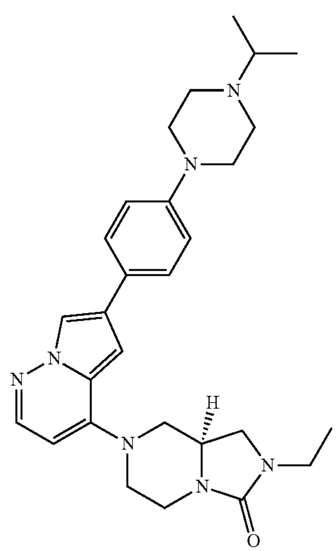 [SMILES: CCN1C[C@@H]2CN(c3ccnn4cc(-c5ccc(N6CCN(C(C)C)CC6)cc5)cc34)CCN2C1=O] | 489 | |

TABLE 1-continued

| # | Structure | LCMS (M + 1) | NMR |
|---|---|---|---|
| 331 | 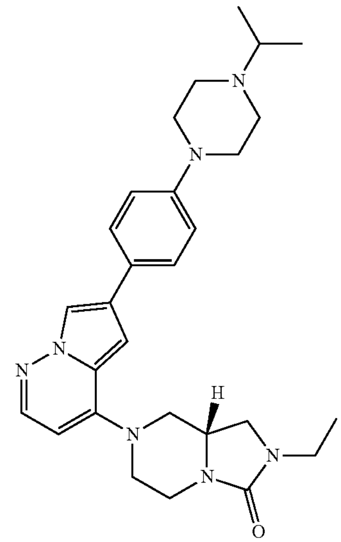 [SMILES: CCN1C[C@H]2CN(c3ccnn4cc(-c5ccc(N6CCN(C(C)C)CC6)cc5)cc34)CCN2C1=O] | 489 | |
| 332 | 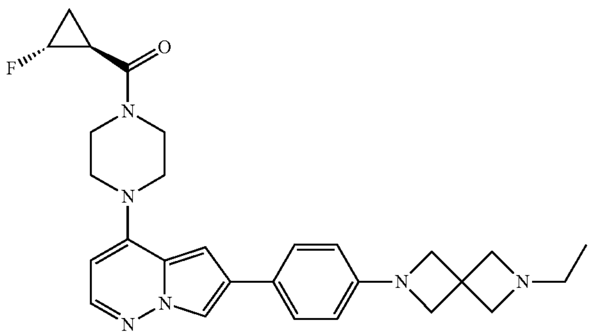 [SMILES: CCN1CC2(C1)CN(c1ccc(-c3cc4c(N5CCN(C(=O)[C@@H]6C[C@H]6F)CC5)ccnn4c3)cc1)C2] | 489 | 1H-NMR (400 MHz, CDCl3) δ ppm 7.85 (d, 1H, J = 1.6 Hz), 7.82 (d, 1H, J = 5.2 Hz), 7.51 (d, 2H, J = 8.4 Hz), 6.62 (d, 1H, J = 1.6 Hz), 6.51 (d, 1H, J = 8.4 Hz), 5.83 (d, 1H, J = 5.2 Hz), 4.93-4.70 (m, 1H), 4.13-4.05 (m, 1H), 4.03-3.95 (m, 1H), 3.93-3.84 (m, 1H), 3.80-3.71 (m, 1H), 3.68-3.60 (m, 1H), 3.58-3.50 (m, 1H), 3.47-3.41 (m, 1H), 3.38 (s, 1H), 3.38-3.32 (m, 1H), 2.46 (q, 2H, J = 7.2 Hz), 1.97-1.95 (m, 1H), 1.95-1.90 (m, 1H), 1.14-1.06 (m, 1H), 0.98 (t, 3H, J = 7.2 Hz). |
| 333 | 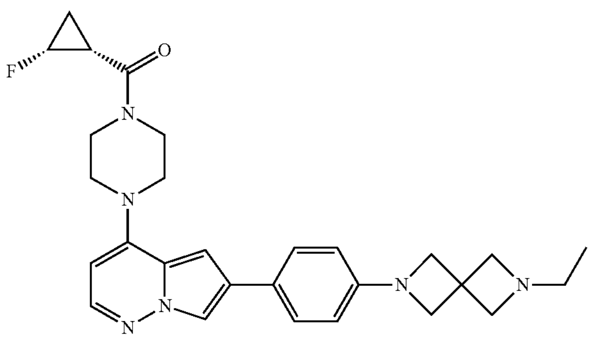 [SMILES: CCN1CC2(C1)CN(c1ccc(-c3cc4c(N5CCN(C(=O)[C@H]6C[C@H]6F)CC5)ccnn4c3)cc1)C2] | 489 | 1H-NMR (400 MHz, CDCl3) δ ppm 8.56 (s, 1H), 7.86 (d, 1H, J = 1.6 Hz), 7.83 (d, 1H, J = 5.2 Hz), 7.52 (d, 2H, J = 8.4 Hz), 6.63 (d, 1H, J = 1.6 Hz), 6.51 (d, 2H, J = 8.4 Hz), 5.84 (d, 1H, J = 5.2 Hz), 4.93-4.70 (m, 1H), 4.13-4.05 (m, 1H), 4.04-4.01 (m, 4H), 4.00-3.95 (m, 1H), 3.94-3.83 (m, 1H), 3.80-3.75 (m, 1H), 3.72-3.70 (m, 4H), 3.68-3.60 (m, 1H), 3.59-3.50 (m, 1H), 3.48-3.45 (m, 1H), 3.42-3.39 (m, 1H), 2.72 (q, 2H, J = 7.2 Hz), 1.98-1.92 (m, 1H), 1.92-1.87 (m, 1H), 1.15-1.05 (m, 4H). |
| 334 | 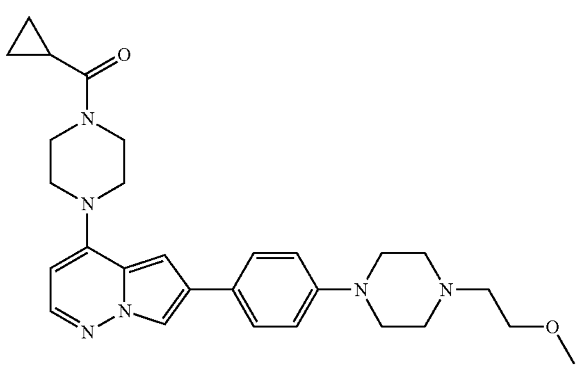 [SMILES: COCCN1CCN(c2ccc(-c3cc4c(N5CCN(C(=O)C6CC6)CC5)ccnn4c3)cc2)CC1] | 489 | 1H-NMR (400 MHz, CDCl3) δ ppm 7.88 (d, 1H, J = 2.0 Hz), 7.82 (d, 1H, J = 5.2 Hz), 7.55 (d, 2H, J = 8.8 Hz), 6.97 (d, 2H, J = 8.8 Hz), 6.66 (d, 1H, J = 2.0 Hz), 5.83 (d, 1H, J = 6.0 Hz), 3.94-3.86 (m, 4H), 3.57 (t, 2H, J = 5.6 Hz), 3.58-3.46 (m, 4H), 3.38 (s, 3H), 3.27 (t, 4H, J = 5.2 Hz), 2.70 (t, 4H, J = 5.2 Hz), 2.67 (t, 2H, J = 5.6 Hz), 1.80-1.76 (m, 1H), 1.06-1.03 (m, 2H), 0.84-0.81 (m, 2H). |

TABLE 1-continued

| # | Structure | LCMS (M + 1) | NMR |
|---|---|---|---|
| 335 | 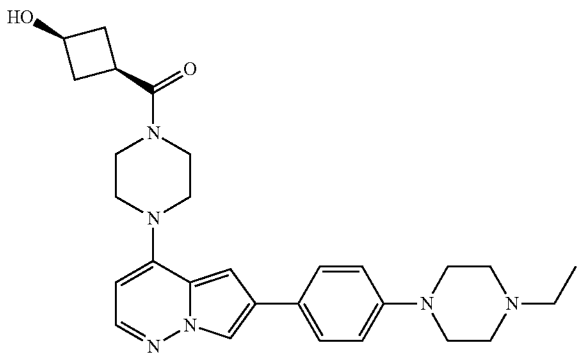 [SMILES: CCN1CCN(c2ccc(-c3cc4c(N5CCN(C(=O)[C@H]6C[C@@H](O)C6)CC5)ccnn4c3)cc2)CC1] | 489 | 1H-NMR (400 MHz, CDCl3) δ ppm 7.87 (d, 1H, J = 1.6 Hz), 7.82 (d, 1H, J = 5.2 Hz), 7.56 (d, 2H, J = 8.8 Hz), 6.98 (d, 2H, J = 8.8 Hz), 6.63 (d, 1H, J = 1.6 Hz), 5.82 (d, 1H, J = 5.2 Hz), 4.24-4.21 (m, 1H), 3.88-3.84 (m, 2H), 3.66-3.62 (m, 2H), 3.45-3.40 (m, 4H), 3.37-3.30 (m, 4H), 2.82-2.78 (m, 1H), 2.78-2.73 (m, 4H), 2.65-2.57 (m, 4H), 2.26-2.23 (m, 2H), 1.26-1.20 (m, 3H). |
| 336 | 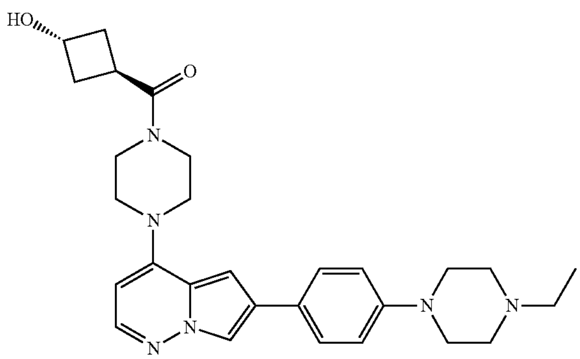 [SMILES: CCN1CCN(c2ccc(-c3cc4c(N5CCN(C(=O)[C@H]6C[C@H](O)C6)CC5)ccnn4c3)cc2)CC1] | 489 | 1H-NMR (400 MHz, CDCl3) δ ppm 7.87 (d, 1H, J = 2.0 Hz), 7.82 (d, 1H, J = 5.6 Hz), 7.56 (d, 2H, J = 8.8 Hz), 6.98 (d, 2H, J = 8.8 Hz), 6.63 (d, 1H, J = 2.0 Hz), 5.82 (d, 1H, J = 5.6 Hz), 4.51 (quintet, 1H, J = 6.4 Hz), 3.88-3.85 (m, 2H), 3.62-3.58 (m, 2H), 3.45-3.42 (m, 4H), 3.30-3.25 (m, 5H), 2.69-2.62 (m, 6H), 2.50 (d, 2H, J = 7.2 Hz), 2.27-2.19 (m, 2H), 1.16 (t, 3H, J = 7.2 Hz). |
| 337 | 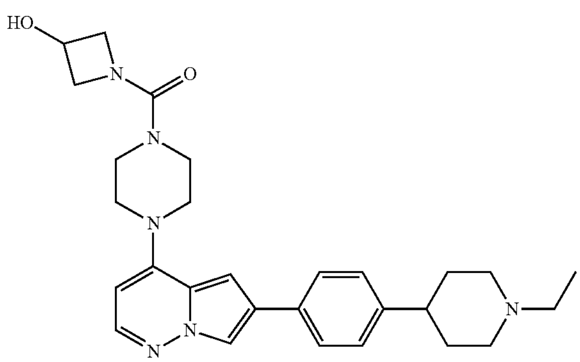 [SMILES: CCN1CCC(c2ccc(-c3cc4c(N5CCN(C(=O)N6CC(O)C6)CC5)ccnn4c3)cc2)CC1] | 489 | 1H-NMR (400 MHz, 6d-DMSO) δ ppm 8.13 (d, 1H, J = 1.2 Hz), 7.88 (d, 1H, J = 5.6 Hz), 7.72 (d, 2H, = 8.0 Hz), 7.25 (d, 2H, J = 8.0 Hz), 7.0 (d, 1H, J = 1.2 Hz), 5.96 (d, 1H, J = 5.6 Hz), 5.09 (d, 1H, J = 5.6 Hz), 4.14-4.09 (m, 1H), 3.69-3.66 (m, 2H), 3.55-3.52 (m, 2H), 3.46-3.41 (m, 4H), 3.26-3.18 (m, 1H), 2.99-2.96 (m, 2H), 2.43-2.37 (m, 3H), 2.34 (q, 2H, J = 7.2 Hz), 2.10-2.02 (m, 2H), 1.97-1.92 (m, 2H), 1.77-1.70 (m, 2H), 1.68-1.61 (m, 2H), 1.02 (t, 3H, J = 7.2 Hz). |
| 338 | 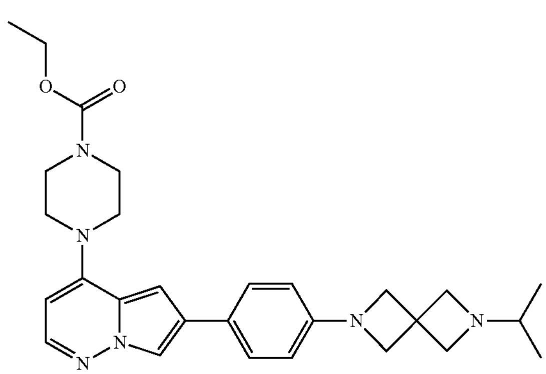 [SMILES: CCOC(=O)N1CCN(c2ccnn3cc(-c4ccc(N5CC6(C5)CN(C(C)C)C6)cc4)cc23)CC1] | 489 | 1H-NMR (400 MHz, 6d-DMSO) δ ppm 8.23 (br s, 1H), 8.03 (d, 1H, J = 1.6 Hz), 7.87 (d, 1H, J = 5.6 Hz), 7.61 (d, 2H, J = 8.4 Hz), 6.88 (d, 1H, J = 1.6 Hz), 6.44 (d, 2H, J = 8.4 Hz), 5.96 (d, 2H, J = 5.6 Hz), 4.09 (q, 2H, J = 7.2 Hz), 3.87 (s, 4H), 3.63-3.57 (m, 4H), 3.47-3.41 (m, 4H), 3.28 (s, 4H), 2.30-2.22 (m, 1H), 1.22 (t, 3H, J = 7.2 Hz), 0.86 (d, 6H, J = 6.4 Hz). |

TABLE 1-continued

| # | Structure | LCMS (M + 1) | NMR |
|---|---|---|---|
| 339 | 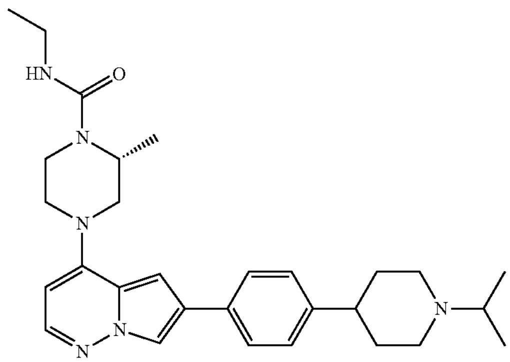 [SMILES: CCNC(=O)N1CCN(c2ccnn3cc(-c4ccc(C5CCN(C(C)C)CC5)cc4)cc23)C[C@H]1C] | 489 | 1H-NMR (400 MHz, 6d-DMSO) δ ppm 8.13 (s, 1H), 7.88 (d, 1H, J = 5.6 Hz), 7.71 (d, 2H, J = 8.0 Hz), 7.26 (d, 2H, J = 8.0 Hz), 6.91 (s, 1H), 6.52 (t, 1H, J = 5.2 Hz), 5.97 (d, 1H, J = 5.6 Hz), 4.32-4.28 (m, 1H), 3.88-3.80 (m, 3H), 3.32-3.31 (m, 1H), 3.29-3.24 (m, 1H), 3.18-3.14 (m, 1H), 3.12-3.06 (m, 2H), 3.02-2.96 (m, 1H), 2.92-2.86 (m, 2H), 2.74-2.68 (m, 1H), 2.46-2.42 (m, 1H), 2.25-2.20 (m, 2H), 1.78-1.72 (m, 2H), 1.66-1.56 (m, 2H), 1.24 (d, 3H, J = 6.0 Hz), 1.04 (t, 3H, J = 7.2 Hz), 1.00 (d, 6H, J = 6.4 Hz). |
| 340 | 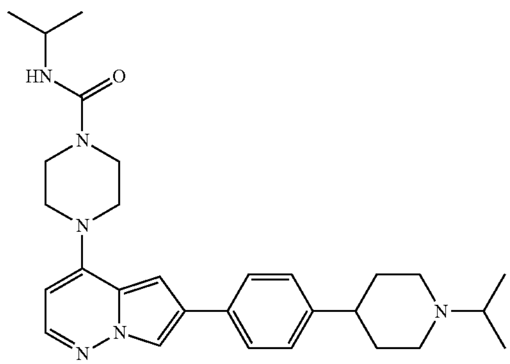 [SMILES: CC(C)NC(=O)N1CCN(c2ccnn3cc(-c4ccc(C5CCN(C(C)C)CC5)cc4)cc23)CC1] | 489 | 1H-NMR (400 MHz, 6d-DMSO) δ ppm 8.26 (s, 1H), 8.14 (d, 1H, J = 1.6 Hz), 7.89 (d, 1H, J = 5.6 Hz), 7.74 (d, 2H, J = 8.4 Hz), 7.25 (d, 2H, J = 8.4 Hz), 7.00 (d, 1H, J = 1.6 Hz), 6.32 (d, 1H, J = 7.6 Hz), 5.98 (d, 1H, J = 5.6 Hz), 3.82-3.75 (m, 1H), 3.54-3.50 (m, 4H), 3.46-3.41 (m, 4H), 3.03-2.98 (m, 2H), 2.92-2.86 (m, 1H), 2.52-2.50 (m, 1H), 2.44-2.36 (m, 2H), 1.85-1.75 (m, 2H), 1.72-1.68 (m, 2H), 1.10-1.05 (m, 12H). |
| 341 | 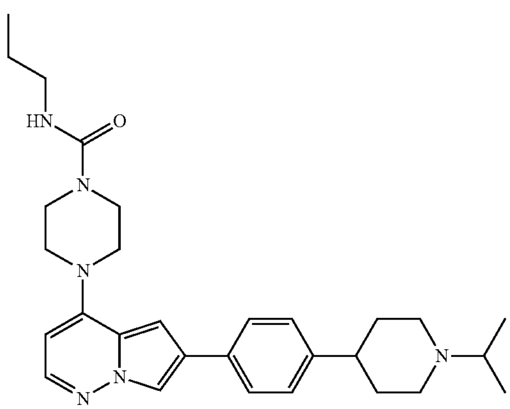 [SMILES: CCCNC(=O)N1CCN(c2ccnn3cc(-c4ccc(C5CCN(C(C)C)CC5)cc4)cc23)CC1] | 489 | 1H-NMR (400 MHz, 6d-DMSO) δ ppm 8.26 (s, 1H), 8.14 (d, 1H, J = 1.6 Hz), 7.89 (d, 1H, J = 5.6 Hz), 7.74 (d, 2H, J = 8.4 Hz), 7.25 (d, 2H, J = 8.4 Hz), 7.00 (d, 1H, J = 1.6 Hz), 6.62 (t, 1H, J = 5.2 Hz), 5.98 (d, 1H, J = 5.6 Hz), 3.54-3.50 (m, 4H), 3.46-3.41 (m, 4H), 3.03-2.94 (m, 4H), 2.88-2.83 (m, 1H), 2.52-2.50 (m, 1H), 2.40-2.32 (m, 2H), 1.84-1.77 (m, 2H), 1.75-1.66 (m, 2H), 1.43 (q, 2H, J = 7.2 Hz), 1.05 (d, 6H, J = 6.8 Hz), 0.85 (t, 3H, J = 7.2 Hz). |
| 342 | 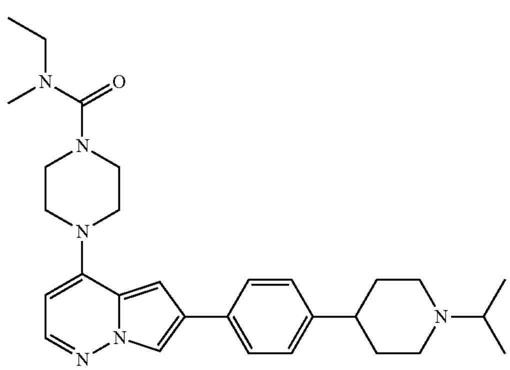 [SMILES: CCN(C)C(=O)N1CCN(c2ccnn3cc(-c4ccc(C5CCN(C(C)C)CC5)cc4)cc23)CC1] | 489 | 1H-NMR (400 MHz, 6d-DMSO) δ ppm 8.25 (s, 1H), 8.15 (d, 1H, J = 1.6 Hz), 7.90 (d, 1H, J = 5.6 Hz), 7.74 (d, 2H, J = 8.4 Hz), 7.25 (d, 2H, J = 8.4 Hz), 7.01 (d, 1H, J = 1.6 Hz), 5.98 (d, 1H, J = 5.6 Hz), 3.50-3.45 (m, 4H), 3.36-3.30 (m, 4H), 3.17 (q, 2H, J = 7.2 Hz), 3.05-3.02 (m, 2H), 2.95-2.92 (m, 1H), 2.79 (s, 3H), 2.59-2.56 (m, 1H), 2.50-2.44 (m, 2H), 1.86-1.80 (m, 2H), 1.78-1.70 (m, 2H), 1.12-1.05 (m, 9H). |

TABLE 1-continued

| # | Structure | LCMS (M + 1) | NMR |
|---|---|---|---|
| 343 | 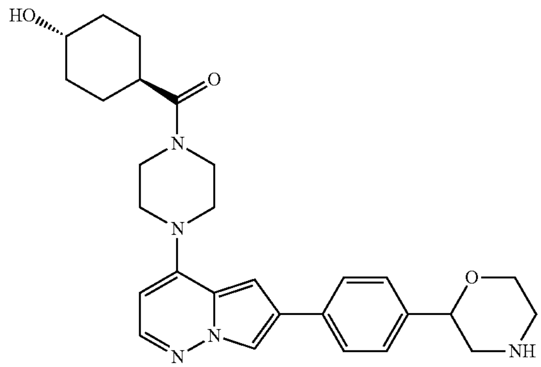 [SMILES: O=C([C@H]1CC[C@H](O)CC1)N1CCN(c2ccnn3cc(-c4ccc(C5CNCCO5)cc4)cc23)CC1] | 490 | 1H-NMR (400 MHz, 6d-DMSO) δ ppm 8.17 (d, 1H, J = 1.6 Hz), 7.89 (d, 1H, J = 5.6 Hz), 7.76 (d, 2H, J = 8.0 Hz), 7.32 (d, 2H, J = 8.0 Hz), 7.03 (d, 1H, J = 1.2 Hz), 5.96 (d, 1H, J = 5.6 Hz), 4.65-4.50 (m, 1H), 4.40-4.30 (m, 1H), 3.95-3.85 (m, 1H), 3.79-3.75 (m, 2H), 3.70-3.65 (m, 2H), 3.60-3.55 (m, 2H), 3.52-3.45 (m, 2H), 3.42-3.38 (m, 2H), 3.00-2.85 (m, 1H), 2.80-2.65 (m, 2H), 2.60-2.52 (m, 2H), 1.90-1.80 (m, 2H), 1.70-1.60 (m, 2H), 1.50-1.30 (m, 2H), 1.25-1.10 (m, 2H). |
| 344 | 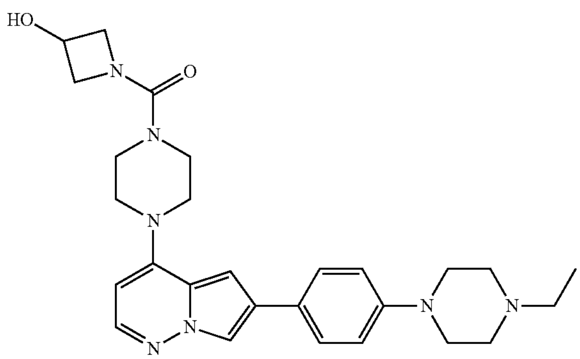 [SMILES: CCN1CCN(c2ccc(-c3cc4c(N5CCN(C(=O)N6CC(O)C6)CC5)ccnn4c3)cc2)CC1] | 490 | 1H-NMR (400 MHz, 6d-DMSO) δ ppm 8.05 (d, 1H, J = 1.6 Hz), 7.86 (d, 1H, J = 5.2 Hz), 7.64 (d, 2H, J = 8.8 Hz), 6.95 (d, 2H, J = 8.8 Hz), 6.91 (d, 1H, J = 1.6 Hz), 5.94 (d, 1H, J = 5.2 Hz), 5.61 (d, 1H, J = 6.0 Hz), 4.43-4.69 (m, 1H), 4.10 (t, 2H, J = 8.8 Hz), 3.70 (dd, 2H, J = 8.8, 4.8 Hz), 2.45-2.41 (m, 8H), 3.35-3.30 (m, 4H), 3.17-3.15 (m, 4H), 2.37 (q, 2H, J = 7.2 Hz), 1.04 (t, 3H, J = 7.2 Hz). |
| 345 | 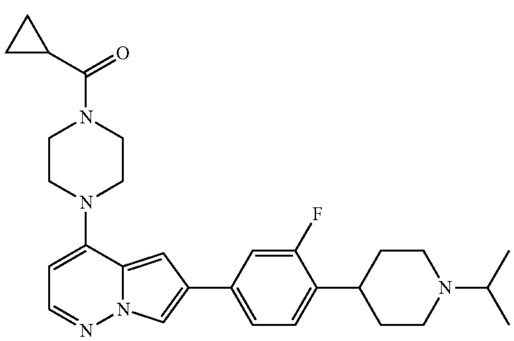 [SMILES: CC(C)N1CCC(c2ccc(-c3cc4c(N5CCN(C(=O)C6CC6)CC5)ccnn4c3)cc2F)CC1] | 490 | 1H-NMR (400 MHz, 6d-DMSO) δ ppm 8.22 (s, 1H), 7.90 (d, 1H, J = 5.6 Hz), 7.65 (s, 1H), 7.62-7.59 (m, 1H), 7.34-7.30 (m, 1H), 7.09 (s, 1H), 5.97 (d, 1H, J = 5.6 Hz), 3.92-3.91 (m, 2H), 3.71-3.69 (m, 2H), 3.54-3.50 (m, 2H), 3.50-3.46 (m, 2H), 2.90-2.87 (m, 2H), 2.73-2.70 (m, 2H), 2.25-2.21 (m, 2H), 2.20-2.19 (m, 1H), 2.00-1.70 (m, 4H), 0.99 (d, 6H, J = 6.4 Hz), 0.77-0.73 (m, 4H). |
| 346 | 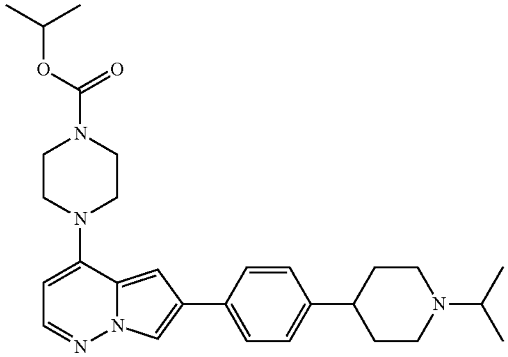 [SMILES: CC(C)OC(=O)N1CCN(c2ccnn3cc(-c4ccc(C5CCN(C(C)C)CC5)cc4)cc23)CC1] | 490 | 1H NMR (400 MHz, DMSO-d6) δ 8.13 (d, J = 1.8 Hz, 1H), 7.89 (d, J = 5.4 Hz, 1H), 7.72 (d, J = 7.8 Hz, 2H), 7.24 (d, J = 8.2 Hz, 2H), 6.99 (d, J = 1.9 Hz, 1H), 5.97 (d, J = 5.5 Hz, 1H), 4.81 (p, J = 6.2 Hz, 1H), 3.58 (q, J = 5.6, 5.1 Hz, 4H), 3.44 (t, J = 5.2 Hz, 4H), 2.91 (s, 2H), 2.23 (s, 1H), 1.73 (d, J = 52.3 Hz, 5H), 1.21 (d, J = 6.2 Hz, 6H), 1.03 (bs, 8H). |

TABLE 1-continued

| # | Structure | LCMS (M + 1) | NMR |
|---|---|---|---|
| 347 | 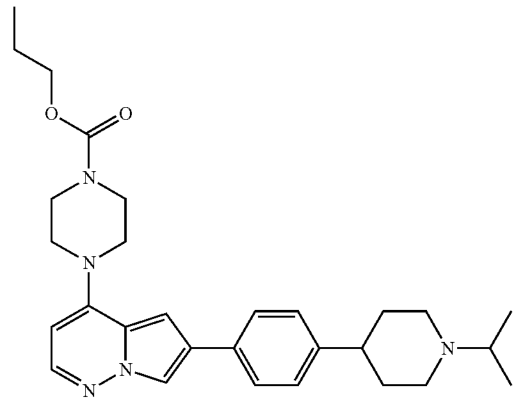 [SMILES: CCCOC(=O)N1CCN(c2ccnn3cc(-c4ccc(C5CCN(C(C)C)CC5)cc4)cc23)CC1] | 491 | 1H NMR (400 MHz, DMSO-d6) δ 8.12 (d, J = 1.7 Hz, 1H), 7.87 (d, J = 5.4 Hz, 1H), 7.71 (d, J = 8.1 Hz, 2H), 7.24 (d, J = 8.2 Hz, 2H), 6.97 (d, J = 1.9 Hz, 1H), 5.96 (d, J = 5.5 Hz, 1H), 5.90 (s, 1H), 3.45 (ddd, J = 28.3, 7.6, 4.0 Hz, 9H), 2.88 (d, J = 10.8 Hz, 2H), 2.80-2.57 (m, 1H), 2.21 (t, J = 11.1 Hz, 2H), 1.76 (d, J = 12.4 Hz, 2H), 1.70-1.49 (m, 2H), 1.27 (s, 9H), 0.99 (d, J = 6.5 Hz, 6H). |
| 348 | 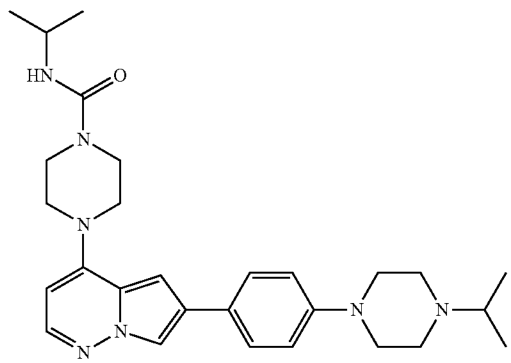 | 490 | 1H-NMR (400 MHz, 6d-DMSO) δ ppm 8.04 (d, 1H, J = 1.6 Hz), 7.85 (d, 1H, J = 5.2 Hz), 7.64 (d, 2H, J = 8.4 Hz), 6.93 (d, 2H, J = 8.4 Hz), 6.90 (d, 1H, J = 1.6 Hz), 6.31 (d, 1H, J = 7.6 Hz), 5.96 (d, 1H, J = 5.6 Hz), 3.80-3.70 (m, 1H), 3.54-3.48 (m, 4H), 3.44-3.36 (m, 4H), 3.20-3.10 (m, 4H), 2.72-2.62 (m, 1H), 2.60-2.54 (m, 4H), 1.07 (d, 6H, J = 6.4 Hz), 1.00 (d, 6H, J = 6.4 Hz). |
| 349 | 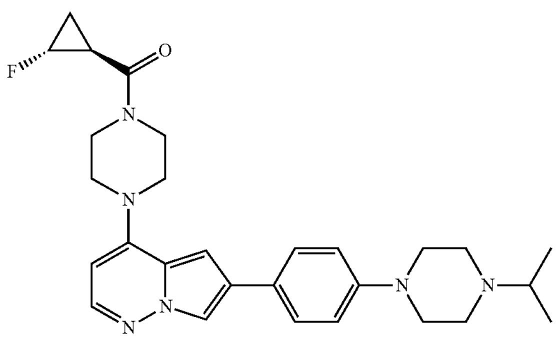 [SMILES: CC(C)N1CCN(c2ccc(-c3cc4c(N5CCN(C(=O)[C@@H]6C[C@H]6F)CC5)ccnn4c3)cc2)CC1] | 491 | 1H-NMR (400 MHz, CDCl3) δ ppm 7.89 (d, 1H, J = 1.6 Hz), 7.84 (d, 1H, J = 5.2 Hz), 7.57 (d, 2H, J = 8.4 Hz), 6.98 (d, 2H, J = 8.4 Hz), 6.66 (d, 1H, J = 1.6 Hz), 5.85 (d, 1H, J = 8.4 Hz), 4.95-4.75 (m, 1H), 3.96-3.92 (m, 2H), 3.90-3.84 (m, 2H), 3.90-3.84 (m, 2H), 3.58-3.54 (m, 2H), 2.49-3.43 (m, 2H), 3.41-3.35 (m, 4H), 2.98-2.90 (m, 1H), 2.90-2.83 (m, 4H), 2.33-2.20 (m, 1H), 1.47-1.40 (m, 2H), 1.22 (d, 6H, J = 5.6 Hz). |
| 350 | 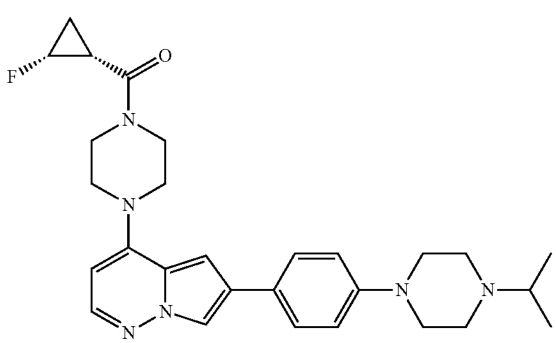 [SMILES: CC(C)N1CCN(c2ccc(-c3cc4c(N5CCN(C(=O)[C@H]6C[C@H]6F)CC5)ccnn4c3)cc2)CC1] | 491 | 1H-NMR (400 MHz, 6d-DMSO) δ ppm 8.06 (d, 1H, J = 1.6 Hz), 7.87 (d, 1H, J = 5.2 Hz), 7.65 (d, 2H, J = 8.8 Hz), 6.95 (d, 1H, J = 1.6 Hz), 6.94 (d, 2H, J = 8.8 Hz), 5.97 (d, 1H, J = 5.2 Hz), 5.06-4.85 (m, 1H), 3.97-3.85 (m, 2H), 3.74-7.71 (m, 2H), 3.60-3.43 (m, 4H), 3.15-3.12 (m, 4H), 2.66 (heptet, 1H, J = 6.4 Hz), 2.51-2.49 (m, 4H), 2.24-2.19 (m, 1H), 1.60-1.50 (m, 1H), 1.08-1.03 (m, 1H), 1.01 (d, 6H, J = 6.4 Hz). |

TABLE 1-continued

| # | Structure | LCMS (M + 1) | NMR |
|---|---|---|---|
| 351 | 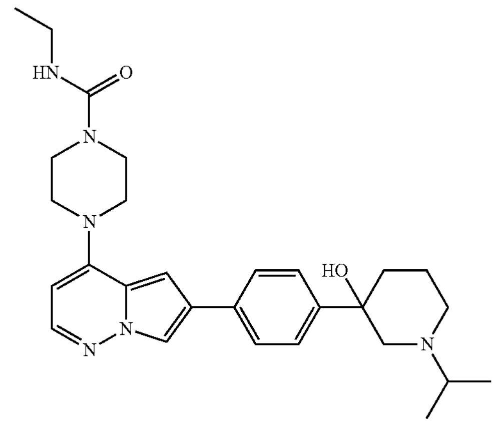 [SMILES: CCNC(=O)N1CCN(c2ccnn3cc(-c4ccc(C5(O)CCCN(C(C)C)C5)cc4)cc23)CC1] | 491 | 1H-NMR (400 MHz, 6d-DMSO) δ ppm 8.17 (s, 1H), 7.90 (d, 1H, J = 6.0 Hz), 7.77 (d, 2H, J = 8.0 Hz), 7.56 (d, 2H, J = 8.0 Hz), 7.02 (s, 1H), 6.61 (t, 1H, J = 5.6 Hz), 5.99 (d, 1H, J = 5.2 Hz), 3.55-3.50 (m, 4H), 3.48-3.43 (m, 4H), 3.43-3.33 (m, 2H), 3.33-3.25 (m, 2H), 3.20-3.05 (m, 2H), 1.91-1.74 (m, 2H), 1.70-1.45 (m, 2H), 1.14-0.95 (m, 9H). |
| 352 | 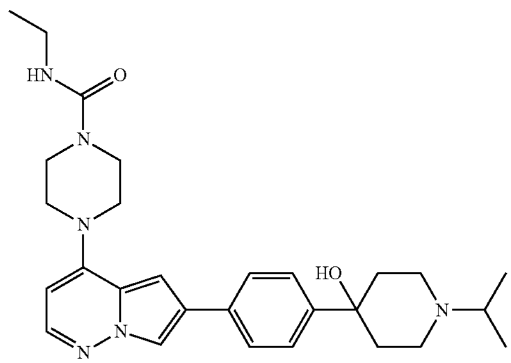 [SMILES: CCNC(=O)N1CCN(c2ccnn3cc(-c4ccc(C5(O)CCN(C(C)C)CC5)cc4)cc23)CC1] | 491 | 1H-NMR (400 MHz, 6d-DMSO) δ ppm 8.15 (s, 1H), 7.88 (d, 1H, J = 5.6 Hz), 7.74 (d, 2H, J = 8.4 Hz), 7.48 (d, 2H, J = 8.4 Hz), 7.01 (d, 1H, J = 1.6 Hz), 6.61 (t, 1H, J = 5.2 Hz), 5.98 (d, 1H, J = 5.6 Hz), 4.74 (s, 1H), 3.52-3.51 (m, 4H), 3.44-3.43 (m, 4H), 3.13-3.05 (m, 2H), 2.74-2.70 (m, 1H), 2.60-2.57 (m, 4H), 1.95-1.85 (m, 2H), 1.63-1.60 (m, 2H), 1.04 (t, 3H, J = 7.2 Hz), 1.00 (d, 6H, J = 6.4 Hz). |
| 353 | 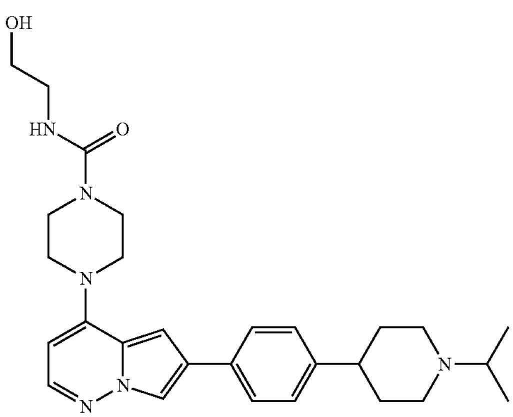 [SMILES: CC(C)N1CCC(c2ccc(-c3cc4c(N5CCN(C(=O)NCCO)CC5)ccnn4c3)cc2)CC1] | 491 | 1H-NMR (400 MHz, 6d-DMSO) δ ppm 8.13 (d, 1H, J = 1.6 Hz), 7.88 (d, 1H, J = 5.6 Hz), 7.72 (d, 2H, J = 8.4 Hz), 7.25 (d, 2H, J = 8.4 Hz), 6.99 (d, 1H, J = 1.6 Hz), 6.63 (t, 1H, J = 5.6 Hz), 5.97 (d, 1H, J = 5.6 Hz), 4.65 (t, 1H, J = 5.6 Hz), 3.55-3.52 (m, 4H), 3.48-3.40 (m, 6H), 3.12 (q, 2H, J = 5.6 Hz), 2.90-2.86 (m, 2H), 2.74-2.68 (m, 1H), 2.50-2.45 (m, 1H), 2.25-2.18 (m, 2H), 1.80-1.74 (m, 2H), 1.65-1.60 (m, 2H), 1.00 (d, 6H, J = 6.4 Hz). |
| 354 | 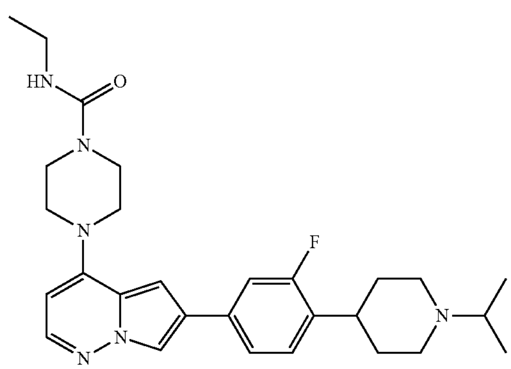 | 493 | 1H-NMR (400 MHz, 6d-DMSO) δ ppm 8.22 (d, 1H, J = 1.6 Hz), 7.91 (d, 1H, J = 5.6 Hz), 7.65 (s, 1H), 7.65-7.60 (m, 1H), 7.33-7.30 (m, 1H), 7.06 (d, 1H, J = 1.6 Hz), 6.61 (t, 1H, J = 5.2 Hz), 5.97 (d, 1H, J = 5.6 Hz), 3.51-3.50 (m, 4H), 3.43-3.40 (m, 4H), 3.07-3.04 (m, 2H), 2.91-2.89 (m, 2H), 2.73-2.71 (m, 2H), 2.30-2.20 (m, 2H), 1.73-1.65 (m, 4H), 1.21-1.20 (m, 9H). |

TABLE 1-continued

| # | Structure | LCMS (M + 1) | NMR |
|---|---|---|---|
| 355 | 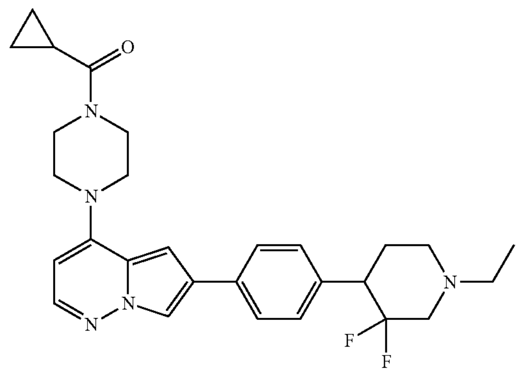 [SMILES: CCN1CCC(c2ccc(-c3cc4c(N5CCN(C(=O)C6CC6)CC5)ccnn4c3)cc2)C(F)(F)C1] | 494 | 1H-NMR (400 MHz, DMSO-d6) δ ppm 8.17 (d, 1H, J = 1.6 Hz), 7.90 (d, 1H, J = 6.0 Hz), 7.76 (d, 2H, J = 8.8 Hz), 7.30 (d, 2H, J = 8.4 Hz), 7.05 (d, 1H, J = 1.2 Hz), 5.97 (d, 1H, J = 4.2 Hz), 3.92 (br. s., 2H), 3.70 (br. s., 2H), 3.54 (br. s., 2H), 3.47 (br. s., 2H), 3.16-2.98 (m, 3H), 2.47-2.43 (m, 2H), 2.36-2.26 (m, 2H), 2.16-2.07 (m, 2H), 2.05-1.98 (m, 1H), 1.82-1.78 (m, 1H), 1.03 (t, 3H, J = 7.2 Hz), 0.77-0.74 (m, 4H). |
| 356 | 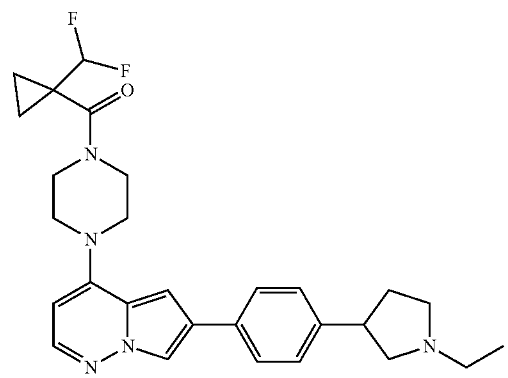 [SMILES: CCN1CCC(c2ccc(-c3cc4c(N5CCN(C(=O)C6(C(F)F)CC6)CC5)ccnn4c3)cc2)C1] | 494 | 1H NMR (400 MHz, 6d-DMSO) δ ppm 8.24 (s, 1H), 8.16 (d, 1H, J = 1.6 Hz), 7.91 (d, 1H, J = 5.2 Hz), 7.74 (d, 2H, J = 8.4 Hz), 7.31 (d, 2H, J = 8.4 Hz), 7.04 (d, 1H, J = 1.6 Hz), 6.12-5.84 (m, 1H), 5.99 (d, 1H, J = 5.2 Hz), 3.79-3.78 (m, 2H), 3.55-3.45 (m, 4H), 3.37-3.31 (m, 3H), 3.03-3.02 (m, 1H), 2.77-2.75 (m, 2H), 2.57-2.53 (m, 4H), 2.25-2.17 (m, 1H), 1.84-1.74 (m, 1H), 1.10-1.07 (m, 6H). |
| 357 | 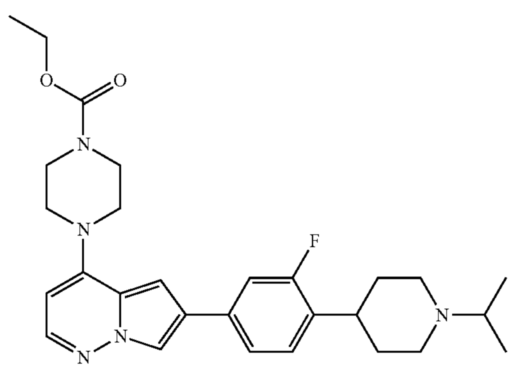 [SMILES: CCOC(=O)N1CCN(c2ccnn3cc(-c4ccc(C5CCN(C(C)C)CC5)c(F)c4)cc23)CC1] | 494 | 1H-NMR (400 MHz, 6d-DMSO) δ ppm 8.22 (d, 1H, J = 1.2 Hz), 7.91 (d, 1H, J = 5.6 Hz), 7.65-7.59 (m, 2H), 7.33-7.30 (m, 1H), 7.06 (d, 1H, J = 1.2 Hz), 5.97 (d, 1H, J = 5.6 Hz), 4.08 (q, 2H, J = 7.2 Hz), 3.61-3.59 (m, 4H), 3.49-3.46 (m, 4H), 2.89-2.88 (m, 2H), 2.72-2.67 (m, 2H), 2.24-2.20 (m, 2H), 1.73-1.65 (m, 4H), 1.21 (t, 3H, J = 7.2 Hz), 0.98 (d, 6H, J = 6.4 Hz). |
| 358 | 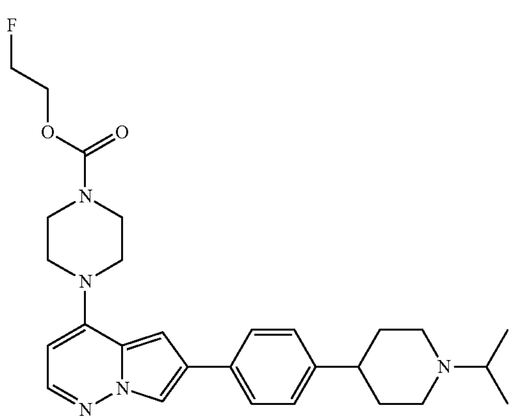 [SMILES: CC(C)N1CCC(c2ccc(-c3cc4c(N5CCN(C(=O)OCCF)CC5)ccnn4c3)cc2)CC1] | 495 | 1H NMR (400 MHz, DMSO-d6) δ 8.13 (s, 1H), 7.89 (d, J = 5.4 Hz, 1H), 7.72 (d, J = 7.8 Hz, 2H), 7.31-7.16 (m, 2H), 6.99 (s, 1H), 5.98 (d, J = 5.5 Hz, 1H), 4.77-4.64 (m, 1H), 4.63-4.52 (m, 1H), 4.37-4.27 (m, 1H), 4.25 (t, J = 4.0 Hz, 1H), 3.62 (s, 4H), 3.47 (t, J = 5.1 Hz, 4H), 2.90 (s, 2H), 2.70 (d, J = 29.0 Hz, 1H), 2.24 (s, 2H), 1.88-1.54 (m, 5H), 1.00 (d, J = 6.6 Hz, 6H). |

TABLE 1-continued

| # | Structure | LCMS (M + 1) | NMR |
|---|---|---|---|
| 359 | 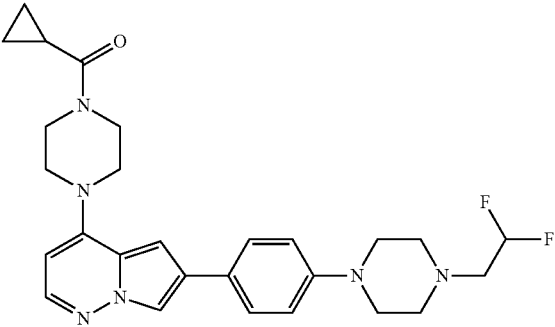 [SMILES: O=C(C1CC1)N1CCN(c2ccnn3cc(-c4ccc(N5CCN(CC(F)F)CC5)cc4)cc23)CC1] | 495 | 1H-NMR (400 MHz, DMSO-d6) δ ppm 8.07 (d, 1H, J = 1.6 Hz), 7.87 (d, 1H, J = 5.6 Hz), 7.66 (d, 2H, J = 8.4 Hz), 6.96-6.94 (m, 3H), 6.20-6.15 (m, 1H), 5.95 (d, 1H, J = 5.6 Hz), 3.92-3.90 (m, 2H), 3.75-3.65 (m, 2H), 3.51-3.44 (m, 4H), 3.15 (t, 4H, J = 4.8 Hz), 2.83-2.74 (m, 2H), 2.68-2.66 (m, 4H), 2.02-1.98 (m, 1H), 0.78-0.72 (m, 4H). |
| 360 | 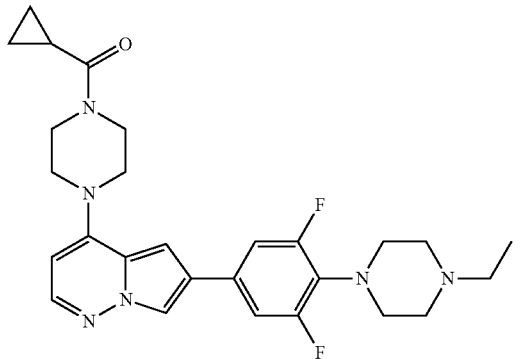 [SMILES: CCN1CCN(c2c(F)cc(-c3cc4c(N5CCN(C(=O)C6CC6)CC5)ccnn4c3)cc2F)CC1] | 495 | 1H-NMR (400 MHz, DMSO-d6) δ ppm 8.27 (s, 1H), 7.90 (d, 1H, J = 4.8 Hz), 7.57 (d, 2H, J = 10.8 Hz), 7.14 (s, 1H), 5.96 (d, 1H, J = 5.6 Hz), 3.92 (br. s., 2H), 3.70 (br. s., 2H), 3.53 (br. s., 2H), 3.47 (br. s., 2H), 3.13 (s, 4H), 2.50 (br. s., 4H), 2.38 (q, 2H, J = 7.2 Hz), 2.02-2.00 (m, 1H), 1.02 (t, 3H, J = 7.2 Hz), 0.78-0.75 (m, 4H). |
| 361 | 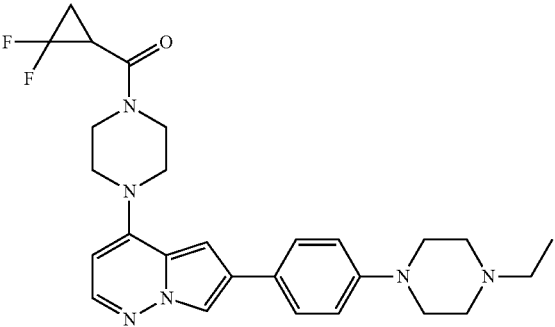 [SMILES: CCN1CCN(c2ccc(-c3cc4c(N5CCN(C(=O)C6CC6(F)F)CC5)ccnn4c3)cc2)CC1] | 495 | 1H-NMR (400 MHz, 6d-DMSO) δ ppm 8.06 (d, 1H, J = 2.0 Hz), 7.87 (d, 1H, J = 5.6 Hz), 7.65 (d, 2H, J = 8.8 Hz), 6.95 (d, 2H, J = 8.8 Hz), 6.94-6.93 (m, 1H), 5.97 (d, 1H, J = 5.6 Hz), 4.00-3.85 (m, 1H), 3.80-3.60 (m, 3H), 3.58-3.40 (m, 4H), 3.30-3.24 (m, 4H), 3.23-3.20 (m, 1H), 3.18-3.10 (m, 4H), 2.37 (q, 2H, J = 7.2 Hz), 2.00-1.90 (m, 2H), 1.03 (t, 3H, J = 7.2 Hz). |
| 362 | 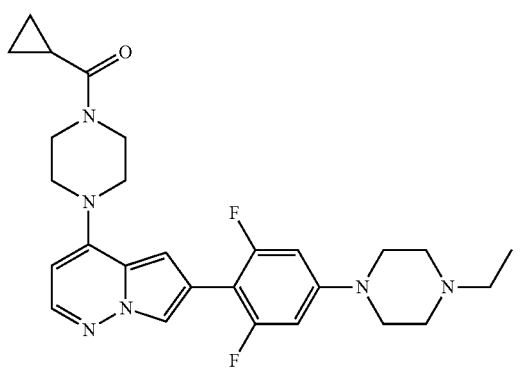 [SMILES: CCN1CCN(c2cc(F)c(-c3cc4c(N5CCN(C(=O)C6CC6)CC5)ccnn4c3)c(F)c2)CC1] | 495 | 1H-NMR (400 MHz, 6d-DMSO) δ ppm 8.17 (s, 1H), 7.94 (d, 1H, J = 5.6 Hz), 7.90 (d, 1H, J = 1.2 Hz), 6.83 (s, 1H), 7.76 (d, 2H, J = 12.8 Hz), 6.01 (d, 1H, J = 5.6 Hz), 3.93-3.91 (m, 2H), 3.69-3.68 (m, 2H), 3.55-3.54 (m, 2H), 3.51-3.50 (m, 2H), 3.25-3.22 (m, 4H), 2.48-2.47 (m, 4H), 2.37 (q, 2H, J = 7.2 Hz), 2.04-2.00 (m, 1H), 1.04 (t, 3H, J = 7.2 Hz), 0.78-0.72 (m, 4H). |

TABLE 1-continued

| # | Structure | LCMS (M + 1) | NMR |
|---|---|---|---|
| 363 | 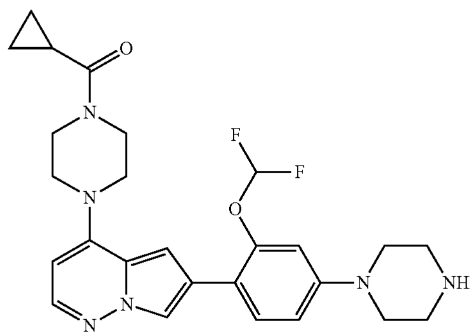 [SMILES: O=C(C1CC1)N1CCN(c2ccnn3cc(-c4ccc(N5CCNCC5)cc4OC(F)F)cc23)CC1] | 497 | 1H-NMR (400 MHz, 6d-DMSO) δ ppm 8.00 (s, 1H), 7.88 (d, 1H, J = 5.6 Hz), 7.75 (d, 1H, J = 8.8 Hz), 7.28 (t, 1H, J = 74 Hz), 6.96 (s, 1H), 6.89 (d, 1H, J = 8.4 Hz), 6.76 (s, 1H), 5.96 (d, 1H, J = 5.6 Hz), 3.91-3.90 (m, 2H), 3.69-3.67 (m, 2H), 3.52-3.46 (m, 4H), 3.24-3.20 (m, 4H), 2.79-2.74 (m, 4H), 2.01-1.98 (m, 1H), 0.84-0.73 (m, 4H). |
| 364 | 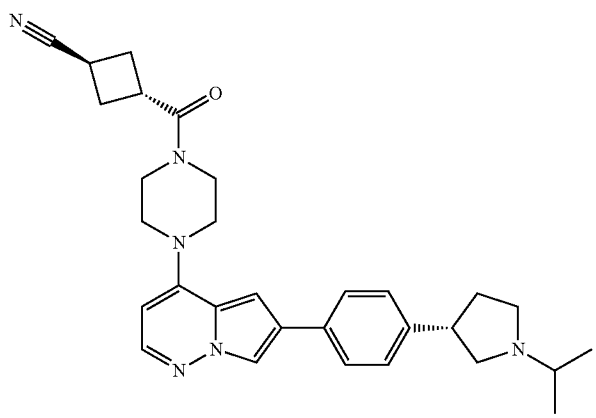 [SMILES: CC(C)N1CC[C@@H](c2ccc(-c3cc4c(N5CCN(C(=O)[C@H]6C[C@H](C#N)C6)CC5)ccnn4c3)cc2)C1] | 497 | 1H-NMR (400 MHz, 6d-DMSO) δ ppm 8.14 (d, 1H, J = 1.6 Hz), 7.89 (d, 1H, J = 5.6 Hz), 7.71 (d, 2H, J = 8.4 Hz), 7.29 (d, 2H, J = 8.4 Hz), 6.99 (d, 1H, J = 1.6 Hz), 5.96 (d, 1H, J = 5.6 Hz), 3.77-3.68 (m, 2H), 3.68-3.62 (m, 1H), 3.57-3.50 (m, 2H), 3.48-3.40 (m, 4H), 3.30-3.20 (m, 2H), 3.05-2.95 (m, 1H), 2.80-2.68 (m, 2H), 2.65-2.55 (m, 2H), 2.50-2.42 (m, 3H), 2.40-2.35 (m, 1H), 2.25-2.15 (m, 1H), 1.80-1.70 (m, 1H), 1.10-1.00 (m, 6H). |
| 365 | 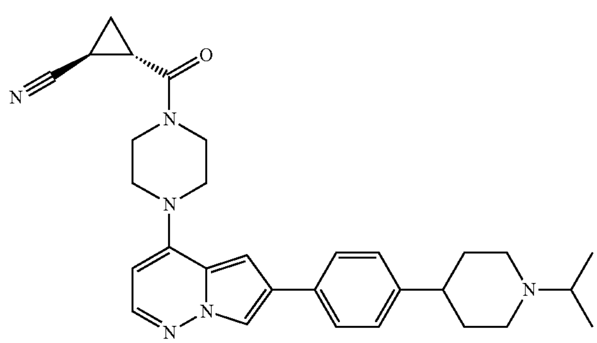 [SMILES: CC(C)N1CCC(c2ccc(-c3cc4c(N5CCN(C(=O)[C@H]6C[C@@H]6C#N)CC5)ccnn4c3)cc2)CC1] | 497 | 1H-NMR (400 MHz, 6d-DMSO) δ ppm 8.16 (d, 1H, J = 1.2 Hz), 7.91 (d, 1H, J = 5.6 Hz), 7.74 (d, 2H), J = 8.4 Hz), 7.26 (d, 2H, J = 8.4 Hz), Hz), 3.97-3.93 (m, 2H), 3.72-3.70 (m, 2H), 2.92 (m, 3H), 2.81-2.77 (m, 1H), 2.52-2.50 (m, 1H), 2.34-2.26 (m, 2H), 2.15-2.05 (m, 1H), 1.82-1.75 (m, 2H), 1.71-1.61 (m, 2H), 1.50-1.44 (m, 1H), 1.38-1.34 (m, 1H), 1.03 (d, 6H, J = 6.8 Hz). |
| 366 | 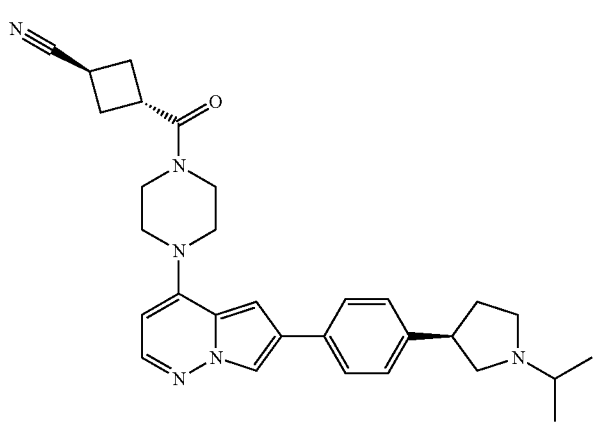 [SMILES: CC(C)N1CC[C@H](c2ccc(-c3cc4c(N5CCN(C(=O)[C@H]6C[C@H](C#N)C6)CC5)ccnn4c3)cc2)C1] | 497 | 1H-NMR (400 MHz, 6d-DMSO) δ ppm 8.15 (d, 1H, J = 1.6 Hz), 7.90 (d, 1H, J = 5.2 Hz), 7.73 (d, 2H, J = 8.4 Hz), 7.30 (d, 2H, J = 8.4 Hz), 7.00 (d, 1H, J = 1.6 Hz), 5.98 (d, 1H, J = 5.2 Hz), 3.73-3.67 (m, 2H), 3.67-3.64 (m, 1H), 3.54-3.50 (m, 2H), 3.45-3.39 (m, 4H), 3.27-3.25 (m, 2H), 3.01-2.96 (m, 1H), 2.75-2.71 (m, 2H), 2.66-2.63 (m, 2H), 2.61-2.53 (m, 2H), 2.50-2.46 (m, 1H), 2.45-2.41 (m, 1H), 2.22-2.19 (m, 1H), 1.79-1.73 (m, 1H), 1.07-1.04 (m, 6H). |

TABLE 1-continued

| # | Structure | LCMS (M + 1) | NMR |
|---|---|---|---|
| 367 | 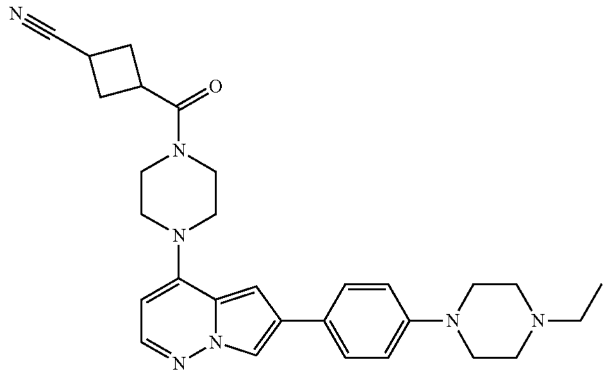 | 498 | 1H-NMR (400 MHz, CDCl3) δ ppm 7.87 (d, 1H, J = 2.0 Hz), 7.82 (d, 1H, J = 5.2 Hz), 7.55 (d, 2H, J = 8.8 Hz), 6.97 (d, 2H, J = 8.8 Hz), 6.62 (d, 1H, J = 2.0 Hz), 5.82 (d, 1H, J = 5.2 Hz), 3.87-3.83 (m, 2H), 3.62-3.58 (m, 1H), 3.57-3.54 (m, 2H), 3.43-3.41 (m, 4H), 3.29-3.24 (m, 4H), 3.22-3.14 (m, 1H), 2.82-2.74 (m, 2H), 2.66-2.62 (m, 4H), 2.61-2.55 (m, 2H), 2.50 (q, 2H, J = 7.2 Hz), 1.15 (t, 3H, J = 7.2 Hz). |
| 368 | 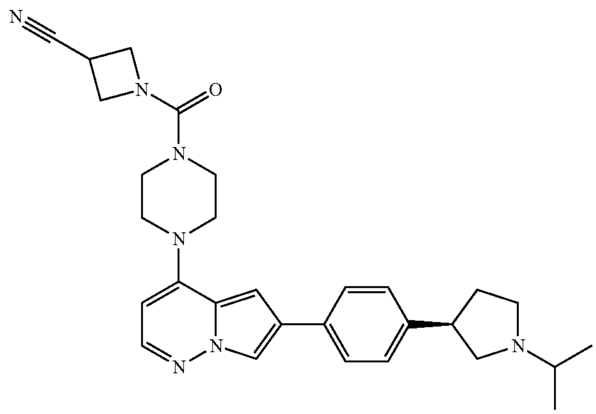 [SMILES: CC(C)N1CC[C@H](c2ccc(-c3cc4c(N5CCN(C(=O)N6CC(C#N)C6)CC5)ccnn4c3)cc2)C1] | 298 | 1H-NMR (400 MHz, 6d-DMSO) δ ppm 8.14 (d, 1H, J = 2.0 Hz), 7.89 (d, 1H, J = 5.2 Hz), 7.71 (d, 2H, J = 8.0 Hz), 7.29 (d, 2H, J = 8.0 Hz), 6.98 (d, 1H, J = 1.2 Hz), 5.95 (d, 1H, J = 5.2 Hz), 4.21 (t, 2H, J = 8.8 Hz), 4.08 (dd, 2H, J = 8.0, 6.4 Hz), 3.80-3.70 (m, 1H), 3.50-3.40 (m, 8H), 3.30-3.20 (m, 1H), 3.10-2.90 (m, 1H), 2.80-2.60 (m, 2H), 2.45-2.35 (m,, 2H), 2.30-2.10 (m, 1H), 1.80-1.70 (m, 1H), 1.05 (t, 6H, J = 6.4 Hz). |
| 369 | 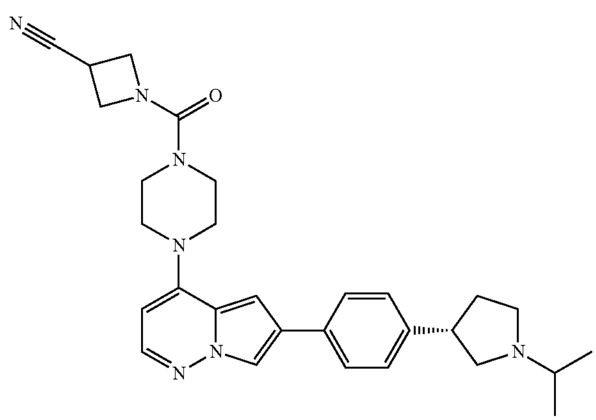 [SMILES: CC(C)N1CC[C@@H](c2ccc(-c3cc4c(N5CCN(C(=O)N6CC(C#N)C6)CC5)ccnn4c3)cc2)C1] | 498 | 1H-NMR (400 MHz, CDCl3) δ ppm 7.92 (d, 1H, J = 1.6 Hz), 7.85 (d, 1H, J = 5.2 Hz), 7.59 (d, 2H, J = 8.0 Hz), 7.32 (d, 2H, J = 8.0 Hz), 6.67 (d, 1H, J = 1.6 Hz), 5.84 (d, 1H, J = 5.2 Hz), 4.33-4.22 (m, 4H), 3.62-3.56 (m, 4H), 3.51-3.47 (m, 4H), 3.50-3.40 (m, 2H), 3.33-3.26 (m, 1H), 3.10-3.00 (m, 1H), 2.79-2.69 (m, 1H), 2.60-2.49 (m, 2H), 2.41-2.30 (m, 1H), 2.01-1.90 (m, 1H), 1.18 (d, 6H, J = 4.4 Hz). |
| 370 | 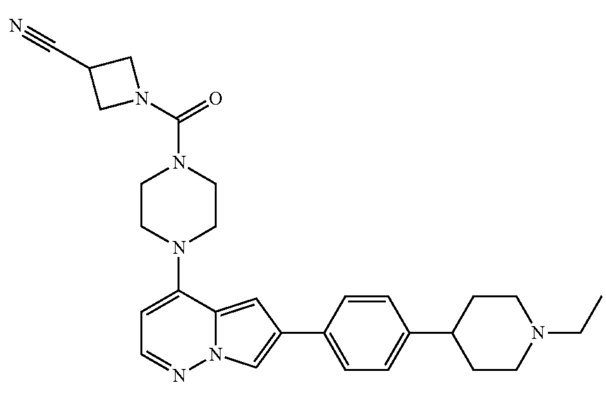 | 498 | 1H-NMR (400 MHz, 6d-DMSO) δ ppm 8.13 (d, 1H, J = 2.0 Hz), 7.88 (d, 1H, J = 5.6 Hz), 7.71 (d, 2H, J = 8.4 Hz), 7.25 (d, 2H, J = 8.4 Hz), 6.98 (d, 1H, J = 1.2 Hz), 5.94 (d, 1H, J = 5.6 Hz), 4.21 (t, 2H, J = 8.4 Hz), 4.08 (dd, 2H, J = 8.4, 6.0 Hz), 3.77-3.75 (m, 1H), 3.46-3.45 (m, 8H), 2.99-2.95 (m, 2H), 2.49-2.44 (m, 1H), 2.34 (q, 2H, J = 7.2 Hz), 1.97-1.92 (m, 2H), 1.76-1.70 (m, 2H), 1.68-1.63 (m, 2H), 1.01 (t, 3H, J = 7.2 Hz). |

TABLE 1-continued

| # | Structure | LCMS (M + 1) | NMR |
|---|---|---|---|
| 371 | 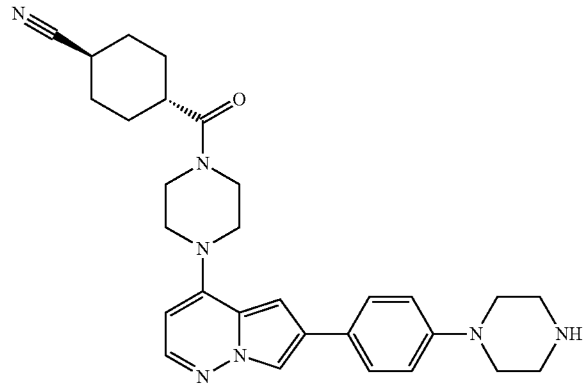 [SMILES: N#C[C@H]1CC[C@H](C(=O)N2CCN(c3ccnn4cc(-c5ccc(N6CCNCC6)cc5)cc34)CC2)CC1] | 498 | 1H-NMR (400 MHz, 6d-DMSO) δ ppm 8.30 (s, 1H), 8.08 (d, 1H, J = 1.6 Hz), 7.87 (d, 1H, J = 5.6 Hz), 7.67 (d, 2H, J = 8.4 Hz), 6.96 (d, 2H, J = 8.4 Hz), 6.94 (d, 1H, J = 1.6 Hz), 5.95 (d, 1H, J = 5.6 Hz), 3.75-3.67 (m, 2H), 3.67-3.60 (m, 2H), 3.50-3.42 (m, 2H), 3.42-3.35 (m, 2H), 3.22-3.14 (m, 4H), 3.06-2.94 (m, 4H), 2.76-2.64 (m, 2H), 2.10-2.00 (m, 2H), 1.78-1.68 (m, 2H), 1.66-1.50 (m, 2H), 1.48-1.34 (m, 2H). |
| 372 | 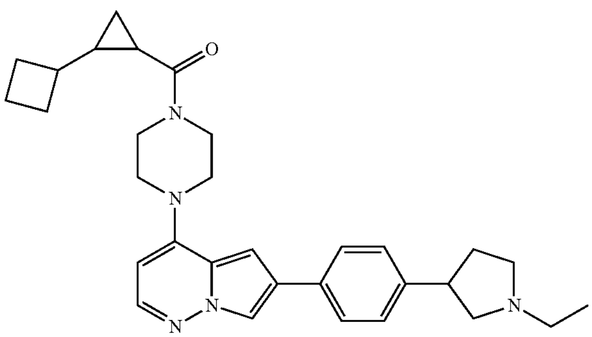 [SMILES: CCN1CCC(c2ccc(-c3cc4c(N5CCN(C(=O)C6CC6C6CCC6)CC5)ccnn4c3)cc2)C1] | 498 | 1H-NMR (400 MHz, 6d-DMSO) δ ppm 8.16 (d, 1H, J = 1.6 Hz), 7.91 (d, 1H, J = 5.2 Hz), 7.73 (d, 2H, J = 8.0 Hz), 7.30 (d, 2H, J = 8.0 Hz), 7.03 (d, 1H, J = 1.6 Hz), 5.98 (d, 1H, J = 5.2 Hz), 3.92-3.86 (m, 2H), 3.72-3.68 (m, 2H), 3.54-3.49 (m, 2H). 3.48-3.43 (m, 2H), 3.31-3.27 (m, 1H), 2.94-2.91 (m, 1H), 2.68-2.62 (m, 2H), 2.46-2.42 (m, 2H), 2.26-2.24 (m, 1H), 2.16-2.10 (m, 1H), 1.98-1.92 (m, 2H), 1.80-1.66 (m, 6H), 1.28-1.22 (m, 2H), 1.06 (t, 3H, J = 7.2 Hz), 0.99-0.95 (m, 1H), 0.65-0.60 (m, 1H). |
| 373 | 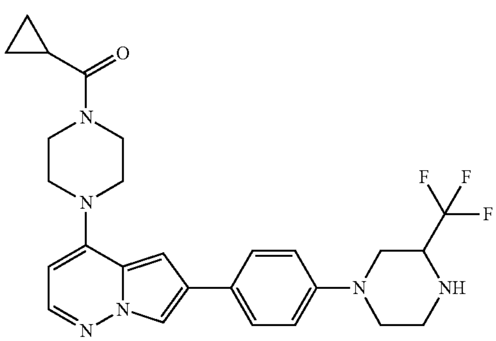 [SMILES: O=C(C1CC1)N1CCN(c2ccnn3cc(-c4ccc(N5CCNC(C(F)(F)F)C5)cc4)cc23)CC1] | 499 | 1H-NMR (400 MHz, DMSO-d6) δ ppm 8.09 (s, 1H), 7.87 (d, 1H, J = 5.6 Hz), 7.67 (d, 2H, J = 8.4 Hz), 6.99 (d, 2H, J = 8.4 Hz), 6.95 (s, 1H), 5.96 (d, 1H, J = 5.6 Hz), 3.92 (br. s., 2H), 3.69-3.63 (m, 3H), 3.51-3.45 (m, 6H), 3.04-3.01 (m, 1H), 2.94-2.89 (m, 1H), 2.86-2.79 (m, 1H), 2.76-2.66 (m, 2H), 2.06-2.00 (m, 1H), 0.78-0.71 (m, 4H). |
| 374 | 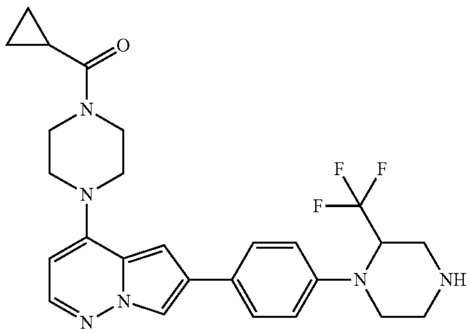 [SMILES: O=C(C1CC1)N1CCN(c2ccnn3cc(-c4ccc(N5CCNCC5C(F)(F)F)cc4)cc23)CC1] | 499 | 1H-NMR (400 MHz, 6d-DMSO) δ ppm 8.34 (s, 1H), 8.07 (d, 1H, J = 1.6 Hz), 7.87 (d, 1H, J = 5.2 Hz), 7.64 (d, 2H, J = 8.8 Hz), 7.01 (d, 2H, J = 8.8 Hz), 6.95 (d, 1H, J = 1.6 Hz), 5.96 (d, 1H, J = 5.2 Hz), 4.71-4.68 (m, 1H), 3.92 (br. s., 2H), 3.71 (br. s., 2H), 3.53-3.35 (m, 4H), 3.28-3.09 (m, 3H), 3.03-2.96 (m, 2H), 2.74-2.67 (m, 1H). |

TABLE 1-continued

| # | Structure | LCMS (M + 1) | NMR |
|---|---|---|---|
| 375 | 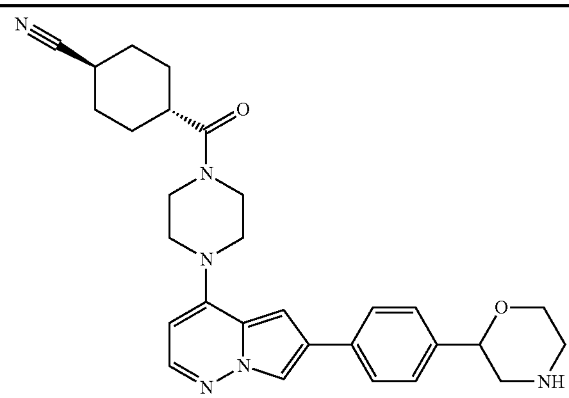 | 499 | 1H-NMR (400 MHz, 6d-DMSO) δ ppm 8.27 (s, 1H), 8.17 (d, 1H, J = 1.6 Hz), 7.90 (d, 1H, J = 5.2 Hz), 7.76 (d, 2H, J = 8.4 Hz), 7.33 (d, 2H, J = 8.4 Hz), 7.04 (d, 1H, J = 1.6 Hz), 5.97 (d, 1H, J = 5.6 Hz), 4.50-4.30 (m, 1H), 3.95-3.85 (m, 1H), 3.79-3.75 (m, 2H), 3.70-3.65 (m, 2H), 3.60-3.55 (m, 2H), 3.52-3.45 (m, 2H), 3.42-3.38 (m, 2H), 3.00-2.90 (m, 2H), 2.80-2.71 (m, 2H), 2.70-2.65 (m, 2H), 2.10-2.00 (m, 2H), 1.80-1.68 (m, 2H), 1.65-1.50 (m, 2H), 1.48-1.30 (m, 2H). |
| 376 | 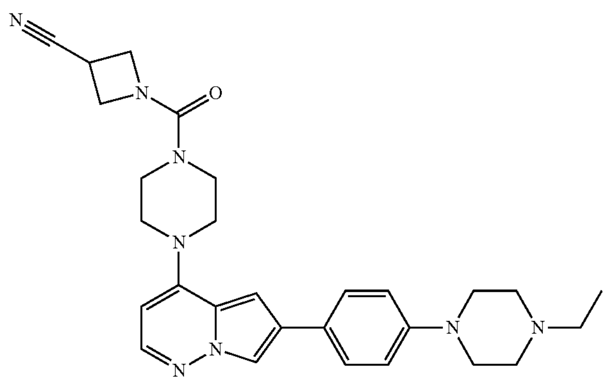 [SMILES: CCN1CCN(c2ccc(-c3cc4c(N5CCN(C(=O)N6CC(C#N)C6)CC5)ccnn4c3)cc2)CC1] | 499 | 1H-NMR (400 MHz, 6d-DMSO) δ ppm 8.17 (s, 1H), 8.06 (d, 1H, J = 1.6 Hz), 7.86 (d, 1H, J = 5.6 Hz), 7.64 (d, 2H, J = 8.8 Hz), 6.96 (d, 2H, J = 8.8 Hz), 6.91 (d, 1H, J = 1.6 Hz), 5.94 (d, 1H, J = 5.6 Hz), 4.22 (t, 2H, J = 8.8 Hz), 4.09 (dd, 2H, J = 8.0, 6.0 Hz), 3.78-3.73 (m, 1H), 2.47-2.46 (m, 4H), 2.45-2.44 (m, 4H), 3.18-3.16 (m, 4H), 2.55-2.53 (m, 4H), 2.40 (q, 2H, J = 7.2 Hz), 1.05 (t, 3H, J = 7.2 Hz). |
| 377 | 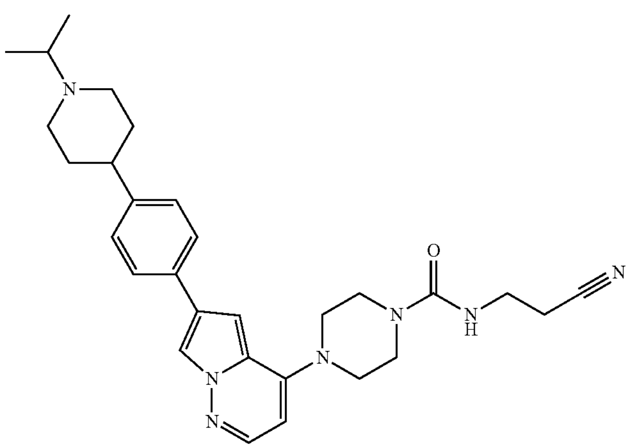 [SMILES: CC(C)N1CCC(c2ccc(-c3cc4c(N5CCN(C(=O)NCCC#N)CC5)ccnn4c3)cc2)CC1] | 500 | 1H-NMR (400 MHz, 6d-DMSO) δ ppm 8.30 (s, 1H), 8.14 (d, 1H, J = 1.6 Hz), 7.89 (d, 1H, J = 5.6 Hz), 7.74 (d, 2H, J = 8.4 Hz), 7.25 (d, 2H, J = 8.4 Hz), 7.07 (t, 1H, J = 5.6 Hz), 7.01 (d, 1H, J = 1.6 Hz), 5.98 (d, 1H, J = 5.6 Hz), 3.58-3.52 (m, 4H), 3.48-3.42 (m, 4H), 3.33-3.24 (m, 2H), 3.03-2.98 (m, 2H), 2.90-2.85 (m, 1H), 2.69-2.64 (m, 2H), 2.55-2.50 (m, 1H), 2.43-2.39 (m, 2H), 1.84-1.75 (m, 2H), 1.74-1.68 (m, 2H), 1.06 (d, 6H, J = 6.4 Hz). |
| 378 | 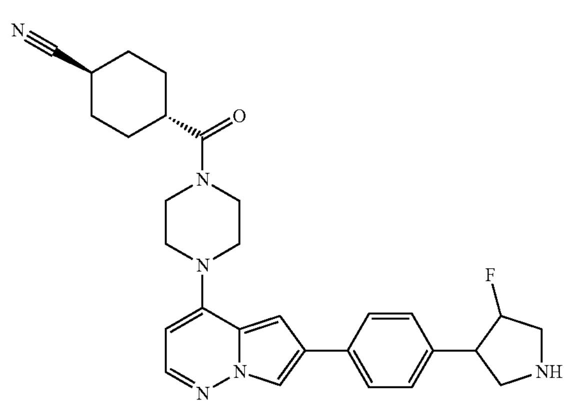 [SMILES: N#C[C@H]1CC[C@H](C(=O)N2CCN(c3ccnn4cc(-c5ccc(C6CNCC6F)cc5)cc34)CC2)CC1] | 501 | 1H-NMR (400 MHz, 6d-DMSO) δ ppm 8.17 (d, 1H, J = 1.2 Hz), 7.90 (d, 1H, J = 5.2 Hz), 7.75 (d, 2H, J = 8.4 Hz), 7.27 (d, 2H, J = 8.4 Hz), 7.03 (d, 1H, J = 1.2 Hz), 5.97 (d, 1H, J = 5.2 Hz), 5.30-5.00 (m, 1H), 3.80-3.70 (m, 2H), 3.70-3.60 (m, 2H), 3.54-3.45 (m, 2H), 3.42-3.33 (m, 4H), 3.18-3.10 (m, 1H), 3.08-3.02 (m, 1H), 2.80-2.60 (m, 3H), 2.10-1.98 (m, 2H), 1.80-1.66 (m, 2H), 1.62-1.50 (m, 2H), 1.46-1.30 (m, 2H). |

TABLE 1-continued

| # | Structure | LCMS (M + 1) | NMR |
|---|---|---|---|
| 379 | 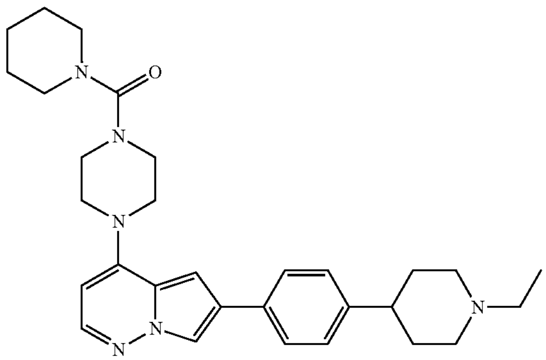 [SMILES: CCN1CCC(c2ccc(-c3cc4c(N5CCN(C(=O)N6CCCCC6)CC5)ccnn4c3)cc2)CC1] | 501 | 1H-NMR (400 MHz, 6d-DMSO) δ ppm 8.13 (d, 1H, J = 1.6 Hz), 7.88 (d, 1H, J = 5.6 Hz), 7.72 (d, 2H, J = 8.0 Hz), 7.25 (d, 2H, J = 8.0 Hz), 6.70 (d, 1H, J = 1.6 Hz), 5.96 (d, 1H, J = 5.6 Hz), 3.45-3.44 (m, 4H), 3.35-3.33 (m, 4H), 3.16-3.13 (m, 4H), 2.99-2.96 (m, 2H), 2.48-2.42 (m, 1H), 2.34 (q, 2H, J = 7.2 Hz), 1.98-1.92 (m, 2H), 1.76-1.71 (m, 2H), 1.70-1.60 (m, 2H), 1.60-1.50 (m, 2H), 1.50-1.40 (m, 4H), 1.02 (t, 3H, J = 7.2 Hz). |
| 380 | 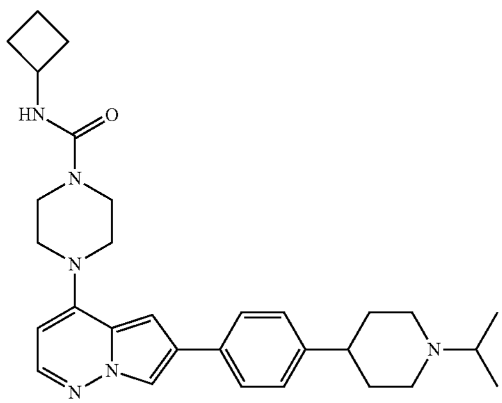 [SMILES: CC(C)N1CCC(c2ccc(-c3cc4c(N5CCN(C(=O)NC6CCC6)CC5)ccnn4c3)cc2)CC1] | 502 | 1H NMR (400 MHz, DMSO-d6) δ 8.12 (d, J = 1.8 Hz, 1H), 7.88 (d, J = 5.4 Hz, 1H), 7.71 (d, J = 8.1 Hz, 2H), 7.24 (d, J = 8.0 Hz, 2H), 6.97 (d, J = 1.9 Hz, 1H), 6.74 (d, J = 7.6 Hz, 1H), 5.97 (d, J = 5.5 Hz, 1H), 4.12 (h, J = 8.3 Hz, 1H), 3.52 (dd, J = 6.9, 3.3 Hz, 4H), 3.42 (dd, J = 6.7, 3.5 Hz, 4H), 2.88 (d, J = 10.6 Hz, 2H), 2.71 (p, J = 6.6 Hz, 1H), 2.27-2.17 (m, 2H), 2.12 (qt, J = 7.7, 2.6 Hz, 2H), 1.93 (pd, J = 9.1, 2.7 Hz, 2H), 1.76 (d, J = 12.3 Hz, 2H), 1.69-1.47 (m, 4H), 0.99 (d, J = 6.5 Hz, 6H). |
| 381 | 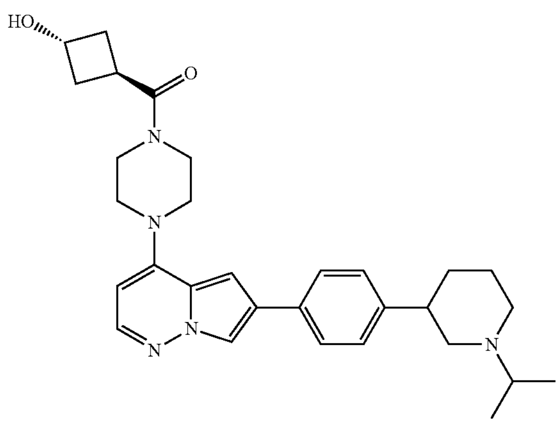 [SMILES: CC(C)N1CCCC(c2ccc(-c3cc4c(N5CCN(C(=O)[C@H]6C[C@H](O)C6)CC5)ccnn4c3)cc2)C1] | 502 | 1H NMR (400 MHz, 6d-DMSO) δ ppm 8.15 (d, 1H, J = 1.6 Hz), 7.90 (d, 1H, J = 5.6 Hz), 7.72 (d, 2H, J = 8.0 Hz), 7.27 (d, 2H, J = 8.0 Hz), 7.00 (d, 1H, J = 1.6 Hz), 5.96 (d, 1H, J = 5.6 Hz), 5.11 (d, 1H, J = 6.0 Hz), 4.15-4.08 (m, 1H), 3.72-3.65 (m, 2H), 3.60-3.50 (m, 2H), 3.48-3.40 (m, 4H), 3.10-2.99 (m, 1H), 3.85-3.78 (m, 2H), 3.78-3.69 (m, 2H), 2.44-2.39 (m, 2H), 2.20-2.10 (m, 2H), 2.09-2.03 (m, 2H), 1.85-1.79 (m, 1H), 1.77-1.70 (m, 1H), 1.60-1.42 (m, 2H), 0.97 (dd, 6H, J = 6.4, 3.2 Hz). |
| 382 | 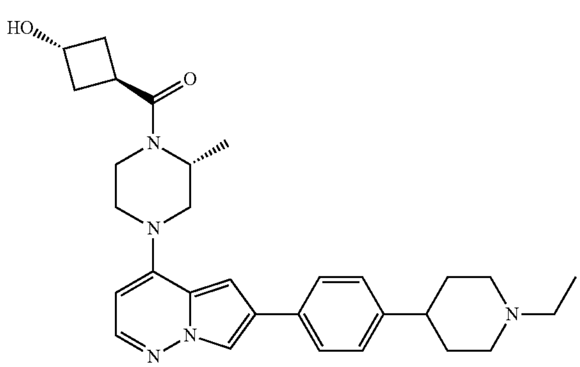 [SMILES: CCN1CCC(c2ccc(-c3cc4c(N5CCN(C(=O)[C@H]6C[C@H](O)C6)[C@H](C)C5)ccnn4c3)cc2)CC1] | 502 | 1H-NMR (400 MHz, 6d-DMSO) δ ppm 8.14 (s, 1H), 7.88 (d, 1H, J = 4.4 Hz), 7.71 (d, 2H, J = 8.4 Hz), 7.26 (d, 2H, J = 8.4 Hz), 6.93 (s, 1H), 5.97-5.93 (m, 1H), 5.10 (d, 1H, J = 2.0 Hz), 4.70-4.30 (m, 1H), 4.12-4.08 (m, 1H), 3.89-3.86 (m, 2H), 3.60-3.50 (m, 1H), 3.21-3.05 (m, 2H), 3.05-3.00 (m, 1H), 3.00-2.96 (m, 2H), 2.49-2.48 (m, 1H), 2.37-2.35 (m, 4H), 2.10-2.00 (m, 2H), 2.00-1.94 (m, 2H), 1.78-1.75 (m, 2H), 1.70-1.67 (m, 2H), 1.37-1.32 (m, 1H) m 1.27-1.21 (m, 2H), 1.03 (t, 3H, J = 7.2 Hz). |

TABLE 1-continued

| # | Structure | LCMS (M + 1) | NMR |
|---|---|---|---|
| 383 | 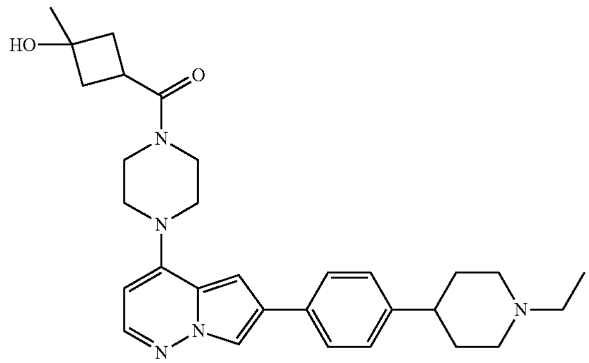 [SMILES: CCN1CCC(c2ccc(-c3cc4c(N5CCN(C(=O)C6CC(C)(O)C6)CC5)ccnn4c3)cc2)CC1] | 503 | 1H NMR (400 MHz, DMSO-d6) δ 8.13 (d, J = 1.7 Hz, 1H), 7.88 (d, J = 5.4 Hz, 1H), 7.71 (d, J = 7.8 Hz, 2H), 7.25 (d, J = 7.9 Hz, 2H), 6.99 (d, J = 1.9 Hz, 1H), 5.95 (d, J = 5.5 Hz, 1H), 4.97 (s, 1H), 3.63 (dt, J = 27.9, 4.8 Hz, 4H), 3.43 (q, J = 5.9, 4.1 Hz, 4H), 2.98 (d, J = 11.0 Hz, 2H), 2.89 (q, J = 8.8 Hz, 1H), 2.34 (q, J = 7.2 Hz, 2H), 2.19 (t, J = 10.1 Hz, 2H), 2.08 (td, J = 8.5, 2.6 Hz, 2H), 2.03-1.88 (m, 2H), 1.75 (d, J = 11.3 Hz, 2H), 1.65 (qd, J = 12.3, 3.5 Hz, 2H), 1.28 (s, 3H), 1.02 (t, J = 7.2 Hz, 3H). |
| 384 | 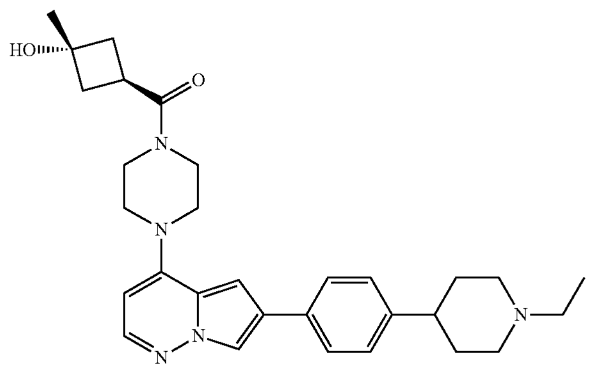 [SMILES: CCN1CCC(c2ccc(-c3cc4c(N5CCN(C(=O)[C@H]6C[C@](C)(O)C6)CC5)ccnn4c3)cc2)CC1] | 503 | |
| 385 | 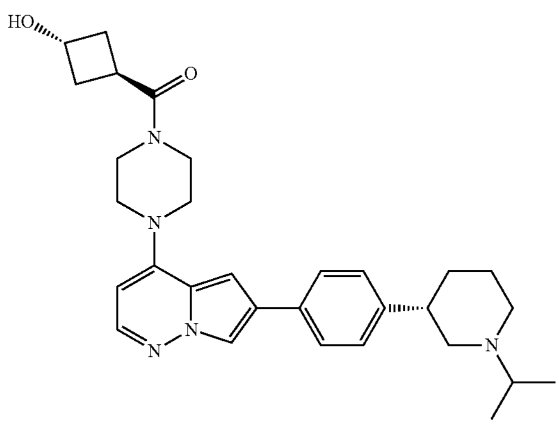 | 502 | 1H-NMR (400 MHz, 6d-DMSO) δ ppm 8.14 (d, 1H, J = 1.2 Hz), 7.90 (d, 1H, J = 5.6 Hz), 7.72 (d, 2H, J = 8.0 Hz), 7.27 (d, 2H, J = 8.0 Hz), 7.00 (d, 1H, J = 1.2 Hz), 5.97 (d, 1H, J = 5.6 Hz), 5.10 (d, 1H, J = 6.0 Hz), 4.13-4.11 (m, 1H), 3.70-3.69 (m, 2H), 3.55-3.54 (m, 2H), 3.45-3.43 (m, 4H), 3.24-3.22 (m, 1H), 2.82-2.77 (m, 2H), 2.76-2.67 (m, 2H), 2.44-2.38 (m, 2H), 2.20-2.14 (m, 2H), 2.10-2.03 (m, 2H), 1.81-1.79 (m, 1H), 1.72-1.70 (m, 1H), 1.59-1.50 (m, 1H), 1.48-1.40 (m, 1H), 0.99-0.96 (m, 6H). |
| 386 | 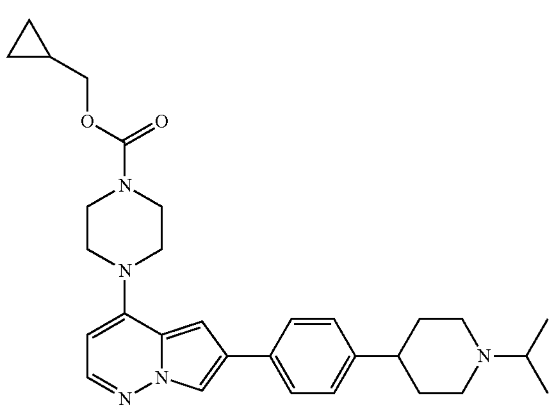 [SMILES: CC(C)N1CCC(c2ccc(-c3cc4c(N5CCN(C(=O)OCC6CC6)CC5)ccnn4c3)cc2)CC1] | 502 | 1H-NMR (400 MHz, 6d-DMSO) δ ppm 8.25 (s, 1H), 8.15 (d, 1H, J = 1.6 Hz), 7.91 (d, 1H, J = .6 Hz), 7.74 (d, 2H, J = 8.4 Hz), 7.25 (d, 2H, J = 8.4 Hz), 7.00 (d, 1H, J = 1.6 Hz), 5.98 (d, 1H, J = 5.6 Hz), 3.89 (d, 2H, J = 6.8 Hz), 3.65-3.59 (m, 4H), 3.50-3.40 (m, 4H), 2.97-2.2.93 (m, 2H), 2.82-2.78 (m, 1H), 2.52-2.50 (m, 1H), 2.35-2.28 (m, 2H), 1.82-1.77 (m, 2H), 1.70-1.64 (m, 2H), 1.14-1.11 (m, 1H), 1.03 (d, 6H, J = 6.8 Hz), 0.54-0.51 (m, 2H), 0.30-0.27 (m, 2H). |

TABLE 1-continued

| # | Structure | LCMS (M + 1) | NMR |
|---|---|---|---|
| 387 | 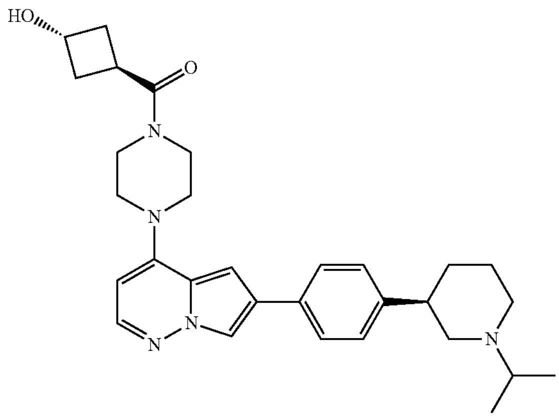 [SMILES: CC(C)N1CCC[C@H](c2ccc(-c3cc4c(N5CCN(C(=O)[C@H]6C[C@H](O)C6)CC5)ccnn4c3)cc2)C1] | 502 | 1H-NMR (400 MHz, 6d-DMSO) δ ppm 8.15 (d, 1H, J = 1.6 Hz), 7.90 (d, 1H, J = 5.6 Hz), 7.72 (d, 2H, J = 8.4 Hz), 7.27 (d, 2H, J = 8.4 Hz), 7.01 (d, 1H, J = 1.6 Hz), 5.98 (d, 1H, J = 5.6 Hz), 5.11 (d, 1H, J = 5.6 Hz), 4.14-4.11 (m, 1H), 3.69-3.68 (m, 2H), 3.55-3.54 (m, 2H), 3.46-3.44 (m, 4H), 3.22-3.21 (m, 1H), 2.81-2.75 (m, 2H), 2.74-2.68 (m, 2H), 2.43-2.38 (m, 2H), 2.19-2.10 (m, 2H), 2.08-2.01 (m, 2H), 1.72-17.71 (m, 1H), 1.70-1.69 (m, 1H), 1.60-1.40 (m, 2H), 0.98-0.96 (m, 6H). |
| 388 | 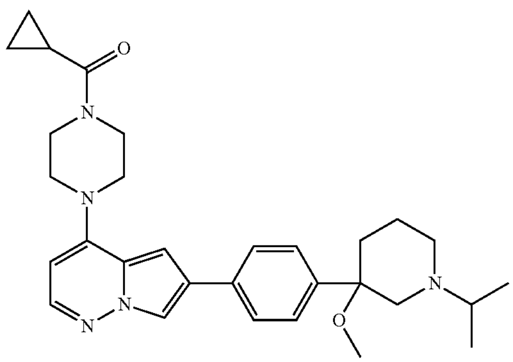 [SMILES: COC1(c2ccc(-c3cc4c(N5CCN(C(=O)C6CC6)CC5)ccnn4c3)cc2)CCCN(C(C)C)C1] | 502 | 1H NMR (400 MHz, 6d-DMSO) δ ppm 8.22 (s, 1H), 8.19 (d, 1H, J = 1.6 Hz), 7.91 (d, 1H, J = 5.2 Hz), 7.80 (d, 2H, J = 8.4 Hz), 7.48 (d, 2H, J = 8.4 Hz), 7.06 (s, 1H), 5.98 (d, 1H, J = 5.2 Hz), 3.94-3.91 (m, 2H), 3.74-3.70 (m, 2H), 3.60-3.52 (m, 2H), 3.50-3.45 (m, 2H), 2.92 (s, 3H), 2.92-2.81 (m, 3H), 2.60-2.50 (m, 1H), 2.03-2.01 (m, 1H), 1.85-1.80 (m, 2H), 1.80-1.75 (m, 1H), 1.45-1.40 (m, 1H), 1.04 (d, 6H, J = 6.4 Hz), 0.78-0.74 (m, 4H). |
| 389 | 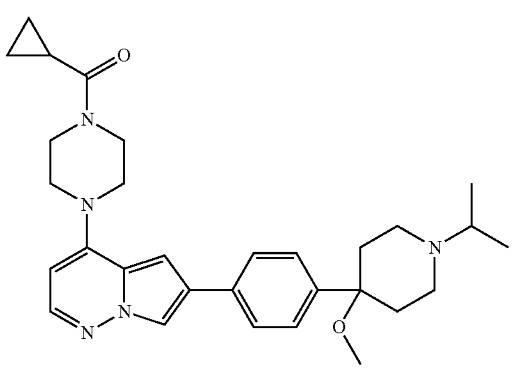 [SMILES: COC1(c2ccc(-c3cc4c(N5CCN(C(=O)C6CC6)CC5)ccnn4c3)cc2)CCN(C(C)C)CC1] | 502 | 1H-NMR (400 MHz, 6d-DMSO) δ ppm 8.19 (s, 1H), 7.91 (d, 1H, J = 5.6 Hz), 7.79 (d, 2H, J = 8.4 Hz), 7.39 (d, 2H, J = 8.4 Hz), 7.06 (s, 1H), 5.98 (d, 1H, J = 5.6 Hz), 4.01-3.91 (m, 2H), 3.76-3.69 (m, 2H), 3.55-3.50 (m, 2H), 3.50-3.45 (m, 2H), 2.89 (s, 3H), 2.71-2.69 (m, 1H), 2.61-2.59 (m, 2H), 2.47-2.45 (m, 2H), 2.03-1.96 (m, 2H), 1.88-1.81 (m, 2H), 1.00 (d, 6H, J = 6.0 Hz), 0.78-0.75 (m, 4H). |

TABLE 1-continued

| # | Structure | LCMS (M + 1) | NMR |
|---|---|---|---|
| 390 | 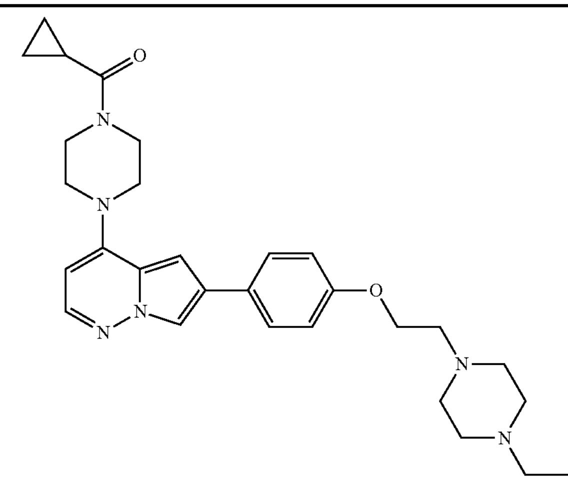 | 503 | 1H-NMR (400 MHz, DMSO-d6) δ ppm 8.11 (d, 1H, J = 1.6 Hz), 7.89 (d, 1H, J = 5.6 Hz), 7.74-7.72 (m, 2H), 6.99-6.96 (m, 3H), 5.97 (d, 1H, J = 5.6 Hz), 4.11 (t, 2H, J = 6.0 Hz), 3.92 (br. s., 2H), 3.70 (br. s., 2H), 3.53-3.37 (m, 6H), 2.71 (t, 2H, J = 5.6 Hz), 2.60-2.48 (m, 4H), 2.43-2.36 (m, 4H), 2.04-2.01 (m, 1H), 1.02 (t, 2H, J = 7.2 Hz), 0.79-0.73 (m, 4H). |
| 391 | 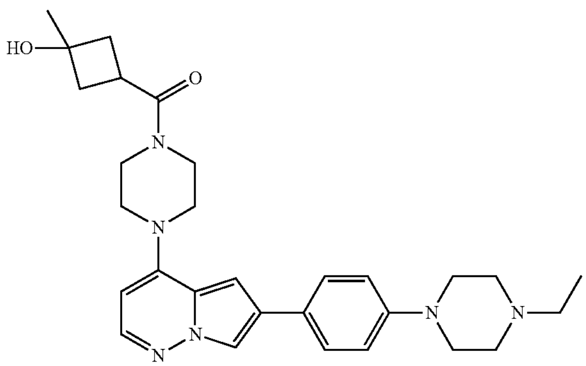 | 503 | 1H-NMR (400 MHz, CDCl3) δ 7.88 (d, 1H, J = 1.6 Hz), 7.83 (d, 1H, J = 5.2 Hz), 7.56 (d, 2H, J = 8.4 Hz), 6.99 (d, 2H, J = 8.4 Hz), 6.63 (d, 1H, J = 1.6 Hz), 5.83 (d, 1H, J = 5.2 Hz), 3.93-3.83 (m, 2H), 3.72-3.62 (m, 2H), 3.51-3.39 (m, 4H), 3.33-3.22 (m, 4H), 2.99-2.88 (m, 1H), 2.71-2.60 (m, 4H), 2.51 (q, 2H, J = 7.2 Hz), 2.44-2.32 (m, 4H), 1.42 (s, 3H), 1.16 (t, J = 7.2 Hz, 3H). |
| 392 | 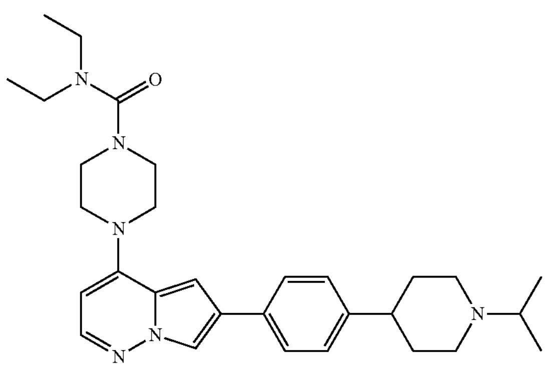 [SMILES: CCN(CC)C(=O)N1CCN(c2ccnn3cc(-c4ccc(C5CCN(C(C)C)CC5)cc4)cc23)CC1] | 503 | 1H-NMR (400 MHz, 6d-DMSO) δ ppm 8.27 (s, 1H), 8.14 (d, 1H, J = 1.6 Hz), 7.89 (d, 1H, J = 5.6 Hz), 7.73 (d, 2H, J = 8.4 Hz), 7.25 (d, 2H, J = 8.4 Hz), 7.01 (d, 1H, J = 1.6 Hz), 5.97 (d, 1H, J = 5.6 Hz), 3.50-3.41 (m, 4H), 3.40-3.30 (m, 4H), 3.18 (q, 4H, J = 6.8 Hz), 3.00-2.95 (m, 2H), 2.85 (heptet, 1H, J = 6.8 Hz), 2.52-2.50 (m, 1H), 2.40-2.31 (m, 2H), 1.82-1.78 (m, 2H), 1.75-1.66 (m, 2H), 1.08 (t, 6H, J = 6.8 Hz), 1.04 (d, 6H, J = 6.8 Hz). |
| 393 | 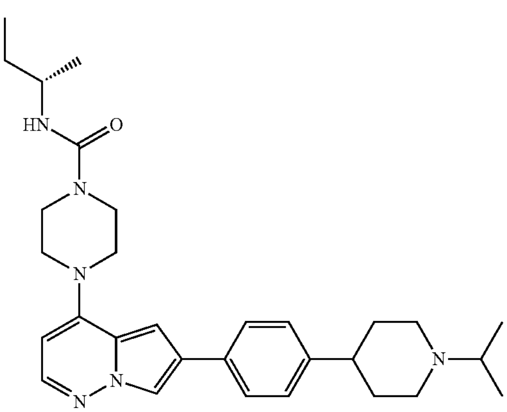 [SMILES: CC[C@H](C)NC(=O)N1CCN(c2ccnn3cc(-c4ccc(C5CCN(C(C)C)CC5)cc4)cc23)CC1] | 503 | 1H-NMR (400 MHz, 6d-DMSO) δ ppm 8.12 (d, 1H, J = 1.6 Hz), 7.88 (d, 1H, J = 5.2 Hz), 7.71 (d, 2H, J = 8.4 Hz), 7.24 (d, 2H, J = 8.4 Hz), 6.99 (d, 1H, J = 1.6 Hz), 6.25 (d, 1H, J = 8.0 Hz), 5.97 (d, 1H, J = 5.6 Hz), 3.66-3.55 (m, 1H), 3.54-3.48 (m, 4H), 3.46-3.38 (m, 4H), 2.92-2.82 (m, 2H), 2.74-2.64 (m, 1H), 2.46-2.40 (m, 1H), 2.26-2.14 (m, 2H), 1.80-1.70 (m, 2H), 1.68-1.54 (m, 2H), 1.50-1.30 (m, 2H), 1.04 (d, 3H, J = 6.8 Hz), 0.98 (d, 6H, J = 6.8 Hz), 0.83 (t, 3H, J = 7.2 Hz). |

TABLE 1-continued

| # | Structure | LCMS (M + 1) | NMR |
|---|-----------|--------------|-----|
| 394 | 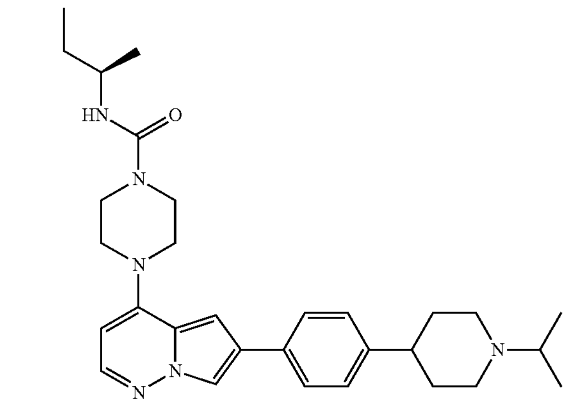 [SMILES: CC[C@@H](C)NC(=O)N1CCN(c2ccnn3cc(-c4ccc(C5CCN(C(C)C)CC5)cc4)cc23)CC1] | 503 | 1H-NMR (400 MHz, 6d-DMSO) δ ppm 8.12 (d, 1H, J = 1.6 Hz), 7.88 (d, 1H, J = 5.6 Hz), 7.71 (d, 2H, J = 8.4 Hz), 7.24 (d, 2H, J = 8.4 Hz), 6.99 (d, 1H, J = 1.6 Hz), 6.25 (d, 1H, J = 8.0 Hz), 5.97 (d, 1H, J = 5.6 Hz), 3.68-3.55 (m, 1H), 3.54-3.48 (m, 4H), 3.46-3.38 (m, 4H), 2.92-2.82 (m, 2H), 2.74-2.64 (m, 1H), 2.46-2.40 (m, 1H), 2.26-2.14 (m, 2H), 1.80-1.70 (m, 2H), 1.68-1.54 (m, 2H), 1.50-1.30 (m, 2H), 1.04 (d, 3H, J = 6.4 Hz), 0.98 (d, 6H, J = 6.4 Hz), 0.83 (t, 3H, J = 7.2 Hz). |
| 395 | 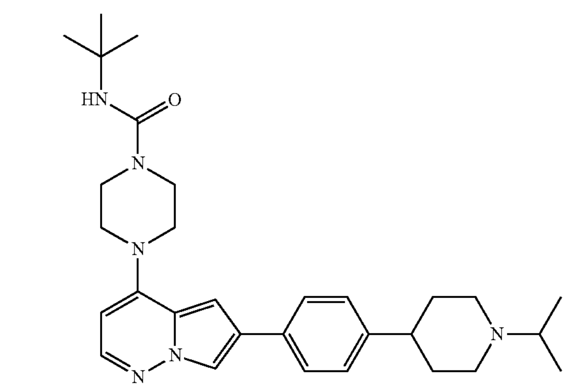 [SMILES: CC(C)N1CCC(c2ccc(-c3cc4c(N5CCN(C(=O)NC(C)(C)C)CC5)ccnn4c3)cc2)CC1] | 504 | 1H NMR (400 MHz, DMSO-d6) δ 8.12 (d, J = 1.7 Hz, 1H), 7.87 (d, J = 5.4 Hz, 1H), 7.71 (d, J = 8.1 Hz, 2H), 7.24 (d, J = 8.2 Hz, 2H), 6.97 (d, J = 1.9 Hz, 1H), 5.96 (d, J = 5.5 Hz, 1H), 5.90 (s, 1H), 3.45 (ddd, J = 28.3, 7.6, 4.0 Hz, 9H), 2.88 (d, J = 10.8 Hz, 2H), 2.80-2.57 (m, 1H), 2.21 (t, J = 11.1 Hz, 2H), 1.76 (d, J = 12.4 Hz, 2H), 1.70-1.49 (m, 2H), 1.27 (s, 9H), 0.99 (d, J = 6.5 Hz, 6H). |
| 396 | 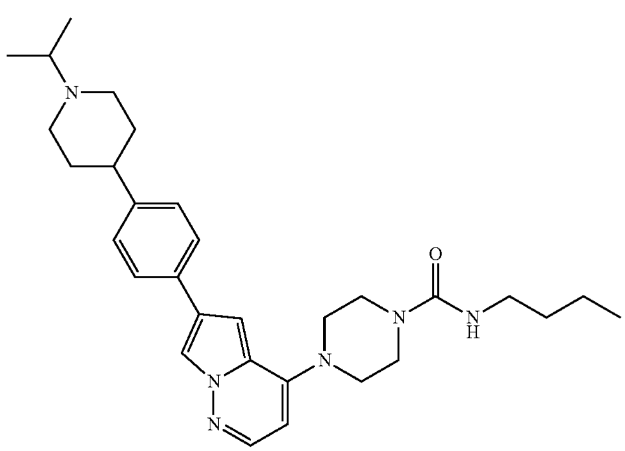 [SMILES: CCCCNC(=O)N1CCN(c2ccnn3cc(-c4ccc(C5CCN(C(C)C)CC5)cc4)cc23)CC1] | 504 | 1H NMR (400 MHz, DMSO-d6) δ 8.21 (s, 1H), 8.12 (d, J = 1.7 Hz, 1H), 7.88 (d, J = 5.4 Hz, 1H), 7.76-7.67 (m, 2H), 7.28-7.19 (m, 2H), 6.98 (d, J = 1.9 Hz, 1H), 6.56 (t, J = 5.5 Hz, 1H), 5.97 (d, J = 5.5 Hz, 1H), 3.56-3.47 (m, 4H), 3.42 (dd, J = 6.8, 3.4 Hz, 4H), 3.09-3.00 (m, 2H), 2.95 (d, J = 11.0 Hz, 2H), 2.81 (p, J = 6.5 Hz, 1H), 2.32 (dd, J = 12.6, 10.1 Hz, 2H), 1.79 (d, J = 12.4 Hz, 2H), 1.74-1.59 (m, 2H), 1.46-1.34 (m, 2H), 1.27 (h, J = 7.2 Hz, 2H), 1.02 (d, J = 6.6 Hz, 5H), 0.87 (t, J = 7.3 Hz, 3H). |

TABLE 1-continued

| # | Structure | LCMS (M + 1) | NMR |
|---|---|---|---|
| 397 | 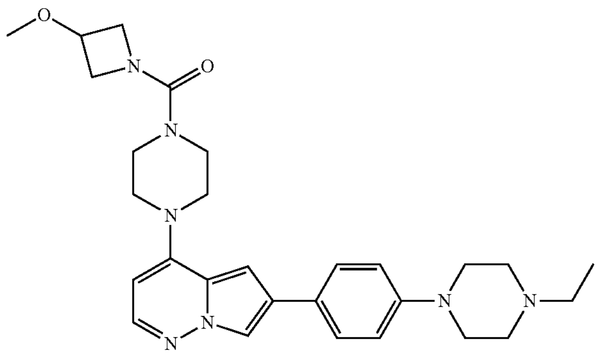 [SMILES: CCN1CCN(c2ccc(-c3cc4c(N5CCN(C(=O)N6CC(OC)C6)CC5)ccnn4c3)cc2)CC1] | 504 | 1H-NMR (400 MHz, 6d-DMSO) δ ppm 8.26 (br. s., 1H), 8.06 (d, 1H, J = 1.6 Hz), 7.86 (d, 1H, J = 5.2 Hz), 7.65 (d, 2H, J = 8.4 Hz), 6.95 (d, 2H, J = 8.4 Hz), 6.91 (d, 1H, J = 1.6 Hz), 5.94 (d, 1H, J = 5.2 Hz), 4.15-4.12 (m, 3H), 3.78-3.75 (m, 2H), 3.46-3.44 (m, 8H), 3.20 (s, 3H), 3.16-3.15 (m, 4H), 2.55-2.54 (m, 4H), 2.41 (q, 2H, J = 7.2 Hz), 1.05 (t, 3H, J = 7.2 Hz). |
| 398 | 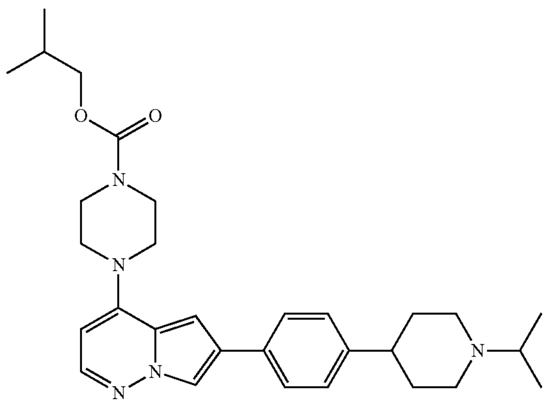 [SMILES: CC(C)COC(=O)N1CCN(c2ccnn3cc(-c4ccc(C5CCN(C(C)C)CC5)cc4)cc23)CC1] | 505 | 1H NMR (400 MHz, DMSO-d6) δ 9.63 (s, 1H), 8.16 (d, J = 1.7 Hz, 1H), 7.90 (d, J = 5.4 Hz, 1H), 7.78 (d, J = 7.9 Hz, 2H), 7.25 (d, J = 8.1 Hz, 2H), 7.01 (d, J = 1.8 Hz, 1H), 5.98 (d, J = 5.5 Hz, 1H), 3.83 (d, J = 6.5 Hz, 2H), 3.61 (br. s, 4H), 3.52-3.41 (m, 7H), 3.15-3.01 (m, 2H), 2.87 (p, J = 9.4, 8.5 Hz, 1H), 2.03 (t, J = 9.3 Hz, 4H), 1.89 (hept, J = 6.8 Hz, 1H), 1.29 (d, J = 6.6 Hz, 6H), 0.91 (d, J = 6.7 Hz, 6H) |
| 399 | 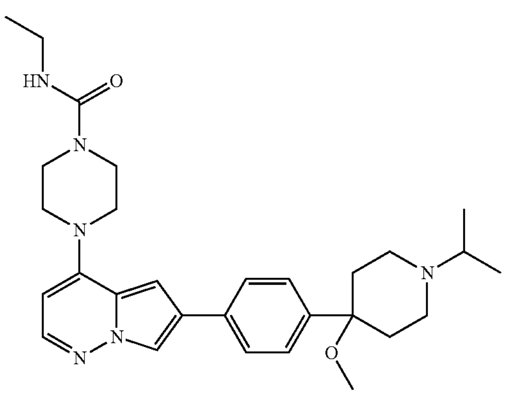 [SMILES: CCNC(=O)N1CCN(c2ccnn3cc(-c4ccc(C5(OC)CCN(C(C)C)CC5)cc4)cc23)CC1] | 505 | 1H-NMR (400 MHz, MeOD) δ ppm 7.98 (d, 1H, J = 1.2 Hz), 7.85 (d, 1H, J = 5.2 Hz), 7.74 (d, 1H, J = 8.4 Hz), 7.45 (d, 1H, J = 8.4 Hz), 6.92 (d, 1H, J = 1.2 Hz), 6.00 (d, 1H, J = 5.2 Hz), 3.67-3.64 (m, 4H), 3.56-3.54 (m, 4H), 3.24 (q, 2H, J = 7.2 Hz), 3.00 (s, 3H), 2.87-2.82 (m, 3H), 2.77-2.71 (m, 2H), 2.20-2.16 (m, 2H), 2.08-2.02 (m, 2H), 1.17 (d, 6H, J = 6.4 Hz), 1.15 (t, 3H, J = 7.2 Hz). |
| 400 | 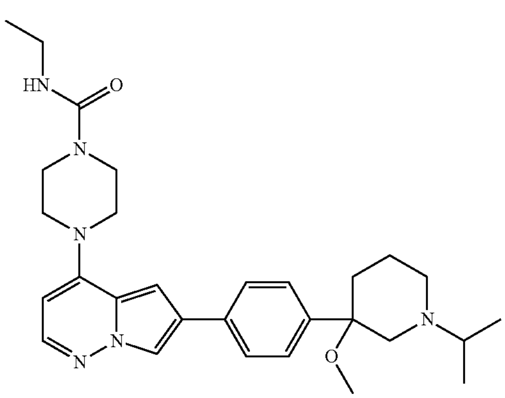 [SMILES: CCNC(=O)N1CCN(c2ccnn3cc(-c4ccc(C5(OC)CCCN(C(C)C)C5)cc4)cc23)CC1] | 505 | 1H NMR (400 MHz, 6d-DMSO) δ ppm 8.17 (s, 1H), 7.90 (d, 1H, J = 5.6 Hz), 7.79 (d, 2H, J = 8.4 Hz), 7.48 (d, 2H, J = 8.4 Hz), 7.03 (d, 1H, J = 1.2 Hz), 6.62 (t, 1H, J = 5.6 Hz), 5.99 (d, 1H, J = 5.6 Hz), 3.53-3.51 (m, 4H), 3.45-3.43 (m, 4H), 3.33-3.30 (m, 1H), 3.20-3.10 (m, 2H), 2.92 (s, 3H), 2.80-2.74 (m, 2H), 2.72-2.60 (m, 1H), 2.50-2.40 (m, 2H), 1.83-1.71 (m, 3H), 1.06-1.01 (m, 9H). |

TABLE 1-continued

| # | Structure | LCMS (M + 1) | NMR |
|---|---|---|---|
| 401 | 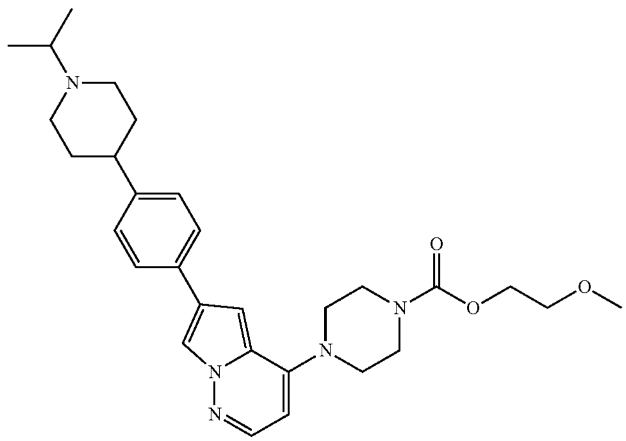 [SMILES: COCCOC(=O)N1CCN(c2ccnn3cc(-c4ccc(C5CCN(C(C)C)CC5)cc4)cc23)CC1] | 507 | 1H NMR (400 MHz, DMSO-d6) δ 8.13 (d, J = 1.7 Hz, 1H), 7.89 (d, J = 5.4 Hz, 1H), 7.71 (d, J = 8.1 Hz, 2H), 7.24 (d, J = 8.2 Hz, 2H), 6.99 (d, J = 1.9 Hz, 1H), 5.97 (d, J = 5.5 Hz, 1H), 4.21-4.10 (m, 2H), 3.68-3.57 (m, 4H), 3.57-3.50 (m, 2H), 3.50-3.41 (m, 4H), 3.28 (s, 3H), 2.87 (s, 2H), 2.68 (d, J = 17.6 Hz, 1H), 2.21 (s, 2H), 1.75 (s, 2H), 1.62 (d, J = 13.0 Hz, 2H), 0.99 (d, J = 6.4 Hz, 6H). |
| 402 | 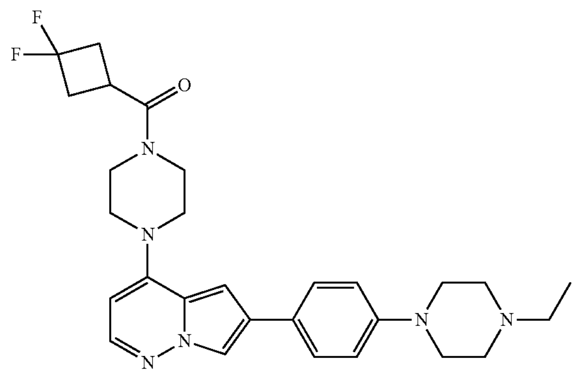 [SMILES: CCN1CCN(c2ccc(-c3cc4c(N5CCN(C(=O)C6CC(F)(F)C6)CC5)ccnn4c3)cc2)CC1] | 509 | 1H-NMR (500 MHz, DMSO-d6) δ ppm 8.07 (s, 1H), 7.88 (d, 1H, J = 5.5 Hz), 7.65 (d, 2H, J = 8.0 Hz), 6.97-6.93 (m, 3H), 5.96 (d, 1H, J = 5.5 Hz), 3.72-3.71 (m, 2H), 3.63-3.62 (m, 2H), 3.47-3.46 (m, 4H), 3.40-3.39 (m, 4H), 3.17-3.16 (m, 4H), 2.86-2.80 (m, 4H), 2.39-2.37 (m, 2H), 1.24 (s, 1H), 1.04 (t, 3H, J = 7.5 Hz). |
| 403 | 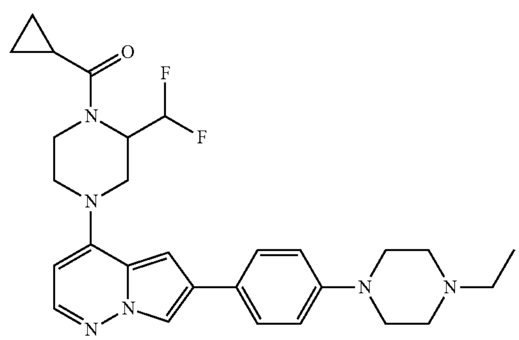 [SMILES: CCN1CCN(c2ccc(-c3cc4c(N5CCN(C(=O)C6CC6)C(C(F)F)C5)ccnn4c3)cc2)CC1] | 509 | 1H-NMR (400 MHz, 6d-DMSO) δ ppm 8.11 (s, 1H), 7.92 (t, 1H, J = 6.0 Hz), 7.60 (d, 2H, J = 8.4 Hz), 6.97 (d, 2H, J = 8.4 Hz), .6.86-6.83 (m, 1H), 6.51 (td, 1H, J = 56 Hz, 5.6 Hz), 6.04 (dd, 1H, J = 13.6 Hz, 5.2 Hz), 4.92-4.90 (m, 1H), 4.43-4.34 (m, 1H), 4.16-4.12 (m, 1H), 3.89-3.85 (m, 1H), 3.30-3.25 (m, 4H), 3.25-3.20 (m, 2H), 3.19-3.15 (m, 4H), 2.90-2.80 (m, 1H), 2.38 (q, 2H, J = 7.2 Hz), 2.10-2.05 (m, 1H), 1.04 (t, 3H, J = 7.2 Hz), 0.86-0.75 (m, 4H). |
| 404 | 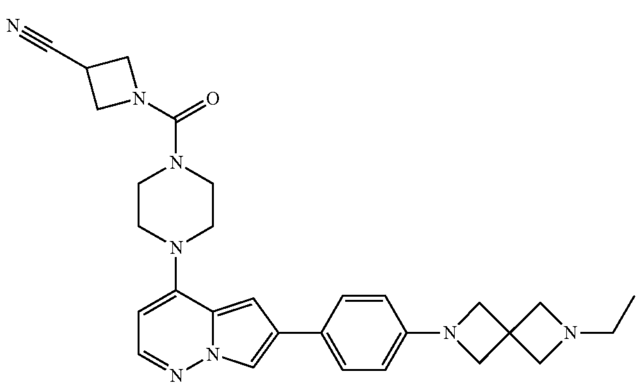 [SMILES: CCN1CC2(C1)CN(c1ccc(-c3cc4c(N5CCN(C(=O)N6CC(C#N)C6)CC5)ccnn4c3)cc1)C2] | 511 | 1H-NMR (400 MHz, CDCl3) δ ppm 7.84 (d, 1H, J = 1.6 Hz), 7.82 (d, 1H, J = 5.6 Hz), 7.50 (d, 2H, J = 8.4 Hz), 6.60 (d, 1H, J = 1.6 Hz), 6.50 (d, 2H, J = 8.4 Hz), 5.81 (d, 2H, J = 6.0 Hz), 4.33-4.22 (m, 4H), 3.98 (s, 4H), 3.65-3.56 (m, 4H), 3.51-3.48 (m, 1H), 3.45-3.38 (m, 4H), 3.36 (s, 4H), 2.46 (q, 2H, J = 7.2 Hz), 0.98 (t, 3H, J = 7.2 Hz). |

TABLE 1-continued

| # | Structure | LCMS (M + 1) | NMR |
|---|---|---|---|
| 405 | 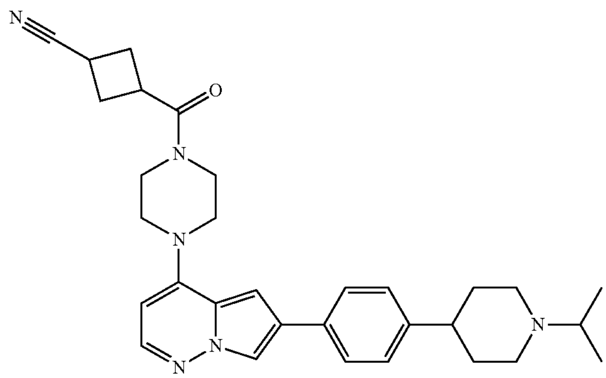 | 511 | 1H-NMR (400 MHz, 6d-DMSO) δ ppm 8.15 (d, 1H, J = 1.6 Hz), 7.90 (d, 1H, J = 5.2 Hz), 7.75 (d, 2H, J = 8.0 Hz), 7.25 (d, 2H, J = 8.0 Hz) 7.00 (d, 1H, J = 1.6 Hz), 5.96 (d, 1H, J = 5.2 Hz), 3.68-3.67 (m, 3H), 3.64-3.62 (m, 1H), 3.53-3.52 (m, 2H), 3.45-3.44 (m, 4H), 3.32-3.29 (m, 2H), 3.28-3.27 (m, 3H), 2.62-2.60 (m, 3H), 2.49-2.46 (m, 2H), 1.90-1.80 (m, 4H), 1.16-1.15 (m, 6H). |
| 406 | 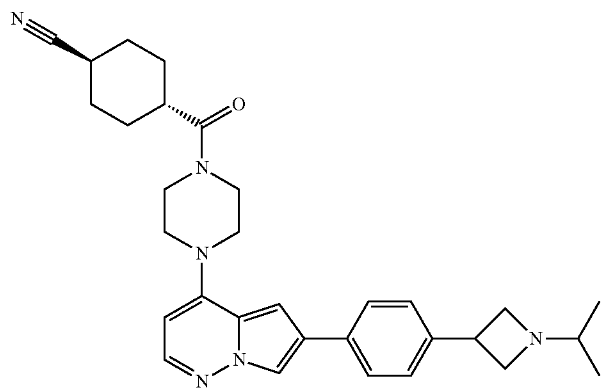 [SMILES: CC(C)N1CC(c2ccc(-c3cc4c(N5CCN(C(=O)[C@H]6CC[C@H](C#N)CC6)CC5)ccnn4c3)cc2)C1] | 511 | 1H-NMR (400 MHz, MeOD) δ ppm 7.98 (d, 1H, J = 1.6 Hz), 7.85 (d, 1H, J = 5.2 Hz), 7.74 (d, 2H, J = 8.4 Hz), 7.36 (d, 2H, J = 8.4 Hz), 6.91 (d, 1H, J = 5.2 Hz), 5.97 (d, 1H, J = 5.2 Hz), 4.12-4.06 (m, 2H), 3.92-3.85 (m, 1H), 3.84-3.78 (m, 4H), 3.66-3.60 (m, 2H), 3.58-3.53 (m, 2H), 3.52-3.47 (m, 2H), 2.98-2.90 (m, 1H), 2.82-2.74 (m, 1H), 2.68-2.60 (m, 1H), 2.20-2.14 (m, 2H), 1.90-1.84 (m, 2H), 1.74-1.62 (m, 2H), 1.60-1.48 (m, 2H), 1.12 (d, 6H, J = 6.4 Hz). |
| 407 | 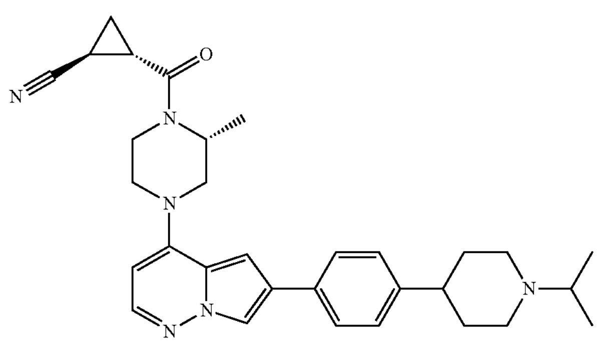 [SMILES: CC(C)N1CCC(c2ccc(-c3cc4c(N5CCN(C(=O)[C@H]6C[C@@H]6C#N)[C@H](C)C5)ccnn4c3)cc2)CC1] | 511 | 1H-NMR (400 MHz, 6d-DMSO) δ ppm 8.33 (br.s., 1H), 8.15 (s, 1H), 7.90 (d, 1H, J = 4.8 Hz), 7.73 (d, 2H, J = 7.6 Hz), 7.27 (d, 2H, J = 7.6 Hz), 6.96 (s, 1H), 5.97 (s, 1H), 4.66-4.62 (m, 1H), 4.22-4.16 (m, 1H), 3.98-3.88 (m, 2H), 3.42-3.16 (m, 2H), 3.08-2.98 (m, 2H), 2.96-2.84 (m, 2H), 2.62-2.52 (m, 1H), 2.46-2.40 (m, 2H), 2.12-2.06 (m, 1H), 1.88-1.72 (m, 4H), 1.50-1.40 (m, 3H), 1.32-1.24 (m, 3H), 1.08 (d, 6H, J = 5.2 Hz). |
| 408 | 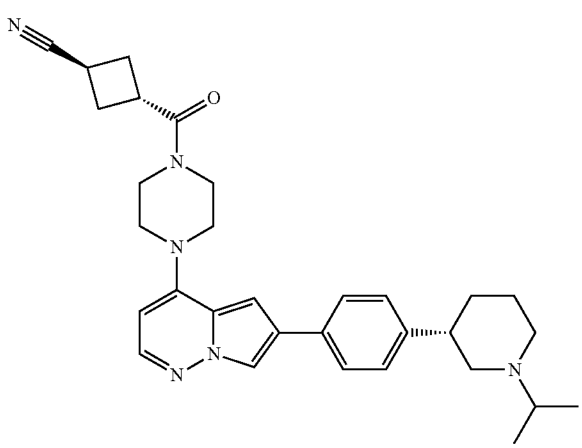 [SMILES: CC(C)N1CCC[C@@H](c2ccc(-c3cc4c(N5CCN(C(=O)[C@H]6C[C@H](C#N)C6)CC5)ccnn4c3)cc2)C1] | 511 | 1H-NMR (400 MHz, 6d-DMSO) δ ppm 8.15 (s, 1H), 7.90 (d, 1H, J = 5.6 Hz), 7.72 (d, 2H, J = 8.0 Hz), 7.27 (d, 2H, J = 8.0 Hz), 6.99 (s, 1H), 5.97 (d, 1H, J = 5.6 Hz), 3.69-3.67 (m, 2H), 3.64-3.60 (m, 1H), 3.54-3.53 (m, 2H), 3.45-3.43 (m, 4H), 3.32-3.30 (m, 1H), 2.80-2.78 (m, 2H), 2.72-2.71 (m, 2H), 2.63-2.61 (m, 2H), 2.52-2.51 (m, 1H), 2.46-2.45 (m, 1H), 2.19-2.11 (m, 2H), 1.83-1.80 (m, 1H), 1.74-1.71 (m, 1H), 1.58-1.50 (m, 1H), 1.49-1.42 (m, 1H), 0.98-0.96 (m, 6H). |

TABLE 1-continued

| # | Structure | LCMS (M + 1) | NMR |
|---|---|---|---|
| 409 | 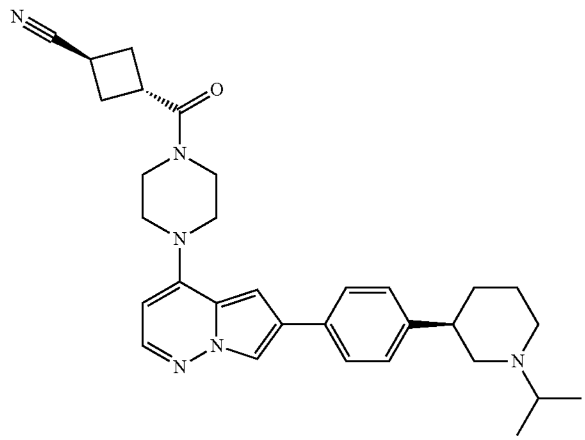 [SMILES: CC(C)N1CCC[C@H](c2ccc(-c3cc4c(N5CCN(C(=O)[C@H]6C[C@H](C#N)C6)CC5)ccnn4c3)cc2)C1] | 511 | 1H-NMR (400 MHz, 6d-DMSO) δ ppm 8.15 (d, 1H, J = 1.6 Hz), 7.90 (d, 1H, J = 5.6 Hz), 7.72 (d, 2H, J = 8.0 Hz), 7.27 (d, 2H, J = 8.0 Hz), 7.00 (d, 1H, J = 1.6 Hz), 5.97 (d, 1H, J = 5.6 Hz), 3.75-3.69 (m, 2H), 3.70-3.67 (m, 1H), 3.54-3.53 (m, 2H), 3.45-3.33 (m, 4H), 3.31-3.28 (m, 1H), 2.81-2.79 (m, 2H), 2.74-2.70 (m, 2H), 2.66-2.63 (m, 2H), 2.50-2.46 (m, 2H), 2.19-2.09 (m, 2H), 1.82-1.81 (m, 1H), 1.72-1.71 (m, 1H), 1.56-1.50 (m, 1H), 1.50-1.42 (m, 1H), 0.98-0.96 (m, 6H). |
| 410 | 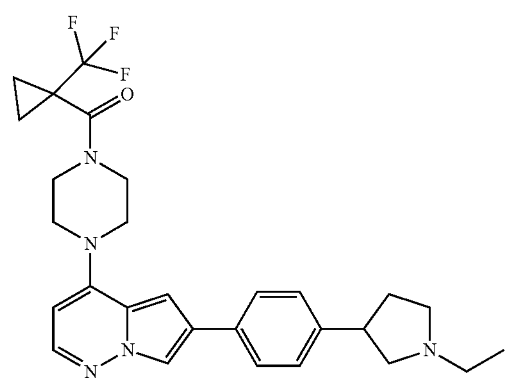 [SMILES: CCN1CCC(c2ccc(-c3cc4c(N5CCN(C(=O)C6(C(F)(F)F)CC6)CC5)ccnn4c3)cc2)C1] | 512 | 1H-NMR (400 MHz, 6d-DMSO) δ ppm 7.92 (d, 1H, J = 1.6 Hz), 7.86 (d, 1H, J = 5.6 Hz), 7.60 (d, 2H, J = 8.0 Hz), 7.33 (d, 2H, J = 8.0 Hz), 6.68 (d, 1H, J = 1.6 Hz), 5.87 (d, 1H, J = 5.6 Hz), 3.92-3.91 (m, 4H), 3.47-3.45 (m, 4H), 3.44-3.43 (m, 1H), 3.18-3.17 (m, 1H), 2.96-2.94 (m, 1H), 2.68-2.67 (m, 2H), 2.53-2.52 (m, 2H), 2.37-2.36 (m, 1H), 1.96-1.94 (m, 1H), 1.39-1.37 (m, 2H), 1.26-1.25 (m, 2H), 1.21-1.16 (m, 3H). |
| 411 | 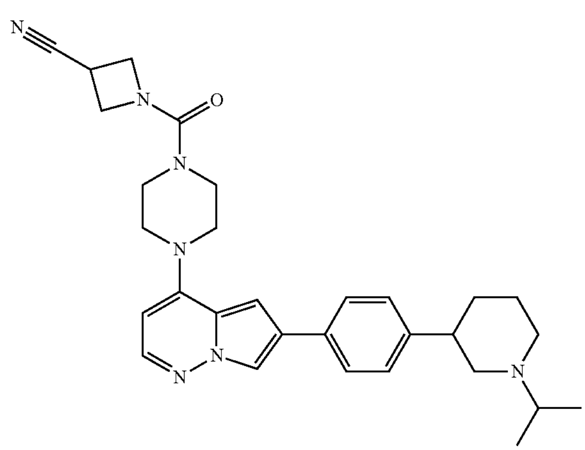 [SMILES: CC(C)N1CCCC(c2ccc(-c3cc4c(N5CCN(C(=O)N6CC(C#N)C6)CC5)ccnn4c3)cc2)C1] | 512 | 1H NMR (400 MHz, 6d-DMSO) δ ppm 8.26 (s, 1H), 8.15 (s, 1H), 7.89 (d, 1H, J = 5.2 Hz), 7.73 (d, 2H, J = 8.4 Hz), 7.27 (d, 2H, J = 8.4 Hz), 6.99 (s, 1H), 5.95 (d, 1H, J = 5.2 Hz), 4.24-4.19 (m, 2H), 4.11-4.01 (m, 2H), 3.77-3.74 (m, 1H), 2.89-2.84 (m, 4H), 2.41-2.27 (m, 2H), 1.85-1.41 (m, 4H), 1.03-1.00 (m, 6H). |

TABLE 1-continued

| # | Structure | LCMS (M + 1) | NMR |
|---|---|---|---|
| 412 | 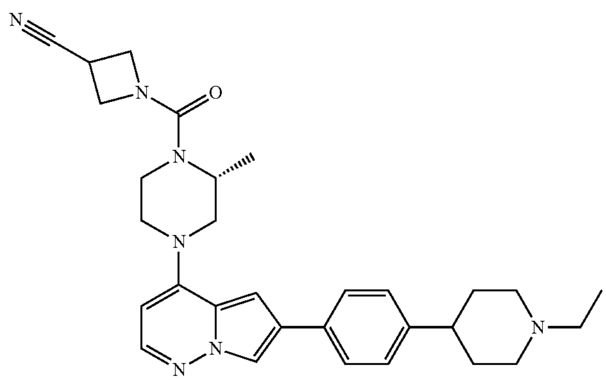 [SMILES: CCN1CCC(c2ccc(-c3cc4c(N5CCN(C(=O)N6CC(C#N)C6)[C@H](C)C5)ccnn4c3)cc2)CC1] | 512 | 1H-NMR (400 MHz, 6d-DMSO) δ ppm 8.24 (br. s., 1H), 8.15 (d, 1H, J = 1.6 Hz), 7.89 (d, 1H, J = 5.6 Hz), 7.70 (d, 2H, J = 8.0 Hz), 7.27 (d, 2H, J = 8.0 Hz), 6.90 (d, 1H, J = 1.6 Hz), 5.95 (d, 1H, J = 5.6 Hz), 4.23-4.20 (m, 2H), 4.19-4.16 (m, 1H), 4.10-4.06 (m, 2H), 3.86-3.83 (m, 2H), 3.75-3.74 (m, 1H), 3.64-3.63 (m, 1H), 3.35-3.34 (m, 2H), 3.16-3.03 (m, 2H), 3.01-2.99 (m, 1H), 2.39 (q, 2H, J = 7.2 Hz), 2.01-1.98 (m, 2H), 1.79-1.74 (m, 2H), 1.72-1.65 (m, 2H), 1.31 (d, 3H, J = 6.4 Hz), 1.04 (t, 3H, J = 7.2 Hz). |
| 413 | 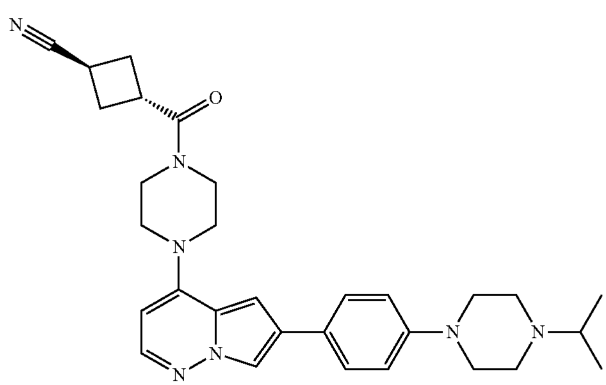 [SMILES: CC(C)N1CCN(c2ccc(-c3cc4c(N5CCN(C(=O)[C@H]6C[C@H](C#N)C6)CC5)ccnn4c3)cc2)CC1] | 512 | 1H-NMR (400 MHz, 6d-DMSO) δ ppm 8.06 (s, 1H), 7.86 (d, 1H, J = 5.6 Hz), 7.64 (d, 2H, J = 8.4 Hz), 6.93 (d, 2H, J = 8.4 Hz), 6.92-6.90 (m, 1H), 5.94 (d, 1H, J = 5.6 Hz), 3.70-3.60 (m, 3H), 3.55-3.48 (m, 2H), 3.45-3.38 (m, 4H), 3.30-3.22 (m, 1H), 3.17-3.08 (m, 4H), 2.70-2.60 (m, 1H), 2.58-2.54 (m, 6H), 2.48-2.42 (m, 2H), 1.00 (d, 6H, J = 6.4 Hz). |
| 414 | 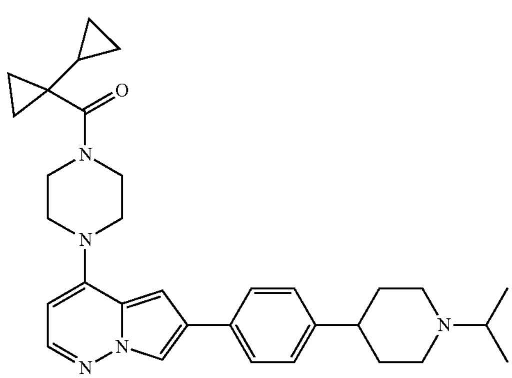 [SMILES: CC(C)N1CCC(c2ccc(-c3cc4c(N5CCN(C(=O)C6(C7CC7)CC6)CC5)ccnn4c3)cc2)CC1] | 512 | 1H-NMR (400 MHz, 6d-DMSO) δ ppm 8.15 (d, 1H, J = 1.6 Hz), 7.91 (d, 1H, J = 5.6 Hz), 7.74 (d, 2H, J = 8.4 Hz), 7.25 (d, 2H, J = 8.4 Hz), 7.00 (d, 1H, J = 1.6 Hz), 6.00 (d, 1H, J = 5.6 Hz), 3.90-3.60 (m, 4H), 3.55-3.45 (m, 4H), 2.91-2.86 (m, 2H), 2.71 (heptet, 1H, J = 6.8 Hz), 2.50-2.46 (m, 1H), 2.26-2.20 (m, 2H), 1.80-1.75 (m, 2H), 1.69-1.56 (m, 2H), 1.24-1.20 (m, 1H), 1.00 (d, 6H, J = 6.8 Hz), 0.78-0.74 (m, 2H), 0.53-0.50 (m, 2H), 0.48-0.43 (m, 2H), 0.15-0.11 (m, 2H). |
| 415 | 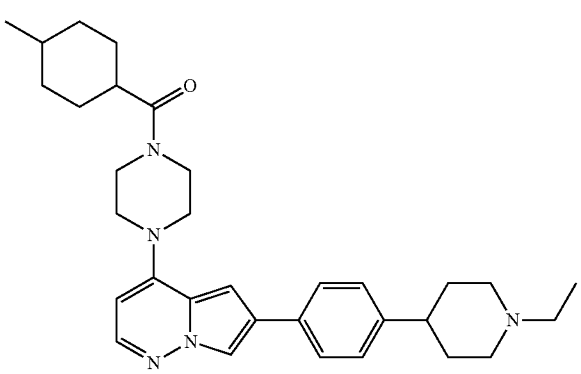 [SMILES: CCN1CCC(c2ccc(-c3cc4c(N5CCN(C(=O)C6CCC(C)CC6)CC5)ccnn4c3)cc2)CC1] | 515 | 1H NMR (400 MHz, Chloroform-d) δ 7.92 (d, J = 1.8 Hz, 1H), 7.85 (d, J = 5.3 Hz, 1H), 7.59 (d, J = 7.9 Hz, 2H), 7.28 (d, J = 8.0 Hz, 3H), 6.69 (d, J = 1.9 Hz, 1H), 5.85 (d, J = 5.4 Hz, 1H), 3.86 (d, J = 26.3 Hz, 5H), 3.49 (d, J = 31.7 Hz, 5H), 3.15 (s, 3H), 2.56 (td, J = 15.0, 5.8 Hz, 3H), 2.34 (ddd, J = 33.9, 16.5, 9.0 Hz, 1H), 2.17-2.06 (m, 7H), 1.89 (bs, 3H), 1.24 (d, J = 5.2 Hz, 3H), 1.16 (t, J = 7.1 Hz, 4H). |

TABLE 1-continued

| # | Structure | LCMS (M + 1) | NMR |
|---|---|---|---|
| 416 | 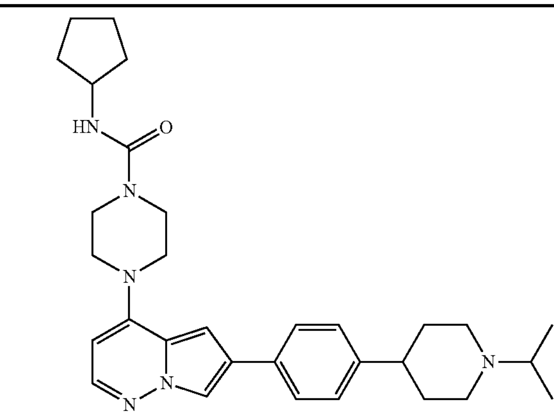 | 516 | 1H NMR (400 MHz, DMSO-d6) δ 8.14 (s, 1H), 7.88 (d, J = 5.4 Hz, 1H), 7.74 (d, J = 7.8 Hz, 2H), 7.28 (dd, J = 24.1, 7.9 Hz, 3H), 6.98 (s, 1H), 6.36 (d, J = 7.0 Hz, 1H), 5.97 (d, J = 5.5 Hz, 1H), 5.75 (s, 1H), 3.93 (p, J = 7.1 Hz, 1H), 3.60-3.40 (m, 10H), 2.11-1.72 (m, 2H), 1.63 (q, J = 6.6, 6.2 Hz, 2H), 1.44 (ddt, J = 27.1, 11.9, 5.6 Hz, 4H), 1.33-0.90 (m, 12H). |
| 417 | 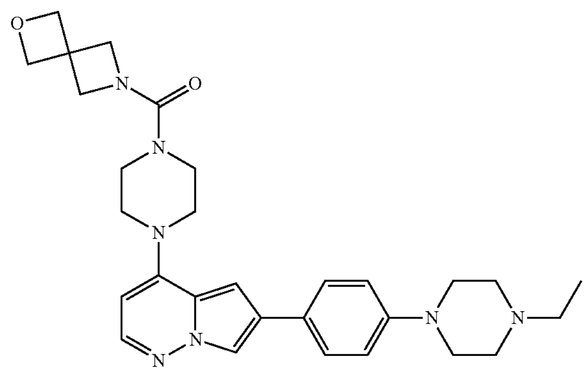 [SMILES: CCN1CCN(c2ccc(-c3cc4c(N5CCN(C(=O)N6CC7(COC7)C6)CC5)ccnn4c3)cc2)CC1] | 516 | 1H-NMR (400 MHz, 6d-DMSO) δ ppm 8.29 (br. s., 1H), 8.06 (d, 1H, J = 1.6 Hz), 7.87 (d, 1H, J = 5.2 Hz), 7.65 (d, 2H, J = 8.8 Hz), 6.95 (d, 2H, J = 8.8 Hz), 6.90 (d, 1H, J = 1.6 Hz), 5.94 (d, 1H, J = 5.2 Hz), 4.66-4.42 (m, 4H), 4.11-4.03 (m, 4H), 3.49-3.45 (m, 4H), 3.44-3.40 (m, 4H), 3.17-3.11 (m, 4H), 2.53-2.50 (m, 4H), 2.38 (q, 2H, J = 7.2 Hz), 1.04 (t, 3H, J = 7.2 Hz). |
| 418 | 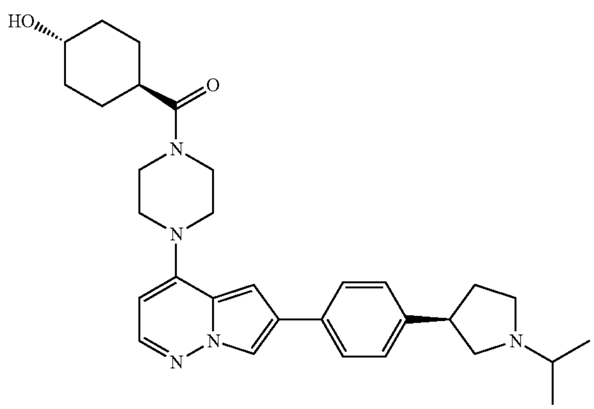 [SMILES: CC(C)N1CC[C@H](c2ccc(-c3cc4c(N5CCN(C(=O)[C@H]6CC[C@H](O)CC6)CC5)ccnn4c3)cc2)C1] | 516 | 1H-NMR (400 MHz, 6d-DMSO) δ ppm 8.14 (d, 1H, J = 1.6 Hz), 7.89 (d, 1H, J = 5.2 Hz), 7.72 (d, 2H, J = 8.0 Hz), 7.29 (d, 2H, J = 8.0 Hz), 7.01 (d, 1H, J = 1.6 Hz), 5.96 (d, 1H, J = 5.2 Hz), 4.58 (d, 1H, J = 4.0 Hz), 3.80-3.70 (m, 2H), 3.70-3.60 (m, 2H), 3.55-3.47 (m, 2H), 3.47-3.40 (m, 2H), 3.39-3.35 (m, 1H), 3.30-3.20 (m, 1H), 3.05-2.95 (m, 1H), 2.80-2.60 (m, 2H), 2.58-2.51 (m, 1H), 2.45-2.30 (m, 2H), 2.28-2.10 (m, 1H), 1.90-1.81 (m, 2H), 1.80-1.75 (m, 1H), 1.70-1.60 (m, 2H), 1.50-1.30 (m, 2H), 1.25-1.10 (m, 2H), 1.08-1.00 (m, 6H). |
| 419 | 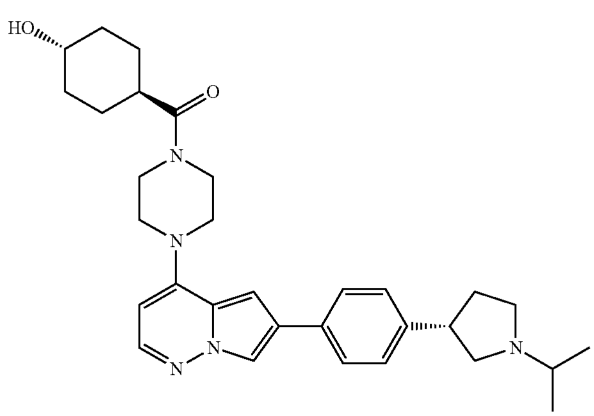 [SMILES: CC(C)N1CC[C@@H](c2ccc(-c3cc4c(N5CCN(C(=O)[C@H]6CC[C@H](O)CC6)CC5)ccnn4c3)cc2)C1] | 516 | 1H-NMR (400 MHz, CDCl3) δ ppm 7.93 (d, 1H, J = 2.0 Hz), 7.86 (d, 1H, J = 5.2 Hz), 7.61 (d, 2H, J = 8.0 Hz), 7.33 (d, 2H, J = 8.0 Hz), 6.69 (d, 1H, J = 1.6 Hz), 5.85 (d, 1H, J = 5.6 Hz), 3.92-3.82 (m, 2H), 3.80-3.70 (m, 2H), 3.69-3.65 (m, 1H), 3.56-3.45 (m, 3H), 3.44-3.41 (m, 2H), 3.40-3.38 (m, 1H), 3.24-3.12 (m, 1H), 2.99-2.87 (m, 1H), 2.80-2.66 (m, 2H), 2.53-2.36 (m, 2H), 2.14-2.00 (m, 4H), 1.90-1.78 (m, 2H), 1.74-1.71 (m, 1H), 1.39-1.34 (m, 2H), 1.27 (d, 6H, J = 6.4 Hz). |

TABLE 1-continued

| # | Structure | LCMS (M + 1) | NMR |
|---|---|---|---|
| 420 | 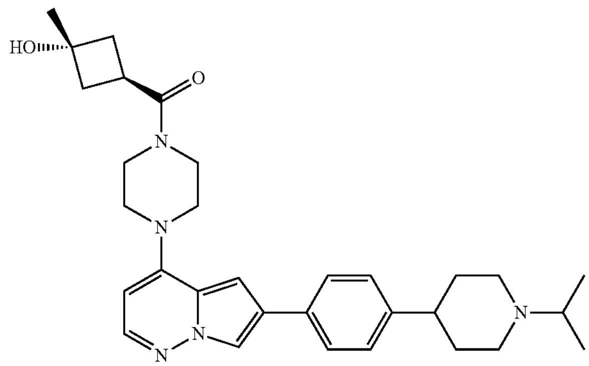 [SMILES: CC(C)N1CCC(c2ccc(-c3cc4c(N5CCN(C(=O)[C@H]6C[C@](C)(O)C6)CC5)ccnn4c3)cc2)CC1] | 517 | 1H NMR (400 MHz, Chloroform-d) δ 7.91 (d, J = 1.8 Hz, 1H), 7.84 (d, J = 5.3 Hz, 1H), 7.58 (d, J = 8.1 Hz, 2H), 7.28 (d, J = 8.2 Hz, 2H), 6.67 (d, J = 1.8 Hz, 1H), 5.83 (d, J = 5.3 Hz, 1H), 4.12 (q, J = 7.1 Hz, 2H), 3.87 (d, J = 5.6 Hz, 2H), 3.66 (s, 2H), 3.45 (s, 2H), 3.03 (d, J = 11.2 Hz, 2H), 2.98-2.86 (m, 1H), 2.78 (p, J = 6.5 Hz, 1H), 2.59-2.44 (m, 2H), 2.44-2.35 (m, 4H), 2.27 (t, J = 11.0 Hz, 2H), 1.94-1.77 (m, 4H), 1.25 (t, J = 7.1 Hz, 3H), 1.10 (d, J = 6.6 Hz, 6H). |
| 421 | 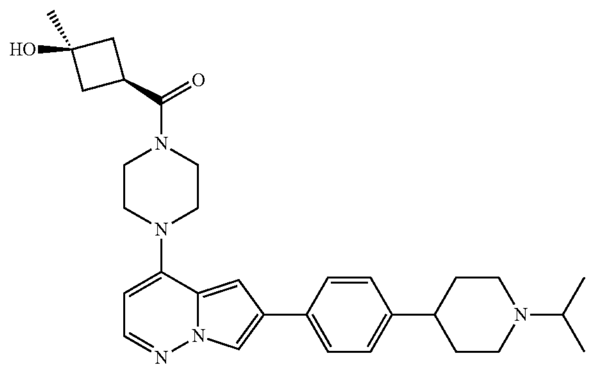 [SMILES: CC(C)N1CCC(c2ccc(-c3cc4c(N5CCN(C(=O)[C@H]6C[C@@](C)(O)C6)CC5)ccnn4c3)cc2)CC1] | 517 | 1H NMR (400 MHz, Chloroform-d) δ 7.91 (d, J = 1.8 Hz, 1H), 7.84 (d, J = 5.3 Hz, 1H), 7.61-7.49 (m, 2H), 7.29 (d, J = 8.2 Hz, 2H), 6.67 (d, J = 1.9 Hz, 1H), 5.83 (d, J = 5.4 Hz, 1H), 4.11 (q, J = 7.1 Hz, 1H), 3.87 (t, J = 5.1 Hz, 2H), 3.73-3.62 (m, 3H), 3.51-3.36 (m, 2H), 3.18 (s, 2H), 2.93 (p, J = 8.1 Hz, 1H), 2.58 (s, 2H), 2.52-2.29 (m, 5H), 1.94 (d, J = 12.9 Hz, 2H), 1.41 (s, 3H), 1.24 (dt, J = 10.8, 6.8 Hz, 10H). |
| 422 | 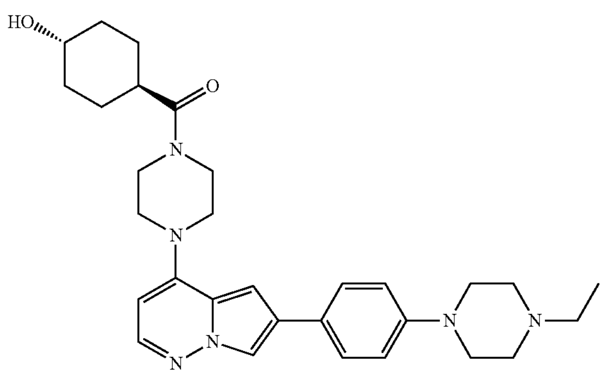 [SMILES: CCN1CCN(c2ccc(-c3cc4c(N5CCN(C(=O)[C@H]6CC[C@H](O)CC6)CC5)ccnn4c3)cc2)CC1] | 517 | 1H-NMR (400 MHz, 6d-DMSO) δ ppm 8.06 (d, 1H, J = 1.6 Hz), 7.86 (d, 1H, J = 6.0 Hz), 7.64 (d, 2H, J = 8.8 Hz), 6.95 (d, 2H, J = 8.8 Hz), 6.93 (d, 1H, J = 1.6 Hz), 5.94 (d, 1H, J = 5.6 Hz), 4.57 (d, 1H, J = 4.4 Hz), 3.73-3.70 (m, 2H), 3.70-3.64 (m, 2H), 3.48-3.45 (m, 2H), 3.44-3.38 (m, 2H), 3.17-3.13 (m, 4H), 2.53-2.58 (m, 4H), 1.86-1.83 (m, 2H), 1.70-1.66 (m, 2H), 1.56-1.53 (m, 1H), 1.43-1.16 (m, 5H), 1.06-1.04 (m, 3H), 0.93 (t, 3H, J = 7.2 Hz). |
| 423 | 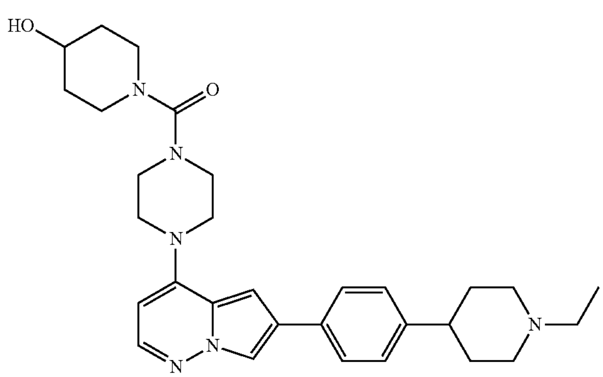 [SMILES: CCN1CCC(c2ccc(-c3cc4c(N5CCN(C(=O)N6CCC(O)CC6)CC5)ccnn4c3)cc2)CC1] | 517 | 1H-NMR (400 MHz, 6d-DMSO) δ ppm 8.13 (d, 1H, J = 1.2 Hz), 7.88 (d, 1H, J = 5.6 Hz), 7.72 (d, 2H, J = 8.0 Hz), 7.25 (d, 2H, J = 8.0 Hz), 6.99 (d, 1H, J = 1.2 Hz), 5.96 (d, 1H, J = 5.6 Hz), 4.72 (d, 1H, J = 3.6 Hz), 3.65-3.60 (m, 1H), 3.52-3.49 (m, 2H), 3.49-3.43 (m, 4H), 3.40-3.35 (m, 4H), 3.40-3.24 (m, 2H), 3.08-2.98 (m, 2H), 2.93-2.87 (m, 2H), 2.41 (q, 2H, J = 7.2 Hz), 2.07-2.01 (m, 2H), 1.78-1.66 (m, 6H), 1.33 (q, 2H, J = 10.4 Hz), 1.03 (t, 3H, J = 7.2 Hz). |

TABLE 1-continued

| # | Structure | LCMS (M + 1) | NMR |
|---|---|---|---|
| 424 | 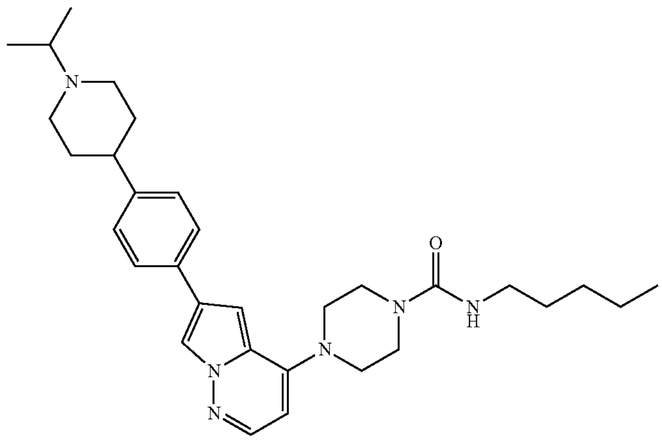 [SMILES: CCCCCNC(=O)N1CCN(c2ccnn3cc(-c4ccc(C5CCN(C(C)C)CC5)cc4)cc23)CC1] | 518 | 1H NMR (400 MHz, DMSO-d6) δ 8.21 (s, 1H), 8.12 (d, J = 1.7 Hz, 1H), 7.88 (d, J = 5.4 Hz, 1H), 7.76-7.65 (m, 2H), 7.29-7.20 (m, 2H), 6.98 (d, J = 1.9 Hz, 1H), 6.57 (t, J = 5.5 Hz, 1H), 5.97 (d, J = 5.5 Hz, 1H), 3.51 (dd, J = 6.9, 3.3 Hz, 4H), 3.42 (dd, J = 6.7, 3.5 Hz, 4H), 3.03 (q, J = 6.6 Hz, 2H), 2.94 (d, J = 11.0 Hz, 2H), 2.79 (p, J = 6.6 Hz, 1H), 2.30 (dd, J = 12.6, 10.0 Hz, 2H), 1.78 (d, J = 12.5 Hz, 2H), 1.66 (tt, J = 12.8, 6.4 Hz, 2H), 1.42 (p, J = 7.3 Hz, 2H), 1.26 (dtd, J = 14.3, 8.3, 7.8, 2.9 Hz, 4H), 1.02 (d, J = 6.5 Hz, 6H), 0.86 (t, J = 6.9 Hz, 3H). |
| 425 | 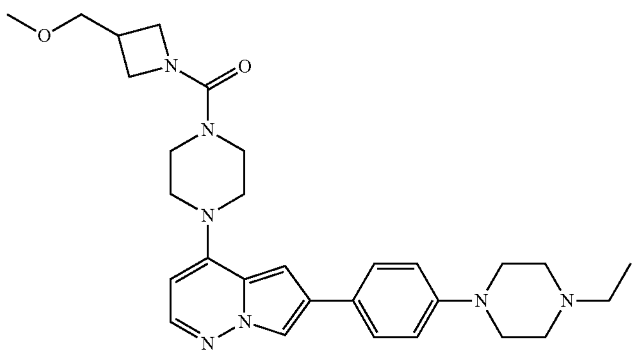 [SMILES: CCN1CCN(c2ccc(-c3cc4c(N5CCN(C(=O)N6CC(COC)C6)CC5)ccnn4c3)cc2)CC1] | 518 | 1H-NMR (400 MHz, 6d-DMSO) δ ppm 8.15 (s, 1H), 8.08 (d, 1H, J = 2.0 Hz), 7.86 (d, 1H, J = 5.2 Hz), 7.67 (d, 2H, J = 8.8 Hz), 6.99 (d, 2H, J = 8.8 Hz), 6.92 (d, 1H, J = 2.0 Hz), 5.94 (d, 1H, J = 5.2 Hz), 3.97 (t, 3H, J = 8.0 Hz), 3.68-3.64 (m, 4H), 3.47-3.46 (m, 2H), 3.45-3.43 (m, 5H), 3.29-3.27 (m, 2H), 3.26 (s, 3H), 2.93-2.91 (m, 4H), 2.79-2.76 (m, 4H), 1.15 (t, 3H, J = 7.2 Hz). |
| 426 | 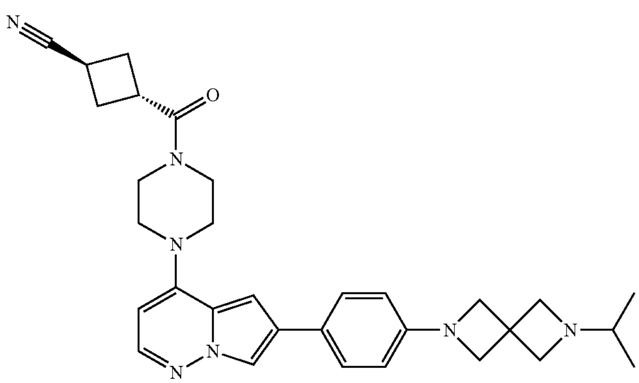 [SMILES: CC(C)N1CC2(CN(c3ccc(-c4cc5c(N6CCN(C(=O)[C@H]7C[C@H](C#N)C7)CC6)ccnn5c4)cc3)C2)C1] | 524 | 1H-NMR (400 MHz, 6d-DMSO) δ ppm 8.03 (d, 1H, J = 1.6 Hz), 7.86 (d, 1H, J = 5.6 Hz), 7.61 (d, 2H, J = 8.4 Hz), 6.89 (d, 1H, J = 1.6 Hz), 6.45 (d, 2H, J = 8.4 Hz), 5.95 (d, 2H, J = 5.6 Hz), 3.90-3.86 (m, 4H), 3.72-3.68 (m, 2H), 3.68-3.65 (m, 1H), 3.54-3.51 (m, 2H), 3.42-3.41 (m, 4H), 3.30-3.24 (m, 4H), 2.65-2.60 (m, 2H), 2.52-2.50 (m, 1H), 2.50-2.48 (m, 2H), 0.90-0.85 (m, 6H). |
| 427 | 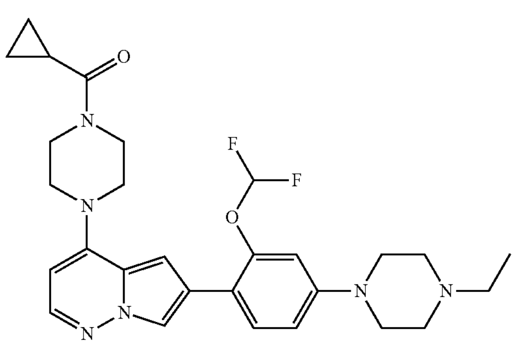 [SMILES: CCN1CCN(c2ccc(-c3cc4c(N5CCN(C(=O)C6CC6)CC5)ccnn4c3)c(OC(F)F)c2)CC1] | 525 | 1H-NMR (400 MHz, 6d-DMSO) δ ppm 7.98 (s, 1H), 7.88 (d, 1H, J = 3.6 Hz), 7.73 (d, 1H, J = 8.4 Hz), 7.26 (t, 1H, J = 74.4 Hz), 6.95 (s, 1H), 6.88 (d, 1H, J = 6.8 Hz), 6.73 (s, 1H), 5.96 (d, 1H, J = 4.4 Hz), 3.91-3.90 (m, 2H), 3.69-3.67 (m, 2H), 3.53-3.45 (m, 4H), 3.23-3.19 (m, 4H), 2.55-2.51 (m, 4H), 2.36 (q, 2H, J = 7.2 Hz), 2.01-2.00 (m, 1H), 1.03 (t, 3H, J = 7.2 Hz), 0.76-0.74 (m, 4H). |

TABLE 1-continued

| # | Structure | LCMS (M + 1) | NMR |
|---|---|---|---|
| 428 | 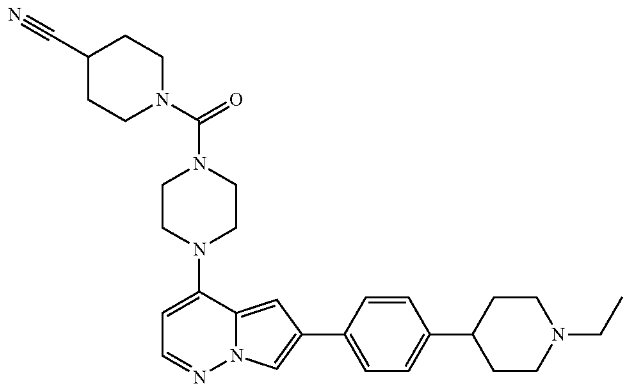 [SMILES: CCN1CCC(c2ccc(-c3cc4c(N5CCN(C(=O)N6CCC(C#N)CC6)CC5)ccnn4c3)cc2)CC1] | 526 | 1H-NMR (400 MHz, 6d-DMSO) δ ppm 8.14 (d, 1H, J = 1.6 Hz), 7.89 (d, 1H, J = 5.6 Hz), 7.73 (d, 2H, J = 8.4 Hz), 7.25 (d, 2H, J = 8.4 Hz), 6.99 (d, 1H, J = 1.6 Hz), 5.96 (d, 1H, J = 5.6 Hz), 3.45-3.44 (m, 4H), 3.39-3.37 (m, 4H), 3.35-3.36 (m, 3H), 3.15-3.04 (m, 6H), 2.58-2.54 (m, 1H), 2.17-2.10 (m, 2H), 1.90-1.86 (m, 2H), 1.82-1.77 (m, 2H), 1.74-1.66 (m, 4H), 1.06 (t, 3H, J = 7.2 Hz). |
| 429 | 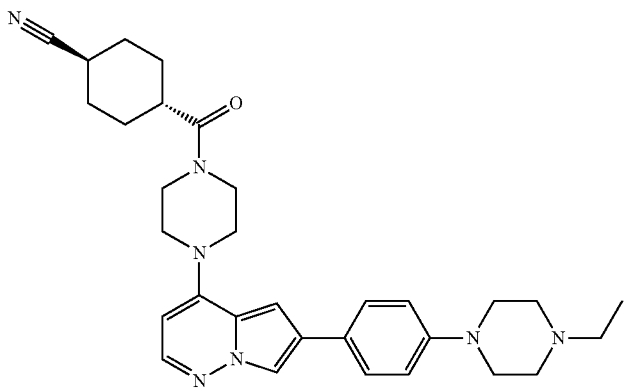 [SMILES: CCN1CCN(c2ccc(-c3cc4c(N5CCN(C(=O)[C@H]6CC[C@H](C#N)CC6)CC5)ccnn4c3)cc2)CC1] | 526 | 1H-NMR (400 MHz, 6d-DMSO) δ ppm 8.06 (s, 1H), 7.86 (d, 1H, J = 5.2 Hz), 7.64 (d, 2H, J = 8.4 Hz), 6.94 (d, 2H, J = 8.4 Hz), 6.93 (s, 1H), 5.94 (d, 1H, J = 5.2 Hz), 3.75-3.70 (m, 2H), 3.69-3.65 (m, 2H), 3.50-3.45 (m, 2H), 3.44-3.40 (m, 2H), 3.15-3.13 (m, 4H), 2.73-2.67 (m, 2H), 2.50-2.49 (m, 4H), 2.37 (q, 2H, J = 6.8 Hz), 2.05-2.02 (m, 2H), 1.73-1.70 (m, 2H), 1.63-1.53 (m, 2H), 1.44-1.36 (m, 2H), 1.03 (t, 3H, J = 6.8 Hz). |
| 430 | 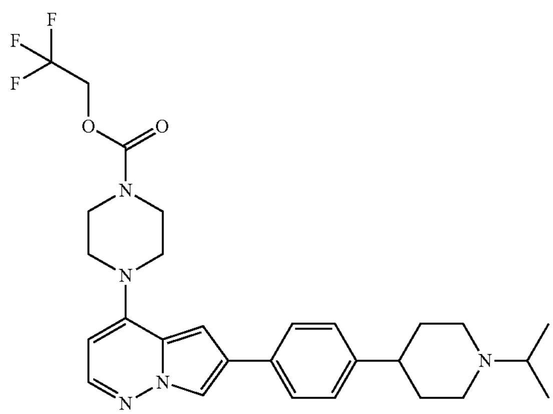 [SMILES: CC(C)N1CCC(c2ccc(-c3cc4c(N5CCN(C(=O)OCC(F)(F)F)CC5)ccnn4c3)cc2)CC1] | 531 | 1H NMR (400 MHz, DMSO-d6) δ 8.13 (d, J = 1.8 Hz, 1H), 7.89 (d, J = 5.4 Hz, 1H), 7.77-7.64 (m, 2H), 7.24 (d, J = 8.1 Hz, 2H), 7.00 (d, J = 1.9 Hz, 1H), 5.98 (d, J = 5.5 Hz, 1H), 4.75 (q, J = 9.1 Hz, 2H), 3.65 (s, 4H), 3.58-3.39 (m, 4H), 2.88 (d, J = 10.9 Hz, 3H), 2.70 (p, J = 6.7 Hz, 1H), 2.21 (t, J = 11.1 Hz, 2H), 1.76 (d, J = 12.4 Hz, 2H), 1.62 (tt, J = 12.6, 6.3 Hz, 2H), 0.99 (d, J = 6.5 Hz, 6H). |
| 431 | 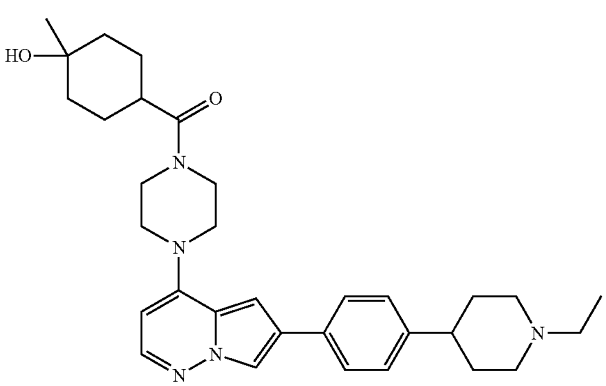 [SMILES: CCN1CCC(c2ccc(-c3cc4c(N5CCN(C(=O)C6CCC(C)(O)CC6)CC5)ccnn4c3)cc2)CC1] | 531 | 1H NMR (400 MHz, Chloroform-d) δ 7.92 (d, J = 1.6 Hz, 1H), 7.84 (d, J = 5.3 Hz, 1H), 7.59 (d, J = 7.9 Hz, 2H), 7.28 (d, J = 8.0 Hz, 2H), 6.69 (d, J = 1.3 Hz, 1H), 5.84 (d, J = 5.4 Hz, 1H), 3.87 (s, 2H), 3.75 (s, 2H), 3.47 (d, J = 25.7 Hz, 5H), 3.15 (s, 2H), 2.54 (d, J = 9.7 Hz, 5H), 2.08 (s, 3H), 1.91 (q, J = 20.9, 17.1 Hz, 3H), 1.81-1.72 (m, 1H), 1.66 (bs, 6H), 1.58-1.39 (m, 1H), 1.31 (s, 2H), 1.24 (d, J = 3.8 Hz, 4H), 1.16 (s, 1H). |

TABLE 1-continued

| # | Structure | LCMS (M + 1) | NMR |
|---|---|---|---|
| 432 | 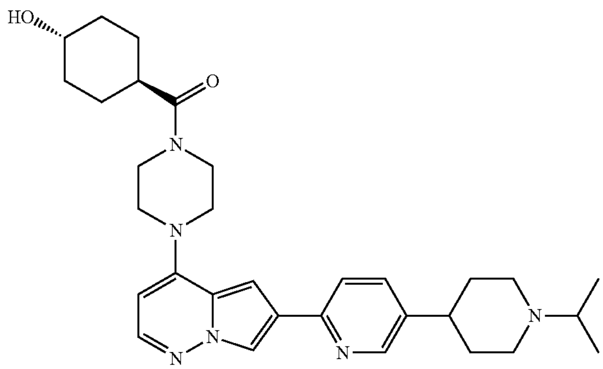 [SMILES: CC(C)N1CCC(c2ccc(-c3cc4c(N5CCN(C(=O)[C@H]6CC[C@H](O)CC6)CC5)ccnn4c3)nc2)CC1] | 531 | 1H-NMR (400 MHz, 6d-DMSO) δ ppm 8.44 (d, 1H, J = 2.0 Hz), 8.24 (d, 1H, J = 1.2 Hz), 7.91 (d, 1H, J = 5.6 Hz), 7.85 (d, 1H, J = 8.0 Hz), 7.67 (dd, 1H, J = 8.4, 2.0 Hz), 7.16 (d, 1H, J = 2.0 Hz), 5.96 (d, 1H, J = 5.6 Hz), 4.58 (d, 1H, J = 4.0 Hz), 3.76-3.72 (m, 2H), 3.68-3.64 (m, 2H), 3.53-3.48 (m, 2H), 3.45-3.40 (m, 2H), 2.93-2.88 (m, 2H), 2.76-2.69 (m, 1H), 2.57-2.54 (m, 1H), 2.25-2.20 (m, 2H), 1.86-1.81 (m, 2H), 1.80-1.72 (m, 2H), 1.70-1.60 (m, 5H), 1.44-1.34 (m, 2H), 1.25-1.14 (m, 2H), 0.99 (d, 6H, J = 6.8 Hz). |
| 433 | 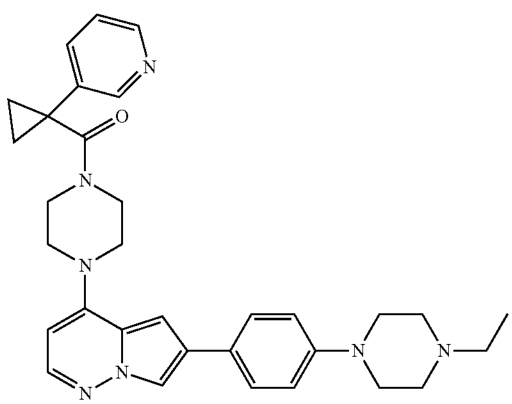 [SMILES: CCN1CCN(c2ccc(-c3cc4c(N5CCN(C(=O)C6(c7cccnc7)CC6)CC5)ccnn4c3)cc2)CC1] | 536 | 1H-NMR (400 MHz, 6d-DMSO) δ ppm 8.43 (d, 1H, J = 2.4 Hz), 8.43 (s, 1H), 8.03 (d, 1H, J = 1.2 Hz), 7.83 (d, 1H, J = 5.6 Hz), 7.62 (d, 2H, = 8.4 Hz), 7.61-7.58 (m, 1H), 7.36 (dd, 1H, J = 8.4, 5.2 Hz), 6.93 (d, 2H, J = 8.4 Hz), 6.88 (d, 1H, J = 1.2 Hz), 5.90 (d, 1H, J = 5.6 Hz), 3.69-3.67 (m, 4H), .42-3.30 (m, 8H), 3.16-3.13 (m, 4H), 2.37 (q, 2H, J = 6.4 Hz), 1.42-1.40 (m, 2H), 1.31-1.28 (m, 2H), 1.04 (t, 3H, J = 7.2 Hz). |
| 434 | 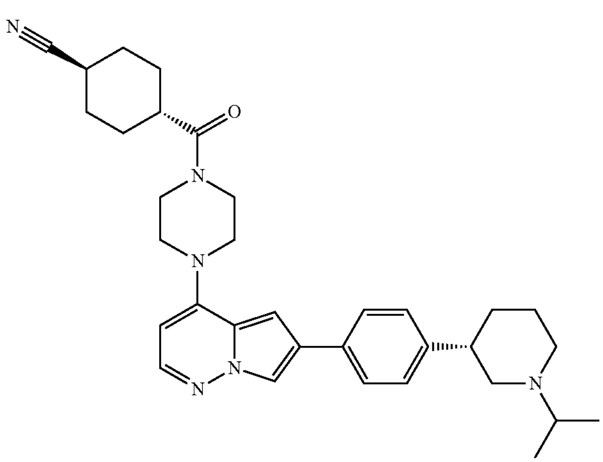 [SMILES: CC(C)N1CCC[C@@H](c2ccc(-c3cc4c(N5CCN(C(=O)[C@H]6CC[C@H](C#N)CC6)CC5)ccnn4c3)cc2)C1] | 539 | 1H-NMR (400 MHz, 6d-DMSO) δ ppm 8.15 (d, 1H, J = 1.2 Hz), 7.90 (d, 1H, J = 5.6 Hz), 7.72 (d, 2H, J = 8.4 Hz), 7.28 (d, 2H, J = 8.4 Hz), 7.01 (d, 1H, J = 1.2 Hz), 5.98 (d, 1H, J = 5.6 Hz), 3.76-3.72 (m, 2H), 3.72-3.68 (m, 2H), 3.51-3.47 (m, 2H), 3.45-3.40 (m, 2H), 2.79-2.75 (m, 2H), 2.72-2.69 (m, 4H), 2.18-2.15 (m, 2H), 2.04-2.03 (m, 2H), 1.82-1.81 (m, 1H), 1.75-1.72 (m, 3H), 1.61-1.57 (m, 3H), 1.43-1.40 (m, 3H), 0.99-0.97 (m, 6H). |

TABLE 1-continued

| # | Structure | LCMS (M + 1) | NMR |
|---|-----------|--------------|-----|
| 435 | 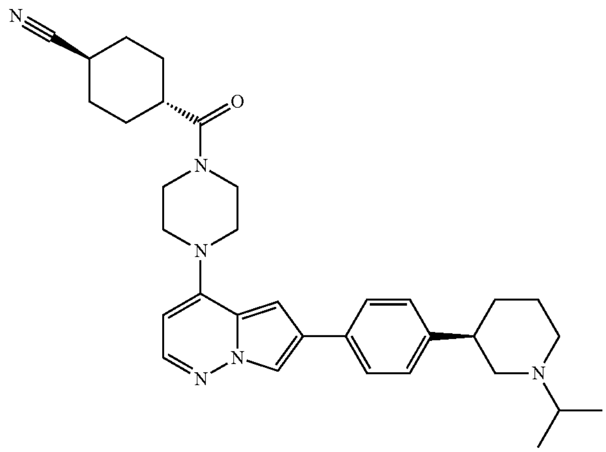 [SMILES: CC(C)N1CCC[C@H](c2ccc(-c3cc4c(N5CCN(C(=O)[C@H]6CC[C@H](C#N)CC6)CC5)ccnn4c3)cc2)C1] | 539 | 1H-NMR (400 MHz, 6d-DMSO) δ ppm 8.15 (d, J = 1.2 Hz), 7.90 (d, 1H, J = 5.2 Hz), 7.72 (d, 2H, J = 8.4 Hz), 7.28 (d, 2H, J = 8.4 Hz), 7.01 (d, 1H, J = 1.2 Hz), 5.98 (d, 1H, J = 5.6 Hz), 3.77-3.72 (m, 2H), 3.70-3.65 (m, 2H), 3.50-3.45 (m, 2H), 3.45-3.40 (m, 2H), 2.82-2.79 (m, 2H), 2.75-2.67 (m, 4H), 2.18-2.15 (m, 2H), 2.07-2.06 (m, 2H), 1.84-1.83 (m, 1H), 1.80-1.75 (m, 3H), 1.60-1.54 (m, 3H), 1.46-1.40 (m, 3H), 0.99-0.96 (m, 6H). |
| 436 | 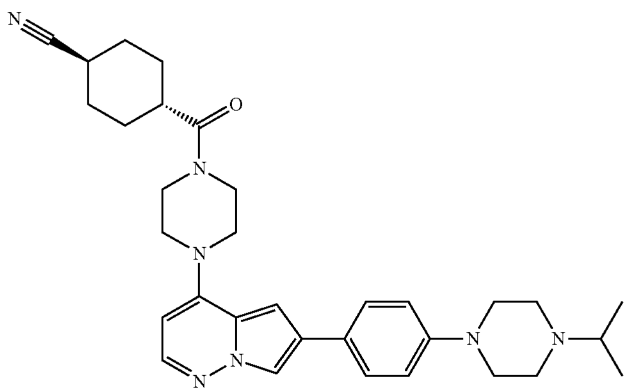 | 540 | 1H-NMR (400 MHz, 6d-DMSO) δ ppm 8.13 (s, 0.3H), 8.09 (d, 1H, J = 1.6 Hz), 7.87 (d, 1H, J = 5.6 Hz), 7.68 (d, 2H, J = 8.4 Hz), 7.00 (d, 2H, J = 8.4 Hz), 6.94 (d, 1H, J = 1.2 Hz), 6.54 (s, 0.4H), 5.96 (d, 1H, J = 5.6 Hz), 3.80-3.70 (m, 2H), 3.70-3.60 (m, 2H), 3.56-3.48 (m, 2H), 3.45-3.38 (m, 2H), 3.35-3.20 (m, 8H), 2.80-2.60 (m, 2H), 2.10-2.00 (m, 2H), 1.78-1.68 (m, 2H), 1.66-1.50 (m, 2H), 1.48-1.34 (m, 2H), 1.24-1.10 (m, 6H). |
| 437 | 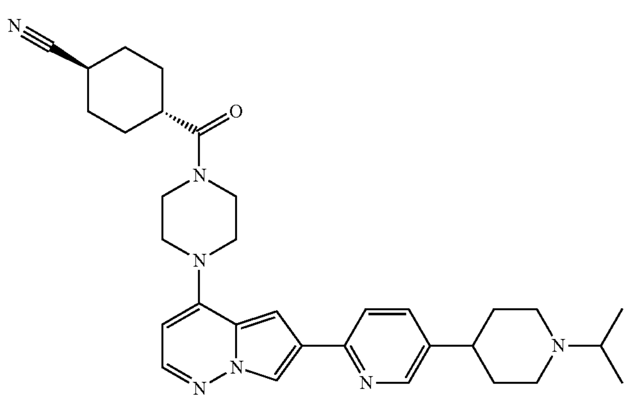 [SMILES: CC(C)N1CCN(c2ccc(-c3cc4c(N5CCN(C(=O)[C@H]6CC[C@H](C#N)CC6)CC5)ccnn4c3)cc2)CC1] | 540 | 1H-NMR (400 MHz, 6d-DMSO) δ ppm 8.45 (s, 1H), 8.24 (s, 1H), 7.91 (d, 1H, J = 6.0 Hz), 7.85 (d, 1H, J = 8.0 Hz), 7.68 (d, 1H, J = 8.0 Hz), 7.16 (s, 1H), 5.97 (d, 1H, J = 5.6 Hz), 3.76-3.73 (m, 2H), 3.69-3.63 (m, 2H), 3.53-3.48 (m, 2H), 3.46-3.42 (m, 2H), 2.90-2.87 (m, 2H), 2.74-2.68 (m, 3H), 2.57-2.49 (m, 1H), 2.24-2.19 (m, 2H), 2.05-2.02 (m, 2H), 1.78-1.70 (m, 4H), 1.70-1.57 (m, 4H), 1.45-1.39 (m, 2H), 0.98 (d, 6H, J = 6.8 Hz). |

TABLE 1-continued

| # | Structure | LCMS (M + 1) | NMR |
|---|---|---|---|
| 438 | 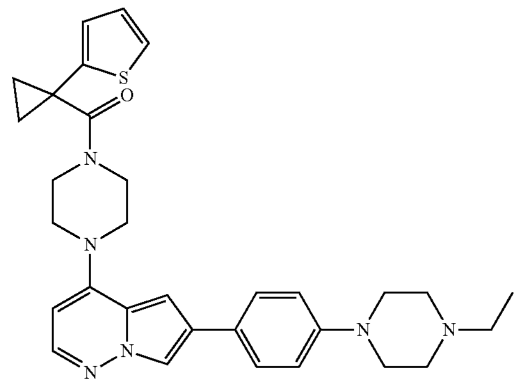 [SMILES: CCN1CCN(c2ccc(-c3cc4c(N5CCN(C(=O)C6(c7cccs7)CC6)CC5)ccnn4c3)cc2)CC1] | 541 | 1H-NMR (400 MHz, 6d-DMSO) δ ppm 8.04 (d, 1H, J = 1.6 Hz), 7.83 (d, 1H, J = 5.6 Hz), 7.63 (d, 2H, J = 9.2 Hz), 7.35 (dd, 1H, J = 4.8, 2.4 Hz), 6.93 (d, 2H, J = 8.4 Hz), 6.96-6.91 (m, 3H), 5.91 (d, 1H, J = 5.6 Hz), 3.73-3.55 (m, 4H), 3.41-3.18 (m, 8H), 3.15-3.13 (m, 4H), 2.36 (q, 2H, J = 7.2 Hz), 1.46-1.43 (m, 2H), 1.21-1.18 (m, 2H), 1.03 (t, 3H, J = 7.2 Hz). |
| 439 | 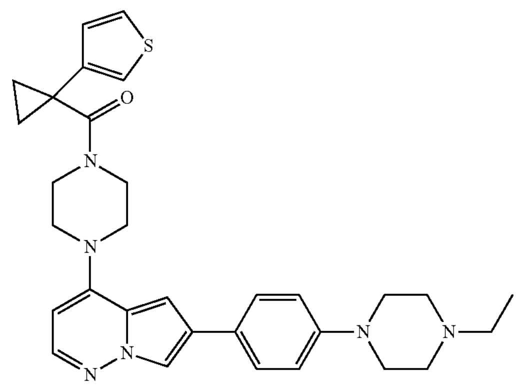 [SMILES: CCN1CCN(c2ccc(-c3cc4c(N5CCN(C(=O)C6(c7ccsc7)CC6)CC5)ccnn4c3)cc2)CC1] | 541 | 1H-NMR (400 MHz, 6d-DMSO) δ ppm 8.04 (d, 1H, J = 2.0 Hz), 7.84 (d, 1H, J = 5.6 Hz), 7.63 (d, 2H, J = 8.8 Hz), 7.50 (dd, 1H, J = 5.2, 2.8 Hz), 7.23 (dd, 1H, J = 2.8, 1.2 Hz), 6.94-6.90 (m, 4H), 5.91 (d, 1H, J = 5.6 Hz), 3.72-3.69 (m, 4H), 3.42-3.30 (m, 8H), 3.16-3.13 (m, 4H), 2.37 (q, 2H, J = 7.2 Hz), 1.35-1.32 (m, 2H), 1.17-1.15 (m, 2H), 1.03 (t, 3H, J = 7.2 Hz). |
| 440 | 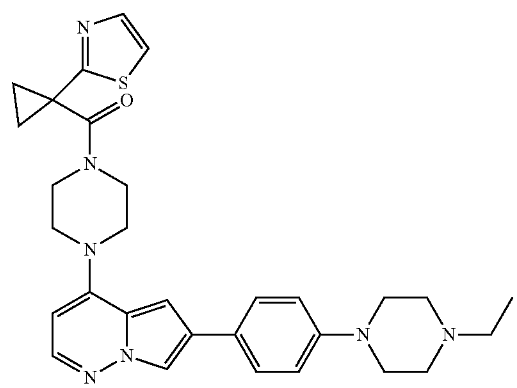 [SMILES: CCN1CCN(c2ccc(-c3cc4c(N5CCN(C(=O)C6(c7nccs7)CC6)CC5)ccnn4c3)cc2)CC1] | 542 | 1H-NMR (400 MHz, 6d-DMSO) δ ppm 8.04 (d, 1H, J = 1.6 Hz), 7.84 (d, 1H, J = 5.2 Hz), 7.69 (d, 1H, J = 3.2 Hz), 7.64 (d, 2H, J = 8.8 Hz), 7.61 (d, 1H, J = 3.2 Hz), 6.93 (d, 2H, J = 8.8 Hz), 6.92 (d, 1H, J = 1.6 Hz), 5.93 (d, 1H, J = 5.2 Hz), 3.80-3.60 (m, 4H), 3.50-3.36 (m, 4H), 3.30-3.28 (m, 4H), 3.20-3.10 (m, 4H), 2.36 (q, 2H, J = 7.2 Hz), 1.60-1.55 (m, 2H), 1.50-1.40 (m, 2H), 1.03 (t, 3H, J = 7.2 Hz). |
| 441 | 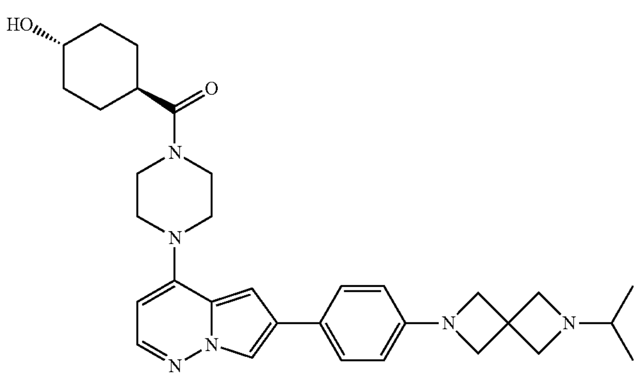 [SMILES: CC(C)N1CC2(CN(c3ccc(-c4cc5c(N6CCN(C(=O)[C@H]7CC[C@H](O)CC7)CC6)ccnn5c4)cc3)C2)C1] | 543 | 1H-NMR (400 MHz, 6d-DMSO) δ ppm 8.25 (br s, 1H), 8.04 (d, 1H, J = 1.6 Hz), 7.87 (d, 1H, J = 5.6 Hz), 7.62 (d, 2H, J = 8.4 Hz), 6.90 (d, 1H, J = 1.6 Hz), 6.45 (d, 2H, J = 8.4 Hz), 5.95 (d, 2H, J = 5.6 Hz), 3.88 (s, 4H), 3.75-3.71 (m, 2H), 3.69-3.64 (m, 2H), 3.52-3.48 (m, 2H), 3.48-3.45 (m, 4H), 3.45-3.33 (m, 3H), 2.56-2.52 (m, 1H), 2.50-2.41 (m, 1H), 1.88-1.82 (m, 2H), 1.72-1.65 (m, 2H), 1.43-1.33 (m, 2H), 1.26-1.18 (m, 2H), 0.87 (d, 6H, J = 6.4 Hz). |

TABLE 1-continued

| # | Structure | LCMS (M + 1) | NMR |
|---|---|---|---|
| 442 | 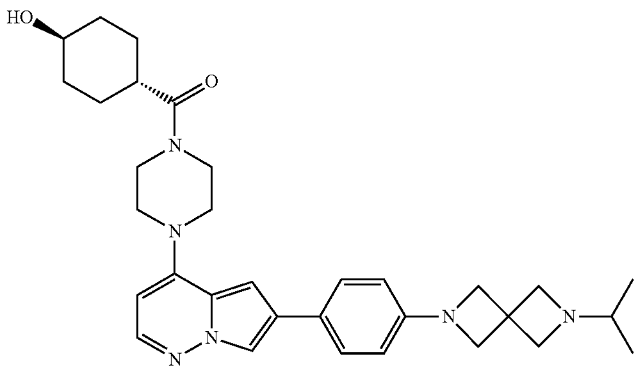 [SMILES: CC(C)N1CC2(CN(c3ccc(-c4cc5c(N6CCN(C(=O)[C@H]7CC[C@H](O)CC7)CC6)ccnn5c4)cc3)C2)C1] | 552 | 1H-NMR (400 MHz, 6d-DMSO) δ ppm 8.34 (s, 1H), 8.03 (d, 1H, J = 1.6 Hz), 7.87 (d, 1H, J = 5.6 Hz), 7.61 (d, 2H, J = 8.8 Hz), 6.90 (d, 2H, J = 1.6 Hz), 6.44 (d, 1H, J = 8.8 Hz), 5.95 (d, 1H, J = 5.6 Hz), 3.86 (s, 4H), 3.78-3.70 (m, 2H), 3.69-3.62 (m, 2H), 3.50-3.45 (m, 2H), 3.44-3.38 (m, 2H), 3.25 (s, 4H), 2.76-2.66 (m, 2H), 2.26-2.20 (m, 1H), 2.10-2.01 (m, 2H), 1.75-1.71 (m, 2H), 1.62-1.55 (m, 2H), 1.46-1.40 (m, 2H), 1.10-1.07 (m, 6H). |
| 443 | 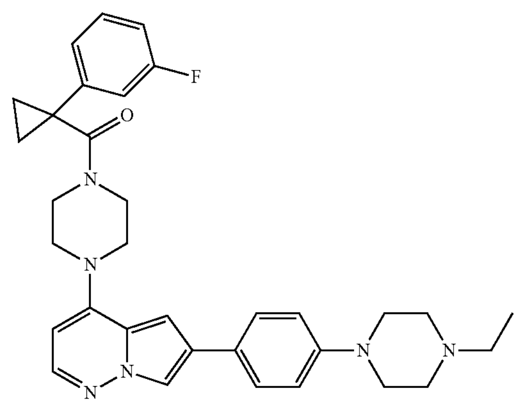 | 553 | 1H-NMR (400 MHz, 6d-DMSO) δ ppm 8.03 (d, 1H, J = 1.2 Hz), 7.83 (d, 1H, J = 5.6 Hz), 7.62 (d, 2H, J = 8.8 Hz), 7.37 (dd, 1H, J = 14.4, 8.0 Hz), 7.07-7.02 (m, 2H), 6.99-6.95 (m, 1H), 6.92 (d, 2H, J = 8.8 Hz), 6.89 (d, 1H, J = 1.2 Hz), 5.90 (d, 1H, J = 5.2 Hz), 3.73-3.55 (m, 4H), 3.41-3.18 (m, 8H), 3.14 (t, 4H, J = 4.4 Hz), 2.36 (q, 2H, J = 7.2 Hz), 1.41-1.37 (m, 2H), 1.27-1.23 (m, 2H), 1.03 (t, 3H, J = 7.2 Hz). |
| 444 | 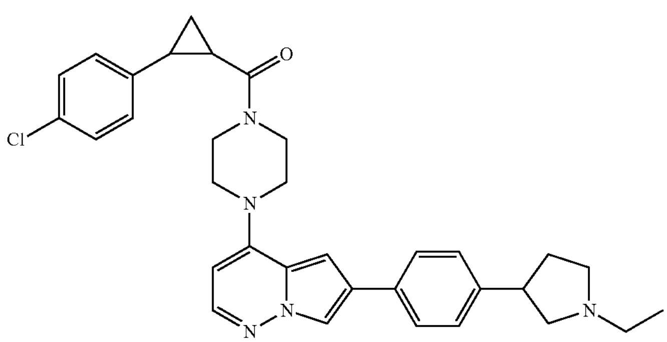 [SMILES: CCN1CCC(c2ccc(-c3cc4c(N5CCN(C(=O)C6CC6c6ccc(Cl)cc6)CC5)ccnn4c3)cc2)C1] | 554 | 1H NMR (400 MHz, 6d-DMSO) δ ppm 8.24 (s, 1H), 8.15 (d, 1H, J = 1.6 Hz), 7.90 (d, 1H, J = 5.6 Hz), 7.73 (d, 2H, J = 8.0 Hz), 7.33 (d, 2H, J = 8.4 Hz), 7.29 (d, 2H, J = 8.0 Hz), 7.24 (d, 2H, J = 8.4 Hz), 7.00 (d, 1H, J = 1.6 Hz), 5.96 (d, 1H, J = 5.6 Hz), 3.97-3.89 (m, 1H), 3.85-3.70 (m, 2H), 3.70-3.66 (m, 1H), 3.36-3.26 (m, 4H), 3.06-2.98 (m, 1H), 2.79-2.71 (m, 2H), 2.61-2.54 (m, 2H), 2.42-2.32 (m, 3H), 2.29-2.17 (m, 1H), 1.84-1.74 (m, 1H), 1.51-1.44 (m, 1H), 1.28-1.21 (m, 1H), 1.08 (t, 3H, J = 7.2 Hz). |
| 445 | 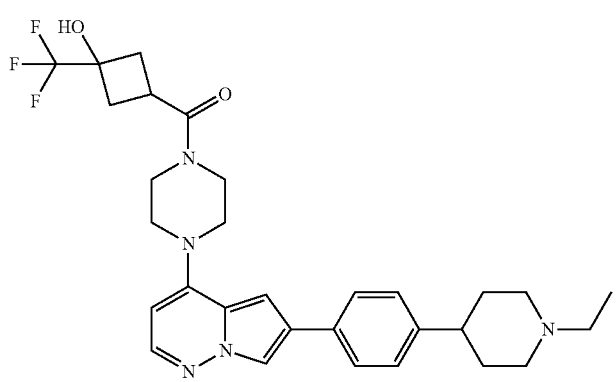 [SMILES: CCN1CCC(c2ccc(-c3cc4c(N5CCN(C(=O)C6CC(O)(C(F)(F)F)C6)CC5)ccnn4c3)cc2)CC1] | 557 | 1H NMR (400 MHz, Methanol-d4) δ 7.93 (d, J = 1.8 Hz, 1H), 7.82 (d, J = 5.4 Hz, 1H), 7.68-7.59 (m, 2H), 7.31-7.21 (m, 2H), 6.86 (d, J = 1.8 Hz, 1H), 5.96 (d, J = 5.5 Hz, 1H), 3.86-3.75 (m, 2H), 3.65 (dd, J = 6.9, 3.5 Hz, 2H), 3.56-3.40 (m, 4H), 3.24-3.06 (m, 3H), 2.80-2.67 (m, 2H), 2.54 (dh, J = 14.0, 7.6 Hz, 4H), 2.14 (td, J = 11.8, 2.9 Hz, 2H), 1.91-1.75 (m, 5H), 1.15 (t, J = 7.3 Hz, 3H). |

TABLE 1-continued

| # | Structure | LCMS (M + 1) | NMR |
|---|---|---|---|
| 446 | 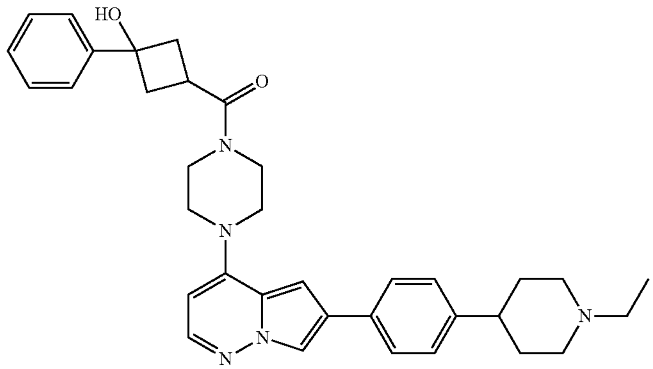 [SMILES: CCN1CCC(c2ccc(-c3cc4c(N5CCN(C(=O)C6CC(O)(c7ccccc7)C6)CC5)ccnn4c3)cc2)CC1] | 565 | 1H NMR (400 MHz, DMSO-d6) δ 8.13 (d, J = 1.8 Hz, 1H), 7.88 (d, J = 5.4 Hz, 1H), 7.76-7.62 (m, 2H), 7.57 (dd, J = 7.6, 1.6 Hz, 2H), 7.36 (t, J = 7.6 Hz, 2H), 7.25 (dd, J = 7.7, 5.4 Hz, 3H), 6.98 (d, J = 1.9 Hz, 1H), 5.95 (d, J = 5.5 Hz, 1H), 5.63 (s, 1H), 3.77-3.63 (m, 2H), 3.58 (d, J = 5.8 Hz, 2H), 3.44 (q, J = 5.4 Hz, 4H), 2.99 (dd, J = 17.5, 9.4 Hz, 3H), 2.59 (ddt, J = 11.7, 9.7, 6.1 Hz, 4H), 2.34 (q, J = 7.1 Hz, 2H), 2.02-1.87 (m, 2H), 1.81-1.55 (m, 4H), 1.02 (t, J = 7.1 Hz, 3H). |
| 447 | 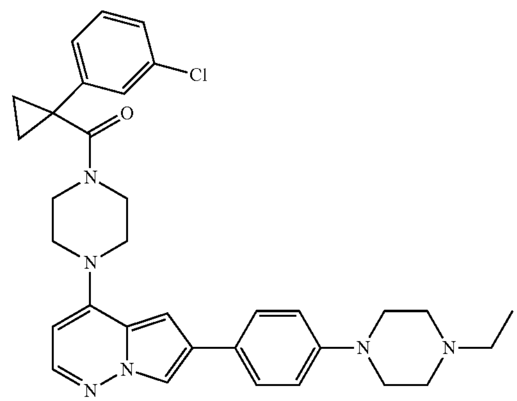 | 569 | 1H-NMR (400 MHz, 6d-DMSO) δ ppm 8.03 (d, 1H, J = 1.6 Hz), 7.83 (d, 1H, J = 5.2 Hz), 7.62 (d, 2H, J = 8.8 Hz), 7.38-7.34 (m, 1H), 7.28 (d, 1H, J = 8.4 Hz), 7.18 (s, 1H), 7.17 (d, 1H, J = 8.0 Hz), 6.92 (d, 2H, J = 8.8 Hz), 6.89 (d, 1H, J = 1.6 Hz), 5.90 (d, 1H, J = 5.6 Hz), 3.73-3.55 (m, 4H), 3.41-3.18 (m, 8H), 3.14 (t, 4H, J = 4.8 Hz), 2.36 (q, 2H, J = 7.2 Hz), 1.41-1.37 (m, 2H), 1.27-1.24 (m, 2H), 1.03 (t, 3H, J = 7.2 Hz). |
| 448 | 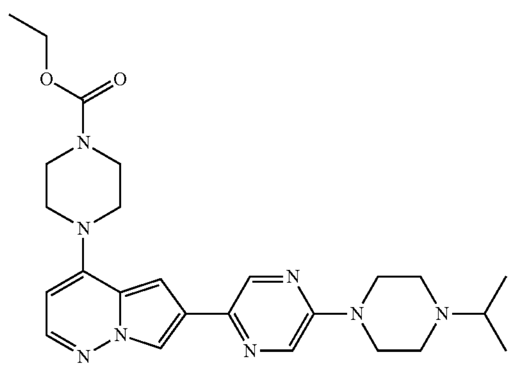 | 479 | 1H-NMR (400 MHz, 6d-DMSO) δ ppm 8.68 (s, 1H), 8.31 (s, 1H), 8.16 (d, 1H, J = 1.6 Hz), 7.91 (d, 1H, J = 5.6 Hz), 7.05 (d, 1H, J = 1.6 Hz), 5.99 (d, 1H, J = 5.2 Hz), 4.08 (q, 2H, J = 7.2 Hz), 3.61-3.60 (m, 4H), 3.56-3.54 (m, 4H), 3.47-3.46 (m, 4H), 2.73-2.67 (m, 1H), 2.57-2.54 (m, 4H), 1.22 (t, 3H, J = 7.2 Hz), 1.00 (d, 6H, J = 6.8 Hz). |
| 449 | 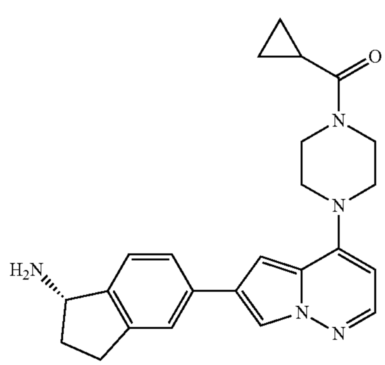 [SMILES: N[C@H]1CCc2cc(-c3cc4c(N5CCN(C(=O)C6CC6)CC5)ccnn4c3)ccc21] | 402 | |

TABLE 1-continued

| # | Structure | LCMS (M + 1) | NMR |
|---|---|---|---|
| 450 | 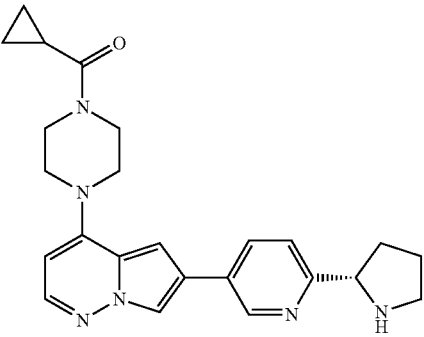 [SMILES: O=C(C1CC1)N1CCN(c2ccnn3cc(-c4ccc([C@@H]5CCCN5)nc4)cc23)CC1] | 417 | 1H-NMR (400 MHz, 6d-DMSO) δ ppm 9.07 (d, 1H, J = 2.0 Hz), 8.38 (d, 1H, J = 1.2 Hz), 8.29 (dd, 1H, J = 8.4, 2.0 Hz), 7.94 (d, 2H, J = 5.6 Hz), 7.54 (d, 1H, J = 8.4 Hz), 7.21 (d, 1H, J = 1.2 Hz), 6.01 (d, 1H, J = 5.6 Hz), 4.66-4.62 (m, 1H), 3.94-3.91 (m, 2H), 3.72-3.70 (m, 2H), 3.57-3.54 (m, 2H), 3.53-3.49 (m, 2H), 3.30-3.19 (m, 2H), 2.40-2.34 (m, 1H), 1.99-1.85 (m, 4H), 0.79-0.75 (m, 4H). |
| 451 | 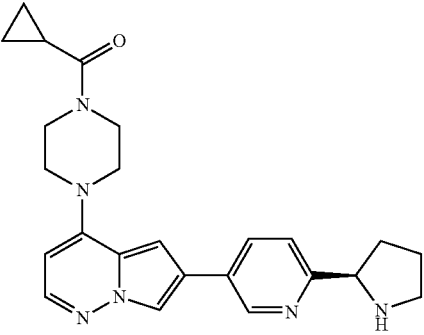 [SMILES: O=C(C1CC1)N1CCN(c2ccnn3cc(-c4ccc([C@H]5CCCN5)nc4)cc23)CC1] | 417 | 1H-NMR (400 MHz, 6d-DMSO) δ ppm 9.06 (s, 1H), 8.36 (s, 1H), 8.26 (dd, 1H, J1 = 8.4 Hz, J2 = 2.0 Hz), 7.94 (d, 1H, J = 5.6 Hz), 7.53 (d, 1H, J = 8.4 Hz), 7.21 (s, 1H), 5.99 (d, 1H, J = 5.6 Hz), 4.62-4.58 (m, 1H), 4.02-3.98 (m, 2H), 3.95-3.91 (m, 2H), 3.72-3.50 (m, 4H), 3.30-3.16 (m, 2H), 2.35-2.30 (m, 1H), 2.08-2.04 (m, 1H), 1.99-1.87 (m, 3H), 0.79-0.73 (m, 4H). |
| 452 | 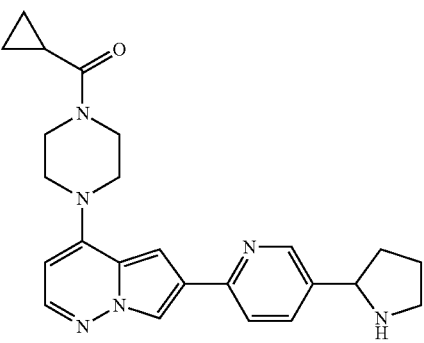 [SMILES: O=C(C1CC1)N1CCN(c2ccnn3cc(-c4ccc(C5CCCN5)cn4)cc23)CC1] | 417 | 1H NMR (400 MHz, DMSO-d6) δ 8.52 (d, J = 2.2 Hz, 1H), 8.25 (d, J = 1.8 Hz, 1H), 7.92 (d, J = 5.4 Hz, 1H), 7.86 (d, J = 8.1 Hz, 1H), 7.75 (dd, J = 8.2, 2.3 Hz, 1H), 7.17 (d, J = 1.8 Hz, 1H), 5.97 (d, J = 5.5 Hz, 1H), 4.06 (t, J = 7.6 Hz, 1H), 3.93 (s, 2H), 3.70 (s, 2H), 3.52 (d, J = 32.7 Hz, 4H), 3.01 (ddd, J = 9.9, 7.6, 5.3 Hz, 1H), 2.89 (ddd, J = 9.9, 8.2, 6.6 Hz, 1H), 2.13 (dtd, J = 12.3, 7.7, 4.9 Hz, 1H), 2.02 (tt, J = 7.7, 4.9 Hz, 1H), 1.85-1.69 (m, 2H), 1.58-1.44 (m, 1H), 0.76 (tt, J = 7.9, 2.9 Hz, 4H). |
| 453 | 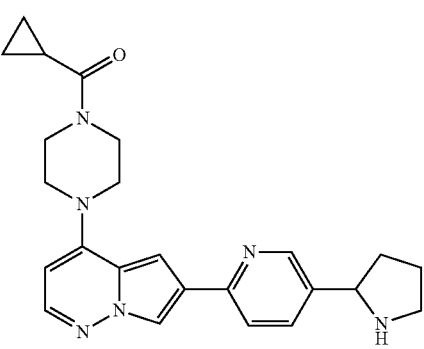 | 417 | 1H NMR (400 MHz, DMSO-d6) δ 8.48 (d, J = 2.2 Hz, 1H), 8.21 (d, J = 1.7 Hz, 1H), 7.88 (d, J = 5.4 Hz, 1H), 7.82 (d, J = 8.1 Hz, 1H), 7.71 (dd, J = 8.2, 2.3 Hz, 1H), 7.14 (d, J = 1.8 Hz, 1H), 5.94 (d, J = 5.5 Hz, 1H), 4.01 (t, J = 7.6 Hz, 1H), 3.89 (s, 2H), 3.67 (s, 2H), 3.53 (s, 2H), 3.45 (s, 2H), 2.98 (ddd, J = 9.9, 7.5, 5.4 Hz, 1H), 2.85 (ddd, J = 9.9, 8.2, 6.6 Hz, 1H), 2.09 (dtd, J = 12.1, 7.6, 4.8 Hz, 1H), 2.02-1.93 (m, 1H), 1.80-1.66 (m, 2H), 1.53-1.42 (m, 1H), 0.72 (tt, J = 7.9, 2.9 Hz, 4H). |

TABLE 1-continued

| # | Structure | LCMS (M + 1) | NMR |
|---|---|---|---|
| 454 | 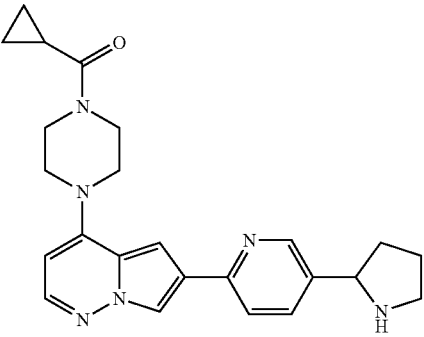 | 417 | |
| 455 | 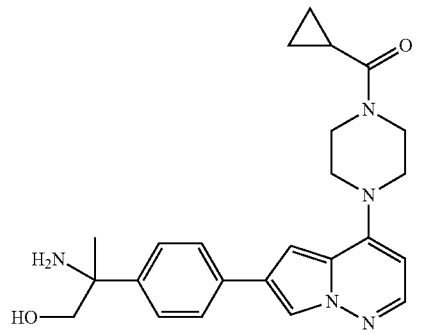 [SMILES: CC(N)(CO)c1ccc(-c2cc3c(N4CCN(C(=O)C5CC5)CC4)ccnn3c2)cc1] | 420 | 1H NMR (400 MHz, Methanol-d4) δ 7.97 (d, J = 1.8 Hz, 1H), 7.84 (d, J = 5.4 Hz, 1H), 7.72 (d, J = 8.2 Hz, 2H), 7.40 (d, J = 8.0 Hz, 2H), 6.93 (d, J = 1.8 Hz, 1H), 5.99 (d, J = 5.4 Hz, 1H), 4.03 (s, 2H), 3.85 (s, 2H), 3.63 (s, 2H), 3.51 (d, J = 25.3 Hz, 4H), 2.80 (s, 2H), 2.60 (d, J = 9.9 Hz, 2H), 2.02 (tt, J = 7.8, 4.7 Hz, 1H), 1.51 (d, J = 6.6 Hz, 3H), 0.92 (dt, J = 4.9, 2.8 Hz, 2H), 0.86 (ddt, J = 7.5, 4.6, 2.6 Hz, 2H). |
| 456 | 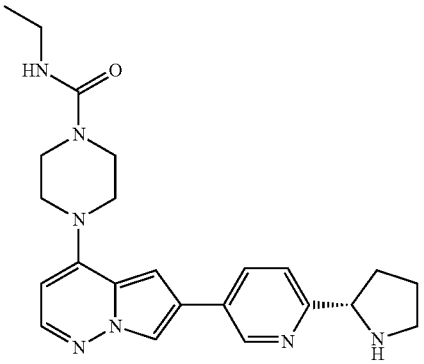 [SMILES: CCNC(=O)N1CCN(c2ccnn3cc(-c4ccc([C@@H]5CCCN5)nc4)cc23)CC1] | 420 | 1H-NMR (400 MHz, 6d-DMSO) δ ppm 9.04 (s, 1H), 8.34 (s, 1H), 8.25 (d, 1H, J = 8.0 Hz), 7.92 (d, 1H, J = 5.6 Hz), 7.52 (d, 1H, J = 8.0 Hz), 7.17 (s, 1H), 6.65-6.62 (m, 1H), 6.00 (d, 1H, J = 5.6 Hz), 4.56-4.54 (m, 1H), 3.53-3.51 (m, 4H), 3.45-3.44 (m, 4H), 3.25-3.22 (m, 1H), 3.21-3.16 (m, 1H), 3.08 (quintet, 2H, J = 7.2 Hz), 2.32-2.30 (m, 1H), 1.91-1.86 (m, 3H), 1.03 (t, 3H, J = 7.2 Hz). |
| 457 | 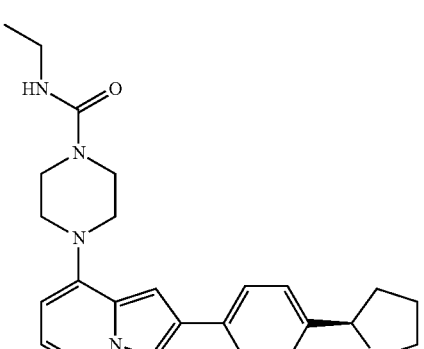 | 420 | 1H-NMR (400 MHz, 6d-DMSO) δ ppm 9.05 (d, 1H, J = 8.4 Hz), 8.36 (s, 1H), 8.26 (dd, 1H, J1 = 8.0 Hz, J2 = 2.0 Hz), 7.93 (d, 1H, J = 5.2 Hz), 7.53 (d, 1H, J = 8.0 Hz), 7.17 (d, 1H, J = 1.2 Hz), 6.64 (t, 1H, J = 5.2 Hz), 6.01 (d, 1H, J = 5.6 Hz), 4.58-4.54 (m, 1H), 3.54-3.52 (m, 4H), 3.46-3.44 (m, 4H), 3.23-3.22 (m, 1H), 3.20-3.11 (m, 1H), 3.09-3.06 (m, 2H), 2.34-2.28 (m, 1H), 1.94-1.85 (m, 3H), 1.04 (t, 3H, J = 7.2 Hz). |

| # | Structure | LCMS (M + 1) | NMR |
|---|---|---|---|
| 458 | 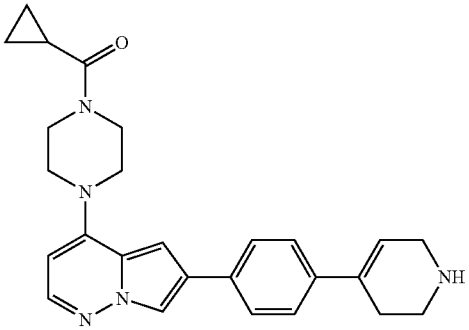 [SMILES: O=C(C1CC1)N1CCN(c2ccnn3cc(-c4ccc(C5=CCNCC5)cc4)cc23)CC1] | 428 | 1H NMR (400 MHz, Methanol-d4) δ 7.99 (d, J = 1.8 Hz, 1H), 7.84 (d, J = 5.5 Hz, 1H), 7.80-7.67 (m, 2H), 7.58-7.46 (m, 2H), 6.94 (d, J = 1.8 Hz, 1H), 6.20 (tt, J = 3.5, 1.7 Hz, 1H), 5.98 (d, J = 5.5 Hz, 1H), 4.01 (s, 2H), 3.93-3.75 (m, 4H), 3.61 (s, 3H), 3.53 (d, J = 5.3 Hz, 3H), 3.48 (t, J = 6.1 Hz, 2H), 2.84 (tq, J = 5.8, 1.9 Hz, 2H), 2.01 (tt, J = 7.8, 4.7 Hz, 1H), 0.99-0.90 (m, 2H), 0.86 (ddt, J = 7.5, 4.6, 2.5 Hz, 2H). |
| 459 | 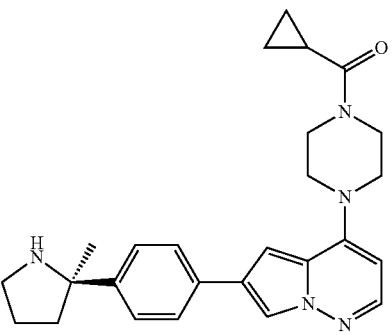 [SMILES: C[C@]1(c2ccc(-c3cc4c(N5CCN(C(=O)C6CC6)CC5)ccnn4c3)cc2)CCCN1] | 430 | 1H NMR (400 MHz, DMSO-d6) δ 8.13 (d, J = 1.7 Hz, 1H), 7.89 (d, J = 5.4 Hz, 1H), 7.76-7.66 (m, 2H), 7.54-7.42 (m, 2H), 7.01 (d, J = 1.9 Hz, 1H), 5.97 (d, J = 5.5 Hz, 1H), 3.91 (qd, J = 5.9, 2.8 Hz, 2H), 3.70 (s, 2H), 3.50 (d, J = 29.4 Hz, 4H), 3.00 (ddd, J = 10.6, 8.3, 5.9 Hz, 1H), 2.76 (ddd, J = 10.3, 8.5, 4.7 Hz, 1H), 2.06-1.95 (m, 2H), 1.82-1.69 (m, 2H), 1.58-1.46 (m, 1H), 1.35 (s, 3H), 0.75 (tt, J = 7.9, 2.9 Hz, 4H). |
| 460 | 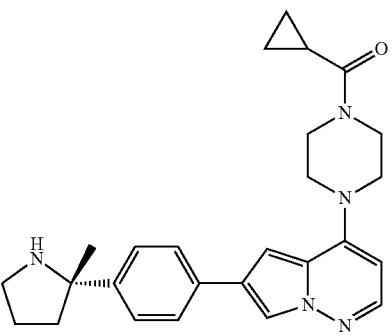 [SMILES: C[C@@]1(c2ccc(-c3cc4c(N5CCN(C(=O)C6CC6)CC5)ccnn4c3)cc2)CCCN1] | 430 | |
| 461 | 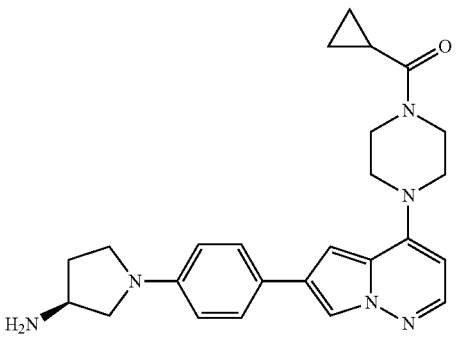 [SMILES: N[C@H]1CCN(c2ccc(-c3cc4c(N5CCN(C(=O)C6CC6)CC5)ccnn4c3)cc2)C1] | 431 | 1H NMR (400 MHz, MeOD) δ ppm 8.55-8.48 (m, 1H), 7.86 (d, 1H, J = 2.0 Hz), 7.82 (d, 1H, J = 5.6 Hz), 7.60 (d, 2H, J = 8.8 Hz), 6.82 (d, 1H, J = 2.0 Hz), 6.70 (d, 2H, J = 8.8 Hz), 5.99 (d, 1H, J = 5.6 Hz), 4.07-4.01 (m, 2H), 3.98-3.95 (m, 1H), 3.89-3.83 (m, 2H), 3.65-3.58 (m, 4H), 3.56-3.50 (m, 2H), 3.42-3.36 (m, 2H), 2.49-2.40 (m, 1H), 2.14-2.07 (m, 1H), 2.05-2.00 (m, 1H), 0.97-0.90 (m, 2H) ), 0.89-0.86 (m, 2H). |

TABLE 1-continued

| # | Structure | LCMS (M + 1) | NMR |
|---|---|---|---|
| 462 | 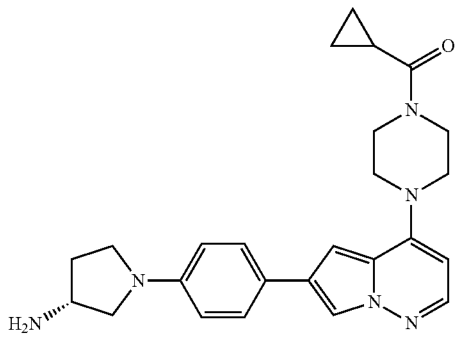 [SMILES: N[C@@H]1CCN(c2ccc(-c3cc4c(N5CCN(C(=O)C6CC6)CC5)ccnn4c3)cc2)C1] | 431 | 1H-NMR (400 MHz, MeOD) δ ppm 8.51 (s, 1H), 7.82 (d, 1H, J = 1.6 Hz), 7.78 (d, 1H, J = 5.2 Hz), 7.57 (d, 2H, J = 8.8 Hz), 6.78 (d, 1H, J = 1.2 Hz), 6.67 (d, 2H, J = 8.8 Hz), 5.94 (d, 1H, J = 5.6 Hz), 3.98-3.95 (m, 3H), 3.82-3.80 (m, 2H), 3.60-3.54 (m, 4H), 3.48-3.46 (m, 2H), 3.40-3.36 (m, 2H), 2.42-2.40 (m, 1H), 2.13-2.11 (m, 1H), 2.00-1.98 (m, 1H), 0.90-0.88 (m, 2H), 0.84-0.80 (m, 2H). |
| 463 | 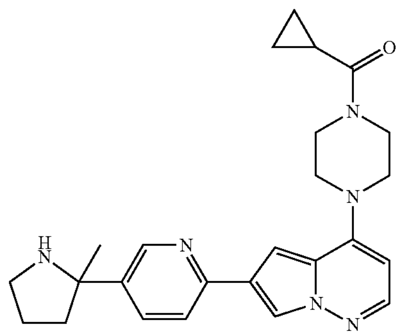 [SMILES: CC1(c2ccc(-c3cc4c(N5CCN(C(=O)C6CC6)CC5)ccnn4c3)nc2)CCCN1] | 431.2 | 1H NMR (400 MHz, DMSO-d6) δ 8.63 (dd, J = 2.1, 1.0 Hz, 1H), 8.21 (d, J = 1.7 Hz, 1H), 7.88 (d, J = 5.4 Hz, 1H), 7.83-7.76 (m, 2H), 7.13 (d, J = 1.8 Hz, 1H), 5.94 (d, J = 5.5 Hz, 1H), 3.90 (br.s, 2H), 3.67 (br.s, 2H), 3.52 (br.s, 2H), 3.44 (br.s, 2H), 2.99 (dt, J = 10.8, 7.1 Hz, 1H), 2.71 (ddd, J = 13.5, 9.2, 4.7 Hz, 1H), 1.98 (ddd, J = 10.8, 8.2, 5.5 Hz, 2H), 1.75 (tt, J = 8.7, 6.2 Hz, 2H), 1.57-1.43 (m, 1H), 1.35 (s, 3H), 0.72 (ddd, J = 10.9, 5.0, 2.4 Hz, 4H). |
| 464 | 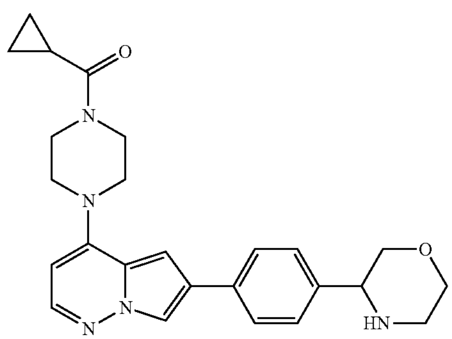 [SMILES: O=C(C1CC1)N1CCN(c2ccnn3cc(-c4ccc(C5COCCN5)cc4)cc23)CC1] | 432 | 1H NMR (400 MHz, Methanol-d4) δ 7.94 (d, J = 1.8 Hz, 1H), 7.81 (d, J = 5.4 Hz, 1H), 7.73-7.65 (m, 2H), 7.39 (d, J = 8.0 Hz, 2H), 6.89 (d, J = 1.8 Hz, 1H), 5.92 (d, J = 5.4 Hz, 1H), 3.96 (d, J = 5.4 Hz, 2H), 3.84 (ddt, J = 16.0, 8.6, 4.2 Hz, 5H), 3.68-3.53 (m, 3H), 3.53-3.38 (m, 3H), 3.31 (p, J = 1.6 Hz, 1H), 3.11-2.91 (m, 2H), 1.98 (ddd, J = 9.3, 6.6, 4.0 Hz, 1H), 0.92 (ddd, J = 5.9, 4.7, 2.5 Hz, 2H), 0.85 (tdd, J = 7.4, 5.4, 1.9 Hz, 2H). |
| 465 | 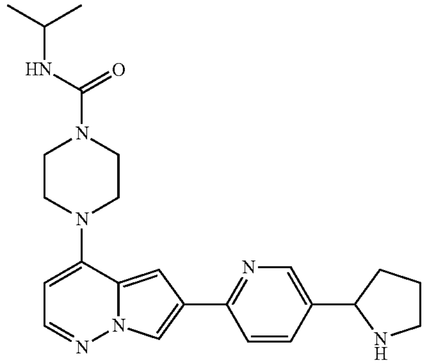 [SMILES: CC(C)NC(=O)N1CCN(c2ccnn3cc(-c4ccc(C5CCCN5)cn4)cc23)CC1] | 434 | 1H NMR (400 MHz, DMSO-d6) δ 8.48 (d, J = 2.2 Hz, 1H), 8.20 (d, J = 1.7 Hz, 1H), 7.87 (d, J = 5.4 Hz, 1H), 7.82 (d, J = 8.2 Hz, 1H), 7.70 (dd, J = 8.2, 2.3 Hz, 1H), 7.10 (d, J = 1.9 Hz, 1H), 6.27 (d, J = 7.6 Hz, 1H), 5.95 (d, J = 5.5 Hz, 1H), 4.01 (t, J = 7.6 Hz, 1H), 3.75 (dt, J = 13.5, 6.7 Hz, 1H), 3.48 (dd, J = 6.8, 3.2 Hz, 4H), 3.44-3.36 (m, 4H), 2.97 (ddd, J = 9.9, 7.6, 5.3 Hz, 1H), 2.85 (ddd, J = 9.9, 8.2, 6.7 Hz, 1H), 2.09 (dtd, J = 12.4, 7.7, 5.0 Hz, 1H), 1.81-1.64 (m, 2H), 1.52-1.42 (m, 1H), 1.04 (d, J = 6.6 Hz, 6H). |

TABLE 1-continued

| # | Structure | LCMS (M + 1) | NMR |
|---|---|---|---|
| 466 | 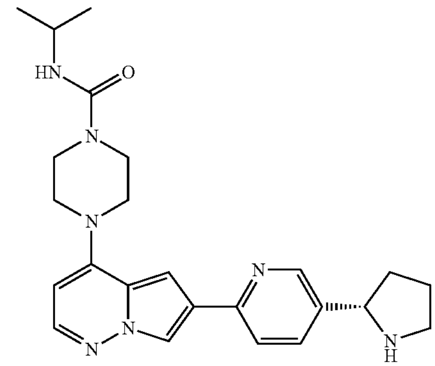 [SMILES: CC(C)NC(=O)N1CCN(c2ccnn3cc(-c4ccc([C@@H]5CCCN5)cn4)cc23)CC1] | 434 | 1H NMR (400 MHz, DMSO-d6) δ 8.48 (d, J = 2.2 Hz, 1H), 8.20 (d, J = 1.7 Hz, 1H), 7.87 (d, J = 5.4 Hz, 1H), 7.82 (d, J = 8.2 Hz, 1H), 7.70 (dd, J = 8.2, 2.3 Hz, 1H), 7.10 (d, J = 1.9 Hz, 1H), 6.27 (d, J = 7.6 Hz, 1H), 5.95 (d, J = 5.5 Hz, 1H), 4.01 (t, J = 7.6 Hz, 1H), 3.75 (dt, J = 13.5, 6.7 Hz, 1H), 3.48 (dd, J = 6.8, 3.2 Hz, 4H), 3.44-3.36 (m, 4H), 2.97 (ddd, J = 9.9, 7.6, 5.3 Hz, 1H), 2.85 (ddd, J = 9.9, 8.2, 6.7 Hz, 1H), 2.09 (dtd, J = 12.4, 7.7, 5.0 Hz, 1H), 1.81-1.64 (m, 2H), 1.52-1.42 (m, 1H), 1.04 (d, J = 6.6 Hz, 6H). |
| 467 | 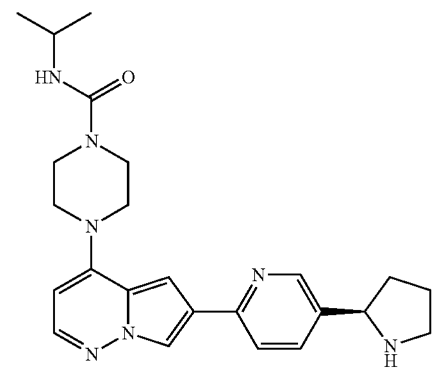 [SMILES: CC(C)NC(=O)N1CCN(c2ccnn3cc(-c4ccc([C@H]5CCCN5)cn4)cc23)CC1] | 434 | |
| 468 | 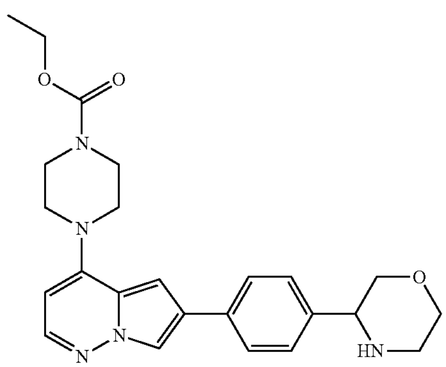 [SMILES: CCOC(=O)N1CCN(c2ccnn3cc(-c4ccc(C5COCCN5)cc4)cc23)CC1] | 436 | 1H NMR (400 MHz, Methanol-d4) δ 7.97 (dd, J = 5.9, 2.5 Hz, 3H), 7.71-7.55 (m, 2H), 4.55 (dd, J = 10.8, 3.6 Hz, 1H), 4.21 (q, J = 7.1 Hz, 2H), 4.18-4.09 (m, 2H), 4.09-3.91 (m, 2H), 3.82-3.69 (m, 4H), 3.63-3.53 (m, 4H), 3.49-3.37 (m, 2H), 3.30 (p, J = 1.7 Hz, 1H), 2.65 (p, J = 1.9 Hz, 1H), 1.33 (t, J = 7.1 Hz, 3H). |
| 469 | 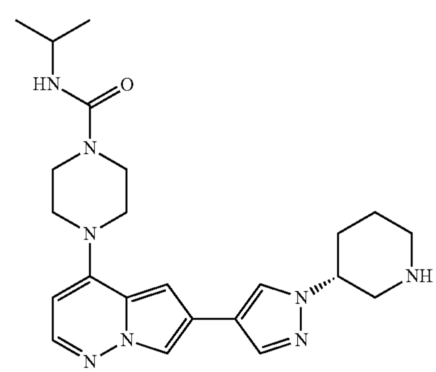 [SMILES: CC(C)NC(=O)N1CCN(c2ccnn3cc(-c4cnn([C@@H]5CCCNC5)c4)cc23)CC1] | 437 | 1H-NMR (400 MHz, 6d-DMSO) δ ppm 8.14 (s, 1H), 7.91 (d, 1H, J = 1.6 Hz), 7.85 (d, 1H, J = 5.6 Hz), 7.80 (s, 1H), 6.79 (d, 1H, J = 1.6 Hz), 6.31 (d, 1H, J = 8.0 Hz), 5.97 (d, 1H, J = 5.2 Hz), 4.11-4.10 (m, 1H), 3.81-3.76 (m, 1H), 3.51-3.50 (m, 4H), 3.41-3.39 (m, 4H), 3.21-3.07 (m, 1H), 2.95-2.90 (m, 1H), 2.75-2.70 (m, 1H), 2.46-2.43 (m, 2H), 2.15-2.11 (m, 1H), 1.90-1.87 (m, 1H), 1.74-1.70 (m, 1H), 1.53-1.50 (m, 1H), 1.08 (d, 6H, J = 6.4 Hz). |

TABLE 1-continued

| # | Structure | LCMS (M + 1) | NMR |
|---|---|---|---|
| 470 | 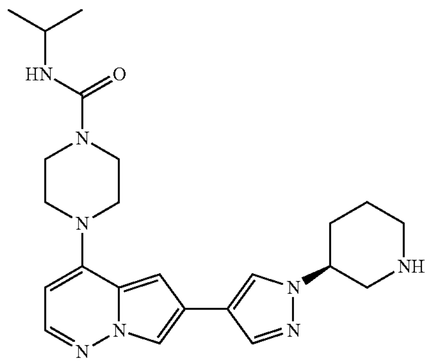 [SMILES: CC(C)NC(=O)N1CCN(c2ccnn3cc(-c4cnn([C@H]5CCCNC5)c4)cc23)CC1] | 437 | 1H-NMR (400 MHz, 6d-DMSO) δ ppm 8.13 (s, 1H), 7.91 (s, 1H), 7.85 (d, 1H, J = 5.6 Hz), 7.80 (s, 1H), 6.78 (s, 1H), 6.33 (d, 1H, J = 8.0 Hz), 5.96 (d, 1H, J = 5.6 Hz), 4.14-4.08 (m, 1H), 3.80-3.74 (m, 1H), 3.48-3.58 (m, 6H), 3.22-3.16 (m, 4H), 2.90-2.86 (m, 1H), 2.78-2.74 (m, 1H), 2.46-2.43 (m, 1H), 2.13-2.10 (m, 1H), 1.89-1.85 (m, 1H), 1.73-1.69 (m, 1H), 1.52-1.48 (m, 1H), 1.08 (d, 6H, J = 6.8 Hz). |
| 471 | 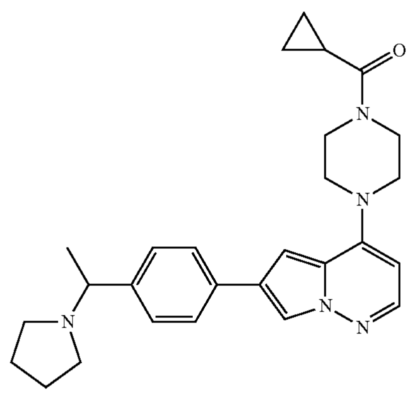 [SMILES: CC(c1ccc(-c2cc3c(N4CCN(C(=O)C5CC5)CC4)ccnn3c2)cc1)N1CCCC1] | 444 | |
| 472 | 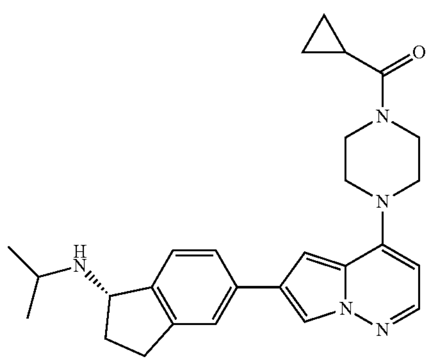 [SMILES: CC(C)N[C@H]1CCc2cc(-c3cc4c(N5CCN(C(=O)C6CC6)CC5)ccnn4c3)ccc21] | 444 | 1H NMR (500 MHz, Methanol-d4) δ 8.02 (d, J = 1.8 Hz, 1H), 7.87 (d, J = 5.4 Hz, 1H), 7.80-7.70 (m, 2H), 7.56 (d, J = 8.0 Hz, 1H), 6.98 (d, J = 2.0 Hz, 1H), 6.02 (d, J = 5.4 Hz, 1H), 4.91 (s, 2H), 4.04 (s, 2H), 3.86 (s, 2H), 3.60 (d, J = 31.4 Hz, 5H), 3.22 (t, J = 7.4 Hz, 6H), 2.22 (s, 1H), 2.03 (s, 1H), 1.44 (t, J = 7.3 Hz, 6H), 0.93 (d, J = 4.1 Hz, 2H), 0.88 (d, J = 7.8 Hz, 1H). |
| 473 | 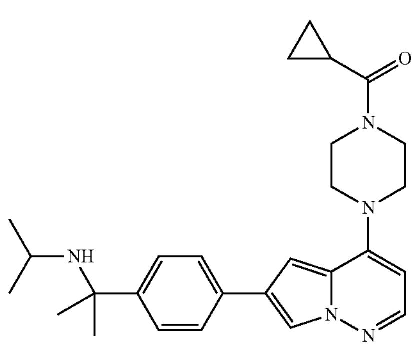 [SMILES: CC(C)NC(C)(C)c1ccc(-c2cc3c(N4CCN(C(=O)C5CC5)CC4)ccnn3c2)cc1] | 446 | 1H-NMR (400 MHz, 6d-DMSO) δ ppm 8.15 (d, 1H, J = 1.6 Hz), 7.89 (d, 1H, J = 5.6 Hz), 7.71 (d, 2H, J = 8.4 Hz), 7.49 (d, 2H, J = 8.4 Hz), 7.02 (d, 1H, J = 1.6 Hz), 5.96 (d, 1H, J = 5.6 Hz), 3.92-3.91 (m, 2H), 3.80-3.60 (m, 2H), 3.60-3.55 (m, 2H), 3.50-3.46 (m, 4H), 3.35-3.29 (m, 1H), 2.54-2.53 (m, 1H), 2.02-1.99 (m, 1H), 1.37 (s, 6H), 0.84 (d, 6H, J = 6.4 Hz), 0.76-0.72 (m, 4H). |

TABLE 1-continued

| # | Structure | LCMS (M + 1) | NMR |
|---|---|---|---|
| 474 | 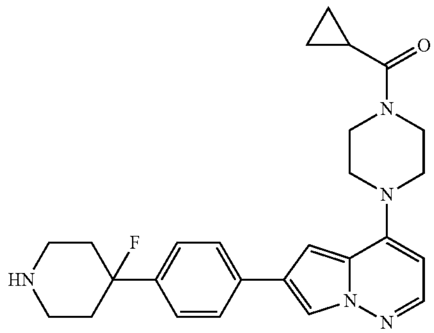 [SMILES: O=C(C1CC1)N1CCN(c2ccnn3cc(-c4ccc(C5(F)CCNCC5)cc4)cc23)CC1] | 428 | 1H NMR (400 MHz, DMSO-d6) δ 8.16 (s, 1H), 7.87 (d, J = 5.4 Hz, 1H), 7.79 (d, J = 8.0 Hz, 2H), 7.37 (d, J = 8.0 Hz, 2H), 7.06-6.98 (m, 1H), 5.94 (d, J = 5.5 Hz, 1H), 3.88 (br.s, 2H), 3.66 (br.s, 2H), 3.47 (br.d, J = 27.3 Hz, 4H), 2.90-2.72 (m, 4H), 2.05-1.72 (m, 5H), 0.72 (dd, J = 9.3, 6.3 Hz, 4H). |
| 475 | 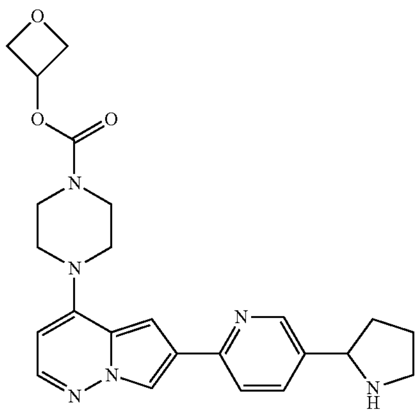 | 449 | 1H NMR (400 MHz, DMSO-d6) δ 8.48 (d, J = 2.1 Hz, 1H), 8.21 (d, J = 1.7 Hz, 1H), 7.89 (d, J = 5.4 Hz, 1H), 7.82 (d, J = 8.1 Hz, 1H), 7.71 (dd, J = 8.2, 2.3 Hz, 1H), 7.11 (d, J = 1.8 Hz, 1H), 5.96 (d, J = 5.5 Hz, 1H), 5.33-5.25 (m, 1H), 4.75 (t, J = 6.9 Hz, 2H), 4.49 (dd, J = 7.5, 5.1 Hz, 2H), 4.02 (t, J = 7.6 Hz, 1H), 3.66 (br.s, 2H), 3.56 (br.s, 2H), 3.50-3.41 (m, 4H), 2.98 (ddd, J = 9.9, 7.6, 5.4 Hz, 1H), 2.85 (ddd, J = 9.9, 8.2, 6.7 Hz, 1H), 2.10 (dtd, J = 12.4, 7.7, 5.0 Hz, 1H), 1.81-1.64 (m, 2H), 1.54-1.41 (m, 1H). |
| 476 | 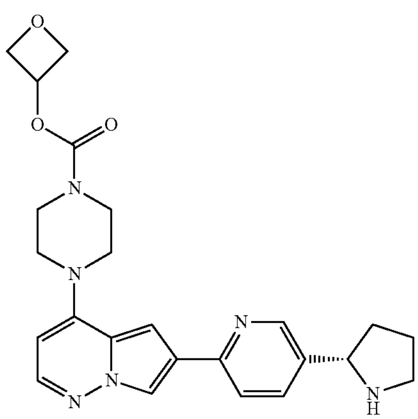 [SMILES: O=C(OC1COC1)N1CCN(c2ccnn3cc(-c4ccc([C@@H]5CCCN5)cn4)cc23)CC1] | 449 | 1H NMR (400 MHz, DMSO-d6) δ 8.48 (d, J = 2.1 Hz, 1H), 8.21 (d, J = 1.7 Hz, 1H), 7.89 (d, J = 5.4 Hz, 1H), 7.82 (d, J = 8.1 Hz, 1H), 7.71 (dd, J = 8.2, 2.3 Hz, 1H), 7.11 (d, J = 1.8 Hz, 1H), 5.96 (d, J = 5.5 Hz, 1H), 5.33-5.25 (m, 1H), 4.75 (t, J = 6.9 Hz, 2H), 4.49 (dd, J = 7.5, 5.1 Hz, 2H), 4.02 (t, J = 7.6 Hz, 1H), 3.66 (br.s, 2H), 3.56 (br.s, 2H), 3.50-3.41 (m, 4H), 2.98 (ddd, J = 9.9, 7.6, 5.4 Hz, 1H), 2.85 (ddd, J = 9.9, 8.2, 6.7 Hz, 1H), 2.10 (dtd, J = 12.4, 7.7, 5.0 Hz, 1H), 1.81-1.64 (m, 2H), 1.54-1.41 (m, 1H). |
| 477 | 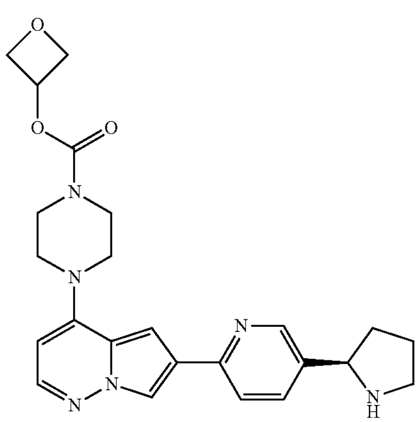 [SMILES: O=C(OC1COC1)N1CCN(c2ccnn3cc(-c4ccc([C@H]5CCCN5)cn4)cc23)CC1] | 449 | |

TABLE 1-continued

| # | Structure | LCMS (M + 1) | NMR |
|---|---|---|---|
| 478 | 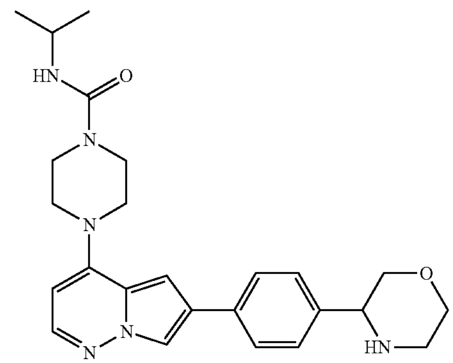 [SMILES: CC(C)NC(=O)N1CCN(c2ccnn3cc(-c4ccc(C5COCCN5)cc4)cc23)CC1] | 449 | 1H NMR (400 MHz, Methanol-d4) δ 8.43 (s, 1H), 8.00 (d, J = 1.8 Hz, 1H), 7.88-7.74 (m, 3H), 7.56-7.40 (m, 2H), 6.93 (d, J = 1.9 Hz, 1H), 5.99 (d, J = 5.5 Hz, 1H), 4.37 (dd, J = 10.7, 3.5 Hz, 1H), 4.08 (dd, J = 12.5, 3.3 Hz, 2H), 3.93 (p, J = 6.6 Hz, 1H), 3.90-3.77 (m, 2H), 3.66-3.58 (m, 4H), 3.58-3.46 (m, 4H), 3.39-3.29 (m, 4H), 1.24-1.07 (m, 6H). |
| 479 | 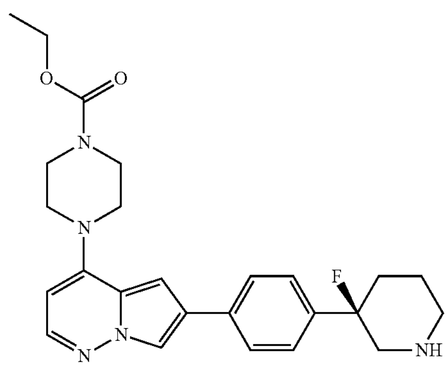 [SMILES: CCOC(=O)N1CCN(c2ccnn3cc(-c4ccc([C@]5(F)CCCNC5)cc4)cc23)CC1] | 452 | 1H-NMR (500 MHz, 6d-DMSO) δ ppm 8.20 (d, 1H, J = 1.5 Hz), 7.91 (d, 1H, J = 5.5 Hz), 7.82 (d, 2H, J = 8.5 Hz), 7.43 (d, 2H, J = 8.5 Hz), 7.04 (d, 1H, J = 2.0 Hz), 5.99 (d, 1H, J = 6.0 Hz), 4.09 (q, 2H, J = 7.0 Hz), 3.65-3.55 (m, 4H), 3.50-3.38 (m, 4H), 2.98-2.85 (m, 3H), 2.70-2.55 (m, 1H), 2.45-2.35 (m, 1H), 2.23-2.05 (m, 1H), 1.99-1.93 (m, 1H), 1.80-1.70 (m, 1H), 1.60-1.50 (m, 1H), 1.22 (t, 3H, J = 7.0 Hz). |
| 480 | 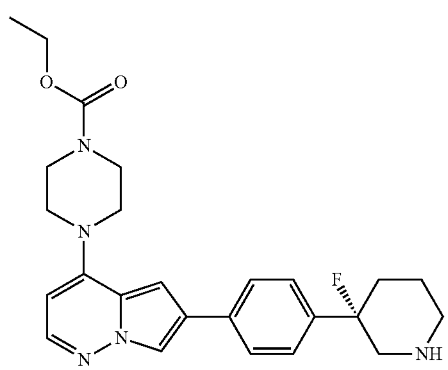 [SMILES: CCOC(=O)N1CCN(c2ccnn3cc(-c4ccc([C@@]5(F)CCCNC5)cc4)cc23)CC1] | 452 | 1H-NMR (400 MHz, 6d-DMSO) δ ppm 8.20 (d, 1H, J = 1.6 Hz), 7.91 (d, 1H, J = 5.2 Hz), 7.82 (d, 2H, J = 8.4 Hz), 7.43 (d, 2H, J = 8.4 Hz), 7.04 (d, 1H, J = 1.6 Hz), 5.99 (d, 1H, J = 5.6 Hz), 4.09 (q, 2H, J = 6.8 Hz), 3.65-3.50 (m, 4H), 3.50-3.38 (m, 4H), 2.98-2.80 (m, 3H), 2.70-2.55 (m, 1H), 2.45-2.15 (m, 2H), 2.03-1.95 (m, 1H), 1.85-1.70 (m, 1H), 1.65-1.48 (m, 1H), 1.22 (t, 3H, J = 6.8 Hz). |
| 481 | 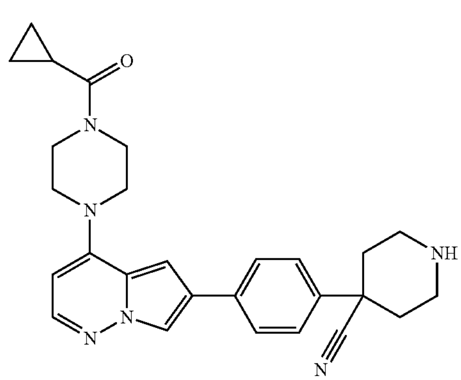 [SMILES: N#CC1(c2ccc(-c3cc4c(N5CCN(C(=O)C6CC6)CC5)ccnn4c3)cc2)CCNCC1] | 455 | 1H NMR (400 MHz, DMSO-d6) δ 8.21 (d, J = 1.7 Hz, 1H), 7.98-7.84 (m, 3H), 7.57-7.44 (m, 2H), 7.07 (d, J = 1.9 Hz, 1H), 5.98 (d, J = 5.5 Hz, 1H), 3.92 (s, 2H), 3.71 (s, 2H), 3.51 (d, J = 25.6 Hz, 4H), 3.27-3.07 (m, 3H), 2.90 (t, J = 12.8 Hz, 2H), 2.13 (d, J = 13.2 Hz, 2H), 2.08-1.90 (m, 4H), 0.89-0.60 (m, 4H). |

TABLE 1-continued

| # | Structure | LCMS (M + 1) | NMR |
|---|---|---|---|
| 482 | 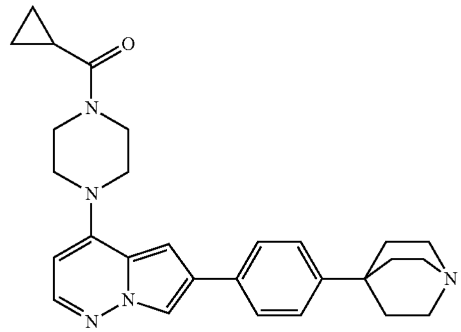 [SMILES: O=C(C1CC1)N1CCN(c2ccnn3cc(-c4ccc(C56CCN(CC5)CC6)cc4)cc23)CC1] | 456 | 1H NMR (400 MHz, DMSO-d6) δ 8.14 (d, J = 1.8 Hz, 1H), 7.89 (d, J = 5.4 Hz, 1H), 7.77-7.67 (m, 2H), 7.34-7.24 (m, 2H), 7.01 (d, J = 1.9 Hz, 1H), 5.97 (d, J = 5.5 Hz, 1H), 3.92 (br.s, 2H), 3.69 (br.s, 2H), 3.50 (br.d, J = 28.4 Hz, 4H), 2.94-2.78 (m, 6H), 2.02 (tt, J = 7.6, 4.9 Hz, 1H), 1.74-1.59 (m, 6H), 0.75 (tt, J = 7.9, 2.9 Hz, 4H). |
| 483 | 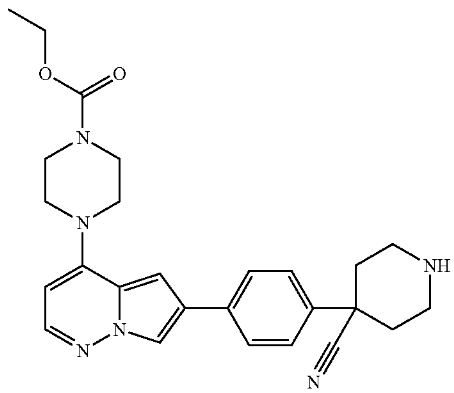 [SMILES: CCOC(=O)N1CCN(c2ccnn3cc(-c4ccc(C5(C#N)CCNCC5)cc4)cc23)CC1] | 459 | 1H NMR (400 MHz, Methanol-d4) δ 8.46 (s, 1H), 8.02 (d, J = 1.8 Hz, 1H), 7.89-7.81 (m, 3H), 7.63-7.52 (m, 2H), 6.94 (d, J = 1.9 Hz, 1H), 6.02 (d, J = 5.4 Hz, 1H), 5.49 (d, J = 5.3 Hz, 1H), 4.18 (q, J = 7.1 Hz, 2H), 3.72 (d, J = 5.8 Hz, 4H), 3.59 (d, J = 13.5 Hz, 2H), 3.52 (t, J = 5.1 Hz, 4H), 3.38 (dd, J = 13.1, 2.9 Hz, 2H), 2.44 (d, J = 14.5 Hz, 2H), 2.39-2.23 (m, 2H), 1.30 (t, J = 7.1 Hz, 3H). |
| 484 | 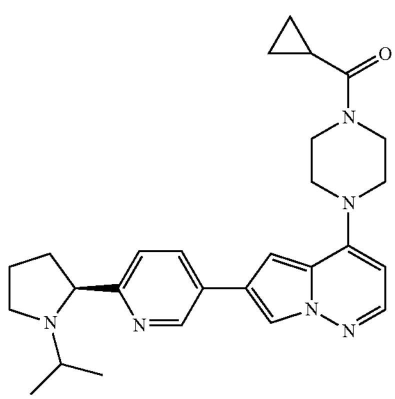 [SMILES: CC(C)N1CCC[C@H]1c1ccc(-c2cc3c(N4CCN(C(=O)C5CC5)CC4)ccnn3c2)cn1] | 459 | 1H-NMR (400 MHz, 6d-DMSO) δ ppm 8.94 (s, 1H), 8.29 (s, 1H), 8.18 (s, 1H), 8.17 (d, 1H, J = 8.0 Hz), 7.92 (d, 1H, J = 5.2 Hz), 7.54 (d, 1H, J = 8.0 Hz), 7.15 (s, 1H), 6.00 (d, 1H, J = 5.2 Hz), 4.02-3.98 (m, 1H), 3.94-3.91 (m, 2H), 3.72-3.70 (m, 2H), 3.55-3.51 (m, 2H), 3.50-3.45 (m, 2H), 3.16-3.14 (m, 1H), 2.86-2.83 (m, 1H), 2.75-2.69 (m, 1H), 2.23-2.18 (m, 1H), 2.04-2.01 (m, 1H), 1.85-1.79 (m, 2H), 1.72-1.69 (m, 1H), 0.99-0.97 (m, 6H), 0.78-0.74 (m, 4H). |
| 485 | 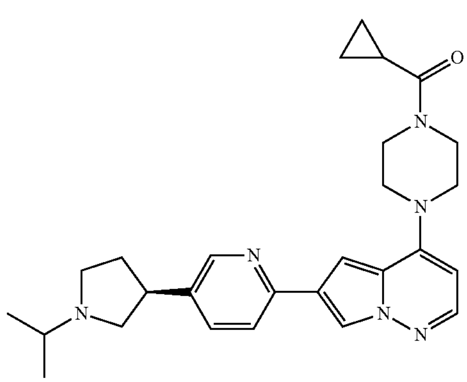 [SMILES: CC(C)N1CC[C@@H](c2ccc(-c3cc4c(N5CCN(C(=O)C6CC6)CC5)ccnn4c3)nc2)C1] | 459 | 1H-NMR (400 MHz, 6d-DMSO) δ ppm 8.48 (d, 1H, J = 1.6 Hz), 8.26 (d, 1H, J = 1.2 Hz), 7.93 (d, 1H, J = 5.2 Hz), 7.86 (d, 1H, J = 8.4 Hz), 7.72 (q, 1H, J1 = 8.4 Hz, J2 = 2.4 Hz), 7.14 (d, 1H, J = 1.6 Hz), 5.98 (d, 1H, J = 5.2 Hz), 4.01-3.92 (m, 2H), 3.73-3.70 (m, 2H), 3.57-3.36 (m, 4H), 3.30-3.28 (m, 1H), 3.02-2.96 (m, 1H), 2.76-2.70 (m, 2H), 2.50-2.48 (m, 1H), 2.44-2.38 (m, 1H), 2.29-2.20 (m, 1H), 2.06-1.99 (m, 1H), 1.81-1.74 (m, 1H), 1.08-1.04 (t, 6H, J = 6.8 Hz), 0.79-0.75 (m, 4H). |

TABLE 1-continued

| # | Structure | LCMS (M + 1) | NMR |
|---|-----------|--------------|-----|
| 486 | 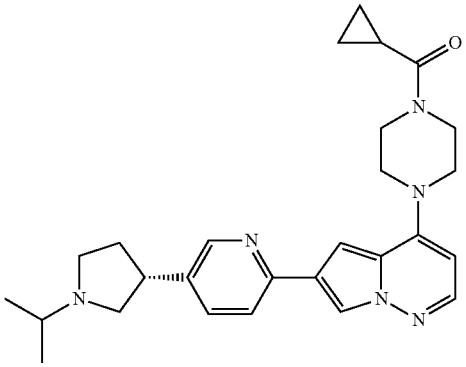 [SMILES: CC(C)N1CC[C@H](c2ccc(-c3cc4c(N5CCN(C(=O)C6CC6)CC5)ccnn4c3)nc2)C1] | 459 | 1H-NMR (400 MHz, CDCl3) δ ppm 8.51 (d, 1H, J = 2.0 Hz), 8.13 (d, 1H, J = 1.6 Hz), 7.85 (d, 1H, J = 5.2 Hz), 7.65 (d, 1H, J = 2.4 Hz), 7.60 (d, 1H, J = 8.0 Hz), 7.03 (d, 1H, J = 1.6 Hz), 5.82 (d, 1H, J = 5.2 Hz), 3.95-3.90 (m, 2H), 3.89-3.85 (m, 2H), 3.62-3.57 (m, 2H), 3.51-3.47 (m, 2H), 3.48-3.42 (m, 1H), 3.35-3.31 (m, 1H), 3.11-3.05 (m, 1H), 2.93-2.85 (m, 1H), 2.71-2.65 (m, 2H), 2.45-2.38 (m, 1H), 2.01-1.89 (m, 1H), 1.79-1.74 (m, 1H), 1.55-1.45 (m, 1H), 1.22-1.19 (m, 6H), 0.84-0.78 (m, 4H). |
| 487 | 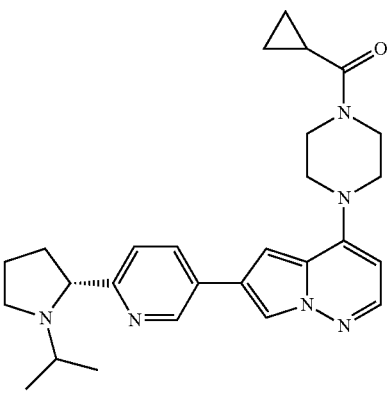 [SMILES: CC(C)N1CCC[C@@H]1c1ccc(-c2cc3c(N4CCN(C(=O)C5CC5)CC4)ccnn3c2)cn1] | 459 | 1H-NMR (400 MHz, 6d-DMSO) δ ppm 8.90 (d, 1H, J = 2.0 Hz), 8.26 (d, 1H, J = 1.6 Hz), 8.13 (dd, 1H, J1 = 8.0 Hz, J2 = 2.0 Hz), 7.93 (d, 1H, J = 5.2 Hz), 7.52 (d, 1H, J = 8.0 Hz), 7.13 (d, 1H, J = 1.2 Hz), 6.00 (d, 1H, J = 5.6 Hz), 3.93-3.92 (m, 2H), 3.85-3.81 (m, 1H), 3.71-3.70 (m, 2H), 3.56-3.49 (m, 4H), 3.10-3.05 (m, 1H), 2.75-2.69 (m, 1H), 2.62-2.59 (m, 1H), 2.20-2.11 (m, 1H), 2.06-2.00 (m, 1H), 1.83-1.72 (m, 2H), 1.68-1.61 (m, 1H), 0.94 (d, 6H, J = 6.4 Hz), 0.79-0.75 (m, 4H). |
| 488 | 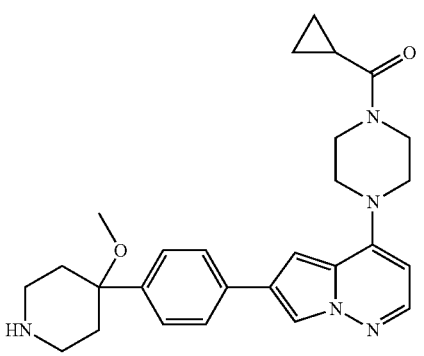 [SMILES: COC1(c2ccc(-c3cc4c(N5CCN(C(=O)C6CC6)CC5)ccnn4c3)cc2)CCNCC1] | 460 | 1H NMR (400 MHz, Methanol-d4) δ 8.00 (dd, J = 5.1, 1.8 Hz, 1H), 7.86 (dd, J = 5.5, 3.8 Hz, 1H), 7.82-7.74 (m, 2H), 7.51-7.40 (m, 2H), 6.96 (t, J = 2.4 Hz, 1H), 6.02 (d, J = 5.5 Hz, 1H), 4.06 (d, J = 12.5 Hz, 2H), 3.86 (s, 2H), 3.64 (s, 2H), 3.56 (s, 2H), 3.27-3.11 (m, 4H), 3.01 (d, J = 11.9 Hz, 3H), 2.27 (d, J = 14.3 Hz, 2H), 2.13-1.96 (m, 1H), 0.99-0.81 (m, 3H). |
| 489 | 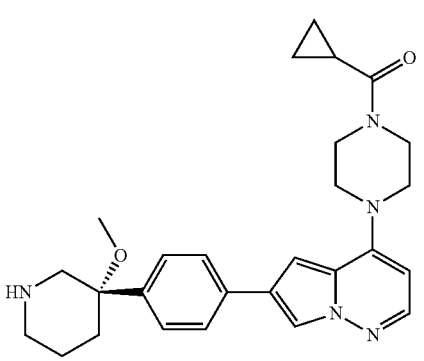 [SMILES: CO[C@]1(c2ccc(-c3cc4c(N5CCN(C(=O)C6CC6)CC5)ccnn4c3)cc2)CCCNC1] | 460 | 1H NMR (400 MHz, 6d-DMSO) δ ppm 9.03-9.00 (m, 1H), 8.46-8.35 (m, 1H), 8.25 (d, 1H, J = 1.6 Hz), 7.93 (d, 1H, J = 5.2 Hz), 7.91 (d, 2H, J = 8.4 Hz), 7.43 (d, 2H, J = 8.4 Hz), 7.09 (d, 1H, J = 1.6 Hz), 6.00 (d, 1H, J = 5.2 Hz), 3.94-3.93 (m, 2H), 3.74-3.73 (m, 2H), 3.57-3.53 (m, 2H), 3.52-3.49 (m, 2H), 3.45-3.42 (m, 1H), 3.24-3.20 (m, 1H), 3.18-3.14 (m, 1H), 3.00 (s, 3H), 2.95-2.92 (m, 1H), 2.23-2.22 (m, 1H), 2.11-2.09 (m, 2H), 2.00-1.83 (m, 2H), 0.79-0.74 (m, 4H). |

TABLE 1-continued

| # | Structure | LCMS (M + 1) | NMR |
|---|---|---|---|
| 490 | 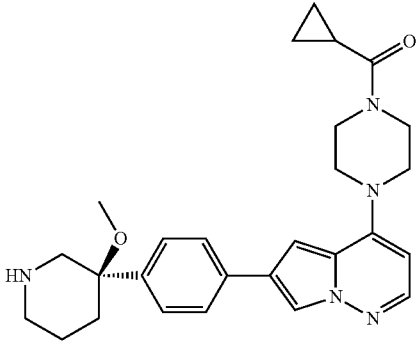 [SMILES: CO[C@@]1(c2ccc(-c3cc4c(N5CCN(C(=O)C6CC6)CC5)ccnn4c3)cc2)CCCNC1] | 460 | 1H NMR (400 MHz, 6d-DMSO) δ ppm 8.34 (s, 1H), 8.22 (d, 1H, J = 1.2 Hz), 7.92 (d, 1H, J = 5.6 Hz), 7.84 (d, 2H, J = 8.4 Hz), 7.42 (d, 2H, J = 8.4 Hz), 7.08 (d, 1H, J = 1.6 Hz), 5.99 (d, 1H, J = 5.2 Hz), 3.93-3.92 (m, 2H), 3.72-3.71 (m, 2H), 3.58-3.53 (m, 2H), 3.51-3.45 (m, 2H), 3.17-3.14 (m, 1H), 3.06-3.035 (m, 1H), 2.98 (s, 3H), 2.91-2.88 (m, 1H), 2.70-2.69 (m, 1H), 2.17-2.16 (m, 1H), 2.05-2.01 (m, 2H), 1.75-1.74 (m, 1H), 1.64-1.60 (m, 1H), 0.79-0.73 (m, 4H). |
| 491 | 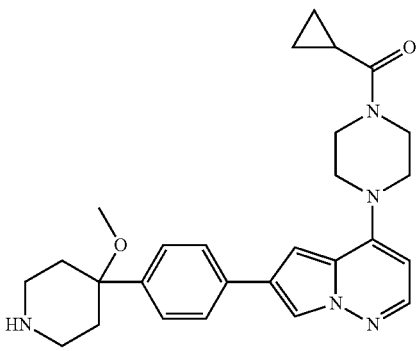 [SMILES: COC1(c2ccc(-c3cc4c(N5CCN(C(=O)C6CC6)CC5)ccnn4c3)cc2)CCNCC1] | 461 | 1H NMR (400 MHz, Methanol-d4) δ 8.53 (d, J = 1.9 Hz, 1H), 8.19 (t, J = 2.3 Hz, 1H), 7.92-7.73 (m, 3H), 7.17 (t, J = 2.1 Hz, 1H), 5.96 (dd, J = 5.6, 1.9 Hz, 1H), 4.03 (d, J = 24.3 Hz, 2H), 3.83 (s, 2H), 3.62 (d, J = 6.6 Hz, 2H), 3.54-3.53 (m, 3H), 3.30 (p, J = 1.6 Hz, 2H), 3.09 (tt, J = 12.4, 2.3 Hz, 2H), 3.01-2.89 (m, 2H), 2.17-2.05 (m, 2H), 2.06-1.88 (m, 3H), 0.97-0.89 (m, 2H), 0.88 (d, J = 2.6 Hz, 2H). |
| 492 | 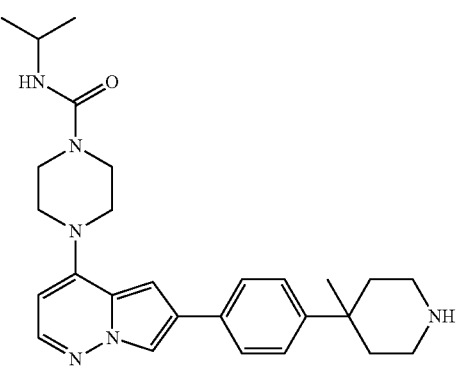 | 461 | 1H-NMR (500 MHz, 6d-DMSO) δ ppm 8.17 (s, 1H), 7.91 (d, 1H, J = 5.5 Hz), 7.78 (d, 2H, J = 8.0 Hz), 7.39 (d, 2H, J = 8.0 Hz), 7.00 (s, 1H), 6.33 (d, 2H, J = 7.5 Hz), 5.99 (d, 1H, J = 5.5 Hz), 3.89-3.80 (m, 1H), 3.79-3.65 (m, 8H), 3.45-3.41 (m, 1H), 3.29-3.19 (m, 2H), 3.13-3.11 (m, 2H), 2.51-2.15 (m, 2H), 1.80-1.79 (m, 2H), 1.23 (s, 3H), 1.08 (d, 6H, J = 6.5 Hz). |
| 493 | 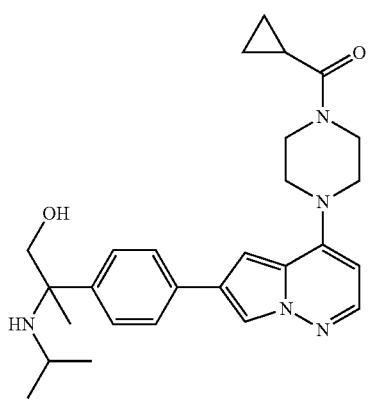 [SMILES: CC(C)NC(C)(CO)c1ccc(-c2cc3c(N4CCN(C(=O)C5CC5)CC4)ccnn3c2)cc1] | 462 | 1H NMR (400 MHz, Methanol-d4) δ 7.98 (d, J = 1.8 Hz, 1H), 7.85 (dd, J = 5.5, 2.3 Hz, 1H), 7.77-7.66 (m, 2H), 7.45-7.33 (m, 2H), 6.94 (d, J = 1.9 Hz, 1H), 6.00 (dd, J = 5.6, 2.2 Hz, 1H), 5.49 (d, J = 2.1 Hz, 1H), 4.04 (s, 2H), 3.85 (s, 2H), 3.63 (s, 2H), 3.54 (s, 2H), 3.42 (s, 1H), 2.75 (s, 2H), 2.53 (s, 2H), 2.03 (tt, J = 7.9, 4.8 Hz, 1H), 1.84 (d, J = 6.9 Hz, 5H), 1.49 (dd, J = 6.7, 2.2 Hz, 3H), 1.00-0.86 (m, 2H), 0.86 (q, J = 2.8 Hz, 1H). |

| # | Structure | LCMS (M + 1) | NMR |
|---|---|---|---|
| 494 | 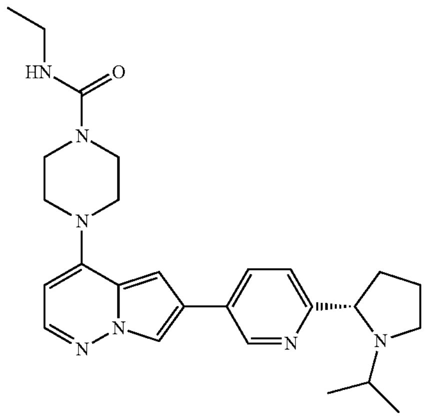 [SMILES: CCNC(=O)N1CCN(c2ccnn3cc(-c4ccc([C@@H]5CCCN5C(C)C)nc4)cc23)CC1] | 462 | 1H-NMR (400 MHz, 6d-DMSO) δ ppm 8.92 (d, 1H, J = 2.0 Hz), 8.27 (s, 1H), 8.27 (s, 1H), 8.16 (dd, 2H, J = 8.4, 2.0 Hz), 7.91 (d, 1H, J = 5.6 Hz), 7.53 (d, 1H, J = 8.4 Hz), 7.11 (s, 1H), 6.62 (t, 1H, J = 5.6 Hz), 6.00 (d, 1H, J = 5.6 Hz), 3.97-3.93 (m, 1H), 3.53-3.51 (m, 4H), 3.45-3.44 (m, 4H), 3.16-3.12 (m, 1H), 3.07 (quintet, 2H, J = 6.8 Hz), 2.84-2.77 (m, 1H), 2.71-2.65 (m, 1H), 2.24-2.15 (m, 1H), 1.86-1.75 (m, 2H), 1.72-1.65 (m, 1H), 1.03 (t, 3H, J = 6.8 Hz), 0.98-0.96 (m, 6H). |
| 495 | 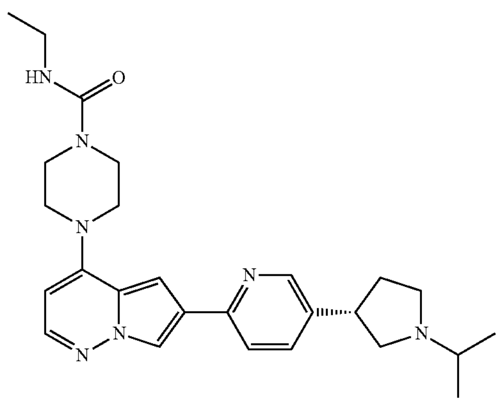 [SMILES: CCNC(=O)N1CCN(c2ccnn3cc(-c4ccc([C@@H]5CCN(C(C)C)C5)cn4)cc23)CC1] | 462 | 1H-NMR (400 MHz, 6d-DMSO) δ ppm 8.47 (d, 1H, J = 1.6 Hz), 8.23 (d, 1H, J = 1.6 Hz), 7.90 (d, 1H, J = 5.6 Hz), 7.85 (d, 1H, J = 8.0 Hz), 7.71 (d, 1H, J = 2.4 Hz), 7.69 (d, 1H, J = 2.0 Hz), 7.13 (d, 1H, J = 1.6 Hz), 6.61 (t, 1H, J = 5.2 Hz), 5.98 (d, 1H, J = 5.6 Hz), 3.52-3.51 (m, 4H), 3.48-3.44 (m, 4H), 3.31-3.25 (m, 1H), 3.11-3.04 (m, 2H), 2.98-2.94 (m, 1H), 2.74-2.68 (m, 2H), 2.49-2.46 (m, 1H), 2.41-2.36 (m, 1H), 2.27-2.18 (m, 1H), 1.77-1.70 (m, 1H), 1.06-1.01 (m, 9H). |
| 496 | 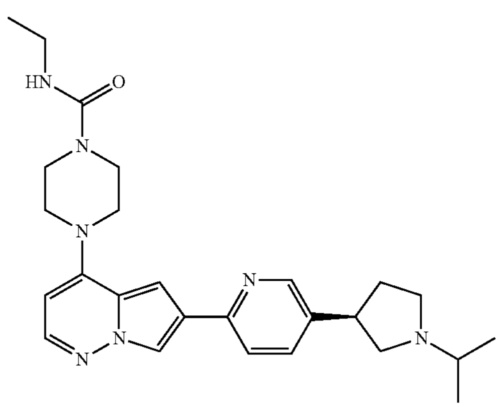 [SMILES: CCNC(=O)N1CCN(c2ccnn3cc(-c4ccc([C@H]5CCN(C(C)C)C5)cn4)cc23)CC1] | 462 | 1H-NMR (400 MHz, CDCl3) δ ppm 8.51 (d, 1H, J = 1.6 Hz), 8.12 (d, 1H, J = 1.6 Hz), 7.84 (d, 1H, J = 5.2 Hz), 7.64 (dd, 1H, J = 8.0, 2.0 Hz), 7.58 (d, 1H, J = 8.0 Hz), 7.01 (d, 1H, J = 1.6 Hz), 5.80 (d, 1H, J = 5.6 Hz), 4.49 (t, 1H, J = 7.2 Hz), 3.64-3.60 (m, 4H), 3.54-3.50 (m, 4H), 3.41-3.36 (m, 1H), 3.36-3.28 (m, 2H), 3.23-3.18 (m, 1H), 2.97-2.94 (m, 1H), 2.77-2.75 (m, 1H), 2.55-2.21 (m, 1H), 2.51-2.49 (m, 1H), 2.41-2.36 (m, 1H), 1.91-1.88 (m, 1H), 1.18 (t, 3H, J = 7.2 Hz), 1.16-1.12 (m, 6H). |

TABLE 1-continued

| # | Structure | LCMS (M + 1) | NMR |
|---|---|---|---|
| 497 | 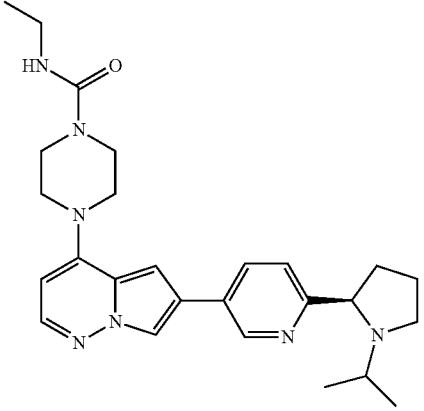 [SMILES: CCNC(=O)N1CCN(c2ccnn3cc(-c4ccc([C@H]5CCCN5C(C)C)nc4)cc23)CC1] | 462 | 1H-NMR (400 MHz, 6d-DMSO) δ ppm 8.90 (d, 1H, J = 1.6 Hz), 8.25 (d, 1H, J = 1.6 Hz), 8.13 (dd, 1H, J1 = 8.4 Hz, J2 = 2.4 Hz), 7.92 (d, 1H, J = 5.6 Hz), 7.52 (d, 1H, J = 8.4 Hz), 7.10 (d, 1H, J = 1.2 Hz), 6.62 (t, 1H, J = 5.2 Hz), 6.00 (d, 1H, J = 5.2 Hz), 3.83 (m, 1H), 3.54-3.52 (m, 4H), 3.45-3.43 (m, 4H), 3.12-3.05 (m, 3H), 2.75-2.69 (m, 1H), 2.62-2.58 (m, 1H), 2.20-2.11 (m, 1H), 1.83-1.73 (m, 2H), 1.68-1.61 (m, 1H), 1.04 (t, 3H, J = 7.2 Hz), 0.94 (d, 6H, J = 6.0 Hz). |
| 498 | 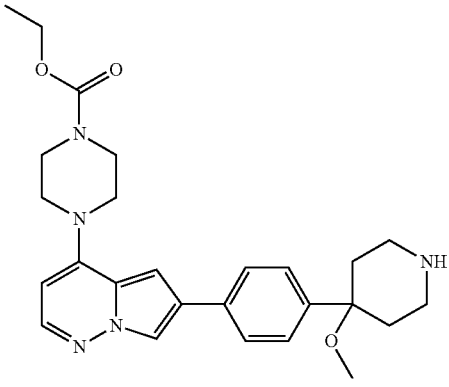 [SMILES: CCOC(=O)N1CCN(c2ccnn3cc(-c4ccc(C5(OC)CCNCC5)cc4)cc23)CC1] | 464 | 1H NMR (400 MHz, Methanol-d4) δ 8.53 (s, 1H), 7.99 (d, J = 1.8 Hz, 1H), 7.85 (d, J = 5.4 Hz, 1H), 7.82-7.73 (m, 2H), 7.53-7.37 (m, 2H), 6.91 (d, J = 1.8 Hz, 1H), 5.99 (d, J = 5.5 Hz, 1H), 4.18 (q, J = 7.1 Hz, 2H), 3.72 (t, J = 4.9 Hz, 4H), 3.50 (dd, J = 6.4, 3.8 Hz, 4H), 3.43-3.24 (m, 6H), 2.35 (dd, J = 15.2, 2.6 Hz, 2H), 2.14 (ddd, J = 14.5, 11.0, 6.5 Hz, 2H), 1.29 (t, J = 7.1 Hz, 3H). |
| 499 | 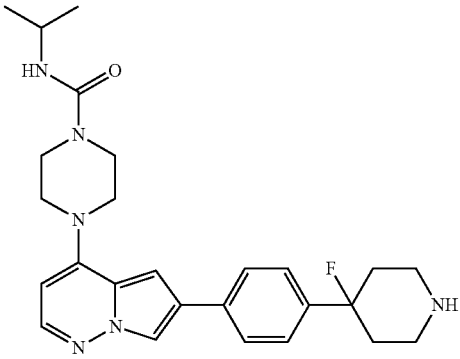 [SMILES: CC(C)NC(=O)N1CCN(c2ccnn3cc(-c4ccc(C5(F)CCNCC5)cc4)cc23)CC1] | 465 | |
| 500 | 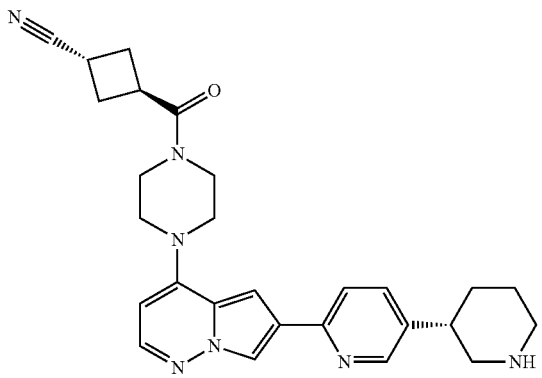 [SMILES: N#C[C@H]1C[C@H](C(=O)N2CCN(c3ccnn4cc(-c5ccc([C@@H]6CCCNC6)cn5)cc34)CC2)C1] | 470 | 1H-NMR (500 MHz, 6d-DMSO) δ ppm 8.45 (d, 1H, J = 2.0 Hz), 8.26 (d, 1H, J = 1.0 Hz), 7.93 (d, 1H, J = 5.5 Hz), 7.86 (d, 1H, J = 8.0 Hz), 7.67 (dd, 1H, J = 8.0, 2.5 Hz), 7.15 (d, 1H, J = 1.5 Hz), 5.98 (d, 1H, J = 6.0 Hz), 3.74-3.3.69 (m, 2H), 3.69-3.62 (m, 1H), 3.60-3.53 (m, 2H), 3.52-3.44 (m, 4H), 3.30-3.20 (m, 4H), 3.04-2.92 (m, 2H), 2.70-2.56 (m, 4H), 1.94-1.86 (m, 1H), 1.72-1.67 (m, 1H), 1.67-1.61 (m, 1H), 1.56-1.44 (m, 1H). |

TABLE 1-continued

| # | Structure | LCMS (M + 1) | NMR |
|---|---|---|---|
| 501 | 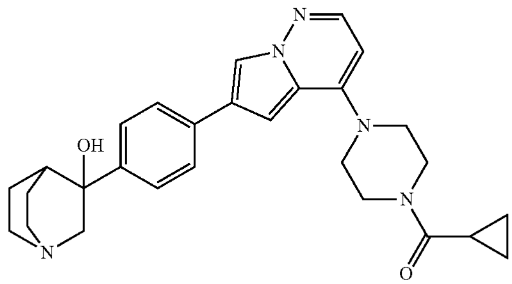 [SMILES: O=C(C1CC1)N1CCN(c2ccnn3cc(-c4ccc(C5(O)CN6CCC5CC6)cc4)cc23)CC1] | 472 | 1H NMR (400 MHz, Methanol-d4) δ 8.52 (s, 1H), 8.01 (d, J = 1.8 Hz, 1H), 7.87 (d, J = 5.5 Hz, 1H), 7.85-7.77 (m, 2H), 7.66-7.54 (m, 2H), 6.97 (d, J = 1.9 Hz, 1H), 6.01 (d, J = 5.5 Hz, 1H), 4.08-3.94 (m, 3H), 3.85 (s, 2H), 3.59 (d, J = 29.0 Hz, 4H), 3.54-3.36 (m, 3H), 2.53 (d, J = 4.0 Hz, 2H), 2.03 (tt, J = 7.9, 4.7 Hz, 1H), 1.99-1.85 (m, 2H), 1.77 (q, J = 10.4 Hz, 1H), 0.93 (dt, J = 5.3, 2.8 Hz, 2H), 0.87 (ddt, J = 7.6, 4.7, 2.4 Hz, 2H). |
| 502 | 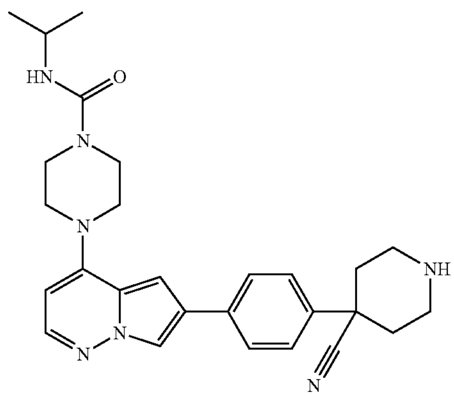 [SMILES: CC(C)NC(=O)N1CCN(c2ccnn3cc(-c4ccc(C5(C#N)CCNCC5)cc4)cc23)CC1] | 472 | 1H NMR (400 MHz, Methanol-d4) δ 8.47 (s, 1H), 8.02 (d, J = 1.8 Hz, 1H), 7.92-7.77 (m, 3H), 7.66-7.44 (m, 2H), 6.94 (d, J = 1.9 Hz, 1H), 6.00 (d, J = 5.5 Hz, 1H), 3.93 (dt, J = 13.1, 6.6 Hz, 1H), 3.65 (dd, J = 6.8, 3.5 Hz, 4H), 3.59-3.48 (m, 7H), 2.43 (d, J = 14.3 Hz, 2H), 2.30 (td, J = 13.7, 3.9 Hz, 2H), 1.18 (d, J = 6.6 Hz, 6H). |
| 503 | 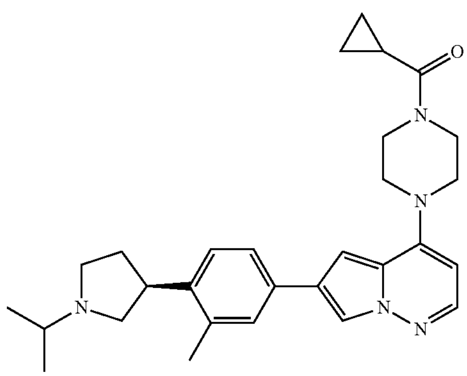 [SMILES: Cc1cc(-c2cc3c(N4CCN(C(=O)C5CC5)CC4)ccnn3c2)ccc1[C@@H]1CCN(C(C)C)C1] | 472 | 1H-NMR (400 MHz, DMSO-d6) δ ppm 8.14 (s, 1H), 7.90 (d, 1H, J = 6.0 Hz), 7.70-7.55 (m, 2H), 7.35 (d, 1H, J = 8.4 Hz), 7.01 (d, 1H, J = 1.6 Hz), 5.98 (d, 1H, J = 5.6 Hz), 4.00-3.80 (m, 2H), 3.80-3.60 (m, 2H), 3.60-3.40 (m, 5H), 3.32-2.54 (m, 5H), 2.35 (s, 3H), 2.30-2.19 (m, 1H), 2.06-1.94 (m, 1H), 1.85-1.65 (m, 1H), 1.21-0.95 (m, 6H), 0.83-0.65 (m, 4H). |
| 504 | 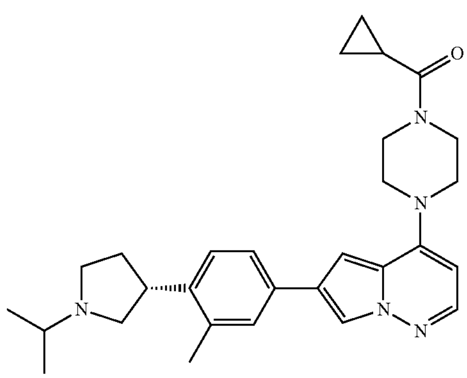 [SMILES: Cc1cc(-c2cc3c(N4CCN(C(=O)C5CC5)CC4)ccnn3c2)ccc1[C@H]1CCN(C(C)C)C1] | 472 | 1H-NMR (400 MHz, DMSO-d6) δ ppm 8.14 (d, 1H, J = 1.2 Hz), 7.90 (d, 1H, J = 5.6 Hz), 7.70-7.55 (m, 2H), 7.35 (d, 1H, J = 8.8 Hz), 7.01 (d, 1H, J = 1.6 Hz), 5.98 (d, 1H, J = 5.6 Hz), 4.00-3.80 (m, 2H), 3.80-3.60 (m, 2H), 3.60-3.40 (m, 5H), 3.32-2.54 (m, 5H), 2.35 (s, 3H), 2.30-2.19 (m, 1H), 2.06-1.94 (m, 1H), 1.85-1.70 (m, 1H), 1.21-0.95 (m, 6H), 0.83-0.65 (m, 4H). |

TABLE 1-continued

| # | Structure | LCMS (M + 1) | NMR |
|---|---|---|---|
| 505 | 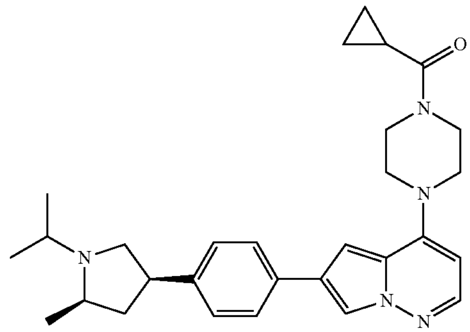 [SMILES: CC(C)N1C[C@@H](c2ccc(-c3cc4c(N5CCN(C(=O)C6CC6)CC5)ccnn4c3)cc2)C[C@H]1C] | 472 | 1H-NMR (400 MHz, MeOD) δ ppm 7.98 (d, 1H, J = 1.6 Hz), 7.86 (d, 1H, J = 5.6 Hz), 7.74 (d, 2H, J = 8.4 Hz), 7.37 (d, 2H, J = 8.0 Hz), 6.94 (d, 1H, J = 1.6 Hz), 6.01 (d, 1H, J = 5.2 Hz), 4.08-4.02 (m, 2H), 3.89-3.81 (m, 2H), 3.79-3.38 (m, 2H), 3.67-3.52 (m, 6H), 3.31-3.20 (m, 2H), 2.64-2.56 (m, 1H), 2.08-2.00 (m, 1 |
| 506 | 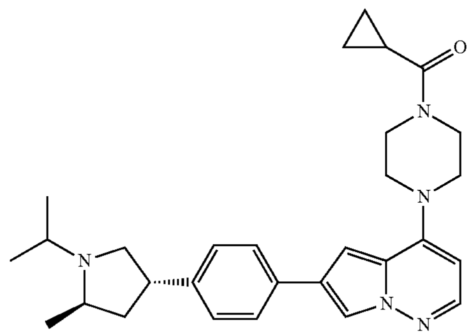 [SMILES: CC(C)N1C[C@H](c2ccc(-c3cc4c(N5CCN(C(=O)C6CC6)CC5)ccnn4c3)cc2)C[C@H]1C] | 472 | 1H-NMR (400 MHz, DMSO-d6) δ ppm 8.14 (s, 1H), 7.88 (d, 1H, J = 5.2 Hz), 7.71 (d, 2H, J = 8.0 Hz), 7.26 (d, 2H, J = 8.4 Hz), 7.01 (s, 1H), 5.96 (s, 1H), 3.96-3.87 (m, 2H), 3.74-3.66 (m, 2H), 3.58-3.42 (m, 4H), 3.31-3.20 (m, 2H), 3.18-3.10 (m, 1H), 3.06-2.96 (m, 1H), 2.92-2.82 (m, 1H), 2.08-1.92 (m, 2H), 1.82-1.76 (m, 1H), 1.08-1.02 (m, 6H), 0.95 (d, 3H, J = 6.8 Hz), 0.79-0.72 (m, 4H). |
| 507 | 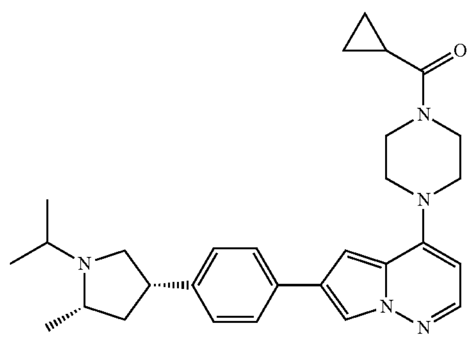 [SMILES: CC(C)N1C[C@H](c2ccc(-c3cc4c(N5CCN(C(=O)C6CC6)CC5)ccnn4c3)cc2)C[C@@H]1C] | 472 | 1H NMR (400 MHz, 6d-DMSO) δ ppm 8.14 (d, 1H, J = 1.2 Hz), 7.89 (d, 1H, J = 5.6 Hz), 7.72 (d, 2H, J = 8.0 Hz), 7.32 (d, 2H, J = 8.4 Hz), 7.02 (d, 1H, J = 5.2 Hz), 5.97 (d, 1H, J = 5.2 Hz), 3.92-3.91 (m, 2H), 3.70-3.60 (m, 2H), 3.53-3.52 (m, 2H), 3.47-3.46 (m, 2H), 3.16-3.15 (m, 3H), 2.81-2.80 (m, 1H), 2.49-2.34 (m, 1H), 2.02-2.01 (m, 1H), 1.46-1.45 (m, 1H), 1.22-1.21 (m, 1H), 1.12-1.11 (m, 6H), 0.96 (s, 3H), 0.78-0.73 (m, 4H). |
| 508 | 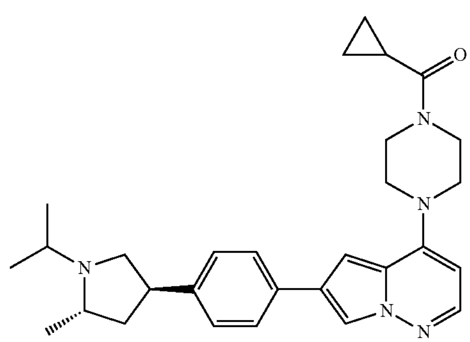 [SMILES: CC(C)N1C[C@@H](c2ccc(-c3cc4c(N5CCN(C(=O)C6CC6)CC5)ccnn4c3)cc2)C[C@@H]1C] | 472 | 1H NMR (400 MHz, 6d-DMSO) δ ppm 8.18 (s, 1H), 7.90 (d, 1H, J = 5.2 Hz), 7.79-7.78 (m, 2H), 7.35-7.34 (m, 2H), 7.05-7.04 (m, 1H), 5.97 (d, 1H, J = 5.6 Hz), 3.92-3.91 (m, 2H), 3.70-3.69 (m, 4H), 3.54-3.47 (m, 6H), 2.02-2.01 (m, 2H), 1.34-1.22 (m, 6H), 1.08-1.03 (m, 5H), 0.78-0.74 (m, 4H). |

TABLE 1-continued

| # | Structure | LCMS (M + 1) | NMR |
|---|---|---|---|
| 509 | 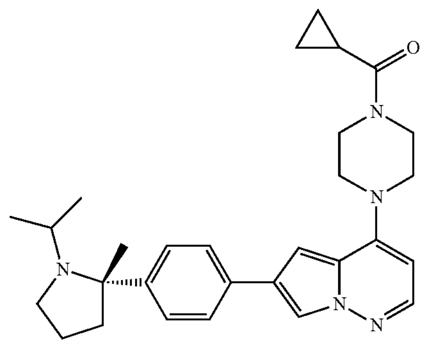 [SMILES: CC(C)N1CCC[C@@]1(C)c1ccc(-c2cc3c(N4CCN(C(=O)C5CC5)CC4)ccnn3c2)cc1] | 472 | 1H NMR (400 MHz, DMSO-d6) δ 8.14 (d, J = 1.7 Hz, 1H), 7.89 (d, J = 5.4 Hz, 1H), 7.71 (d, J = 8.2 Hz, 2H), 7.50 (d, J = 8.4 Hz, 2H), 7.02 (d, J = 1.9 Hz, 1H), 5.97 (d, J = 5.5 Hz, 1H), 3.99-3.85 (m, 2H), 3.70 (s, 2H), 3.54 (s, 2H), 3.47 (s, 2H), 3.14-3.04 (m, 1H), 2.82-2.67 (m, 2H), 2.06-1.96 (m, 1H), 1.77 (d, J = 4.7 Hz, 4H), 1.38 (s, 3H), 0.99 (d, J = 6.3 Hz, 3H), 0.82 (d, J = 6.5 Hz, 3H), 0.79-0.70 (m, 4H). |
| 510 | 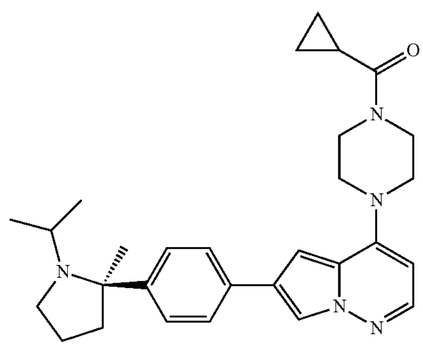 [SMILES: CC(C)N1CCC[C@]1(C)c1ccc(-c2cc3c(N4CCN(C(=O)C5CC5)CC4)ccnn3c2)cc1] | 472 | |
| 511 | 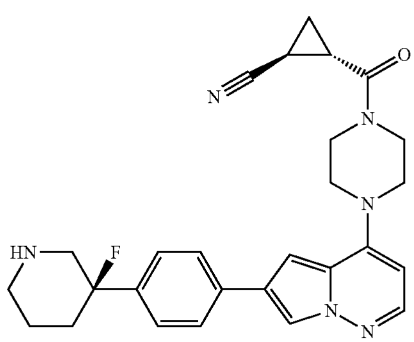 [SMILES: N#C[C@H]1C[C@@H]1C(=O)N1CCN(c2ccnn3cc(-c4ccc([C@]5(F)CCCNC5)cc4)cc23)CC1] | 473 | 1H-NMR (400 MHz, DMSO-d6) δ ppm 8.21 (d, 1H, J = 1.2 Hz), 7.92 (d, 1H, J = 5.6 Hz), 7.83 (d, 2H, J = 8.0 Hz), 7.43 (d, 2H, J = 8.0 Hz), 7.08 (d, 1H, J = 1.2 Hz), 6.00 (d, 1H, J = 5.6 Hz), 4.04-3.90 (m, 2H), 3.80-3.60 (m, 2H), 3.60-3.40 (m, 5H), 3.05-2.85 (m, 3H), 2.70-2.57 (m, 1H), 2.15-1.65 (m, 5H), 1.60-1.50 (m, 1H), 1.50-1.40 (m, 1H), 1.40-1.30 (m, 1H). |
| 512 | 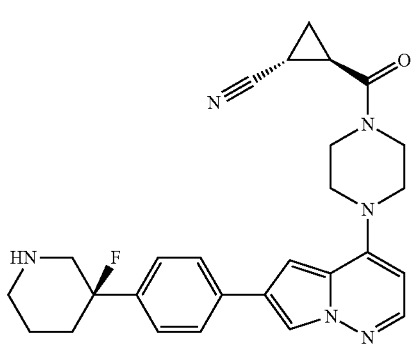 [SMILES: N#C[C@@H]1C[C@H]1C(=O)N1CCN(c2ccnn3cc(-c4ccc([C@]5(F)CCCNC5)cc4)cc23)CC1] | 473 | 1H-NMR (400 MHz, DMSO-d6) δ ppm 8.23 (s, 1H), 7.92 (d, 1H, J = 5.2 Hz), 7.86 (d, 2H, J = 8.0 Hz), 7.45 (d, 2H, J = 8.4 Hz), 7.10 (s, 1H), 6.00 (d, 1H, J = 5.2 Hz), 4.10-3.87 (m, 2H), 3.80-3.65 (m, 2H), 3.65-3.38 (m, 5H), 3.20-2.60 (m, 5H), 2.35-1.70 (m, 4H), 1.70-1.55 (m, 1H), 1.55-1.40 (m, 1H), 1.40-1.30 (m, 1H). |

TABLE 1-continued

| # | Structure | LCMS (M + 1) | NMR |
|---|---|---|---|
| 513 | 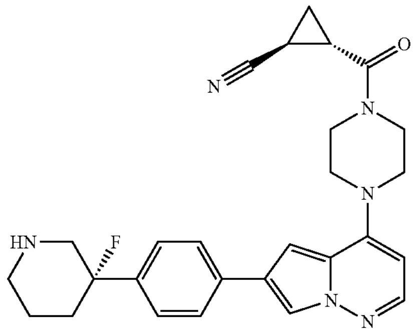 [SMILES: N#C[C@H]1C[C@@H]1C(=O)N1CCN(c2ccnn3cc(-c4ccc([C@@]5(F)CCCNC5)cc4)cc23)CC1] | 473 | 1H-NMR (400 MHz, DMSO-d6) δ ppm 8.22 (d, 1H, J = 1.2 Hz), 7.92 (d, 1H, J = 5.2 Hz), 7.84 (d, 2H, J = 8.4 Hz), 7.43 (d, 2H, J = 8.4 Hz), 7.09 (d, 1H, J = 1.2 Hz), 6.00 (d, 1H, J = 6.0 Hz), 4.04-3.90 (m, 2H), 3.80-3.65 (m, 2H), 3.65-3.40 (m, 5H), 3.25-2.80 (m, 4H), 2.75-2.60 (m, 1H), 2.30-1.90 (m, 3H), 1.90-1.50 (m, 2H), 1.50-1.40 (m, 1H), 1.40-1.30 (m, 1H). |
| 514 | 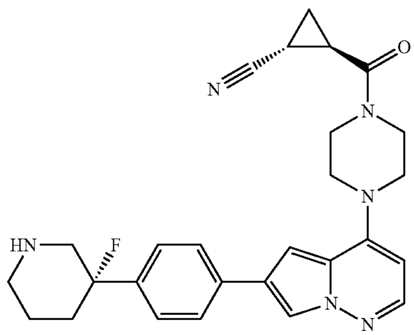 [SMILES: N#C[C@@H]1C[C@H]1C(=O)N1CCN(c2ccnn3cc(-c4ccc([C@@]5(F)CCCNC5)cc4)cc23)CC1] | 473 | 1H-NMR (400 MHz, DMSO-d6) δ ppm 8.22 (d, 1H, J = 1.2 Hz), 7.92 (d, 1H, J = 5.2 Hz), 7.84 (d, 2H, J = 8.0 Hz), 7.44 (d, 2H, J = 8.4 Hz), 7.09 (d, 1H, J = 1.6 Hz), 6.00 (d, 1H, J = 5.6 Hz), 4.04-3.90 (m, 2H), 3.80-3.65 (m, 2H), 3.65-3.40 (m, 5H), 3.25-2.80 (m, 4H), 2.75-2.60 (m, 1H), 2.30-1.90 (m, 3H), 1.90-1.50 (m, 2H), 1.50-1.40 (m, 1H), 1.40-1.30 (m, 1H). |
| 515 | 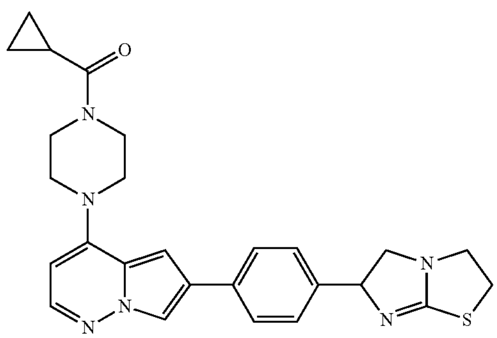 [SMILES: O=C(C1CC1)N1CCN(c2ccnn3cc(-c4ccc(C5CN6CCSC6=N5)cc4)cc23)CC1] | 473 | 1H NMR (400 MHz, Methanol-d4) δ 7.97 (d, J = 1.9 Hz, 1H), 7.85 (d, J = 5.4 Hz, 1H), 7.72 (d, J = 8.2 Hz, 2H), 7.37 (d, J = 7.9 Hz, 2H), 6.94 (d, J = 1.9 Hz, 1H), 6.00 (d, J = 5.5 Hz, 1H), 5.42 (t, J = 9.0 Hz, 1H), 4.04 (s, 2H), 3.85 (s, 2H), 3.75 (dt, J = 18.2, 8.7 Hz, 2H), 3.66 (ddd, J = 11.0, 6.6, 4.2 Hz, 3H), 3.54 (s, 2H), 3.46 (ddd, J = 8.9, 6.5, 4.4 Hz, 1H), 3.23 (td, J = 8.7, 6.6 Hz, 1H), 3.06 (t, J = 9.0 Hz, 1H), 2.07-1.98 (m, 1H), 0.93 (dt, J = 5.3, 2.8 Hz, 2H), 0.87 (dt, J = 8.1, 2.9 Hz, 2H). |
| 516 | 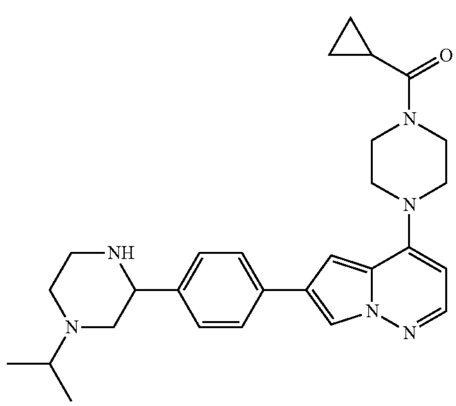 | 473 | 1H-NMR (400 MHz, 6d-DMSO) δ ppm 8.17 (s, 1H), 7.90 (d, 1H, J = 5.2 Hz), 7.76 (d, 2H, J = 7.6 Hz), 7.41 (d, 2H, J = 7.6 Hz), 7.04 (s, 1H), 5.98 (d, 1H, J = 5.2 Hz), 3.94-3.92 (m, 2H), 3.71-3.69 (m, 3H), 3.56-3.50 (m, 2H), 3.50-3.44 (m, 2H), 2.98-2.94 (m, 1H), 2.78-2.72 (m, 1H), 2.71-2.62 (m, 3H), 2.23-2.21 (m, 1H), 2.04-1.98 (m, 2H), 0.97 (d, 6H, J = 6.0 Hz), 0.78-0.74 (m, 4H). |

TABLE 1-continued
| # | Structure | LCMS (M + 1) | NMR |
|---|---|---|---|
| 517 | 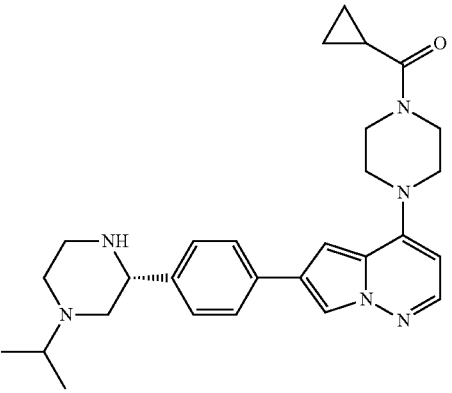 [SMILES: CC(C)N1CCN[C@H](c2ccc(-c3cc4c(N5CCN(C(=O)C6CC6)CC5)ccnn4c3)cc2)C1] | 473 | 1H-NMR (400 MHz, 6d-DMSO) δ ppm 8.18 (d, 1H, J = 1.6 Hz), 7.90 (d, 1H, J = 5.2 Hz), 7.77 (d, 2H, J = 7.6 Hz), 7.42 (d, 2H, J = 7.6 Hz), 7.05 (d, 1H, J = 1.6 Hz), 5.98 (d, 1H, J = 5.2 Hz), 3.94-3.92 (m, 2H), 3.71-3.69 (m, 3H), 3.56-3.40 (m, 5H), 3.01-2.98 (m, 1H), 2.84-2.64 (m, 4H), 2.28-2.22 (m, 1H), 2.10-1.98 (m, 2H), 0.98 (d, 6H, J = 6.0 Hz), 0.80-0.72 (m, 4H). |
| 518 | 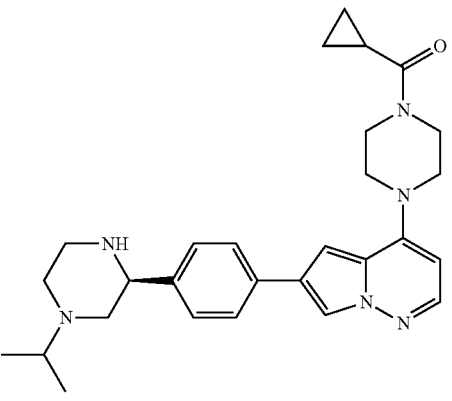 [SMILES: CC(C)N1CCN[C@@H](c2ccc(-c3cc4c(N5CCN(C(=O)C6CC6)CC5)ccnn4c3)cc2)C1] | 473 | 1H-NMR (400 MHz, 6d-DMSO) δ ppm 8.17 (d, 1H, J = 1.6 Hz), 7.90 (d, 1H, J = 5.2 Hz), 7.77 (d, 2H, J = 7.6 Hz), 7.42 (d, 2H, J = 7.6 Hz), 7.05 (d, 1H, J = 1.6 Hz), 5.98 (d, 1H, J = 5.2 Hz), 3.94-3.92 (m, 2H), 3.71-3.69 (m, 3H), 3.56-3.40 (m, 5H), 3.01-2.98 (m, 1H), 2.84-2.64 (m, 4H), 2.28-2.22 (m, 1H), 2.10-1.98 (m, 2H), 0.98 (d, 6H, J = 6.0 Hz), 0.80-0.72 (m, 4H). |
| 519 | 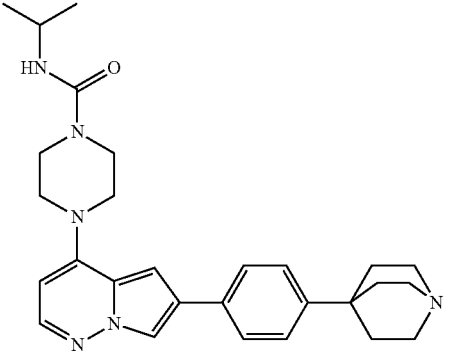 [SMILES: CC(C)NC(=O)N1CCN(c2ccnn3cc(-c4ccc(C56CCN(CC5)CC6)cc4)cc23)CC1] | 473 | |
| 520 | 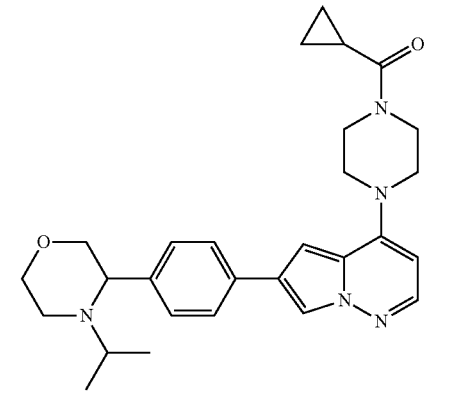 [SMILES: CC(C)N1CCOCC1c1ccc(-c2cc3c(N4CCN(C(=O)C5CC5)CC4)ccnn3c2)cc1] | 474 | 1H NMR (400 MHz, Methanol-d4) δ 7.94 (d, J = 1.8 Hz, 1H), 7.82 (d, J = 5.5 Hz, 1H), 7.73-7.60 (m, 2H), 7.45-7.33 (m, 2H), 6.90 (d, J = 1.9 Hz, 1H), 5.97 (d, J = 5.5 Hz, 1H), 4.00 (s, 2H), 3.91 (d, J = 10.7 Hz, 1H), 3.82 (s, 2H), 3.70 (td, J = 11.3, 2.4 Hz, 1H), 3.66-3.56 (m, 4H), 3.51 (s, 2H), 3.47-3.36 (m, 1H), 2.88 (p, J = 6.7 Hz, 1H), 2.83-2.72 (m, 1H), 2.55 (td, J = 11.7, 3.3 Hz, 1H), 1.99 (tt, J = 7.9, 4.8 Hz, 1H), 1.02 (d, J = 6.9 Hz, 3H), 0.90 (dt, J = 4.8, 2.8 Hz, 2H), 0.84 (dd, J = 7.2, 2.6 Hz, 6H) |

TABLE 1-continued

| # | Structure | LCMS (M + 1) | NMR |
|---|---|---|---|
| 521 | 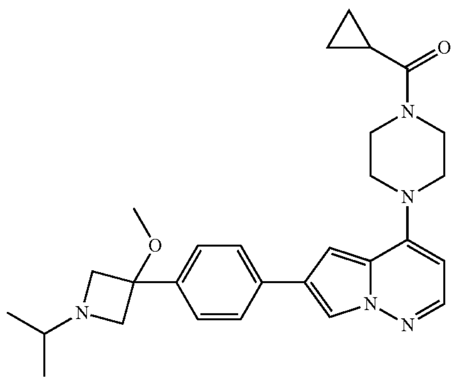 [SMILES: COC1(c2ccc(-c3cc4c(N5CCN(C(=O)C6CC6)CC5)ccnn4c3)cc2)CN(C(C)C)C1] | 474 | 1H-NMR (400 MHz, 6d-DMSO) δ ppm 8.21 (d, 1H, J = 1.6 Hz), 7.92 (d, 1H, J = 5.6 Hz), 7.84 (d, 2H, J = 8.0 Hz), 8.47 (d, 2H, J = 8.0 Hz), 7.07 (d, 1H, J = 1.6 Hz), 5.99 (d, 1H, J = 5.6 Hz), 3.95-3.90 (m, 2H), 3.75-3.70 (m, 2H), 3.58-3.52 (m, 4H), 3.50-3.45 (m, 2H), 3.23-3.21 (m, 2H), 2.95 (s, 3H), 2.35-2.31 (m, 1H), 2.06-2.01 (m, 1H), 0.90 (d, 6H, J = 8.4 Hz), 0.81-0.72 (m, 4H). |
| 522 | 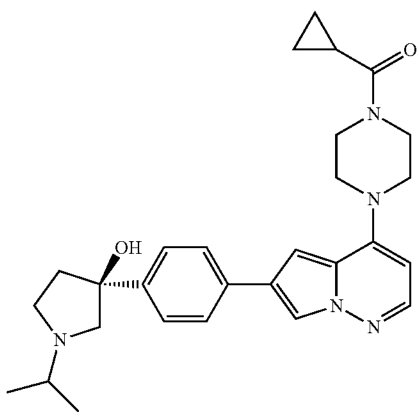 [SMILES: CC(C)N1CC[C@](O)(c2ccc(-c3cc4c(N5CCN(C(=O)C6CC6)CC5)ccnn4c3)cc2)C1] | 474 | 1H NMR (400 MHz, DMSO-d6) δ 8.16 (d, J = 1.8 Hz, 1H), 7.90 (d, J = 5.4 Hz, 1H), 7.82-7.69 (m, 2H), 7.54-7.43 (m, 2H), 7.03 (d, J = 1.9 Hz, 1H), 5.97 (d, J = 5.5 Hz, 1H), 5.14 (s, 1H), 3.92 (s, 2H), 3.70 (s, 2H), 3.50 (d, J = 29.4 Hz, 4H), 2.94-2.71 (m, 4H), 2.18-1.93 (m, 3H), 1.04 (t, J = 6.4 Hz, 7H), 0.76 (tt, J = 7.9, 2.9 Hz, 4H). |
| 523 | 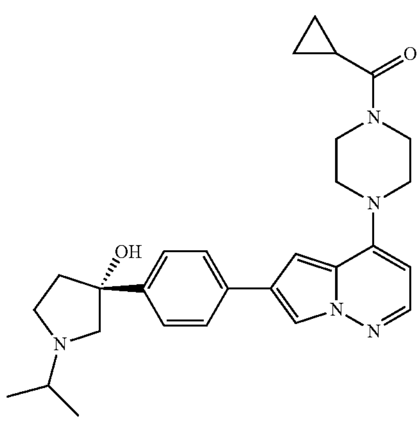 [SMILES: CC(C)N1CC[C@@](O)(c2ccc(-c3cc4c(N5CCN(C(=O)C6CC6)CC5)ccnn4c3)cc2)C1] | 474 | |
| 524 | 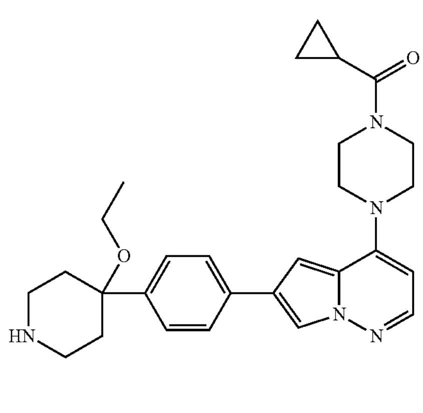 [SMILES: CCOC1(c2ccc(-c3cc4c(N5CCN(C(=O)C6CC6)CC5)ccnn4c3)cc2)CCNCC1] | 474 | 1H NMR (400 MHz, Methanol-d4) δ 7.97 (d, J = 1.8 Hz, 1H), 7.84 (d, J = 5.5 Hz, 1H), 7.79-7.66 (m, 2H), 7.50-7.41 (m, 2H), 6.93 (d, J = 1.8 Hz, 1H), 5.98 (d, J = 5.5 Hz, 1H), 4.02 (s, 2H), 3.84 (s, 2H), 3.62 (s, 2H), 3.53 (s, 2H), 3.20-3.04 (m, 4H), 3.04-2.89 (m, 2H), 2.17-2.04 (m, 2H), 2.04-1.85 (m, 3H), 1.14 (t, J = 7.0 Hz, 3H), 0.92 (dt, J = 4.7, 2.8 Hz, 2H), 0.85 (ddt, J = 7.5, 4.6, 2.6 Hz, 2H). |

US 10,669,277 B2
241                                                                                      242
TABLE 1-continued
| # | Structure | LCMS (M + 1) | NMR |
|---|-----------|--------------|-----|
| 525 | 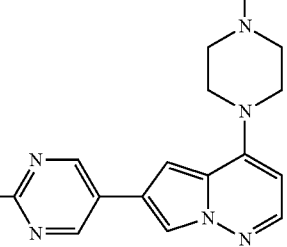 | 474 | 1H NMR (400 MHz, 6d-DMSO) δ ppm 9.18 (s, 2H), 8.36 (d, 1H, J = 1.6 Hz), 7.94 (d, 1H, J = 5.6 Hz), 7.24 (d, 1H, J = 1.6 Hz), 6.00 (d, 1H, J = 5.6 Hz), 3.92-3.91 (m, 2H), 3.70-3.69 (m, 2H), 3.55-3.49 (m, 2H), 3.32-3.21 (m, 2H), 2.88-2.85 (m, 2H), 2.76-2.70 (m, 2H), 2.26-2.21 (m, 2H), 2.03-2.02 (m, 1H), 1.94-1.92 (m, 2H), 1.78-1.75 (m, 2H), 0.98 (d, 6H, J = 6.4 Hz), 0.77-0.74 (m, 4H). |
| 526 | 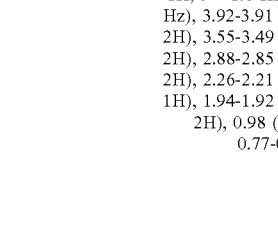 | 475 | 1H NMR (400 MHz, DMSO-d6) δ 8.72-8.64 (m, 1H), 8.26 (d, J = 1.8 Hz, 1H), 7.92 (d, J = 5.4 Hz, 1H), 7.85 (dd, J = 5.6, 1.6 Hz, 2H), 7.18 (d, J = 1.8 Hz, 1H), 5.98 (d, J = 5.5 Hz, 1H), 5.36 (s, 1H), 3.96-3.89 (m, 2H), 3.70 (s, 2H), 3.52 (d, J = 31.6 Hz, 4H), 2.92 (d, J = 9.8 Hz, 1H), 2.87-2.73 (m, 3H), 2.13 (dt, J = 12.9, 8.0 Hz, 1H), 2.03 (dtd, J = 12.7, 7.8, 7.3, 4.8 Hz, 2H), 1.42-1.35 (m, 1H), 1.11 (d, J = 15.0 Hz, 6H), 0.76 (tt, J = 7.9, 2.9 Hz, 4H). |
| 527 | 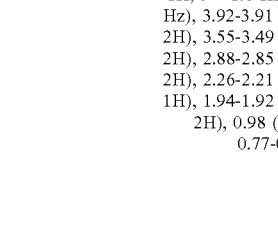 | 475 | |
| 528 | 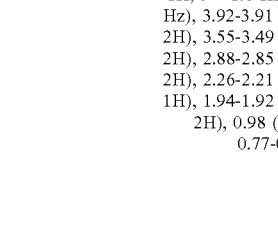 | 475 | 1H-NMR (400 MHz, DMSO-d6) δ ppm 8.84 (s, 2H), 8.18 (d, 1H, J = 1.6 Hz), 8.17 (s, 1H), 7.90 (d, 1H, J = 5.6 Hz), 7.06 (d, 1H, J = 1.6 Hz), 5.99 (d, 1H, J = 5.6 Hz), 3.93-3.90 (m, 2H), 3.78-3.72 (m, 4H), 3.72-3.69 (m, 2H), 3.55-3.45 (m, 4H), 2.77-2.72 (m, 1H), 2.57-2.50 (m, 4H), 2.04-2.00 (m, 1H), 1.01 (d, 6H, J = 6.4 Hz), 0.79-0.74 (m, 4H). |

TABLE 1-continued

| # | Structure | LCMS (M + 1) | NMR |
|---|---|---|---|
| 529 | 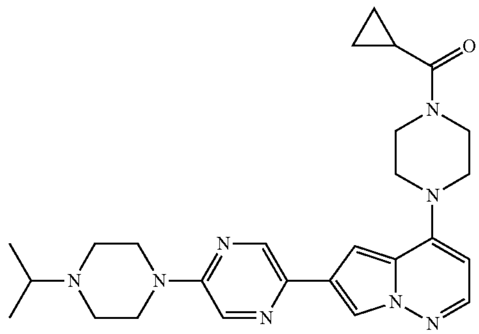 [SMILES: CC(C)N1CCN(c2cnc(-c3cc4c(N5CCN(C(=O)C6CC6)CC5)ccnn4c3)cn2)CC1] | 475 | 1H-NMR (400 MHz, 6d-DMSO) δ ppm 8.68 (d, 1H, J = 0.8 Hz), 8.31 (s, 1H), 8.17 (d, 1H, J = 1.6 Hz), 7.91 (d, 1H, J = 5.6 Hz), 7.08 (d, 1H, J = 1.6 Hz), 5.99 (d, 1H, J = 5.6 Hz), 3.93-3.90 (m, 2H), 3.71-3.70 (m, 2H), 3.56-3.54 (m, 6H), 3.33-3.31 (m, 2H), 2.73-2.67 (m, 1H), 2.57-2.54 (m, 4H), 2.05-1.99 (m, 1H), 1.00 (d, 6H, J = 6.4 Hz), 0.78-0.74 (m, 4H). |
| 530 | 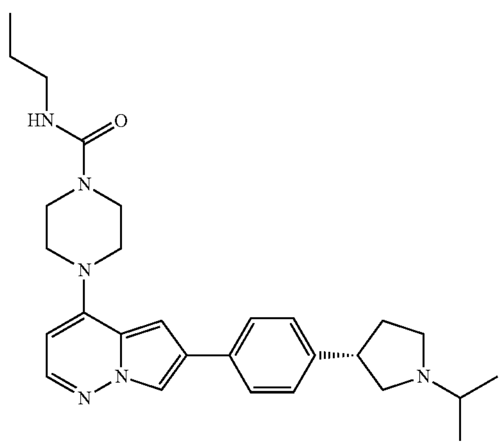 [SMILES: CCCNC(=O)N1CCN(c2ccnn3cc(-c4ccc([C@@H]5CCN(C(C)C)C5)cc4)cc23)CC1] | 475 | 1H-NMR (400 MHz, DMSO-d6) δ ppm 8.14 (d, 1H, J = 0.8 Hz), 7.89 (d, 1H, J = 4.8 Hz), 7.72 (d, 2H, J = 8.4 Hz), 7.29 (d, 2H, J = 8.4 Hz), 6.99 (d, 1H, J = 1.6 Hz), 6.63-6.60 (m, 1H), 5.98 (d, 1H, J = 5.6 Hz), 3.54-3.50 (m, 4H), 3.43-3.40 (m, 4H), 3.29-3.25 (m, 1H), 3.04-2.97 (m, 3H), 2.75-2.69 (m, 2H), 2.47-2.39 (m, 2H), 2.24-2.20 (m, 1H), 1.78-1.73 (m, 1H), 1.46-1.41 (m, 2H), 1.09-1.04 (m, 6H), 0.85 (t, 3H, J = 7.6 Hz). |
| 531 | 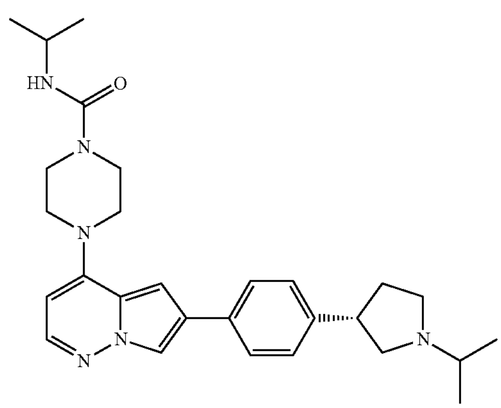 [SMILES: CC(C)NC(=O)N1CCN(c2ccnn3cc(-c4ccc([C@@H]5CCN(C(C)C)C5)cc4)cc23)CC1] | 475 | 1H-NMR (400 MHz, DMSO-d6) δ ppm 8.14 (d, 1H, J = 1.6 Hz), 7.89 (d, 1H, J = 6.0 Hz), 7.72 (d, 2H, J = 7.6 Hz), 7.29 (d, 2H, J = 8.4 Hz), 6.99 (d, 1H, J = 1.6 Hz), 6.31 (d, 1H, J = 7.6 Hz), 5.98 (d, 1H, J = 5.6 Hz), 3.81-3.76 (m, 1H), 3.53-3.51 (m, 4H), 3.44-3.43 (m, 4H), 3.29-3.25 (m, 1H), 3.01-2.97 (m, 1H), 2.75-2.68 (m, 2H), 2.47-2.37 (m, 2H), 2.24-2.19 (m, 1H), 1.78-1.73 (m, 1H), 1.09-1.04 (m, 6H). |

TABLE 1-continued

| # | Structure | LCMS (M + 1) | NMR |
|---|---|---|---|
| 532 | 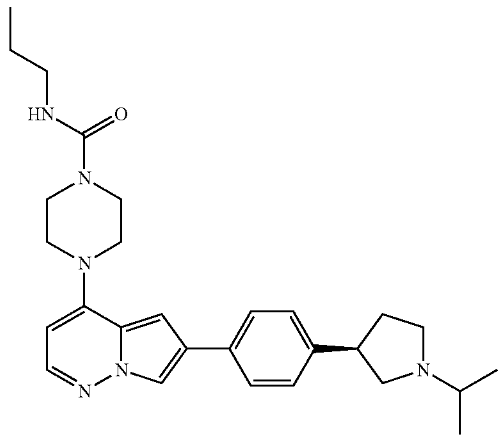 [SMILES: CCCNC(=O)N1CCN(c2ccnn3cc(-c4ccc([C@H]5CCN(C(C)C)C5)cc4)cc23)CC1] | 475 | 1H-NMR (400 MHz, DMSO-d6) δ ppm 8.14 (d, 1H, J = 1.2 Hz), 7.89 (d, 1H, J = 5.6 Hz), 7.72 (d, 2H, J = 8.0 Hz), 7.29 (d, 2H, J = 8.4 Hz), 6.99 (d, 1H, J = 2.0 Hz), 6.63-6.60 (m, 1H), 5.98 (d, 1H, J = 5.6 Hz), 3.53-3.52 (m, 4H), 3.44-3.43 (m, 4H), 3.29-3.25 (m, 1H), 3.04-2.97 (m, 3H), 2.73-2.69 (m, 2H), 2.47-2.39 (m, 2H), 2.23-2.20 (m, 1H), 1.78-1.71 (m, 1H), 1.46-1.41 (m, 2H), 1.07-1.04 (m, 6H), 0.85 (t, 3H, J = 7.6 Hz). |
| 533 | 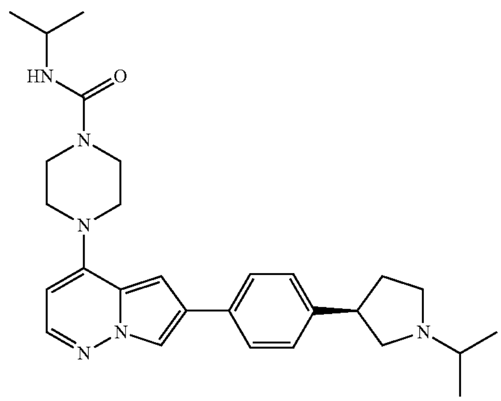 [SMILES: CC(C)NC(=O)N1CCN(c2ccnn3cc(-c4ccc([C@H]5CCN(C(C)C)C5)cc4)cc23)CC1] | 475 | 1H-NMR (400 MHz, DMSO-d6) δ ppm 8.14 (d, 1H, J = 1.2 Hz), 7.89 (d, 1H, J = 5.6 Hz), 7.72 (d, 2H, J = 8.0 Hz), 7.29 (d, 2H, J = 8.0 Hz), 6.99 (d, 1H, J = 1.2 Hz), 6.31 (d, 1H, J = 7.6 Hz), 5.98 (d, 1H, J = 5.6 Hz), 3.81-3.76 (m, 1H), 3.52-3.51 (m, 4H), 3.44-3.43 (m, 4H), 3.29-3.25 (m, 1H), 3.02-2.98 (m, 1H), 2.75-2.69 (m, 2H), 2.47-2.37 (m, 2H), 2.24-2.19 (m, 1H), 1.78-1.75 (m, 1H), 1.09-1.04 (m, 6H). |
| 534 | 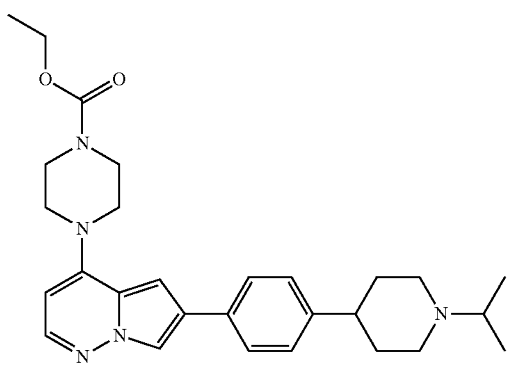 [SMILES: CCOC(=O)N1CCN(c2ccnn3cc(-c4ccc(C5CCN(C(C)C)CC5)cc4)cc23)CC1] | 476 | 1H NMR (400 MHz, Methanol-d4) δ 7.92 (d, J = 1.8 Hz, 1H), 7.81 (d, J = 5.4 Hz, 1H), 7.72-7.58 (m, 2H), 7.31-7.18 (m, 2H), 6.85 (d, J = 1.8 Hz, 1H), 5.97 (d, J = 5.4 Hz, 1H), 4.17 (q, J = 7.1 Hz, 2H), 3.70 (t, J = 5.0 Hz, 4H), 3.56-3.37 (m, 4H), 3.03 (dt, J = 12.2, 3.1 Hz, 2H), 2.77 (hept, J = 6.6 Hz, 1H), 2.53 (tt, J = 11.9, 4.1 Hz, 1H), 2.34 (td, J = 11.8, 2.8 Hz, 2H), 1.95-1.84 (m, 2H), 1.83-1.69 (m, 2H), 1.28 (t, J = 7.1 Hz, 3H), 1.12 (d, J = 6.6 Hz, 6H). |
| 535 | 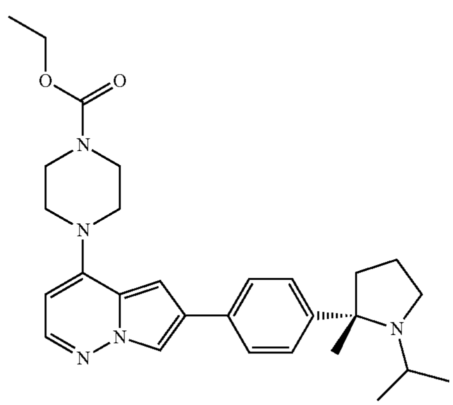 [SMILES: CCOC(=O)N1CCN(c2ccnn3cc(-c4ccc([C@]5(C)CCCN5C(C)C)cc4)cc23)CC1] | 476 | 1H NMR (400 MHz, DMSO-d6) δ 8.14 (d, J = 1.8 Hz, 1H), 7.89 (d, J = 5.4 Hz, 1H), 7.73-7.67 (m, 2H), 7.52-7.43 (m, 2H), 6.99 (d, J = 1.9 Hz, 1H), 5.97 (d, J = 5.5 Hz, 1H), 4.08 (q, J = 7.1 Hz, 2H), 3.59 (s, 4H), 3.49-3.40 (m, 4H), 3.09 (dd, J = 9.4, 4.2 Hz, 1H), 2.82-2.65 (m, 2H), 1.78 (dd, J = 7.2, 4.4 Hz, 4H), 1.38 (s, 3H), 1.21 (t, J = 7.1 Hz, 3H), 0.99 (d, J = 6.4 Hz, 3H), 0.82 (d, J = 6.5 Hz, 3H). |

TABLE 1-continued
| # | Structure | LCMS (M + 1) | NMR |
|---|---|---|---|
| 536 | 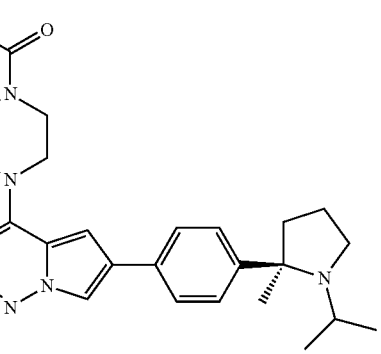 | 476 | |
| 537 | 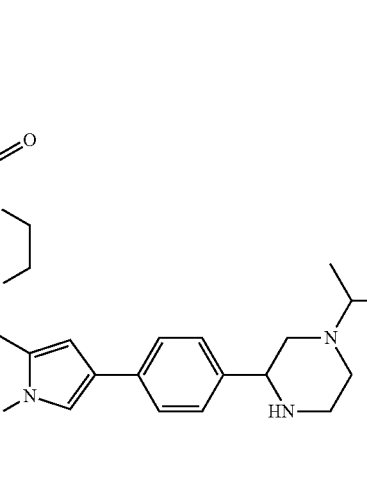 | 476 | 1H-NMR (400 MHz, 6d-DMSO) δ ppm 8.17 (d, 1H, J = 1.6 Hz), 7.91 (d, 1H, J = 5.2 Hz), 7.77 (d, 2H, J = 8.4 Hz), 7.35 (d, 2H, J = 8.0 Hz), 7.04 (d, 1H, J = 1.6 Hz), 6.61 (t, 1H, J = 5.6 Hz), 5.99 (d, 1H, J = 5.2 Hz), 3.77 (d, 1H, J = 8.4 Hz), 3.53-3.51 (m, 4H), 3.45-3.43 (m, 4H), 3.12-3.06 (m, 2H), 3.02-2.98 (m, 1H), 2.85-2.79 (m, 1H), 2.74-2.66 (m, 3H), 2.25 (t, 1H, J = 11.2 Hz), 2.09 (t, 1H, J = 10.4 Hz), 1.04 (t, 3H, J = 7.2 Hz), 0.98 (d, 6H, J = 6.4 Hz). |
| 538 | 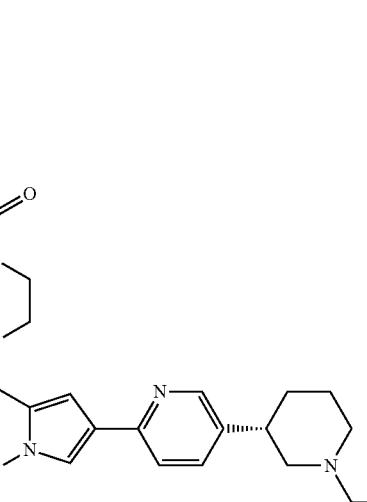 | 476 | 1H-NMR (400 MHz, 6d-DMSO) δ ppm 8.49 (s, 1H), 8.25 (s, 1H), 7.92 (d, 1H, J = 5.6 Hz), 7.86 (d, 1H, J = 8.4 Hz), 7.71 (d, 1H, J = 8.4 Hz), 7.14 (s, 1H), 6.61 (t, 1H, J = 5.2 Hz), 5.99 (d, 1H, J = 5.2 Hz), 3.55-3.50 (m, 4H), 3.47-3.42 (m, 4H), 3.12-3.04 (m, 2H), 2.85-2.71 (m, 4H), 2.25-2.17 (m, 2H), 1.85-1.81 (m, 1H), 1.75-1.71 (m, 1H), 1.59-1.45 (m, 2H), 1.04 (t, 3H, J = 7.2 Hz), 1.04-0.97 (m, 6H). |

TABLE 1-continued

| # | Structure | LCMS (M + 1) | NMR |
|---|---|---|---|
| 539 | 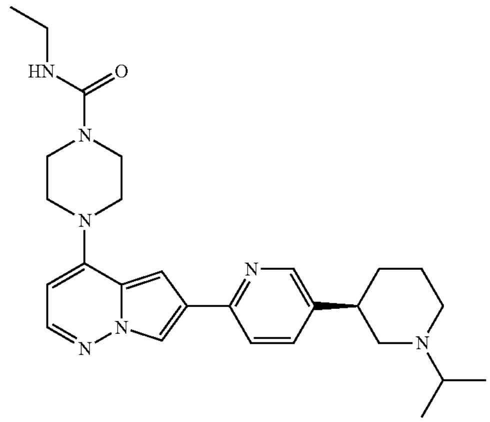 [SMILES: CCNC(=O)N1CCN(c2ccnn3cc(-c4ccc([C@H]5CCCN(C(C)C)C5)cn4)cc23)CC1] | 476 | 1H-NMR (400 MHz, 6d-DMSO) δ ppm 8.48 (d, 1H, J = 1.6 Hz), 8.24 (d, 1H, J = 1.6 Hz), 7.92 (d, 1H, J = 5.2 Hz), 7.85 (d, 1H, J = 8.0 Hz), 7.71-7.68 (m, 1H), 7.14 (d, 1H, J = 1.2 Hz), 6.60 (t, 1H, J = 5.2 Hz), 5.99 (d, 1H, J = 5.6 Hz), 3.53-3.51 (m, 4H), 3.45-3.44 (m, 4H), 3.12-3.05 (m, 2H), 2.81-2.72 (m, 4H), 2.24-2.14 (m, 2H), 1.84-1.81 (m, 1H), 1.76-1.72 (m, 1H), 1.60-1.43 (m, 2H), 1.03 (t, 3H, J = 7.2 Hz), 0.99-0.96 (m, 6H). |
| 540 | 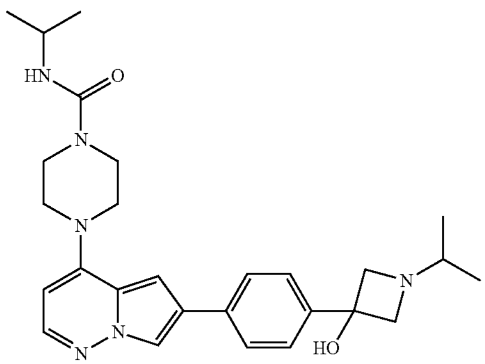 [SMILES: CC(C)NC(=O)N1CCN(c2ccnn3cc(-c4ccc(C5(O)CN(C(C)C)C5)cc4)cc23)CC1] | 477 | 1H-NMR (400 MHz, 6d-DMSO) δ ppm 8.16 (d, 1H, J = 1.6 Hz), 7.89 (d, 1H, J = 5.6 Hz), 7.77 (d, 2H, J = 8.4 Hz), 7.62 (d, 2H, J = 8.4 Hz), 7.01 (d, 1H, J = 1.6 Hz), 6.31 (d, 1H, J = 7.6 Hz), 5.98 (d, 1H, J = 5.6 Hz), 5.79 (s, 1H), 3.82-3.66 (m, 1H), 3.60-3.47 (m, 6H), 3.46-3.38 (m, 4H), 3.24-3.18 (m, 2H), 2.44-2.34 (m, 1H), 1.07 (d, 6H, J = 6.8 Hz), 0.90 (d, 6H, J = 6.0 Hz). |
| 541 | 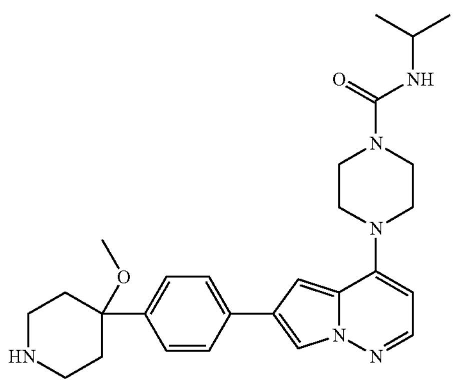 [SMILES: COC1(c2ccc(-c3cc4c(N5CCN(C(=O)NC(C)C)CC5)ccnn4c3)cc2)CCNCC1] | 477 | 1H NMR (400 MHz, Methanol-d4) δ 8.46 (s, 1H), 8.00 (d, J = 1.8 Hz, 1H), 7.86 (d, J = 5.5 Hz, 1H), 7.82-7.69 (m, 2H), 7.54-7.36 (m, 2H), 6.93 (d, J = 1.9 Hz, 1H), 6.00 (d, J = 5.5 Hz, 1H), 3.93 (p, J = 6.6 Hz, 1H), 3.65 (dd, J = 6.6, 3.6 Hz, 4H), 3.54 (dd, J = 6.7, 3.5 Hz, 4H), 3.42-3.34 (m, 4H), 3.04 (s, 3H), 2.38 (d, J = 14.5 Hz, 2H), 2.13 (dd, J = 26.5, 5.7 Hz, 1H), 1.23-1.12 (m, 7H). |
| 542 | 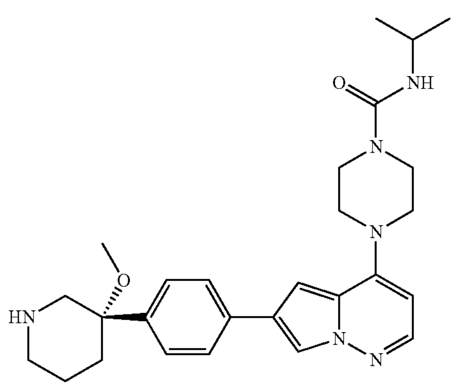 [SMILES: CO[C@]1(c2ccc(-c3cc4c(N5CCN(C(=O)NC(C)C)CC5)ccnn4c3)cc2)CCCNC1] | 477 | 1H NMR (400 MHz, 4d-MeOD) δ ppm 8.55 (m, 1H), 8.04 (dd, 1H, J = 7.6, 1.6 Hz), 7.91 (d, 1H, J = 5.2 Hz), 7.83 (d, 2H, J = 8.4 Hz), 7.52 (d, 2H, J = 8.4 Hz), 6.95 (d, 1H, J = 2.0 Hz), 6.01 (d, 1H, J = 5.6 Hz), 3.96-3.95 (m, 1H), 3.68-3.65 (m, 4H), 3.56-3.55 (m, 4H), 3.44-3.42 (m, 2H), 3.26-3.25 (m, 1H), 3.12 (s, 3H), 3.04-3.00 (m, 2H), 2.25-2.19 (m, 3H), 1.21-1.17 (m, 6H). |

TABLE 1-continued

| # | Structure | LCMS (M + 1) | NMR |
|---|---|---|---|
| 543 | 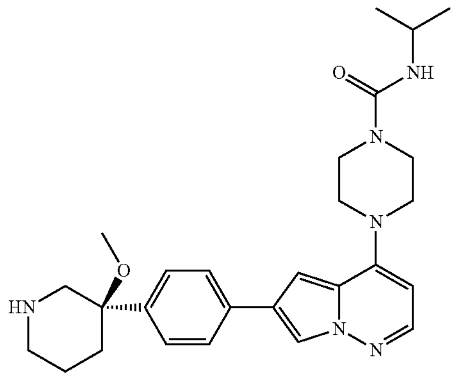 [SMILES: CO[C@@]1(c2ccc(-c3cc4c(N5CCN(C(=O)NC(C)C)CC5)ccnn4c3)cc2)CCCNC1] | 477 | 1H NMR (400 MHz, 6d-DMSO) δ ppm 8.32 (s, 1H), 8.19 (d, 1H, J = 2.0 Hz), 7.91 (d, 1H, J = 5.6 Hz), 7.82 (d, 2H, J = 8.4 Hz), 7.41 (d, 2H, J = 8.4 Hz), 7.04 (d, 1H, J = 6.0 Hz), 6.32 (d, 1H, J = 7.6 Hz), 6.00 (d, 1H, J = 5.6 Hz), 3.80-3.75 (m, 1H), 3.55-3.50 (m, 4H), 3.50-3.45 (m, 4H), 3.18-3.10 (m, 1H), 2.98 (s, 3H), 2.93-2.92 (m, 1H), 2.82-2.80 (m, 1H), 2.70-2.66 (m, 1H), 2.19-2.18 (m, 1H), 2.03-1.98 (m, 1H), 1.73-1.68 (m, 1H), 1.60-1.55 (m, 1H), 1.09-1.06 (m, 6H). |
| 544 | 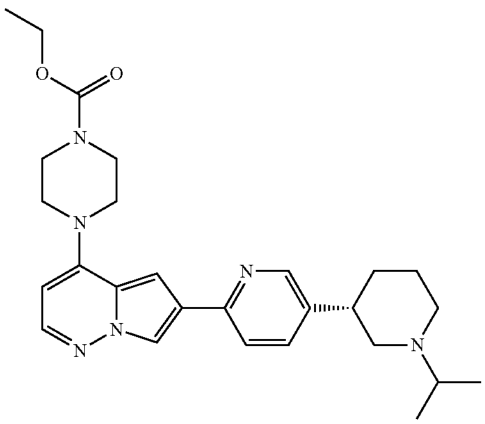 [SMILES: CCOC(=O)N1CCN(c2ccnn3cc(-c4ccc([C@@H]5CCCN(C(C)C)C5)cn4)cc23)CC1] | 477 | 1H-NMR (400 MHz, 6d-DMSO) δ ppm 8.48 (d, 1H, J = 2.0 Hz), 8.24 (d, 1H, J = 2.0 Hz), 7.92 (d, 1H, J = 5.2 Hz), 7.85 (d, 1H, J = 8.4 Hz), 7.71 7.71 (dd 1H, J = 8.4, 2.4 Hz), 7.14 (d, 1H, J = 1.6 Hz), 5.99 (d, 1H, J = 5.6 Hz), 4.09 (q, 2H, J = 7.2 Hz), 3.62-3.59 (m, 4H), 3.48-3.46 (m, 4H), 2.82-2.72 (m, 4H), 2.25-2.14 (m, 2H), 1.84-1.80 (m, 1H), 1.75-1.72 (m, 1H), 1.60-1.45 (m, 2H), 1.22 (t, 3H, J = 7.2 Hz), 0.99-0.96 (m, 6H). |
| 545 | 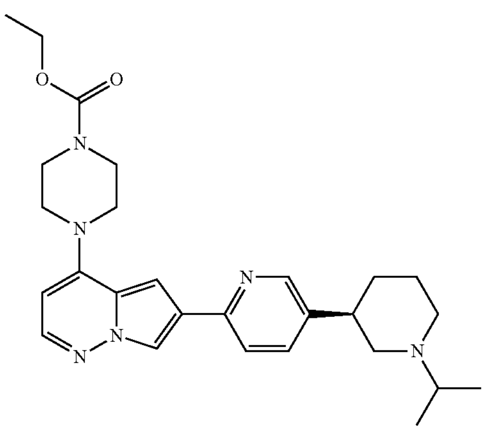 [SMILES: CCOC(=O)N1CCN(c2ccnn3cc(-c4ccc([C@H]5CCCN(C(C)C)C5)cn4)cc23)CC1] | 477 | 1H-NMR (500 MHz, CDCl3) δ ppm 8.53 (s, 1H), 8.14 (d, 1H, J = 1.5 Hz), 7.87 (d, 1H, J = 5.0 Hz), 7.63-7.59 (m, 2H), 7.00 (d, 1H, J = 1.5 Hz), 5.84 (d, 1H, J = 5.5 Hz), 4.21 (q, 2H, J = 7.2 Hz), 3.75-3.70 (m, 4H), 3.52-3.49 (m, 1H), 3.50-3.45 (m, 4H), 3.33-3.20 (m, 3H), 2.60-2.53 (m, 2H), 2.36-2.31 (m, 1H), 2.14-2.10 (m, 1H), 2.01-1.95 (m, 1H), 1.70-1.64 (m, 1H), 1.35-1.28 (m, 9H). |
| 546 | 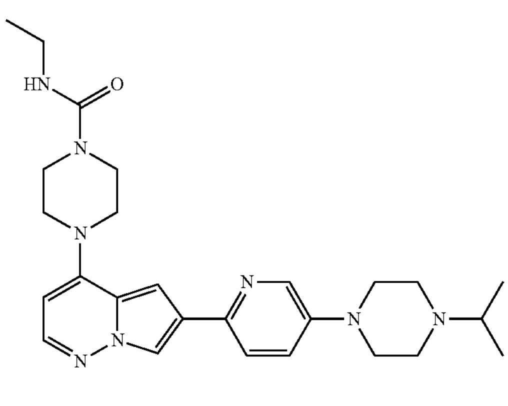 | 477 | 1H-NMR (400 MHz, CDCl3) δ ppm 8.33 (d, 1H, J = 2.8 Hz), 8.06 (d, 1H, J = 1.6 Hz), 7.83 (d, 1H, J = 5.6 Hz), 7.54 (d, 1H, J = 8.4 Hz), 7.26-7.22 (m, 1H), 6.96 (d, 1H, J = 1.6 Hz), 5.80 (d, 1H, J = 5.6 Hz), 4.52-4.48 (m, 1H), 3.65-3.59 (m, 4H), 3.55-3.50 (m, 4H), 3.34 (q, 2H, J = 7.2 Hz), 3.28-3.24 (m, 4H), 2.77-2.70 (m, 5H), 1.19 (t, 3H, J = 7.2 Hz), 1.11 (d, 6H, J = 6.4 Hz). |

TABLE 1-continued

| # | Structure | LCMS (M + 1) | NMR |
|---|---|---|---|
| 547 | 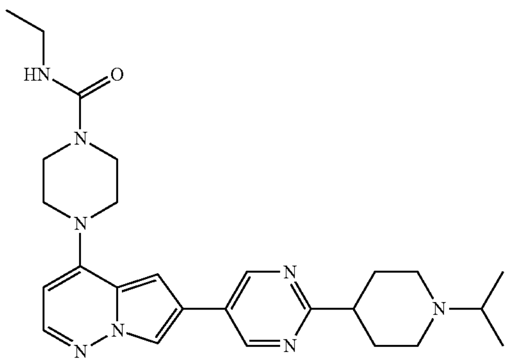 | 477 | 1H NMR (400 MHz, 4d-MeOD) δ ppm 9.08 (s, 2H), 8.14 (d, 1H, J = 1.2 Hz), 7.89 (d, 1H, J = 5.2 Hz), 7.06 (d, 1H, J = 0.8 Hz), 6.02 (d, 1H, J = 5.6 Hz), 3.66-3.65 (m, 4H), 3.65-3.57 (m, 4H), 3.25 (q, 2H, J = 7.2 Hz), 3.11-3.09 (m, 2H), 2.93-2.91 (m, 1H), 2.86-2.83 (m, 1H), 2.48-2.43 (m, 2H), 2.07-2.01 (m, 4H), 1.17-1.13 (m, 9H). |
| 548 | 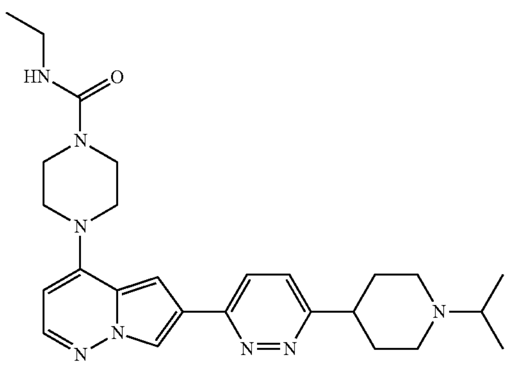 [SMILES: CCNC(=O)N1CCN(c2ccnn3cc(-c4ccc(C5CCN(C(C)C)CC5)nn4)cc23)CC1] | 477 | 1H-NMR (400 MHz, DMSO-d6) δ ppm 8.42 (d, 1H, J = 1.6 Hz), 8.31 (s, 1H), 8.16 (d, 1H, J = 8.8 Hz), 7.96 (d, 1H, J = 6.0 Hz), 7.65 (d, 1H, J = 8.8 Hz), 7.30 (d, 1H, J = 1.2 Hz), 6.66-6.61 (m, 1H), 6.02 (d, 1H, J = 6.0 Hz), 3.56-3.51 (m, 4H), 3.50-3.45 (m, 4H), 3.10-3.05 (m, 4H), 3.00-2.94 (m, 2H), 2.58-2.50 (m, 2H), 2.00-1.90 (m, 4H), 1.10 (d, 6H, J = 6.4 Hz), 1.04 (t, 3H, J = 7.2 Hz). |
| 549 | 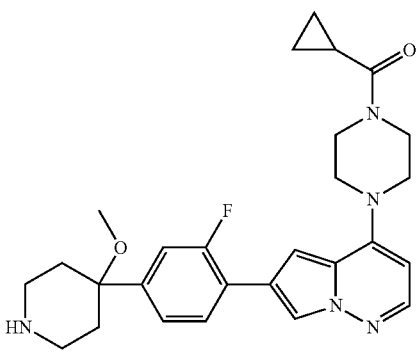 [SMILES: COC1(c2ccc(-c3cc4c(N5CCN(C(=O)C6CC6)CC5)ccnn4c3)c(F)c2)CCNCC1] | 446 | 1H NMR (400 MHz, DMSO-d6) δ 8.04 (t, J = 2.1 Hz, 1H), 7.95-7.84 (m, 2H), 7.28-7.13 (m, 2H), 7.04 (d, J = 1.8 Hz, 1H), 5.96 (d, J = 5.5 Hz, 1H), 3.89 (br.s, 2H), 3.66 (br.s, 2H), 3.48 (br.d, J = 28.4 Hz, 4H), 2.88 (s, 3H), 2.84-2.72 (m, 4H), 1.98 (td, J = 7.7, 3.8 Hz, 1H), 1.89 (d, J = 13.6 Hz, 2H), 1.76 (td, J = 13.5, 12.6, 4.8 Hz, 2H), 0.79-0.65 (m, 4H). |
| 550 | 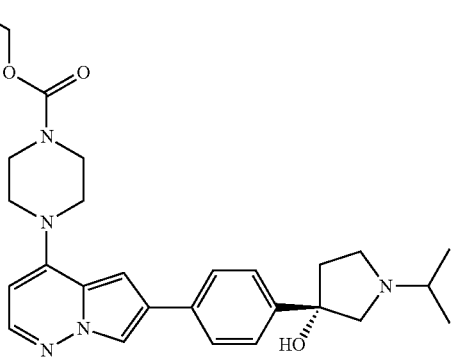 | 478 | 1H NMR (400 MHz, DMSO-d6) δ 8.15 (d, J = 1.8 Hz, 1H), 7.90 (d, J = 5.4 Hz, 1H), 7.79-7.68 (m, 2H), 7.54-7.41 (m, 2H), 7.00 (d, J = 1.9 Hz, 1H), 5.98 (d, J = 5.5 Hz, 1H), 5.14 (s, 1H), 4.08 (q, J = 7.1 Hz, 2H), 3.63-3.56 (m, 4H), 3.45 (t, J = 5.1 Hz, 4H), 2.90 (d, J = 9.7 Hz, 1H), 2.85-2.70 (m, 3H), 2.10 (dt, J = 12.9, 8.0 Hz, 1H), 1.99 (dt, J = 12.5, 5.6 Hz, 1H), 1.21 (t, J = 7.1 Hz, 3H), 1.04 (t, J = 6.4 Hz, 6H). |

TABLE 1-continued

| # | Structure | LCMS (M + 1) | NMR |
|---|---|---|---|
| 551 | 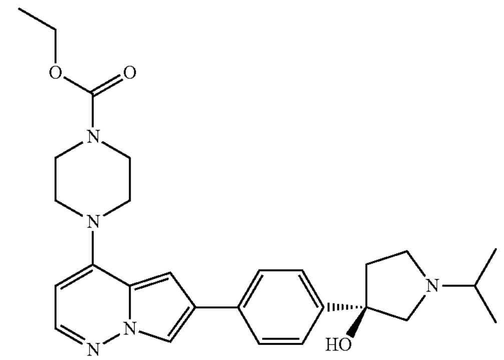 [SMILES: CCOC(=O)N1CCN(c2ccnn3cc(-c4ccc([C@]5(O)CCN(C(C)C)C5)cc4)cc23)CC1] | 478 | |
| 552 | 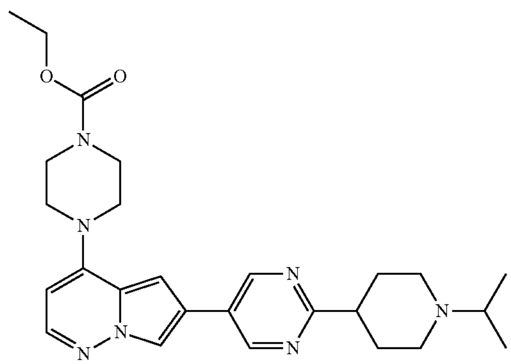 [SMILES: CCOC(=O)N1CCN(c2ccnn3cc(-c4cnc(C5CCN(C(C)C)CC5)nc4)cc23)CC1] | 478 | 1H NMR (400 MHz, 4d-MeOD) δ ppm 9.11 (s, 2H), 8.18 (d, 1H, J = 1.6 Hz), 7.90 (d, 1H, J = 5.6 Hz), 7.07 (d, 1H, J = 2.0 Hz), 6.05 (d, 1H, J = 5.2 Hz), 4.19 (q, 2H, J = 7.2 Hz), 3.74-3.73 (m, 4H), 3.55-3.52 (m, 4H), 3.28-3.27 (m, 2H), 3.14-3.06 (m, 2H), 2.76-2.75 (m, 2H), 2.22-2.10 (m, 4H), 1.31 (t, 3H, J = 7.2 Hz), 1.25 (d, 6H, J = 6.4 Hz). |
| 553 | 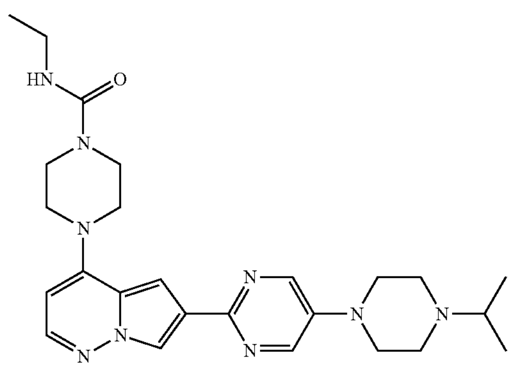 [SMILES: CCNC(=O)N1CCN(c2ccnn3cc(-c4ncc(N5CCN(C(C)C)CC5)cn4)cc23)CC1] | 478 | 1H-NMR (400 MHz, DMSO-d6) δ ppm 8.84 (s, 2H), 8.17 (d, 1H, J = 1.6 Hz), 8.16 (s, 1H), 7.89 (d, 1H, J = 5.6 Hz), 7.03 (d, 1H, J = 1.6 Hz), 6.61 (t, 1H, J = 5.6 Hz), 5.99 (d, 1H, J = 5.6 Hz), 3.78-3.72 (m, 4H), 3.53-3.48 (m, 4H), 3.46-3.40 (m, 4H), 3.08 (q, 2H, J = 7.2 Hz), 2.80-2.70 (m, 1H), 2.56-2.52 (m, 4H), 1.10-1.00 (m, 9H). |
| 554 | 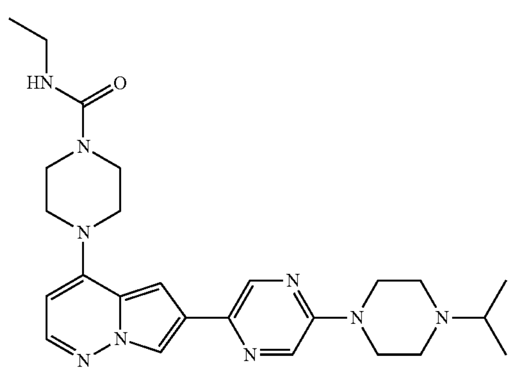 [SMILES: CCNC(=O)N1CCN(c2ccnn3cc(-c4cnc(N5CCN(C(C)C)CC5)cn4)cc23)CC1] | 478 | 1H-NMR (400 MHz, 6d-DMSO) δ ppm 8.68 (s, 1H), 8.31 (s, 1H), 8.16 (d, 1H, J = 1.2 Hz), 7.90 (d, 1H, J = 5.2 Hz), 7.05 (d, 1H, J = 1.2 Hz), 6.60 (t, 1H, J = 5.2 Hz), 5.99 (d, 1H, J = 5.6 Hz), 3.56-3.51 (m, 8H), 3.45-3.43 (m, 4H), 3.11-3.05 (m, 2H), 2.73-2.67 (m, 1H), 2.57-2.54 (m, 4H), 1.05-1.00 (m, 9H). |

| # | Structure | LCMS (M + 1) | NMR |
|---|---|---|---|
| 555 | 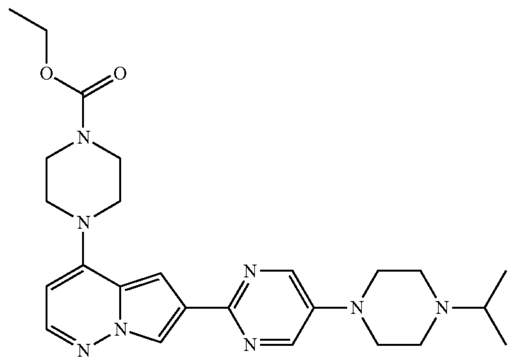 [SMILES: CCOC(=O)N1CCN(c2ccnn3cc(-c4ncc(N5CCN(C(C)C)CC5)cn4)cc23)CC1] | 479 | 1H-NMR (400 MHz, DMSO-d6) δ ppm 8.84 (s, 2H), 8.19 (s, 1H), 8.18 (d, 1H, J = 1.6 Hz), 7.90 (d, 1H, J = 5.6 Hz), 7.03 (d, 1H, J = 1.6 Hz), 5.98 (d, 1H, J = 5.6 Hz), 4.09 (q, 2H, J = 7.2 Hz), 3.80-3.73 (m, 4H), 3.61-3.58 (m, 4H), 3.46-3.42 (m, 4H), 2.79-2.72 (m, 1H), 2.59-2.55 (m, 4H), 1.22 (t, 3H, J = 7.2 Hz), 1.02 (d, 6H, J = 6.4 Hz). |
| 556 | 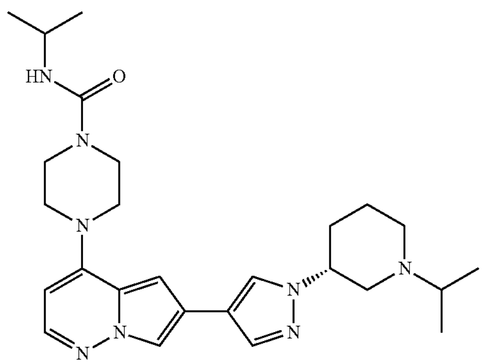 [SMILES: CC(C)NC(=O)N1CCN(c2ccnn3cc(-c4cnn([C@@H]5CCCN(C(C)C)C5)c4)cc23)CC1] | 479 | 1H-NMR (400 MHz, 6d-DMSO) δ ppm 8.17 (s, 1H), 7.91 (d, 1H, J = 1.6 Hz), 7.85 (d, 1H, J = 5.6 Hz), 7.81 (s, 1H), 6.79 (d, 1H, J = 1.6 Hz), 6.32 (d, 1H, J = 7.6 Hz), 5.97 (d, 1H, J = 5.6 Hz), 4.20-4.19 (m, 1H), 3.81-3.76 (m, 1H), 3.51-3.50 (m, 4H), 3.41-3.39 (m, 4H), 3.07-3.04 (m, 1H), 2.80-2.74 (m, 2H), 2.41-2.35 (m, 1H), 2.20-2.17 (m, 1H), 2.09-2.07 (m, 1H), 1.79-1.76 (m, 2H), 1.58-1.55 (m, 1H), 1.23-1.09 (m, 6H), 0.99-0.97 (m, 6H). |
| 557 | 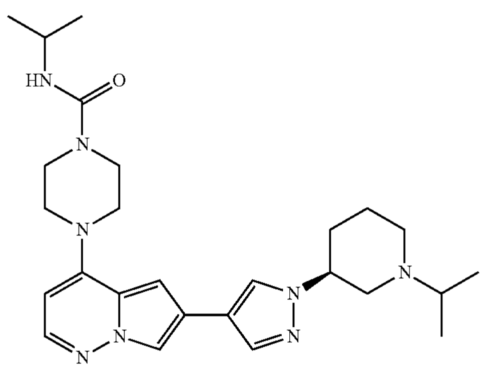 [SMILES: CC(C)NC(=O)N1CCN(c2ccnn3cc(-c4cnn([C@H]5CCCN(C(C)C)C5)c4)cc23)CC1] | 479 | 1H-NMR (400 MHz, 6d-DMSO) δ ppm 8.17 (s, 1H), 7.92 (d, 1H, J = 1.6 Hz), 7.86 (d, 1H, J = 5.6 Hz), 7.81 (s, 1H), 6.80 (d, 1H, J = 1.6 Hz), 6.33 (d, 1H, J = 7.2 Hz), 5.97 (d, 1H, J = 5.2 Hz), 4.20-4.18 (m, 1H), 3.81-3.75 (m, 1H), 3.52-3.50 (m, 4H), 3.41-3.39 (m, 4H), 3.06-3.04 (m, 1H), 2.81-2.74 (m, 2H), 2.40-2.35 (m, 1H), 2.18 (t, 1H, J = 11.2 Hz), 2.10-2.06 (m, 1H), 1.82-1.72 (m, 2H), 1.62-1.56 (m, 1H), 1.08 (d, 6H, J = 6.8 Hz), 0.10-0.96 (m, 6H). |
| 558 | 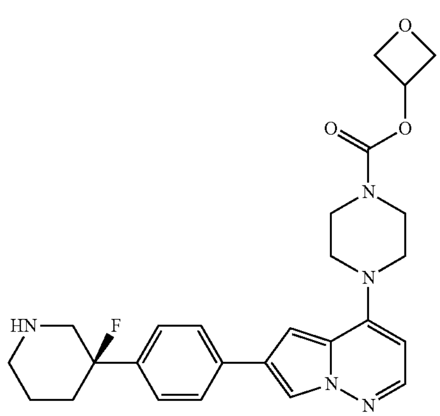 [SMILES: O=C(OC1COC1)N1CCN(c2ccnn3cc(-c4ccc([C@]5(F)CCCNC5)cc4)cc23)CC1] | 480 | 1H-NMR (400 MHz, 6d-DMSO) δ ppm 8.22 (d, 1H, J = 2.0 Hz), 7.92 (d, 1H, J = 5.2 Hz), 7.83 (d, 2H, J = 8.4 Hz), 7.43 (d, 2H, J = 8.4 Hz), 7.05 (d, 1H, J = 1.2 Hz), 5.99 (d, 1H, J = 5.6 Hz), 5.34 (quintet, 1H, J = 5.6 Hz), 4.79 (t, 2H, J = 6.8 Hz), 4.53 (dd, 2H, J = 7.2, 1.2 Hz), 3.72-3.68 (m, 2H), 3.64-3.60 (m, 2H), 3.55-3.40 (m, 4H), 2.99-2.90 (m, 3H), 2.70-2.55 (m, 1H), 2.25-2.15 (m, 1H), 2.10-1.98 (m, 1H), 1.92-1.66 (m, 1H), 1.60-1.50 (m, 1H). |

TABLE 1-continued

| # | Structure | LCMS (M + 1) | NMR |
|---|---|---|---|
| 559 | 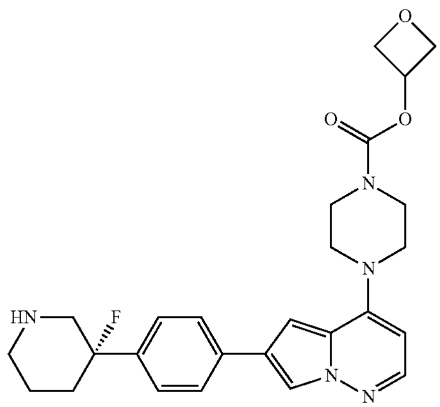 [SMILES: O=C(OC1COC1)N1CCN(c2ccnn3cc(-c4ccc([C@@]5(F)CCCNC5)cc4)cc23)CC1] | 480 | 1H-NMR (400 MHz, 6d-DMSO) δ ppm 8.22 (d, 1H, J = 2.0 Hz), 7.92 (d, 1H, J = 5.2 Hz), 7.83 (d, 2H, J = 8.4 Hz), 7.43 (d, 2H, J = 8.4 Hz), 7.05 (d, 1H, J = 1.2 Hz), 5.99 (d, 1H, J = 5.6 Hz), 5.34 (quintet, 1H, J = 5.6 Hz), 4.79 (t, 2H, J = 6.8 Hz), 4.53 (dd, 2H, J = 7.2, 1.2 Hz), 3.72-3.68 (m, 2H), 3.64-3.60 (m, 2H), 3.55-3.40 (m, 4H), 2.99-2.90 (m, 3H), 2.70-2.55 (m, 1H), 2.25-2.15 (m, 1H), 2.10-1.98 (m, 1H), 1.92-1.66 (m, 1H), 1.60-1.47 (m, 1H). |
| 560 | 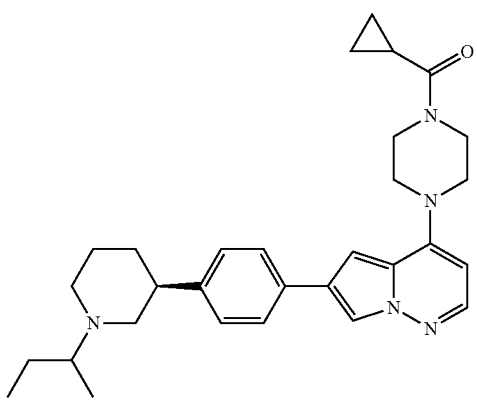 [SMILES: CCC(C)N1CCC[C@@H](c2ccc(-c3cc4c(N5CCN(C(=O)C6CC6)CC5)ccnn4c3)cc2)C1] | 486 | 1H-NMR (400 MHz, DMSO-d6) δ ppm 8.14 (s, 1H), 7.89 (d, 1H, J = 5.2 Hz), 7.71 (d, 2H, J = 8.0 Hz), 7.28-7.25 (m, 2H), 7.01 (s, 1H), 5.97 (d, 1H, J = 5.2 Hz), 4.00-3.82 (m, 2H), 3.80-3.60 (m, 2H), 3.58-3.40 (m, 4H), 2.80-2.60 (m, 3H), 2.47-2.44 (m, 1H), 2.38-2.24 (m, 1H), 2.20-1.96 (m, 2H), 1.86-1.76 (m, 1H), 1.75-1.66 (m, 1H), 1.62-1.38 (m, 3H), 1.32-1.16 (m, 1H), 0.90 (dd, 3H, J = 6.4, 2.8 Hz), 0.85 (t, 3H, J = 7.6 Hz), 0.80-0.70 (m, 4H). |
| 561 | 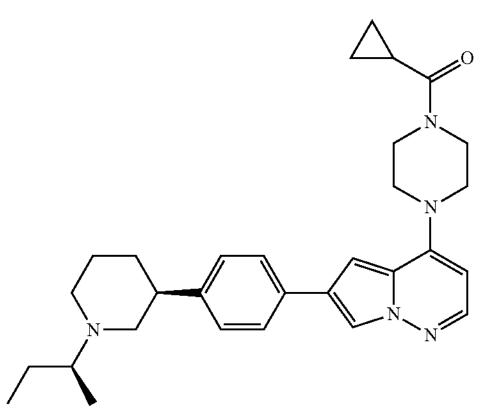 [SMILES: CC[C@H](C)N1CCC[C@@H](c2ccc(-c3cc4c(N5CCN(C(=O)C6CC6)CC5)ccnn4c3)cc2)C1] | 486 | 1H-NMR (400 MHz, DMSO-d6) δ ppm 8.15 (d, 1H, J = 1.2 Hz), 7.89 (d, 1H, J = 5.2 Hz), 7.72 (d, 2H, J = 8.0 Hz), 7.27 (d, 2H, J = 8.0 Hz), 7.01 (d, 1H, J = 1.6 Hz), 5.97 (d, 1H, J = 5.6 Hz), 4.00-3.82 (m, 2H), 3.80-3.60 (m, 2H), 3.58-3.40 (m, 4H), 3.00-2.60 (m, 3H), 2.46-2.40 (m, 1H), 2.38-2.15 (m, 2H), 2.10-1.94 (m, 1H), 1.86-1.70 (m, 2H), 1.66-1.40 (m, 3H), 1.36-1.24 (m, 1H), 1.00-0.90 (m, 3H), 0.86 (t, 3H, J = 7.2 Hz), 0.80-0.70 (m, 4H). |

| # | Structure | LCMS (M + 1) | NMR |
|---|---|---|---|
| 562 | 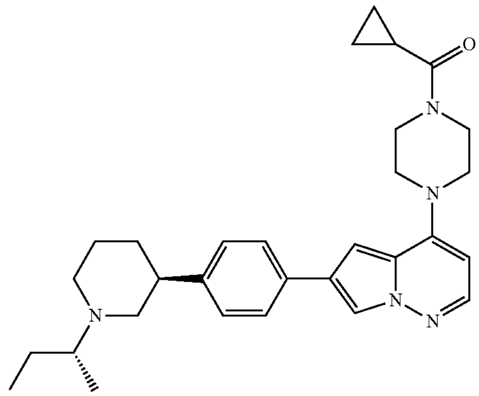 [SMILES: CC[C@@H](C)N1CCC[C@@H](c2ccc(-c3cc4c(N5CCN(C(=O)C6CC6)CC5)ccnn4c3)cc2)C1] | 486 | 1H-NMR (400 MHz, DMSO-d6) δ ppm 8.14 (d, 1H, J = 1.2 Hz), 7.89 (d, 1H, J = 5.6 Hz), 7.71 (d, 2H, J = 8.0 Hz), 7.27 (d, 2H, J = 8.0 Hz), 7.01 (d, 1H, J = 1.6 Hz), 5.96 (d, 1H, J = 5.2 Hz), 4.00-3.82 (m, 2H), 3.80-3.62 (m, 2H), 3.58-3.40 (m, 4H), 2.80-2.65 (m, 3H), 2.47-2.40 (m, 1H), 2.37-2.25 (m, 1H), 2.16-2.06 (m, 1H), 2.05-1.94 (m, 1H), 1.86-1.76 (m, 1H), 1.75-1.66 (m, 1H), 1.60-1.32 (m, 3H), 1.30-1.24 (m, 1H), 0.90 (d, 3H, J = 6.8 Hz), 0.85 (t, 3H, J = 7.2 Hz), 0.80-0.70 (m, 4H). |
| 563 | 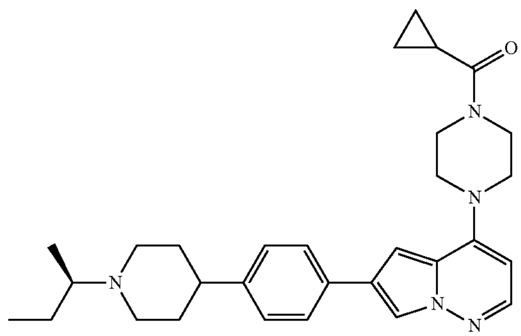 [SMILES: CC[C@@H](C)N1CCC(c2ccc(-c3cc4c(N5CCN(C(=O)C6CC6)CC5)ccnn4c3)cc2)CC1] | 486 | 1H NMR (400 MHz, DMSO-d6) δ ppm 8.14 (d, 1H, J = 1.2 Hz), 7.89 (d, 1H, J = 5.2 Hz), 7.73 (d, 2H, J = 8.4 Hz), 7.26 (d, 2H, J = 8.0 Hz), 7.02 (d, 1H, J = 1.6 Hz), 5.97 (d, 1H, J = 5.6 Hz), 3.94-3.91 (m, 2H), 3.71-3.70 (m, 2H), 3.54-3.46 (m, 4H), 2.84-2.81 (m, 2H), 2.46-2.30 (m, 2H), 2.22-2.19 (m, 1H), 2.03-2.01 (m, 1H), 1.75-1.20 (m, 7H), 0.95-0.71 (m, 10H). |
| 564 | 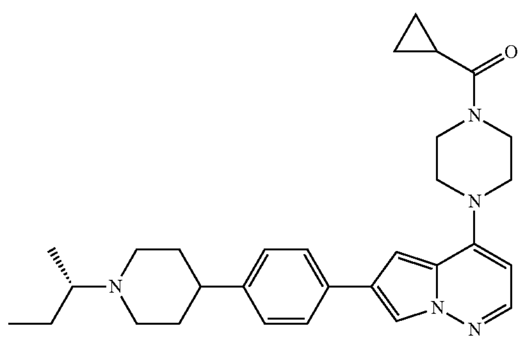 [SMILES: CC[C@H](C)N1CCC(c2ccc(-c3cc4c(N5CCN(C(=O)C6CC6)CC5)ccnn4c3)cc2)CC1] | 486 | 1H NMR (400 MHz, DMSO-d6) δ ppm 8.14 (d, 1H, J = 1.2 Hz), 7.89 (d, 1H, J = 5.2 Hz), 7.73 (d, 2H, J = 8.0 Hz), 7.26 (d, 2H, J = 8.0 Hz), 7.02 (d, 1H, J = 1.2 Hz), 5.97 (d, 1H, J = 5.2 Hz), 3.94-3.91 (m, 2H), 3.71-3.70 (m, 2H), 3.54-3.46 (m, 4H), 2.84-2.81 (m, 2H), 2.46-2.30 (m, 2H), 2.03-2.01 (m, 1H), 1.75-1.20 (m, 8H), 0.95-0.71 (m, 10H). |
| 565 | 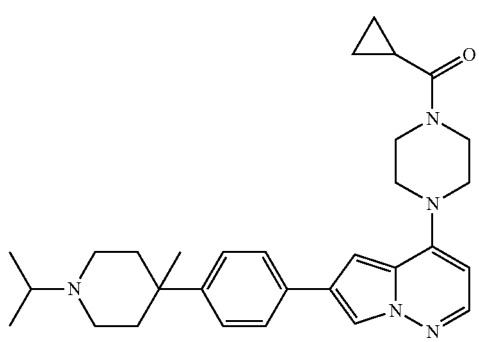 | 486 | 1H-NMR (400 MHz, DMSO-d6) δ ppm 7.97 (d, 1H, J = 1.6 Hz), 7.85 (d, 1H, J = 5.2 Hz), 7.71 (d, 2H, J = 8.4 Hz), 7.42 (d, 2H, J = 8.4 Hz), 6.93 (d, 1H, J = 1.6 Hz), 6.00 (d, 1H, J = 5.6 Hz), 4.08-4.02 (m, 2H), 3.90-3.84 (m, 2H), 3.68-3.62 (m, 2H), 3.58-3.54 (m, 2H), 2.88-2.78 (m, 3H), 2.70-2.60 (m, 2H), 2.36-2.25 (m, 2H), 2.08-2.00 (m, 1H), 1.94-1.84 (m, 2H), 1.34-1.22 (m, 3H), 1.12 (d, 6H, J = 6.8 Hz), 0.97-0.84 (m, 4H) |

TABLE 1-continued

| # | Structure | LCMS (M + 1) | NMR |
|---|---|---|---|
| 566 | 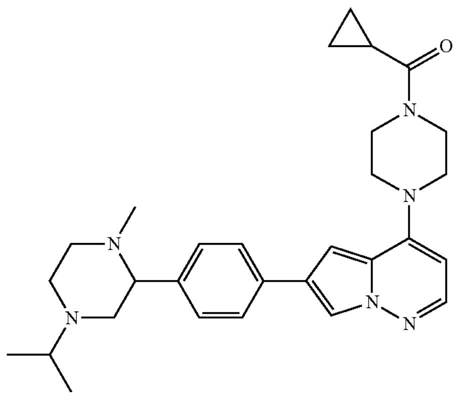 [SMILES: CC(C)N1CCN(C)C(c2ccc(-c3cc4c(N5CCN(C(=O)C6CC6)CC5)ccnn4c3)cc2)C1] | 487 | 1H-NMR (400 MHz, 6d-DMSO) δ ppm 8.17 (d, 1H, J = 1.6 Hz), 7.91 (d, 1H, J = 5.2 Hz), 7.77 (d, 2H, J = 8.4 Hz), 7.35 (d, 2H, J = 8.0 Hz), 7.04 (d, 1H, J = 1.6 Hz), 5.99 (d, 1H, J = 5.2 Hz), 3.94-3.92 (m, 2H), 3.72-3.70 (m, 2H), 3.56-3.46 (m, 4H), 2.97-2.93 (m, 2H), 2.77-2.73 (m, 1H), 2.65-2.61 (m, 2H), 2.36-2.32 (m, 1H), 2.24-2.20 (m, 1H), 2.10 (t, 1H, J = 10.4 Hz), 2.04-2.00 (m, 1H), 1.96 (s, 3H), 0.96 (d, 6H, J = 6.8 Hz), 0.80-0.74 (m, 4H). |
| 567 | 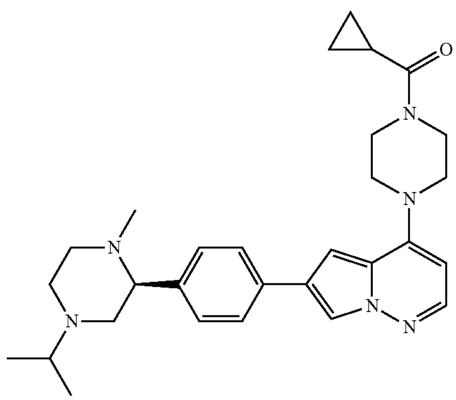 [SMILES: CC(C)N1CCN(C)[C@@H](c2ccc(-c3cc4c(N5CCN(C(=O)C6CC6)CC5)ccnn4c3)cc2)C1] | 487 | 1H-NMR (400 MHz, 6d-DMSO) δ ppm 8.17 (d, 1H, J = 1.6 Hz), 7.91 (d, 1H, J = 5.2 Hz), 7.77 (d, 2H, J = 8.4 Hz), 7.35 (d, 2H, J = 8.0 Hz), 7.04 (d, 1H, J = 1.6 Hz), 5.99 (d, 1H, J = 5.2 Hz), 3.94-3.92 (m, 2H), 3.72-3.70 (m, 2H), 3.56-3.46 (m, 4H), 2.97-2.94 (m, 1H), 2.90-2.86 (m, 1H), 2.77-2.73 (m, 1H), 2.65-2.61 (m, 2H), 2.36-2.32 (m, 1H), 2.24-2.20 (m, 1H), 2.10 (t, 1H, J = 10.4 Hz), 2.04-2.00 (m, 1H), 1.96 (s, 3H), 0.96 (d, 6H, J = 6.8 Hz), 0.80-0.74 (m, 4H). |
| 568 | 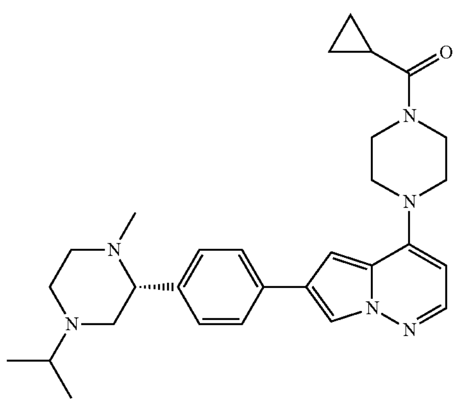 [SMILES: CC(C)N1CCN(C)[C@H](c2ccc(-c3cc4c(N5CCN(C(=O)C6CC6)CC5)ccnn4c3)cc2)C1] | 487 | 1H-NMR (400 MHz, 6d-DMSO) δ ppm 8.17 (d, 1H, J = 1.6 Hz), 7.91 (d, 1H, J = 5.6 Hz), 7.75 (d, 2H, J = 8.4 Hz), 7.34 (d, 2H, J = 8.4 Hz), 7.04 (d, 1H, J = 1.6 Hz), 5.98 (d, 1H, J = 5.6 Hz), 3.94-3.92 (m, 2H), 3.72-3.70 (m, 2H), 3.50-3.45 (m, 2H), 3.37-3.32 (m, 2H), 2.97-2.92 (m, 1H), 2.91-2.86 (m, 1H), 2.77-2.71 (m, 1H), 2.65-2.61 (m, 2H), 2.36-2.32 (m, 1H), 2.24-2.20 (m, 1H), 2.13-2.08 (m, 1H), 2.04-2.00 (m, 1H), 1.96 (s, 3H), 0.96 (d, 6H, J = 6.8 Hz), 0.80-0.74 (m, 4H). |
| 569 | 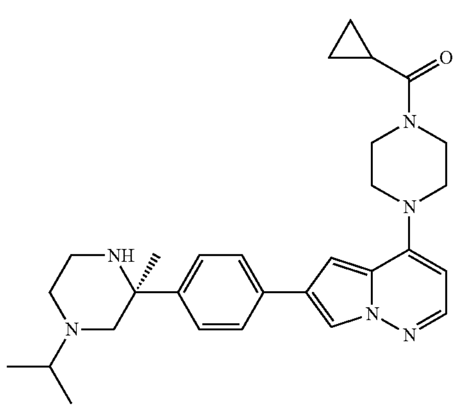 [SMILES: CC(C)N1CCN[C@@](C)(c2ccc(-c3cc4c(N5CCN(C(=O)C6CC6)CC5)ccnn4c3)cc2)C1] | 487 | 1H NMR (400 MHz, CDCl3) δ ppm 7.92 (d, 1H, J = 1.6 Hz), 7.83 (d, 1H, J = 5.2 Hz), 7.63 (d, 2H, J = 8.4 Hz), 7.54 (d, 2H, J = 8.4 Hz), 6.71 (d, 1H, J = 1.6 Hz), 5.82 (d, 1H, J = 5.2 Hz), 3.94-3.90 (m, 2H), 3.90-3.85 (m, 2H), 3.57-3.51 (m, 2H), 3.48-3.43 (m, 2H), 3.21-3.15 (m, 1H), 2.95-2.87 (m, 1H), 2.85-2.77 (m, 1H), 2.74 (heptet, 1H, J = 6.4 Hz), 2.55-2.45 (m, 2H), 2.45-2.38 (m, 1H), 1.79-1.74 (m, 1H), 1.39 (s, 3H), 1.10-1.07 (m, 3H), 1.06-1.01 (m, 5H), 0.84-0.79 (m, 2H). |

TABLE 1-continued
| # | Structure | LCMS (M + 1) | NMR |
|---|---|---|---|
| 570 | 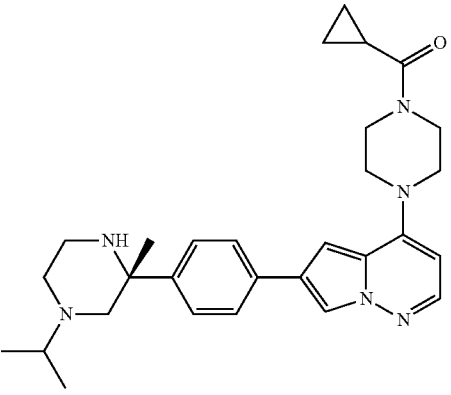 [SMILES: CC(C)N1CCN[C@](C)(c2ccc(-c3cc4c(N5CCN(C(=O)C6CC6)CC5)ccnn4c3)cc2)C1] | 487 | 1H-NMR (400 MHz, 6d-DMSO) δ ppm 8.15 (d, 1H, J = 2.0 Hz), 7.90 (d, 1H, J = 5.6 Hz), 7.72 (d, 2H, J = 8.4 Hz), 7.50 (d, 2H, J = 8.4 Hz), 7.03 (d, 1H, J = 2.0 Hz), 5.97 (d, 1H, J = 5.6 Hz), 3.96-3.90 (m, 2H), 3.73-3.69 (m, 2H), 3.59-3.54 (m, 2H), 3.53-3.47 (m, 2H), 3.10-3.05 (m, 1H), 2.72-2.67 (m, 1H), 2.64-2.56 (m, 2H), 2.41-2.37 (m, 1H), 2.33-2.28 (m, 2H), 2.26-2.22 (m, 1H), 2.06-1.99 (m, 1H), 1.21 (s, 3H), 1.00-0.95 (m, 6H), 0.78-0.74 (m, 4H). |
| 571 | 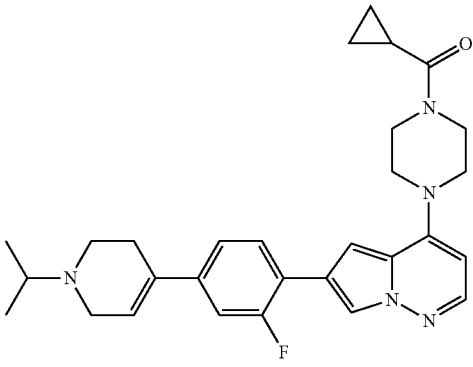 [SMILES: CC(C)N1CC=C(c2ccc(-c3cc4c(N5CCN(C(=O)C6CC6)CC5)ccnn4c3)c(F)c2)CC1] | 488 | |
| 572 | 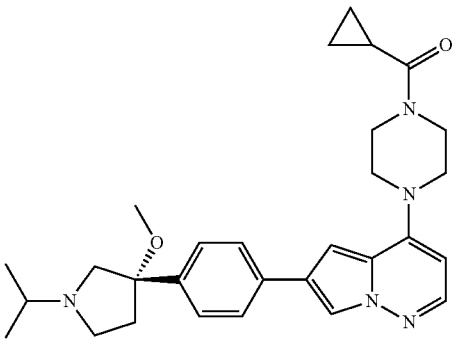 [SMILES: CO[C@]1(c2ccc(-c3cc4c(N5CCN(C(=O)C6CC6)CC5)ccnn4c3)cc2)CCN(C(C)C)C1] | 488 | |
| 573 | 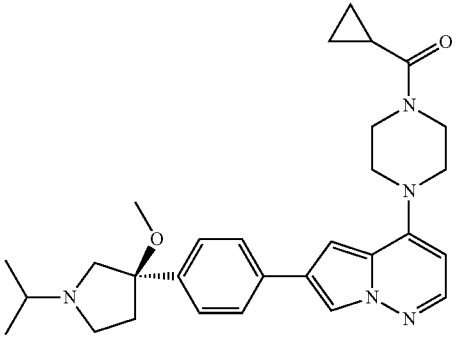 [SMILES: CO[C@@]1(c2ccc(-c3cc4c(N5CCN(C(=O)C6CC6)CC5)ccnn4c3)cc2)CCN(C(C)C)C1] | 488 | |

TABLE 1-continued

| # | Structure | LCMS (M + 1) | NMR |
|---|---|---|---|
| 574 | 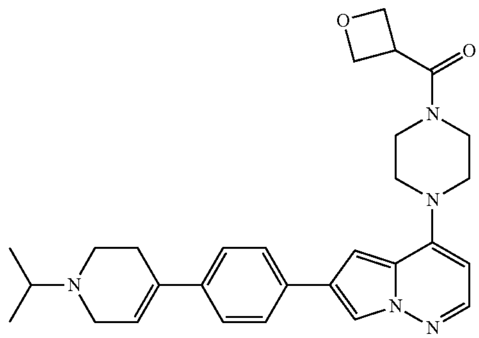 [SMILES: CC(C)N1CC=C(c2ccc(-c3cc4c(N5CCN(C(=O)C6COC6)CC5)ccnn4c3)cc2)CC1] | 488 | 1H NMR (400 MHz, Methanol-d4) δ 8.47 (s, 1H), 7.98 (d, J = 1.8 Hz, 1H), 7.86 (d, J = 5.4 Hz, 1H), 7.81-7.63 (m, 2H), 7.41-7.24 (m, 2H), 6.90 (d, J = 1.9 Hz, 1H), 5.99 (d, J = 5.5 Hz, 1H), 4.87 (s, 2H), 4.26 (p, J = 7.8 Hz, 1H), 3.94-3.83 (m, 2H), 3.63-3.52 (m, 3H), 3.33 (p, J = 1.7 Hz, 4H), 3.21 (td, J = 12.6, 3.0 Hz, 2H), 3.00-2.84 (m, 0H), 2.67 (s, 2H), 2.23-2.12 (m, 2H), 2.12-1.97 (m, 2H), 1.42 (d, J = 6.6 Hz, 6H). |
| 575 | 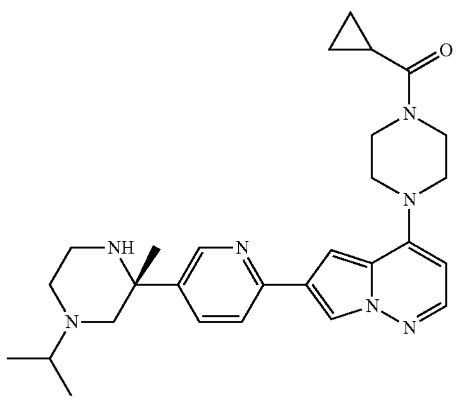 [SMILES: CC(C)N1CCN[C@](C)(c2ccc(-c3cc4c(N5CCN(C(=O)C6CC6)CC5)ccnn4c3)nc2)C1] | 488 | 1H-NMR (400 MHz, CDCl3) δ ppm 8.78 (d, 1H, J = 2.0 Hz), 8.14 (d, 1H, J = 1.2 Hz), 7.98-7.92 (m, 1H), 7.85 (d, 1H, J = 6.4 Hz), 7.64 (d, 1H, J = 8.4 Hz), 7.05 (d, 1H, J = 1.6 Hz), 5.82 (d, 1H, J = 5.2 Hz), 3.97-3.92 (m, 2H), 3.90-3.85 (m, 2H), 3.62-3.57 (m, 2H), 3.52-3.46 (m, 2H), 3.30-3.24 (m, 1H), 3.01-2.93 (m, 1H), 2.81-2.75 (m, 2H), 2.65-2.56 (m, 1H), 2.52-2.45 (m, 3H), 1.80-1.75 (m, 1H), 1.46 (s, 3H), 1.48 (s, 3H), 1.11-1.01 (m, 8H), 0.85-0.79 (m, 2H). |
| 576 | 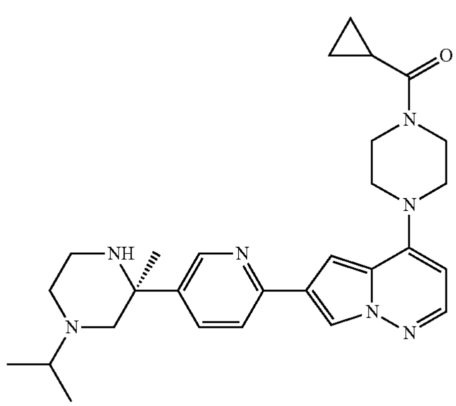 [SMILES: CC(C)N1CCN[C@@](C)(c2ccc(-c3cc4c(N5CCN(C(=O)C6CC6)CC5)ccnn4c3)nc2)C1] | 488 | 1H-NMR (500 MHz, CDCl3) δ ppm 8.81 (d, 1H, J = 1.5 Hz), 8.15 (d, 1H, J = 2.0 Hz), 7.99 (d, 1H, J = 7.5 Hz), 7.87 (d, 1H, J = 5.0 Hz), 7.66 (d, 1H, J = 8.5 Hz), 7.07 (s, 1H), 5.83 (d, 1H, J = 5.0 Hz), 3.98-3.91 (m, 2H), 3.90-3.86 (m, 2H), 3.76-3.80 (m, 1H), 3.68-3.60 (m, 2H), 3.52-3.46 (m, 2H), 3.28-3.25 (m, 1H), 3.08-3.02 (m, 1H), 2.90-2.80 (m, 2H), 2.70-2.62 (m, 2H), 2.62-2.55 (m, 1H), 1.81-1.77 (m, 1H), 2.24-2.21 (m, 1H), 1.54 (s, 3H), 1.14-1.08 (m, 6H), 1.06-1.04 (m, 2H), 0.90-0.82 (m, 2H). |
| 577 | 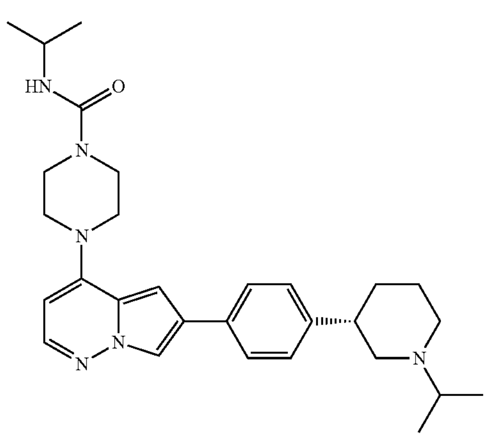 [SMILES: CC(C)NC(=O)N1CCN(c2ccnn3cc(-c4ccc([C@@H]5CCCN(C(C)C)C5)cc4)cc23)CC1] | 489 | 1H-NMR (400 MHz, 6d-DMSO) δ ppm 8.13 (d, 1H, J = 1.6 Hz), 7.88 (d, 1H, J = 5.6 Hz), 7.71 (d, 2H, J = 8.4 Hz), 7.26 (d, 2H, J = 8.4 Hz), 6.98 (d, 1H, J = 1.6 Hz), 6.31 (d, 1H, J = 7.6 Hz), 5.97 (d, 1H, J = 5.6 Hz), 3.85-3.70 (m, 1H), 3.60-3.48 (m, 4H), 3.46-3.38 (m, 4H), 2.84-2.75 (m, 2H), 2.73-2.60 (m, 2H), 2.22-2.08 (m, 2H), 1.86-1.77 (m, 1H), 1.76-1.68 (m, 1H), 1.60-1.50 (m, 1H), 1.50-1.38 (m, 1H), 1.07 (d, 6H, J = 6.4 Hz), 1.00-0.90 (m, 6H). |

TABLE 1-continued

| # | Structure | LCMS (M + 1) | NMR |
|---|---|---|---|
| 578 | 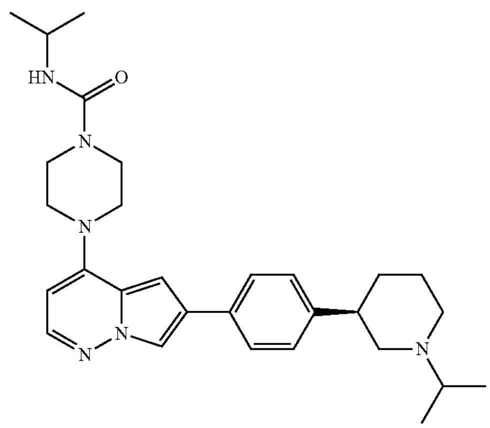 [SMILES: CC(C)NC(=O)N1CCN(c2ccnn3cc(-c4ccc([C@H]5CCCN(C(C)C)C5)cc4)cc23)CC1] | 489 | 1H-NMR (500 MHz, DMSO-d6) δ ppm 8.14 (d, 1H, J = 1.5 Hz), 7.89 (d, 1H, J = 5.0 Hz), 7.72 (d, 2H, J = 8.5 Hz), 7.27 (d, 2H, J = 8.5 Hz), 6.99 (s, 1H), 6.31 (d, 2H, J = 7.5 Hz), 5.98 (d, 1H, J = 5.5 Hz), 3.79-3.78 (m, 1H), 3.52-3.51 (m, 4H), 3.44-3.43 (m, 4H), 2.81-2.79 (m, 2H), 2.74-2.70 (m, 2H), 2.19-2.14 (m, 2H), 1.83-1.81 (m, 1H), 1.74-1.71 (m, 1H), 1.56-1.54 (m, 1H), 1.46-1.44 (m, 1H), 1.09-1.08 (m, 6H), 0.98-0.96 (m, 6H). |
| 579 | 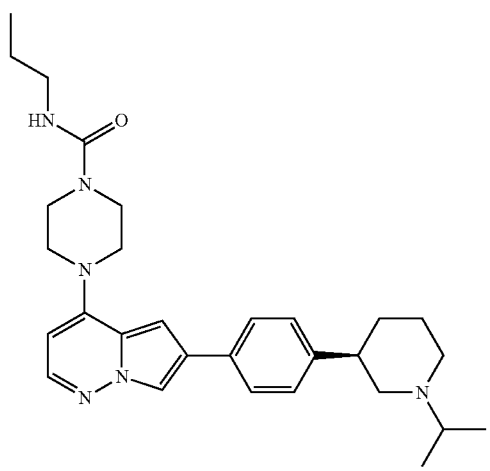 [SMILES: CCCNC(=O)N1CCN(c2ccnn3cc(-c4ccc([C@H]5CCCN(C(C)C)C5)cc4)cc23)CC1] | 489 | 1H-NMR (500 MHz, DMSO-d6) δ ppm 8.14 (s, 1H), 7.89 (d, 1H, J = 5.2 Hz), 7.72 (d, 2H, J = 8.0 Hz), 7.27 (d, 2H, J = 8.0 Hz), 6.99 (s, 1H), 6.63-6.60 (m, 1H), 5.98 (d, 1H, J = 5.6 Hz), 3.54-3.51 (m, 4H), 3.44-3.43 (m, 4H), 3.03-2.99 (m, 2H), 2.81-2.79 (m, 2H), 2.73-2.67 (m, 2H), 2.19-2.14 (m, 2H), 1.84-1.81 (m, 1H), 1.75-1.74 (m, 1H), 1.56-1.41 (m, 4H), 0.98-0.96 (m, 6H), 0.85 (t, 3H, J = 7.6 Hz). |
| 580 | 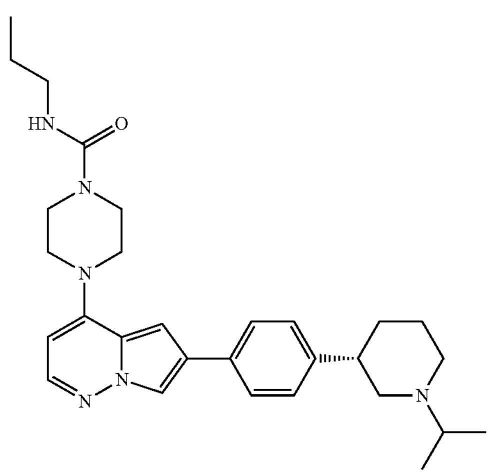 [SMILES: CCCNC(=O)N1CCN(c2ccnn3cc(-c4ccc([C@@H]5CCCN(C(C)C)C5)cc4)cc23)CC1] | 489 | 1H-NMR (400 MHz, DMSO-d6) δ ppm 8.13 (d, 1H, J = 1.2 Hz), 7.88 (d, 1H, J = 5.2 Hz), 7.71 (d, 2H, J = 8.4 Hz), 7.26 (d, 2H, J = 8.0 Hz), 6.98 (d, 1H, J = 1.2 Hz), 6.61 (t, 1H, J = 5.6 Hz), 5.97 (d, 1H, J = 5.6 Hz), 3.60-3.38 (m, 8H), 3.05-2.95 (m, 2H), 2.85-2.60 (m, 4H), 2.22-2.05 (m, 2H), 1.86-1.68 (m, 2H), 1.60-1.34 (m, 4H), 1.00-0.90 (m, 6H), 0.84 (t, 3H, J = 7.2 Hz). |

TABLE 1-continued

| # | Structure | LCMS (M + 1) | NMR |
|---|---|---|---|
| 581 | 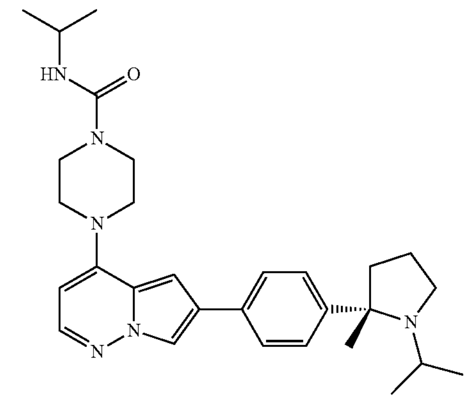 [SMILES: CC(C)NC(=O)N1CCN(c2ccnn3cc(-c4ccc([C@]5(C)CCCN5C(C)C)cc4)cc23)CC1] | 489 | |
| 582 | 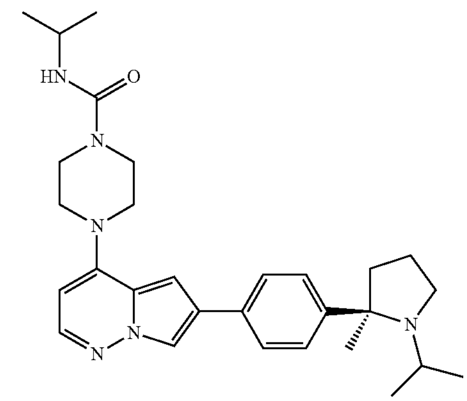 [SMILES: CC(C)NC(=O)N1CCN(c2ccnn3cc(-c4ccc([C@@]5(C)CCCN5C(C)C)cc4)cc23)CC1] | 489 | |
| 583 | 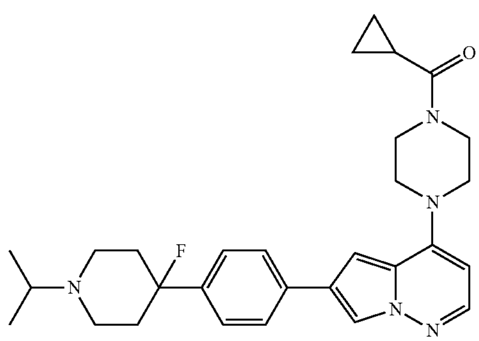 [SMILES: CC(C)N1CCC(F)(c2ccc(-c3cc4c(N5CCN(C(=O)C6CC6)CC5)ccnn4c3)cc2)CC1] | 490 | 1H NMR (400 MHz, DMSO-d6) δ 8.16 (d, J = 1.8 Hz, 1H), 7.86 (d, J = 5.4 Hz, 1H), 7.78 (d, J = 8.1 Hz, 2H), 7.39 (d, J = 8.2 Hz, 2H), 7.03 (d, J = 1.9 Hz, 1H), 5.93 (d, J = 5.5 Hz, 1H), 3.88 (br.s, 2H), 3.66 br. (s, 2H), 3.47 (br.d, J = 27.5 Hz, 4H), 2.70 (d, J = 11.3 Hz, 3H), 2.13-1.80 (m, 5H), 0.98 (d, J = 6.5 Hz, 6H), 0.80-0.64 (m, 4H). |
| 584 | 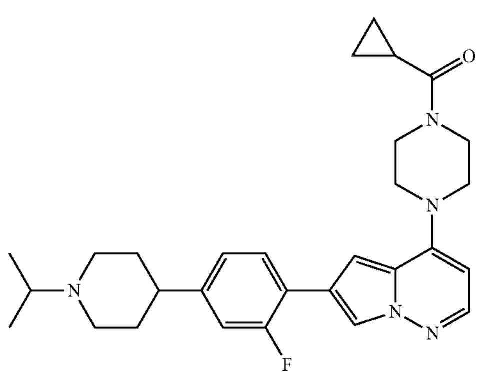 [SMILES: CC(C)N1CCC(c2ccc(-c3cc4c(N5CCN(C(=O)C6CC6)CC5)ccnn4c3)c(F)c2)CC1] | 490 | 1H NMR (500 MHz, Methanol-d4) δ 8.01 (t, J = 2.2 Hz, 1H), 7.87 (d, J = 5.4 Hz, 1H), 7.76 (t, J = 8.1 Hz, 1H), 7.13 (dd, J = 8.0, 1.7 Hz, 1H), 7.07 (dd, J = 12.9, 1.7 Hz, 1H), 6.98 (d, J = 1.8 Hz, 1H), 6.01 (d, J = 5.4 Hz, 1H), 4.04 (s, 2H), 3.86 (s, 2H), 3.65 (s, 2H), 3.55 (s, 2H), 3.09 (d, J = 11.5 Hz, 2H), 2.85 (s, 1H), 2.62 (t, J = 12.4 Hz, 1H), 2.42 (s, 2H), 2.03 (tt, J = 8.2, 4.7 Hz, 1H), 1.93 (d, J = 13.0 Hz, 2H), 1.86-1.72 (m, 2H), 1.15 (d, J = 6.6 Hz, 7H), 0.93 (dt, J = 5.6, 3.0 Hz, 2H), 0.87 (dt, J = 8.0, 3.1 Hz, 2H). |

TABLE 1-continued

| # | Structure | LCMS (M + 1) | NMR |
|---|---|---|---|
| 585 | 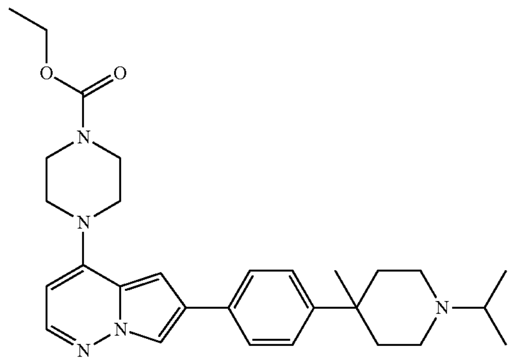 [SMILES: CCOC(=O)N1CCN(c2ccnn3cc(-c4ccc(C5(C)CCN(C(C)C)CC5)cc4)cc23)CC1] | 490 | 1H-NMR (500 MHz, 6d-DMSO) δ ppm 8.34 (s, 1H), 7.15 (d, 1H, J = 1.5 Hz), 7.90 (d, 1H, J = 5.5 Hz), 7.74 (d, 2H, J = 8.5 Hz), 7.37 (d, 2H, J = 8.5 Hz), 6.99 (d, 1H, J = 2.0 Hz), 5.98 (d, 1H, J = 5.5 Hz), 4.09 (q, 2H, J = 7.0 Hz), 3.70-3.41 (m, 8H), 2.68-2.65 (m, 1H), 2.56-2.54 (m, 2H), 2.49-2.45 (m, 2H), 2.05-2.03 (m, 2H), 1.74-1.71 (m, 2H), 1.22 (t, 3H, J = 7.0 Hz), 1.18 (s, 3H), 0.95 (d, 6H, J = 6.5 Hz). |
| 586 | 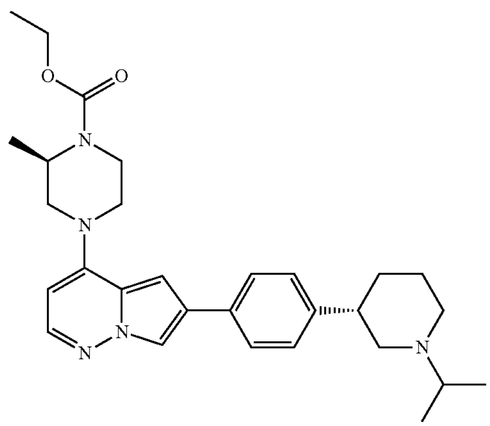 [SMILES: CCOC(=O)N1CCN(c2ccnn3cc(-c4ccc([C@@H]5CCCN(C(C)C)C5)cc4)cc23)C[C@H]1C] | 490 | 1H-NMR (500 MHz, 6d-DMSO) δ ppm 8.26 (s, 1H), 8.14 (d, 1H, J = 1.5 Hz), 7.89 (d, 1H, J = 5.0 Hz), 7.70 (d, 2H, J = 8.0 Hz), 7.28 (d, 2H, J = 8.0 Hz), 6.91 (d, 1H, J = 1.5 Hz), 5.95 (d, 1H, J = 5.5 Hz), 4.29-4.24 (m, 1H), 4.11-4.08 (m, 2H), 3.90-3.86 (m, 3H), 3.41-3.40 (m, 1H), 3.23-3.20 (m, 1H), 3.05-3.04 (m, 1H), 2.85-2.83 (m, 2H), 2.80-2.73 (m, 2H), 2.50-2.20 (m, 2H), 1.75-1.74 (m, 1H), 1.73-1.72 (m, 1H), 1.54-1.53 (m, 1H), 1.52-1.51 (m, 1H), 1.29 (d, 3H, J = 6.5 Hz), 1.22 (t, 3H, J = 7.0 Hz), 1.01-0.99 (m, 6H). |
| 587 | 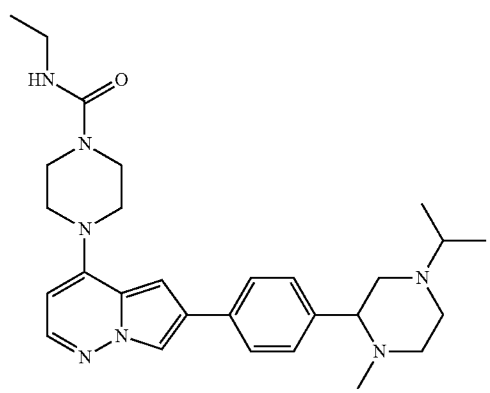 [SMILES: CCNC(=O)N1CCN(c2ccnn3cc(-c4ccc(C5CN(C(C)C)CCN5C)cc4)cc23)CC1] | 490 | 1H-NMR (400 MHz, 6d-DMSO) δ ppm 8.17 (d, 1H, J = 1.2 Hz), 7.90 (d, 1H, J = 5.2 Hz), 7.76 (d, 2H, J = 8.4 Hz), 7.35 (d, 2H, J = 8.0 Hz), 7.01 (d, 1H, J = 1.6 Hz), 6.62 (t, 1H, J = 5.6 Hz), 5.99 (d, 1H, J = 5.2 Hz), 3.53-3.51 (m, 4H), 3.45-3.43 (m, 4H), 3.12-3.06 (m, 2H), 2.98-2.94 (m, 1H), 2.90-2.88 (m, 1H), 2.77-2.75 (m, 1H), 2.66-2.60 (m, 2H), 2.36 (t, 1H, J = 10.8 Hz), 2.22 (t, 1H, J = 9.2 Hz), 2.11 (t, 1H, J = 10.4 Hz), 1.96 (s, 3H), 1.03 (t, 3H, J = 7.6 Hz), 0.98 (d, 6H, J = 6.0 Hz). |
| 588 | 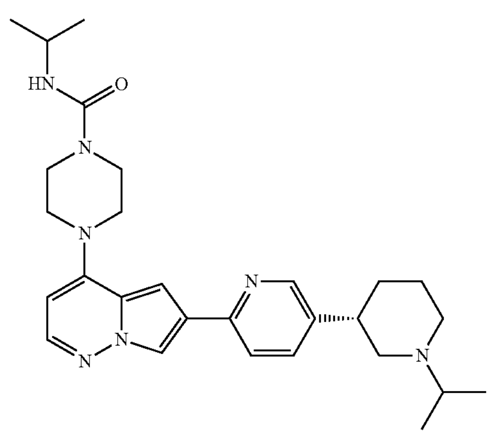 [SMILES: CC(C)NC(=O)N1CCN(c2ccnn3cc(-c4ccc([C@@H]5CCCN(C(C)C)C5)cn4)cc23)CC1] | 490 | 1H-NMR (400 MHz, 6d-DMSO) δ ppm 8.47 (d, 1H, J = 2.0 Hz), 8.24 (d, 1H, J = 2.0 Hz), 7.91 (d, 1H, J = 5.2 Hz), 7.85 (d, 1H, J = 7.6 Hz), 7.69 (dd, 1H, J = 8.0, 2.0 Hz), 7.13 (d, 1H, J = 1.6 Hz), 6.31 (d, 1H, J = 7.6 Hz), 5.98 (d, 1H, J = 5.6 Hz), 3.84-3.74 (m, 1H), 3.53-3.52 (m, 4H), 3.46-3.44 (m, 4H), 2.82-2.72 (m, 4H), 2.25-2.14 (m, 2H), 1.84-1.72 (m, 2H), 1.60-1.45 (m, 2H), 1.08 (d, 6H, J = 6.8 Hz), 0.99-0.96 (m, 6H). |

TABLE 1-continued

| # | Structure | LCMS (M + 1) | NMR |
|---|---|---|---|
| 589 | 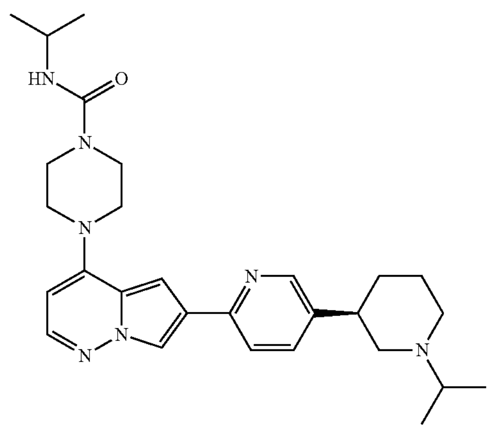 [SMILES: CC(C)NC(=O)N1CCN(c2ccnn3cc(-c4ccc([C@H]5CCCN(C(C)C)C5)cn4)cc23)CC1] | 490 | 1H-NMR (500 MHz, CDCl3) δ ppm 8.52 (s, 1H), 8.13 (d, 1H, J = 1.5 Hz), 7.86 (d, 1H, J = 5.5 Hz), 7.61-7.57 (m, 2H), 7.02 (d, 1H, J = 1.5 Hz), 5.81 (d, 1H, J = 5.0 Hz), 4.31 (d, 1H, J = 7.0 Hz), 4.05-3.98 (m, 1H), 3.64-3.60 (m, 4H), 3.58-3.52 (m, 4H), 3.33-3.29 (m, 1H), 3.25-3.10 (m, 2H), 2.48-2.42 (m, 2H), 2.10-2.04 (m, 2H), 2.00-1.91 (m, 2H), 1.60-1.54 (m, 1H), 1.30-1.20 (m, 6H), 1.20 (d, 6H, J = 6.5 Hz). |
| 590 | 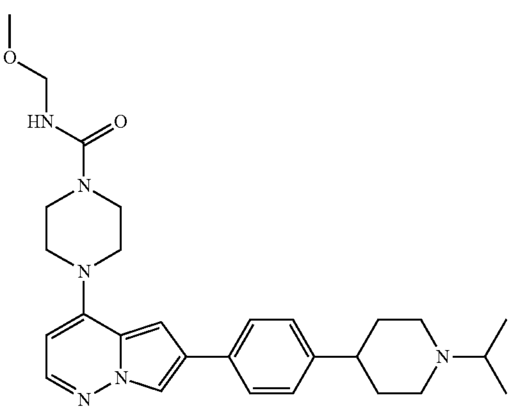 [SMILES: COCNC(=O)N1CCN(c2ccnn3cc(-c4ccc(C5CCN(C(C)C)CC5)cc4)cc23)CC1] | 491 | 1H NMR (400 MHz, DMSO-d6) δ 8.13 (d, J = 1.8 Hz, 1H), 7.88 (d, J = 5.4 Hz, 1H), 7.74 (d, J = 7.8 Hz, 2H), 7.25 (d, J = 8.1 Hz, 2H), 7.00 (d, J = 1.9 Hz, 1H), 5.98 (d, J = 5.5 Hz, 1H), 4.56-4.42 (m, 2H), 3.63-3.51 (m, 4H), 3.44 (t, J = 4.9 Hz, 4H), 3.17 (s, 3H), 1.83 (s, 3H), 1.08 (s, 9H). |
| 591 | 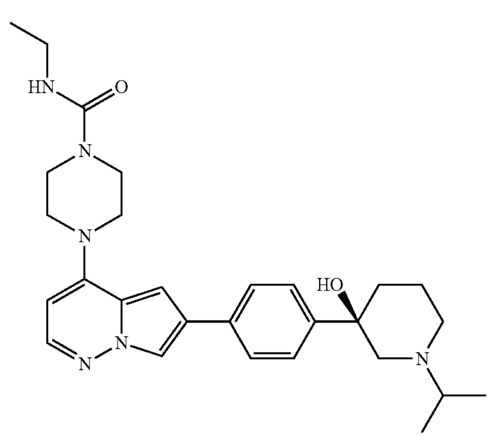 [SMILES: CCNC(=O)N1CCN(c2ccnn3cc(-c4ccc([C@]5(O)CCCN(C(C)C)C5)cc4)cc23)CC1] | 491 | 1H-NMR (400 MHz, DMSO-d6) δ ppm 8.16 (s, 1H), 7.90 (d, 1H, J = 5.2 Hz), 7.75 (d, 2H, J = 8.0 Hz), 7.56 (d, 2H, J = 8.4 Hz), 7.01 (d, 1H, J = 1.2 Hz), 6.63-6.59 (m, 1H), 5.99 (d, 1H, J = 5.6 Hz), 4.56-4.43 (s, 1H), 3.55-3.38 (m, 8H), 3.15-3.00 (m, 2H), 2.90-2.52 (m, 3H), 2.49-2.20 (m, 2H), 1.91-1.70 (m, 2H), 1.70-1.40 (m, 2H), 1.10-0.85 (m, 9H). |

TABLE 1-continued

| # | Structure | LCMS (M + 1) | NMR |
|---|---|---|---|
| 592 | 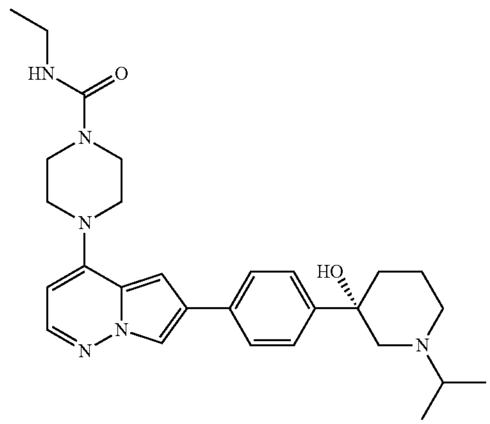 [SMILES: CCNC(=O)N1CCN(c2ccnn3cc(-c4ccc([C@@]5(O)CCCN(C(C)C)C5)cc4)cc23)CC1] | 491 | 1H-NMR (400 MHz, DMSO-d6) δ ppm 8.17 (s, 1H), 7.90 (d, 1H, J = 5.2 Hz), 7.89-7.70 (m, 2H), 7.57 (d, 2H, J = 8.4 Hz), 7.02 (s, 1H), 6.63-6.59 (m, 1H), 5.99 (d, 1H, J = 5.2 Hz), 4.63-4.38 (s, 1H), 3.55-3.38 (m, 8H), 3.15-3.00 (m, 2H), 2.90-2.52 (m, 3H), 2.49-2.20 (m, 2H), 2.00-1.40 (m, 4H), 1.40-0.75 (m, 9H). |
| 593 | 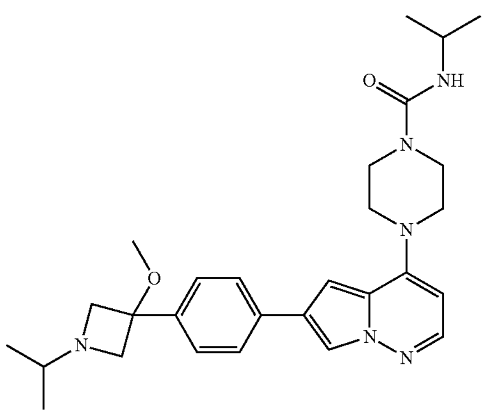 [SMILES: COC1(c2ccc(-c3cc4c(N5CCN(C(=O)NC(C)C)CC5)ccnn4c3)cc2)CN(C(C)C)C1] | 491 | 1H-NMR (400 MHz, 6d-DMSO) δ ppm 8.19 (s, 1H), 7.92 (d, 1H, J = 5.6 Hz), 7.83 (d, 2H, J = 8.0 Hz), 8.46 (d, 2H, J = 8.0 Hz), 7.04 (s, 1H), 6.32 (d, 1H, J = 7.6 Hz), 5.99 (d, 1H, J = 5.2 Hz), 3.82-3.76 (m, 1H), 3.55-3.50 (m, 6H), 3.48-3.43 (m, 4H), 3.22-3.18 (m, 2H), 2.95 (s, 3H), 2.36-2.31 (m, 1H), 1.09 (d, 6H, J = 6.4 Hz), 0.90 (d, 6H, J = 6.0 Hz). |
| 594 | 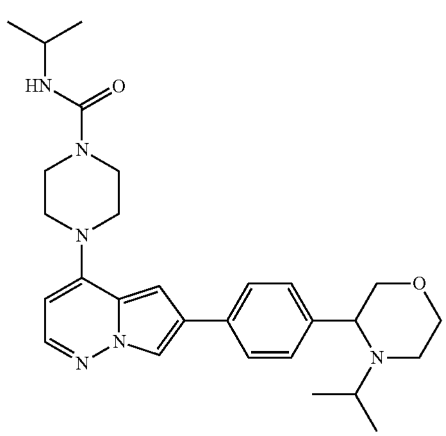 [SMILES: CC(C)NC(=O)N1CCN(c2ccnn3cc(-c4ccc(C5COCCN5C(C)C)cc4)cc23)CC1] | 491 | 1H NMR (400 MHz, Methanol-d4) δ 7.94 (d, J = 1.8 Hz, 1H), 7.87-7.77 (m, 1H), 7.75-7.64 (m, 2H), 7.48-7.35 (m, 2H), 6.88 (d, J = 1.7 Hz, 1H), 5.96 (d, J = 5.5 Hz, 1H), 4.02-3.82 (m, 2H), 3.77-3.59 (m, 7H), 3.55-3.38 (m, 6H), 2.91 (p, J = 6.7 Hz, 1H), 2.80 (dt, J = 11.7, 2.0 Hz, 1H), 2.58 (td, J = 11.7, 3.3 Hz, 1H), 1.17 (d, J = 6.6 Hz, 6H), 1.04 (d, J = 6.9 Hz, 3H), 0.87 (d, J = 6.5 Hz, 3H). |

TABLE 1-continued

| # | Structure | LCMS (M + 1) | NMR |
|---|---|---|---|
| 595 | 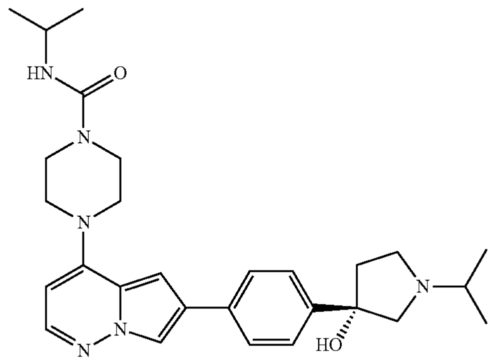 [SMILES: CC(C)NC(=O)N1CCN(c2ccnn3cc(-c4ccc([C@@]5(O)CCN(C(C)C)C5)cc4)cc23)CC1] | 491 | 1H NMR (400 MHz, DMSO-d6) δ 8.11 (d, J = 1.7 Hz, 1H), 7.85 (d, J = 5.4 Hz, 1H), 7.70 (d, J = 8.1 Hz, 2H), 7.45 (d, J = 8.1 Hz, 2H), 6.96 (d, J = 1.8 Hz, 1H), 6.27 (d, J = 7.6 Hz, 1H), 5.94 (d, J = 5.5 Hz, 1H), 5.12 (s, 1H), 3.74 (h, J = 6.7 Hz, 1H), 3.48 (dd, J = 6.8, 3.3 Hz, 4H), 3.38 (dd, J = 6.8, 3.4 Hz, 4H), 2.94-2.66 (m, 4H), 2.11-2.03 (m, 1H), 2.01-1.90 (m, 1H), 1.06-0.97 (m, 12H). |
| 596 | 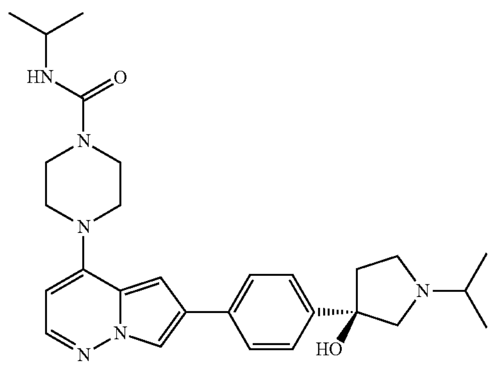 [SMILES: CC(C)NC(=O)N1CCN(c2ccnn3cc(-c4ccc([C@]5(O)CCN(C(C)C)C5)cc4)cc23)CC1] | 491 | |
| 597 | 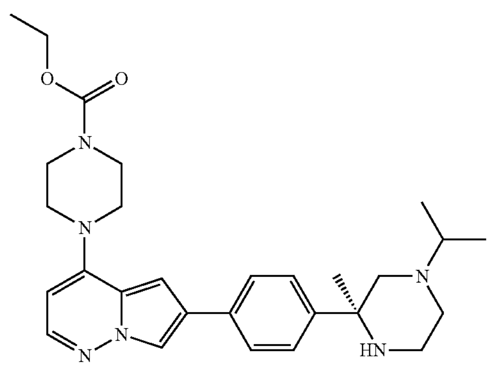 [SMILES: CCOC(=O)N1CCN(c2ccnn3cc(-c4ccc([C@@]5(C)CN(C(C)C)CCN5)cc4)cc23)CC1] | 491 | 1H NMR (400 MHz, CDCl3) δ ppm 7.91 (d, 1H, J = 1.2 Hz), 7.83 (d, 1H, J = 5.2 Hz), 7.62 (d, 2H, J = 8.4 Hz), 7.54 (d, 2H, J = 8.4 Hz), 6.68 (d, 1H, J = 1.2 Hz), 5.82 (d, 1H, J = 5.2 Hz), 4.19 (q, 2H, J = 7.2 Hz), 3.72-3.69 (m, 4H), 3.45-3.41 (m, 4H), 3.14-3.10 (m, 1H), 2.92-2.85 (m, 1H), 2.83-2.74 (m, 1H), 2.72 (heptet, 1H, J = 6.4 Hz), 2.53-2.46 (m, 2H), 2.45-2.38 (m, 1H), 1.39 (s, 3H), 1.29 (t, 3H, J = 7.2 Hz), 1.08 (d, 3H, J = 6.4 Hz), 1.03 (d, 3H, J = 6.4 Hz). |
| 598 | 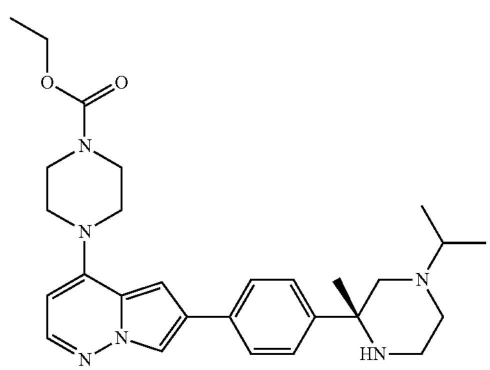 [SMILES: CCOC(=O)N1CCN(c2ccnn3cc(-c4ccc([C@]5(C)CN(C(C)C)CCN5)cc4)cc23)CC1] | 491 | 1H-NMR (400 MHz, 6d-DMSO) δ ppm 8.15 (s, 1H), 7.90 (d, 1H, J = 5.6 Hz), 7.72 (d, 2H, J = 8.0 Hz), 7.50 (d, 2H, J = 8.0 Hz), 7.00 (s, 1H), 5.97 (d, 1H, J = 5.6 Hz), 4.90 (q, 2H, J = 7.2 Hz), 3.62-3.60 (m, 4H), 3.47-3.45 (m, 4H), 3.12-3.04 (m, 1H), 2.72-2.66 (m, 1H), 2.64-2.56 (m, 2H), 2.41-2.37 (m, 1H), 2.33-2.22 (m, 3H), 1.24-1.20 (m, 6H), 1.00-0.95 (m, 6H). |

TABLE 1-continued

| # | Structure | LCMS (M + 1) | NMR |
|---|---|---|---|
| 599 | 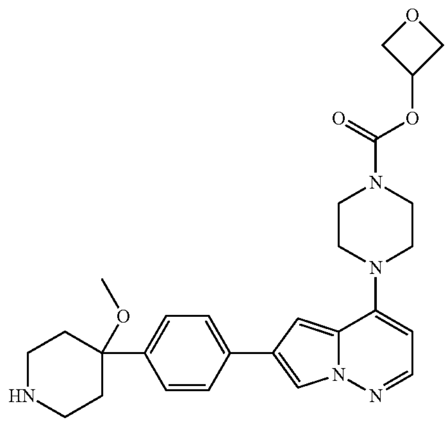 | 492 | 1H NMR (400 MHz, Methanol-d4) δ 7.98 (d, J = 1.8 Hz, 1H), 7.85 (d, J = 5.4 Hz, 1H), 7.78-7.70 (m, 2H), 7.48-7.40 (m, 2H), 6.91 (d, J = 1.8 Hz, 1H), 6.01 (d, J = 5.5 Hz, 1H), 5.41 (tt, J = 6.2, 5.1 Hz, 1H), 4.90 (ddd, J = 7.3, 6.2, 1.0 Hz, 2H), 4.65 (ddd, J = 7.6, 5.1, 0.9 Hz, 2H), 3.75 (d, J = 35.1 Hz, 5H), 3.53 (dd, J = 6.6, 3.9 Hz, 4H), 3.19-3.05 (m, 2H), 3.00 (s, 3H), 2.9.90 (m, 2H), 2.18-2.05 (m, 2H), 1.96 (ddd, J = 13.8, 12.2, 4.4 Hz, 2H). |
| 600 | 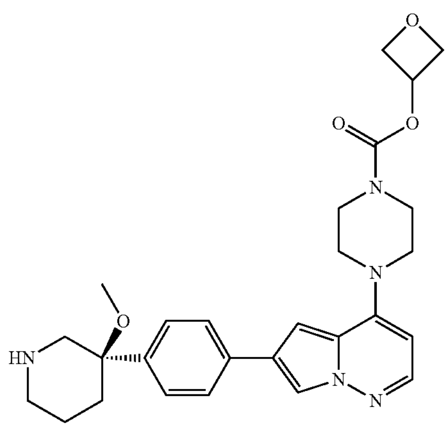 [SMILES: CO[C@@]1(c2ccc(-c3cc4c(N5CCN(C(=O)OC6COC6)CC5)ccnn4c3)cc2)CCCNC1] | 492 | 1H NMR (500 MHz, 4d-MeOD) δ ppm 8.57 (s, 1H), 8.03 (d, 1H, J = 2.0 Hz), 7.88 (d, 1H, J = 5.5 Hz), 7.82 (d, 2H, J = 8.5 Hz), 7.50 (d, 2H, J = 8.5 Hz), 6.95 (d, 1H, J = 1.5 Hz), 6.04 (d, 1H, J = 5.5 Hz), 5.43 (quintet, 1H, J = 5.5 Hz), 4.93 (t, 2H, J = 7.0 Hz), 4.67 (dd, 2H, J = 8.0, 5.5 Hz), 3.83-3.82 (m, 2H), 3.73-3.72 (m, 2H), 3.56-3.54 (m, 4H), 3.47-3.46 (m, 1H), 3.44-3.43 (m, 1H), 3.11 (s, 3H), 3.08-3.06 (m, 1H), 2.99-2.98 (m, 1H), 2.41-2.40 (m, 1H), 2.20-2.19 (m, 1H), 2.16-2.12 (m, 1H), 1.94-1.93 (m, 1H). |
| 601 | 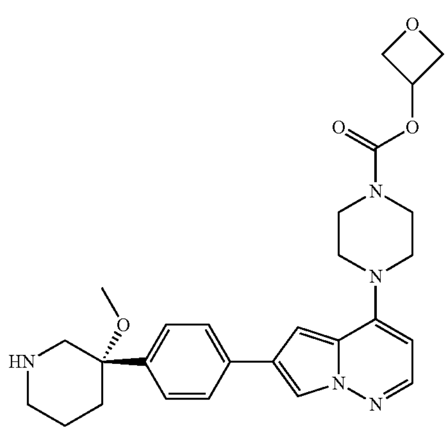 [SMILES: CO[C@]1(c2ccc(-c3cc4c(N5CCN(C(=O)OC6COC6)CC5)ccnn4c3)cc2)CCCNC1] | 492 | 1H NMR (500 MHz, 4d-MeOD) δ ppm 8.57 (s, 1H), 8.03 (d, 1H, J = 2.0 Hz), 7.88 (d, 1H, J = 5.5 Hz), 7.82 (d, 2H, J = 8.5 Hz), 7.50 (d, 2H, J = 8.5 Hz), 6.95 (d, 1H, J = 1.5 Hz), 6.04 (d, 1H, J = 5.5 Hz), 5.43 (quintet, 1H, J = 5.5 Hz), 4.93 (t, 2H, J = 7.0 Hz), 4.67 (dd, 2H, J = 8.0, 5.5 Hz), 3.83-3.82 (m, 2H), 3.73-3.72 (m, 2H), 3.56-3.54 (m, 4H), 3.47-3.46 (m, 1H), 3.44-3.43 (m, 1H), 3.11 (s, 3H), 3.08-3.06 (m, 1H), 2.99-2.98 (m, 1H), 2.41-2.40 (m, 1H), 2.20-2.19 (m, 1H), 2.16-2.12 (m, 1H), 1.94-1.93 (m, 1H). |

TABLE 1-continued

| # | Structure | LCMS (M + 1) | NMR |
|---|---|---|---|
| 602 | 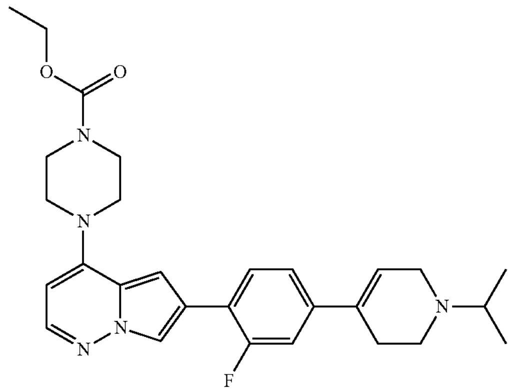 [SMILES: CCOC(=O)N1CCN(c2ccnn3cc(-c4ccc(C5=CCN(C(C)C)CC5)cc4F)cc23)CC1] | 492 | |
| 603 | 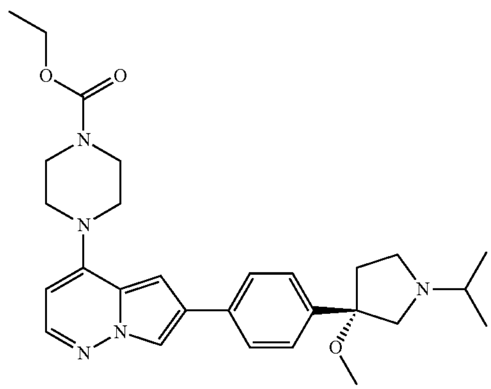 [SMILES: CCOC(=O)N1CCN(c2ccnn3cc(-c4ccc([C@@]5(OC)CCN(C(C)C)C5)cc4)cc23)CC1] | 492 | 1H NMR (400 MHz, DMSO-d6) δ 8.14 (d, J = 1.8 Hz, 1H), 7.86 (d, J = 5.4 Hz, 1H), 7.77-7.71 (m, 2H), 7.38-7.31 (m, 2H), 6.98 (d, J = 1.8 Hz, 1H), 5.94 (d, J = 5.5 Hz, 1H), 4.04 (q, J = 7.1 Hz, 2H), 3.58-3.51 (m, 4H), 3.45-3.38 (m, 4H), 2.95-2.86 (m, 5H), 2.76-2.63 (m, 2H), 2.39 (p, J = 6.3 Hz, 1H), 2.16 (ddd, J = 12.3, 7.2, 4.7 Hz, 1H), 2.04 (dt, J = 13.1, 7.7 Hz, 1H), 1.17 (t, J = 7.1 Hz, 3H), 0.99 (d, J = 6.2 Hz, 6H). |
| 604 | 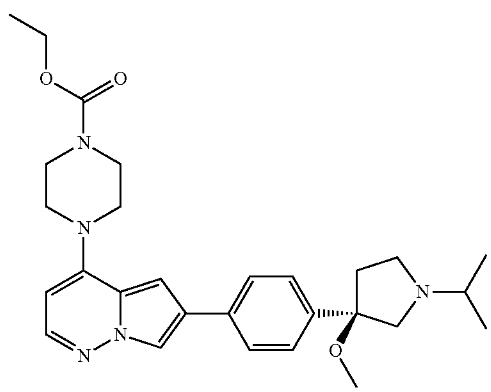 [SMILES: CCOC(=O)N1CCN(c2ccnn3cc(-c4ccc([C@]5(OC)CCN(C(C)C)C5)cc4)cc23)CC1] | 492 | |
| 605 | 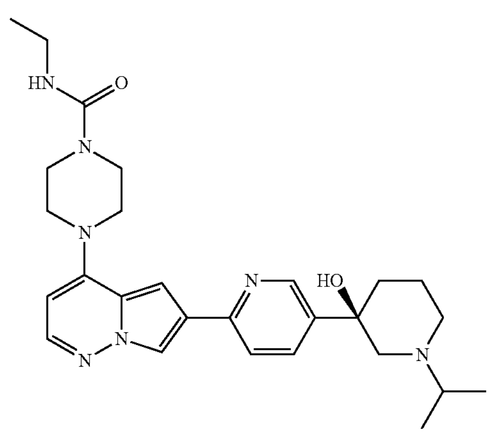 [SMILES: CCNC(=O)N1CCN(c2ccnn3cc(-c4ccc([C@]5(O)CCCN(C(C)C)C5)cn4)cc23)CC1] | 492 | 1H-NMR (400 MHz, DMSO-d6) δ ppm 8.76 (s, 1H), 8.25 (s, 1H), 7.95-7.91 (m, 2H), 7.88-7.85 (m, 1H), 7.15 (s, 1H), 6.61-6.59 (m, 1H), 5.98 (d, 1H, J = 5.6 Hz), 4.76 (s, 1H), 3.53-3.52 (m, 4H), 3.45-3.44 (m, 4H), 3.11-3.05 (m, 2H), 2.81-2.75 (m, 1H), 2.69-2.66 (m, 1H), 2.59-2.56 (m, 1H), 2.46-2.37 (m, 2H), 1.90-1.84 (m, 1H), 1.77-1.74 (m, 1H), 1.61-1.57 (m, 1H), 1.45-1.42 (m, 1H), 1.03 (t, 3H, J = 7.2 Hz), 1.0-0.97 (m, 6H). |

TABLE 1-continued

| # | Structure | LCMS (M + 1) | NMR |
|---|---|---|---|
| 606 | 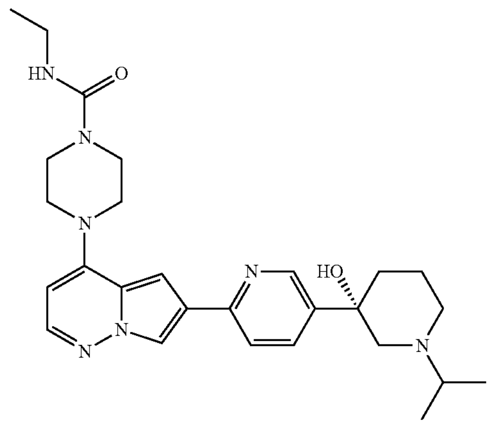 [SMILES: CCNC(=O)N1CCN(c2ccnn3cc(-c4ccc([C@@]5(O)CCCN(C(C)C)C5)cn4)cc23)CC1] | 492 | 1H-NMR (400 MHz, DMSO-d6) δ ppm 8.76 (d, 1H, J = 1.6 Hz), 8.28-8.25 (m, 1H), 7.94-7.90 (m, 2H), 7.87-7.85 (m, 1H), 7.15 (d, 1H, J = 1.2 Hz), 6.61-6.59 (m, 1H), 5.98 (d, 1H, J = 5.6 Hz), 4.76 (s, 1H), 3.53-3.52 (m, 4H), 3.45-3.44 (m, 4H), 3.11-3.05 (m, 2H), 2.81-2.74 (m, 1H), 2.68-2.66 (m, 1H), 2.58-2.56 (m, 1H), 2.46-2.36 (m, 2H), 1.90-1.84 (m, 1H), 1.79-1.74 (m, 1H), 1.60-1.57 (m, 1H), 1.45-1.43 (m, 1H), 1.03 (t, 3H, J = 7.6 Hz), 1.0-0.97 (m, 6H). |
| 607 | 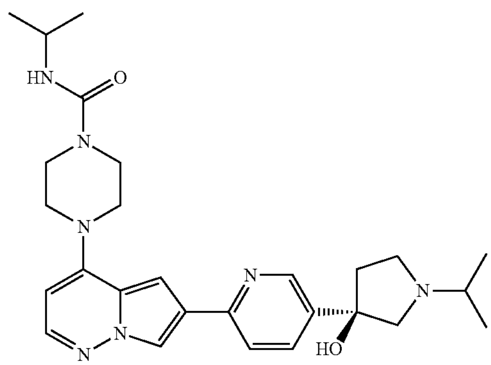 | 492 | 1H NMR (400 MHz, DMSO-d6) δ 8.68 (d, J = 2.1 Hz, 1H), 8.24 (d, J = 1.7 Hz, 1H), 7.91 (d, J = 5.4 Hz, 1H), 7.90-7.80 (m, 2H), 7.14 (d, J = 1.8 Hz, 1H), 6.30 (d, J = 7.6 Hz, 1H), 5.99 (d, J = 5.5 Hz, 1H), 5.36 (s, 1H), 3.78 (h, J = 6.7 Hz, 1H), 3.57-3.48 (m, 4H), 3.48-3.40 (m, 4H), 2.93 (d, J = 9.7 Hz, 1H), 2.88-2.72 (m, 3H), 2.14 (dt, J = 15.1, 7.9 Hz, 1H), 2.09-1.98 (m, 1H), 1.10-1.00 (m, 12H). |
| 608 | 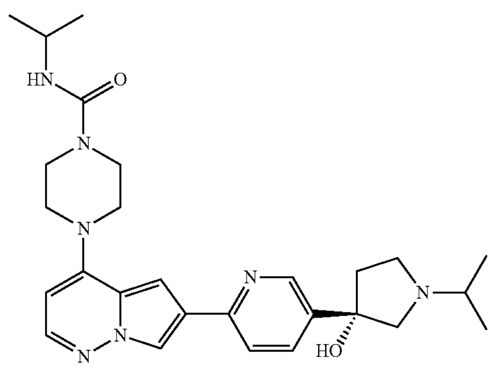 | 492 | |
| 609 | 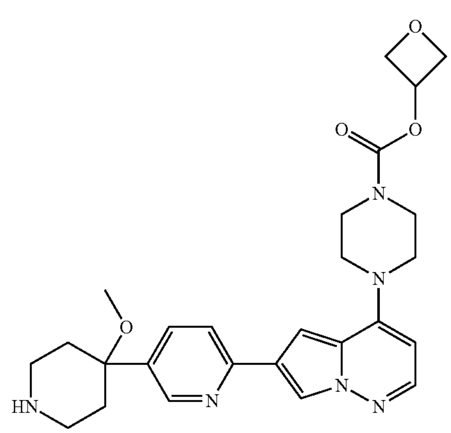 [SMILES: COC1(c2ccc(-c3cc4c(N5CCN(C(=O)OC6COC6)CC5)ccnn4c3)nc2)CCNCC1] | 493 | 1H NMR (400 MHz, Methanol-d4) δ 8.54 (dd, J = 2.2, 1.1 Hz, 1H), 8.20 (d, J = 1.9 Hz, 1H), 7.94-7.78 (m, 3H), 7.24-7.06 (m, 1H), 6.01 (d, J = 5.5 Hz, 1H), 5.41 (tt, J = 6.3, 5.1 Hz, 1H), 4.90 (ddd, J = 7.3, 6.3, 1.0 Hz, 2H), 4.66 (ddd, J = 7.5, 5.1, 0.9 Hz, 2H), 3.89-3.64 (m, 5H), 3.55 (dd, J = 6.5, 3.8 Hz, 4H), 3.30 (p, J = 1.6 Hz, 4H), 3.17-3.06 (m, 2H), 3.01-2.93 (m, 1H), 2.14 (dd, J = 14.5, 2.4 Hz, 2H), 2.04-1.89 (m, 2H). |

TABLE 1-continued

| # | Structure | LCMS (M + 1) | NMR |
|---|---|---|---|
| 610 | 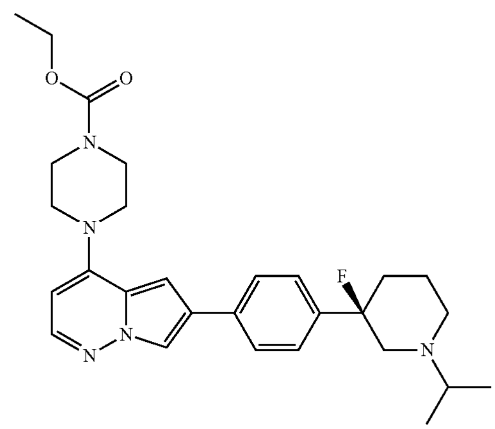 [SMILES: CCOC(=O)N1CCN(c2ccnn3cc(-c4ccc([C@]5(F)CCCN(C(C)C)C5)cc4)cc23)CC1] | 494 | 1H-NMR (400 MHz, 6d-DMSO) δ ppm 8.20 (d, 1H, J = 2.0 Hz), 7.91 (d, 1H, J = 5.2 Hz), 7.82 (d, 2H, J = 8.4 Hz), 7.49 (d, 2H, J = 8.4 Hz), 7.04 (d, 1H, J = 2.0 Hz), 5.99 (d, 1H, J = 5.6 Hz), 4.09 (q, 2H, J = 6.8 Hz), 3.65-3.55 (m, 4H), 3.55-3.40 (m, 4H), 2.82-2.72 (m, 3H), 2.70-2.60 (m, 1H), 2.40-2.25 (m, 1H), 2.05-1.90 (m, 2H), 1.80-1.70 (m, 1H), 1.60-1.50 (m, 1H), 1.22 (t, 3H, J = 6.8 Hz), 1.05-0.92 (m, 6H). |
| 611 | 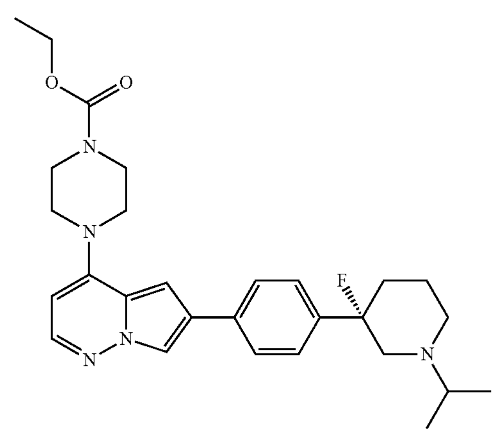 [SMILES: CCOC(=O)N1CCN(c2ccnn3cc(-c4ccc([C@@]5(F)CCCN(C(C)C)C5)cc4)cc23)CC1] | 494 | 1H-NMR (400 MHz, 6d-DMSO) δ ppm 8.20 (d, 1H, J = 2.0 Hz), 7.91 (d, 1H, J = 5.2 Hz), 7.82 (d, 2H, J = 8.4 Hz), 7.49 (d, 2H, J = 8.4 Hz), 7.04 (d, 1H, J = 2.0 Hz), 5.99 (d, 1H, J = 5.6 Hz), 4.09 (q, 2H, J = 6.8 Hz), 3.65-3.55 (m, 4H), 3.55-3.40 (m, 4H), 2.82-2.72 (m, 3H), 2.70-2.60 (m, 1H), 2.40-2.25 (m, 1H), 2.05-1.90 (m, 2H), 1.80-1.70 (m, 1H), 1.60-1.50 (m, 1H), 1.22 (t, 3H, J = 6.8 Hz), 1.05-0.92 (m, 6H). |
| 612 | 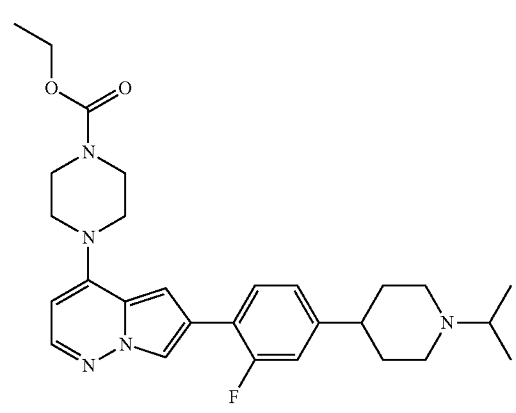 [SMILES: CCOC(=O)N1CCN(c2ccnn3cc(-c4ccc(C5CCN(C(C)C)CC5)cc4F)cc23)CC1] | 494 | 1H NMR (500 MHz, Methanol-d4) δ 8.00 (t, J = 2.2 Hz, 1H), 7.86 (d, J = 5.4 Hz, 1H), 7.75 (t, J = 8.1 Hz, 1H), 7.12 (dd, J = 8.0, 1.7 Hz, 1H), 7.06 (dd, J = 12.9, 1.7 Hz, 1H), 6.94 (d, J = 1.8 Hz, 1H), 6.01 (d, J = 5.5 Hz, 1H), 4.18 (q, J = 7.1 Hz, 2H), 3.72 (d, J = 5.9 Hz, 4H), 3.51 (dd, J = 6.3, 3.9 Hz, 4H), 3.08 (d, J = 11.5 Hz, 2H), 2.91-2.77 (m, 1H), 2.61 (dd, J = 13.9, 10.0 Hz, 1H), 2.42 (t, J = 11.8 Hz, 2H), 1.91 (t, J = 17.0 Hz, 2H), 1.86-1.67 (m, 2H), 1.30 (t, J = 7.1 Hz, 2H), 1.14 (t, J = 6.6 Hz, 7H). |

TABLE 1-continued

| # | Structure | LCMS (M + 1) | NMR |
|---|---|---|---|
| 613 | 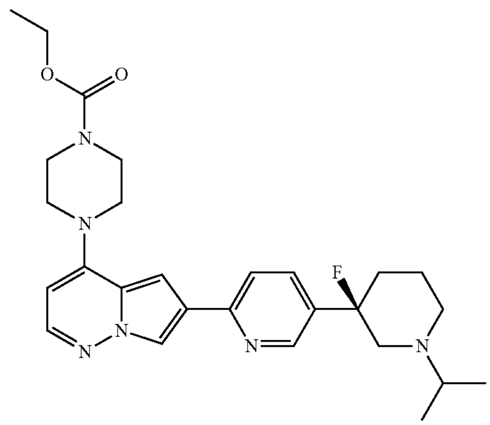 [SMILES: CCOC(=O)N1CCN(c2ccnn3cc(-c4ccc([C@]5(F)CCCN(C(C)C)C5)cn4)cc23)CC1] | 495 | 1H-NMR (500 MHz, 6d-DMSO) δ ppm 8.72 (s, 1H), 8.31 (s, 1H), 7.97-7.91 (m, 3H), 7.20 (s, 1H), 6.02-6.0 (m, 1H), 4.11-4.08 (m, 2H), 3.66-3.58 (m, 4H), 3.52-3.49 (m, 4H), 2.85-2.80 (m, 2H), 2.70-2.65 (m, 2H), 2.43-2.35 (m, 1H), 2.13-1.99 (m, 1H), 1.97-1.89 (m, 1H), 1.85-1.75 (m, 1H), 1.60-1.51 (m, 1H), 1.23 (t, 3H, J = 7.0 Hz), 1.02-0.99 (m, 6H). |
| 614 | 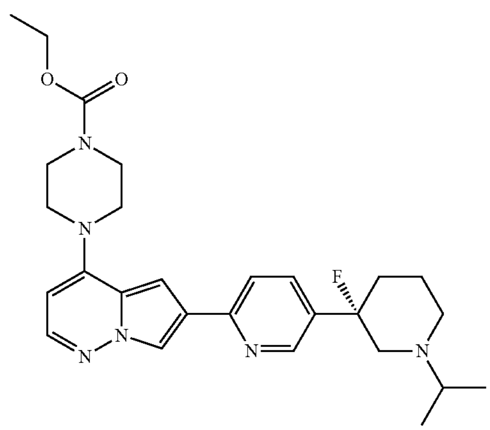 [SMILES: CCOC(=O)N1CCN(c2ccnn3cc(-c4ccc([C@@]5(F)CCCN(C(C)C)C5)cn4)cc23)CC1] | 495 | 1H-NMR (400 MHz, 6d-DMSO) δ ppm 8.73 (s, 1H), 8.31 (s, 1H), 7.96-7.90 (m, 3H), 7.20 (s, 1H), 6.0 (d, 1H, J = 5.6 Hz), 4.08 (q, 2H, J = 7.2 Hz), 3.66-3.59 (m, 4H), 3.53-3.46 (m, 4H), 2.85-2.80 (m, 2H), 2.70-2.65 (m, 2H), 2.43-2.31 (m, 1H), 2.07-1.93 (m, 2H), 1.85-1.71 (m, 1H), 1.61-1.50 (m, 1H), 1.23 (t, 3H, J = 7.2 Hz), 1.01-0.98 (m, 6H). |
| 615 | 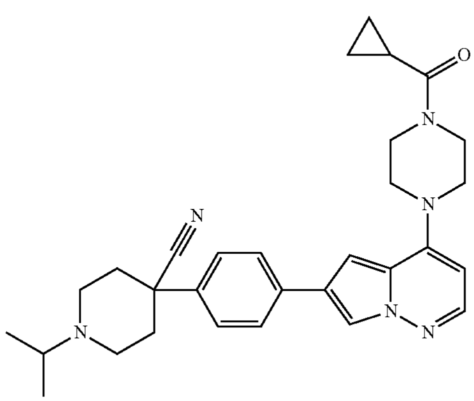 [SMILES: CC(C)N1CCC(C#N)(c2ccc(-c3cc4c(N5CCN(C(=O)C6CC6)CC5)ccnn4c3)cc2)CC1] | 497 | 1H NMR (400 MHz, Methanol-d4) δ 7.99 (d, J = 1.8 Hz, 1H), 7.85 (t, J = 5.2 Hz, 1H), 7.83-7.74 (m, 2H), 7.59-7.48 (m, 2H), 6.94 (d, J = 1.9 Hz, 1H), 5.99 (d, J = 5.5 Hz, 1H), 4.04 (s, 2H), 3.86 (s, 2H), 3.65 (s, 2H), 3.55 (s, 2H), 3.07 (d, J = 12.2 Hz, 2H), 2.86 (p, J = 6.6 Hz, 1H), 2.75-2.62 (m, 2H), 2.26-2.07 (m, 4H), 2.00 (tt, J = 7.9, 4.7 Hz, 1H), 1.16 (d, J = 6.6 Hz, 6H), 0.94 (dt, J = 4.9, 3.0 Hz, 2H), 0.92-0.81 (m, 2H). |

TABLE 1-continued

| # | Structure | LCMS (M + 1) | NMR |
|---|---|---|---|
| 616 | 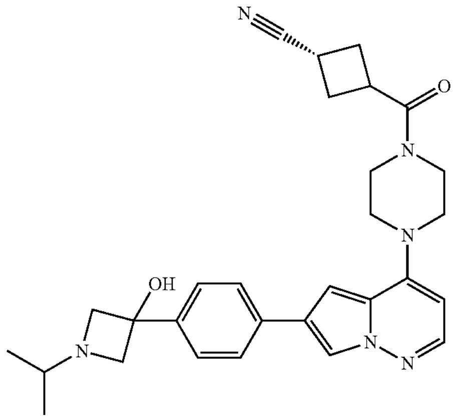 | 499 | 1H-NMR (400 MHz, 6d-DMSO) δ ppm 8.18 (d, 1H, J = 1.6 Hz), 7.92 (d, 1H, J = 5.2 Hz), 7.79 (d, 2H, J = 8.4 Hz), 7.64 (d, 2H, J = 8.4 Hz), 7.03 (d, 1H, J = 1.6 Hz), 5.98 (d, 1H, J = 5.6 Hz), 5.80 (s, 1H), 3.76-3.69 (m, 2H), 3.65-3.62 (m, 1H), 3.60-3.50 (m, 4H), 3.49-3.40 (m, 4H), 3.32-3.27 (m, 1H), 3.26-3.20 (m, 2H), 2.70-2.58 (m, 2H), 2.48-2.30 (m, 3H), 0.92 (d, 6H, J = 6.0 Hz). |
| 617 | 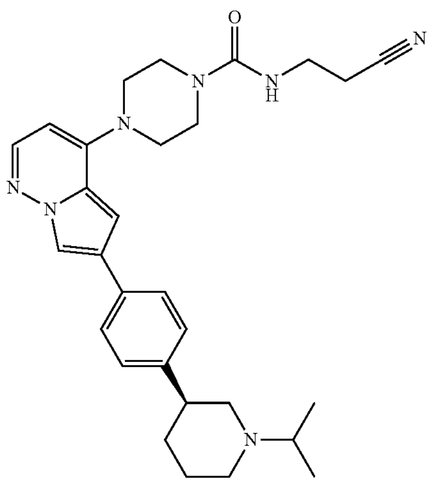 [SMILES: CC(C)N1CCC[C@@H](c2ccc(-c3cc4c(N5CCN(C(=O)NCCC#N)CC5)ccnn4c3)cc2)C1] | 500 | 1H-NMR (500 MHz, DMSO-d6) δ ppm 8.14 (d, 1H, J = 1.6 Hz), 7.89 (d, 1H, J = 5.2 Hz), 7.72 (d, 2H, J = 8.4 Hz), 7.27 (d, 2H, J = 8.4 Hz), 7.08-7.05 (m, 1H), 7.00 (d, 1H, J = 1.2 Hz), 5.98 (d, 1H, J = 5.2 Hz), 3.55-3.51 (m, 4H), 3.45-3.43 (m, 4H), 3.30-3.27 (m, 2H), 2.82-2.80 (m, 2H), 2.74-2.65 (m, 4H), 2.18-2.16 (m, 2H), 1.84-1.81 (m, 1H), 1.75-1.74 (m, 1H), 1.46-1.41 (m, 2H), 0.99-0.97 (m, 6H). |
| 618 | 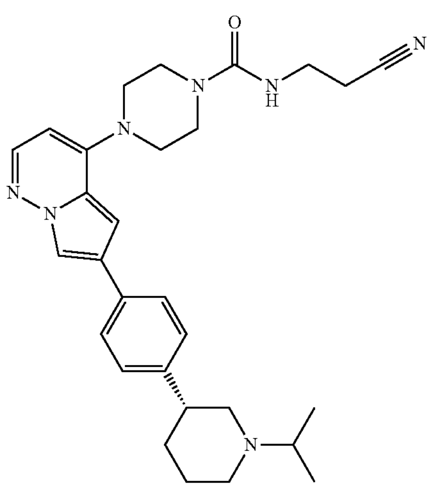 [SMILES: CC(C)N1CCC[C@H](c2ccc(-c3cc4c(N5CCN(C(=O)NCCC#N)CC5)ccnn4c3)cc2)C1] | 500 | 1H-NMR (500 MHz, DMSO-d6) δ ppm 8.14 (d, 1H, J = 1.6 Hz), 7.89 (d, 1H, J = 5.6 Hz), 7.72 (d, 2H, J = 8.4 Hz), 7.27 (d, 2H, J = 8.4 Hz), 7.07-7.04 (m, 1H), 7.00 (d, 1H, J = 1.6 Hz), 5.98 (d, 1H, J = 5.2 Hz), 3.55-3.54 (m, 4H), 3.46-3.45 (m, 4H), 3.30-3.27 (m, 2H), 2.81-2.79 (m, 2H), 2.74-2.65 (m, 4H), 2.19-2.14 (m, 2H), 1.83-1.80 (m, 1H), 1.75-1.71 (m, 1H), 1.56-1.45 (m, 2H), 0.99-0.96 (m, 6H). |

TABLE 1-continued

| # | Structure | LCMS (M + 1) | NMR |
|---|---|---|---|
| 619 | 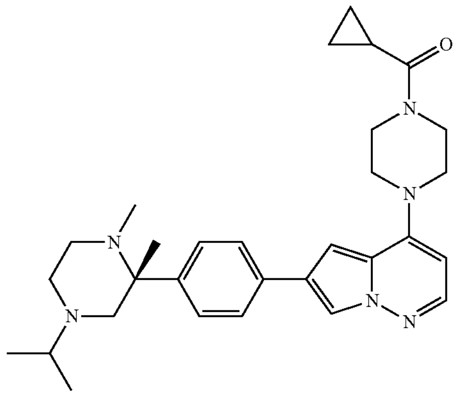 [SMILES: CC(C)N1CCN(C)[C@](C)(c2ccc(-c3cc4c(N5CCN(C(=O)C6CC6)CC5)ccnn4c3)cc2)C1] | 501 | 1H NMR (500 MHz, 6d-DMSO) δ ppm 8.17 (s, 1H), 7.92 (d, 1H, J = 5.5 Hz), 7.75 (d, 2H, J = 7.0 Hz), 7.58 (d, 2H, J = 7.0 Hz), 7.03 (s, 1H), 5.99 (d, 1H, J = 5.0 Hz), 3.94-3.93 (m, 2H), 3.72-3.71 (m, 2H), 3.56-3.52 (m, 2H), 3.48-3.43 (m, 2H), 2.65-2.64 (m, 1H), 2.63-2.60 (m, 3H), 2.39-2.37 (m, 2H), 2.07-2.03 (m, 2H), 1.92 (s, 3H), 1.39 (s, 3H), 0.94-0.91 (m, 6H), 0.79-0.76 (m, 4H). |
| 620 | 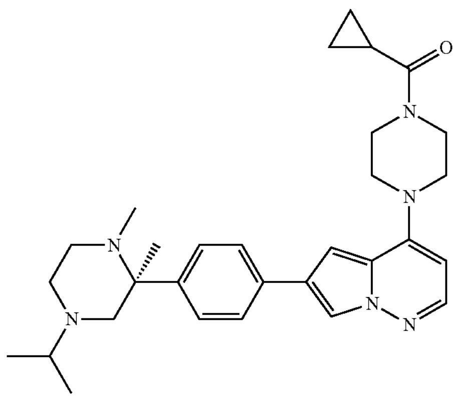 [SMILES: CC(C)N1CCN(C)[C@@](C)(c2ccc(-c3cc4c(N5CCN(C(=O)C6CC6)CC5)ccnn4c3)cc2)C1] | 501 | 1H-NMR (400 MHz, CDCl3) δ ppm 7.95 (d, 1H, J = 1.6 Hz), 7.85 (d, 1H, J = 6.4 Hz), 7.68-7.60 (m, 4H), 6.73 (d, 1H, J = 2.0 Hz), 5.85 (d, 1H, J = 5.2 Hz), 4.00-3.95 (m, 2H), 3.93-3.87 (m, 2H), 3.60-3.55 (m, 2H), 3.55-3.50 (m, 2H), 3.52-3.48 (m, 2H), 2.81-2.71 (m, 2H), 2.70-2.60 (m, 1H), 2.47-2.45 (m, 1H), 2.25-2.22 (m, 1H), 2.02 (s, 3H), 1.48 (s, 3H), 1.16-1.14 (m, 1H), 1.07-1.04 (m, 2H), 1.01-0.94 (m, 6H), 0.85-0.82 (m, 2H). |
| 621 | 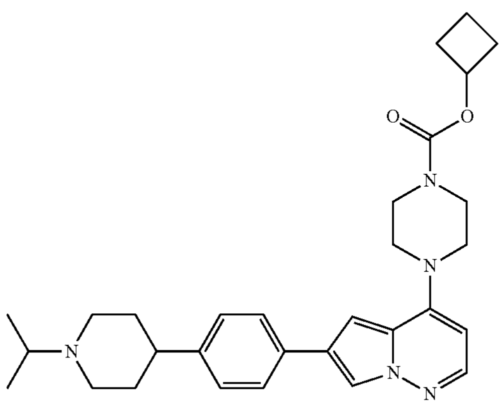 [SMILES: CC(C)N1CCC(c2ccc(-c3cc4c(N5CCN(C(=O)OC6CCC6)CC5)ccnn4c3)cc2)CC1] | 502 | 1H NMR (400 MHz, DMSO-d6) δ 8.13 (d, J = 1.7 Hz, 1H), 7.89 (d, J = 5.4 Hz, 1H), 7.71 (d, J = 7.9 Hz, 2H), 7.24 (d, J = 8.1 Hz, 2H), 6.98 (d, J = 1.8 Hz, 1H), 5.97 (d, J = 5.4 Hz, 1H), 4.87 (p, J = 7.4 Hz, 1H), 3.59 (s, 4H), 3.44 (t, J = 5.1 Hz, 4H), 2.89 (d, J = 10.8 Hz, 3H), 2.69 (d, J = 21.9 Hz, 1H), 2.26 (dtd, J = 12.2, 8.6, 7.7, 3.6 Hz, 4H), 2.01 (ddt, J = 16.1, 10.9, 5.4 Hz, 2H), 1.76 (d, J = 13.2 Hz, 3H), 1.70-1.50 (m, 2H), 0.99 (d, J = 6.5 Hz, 7H). |
| 622 | 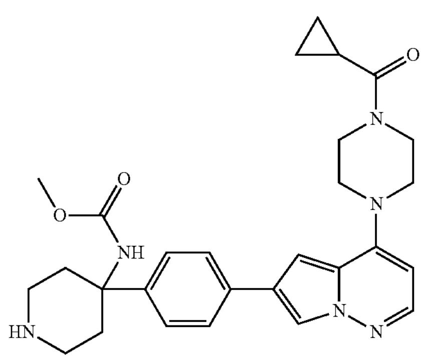 [SMILES: COC(=O)NC1(c2ccc(-c3cc4c(N5CCN(C(=O)C6CC6)CC5)ccnn4c3)cc2)CCNCC1] | 503 | |

TABLE 1-continued

| # | Structure | LCMS (M + 1) | NMR |
|---|---|---|---|
| 623 | 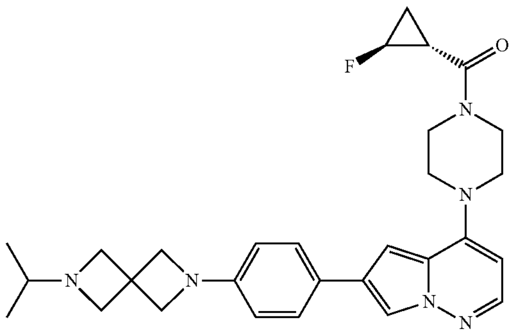 [SMILES: CC(C)N1CC2(CN(c3ccc(-c4cc5c(N6CCN(C(=O)[C@H]7C[C@@H]7F)CC6)ccnn5c4)cc3)C2)C1] | 503 | 1H-NMR (400 MHz, 6d-DMSO) δ ppm 8.04 (d, 1H, J = 1.2 Hz), 7.87 (d, 1H, J = 5.6 Hz), 7.62 (d, 2H, J = 8.4 Hz), 6.91 (d, 1H, J = 1.6 Hz), 6.45 (d, 2H, J = 8.4 Hz), 5.97 (d, 1H, J = 5.2 Hz), 4.93-4.75 (s, 1H), 3.94-3.92 (m, 2H), 3.85 (s, 4H), 3.70-3.66 (m, 2H), 3.54-3.42 (m, 4H), 3.21 (m, 4H), 2.70-2.60 (m, 1H), 2.22-2.16 (m, 1H), 1.48-1.38 (m, 1H), 1.24-1.14 (m, 1H), 0.85 (d, 6H, J = 6.0 Hz). |
| 624 | 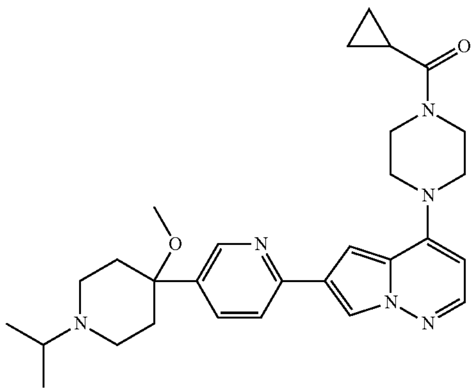 | 503 | 1H-NMR (400 MHz, DMSO-d6) δ ppm 8.58 (d, 1H, J = 2.0 Hz), 8.29 (d, 1H, J = 1.6 Hz), 8.00-7.90 (m, 2H), 7.80-7.75 (m, 1H), 7.21 (d, 1H, J = 1.6 Hz), 5.99 (d, J = 5.6 Hz), 4.00-3.85 (m, 2H), 3.80-3.65 (m, 2H), 3.63-3.40 (m, 4H), 2.92 (s, 3H), 2.75-2.65 (m, 1H), 2.65-2.55 (m, 2H), 2.50-2.40 (m, 2H), 2.10-1.95 (m, 3H), 1.95-1.80 (m, 2H), 1.00 (d, 6H, J = 6.8 Hz), 0.83-0.70 (m, 4H). |
| 625 | 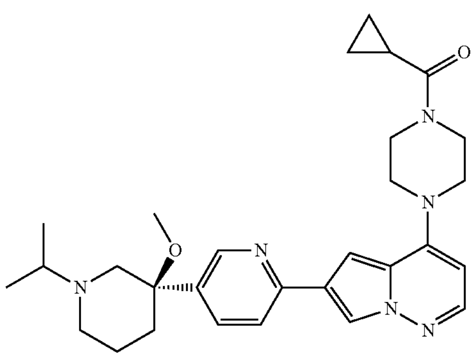 [SMILES: CO[C@@]1(c2ccc(-c3cc4c(N5CCN(C(=O)C6CC6)CC5)ccnn4c3)nc2)CCCN(C(C)C)C1] | 503 | 1H-NMR (400 MHz, DMSO-d6) δ ppm 8.67 (s, 1H), 8.29 (s, 1H), 7.94-7.90 (m, 2H), 7.86-7.84 (m, 1H), 7.20 (s, 1H), 5.98 (d, 1H, J = 5.6 Hz), 3.92-3.94 (m, 2H), 3.70-3.72 (m, 2H), 3.57-3.49 (m, 4H), 2.95-2.94 (m, 1H), 2.93 (s, 3H), 2.81-2.78 (m, 1H), 2.66-2.63 (m, 1H), 2.49-2.45 (m, 2H), 2.03-2.01 (m, 1H), 1.89-1.87 (m, 1H), 1.74-1.72 (m, 2H), 1.34-1.32 (m, 1H), 1.0-1.01 (m, 6H), 0.78-0.74 (m, 4H). |
| 626 | 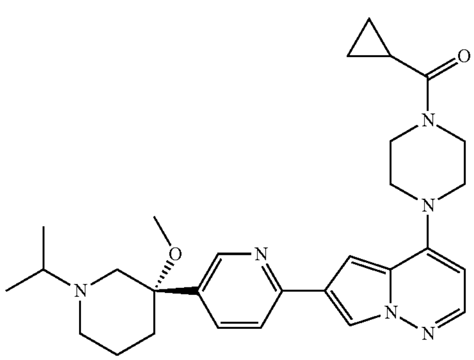 [SMILES: CO[C@]1(c2ccc(-c3cc4c(N5CCN(C(=O)C6CC6)CC5)ccnn4c3)nc2)CCCN(C(C)C)C1] | 503 | 1H-NMR (400 MHz, DMSO-d6) δ ppm 8.67 (s, 1H), 8.29 (s, 1H), 7.94-7.90 (m, 2H), 7.86-7.84 (m, 1H), 7.20 (s, 1H), 5.98 (d, 1H, J = 5.2 Hz), 3.92-3.94 (m, 2H), 3.70-3.72 (m, 2H), 3.57-3.49 (m, 4H), 2.95-2.94 (m, 1H), 2.93 (s, 3H), 2.81-2.78 (m, 1H), 2.65-2.63 (m, 1H), 2.49-2.45 (m, 2H), 2.01-2.0 (m, 1H), 1.95-1.89 (m, 1H), 1.76-1.72 (m, 2H), 1.32-1.29 (m, 1H), 1.0 (d, 6H, J = 2.0 Hz), 0.78-0.74 (m, 4H). |

TABLE 1-continued

| # | Structure | LCMS (M + 1) | NMR |
|---|---|---|---|
| 627 | 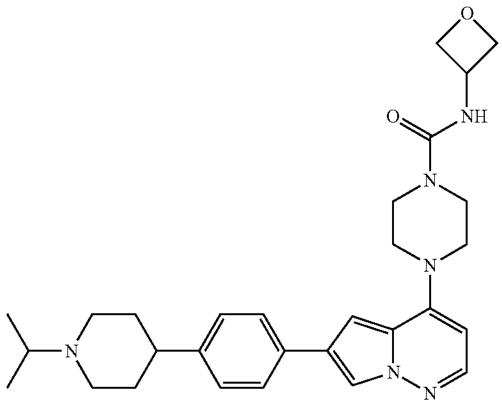 [SMILES: CC(C)N1CCC(c2ccc(-c3cc4c(N5CCN(C(=O)NC6COC6)CC5)ccnn4c3)cc2)CC1] | 503 | 1H NMR (400 MHz, Methanol-d4) δ 7.94 (d, J = 1.8 Hz, 1H), 7.84 (d, J = 5.4 Hz, 1H), 7.70-7.60 (m, 2H), 7.32-7.21 (m, 2H), 6.88 (d, J = 1.9 Hz, 1H), 5.99 (d, J = 5.5 Hz, 1H), 4.67-4.56 (m, 2H), 3.68 (dd, J = 6.6, 3.6 Hz, 4H), 3.54 (dd, J = 6.6, 3.7 Hz, 5H), 3.08 (d, J = 11.3 Hz, 2H), 2.83 (p, J = 6.6 Hz, 1H), 2.57 (ddt, J = 12.0, 8.0, 4.1 Hz, 1H), 2.41 (dd, J = 13.0, 10.3 Hz, 2H), 1.95-1.71 (m, 5H), 1.15 (d, J = 6.6 Hz, 6H). |
| 628 | 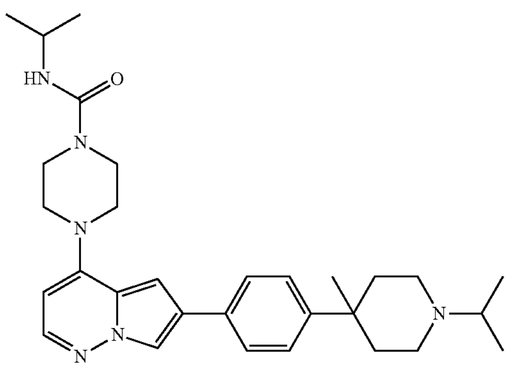 [SMILES: CC(C)NC(=O)N1CCN(c2ccnn3cc(-c4ccc(C5(C)CCN(C(C)C)CC5)cc4)cc23)CC1] | 503 | 1H-NMR (400 MHz, 6d-DMSO) δ ppm 8.35 (s, 1H), 8.15 (d, 1H, J = 1.6 Hz), 7.90 (d, 1H, J = 5.2 Hz), 7.75 (d, 2H, J = 8.4 Hz), 7.39 (d, 2H, J = 8.4 Hz), 7.00 (d, 1H, J = 1.6 Hz), 6.34 (d, 1H, J = 7.6 Hz), 5.98 (d, 1H, J = 5.6 Hz), 3.81-3.78 (m, 1H), 3.55-3.50 (m, 4H), 3.45-3.40 (m, 4H), 2.76-2.73 (m, 1H), 2.65-2.58 (m, 2H), 2.51-2.50 (m, 2H), 2.06-2.03 (m, 2H), 1.75-1.72 (m, 2H), 1.18 (s, 3H), 1.09 (d, 6H, J = 6.4 Hz), 0.97 (d, 6H, J = 6.4 Hz). |
| 629 | 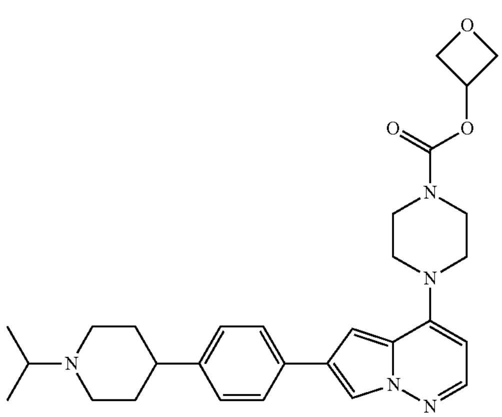 | 504 | 1H NMR (400 MHz, DMSO-d6) δ 8.13 (d, J = 1.8 Hz, 1H), 7.89 (d, J = 5.4 Hz, 1H), 7.76-7.64 (m, 2H), 7.24 (d, J = 8.2 Hz, 2H), 6.99 (d, J = 1.9 Hz, 1H), 5.98 (d, J = 5.5 Hz, 1H), 5.40-5.24 (m, 1H), 4.78 (t, J = 6.9 Hz, 2H), 4.52 (dd, J = 7.6, 5.1 Hz, 2H), 3.63 (d, J = 36.0 Hz, 4H), 3.47 (t, J = 5.0 Hz, 4H), 2.88 (d, J = 10.8 Hz, 2H), 2.77-2.62 (m, 1H), 2.21 (t, J = 11.4 Hz, 2H), 1.76 (d, J = 12.4 Hz, 2H), 1.69-1.53 (m, 2H), 0.99 (d, J = 6.5 Hz, 6H). |

TABLE 1-continued

| # | Structure | LCMS (M + 1) | NMR |
|---|---|---|---|
| 630 | 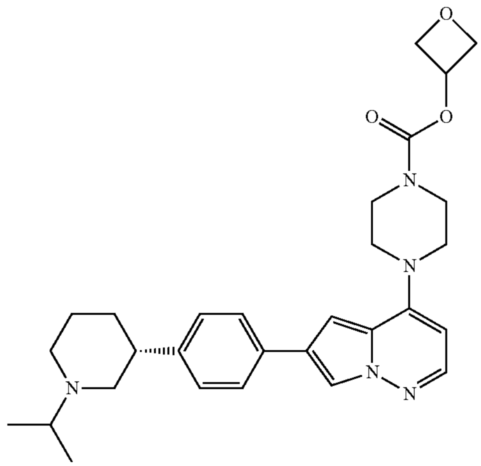 [SMILES: CC(C)N1CCC[C@H](c2ccc(-c3cc4c(N5CCN(C(=O)OC6COC6)CC5)ccnn4c3)cc2)C1] | 504 | 1H-NMR (400 MHz, 6d-DMSO) δ ppm 8.16 (d, 1H, J = 1.6 Hz), 7.91 (d, 1H, J = 6.4 Hz), 7.73 (d, 2H, J = 8.0 Hz), 7.28 (d, 2H, J = 8.0 Hz), 7.00 (d, 1H, J = 2.0 Hz), 5.99 (d, 1H, J = 6.4 Hz), 5.34-5.31 (m, 1H), 4.79 (t, 2H, J = 7.6 Hz), 4.53 (dd, 2H, J = 7.6, 5.6 Hz), 3.71-3.65 (m, 2H), 3.65-3.59 (m, 2H), 3.50-3.47 (m, 4H), 2.82-2.78 (m, 2H), 2.75-2.69 (m, 2H), 2.20-2.14 (m, 2H), 1.80-1.75 (m, 1H), 1.75-1.70 (m, 1H), 1.60-1.50 (m, 1H), 1.50-1.40 (m, 1H), 0.99-0.96 (m, 6H). |
| 631 | 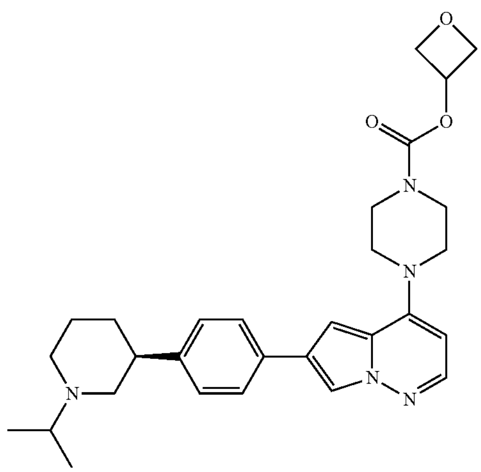 | 504 | 1H-NMR (400 MHz, 6d-DMSO) δ ppm 8.14 (d, 1H, J = 1.6 Hz), 7.90 (d, 1H, J = 5.6 Hz), 7.71 (d, 2H, J = 8.4 Hz), 7.27 (d, 2H, J = 8.4 Hz), 6.99 (d, 1H, J = 1.6 Hz), 5.98 (d, 1H, J = 5.6 Hz), 5.33 (quintet, 1H, J = 5.2 Hz), 4.78 (t, 2H, J = 7.2 Hz), 4.55-4.45 (dd, 2H, J = 7.2, 5.2 Hz), 3.67-3.62 (m, 2H), 3.59-3.53 (m, 2H), 3.50-3.60 (m, 4H), 2.85-2.75 (m, 2H), 2.74-2.63 (m, 2H), 2.20-2.05 (m, 2H), 1.86-1.77 (m, 1H), 1.76-1.66 (m, 1H), 1.60-1.36 (m, 2H), 1.00-0.90 (m, 6H). |
| 632 | 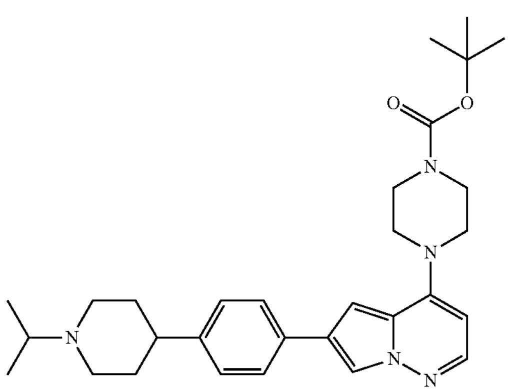 [SMILES: CC(C)N1CCC(c2ccc(-c3cc4c(N5CCN(C(=O)OC(C)(C)C)CC5)ccnn4c3)cc2)CC1] | 504 | 1H NMR (400 MHz, DMSO-d6) δ 8.12 (d, J = 1.7 Hz, 1H), 7.88 (d, J = 5.4 Hz, 1H), 7.76-7.67 (m, 2H), 7.24 (d, J = 8.1 Hz, 2H), 6.98 (d, J = 1.9 Hz, 1H), 5.96 (d, J = 5.5 Hz, 1H), 3.54 (d, J = 5.6 Hz, 4H), 3.43 (dd, J = 6.7, 3.7 Hz, 4H), 2.88 (d, J = 10.9 Hz, 3H), 2.7-2.63 (m, 1H), 2.21 (t, J = 11.3 Hz, 2H), 1.76 (d, J = 12.5 Hz, 2H), 1.70-1.51 (m, 2H), 1.43 (s, 9H), 0.99 (d, J = 6.6 Hz, 7H). |

TABLE 1-continued

| # | Structure | LCMS (M + 1) | NMR |
|---|---|---|---|
| 633 | 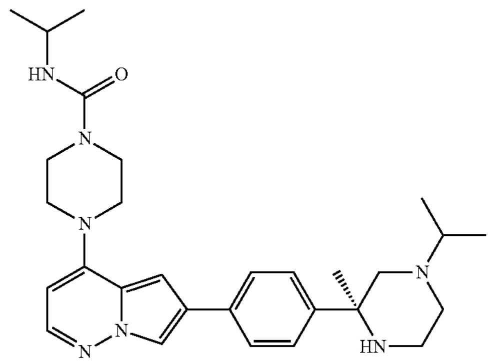 | 504 | 1H NMR (400 MHz, CDCl3) δ ppm 7.90 (d, 1H, J = 1.6 Hz), 7.80 (d, 1H, J = 5.2 Hz), 7.61 (d, 2H, J = 8.4 Hz), 7.52 (d, 2H, J = 8.4 Hz), 6.68 (d, 1H, J = 1.6 Hz), 5.78 (d, 1H, J = 5.2 Hz), 4.39-4.36 (m, 1H), 4.02-3.97 (m, 1H), 3.61-3.56 (m, 4H), 3.50-3.46 (m, 4H), 3.11-3.06 (m, 1H), 2.92-2.85 (m, 1H), 2.83-2.74 (m, 1H), 2.72 (heptet, 1H, J = 6.4 Hz), 2.53-2.45 (m, 2H), 2.45-2.38 (m, 1H), 1.37 (s, 3H), 1.17 (d, 6H, J = 6.8 Hz), 1.07 (d, 3H, J = 6.4 Hz), 1.02 (d, 3H, J = 6.4 Hz). |
| 634 | 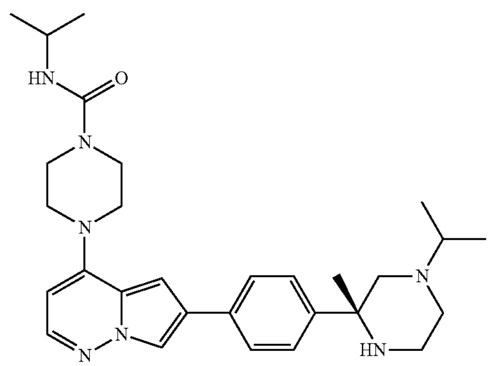 [SMILES: CC(C)NC(=O)N1CCN(c2ccnn3cc(-c4ccc([C@]5(C)CN(C(C)C)CCN5)cc4)cc23)CC1] | 504 | 1H-NMR (400 MHz, 6d-DMSO) δ ppm 8.14 (d, 1H, J = 1.6 Hz), 7.89 (d, 1H, J = 5.6 Hz), 7.71 (d, 2H, J = 8.4 Hz), 7.49 (d, 2H, J = 8.4 Hz), 7.00 (d, 1H, J = 1.6 Hz), 6.31 (d, 1H, J = 8.0 Hz), 5.97 (d, 1H, J = 5.6 Hz), 3.83-3.74 (m, 1H), 3.53-3.51 (m, 4H), 3.44-3.42 (m, 4H), 3.13-3.04 (m, 1H), 2.73-2.66 (m, 1H), 2.63-2.55 (m, 2H), 2.42-2.37 (m, 1H), 2.33-2.28 (m, 2H), 2.26-2.22 (m, 1H), 1.21 (s, 3H), 1.07 (d, 6H, J = 6.4 Hz), 1.00-0.95 (m, 6H). |
| 635 | 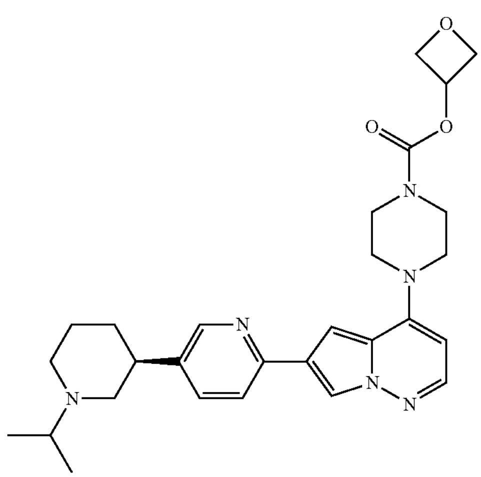 [SMILES: CC(C)N1CCC[C@@H](c2ccc(-c3cc4c(N5CCN(C(=O)OC6COC6)CC5)ccnn4c3)nc2)C1] | 505 | 1H-NMR (400 MHz, 6d-DMSO) δ ppm 8.49 (d, 1H, J = 2.0 Hz), 8.26 (d, 1H, J = 1.6 Hz), 7.94 (d, 1H, J = 5.6 Hz), 7.86 (d, 1H, J = 8.4 Hz), 7.71 (dd, 1H, J = 8.4, 2.0 Hz), 7.16 (d, 1H, J = 1.6 Hz), 6.01 (d, 1H, J = 5.6 Hz), 5.35 (quintet, 1H, J = 5.6 Hz), 4.80 (t, 2H, J = 7.2 Hz), 4.54 (dd, 2H, J = 7.2, 5.6 Hz), 3.73-3.68 (m, 2H), 3.62-3.55 (m, 2H), 3.53-3.45 (m, 4H), 2.85-2.70 (m, 4H), 2.30-2.10 (m, 2H), 1.90-1.80 (m, 1H), 1.78-1.70 (m, 1H), 1.60-1.40 (m, 2H), 1.05-0.90 (m, 6H). |

TABLE 1-continued

| # | Structure | LCMS (M + 1) | NMR |
|---|---|---|---|
| 636 | 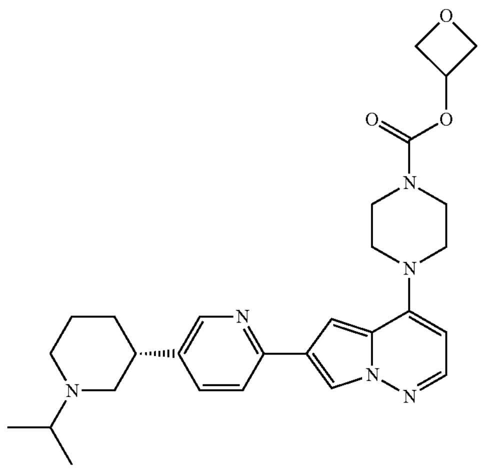 [SMILES: CC(C)N1CCC[C@H](c2ccc(-c3cc4c(N5CCN(C(=O)OC6COC6)CC5)ccnn4c3)nc2)C1] | 505 | 1H-NMR (400 MHz, 6d-DMSO) δ ppm 8.49 (d, 1H, J = 2.0 Hz), 8.26 (d, 1H, J = 1.6 Hz), 7.94 (d, 1H, J = 5.6 Hz), 7.86 (d, 1H, J = 8.4 Hz), 7.71 (dd, 1H, J = 8.4, 2.0 Hz), 7.16 (d, 1H, J = 1.6 Hz), 6.01 (d, 1H, J = 5.6 Hz), 5.35 (quintet, 1H, J = 5.6 Hz), 4.80 (t, 2H, J = 7.2 Hz), 4.54 (dd, 2H, J = 7.2, 5.6 Hz), 3.73-3.68 (m, 2H), 3.62-3.55 (m, 2H), 3.53-3.45 (m, 4H), 2.85-2.70 (m, 4H), 2.30-2.10 (m, 2H), 1.90-1.80 (m, 1H), 1.78-1.70 (m, 1H), 1.60-1.40 (m, 2H), 1.05-0.90 (m, 6H). |
| 637 | 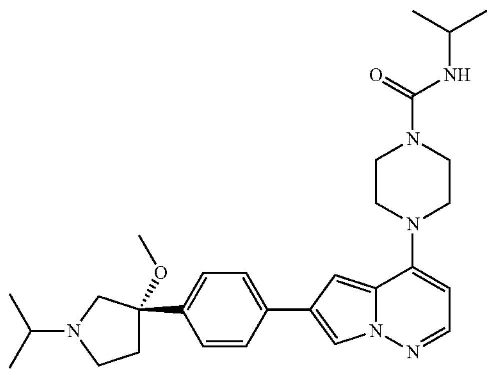 [SMILES: CO[C@]1(c2ccc(-c3cc4c(N5CCN(C(=O)NC(C)C)CC5)ccnn4c3)cc2)CCN(C(C)C)C1] | 505 | 1H NMR (400 MHz, DMSO-d6) δ 8.13 (d, J = 1.8 Hz, 1H), 7.85 (d, J = 5.4 Hz, 1H), 7.78-7.69 (m, 2H), 7.40-7.29 (m, 2H), 6.98 (d, J = 1.8 Hz, 1H), 6.27 (d, J = 7.6 Hz, 1H), 5.94 (d, J = 5.5 Hz, 1H), 3.74 (h, J = 6.7 Hz, 1H), 3.53-3.43 (m, 4H), 3.43-3.32 (m, 4H), 2.89 (d, J = 13.7 Hz, 5H), 2.76-2.61 (m, 2H), 2.45-2.37 (m, 1H), 2.16 (ddd, J = 12.3, 7.2, 4.7 Hz, 1H), 2.04 (dt, J = 13.1, 7.7 Hz, 1H), 1.06-0.97 (m, 12H). |
| 638 | 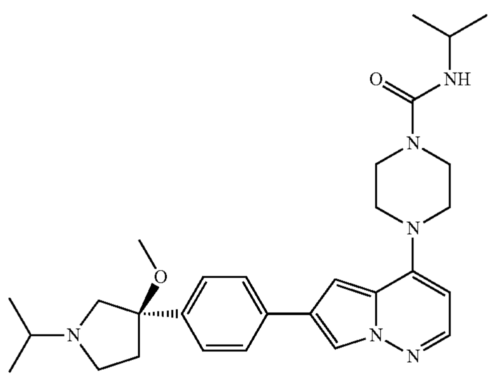 [SMILES: CO[C@@]1(c2ccc(-c3cc4c(N5CCN(C(=O)NC(C)C)CC5)ccnn4c3)cc2)CCN(C(C)C)C1] | 505 | |
| 639 | 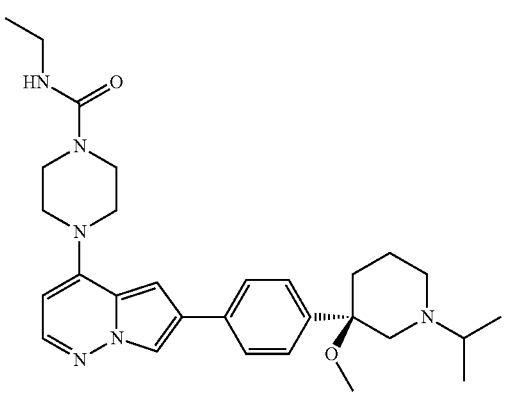 [SMILES: CCNC(=O)N1CCN(c2ccnn3cc(-c4ccc([C@]5(OC)CCCN(C(C)C)C5)cc4)cc23)CC1] | 505 | 1H-NMR (500 MHz, 6d-DMSO) δ ppm 8.18 (s, 1H), 7.90 (d, 1H, J = 5.5 Hz), 7.81 (d, 2H, J = 6.0 Hz), 7.48 (d, 2H, J = 8.5 Hz), 7.03 (s, 1H), 6.63-6.50 (m, 1H), 5.99 (d, 1H, J = 5.5 Hz), 3.53-3.51 (m, 4H), 3.45-3.44 (m, 4H), 3.10-3.07 (m, 3H), 2.94 (s, 3H), 2.90-2.52 (m, 3H), 2.49-2.20 (m, 2H), 1.90-1.40 (m, 4H), 1.06-1.02 (m, 6H), 1.04 (t, 3H, J = 7.0 Hz). |

TABLE 1-continued

| # | Structure | LCMS (M + 1) | NMR |
|---|---|---|---|
| 640 | 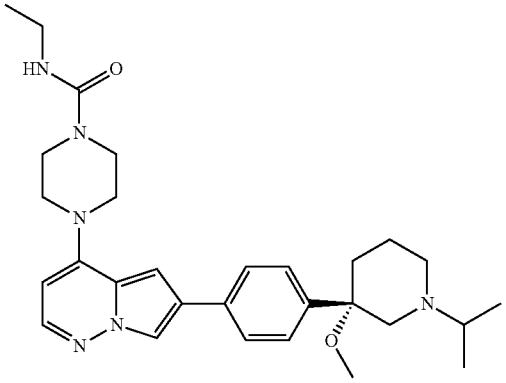 [SMILES: CCNC(=O)N1CCN(c2ccnn3cc(-c4ccc([C@@]5(OC)CCCN(C(C)C)C5)cc4)cc23)CC1] | 505 | 1H-NMR (400 MHz, 6d-DMSO) δ ppm 8.22-8.17 (m, 1H), 7.91 (d, 2H, J = 5.2 Hz), 7.80-7.79 (m, 1H), 7.48 (d, 2H, J = 8.4 Hz), 7.03 (s, 1H), 6.63-6.50 (m, 1H), 5.99 (d, 1H, J = 5.2 Hz), 3.53-3.51 (m, 4H), 3.45-3.44 (m, 4H), 3.10-3.07 (m, 3H), 2.94 (s, 3H), 2.90-2.52 (m, 3H), 2.49-2.20 (m, 2H), 1.90-1.40 (m, 2H), 1.30-1.23 (m, 2H) 1.06-1.02 (m, 9H). |
| 641 | 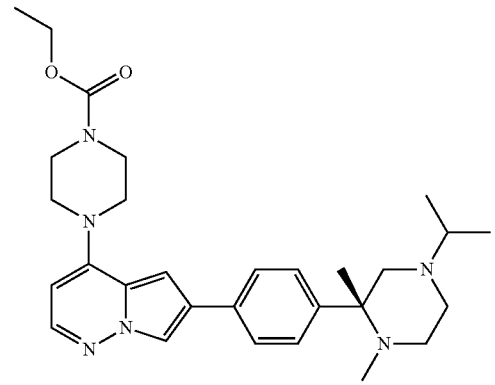 [SMILES: CCOC(=O)N1CCN(c2ccnn3cc(-c4ccc([C@]5(C)CN(C(C)C)CCN5C)cc4)cc23)CC1] | 505 | 1H NMR (500 MHz, 6d-DMSO) δ ppm 8.16 (s, 1H), 7.92 (d, 1H, J = 5.0 Hz), 7.75 (d, 2H, J = 8.0 Hz), 7.57 (d, 2H, J = 8.0 Hz), 7.00 (s, 1H), 6.00 (d, 1H, J = 5.5 Hz), 4.10 (q, 2H, J = 7.0 Hz), 3.61-3.60 (m, 4H), 3.48-3.47 (m, 4H), 2.65-2.64 (m, 1H), 2.61-2.60 (m, 3H), 2.39-2.37 (m, 2H), 2.09-2.08 (m, 1H), 1.91 (s, 3H), 1.38 (s, 3H), 1.23 (t, 3H, J = 7.0 Hz), 0.94-0.90 (m, 6H). |
| 642 | 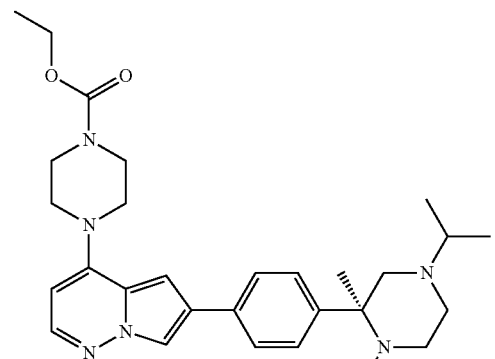 | 505 | 1H-NMR (400 MHz, CDCl3) δ ppm 7.94 (d, 1H, J = 1.6 Hz), 7.85 (d, 1H, J = 5.6 Hz), 7.68-7.60 (m, 4H), 6.70 (d, 1H, J = 1.6 Hz), 5.85 (d, 1H, J = 5.6 Hz), 4.21 (q, 2H, J = 7.2 Hz), 3.80-3.70 (m, 4H), 3.56-3.52 (m, 1H), 3.48-3.42 (m, 4H), 3.42-3.39 (m, 1H), 2.80-2.76 (m, 2H), 2.67-2.62 (m, 1H), 2.48-2.44 (m, 1H), 2.24-2.21 (m, 1H), 2.01 (s, 3H), 1.47 (s, 3H), 1.31 (t, 3H, J = 7.2 Hz), 1.05-0.95 (m, 6H). |
| 643 | 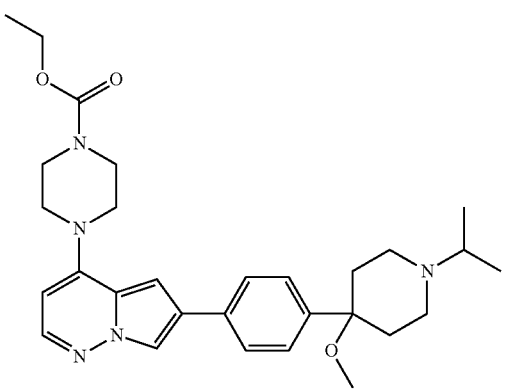 [SMILES: CCOC(=O)N1CCN(c2ccnn3cc(-c4ccc(C5(OC)CCN(C(C)C)CC5)cc4)cc23)CC1] | 506 | 1H-NMR (500 MHz, 6d-DMSO) δ ppm 8.18 (d, 1H, J = 2.0 Hz), 7.92 (d, 1H, J = 5.5 Hz), 7.80 (d, 2H, J = 8.5 Hz), 7.40 (d, 2H, J = 8.5 Hz), 7.03 (d, 1H, J = 2.0 Hz), 5.99 (d, 1H, J = 5.5 Hz), 4.10 (q, 2H, J = 7.0 Hz), 3.70-3.56 (m, 4H), 3.50-3.40 (m, 4H), 2.90 (s, 3H), 2.71 (heptet, 1H, J = 6.5 Hz), 2.64-2.56 (m, 2H), 2.48-2.42 (m, 2H), 2.02-1.94 (m, 2H), 1.92-1.80 (m, 2H), 1.23 (t, 3H, J = 7.0 Hz), 1.01 (d, 6H, J = 6.5 Hz). |

TABLE 1-continued

| # | Structure | LCMS (M + 1) | NMR |
|---|---|---|---|
| 644 | 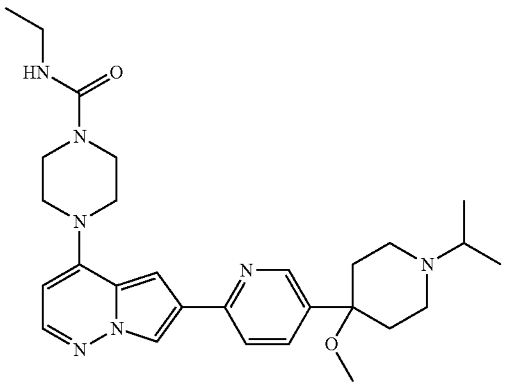 [SMILES: CCNC(=O)N1CCN(c2ccnn3cc(-c4ccc(C5(OC)CCN(C(C)C)CC5)cn4)cc23)CC1] | 506 | 1H-NMR (400 MHz, 6d-DMSO) δ ppm 8.58 (d, 1H, J = 1.6 Hz), 8.28 (d, 1H, J = 1.6 Hz), 7.94-7.90 (m, 2H), 7.77 (dd, 1H, J = 8.4, 2.0 Hz), 7.17 (d, 1H, J = 1.6 Hz), 6.60 (t, 1H, J = 5.2 Hz), 6.00 (d, 1H, J = 5.6 Hz), 3.55-3.50 (m, 4H), 3.47-3.41 (m, 4H), 3.08 (quintet, 2H, J = 5.6 Hz), 2.92 (s, 3H), 2.77-2.70 (m, 1H), 2.68-2.59 (m, 2H), 2.49-2.40 (m, 2H), 2.10-1.95 (m, 2H), 1.95-1.80 (m, 2H), 1.04 (t, 3H, J = 7.2 Hz), 1.00 (d, 6H, J = 6.0 Hz). |
| 645 | 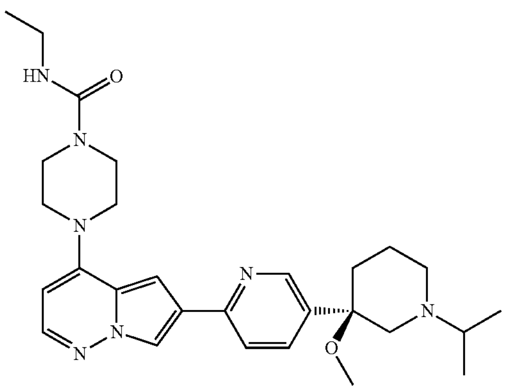 [SMILES: CCNC(=O)N1CCN(c2ccnn3cc(-c4ccc([C@]5(OC)CCCN(C(C)C)C5)cn4)cc23)CC1] | 506 | 1H-NMR (500 MHz, 6d-DMSO) δ ppm 8.68 (d, 1H, J = 1.5 Hz), 8.29 (d, 1H, J = 1.5 Hz), 7.94-7.91 (m, 2H), 7.87-7.85 (m, 1H), 7.18 (d, 1H, J = 1.5 Hz), 6.61 (t, 1H, J = 5.0 Hz), 6.0 (d, 1H, J = 5.0 Hz), 3.54-3.53 (m, 4H), 3.47-3.46 (m, 4H), 3.12-3.07 (m, 2H), 2.99-2.94 (m, 1H), 2.94 (s, 3H), 2.83-2.80 (m, 1H), 2.67-2.65 (m, 1H), 2.45-2.40 (m, 2H), 1.93-1.88 (m, 1H), 1.77-1.71 (m, 2H), 1.35-1.33 (m, 1H), 1.05 (t, 3H, J = 7.0 Hz), 1.04-1.01 (m, 6H). |
| 646 | 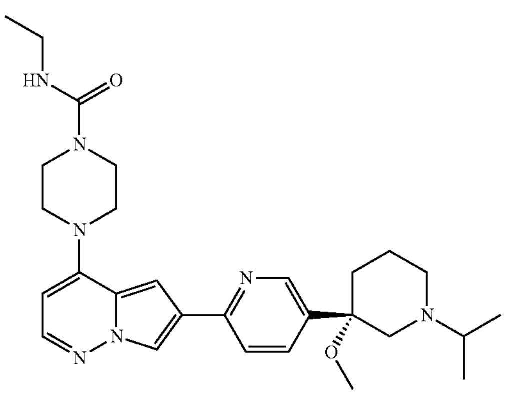 [SMILES: CCNC(=O)N1CCN(c2ccnn3cc(-c4ccc([C@@]5(OC)CCCN(C(C)C)C5)cn4)cc23)CC1] | 506 | 1H-NMR (500 MHz, 6d-DMSO) δ ppm 8.69 (d, 1H, J = 1.5 Hz), 8.27 (d, 1H, J = 1.5 Hz), 7.94-7.91 (m, 2H), 7.87-7.85 (m, 1H), 7.18 (s, 1H), 6.62 (t, 1H, J = 5.0 Hz), 6.00 (d, 1H, J = 5.5 Hz), 3.54-3.53 (m, 4H), 3.47-3.46 (m, 4H), 3.09 (quintet, 2H, J = 7.0 Hz), 2.96-2.92 (m, 1H), 2.94 (s, 3H), 2.82-2.80 (m, 1H), 2.67-2.64 (m, 1H), 2.47-2.44 (m, 2H), 1.92-1.88 (m, 1H), 1.80-1.75 (m, 1H), 1.75-1.71 (m, 1H), 1.35-1.33 (m, 1H), 1.05 (t, 3H, J = 7.0 Hz), 1.03-1.00 (m, 6H). |
| 647 | 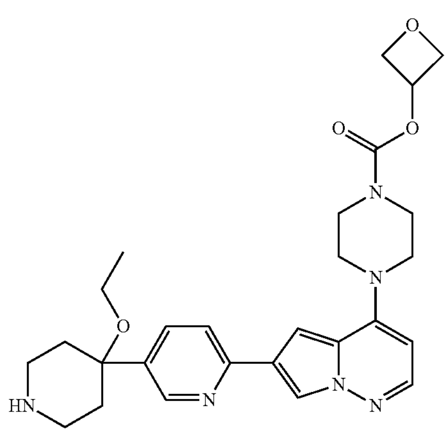 [SMILES: CCOC1(c2ccc(-c3cc4c(N5CCN(C(=O)OC6COC6)CC5)ccnn4c3)nc2)CCNCC1] | 507 | 1H NMR (400 MHz, Methanol-d4) δ 8.66-8.45 (m, 1H), 8.36-8.16 (m, 1H), 7.97-7.68 (m, 3H), 7.17 (d, J = 1.8 Hz, 1H), 6.01 (d, J = 5.4 Hz, 1H), 5.41 (ddd, J = 11.4, 6.3, 5.2 Hz, 1H), 4.98-4.78 (m, 2H), 4.65 (dd, J = 7.7, 5.2 Hz, 2H), 3.87-3.60 (m, 5H), 3.54 (dd, J = 6.6, 3.8 Hz, 4H), 3.30 (p, J = 1.6 Hz, 1H), 3.17 (q, J = 7.0 Hz, 2H), 3.13-3.01 (m, 2H), 2.95 (dt, J = 12.7, 3.5 Hz, 2H), 2.16-2.01 (m, 2H), 1.94 (td, J = 13.2, 4.3 Hz, 2H), 1.23-1.08 (m, 3H). |

TABLE 1-continued

| # | Structure | LCMS (M + 1) | NMR |
|---|---|---|---|
| 648 | 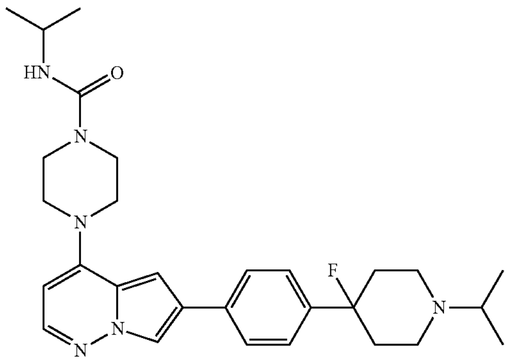 [SMILES: CC(C)NC(=O)N1CCN(c2ccnn3cc(-c4ccc(C5(F)CCN(C(C)C)CC5)cc4)cc23)CC1] | 507 | 1H NMR (400 MHz, DMSO-d6) δ 8.18 (d, J = 1.8 Hz, 1H), 7.89 (d, J = 5.4 Hz, 1H), 7.81 (d, J = 8.0 Hz, 2H), 7.42 (d, J = 8.2 Hz, 2H), 7.03 (d, J = 1.8 Hz, 1H), 6.31 (d, J = 7.6 Hz, 1H), 5.98 (d, J = 5.5 Hz, 1H), 3.77 (h, J = 6.7 Hz, 1H), 3.56-3.47 (m, 4H), 3.42 (dd, J = 6.7, 3.4 Hz, 4H), 2.74 (s, 2H), 2.18-1.84 (m, 4H), 1.07 (d, J = 6.6 Hz, 6H), 1.02 (d, J = 6.6 Hz, 6H). |
| 649 | 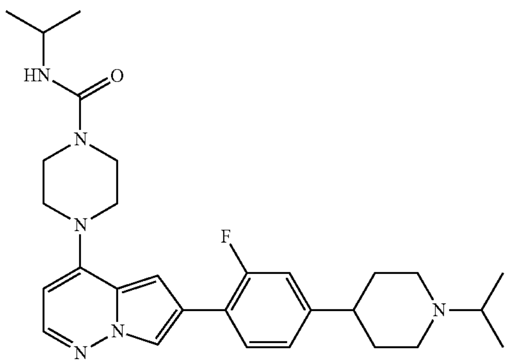 [SMILES: CC(C)NC(=O)N1CCN(c2ccnn3cc(-c4ccc(C5CCN(C(C)C)CC5)cc4F)cc23)CC1] | 507 | 1H NMR (400 MHz, DMSO-d6) δ 7.99 (dd, J = 2.8, 1.7 Hz, 1H), 7.88 (d, J = 5.4 Hz, 1H), 7.80 (t, J = 8.4 Hz, 1H), 7.14-7.06 (m, 2H), 6.97 (d, J = 1.8 Hz, 1H), 6.27 (d, J = 7.6 Hz, 1H), 5.96 (d, J = 5.5 Hz, 1H), 3.74 (h, J = 6.7 Hz, 1H), 3.47 (dd, J = 6.8, 3.2 Hz, 4H), 3.39 (dd, J = 6.7, 3.3 Hz, 4H), 2.84 (d, J = 10.9 Hz, 2H), 2.74-2.60 (m, 1H), 2.18 (t, J = 11.2 Hz, 2H), 1.74 (d, J = 12.2 Hz, 2H), 1.59 (td, J = 12.2, 3.7 Hz, 2H), 1.03 (d, J = 6.6 Hz, 6H), 0.95 (d, J = 6.6 Hz, 5H). |
| 650 | 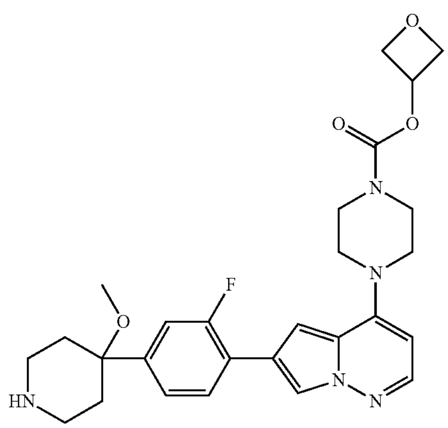 [SMILES: COC1(c2ccc(-c3cc4c(N5CCN(C(=O)OC6COC6)CC5)ccnn4c3)c(F)c2)CCNCC1] | 510 | 1H NMR (400 MHz, DMSO-d6) δ 8.04 (t, J = 2.2 Hz, 1H), 7.95-7.86 (m, 2H), 7.26-7.14 (m, 2H), 7.01 (d, J = 1.8 Hz, 1H), 5.98 (d, J = 5.5 Hz, 1H), 5.34-5.23 (m, 1H), 4.74 (t, J = 6.9 Hz, 2H), 4.48 (dd, J = 7.6, 5.1 Hz, 2H), 3.65 (s, 2H), 3.55 (s, 2H), 3.46 (dd, J = 6.6, 3.7 Hz, 4H), 2.88 (s, 3H), 2.84-2.71 (m, 4H), 1.94-1.83 (m, 2H), 1.83-1.70 (m, 2H). |
| 651 | 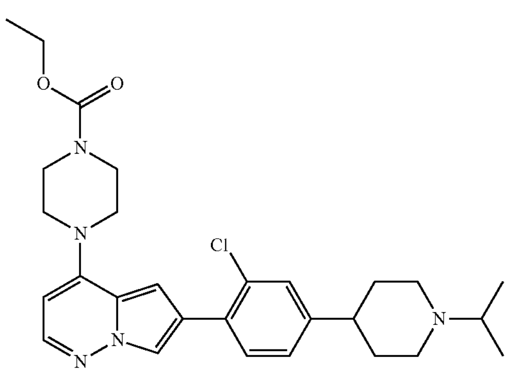 [SMILES: CCOC(=O)N1CCN(c2ccnn3cc(-c4ccc(C5CCN(C(C)C)CC5)cc4Cl)cc23)CC1] | 511 | 1H-NMR (500 MHz, 6d-DMSO) δ ppm 9.24 (br. s., 1H), 8.07 (d, 1H, J = 2.0 Hz), 7.95 (d, 1H, J = 5.5 Hz), 7.73 (d, 1H, J = 8.5 Hz), 7.39 (d, 1H, J = 1.5 Hz), 7.27 (dd, 1H, J = 8.5, 2.0 Hz), 6.91 (d, 1H, J = 2.0 Hz), 6.02 (d, 1H, J = 5.5 Hz), 4.08 (q, 2H, J = 7.5 Hz), 3.64-3.58 (m, 4H), 3.57-3.52 (m, 1H), 3.52-3.45 (m, 6H), 3.13-3.07 (m, 2H), 2.95-2.90 (m, 1H), 2.07-2.01 (m, 2H), 1.97-1.89 (m, 2H), 1.30 (d, 6H, J = 6.5 Hz), 1.22 (t, 3H, J = 7.5 Hz). |

TABLE 1-continued

| # | Structure | LCMS (M + 1) | NMR |
|---|---|---|---|
| 652 | 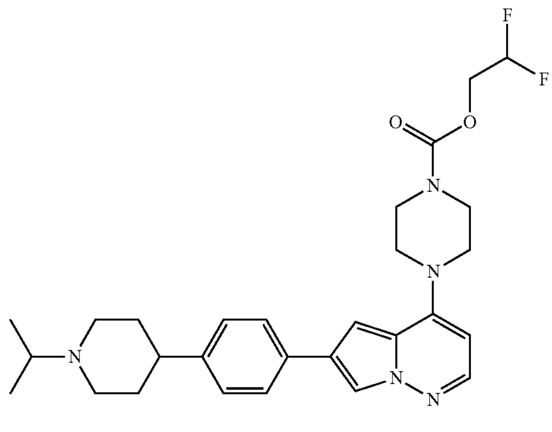 [SMILES: CC(C)N1CCC(c2ccc(-c3cc4c(N5CCN(C(=O)OCC(F)F)CC5)ccnn4c3)cc2)CC1] | 512 | 1H NMR (400 MHz, Methanol-d4) δ 7.93 (dd, J = 6.3, 1.8 Hz, 1H), 7.83 (dd, J = 5.4, 1.8 Hz, 1H), 7.73-7.61 (m, 2H), 7.33-7.20 (m, 2H), 6.87 (dd, J = 6.8, 1.8 Hz, 1H), 6.29-5.88 (m, 2H), 4.34 (td, J = 14.4, 3.7 Hz, 2H), 3.74 (s, 5H), 3.51 (t, J = 5.2 Hz, 5H), 3.22-2.95 (m, 2H), 2.70-2.50 (m, 2H), 2.01-1.77 (m, 3H), 1.31 (dd, J = 85.1, 6.5 Hz, 6H). |
| 653 | 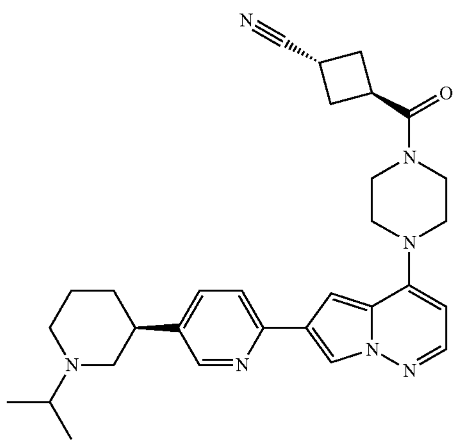 [SMILES: CC(C)N1CCC[C@@H](c2ccc(-c3cc4c(N5CCN(C(=O)[C@H]6C[C@H](C#N)C6)CC5)ccnn4c3)nc2)C1] | 512 | 1H-NMR (500 MHz, 6d-DMSO) δ ppm 8.49 (d, 1H, J = 2.0 Hz), 8.26 (d, 1H, J = 1.5 Hz), 7.93 (d, 1H, J = 5.5 Hz), 7.86 (d, 1H, J = 8.5 Hz), 7.71 (dd, 1H, J = 8.5, 2.0 Hz), 7.16 (d, 1H, J = 2.0 Hz), 5.99 (d, 1H, J = 5.0 Hz), 3.74-3.69 (m, 2H), 3.69-3.62 (m, 1H), 3.60-3.53 (m, 2H), 3.52-3.44 (m, 4H), 3.33-3.24 (m, 3H), 2.84-2.80 (m, 2H), 2.80-2.76 (m, 2H), 2.68-2.60 (m, 2H), 2.26-2.20 (m, 1H), 2.20-2.14 (m, 1H), 1.88-1.80 (m, 1H), 1.78-1.70 (m, 1H), 1.60-1.55 (m, 1H), 1.55-1.47 (m, 1H), 1.02-0.90 (m, 6H). |
| 654 | 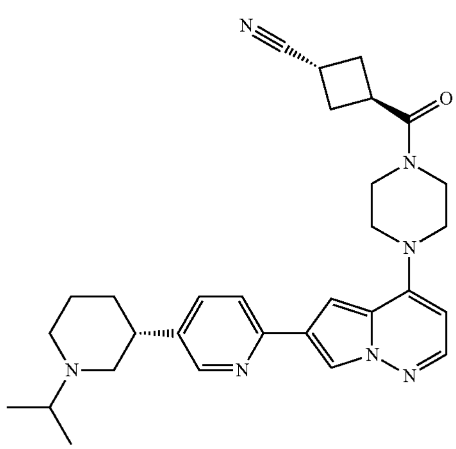 [SMILES: CC(C)N1CCC[C@H](c2ccc(-c3cc4c(N5CCN(C(=O)[C@H]6C[C@H](C#N)C6)CC5)ccnn4c3)nc2)C1] | 512 | 1H-NMR (400 MHz, 6d-DMSO) δ ppm 8.49 (d, 1H, J = 1.6 Hz), 8.26 (d, 1H, J = 1.6 Hz), 7.93 (d, 1H, J = 5.6 Hz), 7.86 (d, 1H, J = 8.0 Hz), 7.72 (dd, 1H, J = 8.0, 2.0 Hz), 7.16 (d, 1H, J = 1.2 Hz), 5.98 (d, 1H, J = 5.6 Hz), 3.74-3.69 (m, 2H), 3.69-3.62 (m, 1H), 3.60-3.53 (m, 2H), 3.52-3.44 (m, 4H), 3.33-3.24 (m, 3H), 2.90-2.70 (m, 4H), 2.68-2.56 (m, 2H), 2.40-2.10 (m, 2H), 1.90-1.85 (m, 1H), 1.82-1.75 (m, 1H), 1.65-1.40 (m, 2H), 1.10-0.90 (m, 6H). |

TABLE 1-continued

| # | Structure | LCMS (M + 1) | NMR |
|---|---|---|---|
| 655 | 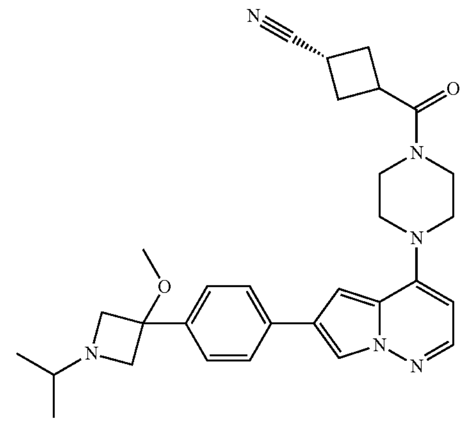 | 513 | 1H-NMR (400 MHz, 6d-DMSO) δ ppm 8.23 (s, 1H), 8.22 (d, 1H, J = 1.6 Hz), 7.92 (d, 1H, J = 5.6 Hz), 7.84 (d, 2H, J = 8.4 Hz), 8.47 (d, 2H, J = 8.4 Hz), 7.06 (d, 1H, J = 1.6 Hz), 5.98 (d, 1H, J = 5.6 Hz), 3.71-3.68 (m, 2H), 3.67-3.63 (m, 3H), 3.56-3.52 (m, 2H), 3.48-3.45 (m, 4H), 3.35-3.31 (m, 2H), 3.30-3.25 (m, 2H), 2.96 (s, 3H), 2.65-2.59 (m, 2H), 2.53-2.45 (m, 2H), 0.93 (d, 6H, J = 6.4 Hz). |
| 656 | 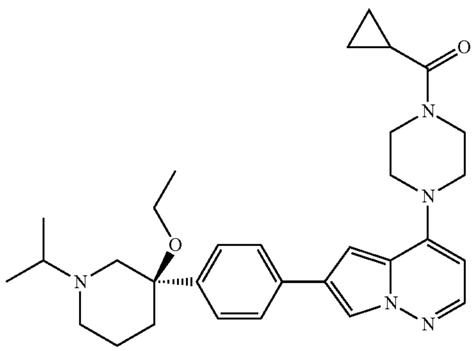 [SMILES: CCO[C@@]1(c2ccc(-c3cc4c(N5CCN(C(=O)C6CC6)CC5)ccnn4c3)cc2)CCCN(C(C)C)C1] | 516 | 1H-NMR (400 MHz, 6d-DMSO) δ ppm 8.18 (d, 1H, J = 1.2 Hz), 7.91 (d, 1H, J = 5.6 Hz), 7.78 (d, 2H, J = 8.0 Hz), 7.51 (d, 2H, J = 8.4 Hz), 7.06 (d, 1H, J = 1.2 Hz), 5.98 (d, 1H, J = 5.6 Hz), 3.94-3.93 (m, 2H), 3.72-3.71 (m, 2H), 3.55-3.48 (m, 4H), 3.19-3.16 (m, 1H), 3.05-3.00 (m, 1H), 2.88-2.80 (m, 2H), 2.69-2.64 (m, 1H), 2.43-2.33 (m, 2H), 2.05-2.00 (m, 1H), 1.82-1.69 (m, 3H), 1.41-1.29 (m, 1H), 1.05-1.02 (m, 9H), 0.79-0.74 (m, 4H). |
| 657 | 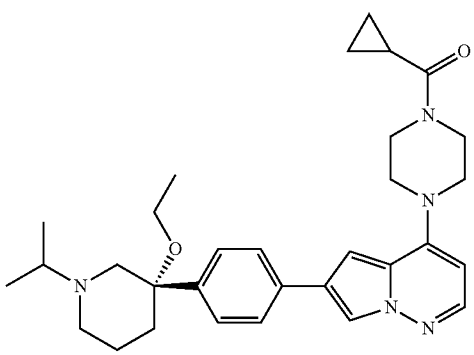 [SMILES: CCO[C@]1(c2ccc(-c3cc4c(N5CCN(C(=O)C6CC6)CC5)ccnn4c3)cc2)CCCN(C(C)C)C1] | 516 | 1H-NMR (400 MHz, DMSO-d6) δ ppm 8.18 (d, 1H, J = 1.6 Hz), 7.91 (d, 1H, J = 5.6 Hz), 7.78 (d, 2H, J = 8.4 Hz), 7.51 (d, 2H, J = 8.8 Hz), 7.06 (d, 1H, J = 1.2 Hz), 5.98 (d, 1H, J = 5.6 Hz), 3.94-3.92 (m, 2H), 3.71-3.70 (m, 2H), 3.54-3.48 (m, 4H), 3.32-3.31 (m, 1H), 3.23-3.19 (m, 1H), 3.03-2.99 (m, 1H), 2.87-2.77 (m, 2H), 2.68-2.65 (m, 1H), 2.42-2.41 (m, 1H), 2.05-2.01 (m, 1H), 1.81-1.73 (m, 3H), 1.37-1.35 (m, 1H), 1.05-0.99 (m, 9H), 0.79-0.73 (m, 4H). |
| 658 | 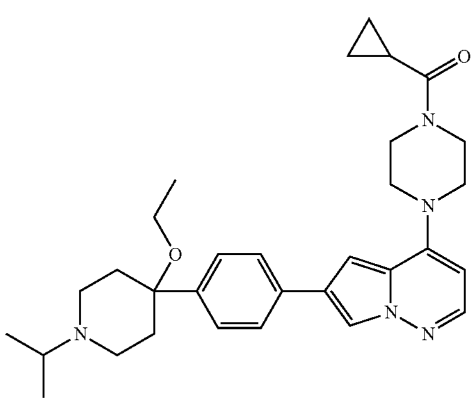 [SMILES: CCOC1(c2ccc(-c3cc4c(N5CCN(C(=O)C6CC6)CC5)ccnn4c3)cc2)CCN(C(C)C)CC1] | 516 | 1H NMR (400 MHz, 4d-MeOD) δ ppm 8.00 (d, 1H, J = 2.0 Hz), 7.86 (d, 1H, J = 5.2 Hz), 7.75 (d, 2H, J = 8.4 Hz), 7.47 (d, 2H, J = 8.0 Hz), 6.95 (d, 1H, J = 1.6 Hz), 6.01 (d, 1H, J = 5.6 Hz), 4.05-4.04 (m, 2H), 3.87-3.86 (m, 2H), 3.64-3.63 (m, 2H), 3.56-3.55 (m, 2H), 3.15 (q, 2H, J = 6.8 Hz), 3.01-2.85 (m, 5H), 2.24-2.20 (m, 2H), 2.11-2.03 (m, 3H), 1.22 (d, 6H, J = 6.4 Hz), 1.15 (t, 3H, J = 6.8 Hz), 0.95-0.93 (m, 2H), 0.89-0.86 (m, 2H). |

TABLE 1-continued

| # | Structure | LCMS (M + 1) | NMR |
|---|---|---|---|
| 659 | 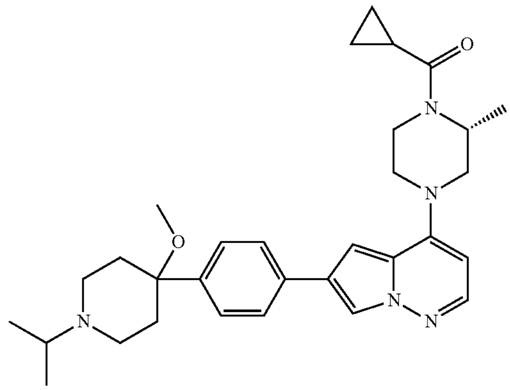 [SMILES: COC1(c2ccc(-c3cc4c(N5CCN(C(=O)C6CC6)[C@H](C)C5)ccnn4c3)cc2)CCN(C(C)C)CC1] | 516 | 1H-NMR (500 MHz, 6d-DMSO) δ ppm 8.23 (br.s, 1H), 8.18 (d, 1H, J = 1.5 Hz), 7.90 (d, 1H, J = 5.0 Hz), 7.78 (d, 2H, J = 8.5 Hz), 7.40 (d, 2H, J = 8.5 Hz), 6.98 (d, 1H, J = 1.0 Hz), 5.96 (d, 1H, J = 5.5 Hz), 4.63-4.62 (m, 1H), 4.20-4.19 (m, 1H), 3.93-3.92 (m, 2H), 2.89 (s, 3H), 2.75-2.74 (m, 1H), 2.63-2.62 (m, 2H), 2.56-2.55 (m, 2H), 2.01-1.98 (m, 4H), 1.90-1.87 (m, 2H), 1.41-1.40 (m, 2H), 1.25-1.21 (m, 3H), 1.04-1.01 (m, 6H), 0.78-0.76 (m, 4H). |
| 660 | 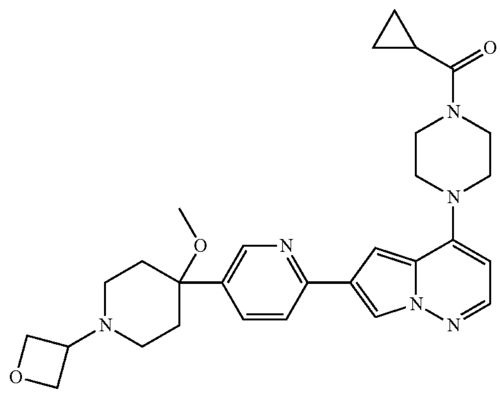 [SMILES: COC1(c2ccc(-c3cc4c(N5CCN(C(=O)C6CC6)CC5)ccnn4c3)nc2)CCN(C2COC2)CC1] | 517 | 1H-NMR (400 MHz, 6d-DMSO) δ ppm 8.60 (d, 1H, J = 1.6 Hz), 8.31 (d, 1H, J = 1.6 Hz), 7.95 (s, 1H), 7.93 (d, 1H, J = 1.6 Hz), 7.80 (dd, 1H, J = 8.4, 2.4 Hz), 7.22 (d, 1H, J = 2.0 Hz), 6.00 (d, 1H, J = 5.6 Hz), 4.56 (t, 2H, J = 6.4 Hz), 4.45 (t, 2H, J = 6.4 Hz), 4.00-3.80 (m, 2H), 3.70-3.55 (m, 2H), 3.60-3.55 (m, 2H), 3.54-3.48 (m, 2H), 3.47-3.40 (m, 1H), 2.93 (s, 3H), 2.60-2.52 (m, 2H), 2.22-2.10 (m, 2H), 2.08-1.88 (m, 5H), 0.82-0.70 (m, 4H). |
| 661 | 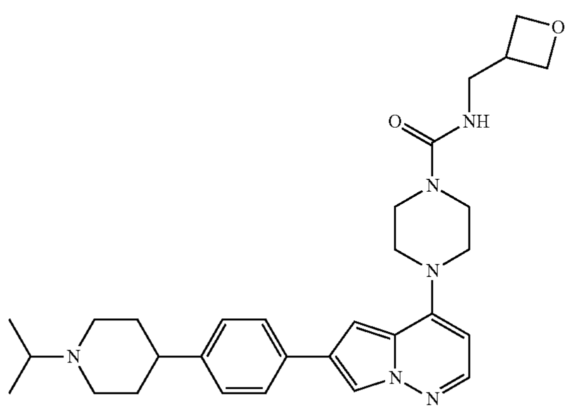 | 517 | 1H NMR (400 MHz, DMSO-d6) δ 8.13 (s, 1H), 7.88 (d, J = 5.4 Hz, 1H), 7.74 (d, J = 8.1 Hz, 2H), 7.24 (d, J = 8.0 Hz, 2H), 6.99 (s, 1H), 6.77 (s, 1H), 5.97 (d, J = 5.4 Hz, 1H), 4.59 (dd, J = 7.8, 6.0 Hz, 2H), 4.29 (t, J = 6.0 Hz, 2H), 3.51 (s, 4H), 3.44 (s, 4H), 3.25-2.94 (m, 2H), 1.95-1.63 (m, 4H), 1.11 (s, 6H). |
| 662 | 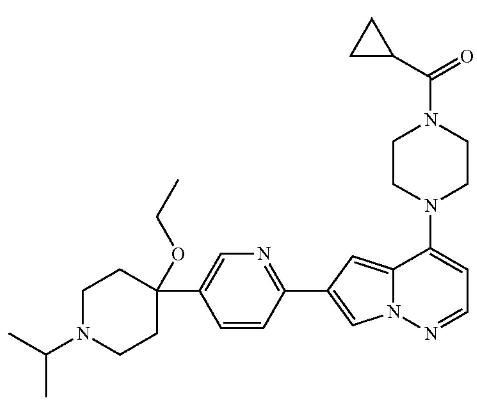 | 517 | 1H-NMR (500 MHz, 6d-DMSO) δ ppm 8.59 (d, 1H, J = 2.5 Hz), 8.30 (d, 1H, J = 1.5 Hz), 7.94 (d, 1H, J = 5.5 Hz), 7.92 (s, 1H), 7.79 (dd, 1H, J = 8.5, 2.5 Hz), 7.21 (d, 1H, J = 1.5 Hz), 6.00 (d, 1H, J = 5.5 Hz), 3.96-3.94 (m, 2H), 3.72-3.71 (m, 2H), 3.60-3.55 (m, 2H), 3.55-3.50 (m, 2H), 3.08 (q, 2H, J = 7.0 Hz), 2.70-2.64 (m, 1H), 2.62-2.58 (m, 2H), 2.59-2.54 (m, 2H), 2.04-2.00 (m, 3H), 1.99-1.90 (m, 2H), 1.09 (t, 3H, J = 7.0 Hz), 1.01 (d, 6H, J = 5.5 Hz), 0.78-0.72 (m, 4H). |

TABLE 1-continued

| # | Structure | LCMS (M + 1) | NMR |
|---|---|---|---|
| 663 | 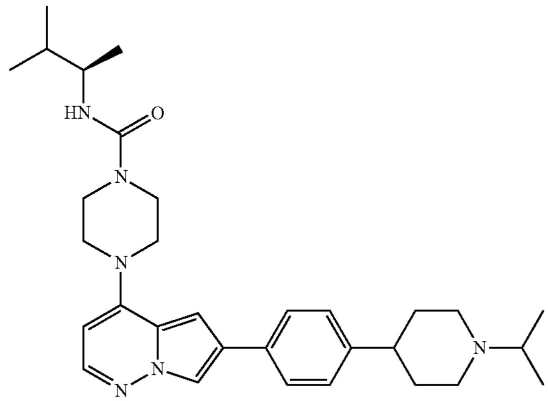 [SMILES: CC(C)[C@@H](C)NC(=O)N1CCN(c2ccnn3cc(-c4ccc(C5CCN(C(C)C)CC5)cc4)cc23)CC1] | 517 | 1H NMR (400 MHz, DMSO-d6) δ 8.12 (d, J = 1.7 Hz, 1H), 7.88 (d, J = 5.4 Hz, 1H), 7.71 (d, J = 7.9 Hz, 2H), 7.24 (d, J = 8.1 Hz, 2H), 6.98 (d, J = 1.8 Hz, 1H), 6.20 (d, J = 8.3 Hz, 1H), 5.97 (d, J = 5.5 Hz, 1H), 3.5.47 (m, 5H), 3.42 (t, J = 5.0 Hz, 4H), 2.88 (d, J = 10.8 Hz, 2H), 2.7.62 (m, 1H), 2.21 (t, J = 11.4 Hz, 2H), 1.76 (d, J = 12.2 Hz, 2H), 1.69-1.51 (m, 3H), 1.00 (t, J = 6.4 Hz, 9H), 0.84 (dd, J = 6.7, 4.1 Hz, 6H). |
| 664 | 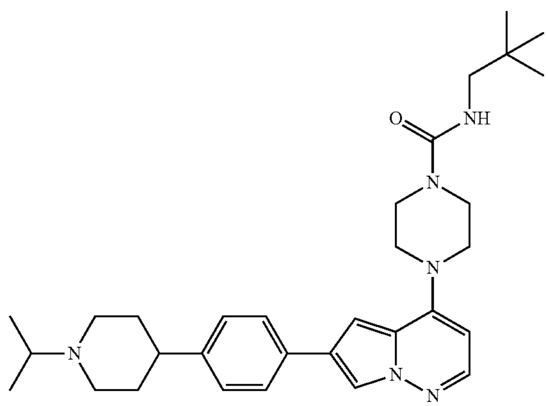 [SMILES: CC(C)N1CCC(c2ccc(-c3cc4c(N5CCN(C(=O)NCC(C)(C)C)CC5)ccnn4c3)cc2)CC1] | 517 | 1H NMR (400 MHz, DMSO-d6) δ 8.12 (d, J = 1.8 Hz, 1H), 7.88 (d, J = 5.4 Hz, 1H), 7.77-7.66 (m, 2H), 7.24 (d, J = 8.1 Hz, 2H), 6.99 (d, J = 1.8 Hz, 1H), 6.49 (t, J = 6.2 Hz, 1H), 5.97 (d, J = 5.5 Hz, 1H), 3.62-3.47 (m, 4H), 3.43 (dd, J = 6.7, 3.6 Hz, 4H), 2.89 (dd, J = 14.5, 8.5 Hz, 4H), 2.70 (p, J = 6.6 Hz, 1H), 2.52-2.35 (m, 1H), 2.20 (td, J = 11.5, 2.3 Hz, 2H), 1.83-1.70 (m, 2H), 1.61 (qd, J = 12.2, 3.7 Hz, 2H), 0.98 (d, J = 6.6 Hz, 6H), 0.83 (s, 8H). |
| 665 | 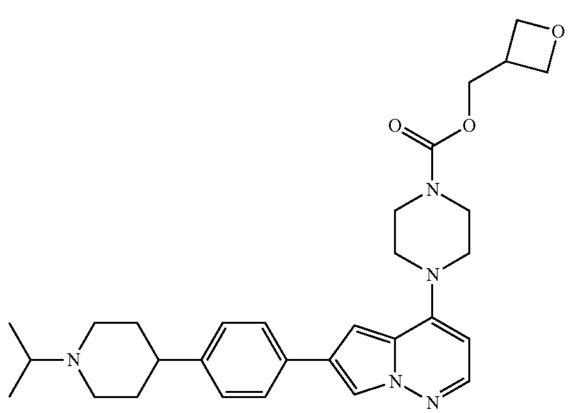 [SMILES: CC(C)N1CCC(c2ccc(-c3cc4c(N5CCN(C(=O)OCC6COC6)CC5)ccnn4c3)cc2)CC1] | 518 | 1H NMR (400 MHz, DMSO-d6) δ 8.13 (d, J = 1.8 Hz, 1H), 7.89 (d, J = 5.4 Hz, 1H), 7.75-7.68 (m, 2H), 7.28-7.20 (m, 2H), 6.99 (d, J = 1.9 Hz, 1H), 5.97 (d, J = 5.5 Hz, 1H), 4.65 (dd, J = 8.0, 6.1 Hz, 2H), 4.39-4.35 (m, 2H), 4.24 (d, J = 6.3 Hz, 2H), 3.61 (s, 4H), 3.46 (dd, J = 6.7, 3.7 Hz, 4H), 3.29-3.21 (m, 1H), 2.88 (d, J = 10.9 Hz, 2H), 2.74-2.65 (m, 1H), 2.21 (t, J = 11.3 Hz, 2H), 1.76 (d, J = 12.3 Hz, 2H), 1.69-1.54 (m, 2H), 0.99 (d, J = 6.5 Hz, 6H). |

TABLE 1-continued

| # | Structure | LCMS (M + 1) | NMR |
|---|---|---|---|
| 666 | 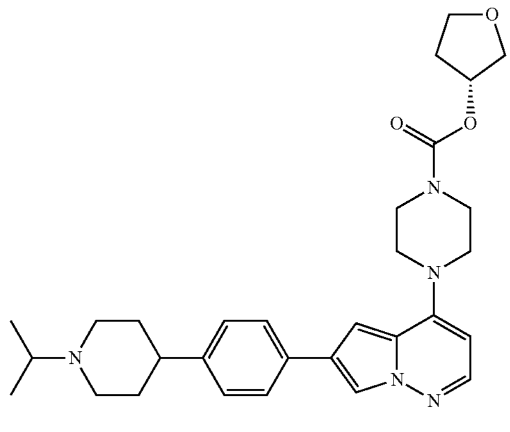 [SMILES: CC(C)N1CCC(c2ccc(-c3cc4c(N5CCN(C(=O)O[C@@H]6CCOC6)CC5)ccnn4c3)cc2)CC1] | 518 | 1H NMR (400 MHz, DMSO-d6) δ 8.12 (d, J = 1.8 Hz, 1H), 7.88 (d, J = 5.4 Hz, 1H), 7.74-7.68 (m, 2H), 7.26-7.19 (m, 2H), 6.97 (d, J = 1.9 Hz, 1H), 5.96 (d, J = 5.5 Hz, 1H), 5.17 (ddt, J = 6.5, 4.3, 1.9 Hz, 1H), 3.82-3.68 (m, 4H), 3.58 (d, J = 5.5 Hz, 4H), 3.45 (dd, J = 6.6, 3.7 Hz, 4H), 2.91 (d, J = 11.1 Hz, 2H), 2.75 (p, J = 6.5 Hz, 1H), 2.30-2.21 (m, 2H), 2.12 (dtd, J = 13.6, 8.3, 6.3 Hz, 1H), 1.92 (dt, J = 11.9, 5.3 Hz, 1H), 1.77 (d, J = 12.1 Hz, 2H), 1.63 (qd, J = 12.2, 3.7 Hz, 2H), 1.00 (d, J = 6.5 Hz, 6H). |
| 667 | 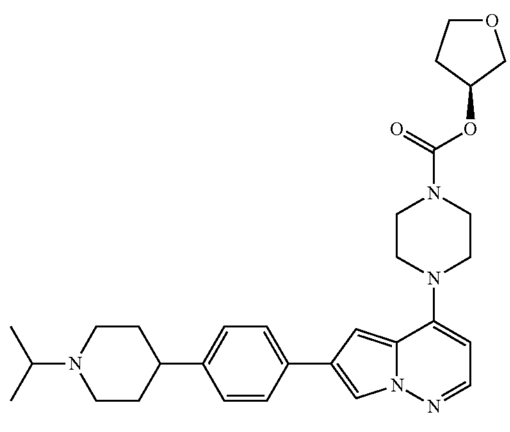 [SMILES: CC(C)N1CCC(c2ccc(-c3cc4c(N5CCN(C(=O)O[C@H]6CCOC6)CC5)ccnn4c3)cc2)CC1] | 518 | 1H NMR (400 MHz, DMSO-d6) δ 8.12 (d, J = 1.8 Hz, 1H), 7.88 (d, J = 5.4 Hz, 1H), 7.75-7.67 (m, 2H), 7.26-7.20 (m, 2H), 6.98 (d, J = 1.8 Hz, 1H), 5.96 (d, J = 5.5 Hz, 1H), 5.17 (ddt, J = 6.5, 4.3, 1.9 Hz, 1H), 3.83-3.68 (m, 4H), 3.58 (d, J = 5.5 Hz, 4H), 3.45 (d, J = 5.7 Hz, 4H), 2.96 (d, J = 11.2 Hz, 2H), 2.83 (p, J = 6.6 Hz, 1H), 2.40-2.27 (m, 2H), 2.12 (dtd, J = 13.6, 8.3, 6.3 Hz, 1H), 1.97-1.88 (m, 1H), 1.84-1.75 (m, 2H), 1.73-1.60 (m, 2H), 1.03 (d, J = 6.6 Hz, 6H). |
| 668 | 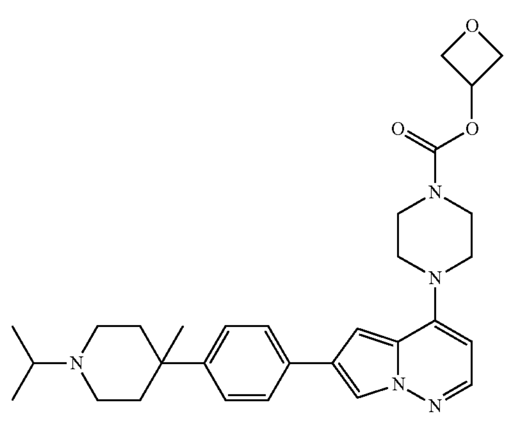 [SMILES: CC(C)N1CCC(C)(c2ccc(-c3cc4c(N5CCN(C(=O)OC6COC6)CC5)ccnn4c3)cc2)CC1] | 518 | 1H-NMR (500 MHz, 6d-DMSO) δ ppm 8.15 (s, 1H), 7.91 (d, 1H, J = 5.0 Hz), 7.73 (d, 2H, J = 8.5 Hz), 7.37 (d, 2H, J = 8.5 Hz), 7.00 (s, 1H), 6.00 (d, 1H, J = 5.0 Hz), 4.43-4.40 (m, 1H), 3.88-3.84 (m, 1H), 3.62-3.64 (m, 4H), 3.46-3.48 (m, 4H), 3.32-3.30 (m, 4H), 2.81-2.79 (m, 1H), 2.66-2.64 (m, 2H), 2.46-2.38 (m, 2H), 2.08-1.98 (m, 2H), 1.76-1.68 (m, 2H), 1.17 (s, 3H), 0.94 (d, 1H, J = 6.0 Hz). |

TABLE 1-continued

| # | Structure | LCMS (M + 1) | NMR |
|---|---|---|---|
| 669 | 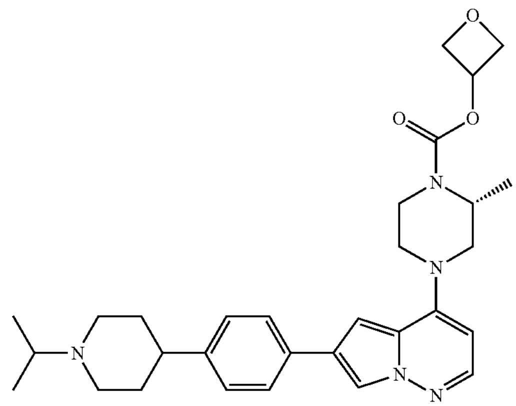 [SMILES: CC(C)N1CCC(c2ccc(-c3cc4c(N5CCN(C(=O)OC6COC6)[C@H](C)C5)ccnn4c3)cc2)CC1] | 518 | 1H-NMR (500 MHz, 6d-DMSO) δ ppm 8.25 (s, 1H), 8.14 (d, 1H, J = 2.0 Hz), 7.89 (d, 1H, J = 5.5 Hz), 7.71 (d, 2H, J = 8.0 Hz), 7.26 (d, 2H, J = 8.0 Hz), 6.93 (d, 1H, J = 1.5 Hz), 5.97 (d, 1H, J = 5.0 Hz), 5.36-5.33 (m, 1H), 4.79 (t, 2H, J = 7.0 Hz), 4.53-4.51 (m, 2H), 3.93-3.91 (m, 2H), 3.25-3.21 (m, 2H), 3.07-3.03 (m, 1H), 2.94-2.92 (m, 2H), 2.78-2.77 (m, 1H), 2.28-2.27 (m, 2H), 2.00-1.99 (m, 1H), 1.79-1.77 (m, 2H), 1.67-1.64 (m, 2H), 1.34-1.32 (m, 2H), 1.25-1.20 (m, 3H), 1.06-1.01 (m, 6H). |
| 670 | 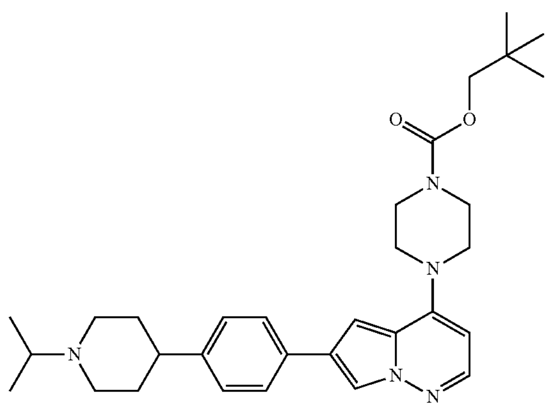 [SMILES: CC(C)N1CCC(c2ccc(-c3cc4c(N5CCN(C(=O)OCC(C)(C)C)CC5)ccnn4c3)cc2)CC1] | 518 | 1H NMR (400 MHz, DMSO-d6) δ 8.16 (d, J = 1.7 Hz, 1H), 7.90 (d, J = 5.4 Hz, 1H), 7.78 (d, J = 8.0 Hz, 2H), 7.25 (d, J = 8.0 Hz, 2H), 7.01 (d, J = 1.9 Hz, 1H), 5.98 (d, J = 5.5 Hz, 1H), 3.63 (s, 5H), 3.48 (d, J = 5.6 Hz, 6H), 2.01 (s, 6H), 1.28 (s, 8H), 0.93 (s, 10H) |
| 671 | 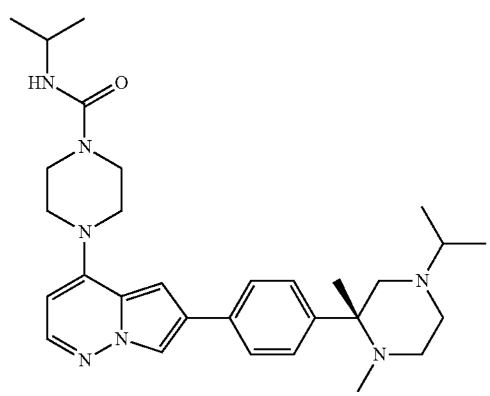 [SMILES: CC(C)NC(=O)N1CCN(c2ccnn3cc(-c4ccc([C@]5(C)CN(C(C)C)CCN5C)cc4)cc23)CC1] | 518 | 1H NMR (500 MHz, 6d-DMSO) δ ppm 8.15 (s, 1H), 7.90 (d, 1H, J = 5.5 Hz), 7.74 (d, 2H, J = 8.0 Hz), 7.57 (d, 2H, J = 8.0 Hz), 6.99 (d, 1H, J = 1.0 Hz), 6.32 (d, 1H, J = 7.5 Hz), 6.00 (d, 1H, J = 5.5 Hz), 3.79-3.78 (m, 1H), 3.54-3.52 (m, 4H), 3.45-3.43 (m, 4H), 2.75-2.74 (m, 1H), 2.62-2.61 (m, 3H), 2.37-2.36 (rn, 2H), 2.09-2.08 (m, 1H), 1.92 (s, 3H), 1.39 (s, 3H), 1.08 (d, 6H, J = 6.5 Hz), 0.95-0.90 (m, 6H). |
| 672 | 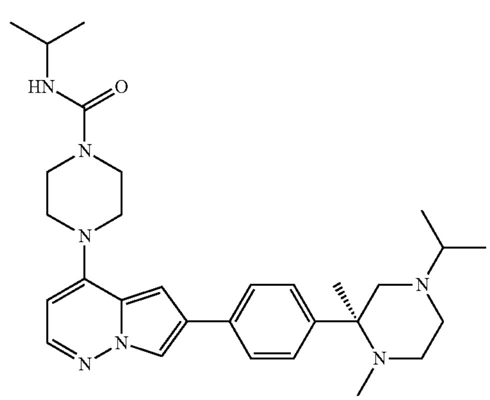 [SMILES: CC(C)NC(=O)N1CCN(c2ccnn3cc(-c4ccc([C@@]5(C)CN(C(C)C)CCN5C)cc4)cc23)CC1] | 518 | 1H-NMR (400 MHz, CDCl3) δ ppm 7.94 (d, 1H, J = 1.6 Hz), 7.84 (d, 1H, J = 6.4 Hz), 7.68-7.60 (m, 4H), 6.72 (d, 1H, J = 1.6 Hz), 5.83 (d, 1H, J = 6.4 Hz), 4.28 (d, 1H, J = 7.2 Hz), 4.10-4.00 (m, 1H), 3.65-3.58 (m, 4H), 3.56-3.46 (m, 4H), 3.45-3.40 (m, 1H), 2.80-2.75 (m, 2H), 2.74-2.70 (m, 1H), 2.50-2.45 (m, 1H), 2.25-2.21 (m, 1H), 2.02 (s, 3H), 1.48 (s, 3H), 1.20 (d, 6H, J = 6.4 Hz), 1.05-0.95 (m, 6H). |

TABLE 1-continued

| # | Structure | LCMS (M + 1) | NMR |
|---|---|---|---|
| 673 | 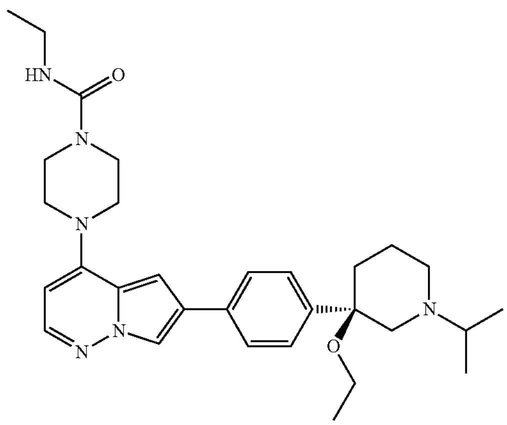 [SMILES: CCNC(=O)N1CCN(c2ccnn3cc(-c4ccc([C@]5(OCC)CCCN(C(C)C)C5)cc4)cc23)CC1] | 519 | 1H-NMR (400 MHz, 6d-DMSO) δ ppm 8.17 (d, 1H, J = 1.2 Hz), 7.90 (d, 1H, J = 5.6 Hz), 7.77 (d, 2H, J = 8.4 Hz), 7.51 (d, 2H, J = 8.0 Hz), 7.03 (d, 1H, J = 1.6 Hz), 6.62 (t, 1H, J = 5.2 Hz), 5.99 (d, 1H, J = 5.2 Hz), 3.53-3.51 (m, 4H), 3.45-3.43 (m, 4H), 3.23-3.18 (m, 1H), 3.12-3.07 (m, 2H), 3.01-2.99 (m, 1H), 2.89-2.77 (m, 2H), 2.67-2.65 (m, 1H), 2.45-2.40 (m, 2H), 1.81-1.70 (m, 3H), 1.40-1.30 (m, 1H), 1.05-0.99 (m, 12H). |
| 674 | 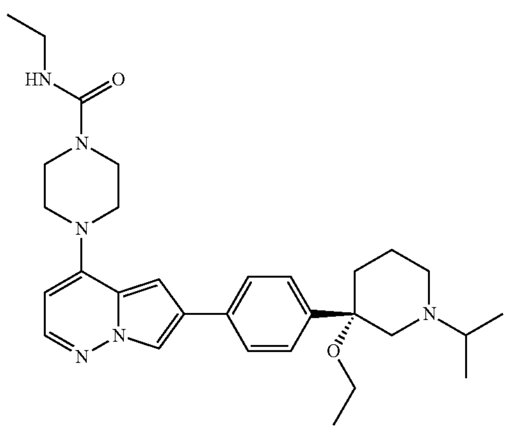 [SMILES: CCNC(=O)N1CCN(c2ccnn3cc(-c4ccc([C@@]5(OCC)CCCN(C(C)C)C5)cc4)cc23)CC1] | 519 | 1H-NMR (400 MHz, DMSO-d6) δ ppm 8.17 (d, 1H, J = 1.2 Hz), 7.90 (d, 1H, J = 5.2 Hz), 7.77 (d, 2H, J = 8.4 Hz), 7.51 (d, 2H, J = 8.0 Hz), 7.03 (d, 1H, J = 1.2 Hz), 6.62 (s, 1H), 5.98 (d, 1H, J = 5.6 Hz), 3.53-3.52 (m, 4H), 3.45-3.43 (m, 4H), 3.34-3.33 (m, 1H), 3.23-3.21 (m, 1H), 3.12-3.00 (m, 3H), 2.87-2.77 (m, 2H), 2.68-2.65 (m, 1H), 2.41-2.40 (m, 1H), 1.81-1.73 (m, 3H), 1.37-1.35 (m, 1H), 1.06-0.99 (m, 12H). |
| 675 | 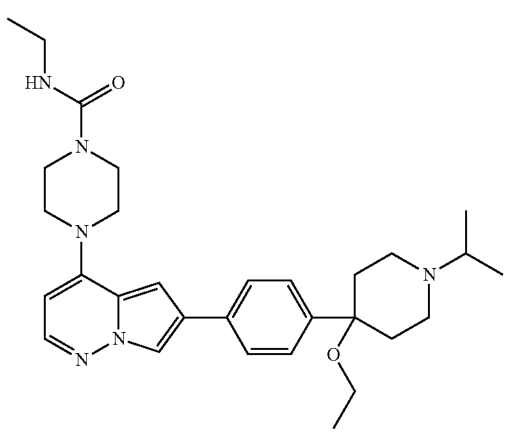 [SMILES: CCNC(=O)N1CCN(c2ccnn3cc(-c4ccc(C5(OCC)CCN(C(C)C)CC5)cc4)cc23)CC1] | 519 | 1H NMR (400 MHz, 4d-MeOD) δ ppm 7.99 (d, 1H, J = 1.6 Hz), 7.86 (d, 1H, J = 5.6 Hz), 7.76 (d, 2H, J = 8.4 Hz), 7.48 (d, 2H, J = 8.4 Hz), 6.92 (d, 1H, J = 1.6 Hz), 6.01 (d, 1H, J = 5.2 Hz), 3.67-3.65 (m, 4H), 3.56-3.54 (m, 4H), 3.24 (q, 2H, J = 7.2 Hz), 3.17 (d, 2H, J = 6.8 Hz), 3.11-3.10 (m, 2H), 3.07-3.06 (m, 2H), 2.32-2.28 (m, 2H), 2.12-2.11 (m, 2H), 1.29 (d, 6H, J = 6.4 Hz), 1.18-1.14 (m, 7H). |

TABLE 1-continued

| # | Structure | LCMS (M + 1) | NMR |
|---|---|---|---|
| 676 | 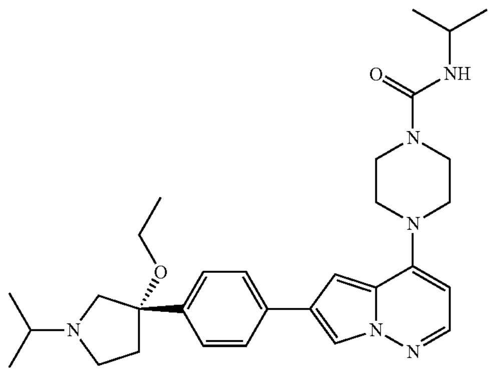 [SMILES: CCO[C@]1(c2ccc(-c3cc4c(N5CCN(C(=O)NC(C)C)CC5)ccnn4c3)cc2)CCN(C(C)C)C1] | 519 | |
| 677 | 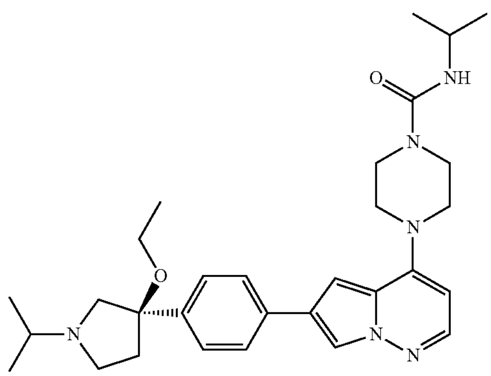 [SMILES: CCO[C@@]1(c2ccc(-c3cc4c(N5CCN(C(=O)NC(C)C)CC5)ccnn4c3)cc2)CCN(C(C)C)C1] | 519 | |
| 678 | 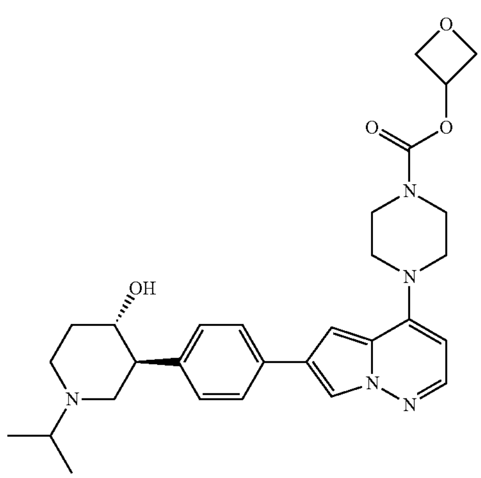 [SMILES: CC(C)N1CC[C@H](O)[C@@H](c2ccc(-c3cc4c(N5CCN(C(=O)OC6COC6)CC5)ccnn4c3)cc2)C1] | 520 | 1H-NMR (400 MHz, 6d-DMSO) δ ppm 8.16 (d, 1H, J = 1.6 Hz), 7.91 (d, 1H, J = 5.2 Hz), 7.72 (d, 2H, J = 8.4 Hz), 7.28 (d, 2H, J = 8.4 Hz), 7.0 (d, 1H, J = 1.6 Hz), 5.99 (d, 1H, J = 5.6 Hz), 5.34 (quintet, 1H, J = 5.2 Hz), 4.80 (t, 2H, J = 7.2 Hz), 4.54 (dd, 2H, J = 7.2, 5.6 Hz), 4.54-4.49 (m, 1H), 3.69-3.65 (m, 2H), 3.65-3.60 (m, 3H), 3.51-3.49 (m, 4H), 2.89-2.75 (m, 3H), 2.65-2.59 (m, 1H), 2.33-2.24 (m, 2H), 1.94-1.92 (m, 1H), 1.53-1.50 (m, 1H), 0.98 (s, 6H). |

| # | Structure | LCMS (M + 1) | NMR |
|---|---|---|---|
| 679 | 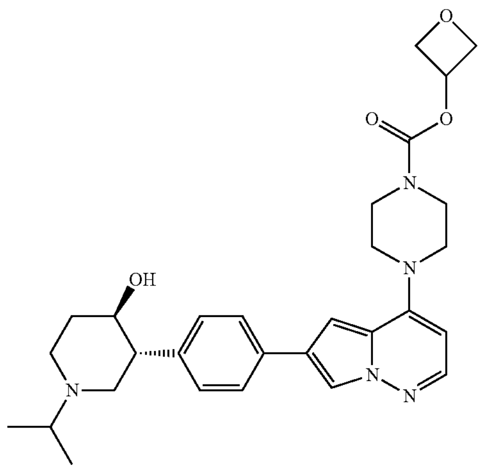 [SMILES: CC(C)N1CC[C@@H](O)[C@H](c2ccc(-c3cc4c(N5CCN(C(=O)OC6COC6)CC5)ccnn4c3)cc2)C1] | 520 | 1H-NMR (400 MHz, 6d-DMSO) δ ppm 8.25 (s, 1H), 8.16 (d, 1H, J = 1.6 Hz), 7.91 (d, 1H, J = 5.2 Hz), 7.73 (d, 2H, J = 8.0 Hz), 7.28 (d, 2H, J = 8.0 Hz), 7.01 (d, 1H, J = 1.6 Hz), 5.99 (d, 1H, J = 5.2 Hz), 5.34 (quintet, 1H, J = 5.2 Hz), 4.80 (t, 2H, J = 6.8 Hz), 4.54 (dd, 2H, J = 7.2, 5.2 Hz), 3.79-3.70 (m, 5H), 3.57-3.50 (m, 4H), 2.90-2.78 (m, 4H), 2.69-2.60 (m, 1H), 2.41-2.32 (m, 2H), 1.95-1.92 (m, 1H), 1.61-1.49 (m, 1H), 1.01-0.99 (m, 6H). |
| 680 | 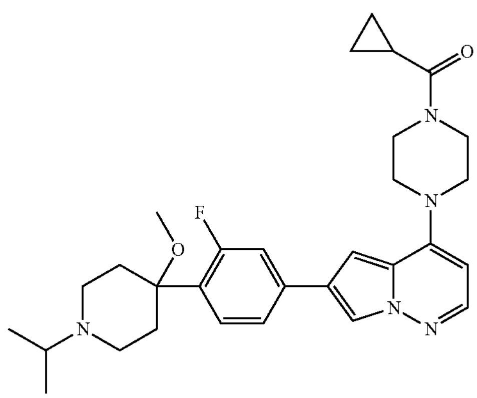 [SMILES: COC1(c2ccc(-c3cc4c(N5CCN(C(=O)C6CC6)CC5)ccnn4c3)cc2F)CCN(C(C)C)CC1] | 520 | 1H-NMR (400 MHz, 6d-DMSO) δ ppm 8.26 (d, 1H, J = 1.6 Hz), 7.91 (d, 1H, J = 5.2 Hz), 7.68-7.62 (m, 2H), 7.37-7.33 (m, 1H), 7.13 (d, 1H, J = 1.6 Hz), 5.96 (d, 1H, J = 5.2 Hz), 3.93-3.91 (m, 2H), 3.67-3.66 (m, 2H), 3.56-3.47 (m, 4H), 2.96 (s, 3H), 2.67-2.57 (m, 3H), 2.49-2.45 (m, 2H), 2.13-1.95 (m, 5H), 0.98 (d, 6H, J = 6.8 Hz), 0.78-0.73 (m, 4H). |
| 681 | 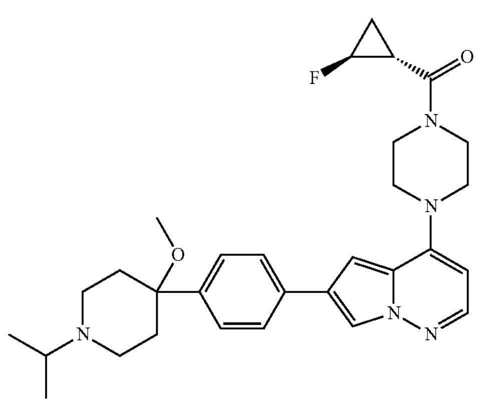 [SMILES: COC1(c2ccc(-c3cc4c(N5CCN(C(=O)[C@H]6C[C@@H]6F)CC5)ccnn4c3)cc2)CCN(C(C)C)CC1] | 520 | 1H-NMR (400 MHz, 6d-DMSO) δ ppm 8.18 (d, 1H, J = 1.6 Hz), 7.91 (d, 1H, J = 5.6 Hz), 7.79 (d, 2H, J = 8.4 Hz), 7.39 (d, 2H, J = 8.4 Hz), 7.05 (d, 1H, J = 1.6 Hz), 5.98 (d, 1H, J = 5.6 Hz), 5.00-4.70 (m, 1H), 4.00-3.90 (m, 2H), 3.75-3.65 (m, 2H), 3.61-3.49 (m, 2H), 3.37-3.40 (m, 2H), 2.88 (s, 3H), 2.72-2.65 (m, 2H), 2.60-2.54 (m, 2H), 2.48-2.42 (m, 2H), 2.00-1.92 (m, 2H), 1.90-1.76 (m, 2H), 1.50-1.36 (m, 1H), 1.24-1.10 (m, 1H), 0.99 (d, 6H, J = 6.4 Hz). |

TABLE 1-continued

| # | Structure | LCMS (M + 1) | NMR |
|---|---|---|---|
| 682 | 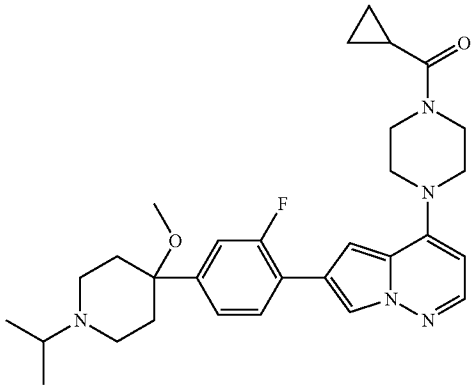 [SMILES: COC1(c2ccc(-c3cc4c(N5CCN(C(=O)C6CC6)CC5)ccnn4c3)c(F)c2)CCN(C(C)C)CC1] | 520 | 1H-NMR (400 MHz, 6d-DMSO) δ ppm 8.27 (d, 1H, J = 1.6 Hz), 7.92 (d, 1H, J = 5.6 Hz), 7.68-7.62 (m, 2H), 7.36 (t, 1H, J = 8.4 Hz), 7.14 (d, 1H, J = 1.6 Hz), 5.99 (d, 1H, J = 5.6 Hz), 3.94-3.92 (m, 2H), 3.72-3.70 (m, 2H), 3.56-3.51 (m, 2H), 3.50-3.45 (m, 2H), 2.97 (s, 3H), 2.69-2.65 (m, 1H), 2.60-2.56 (m, 2H), 2.46-2.44 (m, 2H), 2.14-2.10 (m, 2H), 2.04-2.00 (m, 1H), 1.98-1.92 (m, 2H), 1.00 (d, 6H, J = 6.8 Hz), 0.78-0.74 (m, 4H). |
| 683 | 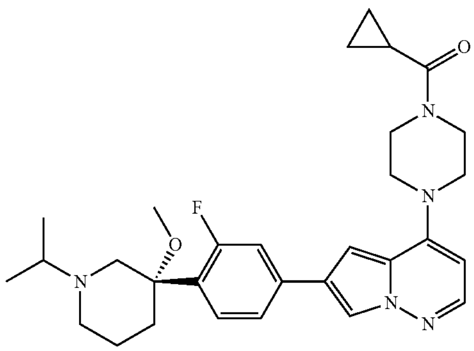 | 520 | 1H-NMR (400 MHz, 6d-DMSO) δ ppm 8.26 (d, 1H, J = 1.6 Hz), 7.92 (d, 1H, J = 5.6 Hz), 7.65-7.63 (m, 2H), 7.51 (t, 1H, J = 8.4 Hz), 7.14 (d, 1H, J = 1.6 Hz), 5.98 (d, 1H, J = 5.6 Hz), 3.93-3.80 (m, 2H), 3.72-3.70 (m, 2H), 3.65-3.54 (m, 2H), 3.55-3.46 (m, 2H), 3.03-3.00 (m, 1H), 2.98 (s, 3H), 2.80-2.76 (m, 1H), 2.68-2.64 (m, 1H), 2.50-2.42 (m, 2H), 2.07-2.00 (m, 2H), 1.76-1.71 (m, 2H), 1.39-1.36 (m, 1H), 1.01-0.99 (m, 6H), 0.79-0.73 (m, 4H). |
| 684 | 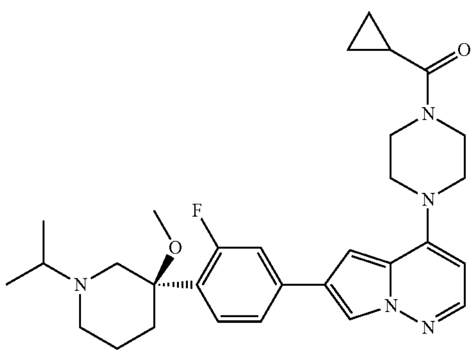 [SMILES: CO[C@@]1(c2ccc(-c3cc4c(N5CCN(C(=O)C6CC6)CC5)ccnn4c3)cc2F)CCCN(C(C)C)C1] | 520 | 1H-NMR (400 MHz, 6d-DMSO) δ ppm 8.26 (d, 1H, J = 1.6 Hz), 7.92 (d, 1H, J = 5.6 Hz), 7.65-7.63 (m, 2H), 7.52 (t, 1H, J = 8.4 Hz), 7.14 (d, 1H, J = 1.6 Hz), 5.98 (d, 1H, J = 5.6 Hz), 3.93-3.80 (m, 2H), 3.72-3.70 (m, 2H), 3.65-3.54 (m, 2H), 3.55-3.46 (m, 2H), 3.30 (s, 3H), 2.80-2.76 (m, 1H), 2.68-2.64 (m, 1H), 2.50-2.42 (m, 3H), 2.07-2.00 (m, 2H), 1.76-1.71 (m, 2H), 1.39-1.36 (m, 1H), 1.01-0.99 (m, 6H), 0.79-0.73 (m, 4H). |
| 685 | 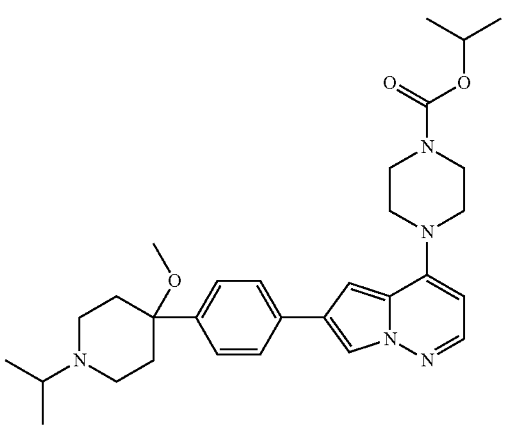 [SMILES: COC1(c2ccc(-c3cc4c(N5CCN(C(=O)OC(C)C)CC5)ccnn4c3)cc2)CCN(C(C)C)CC1] | 520 | 1H-NMR (400 MHz, 6d-DMSO) δ ppm 8.29 (s, 1H), 8.19 (d, 1H, J = 1.6 Hz), 7.91 (d, 1H, J = 5.2 Hz), 7.80 (d, 2H, J = 8.4 Hz), 7.39 (d, 2H, J = 8.4 Hz), 7.03 (d, 1H, J = 1.6 Hz), 5.98 (d, 1H, J = 5.2 Hz), 4.82 (heptet, 1H. J = 6.4 Hz), 3.60-3.59 (m, 4H), 3.46-3.45 (m, 4H), 2.90 (s, 3H), 2.84 (heptet, 1H. J = 6.8 Hz), 2.74-2.71 (m, 2H), 2.64-2.58 (m, 2H), 2.04-1.97 (m, 2H), 1.96-1.91 (m, 2H), 1.22 (d, 6H, J = 6.4 Hz), 1.05 (d, 6H, J = 6.8 Hz). |

TABLE 1-continued

| # | Structure | LCMS (M + 1) | NMR |
|---|---|---|---|
| 686 | 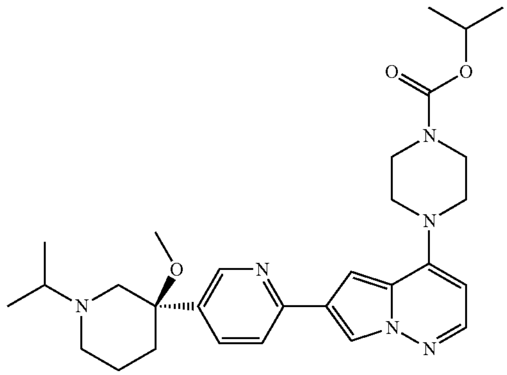 [SMILES: CO[C@@]1(c2ccc(-c3cc4c(N5CCN(C(=O)OC(C)C)CC5)ccnn4c3)nc2)CCCN(C(C)C)C1] | 520 | 1H-NMR (400 MHz, DMSO-d6) δ ppm 8.66 (d, 1H, J = 1.6 Hz), 8.27 (d, 1H, J = 1.6 Hz), 7.93-7.90 (m, 2H), 7.86-7.84 (m, 1H), 7.16 (d, 1H, J = 1.6 Hz), 6.30 (d, 1H, J = 7.6 Hz), 5.99 (d, 1H, J = 5.6 Hz), 3.82-3.73 (m, 1H), 3.53-3.52 (m, 4H), 3.45-3.44 (m, 4H), 2.98-2.88 (m, 1H), 2.93 (s, 3H), 2.83-2.78 (m, 1H), 2.66-2.63 (m, 1H), 2.46-2.40 (m, 2H), 1.93-1.87 (m, 1H), 1.75-1.68 (m, 2H), 1.37-1.33 (m, 1H), 1.08 (d, 6H, J = 6.8 Hz), 1.02-0.99 (m, 6H). |
| 687 | 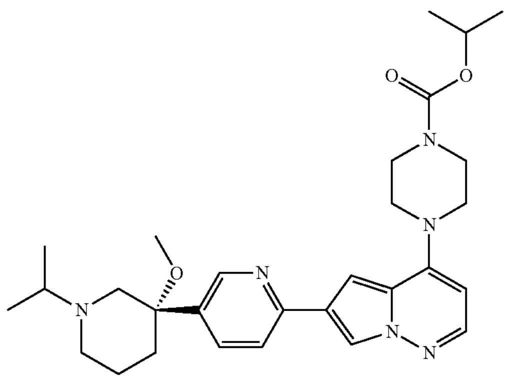 [SMILES: CO[C@]1(c2ccc(-c3cc4c(N5CCN(C(=O)OC(C)C)CC5)ccnn4c3)nc2)CCCN(C(C)C)C1] | 520 | 1H-NMR (400 MHz, DMSO-d6) δ ppm 8.66 (d, 1H, J = 1.6 Hz), 8.27 (d, 1H, J = 1.6 Hz), 7.93-7.90 (m, 2H), 7.86-7.84 (m, 1H), 7.16 (d, 1H, J = 2.0 Hz), 6.30 (d, 1H, J = 7.2 Hz), 5.99 (d, 1H, J = 5.6 Hz), 3.82-3.74 (m, 1H), 3.53-3.52 (m, 4H), 3.45-3.44 (m, 4H), 2.98-2.89 (m, 1H), 2.93 (s, 3H), 2.83-2.75 (m, 1H), 2.66-2.63 (m, 1H), 2.46-2.43 (m, 2H), 1.93-1.84 (m, 1H), 1.78-1.65 (m, 2H), 1.38-1.29 (m, 1H), 1.08 (d, 6H, J = 6.4 Hz), 1.02-0.99 (m, 6H). |
| 688 | 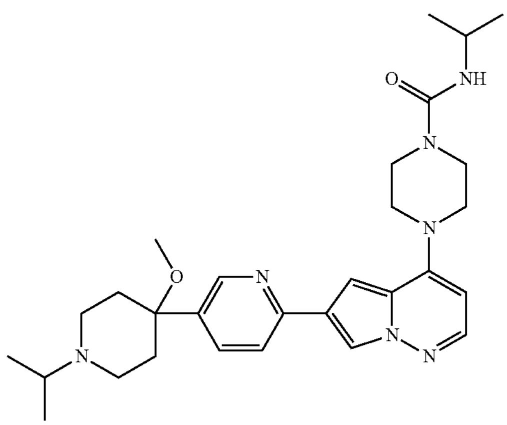 [SMILES: COC1(c2ccc(-c3cc4c(N5CCN(C(=O)NC(C)C)CC5)ccnn4c3)nc2)CCN(C(C)C)CC1] | 520 | 1H-NMR (400 MHz, 6d-DMSO) δ ppm 8.58 (d, 1H, J = 2.0 Hz), 8.28 (d, 1H, J = 1.2 Hz), 7.94-7.90 (m, 2H), 7.77 (dd, 1H, J = 8.0, 2.0 Hz), 7.17 (d, 1H, J = 1.6 Hz), 6.30 (d, 1H, J = 7.6 Hz), 6.00 (d, 1H, J = 5.2 Hz), 3.82-3.75 (m, 1H), 3.55-3.50 (m, 4H), 3.47-3.42 (m, 4H), 2.92 (s, 3H), 2.92 (s, 3H), 2.77-2.70 (m, 1H), 2.60-2.50 (m, 1H), 2.49-2.40 (m, 1H), 2.10-1.95 (m, 2H), 1.95-1.80 (m, 2H), 1.08 (d, 6H, J = 6.4 Hz), 1.00 (d, 6H, J = 6.4 Hz). |
| 689 | 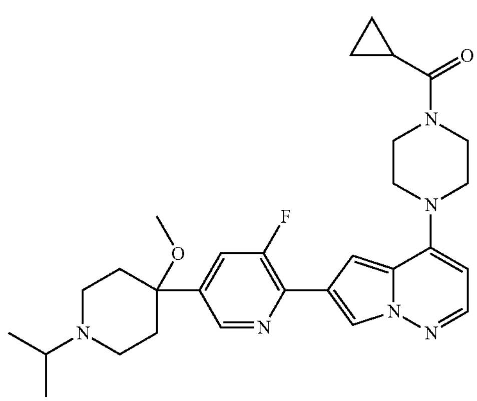 | 521 | 1H-NMR (400 MHz, 6d-DMSO) δ ppm 8.46 (d, 1H, J = 5.2 Hz), 8.19 (s, 1H), 7.98 (d, 1H, J = 5.2 Hz), 7.29 (t, 1H, J = 5.2 Hz), 7.21 (s, 1H), 6.02 (d, 1H, J = 5.6 Hz), 3.96-3.94 (m, 2H), 3.72-3.71 (m, 2H), 3.62-3.60 (m, 2H), 3.51-3.50 (m, 2H), 3.04 (s, 3H), 2.74-2.66 (m, 3H), 2.55-2.50 (m, 1H), 2.18-2.14 (m, 2H), 2.07-2.01 (m, 2H), 1.02 (d, 6H, J = 6.0 Hz), 0.78-0.74 (m, 4H). |

TABLE 1-continued

| # | Structure | LCMS (M + 1) | NMR |
|---|---|---|---|
| 690 | 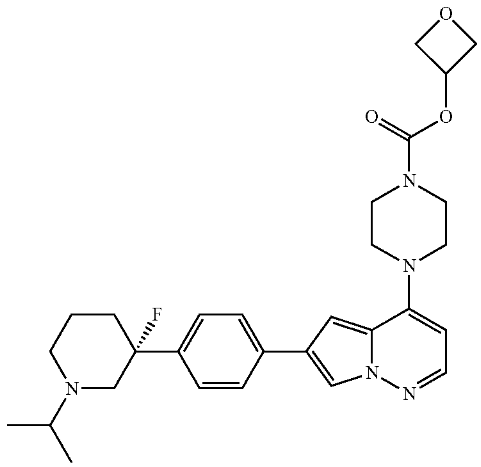 [SMILES: CC(C)N1CCC[C@@](F)(c2ccc(-c3cc4c(N5CCN(C(=O)OC6COC6)CC5)ccnn4c3)cc2)C1] | 522 | 1H-NMR (500 MHz, 6d-DMSO) δ ppm 8.20 (d, 1H, J = 1.5 Hz), 7.92 (d, 1H, J = 5.5 Hz), 7.82 (d, 2H, J = 8.5 Hz), 7.50 (d, 2H, J = 8.5 Hz), 7.05 (d, 1H, J = 2.0 Hz), 5.99 (d, 1H, J = 5.5 Hz), 5.34 (quintet, 1H, J = 5.5 Hz), 4.79 (t, 2H, J = 7.5 Hz), 4.53 (dd, 2H, J = 7.5, 5.5 Hz), 3.78-3.74 (m, 2H), 3.62-3.55 (m, 2H), 3.55-3.40 (m, 4H), 2.83-2.75 (m, 2H), 2.75-2.70 (m, 1H), −2.68-2.58 (m, 1H), 2.38-2.27 (m, 1H), 2.08-2.00 (m, 1H), 1.98-1.90 (m, 1H), 1.87-1.75 (m, 1H), 1.61-1.51 (m, 1H), 1.03-0.90 (m, 6H). |
| 691 | 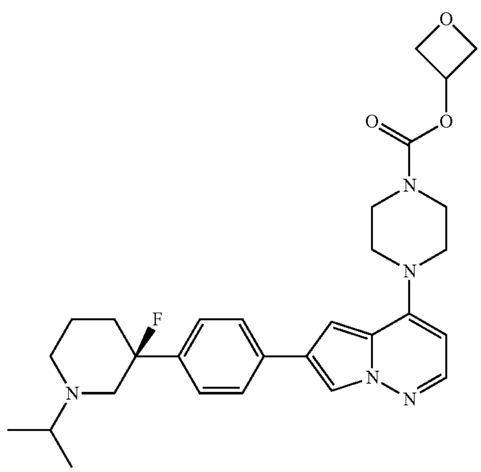 [SMILES: CC(C)N1CCC[C@](F)(c2ccc(-c3cc4c(N5CCN(C(=O)OC6COC6)CC5)ccnn4c3)cc2)C1] | 522 | 1H-NMR (500 MHz, 6d-DMSO) δ ppm 8.20 (d, 1H, J = 1.5 Hz), 7.92 (d, 1H, J = 5.5 Hz), 7.82 (d, 2H, J = 8.5 Hz), 7.50 (d, 2H, J = 8.5 Hz), 7.05 (d, 1H, J = 2.0 Hz), 5.99 (d, 1H, J = 5.5 Hz), 5.34 (quintet, 1H, J = 5.5 Hz), 4.79 (t, 2H, J = 7.5 Hz), 4.53 (dd, 2H, J = 7.5, 5.5 Hz), 3.78-3.74 (m, 2H), 3.62-3.55 (m, 2H), 3.55-3.40 (m, 4H), 2.83-2.75 (m, 2H), 2.75-2.70 (m, 1H), −2.68-2.58 (m, 1H), 2.38-2.27 (m, 1H), 2.08-2.00 (m, 1H), 1.98-1.90 (m, 1H), 1.87-1.75 (m, 1H), 1.61-1.51 (m, 1H), 1.03-0.90 (m, 6H). |
| 692 | 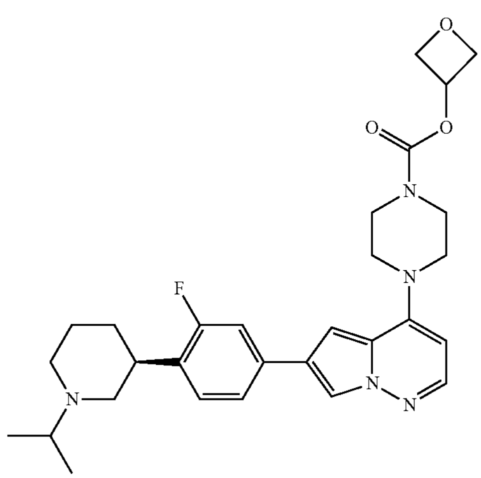 [SMILES: CC(C)N1CCC[C@@H](c2ccc(-c3cc4c(N5CCN(C(=O)OC6COC6)CC5)ccnn4c3)cc2F)C1] | 522 | 1H NMR (500 MHz, 6d-DMSO) δ ppm 8.24 (d, 1H, J = 1.5 Hz), 7.92 (d, 1H, J = 5.5 Hz), 7.66 (d, 1H, J = 11.5 Hz), 7.61 (d, 1H, J = 7.5 Hz), 7.38 (t, 1H, J = 6.5 Hz), 7.09 (d, 1H, J = 1.5 Hz), 6.00 (d, 1H, J = 5.5 Hz), 5.35 (quintet, 1H, J = 5.5 Hz), 4.80 (t, 2H, J = 7.5 Hz), 4.54 (dd, 2H, J = 7.5, 5.5 Hz), 3.70-3.60 (m, 2H), 3.60-3.55 (m, 2H), 3.50-3.48 (m, 4H), 3.10-2.98 (m, 1H), 2.82-2.81 (m, 2H), 2.21-2.19 (m, 2H), 1.79-1.76 (m, 2H), 1.56-1.55 (m, 2H) ), 1.00-0.99 (m, 6H). |

TABLE 1-continued

| # | Structure | LCMS (M + 1) | NMR |
|---|---|---|---|
| 693 | 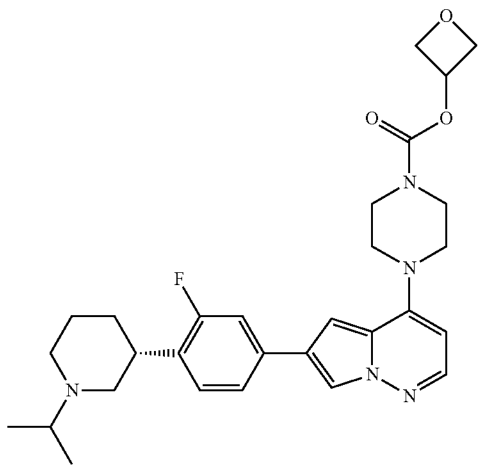 [SMILES: CC(C)N1CCC[C@H](c2ccc(-c3cc4c(N5CCN(C(=O)OC6COC6)CC5)ccnn4c3)cc2F)C1] | 522 | 1H NMR (500 MHz, 6d-DMSO) δ ppm 8.24 (d, 1H, J = 1.5 Hz), 7.92 (d, 1H, J = 5.5 Hz), 7.66 (d, 1H, J = 11.5 Hz), 7.61 (d, 1H, J = 7.5 Hz), 7.38 (t, 1H, J = 6.5 Hz), 7.09 (d, 1H, J = 1.5 Hz), 6.00 (d, 1H, J = 5.5 Hz), 5.35 (quintet, 1H, J = 5.5 Hz), 4.80 (t, 2H, J = 7.5 Hz), 4.54 (dd, 2H, J = 7.5, 5.5 Hz), 3.70-3.60 (m, 2H), 3.60-3.55 (m, 2H), 3.50-3.48 (m, 4H), 3.10-2.98 (m, 1H), 2.82-2.81 (m, 2H), 2.21-2.19 (m, 2H), 1.79-1.76 (m, 2H), 1.56-1.55 (m, 2H)), 1.00-0.99 (m, 6H). |
| 694 | 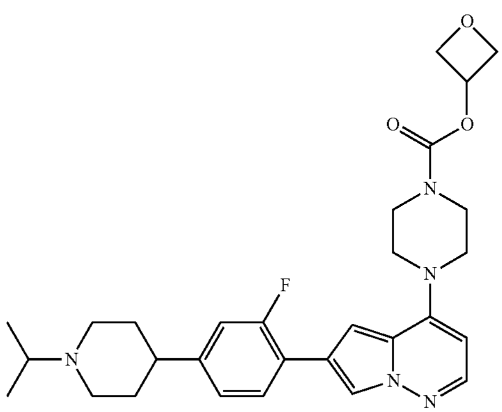 | 552 | 1H NMR (400 MHz, DMSO-d6) δ 8.00 (dd, J = 2.8, 1.7 Hz, 1H), 7.90 (d, J = 5.4 Hz, 1H), 7.81 (t, J = 8.4 Hz, 1H), 7.17-7.05 (m, 2H), 6.98 (d, J = 1.8 Hz, 1H), 5.97 (d, J = 5.5 Hz, 1H), 5.29 (tt, J = 6.3, 5.1 Hz, 1H), 4.81-4.68 (m, 2H), 4.48 (dd, J = 7.6, 5.1 Hz, 2H), 3.59 (d, J = 40.5 Hz, 4H), 3.45 (dd, J = 6.7, 3.7 Hz, 4H), 2.84 (d, J = 10.9 Hz, 2H), 2.72-2.60 (m, 1H), 2.22-2.10 (m, 2H), 1.74 (d, J = 12.4 Hz, 2H), 1.67-1.49 (m, 2H), 0.95 (d, J = 6.6 Hz, 6H). |
| 695 | 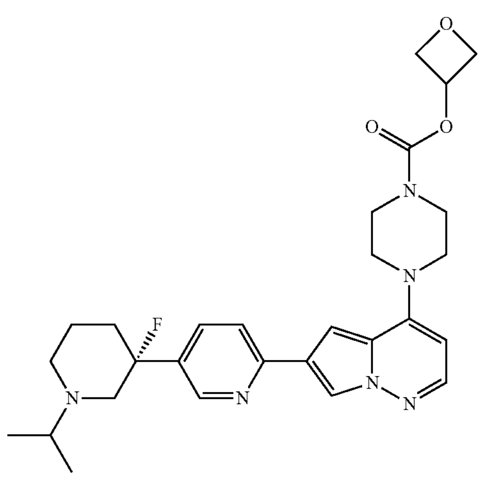 [SMILES: CC(C)N1CCC[C@@](F)(c2ccc(-c3cc4c(N5CCN(C(=O)OC6COC6)CC5)ccnn4c3)nc2)C1] | 523 | 1H-NMR (500 MHz, 6d-DMSO) δ ppm 8.73 (s, 1H), 8.31 (s, 1H), 7.96-7.92 (m, 3H), 7.21 (s, 1H), 6.06-6.01 (m, 1H), 5.37-5.32 (m, 1H), 4.81-4.78 (m, 2H), 4.55-4.53 (m, 2H), 3.74-3.69 (m, 2H), 3.68-3.62 (m, 2H), 3.52-3.49 (m, 4H), 2.90-2.85 (m, 2H), 2.69-2.64 (m, 2H), 2.44-2.36 (m, 1H), 2.12-1.98 (m, 1H), 1.96-1.93 (m, 1H), 1.80-1.75 (m, 1H), 1.61-1.53 (m, 1H), 1.01-0.98 (m, 6H). |

TABLE 1-continued
| # | Structure | LCMS (M + 1) | NMR |
|---|---|---|---|
| 696 | 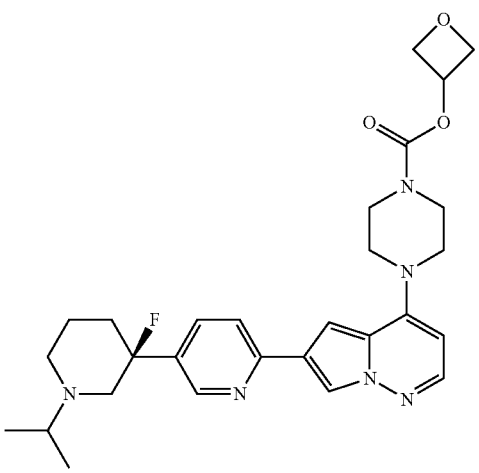 | 523 | 1H-NMR (400 MHz, 6d-DMSO) δ ppm 8.72 (s, 1H), 8.31 (d, 1H, J = 1.6 Hz), 7.97-7.91 (m, 3H), 7.21 (s, 1H), 6.02 (d, 1H, J = 5.6 Hz), 5.34 (quintet, 1H, J = 5.6 Hz), 4.80 (d, 2H, J = 7.2 Hz), 4.53 (dd, 2H, J = 7.2, 5.2 Hz), 3.75-3.70 (m, 2H), 3.65-3.60 (m, 2H), 3.56-3.46 (m, 4H), 2.85-2.79 (m, 2H), 2.75-2.68 (m, 2H), 2.41-2.33 (m, 1H), 2.15-2.09 (m, 1H), 2.01-1.73 (m, 2H), 1.60-1.53 (m, 1H), 1.02-0.97 (m, 6H). |
| 697 | 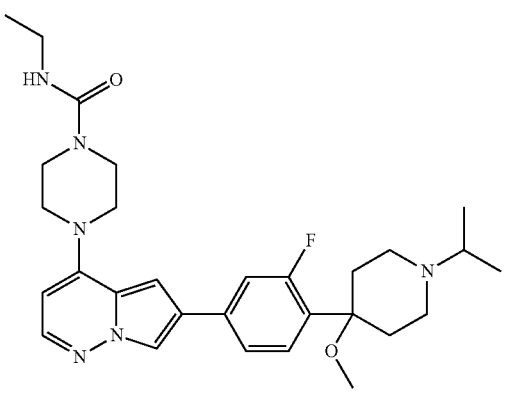 [SMILES: CCNC(=O)N1CCN(c2ccnn3cc(-c4ccc(C5(OC)CCN(C(C)C)CC5)c(F)c4)cc23)CC1] | 523 | 1H-NMR (400 MHz, 6d-DMSO) δ ppm 8.25 (d, 1H, J = 1.6 Hz), 7.90 (d, 1H, J = 5.2 Hz), 7.68-7.62 (m, 2H), 7.37-7.32 (m, 1H), 7.10 (s, 1H), 6.59 (t, 1H, J = 5.6 Hz), 5.98 (d, 1H, J = 5.2 Hz), 3.52-3.51 (m, 4H), 3.44-3.43 (m, 4H), 3.10-3.04 (m, 2H), 2.96 (s, 3H), 2.67-2.57 (m, 3H), 2.49-2.45 (m, 2H), 2.13-2.09 (m, 2H), 2.01-1.92 (m, 2H), 1.03 (t, 3H, J = 7.2 Hz), 0.99 (d, 6H, J = 6.8 Hz). |
| 698 | 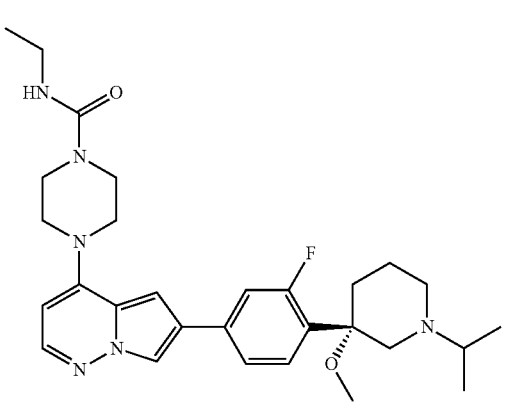 [SMILES: CCNC(=O)N1CCN(c2ccnn3cc(-c4ccc([C@@]5(OC)CCCN(C(C)C)C5)c(F)c4)cc23)CC1] | 523 | 1H-NMR (400 MHz, 6d-DMSO) δ ppm 8.26 (d, 1H, J = 1.6 Hz), 7.92 (d, 1H, J = 5.6 Hz), 7.65-7.63 (m, 2H), 7.52 (t, 1H. J = 8.4 Hz), 7.11 (d, 1H, J = 1.6 Hz), 6.62 (t, 1H, J = 5.6 Hz), 5.99 (d, 1H, J = 5.6 Hz), 3.56-3.52 (m, 4H), 3.46-3.44 (m, 4H), 3.10-3.08 (m, 2H), 3.05-3.00 (m, 1H), 2.99 (s, 3H), 2.80-2.77 (m, 1H), 2.77-2.68 (m, 1H), 2.50-2.42 (m, 2H), 2.08-2.07 (m, 1H), 1.76-1.70 (m, 2H), 1.37-1.36 (m, 1H), 1.06-1.00 (m, 9H). |

TABLE 1-continued

| # | Structure | LCMS (M + 1) | NMR |
|---|---|---|---|
| 699 | 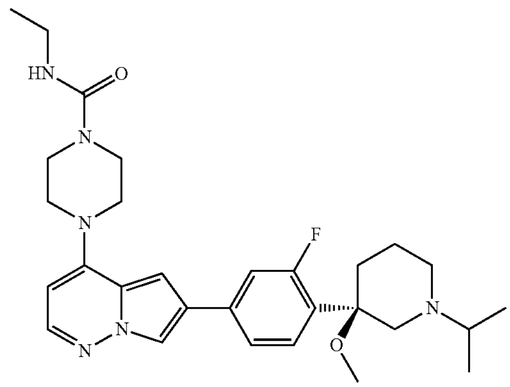 [SMILES: CCNC(=O)N1CCN(c2ccnn3cc(-c4ccc([C@]5(OC)CCCN(C(C)C)C5)c(F)c4)cc23)CC1] | 523 | 1H-NMR (400 MHz, 6d-DMSO) δ ppm 8.26 (d, 1H, J = 1.6 Hz), 7.92 (d, 1H, J = 5.6 Hz), 7.65-7.63 (m, 2H), 7.52 (t, 1H. J = 8.4 Hz), 7.11 (d, 1H, J = 1.6 Hz), 6.61 (t, 1H, J = 5.6 Hz), 5.98 (d, 1H, J = 5.6 Hz), 3.56-3.52 (m, 4H), 3.46-3.44 (m, 4H), 3.10-3.08 (m, 2H), 3.05-3.00 (m, 1H), 2.99 (s, 3H), 2.80-2.77 (m, 1H), 2.77-2.68 (m, 1H), 2.50-2.42 (m, 2H), 2.08-2.07 (m, 1H), 1.76-1.70 (m, 2H), 1.37-1.36 (m, 1H), 1.06-1.00 (m, 9H). |
| 700 | 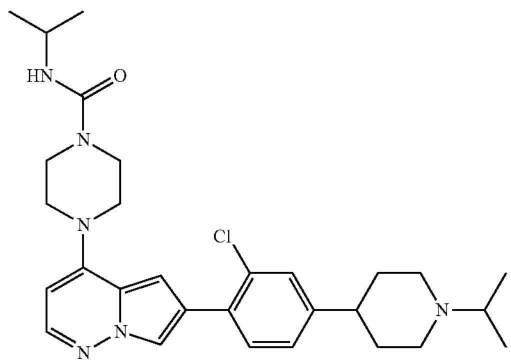 [SMILES: CC(C)NC(=O)N1CCN(c2ccnn3cc(-c4ccc(C5CCN(C(C)C)CC5)cc4Cl)cc23)CC1] | 524 | 1H-NMR (500 MHz, 6d-DMSO) δ ppm 9.24 (br. s., 1H), 8.07 (d, 1H, J = 1.0 Hz), 7.95 (d, 1H, J = 5.5 Hz), 7.73 (d, 1H, J = 7.5 Hz), 7.39 (s, 1H), 7.27 (d, 1H, J = 7.0 Hz), 6.91 (d, 1H, J = 1.5 Hz), 6.31 (d, 1H, J = 7.0 Hz), 6.02 (d, 1H, J = 6.0 Hz), 3.80-3.76 (m, 1H), 3.55-3.51 (m, 6H), 3.51-3.49 (m, 1H), 3.49-3.42 (m, 4H), 3.13-3.07 (m, 2H), 2.95-2.90 (m, 1H), 2.11-2.08 (m, 2H), 1.97-1.90 (m, 2H), 1.29 (d, 6H, J = 6.5 Hz), 1.07 (d, 6H, J = 6.5 Hz). |
| 701 | 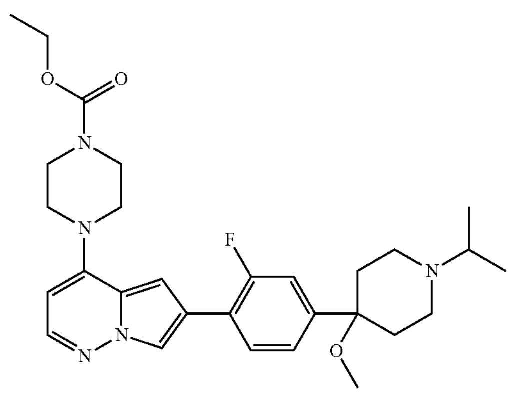 [SMILES: CCOC(=O)N1CCN(c2ccnn3cc(-c4ccc(C5(OC)CCN(C(C)C)CC5)cc4F)cc23)CC1] | 524 | 1H NMR (400 MHz, DMSO-d6) δ 8.03 (t, J = 2.2 Hz, 1H), 7.93-7.84 (m, 2H), 7.25-7.16 (m, 2H), 7.00 (d, J = 1.8 Hz, 1H), 5.97 (d, J = 5.5 Hz, 1H), 4.04 (q, J = 7.1 Hz, 2H), 3.55 (d, J = 5.8 Hz, 4H), 3.43 (dd, J = 6.7, 3.7 Hz, 4H), 2.87 (s, 3H), 2.60 (dd, J = 32.7, 8.3 Hz, 3H), 1.93 (d, J = 13.0 Hz, 2H), 1.81 (t, J = 11.6 Hz, 2H), 1.17 (t, J = 7.1 Hz, 3H), 0.95 (d, J = 6.5 Hz, 6H). |
| 702 | 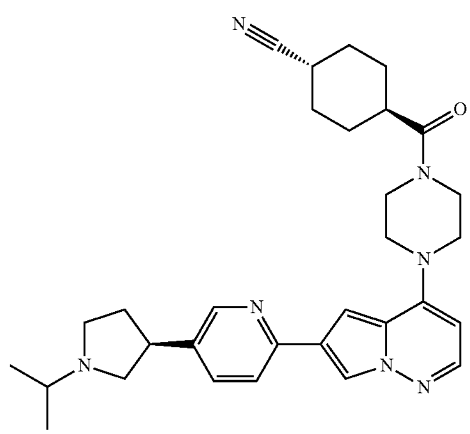 [SMILES: CC(C)N1CC[C@@H](c2ccc(-c3cc4c(N5CCN(C(=O)[C@H]6CC[C@H](C#N)CC6)CC5)ccnn4c3)nc2)C1] | 526 | 1H-NMR (400 MHz, 6d-DMSO) δ ppm 8.34 (s, 1H), 8.07 (d, 1H, J = 2.0 Hz), 7.77 (d, 1H, J = 5.2 Hz), 7.73-7.68 (m, 2H), 7.04 (d, 1H, J = 1.6 Hz), 5.87 (d, 1H, J = 5.6 Hz), 3.77-3.69 (m, 4H), 3.48-3.42 (m, 4H), 3.39-3.33 (m, 1H), 3.31-3.14 (m, 1H), 2.94-2.88 (m, 1H), 2.79-2.73 (m, 1H), 2.71-2.64 (m, 1H), 2.57-2.46 (m, 3H), 2.31-2.23 (m, 1H), 2.09-2.04 (m, 2H), 1.88-1.81 (m, 1H), 1.79-1.70 (m, 2H), 1.62-1.52 (m, 2H), 1.48-1.39 (m, 2H), 1.08 (m, 6H). |

TABLE 1-continued

| # | Structure | LCMS (M + 1) | NMR |
|---|---|---|---|
| 703 | 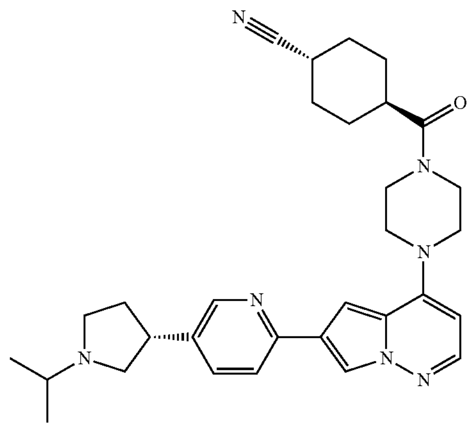 [SMILES: CC(C)N1CC[C@H](c2ccc(-c3cc4c(N5CCN(C(=O)[C@H]6CC[C@H](C#N)CC6)CC5)ccnn4c3)nc2)C1] | 526 | 1H-NMR (400 MHz, CDCl3) δ ppm 8.52 (d, 1H, J = 2.0 Hz), 8.13 (d, 1H, J = 1.6 Hz), 7.87 (d, 1H, J = 5.2 Hz), 7.64 (dd, 1H, J = 8.0, 2.0 Hz), 7.59 (d, 1H, J = 8.0 Hz), 7.01 (d, 1H, J = 1.6 Hz), 5.83 (d, 1H, J = 5.6 Hz), 3.88-3.83 (m, 2H), 3.77-3.72 (m, 2H), 3.57-3.52 (m, 2H), 3.47-3.42 (m, 2H), 3.41-3.37 (m, 1H), 3.23-3.18 (m, 1H), 2.98-2.93 (m, 1H), 2.78-2.73 (m, 1H), 2.60-2.47 (m, 4H), 2.45-2.38 (m, 1H), 2.26-2.23 (m, 2H), 1.91-1.85 (m, 3H), 1.71-1.65 (m, 2H), 1.64-1.59 (m, 2H), 1.17-1.13 (m, 6H). |
| 704 | 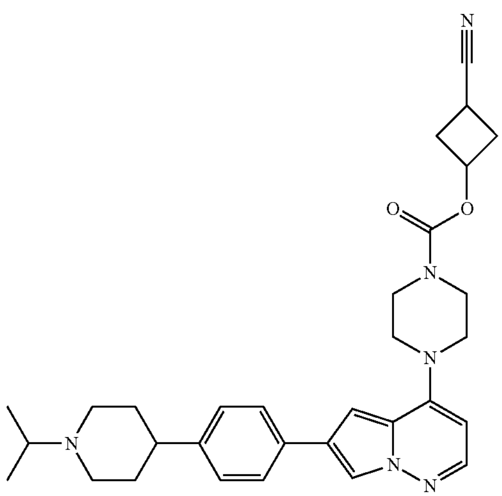 [SMILES: CC(C)N1CCC(c2ccc(-c3cc4c(N5CCN(C(=O)OC6CC(C#N)C6)CC5)ccnn4c3)cc2)CC1] | 527 | 1H NMR (400 MHz, DMSO-d6) δ 8.19 (s, 1H), 8.13 (d, J = 1.7 Hz, 1H), 7.89 (d, J = 5.4 Hz, 1H), 7.72 (d, J = 8.0 Hz, 2H), 7.25 (d, J = 8.1 Hz, 2H), 6.98 (d, J = 1.9 Hz, 1H), 5.97 (d, J = 5.5 Hz, 1H), 4.86 (p, J = 7.3 Hz, 1H), 3.58 (d, J = 17.1 Hz, 5H), 3.46 (t, J = 5.2 Hz, 4H), 3.06 (t, J = 8.8 Hz, 1H), 2.93 (d, J = 11.2 Hz, 2H), 2.83-2.70 (m, 2H), 2.59 (d, J = 7.0 Hz, 1H), 2.42-2.22 (m, 3H), 1.78 (d, J = 12.0 Hz, 2H), 1.73-1.57 (m, 2H), 0.99 (d, J = 8.3 Hz, 4H). |
| 705 | 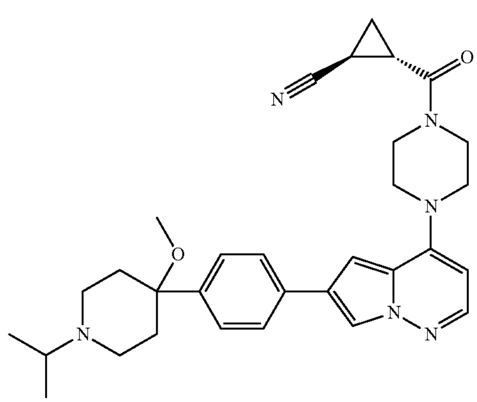 [SMILES: COC1(c2ccc(-c3cc4c(N5CCN(C(=O)[C@H]6C[C@@H]6C#N)CC5)ccnn4c3)cc2)CCN(C(C)C)CC1] | 527 | 1H-NMR (400 MHz, 6d-DMSO) δ ppm 8.19 (d, 1H, J = 1.6 Hz), 7.91 (d, 1H, J = 5.2 Hz), 7.79 (d, 2H, J = 8.4 Hz), 7.39 (d, 2H, J = 8.4 Hz), 7.06 (d, 1H, J = 1.6 Hz), 5.99 (d, 1H, J = 5.2 Hz), 4.00-3.90 (m, 2H), 3.76-3.68 (m, 2H), 3.64-3.52 (m, 2H), 3.51-3.40 (m, 2H), 3.00-2.90 (m, 1H), 2.88 (s, 3H), 2.70 (heptet, 1H, J = 6.4 Hz), 2.62-2.54 (m, 2H), 2.48-2.42 (m, 2H), 2.15-2.05 (m, 1H), 2.00-1.92 (m, 2H), 1.90-1.78 (m, 2H), 1.50-1.40 (m, 1H), 1.38-1.30 (m, 1H), 0.99 (d, 6H, J = 6.4 Hz). |

TABLE 1-continued
| # | Structure | LCMS (M + 1) | NMR |
|---|---|---|---|
| 706 | 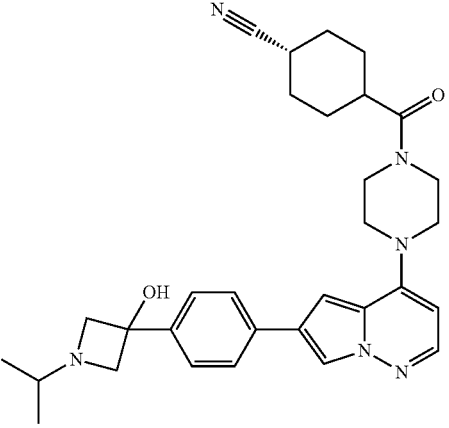 | 527 | 1H-NMR (400 MHz, 6d-DMSO) δ ppm 8.17 (d, 1H, J = 2.0 Hz), 7.90 (d, 1H, J = 5.2 Hz), 7.78 (d, 2H, J = 8.4 Hz), 7.63 (d, 2H, J = 8.4 Hz), 7.03 (d, 1H, J = 1.6 Hz), 5.97 (d, 1H, J = 5.6 Hz), 5.80 (s, 1H), 3.80-3.70 (m, 2H), 3.68-3.60 (m, 2H), 3.56-3.47 (m, 4H), 3.45-3.40 (m, 2H), 3.26-3.16 (m, 2H), 2.80-2.60 (m, 2H), 2.44-2.34 (m, 1H), 2.10-1.94 (m, 2H), 1.80-1.68 (m, 2H), 1.66-1.50 (m, 2H), 1.48-1.32 (m, 2H), 0.90 (d, 6H, J = 6.0 Hz). |
| 707 | 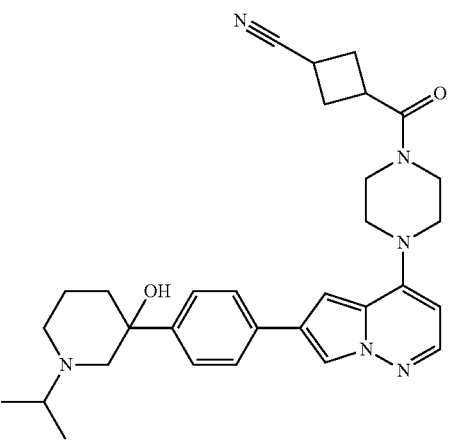 [SMILES: CC(C)N1CCCC(O)(c2ccc(-c3cc4c(N5CCN(C(=O)C6CC(C#N)C6)CC5)ccnn4c3)cc2)C1] | 527 | 1H-NMR (400 MHz, 6d-DMSO) δ ppm 8.16 (d, 1H, J = 1.2 Hz), 7.90 (d, 1H, J = 5.6 Hz), 7.75 (d, 2H, J = 8.4 Hz), 7.56 (d, 2H, J = 8.4 Hz), 7.02 (d, 1H, J = 1.6 Hz), 5.98 (d, 1H, J = 5.6 Hz), 4.51 (s, 1H), 3.71-3.64 (m, 3H), 3.56-3.54 (m, 2H), 3.46-3.45 (m, 4H), 3.31-3.24 (m, 2H), 2.81-2.76 (m, 1H), 2.67-2.59 (m, 4H), 2.46-2.43 (m, 2H), 2.34-2.30 (m, 1H), 1.84-1.80 (m, 2H), 1.56-1.51 (m, 2H), 0.99 (t, 6H, J = 5.6 Hz). |
| 708 | 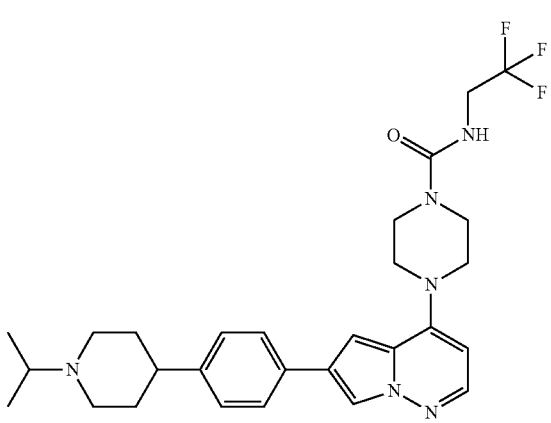 [SMILES: CC(C)N1CCC(c2ccc(-c3cc4c(N5CCN(C(=O)NCC(F)(F)F)CC5)ccnn4c3)cc2)CC1] | 529 | 1H NMR (400 MHz, DMSO-d6) δ 8.19 (s, 1H), 8.13 (d, J = 1.7 Hz, 1H), 7.88 (d, J = 5.4 Hz, 1H), 7.72 (d, J = 8.1 Hz, 2H), 7.26 (dd, J = 9.8, 7.1 Hz, 3H), 7.00 (d, J = 1.9 Hz, 1H), 5.97 (d, J = 5.5 Hz, 1H), 3.86 (qd, J = 9.8, 6.3 Hz, 2H), 3.59-3.53 (m, 4H), 3.45 (dd, J = 6.6, 3.6 Hz, 4H), 2.97 (d, J = 11.3 Hz, 2H), 2.83 (p, J = 6.6 Hz, 1H), 2.42-2.26 (m, 2H), 1.88-1.74 (m, 2H), 1.67 (qd, J = 12.3, 3.7 Hz, 2H), 1.03 (d, J = 6.6 Hz, 6H). |

TABLE 1-continued

| # | Structure | LCMS (M + 1) | NMR |
|---|---|---|---|
| 709 | 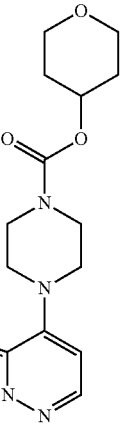 | 532 | 1H NMR (400 MHz, DMSO-d6) δ 8.21 (s, 1H), 8.13 (d, J = 1.6 Hz, 1H), 7.89 (d, J = 5.4 Hz, 1H), 7.72 (d, J = 8.0 Hz, 2H), 7.24 (d, J = 8.1 Hz, 2H), 6.99 (d, J = 1.9 Hz, 1H), 5.97 (d, J = 5.5 Hz, 1H), 4.79 (tt, J = 8.1, 4.0 Hz, 1H), 3.79 (dt, J = 10.4, 4.5 Hz, 2H), 3.61 (s, 4H), 3.48 (ddd, J = 11.4, 8.4, 3.4 Hz, 6H), 2.96 (d, J = 11.0 Hz, 2H), 2.83 (p, J = 6.6 Hz, 1H), 2.34 (dd, J = 12.5, 10.0 Hz, 2H), 1.88 (dd, J = 12.8, 4.6 Hz, 2H), 1.83-1.75 (m, 2H), 1.68 (tt, J = 12.5, 6.3 Hz, 2H), 1.56 (dtd, J = 12.6, 8.5, 4.0 Hz, 2H), 1.03 (d, J = 6.6 Hz, 6H). |
| 710 | 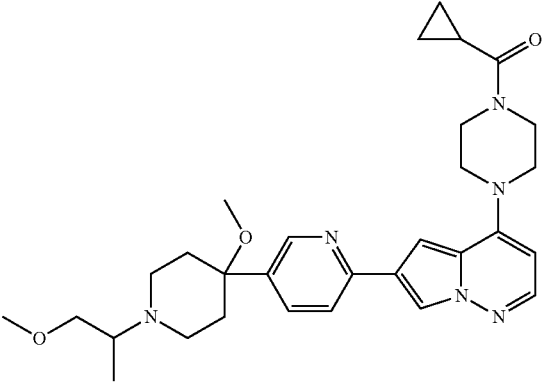 [SMILES: COCC(C)N1CCC(OC)(c2ccc(-c3cc4c(N5CCN(C(=O)C6CC6)CC5)ccnn4c3)nc2)CC1] | 533 | 1H-NMR (400 MHz, 6d-DMSO) δ ppm 8.57 (d, 1H, J = 2.0 Hz), 8.29 (d, 1H, J = 1.6 Hz), 7.96-7.88 (m, 2H), 7.76 (dd, 1H, J = 8.4, 2.4 Hz), 7.20 (d, 1H, J = 1.6 Hz), 5.98 (d, 1H, J = 5.6 Hz), 4.00-3.90 (m, 2H), 3.80-3.65 (m, 2H), 3.61-3.55 (m, 2H), 3.53-3.47 (m, 2H), 3.46-3.40 (m, 1H), 3.26-3.22 (m, 1H), 3.24 (s, 3H), 2.91 (s, 3H), 2.80-2.70 (m, 1H), 2.68-2.56 (m, 4H), 2.10-1.94 (m, 3H), 1.92-1.80 (m, 2H), 0.98 (d, 3H, J = 6.4 Hz), 0.80-0.70 (m, 4H). |
| 711 | 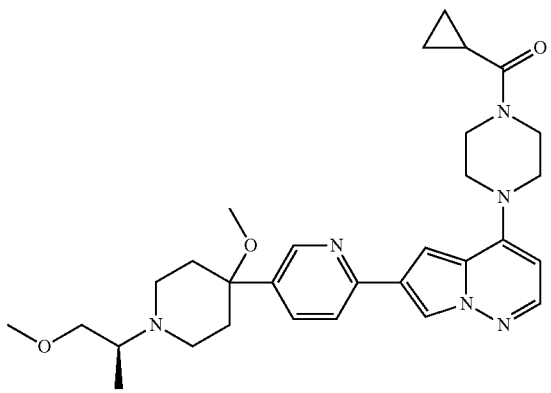 [SMILES: COC[C@H](C)N1CCC(OC)(c2ccc(-c3cc4c(N5CCN(C(=O)C6CC6)CC5)ccnn4c3)nc2)CC1] | 533 | 1H-NMR (400 MHz, 6d-DMSO) δ ppm 8.58 (d, 1H, J = 2.0 Hz), 8.30 (d, 1H, J = 1.6 Hz), 8.00-7.90 (m, 2H), 7.78 (dd, 1H, J = 8.4, 2.0 Hz), 7.21 (d, 1H, J = 1.6 Hz), 6.00 (d, 1H, J = 5.6 Hz), 4.00-3.90 (m, 2H), 3.80-3.65 (m, 2H), 3.65-3.59 (m, 2H), 3.55-3.47 (m, 1H), 3.47-3.40 (m, 1H), 3.28-3.24 (m, 1H), 3.27 (s, 3H), 2.92 (s, 3H), 2.80-2.70 (m, 1H), 2.68-2.55 (m, 4H), 2.10-1.95 (m, 3H), 1.94-1.80 (m, 2H), 0.98 (d, 3H, J = 6.4 Hz), 0.82-0.70 (m, 4H). |

TABLE 1-continued

| # | Structure | LCMS (M + 1) | NMR |
|---|---|---|---|
| 712 | 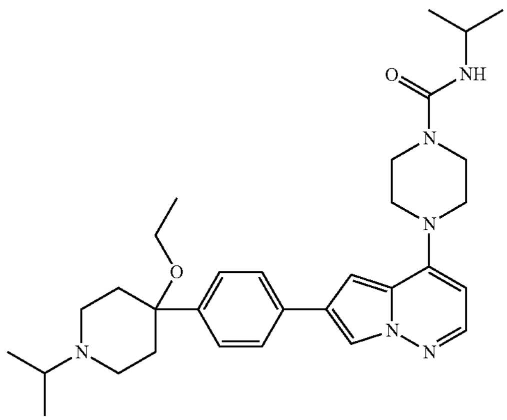 | 533 | 1H NMR (400 MHz, CD30D) δ ppm 7.98 (d, 1H, J = 2.0 Hz), 7.85 (d, 1H, J = 5.6 Hz), 7.74 (d, 2H, J = 8.0 Hz), 7.47 (d, 2H, J = 8.0 Hz), 6.92 (d, 1H, J = 2.0 Hz), 6.00 (d, 1H, J = 5.6 Hz), 3.95-3.90 (m, 1H), 3.67-3.65 (m, 4H), 3.55-3.53 (m, 4H), 3.17-3.16 (q, 2H, J = 7.2 Hz), 2.95-2.94 (m, 3H), 2.93-2.90 (m, 2H), 2.17-2.16 (m, 2H), 2.09-2.05 (m, 2H), 1.21-1.18 (m, 12H), 1.17-1.13 (t, 3H, J = 7.2 Hz). |
| 713 | 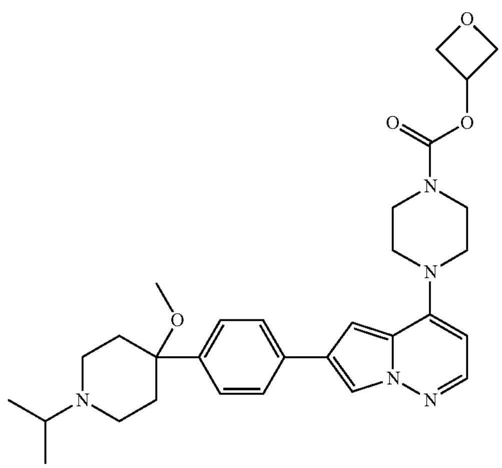 [SMILES: COC1(c2ccc(-c3cc4c(N5CCN(C(=O)OC6COC6)CC5)ccnn4c3)cc2)CCN(C(C)C)CC1] | 534 | 1H-NMR (400 MHz, 6d-DMSO) δ ppm 8.30 (s, 1H), 8.20 (d, 1H, J = 1.6 Hz), 7.92 (d, 1H, J = 5.6 Hz), 7.81 (d, 2H, J = 8.4 Hz), 7.39 (d, 2H, J = 8.4 Hz), 7.04 (d, 1H, J = 1.6 Hz), 5.99 (d, 1H, J = 5.6 Hz), 5.36-5.33 (m, 1H), 4.79 (t, 2H, J = 6.4 Hz), 4.53 (dd, 2H, J = 7.2, 5.2 Hz), 3.60-3.59 (m, 4H), 3.50-3.49 (m, 4H), 2.93-2.91 (m, 1H), 2.90 (s, 3H), 2.82-2.79 (m, 2H), 2.70-2.65 (m, 2H), 2.07-1.98 (m, 4H), 1.08 (d, 6H, J = 6.4 Hz). |
| 714 | 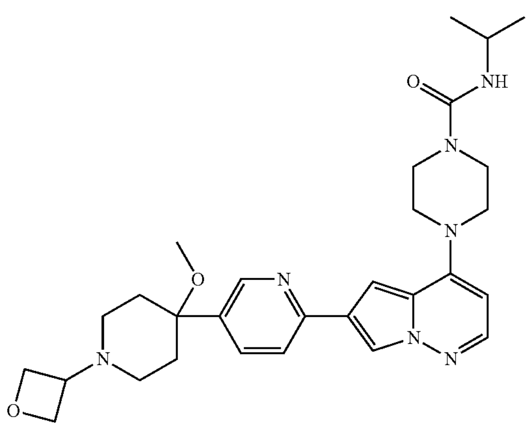 [SMILES: COC1(c2ccc(-c3cc4c(N5CCN(C(=O)NC(C)C)CC5)ccnn4c3)nc2)CCN(C2COC2)CC1] | 534 | 1H-NMR (400 MHz, 6d-DMSO) δ ppm 8.58 (d, 1H, J = 2.0 Hz), 8.28 (d, 1H, J = 1.6 Hz), 7.96-7.90 (m, 2H), 7.78 (dd, 1H, J = 8.4, 2.4 Hz), 7.17 (d, 1H, J = 1.6 Hz), 6.31 (d, 1H, J = 7.2 Hz), 5.99 (d, 1H, J = 5.6 Hz), 4.60-4.51 (m, 2H), 4.50-4.40 (m, 2H), 3.84-3.72 (m, 1H), 3.56-3.50 (m, 4H), 3.48-3.40 (m, 4H), 2.91 (s, 3H), 2.60-2.46 (m, 3H), 2.30-2.10 (m, 2H), 2.08-1.88 (m, 4H), 1.08 (d, 6H, J = 6.4 Hz). |

TABLE 1-continued

| # | Structure | LCMS (M + 1) | NMR |
|---|---|---|---|
| 715 | 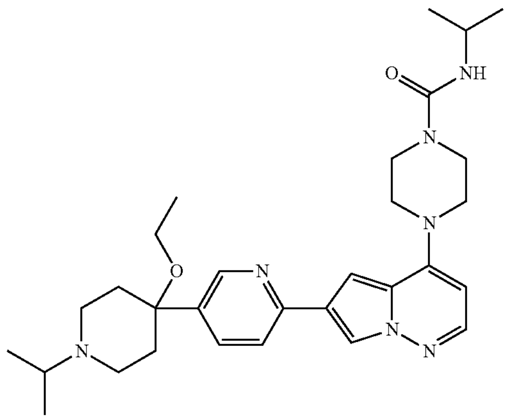 [SMILES: CCOC1(c2ccc(-c3cc4c(N5CCN(C(=O)NC(C)C)CC5)ccnn4c3)nc2)CCN(C(C)C)CC1] | 534 | 1H-NMR (500 MHz, 6d-DMSO) δ ppm 8.59 (d, 1H, J = 2.5 Hz), 8.27 (d, 1H, J = 2.0 Hz), 7.93 (d, 1H, J = 5.5 Hz), 7.91 (s, 1H), 7.78 (dd, 1H, J = 8.5, 2.0 Hz), 7.17 (d, 1H, J = 1.5 Hz), 6.31 (d, 1H, J = 7.5 Hz), 6.00 (d, 1H, J = 5.5 Hz), 3.81-3.76 (m, 1H), 3.53-3.50 (m, 4H), 3.46-3.45 (m, 4H), 3.08 (q, 2H, J = 7.0 Hz), 2.70-2.62 (m, 1H), 2.60-2.54 (m, 2H), 2.54-2.50 (m, 2H), 2.01-1.98 (m, 2H), 1.91-1.87 (m, 2H), 1.09-1.04 (m, 9H), 1.01-0.99 (m, 6H). |
| 716 | 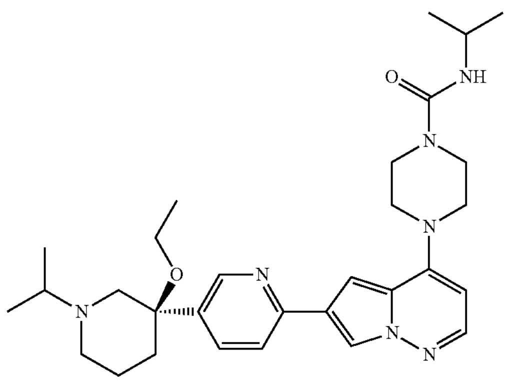 [SMILES: CCO[C@@]1(c2ccc(-c3cc4c(N5CCN(C(=O)NC(C)C)CC5)ccnn4c3)nc2)CCCN(C(C)C)C1] | 534 | 1H-NMR (400 MHz, 6d-DMSO) δ ppm 8.69 (s, 1H), 8.27 (d, 1H, J = 1.2 Hz), 7.92 (d, 1H, J = 5.6 Hz), 7.90-7.88 (m, 2H), 7.16 (d, 1H, J = 1.6 Hz), 6.31 (d, 1H, J = 7.6 Hz), 5.99 (d, 1H, J = 5.6 Hz), 3.80-3.75 (m, 1H), 3.53-3.52 (m, 4H), 3.45-3.44 (m, 4H), 3.26-3.22 (m, 1H), 3.03-2.98 (m, 2H), 2.82-2.78 (m, 1H), 2.62-2.60 (m, 1H), 2.45-2.41 (m, 2H), 1.94-1.85 (m, 1H), 1.74-1.66 (m, 2H), 1.36-1.26 (m, 1H), 1.07 (d, 6H, J = 6.4 Hz), 1.04-0.99 (m, 9H). |
| 717 | 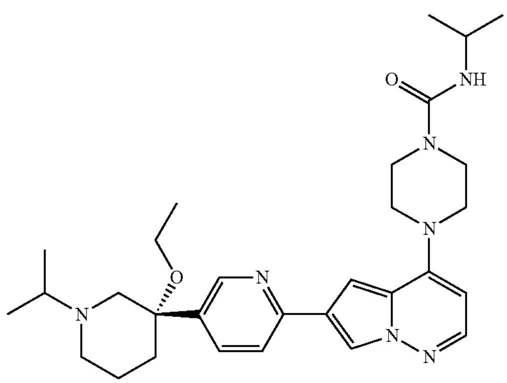 [SMILES: CCO[C@]1(c2ccc(-c3cc4c(N5CCN(C(=O)NC(C)C)CC5)ccnn4c3)nc2)CCCN(C(C)C)C1] | 534 | 1H-NMR (400 MHz, 6d-DMSO) δ ppm 8.68 (s, 1H), 8.26 (d, 1H, J = 1.2 Hz), 7.92 (d, 1H, J = 5.6 Hz), 7.90-7.88 (m, 2H), 7.16 (d, 1H, J = 1.6 Hz), 6.31 (d, 1H, J = 7.6 Hz), 5.98 (d, 1H, J = 5.6 Hz), 3.81-3.75 (m, 1H), 3.53-3.52 (m, 4H), 3.45-3.44 (m, 4H), 3.26-3.22 (m, 1H), 3.03-3.0 (m, 2H), 2.81-2.78 (m, 1H), 2.62-2.59 (m, 1H), 2.45-2.40 (m, 2H), 1.94-1.85 (m, 1H), 1.78-1.63 (m, 2H), 1.35-1.24 (m, 1H), 1.07 (d, 6H, J = 6.4 Hz), 1.04-0.99 (m, 9H). |
| 718 | 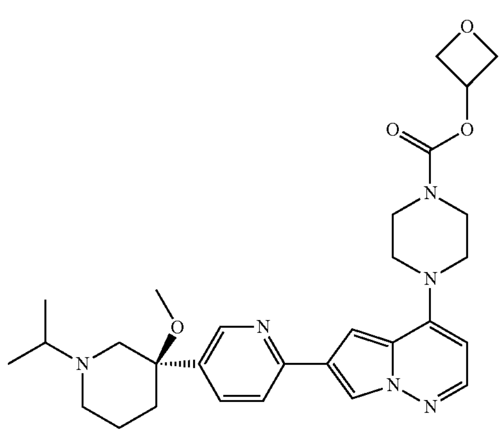 [SMILES: CO[C@@]1(c2ccc(-c3cc4c(N5CCN(C(=O)OC6COC6)CC5)ccnn4c3)nc2)CCCN(C(C)C)C1] | 535 | 1H-NMR (400 MHz, 6d-DMSO) δ ppm 8.68 (d, 1H, J = 1.6 Hz), 8.30 (d, H, J = 1.2 Hz), 8.20 (s, 1H), 7.94 (d, 1H, J = 5.6 Hz), 7.91 (s, 1H), 7.85 (dd, 1H, J = 8.0, 2.4 Hz), 7.18 (d, 1H, J = 1.6 Hz), 6.00 (d, 1H, J = 5.6 Hz), 5.35-5.30 (m, 1H), 4.78 (t, 2H, J = 7.2 Hz), 4.52 (dd, 2H, J = 7.6, 5.6 Hz), 3.72-3.66 (m, 2H), 3.65-3.59 (m, 2H), 3.51-3.50 (m, 4H), 2.98-2.95 (m, 1H), 2.94 (s, 3H), 2.90-2.84 (m, 1H), 2.76-2.73 (m, 1H), 2.59-2.53 (m, 1H), 1.95-1.90 (m, 1H), 1.83-1.81 (m, 1H), 1.74-1.71 (m, 1H), 1.45-1.33 (m, 1H), 1.03 (d, 6H, J = 6.4 Hz). |

TABLE 1-continued
| # | Structure | LCMS (M + 1) | NMR |
|---|---|---|---|
| 719 | 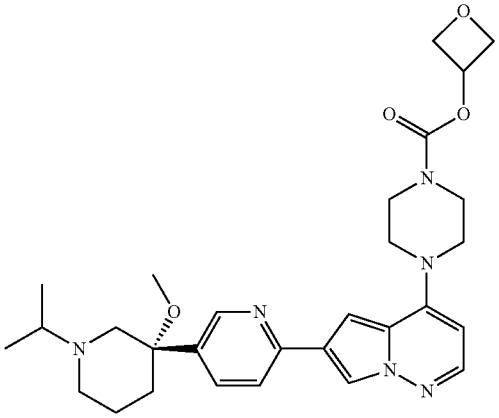 [SMILES: CO[C@]1(c2ccc(-c3cc4c(N5CCN(C(=O)OC6COC6)CC5)ccnn4c3)nc2)CCCN(C(C)C)C1] | 535 | 1H-NMR (400 MHz, 6d-DMSO) δ ppm 8.66 (d, 1H, J = 1.6 Hz), 8.29 (d, 1H, J = 1.6 Hz), 8.21-8.17 (m, 1H), 7.94 (d, 1H, J = 5.6 Hz), 7.91 (s, 1H), 7.85 (dd, 1H, J = 8.0, 2.0 Hz), 7.18 (d, 1H, J = 1.6 Hz), 6.0 (d, 1H, J = 5.2 Hz), 5.34-5.30 (m, 1H), 4.78 (t, 2H, J = 7.2 Hz), 4.52 (dd, 2H, J = 7.6, 5.6 Hz), 3.72-3.66 (m, 2H), 3.65-3.59 (m, 2H), 3.51-3.50 (m, 4H), 2.98-2.95 (m, 1H), 2.94 (s, 3H), 2.90-2.84 (m, 1H), 2.78-2.75 (m, 1H), 2.58-2.53 (m, 1H), 1.96-1.90 (m, 1H), 1.84-1.72 (m, 2H), 1.46-1.36 (m, 1H), 1.04 (d, 6H, J = 6.4 Hz). |
| 720 | 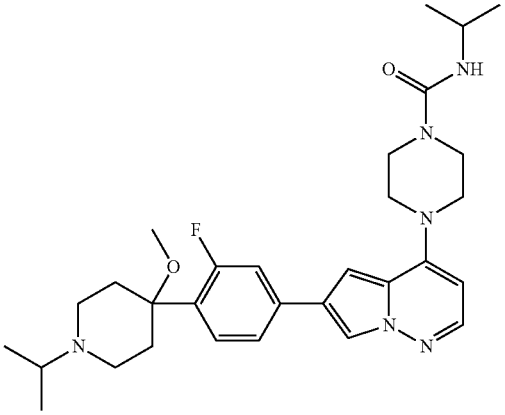 [SMILES: COC1(c2ccc(-c3cc4c(N5CCN(C(=O)NC(C)C)CC5)ccnn4c3)cc2F)CCN(C(C)C)CC1] | 537 | 1H-NMR (400 MHz, 6d-DMSO) δ ppm 8.25 (d, 1H, J = 1.6 Hz), 7.90 (d, 1H, J = 5.2 Hz), 7.68-7.62 (m, 2H), 7.37-7.32 (m, 1H), 7.10 (s, 1H), 6.32 (d, 1H, J = 7.6 Hz), 5.98 (d, 1H, J = 5.2 Hz), 3.80-3.77 (m, 1H), 3.60-3.57 (m, 4H), 3.52-3.51 (m, 4H), 2.96 (s, 3H), 2.67-2.57 (m, 3H), 2.49-2.45 (m, 2H), 2.13-2.09 (m, 2H), 2.01-1.97 (m, 2H), 1.07 (d, 6H, J = 6.4 Hz), 0.98 (d, 6H, J = 6.8 Hz). |
| 721 | 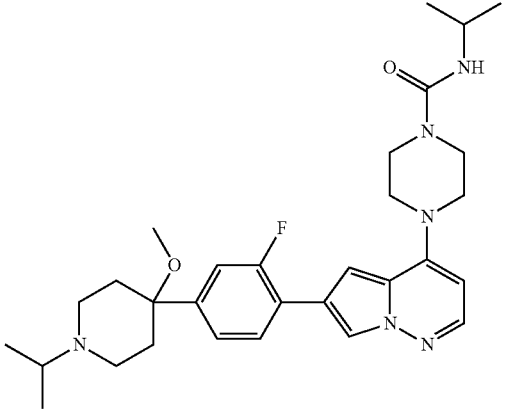 [SMILES: COC1(c2ccc(-c3cc4c(N5CCN(C(=O)NC(C)C)CC5)ccnn4c3)c(F)c2)CCN(C(C)C)CC1] | 537 | 1H-NMR (400 MHz, 6d-DMSO) δ ppm 8.26 (d, 1H, J = 1.6 Hz), 7.91 (d, 1H, J = 5.6 Hz), 7.68-7.62 (m, 2H), 7.36 (t, 1H, J = 8.4 Hz), 7.11 (d, 1H, J = 1.6 Hz), 6.33 (d, 1H, J = 7.6 Hz), 5.99 (d, 1H, J = 5.6 Hz), 3.82-3.76 (m, 1H), 3.54-3.50 (m, 4H), 3.44-3.40 (m, 4H), 2.96 (s, 3H), 2.70-2.67 (m, 1H), 2.60-2.56 (m, 2H), 2.48-2.46 (m, 2H), 2.14-2.10 (m, 2H), 2.00-1.92 (m, 2H), 1.09 (d, 6H, J = 6.8 Hz), 1.00 (d, 6H, J = 6.8 Hz). |

TABLE 1-continued

| # | Structure | LCMS (M + 1) | NMR |
|---|---|---|---|
| 722 | 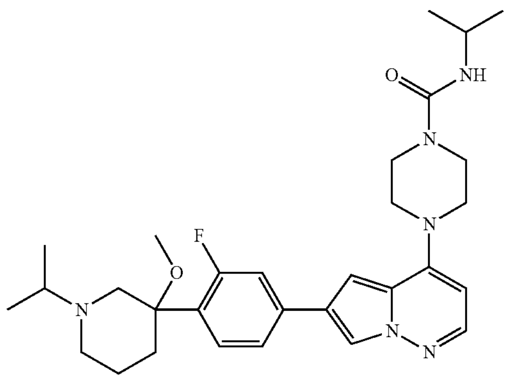 [SMILES: COC1(c2ccc(-c3cc4c(N5CCN(C(=O)NC(C)C)CC5)ccnn4c3)cc2F)CCCN(C(C)C)C1] | 537 | 1H-NMR (400 MHz, 6d-DMSO) δ ppm 8.26 (s, 1H), 7.91 (d, 1H, J = 5.2 Hz), 7.65-7.63 (m, 2H), 7.52 (t, 1H, J = 8.4 Hz), 7.12 (s, 1H), 6.33 (d, 1H, J = 7.2 Hz), 5.99 (d, 1H, J = 5.6 Hz), 3.81-3.76 (m, 1H), 3.56-3.52 (m, 4H), 3.46-3.44 (m, 4H), 2.99 (s, 3H), 2.80-2.70 (m, 3H), 2.52-2.49 (m, 2H), 2.08-2.07 (m, 1H), 1.76-1.70 (m, 2H), 1.38-1.36 (m, 1H), 1.09 (d, 6H, J = 6.8 Hz), 1.10-0.90 (m, 6H). |
| 723 | 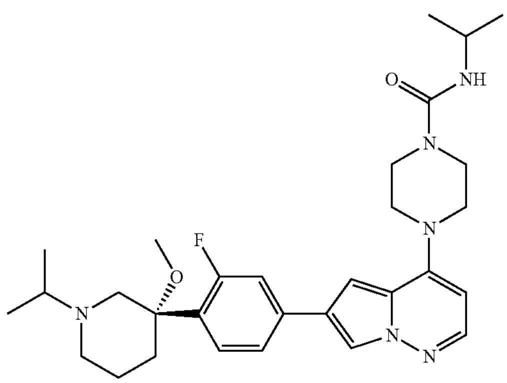 [SMILES: CO[C@]1(c2ccc(-c3cc4c(N5CCN(C(=O)NC(C)C)CC5)ccnn4c3)cc2F)CCCN(C(C)C)C1] | 537 | 1H-NMR (400 MHz, 6d-DMSO) δ ppm 8.26 (d, 1H, J = 1.6 Hz), 8.21 (s, 1H), 7.91 (d, 1H, J = 5.2 Hz), 7.68-7.65 (m, 2H), 7.64 (s, 1H), 7.54-7.50 (m, 1H), 7.11 (s, 1H), 6.33 (d, 1H, J = 7.2 Hz), 5.99 (d, 1H, J = 5.6 Hz), 3.81-3.76 (m, 1H), 3.56-3.52 (m, 4H), 3.46-3.44 (m, 4H), 3.02-2.97 (m, 1H), 2.99 (s, 3H), 2.90-2.80 (m, 1H), 2.79-2.70 (m, 1H), 2.61-2.55 (m, 1H), 2.08-2.07 (m, 1H), 1.89-1.79 (m, 1H), 1.79-1.70 (m, 1H), 1.38-1.36 (m, 1H), 1.09 (d, 6H, J = 6.8 Hz), 1.10-0.90 (m, 6H). |
| 724 | 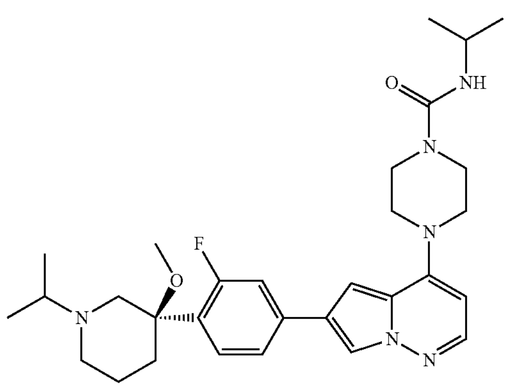 [SMILES: CO[C@@]1(c2ccc(-c3cc4c(N5CCN(C(=O)NC(C)C)CC5)ccnn4c3)cc2F)CCCN(C(C)C)C1] | 537 | 1H-NMR (400 MHz, 6d-DMSO) δ ppm 8.88-8.85 (m, 1H), 8.33 (d, 1H, J = 1.6 Hz), 7.93 (d, 1H, J = 5.6 Hz), 7.65-7.63 (m, 2H), 7.43 (t, 1H, J = 8.4 Hz), 7.15 (d, 1H, J = 1.2 Hz), 6.45-6.41 (m, 1H), 6.00 (d, 1H, J = 5.6 Hz), 3.81-3.80 (m, 1H), 3.78-3.77 (m, 1H), 3.56-3.52 (m, 4H), 3.46-3.44 (m, 4H), 3.30-3.27 (m, 2H), 3.25-3.06 (m, 2H), 3.06 (s, 3H), 2.50-2.49 (m, 1H), 2.39-2.36 (m, 1H), 2.13-2.12 (m, 1H), 1.98-1.91 (m, 1H), 1.29-1.26 (m, 6H), 1.09 (d, 6H, J = 6.4 Hz). |
| 725 | 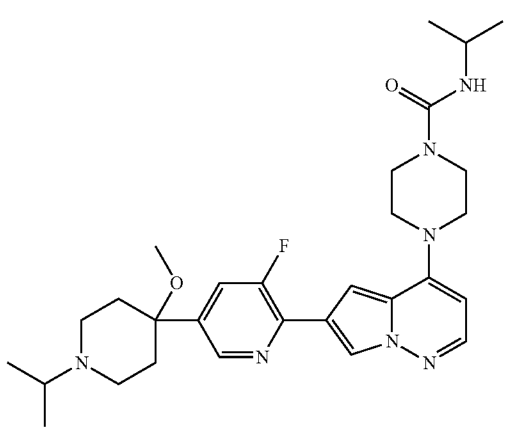 [SMILES: COC1(c2cnc(-c3cc4c(N5CCN(C(=O)NC(C)C)CC5)ccnn4c3)c(F)c2)CCN(C(C)C)CC1] | 538 | 1H-NMR (400 MHz, 6d-DMSO) δ ppm 8.46 (d, 1H, J = 4.8 Hz), 8.18 (s, 1H), 7.98 (d, 1H, J = 5.6 Hz), 7.29 (t, 1H, J = 5.6 Hz), 7.17 (s, 1H), 6.29 (d, 1H, J = 7.6 Hz), 6.03 (d, 1H, J = 5.6 Hz), 3.80-3.76 (m, 1H), 3.54-3.52 (m, 4H), 3.48-3.47 (m, 4H), 3.04 (s, 3H), 2.74-2.72 (m, 2H), 2.58-2.50 (m, 2H), 2.20-2.16 (m, 2H), 2.10-2.04 (m, 2H), 1.09 (d, 6H, J = 6.8 Hz), 1.05 (d, 6H, J = 6.0 Hz). |

TABLE 1-continued

| # | Structure | LCMS (M + 1) | NMR |
|---|---|---|---|
| 726 | 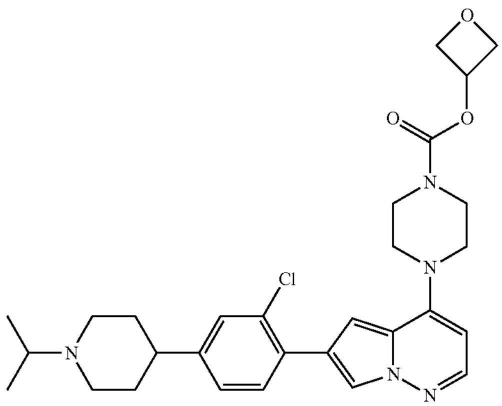 [SMILES: CC(C)N1CCC(c2ccc(-c3cc4c(N5CCN(C(=O)OC6COC6)CC5)ccnn4c3)c(Cl)c2)CC1] | 539 | 1H-NMR (500 MHz, 4d-MeOD) δ ppm 8.00 (d, 1H, J = 1.5 Hz), 7.90 (d, 1H, J = 5.5 Hz), 7.63 (d, 1H, J = 8.0 Hz), 7.41 (d, 1H, J = 1.0 Hz), 7.27 (dd, 1H, J = 8.0, 1.0 Hz), 6.86 (d, 1H, J = 1.0 Hz), 6.03 (d, 1H, J = 5.0 Hz), 5.43-5.41 (m, 1H), 4.92-4.90 (m, 2H), 4.68-4.66 (m, 2H), 3.80-3.75 (m, 2H), 3.75-3.70 (m, 2H), 3.56-3.52 (m, 4H), 3.37-3.32 (m, 2H), 3.25-3.18 (m, 1H), 2.84-2.76 (m, 3H), 2.09-2.05 (m, 2H), 1.96-1.88 (m, 2H), 1.30 (d, 6H, J = 6.5 Hz). |
| 727 | 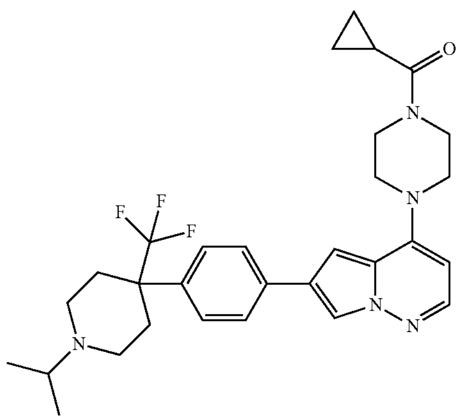 [SMILES: CC(C)N1CCC(c2ccc(-c3cc4c(N5CCN(C(=O)C6CC6)CC5)ccnn4c3)cc2)(C(F)(F)F)CC1] | 540 | 1H-NMR (400 MHz, 6d-DMSO) δ ppm 8.24 (d, 1H, J = 1.6 Hz), 7.92 (d, 1H, J = 5.6 Hz), 7.84 (d, 2H, J = 8.4 Hz), 7.53 (d, 2H, J = 8.4 Hz), 7.09 (d, 1H, J = 1.6 Hz), 6.00 (d, 1H, J = 5.6 Hz), 4.00-3.82 (m, 2H), 3.82-3.65 (m, 2H), 3.58-3.54 (m, 2H), 3.52-3.48 (m, 2H), 2.80-2.65 (m, 2H), 2.65-2.50 (m, 3H), 2.08-1.90 (m, 5H), 0.85 (d, 6H, J = 6.4 Hz), 0.84-.074 (m, 4H). |
| 728 | 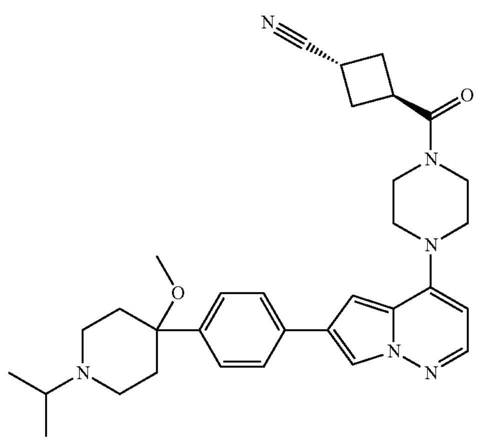 [SMILES: COC1(c2ccc(-c3cc4c(N5CCN(C(=O)[C@H]6C[C@H](C#N)C6)CC5)ccnn4c3)cc2)CCN(C(C)C)CC1] | 541 | 1H-NMR (400 MHz, 6d-DMSO) δ ppm 8.18 (d, 1H, J = 1.6 Hz), 7.90 (d, 1H, J = 5.6 Hz), 7.78 (d, 2H, J = 8.4 Hz), 7.39 (d, 2H, J = 8.4 Hz), 7.03 (d, 1H, J = 1.6 Hz), 5.97 (d, 1H, J = 5.6 Hz), 3.74-3.68 (m, 2H), 3.68-3.62 (m, 1H), 3.58-3.50 (m, 2H), 3.48-3.40 (m, 4H), 3.30-3.20 (m, 1H), 2.88 (s, 3H), 2.74-2.70 (m, 1H), 2.68-2.56 (m, 4H), 2.54-2.50 (m, 2H), 2.47-2.40 (m, 2H), 2.03-1.92 (m, 2H), 1.90-1.78 (m, 2H), 0.99 (d, 6H, J = 6.4 Hz). |

TABLE 1-continued
| # | Structure | LCMS (M + 1) | NMR |
|---|---|---|---|
| 729 | 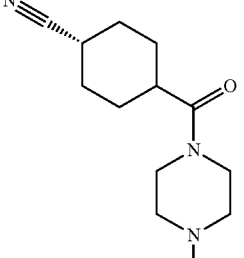 | 541 | 1H-NMR (400 MHz, 6d-DMSO) δ ppm 8.23 (s, 1H), 7.92 (d, 1H, J = 5.2 Hz), 7.85 (d, 2H, J = 7.2 Hz), 8.46 (d, 2H, J = 7.2 Hz), 7.07 (s, 1H), 5.99 (d, 1H, J = 5.2 Hz), 3.78-3.74 (m, 2H), 3.70-3.65 (m, 2H), 3.52-3.43 (m, 1H), 3.52-3.48 (m, 2H), 3.47-3.44 (m, 2H), 3.30-3.21 (m, 2H), 2.96 (s, 3H), 2.75-2.70 (m, 2H), 2.35-2.30 (m, 2H), 2.10-2.01 (m, 2H), 1.75-1.71 (m, 2H), 1.62-1.57 (m, 2H), 1.43-1.39 (m, 2H), 1.01-0.80 (m, 6H). |
| 730 | 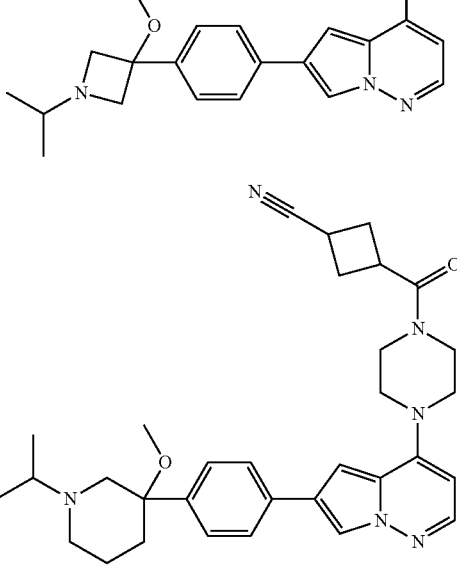 | 541 | 1H-NMR (500 MHz, 6d-DMSO) δ ppm 8.18 (d, 1H, J = 1.0 Hz), 7.90 (d, 1H, J = 5.5 Hz), 7.77 (d, 2H, J = 8.0 Hz), 7.48 (d, 2H, J = 8.0 Hz), 7.03 (d, 1H, J = 1.5 Hz), 5.98 (d, 1H, J = 5.5 Hz), 3.71-3.68 (m, 2H), 3.68-3.65 (m, 1H), 3.55-3.53 (m, 2H), 3.47-3.43 (m, 4H), 3.30-3.25 (m, 2H), 2.91 (s, 3H), 2.81-2.77 (m, 2H), 2.71-2.68 (m, 1H), 2.65-2.60 (m, 2H), 2.54-2.51 (m, 2H), 2.39-2.36 (m, 1H), 1.80-1.78 (m, 2H), 1.72-1.69 (m, 1H), 1.40-1.35 (m, 1H), 1.01 (t, 6H, J = 6.0 Hz ). |
| 731 | 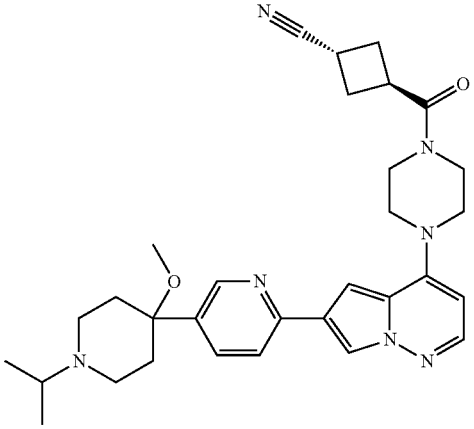 [SMILES: COC1(c2ccc(-c3cc4c(N5CCN(C(=O)[C@H]6C[C@H](C#N)C6)CC5)ccnn4c3)nc2)CCN(C(C)C)CC1] | 542 | 1H-NMR (500 MHz, 6d-DMSO) δ ppm 8.58 (d, 1H, J = 2.5 Hz), 8.29 (d, 1H, J = 1.5 Hz), 7.94-7.91 (m, 2H), 7.77 (dd, 1H, J = 8.5, 2.0 Hz), 7.19 (d, 1H, J = 1.5 Hz), 5.98 (d, 1H, J = 5.0H), 3.71-3.66 (m, 2H), 3.65-3.63 (m, 1H), 3.56-3.55 (m, 2H), 3.48-3.46 (m, 4H), 3.30-3.25 (m, 1H), 2.92 (s, 3H), 2.72-2.69 (m, 1H), 2.63-2.60 (m, 4H), 2.52-2.47 (m, 4H), 2.02-2.00 (m, 2H), 1.92-1.86 (m, 2H), 1.00 (d, 6H, J = 6.5 Hz). |
| 732 | 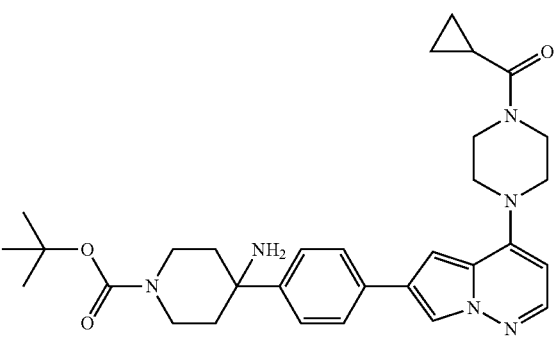 [SMILES: CC(C)(C)OC(=O)N1CCC(N)(c2ccc(-c3cc4c(N5CCN(C(=O)C6CC6)CC5)ccnn4c3)cc2)CC1] | 545 | |

TABLE 1-continued

| # | Structure | LCMS (M + 1) | NMR |
|---|---|---|---|
| 733 | 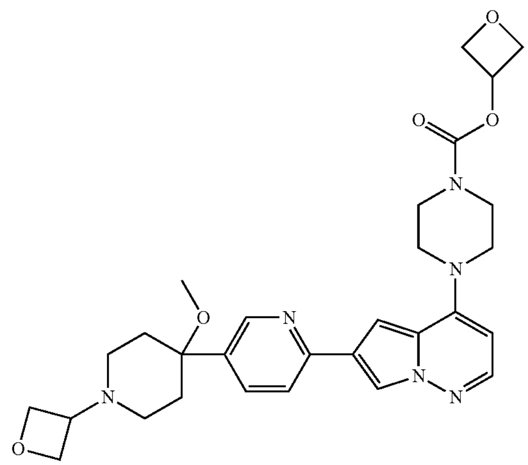 [SMILES: COC1(c2ccc(-c3cc4c(N5CCN(C(=O)OC6COC6)CC5)ccnn4c3)nc2)CCN(C2COC2)CC1] | 549 | 1H-NMR (500 MHz, 6d-DMSO) δ ppm 8.59 (d, 1H, J = 2.0 Hz), 8.29 (d, 1H, J = 1.5 Hz), 7.95-7.93 (m, 2H), 7.79 (dd, 1H, J = 8.5, 2.5 Hz), 7.19 (d, 1H, J = 1.5 Hz), 6.01 (d, 1H, J = 5.5 Hz), 5.34 (quintet, 1H, J = 6.0 Hz), 4.79 (t, 2H, J = 7.0 Hz), 4.56-4.52 (m, 4H), 4.45 (t, 2H, J = 6.0 Hz), 3.72-3.68 (m, 2H), 3.63-3.59 (m, 2H), 3.52-3.50 (m, 4H), 3.45-3.43 (m, 1H), 2.92 (s, 3H), 2.54-2.52 (m, 2H), 2.19-2.15 (m, 2H), 2.04-1.98 (m, 2H), 1.95-1.91 (m, 2H). |
| 734 | 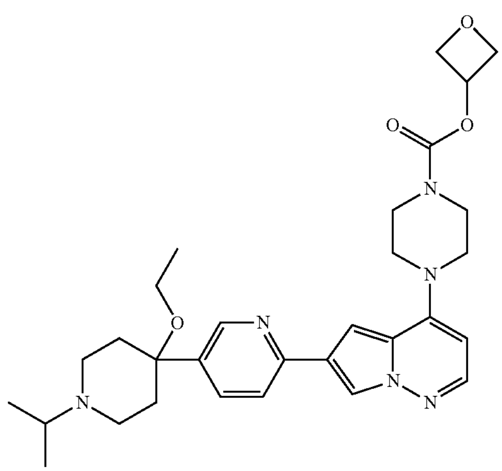 [SMILES: CCOC1(c2ccc(-c3cc4c(N5CCN(C(=O)OC6COC6)CC5)ccnn4c3)nc2)CCN(C(C)C)CC1] | 549 | 1H-NMR (500 MHz, 6d-DMSO) δ ppm 8.59 (d, 1H, J = 2.5 Hz), 8.29 (d, 1H, J = 2.0 Hz), 7.95-7.92 (m, 2H), 7.79 (dd, 1H, J = 8.5, 2.0 Hz), 7.19 (d, 1H, J = 2.0 Hz), 6.01 (d, 1H, J = 5.5 Hz), 5.35 (quintet, 1H, J = 5.5 Hz), 4.80 (t, 2H, J = 6.5 Hz), 4.54 (dd, 2H, J = 7.5, 5.5 Hz), 3.71-3.70 (m, 2H), 3.67-3.60 (m, 2H), 3.52-3.51 (m, 4H), 3.33-3.30 (m, 1H), 3.09 (q, 2H, J = 6.5 Hz), 2.70-2.55 (m, 2H), 2.55-2.50 (m, 2H), 2.02-1.98 (m, 2H), 1.09 (t, 3H, J = 6.5 Hz), 1.01 (d, 6H, J = 6.5 Hz). |
| 735 | 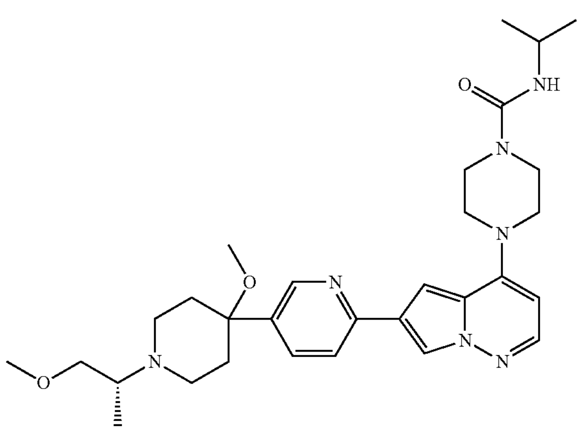 [SMILES: COC[C@@H](C)N1CCC(OC)(c2ccc(-c3cc4c(N5CCN(C(=O)NC(C)C)CC5)ccnn4c3)nc2)CC1] | 550 | 1H-NMR (400 MHz, 6d-DMSO) δ ppm 8.57 (d, 1H, J = 1.6 Hz), 8.27 (d, 1H, J = 1.2 Hz), 7.96-7.88 (m, 2H), 7.78 (dd, 1H, J = 8.0, 2.0 Hz), 7.17 (d, 1H, J = 1.6 Hz), 6.30 (d, 1H, J = 7.6 Hz), 5.99 (d, 1H, J = 5.6 Hz), 3.80-3.70 (m, 1H), 3.60-3.50 (m, 4H), 3.48-3.42 (m, 4H), 3.44-3.41 (m, 1H), 3.26-3.20 (m, 1H), 3.25 (s, 3H), 2.91 (s, 3H), 2.80-2.70 (m, 1H), 2.67-2.55 (m, 4H), 2.05-1.95 (m, 2H), 1.92-1.80 (m, 2H), 1.08 (d, 6H, J = 6.8 Hz), 0.98 (d, 3H, J = 7.2 Hz). |

TABLE 1-continued
| # | Structure | LCMS (M + 1) | NMR |
|---|---|---|---|
| 736 | 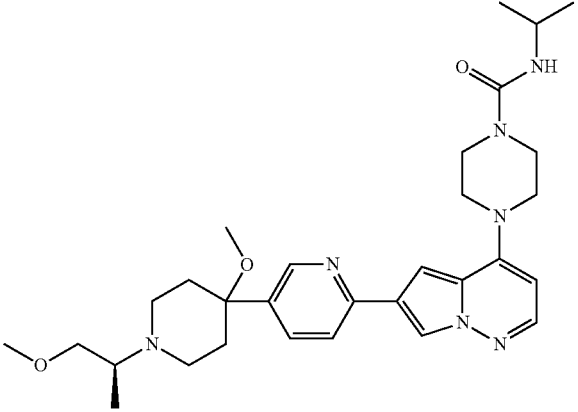 [SMILES: COC[C@H](C)N1CCC(OC)(c2ccc(-c3cc4c(N5CCN(C(=O)NC(C)C)CC5)ccnn4c3)nc2)CC1] | 550 | 1H-NMR (400 MHz, 6d-DMSO) δ ppm 8.58 (d, 1H, J = 2.0 Hz), 8.29 (d, 1H, J = 1.6 Hz), 8.00-7.90 (m, 2H), 7.77 (dd, 1H, J = 8.0, 2.0 Hz), 7.18 (d, 1H, J = 1.6 Hz), 6.32 (d, 1H, J = 7.6 Hz), 6.00 (d, 1H, J = 5.2 Hz), 3.90-3.70 (m, 1H), 3.60-3.50 (m, 4H), 3.47-3.42 (m, 4H), 3.43-3.40 (m, 1H), 3.30-3.20 (m, 1H), 3.25 (s, 3H), 2.92 (s, 3H), 2.80-2.72 (m, 1H), 2.70-2.58 (m, 4H), 2.40-1.96 (m, 2H), 1.94-1.80 (m, 2H), 1.09 (d, 6H, J = 6.8 Hz), 0.99 (d, 3H, J = 6.8 Hz). |
| 737 | 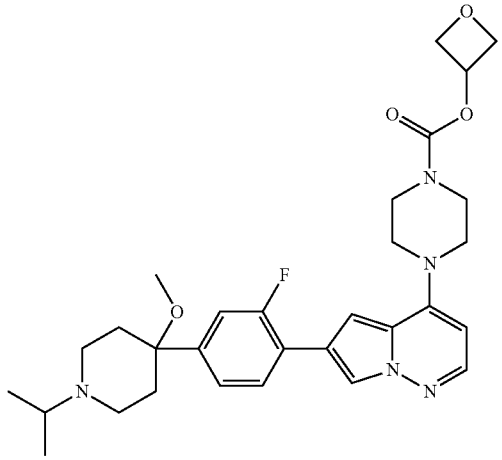 [SMILES: COC1(c2ccc(-c3cc4c(N5CCN(C(=O)OC6COC6)CC5)ccnn4c3)c(F)c2)CCN(C(C)C)CC1] | 552 | 1H NMR (400 MHz, DMSO-d6) δ 8.04 (t, J = 2.2 Hz, 1H), 7.97-7.81 (m, 2H), 7.26-7.16 (m, 2H), 7.01 (d, J = 1.8 Hz, 1H), 5.98 (d, J = 5.5 Hz, 1H), 5.33-5.23 (m, 1H), 4.74 (t, J = 6.9 Hz, 2H), 4.48 (dd, J = 7.6, 5.1 Hz, 2H), 3.65 (br.s, 2H), 3.55 (br.s, 2H), 3.45 (dd, J = 6.7, 3.7 Hz, 4H), 3.29 (s, 5H), 2.87 (s, 3H), 2.72-2.50 (m, 3H), 1.93 (d, J = 13.0 Hz, 2H), 1.82 (d, J = 13.1 Hz, 2H), 0.95 (d, J = 6.5 Hz, 6H). |
| 738 | 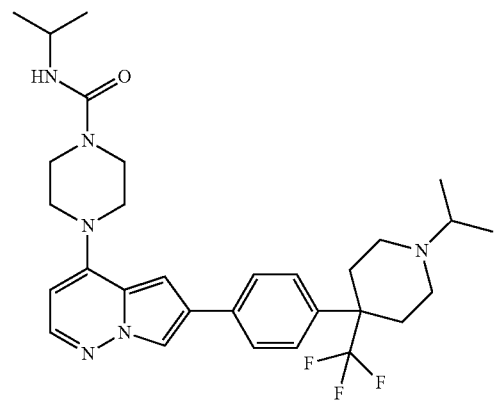 [SMILES: CC(C)NC(=O)N1CCN(c2ccnn3cc(-c4ccc(C5(C(F)(F)F)CCN(C(C)C)CC5)cc4)cc23)CC1] | 557 | 1H-NMR (400 MHz, 6d-DMSO) δ ppm 8.22 (d, 1H, J = 1.6 Hz), 7.91 (d, 1H, J = 5.6 Hz), 7.84 (d, 2H, J = 8.4 Hz), 7.53 (d, 2H, J = 8.4 Hz), 7.06 (d, 1H, J = 1.6 Hz), 6.32 (d, 1H, J = 7.6 Hz), 6.00 (d, 1H, J = 5.2 Hz), 3.85-3.75 (m, 1H), 3.55-3.50 (m, 4H), 3.47-3.42 (m, 4H), 2.80-2.65 (m, 2H), 2.65-2.50 (m, 3H), 2.08-1.90 (m, 4H), 1.08 (d, 6H, J = 6.4 Hz), 0.85 (d, 6H, J = 6.4 Hz). |

TABLE 1-continued

| # | Structure | LCMS (M + 1) | NMR |
|---|---|---|---|
| 739 | 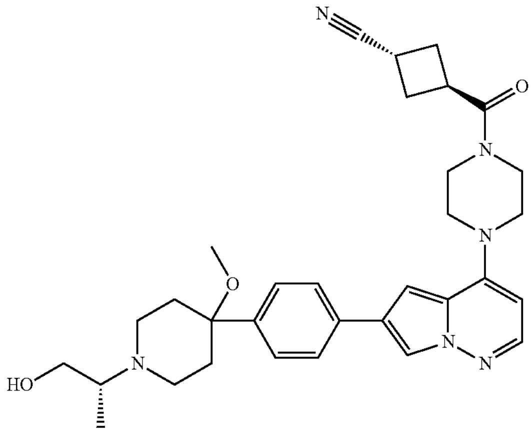 [SMILES: COC1(c2ccc(-c3cc4c(N5CCN(C(=O)[C@H]6C[C@H](C#N)C6)CC5)ccnn4c3)cc2)CCN([C@H](C)CO)CC1] | 557 | 1H-NMR (400 MHz, 6d-DMSO) δ ppm 8.18 (d, 1H, J = 1.2 Hz), 7.91 (d, 1H, J = 5.2 Hz), 7.79 (d, 2H, J = 8.4 Hz), 7.39 (d, 2H, J = 8.4 Hz), 7.04 (s, 1H), 5.97 (d, 1H, J = 5.6 Hz), 4.23-4.2.2 (m, 1H), 3.69-3.65 (m, 2H), 3.65-3.63 (m, 1H), 3.55-3.54 (m, 2H), 3.52-3.50 (m, 1H), 3.49-3.45 (m, 4H), 3.30-3.26 (m, 3H), 2.89 (s, 3H), 2.74-2.66 (m, 2H), 2.65-2.50 (m, 6H), 1.98-1.93 (m, 2H), 1.92-1.88 (m, 2H), 0.95 (d, 3H, J = 6.4 Hz). |
| 740 | 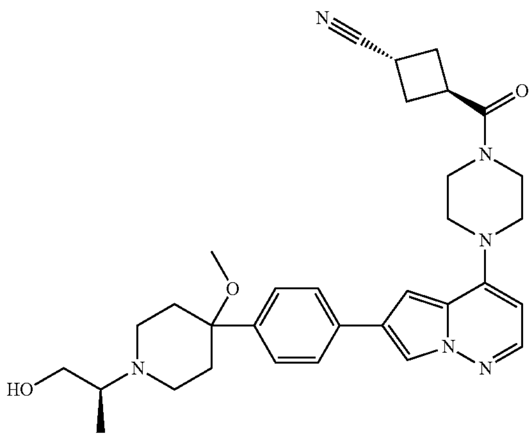 [SMILES: COC1(c2ccc(-c3cc4c(N5CCN(C(=O)[C@H]6C[C@H](C#N)C6)CC5)ccnn4c3)cc2)CCN([C@@H](C)CO)CC1] | 557 | 1H-NMR (500 MHz, 6d-DMSO) δ ppm 8.18 (d, 1H, J = 1.5 Hz), 7.91 (d, 1H, J = 5.5 Hz), 7.79 (d, 2H, J = 8.5 Hz), 7.39 (d, 2H, J = 8.5 Hz), 7.04 (d, 1H, J = 1.5 Hz), 5.97 (d, 1H, J = 5.5 Hz), 4.30-4.20 (m, 1H), 3.69-3.65 (m, 2H), 3.65-3.61 (m, 1H), 3.55-3.54 (m, 2H), 3.51-3.48 (m, 1H), 3.49-3.45 (m, 4H), 3.30-3.26 (m, 3H), 2.89 (s, 3H), 2.69-2.65 (m, 2H), 2.65-2.50 (m, 6H), 1.98-1.95 (m, 2H), 1.90-1.88 (m, 2H), 0.95 (d, 3H, J = 6.5 Hz). |
| 741 | 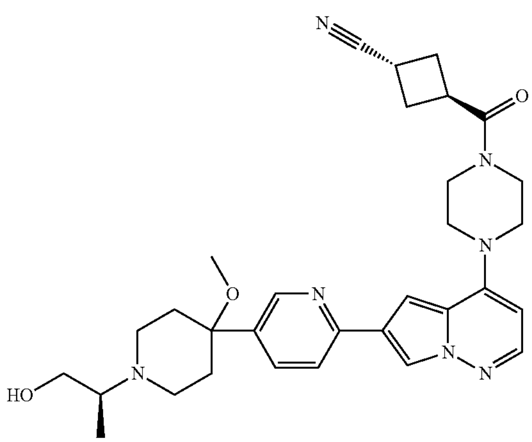 [SMILES: COC1(c2ccc(-c3cc4c(N5CCN(C(=O)[C@H]6C[C@H](C#N)C6)CC5)ccnn4c3)nc2)CCN([C@@H](C)CO)CC1] | 558 | 1H NMR (500 MHz, 6d-DMSO) δ ppm 8.58 (d, 1H, J = 2.5 Hz), 8.30 (d, 1H, J = 1.5 Hz), 7.95-7.91 (m, 2H), 7.80-7.78 (m, 1H), 7.19 (d, 1H, J = 1.5 Hz), 5.99 (d, 1H, J = 5.0 Hz), 4.23-4.21 (m, 1H), 3.74-3.69 (m, 2H), 3.70-3.65 (m, 1H), 3.56-3.55 (m, 2H), 3.49-3.47 (m, 5H), 3.31-3.29 (m, 3H), 2.93 (s, 3H), 2.65-2.64 (m, 1H), 2.64-2.60 (m, 6H), 2.51-2.50 (m, 1H), 2.05-2.01 (m, 2H), 1.99-1.98 (m, 2H), 0.96-0.95 (d, 3H, J = 6.5 Hz). |

TABLE 1-continued

| # | Structure | LCMS (M + 1) | NMR |
|---|---|---|---|
| 742 | 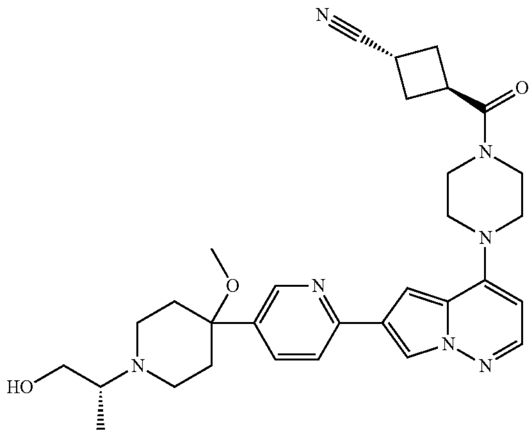 [SMILES: COC1(c2ccc(-c3cc4c(N5CCN(C(=O)[C@H]6C[C@H](C#N)C6)CC5)ccnn4c3)nc2)CCN([C@H](C)CO)CC1] | 558 | 1H NMR (500 MHz, 6d-DMSO) δ ppm 8.59 (d, 1H, J = 2.0 Hz), 8.30 (d, 1H, J = 2.0 Hz), 7.96-7.93 (m, 2H), 7.79 (dd, 1H, J = 8.0, 2.0 Hz), 7.19 (d, 1H, J = 1.5 Hz), 5.99 (d, 1H, J = 5.5 Hz), 3.73-3.68 (m, 2H), 3.69-3.65 (m, 1H), 3.67-3.56 (m, 2H), 3.55-3.49 (m, 4H), 3.31-3.28 (m, 4H), 2.94 (s, 3H), 2.95-2.85 (m, 2H), 2.66-2.65 (m, 2H), 2.56-2.53 (m, 2H), 2.49-2.48 (m, 2H), 2.18-1.99 (m, 4H), 1.04-1.03 (m, 3H). |
| 743 | 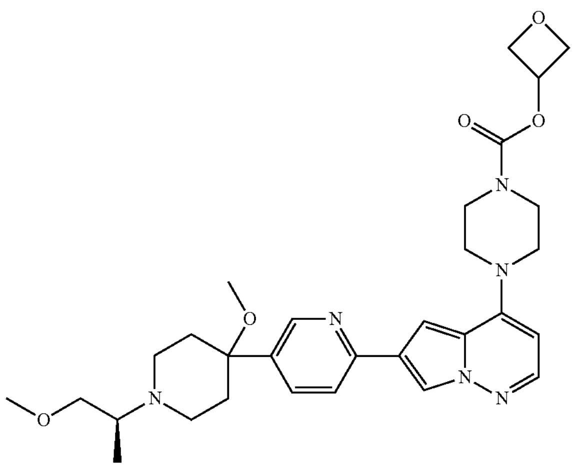 [SMILES: COC[C@H](C)N1CCC(OC)(c2ccc(-c3cc4c(N5CCN(C(=O)OC6COC6)CC5)ccnn4c3)nc2)CC1] | 565 | 1H-NMR (400 MHz, 6d-DMSO) δ ppm 8.57 (d, 1H, J = 2.0 Hz), 8.29 (d, 1H, J = 1.6 Hz), 7.95-7.90 (m, 2H), 7.77 (dd, 1H, J = 8.0 Hz, 2.0 Hz), 7.18 (d, 1H, J = 1.6 Hz), 6.01 (d, 1H, J = 5.2 Hz), 5.39-5.28 (m, 1H), 4.79 (t, 2H, J = 7.2 Hz), 4.53 (dd, 2H, J = 7.2, 5.2 Hz), 3.80-3.75 (m, 2H), 3.72-3.67 (m, 2H), 3.63-3.58 (m, 4H), 3.53-3.49 (m, 1H), 3.32-3.20 (m, 1H), 3.26 (s, 3H), 2.91 (s, 3H), 2.80-3.75 (m, 1H), 2.70-2.56 (m, 4H), 2.05-1.98 (m, 2H), 1.95-1.79 (m, 2H), 0.98 (d, 3H, J = 6.8 Hz). |
| 744 | 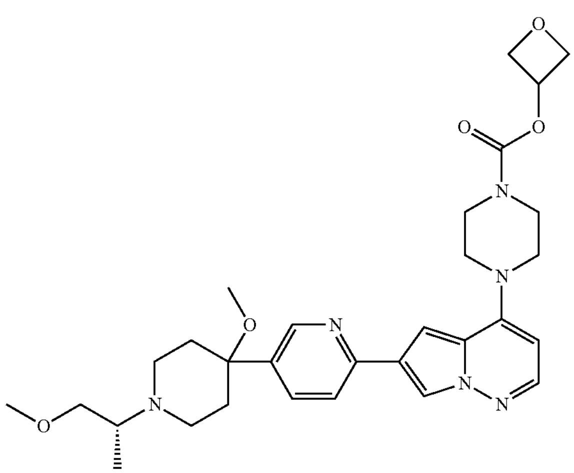 [SMILES: COC[C@@H](C)N1CCC(OC)(c2ccc(-c3cc4c(N5CCN(C(=O)OC6COC6)CC5)ccnn4c3)nc2)CC1] | 565 | 1H-NMR (400 MHz, 6d-DMSO) δ ppm 8.57 (d, 1H, J = 2.0 Hz), 8.29 (d, 1H, J = 1.6 Hz), 7.95-7.90 (m, 2H), 7.77 (dd, 1H, J = 8.0 Hz, 2.0 Hz), 7.18 (d, 1H, J = 1.6 Hz), 6.01 (d, 1H, J = 5.2 Hz), 5.39-5.28 (m, 1H), 4.79 (t, 2H, J = 7.2 Hz), 4.53 (dd, 2H, J = 7.2, 5.2 Hz), 3.80-3.75 (m, 2H), 3.72-3.67 (m, 2H), 3.63-3.58 (m, 4H), 3.53-3.49 (m, 1H), 3.32-3.20 (m, 1H), 3.26 (s, 3H), 2.91 (s, 3H), 2.80-3.75 (m, 1H), 2.70-2.56 (m, 4H), 2.05-1.98 (m, 2H), 1.95-1.79 (m, 2H), 0.98 (d, 3H, J = 6.8 Hz). |

TABLE 1-continued

| # | Structure | LCMS (M + 1) | NMR |
|---|---|---|---|
| 745 | 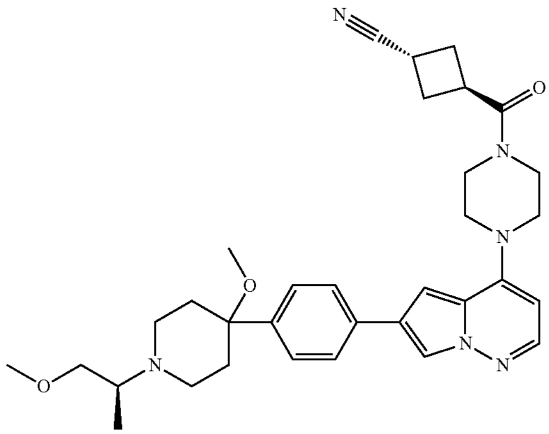 [SMILES: COC[C@H](C)N1CCC(OC)(c2ccc(-c3cc4c(N5CCN(C(=O)[C@H]6C[C@H](C#N)C6)CC5)ccnn4c3)cc2)CC1] | 571 | 1H-NMR (500 MHz, 6d-DMSO) δ ppm 8.18 (d, 1H, J = 1.5 Hz), 7.90 (d, 1H, J = 5.5 Hz), 7.78 (d, 2H, J = 8.5 Hz), 7.38 (d, 2H, J = 8.5 Hz), 7.03 (d, 1H, J = 1.0 Hz), 5.96 (d, 1H, J = 5.5 Hz), 3.70-3.65 (m, 2H), 3.65-3.58 (m, 1H), 3.55-3.51 (m, 2H), 3.46-3.41 (m, 6H), 3.30-3.22 (m, 2H), 3.24 (s, 3H), 2.87 (s, 3H), 2.77-2.73 (m, 1H), 2.65-2.58 (m, 6H), 2.50-2.47 (m, 1H), 1.97-1.94 (m, 2H), 1.86-1.82 (m, 2H), 1.00 (d, 3H, J = 6.0 Hz). |
| 746 | 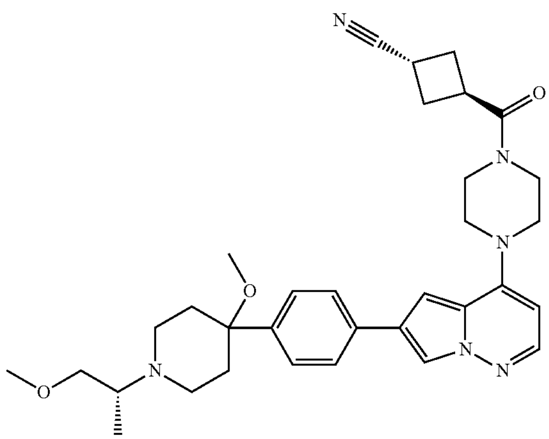 [SMILES: COC[C@@H](C)N1CCC(OC)(c2ccc(-c3cc4c(N5CCN(C(=O)[C@H]6C[C@H](C#N)C6)CC5)ccnn4c3)cc2)CC1] | 571 | 1H-NMR (500 MHz, 6d-DMSO) δ ppm 8.18 (d, 1H, J = 1.5 Hz), 7.90 (d, 1H, J = 5.5 Hz), 7.78 (d, 2H, J = 8.5 Hz), 7.38 (d, 2H, J = 8.5 Hz), 7.03 (d, 1H, J = 1.0 Hz), 5.96 (d, 1H, J = 5.5 Hz), 3.70-3.65 (m, 2H), 3.65-3.58 (m, 1H), 3.55-3.51 (m, 2H), 3.46-3.41 (m, 6H), 3.30-3.22 (m, 2H), 3.24 (s, 3H), 2.87 (s, 3H), 2.77-2.73 (m, 1H), 2.65-2.58 (m, 6H), 2.50-2.47 (m, 1H), 1.97-1.94 (m, 2H), 1.86-1.82 (m, 2H), 1.00 (d, 3H, J = 6.0 Hz). |
| 747 | 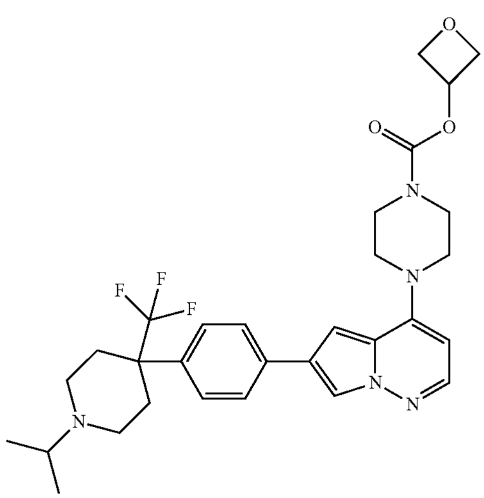 [SMILES: CC(C)N1CCC(c2ccc(-c3cc4c(N5CCN(C(=O)OC6COC6)CC5)ccnn4c3)cc2)(C(F)(F)F)CC1] | 572 | 1H-NMR (400 MHz, 6d-DMSO) δ ppm 8.24 (d, 1H, J = 1.6 Hz), 7.93 (d, 1H, J = 5.6 Hz), 7.84 (d, 2H, J = 8.4 Hz), 7.53 (d, 2H, J = 8.4 Hz), 7.06 (d, 1H, J = 2.0 Hz), 6.01 (d, 1H, J = 5.6 Hz), 5.34 (quintet, 1H, J = 5.6 Hz), 4.79 (t, 2H, J = 7.2 Hz), 4.53 (dd, 2H, J = 8.0, 5.6 Hz), 3.80-3.75 (m, 2H), 3.70-3.65 (m, 2H), 3.55-3.45 (m, 4H), 2.78-2.70 (m, 2H), 2.65-2.50 (m, 3H), 2.08-1.80 (m, 4H), 0.85 (d, 6H, J = 6.4 Hz). |

TABLE 1-continued

| # | Structure | LCMS (M + 1) | NMR |
|---|---|---|---|
| 748 | 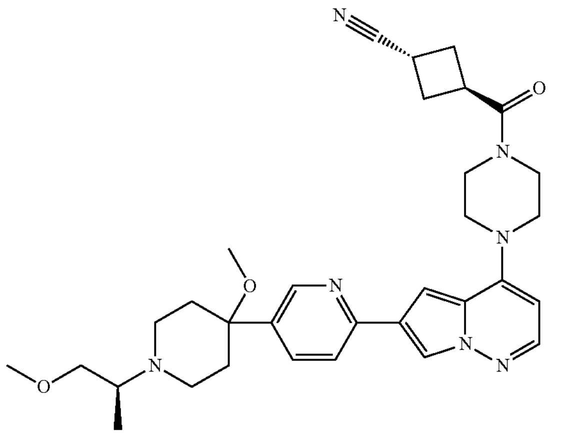 [SMILES: COC[C@H](C)N1CCC(OC)(c2ccc(-c3cc4c(N5CCN(C(=O)[C@H]6C[C@H](C#N)C6)CC5)ccnn4c3)nc2)CC1] | 572 | 1H-NMR (400 MHz, 6d-DMSO) δ ppm 8.57 (d, 1H, J = 2.0 Hz), 8.29 (d, 1H, J = 2.0 Hz), 7.95-7.90 (m, 2H), 7.77 (dd, 1H, J = 8.0, 2.0 Hz), 7.18 (d, 1H, J = 1.2 Hz), 5.99 (d, 1H, J = 5.6 Hz), 3.73-3.67 (m, 2H), 3.58-3.53 (m, 2H), 3.49-3.40 (m, 4H), 3.40-3.35 (m, 2H), 3.32-3.20 (m, 4H), 3.25 (s, 3H), 2.92 (s, 3H), 2.81-2.75 (m, 2H), 2.60-2.52 (m, 4H), 2.50-2.47 (m, 1H), 2.03-1.95 (m, 2H), 1.90-1.84 (m, 2H), 0.99 (d, 3H, J = 6.8 Hz). |
| 749 | 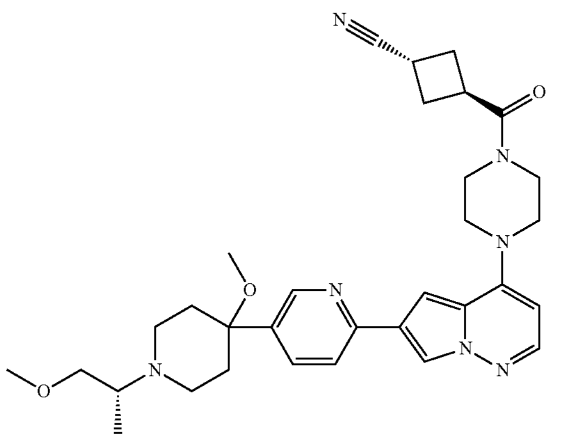 [SMILES: COC[C@@H](C)N1CCC(OC)(c2ccc(-c3cc4c(N5CCN(C(=O)[C@H]6C[C@H](C#N)C6)CC5)ccnn4c3)nc2)CC1] | 572 | 1H-NMR (400 MHz, 6d-DMSO) δ ppm 8.57 (d, 1H, J = 2.0 Hz), 8.29 (d, 1H, J = 2.0 Hz), 7.95-7.90 (m, 2H), 7.77 (dd, 1H, J = 8.0, 2.0 Hz), 7.18 (d, 1H, J = 1.2 Hz), 5.99 (d, 1H, J = 5.6 Hz), 3.73-3.67 (m, 2H), 3.58-3.53 (m, 2H), 3.49-3.40 (m, 4H), 3.40-3.35 (m, 2H), 3.32-3.20 (m, 4H), 3.25 (s, 3H), 2.92 (s, 3H), 2.81-2.75 (m, 2H), 2.60-2.52 (m, 4H), 2.50-2.47 (m, 1H), 2.03-1.95 (m, 2H), 1.90-1.84 (m, 2H), 0.99 (d, 3H, J = 6.8 Hz). |
| 750 | 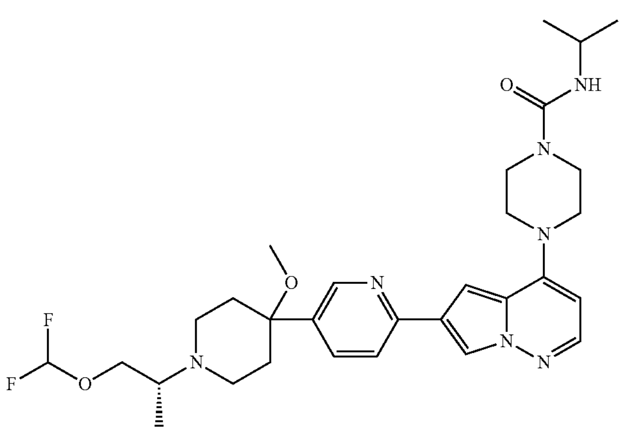 [SMILES: COC1(c2ccc(-c3cc4c(N5CCN(C(=O)NC(C)C)CC5)ccnn4c3)nc2)CCN([C@H](C)COC(F)F)CC1] | 586 | 1H-NMR (500 MHz, 6d-DMSO) δ ppm 8.58 (d, 1H, J = 2.5 Hz), 8.28 (d, 1H, J = 1.0 Hz), 7.93-7.92 (m, 2H), 7.78 (dd, 1H, J = 7.0, 2.0 Hz), 7.18 (s, 1H), 6.69 (d, 1H, J = 76.0 Hz), 6.31 (d, 1H, J = 7.5 Hz), 6.00 (d, 1H, J = 5.0 Hz), 3.94-3.89 (m, 1H), 3.84-3.75 (m, 1H), 3.55-3.52 (m, 4H), 3.48-3.45 (m, 4H), 2.93 (s, 3H), 2.87-2.81 (m, 1H), 2.70-2.61 (m, 4H), 2.06-2.00 (m, 2H), 1.95-1.86 (m, 2H), 1.09 (d, 6H, J = 6.5 Hz), 1.02 (d, 3H, J = 6.5 Hz). |

TABLE 1-continued

| # | Structure | LCMS (M + 1) | NMR |
|---|---|---|---|
| 751 | 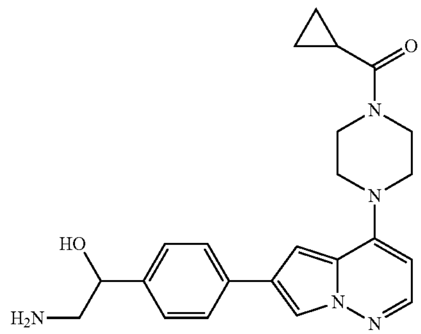 [SMILES: NCC(O)c1ccc(-c2cc3c(N4CCN(C(=O)C5CC5)CC4)ccnn3c2)cc1] | 407 | 1H NMR (400 MHz, Methanol-d4) δ 8.54 (s, 1H), 7.98 (d, J = 1.8 Hz, 1H), 7.85 (d, J = 5.5 Hz, 1H), 7.81-7.70 (m, 2H), 7.55-7.38 (m, 2H), 6.94 (d, J = 1.8 Hz, 1H), 6.00 (d, J = 5.5 Hz, 1H), 4.86 (d, J = 3.6 Hz, 1H), 4.03 (s, 2H), 3.85 (s, 2H), 3.62 (s, 2H), 3.59-3.47 (m, 3H), 3.16-3.07 (m, 1H), 3.00 (dd, J = 12.8, 9.3 Hz, 1H), 2.09-1.96 (m, 1H), 0.92 (dt, J = 4.8, 2.8 Hz, 2H), 0.86 (ddt, J = 7.5, 4.6, 2.5 Hz, 2H). |
| 752 | 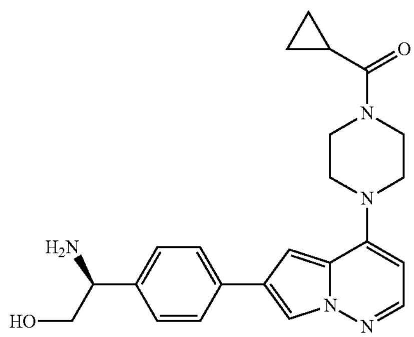 [SMILES: N[C@H](CO)c1ccc(-c2cc3c(N4CCN(C(=O)C5CC5)CC4)ccnn3c2)cc1] | 407 | 1H NMR (400 MHz, Methanol-d4) δ 7.95 (d, J = 1.8 Hz, 1H), 7.83 (d, J = 5.4 Hz, 1H), 7.79-7.66 (m, 2H), 7.44-7.35 (m, 2H), 6.92 (d, J = 1.8 Hz, 1H), 5.99 (d, J = 5.5 Hz, 1H), 5.48 (s, 1H), 4.02 (s, 2H), 3.97 (dd, J = 8.0, 4.7 Hz, 1H), 3.84 (s, 2H), 3.71 (dd, J = 10.9, 4.7 Hz, 1H), 3.63 (s, 2H), 3.60-3.55 (m, 1H), 3.54 (d, J = 8.0 Hz, 2H), 2.01 (tt, J = 8.0, 4.7 Hz, 1H), 0.92 (dt, J = 4.8, 2.8 Hz, 2H), 0.85 (ddt, J = 7.4, 4.6, 2.5 Hz, 2H). |
| 753 | 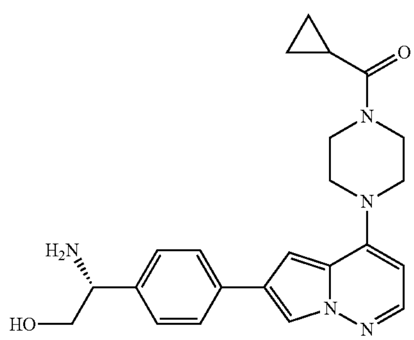 [SMILES: N[C@@H](CO)c1ccc(-c2cc3c(N4CCN(C(=O)C5CC5)CC4)ccnn3c2)cc1] | 407 | 1H NMR (400 MHz, Methanol-d4) δ 7.96 (d, J = 1.8 Hz, 1H), 7.84 (d, J = 5.5 Hz, 1H), 7.77-7.63 (m, 2H), 7.48-7.35 (m, 2H), 6.92 (d, J = 1.8 Hz, 1H), 5.99 (d, J = 5.5 Hz, 1H), 4.03 (s, 2H), 3.98 (dd, J = 8.0, 4.7 Hz, 1H), 3.85 (s, 2H), 3.72 (dd, J = 10.9, 4.8 Hz, 1H), 3.63 (s, 2H), 3.58 (dd, J = 10.8, 8.0 Hz, 1H), 3.54 (s, 2H), 2.02 (tt, J = 7.9, 4.7 Hz, 1H), 0.92 (dt, J = 4.8, 2.8 Hz, 2H), 0.86 (ddt, J = 7.5, 4.6, 2.5 Hz, 2H). |
| 754 | 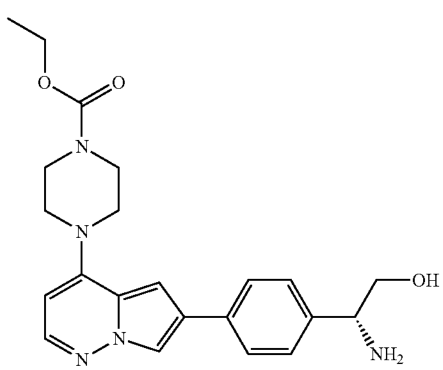 [SMILES: CCOC(=O)N1CCN(c2ccnn3cc(-c4ccc([C@@H](N)CO)cc4)cc23)CC1] | 411 | 1H NMR (400 MHz, Methanol-d4) δ 8.05 (d, J = 1.8 Hz, 1H), 7.89 (d, J = 5.4 Hz, 1H), 7.84-7.69 (m, 2H), 7.51-7.33 (m, 2H), 6.96 (d, J = 1.8 Hz, 1H), 6.04 (d, J = 5.4 Hz, 1H), 4.19 (q, J = 7.1 Hz, 2H), 4.02 (dd, J = 7.9, 4.7 Hz, 1H), 3.80-3.68 (m, 5H), 3.63-3.48 (m, 5H), 2.63 (p, J = 1.9 Hz, 3H), 1.31 (t, J = 7.1 Hz, 3H). |

| # | Structure | LCMS (M + 1) | NMR |
|---|---|---|---|
| 755 | 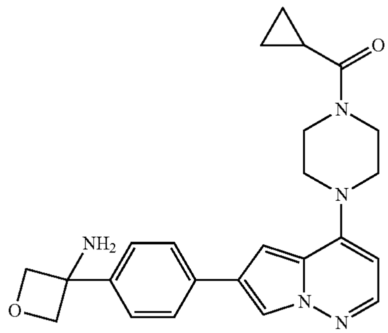 [SMILES: NC1(c2ccc(-c3cc4c(N5CCN(C(=O)C6CC6)CC5)ccnn4c3)cc2)COC1] | 419 | 1H NMR (400 MHz, DMSO-d6) δ 8.18 (d, J = 1.8 Hz, 1H), 7.89 (d, J = 5.4 Hz, 1H), 7.86-7.77 (m, 2H), 7.63-7.53 (m, 2H), 7.05 (d, J = 1.8 Hz, 1H), 5.96 (d, J = 5.5 Hz, 1H), 4.72 (d, J = 6.1 Hz, 2H), 4.65 (d, J = 6.0 Hz, 2H), 3.91 (s, 2H), 3.70 (s, 2H), 3.51 (d, J = 27.0 Hz, 5H), 2.01 (tt, J = 7.7, 4.9 Hz, 1H), 0.81-0.65 (m, 4H). |
| 756 | 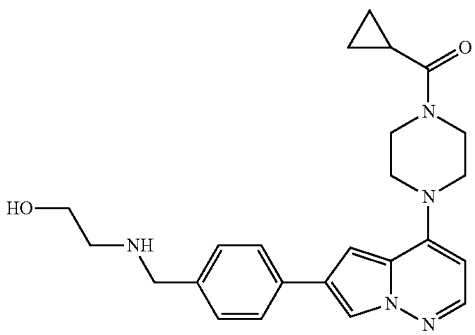 [SMILES: O=C(C1CC1)N1CCN(c2ccnn3cc(-c4ccc(CNCCO)cc4)cc23)CC1] | 421 | 1H NMR (400 MHz, Methanol-d4) δ 7.97 (d, J = 1.8 Hz, 1H), 7.84 (d, J = 5.4 Hz, 1H), 7.74-7.66 (m, 2H), 7.42-7.35 (m, 2H), 7.36-7.21 (m, 1H), 6.93 (d, J = 1.8 Hz, 1H), 5.99 (d, J = 5.5 Hz, 1H), 4.04 (d, J = 9.6 Hz, 2H), 3.91-3.85 (m, 0H), 3.83-3.72 (m, 7H), 3.69-3.61 (m, 6H), 3.55 (d, J = 6.9 Hz, 2H), 2.77 (t, J = 5.6 Hz, 2H), 2.72 (dt, J = 11.3, 5.6 Hz, 5H), 2.02 (tt, J = 7.8, 4.7 Hz, 1H), 0.92 (dt, J = 4.8, 2.8 Hz, 2H), 0.86 (ddt, J = 7.5, 4.6, 2.6 Hz, 2H). |
| 757 | 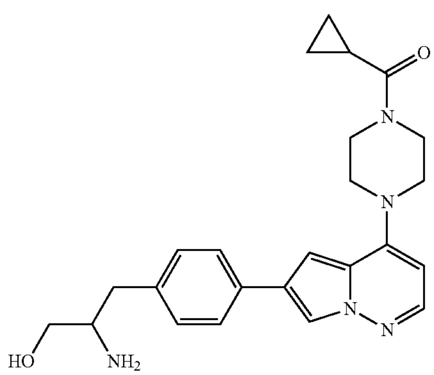 [SMILES: NC(CO)Cc1ccc(-c2cc3c(N4CCN(C(=O)C5CC5)CC4)ccnn3c2)cc1] | 421 | |
| 758 | 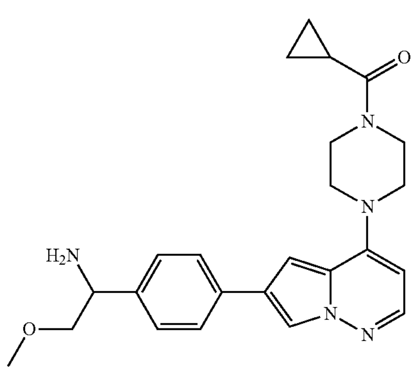 [SMILES: COCC(N)c1ccc(-c2cc3c(N4CCN(C(=O)C5CC5)CC4)ccnn3c2)cc1] | 421 | |

TABLE 1-continued

| # | Structure | LCMS (M + 1) | NMR |
|---|---|---|---|
| 759 | 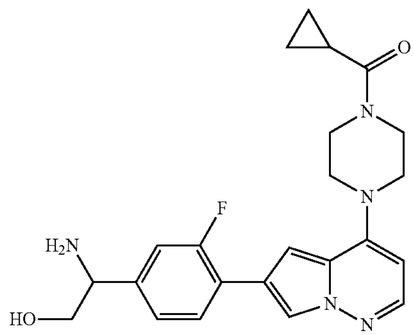 [SMILES: NC(CO)c1ccc(-c2cc3c(N4CCN(C(=O)C5CC5)CC4)ccnn3c2)c(F)c1] | 425 | 1H NMR (400 MHz, Methanol-d4) δ 8.02 (dd, J = 2.8, 1.8 Hz, 1H), 7.86 (d, J = 5.4 Hz, 1H), 7.81 (t, J = 8.2 Hz, 1H), 7.30-7.15 (m, 2H), 7.04-6.95 (m, 1H), 6.00 (d, J = 5.5 Hz, 1H), 4.10-3.94 (m, 3H), 3.85 (s, 2H), 3.72 (dd, J = 10.9, 4.9 Hz, 1H), 3.68-3.48 (m, 5H), 2.02 (tt, J = 7.9, 4.8 Hz, 1H), 0.92 (dt, J = 4.9, 2.8 Hz, 2H), 0.86 (ddt, J = 7.5, 4.7, 2.5 Hz, 2H). |
| 760 | 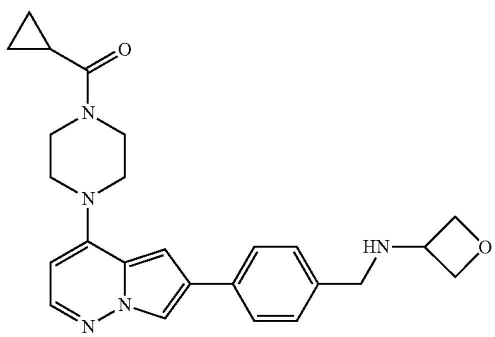 [SMILES: O=C(C1CC1)N1CCN(c2ccnn3cc(-c4ccc(CNC5COC5)cc4)cc23)CC1] | 433 | 1H NMR (400 MHz, Methanol-d4) δ 7.96 (d, J = 1.8 Hz, 1H), 7.84 (d, J = 5.4 Hz, 1H), 7.73-7.63 (m, 2H), 7.41-7.32 (m, 2H), 6.93 (d, J = 1.8 Hz, 1H), 5.99 (d, J = 5.5 Hz, 1H), 4.70 (t, J = 6.8 Hz, 2H), 4.44 (t, J = 6.4 Hz, 2H), 4.08-3.98 (m, 3H), 3.85 (s, 2H), 3.71 (s, 2H), 3.63 (s, 2H), 3.54 (s, 2H), 2.02 (tt, J = 7.9, 4.8 Hz, 1H), 0.92 (dt, J = 4.8, 2.8 Hz, 2H), 0.86 (ddt, J = 7.5, 4.6, 2.5 Hz, 2H). |
| 761 | 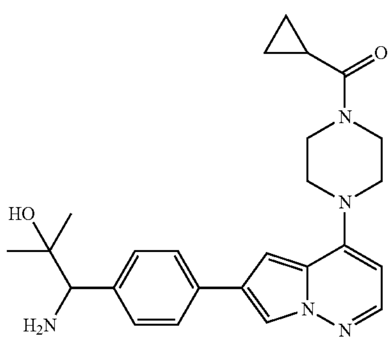 [SMILES: CC(C)(O)C(N)c1ccc(-c2cc3c(N4CCN(C(=O)C5CC5)CC4)ccnn3c2)cc1] | 435 | 1H NMR (400 MHz, Methanol-d4) δ 7.96 (d, J = 1.8 Hz, 1H), 7.84 (d, J = 5.4 Hz, 1H), 7.73-7.65 (m, 2H), 7.42-7.36 (m, 2H), 6.92 (d, J = 1.8 Hz, 1H), 5.98 (d, J = 5.5 Hz, 1H), 4.02 (s, 2H), 3.84 (s, 2H), 3.79 (s, 1H), 3.62 (s, 2H), 3.59-3.47 (m, 2H), 3.34 (s, 6H), 2.01 (tt, J = 7.9, 4.7 Hz, 1H), 1.20 (s, 3H), 1.12 (s, 3H), 0.96-0.90 (m, 2H), 0.86 (tdd, J = 7.5, 5.3, 2.4 Hz, 2H). |
| 762 | 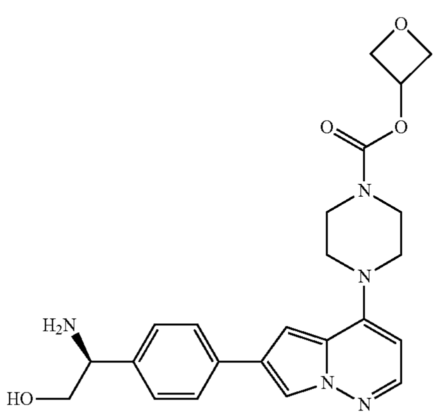 [SMILES: N[C@H](CO)c1ccc(-c2cc3c(N4CCN(C(=O)OC5COC5)CC4)ccnn3c2)cc1] | 439 | 1H NMR (400 MHz, Chloroform-d) δ 7.95 (d, J = 1.8 Hz, 1H), 7.84 (d, J = 5.5 Hz, 1H), 7.75-7.67 (m, 2H), 7.43-7.34 (m, 2H), 6.89 (d, J = 1.9 Hz, 1H), 6.00 (d, J = 5.5 Hz, 1H), 5.41 (tt, J = 6.2, 5.1 Hz, 1H), 4.89 (ddd, J = 7.4, 6.2, 1.0 Hz, 2H), 4.65 (ddd, J = 7.5, 5.2, 0.9 Hz, 2H), 3.97 (dd, J = 8.0, 4.7 Hz, 1H), 3.74-3.68 (m, 3H), 3.57 (dd, J = 10.8, 8.0 Hz, 1H), 3.53 (dd, J = 6.5, 3.9 Hz, 4H). |

TABLE 1-continued

| # | Structure | LCMS (M + 1) | NMR |
|---|---|---|---|
| 763 | 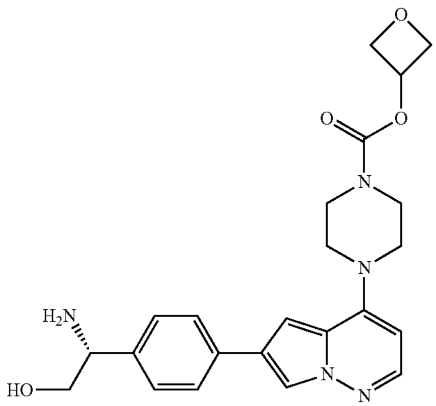 [SMILES: N[C@@H](CO)c1ccc(-c2cc3c(N4CCN(C(=O)OC5COC5)CC4)ccnn3c2)cc1] | 439 | 1H NMR (400 MHz, Methanol-d4) δ 7.96 (d, J = 1.8 Hz, 1H), 7.84 (d, J = 5.4 Hz, 1H), 7.77-7.62 (m, 2H), 7.47-7.33 (m, 2H), 6.89 (d, J = 1.8 Hz, 1H), 6.01 (d, J = 5.5 Hz, 1H), 5.41 (tt, J = 6.3, 5.1 Hz, 1H), 4.90 (ddd, J = 7.4, 6.2, 1.0 Hz, 2H), 4.66 (ddd, J = 7.5, 5.1, 0.9 Hz, 2H), 3.99 (dd, J = 7.9, 4.7 Hz, 1H), 3.80 (s, 3H), 3.77-3.64 (m, 2H), 3.59 (dd, J = 10.9, 8.0 Hz, 1H), 3.54-3.44 (m, 4H). |
| 764 | 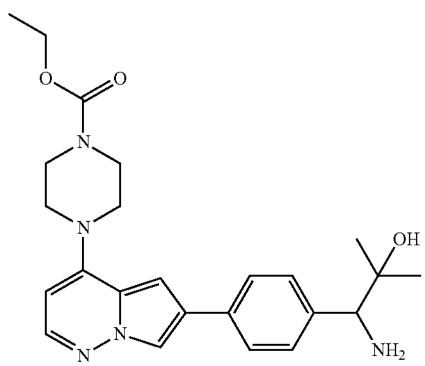 [SMILES: CCOC(=O)N1CCN(c2ccnn3cc(-c4ccc(C(N)C(C)(C)O)cc4)cc23)CC1] | 439 | 1H NMR (400 MHz, Methanol-d4) δ 7.95 (d, J = 1.8 Hz, 1H), 7.84 (d, J = 5.5 Hz, 1H), 7.76-7.59 (m, 2H), 7.49-7.32 (m, 2H), 6.89 (d, J = 1.8 Hz, 1H), 6.00 (d, J = 5.5 Hz, 1H), 4.17 (q, J = 7.1 Hz, 2H), 3.79 (s, 1H), 3.72 (d, J = 6.1 Hz, 4H), 3.57-3.41 (m, 4H), 1.29 (t, J = 7.1 Hz, 3H), 1.20 (s, 3H), 1.12 (s, 3H). |
| 765 | 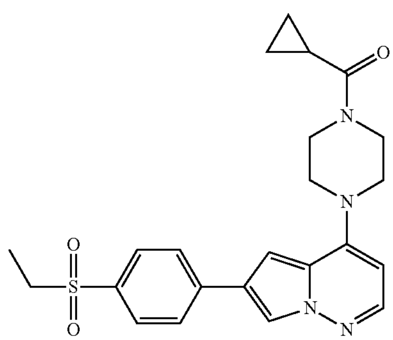 [SMILES: CCS(=O)(=O)c1ccc(-c2cc3c(N4CCN(C(=O)C5CC5)CC4)ccnn3c2)cc1] | 440 | |
| 766 | 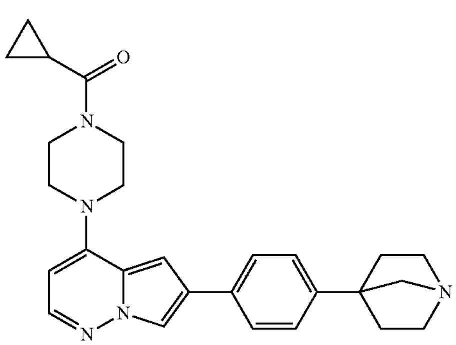 [SMILES: O=C(C1CC1)N1CCN(c2ccnn3cc(-c4ccc(C56CCN(CC5)C6)cc4)cc23)CC1] | 443 | 1H NMR (500 MHz, Methanol-d4) δ 7.98 (dd, J = 12.3, 1.8 Hz, 1H), 7.86 (d, J = 5.4 Hz, 1H), 7.69 (dd, J = 16.3, 7.9 Hz, 2H), 7.25 (t, J = 7.2 Hz, 2H), 6.94 (dd, J = 10.9, 1.8 Hz, 1H), 6.42 (s, 0H), 6.02 (d, J = 5.4 Hz, 1H), 5.57 (s, 1H), 4.07 (d, J = 18.4 Hz, 2H), 3.87 (s, 2H), 3.65 (s, 2H), 3.57 (s, 2H), 3.48 (s, 1H), 3.38 (s, 2H), 3.05 (dt, J = 18.3, 6.0 Hz, 2H), 2.94 (t, J = 5.8 Hz, 1H), 2.61 (t, J = 5.9 Hz, 1H), 2.46 (t, J = 5.9 Hz, 1H), 2.15 (s, 1H), 2.04 (tt, J = 8.2, 5.0 Hz, 1H), 0.95 (dt, J = 5.5, 3.1 Hz, 2H), 0.88 (dq, J = 10.4, 4.0, 3.6 Hz, 2H). |

TABLE 1-continued

| # | Structure | LCMS (M + 1) | NMR |
|---|---|---|---|
| 767 | 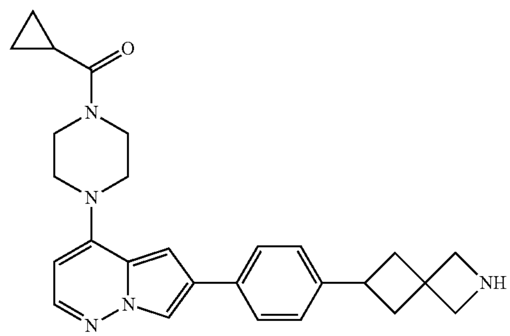 [SMILES: O=C(C1CC1)N1CCN(c2ccnn3cc(-c4ccc(C5CC6(CNC6)C5)cc4)cc23)CC1] | 443 | 1H NMR (400 MHz, Methanol-d4) δ 7.94 (d, J = 1.8 Hz, 1H), 7.84 (d, J = 5.5 Hz, 1H), 7.66 (d, J = 8.3 Hz, 2H), 7.24 (d, J = 8.0 Hz, 2H), 6.90 (d, J = 1.9 Hz, 1H), 6.00 (d, J = 5.5 Hz, 1H), 4.25 (s, 3H), 4.03 (s, 3H), 3.84 (s, 2H), 3.58 (d, J = 26.6 Hz, 5H), 2.75-2.66 (m, 2H), 2.42 (td, J = 9.7, 2.9 Hz, 2H), 2.06-1.99 (m, 1H), 1.30 (d, J = 14.4 Hz, 1H), 0.99-0.81 (m, 4H). |
| 768 | 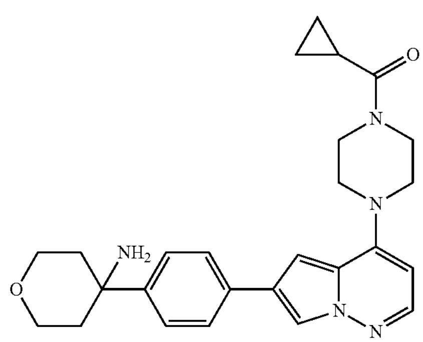 [SMILES: NC1(c2ccc(-c3cc4c(N5CCN(C(=O)C6CC6)CC5)ccnn4c3)cc2)CCOCC1] | 447 | 1H NMR (400 MHz, DMSO-d6) δ 8.14 (d, J = 1.8 Hz, 1H), 7.88 (d, J = 5.4 Hz, 1H), 7.78-7.68 (m, 2H), 7.56-7.47 (m, 2H), 7.02 (d, J = 1.9 Hz, 1H), 5.96 (d, J = 5.5 Hz, 1H), 3.91 (s, 2H), 3.86 (td, J = 11.2, 2.3 Hz, 2H), 3.69 (s, 2H), 3.62 (dt, J = 11.1, 3.8 Hz, 2H), 3.50 (d, J = 25.8 Hz, 4H), 2.07-1.91 (m, 3H), 1.53 (d, J = 13.1 Hz, 2H), 0.84-0.67 (m, 4H). |
| 769 | 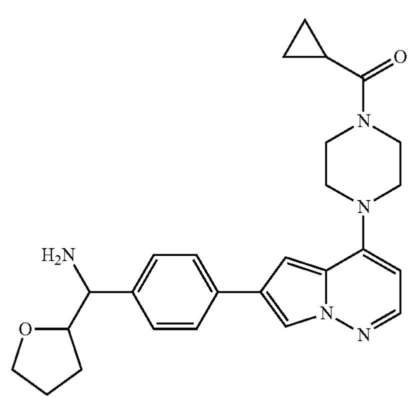 [SMILES: NC(c1ccc(-c2cc3c(N4CCN(C(=O)C5CC5)CC4)ccnn3c2)cc1)C1CCCO1] | 447 | |
| 770 | 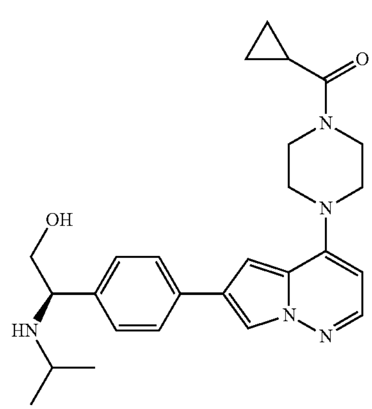 [SMILES: CC(C)N[C@@H](CO)c1ccc(-c2cc3c(N4CCN(C(=O)C5CC5)CC4)ccnn3c2)cc1] | 449 | 1H NMR (400 MHz, Methanol-d4) δ 8.54 (s, 2H), 7.98 (d, J = 1.8 Hz, 1H), 7.85 (d, J = 5.4 Hz, 1H), 7.75 (d, J = 8.0 Hz, 2H), 7.43 (d, J = 8.0 Hz, 2H), 6.94 (d, J = 1.8 Hz, 1H), 6.00 (d, J = 5.5 Hz, 1H), 4.55 (s, 1H), 4.03 (s, 3H), 3.82 (d, J = 23.8 Hz, 2H), 3.79-3.67 (m, 1H), 3.63 (s, 2H), 3.53 (d, J = 18.9 Hz, 2H), 2.05-1.94 (m, 1H), 1.28 (s, 1H), 1.16 (dd, J = 16.5, 9.4 Hz, 6H), 0.96-0.81 (m, 5H). |

TABLE 1-continued

| # | Structure | LCMS (M + 1) | NMR |
|---|---|---|---|
| 771 | 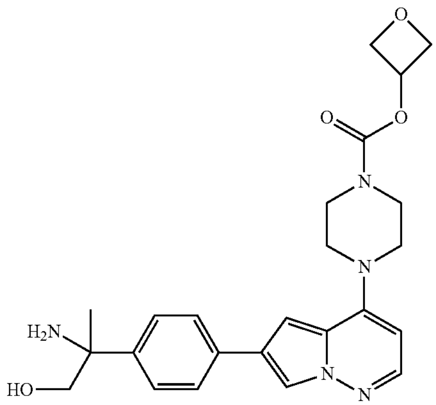 [SMILES: CC(N)(CO)c1ccc(-c2cc3c(N4CCN(C(=O)OC5COC5)CC4)ccnn3c2)cc1] | 453 | 1H NMR (500 MHz, Methanol-d4) δ 8.45 (s, 2H), 8.11-7.96 (m, 1H), 7.87 (dd, J = 17.6, 6.7 Hz, 3H), 7.51 (d, J = 8.2 Hz, 2H), 6.96 (d, J = 1.9 Hz, 1H), 6.05 (d, J = 5.5 Hz, 1H), 5.44 (p, J = 5.6 Hz, 1H), 4.93 (t, J = 6.9 Hz, 2H), 4.68 (dd, J = 7.6, 5.1 Hz, 2H), 3.96-3.66 (m, 6H), 3.56 (t, J = 5.1 Hz, 4H), 3.01 (s, 2H), 2.88 (s, 1H), 1.74 (s, 3H). |
| 772 | 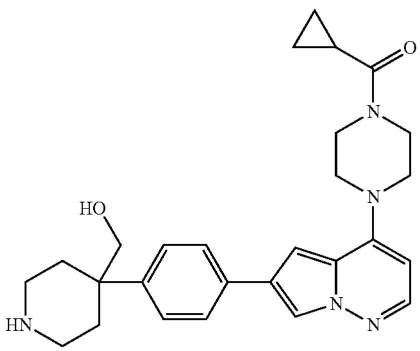 [SMILES: O=C(C1CC1)N1CCN(c2ccnn3cc(-c4ccc(C5(CO)CCNCC5)cc4)cc23)CC1] | 561 | 1H NMR (400 MHz, DMSO-d6) δ 8.55 (s, 0H), 8.14 (d, J = 2.0 Hz, 1H), 7.89 (d, J = 5.4 Hz, 1H), 7.71 (d, J = 8.0 Hz, 2H), 7.33 (d, J = 8.2 Hz, 2H), 7.01 (d, J = 1.9 Hz, 1H), 5.97 (d, J = 5.5 Hz, 1H), 4.13 (s, 2H), 3.92 (s, 2H), 3.70 (s, 2H), 3.57 (d, J = 25.1 Hz, 3H), 3.46 (s, 1H), 3.15 (s, 4H), 2.79 (d, J = 10.7 Hz, 1H), 2.07-1.98 (m, 1H), 1.94-1.80 (m, 2H), 1.63 (d, J = 10.9 Hz, 1H), 1.51 (s, 1H), 1.22 (s, 1H), 0.75 (tt, J = 7.9, 2.9 Hz, 4H). |
| 773 | 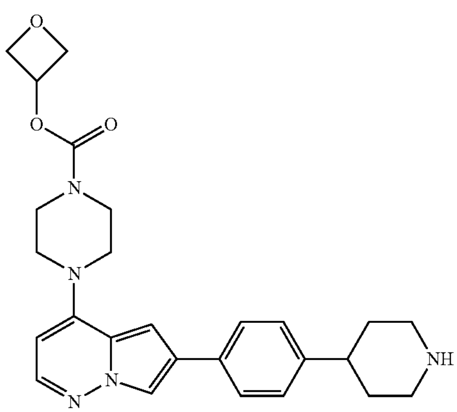 [SMILES: O=C(OC1COC1)N1CCN(c2ccnn3cc(-c4ccc(C5CCNCC5)cc4)cc23)CC1] | 462 | 1H-NMR (500 MHz, 6d-DMSO) δ ppm 8.16 (s, 1H), 7.91 (d, 1H, J = 5.5 Hz), 7.74 (d, 2H, J = 8.0 Hz), 7.25 (d, 2H, J = 8.0 Hz), 7.01 (s, 1H), 5.99 (d, 1H, J = 5.5 Hz), 5.34 (quintet, 1H, d, 1H, J = 5.5 Hz), 4.80 (t, 2H, d, 1H, J = 7.0 Hz), 4.53 (dd, 2H, d, 1H, J = 7.0, 5.5 Hz), 3.72-3.67 (m, 2H), 3.63-3.58 (m, 2H), 3.55-3.45 (m, 4H), 3.20-3.15 (m, 1H), 3.06-3.02 (m, 2H), 2.64-2.59 (m, 2H), 1.75-1.70 (m, 2H), 1.57-1.52 (m, 2H). |
| 774 | 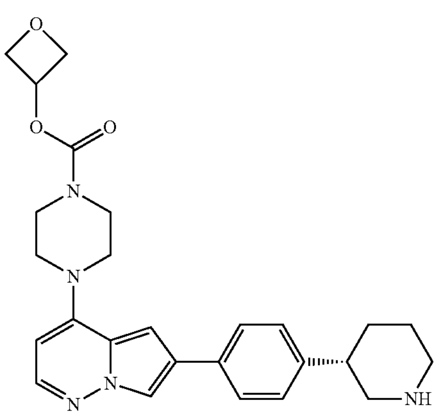 [SMILES: O=C(OC1COC1)N1CCN(c2ccnn3cc(-c4ccc([C@@H]5CCCNC5)cc4)cc23)CC1] | 462 | 1H-NMR (400 MHz, 6d-DMSO) δ ppm 8.15 (d, 1H, J = 1.2 Hz), 7.91 (d, 1H, J = 5.6 Hz), 7.72 (d, 2H, J = 8.4 Hz), 7.24 (d, 2H, J = 8.4 Hz), 7.00 (s, 1H), 6.00 (d, 1H, J = 5.6 Hz), 5.34 (quintet, 1H, J = 5.2 Hz), 4.79 (t, 2H, J = 7.2 Hz), 4.53 (dd, 2H, J = 7.2, 5.2 Hz), 3.69 (m, 2H), 3.59 (m, 2H), 3.49-3.48 (m, 4H), 2.96-2.93 (m, 2H), 2.60-2.52 (m, 2H), 2.47 (m, 1H), 1.89-1.87 (m, 1H), 1.70-1.65 (m, 1H), 1.62-1.58 (m, 1H), 1.55-1.40 (m, 2H). |

TABLE 1-continued

| # | Structure | LCMS (M + 1) | NMR |
|---|---|---|---|
| 775 | 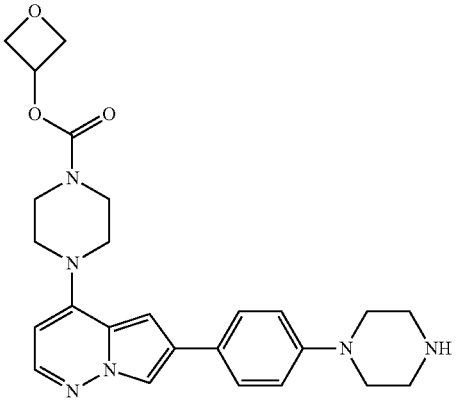 [SMILES: O=C(OC1COC1)N1CCN(c2ccnn3cc(-c4ccc(N5CCNCC5)cc4)cc23)CC1] | 463 | 1H-NMR (500 MHz, 6d-DMSO) δ ppm 8.27 (s, 1H), 8.08 (d, 1H, J = 1.5 Hz), 7.88 (d, 1H, J = 5.5 Hz), 7.67 (d, 2H, J = 9.0 Hz), 6.97 (d, 2H, J = 9.0 Hz), 6.93 (d, 1H, J = 1.5 Hz), 5.98 (d, 1H, J = 5.5 Hz), 5.33 (quintet, 1H, J = 5.0 Hz), 4.79 (t, 2H, J = 7.0 Hz), 4.53 (dd, 2H, J = 7.5, 5.0 Hz), 3.70-3.68 (m, 2H), 3.65-3.64 (m, 2H), 3.48-3.46 (m, 4H), 3.18-3.16 (m, 4H), 2.99-2.97 (m, 4H). |
| 776 | 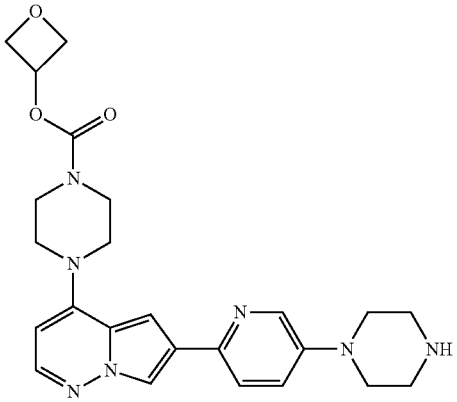 [SMILES: O=C(OC1COC1)N1CCN(c2ccnn3cc(-c4ccc(N5CCNCC5)cn4)cc23)CC1] | 464 | 1H-NMR (400 MHz, 6d-DMSO) δ ppm 8.28 (d, 1H, J = 2.4 Hz), 8.15 (d, 1H, J = 1.2 Hz), 7.90 (d, 1H, J = 5.6 Hz), 7.70 (d, 1H, J = 8.8 Hz), 7.73 (dd, 1H, J = 8.8, 2.4 Hz), 7.06 (d, 1H, J = 1.2 Hz), 5.98 (d, 1H, J = 5.6 Hz), 5.33 (quintet, 1H, J = 5.6 Hz), 4.78 (t, 2H, J = 7.2 Hz), 4.52 (dd, 2H, J = 7.2, 5.6 Hz), 3.70-3.65 (m, 2H), 3.65-3.58 (m, 2H), 3.51-3.45 (m, 4H), 3.25-3.15 (m, 4H), 3.05-2.93 (m, 4H). |
| 777 | 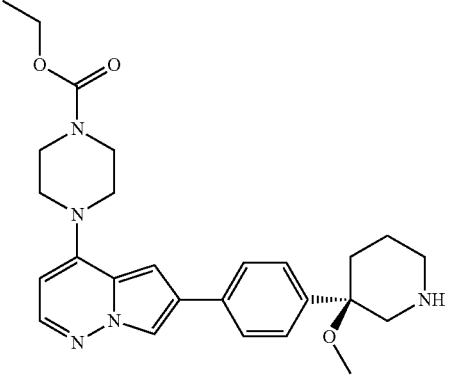 [SMILES: CCOC(=O)N1CCN(c2ccnn3cc(-c4ccc([C@]5(OC)CCCNC5)cc4)cc23)CC1] | 464 | 1H-NMR (400 MHz, 6d-DMSO) δ ppm 8.18 (d, 1H, J = 1.6 Hz), 7.91 (d, 1H, J = -5.6 Hz), 7.79 (d, 2H, J = 8.4 Hz), 7.39 (d, 2H, J = 8.4 Hz), 7.02 (d, 1H, J = 1.6 Hz), 5.98 (d, 1H, J = 5.6 Hz), 4.09 (q, 2H, J = 7.2 Hz), 3.62-3.60 (m, 4H), 3.47-3.46 (m, 4H), 2.96-2.87 (m, 5H), 2.70-2.67 (m, 1H), 2.49-2.46 (m, 1H), 2.11-2.07 (m, 1H), 1.98-1.92 (m, 1H), 1.69-1.59 (m, 1H), 1.46-1.42 (m, 1H), 1.22 (t, 3H, J = 7.2 Hz). |
| 778 | 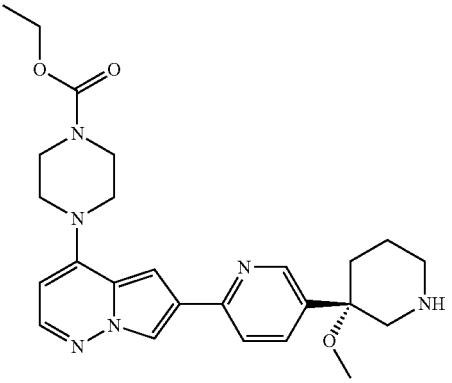 [SMILES: CCOC(=O)N1CCN(c2ccnn3cc(-c4ccc([C@@]5(OC)CCCNC5)cn4)cc23)CC1] | 465 | 1H-NMR (500 MHz, 6d-DMSO) δ ppm 8.61 (s, 1H), 8.32 (d, 1H, J = 1.5 Hz), 8.29 (s, 1H), 7.99 (d, 1H, J = 8.0 Hz), 7.95 (d, 1H, J = 5.0 Hz), 7.82 (d, 1H, J = 7.5 Hz), 7.20 (d, 1H, J = 1.5 Hz), 6.01 (d, 1H, J = 5.5 Hz), 4.10 (q, 2H, J = 7.0 Hz), 3.70-3.58 (m, 4H), 3.54-3.46 (m, 4H), 3.38-3.25 (m, 1H), 3.15-3.05 (m, 2H), 3.02 (s, 3H), 2.90-2.76 (m, 1H), 2.26-2.18 (m, 1H), 2.14-2.04 (m, 1H), 1.90-1.78 (m, 1H), 1.76-1.66 (m, 1H), 1.23 (t, 3H, J = 7.0 Hz). |

TABLE 1-continued

| # | Structure | LCMS (M + 1) | NMR |
|---|---|---|---|
| 779 | 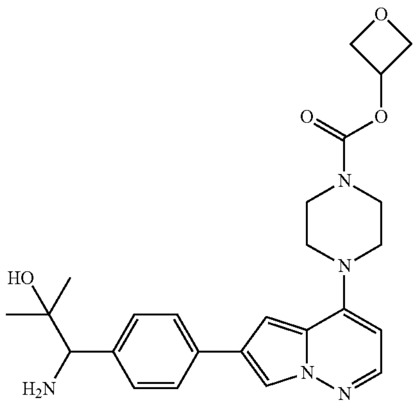 [SMILES: CC(C)(O)C(N)c1ccc(-c2cc3c(N4CCN(C(=O)OC5COC5)CC4)ccnn3c2)cc1] | 467 | 1H NMR (400 MHz, Methanol-d4) δ 7.96 (d, J = 1.8 Hz, 1H), 7.84 (d, J = 5.4 Hz, 1H), 7.73-7.62 (m, 2H), 7.43-7.36 (m, 2H), 6.90 (d, J = 1.9 Hz, 1H), 6.01 (d, J = 5.5 Hz, 1H), 5.41 (tt, J = 6.2, 5.1 Hz, 1H), 4.90 (ddd, J = 7.4, 6.2, 1.0 Hz, 2H), 4.66 (ddd, J = 7.5, 5.1, 0.9 Hz, 2H), 3.76 (d, J = 26.0 Hz, 1H), 3.58-3.47 (m, 4H), 1.16 (d, J = 29.4 Hz, 6H). |
| 780 | 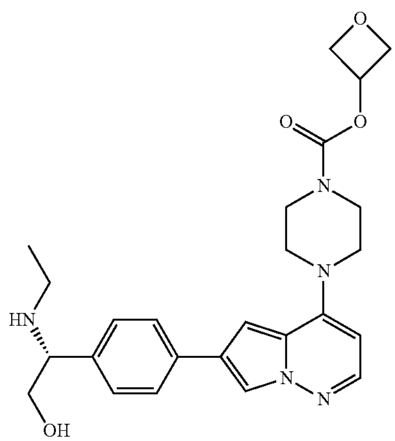 [SMILES: CCN[C@@H](CO)c1ccc(-c2cc3c(N4CCN(C(=O)OC5COC5)CC4)ccnn3c2)cc1] | 467 | 1H NMR (400 MHz, Methanol-d4) δ 7.97 (d, J = 1.8 Hz, 1H), 7.85 (d, J = 5.4 Hz, 1H), 7.72 (d, J = 8.1 Hz, 2H), 7.38 (d, J = 8.2 Hz, 2H), 6.90 (d, J = 1.8 Hz, 1H), 6.01 (d, J = 5.4 Hz, 1H), 5.4.35 (m, 1H), 4.90 (dd, J = 7.5, 6.5 Hz, 2H), 4.66 (dd, J = 7.8, 5.2 Hz, 2H), 3.88-3.61 (m, 8H), 3.61-3.46 (m, 5H), 2.58 (q, J = 7.0 Hz, 2H), 1.29 (s, 2H), 1.13 (t, J = 7.2 Hz, 3H). |
| 781 | 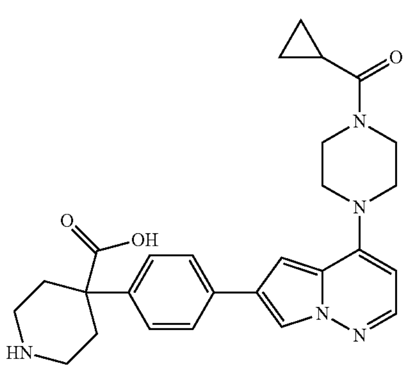 [SMILES: O=C(C1CC1)N1CCN(c2ccnn3cc(-c4ccc(C5(C(=O)O)CCNCC5)cc4)cc23)CC1] | 475 | |

TABLE 1-continued

| # | Structure | LCMS (M + 1) | NMR |
|---|---|---|---|
| 782 | 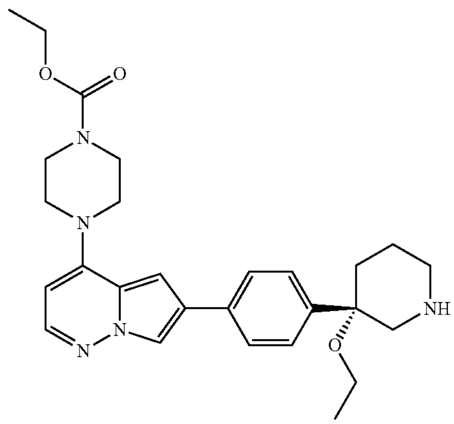 [SMILES: CCOC(=O)N1CCN(c2ccnn3cc(-c4ccc([C@@]5(OCC)CCCNC5)cc4)cc23)CC1] | 478 | 1H-NMR (400 MHz, 6d-DMSO) δ ppm 8.18 (d, 1H, J = 1.6 Hz), 7.91 (d, 1H, J = 5.2 Hz), 7.78 (d, 2H, J = 8.4 Hz), 7.41 (d, 2H, J = 8.4 Hz), 7.02 (d, 1H, J = 1.6 Hz), 5.98 (d, 1H, J = 5.2 Hz), 4.09 (q, 2H, J = 7.2 Hz), 3.62-3.61 (m, 4H), 3.47-3.46 (m, 4H), 3.19-3.15 (m, 1H), 3.08-3.04 (m, 1H), 2.90-2.87 (m, 2H), 2.68-2.65 (m, 1H), 2.51-2.50 (m, 1H), 2.05-2.04 (m, 1H), 1.97-1.96 (m, 1H), 1.62-1.60 (m, 1H), 1.41-1.39 (m, 1H), 1.22 (t, 3H, J = 7.2 Hz), 1.09 (t, 3H, J = 6.4 Hz). |
| 783 | 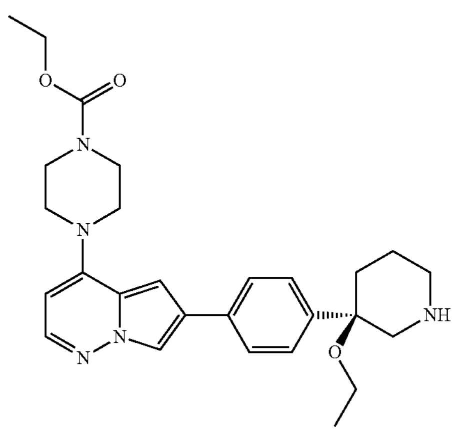 [SMILES: CCOC(=O)N1CCN(c2ccnn3cc(-c4ccc([C@]5(OCC)CCCNC5)cc4)cc23)CC1] | 478 | 1H-NMR (400 MHz, 6d-DMSO) δ ppm 8.18 (d, 1H, J = 1.6 Hz), 7.91 (d, 1H, J = 5.2 Hz), 7.79 (d, 2H, J = 8.4 Hz), 7.40 (d, 2H, J = 8.4 Hz), 7.02 (d, 1H, J = 1.6 Hz), 5.98 (d, 1H, J = 5.2 Hz), 4.09 (q, 2H, J = 7.2 Hz), 3.62-3.55 (m, 4H), 3.20-3.45 (m, 4H), 3.20-3.15 (m, 1H), 3.08-3.03 (m, 1H), 2.95-2.88 (m, 2H), 2.73-2.68 (m, 1H), 2.54-2.50 (m, 1H), 2.08-2.04 (m, 1H), 2.00-1.95 (m, 1H), 1.69-1.64 (m, 1H), 1.48-1.43 (m, 1H), 1.22 (t, 3H, J = 7.2 Hz), 1.11 (t, 3H, J = 7.2 Hz). |
| 784 | 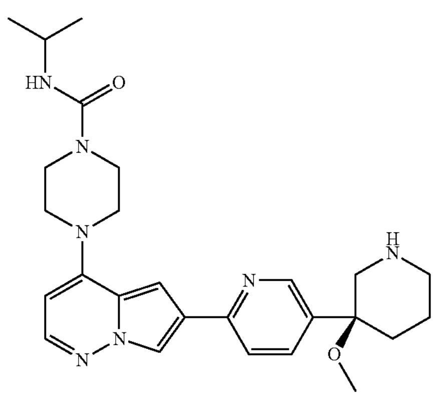 [SMILES: CO[C@]1(c2ccc(-c3cc4c(N5CCN(C(=O)NC(C)C)CC5)ccnn4c3)nc2)CCCNC1] | 478 | 1H-NMR (400 MHz, 6d-DMSO) δ ppm 8.59 (s, 1H), 8.29 (d, 1H, J = 1.6 Hz), 8.27 (s, 1H), 7.97 (d, 1H, J = 8.0 Hz), 7.93 (d, 1H, J = 5.2 Hz), 7.80 (d, 1H, J = 7.6 Hz), 7.18 (d, 1H, J = 1.2 Hz), 6.32 (d, 1H, J = 7.6 Hz), 5.99 (d, 1H, J = 5.6 Hz), 3.75-3.60 (m, 1H), 3.67-3.48 (m, 4H), 3.47-3.40 (m, 4H), 3.30-3.20 (m, 1H), 3.12-3.02 (m, 2H), 3.00 (s, 3H), 2.84-2.66 (m, 1H), 2.24-2.14 (m, 1H), 2.12-2.00 (m, 1H), 1.86-1.72 (m, 1H), 1.70-1.60 (m, 1H), 1.07 (d, 6H, J = 6.4 Hz). |

TABLE 1-continued

| # | Structure | LCMS (M + 1) | NMR |
|---|---|---|---|
| 785 | 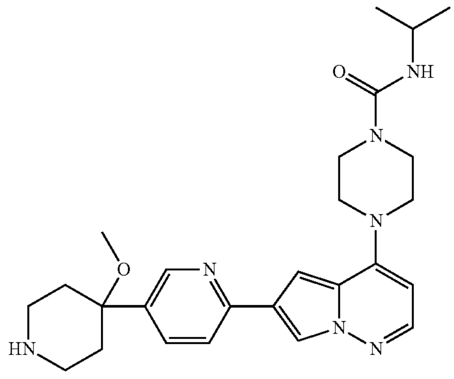 [SMILES: COC1(c2ccc(-c3cc4c(N5CCN(C(=O)NC(C)C)CC5)ccnn4c3)nc2)CCNCC1] | 478 | 1H-NMR (400 MHz, 6d-DMSO) δ ppm 8.56 (d, 1H, J = 1.6 Hz), 8.27 (d, 1H, J = 1.6 Hz), 7.96-7.90 (m, 2H), 7.75 (dd, 1H, J = 8.0, 2.0 Hz), 7.16 (d, 1H, J = 1.6 Hz), 6.30 (d, 1H, J = 7.2 Hz), 5.99 (d, 1H, J = 5.6 Hz), 3.80-3.70 (m, 1H), 3.60-3.50 (m, 4H), 3.48-3.40 (m, 4H), 2.91 (s, 3H), 2.90-2.80 (m, 2H), 2.78-2.70 (m, 2H), 2.00-1.88 (m, 2H), 1.86-1.74 (m, 2H), 1.08 (d, 6H, J = 6.4 Hz). |
| 786 | 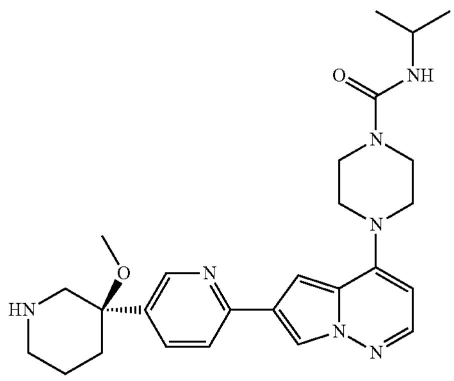 | 478 | 1H-NMR (500 MHz, 6d-DMSO) δ ppm 8.60 (d, 1H, J = 1.5 Hz), 8.29 (d, 1H, J = 1.0 Hz), 7.96-7.93 (m, 2H), 7.80 (dd, 1H, J = 8.0, 2.0 Hz), 7.18 (d, 1H, J = 1.5 Hz), 6.31 (d, 1H, J = 7.0 Hz), 6.00 (d, 1H, J = 5.5 Hz), 3.81-3.75 (m, 1H), 3.54-3.53 (m, 4H), 3.46-3.45 (m, 4H), 3.17-3.14 (m, 1H), 3.03-3.01 (m, 1H), 3.01 (s, 3H), 3.00-2.92 (m, 1H), 2.70-2.64 (m, 1H), 2.18 (m, 1H), 2.07-2.02 (m, 1H), 1.75-1.72 (m, 1H), 1.60-1.58 (m, 1H), 1.08 (d, 6H, J = 6.5 Hz). |
| 787 | 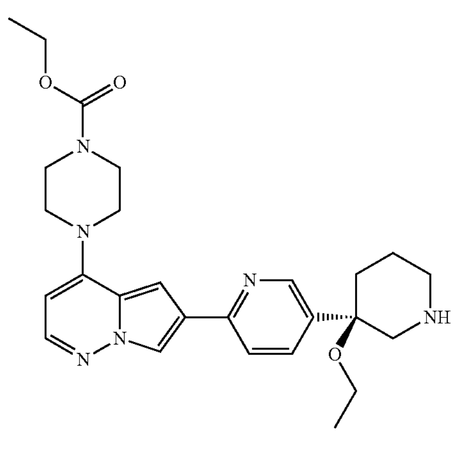 [SMILES: CCOC(=O)N1CCN(c2ccnn3cc(-c4ccc([C@]5(OCC)CCCNC5)cn4)cc23)CC1] | 479 | 1H-NMR (400 MHz, 6d-DMSO) δ ppm 8.59 (d, 1H, J = 2.4 Hz), 8.28 (d, 1H, J = 1.6 Hz), 7.95-7.90 (m, 2H), 7.79 (dd, 1H, J = 8.4, 2.4 Hz), 7.17 (d, 1H, J = 1.6 Hz), 6.00 (d, 1H, J = 5.6 Hz), 4.09 (q, 2H, J = 7.2 Hz), 3.64-3.60 (m, 4H), 3.50-3.45 (m, 4H), 3.22-3.18 (m, 1H), 3.11-3.07 (m, 1H), 2.92-2.84 (m, 2H), 2.78-2.74 (m, 1H), 2.51-2.50 (m, 1H), 2.05-1.99 (m, 2H), 1.54-1.53 (m, 1H), 1.44-1.43 (m, 1H), 1.22 (t, 3H, J = 7.2 Hz), 1.12 (t, 3H, J = 7.2 Hz). |

TABLE 1-continued
| # | Structure | LCMS (M + 1) | NMR |
|---|---|---|---|
| 788 | 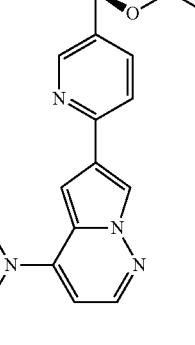 | 479 | 1H-NMR (400 MHz, 6d-DMSO) δ ppm 8.59 (d, 1H, J = 2.0 Hz), 8.31 (s, 1H), 8.29 (d, 1H, J = 2.0 Hz), 7.97-7.91 (m, 2H), 7.79 (dd, 1H, J = 8.4, 2.4 Hz), 7.17 (d, 1H, J = 1.6 Hz), 5.99 (d, 1H, J = 5.2 Hz), 4.08 (q, 2H, J = 7.2 Hz), 3.68-3.56 (m, 4H), 3.52-3.42 (m, 4H), 3.26-3.12 (m, 2H), 3.10-2.98 (m, 2H), 2.97-2.90 (m, 1H), 2.76-2.64 (m, 1H), 2.20-2.00 (m, 2H), 1.84-1.68 (m, 1H), 1.66-1.54 (m, 1H), 1.21 (t, 3H, J = 6.8 Hz), 1.13 (t, 3H, J = 6.8 Hz). |
| 789 | 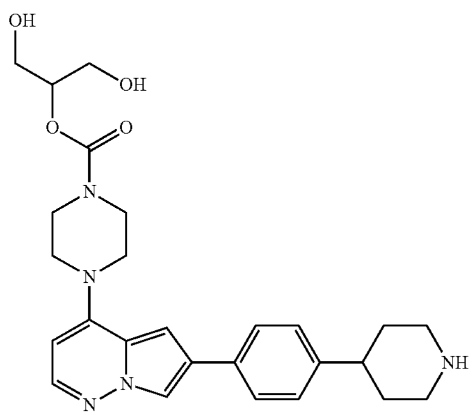 [SMILES: O=C(OC(CO)CO)N1CCN(c2ccnn3cc(-c4ccc(C5CCNCC5)cc4)cc23)CC1] | 480 | 1H-NMR (500 MHz, 4d-MeOD) δ ppm 7.97 (d, 1H, J = 1.5 Hz), 7.86 (d, 1H, J = 5.0 Hz), 7.71 (d, 2H, J = 8.5 Hz), 7.32 (d, 2H, J = 8.5 Hz), 6.90 (d, 1H, J = 1.5 Hz), 6.02 (d, 1H, J = 5.5 Hz), 4.85-4.81 (m, 1H), 4.26-4.23 (m, 1H), 4.16-4.13 (m, 1H), 3.91-3.86 (m, 1H), 3.78-3.71 (m, 4H), 3.61-3.59 (m, 1H), 3.55-3.51 (m, 6H), 3.14 (td, 2H, J = 12.5, 2.5 Hz), 2.93 (tt, 1H, J = 12.5, 3.5 Hz), 2.12-2.09 (m, 2H), 1.98-1.89 (m, 2H). |
| 790 | 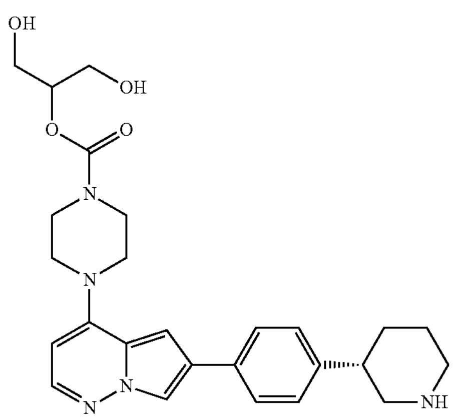 [SMILES: O=C(OC(CO)CO)N1CCN(c2ccnn3cc(-c4ccc([C@@H]5CCCNC5)cc4)cc23)CC1] | 480 | 1H-NMR (500 MHz, 6d-DMSO) δ ppm 8.38 (s, 1H), 8.16 (s, 1H), 7.91 (d, 1H, J = 5.0 Hz), 7.75 (d, 2H, J = 8.0 Hz), 7.27 (d, 2H, J = 8.0 Hz), 7.01 (s, 1H), 5.99 (d, 1H, J = 5.5 Hz), 4.62 (quintet, 1H, J = 5.5 Hz), 3.60-3.55 (m, 12H), 3.20-3.14 (m, 2H), 2.81-2.28 (m, 3H), 2.74-2.71 (m, 1H), 1.91-1.89 (m, 1H), 1380-1.78 (m, 1H), 1.69-1.64 (m, 2H). |

TABLE 1-continued

| # | Structure | LCMS (M + 1) | NMR |
|---|-----------|--------------|-----|
| 791 | 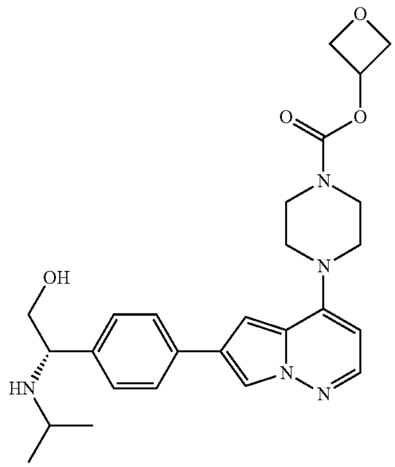 [SMILES: CC(C)N[C@H](CO)c1ccc(-c2cc3c(N4CCN(C(=O)OC5COC5)CC4)ccnn3c2)cc1] | 481 | |
| 792 | 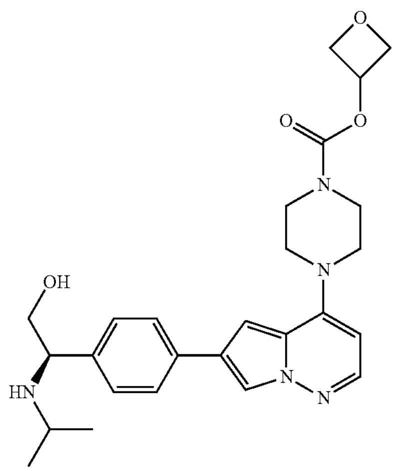 [SMILES: CC(C)N[C@@H](CO)c1ccc(-c2cc3c(N4CCN(C(=O)OC5COC5)CC4)ccnn3c2)cc1] | 481 | 1H NMR (400 MHz, Methanol-d4) δ 7.96 (d, J = 1.8 Hz, 1H), 7.84 (d, J = 5.4 Hz, 1H), 7.71 (d, J = 8.2 Hz, 2H), 7.38 (d, J = 8.2 Hz, 2H), 6.90 (d, J = 1.9 Hz, 1H), 6.01 (d, J = 5.5 Hz, 1H), 5.41 (tt, J = 6.3, 5.1 Hz, 1H), 4.90 (ddd, J = 7.3, 6.2, 0.9 Hz, 2H), 4.70-4.59 (m, 2H), 3.92 (t, J = 6.3 Hz, 1H), 3.87-3.59 (m, 7H), 3.53 (t, J = 5.2 Hz, 4H), 2.81-2.68 (m, 1H), 1.07 (dd, J = 15.0, 6.3 Hz, 6H). |
| 793 | 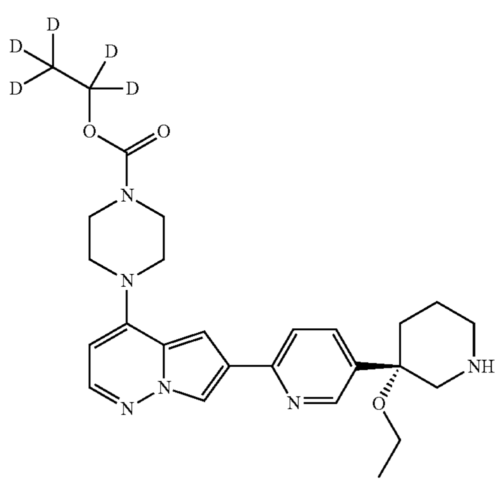 [SMILES: [2H]C([2H])([2H])C([2H])([2H])OC(=O)N1CCN(c2ccnn3cc(-c4ccc([C@@]5(OCC)CCCNC5)cn4)cc23)CC1] | 484 | 1H-NMR (400 MHz, 6d-DMSO) δ ppm 8.61 (d, 1H, J = 1.6 Hz), 8.36 (s, 1H), 8.31 (d, 1H, J = 1.6 Hz), 7.97-7.93 (m, 2H), 7.82-7.79 (m, 1H), 7.19 (d, 1H, J = 1.6 Hz), 6.00 (d, 1H, J = 6.4 Hz), 3.64-3.60 (m, 4H), 3.52-3.44 (m, 4H), 3.23-3.19 (m, 2H), 3.14-3.04 (m, 2H), 3.00-2.95 (m, 1H), 2.77-2.70 (m, 1H), 2.20-2.02 (m, 2H), 1.82-1.61 (m, 2H), 1.14 (t, 3H, J = 7.2 Hz). |

| # | Structure | LCMS (M + 1) | NMR |
|---|---|---|---|
| 794 | 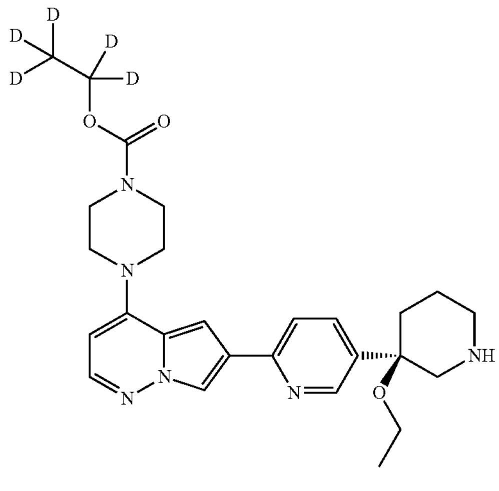 [SMILES: [2H]C([2H])([2H])C([2H])([2H])OC(=O)N1CCN(c2ccnn3cc(-c4ccc([C@]5(OCC)CCCNC5)cn4)cc23)CC1] | 484 | 1H-NMR (400 MHz, 6d-DMSO) δ ppm 8.61 (d, 1H, J = 1.6 Hz), 8.36 (s, 1H), 8.31 (d, 1H, J = 1.6 Hz), 7.97-7.93 (m, 2H), 7.82-7.79 (m, 1H), 7.19 (d, 1H, J = 1.6 Hz), 6.00 (d, 1H, J = 6.4 Hz), 3.64-3.60 (m, 4H), 3.52-3.44 (m, 4H), 3.24-3.19 (m, 2H), 3.12-3.03 (m, 2H), 3.00-2.94 (m, 1H), 2.77-2.70 (m, 1H), 2.20-2.02 (m, 2H), 1.82-1.60 (m, 2H), 1.14 (t, 3H, J = 7.2 Hz). |
| 795 | 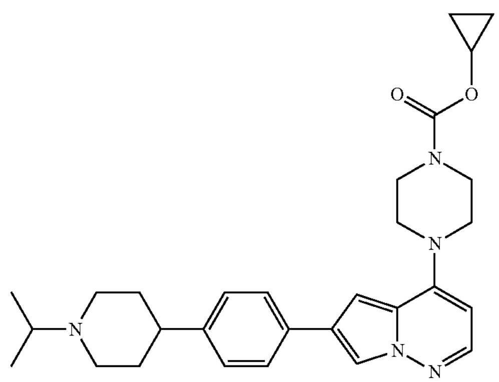 [SMILES: CC(C)N1CCC(c2ccc(-c3cc4c(N5CCN(C(=O)OC6CC6)CC5)ccnn4c3)cc2)CC1] | 489 | 1H NMR (400 MHz, Methanol-d4) δ 7.93 (d, J = 1.8 Hz, 1H), 7.83 (d, J = 5.5 Hz, 1H), 7.73-7.56 (m, 2H), 7.30-7.19 (m, 2H), 6.85 (d, J = 1.8 Hz, 1H), 5.99 (d, J = 5.5 Hz, 1H), 4.17-4.00 (m, 1H), 3.69 (s, 4H), 3.48 (d, J = 7.0 Hz, 4H), 3.19-2.99 (m, 3H), 2.82 (p, J = 6.6 Hz, 1H), 2.47 (m, 1H), 2.40 (t, J = 11.6 Hz, 2H), 1.98-1.67 (m, 4H), 1.14 (d, J = 6.6 Hz, 6H), 0.77-0.64 (m, 4H). |
| 796 | 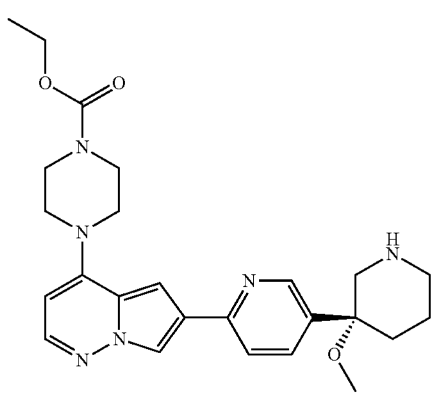 [SMILES: CCOC(=O)N1CCN(c2ccnn3cc(-c4ccc([C@]5(OC)CCCNC5)cn4)cc23)CC1] | 465 | 1H-NMR (500 MHz, 6d-DMSO) δ ppm 8.59 (d, 1H, J = 1.5 Hz), 8.32 (s, 1H), 8.30 (d, 1H, J = 1.5 Hz), 7.96-7.94 (m, 2H), 7.79 (dd, 1H, J = 8.5, 2.0 Hz), 7.18 (d, 1H, J = 1.5 Hz), 6.00 (d, 1H, J = 5.5 Hz), 4.09 (q, 2H, J = 6.5 Hz), 3.62-3.61 (m, 4H), 3.49-3.48 (m, 4H), 3.16-3.13 (m, 1H), 3.00 (s, 3H), 2.95-2.92 (m, 2H), 2.70-2.65 (m, 1H), 2.18-2.15 (m, 1H), 2.07-2.02 (m, 1H), 1.75-1.73 (m, 1H), 1.60-1.57 (m, 1H), 1.22 (t, 3H, J = 6.5 Hz). |

TABLE 1-continued

| # | Structure | LCMS (M + 1) | NMR |
|---|---|---|---|
| 797 | 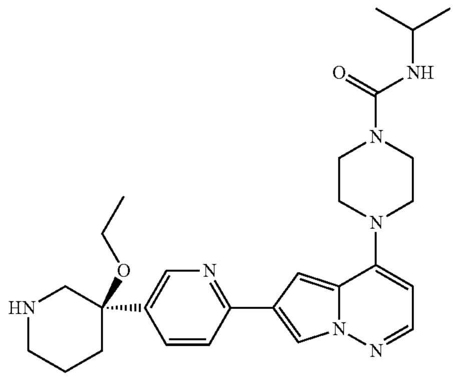 [SMILES: CCO[C@@]1(c2ccc(-c3cc4c(N5CCN(C(=O)NC(C)C)CC5)ccnn4c3)nc2)CCCNC1] | 492 | 1H-NMR (400 MHz, 6d-DMSO) δ ppm 8.61 (d, 1H, J = 2.0 Hz), 8.29 (d, 1H, J = 1.6 Hz), 7.97-7.92 (m, 2H), 7.81 (dd, 1H, J = 8.4, 2.4 Hz), 7.18 (d, 1H, J = 1.6 Hz), 6.33 (d, 1H, J = 7.6 Hz), 6.01 (d, 1H, J = 5.6 Hz), 3.80-3.78 (m, 1H), 3.54-3.53 (m, 4H), 3.46-3.45 (m, 4H), 3.25-3.18 (m, 2H), 3.17-3.07 (m, 2H), 3.05-2.97 (m, 2H), 2.70-2.63 (m, 1H), 2.10-2.01 (m, 2H), 1.76-1.75 (m, 1H), 1.74-1.73 (m, 1H), 1.14 (t, 3H, J = 6.8 Hz), 1.08 (d, 6H, J = 6.8 Hz). |
| 798 | 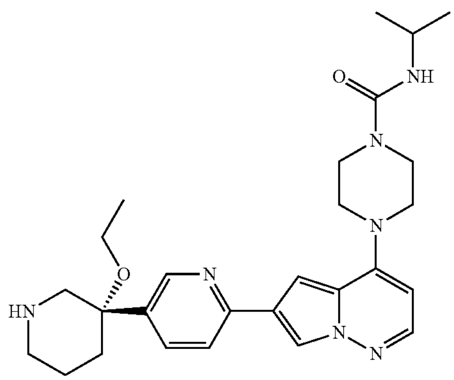 [SMILES: CCO[C@]1(c2ccc(-c3cc4c(N5CCN(C(=O)NC(C)C)CC5)ccnn4c3)nc2)CCCNC1] | 492 | 1H-NMR (400 MHz, 6d-DMSO) δ ppm 8.59 (d, 1H, J = 1.6 Hz), 8.30-8.25 (m, 2H), 8.00-7.90 (m, 2H), 7.79 (dd, 1H, J = 8.4, 2.0 Hz), 7.17 (d, 1H, J = 1.6 Hz), 6.30 (d, 1H, J = 8.4 Hz), 5.99 (d, 1H, J = 5.6 Hz), 3.84-3.70 (m, 1H), 3.56-3.50 (m, 4H), 3.48-3.40 (m, 4H), 3.26-3.16 (m, 1H), 3.14-3.04 (m, 2H), 3.02-2.86 (m, 2H), 2.72-2.60 (m, 1H), 2.18-1.94 (m, 2H), 1.80-1.64 (m, 1H), 1.62-1.50 (m, 1H), 1.13 (t, 3H, J = 6.8 Hz), 1.07 (d, 6H, J = 6.8 Hz). |
| 799 | 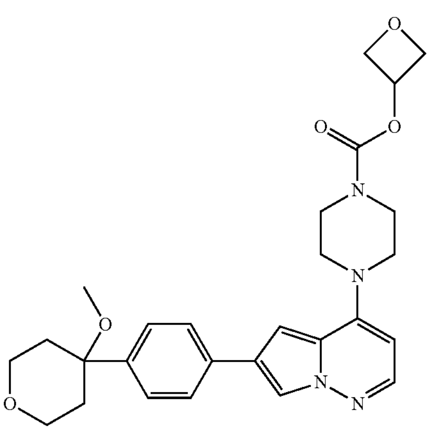 [SMILES: COC1(c2ccc(-c3cc4c(N5CCN(C(=O)OC6COC6)CC5)ccnn4c3)cc2)CCOCC1] | 493 | 1H-NMR (400 MHz, 6d-DMSO) δ ppm 8.21 (s, 1H), 7.93 (d, 1H, J = 5.2 Hz), 7.83 (d, 2H, J = 8.4 Hz), 7.21 (d, 2H, J = 8.4 Hz), 7.06 (s, 1H), 6.01 (d, 1H, J = 5.6 Hz), 5.35 (quintet, 1H, J = 5.2 Hz), 4.80 (t, 2H, J = 6.8 Hz), 4.55-4.52 (m, 2H), 3.75-3.70 (m, 4H), 3.70-3.65 (m, 2H), 3.65-3.60 (m, 2H), 3.50-3.49 (m, 4H), 2.91 (s, 3H), 1.99-1.94 (m, 4H). |

TABLE 1-continued

| # | Structure | LCMS (M + 1) | NMR |
|---|---|---|---|
| 800 | 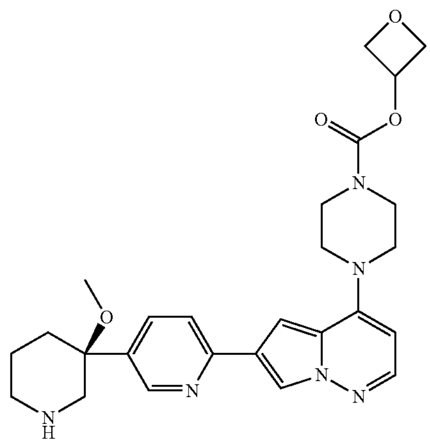 [SMILES: CO[C@]1(c2ccc(-c3cc4c(N5CCN(C(=O)OC6COC6)CC5)ccnn4c3)nc2)CCCNC1] | 493 | 1H-NMR (500 MHz, 6d-DMSO) δ ppm 8.61 (d, 1H, J = 1.5 Hz), 8.32 (d, 1H, J = 2.0 Hz), 7.99-7.95 (m, 2H), 7.81 (d, 1H, J = 9.5 Hz), 7.20 (d, 1H, J = 1.5 Hz), 6.02 (d, 1H, J = 4.5 Hz), 5.34 (quintet, 1H, J = 5.5 Hz), 4.80 (t, 2H, J = 7.5 Hz), 4.53 (dd, 2H, J = 7.5, 5.5 Hz), 3.71-3.65 (m, 2H), 3.65-3.60 (m, 2H), 3.53-3.51 (m, 4H), 3.34-3.31 (m, 1H), 3.13-3.06 (m, 2H), 3.01 (s, 3H), 2.82-2.77 (m, 1H), 2.24-2.21 (m, 1H), 2.11-2.06 (m, 1H), 1.83-1.80 (m, 1H), 1.72-1.69 (m, 1H). |
| 801 | 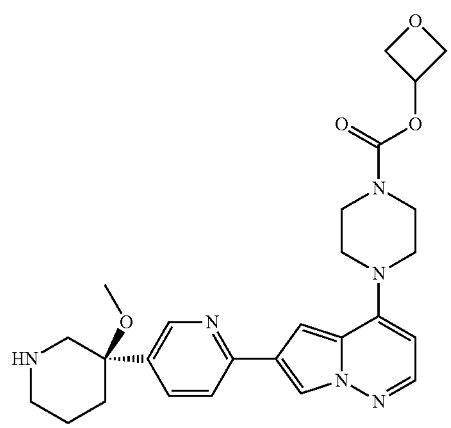 [SMILES: CO[C@@]1(c2ccc(-c3cc4c(N5CCN(C(=O)OC6COC6)CC5)ccnn4c3)nc2)CCCNC1] | 493 | 1H-NMR (400 MHz, 6d-DMSO) δ ppm 8.58 (d, 1H, J = 2.0 Hz), 8.28 (d, 1H, J = 1.2 Hz), 7.94 (d, 1H, J = 5.6 Hz), 7.92 (d, 1H, J = 8.8 Hz), 7.77 (dd, 1H, J = 8.4, 2.4 Hz), 7.17 (d, 1H, J = 2.0 Hz), 6.00 (d, 1H, J = 5.6 Hz), 5.40-5.25 (m, 1H), 4.78 (t, 2H, J = 7.2 Hz), 4.55-4.50 (m, 2H), 3.80-3.72 (m, 2H), 3.72-3.65 (m, 2H), 3.54-3.46 (m, 4H), 2.97 (s, 3H), 2.96-2.91 (m, 1H), 2.90-2.82 (m, 1H), 2.80-2.72 (m, 1H), 2.56-2.51 (m, 1H), 2.15-2.05 (m, 1H), 2.05-1.95 (m, 1H), 1.70-1.55 (m, 1H), 1.50-1.35 (m, 1H). |
| 802 | 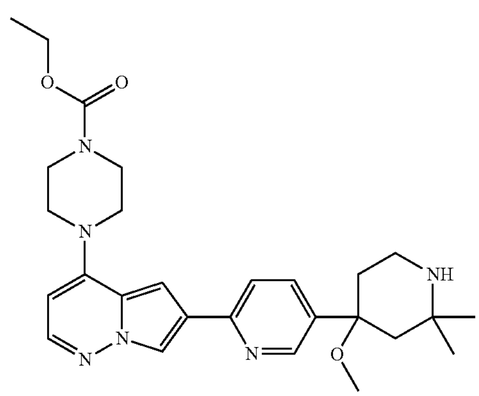 [SMILES: CCOC(=O)N1CCN(c2ccnn3cc(-c4ccc(C5(OC)CCNC(C)(C)C5)cn4)cc23)CC1] | 494 | 1H NMR (400 MHz, Methanol-d4) δ 8.59-8.47 (m, 1H), 8.20 (d, J = 1.8 Hz, 1H), 8.00-7.77 (m, 3H), 7.16 (d, J = 1.8 Hz, 1H), 6.02 (d, J = 5.5 Hz, 1H), 4.18 (q, J = 7.1 Hz, 2H), 3.73 (d, J = 5.4 Hz, 4H), 3.54 (dd, J = 6.6, 3.9 Hz, 4H), 3.28-3.14 (m, 1H), 3.00 (s, 3H), 2.94-2.82 (m, 1H), 2.25-2.05 (m, 2H), 1.91 (td, J = 0 13.1, 4.3 Hz, 1H), 1.66 (d, J = 14.2 Hz, 1H), 1.40 (s, 3H), 1.29 (t, J = 7.1 Hz, 4H), 1.14 (s, 3H) |

TABLE 1-continued

| # | Structure | LCMS (M + 1) | NMR |
|---|---|---|---|
| 803 | 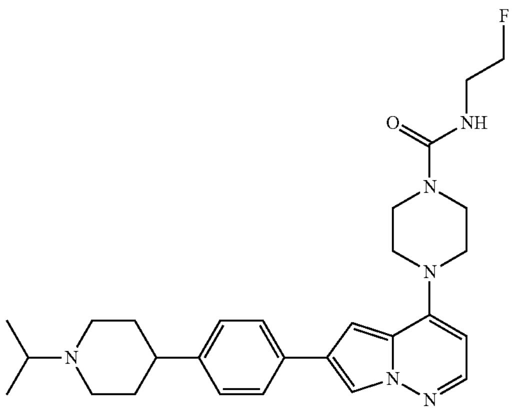 [SMILES: CC(C)N1CCC(c2ccc(-c3cc4c(N5CCN(C(=O)NCCF)CC5)ccnn4c3)cc2)CC1] | 494 | 1H NMR (400 MHz, Methanol-d4) δ 8.37-8.28 (m, 1H), 7.95 (dd, J = 3.6, 1.8 Hz, 1H), 7.85 (dd, J = 5.4, 3.6 Hz, 1H), 7.76-7.62 (m, 2H), 7.51-7.33 (m, 1H), 7.28 (d, J = 7.9 Hz, 2H), 6.90 (dd, J = 3.9, 1.8 Hz, 1H), 6.88-6.68 (m, 1H), 6.10-5.98 (m, 1H), 3.97 (s, 1H), 3.80 (d, J = 18.0 Hz, 1H), 3.62 (s, 4H), 3.14-3.04 (m, 3H), 2.88 (d, J = 15.9 Hz, 1H), 2.60 (t, J = 12.2 Hz, 1H), 2.43 (d, J = 12.3 Hz, 2H), 2.00-1.73 (m, 5H), 1.28 (s, 1H), 1.16 (d, J = 6.5 Hz, 6H). |
| 804 | 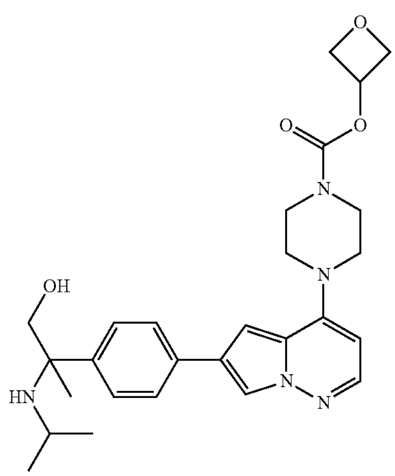 [SMILES: CC(C)NC(C)(CO)c1ccc(-c2cc3c(N4CCN(C(=O)OC5COC5)CC4)ccnn3c2)cc1] | 495 | 1H NMR (400 MHz, Methanol-d4) δ 7.97 (d, J = 1.8 Hz, 1H), 7.84 (d, J = 5.4 Hz, 1H), 7.76-7.64 (m, 2H), 7.59-7.47 (m, 2H), 6.90 (d, J = 1.8 Hz, 1H), 6.01 (d, J = 5.5 Hz, 1H), 5.41 (tt, J = 6.2, 5.1 Hz, 1H), 4.90 (ddd, J = 7.4, 6.3, 1.0 Hz, 2H), 4.66 (ddd, J = 7.5, 5.1, 1.0 Hz, 2H), 3.76 (d, J = 36.2 Hz, 5H), 3.61 (d, J = 13.2 Hz, 1H), 3.57-3.48 (m, 4H), 2.82-2.73 (m, 1H), 1.57 (s, 3H), 1.03 (d, J = 6.3 Hz, 3H), 0.91 (d, J = 6.4 Hz, 3H). |
| 805 | 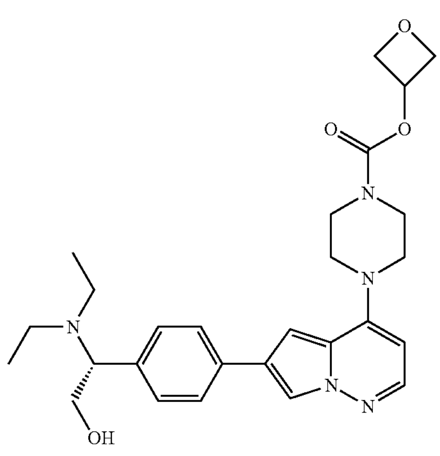 [SMILES: CCN(CC)[C@@H](CO)c1ccc(-c2cc3c(N4CCN(C(=O)OC5COC5)CC4)ccnn3c2)cc1] | 495 | |

| # | Structure | LCMS (M + 1) | NMR |
|---|---|---|---|
| 806 | 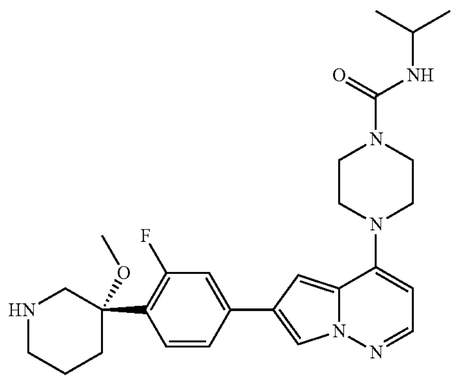 [SMILES: CO[C@]1(c2ccc(-c3cc4c(N5CCN(C(=O)NC(C)C)CC5)ccnn4c3)cc2F)CCCNC1] | 495 | 1H-NMR (400 MHz, 6d-DMSO) δ ppm 8.30-8.28 (m, 2H), 7.92 (d, 1H, J = 5.6 Hz), 7.72 (s, 1H), 7.69-7.67 (m, 1H), 7.39 (t, 1H, J = 7.2 Hz), 7.12 (d, 1H, J = 2.0 Hz), 6.32 (d, 1H, J = 7.5 Hz), 5.99 (d, 1H, J = 5.6 Hz), 3.80-3.76 (m, 1H), 3.54-3.52 (m, 4H), 3.46-3.44 (m, 4H), 3.26-3.22 (m, 1H), 3.05 (s, 3H), 3.05-2.96 (m, 2H), 2.68-2.64 (m, 1H), 2.24-2.20 (m, 1H), 2.09-2.04 (m, 1H), 1.77-1.75 (m, 1H), 1.59-1.56 (m, 1H), 1.09-1.03 (d, 6H, J = 6.8 Hz). |
| 807 | 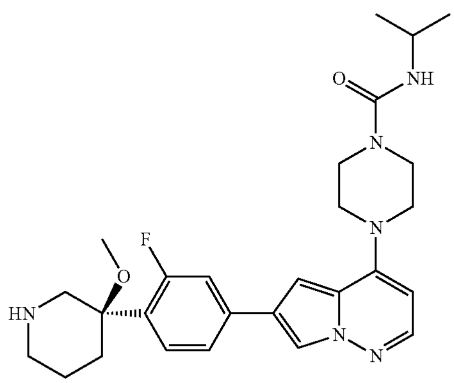 [SMILES: CO[C@@]1(c2ccc(-c3cc4c(N5CCN(C(=O)NC(C)C)CC5)ccnn4c3)cc2F)CCCNC1] | 495 | 1H-NMR (500 MHz, 6d-DMSO) δ ppm 8.30-8.28 (m, 2H), 7.92 (d, 1H, J = 5.5 Hz), 7.72 (s, 1H), 7.68 (d, 1H, J = 7.0 Hz), 7.38 (t, 1H, J = 7.5 Hz), 7.12 (d, 1H, J = 1.5 Hz), 6.32 (d, 1H, J = 7.5 Hz), 5.99 (d, 1H, J = 5.5 Hz), 3.80-3.76 (m, 1H), 3.54-3.52 (m, 4H), 3.46-3.44 (m, 4H), 3.26-3.22 (m, 2H), 3.05 (s, 3H), 3.05-2.96 (m, 2H), 2.68-2.64 (m, 1H), 2.24-2.20 (m, 1H), 2.09-2.04 (m, 1H), 1.77-1.75 (m, 1H), 1.59-1.56 (m, 1H), 1.09-1.03 (d, 6H, J = 6.5 Hz). |
| 808 | 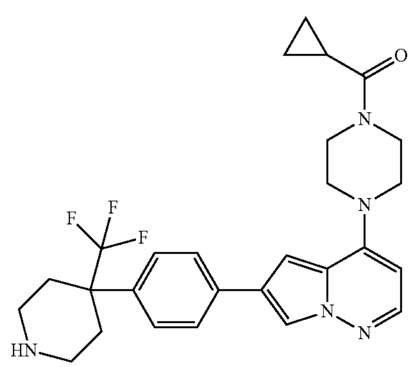 [SMILES: O=C(C1CC1)N1CCN(c2ccnn3cc(-c4ccc(C5(C(F)(F)F)CCNCC5)cc4)cc23)CC1] | 498 | 1H-NMR (400 MHz, 6d-DMSO) δ ppm 8.23 (d, 1H, J = 1.6 Hz), 7.92 (d, 1H, J = 5.6 Hz), 7.85 (d, 2H, J = 8.4 Hz), 7.53 (d, 2H, J = 8.4 Hz), 7.09 (d, 1H, J = 2.0 Hz), 6.00 (d, 1H, J = 5.6 Hz), 4.00-3.82 (m, 2H), 3.82-3.65 (m, 2H), 3.57-3.52 (m, 2H), 3.52-3.47 (m, 2H), 2.87-2.80 (m, 2H), 2.50-2.25 (m, 4H), 2.10-1.95 (m, 1H), 1.95-1.75 (m, 2H), 0.82-.074 (m, 4H). |
| 809 | 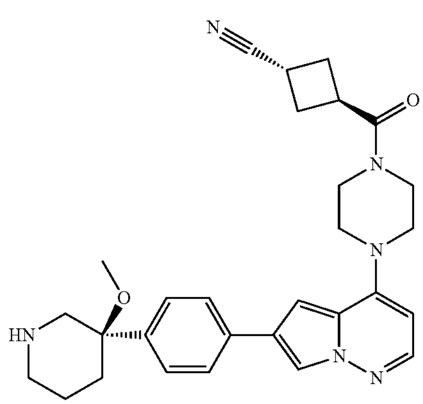 [SMILES: CO[C@@]1(c2ccc(-c3cc4c(N5CCN(C(=O)[C@H]6C[C@H](C#N)C6)CC5)ccnn4c3)cc2)CCCNC1] | 499 | 1H-NMR (400 MHz, 6d-DMSO) δ ppm 8.31 (s, 1H), 8.21 (d, 1H, J = 1.6 Hz), 7.91 (d, 1H, J = 5.6 Hz), 7.83 (d, 2H, J = 8.0 Hz), 7.41 (d, 2H, J = 8.4 Hz), 7.05 (d, 1H, J = 1.6 Hz), 5.97 (d, 1H, J = 5.6 Hz), 3.70-3.62 (m, 3H), 3.54-3.53 (m, 2H), 3.47-3.45 (m, 4H), 3.32-3.25 (m, 1H), 3.16-3.13 (m, 2H), 3.05-3.02 (m, 1H), 2.97 (s, 3H), 2.91-2.87 (m, 1H), 2.73-2.58 (m, 3H), 2.49-2.45 (m, 2H), 2.17-2.14 (m, 1H), 2.05-1.97 (m, 2H), 1.81-1.70 (m, 1H), 1.63-1.59 (m, 1H). |

TABLE 1-continued

| # | Structure | LCMS (M + 1) | NMR |
|---|---|---|---|
| 810 | 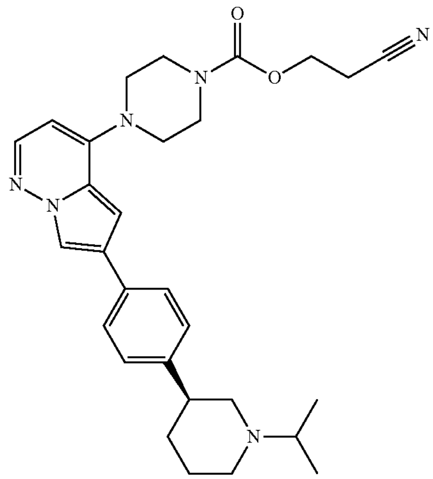 [SMILES: CC(C)N1CCC[C@@H](c2ccc(-c3cc4c(N5CCN(C(=O)OCCC#N)CC5)ccnn4c3)cc2)C1] | 501 | 1H-NMR (400 MHz, 6d-DMSO) δ ppm 8.14 (d, 1H, J = 1.2 Hz), 7.89 (d, 1H, J = 5.2 Hz), 7.72 (d, 2H, J = 8.4 Hz), 7.26 (d, 2H, J = 8.4 Hz), 7.01 (d, 1H, J = 1.6 Hz), 5.98 (d, 1H, J = 5.2 Hz), 4.22 (t, 2H, J = 6.0 Hz), 3.74-3.56 (m, 4H), 3.52-3.42 (m, 4H), 2.91 (t, 2H, J = 6.0 Hz), 2.82-2.77 (m, 2H), 2.74-2.65 (m, 2H), 2.22-2.08 (m, 2H), 1.86-1.66 (m, 2H), 1.62-1.38 (m, 2H), 1.00-0.90 (m, 6H). |
| 811 | 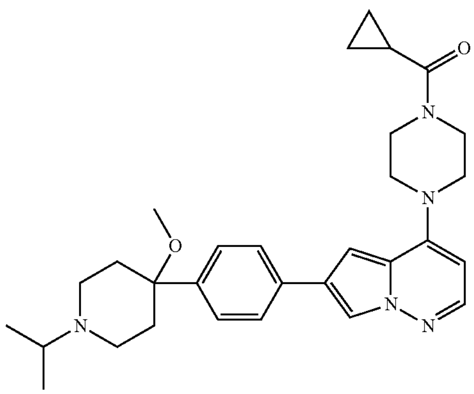 [SMILES: COC1(c2ccc(-c3cc4c(N5CCN(C(=O)C6CC6)CC5)ccnn4c3)cc2)CCN(C(C)C)CC1] | 503 | 1H NMR (400 MHz, DMSO-d6) δ 8.25 (s, 1H), 8.13 (d, J = 1.8 Hz, 1H), 7.88 (d, J = 5.4 Hz, 1H), 7.71 (d, J = 8.4 Hz, 2H), 7.34 (d, J = 8.5 Hz, 2H), 7.00 (d, J = 1.9 Hz, 1H), 5.96 (d, J = 5.5 Hz, 1H), 4.51 (s, 1H), 3.91 (s, 2H), 3.69 (s, 2H), 3.50 (d, J = 25.3 Hz, 4H), 2.59 (t, J = 6.5 Hz, 2H), 2.32-2.18 (m, 2H), 2.08-1.95 (m, 3H), 1.84 (t, J = 11.2 Hz, 2H), 0.89 (d, J = 6.5 Hz, 6H), 0.83-0.66 (m, 4H). |
| 812 | 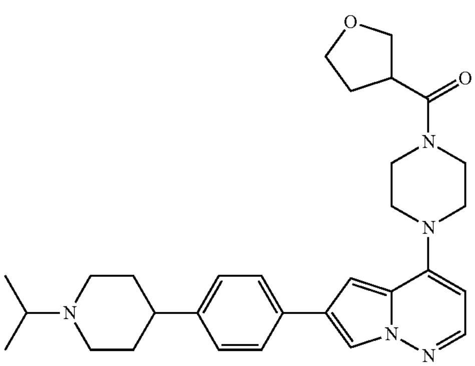 [SMILES: CC(C)N1CCC(c2ccc(-c3cc4c(N5CCN(C(=O)C6CCOC6)CC5)ccnn4c3)cc2)CC1] | 503 | 1H NMR (400 MHz, Methanol-d4) δ 7.94 (d, J = 1.8 Hz, 1H), 7.83 (d, J = 5.4 Hz, 1H), 7.72-7.60 (m, 2H), 7.31-7.22 (m, 2H), 6.89 (d, J = 1.8 Hz, 1H), 5.99 (d, J = 5.5 Hz, 1H), 5.48 (s, 0H), 4.00 (t, J = 8.2 Hz, 1H), 3.91 (dd, J = 8.3, 6.0 Hz, 2H), 3.88-3.80 (m, 5H), 3.57 (t, J = 5.1 Hz, 2H), 3.55-3.46 (m, 3H), 3.17-3.02 (m, 2H), 2.86 (p, J = 6.6 Hz, 1H), 2.58 (ddt, J = 11.8, 7.9, 4.0 Hz, 1H), 2.44 (dd, J = 13.0, 10.3 Hz, 2H), 2.2.08 (m, 2H), 1.91 (d, J = 12.9 Hz, 2H), 1.82 (qd, J = 12.4, 3.7 Hz, 2H), 1.15 (d, J = 6.6 Hz, 6H). |
| 813 | 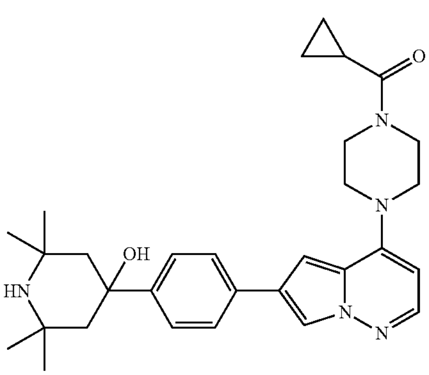 [SMILES: CC1(C)CC(O)(c2ccc(-c3cc4c(N5CCN(C(=O)C6CC6)CC5)ccnn4c3)cc2)CC(C)(C)N1] | 503 | |

| # | Structure | LCMS (M + 1) | NMR |
|---|---|---|---|
| 814 | 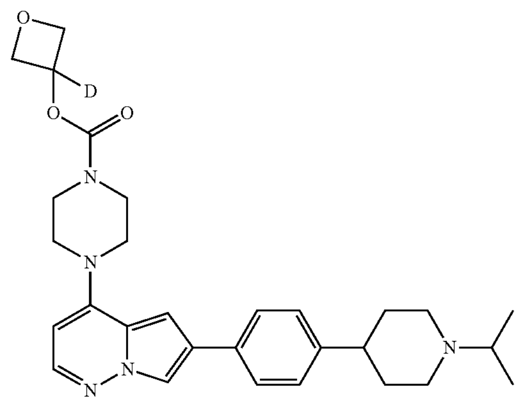 [SMILES: [2H]C1(OC(=O)N2CCN(c3ccnn4cc(-c5ccc(C6CCN(C(C)C)CC6)cc5)cc34)CC2)COC1] | 506 | 1H NMR (400 MHz, Methanol-d4) δ 7.95 (d, J = 1.8 Hz, 1H), 7.85 (d, J = 5.5 Hz, 1H), 7.68 (d, J = 8.1 Hz, 2H), 7.29 (d, J = 8.1 Hz, 2H), 6.88 (d, J = 1.8 Hz, 1H), 6.01 (d, J = 5.5 Hz, 1H), 4.89 (d, J = 7.7 Hz, 2H), 4.65 (d, J = 7.8 Hz, 2H), 3.80 (s, 2H), 3.58-3.49 (m, 4H), 2.76 (s, 5H), 2.03 (s, 2H), 1.91 (d, J = 12.2 Hz, 1H), 1.27 (d, J = 6.7 Hz, 6H). |
| 815 | 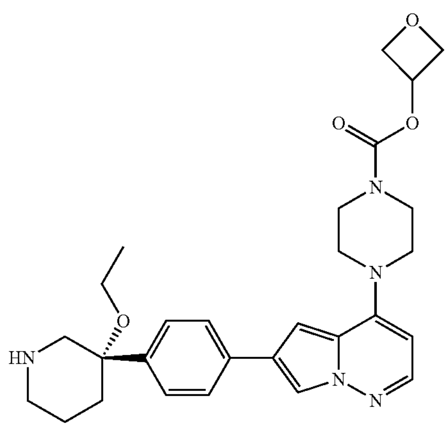 [SMILES: CCO[C@]1(c2ccc(-c3cc4c(N5CCN(C(=O)OC6COC6)CC5)ccnn4c3)cc2)CCCNC1] | 506 | 1H-NMR (400 MHz, 6d-DMSO) δ ppm 8.18 (d, 1H, J = 1.2 Hz), 7.91 (d, 1H, J = 5.6 Hz), 7.79 (d, 2H, J = 8.4 Hz), 7.41 (d, 2H, J = 8.4 Hz), 7.03 (s, 1H), 6.00 (d, 1H, J = 5.6 Hz), 5.33 (quintet, 1H, J = 5.6 Hz), 4.79 (t, 2H, J = 7.2 Hz), 4.53 (dd, 2H, J = 7.2, 5.6 Hz), 3.72-3.66 (m, 2H), 3.66-3.60 (m, 2H), 3.55-3.48 (m, 4H), 3.18-3.16 (m, 1H), 3.08-3.04 (m, 1H), 2.90-2.87 (m, 2H), 2.69-2.65 (m, 1H), 2.51-2.50 (m, 1H), 2.06-2.05 (m, 1H), 1.96-1.95 (m, 1H), 1.55-1.52 (m, 1H), 1.46-1.45 (m, 1H), 1.11 (t, 3H, J = 6.8 Hz). |
| 816 | 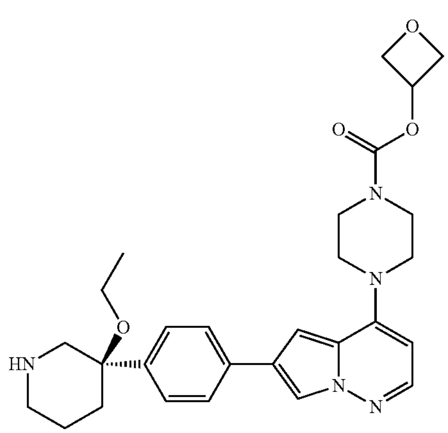 [SMILES: CCO[C@@]1(c2ccc(-c3cc4c(N5CCN(C(=O)OC6COC6)CC5)ccnn4c3)cc2)CCCNC1] | 506 | 1H-NMR (400 MHz, 6d-DMSO) δ ppm 8.18 (d, 1H, J = 1.2 Hz), 7.91 (d, 1H, J = 5.6 Hz), 7.79 (d, 2H, J = 8.4 Hz), 7.41 (d, 2H, J = 8.4 Hz), 7.03 (d, 1H, J = 1.2 Hz), 5.99 (d, 1H, J = 5.6 Hz), 5.34 (quintet, 1H, J = 5.6 Hz), 4.79 (t, 2H, J = 7.2 Hz), 4.53 (dd, 1H, J = 7.2, 5.6 Hz), 3.72-3.65 (m, 2H), 3.65-3.57 (m, 2H), 3.54-3.44 (m, 4H), 3.20-3.15 (m, 1H), 3.08-3.03 (m, 1H), 2.95-2.88 (m, 2H), 2.73-2.68 (m, 1H), 2.54-2.50 (m, 1H), 2.08-2.04 (m, 1H), 2.00-1.95 (m, 1H), 1.70-1.62 (m, 1H), 1.50-1.44 (m, 1H), 1.11 (t, 3H, J = 7.2 Hz). |

TABLE 1-continued

| # | Structure | LCMS (M + 1) | NMR |
|---|---|---|---|
| 817 | 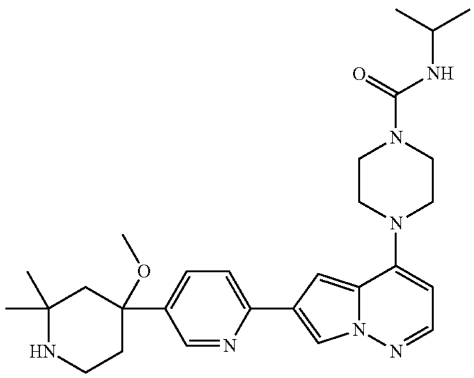 [SMILES: COC1(c2ccc(-c3cc4c(N5CCN(C(=O)NC(C)C)CC5)ccnn4c3)nc2)CCNC(C)(C)C1] | 506 | 1H NMR (400 MHz, Methanol-d4) δ 8.54 (t, J = 1.6 Hz, 1H), 8.20 (d, J = 1.8 Hz, 1H), 7.88 (dd, J = 3.5, 1.8 Hz, 3H), 7.17 (d, J = 1.8 Hz, 1H), 6.00 (d, J = 5.6 Hz, 1H), 3.93 (hept, J = 6.4 Hz, 1H), 3.65 (dd, J = 6.7, 3.5 Hz, 4H), 3.60-3.48 (m, 5H), 3.01 (s, 4H), 2.31-2.11 (m, 2H), 2.06-1.87 (m, 1H), 1.73 (d, J = 14.4 Hz, 1H), 1.47 (s, 3H), 1.22 (s, 3H), 1.17 (d, J = 6.6 Hz, 6H). |
| 818 | 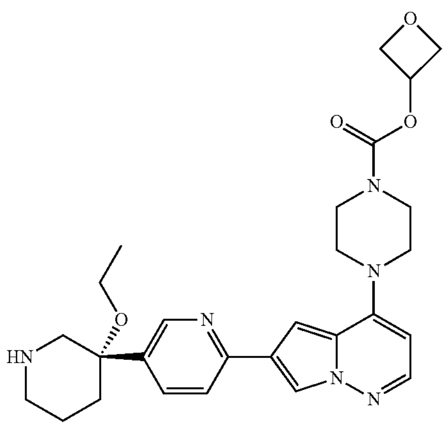 [SMILES: CCO[C@]1(c2ccc(-c3cc4c(N5CCN(C(=O)OC6COC6)CC5)ccnn4c3)nc2)CCCNC1] | 507 | 1H-NMR (400 MHz, 6d-DMSO) δ ppm 8.60 (d, 1H, J = 2.0 Hz), 8.35-8.25 (m, 2H), 8.00-7.90 (m, 2H), 7.80 (dd, 1H, J = 8.4, 2.4 Hz), 7.19 (d, 1H, J = 1.6 Hz), 6.00 (d, 1H, J = 5.6 Hz), 5.33 (quintet, 1H, J = 5.6 Hz), 4.78 (t, 2H, J = 7.2 Hz), 4.56-4.50 (m, 2H), 3.70-3.65 (m, 2H), 3.65-3.59 (m, 2H), 3.54-3.46 (m, 4H), 3.26-3.14 (m, 2H), 3.12-23.00 (m, 2H), 2.98-2.90 (m, 1H), 2.78-2.64 (m, 1H), 2.20-2.11 (m, 1H), 2.10-2.00 (m, 1H), 1.84-1.70 (m, 1H), 1.66-1.56 (m, 1H), 1.13 (t, 3H, J = 7.2 Hz). |
| 819 | 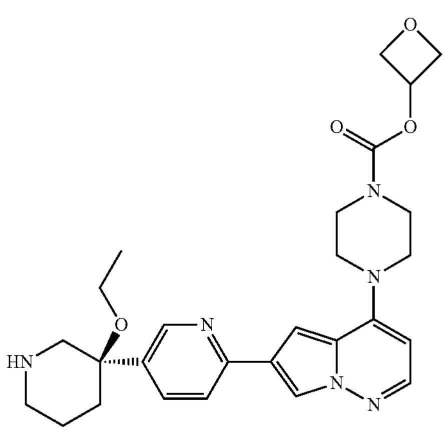 [SMILES: CCO[C@@]1(c2ccc(-c3cc4c(N5CCN(C(=O)OC6COC6)CC5)ccnn4c3)nc2)CCCNC1] | 507 | 1H-NMR (400 MHz, 6d-DMSO) δ ppm 8.60 (d, 1H, J = 1.6 Hz), 8.30 (d, 1H, J = 2.0 Hz), 7.96-7.91 (m, 2H), 7.80 (dd, 1H, J = 8.4, 2.4 Hz), 7.19 (d, 1H, J = 1.6 Hz), 6.01 (d, 1H, J = 5.6 Hz), 5.34 (quintet, 1H, J = 5.2 Hz), 4.79 (t, 2H, J = 7.2 Hz), 4.53 (dd, 2H, J = 7.2, 5.2 Hz), 3.70-3.65 (m, 2H), 3.65-3.60 (m, 2H), 3.52-3.45 (m, 4H), 3.23-3.18 (m, 1H), 3.11-3.05 (m, 2H), 2.98-2.95 (m, 1H), 2.89-2.86 (m, 1H), 2.66-2.60 (m, 1H), 2.14-2.10 (m, 2H), 1.73-1.70 (m, 1H), 1.55-1.52 (m, 1H), 1.13 (t, 3H, J = 7.2 Hz). |

TABLE 1-continued

| # | Structure | LCMS (M + 1) | NMR |
|---|---|---|---|
| 820 | 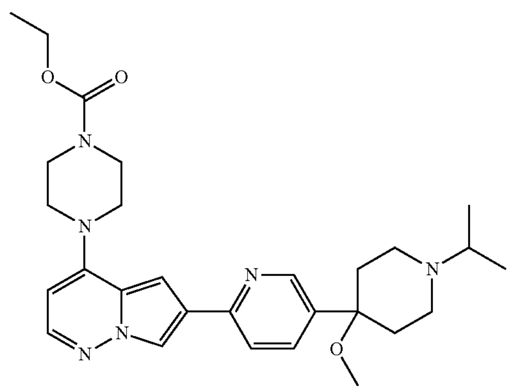 [SMILES: CCOC(=O)N1CCN(c2ccnn3cc(-c4ccc(C5(OC)CCN(C(C)C)CC5)cn4)cc23)CC1] | 507 | 1H-NMR (500 MHz, 6d-DMSO) δ ppm 8.58 (d, 1H, J = 2.0 Hz), 8.29 (d, 1H, J = 1.5 Hz), 8.22 (s, 1H), 7.96-7.91 (m, 2H), 7.78 (dd, 1H, J = 2.0 Hz, 8.0 Hz), 7.18 (d, 1H, J = 1.5 Hz), 6.00 (d, 1H, J = 6.0 Hz), 4.09 (q, 2H, J = 6.5 Hz), 3.70-3.55 (m, 4H), 3.55-3.40 (m, 4H), 2.93 (s, 3H), 2.90-2.80 (m, 1H), 2.80-2.70 (m, 2H), 2.70-2.55 (m, 2H), 2.15-2.03 (m, 2H), 2.03-1.90 (m, 2H), 1.22 (t, 3H, J = 6.5 Hz), 1.05 (d, 6H, J = 6.0 Hz). |
| 821 | 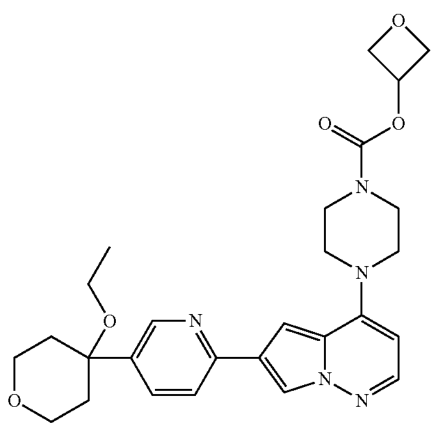 [SMILES: CCOC1(c2ccc(-c3cc4c(N5CCN(C(=O)OC6COC6)CC5)ccnn4c3)nc2)CCOCC1] | 508 | 1H-NMR (500 MHz, 6d-DMSO) δ ppm 8.60 (d, 1H, J = 1.5 Hz), 8.30 (d, 1H, J = 1.5 Hz), 7.96 (s, 1H), 7.95-7.93 (m, 1H), 7.80 (dd, 1H, J = 8.5, 2.0 Hz), 7.19 (d, 1H, J = 1.0 Hz), 6.01 (d, 1H, J = 5.5 Hz), 5.33 (quintet, 1H, J = 5.5 Hz), 4.79 (t, 2H, J = 7.0 Hz), 4.53 (dd, 2H, J = 7.0, 5.5 Hz), 3.77-3.74 (m, 2H), 3.74-3.70 (m, 4H), 3.62-3.58 (m, 2H), 3.54-3.50 (m, 2H), 3.09 (q, 2H, J = 7.0 Hz), 2.02-1.97 (m, 4H), 1.10 (t, 3H, J = 7.0 Hz). |
| 822 | 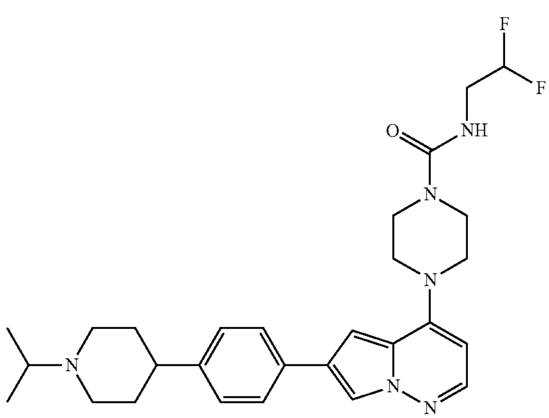 [SMILES: CC(C)N1CCC(c2ccc(-c3cc4c(N5CCN(C(=O)NCC(F)F)CC5)ccnn4c3)cc2)CC1] | 512 | 1H NMR (400 MHz, Methanol-d4) δ 8.39-8.24 (m, 2H), 8.03 (d, J = 1.8 Hz, 1H), 7.90 (d, J = 5.4 Hz, 1H), 7.79-7.67 (m, 2H), 7.52-7.41 (m, 2H), 7.41-7.23 (m, 2H), 6.96 (d, J = 1.8 Hz, 1H), 6.08 (d, J = 5.5 Hz, 1H), 3.96 (d, J = 16.6 Hz, 2H), 3.87 (d, J = 27.2 Hz, 2H), 3.70-3.57 (m, 5H), 3.57-3.37 (m, 4H), 3.15-2.97 (m, 2H), 2.95-2.75 (m, 1H), 2.13 (d, J = 13.9 Hz, 2H), 2.08-1.96 (m, 2H), 1.93 (s, 3H), 1.40-1.31 (m, 8H), 1.23-1.12 (m, 3H). |

TABLE 1-continued

| # | Structure | LCMS (M + 1) | NMR |
|---|---|---|---|
| 823 | 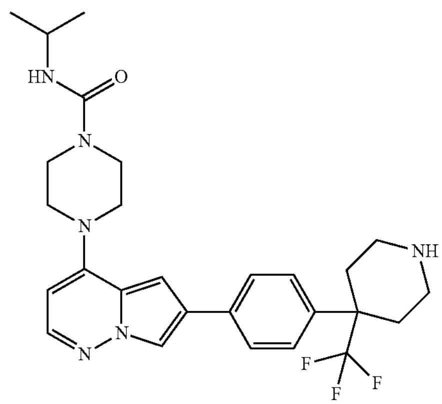 [SMILES: CC(C)NC(=O)N1CCN(c2ccnn3cc(-c4ccc(C5(C(F)(F)F)CCNCC5)cc4)cc23)CC1] | 515 | 1H-NMR (400 MHz, 6d-DMSO) δ ppm 8.23 (d, 1H, J = 2.0 Hz), 7.91 (d, 1H, J = 5.2 Hz), 7.86 (d, 2H, J = 8.4 Hz), 7.53 (d, 2H, J = 8.4 Hz), 7.06 (d, 1H, J = 1.6 Hz), 6.32 (d, 1H, J = 7.2 Hz), 6.00 (d, 1H, J = 5.6 Hz), 3.85-3.70 (m, 1H), 3.55-3.50 (m, 4H), 3.50-3.45 (m, 4H), 2.91-2.87 (m, 2H), 2.50-2.25 (m, 4H), 1.95-1.80 (m, 2H), 1.08 (d, 6H, J = 7.2 Hz). |
| 824 | 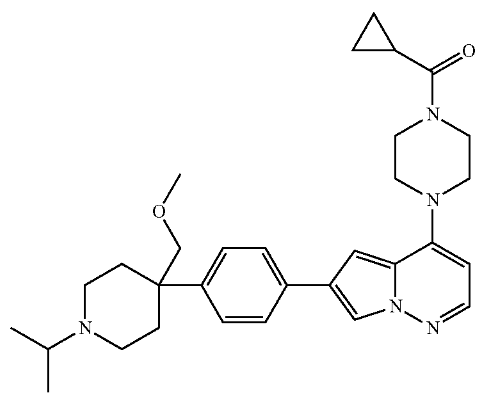 | 517 | 1H NMR (500 MHz, Methanol-d4) δ 8.01 (d, J = 1.8 Hz, 1H), 7.88 (d, J = 5.4 Hz, 1H), 7.79 (d, J = 8.0 Hz, 2H), 7.48 (d, J = 8.1 Hz, 2H), 6.96 (d, J = 1.9 Hz, 1H), 6.03 (d, J = 5.4 Hz, 1H), 5.51 (s, 0H), 4.06 (s, 2H), 3.87 (s, 2H), 3.74 (q, J = 6.6 Hz, 4H), 3.68 (d, J = 24.2 Hz, 2H), 3.58 (s, 2H), 3.23 (q, J = 7.6 Hz, 5H), 2.88 (s, 0H), 2.50 (s, 2H), 2.28 (s, 2H), 2.05 (dd, J = 8.9, 4.3 Hz, 1H), 1.25 (d, J = 6.5 Hz, 6H), 0.95 (q, J = 3.3 Hz, 2H), 0.91-0.86 (m, 2H). |
| 825 | 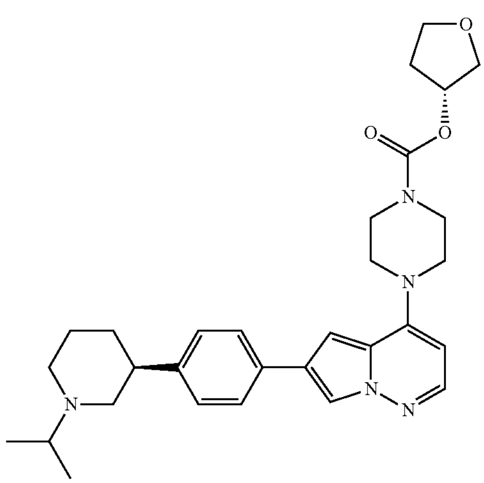 [SMILES: CC(C)N1CCC[C@@H](c2ccc(-c3cc4c(N5CCN(C(=O)O[C@@H]6CCOC6)CC5)ccnn4c3)cc2)C1] | 518 | 1H-NMR (400 MHz, 6d-DMSO) δ ppm 8.14 (d, 1H, J = 1.6 Hz), 7.89 (d, 1H, J = 5.6 Hz), 7.71 (d, 2H, J = 8.4 Hz), 7.26 (d, 2H, J = 8.4 Hz), 6.99 (d, 1H, J = 1.6 Hz), 5.97 (d, 1H, J = 5.6 Hz), 5.19-5.14 (m, 1H), 3.83-3.76 (m, 2H), 3.76-3.68 (m, 2H), 3.65-3.55 (m, 4H), 3.50-3.40 (m, 4H), 2.80-2.75 (m, 2H), 2.72-2.65 (m, 2H), 2.20-2.05 (m, 3H), 2.00-1.88 (m, 1H), 1.86-1.76 (m, 1H), 1.75-1.68 (m, 1H), 1.59-1.49 (m, 1H), 1.49-1.40 (m, 1H), 1.00-0.94 (m, 6H). |

TABLE 1-continued
| # | Structure | LCMS (M + 1) | NMR |
|---|---|---|---|
| 826 | 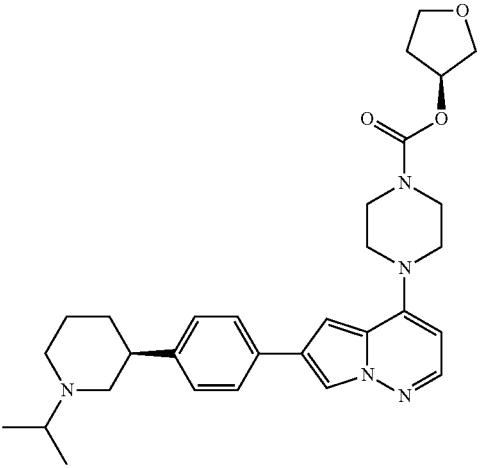 [SMILES: CC(C)N1CCC[C@@H](c2ccc(-c3cc4c(N5CCN(C(=O)O[C@H]6CCOC6)CC5)ccnn4c3)cc2)C1] | 518 | 1H-NMR (400 MHz, 6d-DMSO) δ ppm 8.14 (d, 1H, J = 1.6 Hz), 7.89 (d, 1H, J = 5.6 Hz), 7.71 (d, 2H, J = 8.4 Hz), 7.26 (d, 2H, J = 8.4 Hz), 6.99 (d, 1H, J = 1.6 Hz), 5.97 (d, 1H, J = 5.6 Hz), 5.19-5.14 (m, 1H), 3.83-3.76 (m, 2H), 3.76-3.68 (m, 2H), 3.65-3.55 (m, 4H), 3.50-3.40 (m, 4H), 2.80-2.75 (m, 2H), 2.72-2.65 (m, 2H), 2.20-2.05 (m, 3H), 2.00-1.88 (m, 1H), 1.86-1.76 (m, 1H), 1.75-1.68 (m, 1H), 1.59-1.49 (m, 1H), 1.49-1.40 (m, 1H), 1.00-0.94 (m, 6H). |
| 827 | 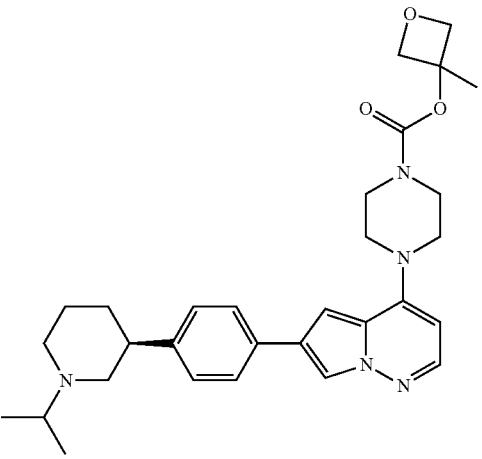 [SMILES: CC(C)N1CCC[C@@H](c2ccc(-c3cc4c(N5CCN(C(=O)OC6(C)COC6)CC5)ccnn4c3)cc2)C1] | 518 | 1H-NMR (400 MHz, 6d-DMSO) δ ppm 8.13 (d, 1H, J = 1.6 Hz), 7.90 (d, 1H, J = 5.6 Hz), 7.71 (d, 2H, J = 8.4 Hz), 7.27 (d, 2H, J = 8.4 Hz), 6.98 (d, 1H, J = 2.0 Hz), 5.98 (d, 1H, J = 5.6 Hz), 4.65 (d, 2H, J = 7.2 Hz), 4.41 (d, 2H, J = 7.2 Hz), 3.65-3.60 (m, 2H), 3.60-3.54 (m, 2H), 3.52-3.42 (m, 4H), 2.83-2.74 (m, 2H), 2.72-2.66 (m, 2H), 2.22-2.08 (m, 2H), 1.86-1.68 (m, 2H), 1.66 (s, 3H), 1.60-1.36 (m, 2H), 1.00-0.94 (m, 6H). |
| 828 | 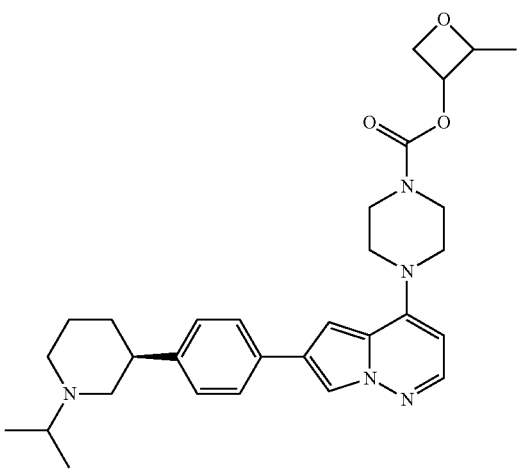 [SMILES: CC1OCC1OC(=O)N1CCN(c2ccnn3cc(-c4ccc([C@@H]5CCCN(C(C)C)C5)cc4)cc23)CC1] | 518 | 1H-NMR (500 MHz, 6d-DMSO) δ ppm 8.14 (d, 1H, J = 1.0 Hz), 7.90 (d, 1H, J = 5.5 Hz), 7.72 (d, 2H, J = 8.5 Hz), 7.27 (d, 2H, J = 8.0 Hz), 7.00-6.99 (m, 1H), 5.99 (d, 1H, J = 5.5 Hz), 5.40-5.30 (m, 0.25H), 5.05-4.95 (m, 0.25H), 4.95-4.85 (m, 0.75H), 4.74-4.61 (m, 1H), 4.60-4.55 (m, 0.75H), 4.45-4.35 (m, 1H), 3.65-3.60 (m, 2H), 3.60-3.55 (m, 2H), 3.52-3.45 (m, 4H), 2.90-2.80 (m, 2H), 2.80-2.70 (m, 2H), 2.25-2.10 (m, 2H), 1.90-1.80 (m, 1H), 1.80-1.70 (m, 1H), 1.6-1.50 (m, 1H), 1.50-1.40 (m, 1H), 1.38 (d, 2.25H, J = 6.5 Hz), 1.30 (d, 0.75H, J = 6.5 Hz), 1.05-0.90 (m, 6H). |

TABLE 1-continued

| # | Structure | LCMS (M + 1) | NMR |
|---|---|---|---|
| 829 | 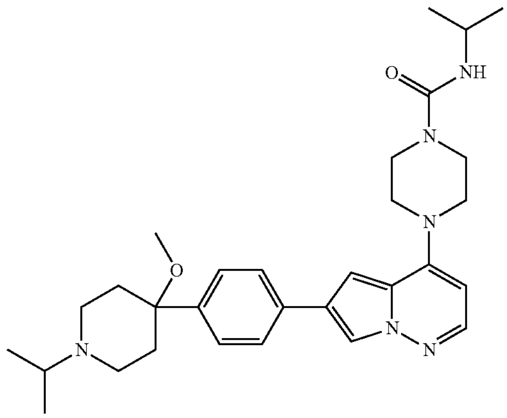 [SMILES: COC1(c2ccc(-c3cc4c(N5CCN(C(=O)NC(C)C)CC5)ccnn4c3)cc2)CCN(C(C)C)CC1] | 519 | 1H-NMR (400 MHz, 6d-DMSO) δ ppm 8.17 (s, 1H), 7.89 (d, 1H, J = 5.6 Hz), 7.79 (d, 2H, J = 7.6 Hz), 7.39 (d, 2H, J = 8.4 Hz), 7.03 (s, 1H), 6.31 (s, 1H), 5.98 (d, 1H, J = 5.2 Hz), 3.81-3.76 (m, 1H), 3.53-3.50 (m, 4H), 3.45-3.42 (m, 4H), 2.89 (s, 3H), 2.71-2.67 (m, 1H), 2.60-2.58 (m, 2H), 2.48-2.46 (m, 2H), 1.99-1.96 (m, 2H), 1.87-1.81 (m, 2H), 1.08 (d, 6H, J = 6.4 Hz), 0.99 (d, 6H, J = 6.8 Hz). |
| 830 | 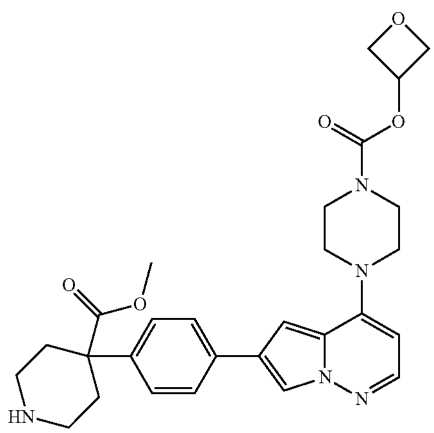 [SMILES: COC(=O)C1(c2ccc(-c3cc4c(N5CCN(C(=O)OC6COC6)CC5)ccnn4c3)cc2)CCNCC1] | 521 | 1H NMR (400 MHz, DMSO-d6) δ 8.32 (s, 1H), 8.19 (d, J = 1.8 Hz, 1H), 7.91 (d, J = 5.4 Hz, 1H), 7.80 (dd, J = 8.0, 5.9 Hz, 2H), 7.36 (d, J = 8.5 Hz, 2H), 7.03 (d, J = 1.9 Hz, 1H), 5.99 (d, J = 5.6 Hz, 1H), 4.88-4.76 (m, 1H), 3.90-3.74 (m, 2H), 3.60-3.53 (m, 2H), 3.46 (t, J = 5.2 Hz, 5H), 3.11 (d, J = 12.6 Hz, 2H), 2.94 (s, 0H), 2.79 (t, J = 11.9 Hz, 2H), 1.99 (t, J = 12.3 Hz, 2H). |
| 831 | 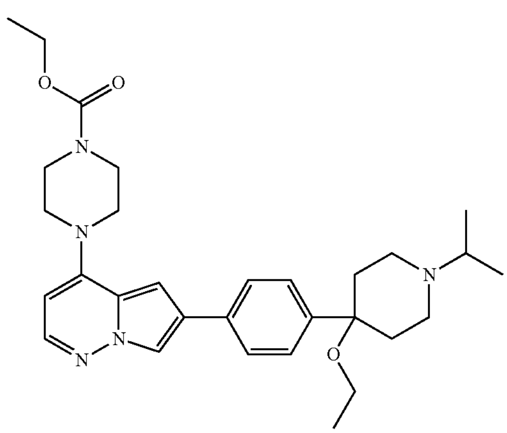 | 520 | 1H-NMR (500 MHz, 6d-DMSO) δ ppm 8.30 (s, 1H), 8.18 (s, 1H), 7.91 (d, 1H, J = 5.0 Hz), 7.89 (d, 2H, J = 8.5 Hz), 7.40 (d, 2H, J = 8.5 Hz), 7.03 (s, 1H), 5.98 (d, 1H, J = 5.0 Hz), 4.09 (q, 2H, J = 7.0 Hz), 4.65-4.55 (m, 4H), 4.51-4.41 (m, 4H), 3.06 (q, 2H, J = 6.5 Hz), 2.82-2.77 (m, 1H), 2.72-2.68 (m, 2H), 2.63-2.56 (m, 2H), 2.03-1.98 (m, 2H), 1.93-1.88 (m, 2H), 1.22 (t, 3H, J = 6.5 Hz), 1.07 (t, 3H, J = 7.0 Hz), 1.03 (d, 6H, J = 7.0 Hz). |

TABLE 1-continued

| # | Structure | LCMS (M + 1) | NMR |
|---|---|---|---|
| 832 | 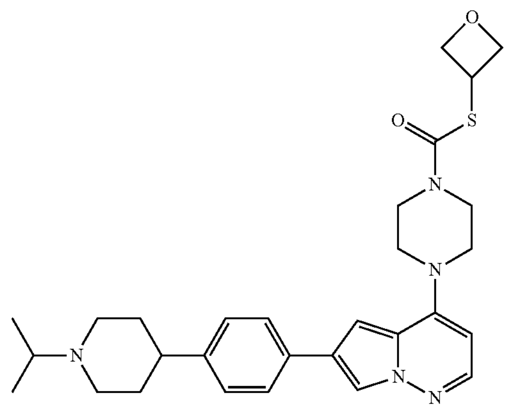 [SMILES: CC(C)N1CCC(c2ccc(-c3cc4c(N5CCN(C(=O)SC6COC6)CC5)ccnn4c3)cc2)CC1] | 521 | 1H NMR (400 MHz, Methanol-d4) δ 7.98 (d, J = 1.8 Hz, 1H), 7.86 (d, J = 5.4 Hz, 1H), 7.76-7.62 (m, 2H), 7.34-7.22 (m, 2H), 6.91 (d, J = 1.8 Hz, 1H), 6.01 (d, J = 5.4 Hz, 1H), 5.14-5.01 (m, 2H), 4.66-4.54 (m, 3H), 3.78 (s, 4H), 3.60-3.47 (m, 4H), 3.34 (s, 4H), 3.10-2.99 (m, 2H), 2.80 (h, J = 6.5 Hz, 1H), 2.62 (p, J = 1.9 Hz, 1H), 2.56 (dq, J = 11.9, 4.0 Hz, 1H), 2.38 (td, J = 11.8, 2.7 Hz, 2H), 1.96-1.68 (m, 4H), 1.14 (d, J = 6.6 Hz, 6H). |
| 833 | 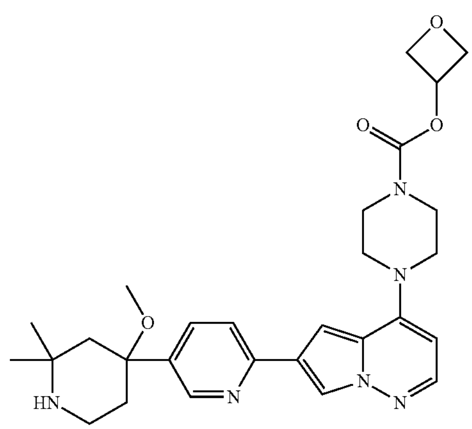 [SMILES: COC1(c2ccc(-c3cc4c(N5CCN(C(=O)OC6COC6)CC5)ccnn4c3)nc2)CCNC(C)(C)C1] | 522 | 1H NMR (400 MHz, Methanol-d4) δ 8.54 (t, J = 1.5 Hz, 1H), 8.20 (d, J = 1.8 Hz, 1H), 8.01-7.79 (m, 3H), 7.16 (d, J = 1.8 Hz, 1H), 6.02 (d, J = 5.5 Hz, 1H), 5.42 (tt, J = 6.2, 5.1 Hz, 1H), 4.90 (ddd, J = 7.3, 6.2, 0.9 Hz, 2H), 4.66 (ddd, J = 7.5, 5.1, 0.9 Hz, 2H), 3.77 (d, J = 35.0 Hz, 5H), 3.56 (t, J = 5.2 Hz, 4H), 3.48 (q, J = 7.0 Hz, 1H), 3.26-3.07 (m, 1H), 3.00 (s, 3H), 2.87 (dt, J = 13.2, 3.6 Hz, 1H), 2.22-2.00 (m, 3H), 1.96-1.78 (m, 1H), 1.65 (d, J = 14.2 Hz, 1H), 1.40 (s, 3H), 1.20-1.11 (m, 4H). |
| 834 | 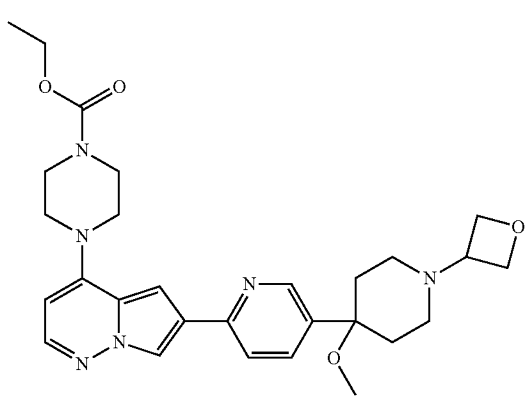 [SMILES: CCOC(=O)N1CCN(c2ccnn3cc(-c4ccc(C5(OC)CCN(C6COC6)CC5)cn4)cc23)CC1] | 521 | 1H-NMR (400 MHz, 6d-DMSO) δ ppm 8.58 (d, 1H, J = 2.0 Hz), 8.28 (d, 1H, J = 1.6 Hz), 7.96-7.90 (m, 2H), 7.78 (dd, 1H, J = 8.4, 2.4 Hz), 7.17 (d, 1H, J = 2.0 Hz), 5.99 (d, 1H, J = 5.6 Hz), 4.60-4.50 (m, 2H), 4.48-4.40 (m, 2H), 4.08 (q, 2H, J = 7.2 Hz), 3.66-3.56 (m, 4H), 3.52-3.38 (m, 5H), 2.91 (s, 3H), 2.60-2.52 (m, 2H), 2.20-2.10 (m, 2H), 2.05-1.85 (m, 4H), 1.21 (t, 3H, J = 6.8 Hz). |

TABLE 1-continued

| # | Structure | LCMS (M + 1) | NMR |
|---|---|---|---|
| 835 | 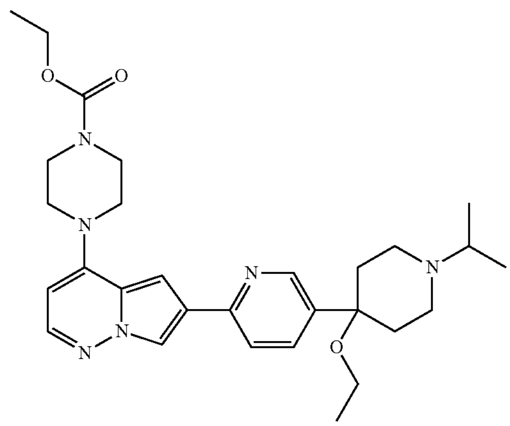 [SMILES: CCOC(=O)N1CCN(c2ccnn3cc(-c4ccc(C5(OCC)CCN(C(C)C)CC5)cn4)cc23)CC1] | 521 | 1H-NMR (500 MHz, 6d-DMSO) δ ppm 8.59 (d, 1H, J = 2.5 Hz), 8.28 (d, 1H, J = 2.0 Hz), 7.94-7.91 (m, 2H), 7.78 (dd, 1H, J = 8.0, 2.0 Hz), 7.17 (d, 1H, J = 1.5 Hz), 6.00 (d, 1H, J = 5.5 Hz), 4.09 (q, 2H, J = 7.0 Hz), 3.62-3.61 (m, 4H), 3.49-3.48 (m, 4H), 3.08 (q, 2H, J = 7.0 Hz), 2.69-2.68 (m, 1H), 2.62-2.60 (m, 2H), 2.53-2.51 (m, 2H), 2.01-1.98 (m, 2H), 1.91-1.89 (m, 2H), 1.22 (d, 3H, J = 7.0 Hz), 1.08 (t, 3H, J = 7.0 Hz), 1.00-0.99 (m, 6H). |
| 836 | 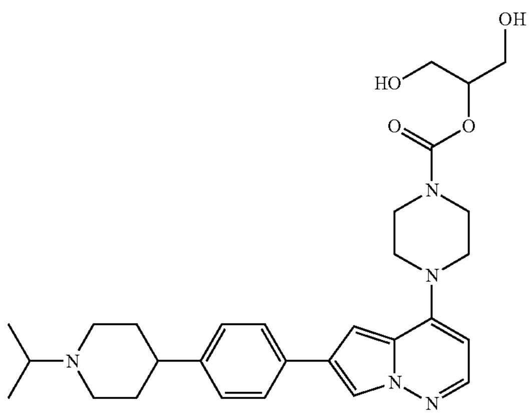 [SMILES: CC(C)N1CCC(c2ccc(-c3cc4c(N5CCN(C(=O)OC(CO)CO)CC5)ccnn4c3)cc2)CC1] | 522 | 1H-NMR (500 MHz, 4d-MeOD) δ ppm 7.95 (d, 1H, J = 1.5 Hz), 7.83 (d, 1H, J = 5.0 Hz), 7.65 (d, 2H, J = 8.5 Hz), 7.27 (d, 2H, J = 8.5 Hz), 6.86 (d, 1H, J = 1.5 Hz), 5.98 (d, 1H, J = 5.5 Hz), 4.85-4.81 (m, 0.5H), 4.26-4.13 (m, 1H), 3.90-3.86 (m, 0.5H), 3.78-3.71 (m, 6H), 3.61-3.60 (m, 1H), 3.52-3.49 (m, 4H), 3.06-3.03 (m, 2H), 2.81-2.76 (m, 1H), 2.57-2.52 (m, 1H), 2.38-2.32 (m, 2H), 1.89-1.87 (m, 2H), 1.85-1.79 (m, 2H), 1.13 (d, 6H, J = 6.5 Hz) |
| 837 | 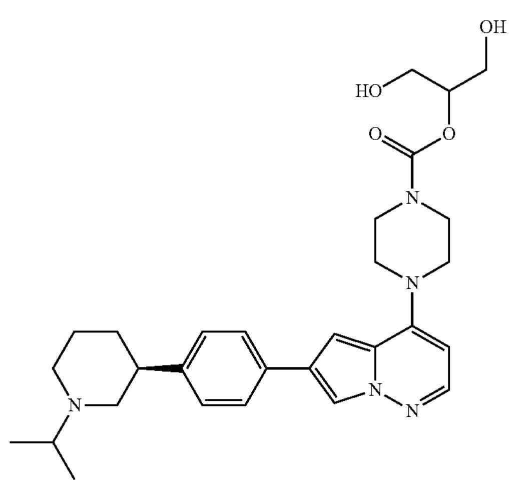 [SMILES: CC(C)N1CCC[C@@H](c2ccc(-c3cc4c(N5CCN(C(=O)OC(CO)CO)CC5)ccnn4c3)cc2)C1] | 522 | 1H-NMR (400 MHz, 6d-DMSO) δ ppm 8.27 (s, 1H), 8.16 (d, 1H, J = 2.4 Hz), 7.90 (d, 1H, J = 5.2 Hz), 7.74 (d, 2H, J = 8.4 Hz), 7.29 (d, 2H, J = 8.4 Hz), 7.00 (d, 1H, J = 1.6 Hz), 5.98 (d, 1H, J = 5.2 Hz), 4.62 (quintet, 1H, J = 5.2 Hz), 3.57-3.47 (m, 12H, mixed with H2O peak), 2.99-2.95 (m, 2H), 2.95-2.91 (m, 1H), 2.81-2.80 (m, 1H), 2.43-2.36 (m, 2H), 1.58-1.77 (m, 2H), 1.69-1.60 (m, 1H), 1.53-1.47 (m, 1H), 1.07-1.04 (m, 6H). |

TABLE 1-continued

| # | Structure | LCMS (M + 1) | NMR |
|---|---|---|---|
| 838 | 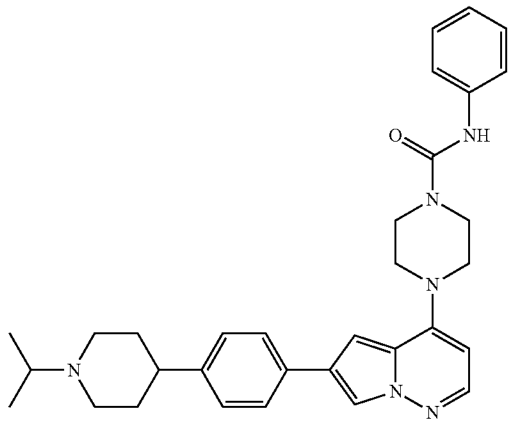 [SMILES: CC(C)N1CCC(c2ccc(-c3cc4c(N5CCN(C(=O)Nc6ccccc6)CC5)ccnn4c3)cc2)CC1] | 524 | |
| 839 | 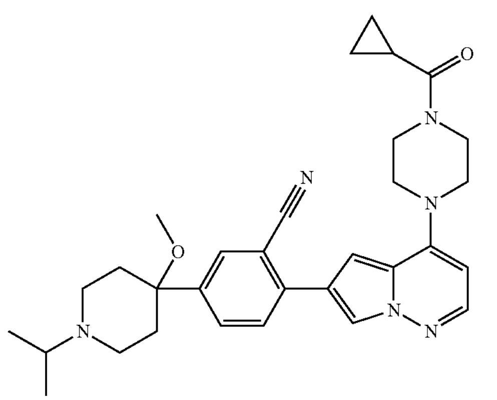 [SMILES: COC1(c2ccc(-c3cc4c(N5CCN(C(=O)C6CC6)CC5)ccnn4c3)c(C#N)c2)CCN(C(C)C)CC1] | 527 | 1H-NMR (400 MHz, 6d-DMSO) δ ppm 8.24 (d, 1H, J = 1.6 Hz), 7.99 (d, 1H, J = 5.6 Hz), 7.92 (d, 1H, J = 8.4 Hz), 7.82 (d, 1H, J = 1.6 Hz), 7.75 (dd, 1H, J = 8.4, 2.0 Hz), 7.13 (d, 1H, J = 1.6 Hz), 6.03 (d, 1H, J = 5.6 Hz), 3.93-3.91 (m, 2H), 3.72-3.70 (m, 2H), 3.59-3.58 (m, 2H), 3.53-3.51 (m, 2H), 2.91 (s, 3H), 2.72-2.68 (m, 1H), 2.63-2.59 (m, 2H), 2.48-2.44 (m, 2H), 2.04-1.99 (m, 3H), 1.91-1.85 (m, 2H), 1.01 (d, 6H, J = 6.8 Hz), 0.79-0.73 (m, 4H). |
| 840 | 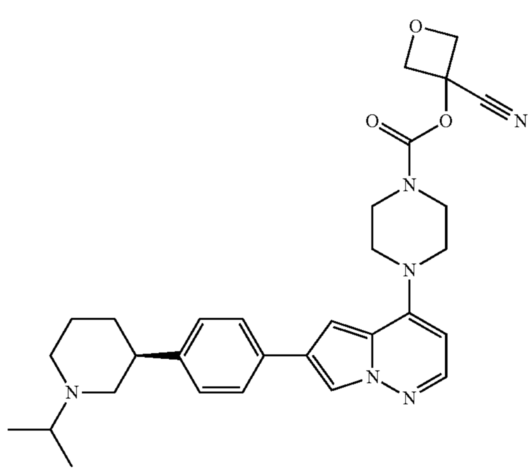 [SMILES: CC(C)N1CCC[C@@H](c2ccc(-c3cc4c(N5CCN(C(=O)OC6(C#N)COC6)CC5)ccnn4c3)cc2)C1] | 529 | 1H-NMR (400 MHz, 6d-DMSO) δ ppm 8.15 (d, 1H, J = 1.6 Hz), 7.91 (d, 1H, J = 5.6 Hz), 7.72 (d, 2H, J = 8.4 Hz), 7.27 (d, 2H, J = 8.4 Hz), 7.00 (d, 1H, J = 1.6 Hz), 6.00 (d, 1H, J = 5.2 Hz), 5.01 (d, 2H, J = 8.8 Hz), 4.82 (d, 2H, J = 8.8 Hz), 3.73-3.68 (m, 2H), 3.66-3.60 (m, 2H), 3.55-3.45 (m, 4H), 2.85-2.75 (m, 2H), 2.74-2.64 (m, 2H), 2.22-2.08 (m, 2H), 1.86-1.77 (m, 1H), 1.76-1.66 (m, 1H), 1.60-1.40 (m, 2H), 1.00-0.90 (m, 6H). |

TABLE 1-continued

| # | Structure | LCMS (M + 1) | NMR |
|---|---|---|---|
| 841 | 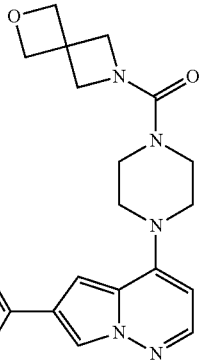 | 530 | 1H NMR (400 MHz, Methanol-d4) δ 7.93 (d, J = 1.7 Hz, 1H), 7.82 (d, J = 5.5 Hz, 1H), 7.71-7.58 (m, 2H), 7.35-7.21 (m, 2H), 6.87 (d, J = 1.8 Hz, 1H), 5.97 (d, J = 5.5 Hz, 1H), 4.79 (s, 4H), 4.22 (s, 4H), 3.63-3.56 (m, 4H), 3.52 (dd, J = 6.7, 3.5 Hz, 4H), 3.16-3.07 (m, 2H), 2.89 (d, J = 10.8 Hz, 1H), 2.60 (t, J = 12.0 Hz, 1H), 2.46 (t, J = 11.6 Hz, 2H), 1.93 (d, J = 13.0 Hz, 2H), 1.88-1.74 (m, 2H), 1.16 (d, J = 6.6 Hz, 6H). |
| 842 | 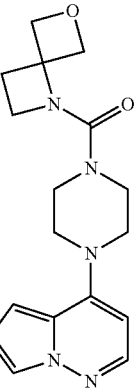 | 530 | 1H NMR (400 MHz, Methanol-d4) δ 7.93 (d, J = 1.8 Hz, 1H), 7.83 (dd, J = 5.4, 2.9 Hz, 1H), 7.65 (d, J = 8.0 Hz, 2H), 7.27 (d, J = 8.2 Hz, 2H), 6.87 (dd, J = 3.8, 1.8 Hz, 1H), 5.98 (dd, J = 10.4, 5.5 Hz, 1H), 5.46 (d, J = 6.7 Hz, 1H), 4.63 (d, J = 6.8 Hz, 1H), 4.10 (t, J = 7.3 Hz, 1H), 3.68-3.60 (m, 1H), 3.60-3.45 (m, 4H), 3.19-3.05 (m, 2H), 2.64-2.40 (m, 4H), 1.99-1.70 (m, 4H), 1.17 (d, J = 6.5 Hz, 6H). |
| 843 | 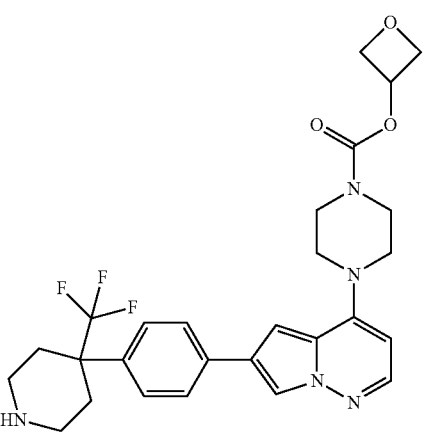 [SMILES: O=C(OC1COC1)N1CCN(c2ccnn3cc(-c4ccc(C5(C(F)(F)F)CCNCC5)cc4)cc23)CC1] | 530 | 1H-NMR (400 MHz, 6d-DMSO) δ ppm 8.24 (d, 1H, J = 1.6 Hz), 7.93 (d, 1H, J = 5.2 Hz), 7.85 (d, 2H, J = 8.4 Hz), 7.53 (d, 2H, J = 8.4 Hz), 7.06 (d, 1H, J = 1.6 Hz), 6.01 (d, 1H, J = 5.2 Hz), 5.34 (quintet, 1H, J = 5.2 Hz), 4.79 (t, 2H, J = 7.2 Hz), 4.53 (dd, 2H, J = 7.2, 5.2 Hz), 3.72-3.67 (m, 2H), 3.62-3.56 (m, 2H), 3.52-3.47 (m, 4H), 2.87-2.80 (m, 2H), 2.50-2.25 (m, 4H), 1.95-1.80 (m, 2H). |

TABLE 1-continued

| # | Structure | LCMS (M + 1) | NMR |
|---|---|---|---|
| 844 | 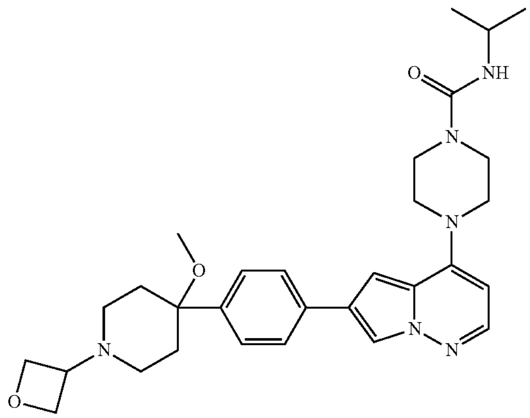 [SMILES: COC1(c2ccc(-c3cc4c(N5CCN(C(=O)NC(C)C)CC5)ccnn4c3)cc2)CCN(C2COC2)CC1] | 533 | 1H-NMR (400 MHz, 6d-DMSO) δ ppm 8.23 (s, 0.26H), 8.18 (d, 1H, J = 1.6 Hz), 7.90 (d, 1H, J = 4.2 Hz), 7.80 (d, 2H, J = 8.4 Hz), 7.40 (d, 2H, J = 8.4 Hz), 7.03 (d, 1H, J = 1.2 Hz), 6.32 (d, 1H, J = 4.0 Hz), 5.98 (d, 1H, J = 4.2 Hz), 4.56-4.53 (m, 2H), 4.46-4.43 (m, 2H), 3.80-3.76 (m, 1H), 3.53-3.51 (m, 4H), 3.47-3.43 (m, 4H), 3.43-3.33 (m, 1H), 2.89 (s, 3H), 2.53-2.49 (m, 2H), 2.18-2.13 (m, 2H), 2.01-1.92 (m, 4H), 1.08 (d, 6H, J = 6.4 Hz). |
| 845 | 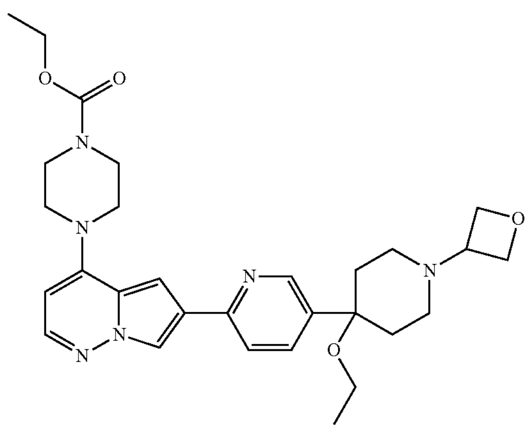 [SMILES: CCOC(=O)N1CCN(c2ccnn3cc(-c4ccc(C5(OCC)CCN(C6COC6)CC5)cn4)cc23)CC1] | 535 | 1H-NMR (400 MHz, 6d-DMSO) δ ppm 8.60 (d, 1H, J = 2.0 Hz), 8.30 (d, 1H, J = 1.6 Hz), 7.96-7.93 (m, 1H), 7.93 (d, 1H, J = 5.6 Hz), 7.81 (dd, 1H, J = 8.4, 2.4 Hz), 7.19 (d, 1H, J = 1.6 Hz), 6.00 (d, 1H, J = 5.6 Hz), 4.56 (t, 2H, J = 6.4 Hz), 4.45 (t, 2H, J = 6.4 Hz), 4.10 (q, 2H, J = 7.2 Hz), 3.68-3.58 (m, 4H), 3.52-3.43 (m, 4H)m 3.43-3.40 (m, 1H), 3.08 (q, 2H, J = 6.8 Hz), 2.60-2.52 (m, 2H), 2.24-2.12 (m, 2H), 2.06-1.86 (m, 4H), 1.23 (t, 3H, J = 7.2 Hz), 1.08 (t, 3H, J = 6.8 Hz). |
| 846 | 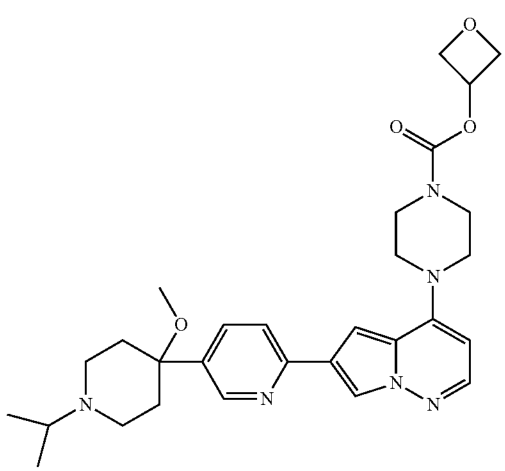 [SMILES: COC1(c2ccc(-c3cc4c(N5CCN(C(=O)OC6COC6)CC5)ccnn4c3)nc2)CCN(C(C)C)CC1] | 535 | 1H-NMR (500 MHz, 6d-DMSO) δ ppm 8.58 (d, 1H, J = 2.0 Hz), 8.31-8.26 (m, 2H), 7.96-7.91 (m, 2H), 7.78 (dd, 1H, J = 2.0 Hz, 8.0 Hz), 7.18 (d, 1H, J = 1.5 Hz), 6.00 (d, 1H, J = 5.5 Hz), 5.40-5.30 (m, 1H), 4.82-4.75 (m, 2H), 4.58-4.50 (m, 2H), 3.80-3.55 (m, 4H), 3.55-3.45 (m, 4H), 2.93 (s, 3H), 2.85-2.75 (m, 1H), 2.75-2.65 (m, 2H), 2.65-2.55 (m, 2H), 2.12-1.90 (m, 4H), 1.04 (d, 6H, J = 6.5 Hz). |

TABLE 1-continued

| # | Structure | LCMS (M + 1) | NMR |
|---|---|---|---|
| 847 | 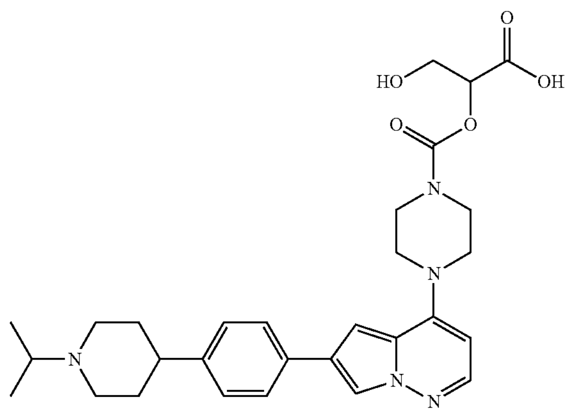 [SMILES: CC(C)N1CCC(c2ccc(-c3cc4c(N5CCN(C(=O)OC(CO)C(=O)O)CC5)ccnn4c3)cc2)CC1] | 536 | 1H-NMR (500 MHz, 6d-DMSO) δ ppm 8.13 (s, 1H), 7.90 (d, 1H, J = 5.5 Hz), 7.72 (d, 2H, J = 8.0 Hz), 7.24 (d, 2H, J = 8.0 Hz), 6.99 (s, 1H), 5.99 (d, 1H, J = 6.0 Hz), 4.78-4.46 (m, 1H), 3.75-3.65 (m, 4H), 3.65-3.58 (m, 2H), 3.51-3.42 (m, 4H), 3.08-3.00 (m, 2H), 2.93-2.90 (m, 1H), 2.56-2.51 (m, 1H), 2.49-2.42 (m, 2H), 1.83-1.79 (m, 2H), 1.79-1.72 (m, 2H), 1.08 (d, 6H, J = 7.0 Hz). |
| 848 | 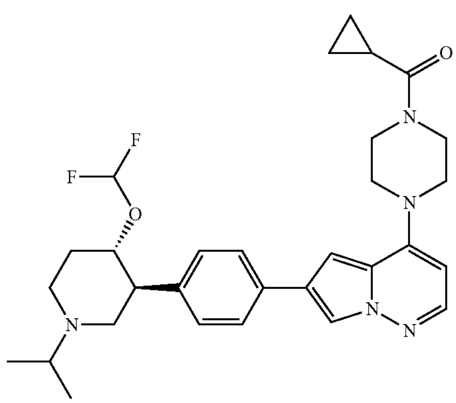 [SMILES: CC(C)N1CC[C@H](OC(F)F)[C@@H](c2ccc(-c3cc4c(N5CCN(C(=O)C6CC6)CC5)ccnn4c3)cc2)C1] | 538 | 1H-NMR (500 MHz, 6d-DMSO) δ ppm 8.18 (d, 1H, J = 1.5 Hz), 7.91 (d, 1H, J = 5.5 Hz), 7.75 (d, 2H, J = 8.5 Hz), 7.34 (d, 2H, J = 8.5 Hz), 7.05 (d, 1H, J = 1.5 Hz), 6.49 (t, 1H, J = 76.5 Hz), 5.98 (d, 1H, J = 5.5 Hz), 4.35-4.29 (m, 1H), 3.93-3.91 (m, 2H), 3.72-3.70 (m, 2H), 3.54-3.50 (m, 2H), 3.50-3.46 (m, 2H), 2.88-2.80 (m, 2H), 2.80-2.72 (m, 2H), 2.31 (t, 2H, J = 11.0 Hz), 2.12-2.10 (m, 1H), 2.04-2.00 (m, 1H), 1.68-1.63 (m, 1H), 0.98-0.95 (m, 6H), 0.79-0.74 (m, 4H). |
| 849 | 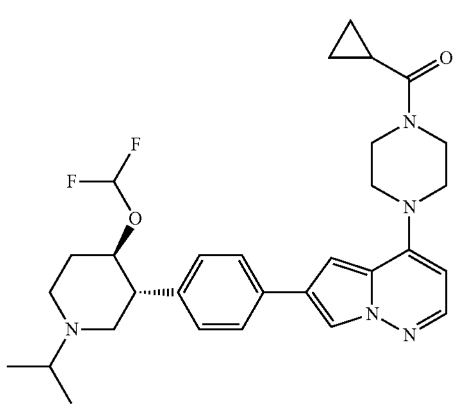 [SMILES: CC(C)N1CC[C@@H](OC(F)F)[C@H](c2ccc(-c3cc4c(N5CCN(C(=O)C6CC6)CC5)ccnn4c3)cc2)C1] | 538 | 1H-NMR (400 MHz, 6d-DMSO) δ ppm 8.17 (d, 1H, J = 2.0 Hz), 7.91 (d, 1H, J = 5.6 Hz), 7.75 (d, 2H, J = 8.4 Hz), 7.34 (d, 2H, J = 8.4 Hz), 7.04 (d, 1H, J = 1.6 Hz), 6.49 (t, 1H, J = 76.4 Hz), 5.98 (d, 1H, J = 5.6 Hz), 4.35-4.29 (m, 1H), 3.93-3.91 (m, 2H), 3.72-3.70 (m, 2H), 3.55-3.50 (m, 2H), 3.50-3.45 (m, 2H), 2.86-2.79 (m, 2H), 2.79-2.72 (m, 2H), 2.31 (t, 2H, J = 11.2 Hz), 2.12-2.10 (m, 1H), 2.04-2.00 (m, 1H), 1.68-1.63 (m, 1H), 0.98-0.94 (m, 6H), 0.80-0.74 (m, 4H). |

TABLE 1-continued

| # | Structure | LCMS (M + 1) | NMR |
|---|---|---|---|
| 850 | 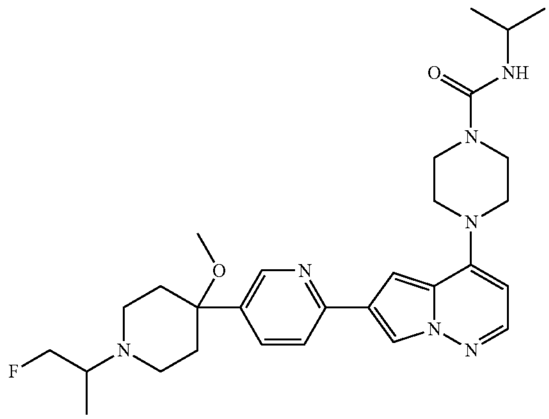 [SMILES: COC1(c2ccc(-c3cc4c(N5CCN(C(=O)NC(C)C)CC5)ccnn4c3)nc2)CCN(C(C)CF)CC1] | 538 | 1H-NMR (400 MHz, 6d-DMSO) δ ppm 8.59 (d, 1H, J = 1.6 Hz), 8.29 (d, 1H, J = 1.2 Hz), 8.14 (s, 1H), 7.96-7.92 (m, 2H), 7.78 (dd, 1H, J = 8.0, 2.0 Hz), 7.18 (d, 1H, J = 1.6 Hz), 6.31 (d, 1H, J = 7.2 Hz), 6.00 (d, 1H, J = 5.6 Hz), 4.60-4.43 (m, 2H), 3.81-3.77 (m, 1H), 3.55-3.51 (m, 4H), 3.50-3.45 (m, 4H), 3.08-3.00 (m, 1H), 2.93 (s, 3H), 2.80-2.72 (m, 4H), 2.11-2.00 (m, 2H), 2.00-1.92 (m, 2H), 1.15-1.05 (m, 9H). |
| 851 | 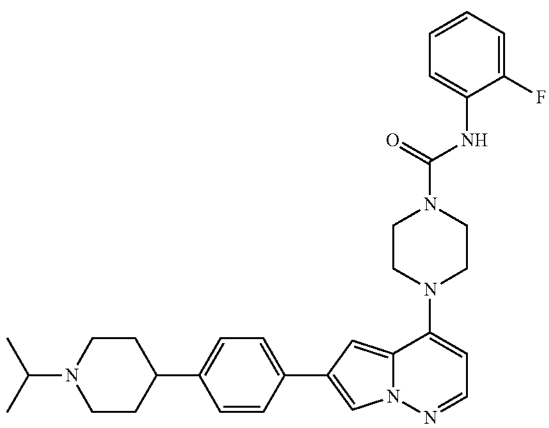 [SMILES: CC(C)N1CCC(c2ccc(-c3cc4c(N5CCN(C(=O)Nc6ccccc6F)CC5)ccnn4c3)cc2)CC1] | 542 | 1H NMR (400 MHz, Methanol-d4) δ 8.54 (s, 3H), 7.96 (d, J = 1.8 Hz, 1H), 7.85 (d, J = 5.4 Hz, 1H), 7.70 (d, J = 8.2 Hz, 2H), 7.56-7.43 (m, 1H), 7.30 (d, J = 8.1 Hz, 2H), 7.22-7.07 (m, 3H), 6.91 (d, J = 1.8 Hz, 1H), 6.02 (d, J = 5.6 Hz, 1H), 3.90-3.75 (m, 4H), 3.68-3.58 (m, 4H), 3.50 (d, J = 13.0 Hz, 4H), 3.18-3.02 (m, 2H), 2.88 (s, 1H), 2.15 (d, J = 14.4 Hz, 3H), 2.00 (t, J = 13.1 Hz, 2H), 1.37 (d, J = 6.6 Hz, 6H). |
| 852 | 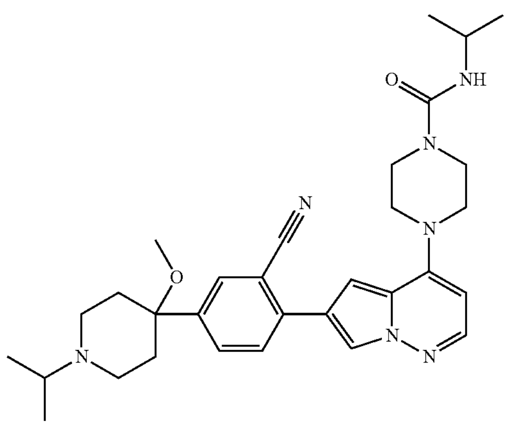 [SMILES: COC1(c2ccc(-c3cc4c(N5CCN(C(=O)NC(C)C)CC5)ccnn4c3)c(C#N)c2)CCN(C(C)C)CC1] | 544 | 1H-NMR (400 MHz, 6d-DMSO) δ ppm 8.23 (d, 1H, J = 2.0 Hz), 7.99 (d, 1H, J = 5.2 Hz), 7.92 (d, 1H, J = 8.8 Hz), 7.82 (d, 1H, J = 1.6 Hz), 7.75 (dd, 1H, J = 8.8, 2.0 Hz), 7.12 (d, 1H, J = 1.6 Hz), 6.34 (d, 1H, J = 7.6 Hz), 6.05 (d, 1H, J = 5.6 Hz), 3.81-3.75 (m, 1H), 3.52-3.50 (m, 4H), 3.46-3.44 (m, 4H), 2.91 (s, 3H), 2.72-2.68 (m, 1H), 2.63-2.59 (m, 2H), 2.48-2.44 (m, 2H), 2.01-1.97 (m, 2H), 1.91-1.85 (m, 2H), 1.08 (d, 6H, J = 6.8 Hz), 1.00 (d, 6H, J = 6.4 Hz). |

TABLE 1-continued

| # | Structure | LCMS (M+1) | NMR |
|---|---|---|---|
| 853 | 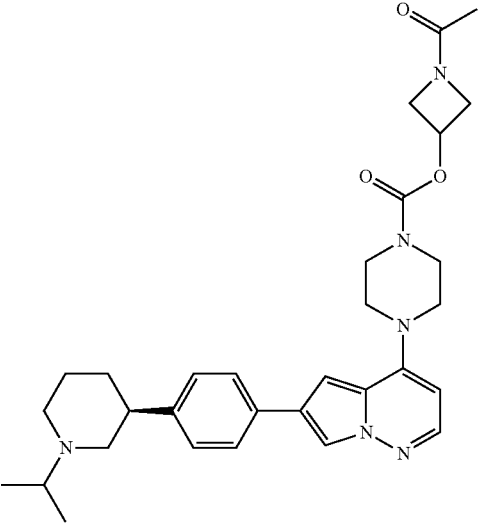 [SMILES: CC(=O)N1CC(OC(=O)N2CCN(c3ccnn4cc(-c5ccc([C@@H]6CCCN(C(C)C)C6)cc5)cc34)CC2)C1] | 545 | 1H-NMR (400 MHz, 6d-DMSO) δ ppm 8.14 (d, 1H, J = 1.6 Hz), 7.90 (d, 1H, J = 5.6 Hz), 7.71 (d, 2H, J = 7.8 Hz), 7.27 (d, 2H, J = 8.0 Hz), 6.99 (d, 1H, J = 1.6 Hz), 5.98 (d, 1H, J = 5.6 Hz), 5.11-5.05 (m, 1H), 4.43 (dd, 1H, J = 9.6, 7.2 Hz), 4.14 (dd, 1H, J = 10.4, 7.2 Hz), 4.09 (dd, 1H, J = 9.6, 4.0 Hz), 3.78 (dd, 1H, J = 10.4, 4.0 Hz), 3.72-3.65 (m, 2H), 3.65-3.58 (m, 2H), 3.51-3.45 (m, 4H), 2.83-2.76 (m, 2H), 2.73-2.65 (m, 2H), 2.22-2.08 (m, 2H), 1.84-1.77 (m, 1H), 1.77 (s, 3H), 1.76-1.71 (m, 1H), 1.60-1.50 (m, 1H), 1.49-1.39 (m, 1H), 1.00-0.92 (m, 6H). |
| 854 | 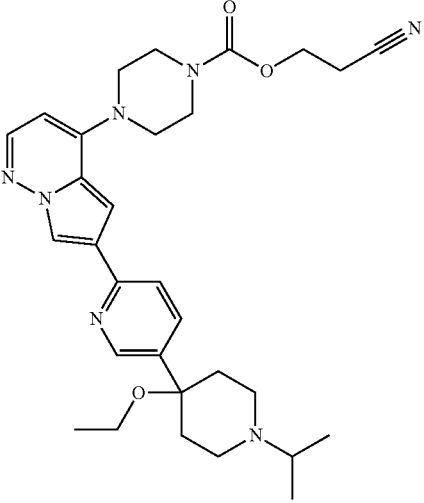 [SMILES: CCOC1(c2ccc(-c3cc4c(N5CCN(C(=O)OCCC#N)CC5)ccnn4c3)nc2)CCN(C(C)C)CC1] | 546 | 1H-NMR (500 MHz, 6d-DMSO) δ ppm 8.59 (d, 1H, J = 2.0 Hz), 8.28 (d, 1H, J = 1.5 Hz), 8.21 (s, 1H), 7.95-7.92 (m, 2H), 7.79 (dd, 1H, J = 8.5, 2.5 Hz), 7.19 (d, 1H, J = 1.5 Hz), 6.01 (d, 1H, J = 5.0 Hz), 4.24 (t, 2H, J = 6.0 Hz), 3.68-3.64 (m, 4H), 3.53-3.48 (m, 4H), 3.09 (q, 2H, J = 7.0 Hz), 2.92 (t, 2H, J = 6.0 Hz), 2.83-2.82 (m, 1H), 2.74-2.72 (m, 2H), 2.64-2.60 (m, 2H), 2.06-2.04 (m, 2H), 1.98-1.95 (m, 2H), 1.08 (t, 3H, J = 7.0 Hz), 1.05 (d, 6H, J = 7.0 Hz). |
| 855 | 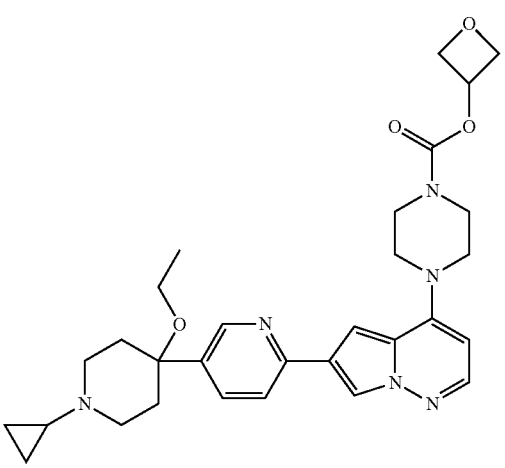 [SMILES: CCOC1(c2ccc(-c3cc4c(N5CCN(C(=O)OC6COC6)CC5)ccnn4c3)nc2)CCN(C2CC2)CC1] | 547 | 1H-NMR (400 MHz, 6d-DMSO) δ ppm 8.58 (d, 1H, J = 1.6 Hz), 8.29 (d, 1H, J = 1.6 Hz), 8.17 (s, 1H), 7.95-7.90 (m, 2H), 7.80-7.76 (m, 1H), 7.18 (d, 1H, J = 1.6 Hz), 6.01 (d, 1H, J = 5.6 Hz), 5.36-5.31 (m, 1H), 4.82-4.76 (m, 2H), 4.55-4.51 (m, 2H), 3.80-3.55 (m, 4H), 3.51-3.48 (m, 4H), 3.10 (q, 2H, J = 7.2 Hz), 2.79-2.75 (m, 2H), 2.61-2.55 (m, 2H), 2.00-1.96 (m, 2H), 1.88-1.84 (m, 2H), 1.67-1.65 (m, 1H), 1.10 (t, 3H, J = 7.2 Hz), 0.44-0.41 (m, 2H), 0.31-0.29 (m, 2H). |

TABLE 1-continued

| # | Structure | LCMS (M + 1) | NMR |
|---|---|---|---|
| 856 | 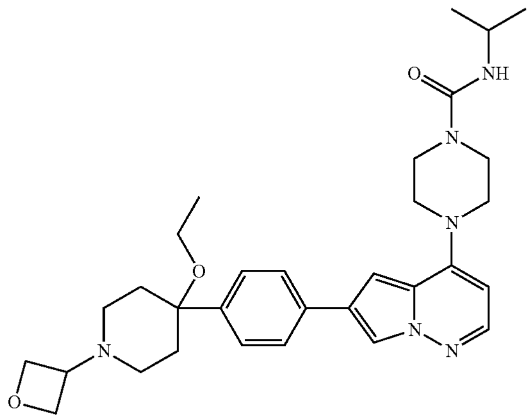 [SMILES: CCOC1(c2ccc(-c3cc4c(N5CCN(C(=O)NC(C)C)CC5)ccnn4c3)cc2)CCN(C2COC2)CC1] | 547 | 1H-NMR (400 MHz, 6d-DMSO) δ ppm 8.19 (s, 1H), 8.17 (d, 1H, J = 1.6 Hz), 7.90 (d, 1H, J = 5.6 Hz), 7.78 (d, 2H, J = 8.4 Hz), 7.40 (d, 2H, J = 8.0 Hz), 7.02 (d, 1H, J = 1.2 Hz), 6.31 (d, 1H, J = 7.6 Hz), 5.97 (d, 1H, J = 5.2 Hz), 4.60-4.50 (m, 2H), 4.48-4.40 (m, 2H), 3.80-3.70 (m, 1H), 3.60-3.48 (m, 4H), 3.46-3.36 (m, 5H), 3.03 (q, 2H, J = 6.8 Hz), 2.60-2.50 (m, 2H), 2.22-2.10 (m, 2H), 2.00-1.80 (m, 4H), 1.12-1.00 (m, 9H). |
| 857 | 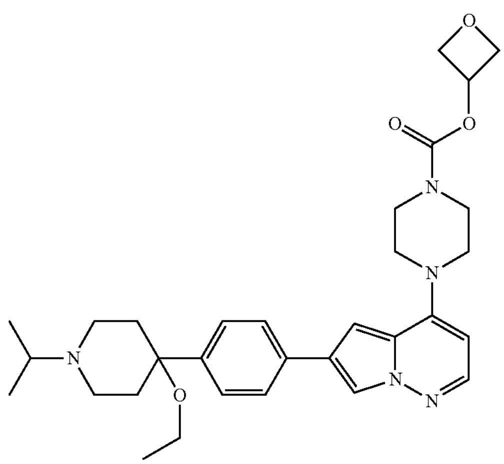 [SMILES: CCOC1(c2ccc(-c3cc4c(N5CCN(C(=O)OC6COC6)CC5)ccnn4c3)cc2)CCN(C(C)C)CC1] | 548 | 1H-NMR (500 MHz, 6d-DMSO) δ ppm 8.30 (s, 1H), 8.18 (d, 1H, J = 1.5 Hz), 7.91 (d, 1H, J = 5.5 Hz), 7.80 (d, 2H, J = 8.5 Hz), 7.40 (d, 2H, J = 8.5 Hz), 7.04 (d, 1H, J = 1.5 Hz), 5.99 (d, 1H, J = 5.5 Hz), 5.34 (quintet, 1H, J = 5.5 Hz), 4.79 (t, 2H, J = 7.0 Hz), 4.53 (dd, 2H, d, 2H, J = 7.0, 5.5 Hz), 3.80-3.65 (m, 2H), 3.65-3.50 (m, 2H), 3.50-3.40 (m, 4H), 3.06 (q, 2H, J = 6.5 Hz), 2.90-2.80 (m, 1H), 2.80-2.70 (m, 2H), 2.68-2.61 (m, 2H), 2.03-2.00 (m, 2H), 1.98-1.92 (m, 2H), 1.09-1.05 (m, 9H). |
| 858 | 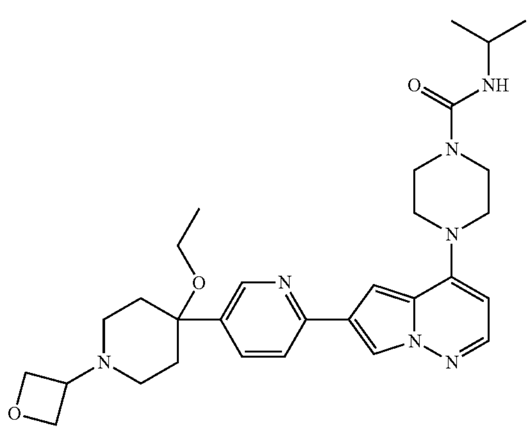 [SMILES: CCOC1(c2ccc(-c3cc4c(N5CCN(C(=O)NC(C)C)CC5)ccnn4c3)nc2)CCN(C2COC2)CC1] | 548 | 1H-NMR (400 MHz, 6d-DMSO) δ ppm 8.59 (d, 1H, J = 2.0 Hz), 8.27 (d, 1H, J = 1.2 Hz), 8.16 (s, 1H), 7.92 (d, 1H, J = 5.6 Hz), 7.91-7.88 (m, 1H), 7.78 (dd, 1H, J = 8.4, 2.4 Hz), 7.17 (d, 1H, J = 1.6 Hz), 6.30 (d, 1H, J = 7.6 Hz), 5.99 (d, 1H, J = 5.6 Hz), 4.54 (t, 2H, J = 6.4 Hz), 4.43 (t, 2H, J = 6.4 Hz), 3.84-3.72 (m, 1H), 3.56-3.49 (m, 4H), 3.48-3.43 (m, 4H), 3.44-3.40 (m, 1H), 3.06 (q, 2H, J = 6.8 Hz), 2.56-2.51 (m, 2H), 2.22-2.12 (m, 2H), 2.06-1.86 (m, 4H), 1.08 (d, 6H, J = 6.4 Hz), 1.06 (t, 3H, J = 6.8 Hz). |

TABLE 1-continued

| # | Structure | LCMS (M + 1) | NMR |
|---|---|---|---|
| 859 | 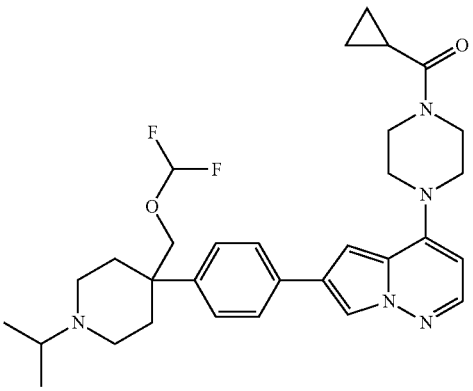 [SMILES: CC(C)N1CCC(COC(F)F)(c2ccc(-c3cc4c(N5CCN(C(=O)C6CC6)CC5)ccnn4c3)cc2)CC1] | 552 | 1H-NMR (400 MHz, 6d-DMSO) δ ppm 8.18 (d, 1H, J = 1.6 Hz), 7.91 (d, 1H, J = 5.6 Hz), 7.76 (d, 2H, J = 8.4 Hz), 7.40 (d, 2H, J = 8.4 Hz), 7.05 (d, 1H, J = 1.6 Hz), 6.54 (t, 1H, J = 75.6 Hz), 5.99 (d, 1H, J = 5.6 Hz), 3.92 (m, 2H), 3.83 (s, 2H), 3.71 (m, 2H), 3.57-3.50 (m, 2H), 3.50-3.43 (m, 2H), 2.60-2.57 (m, 3H), 2.30-2.25 (m, 2H), 2.15-2.11 (m, 2H), 2.14-1.99 (m, 1H), 1.88-1.83 (m, 2H), 0.90 (d, 6H, J = 6.8 Hz), 0.79-0.77 (m, 4H). |
| 860 | 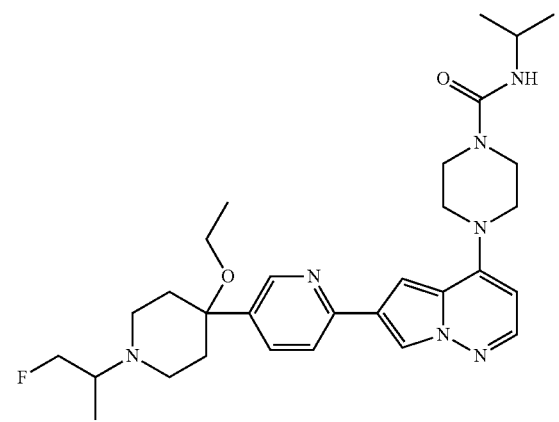 [SMILES: CCOC1(c2ccc(-c3cc4c(N5CCN(C(=O)NC(C)C)CC5)ccnn4c3)nc2)CCN(C(C)CF)CC1] | 552 | 1H-NMR (400 MHz, 6d-DMSO) δ ppm 8.59 (d, 1H, J = 2.0 Hz), 8.28 (d, 1H, J = 1.6 Hz), 7.94-7.90 (m, 2H), 7.79 (dd, 1H, J = 8.4, 2.4 Hz), 7.17 (d, 1H, J = 2.0 Hz), 6.31 (d, 1H, J = 7.6 Hz), 6.00 (d, 1H, J = 5.6 Hz), 4.56-4.32 (m, 2H), 3.82-3.76 (m, 1H), 3.55-3.50 (m, 4H), 3.48-3.43 (m, 4H), 3.08 (q, 2H, J = 7.2 Hz), 2.93-2.84 (m, 1H), 2.71-2.63 (m, 4H), 2.03-1.95 (m, 2H), 1.95-1.85 (m, 2H), 1.09-1.06 (m, 9H), 1.18 (d, 3H, J = 5.6 Hz). |
| 861 | 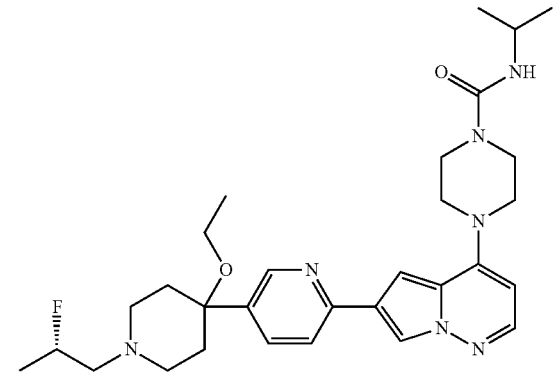 [SMILES: CCOC1(c2ccc(-c3cc4c(N5CCN(C(=O)NC(C)C)CC5)ccnn4c3)nc2)CCN(C[C@H](C)F)CC1] | 552 | 1H-NMR (400 MHz, 6d-DMSO) δ ppm 8.60 (d, 1H, J = 1.6 Hz), 8.28 (d, 1H, J = 1.6 Hz), 8.17 (s, 1H), 7.95-7.91 (m, 2H), 7.81-7.77 (m, 1H), 7.18 (d, 1H, J = 1.6 Hz), 6.31 (d, 1H, J = 7.6 Hz), 6.00 (d, 1H, J = 5.6 Hz), 4.95-4.78 (m, 1H), 3.82-3.76 (m, 1H), 3.55-3.51 (m, 4H), 3.48-3.45 (m, 4H), 3.07 (q, 2H, J = 7.2 Hz), 2.80-2.65 (m, 2H), 2.64-2.50 (m, 2H), 2.50-2.45 (m, 2H), 2.08-1.93 (m, 4H), 1.27 (dd, 2H, J = 23.6 Hz, J = 6.4 Hz), 1.10-1.06 (m, 9H). |
| 862 | 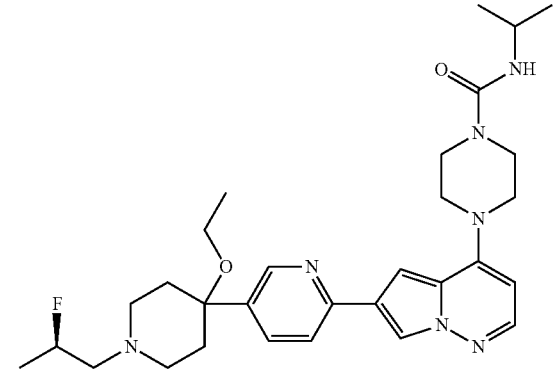 [SMILES: CCOC1(c2ccc(-c3cc4c(N5CCN(C(=O)NC(C)C)CC5)ccnn4c3)nc2)CCN(C[C@@H](C)F)CC1] | 552 | 1H-NMR (400 MHz, 6d-DMSO) δ ppm 8.60 (d, 1H, J = 1.6 Hz), 8.28 (d, 1H, J = 1.6 Hz), 8.16 (s, 1H), 7.95-7.91 (m, 2H), 7.81-7.77 (m, 1H), 7.18 (d, 1H, J = 1.6 Hz), 6.31 (d, 1H, J = 7.6 Hz), 6.00 (d, 1H, J = 5.6 Hz), 4.97-4.78 (m, 1H), 3.82-3.76 (m, 1H), 3.55-3.51 (m, 4H), 3.48-3.45 (m, 4H), 3.08 (q, 2H, J = 7.2 Hz), 2.80-2.65 (m, 2H), 2.64-2.50 (m, 2H), 2.50-2.43 (m, 2H), 1.99-1.93 (m, 4H), 1.27 (dd, 2H, J = 23.6 Hz, J = 6.4 Hz), 1.10-1.06 (m, 9H). |

TABLE 1-continued
| # | Structure | LCMS (M + 1) | NMR |
|---|---|---|---|
| 863 | 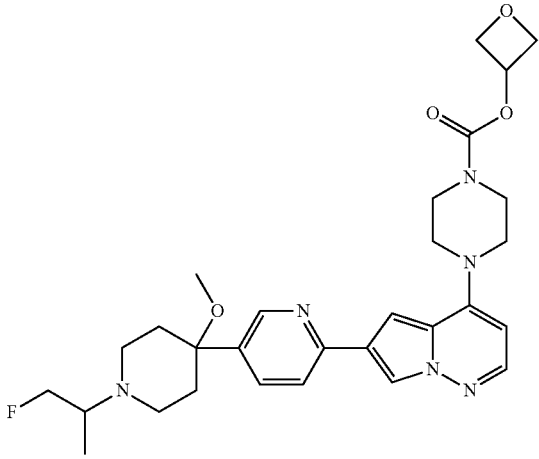 [SMILES: COC1(c2ccc(-c3cc4c(N5CCN(C(=O)OC6COC6)CC5)ccnn4c3)nc2)CCN(C(C)CF)CC1] | 553 | 1H-NMR (400 MHz, 6d-DMSO) δ ppm 8.59 (d, 1H, J = 2.0 Hz), 8.30 (d, 1H, J = 2.0 Hz), 8.16 (s, 1H), 7.96-7.92 (m, 2H), 7.78 (dd, 1H, J = 8.4, 2.0 Hz), 7.19 (d, 1H, J = 1.6 Hz), 6.01 (d, 1H, J = 5.2 Hz), 5.34 (quintet, 1H, J = 5.2 Hz), 4.80 (t, 2H, J = 7.2 Hz), 4.55 (dd, 2H, J = 7.2, 5.2 Hz) 4.60-4.41 (m, 2H), 3.73-3.68 (m, 2H), 3.68-3.60 (m, 2H), 3.55-3.50 (m, 4H), 3.10-2.95 (m, 1H), 2.93 (s, 3H), 2.85-2.70 (m, 4H), 2.10-2.00 (m, 2H), 2.00-1.92 (m, 2H), 1.06 (d, 3H, J = 6.4 Hz). |
| 864 | 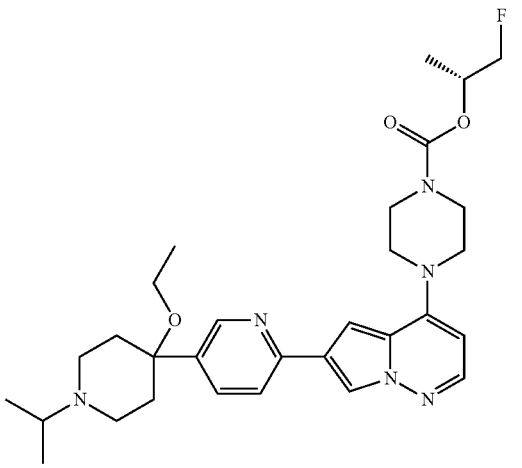 [SMILES: CCOC1(c2ccc(-c3cc4c(N5CCN(C(=O)O[C@H](C)CF)CC5)ccnn4c3)nc2)CCN(C(C)C)CC1] | 553 | 1H-NMR (400 MHz, 6d-DMSO) δ ppm 8.59 (d, 1H, J = 2.0 Hz), 8.28 (s, 1H), 7.94-7.91 (m, 2H), 7.80-7.77 (m, 1H), 7.18 (s, 1H), 6.00 (d, 1H, J = 5.2 Hz), 5.01-4.92 (m, 1H), 4.61-4.38 (m, 2H), 3.63-3.62 (m, 4H), 3.50-3.49 (m, 4H), 3.08 (q, 2H, J = 6.8 Hz), 2.70-2.54 (m, 4H), 2.44-2.33 (m, 1H), 2.01-1.98 (m, 2H), 1.91-1.85 (m, 2H), 1.22 (d, 3H, J = 6.4 Hz), 1.08 (t, 3H, J = 6.8 Hz), 1.00 (d, 3H, J = 6.8 Hz). |
| 865 | 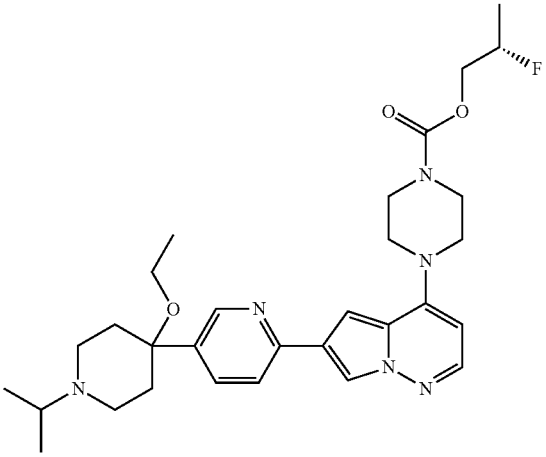 [SMILES: CCOC1(c2ccc(-c3cc4c(N5CCN(C(=O)OC[C@H](C)F)CC5)ccnn4c3)nc2)CCN(C(C)C)CC1] | 553 | 1H-NMR (400 MHz, 6d-DMSO) δ ppm 8.59 (d, 1H, J = 2.4 Hz), 8.28 (d, 1H, J = 1.6 Hz), 7.95-7.91 (m, 2H), 7.80-7.77 (m, 1H), 7.18 (d, 1H, J = 1.2 Hz), 6.00 (d, 1H, J = 5.2 Hz), 5.00-4.81 (m, 1H), 4.28-4.06 (m, 2H), 3.65-3.64 (m, 4H), 3.52-3.50 (m, 4H), 3.08 (q, 2H, J = 6.8 Hz), 2.73-2.61 (m, 5H), 2.03-1.91 (m, 4H), 1.31 (dd, 3H, J = 24.0, 6.8 Hz), 1.07 (t, 3H, J = 6.8 Hz), 0.99 (d, 6H, J = 6.4 Hz). |

TABLE 1-continued

| # | Structure | LCMS (M + 1) | NMR |
|---|---|---|---|
| 866 | 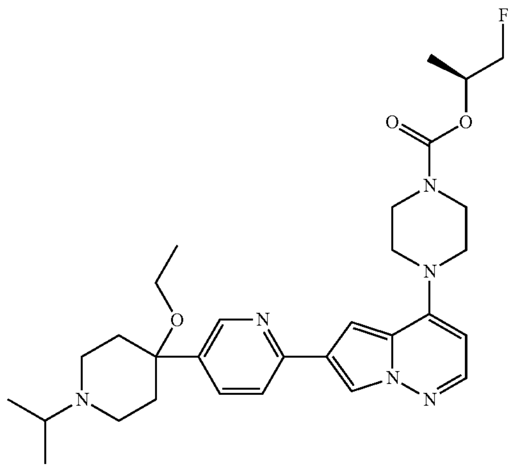 [SMILES: CCOC1(c2ccc(-c3cc4c(N5CCN(C(=O)O[C@@H](C)CF)CC5)ccnn4c3)nc2)CCN(C(C)C)CC1] | 553 | 1H-NMR (400 MHz, 6d-DMSO) δ ppm 8.59 (d, 1H, J = 2.0 Hz), 8.28 (s, 1H), 7.94-7.91 (m, 2H), 7.80-7.77 (m, 1H), 7.18 (s, 1H), 6.00 (d, 1H, J = 5.2 Hz), 5.01-4.92 (m, 1H), 4.61-4.38 (m, 2H), 3.63-3.62 (m, 4H), 3.50-3.49 (m, 4H), 3.08 (q, 2H, J = 6.8 Hz), 2.70-2.54 (m, 4H), 2.44-2.33 (m, 1H), 2.01-1.98 (m, 2H), 1.91-1.85 (m, 2H), 1.22 (d, 3H, J = 6.4 Hz), 1.08 (t, 3H, J = 6.8 Hz), 1.00 (d, 3H, J = 6.8 Hz). |
| 867 | 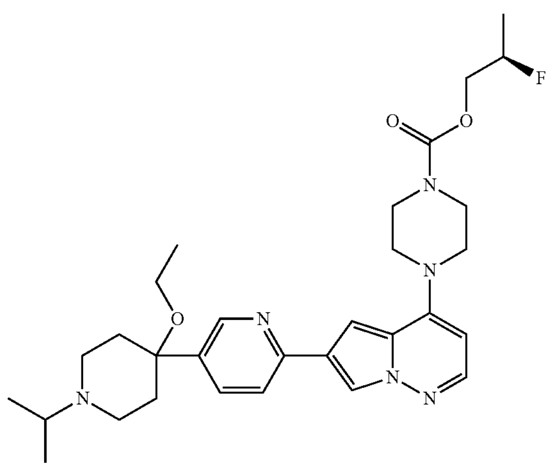 [SMILES: CCOC1(c2ccc(-c3cc4c(N5CCN(C(=O)OC[C@@H](C)F)CC5)ccnn4c3)nc2)CCN(C(C)C)CC1] | 553 | 1H-NMR (400 MHz, 6d-DMSO) δ ppm 8.59 (d, 1H, J = 2.4 Hz), 8.28 (d, 1H, J = 1.6 Hz), 7.95-7.91 (m, 2H), 7.80-7.77 (m, 1H), 7.18 (d, 1H, J = 1.2 Hz), 6.00 (d, 1H, J = 5.2 Hz), 5.00-4.81 (m, 1H), 4.28-4.06 (m, 2H), 3.65-3.64 (m, 4H), 3.52-3.50 (m, 4H), 3.08 (q, 2H, J = 6.8 Hz), 2.73-2.61 (m, 5H), 2.03-1.91 (m, 4H), 1.31 (dd, 3H, J = 24.0, 6.8 Hz), 1.07 (t, 3H, J = 6.8 Hz), 0.99 (d, 6H, J = 6.4 Hz). |
| 868 | 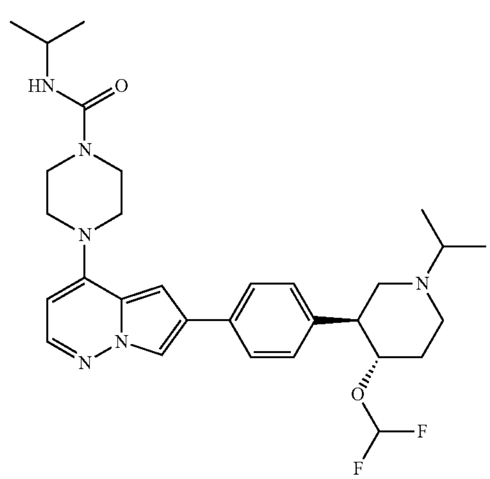 [SMILES: CC(C)NC(=O)N1CCN(c2ccnn3cc(-c4ccc([C@H]5CN(C(C)C)CC[C@@H]5OC(F)F)cc4)cc23)CC1] | 555 | 1H-NMR (400 MHz, 6d-DMSO) δ ppm 8.16 (d, 1H, J = 2.0 Hz), 7.90 (d, 1H, J = 5.2 Hz), 7.75 (d, 2H, J = 8.4 Hz), 7.33 (d, 2H, J = 8.4 Hz), 7.01 (d, 1H, J = 1.6 Hz), 6.49 (t, 1H, J = 75.2 Hz), 6.32 (s, 1H), 5.99 (d, 1H, J = 5.6 Hz), 4.35-4.29 (m, 1H), 3.82-3.74 (m, 1H), 3.53-3.51 (m, 4H), 3.46-3.43 (m, 4H), 2.89-2.80 (m, 2H), 2.80-2.74 (m, 2H), 2.31 (t, 2H, J = 10.8 Hz), 2.12-2.10 (m, 1H), 1.68-1.64 (m, 1H), 1.09 (d, 6H, J = 6.4 Hz), 0.98-0.94 (m, 6H). |

TABLE 1-continued

| # | Structure | LCMS (M + 1) | NMR |
|---|---|---|---|
| 869 | 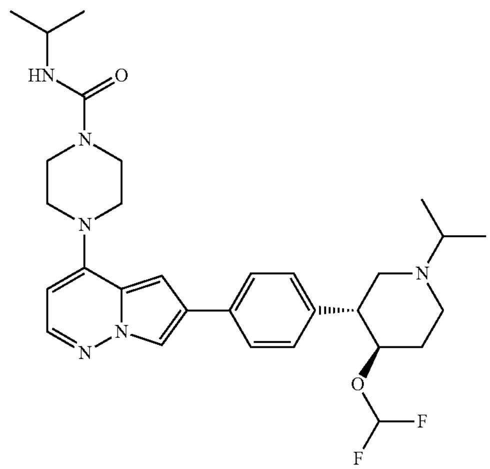 [SMILES: CC(C)NC(=O)N1CCN(c2ccnn3cc(-c4ccc([C@@H]5CN(C(C)C)CC[C@H]5OC(F)F)cc4)cc23)CC1] | 555 | 1H-NMR (400 MHz, 6d-DMSO) δ ppm 8.16 (d, 1H, J = 1.6 Hz), 7.90 (d, 1H, J = 5.6 Hz), 7.75 (d, 2H, J = 8.4 Hz), 7.33 (d, 2H, J = 8.4 Hz), 7.01 (d, 1H, J = 1.6 Hz), 6.49 (t, 1H, J = 76.4 Hz), 6.32-6.30 (m, 1H), 5.98 (d, 1H, J = 5.2 Hz), 4.32 (td, 1H, J = 10.4, 4.4 Hz), 3.82-3.74 (m, 1H), 3.53-3.51 (m, 4H), 3.46-3.43 (m, 4H), 2.89-2.80 (m, 2H), 2.80-2.74 (m, 2H), 2.31 (t, 2H, J = 10.8 Hz), 2.12-2.10 (m, 1H), 1.68-1.64 (m, 1H), 1.09 (d, 6H, J = 6.4 Hz), 0.98-0.94 (m, 6H). |
| 870 | 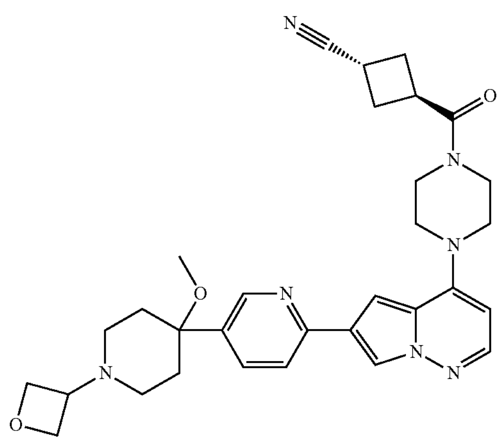 [SMILES: COC1(c2ccc(-c3cc4c(N5CCN(C(=O)[C@H]6C[C@H](C#N)C6)CC5)ccnn4c3)nc2)CCN(C2COC2)CC1] | 556 | 1H-NMR (400 MHz, 6d-DMSO) δ ppm 8.58 (d, 1H, J = 2.0 Hz), 8.29 (d, 1H, J = 1.6 Hz), 7.96-7.90 (m, 2H), 7.78 (dd, 1H, J = 8.0, 2.4 Hz), 7.18 (d, 1H, J = 1.6 Hz), 5.98 (d, 1H, J = 5.6 Hz), 4.58-4.50 (m, 2H), 4.48-4.40 (m, 2H), 3.72-3.60 (m, 3H), 3.58-3.52 (m, 2H), 3.50-3.38 (m, 5H), 3.30-3.20 (m, 1H), 2.91 (s, 3H), 2.68-2.57 (m, 2H), 2.56-2.50 (m, 4H), 2.20-2.10 (m, 2H), 2.05-1.85 (m, 4H). |
| 871 | 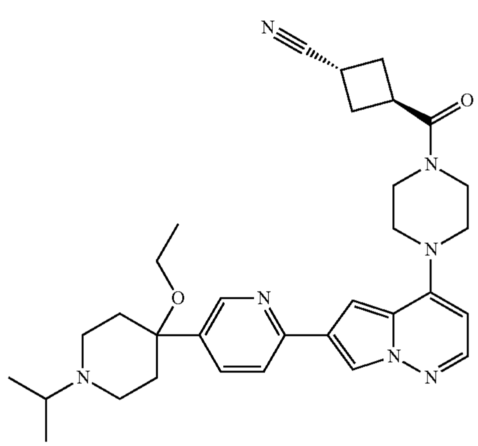 [SMILES: CCOC1(c2ccc(-c3cc4c(N5CCN(C(=O)[C@H]6C[C@H](C#N)C6)CC5)ccnn4c3)nc2)CCN(C(C)C)CC1] | 556 | 1H-NMR (500 MHz, 6d-DMSO) δ ppm 8.59 (d, 1H, J = 2.0 Hz), 8.30 (d, 1H, J = 2.0 Hz), 8.17 (s, 1H), 7.96-7.91 (m, 2H), 7.80 (dd, 1H, J = 2.5 Hz, 8.0 Hz), 7.19 (d, 1H, J = 1.5 Hz), 5.99 (d, 1H, J = 5.5 Hz), 3.75-3.60 (m, 3H), 3.60-3.52 (m, 2H), 3.52-3.40 (m, 4H), 3.35-3.20 (m, 3H), 3.15-3.05 (m, 2H), 3.00-2.88 (m, 1H), 2.88-2.75 (m, 2H), 2.75-2.55 (m, 4H), 2.15-1.90 (m, 4H), 1.15-1.00 (m, 9H). |

TABLE 1-continued

| # | Structure | LCMS (M + 1) | NMR |
|---|---|---|---|
| 872 | 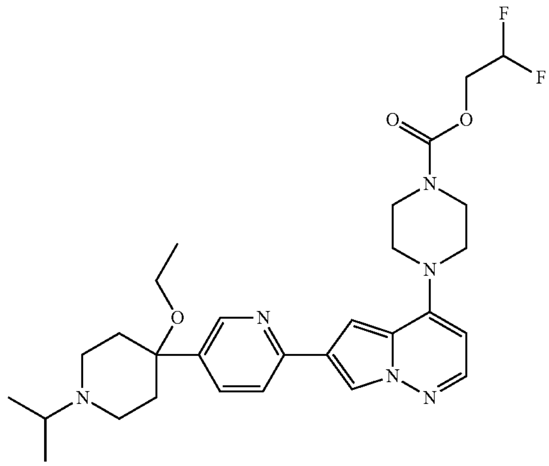 [SMILES: CCOC1(c2ccc(-c3cc4c(N5CCN(C(=O)OCC(F)F)CC5)ccnn4c3)nc2)CCN(C(C)C)CC1] | 557 | 1H-NMR (500 MHz, 6d-DMSO) δ ppm 8.58 (d, 1H, J = 2.0 Hz), 8.28 (d, 1H, J = 1.0 Hz), 7.95-7.91 (m, 2H), 7.78 (dd, 1H, J = 8.0, 2.0 Hz), 7.19 (d, 1H, J = 1.0 Hz), 6.28 (tt, 1H, J = 54.5, 3.5 Hz), 6.01 (d, 1H, J = 5.0 Hz), 4.35 (td, 2H, J = 15.5, 3.5 Hz), 3.66-3.65 (m, 4H), 3.52-3.49 (m, 4H), 3.08 (q, 2H, J = 6.5 Hz), 2.70-2.67 (m, 1H), 2.62-2.60 (m, 2H), 2.53-2.51 (m, 2H), 2.01-1.98 (m, 2H), 1.91-1.87 (m, 2H), 1.08 (t, 3H, J = 6.5 Hz), 1.00 (d, 6H, J = 6.5 Hz). |
| 873 | 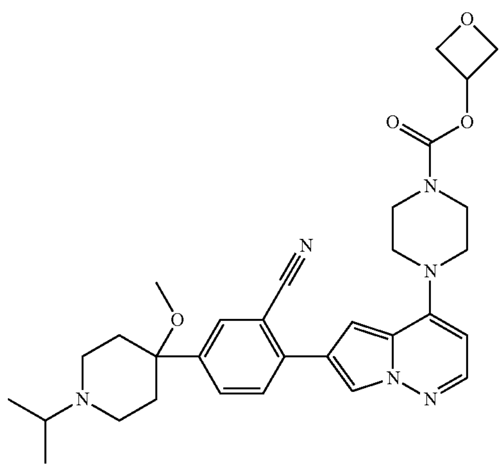 [SMILES: COC1(c2ccc(-c3cc4c(N5CCN(C(=O)OC6COC6)CC5)ccnn4c3)c(C#N)c2)CCN(C(C)C)CC1] | 559 | 1H-NMR (400 MHz, 6d-DMSO) δ ppm 8.24 (d, 1H, J = 1.6 Hz), 8.00 (d, 1H, J = 5.2 Hz), 7.92 (d, 1H, J = 8.4 Hz), 7.82 (d, 1H, J = 1.6 Hz), 7.75 (dd, 1H, J = 8.4, 2.0 Hz), 7.12 (d, 1H, J = 2.0 Hz), 6.07 (d, 1H, J = 5.6 Hz), 5.34 (quintet, 1H, J = 5.2 Hz), 4.79 (t, 2H, J = 7.2 Hz), 4.53 (dd, 2H, J = 7.2, 5.2 Hz), 3.69-3.67 (m, 2H), 3.59-3.57 (m, 2H), 3.53-3.51 (m, 4H), 2.91 (s, 3H), 2.72-2.68 (m, 1H), 2.63-2.59 (m, 2H), 2.48-2.44 (m, 2H), 2.01-1.97 (m, 2H), 1.91-1.85 (m, 2H), 1.01 (d, 6H, J = 6.4 Hz). |
| 874 | 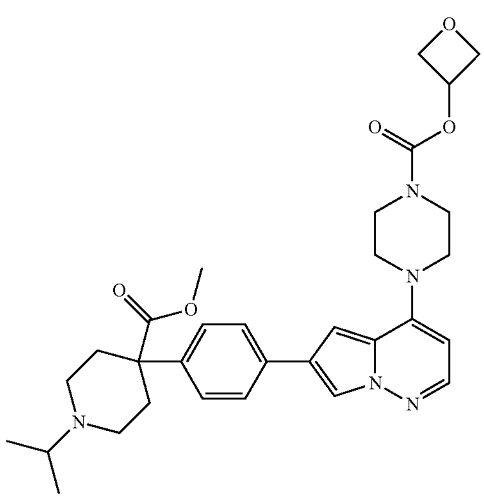 [SMILES: COC(=O)C1(c2ccc(-c3cc4c(N5CCN(C(=O)OC6COC6)CC5)ccnn4c3)cc2)CCN(C(C)C)CC1] | 563 | 1H NMR (500 MHz, Methanol-d4) δ 8.51 (s, 1H), 8.00 (d, J = 1.8 Hz, 1H), 7.87 (d, J = 5.4 Hz, 1H), 7.78 (d, J = 8.0 Hz, 2H), 7.46 (d, J = 8.1 Hz, 2H), 6.92 (d, J = 1.9 Hz, 1H), 6.03 (d, J = 5.5 Hz, 1H), 4.99-4.92 (m, 1H), 3.88-3.63 (m, 8H), 3.55 (s, 5H), 3.44 (d, J = 15.6 Hz, 1H), 3.12 (d, J = 53.8 Hz, 2H), 2.97-2.67 (m, 2H), 2.23 (s, 2H), 1.35 (d, J = 6.6 Hz, 6H). |

TABLE 1-continued

| # | Structure | LCMS (M + 1) | NMR |
|---|---|---|---|
| 875 | 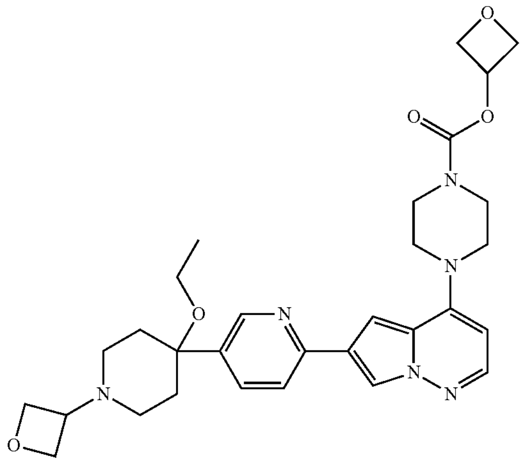 [SMILES: CCOC1(c2ccc(-c3cc4c(N5CCN(C(=O)OC6COC6)CC5)ccnn4c3)nc2)CCN(C2COC2)CC1] | 563 | 1H-NMR (400 MHz, 6d-DMSO) δ ppm 8.59 (d, 1H, J = 2.0 Hz), 8.29 (d, 1H, J = 1.6 Hz), 7.94 (d, 1H, J = 5.2 Hz), 7.93-7.90 (m, 1H), 7.79 (dd, 1H, J = 8.4, 2.4 Hz), 7.18 (d, 1H, J = 2.0 Hz), 6.00 (d, 1H, J = 5.2 Hz), 5.33 (quintet, 1H, J = 5.2 Hz), 4.78 (t, 2H, J = 7.2 Hz), 4.60-4.50 (m, 4H), 4.44 (t, 2H, J = 5.6 Hz), 3.73-3.66 (m, 2H), 3.66-3.58 (m, 2H), 3.54-3.47 (m, 4H), 3.46-3.36 (m, 1H), 3.06 (q, 2H, J = 6.8 Hz), 2.58-2.51 (m, 2H), 2.24-2.10 (m, 2H), 2.06-1.86 (m, 4H), 1.07 (t, 3H, J = 6.8 Hz). |
| 876 | 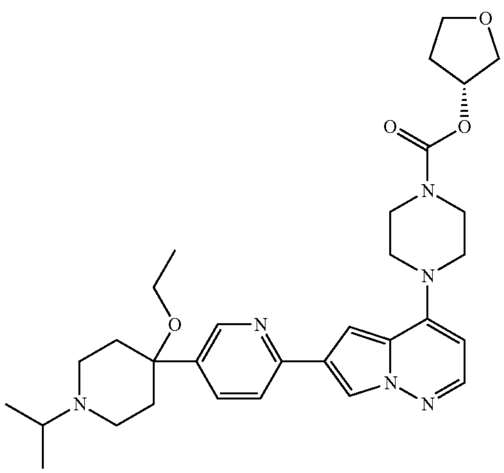 [SMILES: CCOC1(c2ccc(-c3cc4c(N5CCN(C(=O)O[C@@H]6CCOC6)CC5)ccnn4c3)nc2)CCN(C(C)C)CC1] | 563 | 1H-NMR (500 MHz, 6d-DMSO) δ ppm 8.58 (d, 1H, J = 2.0 Hz), 8.28 (d, 1H, J = 1.5 Hz), 7.94-7.91 (m, 2H), 7.78 (dd, 1H, J = 8.0, 2.5 Hz), 7.18 (d, 1H, J = 2.0 Hz), 6.00 (d, 1H, J = 6.0 Hz), 5.19-5.18 (m, 1H), 3.82-3.79 (m, 2H), 3.76-3.71 (m, 2H), 3.62-3.60 (m, 4H), 3.50-3.48 (m, 4H), 3.08 (q, 2H, J = 7.0 Hz), 2.70-2.68 (m, 1H), 2.62-2.60 (m, 2H), 2.54-2.51 (m, 2H), 2.16-2.12 (m, 1H), 2.01-1.92 (m, 3H), 1.92-1.86 (m, 2H), 1.08 (t, 3H, J = 7.0 Hz), 1.00 (d, 6H, J = 7.0 Hz). |
| 877 | 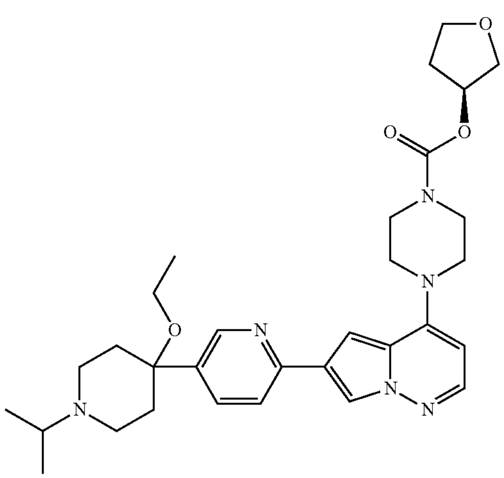 [SMILES: CCOC1(c2ccc(-c3cc4c(N5CCN(C(=O)O[C@H]6CCOC6)CC5)ccnn4c3)nc2)CCN(C(C)C)CC1] | 563 | 1H-NMR (500 MHz, 6d-DMSO) δ ppm 8.58 (d, 1H, J = 2.0 Hz), 8.28 (d, 1H, J = 1.5 Hz), 7.94-7.91 (m, 2H), 7.78 (dd, 1H, J = 8.0, 2.5 Hz), 7.18 (d, 1H, J = 2.0 Hz), 6.00 (d, 1H, J = 6.0 Hz), 5.19-5.18 (m, 1H), 3.82-3.79 (m, 2H), 3.76-3.71 (m, 2H), 3.62-3.60 (m, 4H), 3.50-3.48 (m, 4H), 3.08 (q, 2H, J = 7.0 Hz), 2.70-2.68 (m, 1H), 2.62-2.60 (m, 2H), 2.54-2.51 (m, 2H), 2.16-2.12 (m, 1H), 2.01-1.92 (m, 3H), 1.92-1.86 (m, 2H), 1.08 (t, 3H, J = 7.0 Hz), 1.00 (d, 6H, J = 7.0 Hz). |

| # | Structure | LCMS (M + 1) | NMR |
|---|---|---|---|
| 878 | 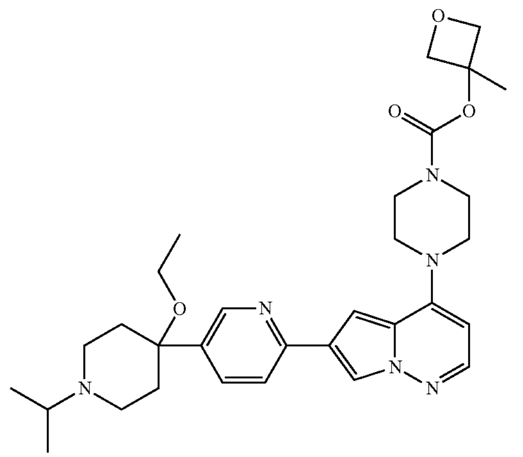 [SMILES: CCOC1(c2ccc(-c3cc4c(N5CCN(C(=O)OC6(C)COC6)CC5)ccnn4c3)nc2)CCN(C(C)C)CC1] | 563 | 1H-NMR (400 MHz, 6d-DMSO) δ ppm 8.59 (s, 1H), 8.29 (s, 1H), 7.94 (d, 1H, J = 5.2 Hz), 7.93-7.91 (m, 1H), 7.79 (d, 1H, J = 8.0 Hz), 7.18 (s, 1H), 6.00 (d, 1H, J = 5.2 Hz), 4.66 (d, 2H, J = 7.2 Hz), 4.42 (d, 2H, J = 7.2 Hz), 3.66-3.63 (m, 2H), 3.63-3.58 (m, 2H), 3.51-3.48 (m, 4H), 3.08 (q, 2H, J = 7.2 Hz), 2.80-2.70 (m, 2H), 2.70-2.60 (m, 2H), 2.02-1.99 (m, 2H), 1.92-1.90 (m, 2H), 1.67 (s, 3H), 1.08 (t, 3H, J = 7.2 Hz), 1.01-0.99 (m, 6H). |
| 879 | 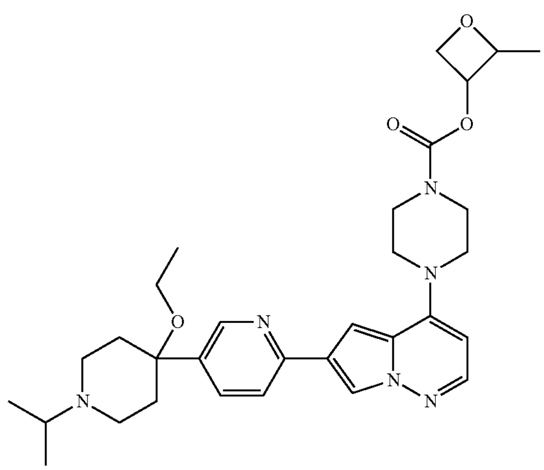 [SMILES: CCOC1(c2ccc(-c3cc4c(N5CCN(C(=O)OC6COC6C)CC5)ccnn4c3)nc2)CCN(C(C)C)CC1] | 563 | 1H-NMR (500 MHz, 6d-DMSO) δ ppm 8.61 (s, 1H), 8.31 (d, 1H, J = 1.0 Hz), 7.98-7.94 (m, 2H), 7.81-7.78 (m, 1H), 7.21-7.18 (m, 1H), 6.02-6.00 (m, 1H), 5.40-5.30 (m, 0.25H), 5.05-4.95 (m, 0.25H), 4.95-4.85 (m, 0.75H), 4.80-4.70 (m, 1H), 4.65-4.58 (m, 0.75H), 4.45-4.30 (m, 1H), 3.75-3.40 (br., 2H), 3.70-3.62 (m, 2H), 3.62-3.55 (m, 2H), 3.55-3.48 (m, 4H), 3.30-3.25 (m, 1H), 3.11 (q, 2H, J = 7.0 Hz), 2.45-2.10 (m, 4H), 1.38 (d, 6H, J = 7.0 Hz), 1.30 (d, 3H, J = 6.0 Hz), 1.30-1.20 (m, 2H), 1.11 (t, 3H, J = 7.0 Hz). |
| 880 | 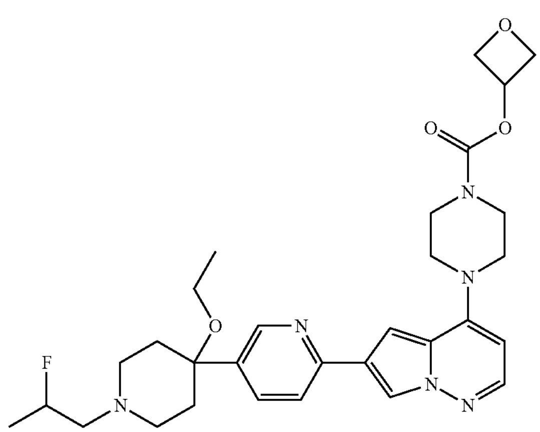 [SMILES: CCOC1(c2ccc(-c3cc4c(N5CCN(C(=O)OC6COC6)CC5)ccnn4c3)nc2)CCN(CC(C)F)CC1] | 567 | 1H-NMR (400 MHz, 6d-DMSO) δ ppm 8.59 (d, 1H, J = 1.6 Hz), 8.29 (d, 1H, J = 1.6 Hz), 7.95-7.92 (m, 2H), 7.80 (dd, 1H, J = 8.0, 2.4 Hz), 7.18 (d, 1H, J = 1.6 Hz), 6.01 (d, 1H, J = 5.6 Hz), 5.34 (quintet, 1H, J = 5.2 Hz), 4.97-4.90 (m, 1H), 4.79 (t, 2H, J = 7.2 Hz), 4.53 (dd, 2H, J = 7.2, 5.2 Hz), 3.73-3.65 (m, 2H), 3.65-3.59 (m, 2H), 3.52-3.50 (m, 4H), 3.33-3.31 (m, 2H), 3.08 (q, 2H, J = 6.8 Hz), 2.75-2.66 (m, 2H), 2.50-2.49 (m, 2H), 1.91-1.75 (m, 4H), 1.27 (dd, 3H, J = 24.0, 6.4 Hz), 1.08 (t, 3H, J = 6.8 Hz). |

TABLE 1-continued

| # | Structure | LCMS (M + 1) | NMR |
|---|---|---|---|
| 881 | 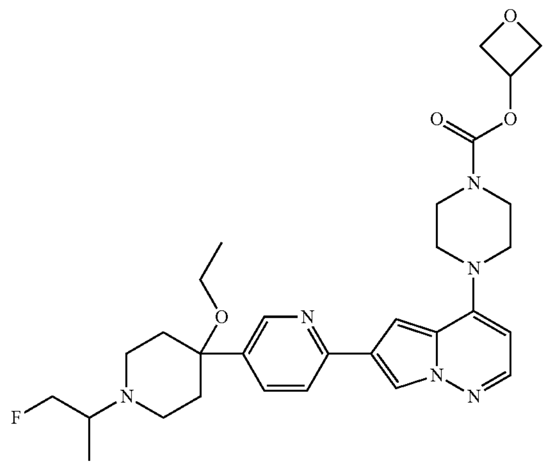 [SMILES: CCOC1(c2ccc(-c3cc4c(N5CCN(C(=O)OC6COC6)CC5)ccnn4c3)nc2)CCN(C(C)CF)CC1] | 567 | 1H-NMR (400 MHz, 6d-DMSO) δ ppm 8.59 (d, 1H, J = 1.6 Hz), 8.30 (d, 1H, J = 1.6 Hz), 8.22 (s, 1H), 7.96-7.91 (m, 2H), 7.79 (dd, 1H, J = 8.4, 2.4 Hz), 7.19 (d, 1H, J = 1.2 Hz), 6.01 (d, 1H, J = 5.6 Hz), 5.34 (quintet, 1H, J = 5.6 Hz), 4.79 (t, 2H, J = 7.2 Hz), 4.54 (dd, 2H, J = 7.2, 5.6 Hz), 4.50-4.33 (m, 2H), 3.75-3.65 (m, 2H), 3.65-3.55 (m, 2H), 3.55-3.48 (m, 4H), 3.08 (q, 2H, J = 7.2 Hz), 2.95-2.85 (m, 1H), 2.73-2.65 (m, 4H), 2.05-1.95 (m, 2H), 1.95-1.85 (m, 2H), 1.08 (t, 3H, J = 7.2 Hz), 1.26 (d, 3H, J = 6.8 Hz). |
| 882 | 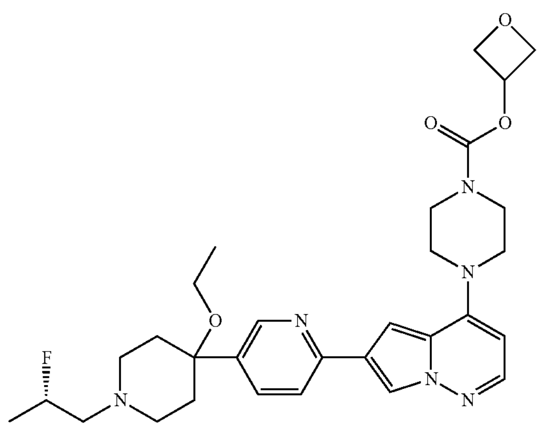 [SMILES: CCOC1(c2ccc(-c3cc4c(N5CCN(C(=O)OC6COC6)CC5)ccnn4c3)nc2)CCN(C[C@H](C)F)CC1] | 567 | 1H-NMR (400 MHz, 6d-DMSO) δ ppm 8.60 (d, 1H, J = 2.0 Hz), 8.30 (d, 1H, J = 1.6 Hz), 8.18 (s, 1H), 7.96-7.91 (m, 2H), 7.79 (dd, 1H, J = 8.0, 2.4 Hz), 7.19 (d, 1H, J = 1.2 Hz), 6.01 (d, 1H, J = 5.6 Hz), 5.33 (quintet, 1H, J = 5.2 Hz), 4.95-4.77 (m, 1H), 4.80 (t, 2H, J = 7.2 Hz), 4.54 (dd, 2H, J = 7.2, 5.2 Hz), 3.72-3.65 (m, 2H), 3.65-3.57 (m, 2H), 3.57-3.48 (m, 4H), 3.07 (q, 2H, J = 7.2 Hz), 2.80-2.71 (m, 2H), 2.70-2.50 (m, 2H), 2.50-2.48 (m, 2H), 2.02-1.90 (m, 4H), 1.27 (dd, 3H, J = 23.6 Hz, 6.4 Hz), 1.08 (t, 3H, J = 7.2 Hz). |
| 883 | 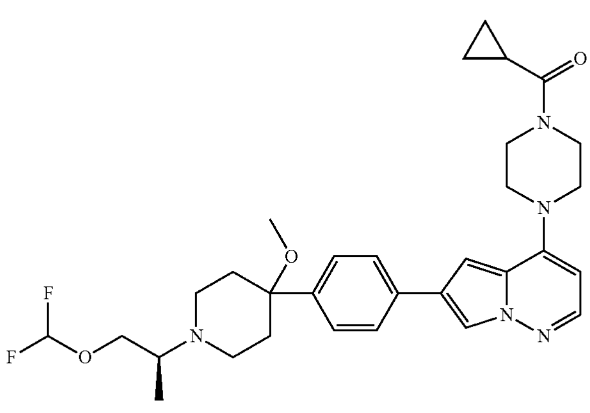 | 568 | 1H-NMR (400 MHz, 6d-DMSO) δ ppm 8.18 (d, 1H, J = 1.6 Hz), 7.91 (d, 1H, J = 5.6 Hz), 7.79 (d, 2H, J = 8.4 Hz), 7.39 (d, 2H, J = 8.4 Hz), 7.05 (d, 1H, J = 1.6 Hz), 6.69 (d, 1H, J = 76.4 Hz), 5.98 (d, 1H, J = 5.6 Hz), 4.00-3.85 (m, 3H), 3.82-3.65 (m, 3H), 3.55-3.50 (m, 2H), 3.50-3.45 (m, 2H), 2.89 (s, 3H), 2.88-2.82 (m, 1H), 2.75-2.53 (m, 4H), 2.08-1.95 (m, 3H), 1.92-1.85 (m, 2H), 1.01 (d, 3H, J = 6.8 Hz), 0.82-.072 (m, 4H). |

TABLE 1-continued
| # | Structure | LCMS (M + 1) | NMR |
|---|---|---|---|
| 884 | 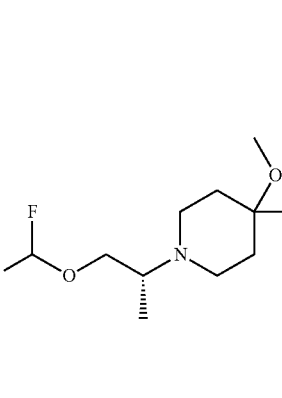 | 568 | 1H-NMR (400 MHz, 6d-DMSO) δ ppm 8.18 (d, 1H, J = 1.6 Hz), 7.91 (d, 1H, J = 5.6 Hz), 7.79 (d, 2H, J = 8.4 Hz), 7.39 (d, 2H, J = 8.4 Hz), 7.05 (d, 1H, J = 1.6 Hz), 6.69 (d, 1H, J = 76.4 Hz), 5.98 (d, 1H, J = 5.6 Hz), 4.00-3.85 (m, 3H), 3.82-3.65 (m, 3H), 3.55-3.50 (m, 2H), 3.50-3.45 (m, 2H), 2.89 (s, 3H), 2.88-2.82 (m, 1H), 2.75-2.53 (m, 4H), 2.08-1.95 (m, 3H), 1.92-1.85 (m, 2H), 1.01 (d, 3H, J = 6.8 Hz), 0.82-.072 (m, 4H). |
| 885 | 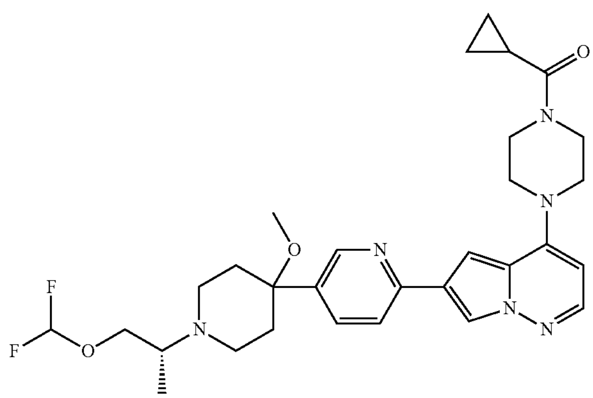 [SMILES: COC1(c2ccc(-c3cc4c(N5CCN(C(=O)C6CC6)CC5)ccnn4c3)cc2)CCN([C@H](C)COC(F)F)CC1] | 569 | 1H-NMR (400 MHz, 6d-DMSO) δ ppm 8.58 (s, 1H), 8.29 (s, 1H), 8.27 (s, 0.4H, HCOOH), 7.93 (d, 1H, J = 4.8 Hz), 7.92 (d, 1H, J = 8.4 Hz), 7.78 (d, 1H, J = 8.0 Hz), 7.21 (s, 1H), 6.68 (t, 1H, J = 76.0 Hz), 5.98 (d, 1H, J = 5.2 Hz), 3.93-3.89 (m, 3H), 3.76-3.72 (m, 3H), 3.57-3.51 (m, 4H), 2.92 (s, 3H), 2.89-2.84 (m, 1H), 2.67-2.61 (m, 4H), 2.03-2.00 (m, 3H), 1.89-1.86 (m, 2H), 1.01 (d, 3H, J = 6.8 Hz), 0.78-0.75 (m, 4H). |
| 886 | 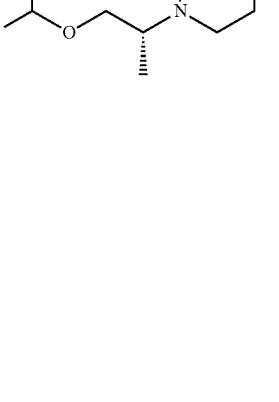 | 569 | 1H-NMR (500 MHz, 6d-DMSO) δ ppm 8.58 (d, 1H, J = 2.0 Hz), 8.30 (d, 1H, J = 1.5 Hz), 7.94-7.92 (m, 2H), 7.77 (dd, 1H, J = 8.5, 2.0 Hz), 7.21 (d, 1H, J = 1.5 Hz), 6.69 (t, 1H, J = 76.0 Hz), 5.99 (d, 1H, J = 5.5 Hz), 3.94-3.89 (m, 3H), 3.76-3.72 (m, 3H), 3.58-3.54 (m, 2H), 3.54-3.50 (m, 2H), 2.92 (s, 3H), 2.87-2.86 (m, 1H), 2.65-2.62 (m, 1H), 2.61-2.57 (m, 3H), 2.03-2.01 (m, 3H), 1.90-1.89 (m, 2H), 1.02 (d, 3H, J = 6.5 Hz), 0.80-0.75 (m, 4H). |

TABLE 1-continued

| # | Structure | LCMS (M + 1) | NMR |
|---|---|---|---|
| 887 | 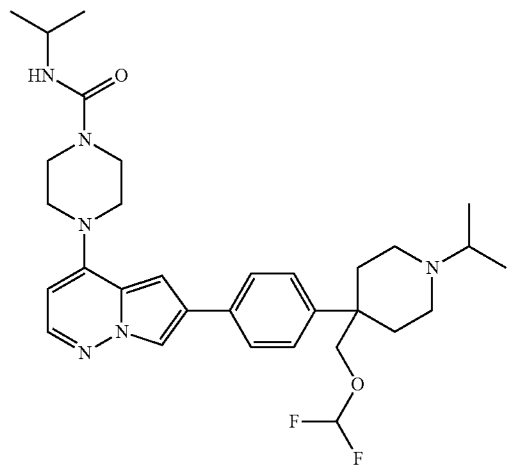 [SMILES: CC(C)NC(=O)N1CCN(c2ccnn3cc(-c4ccc(C5(COC(F)F)CCN(C(C)C)CC5)cc4)cc23)CC1] | 569 | 1H-NMR (500 MHz, 6d-DMSO) δ ppm 8.27 (s, 1H), 8.17 (d, 1H, J = 2.0 Hz), 7.90 (d, 1H, J = 5.5 Hz), 7.76 (d, 2H, J = 8.5 Hz), 7.40 (d, 2H, J = 8.5 Hz), 7.01 (d, 1H, J = 2.0 Hz), 6.53 (t, 1H, J = 76.0 Hz), 6.31 (d, 1H, J = 7.5 Hz), 5.98 (d, 1H, J = 5.0 Hz), 3.83 (s, 2H), 3.81-3.76 (m, 1H), 3.54-3.50 (m, 4H), 3.48-3.42 (m, 4H), 2.65-2.60 (m, 3H), 2.32-2.28 (m, 2H), 2.15-2.13 (m, 2H), 1.89-1.85 (m, 2H), 1.07 (d, 6H, J = 7.0 Hz), 0.92 (d, 6H, J = 6.5 Hz). |
| 888 | 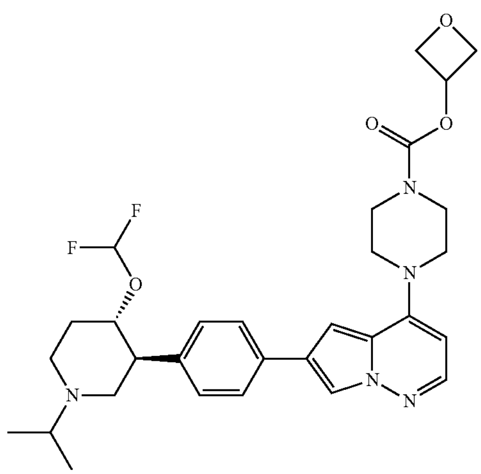 [SMILES: CC(C)N1CC[C@H](OC(F)F)[C@@H](c2ccc(-c3cc4c(N5CCN(C(=O)OC6COC6)CC5)ccnn4c3)cc2)C1] | 570 | 1H-NMR (500 MHz, 6d-DMSO) δ ppm 8.17 (d, 1H, J = 1.5 Hz), 7.91 (d, 1H, J = 6.0 Hz), 7.75 (d, 2H, J = 8.0 Hz), 7.34 (d, 2H, J = 8.0 Hz), 7.03 (d, 1H, J = 1.5 Hz), 6.49 (t, 1H, J = 76.5 Hz), 5.99 (d, 1H, J = 5.0 Hz), 5.34 (quintet, 1H, J = 6.5 Hz), 4.79 (t, 2H, J = 7.0 Hz), 4.53 (dd, 2H, J = 7.5, 5.5 Hz), 4.35-4.29 (m, 1H), 3.71-3.69 (m, 2H), 3.61-3.59 (m, 2H), 3.50-3.48 (m, 4H), 2.89-2.80 (m, 2H), 2.80-2.72 (m, 2H), 2.31 (t, 2H, J = 11.0 Hz), 2.12-2.10 (m, 1H), 1.68-1.62 (m, 1H), 1.51-1.47 (m, 1H), 0.97-0.94 (m, 6H). |
| 889 | 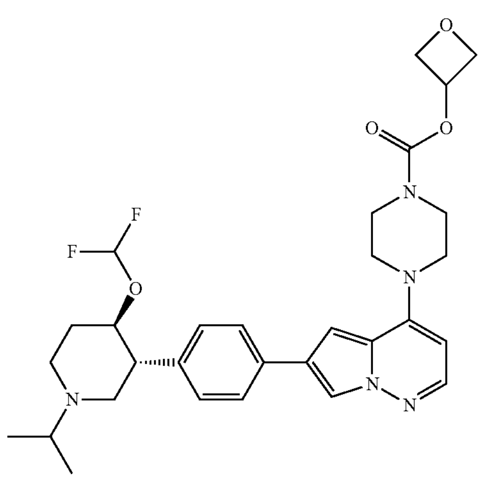 [SMILES: CC(C)N1CC[C@@H](OC(F)F)[C@H](c2ccc(-c3cc4c(N5CCN(C(=O)OC6COC6)CC5)ccnn4c3)cc2)C1] | 570 | 1H-NMR (400 MHz, 6d-DMSO) δ ppm 8.18 (d, 1H, J = 1.6 Hz), 7.91 (d, 1H, J = 5.2 Hz), 7.75 (d, 2H, J = 8.4 Hz), 7.34 (d, 2H, J = 8.4 Hz), 7.03 (d, 1H, J = 1.6 Hz), 6.49 (t, 1H, J = 76.4 Hz), 5.99 (d, 1H, J = 5.6 Hz), 5.34 (quintet, 1H, J = 5.6 Hz), 4.79 (t, 2H, J = 7.2 Hz), 4.53 (dd, 2H, J = 8.0, 5.6 Hz), 4.35-4.29 (m, 1H), 3.70-3.65 (m, 2H), 3.65-3.59 (m, 2H), 3.50-3.48 (m, 4H), 2.86-2.79 (m, 2H), 2.79-2.72 (m, 2H), 2.31 (t, 2H, J = 11.2 Hz), 2.12-2.10 (m, 1H), 1.68-1.62 (m, 1H), 0.98-0.94 (m, 6H). |

TABLE 1-continued

| # | Structure | LCMS (M + 1) | NMR |
|---|---|---|---|
| 890 | 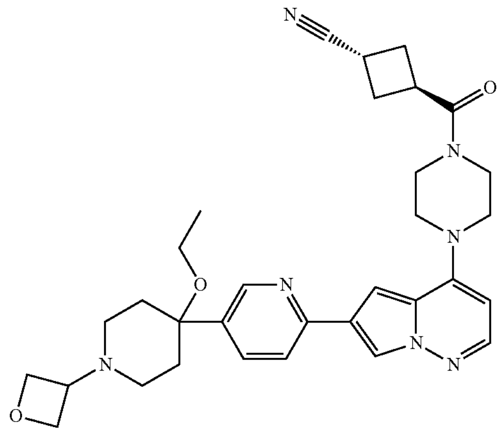 [SMILES: CCOC1(c2ccc(-c3cc4c(N5CCN(C(=O)[C@H]6C[C@H](C#N)C6)CC5)ccnn4c3)nc2)CCN(C2COC2)CC1] | 570 | 1H-NMR (400 MHz, 6d-DMSO) δ ppm 8.60 (d, 1H, J = 1.6 Hz), 8.30 (d, 1H, J = 1.6 Hz), 8.17 (s, 1H), 7.95-7.91 (m, 2H), 7.81-7.78 (m, 1H), 7.19 (d, 1H, J = 1.6 Hz), 5.98 (d, 1H, J = 5.6 Hz), 4.55 (t, 2H, J = 6.4 Hz), 4.44 (t, 2H, J = 6.4 Hz), 3.71-3.65 (m, 3H), 3.57-3.54 (m, 2H), 3.49-3.46 (m, 4H), 3.45-3.42 (m, 1H), 3.31-3.26 (m, 1H), 3.07 (q, 2H, J = 7.2 Hz), 2.67-2.59 (m, 2H), 2.54-2.51 (m, 2H), 2.50-2.48 (m, 2H), 2.21-2.15 (m, 2H), 2.03-1.90 (m, 4H), 1.08 (t, 3H, J = 7.2 Hz). |
| 891 | 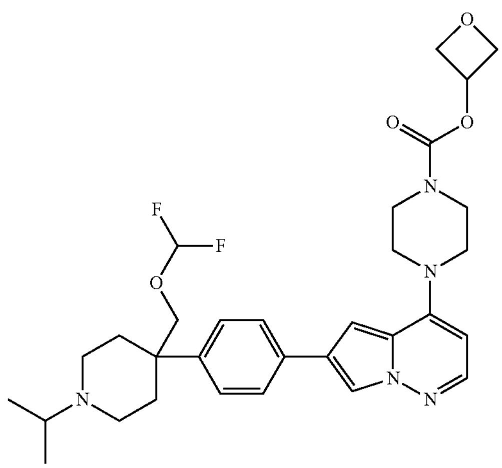 [SMILES: CC(C)N1CCC(COC(F)F)(c2ccc(-c3cc4c(N5CCN(C(=O)OC6COC6)CC5)ccnn4c3)cc2)CC1] | 584 | 1H-NMR (500 MHz, 6d-DMSO) δ ppm 8.18 (s, 1H), 7.92 (d, 1H, J = 5.5 Hz), 7.76 (d, 2H, J = 8.0 Hz), 7.40 (d, 2H, J = 8.0 Hz), 7.02 (s, 1H), 6.53 (t, 1H, J = 76.0 Hz), 6.00 (d, 1H, J = 5.5 Hz), 5.33 (quintet, 1H, J = 5.0 Hz), 4.79 (t, 2H, J = 7.0 Hz), 4.53 (dd, 2H, J = 7.0, 5.0 Hz), 3.83 (s, 2H), 3.75-3.70 (m, 2H), 3.70-3.65 (m, 2H), 3.52-3.47 (m, 4H), 2.60-2.56 (m, 3H), 2.32-2.28 (m, 2H), 2.15-2.13 (m, 2H), 1.90-1.87 (m, 2H), 0.91 (d, 6H, J = 7.0 Hz). |
| 892 | 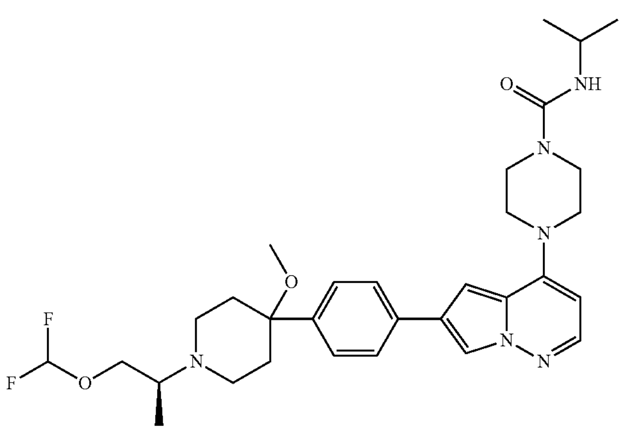 [SMILES: COC1(c2ccc(-c3cc4c(N5CCN(C(=O)NC(C)C)CC5)ccnn4c3)cc2)CCN([C@@H](C)COC(F)F)CC1] | 585 | 1H-NMR (400 MHz, 6d-DMSO) δ ppm 8.17 (d, 1H, J = 1.6 Hz), 7.90 (d, 1H, J = 5.6 Hz), 7.79 (d, 2H, J = 8.4 Hz), 7.39 (d, 2H, J = 8.4 Hz), 7.01 (d, 1H, J = 1.2 Hz), 6.68 (t, 1H, J = 76.4 Hz), 6.30 (d, 1H, J = 7.6 Hz), 5.99 (d, 1H, J = 5.2 Hz), 3.91-3.87 (m, 1H), 3.80-3.73 (m, 2H), 3.53-3.48 (m, 4H), 3.46-3.41 (m, 4H), 2.89 (s, 3H), 2.88-2.83 (m, 1H), 2.75-2.53 (m, 4H), 2.03-1.93 (m, 2H), 1.90-1.82 (m, 2H), 1.06 (d, 6H, J = 8.4 Hz), 1.01 (d, 3H, J = 6.4 Hz). |

TABLE 1-continued

| # | Structure | LCMS (M + 1) | NMR |
|---|---|---|---|
| 893 | 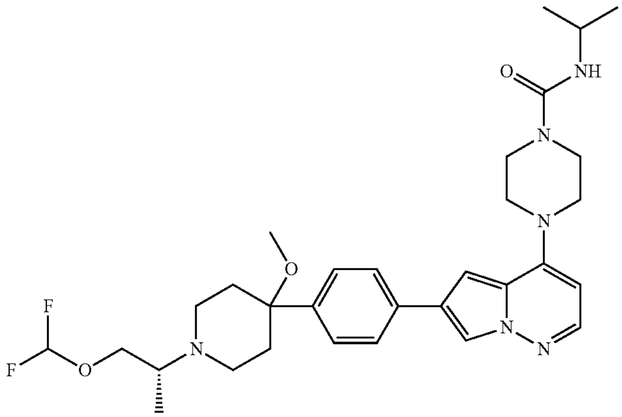 [SMILES: COC1(c2ccc(-c3cc4c(N5CCN(C(=O)NC(C)C)CC5)ccnn4c3)cc2)CCN([C@H](C)COC(F)F)CC1] | 585 | 1H-NMR (400 MHz, 6d-DMSO) δ ppm 8.17 (d, 1H, J = 1.6 Hz), 7.90 (d, 1H, J = 5.6 Hz), 7.79 (d, 2H, J = 8.4 Hz), 7.39 (d, 2H, J = 8.4 Hz), 7.01 (d, 1H, J = 1.2 Hz), 6.68 (t, 1H, J = 76.4 Hz), 6.30 (d, 1H, J = 7.6 Hz), 5.99 (d, 1H, J = 5.2 Hz), 3.91-3.87 (m, 1H), 3.80-3.73 (m, 2H), 3.53-3.48 (m, 4H), 3.46-3.41 (m, 4H), 2.89 (s, 3H), 2.88-2.83 (m, 1H), 2.75-2.53 (m, 4H), 2.03-1.93 (m, 2H), 1.90-1.82 (m, 2H), 1.06 (d, 6H, J = 8.4 Hz), 1.01 (d, 3H, J = 6.4 Hz). |
| 894 | 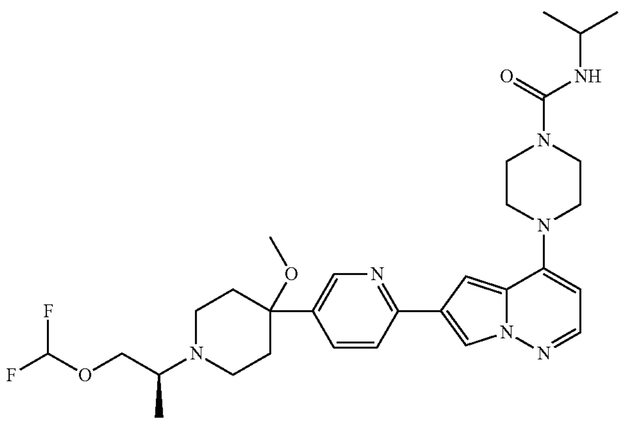 [SMILES: COC1(c2ccc(-c3cc4c(N5CCN(C(=O)NC(C)C)CC5)ccnn4c3)nc2)CCN([C@@H](C)COC(F)F)CC1] | 586 | 1H-NMR (400 MHz, 6d-DMSO) δ ppm 8.58 (d, 1H, J = 1.6 Hz), 8.28 (d, 1H, J = 1.6 Hz), 7.93-7.91 (m, 2H), 7.77 (dd, 1H, J = 8.4, 2.0 Hz), 7.17 (d, 1H, J = 1.6 Hz), 6.68 (t, 1H, J = 76.4 Hz), 6.30 (d, 1H, J = 7.6 Hz), 5.99 (d, 1H, J = 5.2 Hz), 3.93-3.89 (m, 1H), 3.80-3.77 (m, 1H), 3.77-3.72 (m, 1H), 3.54-3.53 (m, 4H), 3.47-3.46 (m, 4H), 2.92 (s, 3H), 2.89-2.86 (m, 1H), 2.67-2.62 (m, 1H), 2.61-2.56 (m, 3H), 2.04-2.01 (m, 2H), 1.89-1.86 (m, 2H), 1.08 (d, 6H, J = 6.8 Hz), 1.02 (d, 3H, J = 6.4 Hz). |
| 895 | 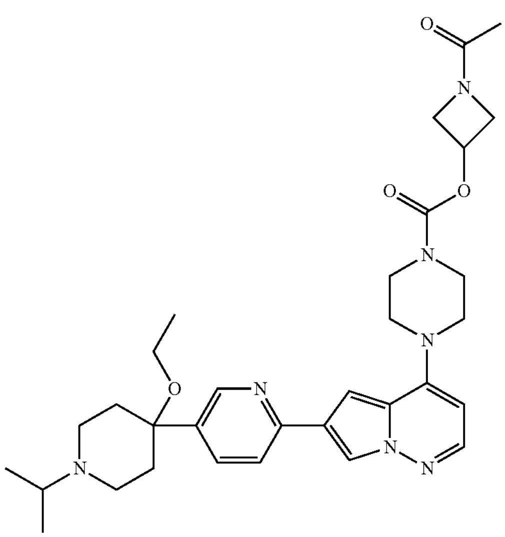 [SMILES: CCOC1(c2ccc(-c3cc4c(N5CCN(C(=O)OC6CN(C(C)=O)C6)CC5)ccnn4c3)nc2)CCN(C(C)C)CC1] | 590 | 1H-NMR (500 MHz, 6d-DMSO) δ ppm 8.59 (d, 1H, J = 2.0 Hz), 8.28 (d, 1H, J = 1.5 Hz), 7.94 (d, 1H, J = 5.5 Hz), 7.91 (d, 1H, J = 8.0 Hz), 7.78 (dd, 1H, J = 8.0, 2.0 Hz), 7.18 (d, 1H, J = 1.5 Hz), 6.01 (d, 1H, J = 5.5 Hz), 5.10-5.08 (m, 1H), 4.43 (dd, 1H, J = 9.5, 7.0 Hz), 4.14 (dd, 1H, J = 10.5, 7.0 Hz), 4.09 (dd, 1H, J = 9.5, 4.0 Hz), 3.78 (dd, 1H, J = 10.5, 4.0 Hz), 3.71-3.65 (m, 2H), 3.65-3.59 (m, 2H), 3.52-3.51 (m, 4H), 3.08 (q, 2H, J = 7.0 Hz), 2.70-2.68 (m, 1H), 2.62-2.60 (m, 2H), 2.54-2.51 (m, 2H), 2.01-1.98 (m, 2H), 1.91-1.89 (m, 2H), 1.78 (s, 3H), 1.08 (t, 3H, J = 7.0 Hz), 1.00 (d, 6H, J = 7.0 Hz). |

TABLE 1-continued

| # | Structure | LCMS (M + 1) | NMR |
|---|---|---|---|
| 896 | 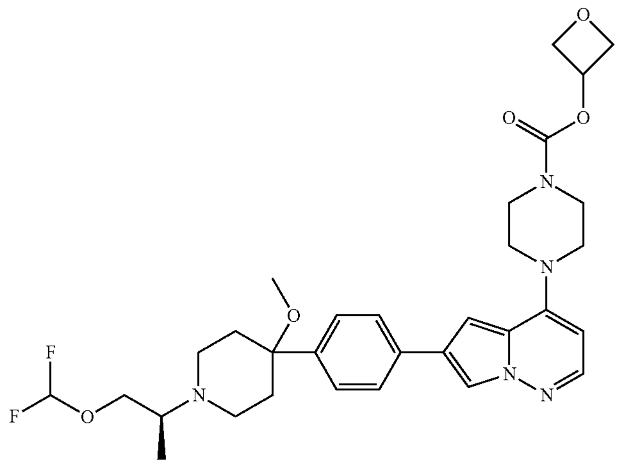 [SMILES: COC1(c2ccc(-c3cc4c(N5CCN(C(=O)OC6COC6)CC5)ccnn4c3)cc2)CCN([C@@H](C)COC(F)F)CC1] | 600 | 1H-NMR (400 MHz, 6d-DMSO) δ ppm 8.18 (d, 1H, J = 1.2 Hz), 7.92 (d, 1H, J = 5.2 Hz), 7.79 (d, 2H, J = 8.4 Hz), 7.39 (d, 2H, J = 8.4 Hz), 7.03 (d, 1H, J = 1.6 Hz), 6.69 (d, 1H, J = 76.4 Hz), 6.00 (d, 1H, J = 5.2 Hz), 5.34 (quintet, 1H, J = 5.6 Hz), 4.79 (t, 2H, J = 6.8 Hz), 4.53 (dd, 2H, J = 6.8, 5.6 Hz), 3.92-3.87 (m, 1H), 3.77-3.72 (m, 1H), 3.75-3.69 (m, 2H), 3.69-3.66 (m, 2H), 3.62-3.58 (m, 4H), 2.89 (s, 3H), 2.88-2.83 (m, 1H), 2.75-2.55 (m, 4H), 2.03-1.96 (m, 2H), 1.90-1.81 (m, 2H), 1.01 (d, 3H, J = 6.4 Hz). |
| 897 | 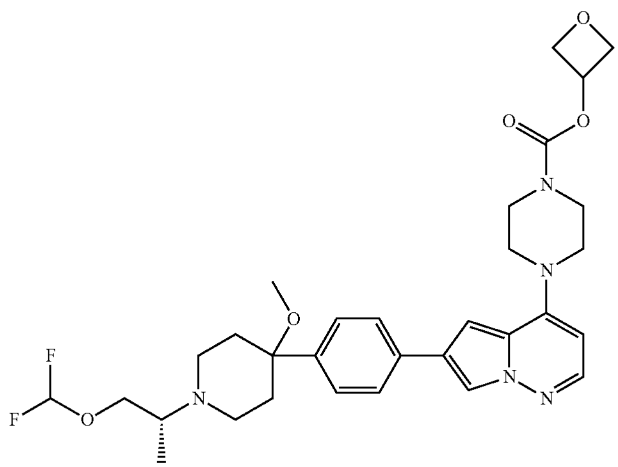 [SMILES: COC1(c2ccc(-c3cc4c(N5CCN(C(=O)OC6COC6)CC5)ccnn4c3)cc2)CCN([C@H](C)COC(F)F)CC1] | 600 | 1H-NMR (400 MHz, 6d-DMSO) δ ppm 8.18 (d, 1H, J = 1.2 Hz), 7.92 (d, 1H, J = 5.2 Hz), 7.79 (d, 2H, J = 8.4 Hz), 7.39 (d, 2H, J = 8.4 Hz), 7.03 (d, 1H, J = 1.6 Hz), 6.69 (d, 1H, J = 76.4 Hz), 6.00 (d, 1H, J = 5.2 Hz), 5.34 (quintet, 1H, J = 5.6 Hz), 4.79 (t, 2H, J = 6.8 Hz), 4.53 (dd, 2H, J = 6.8, 5.6 Hz), 3.92-3.87 (m, 1H), 3.77-3.72 (m, 1H), 3.75-3.69 (m, 2H), 3.69-3.66 (m, 2H), 3.62-3.58 (m, 4H), 2.89 (s, 3H), 2.88-2.83 (m, 1H), 2.75-2.55 (m, 4H), 2.03-1.96 (m, 2H), 1.90-1.81 (m, 2H), 1.01 (d, 3H, J = 6.4 Hz). |
| 898 | 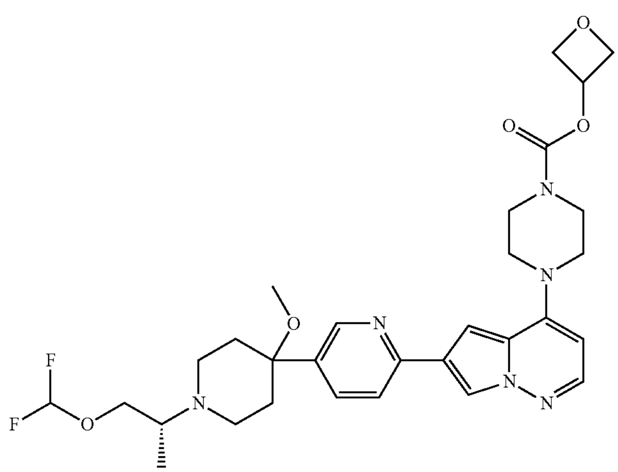 | 601 | 1H-NMR (400 MHz, 6d-DMSO) δ ppm 8.58 (s, 1H), 8.29 (s, 1H), 8.27 (s, 0.4H, HCOOH), 7.94 (d, 1H, J = 5.6 Hz), 7.92 (d, 1H, J = 4.4 Hz), 7.78 (d, 1H, J = 4.4 Hz), 7.19 (s, 1H), 6.69 (t, 1H, J = 76.4 Hz), 6.01 (d, 1H, J = 5.2 Hz), 5.35-5.31 (m, 1H), 4.81-4.77 (m, 2H), 4.55-4.51 (m, 2H), 3.93-3.89 (m, 1H), 3.78-3.68 (m, 8H), 2.92 (s, 3H), 2.89-2.84 (m, 2H), 2.70-2.58 (m, 4H), 2.03-2.00 (m, 2H), 1.89-1.78 (m, 2H), 1.01 (d, 3H, J = 6.4 Hz). |

| # | Structure | LCMS (M + 1) | NMR |
|---|---|---|---|
| 899 | 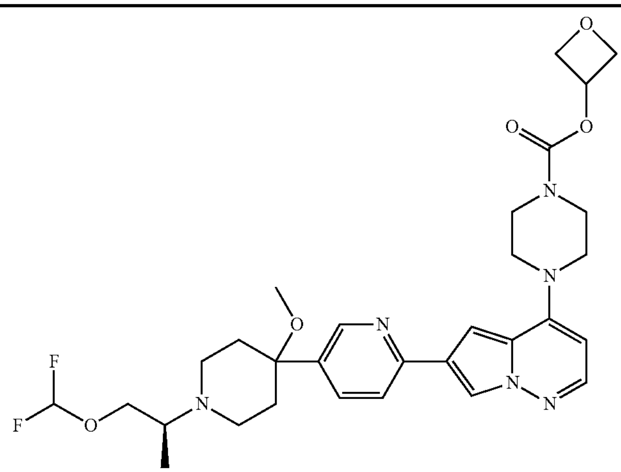 | 601 | 1H-NMR (500 MHz, 6d-DMSO) δ ppm 8.58 (d, 1H, J = 2.0 Hz), 8.29 (d, 1H, J = 1.5 Hz), 7.95-7.92 (m, 2H), 7.78 (dd, 1H, J = 8.5, 2.5 Hz), 7.19 (d, 1H, J = 1.5 Hz), 6.69 (t, 1H, J = 76.0 Hz), 6.01 (d, 1H, J = 5.5 Hz), 5.34 (quintet, 1H, J = 5.5 Hz), 4.79 (t, 2H, J = 7.5 Hz), 4.53 (dd, 2H, J = 7.5, 5.5 Hz), 3.91-3.89 (m, 1H), 3.76-3.74 (m, 1H), 3.75-3.70 (m, 2H), 3.62-3.57 (m, 2H), 3.51-3.49 (m, 4H), 2.92 (s, 3H), 2.87-2.86 (m, 1H), 2.70-2.67 (m, 1H), 2.67-2.61 (m, 3H), 2.03-2.01 (m, 2H), 1.90-1.89 (m, 2H), 1.02 (d, 3H, J = 6.5 Hz). |

In another aspect, the present disclosure features a method of treating or ameliorating fibrodysplasia ossificans progressiva in a subject, comprising administering to the subject a pharmaceutically effective amount of a compound described herein (e.g., a compound in Table 1) or a pharmaceutically acceptable salt thereof, or a pharmaceutical composition thereof.

In another aspect, the present disclosure features a method of treating or ameliorating diffuse intrinsic pontine glioma in a subject, comprising administering to the subject a pharmaceutically effective amount of a compound described herein (e.g., a compound in Table 1) or a pharmaceutically acceptable salt thereof, or a pharmaceutical composition thereof.

In another aspect, the present disclosure features a method of inhibiting aberrant ALK2 activity in a subject, comprising administering to the subject a therapeutically effective amount of a compound described herein (e.g., a compound in Table 1) or a pharmaceutically acceptable salt thereof, or a pharmaceutical composition thereof.

Pharmaceutically acceptable salts of these compounds are also contemplated for the uses described herein.

"Pharmaceutically acceptable salt" refers to any salt of a compound of the disclosure which retains its biological properties and which is not toxic or otherwise undesirable for pharmaceutical use. Pharmaceutically acceptable salts may be derived from a variety of organic and inorganic counter-ions. Such salts include one or more of: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. A pharmaceutically acceptable salt according to the disclosure includes at least one salt, and also may be mixtures of more than one salt.

Pharmaceutical Compositions

Pharmaceutical compositions of the disclosure comprise one or more compounds of the disclosure and one or more pharmaceutically acceptable carrier(s). The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In an embodiment, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present disclosure that may be combined with the carrier to produce a composition in a single dosage form will vary depending upon the host treated, the particular mode of administration, and other factors determined by the person administering the single dosage form.

Dosages

Toxicity and therapeutic efficacy of compounds of the disclosure, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including but not limited to the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

Treatment

Mutations in ALK2 cause the kinase to be inappropriately active and are associated with various diseases. The disclosure provides compounds that inhibit a mutant ALK2 gene, e.g., a mutant ALK2 gene that results in the expression of an ALK2 enzyme having an amino acid modification. In another aspect, the disclosure provides compounds that inhibit both wild type (WT) ALK2 protein and mutant forms of ALK2 protein. For the purposes of this disclosure, sequence information for ALK2 is found on the National Center for Biological Information (NCBI) webpage (https://www.ncbi.nlm.nih.gov/) under ACVR1 activin A receptor type 1 [Homo sapiens (human)]; Entrez Gene ID (NCBI): 90. It is also known as: FOP; ALK2; SKR1; TSRI; ACTRI; ACVR1A; ACVRLK2 said sequence information is incorporated herein.

In an embodiment, the disclosure provides a method of inhibiting aberrant ALK2 activity in a subject comprising the step of administering to the subject in need thereof a pharmaceutically effective amount of at least one compound or pharmaceutical composition described herein. In an embodiment, the aberrant ALK2 activity is caused by a mutation in an ALK2 gene that results in the expression of an ALK2 enzyme having an amino acid modification selected from one or more of L196P, PF197-8L, R202I, R206H, Q207E, R258S, R258G, G328A, G328V, G328W, G328E, G328R, G356D, and R375P. In an embodiment, the ALK2 enzyme has the amino acid modification R206H.

Because of their activity against ALK2, the compounds described herein can be used to treat a patient with a condition associated with aberrant ALK2 activity. In an embodiment, the condition associated with aberrant ALK2 activity is fibrodysplasia ossificans progressiva. FOP diagnosis is based on the presence of congenital malformations of the great toes (hallux valgus) and the formation of fibrous nodules in soft tissues. The nodules may or may not transform into heterotopic bone. These soft tissue lesions are often first noted in the head, neck back. ~97% of FOP patients have the same c.617G>A; R206H mutation in the ACVR1 (Alk2) gene. There is a genetic test available through the University of Pennsylvania (Kaplan et all, *Pediatrics* 2008, 121(5): e1295-e1300).

Other common congenital anomalies include malformations of the thumbs, short broad femoral necks, tibial osteochondromas and fused facet joints of the cervical spine. The fused facet joints in the neck often cause toddlers to scoot on their buttocks rather than crawl. FOP is commonly misdiagnosed (~80%; cancer or fibromatosis) and patients are frequently subjected to inappropriate diagnostic procedures such as biopsies that exacerbate disease and cause permanent disability.

In an embodiment, the present disclosure provides a method of treating or ameliorating fibrodysplasia ossificans progressiva in a subject, comprising administering to the subject in need thereof a pharmaceutically effective amount of a compound or pharmaceutical composition described herein.

In an embodiment, the condition associated with aberrant ALK2 activity is fibrodysplasia ossificans progressiva (FOP) and the subject has a mutation in an ALK2 gene that results in the expression of an ALK2 enzyme having an amino acid modification selected from one or more of L196P, PF197-8L, R202I, R206H, Q207E, R258S, R258G, G328A, G328W, G328E, G328R, G356D, and R375P. In one aspect of this embodiment, the ALK2 enzyme has the amino acid modification R206H.

The present disclosure includes methods of identifying and/or diagnosing patients for treatment with one or more of the compounds or pharmaceutical compositions described herein. In an embodiment, the disclosure provides a method of detecting a condition associated with aberrant ALK2 activity e.g., FOB in a subject, wherein the method includes a. obtaining a sample e.g., plasma from the subject e.g., a human patient; and b. detecting whether one or more mutations in an ALK2 gene as described herein are present in the sample. In another embodiment, the disclosure provides a method of diagnosing a condition associated with aberrant ALK2 activity in a subject, said method comprising: a. obtaining a sample from the subject; b. detecting whether one or more mutations in an ALK2 gene as described herein are present in the sample using a detection method described herein; and c. diagnosing the subject with the condition when the presence of the one or more mutations is detected. Methods for detecting a mutation include but are not limited to hybridization-based methods, amplification-based methods, microarray analysis, flow cytometry analysis, DNA sequencing, next-generation sequencing (NGS), primer extension, PCR, in situ hybridization, dot blot, and Southern blot. In an embodiment, the present disclosure provides a method of diagnosing and treating a condition associated with aberrant ALK2 activity in a subject, said method comprising a. obtaining a sample from a subject; b. detecting whether one or more mutations in an ALK2 gene as described herein are present in the sample; diagnosing the subject with the condition when the one or more mutations in the sample are detected; and d. administering an effective amount of one or more of the compounds or a pharmaceutical composition described herein to the diagnosed patient. In an embodiment, the disclosure provides a method of treating a condition associated with aberrant ALK2 activity in a subject, said method comprising a. determining if, having determined if, or receiving information that the subject has one or more mutations in an ALK2 gene as described herein; b. identifying the subject as responsive to one or more compounds or a pharmaceutical composition described herein; and c. administering an effective amount of the one or more compounds or pharmaceutical compositions to the subject.

In an embodiment, the condition associated with aberrant ALK2 activity is a brain tumor, e.g., glial tumor. In an embodiment, the glial tumor is diffuse intrinsic pontine glioma (DIPG). In an embodiment, the disclosure provides a method of treating or ameliorating diffuse intrinsic pontine glioma in a subject, comprising administering to the subject in need thereof a pharmaceutically effective amount of a compound or pharmaceutical composition described herein.

In an embodiment, the condition associated with aberrant ALK2 activity is diffuse intrinsic pontine glioma and the subject has a mutation in an ALK2 gene that results in the expression of an ALK2 enzyme having an amino acid modification selected from one or more of R206H, G328V, G328W, G328E, and G356D. In one aspect of this embodiment, the ALK2 enzyme has the amino acid modification R206H.

In an embodiment, the condition associated with aberrant ALK2 activity is anemia associated with inflammation, cancer or chronic disease.

In an embodiment, the condition associated with aberrant ALK2 activity is trauma- or surgery-induced heterotopic ossification.

In an embodiment, a compound of the disclosure is co-administered (either as part of a combination dosage form or as a separate dosage form administered prior to, sequentially with, of after administration) with a second therapeutic agent useful in treating the disease to be treated e.g., FOP. In one aspect of this embodiment, a compound of the disclosure is co-administered with a steroid (e.g., prednisone) or other anti-allergenic agents such as omalizumab.

In an embodiment, a compound of the disclosure is co-administered with a RAR-γ agonist or an antibody against activating for treating the disease to be treated e.g., FOP. In an embodiment, the RAR-γ agonist to be co-administered is palovarotene. In an embodiment, the antibody against activin to be co-administered is REGN2477.

In an embodiment, a compound of the disclosure is co-administered with therapies that target mast cells useful in treating FOP. In an embodiment, a compound of the disclosure is co-administered with a mast cell inhibitor including, but not limited to a KIT inhibitor. In an embodiment, the mast cell inhibitor to be co-administered is selected from cromolyn sodium (or sodium cromoglicate); brentuximab (ADCETRIS®); ibrutinib (IMBRUVICA®); omalizumab (XOLAIR®); anti-leukotriene agents (e.g., montelukast (SINGULAIR®) or zileuton (ZYFLO® or ZYFLO CR®)); and KIT inhibitors (e.g., imatinib (GLEEVEC®), midostaurin (PKC412A), masitinib (MASIVET® or KINAVET®), BLU-285, DCC-2618, PLX9486).

Synthesis

The Schemes below are meant to provide general guidance in connection with preparing the compounds of the disclosure. One skilled in the art would understand that the preparations shown in the Schemes can be modified or optimized using general knowledge of organic chemistry to prepare various compounds of the disclosure.

Synthetic Protocol 1

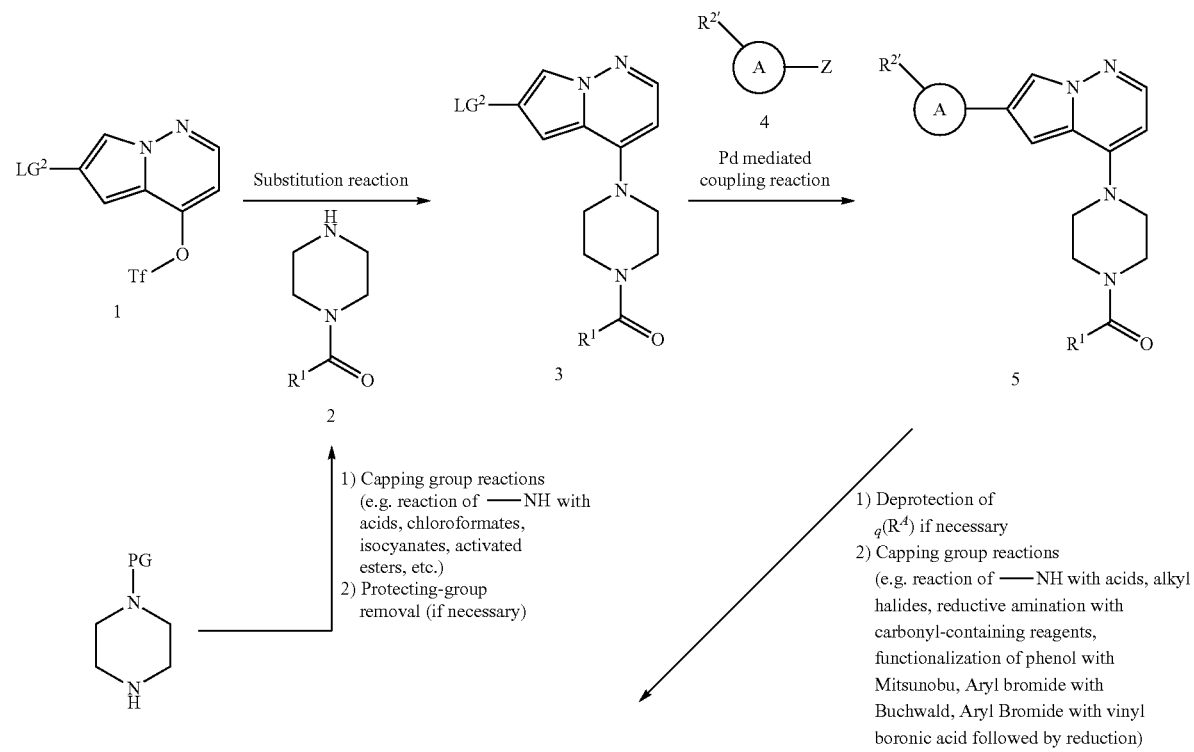

-continued

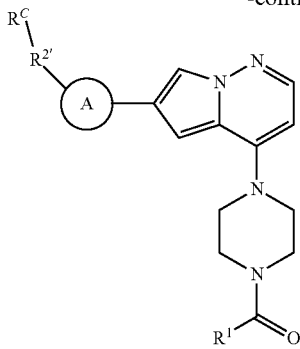
6

Tf=trifluoromethyl sulfonyl; LG²=leaving group; PG=protecting group; R^C is an optional capping group; R²'=R² or a precursor to R² if capped with R^C; Z=a Pd-mediated cross coupling partner for a halide, e.g.; a boronic ester/acid, a tin group or a zinc group.

The pyrrolopyridazine 1 having a leaving group (LG₂) can be coupled with a functionalized piperazine 2 via a substitution reaction to provide an intermediate 3 with a new carbon-nitrogen bond formed. The functionalized piperazine 2 can be formed by reaction with such groups as carboxylic acids/acid chlorides, chloroformates and isocyanates (or activated carbamates, etc.) to form amides, carbamates and ureas, respectively, via well-established reaction protocols; followed by deprotection (if necessary). The resulting pyrrolopyridazine 3 can be coupled to intermediate 4 via a palladium-mediated coupling reaction, e.g., Suzuki, Stille, or Negishi coupling, to provide an intermediate (5) with a new carbon-carbon bond formed. (LG² can be, e.g., Cl, Br, or I. Z can be boronate, boronate ester, or trialkyltin. R²' can be, for example, Br, OH, N-linked alkyl or cycloalkylamine, or C-linked alkyl or cycloalkylamine. The resulting intermediate 5 can be further functionalized (following protecting group removal, if necessary) by capping reactions including alkylation, reductive amination with carbonyl containing compounds, acylation, ether formation via Mitsunobu coupling, amination using the Buchwald reaction, or alkyl/cycloalkylamine formation achieved through vinylboronic acid addition followed by hydrogenation. Synthesis of exemplary compounds prepared using Synthetic Protocol 1 are disclosed in certain of the Examples below.

Synthetic Protocol 2

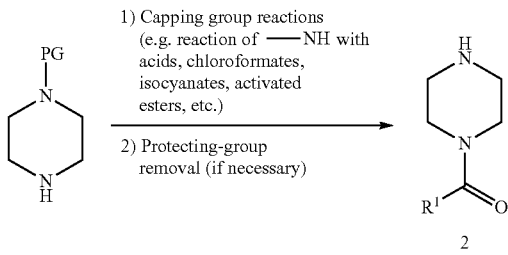

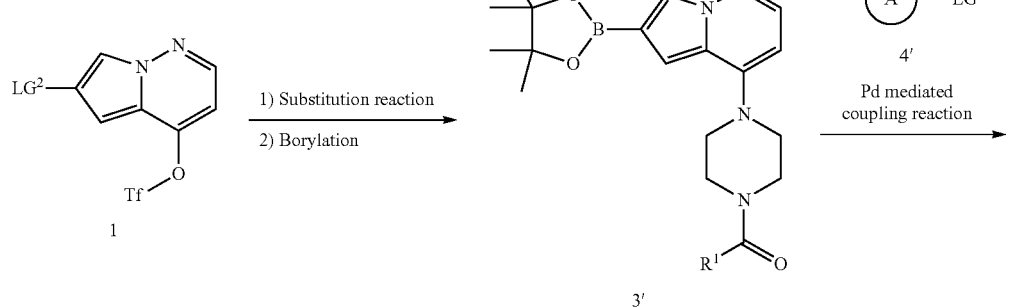

-continued

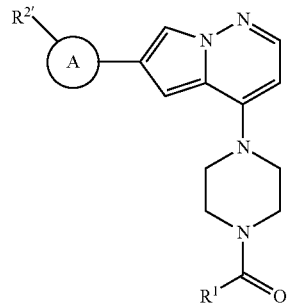
5

1) Deprotection of $_q(R^4)$ if necessary
2) Capping group reactions (e.g. reaction of ——NH with acids, alkyl halides, reductive amination with carbonyl-containing reagents, functionalization of phenol with Mitsunobu, Aryl bromide with Buchwald, Aryl Bromide with vinyl boronic acid followed by reduction)

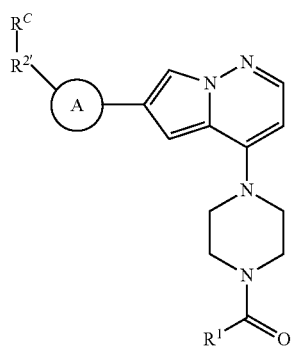
6

The pyrrolopyridazine 1 can be coupled with a functionalized piperazine 2 via a substitution reaction to provide an intermediate with a new carbon-nitrogen bond formed. The resulting intermediate can be converted to a boronate ester by palladium mediated coupling with bis-pinacolato diboron to give intermediate 3'. In some instances, the $R^1$ group can be replaced with a different $R^1$ group e.g., replacement nitrophenyloxy with oxetanyloxy. The resulting pyrrolopyridazine boronate can be coupled to an aryl halide (4') via a palladium-mediated coupling reaction, e.g., Suzuki coupling, to provide an intermediate with a new carbon-carbon bond formed. ($LG^2$ can be Cl, Br, I, OTf; $R^{2'}$ can be, for example, Br, OH, N-linked alkyl or cycloalkylamine, or C-linked alkyl or cycloalkylamine.) This resulting di-substituted pyrrolopyridazine, intermediate 5, can be further functionalized (following protecting group removal, if necessary) by capping reactions including alkylation, reductive amination with carbonyl containing compounds, acylation, ether formation via Mitsunobu coupling between a phenol and alcohols, amination using the Buchwald reaction or alkyl/cycloalkylamine formation achieved through vinylboronic acid addition followed by hydrogenation via well-established reaction protocols. Synthesis of exemplary compounds prepared using Synthetic Protocol 2 are disclosed in certain of the Examples below.

Synthetic Protocol 3

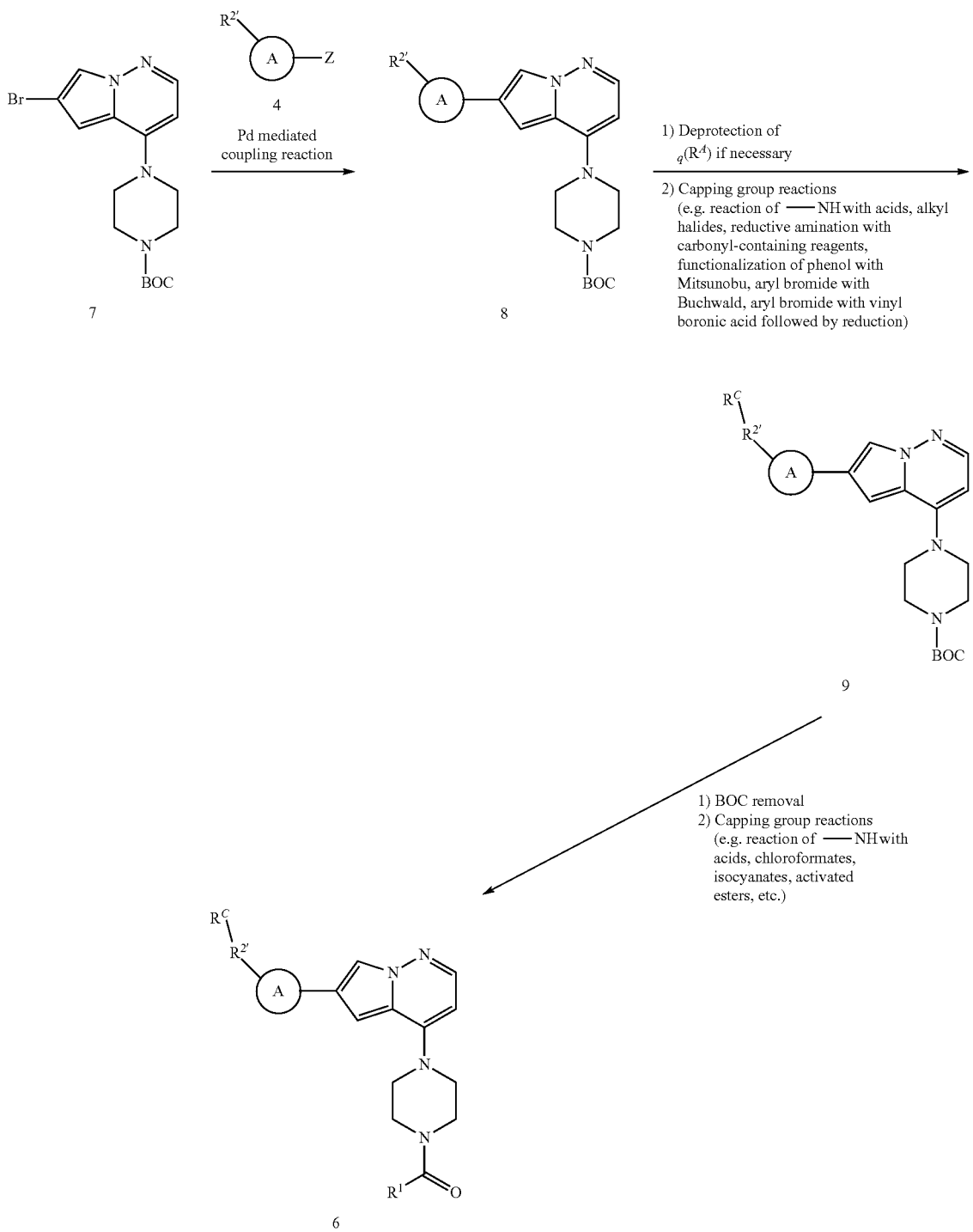

The pyrrolopyridazine 7 can be coupled with substituted aryl boronic acids 4 ($R^{2'}$ can be, for example, Br, OH, N-linked alkyl or cycloalkylamine, or C-linked alkyl or cycloalkylamine) to form a new carbon-carbon bond. The resulting intermediate 8 can be further functionalized (following protecting group removal, if necessary) by capping reactions including alkylation, reductive amination with carbonyl containing compounds, acylation, ether formation via Mitsunobu coupling, or amination using the Buchwald reaction. Removal of the BOC group in intermediate 9 can be followed by capping reactions of the resulting free NH using activated carboxylic acids, chloroformates, carbamoyl chlorides/isocyanates to give amides, carbamates, or ureas respectively via well-established reaction protocols. Synthesis of exemplary compounds prepared using Synthetic Protocol 3 are disclosed in certain of the Examples below.

Synthetic Protocol 4

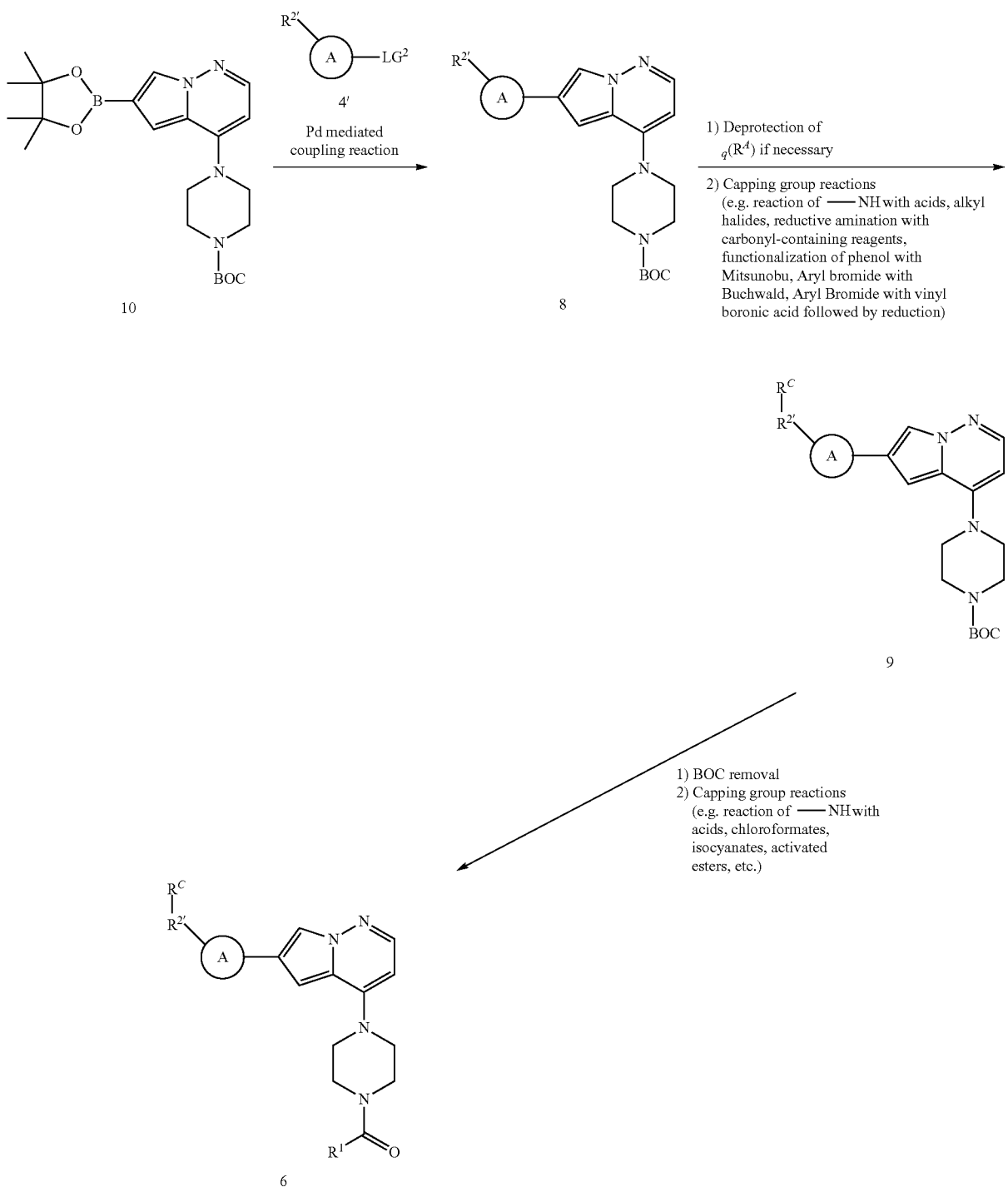

The pyrrolopyridazine boronate ester 10 can be coupled with aryl halides 4' to provide intermediate 8. (LG² can be, e.g., Cl, Br, or I. R²' can be, for example, Br, OH, N-linked alkyl or cycloalkylamine, or C-linked alkyl or cycloalkylamine). Intermediate 8 can be further functionalized (following protecting group removal, if necessary) by capping reactions including alkylation, reductive amination with carbonyl containing compounds, acylation, ether formation via Mitsunobu coupling, or amination using the Buchwald reaction to provide intermediate 9. Removal of the BOC group in intermediate 9 can be followed by capping reactions of the resulting free NH using activated carboxylic acids, chloroformates, carbamoyl chlorides/isocyanates to give amides, carbamates, or ureas respectively via well-established reaction protocols. Synthesis of exemplary compounds prepared using Synthetic Protocol 4 are disclosed in certain of the Examples below.

Synthetic Protocol 5

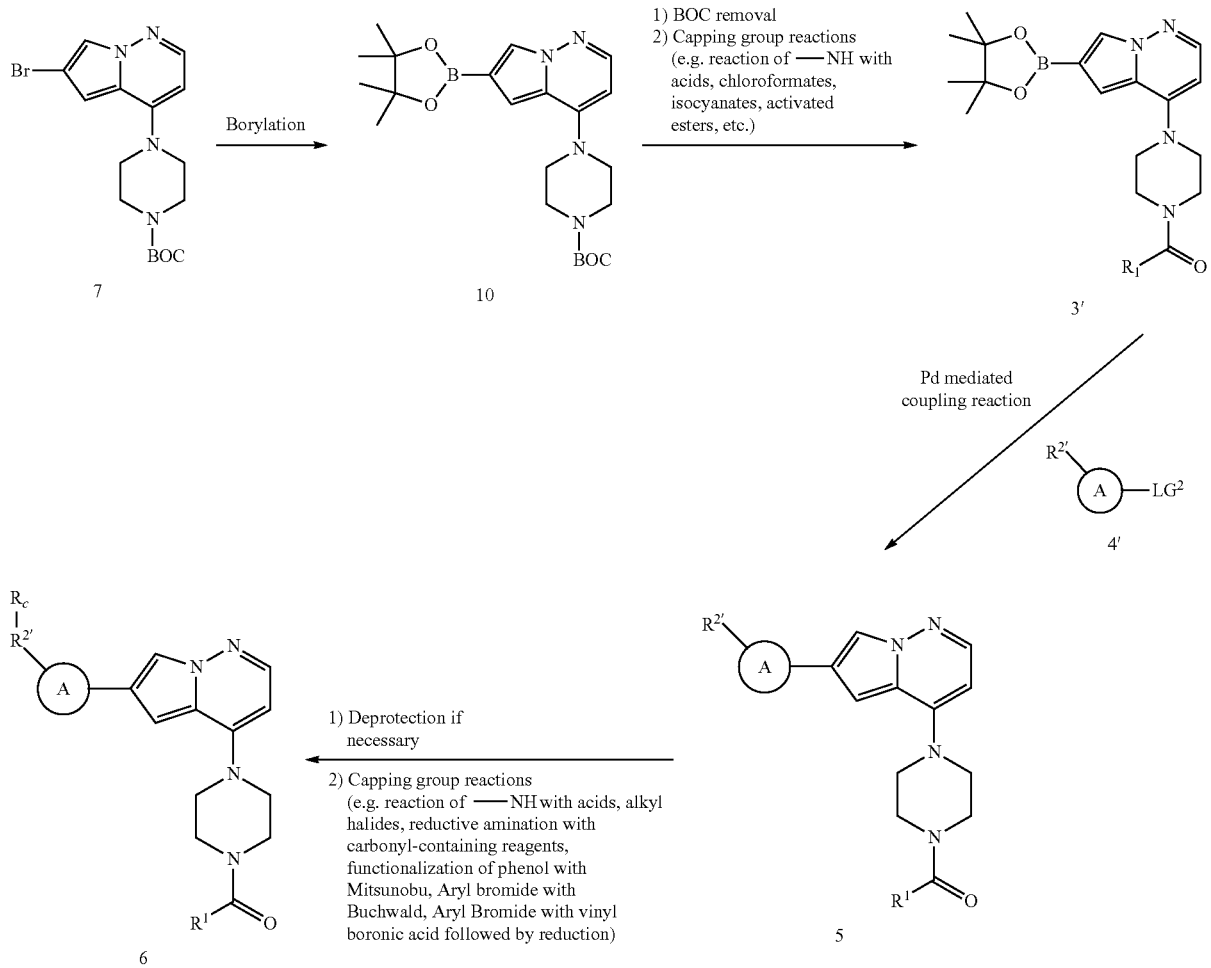

The pyrrolopyridazine bromide 7 can be converted to the boronate ester 10, via a Pd-mediate reaction. Removal of the BOC group in intermediate 10 can be followed by capping reactions of the resulting free NH using activated carboxylic acids, chloroformates, carbamoyl chlorides/isocyanates to give amides, carbamates, or ureas respectively via well-established reaction protocols. The pyrrolopyridazine boronate ester 3' can be coupled with aryl halides 4' to provide intermediate 5. ($LG^2$ can be, e.g., Cl, Br, or I. $R^{2'}$ can be, for example, Br, OH, N-linked alkyl or cycloalkylamine, or C-linked alkyl or cycloalkylamine). Intermediate 5 can be further functionalized (following protecting group removal, if necessary) by capping reactions including alkylation, reductive amination with carbonyl containing compounds, acylation, ether formation via Mitsunobu coupling, or amination using the Buchwald reaction to provide 6. Synthesis of exemplary compounds prepared using Synthetic Protocol 5 are disclosed in certain of the Examples below.

In yet another embodiment, the disclosure provides an intermediate for synthesizing compounds of the disclosure. The intermediate is 6-bromopyrrolo[1,2-b]pyridazin-4-ol:

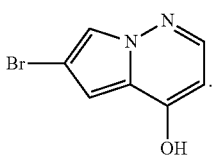

In another embodiment, the disclosure provides a process for synthesizing said intermediate. The method of synthesizing 6-bromopyrrolo[1,2-b]pyridazin-4-ol comprises the step of combining a compound of Formula C-1:

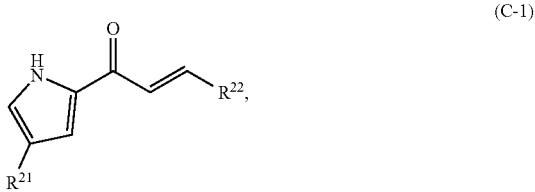

(C-1)

with a compound of Formula D-1:

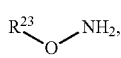
(D-1)

wherein:
R$^{21}$ is selected from chloro, bromo, and iodo;
R$^{22}$ is a leaving group; and
R$^{23}$ is an electron withdrawing group.
In some embodiments, R$^{2'}$ is bromo.
In some embodiments, R$^{22}$ is selected from —N(R$^{24}$)(R$^{25}$) and —OR$^{24}$, wherein each of R$^{24}$ and R$^{25}$ is an independently selected C$_1$-C$_4$ alkyl. In more specific aspects of these embodiments, R$^{22}$ is —N(CH$_3$)$_2$.
In some embodiments, R$^{23}$ is selected from methylcarbonyl, t-butylcarbonyl, 4-nitrophenylcarbonyl, 4-cyanophenylcarbonyl, 4-trifluoromethylphenylcarbonyl, 4-fluorophenylcarbonyl, 4-trifluoromethylcarbonylphenylcarbonyl, 4-ethoxycarbonylphenylcarbonyl, 4-trifluoromethylsulfonylphenylcarbonyl, 2,4,6-trimethylphenylcarbonyl, 2,4,6-trimethyl-3,5-dinitrophenylcarbonyl, 2-trifluoromethyl-4-nitrophenyl, 2,4-dinitrophenyl, and diphenylphosphinyl. In more specific aspects of these embodiments, R$^{23}$ is 4-nitrophenylcarbonyl.

In the method of synthesizing 6-bromopyrrolo[1,2-b]pyridazin-4-ol from C-1 and D-1, the starting materials are dissolved in a polar solvent. The choice of polar solvent can be made from any known in the art. More specifically, the polar solvent is selected from N-methyl-2-pyrrolidine ("NMP"), N,N-dimethylacetamide ("DMAC"), dimethylformamide ("DMF"), tetrahydrofuran ("THF"), methyl-tetrahydrofuran ("MeTHF"), dimethyl sulfoxide ("DMSO"), and cyclopentylmethyl ether ("CPME"). Even more specifically, the polar solvent is NMP or DMAC.

In the first step of the synthesis method C-1 dissolved in the polar solvent. This is done at the lowest temperature possible which allows dissolution. Dissolved C-1 is then treated with a base, typically 1.15-1.5 equivalents thereof, optionally maintained under a N$_2$ atmosphere. The choice of base can be made from any known in the art. More specifically, the base is selected from KOC(CH$_3$)$_3$, NaOC(CH$_3$)$_3$, LiOC(CH$_3$)$_3$, LiC(CH$_3$)$_3$, Li(CH$_2$)$_3$CH$_3$, LiN(C$_3$H$_7$)$_2$, NaOCH$_3$, NaOCH$_2$CH$_3$, KOCH$_3$, LiOCH$_3$, LiOCH$_2$CH$_3$, and KOCH$_2$CH$_3$. Even more specifically, the base is KOC(CH$_3$)$_3$.

Treatment of C-1 with a base is performed at a temperature of between about 15 to 30° C. for 0.5-2 hours with stirring. The base-treated C-1 solution is then optionally cooled to −8 to −5° C. before adding reagent D-1.

D-1 is also dissolved in a polar solvent at a temperature of between −5 to 30° C. optionally under a N$_2$ atmosphere and then slowly added to base-treated C-1. The resulting mixture is stirred for 1-2 hrs until at least 90% of C-1 has disappeared as determined by LCMS or IPC.

At that point a protonating agent is added at acid pH and at a temperature of between about −5 to 10° C. The choice of protonating agent can be made from any known in the art. More specifically, the protonating agent is selected from NH$_4$C$_1$, NaHCO$_3$, KHCO$_3$, LiHCO$_3$, acetic acid, HCl, HBr, and H$_2$SO$_4$. Even more specifically, the protonating agent is NH$_4$C$_1$. In some specific aspects, the pH of the reaction with the protonating agent is adjusted to between about 1 and 5, more specifically between about 2 and 4 with an acidifying agent. In certain specific embodiments, the acidifying agent is HCl. The protonation reaction is allowed to proceed for between 0.5-2 hrs at 0-10° C.

The resulting mixture is then optionally filtered before extracting the insoluble material with an extraction agent. If filtered, the filter cake is extracted multiple times with the extraction agent and filtered after each extraction. The original filtrate is then combined with all of the extraction filtrates and the resulting solution is allowed to separate into an organic and an aqueous phase. The aqueous phase is then extracted several more times with the extraction agent and all organic phases are combined. If the mixture resulting from the protonation reaction is not filtered, it is extracted multiple times with the extraction agent, with all organic phases resulting from the extractions being pooled.

The choice of extraction agent may be made from any agent known in the art that is capable of extracting material from an aqueous phase into an organic phase. More specifically, the extraction agent is selected from methyl tert-butyl ether ("MTBE"), MeTHF, dichloromethane ("DCM"), CPME, diethyl ether, ethyl acetate, toluene, and isopropyl acetate. Even more specifically, the extraction agent is MTBE.

The pooled organic layers resulting from the extractions are optionally washed with saturated NaCl, dried over anhydrous Na$_2$SO$_4$, filtered if any insoluble material remains, and the soluble material then concentrated to dryness. This process typically results in at least 90% pure 6-bromopyrrolo[1,2-b]pyridazin-4-ol as determined by LCMS, HPLC or quantitative $^1$H-NMR.

EXAMPLES

The following examples are intended to be illustrative, and are not meant in any way to be limiting.

Compounds of the disclosure, including salts and N-oxides thereof, can be prepared using known organic synthesis techniques and can be synthesized according to any of numerous possible synthetic routes, such as those in the Schemes below. The reactions for preparing compounds of the disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, *Protective Groups in Organic Synthesis*, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization include the following:

LC-MS:

Unless otherwise indicated, all liquid chromatography-mass spectrometry (LC-MS) data (sample analyzed for purity and identity) were obtained with an Agilent model-1260 LC system using an Agilent model 6120 or model 1956 mass spectrometer utilizing ES-API ionization fitted with an Agilent Poroshel 120 (EC-C18, 2.7 µm particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Alternatively, LC-MS data was obtained using the following columns and mobile phases. Basic Mobile Phase: A: water (10 mM $NH_4HCO_3$) B: ACN; Gradient: 5% B increase to 95% B within 1.2 min, 95% B for 1.3 min, back to 5% B within 0.01 min; Flow Rate: 2 mL/min; Column: XBridge, 3.5 um, 50*4.6 mm; Oven Temperature: 50° C. Acidic Mobile Phase: A: water (0.01% TFA) B: CAN (0.01% TFA); Gradient: 5% B increase to 95% B within 1.2 min, 95% B for 1.3 min, back to 5% B within 0.01 min; Flow Rate: 2 mL/min; Column: Sunfire, 3.5 um, 50*4.6 mm; Oven Temperature: 50° C.

Alternatively, HPLC data was obtained using the following columns and mobile phases. Basic Mobile Phase: A: water (10 mM $NH_4HCO_3$) B: ACN; Gradient: 5% B increase to 95% B within 1.2 min, 95% B for 1.3 min, back to 5% B within 0.01 min; Flow Rate: 2 mL/min; Column: XBridge, 3.5 um, 50*4.6 mm; Oven Temperature: 50° C. Acidic Mobile Phase: A: water (0.01% TFA) B: ACN (0.01% TFA); Gradient: 0 min 5% B, 3 min 5% B, 10 min 95% B, 15 min 95% B; Flow Rate: 1.2 mL/min; Column: Eclipse XDB-C18, 4.6*150 mm, 5 um; Oven Temperature: 40° C.

Prep LC-MS:

Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Chiral HPLC:

Preparative HPLC to resolve chiral mixtures was performed on one of the following systems. For SFC using either a SFC-80 or SFC-200 (Thar, Waters) instrument, we used an AD-H 20×250 mm, 5 µm Diacel column run at 35° C. using a mobile phase gradient of $CO_2$/Methanol (0.1% $NH_4OH$)=40:60-90:10 at a flow rate of 80-180 g/min and detection at 214-360 nm. For HPLC using a Gilson-281 instrument, we used an AD-H 20×250 mm, 10 µm Diacel column run at 40° C. using a mobile phase gradient of Hexane (0.1% DEA): EtOH (0.1% DEA)=0:100–100:0.

Silica Gel Chromatography:

Silica gel chromatography was performed on either a Teledyne Isco COMBIFLASH® Rf unit or a BIOTAGE® Isolera Four unit.

Proton NMR:

Unless otherwise indicated, all $^1H$ NMR spectra were obtained with a Varian 400 MHz Unity Inova 400 MHz NMR instrument (acquisition time=3.5 seconds with a 1 second delay; 16 to 64 scans), a Bruker, AVANCE III 500 MHz UltraShield-Plus digital NMR spectrometer, or a Bruker, AVANCE III 400 MHz UltraShield-Plus digital NMR spectrometer. Where characterized, all protons were reported in DMSO-d6 solvent as parts-per million (ppm) with respect to residual DMSO (2.50 ppm).

Examples

The following examples are intended to be illustrative, and are not meant in any way to be limiting.

The below Schemes are meant to provide general guidance in connection with preparing the compounds of the disclosure. One skilled in the art would understand that the preparations shown in the Schemes can be modified or optimized using general knowledge of organic chemistry to prepare various compounds of the disclosure.

Example 1. Synthesis of 6-bromopyrrolo[1,2-b]pyridazin-4-yl trifluoromethanesulfonate Step 1: Synthesis of 1-(4-bromo-1H-pyrrol-2-yl)ethanone (Intermediate B)

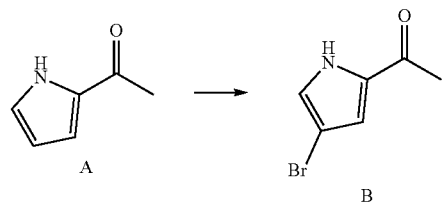

Amberlyst 15 (0.09 g/g-bulk-LR) was added to a solution of commercially available 1-(1H-pyrrol-2-yl)ethanone (70 g; 1.00 equiv; 641.45 mmoles) in tetrahydrofuran (10 mL/g-bulk-LR; 9.71 moles; 700.00 mL; 700.00 g) at room temperature (RT) (around 25° C.). Next, 1-bromopyrrolidine-2,5-dione (1 equiv (molar); 641.45 mmoles; 114.17 g) was added in portions at −30 to −20° C. and stirred for approximately 1 h until LCMS indicated that the reaction was complete. The reaction mixture was then filtered and the filtrate quenched with saturated $Na_2SO_3$ aqueous (350 mL) and extracted with DCM (700 mL×2). The organic layer was concentrated and then diluted with MTBE (700 mL). The organic layers were combined and then washed with sat. $NaHCO_3$ (350 mL×2) and concentrated on a rotavapor under reduced pressure to give 1-(4-bromo-1H-pyrrol-2-yl)ethanone (Intermediate B; 91 g; 0.75 equiv; 483.98 mmoles; 91.00 g; 75.45% yield) as a white solid. LCMS: 100% purity.

Step 2: Synthesis of (E)-1-(4-bromo-1H-pyrrol-2-yl)-3-(dimethylamino)prop-2-en-1-one (Intermediate C)

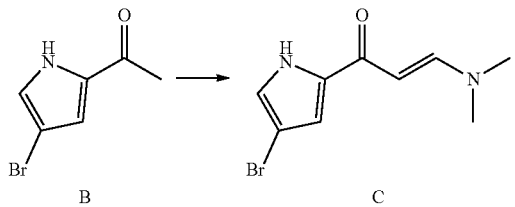

1-(4-bromo-1H-pyrrol-2-yl)ethanone (50 g; 1.00 equiv; 265.92 mmoles; 50.00 g) was added to 1,1-dimethoxy-N,N-dimethylmethanamine (5 mL/g-pure-LR; 2.10 moles; 250.00 mL; 250.00 g;) at room temperature (around 25° C.) and then the reaction mixture was heated at 70-80° C. for 12 h when LCMS indicated that the reaction was complete resulting in a suspension. The reaction mixture was filtered and the cake washed with PE (300 mL). The wet cake was dried in air for 16 h to give (E)-1-(4-bromo-1H-pyrrol-2-yl)-3-(dimethylamino)prop-2-en-1-one (35 g; 0.54 equiv; 143.97 mmoles; 35.00 g; 54.14% yield) as a yellow solid. LCMS: >95%.

Step 3: Synthesis of 6-bromopyrrolo[1,2-b]pyridazin-4-ol (Intermediate E)

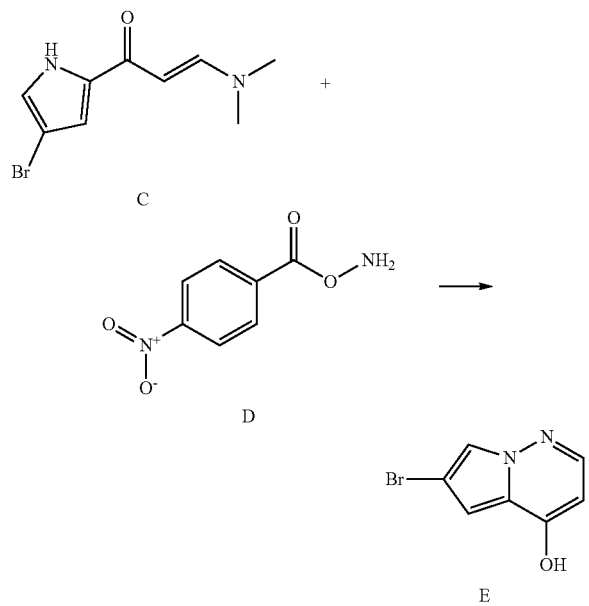

(E)-1-(4-bromo-1H-pyrrol-2-yl)-3-(dimethylamino)prop-2-en-1-one (C; 20 g; 1.00 equiv; 82.27 mmoles; 20.00 g;) was taken up in 1-methylpyrrolidin-2-one (30 mL/g-bulk-LR; 6.05 moles; 600.00 mL; 600.00 g) to form a solution. Potassium 2-methylpropan-2-olate (1.5 equiv (molar); 123.40 mmoles; 13.85 g) was then added in portions. The solution temperature was kept at 10 to 25° C. and the solution was then stirred at 15 to 25° C. for 0.5 h. Commercially available O-(4-nitrobenzoyl)hydroxylamine (D; 1.5 equiv (molar); 123.40 mmoles; 22.48 g) was then added into the reaction mixture maintaining the temperature at 20 to 30° C. and then stirred at 30° C. for 2 h until LCMS indicated that the starting material was gone. Saturated aqueous ammonium chloride (200 mL) was added dropwise into the reaction mixture cooled in an ice bath (0° C.), diluted with water (200 mL), and the pH was adjusted to between 3 and 4 with hydrochloric acid (1 M). The resulting solution was extracted with MTBE (3×150 mL), the combined organic layers were dried over anhydrous sodium sulfate, and then filtered and concentrated to dryness. The residue was purified by silica gel chromatography (petroleum ether: ethyl acetate=10:1-5:1) to give 6-bromopyrrolo[1,2-b]pyridazin-4-ol (E; 16 g, 90% yield; Purity: 91.6%) and isolated as a yellow solid, which is used for next step without further purifications. LCMS: 91.6%.

Step 3 Alternate: Synthesis of 6-bromopyrrolo[1,2-b]pyridazin-4-ol (Intermediate E)

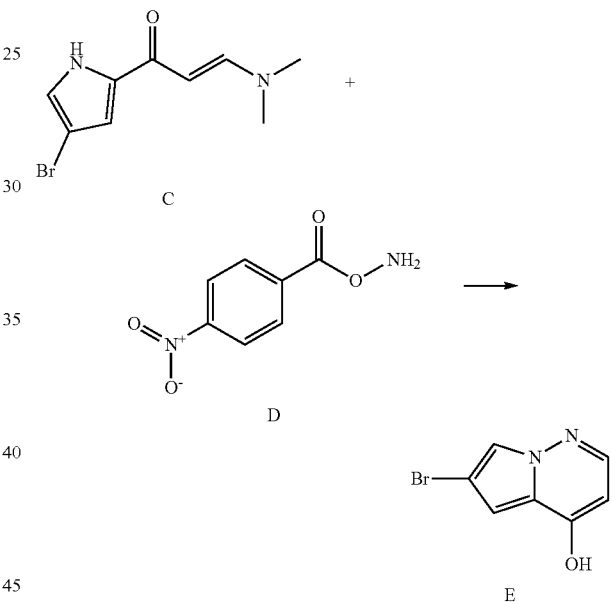

A synthesis of Intermediate E using the same reagents, but different conditions, is described in this Step 3 Alternate.

Two hundred kilograms of DMAc was added into a reactor to which was then quickly added. potassium tert-butoxide (1.15 equiv) under protection of $N_2$. The mixture was stirred until the reagents were dissolved. ((E)-1-(4-bromo-1H-pyrrol-2-yl)-3-(dimethylamino)prop-2-en-1-one) (C; 20.5 kg, 84.32 mol, 1 equiv) was added and was kept stirring at 20-30° C. for 1-2 hours. The reaction mixture was then cooled to −8 to −5° C. O-(4-nitrobenzoyl)hydroxylamine (D; 16.1 kg, 88.54 mol, 1.05 equiv) was then dissolved into DMAc (100 kg) in a separate container and the solution maintained at −5-0° C., then slowly the resulting solution of D was added to the reaction mixture. During addition, the temperature of solution D was maintained at −5-0° C. and kept under $N_2$ protection. The addition of D was completed after about 4 hrs. The resulting mixture was continually stirred at −5-0° C. for an additional 1-2 hr, until less than 8% of starting material C was present as determined by IPC. Saturated $NH_4Cl$ (150 kg) was added at −5-10° C. and the pH was adjusted to 2-2.5 with hydrochloric acid also maintained at −5-10° C. The mixture was continually stirred for an additional 1-2 hrs at 0-10° C. The resulting mixture was then filtered, and the filter cake washed twice with MTBE (100 kg×2). The filtrates were combined, and the aqueous layer separated from the organic layer. The aqueous layer was then extracted with MTBE 4-5 times and all of the organic phases were combined. The organic phases were then washed with sat. NaCl (40 kg×3). The organic phases were dried over anhydrous $Na_2SO_4$, filtered and the filtrate was concentrated at 35-45° C. under vacuum until the solution volume was ~50L (this concentration process should be completed within 3 hrs). The resulting concentrated solution was separated into several smaller batches and each batch transferred to a rotary evaporator for further and faster concentration to give wet solid (this process should be completed within 2 hrs). The resulting wet solids were combined and then DCM (40 kg) was added to slurry wash the solid at 10-15° C. for 0.5 h. The slurry was then filtered and dried to give 7.45 kg of E (HPLC: 98.51%, RRT=~1.4 impurity is 1.28%, QHNMR: 96.72%, assay by external standard method is 94.5%, yield is 41.4%).

Step 4: Synthesis of
6-bromopyrrolo[1,2-b]pyridazin-4-yl
trifluoromethanesulfonate (Intermediate F)

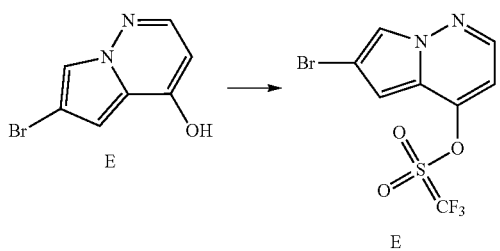

6-bromopyrrolo[1,2-b]pyridazin-4-ol (E; 10 g; 1.00 equiv; 46.94 mmoles; 10.00 g), dichloromethane (15 mL/g-bulk-LR; 2.34 moles; 150.00 mL; 198.75 g) and triethylamine (1.18 equiv (molar); 55.39 mmoles; 7.68 mL; 5.61 g) were combined in a 250 mL reactor. Trifluoromethanesulfonic anhydride (1.15 equiv (molar); 1.15 equiv; 53.98 mmoles; 9.08 mL; 15.23 g) was added dropwise and the temperature was kept between 0-20° C. The reaction mixture was warmed to 25° C. and stirred for an additional 2 h until LC-MS showed the reaction was completed. The mixture was then diluted with DCM (160 mL) and washed with sat.$NaHCO_3$ solution (2×80 mL). The organic phases were combined and dried over $Na_2SO_4$, filtered and concentrated under reduced pressure. MTBE (80 mL) and PE (80 mL) were added to dilute the crude product with stirring. Any solid that precipitated out at the bottom was removed by filtration. The filtrate was washed with sat. $NaHCO_3$ (40 mL×2) and water (40 mL) and sat. NaCl (40 mL) and then concentrated to give a crude product. Further purification was achieved with silica chromatography (PE/MTBE=100/0 to 50/1) to give 6-bromopyrrolo[1,2-b]pyridazin-4-yl trifluoromethanesulfonate (F; 9 g; 0.56 equiv; 26.08 mmoles; 9.00 g; 55.56% yield; [Actual]) as a dark green liquid. LC-MS: 345 $(M+H)^+$, 98% purity (214 nm).

Alternate Synthesis of Intermediate E
An alternate synthesis of Intermediate E was carried out as follows Step 1: 6-bromo-4-hydroxy-pyrrolo[1,2-b]
pyridazine-3-carbonitrile

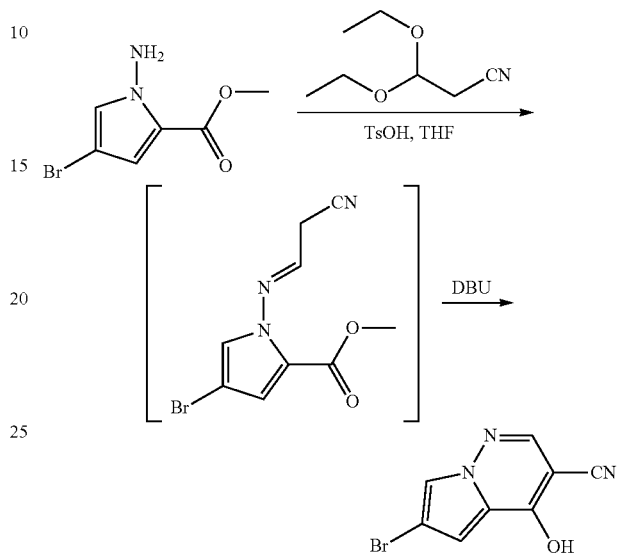

To a solution of methyl 1-amino-4-bromo-pyrrole-2-carboxylate (4.0 g, 18 mmol, 1.0 eq) and 3,3-dimethoxypropanenitrile (12.6 g, 109 mmol, 6.0 eq) was added TsOH (629 mg, 4 mmol, 0.2 eq). The reaction mixture was stirred at 80° C. for 6 h. Then, DBU (16.7 g, 109 mmol, 6.0 eq) was added into the reaction mixture and stirred for another 10 h at 80° C. TLC showed the reaction was complete. The mixture was diluted with water (5 mL) and extracted with EA (10 mL×2). The combined organic phases were washed with brine, dried over $Na_2SO_4$ and concentrated in vacuo. The residue was purified by silica gel column chromatography (DCM:MeOH=10:1) to give the title product (3.7 g, 15 mmol, 85% yield) as a yellow solid.

Step 2: 6-bromo-4-hydroxypyrrolo[1,2-b]
pyridazine-3-carboxamide

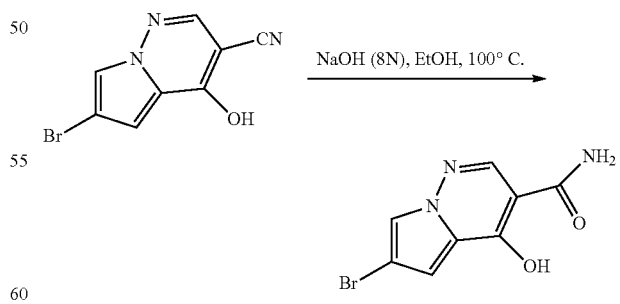

To the solution of 6-bromo-4-hydroxy-pyrrolo[1,2-b]pyridazine-3-carbonitrile (2.0 g, 8.4 mmol, 1.0 eq) in EtOH (20 mL) was added a solution of NaOH (16.0 g, 400 mmol) in $H_2O$ (50 mL). The reaction mixture was stirred for 48 h at 100° C. until TLC (petroleum ether (PE): ethyl acetate (EA)=0:1) indicated that most of the starting material was consumed. The reaction mixture was concentrated to remove the EtOH. The pH of the resulting aqueous solution was adjusted to 5-6 and then extracted with ethyl acetate. The combined organic layer was dried over sodium sulfate, filtered and concentrated to dryness. The residue was purified by silica gel column chromatography (petroleum ether: ethyl acetate=5:1-1:1) to afford the title product (1.1 g, 4 mmol, 51% yield) as a yellow solid.

Step 3: 6-bromopyrrolo[1,2-b]pyridazin-4-ol (Intermediate E)

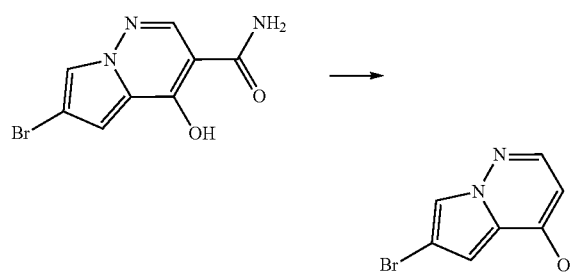

To a solution of 6-bromo-4-hydroxypyrrolo[1,2-b]pyridazine-3-carboxamide (1.0 g, 4 mmol) in concentrated HCl (aq., 30 mL) was added dioxane (2 mL) and EtOH (2 mL). The reaction mixture was stirred for 48 h at 100° C. TLC (petroleum ether: ethyl acetate=0:1) indicated that most of the starting material was consumed and the reaction mixture was concentrated to remove organic solvents. The pH of the resulting aqueous solution was adjusted to 4-6 and then extracted (twice) with ethyl acetate. The combined organic layer was dried over sodium sulfate, filtered and concentrated to dryness. The residue was purified by silica gel column chromatography (petroleum ether: ethyl acetate=10:1-5:1) to afford crude Intermediate E (150 mg, contains two byproducts (halogen-exchange and de-halogen)) as a yellow solid.

Example 2. Synthesis of cyclopropyl(4-(6-(4-(piperazin-1-yl)phenyl)pyrrolo[2-b]pyridazin-4-yl)piperazin-1-yl)methanone (Compound 127)

Step 1: Synthesis of (4-(6-bromopyrrolo[1,2-b]pyridazin-4-yl)piperazin-1-yl) (cyclopropyl)methanone

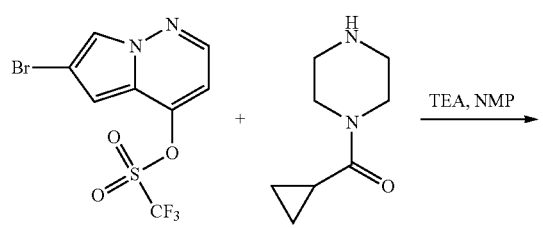

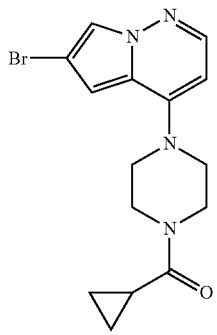

A mixture of 6-bromopyrrolo[1,2-b]pyridazin-4-yl trifluoromethanesulfonate (30 g, 86.9 mmol), cyclopropyl(piperazin-1-yl)methanone (16.0 g, 104 mmol), and triethylamine (13.1 g, 130 mmol) in NMP (300 mL) was stirred at 100° C. for 30 min. The reaction mixture was cooled and diluted with EA. The organic layer was washed with water and brine, concentrated and purified by silica gel column to give the title product (26.0 g, yield 86%) as a yellow solid. MS (ES+) $C_{15}H_{17}BrN_4O$ requires: 348, found: 349 [M+H]$^+$.

Step 2: Synthesis of cyclopropyl(4-(6-(4-(piperazin-1-yl)phenyl)pyrrolo[1,2-b]pyridazin-4-yl) piperazin-1-yl)methanone (Compound 127)

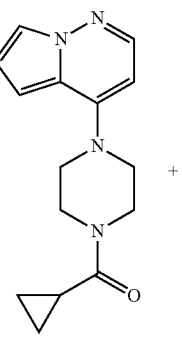

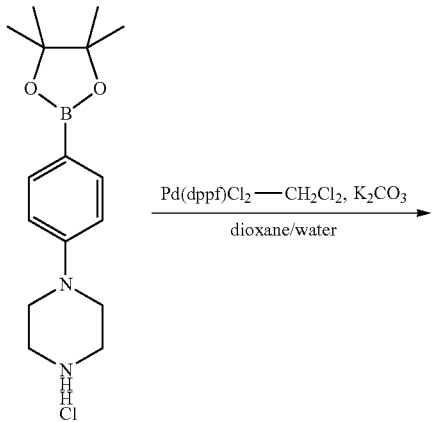

-continued

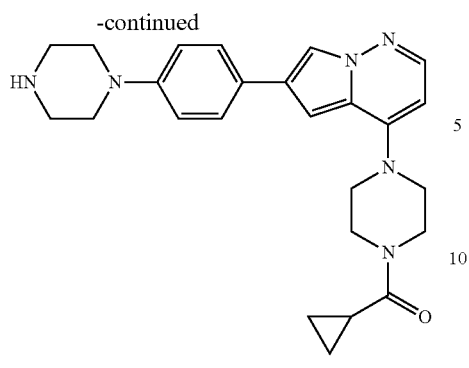

127

A mixture of (4-(6-bromopyrrolo[1,2-b]pyridazin-4-yl)piperazin-1-yl)(cyclopropyl)methanone (3.0 g, 8.59 mmol), 1-(4-(4,4,5,5-tetramethyl-1,3,2-dioxaborolan-2-yl)phenyl)piperazine hydrochloride (3.10 g, 12.8 mmol), $K_2CO_3$ (4.73 g, 34.3 mmol) and Pd(dppf)$Cl_2$·$CH_2Cl_2$ (700 mg, 859 μmol) in 1,4-dioxane/water (30 mL/5 mL) was degassed with $N_2$, and then stirred at 100° C. for 16 h under $N_2$. The mixture was cooled to RT and concentrated. The residue was purified by silica gel column to give the title product (1.95 g, yield 52.8%) as a white solid. MS (ES+) $C_{25}H_{30}N_6O$ requires: 430, found: 431 [M+H]$^+$.

Example 3. Synthesis of cyclopropyl(4-(6-(4-(4-(2-hydroxyethyl)piperazin-1-yl) phenyl)pyrrolo[1,2-b]pyridazin-4-yl)piperazin-1-yl)methanone (Compound 274)

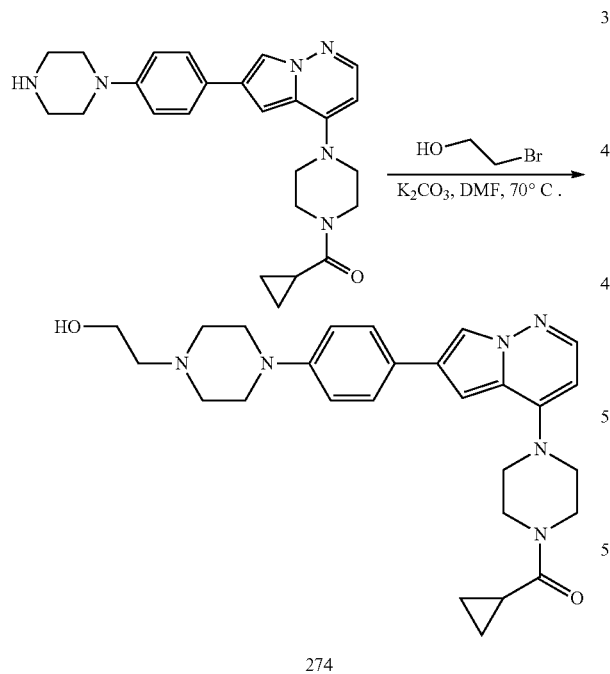

274

A mixture of cyclopropyl(4-(6-(4-(piperazin-1-yl)phenyl)pyrrolo[1,2-b]pyridazin-4-yl) piperazin-1-yl)methanone (100 mg, 232 μmol), 2-bromoethanol (57.9 mg, 464 μmol) and potassium carbonate (32 mg, 0.232 mmol) was stirred at 70° C. overnight (~12 h). The reaction mixture was cooled and concentrated. The residue was purified by Prep-HPLC to afford the title compound as a white solid (10.5 mg, yield 9.5%). MS (ES+) $C_{27}H_{34}N_6O_2$, requires: 474, found: 475 [M+H]$^+$.

Example 4. Synthesis of cyclopropyl(4-(6-(4-(4-(oxetan-3-yl)piperazin-1-yl)phenyl)pyrrolo[1,2-b]pyridazin-4-yl)piperazin-1-yl)methanone (Compound 314)

Step 1: Synthesis of tert-butyl 4-(4-(4-(4-(cyclopropanecarbonyl)piperazin-1-yl)pyrrolo[1,2-b]pyridazin-6-yl)phenyl)piperazine-1-carboxylate

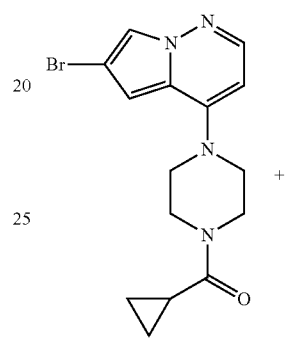

+

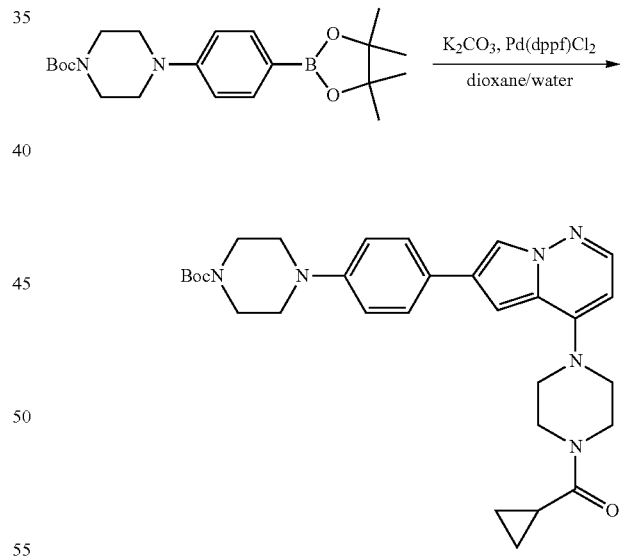

A mixture of (4-(6-bromopyrrolo[1,2-b]pyridazin-4-yl)piperazin-1-yl) (cyclopropyl)methanone (65 mg, 0.19 mmol), tert-butyl 4-(4-(4,4,5,5-tetramethyl-1,3,2-dioxaborolan-2-yl)phenyl)piperazine-1-carboxylate (86 mg, 0.22 mmol), $K_2CO_3$ (51 mg, 0.37 mmol) and Pd(dppf)$Cl_2$ (14 mg, 0.019 mmol) in dioxane/water (10/1) was irradiated in the microwave at 100° C. for 1 h. Concentrated and purified by flash column (PE/EA=2/1 to 1/10) to give the title product (66 mg, yield 65.4%). MS (ES+) $C_{30}H_{38}N_6O_3$, requires: 530, found 531[M+H]$^+$.

493

Step 2: Synthesis of cyclopropyl(4-(6-(4-(piperazin-1-yl)phenyl)pyrrolo[1,2-b]pyridazin-4-yl) piperazin-1-yl)methanone

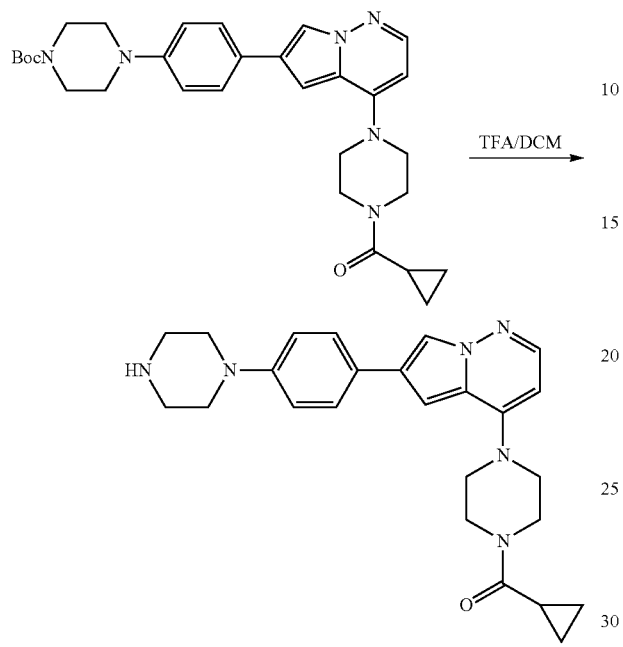

To a solution of tert-butyl 4-(4-(4-(4-(cyclopropanecarbonyl)piperazin-1-yl)pyrrolo[1,2-b]pyridazin-6-yl)phenyl) piperazine-1-carboxylate (66 mg, 0.12 mmol) in DCM was added TFA (TFA/DCM, 10:1). The reaction mixture was stirred at RT for 1 h. Saturated NaHCO$_3$ solution was added to the mixture to bring the pH to 8-9, and then the mixture was extracted with DCM. The combined organic layers were washed with brine, dried over Na$_2$SO$_4$, and concentrated to give the title product (55 mg, crude). MS (ES+) C$_{25}$H$_{30}$N$_6$O, requires: 430, found 431 [M+H]$^+$.

Step 3: Synthesis of cyclopropyl(4-(6-(4-(4-(oxetan-3-yl)piperazin-1-yl)phenyl)pyrrolo[1,2-b]pyridazin-4-yl)piperazin-1-yl)methanone

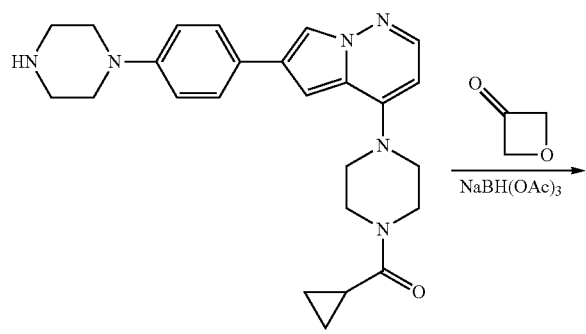

494

-continued

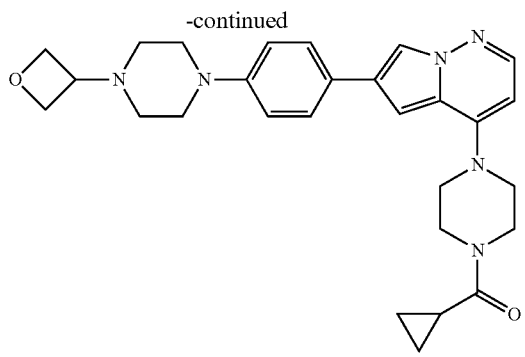

314

To a solution of cyclopropyl(4-(6-(4-(piperazin-1-yl)phenyl)pyrrolo[1,2-b]pyridazin-4-yl) piperazin-1-yl)methanone (55 mg, crude) in 1,2-dichloroethane was added oxetan-3-one (92 mg, 1.27 mmol), followed by addition of NaBH(OAc)$_3$ (269 mg, 1.27 mmol). The reaction mixture was stirred at RT overnight. Concentration and purification by Prep-HPLC gave the title product (3.7 mg, yield 6.3%). MS (ES+) C$_{28}$H$_{34}$N$_6$O$_2$ requires: 486, found 487 [M+H]$^+$.

Example 5. Synthesis of cyclopropyl(4-(6-(4-(2-(piperazin-1-yl)ethoxy)phenyl)pyrrolo[1,2-b]pyridazin-4-yl)piperazin-1-yl)methanone (Compound 273) and (4-(6-(4-(2-(4-ethylpiperazin-1-yl)ethoxy)phenyl)pyrrolo[1,2-b]pyridazin-4-yl) piperazin-1-yl)methanone (Compound 390)

Step 1: Synthesis of tert-butyl 4-(2-(4-bromophenoxy)ethyl)piperazine-1-carboxylate

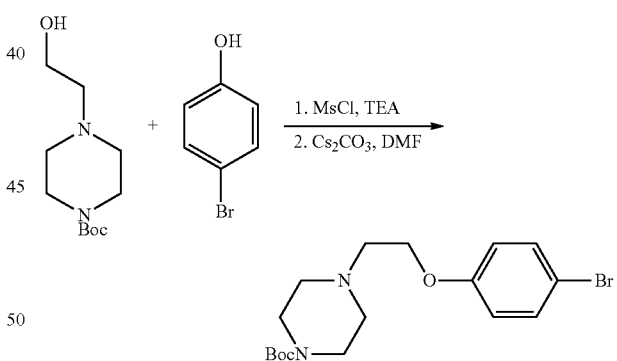

A mixture of tert-butyl 4-(2-hydroxyethyl)piperazine-1-carboxylate (400 mg, 1.73 mmol), MsCl (596 mg, 5.19 mmol) and triethylamine (524 mg, 5.19 mmol) in DCM (25 mL) was stirred at RT for 2 h. The solution was diluted with DCM, and washed with sat. NaHCO$_3$ and brine. The organic layer was concentrated. The residue was dissolved in DMF (15 mL), followed by addition of 4-bromophenol (451 mg, 2.61 mmol) and Cs$_2$CO$_3$ (1.70 g, 5.22 mmol) at RT. The resultant mixture was stirred at 100° C. for 18 h. After that, the solution was diluted with EA and washed with brine. The organic layer was concentrated and purified by silica gel chromatography to get the title compound (320 mg, yield 48%) as a colorless oil. MS (ES+) C$_{17}$H$_{25}$BrN$_2$O$_3$ requires: 384, 386 found: 385, 387 [M+H]$^+$.

495

Step 2: Synthesis of tert-butyl 4-(2-(4-(4,4,5,5-tetramethyl-1,3,2-dioxaborolan-2-yl) phenoxy)ethyl)piperazine-1-carboxylate

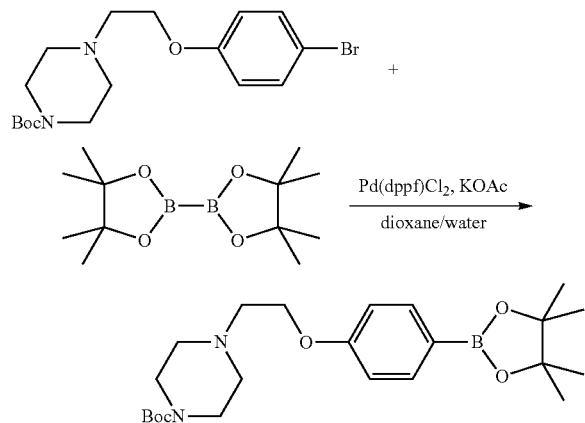

A mixture of tert-butyl 4-(2-(4-bromophenoxy)ethyl)piperazine-1-carboxylate (320 mg, 830 μmol), 4,4,4',4',5,5,5',5'-octamethyl-2,2'-bi(1,3,2-dioxaborolane) (271 mg, 1.07 mmol), Pd(dppf)Cl₂ (60.6 mg, 83.0 μmol) and KOAc (325 mg, 3.32 mmol) in dioxane/water (10 mL) was purged with N₂, and stirred at 100° C. for 18 h under N₂. After that, the solution was cooled and concentrated. The residue was purified by silica gel chromatography (EA/PE=1/3) to get the title compound (300 mg, yield 84%) as a brown oil. MS (ES+) $C_{23}H_{27}BN_2O_5$ requires: 432, found: 433 [M+H]⁺.

Step 3: Synthesis of tert-butyl 4-(2-(4-(4-(4-(cyclopropanecarbonyl)piperazin-1-yl)pyrrolo[1,2-b]pyridazin-6-yl)phenoxy)ethyl)piperazine-1-carboxylate

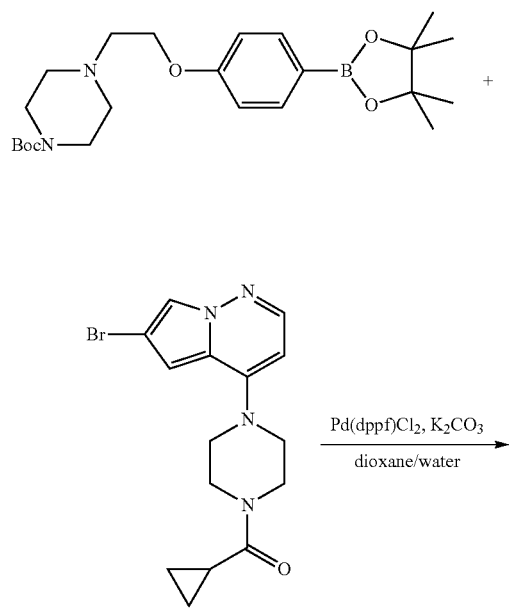

496

-continued

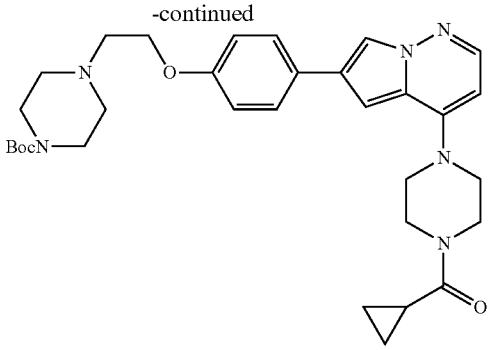

A mixture of (4-(6-bromopyrrolo[1,2-b]pyridazin-4-yl)piperazin-1-yl) (cyclopropyl)methanone (200 mg, 572 mol), tert-butyl 4-(2-(4-(4,4,5,5-tetramethyl-1,3,2-dioxaborolan-2-yl)phenoxy)ethyl)piperazine-1-carboxylate (271 mg, 629 μmol), Pd(dppf)Cl₂ (41.8 mg, 57.2 μmol), and K₂CO₃ (314 mg, 2.28 mmol) in dioxane (5 mL) and water (1 mL) was purged with N₂, and then stirred at 100° C. for 18 h under N₂. After that, the solution was cooled and concentrated. The residue was purified by silica gel chromatography to get the title compound (160 mg, yield 49%) as a yellow oil. MS (ES+) $C_{32}H_{42}N_6O_4$ requires: 574, found: 575 [M+H]⁺.

Step 4: Synthesis of cyclopropyl(4-(6-(4-(2-(piperazin-1-yl)ethoxy)phenyl)pyrrolo[1,2-b]pyridazin-4-yl)piperazin-1-yl)methanone (Compound 273)

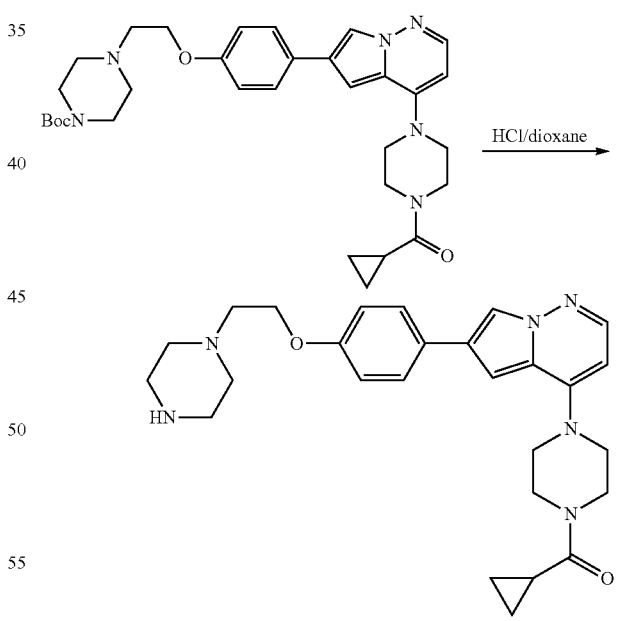

A mixture of tert-butyl 4-(2-(4-(4-(4-(cyclopropanecarbonyl)piperazin-1-yl)pyrrolo[1,2-b]pyridazin-6-yl)phenoxy)ethyl)piperazine-1-carboxylate (80 mg, 139 μmol) in HCl/dioxane (4 N, 1 mL) was stirred at RT for 2 h. After that, the solution was concentrated to afford the title compound (80 mg, crude) as a yellow solid. MS (ES+) $C_{27}H_{34}N_6O_2$ requires: 474 found: 475 [M+H]⁺.

Step 5: Synthesis of cyclopropyl(4-(6-(4-(2-(4-eth-ylpiperazin-1-yl)ethoxy)phenyl)pyrrolo[1,2-b]pyridazin-4-yl)piperazin-1-yl)methanone (Compound 390)

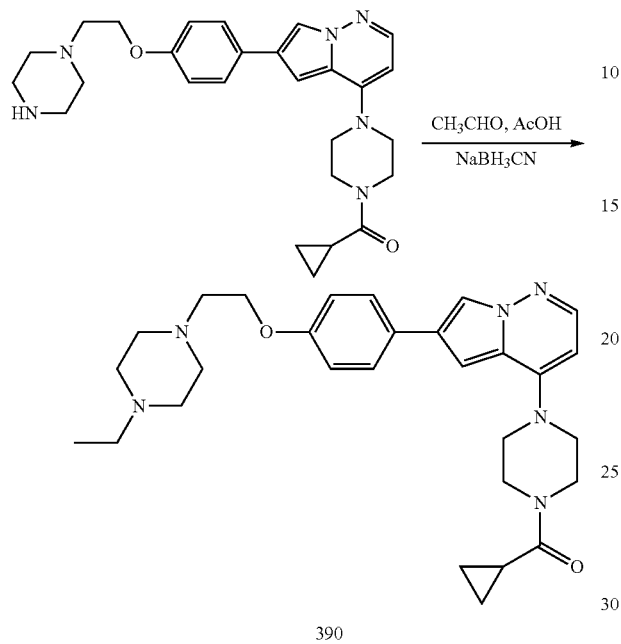

390

A mixture of tert-butyl 4-(2-(4-(4-(4-(cyclopropanecarbonyl)piperazin-1-yl)pyrrolo[1,2-b]pyridazin-6-yl)phenoxy)ethyl)piperazine-1-carboxylate (40 mg, 84.2 μmol), $CH_3CHO$ (11.0 mg, 252 μmol), $NaBH_3CN$ (7.93 mg, 126 μmol) and AcOH (5.05 mg, 84.2 μmol) in DCM (5 mL) and MeOH (2 mL) was stirred at RT for 2 h. After that, the solution was concentrated and purified by Prep-HPLC to give the title compound (12 mg, 28%) as a yellow solid. MS (ES+) $C_{29}H_{38}N_6O_2$ requires: 502 found: 503 $[M+H]^+$.

Example 6. Synthesis of cyclopropyl(4-(6-(1-(5,5-difluoropiperidin-3-yl)-1H-pyrazol-4-yl) pyrrolo[1,2-b]pyridazin-4-yl)piperazin-1-yl)methanone (Compound 194)

Step 1: Synthesis of tert-butyl 5-oxo-5,6-dihydropyridine-1(2H)-carboxylate

To a solution of 1-(tert-butoxycarboxyl)-1,2,3,6-tetrahydropyridin-3-ol (300 mg, 1.50 mmol) in DCM (25 mL) was added Dess-Martin Oxidant (1.27 g, 3.00 mmol). The reaction solution was stirred at RT for 12 hours and then filtered. The filtrate was washed with saturated aqueous $Na_2CO_3$ (50 mL) and concentrated in vacuo. The residue was purified by silica gel column chromatography (PE/EtOAc (v/v)=2/1) to give the title compound as a colorless oil (280 mg, yield 94%). MS (ES+) $C_{10}H_{15}NO_3$ requires: 197, found: 142 $[M+H-56]^+$.

Step 2: Synthesis of (4-(6-(1H-pyrazol-4-yl)pyrrolo[1,2-b]pyridazin-4-yl)piperazin-1-yl) (cyclopropyl)methanone

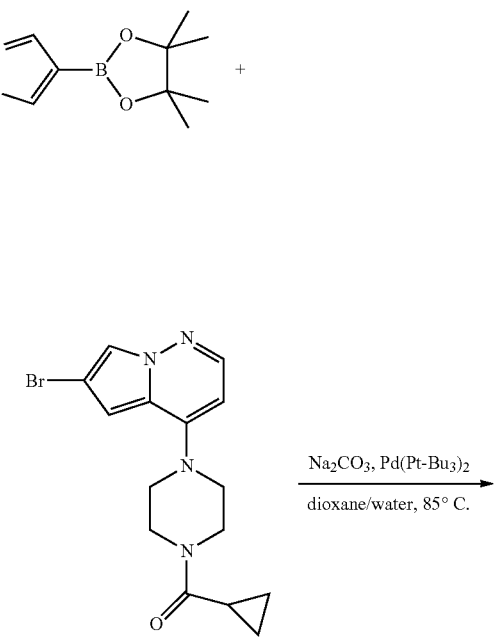

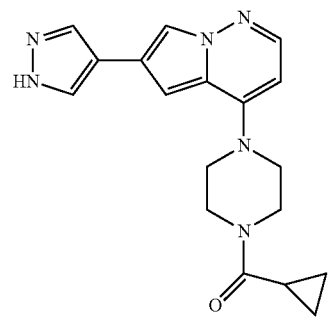

A mixture of tert-butyl 4-(4,4,5,5-tetramethyl-1,3,2-dioxaborolan-2-yl)-1H-pyrazole-1-carboxylate (335 mg, 1.14 mmol), (4-(6-bromopyrrolo[1,2-b]pyridazin-4-yl)piperazin-1-yl) (cyclopropyl)methanone (400 mg, 1.14 mmol), $Na_2CO_3$ (362 mg, 3.42 mmol) and $Pd(t-Bu_3P)_2$ (116 mg, 0.228 mmol) in dioxane/water (v/v=3:1, 10 mL) was degassed with $N_2$ three times, and then stirred at 85° C. for 12 hours. The reaction mixture was cooled and evaporated in vacuo. The residue was purified by flash column (PE: EA=3:1 to 1:3) to give the title compound as a yellow solid (340 mg, yield 88%). MS (ES+) $C_{18}H_{20}N_6O$ requires: 336, found: 337 $[M+H]^+$.

Step 3: Synthesis of tert-butyl 3-(4-(4-(4-(cyclopropanecarbonyl)piperazin-1-yl)pyrrolo[1,2-b]pyridazin-6-yl)-1H-pyrazol-1-yl)-5-oxopiperidine-1-carboxylate

Step 4: Synthesis of tert-butyl 5-(4-(4-(4-(cyclopropanecarbonyl)piperazin-1-yl)pyrrolo[1,2-b]pyridazin-6-yl)-1H-pyrazol-1-yl)-3,3-difluoropiperidine-1-carboxylate

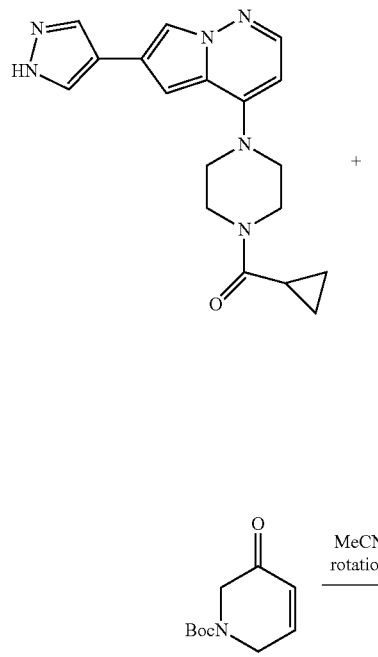

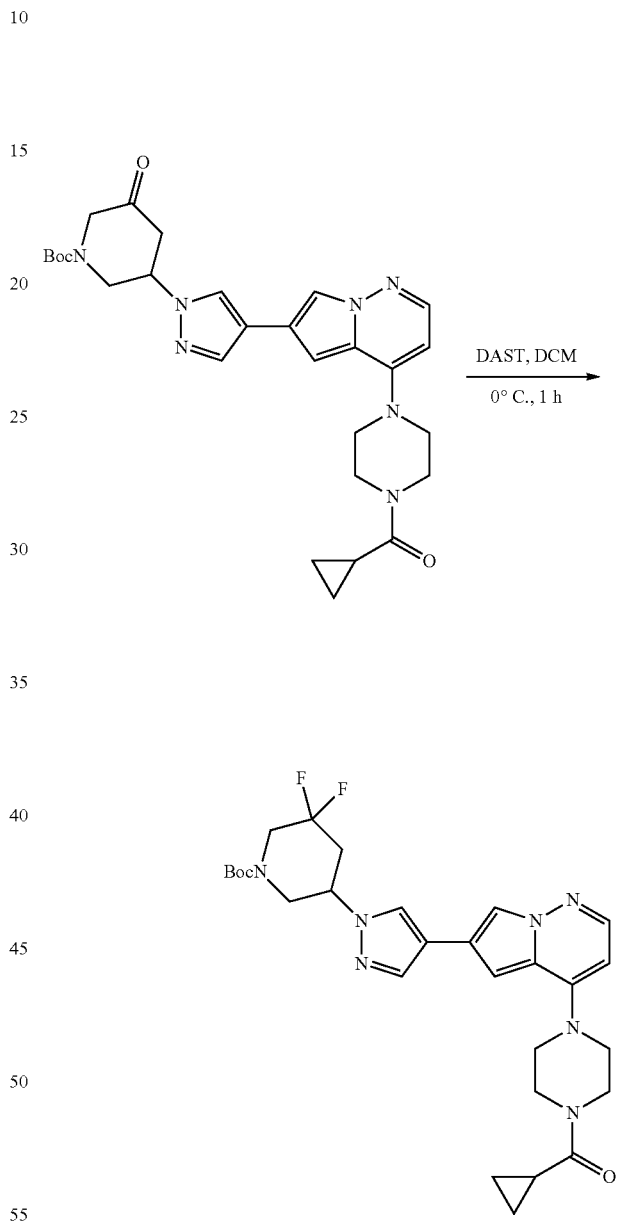

A mixture of tert-butyl 5-oxo-5,6-dihydropyridine-1(2H)-carboxylate (100 mg, 0.51 mmol) and (4-(6-(1H-pyrazol-4-yl)pyrrolo[1,2-b]pyridazin-4-yl)piperazin-1-yl) (cyclopropyl)methanone (180 mg, 0.54 mmol) in MeCN (5 mL) in a flask was evaporated in vacuo at 50° C. The residue was diluted with 5 mL of MeCN, and then evaporated to dryness. The dilution/evaporation was repeated three times. Purification by flash column (PE/EA to EA) gave the title compound as an off-white solid (140 mg, yield 49%). MS (ES+) $C_{28}H_{35}N_7O_4$ requires: 533, found: 534 [M+H]$^+$.

To a solution of tert-butyl 3-(4-(4-(4-(cyclopropanecarbonyl)piperazin-1-yl)pyrrolo[1,2-b]pyridazin-6-yl)-1H-pyrazol-1-yl)-5-oxopiperidine-1-carboxylate (60 mg, 0.1124 mmol) in DCM (4 mL) was added DAST (180 mg, 1.12 mmol) at 0° C. The reaction mixture was then stirred at 0° C. for 10 minutes. Quenched by water and extracted with DCM. The organic layers were evaporated and purified by flash column (PE/EA=1:4 to 4:1) to give the title compound as a yellow solid (12 mg, yield 19%). MS (ES+) $C_{28}H_{35}F_2N_7O_3$ requires: 555, found: 556[M+H]$^+$.

501

Step 5: Synthesis of cyclopropyl(4-(6-(1-(5,5-difluoropiperidin-3-yl)-1H-pyrazol-4-yl)pyrrolo[1,2-b]pyridazin-4-yl)piperazin-1-yl)methanone

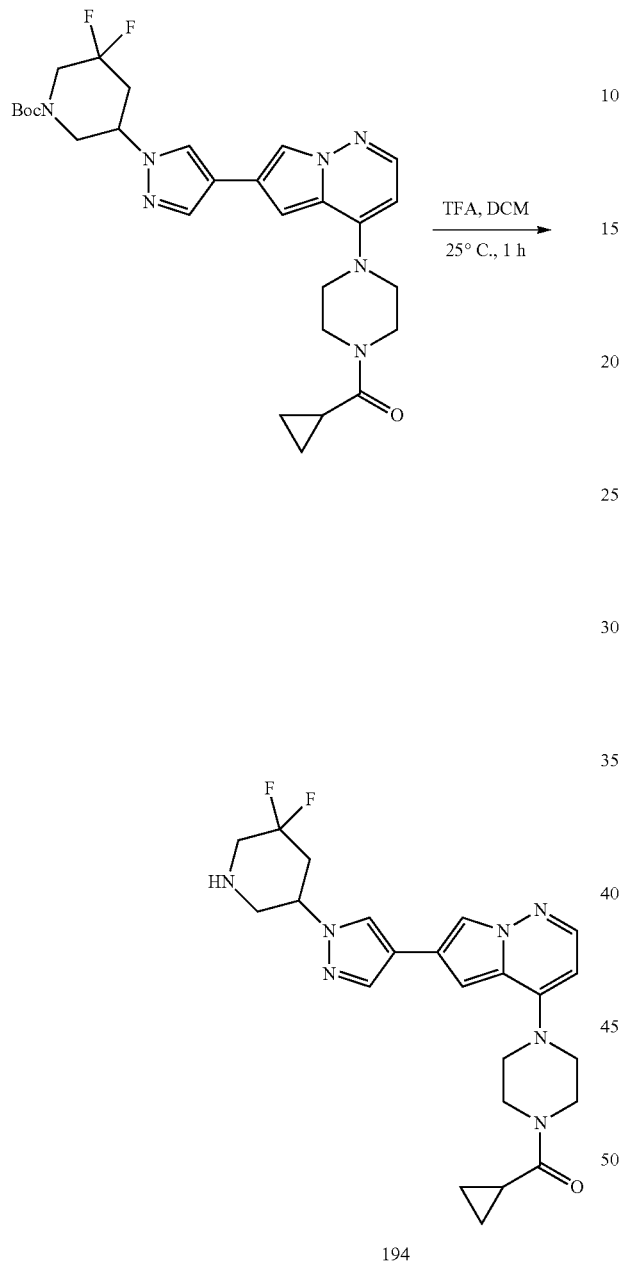

194

To a solution of tert-butyl 5-(4-(4-(4-(cyclopropanecarbonyl)piperazin-1-yl)pyrrolo[1,2-b]pyridazin-6-yl)-1H-pyrazol-1-yl)-3,3-difluoropiperidine-1-carboxylate (12 mg, 0.02159 mmol) in DCM (2.0 mL) was added TFA (1.0 mL). The reaction solution was stirred at 25° C. for 1 hour. The reaction solution was concentrated in vacuo. The residue was dissolved in DCM and neutralized by sat. aqueous NaHCO$_3$. The organic layer was washed with brine, dried and concentrated to give the title compound (8.5 mg, yield 86%) as a yellow solid. MS (ES+) C$_{23}$H$_{27}$F$_2$N$_7$O requires: 455, found 456[M+H]$^+$.

502

Example 7. Synthesis of (S)-cyclopropyl(4-(6-(4-(morpholin-2-yl)phenyl)pyrrolo[1,2-b]pyridazin-4-yl)piperazin-1-yl)methanone (Compound 130) and (R)-cyclopropyl(4-(6-(4-(morpholin-2-yl)phenyl)pyrrolo[1,2-b]pyridazin-4-yl)piperazin-1-yl)methanone (Compound 131)

Step 1: Synthesis of cyclopropyl(4-(6-(4,4,5,5-tetramethyl-1,3,2-dioxaborolan-2-yl)pyrrolo[1,2-b]pyridazin-4-yl)piperazin-1-yl)methanone

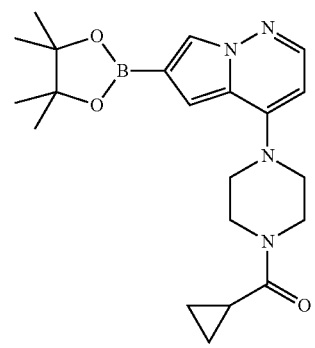

A mixture of (4-(6-bromopyrrolo[1,2-b]pyridazin-4-yl)piperazin-1-yl) (cyclopropyl)methanone (11.6 g, 33.2 mmol), 4,4,4',4',5,5,5',5'-octamethyl-2,2'-bi(1,3,2-dioxaborolane) (16.8 g, 66.4 mmol), Pd(dppf)Cl$_2$ (3.63 g, 4.97 mmol) and KOAc (9.76 g, 99.6 mmol) in CH$_3$CN (300 mL) was purged with N$_2$ and then stirred at 65° C. for 24 hrs under N$_2$. The reaction mixture was concentrated and purified by flash chromatography (PE/EA=10:1 to 2:1) to afford the title compound (11.2 g, 80% yield) as a yellow solid. MS (ES+) C$_{21}$H$_{29}$BN$_4$O$_3$ requires: 396, found: 397[M+H]$^+$.

Step 2: Synthesis of (S)-cyclopropyl(4-(6-(4-(morpholin-2-yl)phenyl)pyrrolo[1,2-b]pyridazin-4-yl)piperazin-1-yl)methanone (Compound 130) and (R)-cyclopropyl(4-(6-(4-(morpholin-2-yl)phenyl)pyrrolo[1,2-b]pyridazin-4-yl)piperazin-1-yl)methanone (Compound 131)

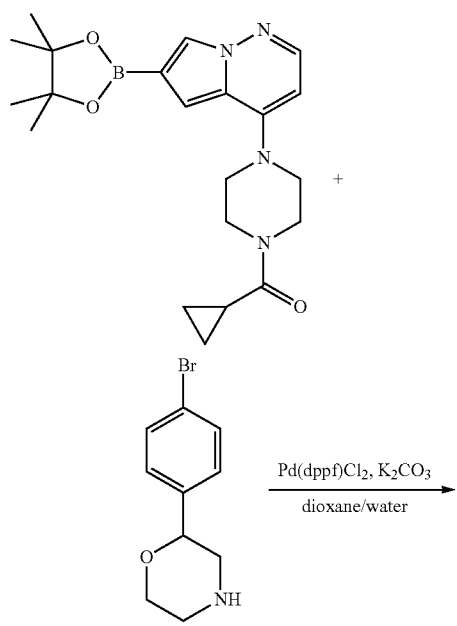

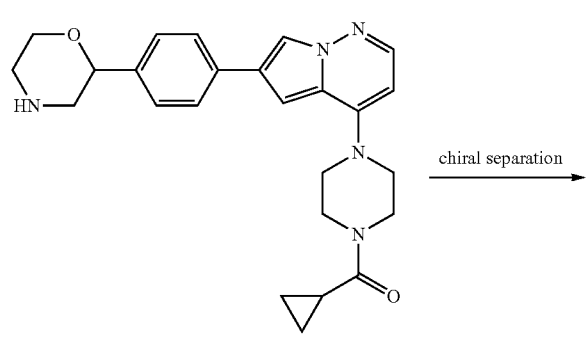

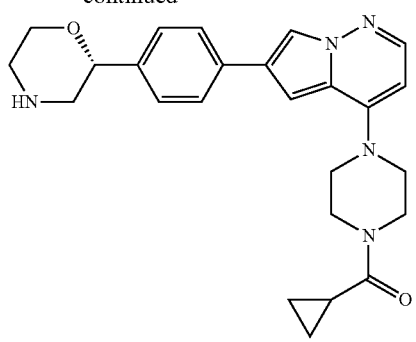

130

A mixture of cyclopropyl(4-(6-(4,4,5,5-tetramethyl-1,3,2-dioxaborolan-2-yl)pyrrolo[1,2-b]pyridazin-4-yl)piperazin-1-yl)methanone (300 mg, 757 µmol), 2-(4-bromophenyl)morpholine (183 mg, 757 µmol), Pd(dppf)Cl$_2$—CH$_2$Cl$_2$ (61.7 mg, 75.7 µmol) and K$_2$CO$_3$ (208 mg, 1.51 mmol) in dioxane/water (3 mL/0.5 mL) was purged with N$_2$, and then stirred at 100° C. for 16 hrs under N$_2$. The mixture was concentrated and purified by flash column chromatography (DCM/MeOH=10:1) to give a yellow oil (300 mg, crude). Chiral separation was performed to afford the title compounds using a CE-3 column. Mobile Phase: Hexane/EtOH/DEA=30/70/0.1; flow rate: 50 mL/min; 0.4 ml injection; 25 minute run time; sample solution: 3.2 g in 30 mL MeOH; elution measured at 214 and 254 nm using a Gilson-281. Compound 130: (56.3 mg, 17% yield) as a yellow solid MS (ES+) C$_{25}$H$_{29}$N$_5$O$_2$ requires: 431, found: 432[M+H]$^+$. Compound 131: (32.6 mg, 10% yield) as a yellow solid. MS (ES+) C$_{25}$H$_{29}$N$_5$O$_2$ requires: 431, found: 432[M+H]+.

Example 8. Synthesis of cyclopropyl(4-(6-(4-(4-ethylmorpholin-2-yl)phenyl)pyrrolo[1,2-b]pyridazin-4-yl)piperazin-1-yl)methanone (Compound 214)

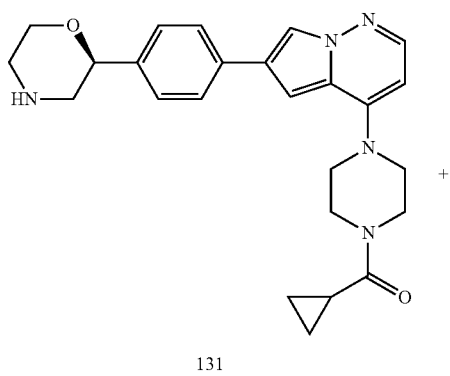

131

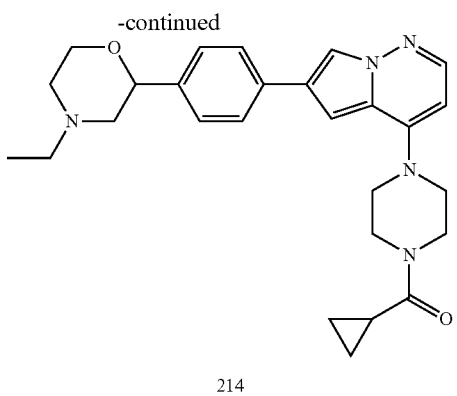

214

A mixture of cyclopropyl(4-(6-(4-(morpholin-2-yl)phenyl)pyrrolo[1,2-b]pyridazin-4-yl) piperazin-1-yl)methanone (100 mg, 231 μmol) and acetaldehyde (40.7 mg, 924 μmol) in DCM/MeOH/CH$_3$COOH (2 mL/2 mL/0.5 mL) was stirred at 25° C. for 30 min, followed by addition of NaBH$_3$CN (72.2 mg, 1.15 mmol). The mixture was stirred at 25° C. for 2 hours. The mixture was purified by Prep-HPLC to afford the title compound (8.4 mg, yield 8%) as a yellow solid. MS (ES+) C$_{27}$H$_{33}$N$_5$O$_2$ requires: 459, found: 460[M+H]$^+$.

Example 9. Synthesis of cyclopropyl(4-(6-(4-(2-(trifluoromethyl)piperazin-1-yl) phenyl)pyrrolo[1,2-b]pyridazin-4-yl)piperazin-1-yl)methanone (Compound 374)

Step 1: Synthesis of 4-benzyl-1-(4-bromophenyl)-2-(trifluoromethyl)piperazine

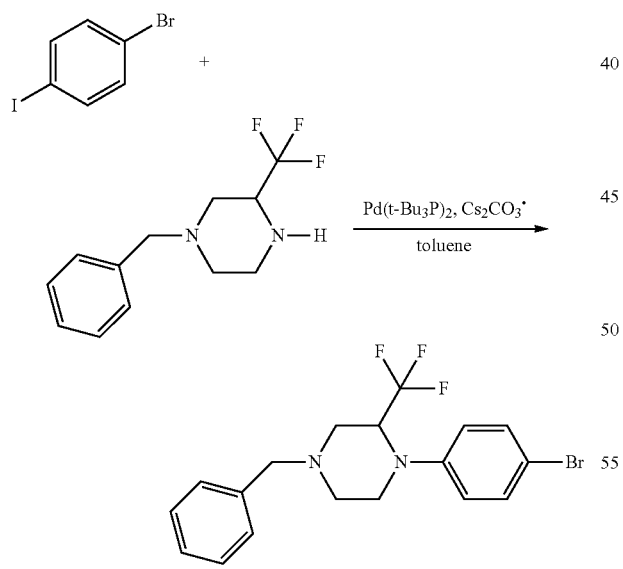

A mixture of 1-benzyl-3-(trifluoromethyl)piperazine (200 mg, 818 μmol), 1-bromo-4-iodobenzene (461 mg, 1.63 mmol), bis(tri-t-butylphosphine)palladium (83.3 mg, 163 μmol) and cesium carbonate (798 mg, 2.45 mmol) in toluene (4 mL) was purged with N$_2$ and stirred at 80° C. overnight. TLC and LCMS showed completed reaction. The mixture was cooled to RT and concentrated. The residue was purified by silica gel column (PE/EA=10/1) to give the title compound (40 mg, yield 12%) as a yellow solid. MS (ES+) C$_{18}$H$_{18}$BrF$_3$N$_2$ requires: 398, found: 399 [M+H]$^+$.

Step 2: Synthesis of (4-(6-(4-(4-benzyl-2-(trifluoromethyl)piperazin-1-yl)phenyl)pyrrolo[1,2-b]pyridazin-4-yl)piperazin-1-yl)(cyclopropyl)methanone

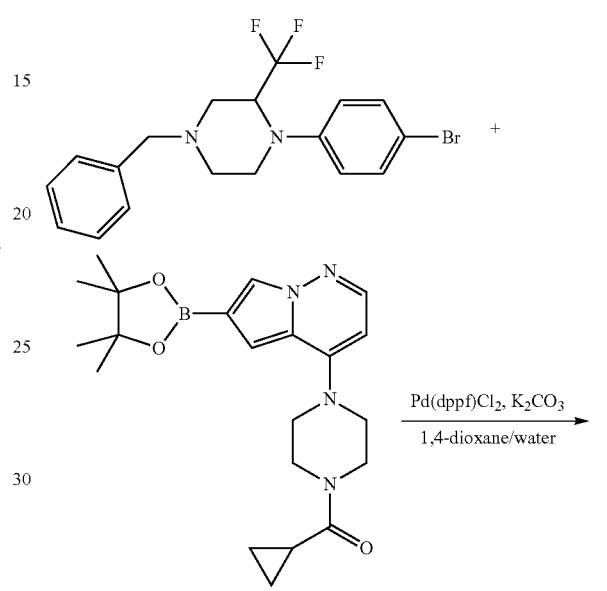

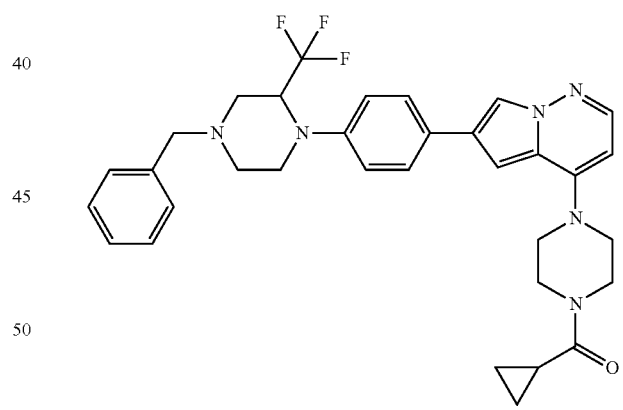

A mixture of 4-benzyl-1-(4-bromophenyl)-2-(trifluoromethyl)piperazine (60 mg, 150 μmol), cyclopropyl(4-(6-(4,4,5,5-tetramethyl-1,3,2-dioxaborolan-2-yl)pyrrolo[1,2-b]pyridazin-4-yl)piperazin-1-yl)methanone (118 mg, 300 μmol), Pd(dppf)Cl$_2$ (21.9 mg, 30.0 mop and potassium carbonate (62.1 mg, 450 μmol) in dioxane/water (4 mL) was purged with N$_2$ and stirred at 100° C. for 2 h. TLC and LCMS showed completed reaction. The mixture was cooled to RT and concentrated. The residue was purified by silica gel column (PE/EA=2/1) to give the title compound (80 mg, crude) as a yellow solid. MS (ES+) C$_{33}$H$_{35}$F$_3$N$_6$O requires: 588, found: 589[M+H]$^+$.

Step 3: Synthesis of cyclopropyl(4-(6-(4-(2-(trifluoromethyl)piperazin-1-yl)phenyl)pyrrolo[1,2-b]pyridazin-4-yl)piperazin-1-yl)methanone (Compound 374)

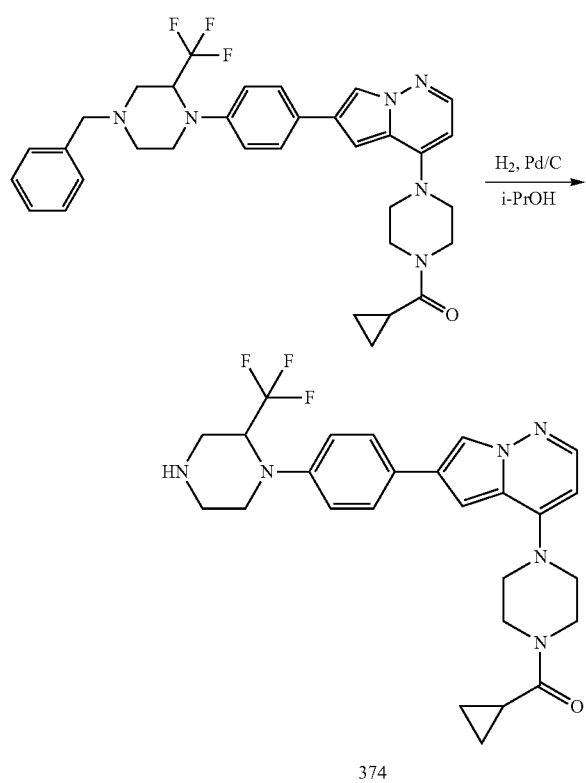

374

A mixture of (4-(6-(4-(4-benzyl-2-(trifluoromethyl)piperazin-1-yl)phenyl)pyrrolo[1,2-b]pyridazin-4-yl)piperazin-1-yl)(cyclopropyl)methanone (70 mg, 118 µmol) and Pd/C (14 mg, 20% wt) in i-PrOH (4 mL) was stirred at 45° C. overnight under hydrogen (balloon). The mixture was filtered and concentrated. The residue was purified by Prep-HPLC to give the title compound (1.6 mg, yield 3%) as a white solid. MS (ES+) $C_{26}H_{29}F_3N_6O$ requires: 498, found: 499[M+H]$^+$.

Example 10. Synthesis of N-ethyl 4-(6-(4-(1-ethylpiperidin-4-yl)phenyl)pyrrolo[1,2-b]pyridazin-4-yl)piperazine-1-carboxylate (Compound 230)

Step 1: Synthesis of 6-(4-(1-ethylpiperidin-4-yl)phenyl)-4-(piperazin-1-yl)pyrrolo[1,2-b]pyridazine

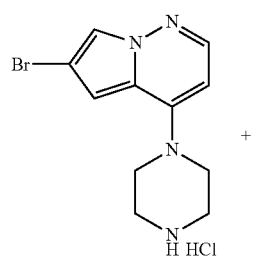

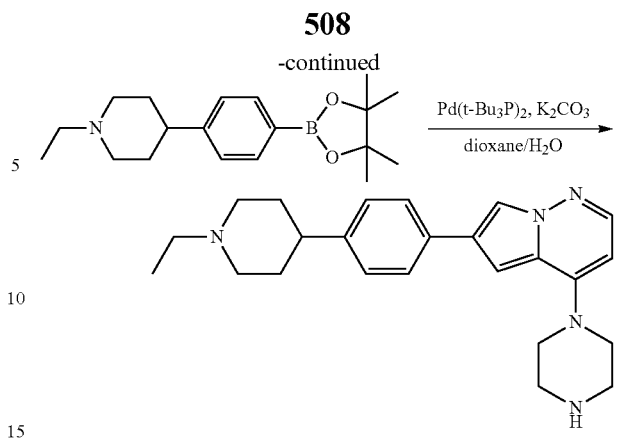

A mixture of 6-bromo-4-(piperazin-1-yl)pyrrolo[1,2-b]pyridazine hydrochloride (1.2 g, 3.77 mmol), 1-ethyl-4-(4-(4,4,5,5-tetramethyl-1,3,2-dioxaborolan-2-yl)phenyl)piperidine (1.78 g, 5.65 mmol), $K_2CO_3$ (1.57 g, 11.3 mmol) and Pd(t-Bu$_3$P)$_2$ in dioxane/water (20 mL/5 mL) was degassed with nitrogen three times. The mixture was then heated to 70° C. and the temperature maintained overnight. The reaction mixture was cooled to RT and concentrated to give a residue, which was purified by silica gel chromatography to afford the title compound (1.2 g, yield 82%) as a yellow oil. MS (ES+) $C_{24}H_{31}N_5$ requires: 389, found: 390[M+H]$^+$.

Step 2: Synthesis of ethyl 4-(6-(4-(1-ethylpiperidin-4-yl)phenyl)pyrrolo[1,2-b]pyridazin-4-yl) piperazine-1-carboxylate (Compound 230)

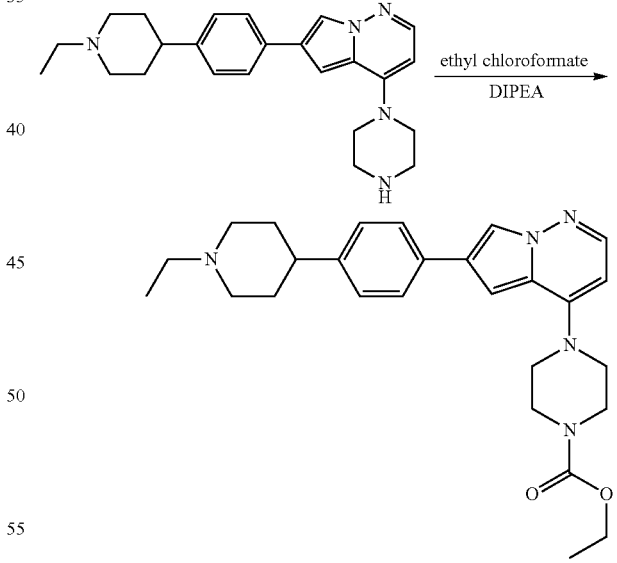

230

To a solution 6-(4-(1-ethylpiperidin-4-yl)phenyl)-4-(piperazin-1-yl)pyrrolo[1,2-b]pyridazine (50 mg, 128 µmol) and DIPEA (82 mg, 640 µmol) in DCM (10 mL) was added ethyl chloroformate (41.5 mg, 384 µmol). The reaction mixture was stirred at RT for 3 h. The mixture was concentrated under reduced pressure. The residue was purified by Prep-HPLC to afford the title compound (9 mg, yield 15%). MS (ES+) $C_{27}H_{35}N_5O_2$ requires: 461, found: 462[M+H]$^+$.

509

Example 11. Synthesis of N-ethyl-4-(6-(4-(1-isopropylpiperidin-4-yl)phenyl)pyrrolo[1,2-b]pyridazin-4-yl)piperazine-1-carboxamide (Compound 275)

Step 1: Synthesis of tert-butyl-4-(6-bromo-pyrrolo[1,2-b]pyridazin-4-yl)piperazine-1-carboxylate

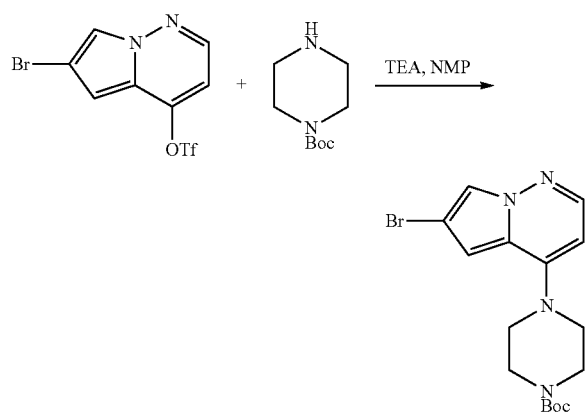

A mixture of 6-bromopyrrolo[1,2-b]pyridazin-4-yl trifluoromethanesulfonate (200 g, 579.7 mmol), tert-butyl piperazine-1-carboxylate (113.2 g, 609 mmol) and triethylamine (176 g, 1740 mmol) in NMP (180 mL) was stirred at 100° C. for 1 hr. Monitored by LC-MS, the reaction was completed. The mixture was diluted with EtOAc, washed with water and brine, and dried over sodium sulfate. The organic layer was concentrated and purified by flash chromatography (silica gel, 10-40% EtOAc in PE) to afford the title compound (220.0 g, crude). MS (ES+) $C_{16}H_{21}BrN_4O_2$ require: 380, 382, found: 381, 383[M+H]+.

Step 2: Synthesis of tert-butyl-4-(6-(4,4,5,5-tetramethyl-1,3,2-dioxaborolan-2-yl)pyrrolo[1,2-b]pyridazin-4-yl)piperazine-1-carboxylate

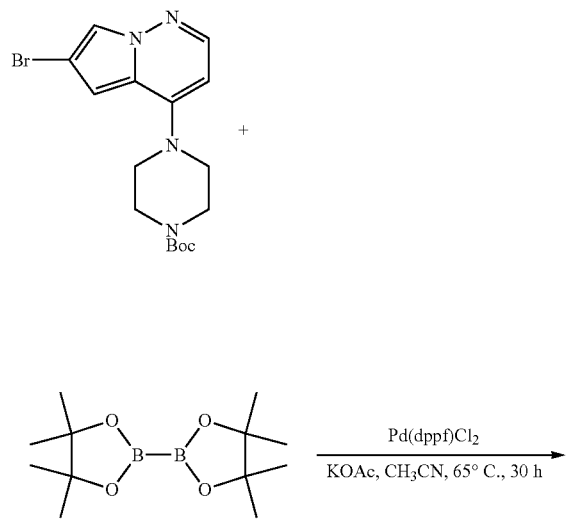

510

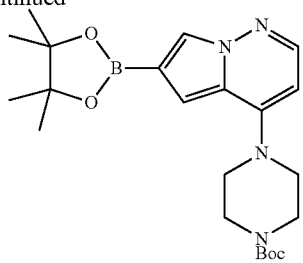

A mixture of tert-butyl 4-(6-bromopyrrolo[1,2-b]pyridazin-4-yl)piperazine-1-carboxylate (220 g crude, 0.58 mol), 4,4,4',4',5,5,5',5'-octamethyl-2,2'-bi(1,3,2-dioxaborolane) (294 g, 1.158 mol), Pd(dppf) Cl$_2$—CH$_2$C$_{12}$ (42.4 g, 0.058 mol) and KOAc (170.2 g, 1.737 mol) in CH$_3$CN (500 mL) was purged with N$_2$ and stirred at 65° C. for 24 hrs under N$_2$. Monitored by LC-MS, the reaction was completed. The mixture was cooled to RT, concentrated and purified by flash column chromatography (Petroleum ether/ethyl acetate=10:1 to 2:1) to afford the title compound (189.0 g, 76%) as a white solid. MS (ES+) $C_{22}H_{33}BN_4O_4$ requires: 428, found: 429[M+H]+.

Step 3: Synthesis of tert-butyl tert-butyl 4-(6-(4-(1-isopropylpiperidin-4-yl)phenyl)pyrrolo[1,2-b]pyridazin-4-yl)piperazine-1-carboxylate

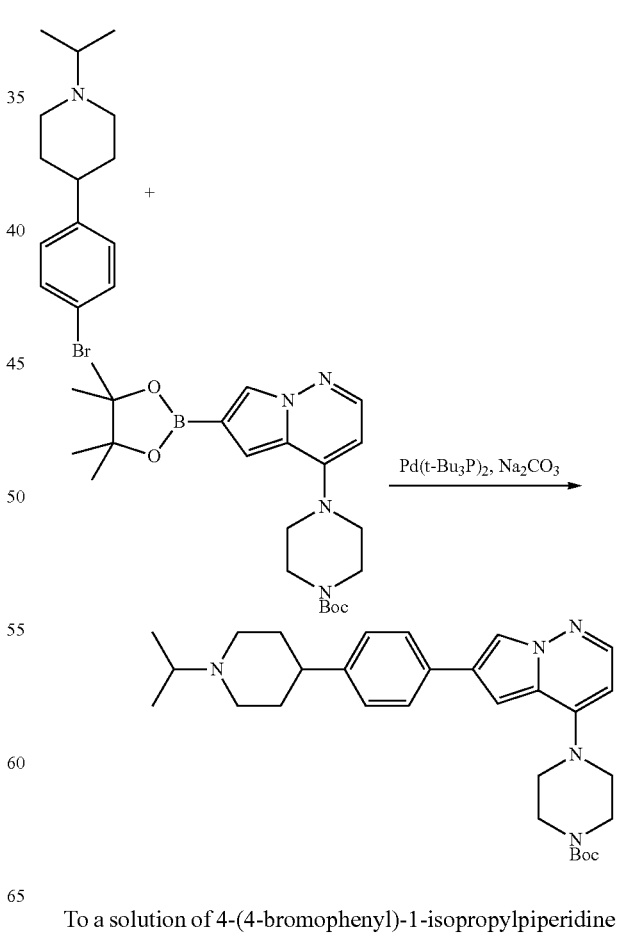

To a solution of 4-(4-bromophenyl)-1-isopropylpiperidine (300 mg, 1.06 mmol) and tert-butyl-4-(6-(4,4,5,5-tetramethyl-1,3,2-dioxaborolan-2-yl)pyrrolo[1,2]pyridazin-4-yl)piperazine-1-carboxylate (550 mg, 1.59 mmol) in dioxane/water (30 mL/10 mL) was added Pd(t-Bu$_3$P)$_2$ (108.3 mg, 0.212 mmol) and Na$_2$CO$_3$ (337.1 mg, 3.18 mmol) at RT under nitrogen. The resulting mixture was heated at 75° C. for 3 hours; LCMS showed that the reaction was completed. Water (50 mL) was added and extracted with EtOAc (50 mL×2). The organic layer was washed with brine (50 mL), dried over Na$_2$SO$_4$, and concentrated to dryness to afford crude product, which was purified with flash column (DCM/MeOH, 10:1) to give the title compound (346 mg, yield 65%) as a white powder. MS (ES+) C$_{30}$H$_{41}$N$_5$O$_2$, requires: 503, found: 504[M+H]$^+$.

Step 4: Synthesis of 6-(4-(1-isopropylpiperidin-4-yl)phenyl)-4-(piperazin-1-yl)pyrrolo[1,2-b]pyridazine hydrochloride

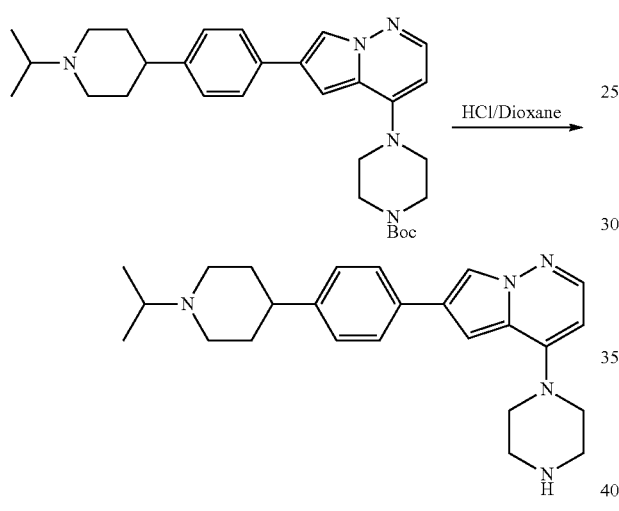

To a solution of tert-butyl 4-(6-(4-(1-isopropylpiperidin-4-yl)phenyl)pyrrolo[1,2-b]pyridazin-4-yl)piperazine-1-carboxylate (346 mg, 0.69 mmol) in dioxane (10 mL) was added 6 M HCl/dioxane (3 mL) at RT. The resulting mixture was stirred for 6 hours; LCMS showed that the reaction was completed. The mixture was then evaporated to dryness to afford the title product (282 mg, 93% yield) as a white solid. MS (ES+) C$_{25}$H$_{33}$N$_5$ requires: 403, found: 404[M+H]$^+$.

Step 5: Synthesis of N-ethyl-4-(6-(4-(1-isopropylpiperidin-4-yl)phenyl)pyrrolo[1,2-b]pyridazin-4-yl)piperazine-1-carboxamide (Compound 275)

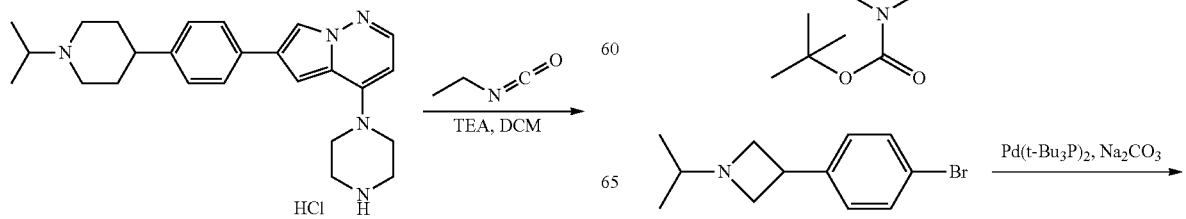

275

To a solution of 6-(4-(1-isopropylpiperidin-4-yl)phenyl)-4-(piperazin-1-yl)pyrrolo[1,2-b]pyridazine hydrochloride (282 mg, 0.64 mmol) in DCM (10 mL) was added triethylamine (0.5 mL) and isocyanatoethane (0.1 mL) at 0° C. The resulting mixture was stirred at RT for 30 min; LCMS indicated that the reaction was completed. Extracted with EtOAc (50 mL×2) after water (50 mL) was added. The organic layer was washed with brine (50 mL), dried over Na$_2$SO$_4$, and concentrated to dryness to afford crude product which was purified by Prep-HPLC to give the title compound (89.9 mg, yield 30%) as a white powder. MS (ES+) C$_{27}$H$_{37}$N$_7$O, requires: 475, found: 476[M+H]$^+$.

Example 12. Synthesis of cyclopropyl(4-(6-(4-(1-isopropylazetidin-3-yl)phenyl)pyrrolo[1,2-b]pyridazin-4-yl)piperazin-1-yl)methanone (Compound 150)

Step 1: Synthesis of tert-butyl 4-(6-(4-(1-isopropylazetidin-3-yl)phenyl)pyrrolo[1,2-b]pyridazin-4-yl)piperazine-1-carboxylate

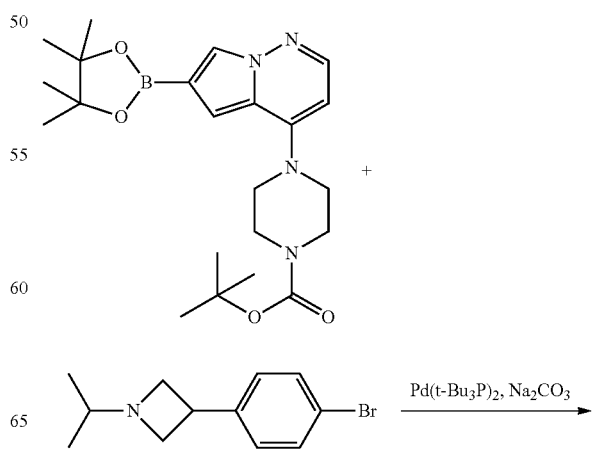

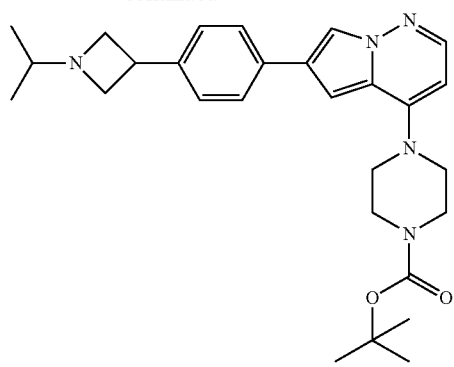

To a solution of tert-butyl 4-(6-(4,4,5,5-tetramethyl-1,3,2-dioxaborolan-2-yl)pyrrolo[1,2-b]pyridazin-4-yl)piperazine-1-carboxylate (680 mg, 1.59 mmol) in dioxane/water (15 mL) was added 3-(4-bromophenyl)-1-isopropylazetidine (480 mg, 1.9 mmol), Pd(t-Bu₃P)₂ (81 mg, 0.16 mmol) and Na₂CO₃ (337 mg, 3.18 mmol) at room temperature under nitrogen. The resulting mixture was stirred at 70° C. for 3 h under nitrogen. Water was added and extracted with EtOAc. The combined organic layers were washed with brine, dried over Na₂SO₄, and concentrated to dryness to afford crude compound, which was purified by flash chromatography on silica gel eluting with DCM/MeOH (10:1) to give the title compound (430 mg, 57% yield) as a light yellow powder. MS (ES+) $C_{28}H_{37}N_5O_2$ requires: 475, found 476[M+H]⁺.

Step 2: Synthesis of 6-(4-(1-isopropylazetidin-3-yl)phenyl)-4-(piperazin-1-yl)pyrrolo[1,2-b]pyridazine

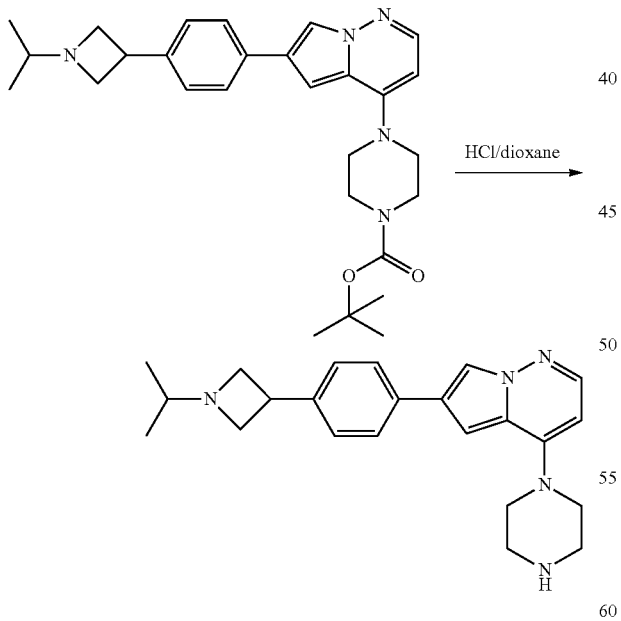

To a solution of tert-butyl 4-(6-(4-(1-isopropylazetidin-3-yl)phenyl)pyrrolo[1,2-b]pyridazin-4-yl)piperazine-1-carboxylate (430 mg, 0.91 mmol) in dioxane (10 mL) was added HCl/dioxane (3 mL, 4.0 M) at RT. The resulting mixture was stirred for 5 hours. LC-MS showed that the reaction was completed. The mixture was evaporated to dryness to afford the title compound (360 mg, 99% yield) as a white powder. MS (ES+) $C_{23}H_{29}N_5$ requires: 375, found 376[M+H]⁺.

Step 3: Synthesis of cyclopropyl(4-(6-(4-(1-isopropylazetidin-3-yl)phenyl)pyrrolo[1,2-b]pyridazin-4-yl)piperazin-1-yl)methanone

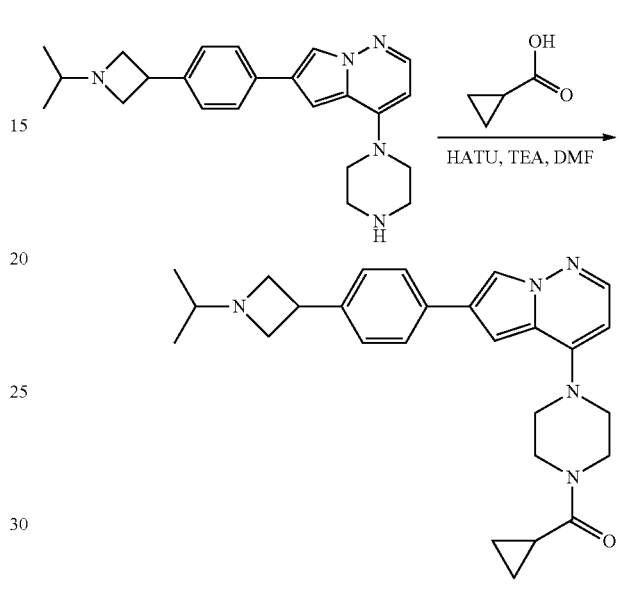

150

To a solution of 6-(4-(1-isopropylazetidin-3-yl)phenyl)-4-(piperazin-1-yl)pyrrolo[1,2-b]pyridazine (120 mg, 0.32 mmol) in DMF (10 mL) was added cyclopropanecarboxylic acid (33 mg, 0.38 mmol) and triethylamine (80 mg, 0.8 mmol) at RT, followed by addition of HATU (144 mg, 0.38 mmol). The resulting mixture was stirred at RT for 2 h, diluted with water and extracted with EtOAc. The combined organic layers were washed with brine, dried over Na₂SO₄, and concentrated to dryness to afford crude product, which was purified by flash chromatography on silica gel eluting with DCM/MeOH (5:1) to give the title compound (101 mg, 72% yield) as a white powder. MS (ES+) $C_{27}H_{33}N_5O$ requires: 443, found 444[M+H]⁺.

Example 13. Synthesis of ethyl 4-(6-(5-(4-isopropylpiperazin-1-yl)pyrazin-2-yl)pyrrolo[1,2-b]pyridazin-4-yl)piperazine-1-carboxylate (Compound 448)

Step 1: Synthesis of tert-butyl 4-(5-bromopyrazin-2-yl)piperazine-1-carboxylate

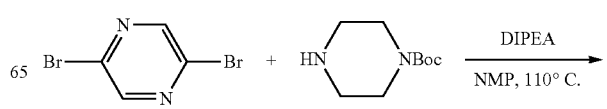

-continued

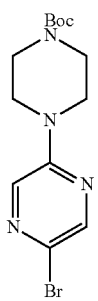

A mixture of 2,5-dibromopyrazine (2 g, 8.40 mmol), tert-butyl piperazine-1-carboxylate (1.86 g, 10.0 mmol) and DIPEA (1.62 g, 12.6 mmol) in NMP (40 mL) was stirred at 110° C. for 2 h. Diluted with ethyl acetate, washed with water and brine, dried over Na$_2$SO$_4$, and concentrated to give the title product (2.8 g, yield 97%). MS (ES+) C$_{13}$H$_{19}$BrN$_4$O$_2$ requires: 342, found: 343[M+H]$^+$.

Step 2: Synthesis of 2-bromo-5-(piperazin-1-yl)pyrazine

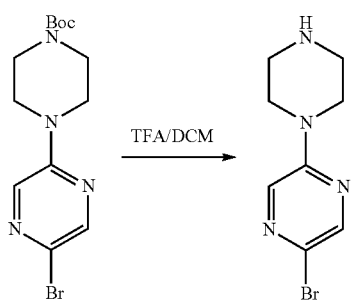 [SMILES: CC(C)(C)OC(=O)N1CCN(c2cnc(Br)cn2)CC1 ; Brc1cnc(N2CCNCC2)cn1]

To a solution of tert-butyl 4-(5-bromopyrazin-2-yl)piperazine-1-carboxylate (2.8 g, 8.15 mmol) in DCM (20 mL) was added TFA (5 mL). The mixture was stirred at 20° C. for 1 h. Concentrated and diluted with ethyl acetate. Adjusted pH to 7-8 with sat. NaHCO$_3$ solution. The organic layer was washed with brine, dried over Na$_2$SO$_4$ and concentrated to give the title product (1.98 g, crude). MS (ES+) C$_8$H$_{11}$BrN$_4$ requires: 242, found: 243[M+H]$^+$.

Step 3: Synthesis of 2-bromo-5-(4-isopropylpiperazin-1-yl)pyrazine

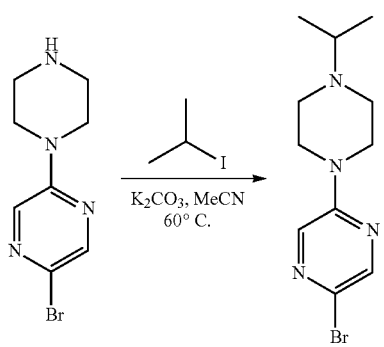

A mixture of 2-bromo-5-(piperazin-1-yl)pyrazine (458 mg, 1.88 mmol), 2-iodopropane (479 mg, 2.82 mmol) and K$_2$CO$_3$ (518 mg, 3.76 mmol) in MeCN (10 mL) was stirred at 60° C. overnight. Concentrated and purified by silica gel column (MeOH/EA=1:10) to give the title product (388 mg, yield 72%). MS (ES+) C$_{11}$H$_{17}$BrN$_4$ requires: 284, found: 285[M+H]$^+$.

Step 4: Synthesis of tert-butyl 4-(6-(5-(4-isopropylpiperazin-1-yl)pyrazin-2-yl)pyrrolo[1,2-b]pyridazin-4-yl)piperazine-1-carboxylate

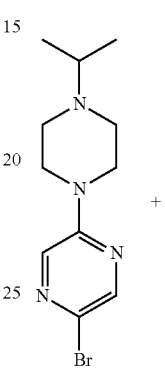

+

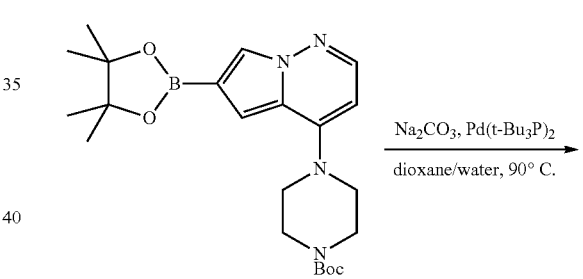

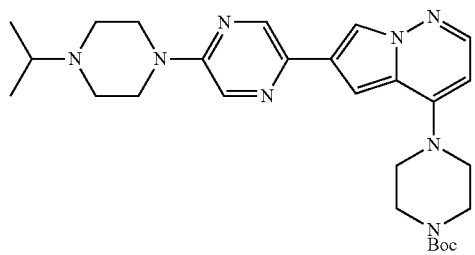

A mixture of 2-bromo-5-(4-isopropylpiperazin-1-yl)pyrazine (350 mg, 1.22 mmol), tert-butyl 4-(6-(4,4,5,5-tetramethyl-1,3,2-dioxaborolan-2-yl)pyrrolo[1,2-b]pyridazin-4-yl)piperazine-1-carboxylate (625 mg, 1.46 mmol), Na$_2$CO$_3$ (193 mg, 1.83 mmol) and Pd(t-Bu$_3$P)$_2$ (62.3 mg, 122 μmol) in dioxane/water (20 mL) was purged with N$_2$, and then stirred at 90° C. overnight under nitrogen. Concentrated and purified by silica gel column (MeOH/EA=1:10) to give the title product (388 mg, yield 63%). MS (ES+) C$_{27}$H$_{33}$N$_8$O$_2$ requires: 506, found: 507[M+H]$^+$.

Step 5: Synthesis of 6-(5-(4-isopropylpiperazin-1-yl)pyrazin-2-yl)-4-(piperazin-1-yl)pyrrolo[1,2-b]pyridazine Hydrochloride

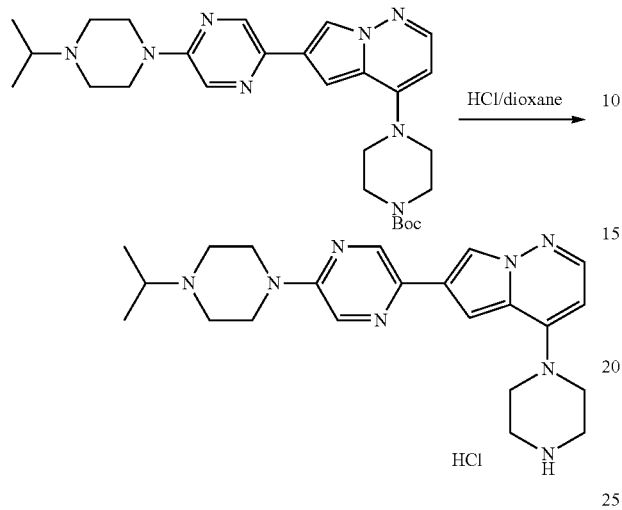

To a solution of tert-butyl 4-(6-(5-(4-isopropylpiperazin-1-yl)pyrazin-2-yl)pyrrolo[1,2-b]pyridazin-4-yl)piperazine-1-carboxylate (388 mg, 765 mol) in DCM (4 mL) was added HCl/dioxane (4 mL, 4 M). The mixture was stirred at 20° C. overnight and then concentrated to give the title product (338 mg, crude). MS (ES+) $C_{22}H_{31}ClN_8$ requires: 406, found: 407[M+H]⁺.

Step 6: Synthesis of ethyl 4-(6-(5-(4-isopropylpiperazin-1-yl)pyrazin-2-yl)pyrrolo[1,2-b]pyridazin-4-yl)piperazine-1-carboxylate (Compound 448)

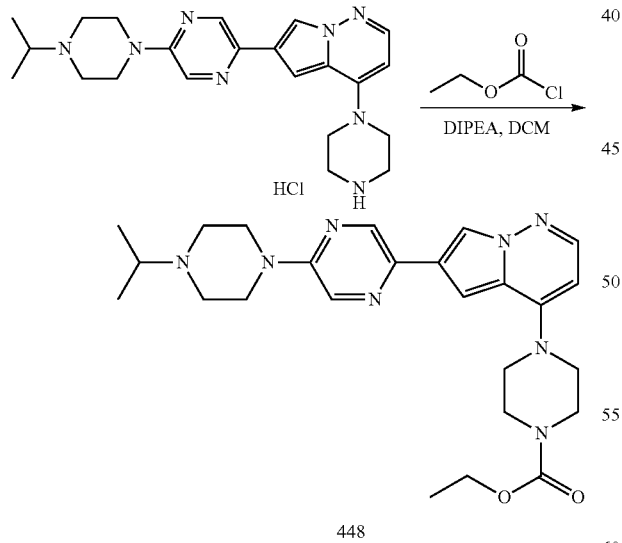

To a solution of 6-(5-(4-isopropylpiperazin-1-yl)pyrazin-2-yl)-4-(piperazin-1-yl)pyrrolo[1,2-b]pyridazine hydrochloride (100 mg, 225 μmol) and DIPEA (87.0 mg, 675 μmol) in DCM (10 mL) was added ethyl chloroformate (48.8 mg, 450 μmol). The mixture was stirred at 20° C. for 1 h and then concentrated and purified by Prep-HPLC to give the title product (30.0 mg, yield 28%). MS (ES+) $C_{25}H_{34}N_8O_2$ requires: 478, found: 479[M+H]⁺.

Example 14. Synthesis of 1-(4-(6-(4-(1-ethylpyrrolidin-3-yl)phenyl)pyrrolo[1,2-b]pyridazin-4-yl)piperazine-1-carbonyl)azetidine-3-carbonitrile (Compound 300)

Step 1: Synthesis of tert-butyl 4-(6-(4-(1-ethylpyrrolidin-3-yl)phenyl)pyrrolo[1,2-b]pyridazin-4-yl)piperazine-1-carboxylate

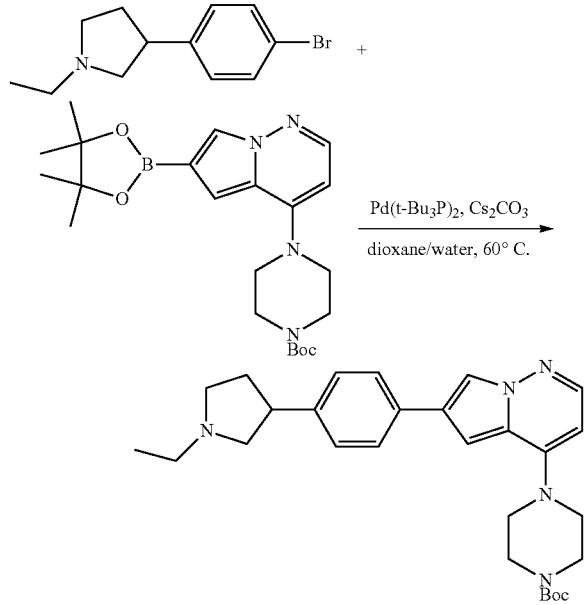

A solution of 3-(4-bromophenyl)-1-ethylpyrrolidine (200 mg, 786 μmol) in dioxane/water (5 mL) was added tert-butyl 4-(6-(4,4,5,5-tetramethyl-1,3,2-dioxaborolan-2-yl)pyrrolo[1,2-b]pyridazin-4-yl)piperazine-1-carboxylate (336 mg, 786 μmol), Pd(t-Bu₃P)₂ (40.1 mg, 78.6 μmol) and Cs₂CO₃ (763 mg, 2.35 mmol) was degassed with nitrogen, and then heated at 60° C. under MW for 1 h. The reaction mixture was cooled to RT and concentrated. The residue was purified by flash chromatography to afford the title compound (300 mg, yield 80%). MS (ES+) $C_{28}H_{37}N_5O_2$, requires: 475, found: 476[M+H]⁺.

Step 2: Synthesis of 6-(4-(1-ethylpyrrolidin-3-yl)phenyl)-4-(piperazin-1-yl)pyrrolo[1,2-b]pyridazine

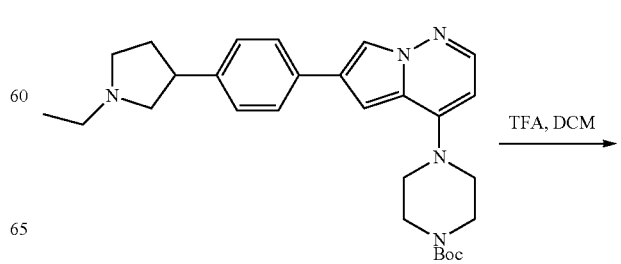

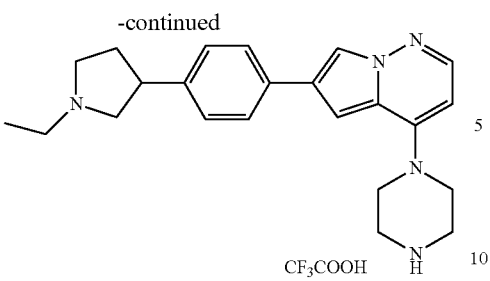

To a solution of tert-butyl 4-(6-(4-(1-ethylpyrrolidin-3-yl)phenyl)pyrrolo[1,2-b]pyridazin-4-yl)piperazine-1-carboxylate (300 mg, 630 μmol) in DCM (8 mL) was added TFA (5 mL). The reaction mixture was stirred at 20° C. for 18 h. The mixture was concentrated to give the title compound (230 mg, yield 97%). MS (ES+) $C_{28}H_{34}N_6O_2$, requires: 375, found: 376[M+H]$^+$.

Step 3: Synthesis of 1-(4-(6-(4-(1-ethylpyrrolidin-3-yl)phenyl)pyrrolo[1,2-b]pyridazin-4-yl) piperazine-1-carbonyl)azetidine-3-carbonitrile

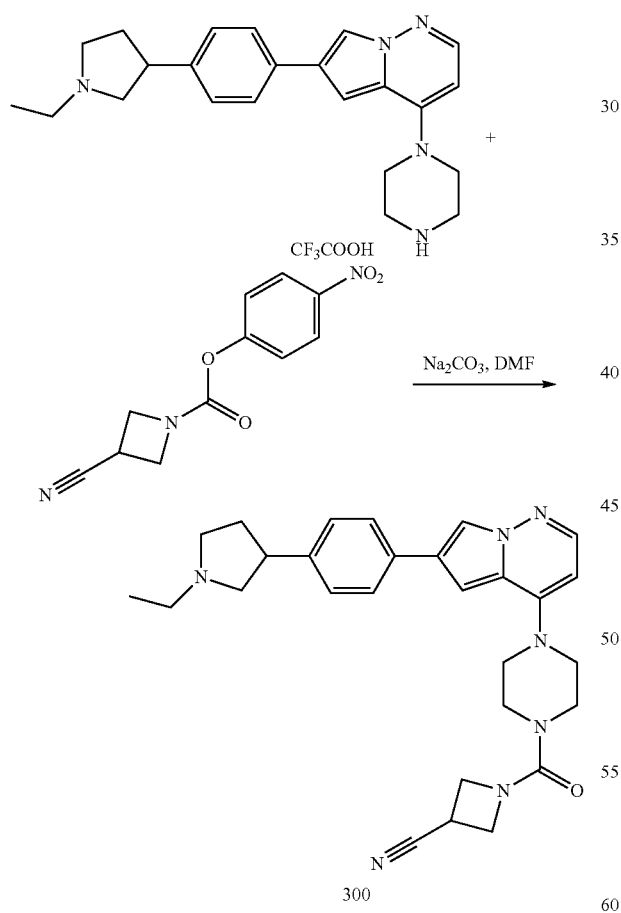

To a solution of 6-(4-(1-ethylpyrrolidin-3-yl)phenyl)-4-(piperazin-1-yl)pyrrolo[1,2-b]pyridazine (200 mg, 532 μmol) in DMF (5 mL) was added 4-nitrophenyl 3-cyanoazetidine-1-carboxylate (131 mg, 532 μmol) and Na$_2$CO$_3$ (168 mg, 1.59 mmol). The reaction mixture was stirred at 20° C. for 18 hrs. Water was added and extracted with DCM/MeOH (10/1). The mixture was concentrated to give a residue, which was purified by Prep-HPLC to give the title compound (130 mg, yield 51%). MS (ES+) $C_{28}H_{33}N_7O$, requires: 483, found: 484[M+H]$^+$.

Example 15. Synthesis of (4-(6-(4-(2-oxa-5,8-diazaspiro[3.5]nonan-8-yl)phenyl)pyrrolo[1,2-b]pyridazin-4-yl)piperazin-1-yl)(cyclopropyl)methanone (Compound 260)

Step 1: Synthesis of 2-oxa-5,8-diazaspiro[3.5]nonane

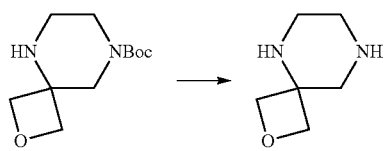 [SMILES: CC(C)(C)OC(=O)N1CCNC2(COC2)C1 ; C1CNC2(CN1)COC2]

To a mixture of tert-butyl 2-oxa-5,8-diazaspiro[3.5]nonane-8-carboxylate (100 mg, 438 μmol) in DCM (3 mL) was added TFA ((1 mL). The reaction mixture was stirred at 25° C. for 16 h. NH$_3$ (7 N in MeOH) was added to adjust pH to 8-9. The reaction mixture was concentrated in vacuo to afford the title compound (56 mg, crude) as a white solid MS (ES+) $C_6H_{12}N_2O$ requires: 128, found 129[M+H]$^+$.

Step 2: Synthesis of (4-(6-(4-(2-oxa-5,8-diazaspiro[3.5]nonan-8-yl)phenyl)pyrrolo[1,2-b]pyridazin-4-yl)piperazin-1-yl)(cyclopropyl)methanone (Compound 260)

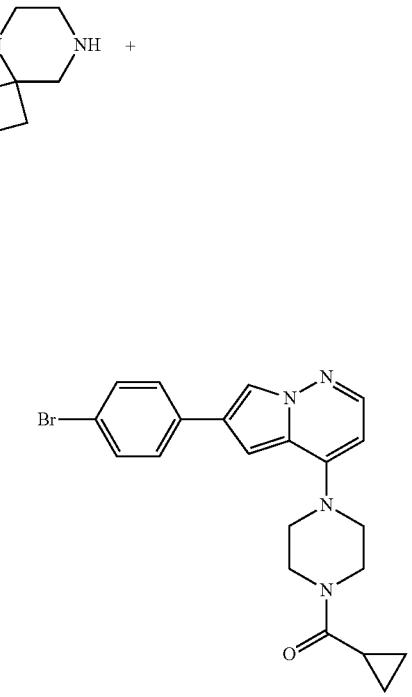

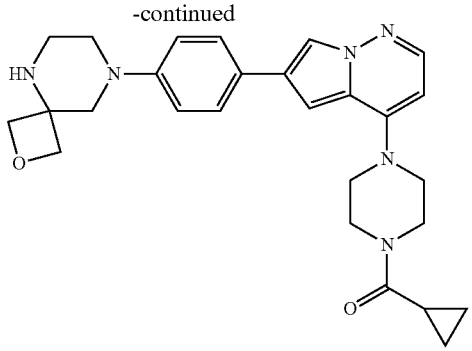

260

A mixture of 2-oxa-5,8-diazaspiro[3.5]nonane (30 mg, 234 μmol), (4-(6-(4-bromophenyl)pyrrolo[1,2-b]pyridazin-4-yl)piperazin-1-yl)(cyclopropyl)methanone (129 mg, 304 μmol), Pd[(t-Bu)$_3$P]$_2$ (11.9 mg, 23.4 μmol) and Na$_2$CO$_3$ (49.6 mg, 468 μmol) in toluene (3 mL) was degassed with nitrogen and stirred at 100° C. for 16 h under N$_2$. LCMS showed the reaction was completed. Concentrated in vacuo, the residue was purified by Prep-HPLC to afford the title compound (7.2 mg, yield 6%) as a yellow solid MS (ES+) C$_{27}$H$_{32}$N$_6$O$_2$ requires: 472, found 473[M+H]$^+$.

Example 16. Synthesis of 2-(6-(4-(4-ethylpiperazin-1-yl)phenyl)pyrrolo[1,2-b]pyridazin-4-yl) hexahydropyrrolo[1,2-a]pyrazin-6(7H)-one (Compound 157)

Step 1: Synthesis of 1-(4-bromophenyl)-4-ethylpiperazine

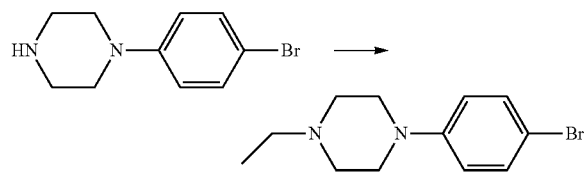

A mixture of 1-(4-bromophenyl)piperazine (40 g, 165 mmol), bromoethane (17.9 g, 165 mmol) and triethylamine (16.6 g, 165 mmol) in THF (500 ml) was stirred at 60° C. overnight. The reaction was cooled to RT, diluted with EA and washed with water. The organic layer was concentrated to give the title compound (50 g, crude). MS (ES+) C$_{12}$H$_{17}$BrN$_2$ requires: 268, found 269[M+H]$^+$.

Step 2: Synthesis of 1-ethyl-4-(4-(4,4,5,5-tetramethyl-1,3,2-dioxaborolan-2-yl)phenyl)piperazine

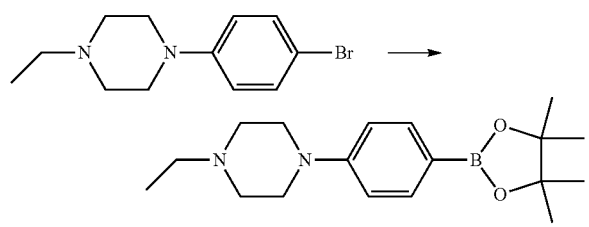

A mixture of 1-(4-bromophenyl)-4-ethylpiperazine (50 g, 185 mmol), KOAc (54.3 g, 554 mmol) and Pd(dppf)Cl$_2$ (13.5 g, 18.5 mmol) in dioxane (500 mL) was purged with N$_2$ and stirred at 60° C. overnight. The reaction mixture was cooled, concentrated and purified by silica gel column (PE/EA=5/1 to EA) to give the title compound (40 g, 69.5%). MS (ES+) C$_{18}$H$_{29}$BN$_2$O$_2$ requires: 316, found 317 [M+H]$^+$.

Step 3: Synthesis of 6-bromo-4-((2-(trimethylsilyl)ethoxy)methoxy)pyrrolo[1,2-b]pyridazine

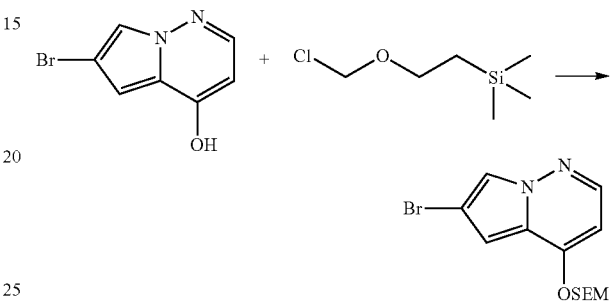

To a mixture of 6-bromopyrrolo[1,2-b]pyridazin-4-ol (22.0 g, 103 mmol) and triethylamine (31.2 g, 309 mmol) in THF (100 mL) was added (2-(chloromethoxy)ethyl)trimethylsilane (20.5 g, 123 mmol) dropwise at 0° C. The reaction mixture was stirred at 20° C. for 1 h. The mixture was concentrated, diluted with EA and washed with water. The organic layer was concentrated and purified by flash column chromatography (PE/EA=5:1) to afford the title compound (31 g, yield 87%) as a yellow oil MS (ES+) C$_{13}$H$_{19}$BrN$_2$O$_2$Si requires: 342, found 343[M+H]$^+$.

Step 4: Synthesis of 6-(4-(4-ethylpiperazin-1-yl)phenyl)-4-((2-(trimethylsilyl)ethoxy)methoxy)pyrrolo[1,2-b]pyridazine

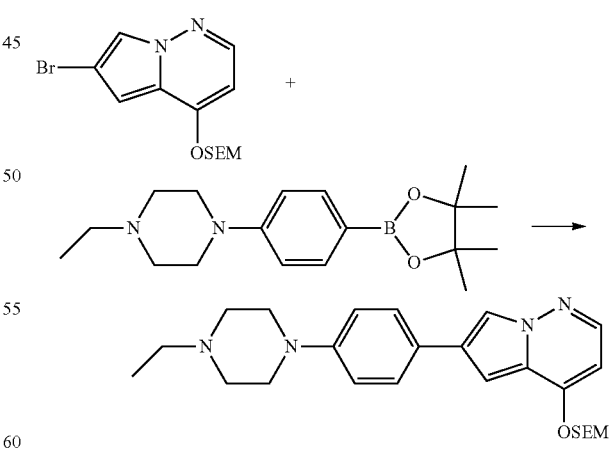

A mixture of 6-bromo-4-((2-(trimethylsilyl)ethoxy)methoxy)pyrrolo[1,2-b]pyridazine (5 g, 14.5 mmol), 1-ethyl-4-(4-(4,4,5,5-tetramethyl-1,3,2-dioxaborolan-2-yl)phenyl)piperazine (5.94 g, 18.8 mmol), K$_2$CO$_3$ (6.0 g, 43.5 mmol) and Pd[(t-Bu)$_3$P]$_2$ (370 mg, 725 μmol) in dioxane/water (30 mL, 4/1) was purged with N$_2$ and then stirred at 70° C. for 4 h under N₂. The mixture was purified by flash column chromatography (PE/EA=10:1 to 1:2) to afford the title compound (6 g, yield 91%) as a grey solid. MS (ES+) C$_{25}$H$_{36}$N$_4$O$_2$Si requires: 452, found 453[M+H]⁺.

Step 5: Synthesis of 6-(4-(4-ethylpiperazin-1-yl) phenyl)pyrrolo[1,2-b]pyridazin-4-ol

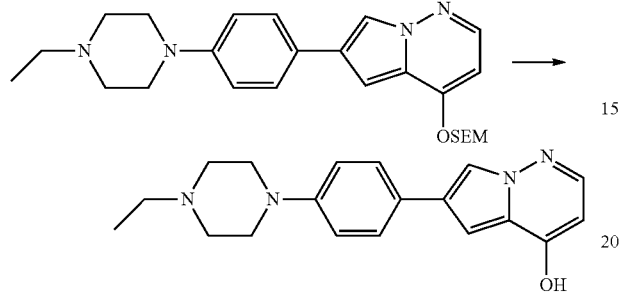

To a mixture of 6-(4-(4-ethylpiperazin-1-yl)phenyl)-4-((2-(trimethylsilyl)ethoxy)methoxy)pyrrolo[1,2-b]pyridazine (8.0 g, 17.6 mmol) in dioxane (20 mL) was added HCl (4 N in dioxane, 40 mL). The mixture was stirred at 25° C. for 1 h. The mixture was concentrated in vacuo to afford the title compound (4.77 g, crude) as a yellow solid. MS (ES+) C$_{19}$H$_{22}$N$_4$O requires: 322, found: 323[M+H]⁺.

Step 6: Synthesis of 6-(4-(4-ethylpiperazin-1-yl) phenyl)pyrrolo[1,2-b]pyridazin-4-yl trifluoromethanesulfonate

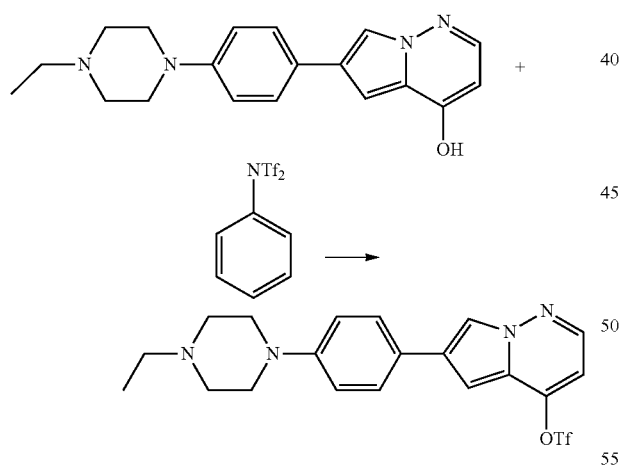

To a solution of 6-(4-(4-ethylpiperazin-1-yl)phenyl)pyrrolo[1,2-b]pyridazin-4-ol (3.0 g, 9.30 mmol) in DCM (30 mL) at 0° C. was added triethylamine (2.82 g, 27.9 mmol), followed by addition of 1,1,1-trifluoro-N-phenyl-N-((trifluoromethyl)sulfonyl)methanesulfonamide (3.96 g, 11.1 mmol). The reaction mixture was stirred at 0° C. for 2 h. The mixture was diluted with DCM and washed with brine. The organic layer was evaporated and purified by flash column (PE:EA=5:1) to afford the title compound (1.9 g, yield 45%) as a yellow solid MS (ES+) C$_{20}$H$_{21}$F$_3$N$_4$O$_3$S requires: 454, found 455[M+H]⁺.

Step 7: Synthesis of 2-(6-(4-(4-ethylpiperazin-1-yl) phenyl)pyrrolo[1,2-b]pyridazin-4-yl) hexahydropyrrolo[1,2-a]pyrazin-6(7H)-one

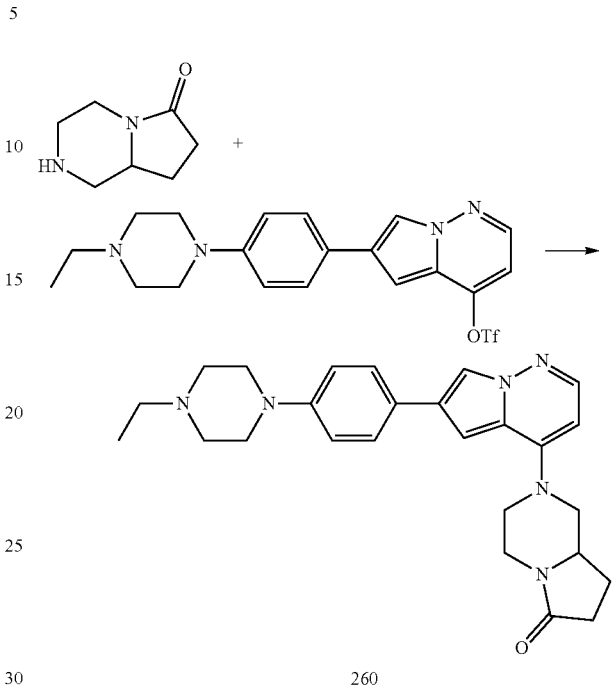

260

A mixture of hexahydropyrrolo[1,2-a]pyrazin-6(2H)-one (30 mg, 214 μmol), 6-(4-(4-ethylpiperazin-1-yl)phenyl)pyrrolo[1,2-b]pyridazin-4-yl trifluoromethanesulfonate (116 mg, 256 μmol) and triethylamine (64.9 mg, 642 μmol) in NMP (2 mL) was stirred at 100° C. for 1 h. The mixture was concentrated and purified by Prep-HPLC to afford the title compound (4.0 mg, yield 4%) as a white solid MS (ES+) C$_{26}$H$_{32}$N$_6$O requires: 444, found 445 [M+H]⁺.

Example 17. Synthesis of cyclopropyl(2-(difluoromethyl)-4-(6-(4-(4-ethylpiperazin-1-yl) phenyl) pyrrolo[1,2-b]pyridazin-4-yl)piperazin-1-yl)methanone (Compound 403)

Step 1: Synthesis of 2-(difluoromethyl)piperazine

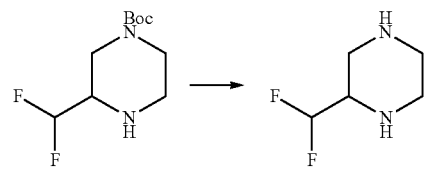 [SMILES: CC(C)(C)OC(=O)N1CCNC(C(F)F)C1 ; FC(F)C1CNCCN1]

To a solution of tert-butyl 3-(difluoromethyl)piperazine-1-carboxylate (30 mg, 0.127 mmol) in dioxane (2.0 mL) was added HCl/dioxane (4 N, 1.0 mL). The reaction solution was stirred at 25° C. for 1 h. The reaction mixture was concentrated. The residue was used in next step directly without any further purification.

Step 2: Synthesis of 4-(3-(difluoromethyl)piperazin-1-yl)-6-(4-(4-ethylpiperazin-1-yl) phenyl)pyrrolo[1,2-b]pyridazine

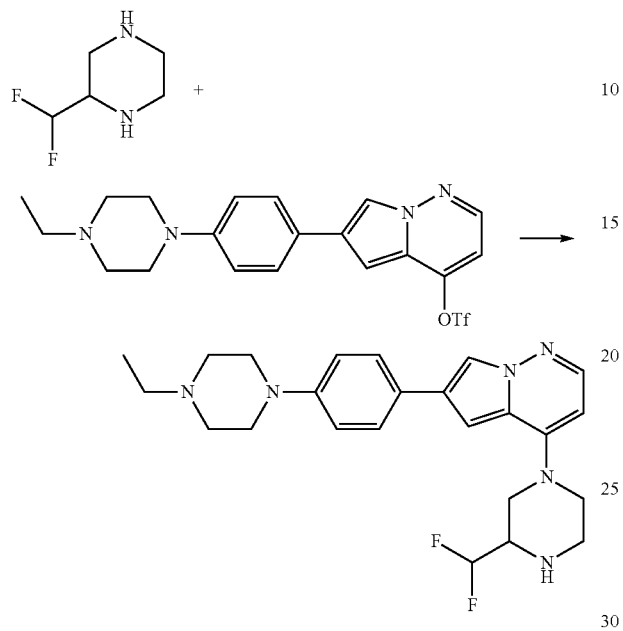

A mixture of 6-(4-(4-ethylpiperazin-1-yl)phenyl)pyrrolo[1,2-b]pyridazin-4-yl trifluoromethanesulfonate (60 mg, 0.13 mmol) and 2-(difluoromethyl)piperazine (17 mg, 0.13 mmol) and triethylamine (40 mg, 0.40 mmol) in NMP (3 mL) was stirred at 100° C. for 2 h. The reaction solution was used in next step directly without any further purification. MS (ES+) $C_{24}H_{30}F_2N_6$ requires: 440, found 441 [M+H]$^+$.

Step 3: Synthesis of cyclopropyl(2-(difluoromethyl)-4-(6-(4-(4-ethylpiperazin-1-yl) phenyl)pyrrolo[1,2-b]pyridazin-4-yl)piperazin-1-yl)methanone (Compound 403)

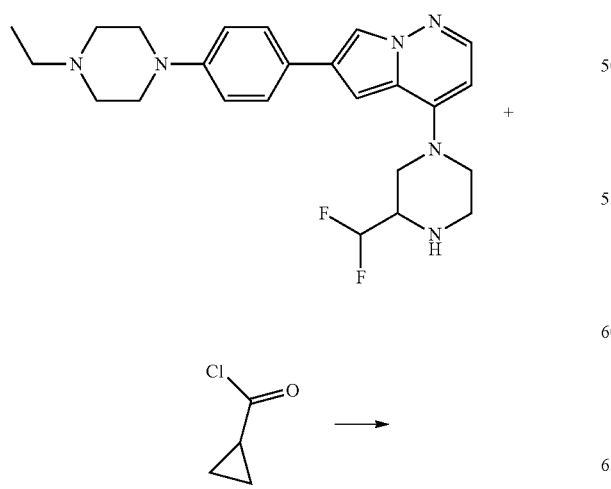

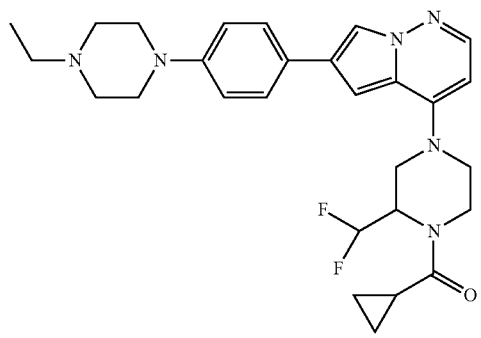

403

To above reaction mixture was added triethylamine (40 mg, 0.40 mmol) and cyclopropanecarbonyl chloride (27 mg, 0.26 mmol). The mixture was stirred at RT for 2 h. The reaction mixture was concentrated and purified by Prep-HPLC to give the title product as a yellow solid (3.8 mg, yield 7.6%). MS (ES+) $C_{28}H_{34}F_2N_6O$ requires: 508, found 509[M+H]$^+$.

Example 18. Synthesis of cyclopropyl(4-(6-(4-(4,5-dihydro-1H-imidazol-2-yl) phenyl)pyrrolo[1,2-b]pyridazin-4-yl)piperazin-1-yl)methanone (Compound 111)

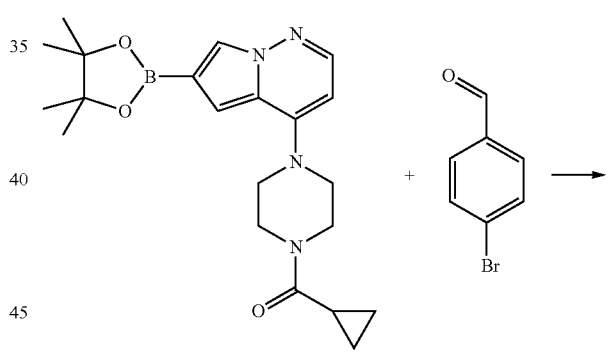

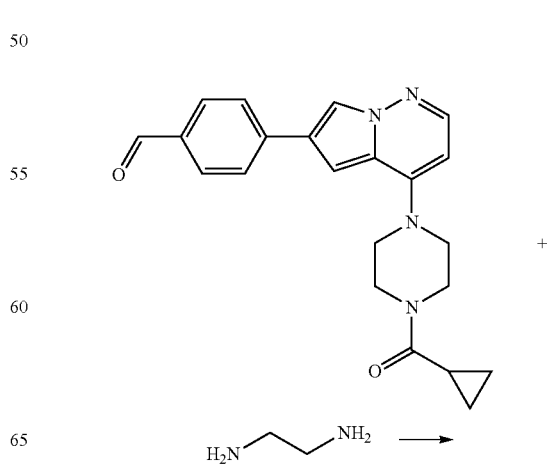

-continued

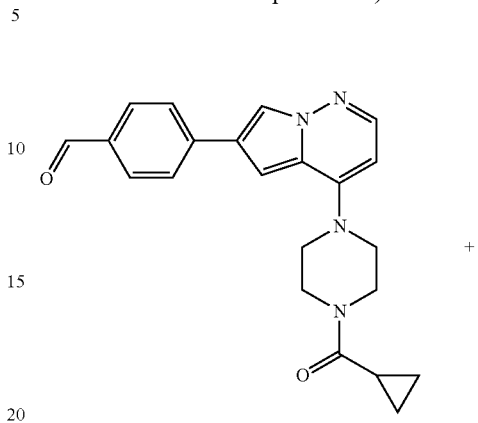

Ex ??

Step 1: Synthesis of 4-(4-(4-(cyclopropanecarbonyl)piperazin-1-yl)pyrrolo[1,2-b]pyridazin-6-yl)benzaldehyde

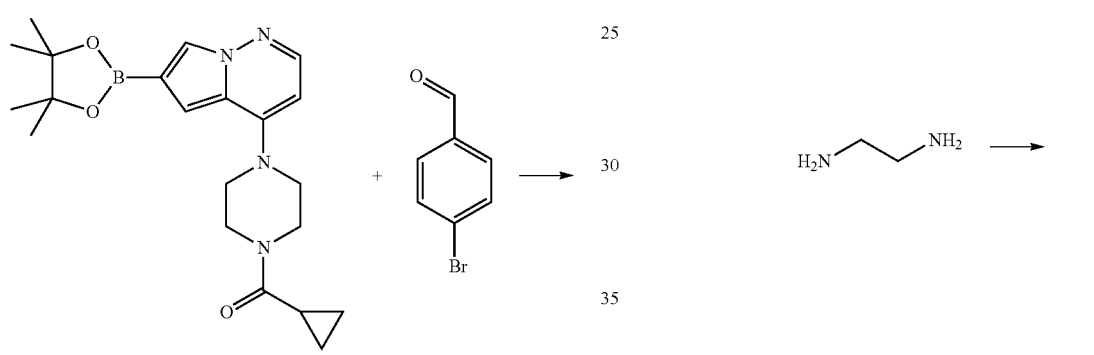

A mixture of cyclopropyl(4-(6-(4,4,5,5-tetramethyl-1,3,2-dioxaborolan-2-yl)pyrrolo[1,2-b]pyridazin-4-yl)piperazin-1-yl)methanone (250 mg, 0.63 mmol), 4-bromobenzaldehyde (120 mg, 0.65 mmol), sodium carbonate (200 mg, 1.89 mmol) and Pd(t-Bu$_3$P)$_2$ (65 mg, 0.13 mmol) in dioxane/water (15 mL) was purged with N$_2$, and then stirred at 75° C. for 3 h. Cooled to RT and diluted with EtOAc. The organic layer was washed with water and brine, concentrated and purified by flash column (PE/EtOAc=10/1 to 5/1) to give the title product (180 mg, crude). MS (ES+) $C_{22}H_{22}N_4O_2$ requires: 374, found 375[M+H]$^+$.

Step 2: Synthesis of cyclopropyl(4-(6-(4-(4,5-di-hydro-1H-imidazol-2-yl)phenyl)pyrrolo[1,2-b]pyridazin-4-yl)piperazin-1-yl)methanone (Compound 111)

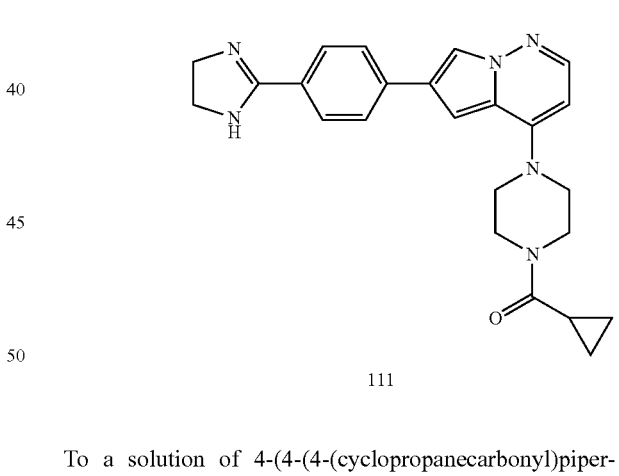

111

To a solution of 4-(4-(4-(cyclopropanecarbonyl)piperazin-1-yl)pyrrolo[1,2-b]pyridazin-6-yl)benzaldehyde (180 mg, 0.48 mmol) in t-BuOH (20 mL) was added potassium carbonate (200 mg, 1.44 mmol) and iodine (122 mg, 0.48 mmol). The reaction mixture was heated at 70 degrees for 2 h. Quenched by sat. aq. Na$_2$S$_2$O$_3$ (20 mL) and diluted with EtOAc. The organic layer was washed with water and brine, concentrated and purified by column (DCM/MeOH=20/1 to 5/1) to give the title product (98.99 mg, 49.7%). MS (ES+) $C_{24}H_{26}N_6O$ requires: 414, found 415[M+H]$^+$.

Example 19. Synthesis of cyclopropyl(4-(6-(4-(4,5-dihydro-1H-imidazol-2-ylamino) phenyl)pyrrolo[1,2-b]pyridazin-4-yl)piperazin-1-yl)methanone (Compound 121)

Step 1: Synthesis of (4-(6-(4-aminophenyl)pyrrolo[1,2-b]pyridazin-4-yl)piperazin-1-yl) (cyclopropyl)methanone

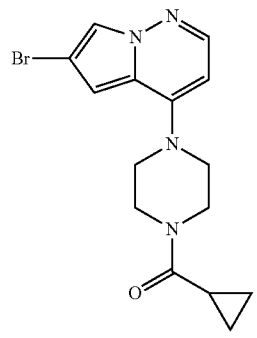

+

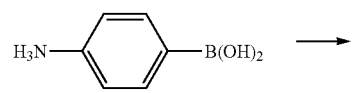

→

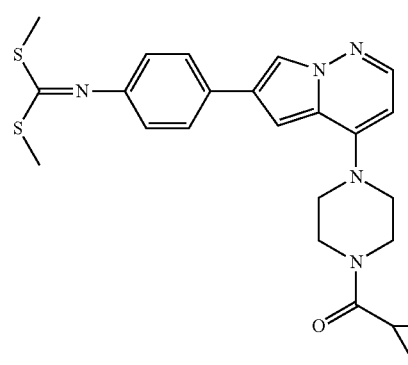

A mixture of (4-(6-bromopyrrolo[1,2-b]pyridazin-4-yl)piperazin-1-yl)(cyclopropyl)methanone (250 mg, 0.72 mmol), 4-aminophenylboronic acid (150 mg, 1.08 mmol), $K_2CO_3$ (300 mg, 2.16 mmol) and Pd(dppf)Cl$_2$ (100 mg) in 1,4-dioane (20 mL) and water (4 mL) was purged with $N_2$, and then stirred at 100° C. for 6 h. Cooled to RT and diluted with DCM. The organic layer was washed with water and brine, concentrated and purified by flash column (DCM/MeOH=100/1 to 20/1) to give the title product (130 mg, yield: 50%). MS (ES+) $C_{21}H_{23}N_5O$ requires: 361, found 362 [M+H]$^+$.

Step 2: Synthesis of dimethyl 4-(4-(4-(cyclopropanecarbonyl)piperazin-1-yl)pyrrolo[1,2-b]pyridazin-6-yl)phenylcarbonimidodithioate

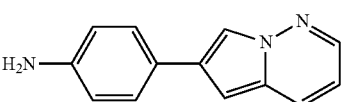

→

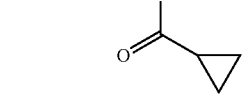
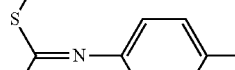

To a solution of (4-(6-(4-aminophenyl)pyrrolo[1,2-b]pyridazin-4-yl)piperazin-1-yl) (cyclopropyl)methanone (100 mg, 0.28 mmol) in DMF (6 mL) was added CS$_2$ (1 mL). The reaction mixture was added 6 ml of NaOH in water (1 N) and stirred at RT for 30 min. The reaction mixture was added methyl iodide (0.3 ml) and stirred overnight at RT. The mixture was extracted with DCM. The combined organic layer was washed with brine, dried over Na$_2$SO$_4$ and concentrated to give the title product (120 mg, crude). MS (ES+) $C_{24}H_{27}N_5OS_2$ requires: 465, found 466[M+H]$^+$.

Step 3: Synthesis of cyclopropyl(4-(6-(4-(4,5-dihydro-1H-imidazol-2-ylamino) phenyl)pyrrolo[1,2-b]pyridazin-4-yl)piperazin-1-yl)methanone (Compound 121)

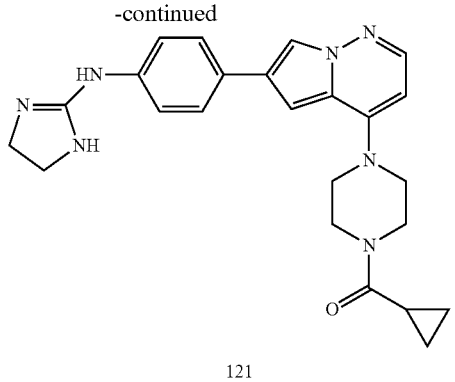

121

A mixture of dimethyl 4-(4-(4-(cyclopropanecarbonyl)piperazin-1-yl)pyrrolo[1,2-b]pyridazin-6-yl)phenylcarbonimidodithioate (120 mg, crude) and ethane-1,2-diamine (300 mg) in DMF (5 mL) was heated to 120° C. for 10 h. The reaction mixture was concentrated and purification by Pre-HPLC to give the title product as a white solid (48.2 mg, yield 40.2%). MS (ES+) $C_{24}H_{27}N_7O$ requires: 429, found 430[M+H]$^+$.

Example 20. Synthesis of ethyl 4-(6-(2-fluoro-4-(1-isopropyl-4-methoxypiperidin-4-yl) phenyl)pyrrolo[1,2-b]pyridazin-4-yl)piperazine-1-carboxylate (Compound 701)

Step 1: Synthesis of 4-(piperazin-1-yl)-6-(4-(4,4,5,5-tetramethyl-1,3,2-dioxaborolan-2-yl) phenyl)pyrrolo[1,2-b]pyridazine

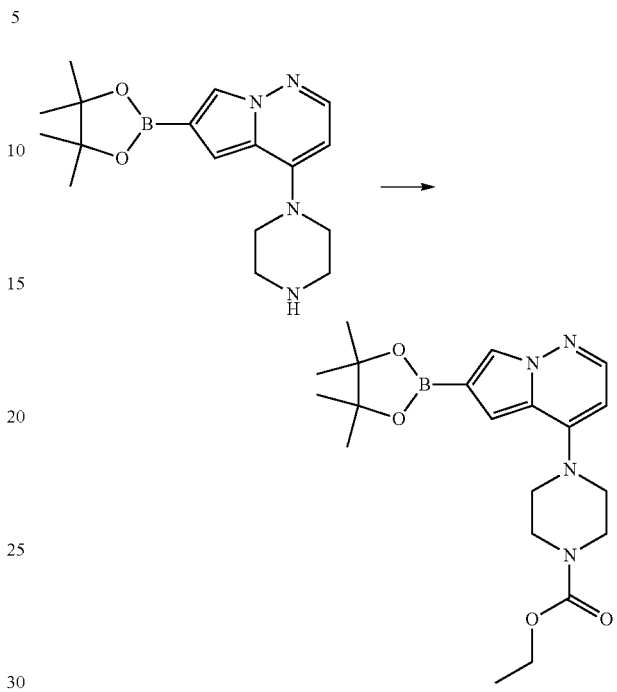

A mixture of tert-butyl 4-(6-(4,4,5,5-tetramethyl-1,3,2-dioxaborolan-2-yl)pyrrolo[1,2-b]pyridazin-4-yl)piperazine-1-carboxylate (100 g, 0.234 mol) in DCM (200 mL) was added HCl in dioxane (584 mL, 2.34 mol) at 15° C. for 16 hrs. The reaction mixture was cooled to RT and concentrated to afford the title product (100 g, crude) as a yellow solid. MS (ES+) $C_{17}H_{25}BN_4O_2$ requires: 328, found: 329[M+H]+.

Step 2: Synthesis of ethyl 4-(6-(4-(4,4,5,5-tetramethyl-1,3,2-dioxaborolan-2-yl) phenyl)pyrrolo[1,2-b]pyridazin-4-yl)piperazine-1-carboxylate

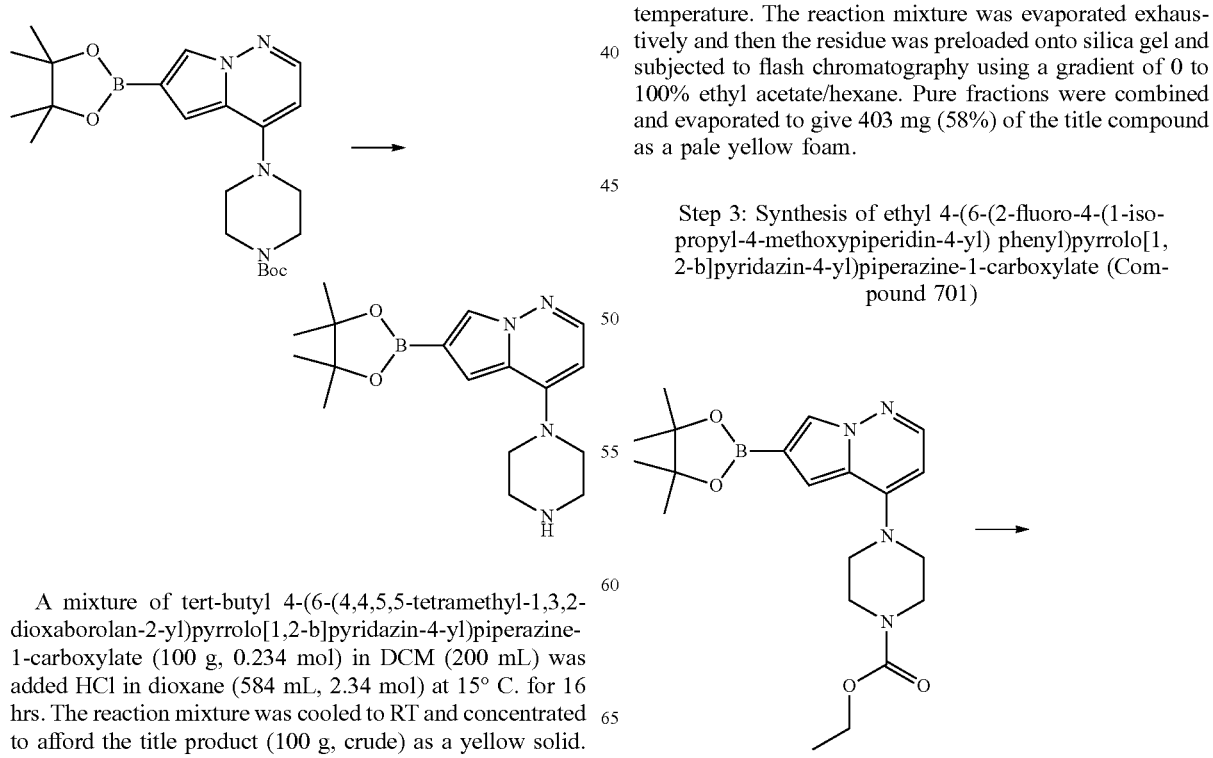

4-(piperazin-1-yl)-6-(4-(4,4,5,5-tetramethyl-1,3,2-dioxaborolan-2-yl)phenyl)pyrrolo[1,2-b]pyridazine, 2TFA (917 mg, 1.45 mmole) was dissolved in 7 mL dichloromethane and Hunig's base (1.0 mmole, 5.8 mmole) was added followed by ethyl chloroformate (167 uL, 1.7 mmole) and the reaction mixture allowed to stir overnight at room temperature. The reaction mixture was evaporated exhaustively and then the residue was preloaded onto silica gel and subjected to flash chromatography using a gradient of 0 to 100% ethyl acetate/hexane. Pure fractions were combined and evaporated to give 403 mg (58%) of the title compound as a pale yellow foam.

Step 3: Synthesis of ethyl 4-(6-(2-fluoro-4-(1-isopropyl-4-methoxypiperidin-4-yl) phenyl)pyrrolo[1,2-b]pyridazin-4-yl)piperazine-1-carboxylate (Compound 701)

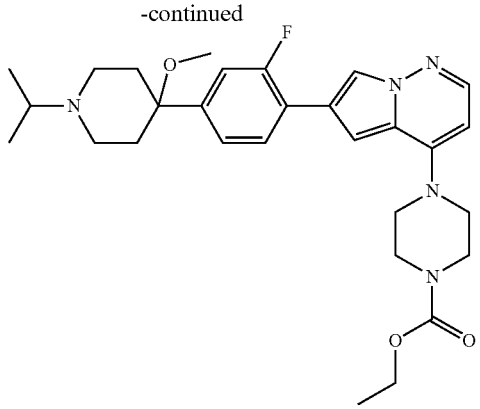

Ethyl 4-(6-(4-(4,4,5,5-tetramethyl-1,3,2-dioxaborolan-2-yl)phenyl)pyrrolo[1,2-b]pyridazin-4-yl)piperazine-1-carboxylate (106 mg, 0.22 mmole), 4-(4-bromo-3-fluorophenyl)-1-isopropyl-4-methoxypiperidine (70 mg, 0.21 mmole), palladium (II) acetate (1.0 mg, 2 mol %), SPhos (3.5 mg, 4 mol %), and potassium carbonate (88 mg, 0.64 mmole) were combined in a vial and purged with nitrogen. Acetonitrile (0.8 mL) and water (0.4 mL) were added and then the reaction was heated to 100 degrees in an oil bath for 3 hours. The reaction mixture was diluted with ethyl acetate and then filtered through celite and transferred to a separatory funnel. The organic layer was washed with brine and dried over sodium sulfate. Filtration and evaporation gave the crude product, which was subjected to flash chromatography using a gradient of 0 to 10% methanol/dichloromethane containing 1% ammonium hydroxide. Pure fractions were combined and evaporated to give 96 mg (87%) of the title compound as a tan-colored foam.

Example 21. Synthesis of 3-hydroxy-2-(4-(6-(4-(1-isopropylpiperidin-4-yl)phenyl) pyrrolo[1,2-b]pyridazin-4-yl)piperazine-1-carbonyloxy)propanoic Acid (Compound 847)

Step 1. Synthesis of benzyl 2,3-dihydroxypropanoate

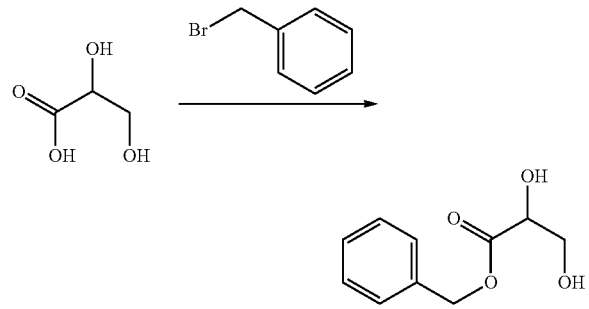

To a solution of 2,3-dihydroxypropanoic acid (10.0 g, 18.8 mmol, 20% aq) in DMF (20 mL) was added (bromomethyl)benzene (8.0 g, 47.1 mmol) and K$_2$CO$_3$ (6.5 g, 47.1 mmol). The resulting mixture was stirred at room temperature for 48 h. LC-MS showed that the reaction was completed. The solvent was evaporated. The residue was dissolved in EtOAc and washed with brine. The organic layer was dried over Na$_2$SO$_4$, filtered and evaporated. The crude product was purified by flash chromatography on silica gel eluting with EtOAc/petroleum ether (3:1) to give the title compound (1.7 g, 46% yield) as a colorless oil.

Step 2. Synthesis of benzyl 3-(tert-butyldiphenylsilyloxy)-2-hydroxypropanoate

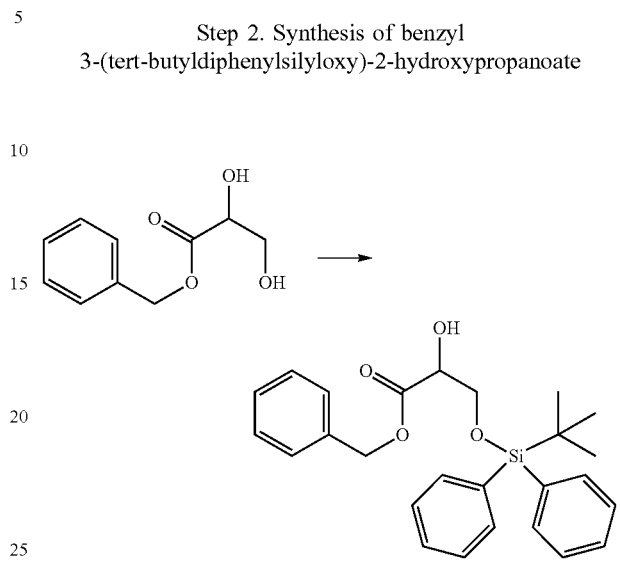

To a solution of benzyl 2,3-dihydroxypropanoate (1.7 g, 8.6 mmol) in DMF (10 mL) was added tert-butylchlorodiphenylsilane (2.6 g, 9.5 mmol) and imidazole (1.2 g, 17.2 mmol). The resulting mixture was stirred at room temperature for 16 hours; LC-MS showed that the reaction was completed. Water was added and extracted with DCM. The organic was washed with brine, dried over Na$_2$SO$_4$ and concentrated to afford crude product which was purified by flash chromatography on silica gel eluting with PE/EA (3:1) to give the title product (510 mg, 14% yield) as a colorless oil.

Step 3. Synthesis of 1-(benzyloxy)-3-(tert-butyldiphenylsilyloxy)-1-oxopropan-2-yl 4-(6-(4-(1-isopropylpiperidin-4-yl)phenyl)pyrrolo[1,2-b]pyridazin-4-yl)piperazine-1-carboxylate

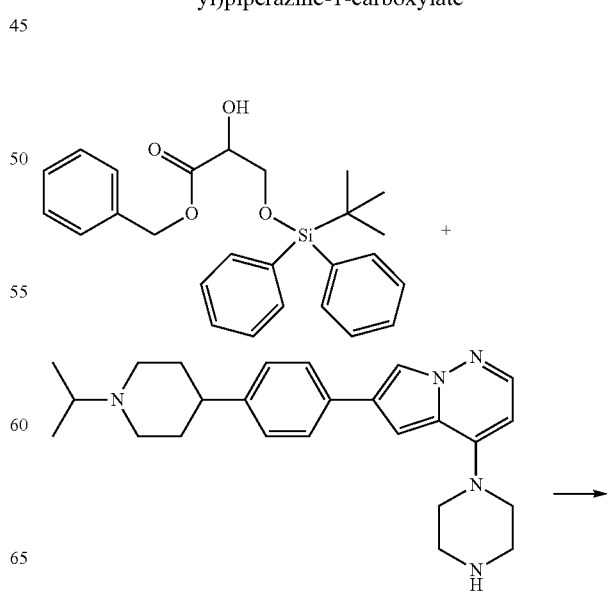

535

-continued

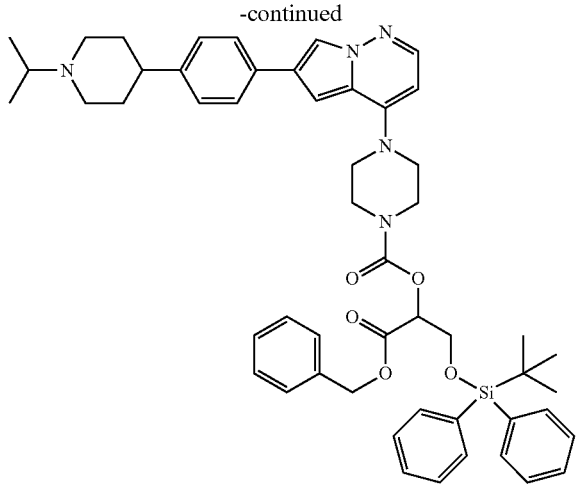

To a solution of benzyl 3-(tert-butyldiphenylsilyloxy)-2-hydroxypropanoate (510 mg, 1.2 mmol) in DCM (10 mL) was added CDI (194 mg, 1.2 mmol). The solution was stirred at room temperature for 6 h.

In another flask, 6-(4-(1-isopropylpiperidin-4-yl)phenyl)-4-(piperazin-1-yl)pyrrolo [1,2-b]pyridazine (322 mg, 0.8 mmol) was dissolved in DCM (5 mL) and TEA (244 mg, 2.4 mmol) was added thereto. The above solution of benzyl 3-(tert-butyldiphenylsilyloxy)-2-hydroxypropanoate and CDI was added the solution. The mixture was stirred at room temperature for 16 hours; LC-MS showed that the reaction was completed. Water was added and extracted with EtOAc. The organic was washed with brine, dried over Na$_2$SO$_4$ and concentrated to afford crude product, which was purified by silica gel chromatography eluting with PE/EA (1:1) to give the title compound (310 mg, 45% yield) as a light yellow solid.

Step 4. Synthesis of 1-(benzyloxy)-3-hydroxy-1-oxopropan-2-yl 4-(6-(4-(1-isopropylpiperidin-4-yl)phenyl)pyrrolo[1,2-b]pyridazin-4-yl)piperazine-1-carboxylate

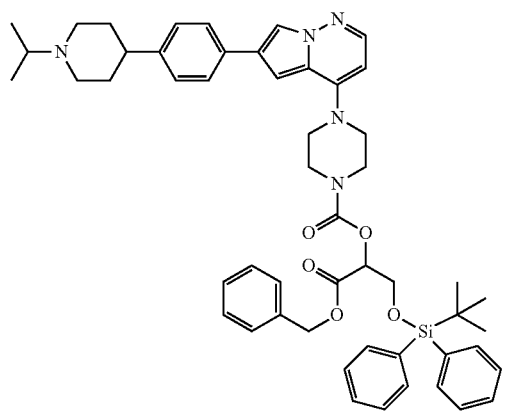

536

-continued

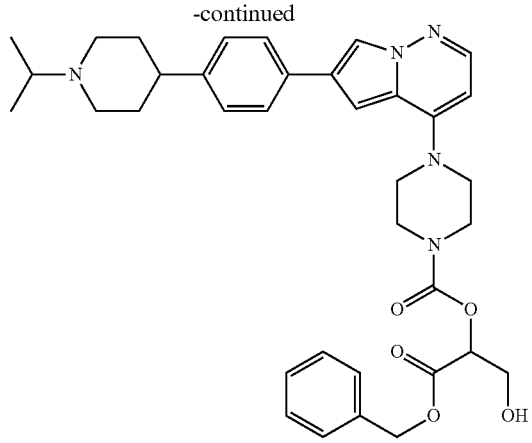

To a solution of 1-(benzyloxy)-3-(tert-butyldiphenylsilyloxy)-1-oxopropan-2-yl 4-(6-(4-(1-isopropylpiperidin-4-yl)phenyl)pyrrolo[1,2-b]pyridazin-4-yl)piperazine-1-carboxylate (250 mg, 0.29 mmol) in THF (5 mL) was added TBAF (2.0 mL, 1.0 M). The solution was heated at 70° C. for 6 hours. The reaction mixture was concentrated and subjected to silica gel eluting with DCM/MeOH (10:1) to give the title compound (80 mg, 44% yield) as a light yellow solid.

Step 5. Synthesis of 3-hydroxy-2-(4-(6-(4-(1-isopropylpiperidin-4-yl)phenyl) pyrrolo[1,2-b]pyridazin-4-yl)piperazine-1-carbonyloxy)propanoic Acid

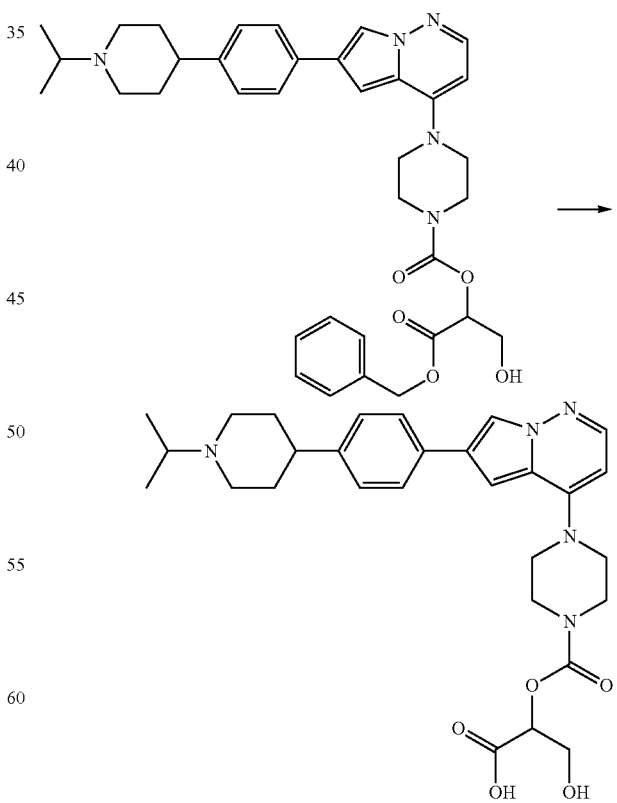

To a solution of 1-(benzyloxy)-3-hydroxy-1-oxopropan-2-yl 4-(6-(4-(1-isopropylpiperidin-4-yl)phenyl)pyrrolo[1,2- b]pyridazin-4-yl)piperazine-1-carboxylate (80 mg, 0.12 mmol) in MeOH (5 mL) was added Pd/C (50 mg, 10% wet). The suspension was hydrogenated with $H_2$ balloon at room temperature for 16 hours. Filtered off and the filtrate was evaporated to afford crude product which was purified by Prep-HPLC to give the title compound (5.3 mg, 8% yield) as a light white solid.

Example 22. Synthesis of 1,3-dihydroxypropan-2-yl 4-(6-(4-(piperidin-4-yl)phenyl) pyrrolo[1,2-b]pyridazin-4-yl)piperazine-1-carboxylate (Compound 789)

Step 1. Synthesis of 2-phenyl-1,3-dioxan-5-yl 4-(6-(4-(1-(tert-butoxycarbonyl)piperidin-4-yl) phenyl) pyrrolo[1,2-b]pyridazin-4-yl)piperazine-1-carboxylate

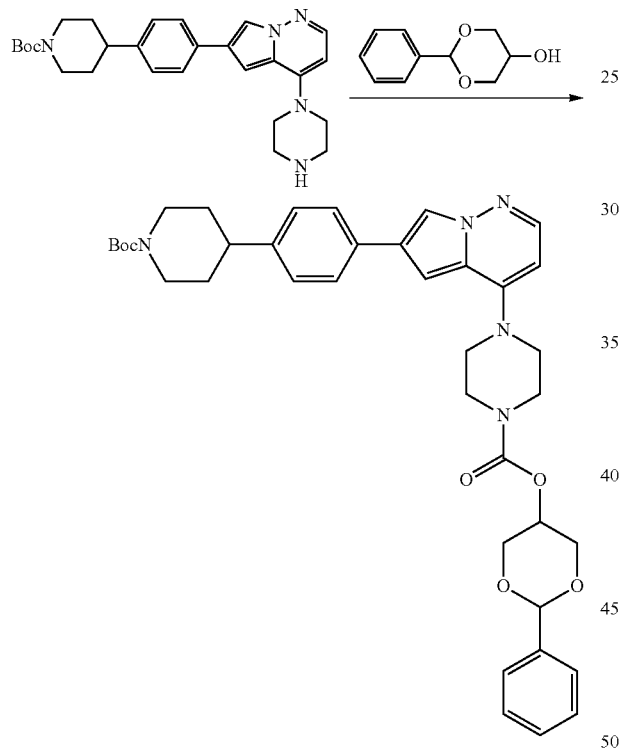

To a solution of 2-phenyl-1,3-dioxan-5-ol (327 mg, 1.82 mmol) in DCM (5 mL) was added CDI (295 mg, 1.82 mmol). The resulting mixture was stirred at room temperature for 6 h. In another flask, tert-butyl 4-(4-(4-(piperazin-1-yl)pyrrolo-[1,2-b]pyridazin-6-yl) phenyl)piperidine-1-carboxylate (420 mg, 0.91 mmol) was dissolved in DCM (5 mL) and TEA (278 mg, 2.73 mmol) was added thereto. The above solution of 2-phenyl-1,3-dioxan-5-ol and CDI was added into the solution. The reaction mixture was stirred at room temperature for 16 hours where LC-MS showed that the reaction was completed. Water was added and extracted with EtOAc. The organic layers were washed with brine, dried over $Na_2SO_4$ and concentrated. The residue was purified by PE/EA (2:1) to give the title compound (340 mg, 56%) as a yellow powder.

Step 2. Synthesis of 1,3-dihydroxypropan-2-yl 4-(6-(4-(1-(tert-butoxycarbonyl) piperidin-4-yl) phenyl) pyrrolo[1,2-b]pyridazin-4-yl)piperazine-1-carboxylate

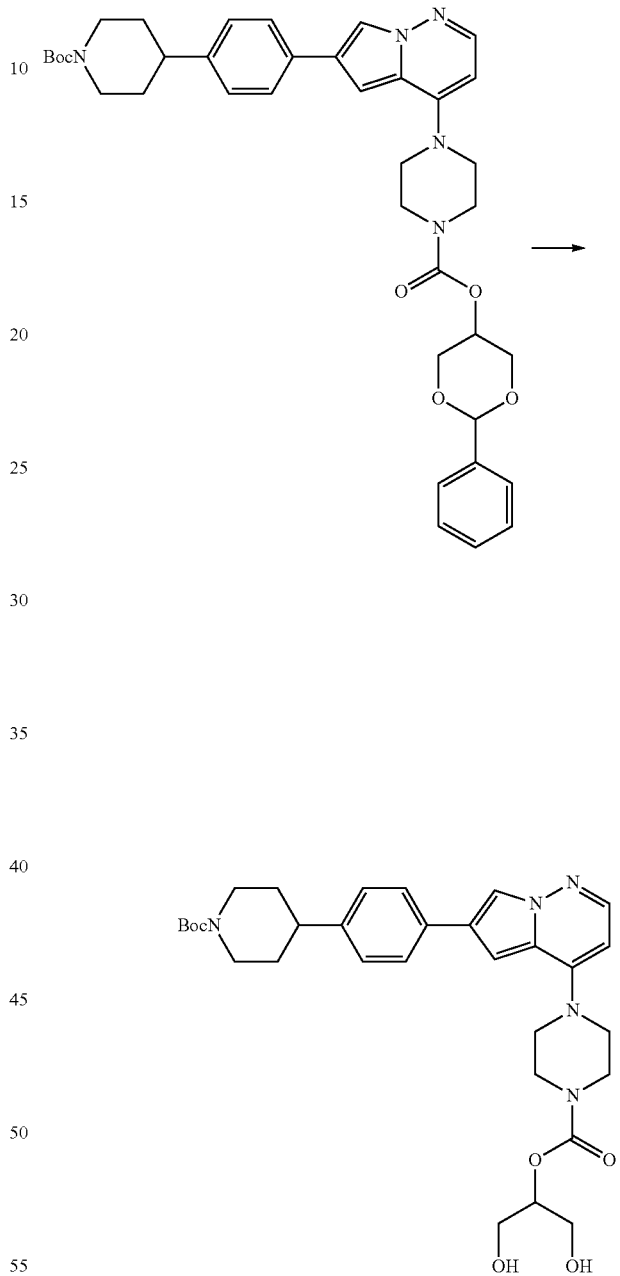

To a solution of 2-phenyl-1,3-dioxan-5-yl 4-(6-(4-(1-(tert-butoxycarbonyl)piperidin-4-yl) phenyl)pyrrolo[1,2-b] pyridazin-4-yl)piperazine-1-carboxylate (310 mg, 0.46 mmol) in MeOH (10 mL) was added $Pd(OH)_2/C$ (100 mg). The suspension was hydrogenated with hydrogen balloon at room temperature for 16 hours. LC-MS showed that the reaction was completed. The suspension was then filtered and the solvent was removed under reduced pressure to give the title product (210 mg, 78% yield) as a yellow solid.

539

Step 3. Synthesis of 1,3-dihydroxypropan-2-yl 4-(6-(4-(piperidin-4-yl)phenyl) pyrrolo[1,2-b]pyridazin-4-yl)piperazine-1-carboxylate

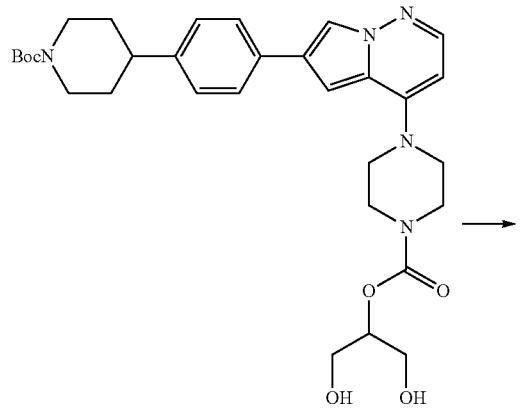

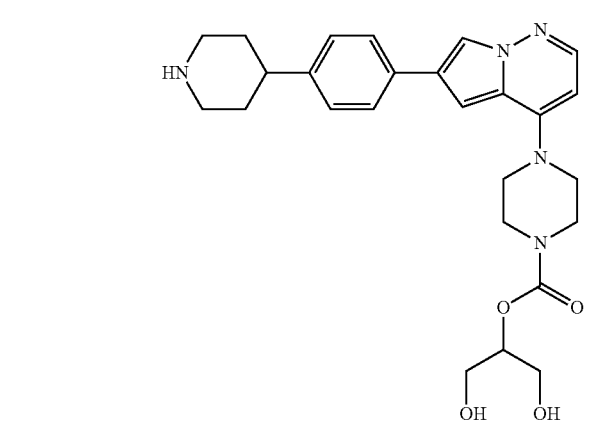

To a solution of 1,3-dihydroxypropan-2-yl 4-(6-(4-(1-(tert-butoxycarbonyl) piperidin-4-yl) phenyl)pyrrolo[1,2-b]pyridazin-4-yl)piperazine-1-carboxylate (210 mg, 0.36 mmol) in DCM (5 mL) was added TFA (2.5 mL) at 0° C. The resulting mixture was stirred at room temperature for 3 hours. LC-MS indicated that the reaction was completed. The resulting mixture was evaporated to dryness to afford crude product which was purified by Prep-HPLC to give the title compound as a white powder.

540

Example 23. Synthesis of (S)-oxetan-3-yl 4-(6-(4-(1-isopropylpiperidin-3-yl)phenyl)pyrrolo[1,2-b]pyridazin-4-yl)piperazine-1-carboxylate (Compound 631)

Step 1: Synthesis of 4-(piperazin-1-yl)-6-(4,4,5,5-tetramethyl-1,3,2-dioxaborolan-2-yl) pyrrolo[1,2-b]pyridazine Hydrochloride

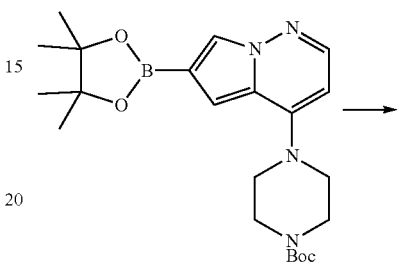

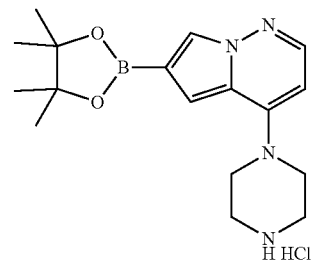

To a solution of tert-butyl 4-(6-(4,4,5,5-tetramethyl-1,3,2-dioxaborolan-2-yl)pyrrolo[1,2-b]pyridazin-4-yl)piperazine-1-carboxylate (7 g, 16.3 mmol) in dioxane (200 mL) was added HCl/dioxane (4 M, 16 mL). The reaction mixture was stirred at 20° C. overnight. The resulting mixture was concentrated to give the title compound as a yellow solid (9 g, crude). MS (ES+) $C_{17}H_{26}BClN4O_2$ requires: 328, found: 329[M+H]+.

Step 2: Synthesis of 4-nitrophenyl 4-(6-(4,4,5,5-tetramethyl-1,3,2-dioxaborolan-2-yl)pyrrolo[1,2-b]pyridazin-4-yl)piperazine-1-carboxylate

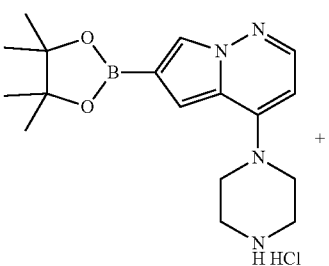

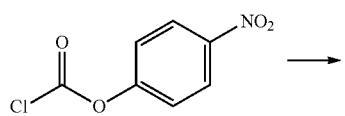

-continued

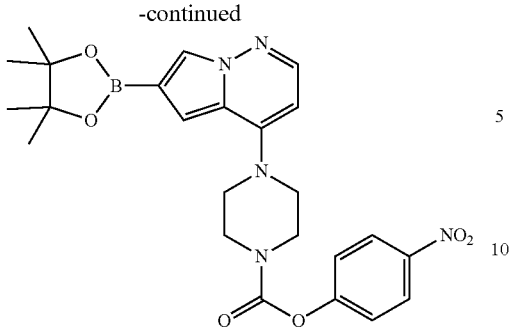

To a solution of 4-(piperazin-1-yl)-6-(4,4,5,5-tetramethyl-1,3,2-dioxaborolan-2-yl)pyrrolo[1,2-b]pyridazine hydrochloride (7 g, 19.1 mmol) in dichloromethane (DCM) (100 mL) was added triethylamine (TEA) (11.6 g, 115 mmol) and 4-nitrophenyl carbonochloridate (4.62 g, 23 mmol). The mixture was stirred at room temperature (RT) for 4 h. The solution was concentrated to give a residue, which was purified by flash chromatography to afford the title compound (7 g, 85%). MS (ES+) $C_{24}H_{28}BN_5O_6$ requires: 493, found: 494[M+H]+.

Step 3: Synthesis of oxetan-3-yl 4-(6-(4,4,5,5-tetramethyl-1,3,2-dioxaborolan-2-yl)pyrrolo[1,2-b]pyridazin-4-yl)piperazine-1-carboxylate

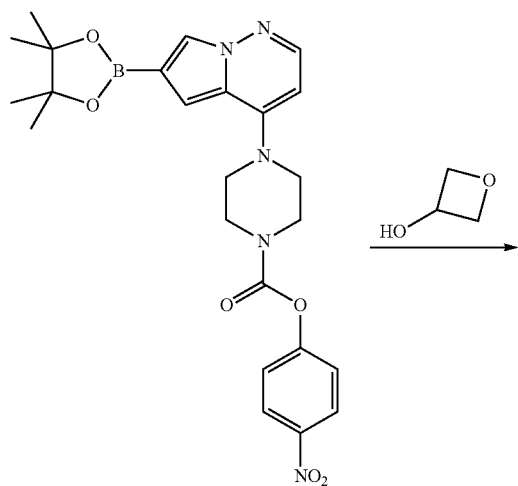

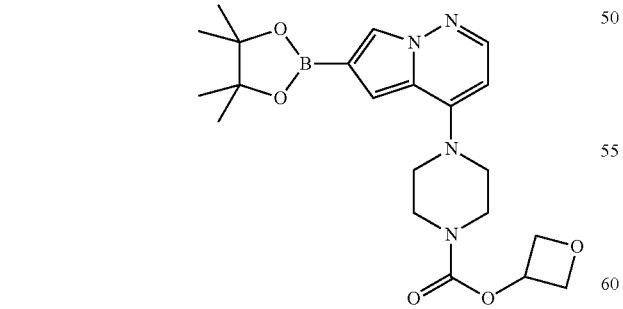

To a solution of oxetan-3-ol (1.56 g, 21.1 mmol) in tetrahydrofuran (THF) (200 mL) at 0° C. was added 60% NaH (2.26 g, 56.4 mmol). The mixture was stirred at 25° C. for 1 h, followed by 4-nitrophenyl 4-(6-(4,4,5,5-tetramethyl-1,3,2-dioxaborolan-2-yl)pyrrolo[1,2-b]pyridazin-4-yl) piperazine-1-carboxylate (7 g, 14.1 mmol). The reaction mixture was stirred at 25° C. for another 5 h. The reaction was quenched with $NH_4Cl$ solution and extracted with ethyl acetate. Combined, dried and concentrated to give the title compound (3.5 g, 71%). MS (ES+) $C_{21}H_{29}BN_4O_5$ requires: 428, found: 429[M+H]+.

Step 4: Synthesis of (S)-oxetan-3-yl 4-(6-(4-(1-isopropylpiperidin-3-yl)phenyl)pyrrolo[1,2-b]pyridazin-4-yl)piperazine-1-carboxylate

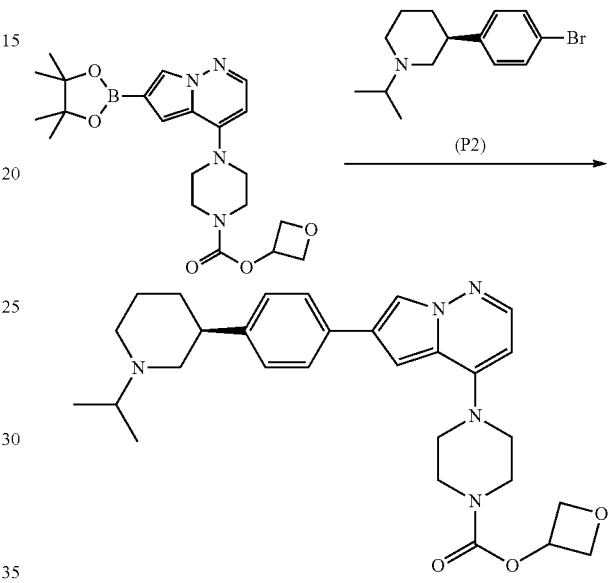

A solution of oxetan-3-yl 4-(6-(4,4,5,5-tetramethyl-1,3,2-dioxaborolan-2-yl)pyrrolo[1,2-b]pyridazin-4-yl)piperazine-1-carboxylate (3 g, 7.00 mmol) in dioxane/water (20 mL, 10/1) was added (S)-3-(4-bromophenyl)-1-isopropylpiperidine (1.77 g, 6.30 mmol), Pd(dppf)Cl₂ (511 mg, 700 μmol) and $K_2CO_3$ (2.89 g, 21.0 mmol) was degassed with nitrogen and heated at 90° C. for 5 h. The reaction mixture was cooled to RT and concentrated to give a residue, which was purified by flash chromatography to afford the title compound (1.5 g, 43%)

Example 24. Building Block Synthesis

A. Synthesis of 1-cyclopentyl-4-(4,4,5,5-tetramethyl-1,3,2-dioxaborolan-2-yl)-1H-pyrazole

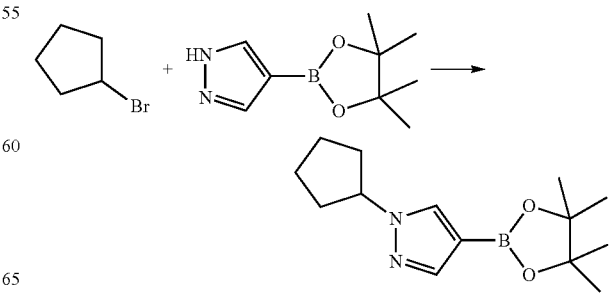

A mixture of bromocyclopentane (1.0 g, 6.71 mmol), 4-(4,4,5,5-tetramethyl-1,3,2-dioxaborolan-2-yl)-1H-pyrazole (1.32 g, 6.84 mmol) and $Cs_2CO_3$ (6.54 g, 20.1 mmol) in $CH_3CN$ (50 mL) was refluxed overnight. The mixture was cooled, concentrated and purified by flash column chromatography (PE:EA=5:1) to give the title compound as a white solid (1.5 g, yield 85.7%). MS (ES+) $C_{14}H_{23}BN_2O_2$ requires: 262, found 263[M+H]+.

B. Synthesis of 1-(2,2-difluoroethyl)-4-(4-(4,4,5,5-tetramethyl-1,3,2-dioxaborolan-2-yl) phenyl)piperazine Step 1: Synthesis of 2,2-difluoroacetaldehyde

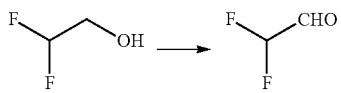

To a solution of 2,2-difluoroethanol (2.0 g, 24.3 mmol) in DMF (20 mL) was added Dess-Martin periodinane (25.7 g, 60.7 mmol) in portions at 0° C. The solution was stirred at RT for 6 h. After that, the solution was used directly for the next reaction.

Step 2: Synthesis of 1-(4-bromophenyl)-4-(2,2-difluoroethyl)piperazine

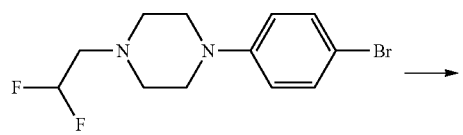

Above solution (24.3 mmol, assumed) in DMF was diluted with DCM (30 mL) and $CH_3OH$ (30 mL). 1-(4-Bromophenyl)piperazine (6.0 g, 24.9 mmol) and acetic acid (1.49 g, 24.9 mmol) was added, followed by addition of sodium cyanoborohydride (2.34 g, 37.3 mmol) at 0° C. The solution was stirred at RT for 12 h. After that, the solution was cooled to 0° C., quenched with $NaHCO_3$ (aq) and brine, and diluted with EtOAc. The organic layer was washed with brine, dried over $Na_2SO_4$, concentrated and purified by flash column (PE/EtOAc=6/1) to get the title compound as a yellow solid (400 mg, 5%). MS (ES+) $C_{12}H_{15}BrF_2N_2$ requires: 304, found 305[M+H]+.

Step 3: Synthesis of 1-(2,2-difluoroethyl)-4-(4-(4,4,5,5-tetramethyl-1,3,2-dioxaborolan-2-yl) phenyl) piperazine

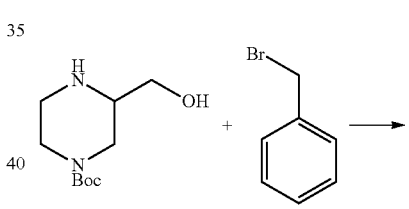

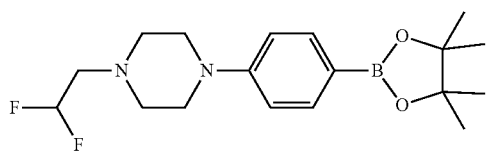

A mixture of 1-(4-bromophenyl)-4-(2,2-difluoroethyl)piperazine (400 mg, 1.31 mmol), 4,4,4',4',5,5,5',5'-octamethyl-2,2'-bi(1,3,2-dioxaborolane) (497 mg, 1.96 mmol), potassium acetate (385 mg, 3.93 mmol) and [1,1'-bis(diphenylphosphino)ferrocene]dichloropalladium(II) (191 mg, 262 mmol) in dioxane (20 mL) was purged with $N_2$, and then stirred at 80° C. for 16 h. After that, the mixture was cooled, concentrated and purified by flash column (PE/EtOAc=5/1) to get the title compound as a white solid (350 mg, 76%). MS (ES+) $C_{18}H_{27}BF_2N_2O_2$ requires: 352, found 353[M+H]+.

C. Synthesis of 1-(4-bromophenyl)-2-(difluoromethyl)piperazine

Step 1: Synthesis of tert-butyl 4-benzyl-3-(hydroxymethyl)piperazine-1-carboxylate

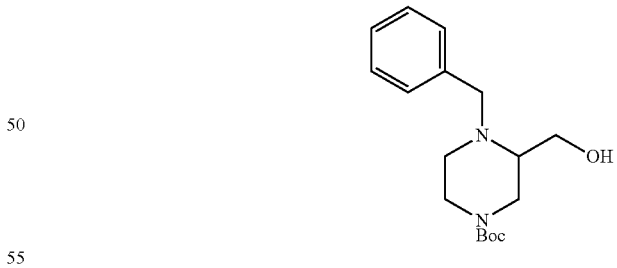

A mixture of tert-butyl 3-(hydroxymethyl)piperazine-1-carboxylate (5 g, 23.1 mmol), (bromomethyl)benzene (4.73 g, 27.7 mmol) and triethylamine (4.67 g, 46.2 mmol) in acetonitrile (40 mL) was stirred at 80° C. overnight. The reaction solution was cooled, concentrated and purified by silica gel chromatograph (EA:PE=1:5) to give the title product (6.0 g, yield: 85%) as colorless oil. MS (ES+) $C_{17}H_{26}N_2O_3$ requires: 306, found: 307[M+H]+.

Step 2: Synthesis of tert-butyl 4-benzyl-3-(hydroxymethyl)piperazine-1-carboxylate

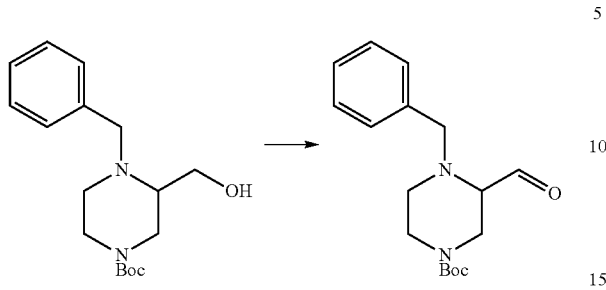

A solution of oxalyl chloride (1.98 g, 15.6 mmol) in DCM (10 mL) was added DMSO (1.52 g, 19.5 mmol) in DCM (10 mL) at −78° C. The mixture was stirred for 15 min, followed by addition of tert-butyl 4-benzyl-3-(hydroxymethyl)piperazine-1-carboxylate (4.00 g, 13.0 mmol). The resulting mixture was stirred at RT for 2 h, followed by addition of Et$_3$N. LC-MS showed full conversion. The reaction mixture was diluted with DCM, washed with water and brine, and dried over sodium sulfate. The organic layer was concentrated to afford the title compound (4.00 g, crude) as a yellow oil, which was used in the next step without further purification. MS (ES+) C$_{17}$H$_{24}$N$_2$O$_3$ requires: 304, found: 305[M+H]$^+$.

Step 3: Synthesis of tert-butyl 4-benzyl-3-(difluoromethyl)piperazine-1-carboxylate

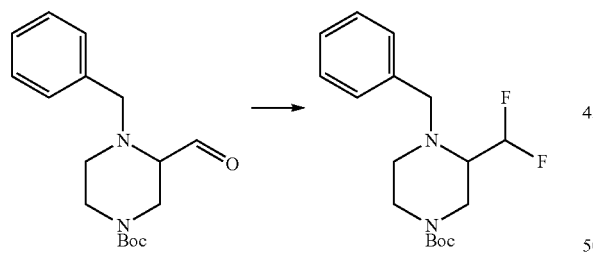

A mixture of tert-butyl 4-benzyl-3-formylpiperazine-1-carboxylate (4.00 g, 13.1 mmol) in DCM (10 mL) was added diethylaminosulfurtrifluoride (3.45 mL, 26.2 mmol) at 0° C. The reaction mixture was stirred at 0° C. for 2 h. LC-MS showed full conversion. The reaction solution was poured into ice water and extracted with DCM. The organic layer was washed with water and brine, dried over sodium sulfate, concentrated and purified by silica gel chromatograph (EA:PE=1:5) to give the title product (1.40 g, yield 33%) as a light yellow oil. MS (ES+) C$_{17}$H$_{24}$F$_2$N$_2$O$_2$ requires: 326, found: 327[M+H]$^+$.

Step 4: Synthesis of tert-butyl 3-(difluoromethyl)piperazine-1-carboxylate

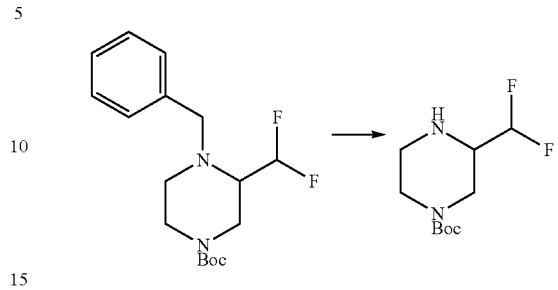

A mixture of tert-butyl 4-benzyl-3-(difluoromethyl)piperazine-1-carboxylate (1.20 g, 3.67 mmol) in methanol (10 mL) was added Pd/C (388 mg). The suspension was stirred at RT overnight under H$_2$ (balloon). LC-MS showed full conversion. The reaction mixture was filtered through a pad of Celite. The filtrate was concentrated to give the title product (800 mg, crude) as a light yellow oil, which was used in the next step without further purification.

Step 5: Synthesis of tert-butyl 4-(4-bromophenyl)-3-(difluoromethyl)piperazine-1-carboxylase

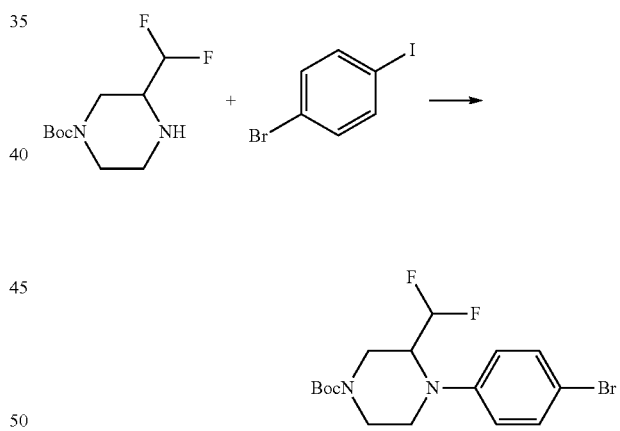

A mixture of tert-butyl 3-(difluoromethyl)piperazine-1-carboxylate (250 mg, 1.05 mmol), 1-bromo-4-iodobenzene (1.48 g, 5.25 mmol), bis(tri-t-butylphosphine)palladium (268 mg, 525 umol) and sodium tert-butoxide (201 mg, 2.10 mmol) in toluene (20 mL) was purged with N$_2$, and then stirred at 60° C. for 15 h. LCMS showed full conversion. The reaction mixture was concentrated. The residue was purified by silica gel chromatograph (EA:PE=1:10 to EA:PE=1:1) to give the title product (310 mg, yield 75%) as a colorless oil. MS (ES+) C$_{16}$H$_{21}$BrF$_2$N$_2$O$_2$ requires: 390, found: 391, [M+H]$^+$.

Step 6: Synthesis of 1-(4-bromophenyl)-2-(difluoromethyl)piperazine

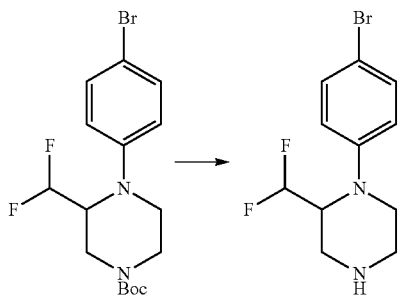 [SMILES: CC(C)(C)OC(=O)N1CCN(c2ccc(Br)cc2)C(C(F)F)C1 ; FC(F)C1CNCCN1c1ccc(Br)cc1]

A mixture of tert-butyl 4-(4-bromophenyl)-3-(difluoromethyl)piperazine-1-carboxylate (150 mg, 383 μmol) in HCl/dioxane (4 M, 2 mL) was stirred at RT for 1.5 h. LCMS showed full conversion. The reaction mixture was concentrated and purified by Prep-HPLC to give the title product (80 mg, yield 72%) as colorless oil. MS (ES+) $C_{11}H_{13}BrF_2N_2$ requires: 290, found: 291[M+H]$^+$.

D. Synthesis of tert-butyl 3-(4-bromophenyl)-3-fluoropiperidine-1-carboxylate

Step 1: Synthesis of tert-butyl 3-(4-bromophenyl)-3-hydroxypiperidine-1-carboxylate

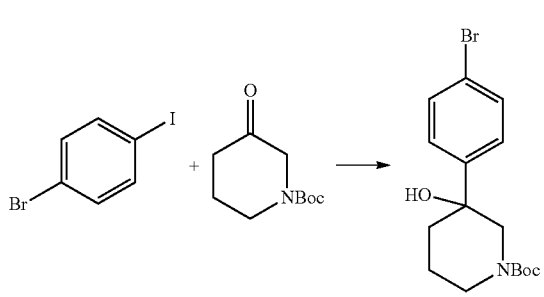

A solution of 1-bromo-4-iodobenzene (1.0 g, 3.53 mmol) in THF (20 mL) was cooled to 78° C., followed by addition of n-BuLi (2.5 N in hexane, 1.4 mL, 3.53 mmol). After 15 minutes, tert-butyl 3-oxopiperidine-1-carboxylate (703 mg, 3.53 mmol) in THF (5 mL) was added slowly. The reaction solution was stirred for 2 h at −78° C., allowed to warm up to 0° C., and quenched using saturated aqueous $NH_4Cl$ and extracted with EA. The organic layer was concentrated and purified by flash column (silica gel, PE:EA=3:1) to give the title product (0.8 g, yield 64%) as a colorless oil. MS (ES+) $C_{16}H_{22}BrNO_3$ requires: 355, found 356 [M+H]$^+$.

Step 2: Synthesis of tert-butyl 3-(4-bromophenyl)-3-fluoropiperidine-1-carboxylate

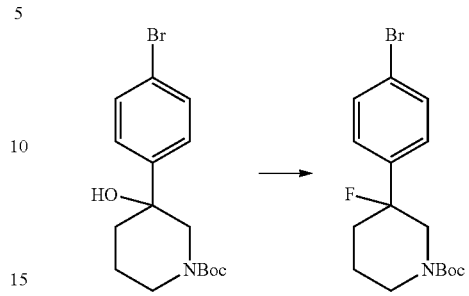

To a solution of tert-butyl 3-(4-bromophenyl)-3-hydroxypiperidine-1-carboxylate (3.0 g, 8.42 mmol) in DCM (30 mL) was added Dast (2.0 g, 12.6 mmol) at 0° C. The reaction mixture was stirred at RT for 5 h. The mixture was diluted with DCM, washed with aq. $NaHCO_3$ and brine, evaporated and purified by flash column (silica gel, PE:EA=5:1) to give the title product (1.5 g, yield 50%) as a colorless oil. MS (ES+) $C_{16}H_{21}BrFNO_2$ requires: 357, found 358[M+H]$^+$.

E. Synthesis of tert-butyl 3-(4-bromophenyl)-4-fluoropyrrolidine-1-carboxylate

Step 1: Synthesis of tert-butyl 3-(4-bromophenyl)-2,5-dihydro-1H-pyrrole-1-carboxylate

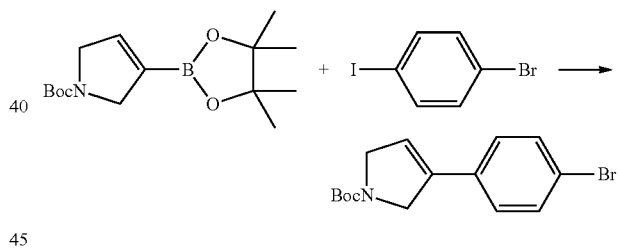

A mixture of tert-butyl 3-(4,4,5,5-tetramethyl-1,3,2-dioxaborolan-2-yl)-2,5-dihydro-1H-pyrrole-1-carboxylate (1.0 g, 3.38 mmol), 1-bromo-4-iodobenzene (1.91 g, 6.76 mmol), Pd(dppf)Cl$_2$ (247 mg, 338 μmol) and $K_2CO_3$ (932 mg, 6.76 mmol) in dioxane/water (5 mL, 4/1) was purged with $N_2$ and stirred at 80° C. for 16 h under $N_2$. The mixture was cooled and concentrated in vacuo. The residue was purified by flash column chromatography (PE/EA=10:1) to afford the title compound (800 mg, yield 73%) as a white solid MS (ES+) $C_{15}H_{18}BrNO_2$ requires: 323, found 324[M+H]$^+$.

Step 2: Synthesis of tert-butyl 3-(4-bromophenyl)-4-hydroxypyrrolidine-1-carboxylate

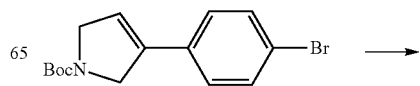

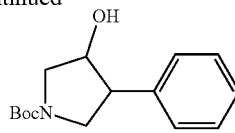

A solution of BH₃ (1 N in THF, 21.5 mL, 21.5 mmol) was added to a stirring solution of tert-butyl 3-(4-bromophenyl)-2,5-dihydro-1H-pyrrole-1-carboxylate (1.4 g, 4.31 mmol) in THF (20 mL) at 0° C. After stirred at RT for 4 h, the mixture was cooled to 0° C., followed by addition of NaOH aqueous (4 N, 6.45 mL, 25.8 mmol). After 10 min, H₂O₂ (2.92 g, 25.8 mmol) was added. The resulting mixture was allowed to warm up to RT and stirred for 90 min. Monitored by LC-MS. Quenched by water and extracted with ethyl acetate. The organic layer was concentrated and purified by flash column chromatography (PE/EA=10:1 to 1:1) to afford the title compound (1.3 g, yield 88%) as a light oil MS (ES+) $C_{15}H_{20}BrNO_3$ requires: 341, found 342[M+H]⁺.

Step 3: Synthesis of tert-butyl 3-(4-bromophenyl)-4-fluoropyrrolidine-1-carboxylate

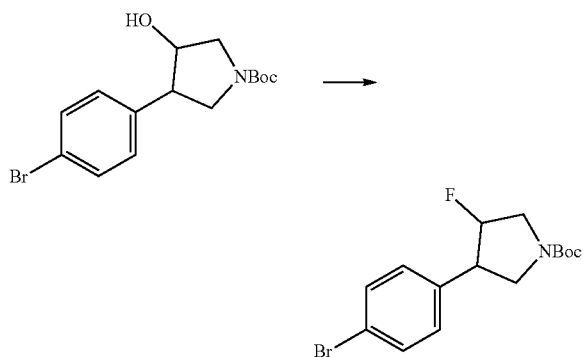

To a mixture of tert-butyl 3-(4-bromophenyl)-4-hydroxypyrrolidine-1-carboxylate (500 mg, 1.46 mmol) in DCM (10 mL) was added dropwise DAST (1.17 g, 7.29 mmol) at −78° C. The mixture was stirred at 25° C. for 2 h. Monitored by LC-MS. Diluted with DCM and quenched with saturated NaHCO₃ solution. The organic layer was separated and concentrated in vacuo to afford the title compound (400 mg, crude) as a yellow oil. MS (ES+) $C_{15}H_{19}BrFNO_2$ requires: 343, found: 344[M+H]⁺.

F. Synthesis of 4-(4-bromophenyl)-4-methoxypiperidine

Step 1: Synthesis of tert-butyl 4-(4-bromophenyl)-4-hydroxypiperidine-1-carboxylate

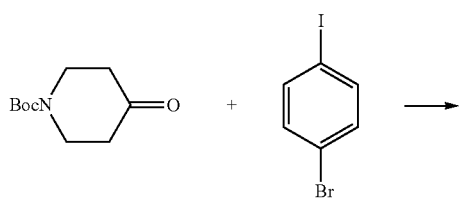

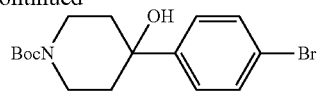

To a solution of 1-bromo-4-iodobenzene (12 g, 42.6 mmol) in THF (60 mL) at −78° C. was added BuLi (20 mL, 2.4 M in hexane) dropwise. The solution was stirred at −78° C. for 2 h. A solution of tert-butyl 4-oxopiperidine-1-carboxylate (8.5 g, 42.4 mmol) in THF (20 mL) was added dropwise. The resulting solution was stirred at −78° C. for 1 h. The reaction was quenched carefully by addition of water and extracted with EtOAc. The organic layer was washed with water and brine, concentrated and purified by flash column (PE/EtOAc=10/1 to 3/1) to give the title product (12.6 g, yield 83.4%). MS (ES+) $C_{16}H_{22}BrNO_3$ requires: 355, found 282 [M−73]⁺.

Step 2: Synthesis of tert-butyl 4-(4-bromophenyl)-4-methoxypiperidine-1-carboxylate

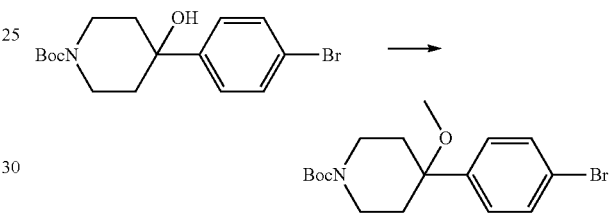

To a solution of tert-butyl 4-(4-bromophenyl)-4-hydroxypiperidine-1-carboxylate (178 mg, 499 μmol) in dry DMF (2 mL) was added NaH (26 mg, 0.646 mmol) at 0° C. The mixture was stirred at 0° C. for 1 h. Iodomethane (106 mg, 0.746 mmol) was added. The mixture was stirred at RT overnight. The reaction was quenched carefully by addition of water, extracted with EtOAc, washed with water and brine, concentrated and purified by flash column (PE/EtOAc=10/1 to 5/1) to give the title product (160 mg, yield 86.5%). MS (ES+) $C_{17}H_{24}BrNO_3$ requires: 369, found 282 [M+H−88]⁺.

Step 3: Synthesis of 4-(4-bromophenyl)-4-methoxypiperidine

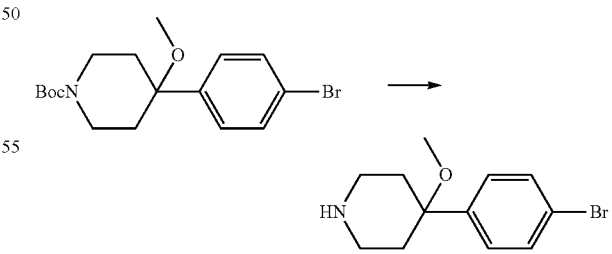

To a solution of tert-butyl 4-(4-bromophenyl)-4-methoxypiperidine-1-carboxylate (740 mg, 1.99 mmol) in dioxane (4 mL) was added HCl (4 M in dioxane, 3 mL). The resulting solution was stirred at RT overnight. The solvent was removed in vacuo to afford the title product (690 mg, crude). MS (ES+) $C_{12}H_{16}BrNO$ requires: 269, found 270 [M+H]⁺.

Step 4: Synthesis of 4-(4-bromophenyl)-4-methoxypiperidine

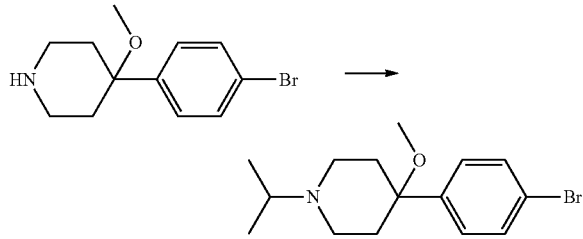

To a solution of 4-(4-bromophenyl)-4-methoxypiperidine (1 g, 3.70 mmol) in CH$_3$CN (50 mL) was added K$_2$CO$_3$ (1.53 g, 11.1 mmol) and 2-bromopropane (2.27 g, 18.5 mmol). The resulting mixture was stirred at 80° C. for 5 h. The solvent was removed in vacuo. The residue was purified by flash column (PE/EtOAc=10/1 to 5/1) to afford the title product (1.06 g, yield 91.8%). MS (ES+) C$_{15}$H$_{22}$BrNO requires: 311, found 312 [M+H]$^+$.

G. Synthesis of 1-isopropyl-4-methoxy-4-(4-(4,4,5,5-tetramethyl-1,3,2-dioxaborolan-2-yl) phenyl)piperidine

Step 1: Synthesis of tert-butyl 4-methoxy-4-(4-(4,4,5,5-tetramethyl-1,3,2-dioxaborolan-2-yl) phenyl) piperidine-1-carboxylate

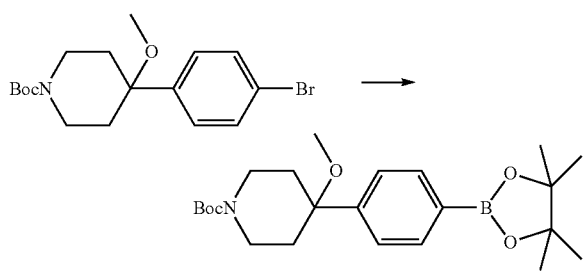

A mixture of tert-butyl 4-(4-bromophenyl)-4-methoxypiperidine-1-carboxylate (200 mg, 540 μmol), 4,4,4',4',5,5,5',5'-octamethyl-2,2'-bi(1,3,2-dioxaborolane) (178 mg, 702 μmol), Pd(dppf)Cl$_2$ (39.5 mg, 54.0 μmol) and K$_2$CO$_3$ (105 mg, 1.08 mmol) in dioxane (10 mL) was stirred at 65° C. for 4 h. The reaction mixture was concentrated and purified by silica gel chromatography (PE:EA=10:1 to 5:1) to give the title product (158 mg, yield: 70%) as a yellow solid. MS (ES+) C$_{23}$H$_{36}$BNO$_5$ requires: 417, found 418[M+H]$^+$.

Step 2: Synthesis of 4-methoxy-4-(4-(4,4,5,5-tetramethyl-1,3,2-dioxaborolan-2-yl) phenyl)piperidine

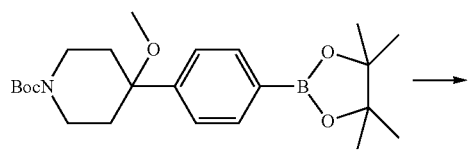

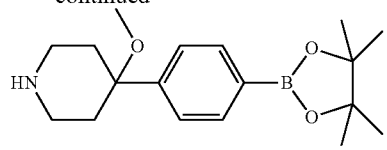

A mixture of tert-butyl 4-methoxy-4-(4-(4,4,5,5-tetramethyl-1,3,2-dioxaborolan-2-yl) phenyl)piperidine-1-carboxylate (6 g, 14.3 mmol) and HCl/dioxane (30 mL) in DCM (30 mL) was stirred at RT for 1 h. The reaction mixture was concentrated to give the title product (4.6 g, crude) as a light yellow solid, which was used for the next step without purification. MS (ES+) C$_{18}$H$_{28}$BNO$_3$ requires: 317, found 318[M+H]$^+$.

Step 3: Synthesis of 1-isopropyl-4-methoxy-4-(4-(4,4,5,5-tetramethyl-1,3,2-dioxaborolan-2-yl) phenyl) piperidine

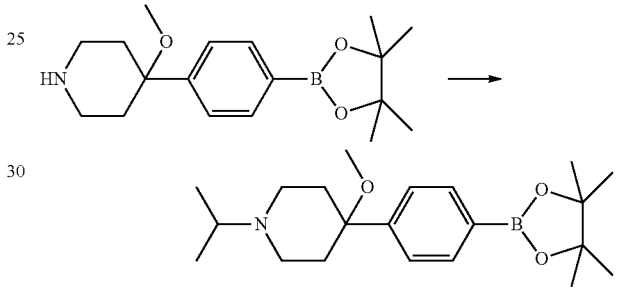

A mixture of 4-methoxy-4-(4-(4,4,5,5-tetramethyl-1,3,2-dioxaborolan-2-yl) phenyl)piperidine (4.5 g, 14.1 mmol), 2-iodopropane (3.58 g, 21.1 mmol) and K$_2$CO$_3$ (5.84 g, 42.3 mmol) in acetonitrile (50 mL) was stirred at 85° C. for 2 h. The reaction mixture was concentrated and purified by silica gel chromatography (DCM:MeOH=15:1) to give the title product (4.8 g, yield: 95%) as a light yellow solid. MS (ES+) C$_{21}$H$_{34}$BNO$_3$ requires: 359, found 360[M+H]$^+$.

H. Synthesis of tert-butyl 4-(3-(difluoromethoxy)-4-(4,4,5,5-tetramethyl-1,3,2-dioxaborolan-2-yl)phenyl) piperazine-1-carboxylate

Step 1: Synthesis of 1,4-dibromo-2-(difluoromethoxy)benzene

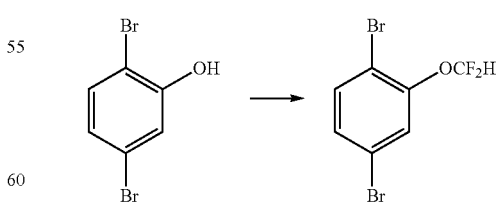

To a solution of 2,5-dibromophenol (1.5 g, 6.0 mmol) in DMF/water (30 mL/10 mL) was added sodium 2-chloro-2,2-difluoroacetate (2.3 g, 15.0 mmol) and Cs$_2$CO$_3$ (3.9 g, 12.0 mmol) at RT. The resulting mixture was stirred at 100° C. for 3 h. Quenched with water and extracted with EtOAc.

The combined organic layer was washed with brine, dried over Na$_2$SO$_4$, and concentrated to dryness. The residue was purified by flash chromatography on silica gel eluting with PE/EtOAc (5:1) to give the title compound (1.2 g, yield 67%) as a light yellow powder. MS (ES+) C$_7$H$_4$Br$_2$F$_2$O requires: 300, found 301[M+H]$^+$ (weak ion mass).

Step 2: Synthesis of tert-butyl 4-(4-bromo-3-(difluoromethoxy)phenyl)piperazine-1-carboxylate

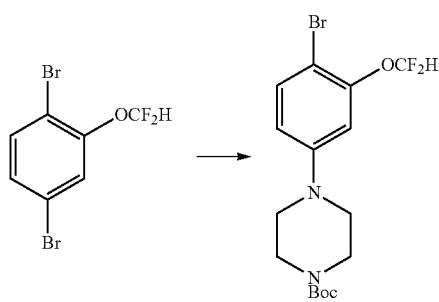

To a solution of 1,4-dibromo-2-(difluoromethoxy)benzene (500 mg, 1.66 mmol) and tert-butyl piperazine-1-carboxylate (309 mg, 1.66 mmol) in DMF (20 mL) was added Pd$_2$(dba)$_3$ (155 mg, 0.17 mmol), XantPhos (98 mg, 0.17 mmol) and Cs$_2$CO$_3$ (1.6 g, 5.0 mmol) at RT under nitrogen. The resulting mixture was stirred at 90° C. for 1 h under Microwave. LC-MS showed that the reaction was completed. Quenched with water and extracted with EtOAc. The combined organic layers were washed with brine, dried over Na$_2$SO$_4$ and concentrated to dryness. The residue was purified by flash chromatography on silica gel eluting with PE/EtOAc (3:1 to 1:1) to give the title compound (370 mg, yield 55%) as while solid. MS (ES+) C$_{16}$H$_{21}$BrF$_2$N$_2$O$_3$ requires: 406, found 351[M+H−56]$^+$.

Step 3: Synthesis of tert-butyl 4-(3-(difluoromethoxy)-4-(4,4,5,5-tetramethyl-1,3,2-dioxaborolan-2-yl)phenyl)piperazine-1-carboxylate

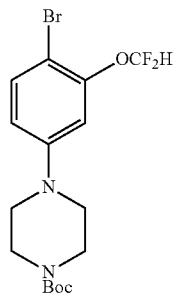

+

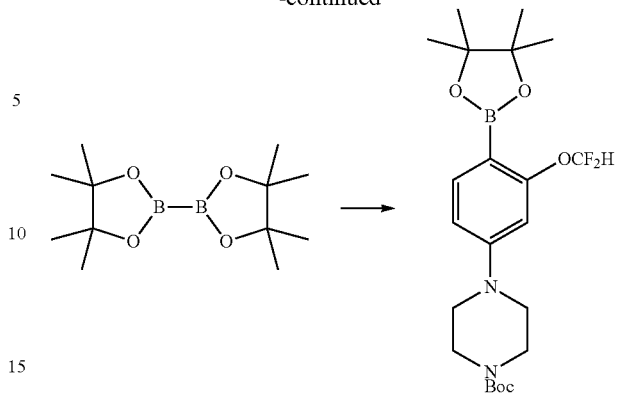

To a solution of tert-butyl 4-(4-bromo-3-(difluoromethoxy)phenyl)piperazine-1-carboxylate (320 mg, 0.78 mmol) and 4,4,4',4',5,5,5',5'-octamethyl-2,2'-bi(1,3,2-dioxaborolane) (309 mg, 1.66 mmol) in dioxane (10 mL) was added Pd(dppf)Cl$_2$ (63 mg, 0.078 mmol) and KOAc (229 mg, 2.34 mmol) at RT under nitrogen. The resulting mixture was stirred at 90° C. for 6 h under nitrogen; LC-MS showed that the reaction was completed. Quenched with water and extracted with EtOAc. The combined organic layers were washed with brine, dried over Na$_2$SO$_4$ and concentrated to dryness to afford crude product, which was purified by flash chromatography on silica gel eluting with PE/EtOAc (10:1 to 3:1) to give the title compound (260 mg, yield 73%) as while solid. MS (ES+) C$_{22}$H$_{33}$BF$_2$N$_2$O$_5$ requires: 454, found 399[M+H−56]$^+$.

I. Synthesis of 2-(4-chlorophenyl)-1-isopropyl-2-methylpyrrolidine

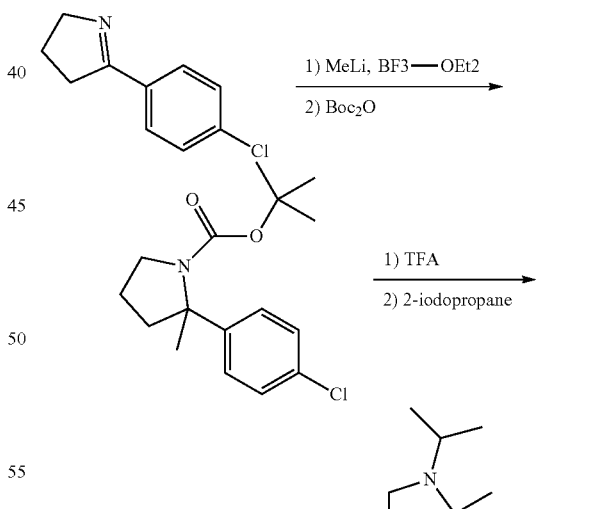

Step 1: Synthesis of tert-butyl 2-(4-chlorophenyl)-2-methylpyrrolidine-1-carboxylate 5-(4-chlorophenyl)-3,4-dihydro-2H-pyrrole (2.00 g, 11.1 mmole) was dissolved in 33 mL dry THF and cooled to −78°

C. Boron trifluoride diethyletherate (2.8 mL, 22.3 mmole) was added dropwise and stirred at −78° C. for 40 minutes and then 0.5M methyllithium in ether (13.9 mL, 22.3 mmole) was added dropwise and then allowed to warm slowly to room temperature overnight. The reaction mixture was quenched with water and diluted with ethyl acetate. The reaction mixture was acidified with 1M HCl and then transferred to a separatory funnel. The aqueous layer was then made basic to pH~12-13 with 6M NaOH and then extracted with ethyl acetate (×2) and combined organics washed with brine and dried over sodium sulfate. Filter and evaporate to give the crude product, which consisted of desired product and the starting material. The two were difficult to separate by chromatography so were converted to the Boc protected product to facilitate separation: The crude product was dissolved in 30 mL dichloromethane and then Boc anhydride (1.74 g, 8.0 mmole) was added as a solution in 5 mL dichloromethane, followed by DMAP (100 mg, 0.8 mmole) and the mixture stirred at room temperature overnight. The reaction mixture was evaporated and then subjected to flash chromatography (0 to 40% ethyl acetate/hexane, collecting all fractions due to low UV activity). Pure fractions combined and evaporated to give 920 mg (28%) of the title compound as a colorless oil that crystallized on standing.

Step 2: Synthesis of 2-(4-chlorophenyl)-1-isopropyl-2-methylpyrrolidine tert-Butyl 2-(4-chlorophenyl)-2-methylpyrrolidine-1-carboxylate (915 mg, 3.1 mmole) was dissolved in 12 mL dichloromethane and trifluoroacetic acid (3.6 mmole, 46.4 mmole) was added and stirred at room temperature for 2 hours. The reaction mixture was evaporated exhaustively and then the residue partitioned between dichloromethane and 1M NaOH. The organic layer was dried over sodium sulfate, filtered and evaporated to give 610 mg (100%) of 2-(4-chlorophenyl)-2-methylpyrrolidine as a viscous orange oil. This material was then dissolved in 10 mL acetonitrile in a heavy-walled pressure vessel and potassium carbonate (646 mg, 4.7 mmole) was added followed by 2-iodopropane (374 uL, 3.7 mmole). The reaction mixture was heated to 90° C. for 3 days and then diluted with ethyl acetate. The reaction was filtered through celite and evaporated. The crude product was subjected to flash chromatography using an Isco amine column, gradient of 0 to 30% ethyl acetate/hexane. Pure fractions were combined and evaporated to give 509 mg (69%) of the desired product as a pale yellow oil.

J. Synthesis of benzyl 4-(4-bromophenyl)-4-fluoropiperidine-1-carboxylate

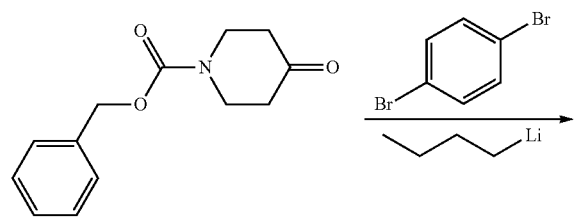

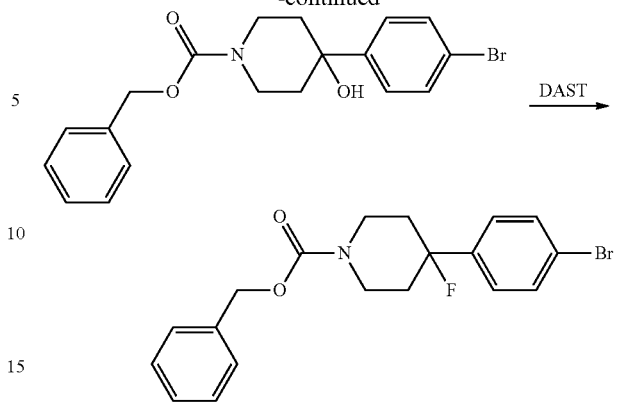

Step 1: Synthesis of benzyl 4-(4-bromophenyl)-4-hydroxypiperidine-1-carboxylate Benzyl 4-oxopiperidine-1-carboxylate (937 mg, 4.0 mmole) and 1,4-dibromobenzene (790 mg, 3.4 mmole) were dissolved in 15 mL THF and cooled to −78° C. nBuLi (1.47 mL of 2.5M solution in hexanes, 3.7 mmole) was added dropwise and the reaction mixture was allowed to warm to room temperature over several hours. The reaction was quenched with saturated ammonium chloride solution and diluted with ethyl acetate and transferred to a reparatory funnel. The organic layer was washed with brine and dried over sodium sulfate. Filtration and evaporation gave the crude product, which was subjected to flash chromatography using a gradient of 0 to 35% ethyl acetate/hexane, collecting all fractions and monitoring by ELSD. Clean fractions combined and evaporated to give 732 mg (56%) of the desired product as a colorless oil.

Step 2: Synthesis of benzyl 4-(4-bromophenyl)-4-fluoropiperidine-1-carboxylate Benzyl 4-(4-bromophenyl)-4-hydroxypiperidine-1-carboxylate (731 mg, 1.87 mmole) was dissolved in 8 mL dichloromethane and cooled to −78° C. DAST (272 uL, 2.06 mmole) was added dropwise and then allowed to warm slowly to room temperature over a couple hours. The reaction was quenched with saturated sodium bicarbonate solution and diluted with dichloromethane and transferred to a separatory funnel. The organic layer was dried over sodium sulfate, filtered and evaporated to give the crude product. Purification by flash chromatography using a gradient of 0 to 35% ethyl acetate/hexane, collecting all fractions and monitoring by ELSD. Clean fractions combined and evaporated to give 236 mg (32%) of the desired product as a colorless oil.

K. Synthesis of tert-butyl 3-(6-chloropyridin-3-yl)-3-methylpiperazine-1-carboxylate

Step 1: Synthesis of ethyl 2-(6-chloropyridin-3-yl)propanoate

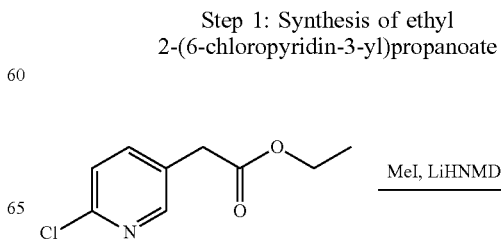

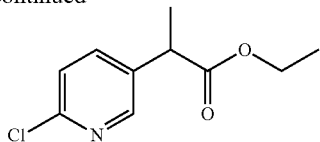

A solution of lithium bis(trimethylsilyl)amide in THF (1 M, 14 mL, 14.0 mmol) was added to a solution of ethyl 2-(6-chloropyridin-3-yl)acetate (2.5 g, 12.5 mmol) in THF at −78° C. under nitrogen. After stirred at −78° C. for 2 h, methyl iodide (1.94 g, 13.7 mmol) was added. The mixture was stirred at 20° C. for another 8 h. Worked up, concentrated and purified with silica gel column chromatography, eluting with 0%-10% EA/PE, to give the title compound (1.5 g, 83% purity in LCMS, yield 46%) as yellow oil. MS (ES+) $C_{10}H_{12}C_1NO_2$ requires: 213, 215, found: 214, 216[M+H]$^+$.

Step 2: Synthesis of ethyl 2-bromo-2-(6-chloropyridin-3-yl)propanoate

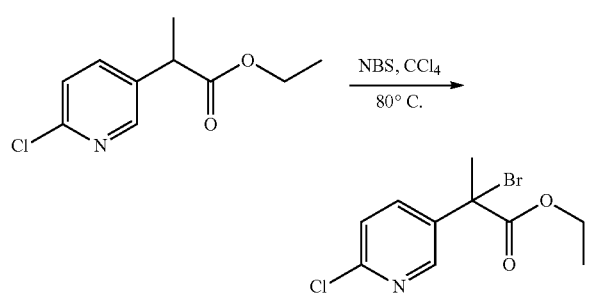

A solution of ethyl 2-(6-chloropyridin-3-yl)propanoate (1.5 g, 5.80 mmol), N-bromosuccinimide (1.23 g, 6.95 mmol) and (E)-azobis(isobutyronitrile) (95 mg, 0.58 mmol) in perchloromethane (50 mL) was stirred at 80° C. for 48 h under nitrogen. The mixture was cooled and concentrated in vacuo. The residue was purified with silica gel column chromatography, eluting with 0%-10% EA/PE, to give the title compound (1.9 g, 75% purity in LCMS, yield 84%) as a yellow oil. MS (ES+) $C_{10}H_{11}BrClNO_2$ requires: 291, 293, found: 292, 294[M+H]$^+$.

Step 3: Synthesis of 3-(6-chloropyridin-3-yl)-3-methylpiperazin-2-one

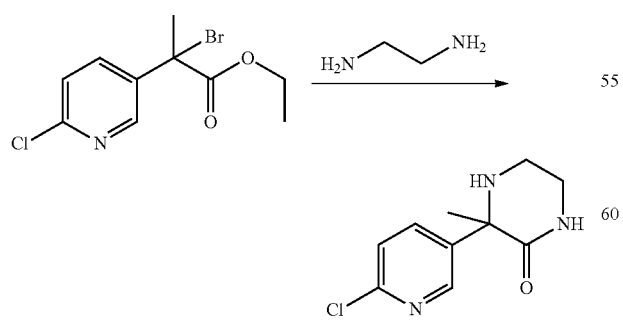

A solution of ethyl 2-bromo-2-(6-chloropyridin-3-yl)propanoate (1.2 g, 4.10 mmol) in ethane-1,2-diamine (5 mL) was stirred at 25° C. for 18 h. Diluted with DCM and washed with brine. Concentrated, the residue was purified with silica gel column chromatography, eluting with 100% EA, to give the title compound (600 mg, yield 63%) as a yellow solid. MS (ES+) $C_{10}H_{12}ClN_3O$ requires: 225, 227, found: 226, 228[M+H]$^+$.

Step 4: Synthesis of tert-butyl 3-(6-chloropyridin-3-yl)-3-methylpiperazine-1-carboxylate

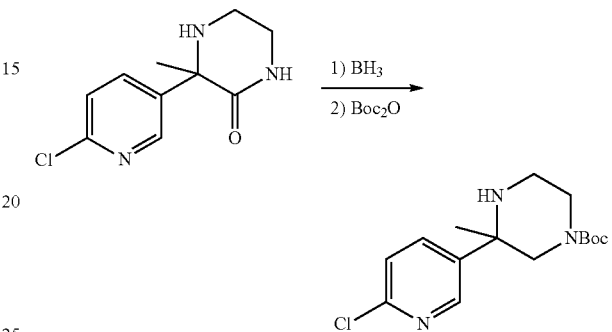

A solution of borane in tetrahydrofuran (22 mL, 1 M, 22.0 mmol) was added dropwise to a solution of 3-(6-chloropyridin-3-yl)-3-methylpiperazin-2-one (500 mg, 2.21 mmol) in tetrahydrofuran (10 mL), and then stirred at 80° C. for 18 h under nitrogen. Cooled, quenched with MeOH and refluxed with HCl/dioxane solution. The mixture was basified with 1 M NaOH solution to pH=10~12, and then di-tert-butyl dicarbonate (1.23 g, 5.64 mmol) was added. Stirred at 20° C. for 18 h. Diluted with EA and washed with water. Concentrated, the residue was purified with silica gel column chromatography, eluting with 0%~10% MeOH/EA, to give the title compound (200 mg, yield 34%) as a white solid. MS (ES+) $C_{15}H_{22}ClN_3O_2$ requires: 311, 313, found: 312, 314 [M+H]$^+$.

L. Synthesis of 2-chloro-3-fluoro-5-(1-isopropyl-4-methoxypiperidin-4-yl)pyridine Step 1: Synthesis of tert-butyl 4-(6-chloro-5-fluoropyridin-3-yl)-4-hydroxypiperidine-1-carboxylate

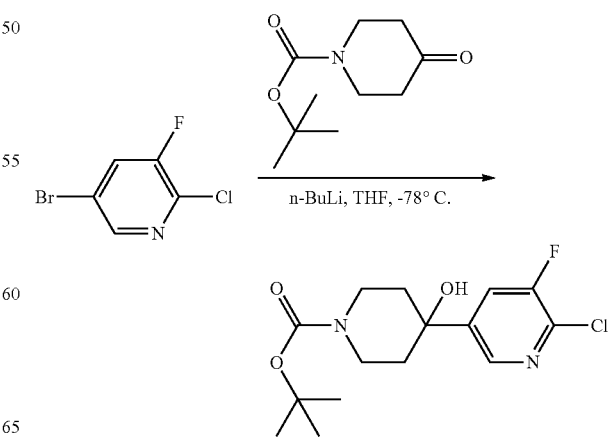

To a solution of 5-bromo-2-chloro-3-fluoropyridine (2 g, 9.50 mmol) in THF (60 mL) at −78° C. was added nBuLi (4 mL, 2.4 M in hexane) dropwise. The solution was stirred at −78° C. for 2 h. Then a solution of tert-butyl 4-oxopiperidine-1-carboxylate (1.89 g, 9.50 mmol) in THF (10 mL) was added dropwise. The resulting solution was stirred at −78° C. for 2 h. The reaction was quenched carefully by addition of water and extracted with EtOAc. The organic layer was washed with water and brine, concentrated and purified by silica gel column chromatography (petroleum ether/ethyl acetate=10/1 to 2/1) to afford the title product (2 g, 64%) as a white solid. MS (ES+) $C_{15}H_{20}ClFN_2O_3$ requires: 330, found: 331[M+H]$^+$.

Step 2: Synthesis of tert-butyl 4-(6-chloro-5-fluoropyridin-3-yl)-4-methoxypiperidine-1-carboxylate

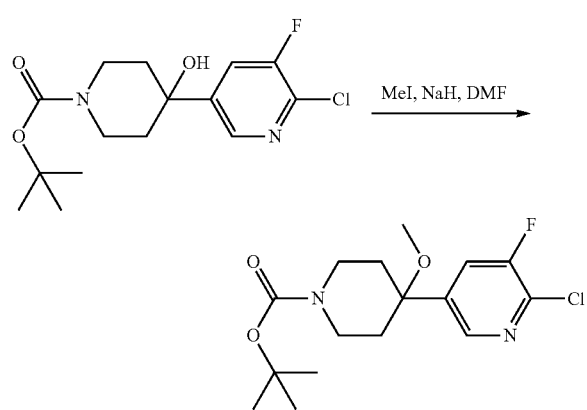

To a solution of tert-butyl 4-(6-chloro-5-fluoropyridin-3-yl)-4-hydroxypiperidine-1-carboxylate (2 g, 6.04 mmol) in dry DMF (20 mL) was added NaH (60%) (313 mg, 7.85 mmol) at 0° C. The mixture was stirred at 0° C. for 1 h. Then iodomethane (1.28 g, 9.06 mmol) was added. The mixture was stirred at RT overnight. After that, the mixture was slowly poured into ice water (200 mL) and stirred for 1 h. The solid was collected by filtration and dried to afford the title compound (1.5 g, 72%) as a white solid. MS (ES+) $C_{16}H_{22}ClFN_2O_3$ requires: 344, found: 345[M+H]$^+$.

Step 3: Synthesis of 2-chloro-3-fluoro-5-(4-methoxypiperidin-4-yl)pyridine

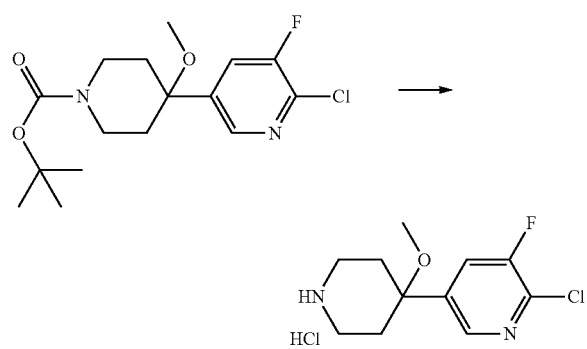

To a solution of tert-butyl 4-(6-chloro-5-fluoropyridin-3-yl)-4-methoxypiperidine-1-carboxylate (1.5 g, 4.35 mmol) in dioxane (10 mL) was added HCl/dioxane (4 N, 10 mL). The mixture was stirred at RT for 12 h. After that, the solution was concentrated. The residue was used in the next step without further purification. MS (ES+) $C_{11}H_{14}ClFN_2O$ requires: 244, found: 245[M+H]$^+$.

Step 4: Synthesis of 2-chloro-3-fluoro-5-(1-isopropyl-4-methoxypiperidin-4-yl)pyridine

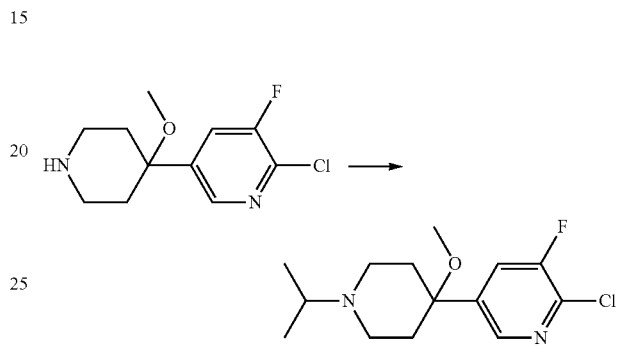

A mixture of 2-chloro-3-fluoro-5-(4-methoxypiperidin-4-yl)pyridine (1 g, 4.08 mmol), 2-iodopropane (693 mg, 4.08 mmol) and triethylamine (1.23 g, 12.2 mmol) in $CH_3CN$ (15 mL) was stirred at 80° C. overnight. After that, the solution was concentrated and purified by silica gel column chromatography (DCM/MeOH=10/1) to afford the title compound (800 mg, 68%) as a yellow solid. MS (ES+) $C_{14}H_{20}ClFN_2O$ requires: 286, found: 287[M+H]$^+$.

M. Synthesis of (R)-3-(4-bromophenyl)-1-isopropylpiperidine and (S)-3-(4-bromophenyl)-1-isopropylpiperidine Step 1: Chiral Separation of 3-(4-bromophenyl)piperidine Hydrochloride

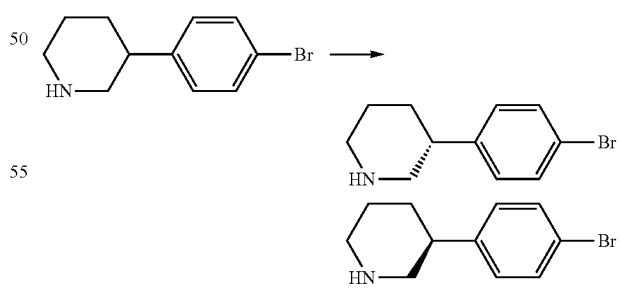

Racemic 3-(4-bromophenyl)piperidine hydrochloride was separated into single enantiomers using the following appropriately scaled chiral HPLC conditions: Column: CD-PH 250×4.6 mm I.D., 5 um Mobile phase:A:water with 0.1% TFA B:acetonitrile with 0.1% TFA A/B=70/30 Flow rate: 1.0 mL/min Wavelength: 220 nm.

Step 2: Synthesis of (S)-3-(4-bromophenyl)-1-isopropylpiperidine

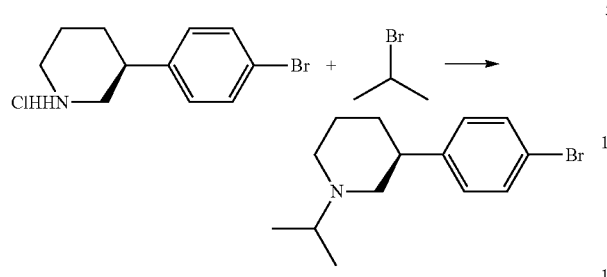

A mixture of (S)-3-(4-bromophenyl)piperidine hydrochloride (3.1 g, 11.2 mmol), 2-bromopropane (2.75 g, 22.4 mmol) and $K_2CO_3$ (4.62 g, 33.5 mmol) in $CH_3CN$ (20 mL) was stirred at 70° C. for 16 hrs. The mixture was diluted with EtOAc and washed with brine. The organic layer was concentrated in vacuo to afford the title compound (2.9 g, yield 91%) as a yellow oil. MS (ES+) $C_{14}H_{20}BrN$ requires: 281, found: 282[M+H]$^+$.

N. Synthesis of 5-(4-bromo-2-fluorophenyl)-1-isopropyl-1,2,3,6-tetrahydropyridine

Step 1: Synthesis of tert-butyl 3-(4-bromo-2-fluorophenyl)-5,6-dihydropyridine-1(2H)-carboxylate

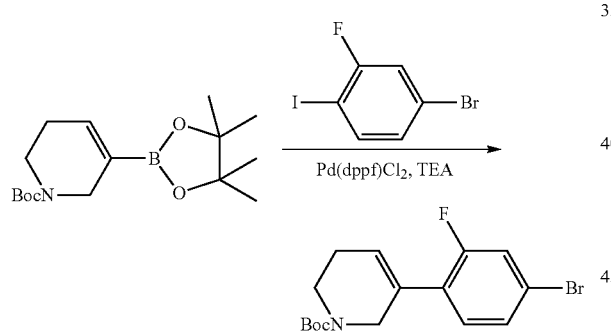

A mixture of tert-butyl 3-(4,4,5,5-tetramethyl-1,3,2-dioxaborolan-2-yl)-5,6-dihydropyridine-1(2H)-carboxylate (4.3 g, 13.9 mmol), 4-bromo-2-fluoro-1-iodobenzene (6.25 g, 20.8 mmol), [1,1'-Bis(diphenylphosphino)ferrocene]dichloropalladium(II) (2.54 g, 2.78 mmol) and potassium carbonate (5.75 g, 41.7 mmol) in dioxane/$H_2O$ (L/10 mL) was degassed with Nitrogen for three times and then heated at 70° C. for 3 h. The reaction mixture was cooled to room temperature and concentrated to get crude product, which was purified by silica gel chromatography (petroleum ether/ethyl acetate=4/1) to afford the title compound (3.7 g, yield 75%) as a brown oil. MS (ES+) $C_{16}H_{19}BrFNO_2$ requires: 355, found: 300 [M−56+H]$^+$.

Step 2: Synthesis of 5-(4-bromo-2-fluorophenyl)-1,2,3,6-tetrahydropyridine HCl Salt

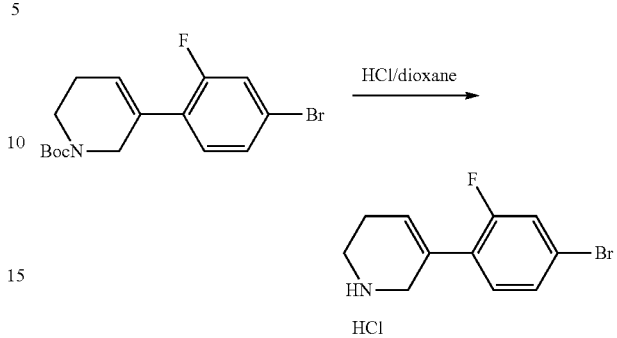

To a mixture of tert-butyl 3-(4-bromo-2-fluorophenyl)-5,6-dihydropyridine-1(2H)-carboxylate (3.7 g, 10.3 mmol) in dioxane (20 ml) was added dioxane/HCl (4 M, 20 mL). The reaction mixture was stirred at room temperature for 3 hours. Concentrated under reduced pressure to afford the title compound (2.6 g, yield 86%) as a brown solid, which was directly used into the next step without further purification. MS (ES+) $C_{11}H_{11}BrFN$ requires: 255, found: 256 [M+H]$^+$.

Step 3: Synthesis of 5-(4-bromo-2-fluorophenyl)-1-isopropyl-1,2,3,6-tetrahydropyridine

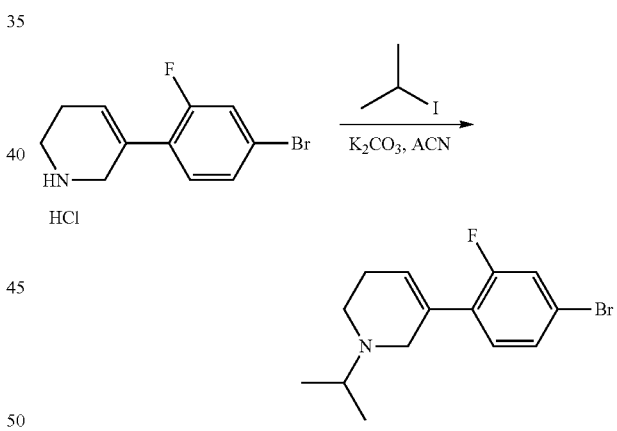

To a solution of 5-(4-bromo-2-fluorophenyl)-1,2,3,6-tetrahydropyridine HCl salt (150 mg, 585 mol) and potassium carbonate (241 mg, 1.75 mmol) in acetonitrile (10 ml) was added 2-iodopropane (496 mg, 2.92 mmol). The solution was stirred at 60° C. for 6 hours. Cooled to room temperature and extracted with EtOAc after water was added. The organic phase was washed with water and brine, dried over $Na_2SO_4$, and concentrated to dryness to afford the title compound as a yellow solid which was used without further purification (140 mg, crude). MS (ES+) $C_{14}H_{17}BrFN$ requires: 297, found: 298 [M+H]$^+$.

O. Synthesis of 3-(4-bromophenyl)-1-isopropyl-3-methylpiperazine

Step 1: Synthesis of methyl 2-(4-bromophenyl)acetate

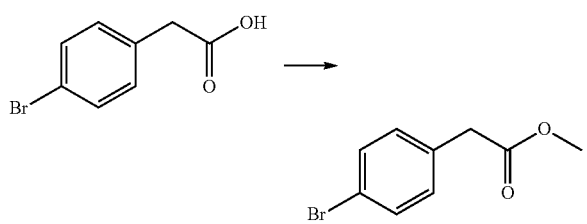

A mixture of 2-(4-bromophenyl)acetic acid (10 g, 46.5 mmol) in MeOH (100 mL, with 2 mL of conc. $H_2SO_4$) was refluxed for 4 h. The mixture was concentrated and diluted with EtOAc. The organic was washed with water and brine, dried and concentrated to give the title product (10.6 g, yield 100%). MS (ES+) $C_9H_9BrO_2$ requires: 229 found 230 $[M+H]^+$.

Step 2: Synthesis of methyl 2-(4-bromophenyl)propanoate

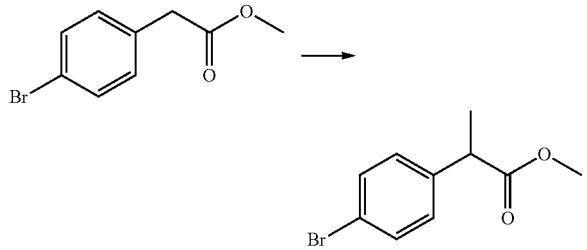

To a solution of methyl 2-(4-bromophenyl)acetate (1 g, 4.36 mmol) in dry THF (20 mL) was added LiHMDS (5.23 mL, 1 M) dropwise at −78° C. under $N_2$. The mixture was stirred at 0° C. for 2 h. After MeI (1.23 g, 8.72 mmol) was added at −78° C., the mixture was stirred at 20° C. for 16 h. Quenched with $NH_4Cl$ sat. and extracted with EtOAc. The organic was concentrated and purified by silica gel column (PE/EtOAc=1/0 to 100/1) to give the title product (642 mg, yield 61%). MS (ES+) $C_{10}H_{11}BrO_2$ requires: 243, found 244 $[M+H]^+$.

Step 3: Synthesis of methyl 2-bromo-2-(4-bromophenyl)propanoate

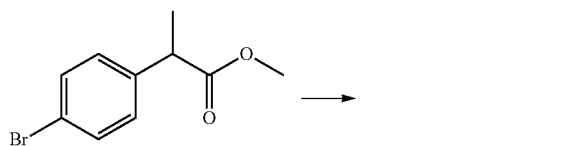

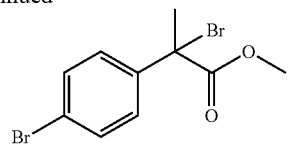

A mixture of methyl 2-(4-bromophenyl)propanoate (30 g, 123 mmol), AIBN (2.01 g, 12.3 mmol) and NBS (32.9 g, 184 mmol) in $CCl_4$ (300 mL) was refluxed for 16 h. Cooled to RT and filtered. After concentrated, the residue was used into the next step without further purification.

Step 4: Synthesis of 3-(4-bromophenyl)-3-methylpiperazin-2-one

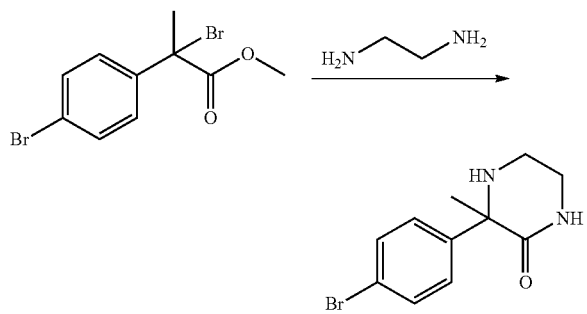

To a solution of methyl 2-bromo-2-(4-bromophenyl)propanoate (39 g, 121 mmol) in EtOH (200 mL) was added ethane-1,2-diamine (14.5 g, 242 mmol). The mixture was stirred at RT for 16 h. Filtered off solid, concentrated and purified by silica gel column (EtOAc) to give the title product (12 g, yield 37%). MS (ES+) $C_{11}H_{13}BrN_2O$ requires: 269, found 270 $[M+H]^+$.

Step 5: Synthesis of tert-butyl 3-(4-bromophenyl)-3-methylpiperazine-1-carboxylate

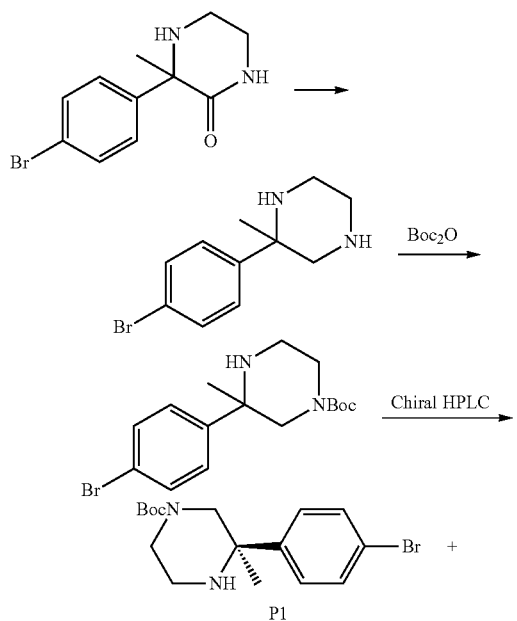

-continued

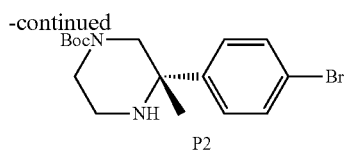

P2

A solution of 3-(4-bromophenyl)-3-methylpiperazin-2-one (12 g, 44.5 mmol) and BH$_3$ (250 mL, 1 M in THF) was stirred at 80° C. overnight. Cooled to RT and quenched with MeOH. After concentrated, the residue was dissolved in MeOH (100 mL), followed by addition of HCl (250 mL, aq, 1 M). The mixture was stirred at 80° C. for 30 min. Cooled to RT. NaOH (12 g, 0.3 mol) was added, followed by addition of Boc$_2$O (11.6 g, 53.3 mmol). The mixture was stirred at RT overnight. Extracted with EtOAc. The organic was concentrated and purified by silica gel column DCM/MeOH (50/1) to give the title product (10 g, yield 63%). MS (ES+) $C_{16}H_{23}BrN_2O_2$ requires: 355, found 356 [M+H]$^+$.

The racemic product (10 g) was separated by chiral-HPLC to give two single enantiomers: P1 (4.63 g) and P2 (4.46 g). Chiral conditions: Co-Solvent: MeOH (0.2% Methanol Ammonia); Column: OZ-H 100*4.6 mm Sum; Column Temperature: 39.9.

Step 6: Synthesis of 2-(4-bromophenyl)-2-methylpiperazine

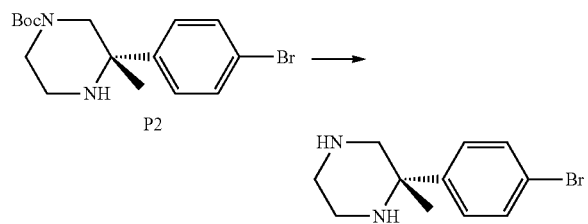

To a mixture of tert-butyl 3-(4-bromophenyl)-3-methylpiperazine-1-carboxylate (1.8 g, 5.06 mmol) in DCM/MeOH (10 mL/10 mL) was added HCl/dioxane (14 mL, 4 M). The mixture was stirred at RT for 1 h, concentrated, and the residue was dissolved in NH$_3$.MeOH (8 mL, 7 mL). DCM (20 mL) was added. Filtered off solid and then concentrated to give the title product (1.2 g, yield 98%). MS (ES+) $C_{16}H_{23}BrN_2O_2$ requires: 255, found 256 [M+H]$^+$.

Step 7: Synthesis of 3-(4-bromophenyl)-1-isopropyl-3-methylpiperazine

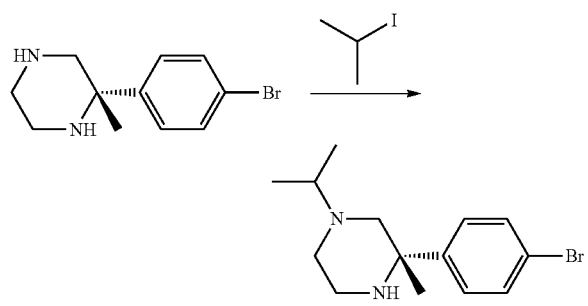

A mixture of 2-(4-bromophenyl)-2-methylpiperazine (1.3 g, 5.09 mmol), 2-iodopropane (994 mg, 5.85 mmol) and DIPEA (3.28 g, 25.4 mmol) in THF (50 mL) was stirred at 60° C. for 16 h. Concentrated and purified by silica gel column (EtOAc) to give the title product (1.3 g, yield 86%). MS (ES+) $C_{14}H_{21}BrN_2$ requires: 297, found 298 [M+H]$^+$.

P. Synthesis of 6'-bromo-1-isopropyl-1,2,5,6-tetrahydro-3,3'-bipyridine

Step 1: Synthesis of tert-butyl 6'-bromo-5,6-dihydro-[3,3'-bipyridine]-1(2H)-carboxylate

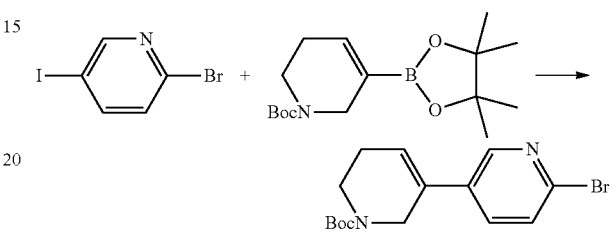

A mixture of 2-bromo-5-iodopyridine (3.66 g, 12.9 mmol), tert-butyl 3-(4,4,5,5-tetramethyl-1,3,2-dioxaborolan-2-yl)-5,6-dihydropyridine-1(2H)-carboxylate (4 g, 12.9 mmol), Pd(dppf)Cl$_2$ (944 mg, 1.29 mmol) and K$_2$CO$_3$ (2.66 g, 19.3 mmol) in dioxane/water (10/1, 20 mL) was irradiated under microwave at 120° C. for 2 h. Concentrated and purified by silica gel column PE/EtOAc (10/1) to give title product (2.12 g, yield 48%). MS (ES+) $C_{15}H_{19}BrN_2O_2$ requires: 339 found 340 [M+H]$^+$.

Step 2: Synthesis of 6'-bromo-1,2,5,6-tetrahydro-3,3'-bipyridine

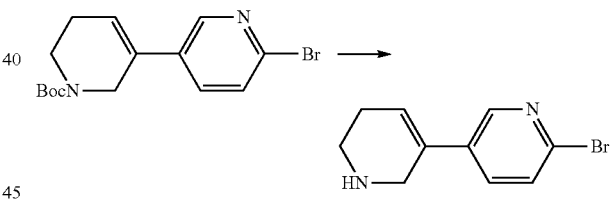

To a solution of tert-butyl 6'-bromo-5,6-dihydro-[3,3'-bipyridine]-1(2H)-carboxylate (2.12 g, 6.24 mmol) in DCM (20 mL) was added TFA (4 mL) at RT, and then stirred for 1 h. The mixture was diluted with water, adjusted pH to 7-8 with NaHCO$_3$ sat., and extracted with DCM.

Dried and concentrated to give the title product (1.49 g, yield 100%). MS (ES+) $C_{10}H_{11}BrN_2$ requires: 239, found 240 [M+H]$^+$.

Step 3: Synthesis of 6'-bromo-1-isopropyl-1,2,5,6-tetrahydro-3,3'-bipyridine

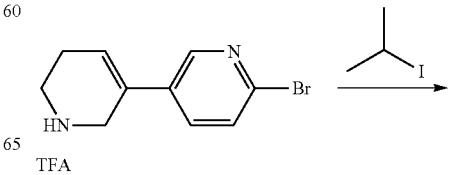

TFA

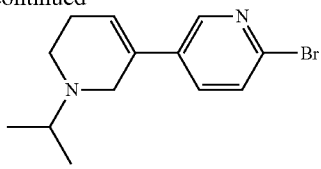

A mixture of 6'-bromo-1,2,5,6-tetrahydro-3,3'-bipyridine (1.49 g, 6.23 mmol), DIPEA (2.39 g, 18.6 mmol) and 2-iodopropane (3.16 g, 18.6 mmol) in MeCN (50 mL) was stirred at 60° C. for 16 h. Concentrated and purified by silica gel column DCM/MeOH (20/1) to give title product (1.75 g, yield 100%). MS (ES+) $C_{13}H_{17}BrN_2$ requires: 281 found 282 $[M+H]^+$.

Q. Synthesis of 2-bromo-5-(4-ethoxy-1-isopropylpiperidin-4-yl)pyridine

Step 1: Synthesis of tert-butyl 4-(6-bromopyridin-3-yl)-4-hydroxypiperidine-1-carboxylate

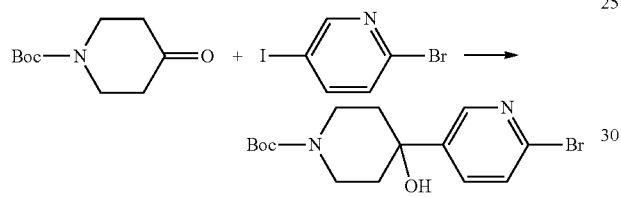

To a solution of 2-bromo-5-iodopyridine (18.5 g, 65.2 mmol) in 150 mL of THF was added n-BuLi (26 mL, 2.5 M in hexane) dropwise under $N_2$ at −78° C. The resulting solution was stirred at −78° C. for 2 h. A solution of tert-butyl 4-oxopiperidine-1-carboxylate (10 g, 50.2 mmol) in 30 mL of THF was added dropwise. The mixture was stirred at −78° C. for another 1 h. The reaction was quenched by addition of sat. $NH_4Cl$ solution and extracted with EtOAc. The organic phase was dried over $Na_2SO_4$ and concentrated. The residue was purified by silica gel chromatography to afford the title product (12.6 g, 70% yield) as a white solid.

Step 2: Synthesis of tert-butyl 4-(6-bromopyridin-3-yl)-4-ethoxypiperidine-1-carboxylate

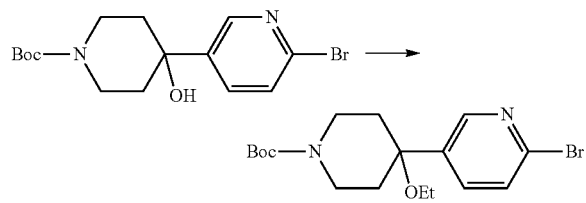

To a solution of tert-butyl 4-(6-bromopyridin-3-yl)-4-hydroxypiperidine-1-carboxylate (2.5 g, 6.99 mmol) in 100 mL of THF was added NaH (60%, 415 mg, 10.4 mmol) at 0° C. The mixture was stirred at 0° C. for 30 min. Then bromoethane (1.13 g, 10.4 mmol) was added. The resulting mixture was stirred at rt for 4 h. The reaction was quenched by addition of water carefully and extracted with EtOAc. The organic phase was washed with brine and water, dried over $Na_2SO_4$ and concentrated in vacuo. The residue was purified by silica gel chromatography to afford the title compound (2.4 g, 89% yield) as a white solid.

Step 3: Synthesis of 2-bromo-5-(4-ethoxypiperidin-4-yl)pyridine

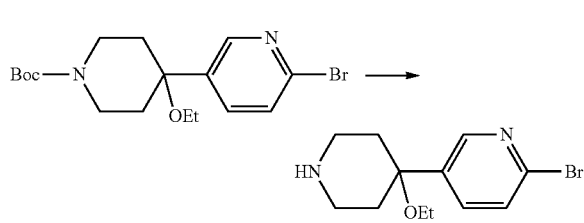

To a solution of tert-butyl 4-(6-bromopyridin-3-yl)-4-ethoxypiperidine-1-carboxylate (2.4 g, 6.22 mmol) in dioxane (80 mL) was added HCl/dioxane (15 mL, 4.0 M) at 25° C., and the resulting mixture was stirred at 25° C. for 2 h. LC-MS showed that the reaction was completed. Evaporated to dryness to afford the title compound (1.5 g) as HCl salt, which was used for the next step without further purification.

Step 4: Synthesis of 2-bromo-5-(4-ethoxy-1-isopropylpiperidin-4-yl)pyridine

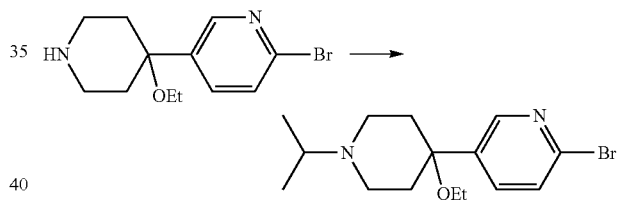

A mixture of 2-bromo-5-(4-ethoxypiperidin-4-yl)pyridine (1.5 g, 5.25 mmol) and potassium carbonate (2.18 g, 15.7 mmol) in MeCN (100 mL) was added iodomethane (2.66 g, 15.7 mmol) and then stirred at 60° C. for 5 h. Concentrated, the residue was diluted with DCM/water (200 mL/200 mL) and extracted with DCM. The combined organic layers were dried over $Na_2SO_4$ and concentrated to give the title product (1.4 g), which was used for the next step without further purification.

R. Synthesis of 2-bromo-5-(1-(1-(difluoromethoxy)propan-2-yl)-4-methoxypiperidin-4-yl)pyridine Step 1: Synthesis of 2-(4-(6-bromopyridin-3-yl)-4-methoxypiperidin-1-yl)propan-1-ol

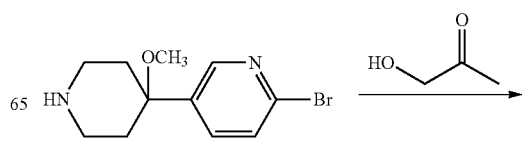

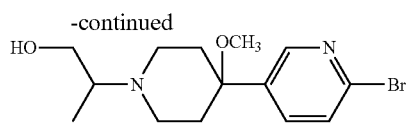

To a solution of 2-bromo-5-(4-methoxypiperidin-4-yl)pyridine (10 g, 36.8 mmol) and 1-hydroxypropan-2-one (54.5 g, 736 mmol) in DCM (100 mL) and CH$_3$OH (100 mL) was added HOAc (1.0 mL) at 0° C., and then sodium cyanoborohydride (11.5 g, 184 mmol) was added. The mixture was stirred at 35° C. for 16 h. After that, the mixture was quenched by addition of NaHCO$_3$ solution and extracted with DCM. The organic layers were concentrated and purified by silica gel column (DCM/CH$_3$OH=10/1) to get the title compound (8.0 g, yield 66%) as a colorless oil. MS (ES+) C$_{14}$H$_{21}$BrN$_2$O$_2$ requires: 328, 330, found 329, 331 [M+H]$^+$.

Step 2: Chiral separation of 2-(4-(6-bromopyridin-3-yl)-4-methoxypiperidin-1-yl)propan-1-ol

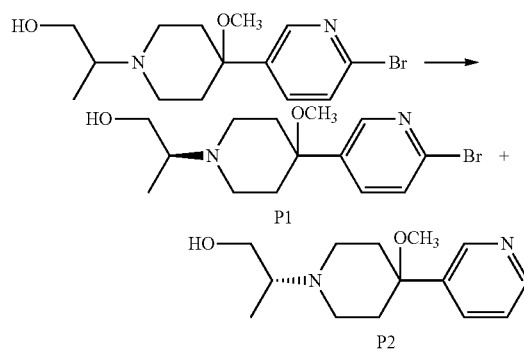

The two enantiomers were separated on an AY-H column (250*4.6 mm, 5 um; Mobile Phase: n-Hexane (0.1% DEA): EtOH (0.1% DEA)=70:30; Temperature: 40° C.; Flow: 1.0 mL/min) and the fractions were measured at wavelengths 214 nm and 254 nm on a SHIMADZU Instrument.

Step 3: Synthesis of 2-bromo-5-(1-(1-(difluoromethoxy)propan-2-yl)-4-methoxypiperidin-4-yl)pyridine

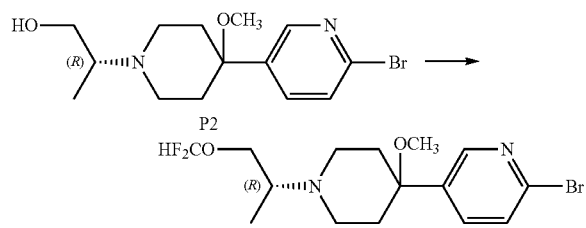

To a mixture of 2-(4-(6-bromopyridin-3-yl)-4-methoxypiperidin-1-yl)propan-1-ol (100 mg, 303 μmol) and CuI (86 mg, 0.45 mmol) in 4 mL of CH$_3$CN was added a solution of 2,2-difluoro-2-(fluorosulfonyl)acetic acid (268 mg, 1.51 mmol) dropwise in 2 mL of CH$_3$CN at 45° C. under N$_2$. The resulting mixture was stirred at 45° C. for 2 hrs. The solvent was removed in vacuo and the residue was purified by silica gel column (EtOAc/CH$_3$OH=20/1) to afford the title product (40 mg, yield 35%) as a yellow oil. MS (ES+) C$_{15}$H$_{21}$BrF$_2$N$_2$O$_2$ requires: 378, 380, found 379, 381 [M+H]$^+$.

S. Synthesis of 2-bromo-5-(4-methoxy-1-(1-methoxypropan-2-yl)piperidin-4-yl)pyrine Step 1: Synthesis of (S)-2-bromo-5-(4-methoxy-1-(1-methoxypropan-2-yl)piperidin-4-yl)pyridine

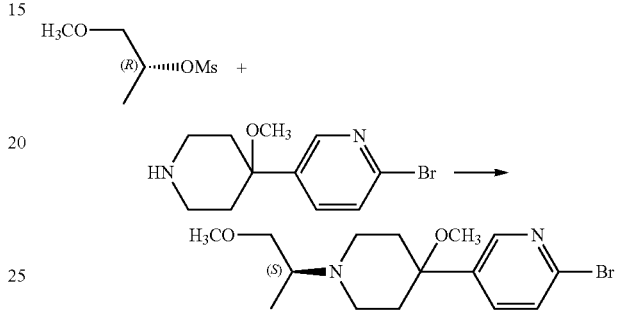

A mixture of 2-bromo-5-(4-methoxypiperidin-4-yl)pyridine (800 mg, 2.95 mmol), (R)-1-methoxypropan-2-yl methanesulfonate (992 mg, 5.90 mmol) and K$_2$CO$_3$ (1.22 g, 8.85 mmol) in CH$_3$CN (30 mL) was heated to 70° C. for 72 h. Concentrated and passed a column (silica gel, DCM:MeOH=20:1) to give the title product (0.5 g, 50%) as a yellow oil. MS (ES+) C$_{15}$H$_{23}$BrN$_2$O$_2$ requires: 342, found 343 [M+H]$^+$.

Step 2: Synthesis of (R)-2-bromo-5-(4-methoxy-1-(1-methoxypropan-2-yl)piperidin-4-yl)pyridine

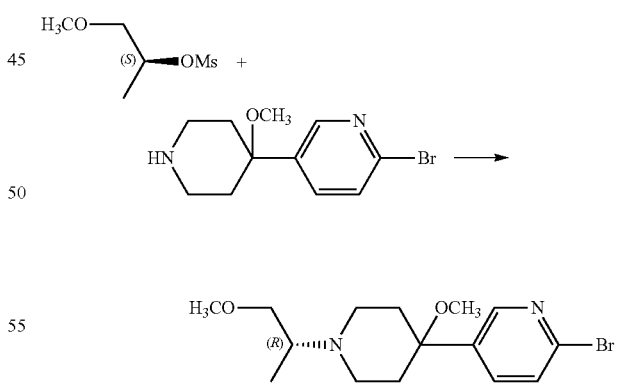

A mixture of 2-bromo-5-(4-methoxypiperidin-4-yl)pyridine hydrochloride (200 mg, 0.65 mmol), (S)-1-methoxypropan-2-yl methanesulfonate (218 mg, 1.30 mmol) and K$_2$CO$_3$ (269 mg, 1.95 mmol) in CH$_3$CN (5 mL) was heated to 70° C. for 72 h. Concentrated and passed a column (silica gel, DCM:MeOH=20:1) to give the title product (100 mg, 45%) as a yellow oil. MS (ES+) C$_{15}$H$_{23}$BrN$_2$O$_2$ requires: 342, found 343 [M+H]$^+$.

T. Synthesis of (3S,4S)-3-(4-bromophenyl)-1-isopropylpiperidin-4-ol

Step 1: Synthesis of tert-butyl 3-(4-bromophenyl)-5,6-dihydropyridine-1(2H)-carboxylate

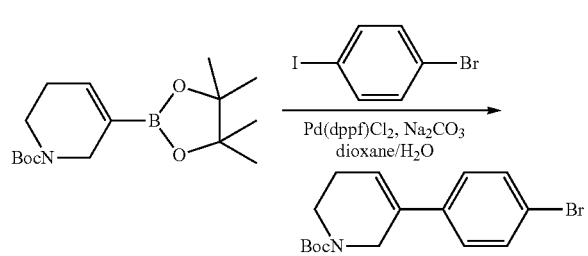

A mixture of tert-butyl 3-(4,4,5,5-tetramethyl-1,3,2-dioxaborolan-2-yl)-5,6-dihydropyridine-1(2H)-carboxylate (10 g, 32.3 mmol), 1-bromo-4-iodobenzene (9.13 g, 32.3 mmol), [1,1'-Bis(diphenylphosphino)ferrocene]dichloropalladium(II) (2.35 g, 3.22 mmol) and sodium carbonate (10.2 g, 96.8 mmol) in dioxane (80 mL) and water (20 mL) was purged with $N_2$ and stirred at 75° C. for 2 h. After that, the solution was cooled to RT and purified by silica gel column chromatography (petroleum ether/ethyl acetate=10/1 to 5/1) to afford the title compound (8 g, 73%) as a colorless oil. MS (ES+) $C_{16}H_{20}BrNO_2$ requires: 337, 339, found: 282, 284 [M−55]$^+$.

Step 2: Synthesis of (3r,4r)-tert-butyl 3-(4-bromophenyl)-4-hydroxypiperidine-1-carboxylate

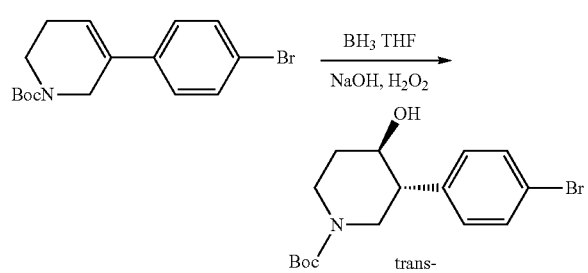

To a cooled solution of borane-methyl sulfide complex (26.5 mL, 26.5 mmol) in anhydrous tetrahydrofuran (80 mL) under an atmosphere of nitrogen was added a solution of tert-butyl 3-(4-bromophenyl)-5,6-dihydropyridine-1(2H)-carboxylate (7.5 g, 22.1 mmol) in tetrahydrofuran (20 mL). The resulting mixture was stirred at room temperature for 17 hours, then cooled in an ice bath, and sodium hydroxide (12.65 mL of a 2 N solution, 24.25 mmol) added in a dropwise manner, followed by hydrogen peroxide (9.2 mL of a 30% solution). The resulting mixture was stirred at RT for 3-5 hours, then poured into water (100 mL) and extracted with ethyl acetate (3×150 mL). The combined organic layers were washed with water (150 mL), saturated $NaHCO_3$ (150 mL) and saturated NaCl (150 mL), dried over $Na_2SO_4$, filtered, concentrated and purified by silica gel column chromatography (petroleum ether/ethyl acetate=5/1 to 1/1) to afford the title compound (trans-, 3.5 g, 44%) as a white solid. MS (ES+) $C_{16}H_{20}BrNO_2$ requires: 355, 357, found: 300, 302 [M−55]$^+$.

Step 3: Separation of (3S,4S)-tert-butyl 3-(4-bromophenyl)-4-hydroxypiperidine-1-carboxylate and (3R,4R)-tert-butyl 3-(4-bromophenyl)-4-hydroxypiperidine-1-carboxylate

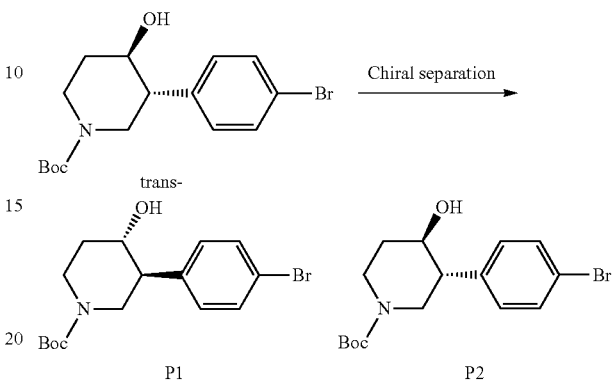

The enantiomers were separated on a S,S-Whelk-O1 column (4.6*100*5 um; Co-Solvent: MeOH (0.2% Methanol Ammonia); Column Temperature: 40° C.; $CO_2$ Flow Rate: 3.6.

Step 4: Synthesis of (3S,4S)-3-(4-bromophenyl)piperidin-4-ol

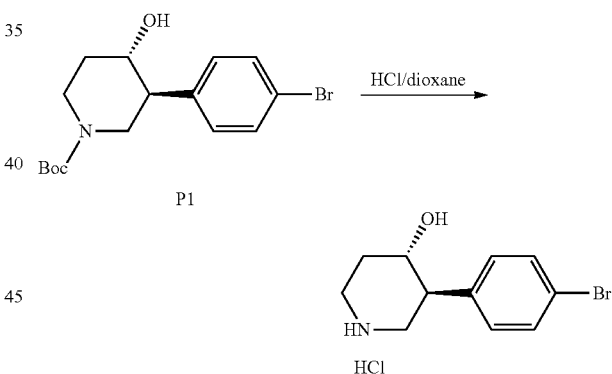

To a solution of (3S,4S)-tert-butyl 3-(4-bromophenyl)-4-hydroxypiperidine-1-carboxylate (1.3 g, 3.64 mmol) in dioxane (20 mL) was added HCl/dioxane (4 mol/L, 10 mL). The mixture was stirred at RT for 12 h. After that, the solution was concentrated, and the residue was used in the next step without further purification. MS (ES+) $C_{11}H_{14}BrNO$ requires: 255, 257, found: 256, 258 [M+H]$^+$.

Step 5: Synthesis of (3S,4S)-3-(4-bromophenyl)-1-isopropylpiperidin-4-ol

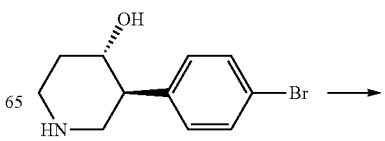

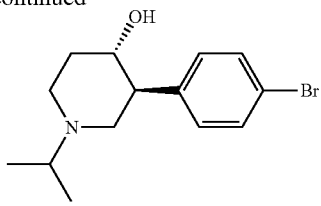

A mixture of (3S,4S)-3-(4-bromophenyl)piperidin-4-ol (900 mg, 3.51 mmol), 2-iodopropane (1.19 g, 7.02 mmol) and triethylamine (1.06 g, 10.5 mmol) in CH$_3$CN (30 mL) was stirred at 70° C. overnight. After that, the solution was concentrated and purified by silica gel column chromatography (petroleum ether/ethyl acetate/NH$_3$.MeOH=10/10/1) to afford the title compound (900 mg, 87%) as a white solid. MS (ES+) C$_{14}$H$_{20}$BrNO requires: 297, 299, found: 298, 300 [M+H]$^+$.

U. Synthesis of 4-(4-bromophenyl)-4-methoxy-1-(1-methoxypropan-2-yl)piperidine

Step 1: Synthesis of tert-butyl 4-(4-bromophenyl)-4-hydroxypiperidine-1-carboxylate

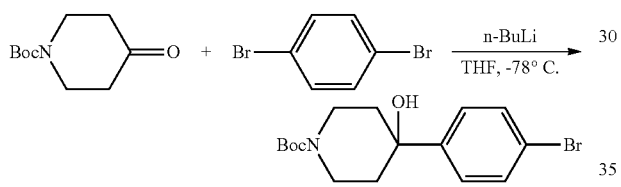

To a solution of 1,4-dibromobenzene (25.9 g, 110 mmol) in dry THF (250 mL) was added n-BuLi (2.5 M, 48.0 mL, 120.0 mmol) dropwise at −78° C. The mixture was stirred at −78° C. for 1 h before tert-butyl 4-oxopiperidine-1-carboxylate (20 g, 100 mmol) in dry THF (100 mL) was added dropwise at −78° C. The reaction mixture was stirred at −78° C. for another 1 h and warmed to RT slowly. LC-MS showed the reaction was completed. The reaction mixture was quenched with saturated NH$_4$Cl and extracted with EA (200 mL×3). The organic layer was washed with water and brine, dried over Na$_2$SO$_4$, filtrated, concentrated and purified by silica gel chromatograph (PE:EA=5:1) to give the title product (22 g, yield: 62%) as a white solid. MS (ES+) C$_{16}$H$_{22}$BrNO$_3$ requires: 355, 357 found 356, 358 [M+H]$^+$.

Step 2: Synthesis of tert-butyl 4-(4-bromophenyl)-4-methoxypiperidine-1-carboxylate

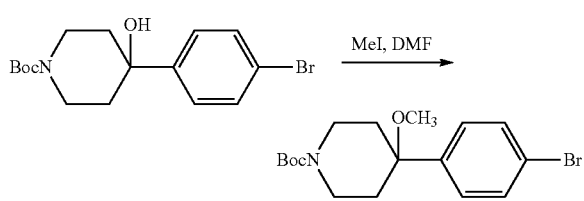

Sodium hydride (60%, 782 mg, 32.6 mmol) was added to a solution of tert-butyl 4-(4-bromophenyl)-4-hydroxypiperidine-1-carboxylate (7.8 g, 21.8 mmol) in DMF. This mixture was stirred at 20° C. for 30 min under nitrogen. Iodomethane (32.6 mmol, 4.62 g) was then added. Stirred at 20° C. for 2 h. Dissolved in water and extracted with EA. EA phase was dried and purified by silica gel chromatograph, eluting with 1/4 EA/PE to give the title product as a yellow oil (8.0 g, ~80% in LCMS, yield 79%). MS (ES+) C$_{17}$H$_{24}$BrNO$_3$ requires: 369, 371, found: 282, 284 [M+H]$^+$.

Step 3: Synthesis of 4-(4-bromophenyl)-4-methoxypiperidine HCl Salt

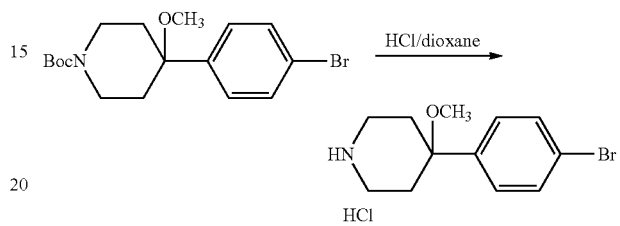

A solution of 4 M HCl in dioxane (25 mL, 100.0 mmol) was added to a stirred solution of tert-butyl 4-(4-bromophenyl)-4-methoxypiperidine-1-carboxylate (3.7 g, 10.0 mmol) in MeOH (20 mL) at 25° C., and stirred for 3 h under N$_2$. After concentrated, the crude product (2.5 g, yield 89%, yellow solid) was used into the next reaction directly without further purification. MS (ES+) C$_{12}$H$_{16}$BrNO requires: 269, 271, found: 270, 272 [M+H]$^+$.

Step 4a: Synthesis of (R)-1-methoxypropan-2-yl methanesulfonate

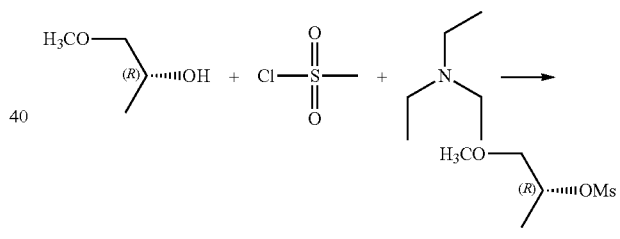

To a mixture of (R)-1-methoxypropan-2-ol (2.0 g, 22.1 mmol) and triethylamine (6.70 g, 66.3 mmol) in DCM (10 mL) was added methanesulfonyl chloride (3.79 g, 33.1 mmol) dropwise at 0° C. The mixture was stirred at rt for 16 hrs. The mixture was quenched with sat. NaHCO$_3$ solution, diluted with DCM, washed with water and dried over Na$_2$SO$_4$ anhydrous. The organic layer was concentrated in vacuo to afford the title compound (3.0 g, yield 80%) as a yellow oil MS (ES+) C$_5$H$_{12}$O$_4$S requires: 168, found: 169 [M+H]$^+$.

Step 4b: Synthesis of (S)-1-methoxypropan-2-yl methanesulfonate

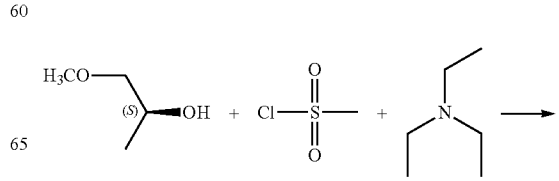

-continued

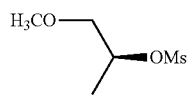

To a mixture of (S)-1-methoxypropan-2-ol (1.5 g, 16.6 mmol) and triethylamine (5.03 g, 49.8 mmol) was added methanesulfonyl chloride (1.92 mL, 24.9 mmol) at 0° C. The mixture was stirred at rt for 16 hrs. The mixture was diluted with DCM, washed with sat. NaHCO$_3$ solution and dried over Na$_2$SO$_4$ anhydrous. The organic layer was concentrated in vacuo to afford the title compound (2.3 g, yield 82%) as a yellow oil MS (ES+) C$_5$H$_{12}$O$_4$S requires: 168, found: 169 [M+H]$^+$.

Step 5a: Synthesis of (S)-4-(4-bromophenyl)-4-methoxy-1-(1-methoxypropan-2-yl)piperidine

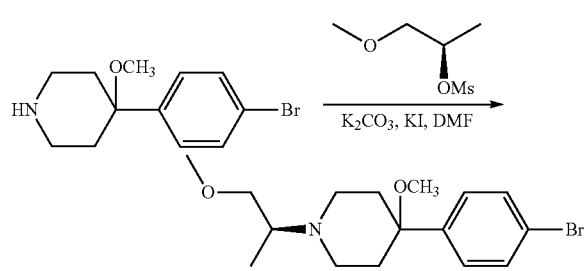

A solution of 4-(4-bromophenyl)-4-methoxypiperidine (250 mg, 0.93 mmol), potassium carbonate (127 mg, 0.93 mmol), potassium iodide (153 mg, 0.93 mmol) and (R)-1-methoxypropan-2-yl methanesulfonate (186 mg, 1.11 mmol) in DMF (5 mL) was stirred at 60° C. for 5 h under N$_2$. Dissolved in EA, and washed with water and brine. After dried and concentrated, the residue was purified by silica gel chromatograph, eluting with 1/10 MeOH/EA to. give desired product (100 mg, 65% purity in LCMS, yield 21%) as a brown paste. MS (ES+) C$_{16}$H$_{24}$BrNO$_2$ requires: 341, found: 342, 344 [M+H]$^+$.

Step 5b: Synthesis of (R)-4-(4-bromophenyl)-4-methoxy-1-(1-methoxypropan-2-yl)piperidine

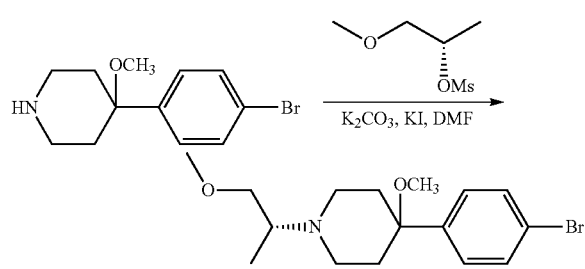

A solution of 4-(4-bromophenyl)-4-methoxypiperidine (250 mg, 0.93 mmol), potassium carbonate (127 mg, 0.93 mmol), potassium iodide (153 mg, 0.93 mmol) and (S)-1-methoxypropan-2-yl methanesulfonate (155 mg, 0.93 mmol) in DMF (5 mL) was stirred at 60° C. for 5 h under N$_2$. Dissolved in EA, and washed with water and brine. After dried and concentrated, the residue was purified by silica gel chromatograph, eluting with 1/10 MeOH/EA, to give the title compound (106 mg, 85% purity in LCMS, yield 34%) as a yellow paste. MS (ES+) C$_{16}$H$_{24}$BrNO$_2$ requires: 341, 343, found: 342, 344 [M+H]$^+$.

V. Synthesis of (S)-5-(1-isopropylpiperidin-3-yl) pyridin-2-yl trifluoromethanesulfonate Step 1: Synthesis of tert-butyl 3-(6-(benzyloxy) pyridin-3-yl)-5,6-dihydropyridine-1(2H)-carboxylate

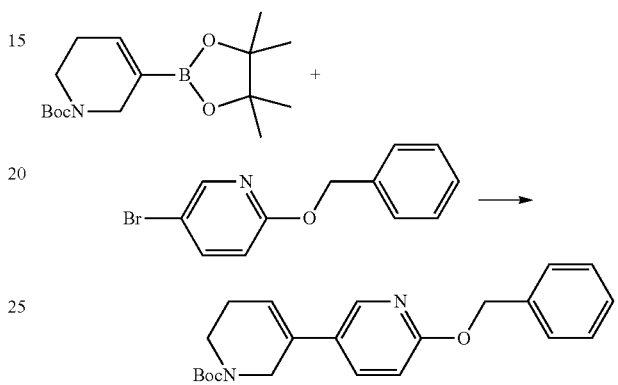

A mixture of tert-butyl 3-(4,4,5,5-tetramethyl-1,3,2-dioxaborolan-2-yl)-5,6-dihydropyridine-1(2H)-carboxylate (5 g, 16.1 mmol), 2-(benzyloxy)-5-bromopyridine (6.36 g, 24.1 mmol), Pd(dppf)Cl$_2$ (818 mg, 1.12 mmol) and K$_2$CO$_3$ (4.44 g, 32.2 mmol) in dioxane/water (40 mL/5 mL) was purged with N$_2$ for three times and stirred at 100° C. for 16 hrs. The mixture was concentrated and purified by flash column chromatography (PE/EtOAc=10:1) to afford the title compound (5.0 g, yield 84%) as a yellow oil. MS (ES+) C$_{22}$H$_{26}$N$_2$O$_3$ requires: 366, found: 367 [M+H]$^+$.

Step 2: Synthesis of (S)-tert-butyl 3-(6-hydroxy-pyridin-3-yl)piperidine-1-carboxylate (P1) and (R)-tert-butyl 3-(6-hydroxypyridin-3-yl)piperidine-1-carboxylate (P2)

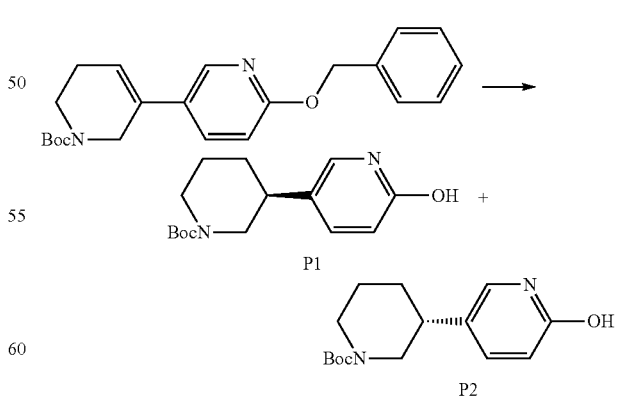

A mixture of tert-butyl 6'-(benzyloxy)-5,6-dihydro-[3,3'-bipyridine]-1(2H)-carboxylate (2.5 g, 6.82 mmol) and Pd/C (1.44 g) in EtOAc (10 mL) was stirred at RT for 16 hrs under H$_2$ (H$_2$ balloon). The mixture was filtered through a pad of Celite and purified by Prep-HPLC to afford racemic compound (1.1 g) as a white solid, which was separated by chiral HPLC (Chiral condition: Co-Solvent: MeOH (0.2% Methanol Ammonia); Column: OZ-H 100*4.6 mm 5 um; Column Temperature: 36.8; CO2 Flow Rate: 3; Co-Solvent Flow Rate: 1) to afford the title compound P1 (500 mg, yield 26%) as a white solid. MS (ES+) $C_{15}H_{22}N_2O_3$ requires: 278, found: 279 [M+H]$^+$ and P2 (500 mg, yield 26%) as a white solid. MS (ES+) $C_{15}H_{22}N_2O_3$ requires: 278, found: 279 [M+H]$^+$.

Step 3: Synthesis of (S)-tert-butyl-3-(6-trifluoromethylsulfonyloxy)pyridin-3-yl)piperidine-1-carboxylate

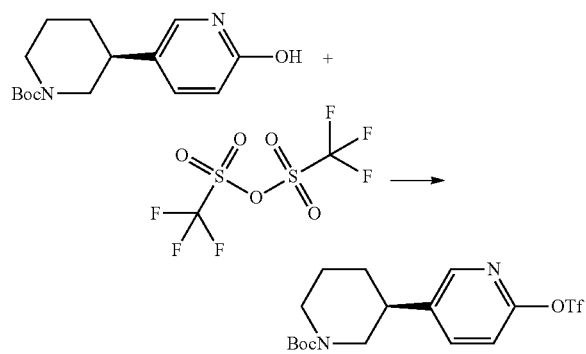

To a mixture of (S)-tert-butyl 3-(6-hydroxypyridin-3-yl)piperidine-1-carboxylate (500 mg, 1.79 mmol) and pyridine (431 μL, 5.37 mmol) in DCM (5 mL) was added trifluoromethanesulfonic anhydride (450 μL, 2.68 mmol) dropwise at 0° C. The mixture was stirred at 0° C. for 30 min, diluted with DCM, washed with ice water and dried over Na$_2$SO$_4$ anhydrous. The organic layer was concentrated in vacuo to afford the title compound (700 mg, yield 95%) as a yellow oil. MS (ES+) $C_{16}H_{21}F_3N_2O_5S$ requires: 410, found: 411 [M+H]$^+$.

Step 4: Synthesis of (S)-5-(piperidin-3-yl)pyridin-2-yl trifluoromethanesulfonate hydrochloride

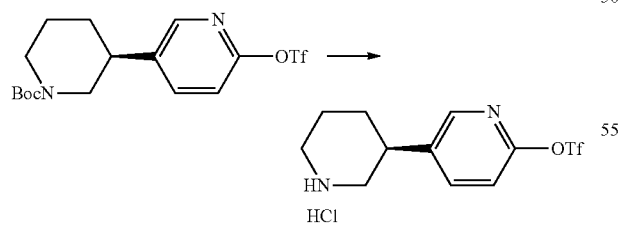

To a mixture of (S)-tert-butyl 3-(6-(((trifluoromethyl)sulfonyl)oxy)pyridin-3-yl)piperidine-1-carboxylate (400 mg, 974 μmol) in DCM (2 mL) was added HCl in dioxane (1.21 mL, 4.84 mmol). The mixture was stirred at RT for 4 hrs. The mixture was concentrated in vacuo to afford the title compound (330 mg, crude) as a yellow solid. MS (ES+) $C_{11}H_{14}ClF_3N_2O_3S$ requires: 310, found: 311 [M+H]$^+$.

Step 5: Synthesis of (S)-5-(1-isopropylpiperidin-3-yl)pyridin-2-yl Trifluoromethanesulfonate

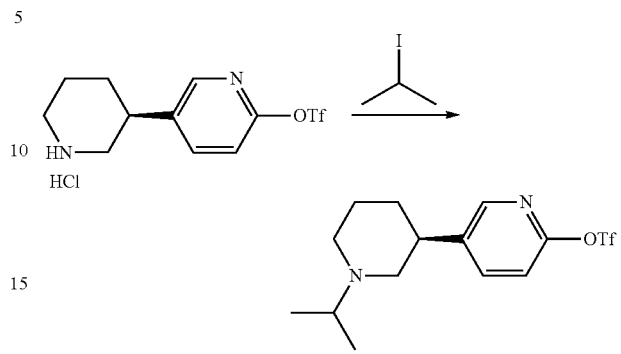

A mixture of (S)-5-(piperidin-3-yl)pyridin-2-yl trifluoromethanesulfonate hydrochloride (330 mg, 951 μmol), 2-iodopropane (322 mg, 1.90 mmol) and triethylamine (288 mg, 2.85 mmol) in ACN (5 mL) was stirred at 60° C. for 16 hrs. The mixture was concentrated and purified by flash column chromatography (DCM/MeOH=10:1) to afford the title compound (250 mg, yield 74%) as a yellow oil MS (ES+) $C_{14}H_{19}F_3N_2O_3S$ requires: 352, found: 353 [M+H]$^+$.

W. Synthesis of 4-(4-bromo-3-chlorophenyl)-1-isopropyl-1,2,3,6-tetrahydropyridine

Step 1: Synthesis of tert-butyl 4-(4-bromo-3-chlorophenyl)-5,6-dihydropyridine-1(2H)-carboxylate

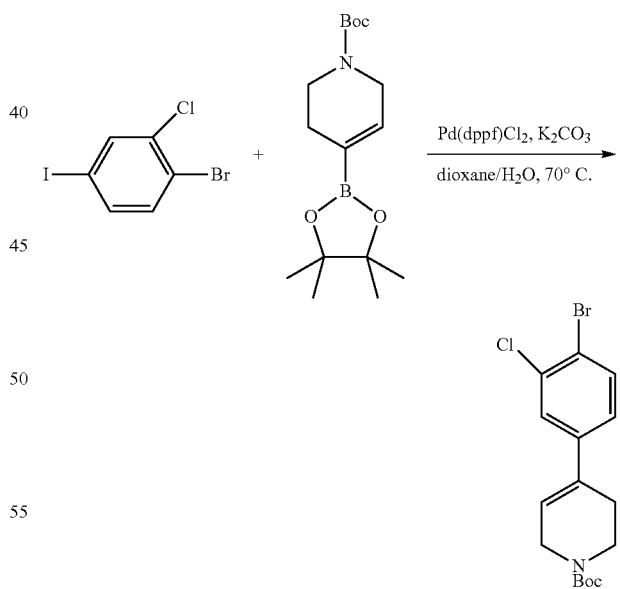

To a solution of 1-bromo-2-chloro-4-iodobenzene (4.9, 15.4 mmol) and tert-butyl 4-(4,4,5,5-tetramethyl-1,3,2-dioxaborolan-2-yl)-5,6-dihydropyridine-1(2H)-carboxylate (4.3 g, 13.9 mmol) in dioxane/H$_2$O (50 mL/20 mL) was added Pd(dppf)Cl$_2$ (626 mg, 0.77 mmol) and K$_2$CO$_3$ (6.4 g, 46.2 mmol) at room temperature under nitrogen. The resulting mixture was stirred at 70° C. for 2 hours. Cooled to room temperature and extracted with EtOAc after additional water was added. The organic was washed with brine, dried over Na₂SO₄ and concentrated to dryness to afford the crude product which was purified by flash chromatography on silica gel eluting with PE/EA (10:1) to afford the title product (3.6 g, yield 70%) as a yellow solid. MS (ES+) $C_{16}H_{19}BrClNO_2$ requires: 371, found 372 [M+H]⁺.

Step 2: Synthesis of 4-(4-bromo-3-chlorophenyl)-1,2,3,6-tetrahydropyridine TFA Salt

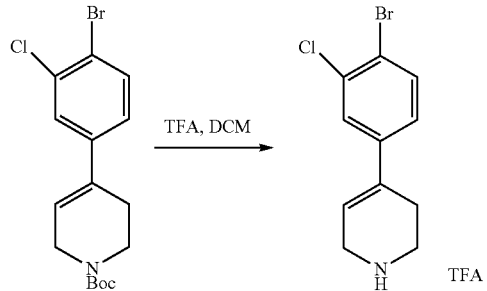 [SMILES: CC(C)(C)OC(=O)N1CC=C(c2ccc(Br)c(Cl)c2)CC1 ; Clc1cc(C2=CCNCC2)ccc1Br]

To a solution of tert-butyl 4-(4-bromo-3-chlorophenyl)-5,6-dihydropyridine-1(2H)-carboxylate (3.6 g, 9.7 mmol) in DCM (20 mL) was added TFA (5 mL) dropwise at room temperature. The resulting mixture was stirred at room temperature for 3 hours; LC-MS showed that the reaction was completed. The solution was evaporated to dryness to afford the crude product which was used for the next step without further purification (3.4 g, TFA salt). MS (ES+) $C_{11}H_{11}BrClN$ requires: 271, found 272 [M+H]⁺.

Step 3: Synthesis of 4-(4-bromo-3-chlorophenyl)-1-isopropyl-1,2,3,6-tetrahydropyridine

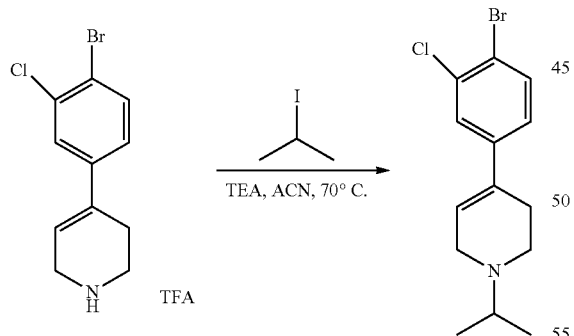

To a solution of 4-(4-bromo-3-chlorophenyl)-1,2,3,6-tetrahydropyridine TFA salt (3.4 g, 9.2 mmol) in acetonitrile (15 mL) was added TEA (2.8 g, 27.6 mmol), followed by addition of isopropyl iodide (4.7 g, 27.6 mmol). The solution was heated at 70° C. for 6 hours; LC-MS showed that the reaction was completed. The crude product was purified by flash chromatography on silica gel eluting with PE/EA (1:1 to 1:3) to give the title product (2.4 g, yield 83%) as viscous oil. MS (ES+) $C_{14}H_{17}BrClN$ requires: 313, found 314 [M+H]⁺.

X. Synthesis of 4-(4-bromo-3-fluorophenyl)-1-isopropyl-4-methoxypiperidine

Step 1: Synthesis of tert-butyl 4-(4-bromo-3-fluorophenyl)-4-hydroxypiperidine-1-carboxylate

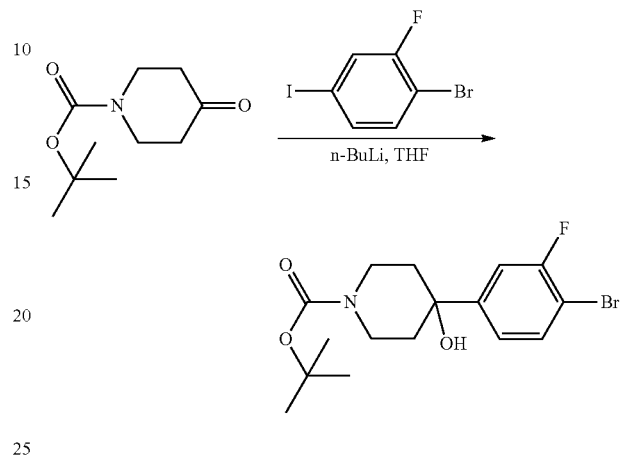

To a solution of 1-bromo-2-fluoro-4-iodobenzene (15.0 g, 50.1 mmol) in THF (150 mL) at −78° C. was added n-BuLi (20 mL, 2.4 M in hexane) dropwise. The solution was stirred at −78° C. for 2 h. Then, a solution of tert-butyl 4-oxopiperidine-1-carboxylate (10 g, 50.1 mmol) in THF (20 mL) was added dropwise. After that, the resulting solution was stirred at −78° C. for 2 h. The reaction was quenched carefully by addition of water and extracted with EtOAc. The organic layer was washed with water and brine, concentrated and purified by silica gel column chromatography (petroleum ether/ethyl acetate=10/1 to 2/1) to afford the title product (3 g, 16%) as a white solid. MS (ES+) $C_{16}H_{21}BrFNO_3$ requires: 373, 375, found: 300, 302 [M-73]⁺.

Step 2: Synthesis of (tert-butyl 4-(4-bromo-3-fluorophenyl)-4-methoxypiperidine-1-carboxylate

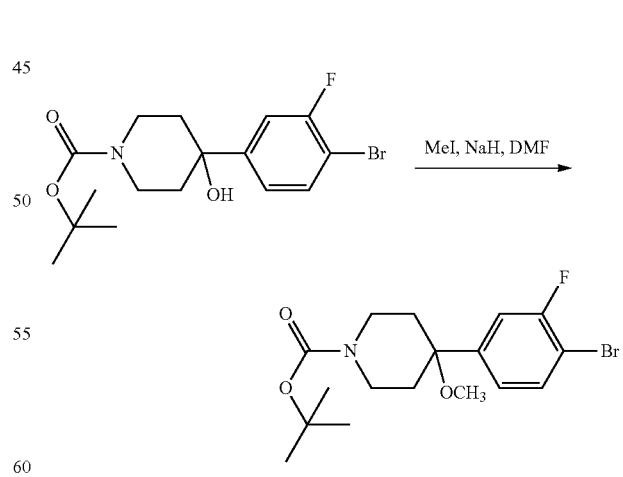

To a solution of tert-butyl 4-(4-bromo-3-fluorophenyl)-4-hydroxypiperidine-1-carboxylate (3 g, 8.01 mmol) in dry DMF (50 mL) was added NaH (60%) (416 mg, 10.4 mmol) at 0° C. The mixture was stirred at 0° C. for 1 h. Then, iodomethane (1.7 g, 12.0 mmol) was added. The mixture was stirred at RT overnight. After that, the mixture was slowly poured into ice water (200 mL) and stirred for 1 h. The solid was collected via filtration and purified by silica gel column chromatography (petroleum ether/ethyl acetate=10/1 to 4/1) to afford the title compound (2.5 g, 80%) as a white solid. MS (ES+) $C_{17}H_{23}BrFNO_3$ requires: 387, 389, found: 300, 302 [M−87]+.

Step 3: Synthesis of 4-(4-bromo-3-fluorophenyl)-4-methoxypiperidine

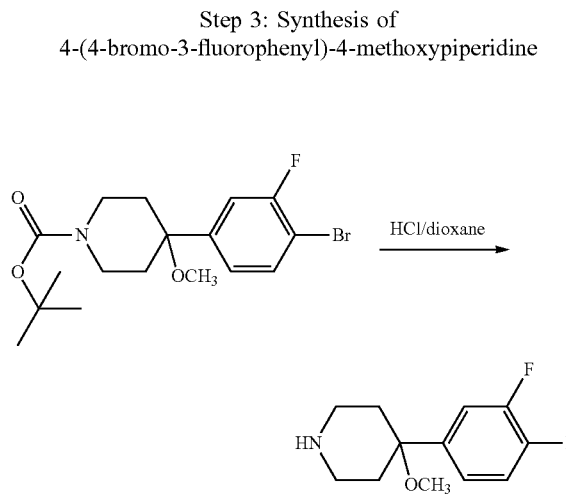

To a solution of tert-butyl 4-(4-bromo-3-fluorophenyl)-4-methoxypiperidine-1-carboxylate (2.5 g, 6.43 mmol) in dioxane (20 mL) was added HCl/dioxane (4 N, 20 mL). The mixture was stirred at RT for 12 h. After that, the solution was concentrated and used in next step without further purification. MS (ES+) $C_{12}H_{15}BrFNO$ requires: 287, 289, found: 288, 290 [M+H]+.

Step 4: Synthesis of 4-(4-bromo-3-fluorophenyl)-1-isopropyl-4-methoxypiperidine

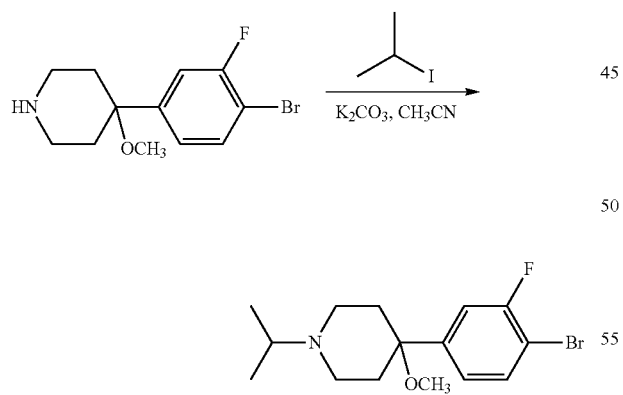

A mixture of 4-(4-bromo-3-fluorophenyl)-4-methoxypiperidine (1.6 g, 5.55 mmol), 2-iodopropane (1.88 g, 11.1 mmol) and triethylamine (1.67 g, 16.6 mmol) in $CH_3CN$ (30 mL) was stirred at 80° C. overnight. After that, the solution was concentrated and purified by silica gel column chromatography (DCM/MeOH=10/1) to afford the title compound (1.5 g, 82%) as a yellow solid. MS (ES+) $C_{15}H_{21}BrFNO$ requires: 329, 331, found: 330, 332 [M+H]+.

Y. Synthesis of tert-butyl 4-methyl-4-(4-(trifluoromethylsulfonyloxy)phenyl)piperidine-1-carboxylate Step 1: Synthesis of tert-butyl 4-(4-methoxyphenyl)-5,6-dihydropyridine-1(2H)-carboxylate

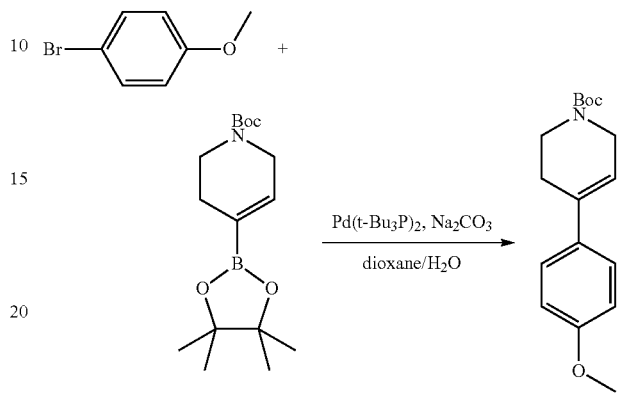

To a solution of 1-bromo-4-methoxybenzene (6.0 g, 32.0 mmol) and tert-butyl 4-(4,4,5,5-tetramethyl-1,3,2-dioxaborolan-2-yl)-5,6-dihydropyridine-1(2H)-carboxylate (10.0 g, 32.0 mmol) in dioxane/$H_2O$ (60 mL/30 mL) was added Pd(t-Bu$_3$P)$_2$ (163 mg, 0.32 mmol) and $Na_2CO_3$ (6.8 g, 64 mmol) at room temperature under nitrogen. The resulting mixture was stirred at 70° C. for 2 hours. LC-MS showed that the reaction was completed. Cooled to room temperature and extracted with EtOAc after additional water was added. The organic was washed with brine, dried over $Na_2SO_4$ and concentrated to dryness to afford the crude product which was purified by flash chromatography on silica gel eluting with PE/EA (10:1) to afford the title product (9.3 g, yield 97%) as a white solid. MS (ES+) $C_{17}H_{23}NO_3$ requires: 289, found 234 [M+H−56]+.

Step 2: Synthesis of tert-butyl 4-(4-methoxyphenyl)-4-methyl-3,4-dihydropyridine-1(2H)-carboxylate

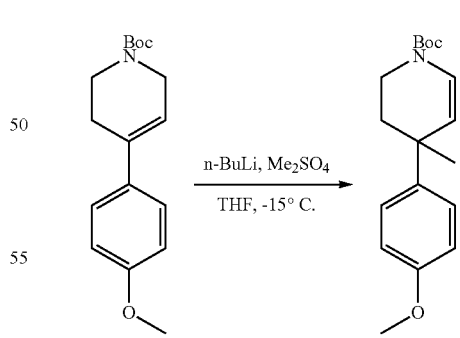

To a solution of tert-butyl 4-(4-methoxyphenyl)-5,6-dihydropyridine-1(2H)-carboxylate (9.3 g, 32.0 mmol) in THF (50 mL) was added n-BuLi (25.6 mL, 2.5 M in hexane) at −15° C. under nitrogen. The blood-red solution formed as the end of dropwise addition of n-BuLi. The reaction mixture was stirred at this temperature for 15 minutes. $Me_2SO_4$ (8.1 g, 64.0 mmol) was added dropwise to the above solution at −15° C. The resulting mixture was stirred at room temperature for 30 minutes. NH$_4$OH (40 mL, 2.0 M) was added and the resulting mixture was extracted with EtOAc after water was added. The combined organics were washed with water and brine, dried over Na$_2$SO$_4$, and concentrated to dryness to afford the crude product which was purified by flash chromatography on silica gel eluting with PE/EA (5:1) to give the title product (1.5 g, yield 15%) MS (ES+) C$_{18}$H$_{25}$NO$_3$ requires: 303, found 248 [M+H-56]$^+$.

Step 3: Synthesis of 4-(4-methyl-1,2,3,4-tetrahydropyridin-4-yl)phenol

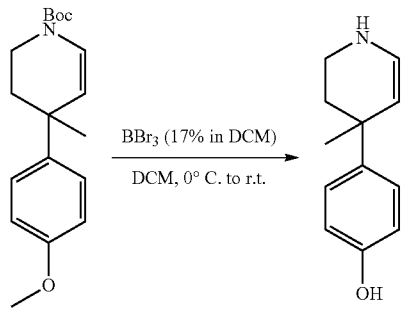 [SMILES: COc1ccc(C2(C)C=CN(C(=O)OC(C)(C)C)CC2)cc1 ; CC1(c2ccc(O)cc2)C=CNCC1]

To a solution of tert-butyl 4-(4-methoxyphenyl)-4-methyl-3,4-dihydropyridine-1(2H)-carboxylate (750 mg, 2.5 mmol) in anhydrous DCM (15 mL) was added BBr$_3$ (2 mL, 17% in DCM) at 0° C. The resulting mixture was stirred at 0° C. for 6 hours; LC-MS showed that reaction was completed. The reaction mixture was used for the next step without work-up and purification.

Step 4: Synthesis of tert-butyl 4-(4-(tert-butoxycarbonyloxy)phenyl)-4-methyl-3,4-dihydropyridine-1(2H)-carboxylate

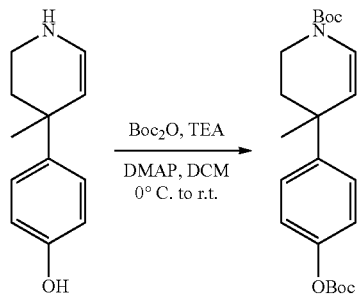

To a solution of 4-(4-methyl-1,2,3,4-tetrahydropyridin-4-yl)phenol from last step was added TEA (7 mL) at 0° C. to adjust pH value to 9.0. Boc$_2$O (1.6 g, 7.5 mmol) and catalytic DMAP (30 mg, 0.25 mmol) was added. The resulting mixture was stirred at room temperature for 16 hours; LC-MS showed that the reaction was completed. Water was added and extracted with EtOAc (×2). The combined organics were washed with brine, dried over Na$_2$SO$_4$, and concentrated to dryness to afford the crude product which was purified by flash chromatography on silica gel eluting with PE/EA (20:1 to 10:1) to afford the title product (470 mg, yield 51%) MS (ES+) C$_{22}$H$_{31}$NO$_5$ requires: 389, found 390 [M+H]$^+$.

Step 5: Synthesis of tert-butyl 4-(4-(tert-butoxycarbonyloxy)phenyl)-4-methylpiperidine-1-carboxylate

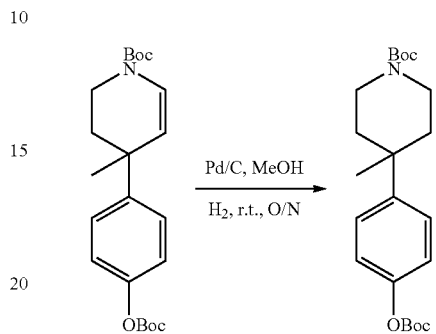

To a solution of tert-butyl 4-(4-(tert-butoxycarbonyloxy)phenyl)-4-methyl-3,4-dihydropyridine-1(2H)-carboxylate (470 mg, 1.2 mmol) in MeOH (10 mL) was added Pd/C (100 mg, 10% wet) at room temperature. The resulting mixture was stirred under hydrogen balloon at room temperature for 16 hours; LC-MS showed that the reaction was completed. Filtered off, the filtration was evaporated to dryness to afford the title product (410 mg, yield 87%) MS (ES+) C$_{22}$H$_{33}$NO$_5$ requires: 391, found 392 [M+H]$^+$.

Step 6: Synthesis of tert-butyl 4-(4-hydroxyphenyl)-4-methylpiperidine-1-carboxylate

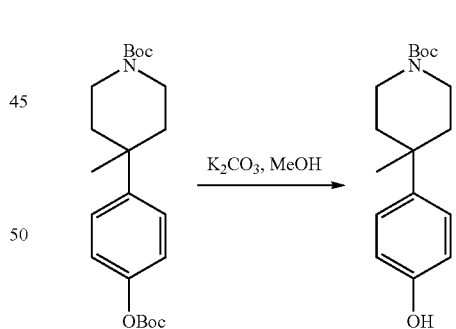

To a solution of tert-butyl 4-(4-(tert-butoxycarbonyloxy)phenyl)-4-methylpiperidine-1-carboxylate (410 mg, 1.0 mmol) in MeOH (5.0 mL) was added K$_2$CO$_3$ (691 mg, 5.0 mmol) at room temperature. The resulting mixture was stirred at room temperature at for 1 hour. LC-MS showed that the reaction was completed. The mixture was then extracted with EtOAc after water was added. The organic was washed with brine, dried over Na$_2$OS$_4$, and concentrated to dryness to afford the title product (310 mg, quantitative) which was used for the next step without further purification MS (ES+) C$_{17}$H$_{25}$NO$_3$ requires: 291, found 236 [M+H-56]$^+$.

Step 7: Synthesis of tert-butyl 4-methyl-4-(4-(trifluoromethylsulfonyloxy)phenyl)piperidine-1-carboxylate

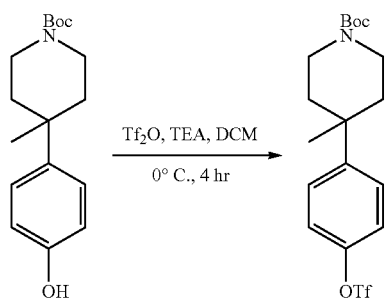 [SMILES: CC(C)(C)OC(=O)N1CCC(C)(c2ccc(O)cc2)CC1 ; CC(C)(C)OC(=O)N1CCC(C)(c2ccc(OS(=O)(=O)C(F)(F)F)cc2)CC1]

To a solution of tert-butyl 4-(4-hydroxyphenyl)-4-methylpiperidine-1-carboxylate (310 mg, 1.1 mmol) in DCM (15.0 mL) was added TEA (333 mg, 3.3 mmol) at room temperature. Tf$_2$O (372 mg, 1.3 mmol) in DCM (3 mL) was added at 0° C. dropwise during 5 minutes. The resulting mixture was stirred at 0° C. for 4 hours; LC-MS showed that the reaction was completed. The mixture was them extracted with EtOAc after water was added. The organic was washed with brine, dried over Na$_2$SO$_4$ and concentrated to dryness to afford the title product, which was used for the next step without further purification (270 mg, 8%) MS (ES+) C$_{18}$H$_{24}$F$_3$NO$_5$S requires: 423, found 424 [M+H]$^+$.

Z. Synthesis of 2-bromo-5-(4-methoxy-1-(oxetan-3-yl)piperidin-4-yl)pyridine

Step 1: Synthesis of tert-butyl 4-(6-bromopyridin-3-yl)-4-hydroxypiperidine-1-carboxylate

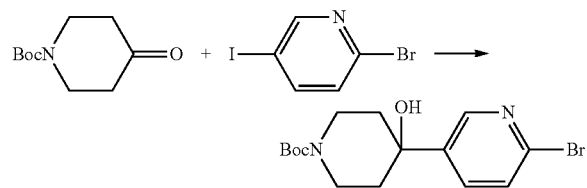

To a solution of 2-bromo-5-iodopyridine (11.3 g, 40 mmol) in 120 mL of THF was added nBuLi (17.6 ml, 2.5M in hexane) dropwise under N$_2$ at −78° C. The resulting solution was stirred at −78° C. for 2 h. Then a solution of tert-butyl 4-oxopiperidine-1-carboxylate (7.96 g, 40.0 mmol) in 20 ml of THF was added dropwise. The mixture was stirred at −78° C. for another 1 h. The reaction was quenched by addition of sat. NH$_4$Cl solution. After extracted with EtOAc, the organic phase was dried over Na$_2$SO$_4$ and concentrated. The residue was purified by silica gel column (PE/EtOAc=10:1) to afford the title product (8 g, yield 56%) as a yellow solid. MS (ES+) C$_{15}$H$_{21}$BrN$_2$O$_3$ requires: 356, 358, found 357, 359 [M+H]$^+$.

Step 2: Synthesis of tert-butyl 4-(6-bromopyridin-3-yl)-4-methoxypiperidine-1-carboxylate

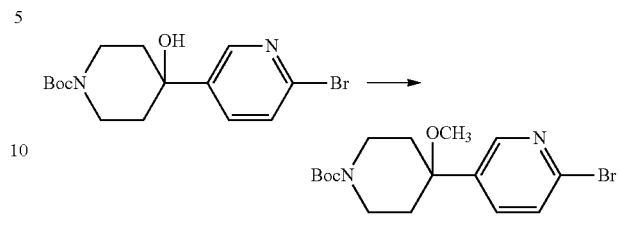

To a solution of tert-butyl 4-(6-bromopyridin-3-yl)-4-hydroxypiperidine-1-carboxylate (6.5 g, 18.1 mmol) in 20 mL of DMF was added NaH (60%, 3.62 g, 90.5 mmol) at 0° C. The mixture was stirred at 0° C. for 30 min. Then MeI (7.7 g, 54.3 mmol) was added. The resulting mixture was stirred at RT overnight. The reaction was quenched by addition of water carefully, and extracted with EtOAc. The organic phase was washed with brine, dried over Na$_2$SO$_4$ and concentrated in vacuo to afford crude product which was used in the next step without purification. MS (ES+) C$_{16}$H$_{23}$BrN$_2$O$_3$ requires: 370, 372, found 315, 317 [M+H−56]$^+$.

Step 3: Synthesis of 2-bromo-5-(4-methoxypiperidin-4-yl)pyridine hydrochloride

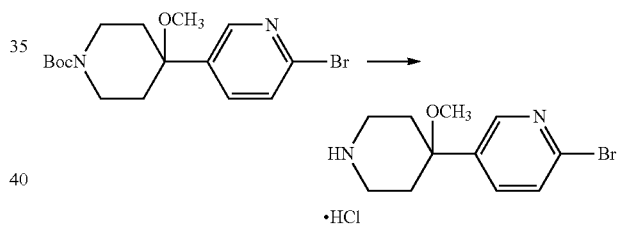

To a solution of tert-butyl 4-(6-bromopyridin-3-yl)-4-methoxypiperidine-1-carboxylate (740 mg, 2 mmol) in 5 mL of dioxane was added HCl (4 mL, 4M in dioxane). The resulting mixture was stirred at RT for 4 h. The solvent was removed in vacuo to afford crude product which was used in the next step without purification. MS (ES+) C$_{11}$H$_{15}$BrN$_2$O requires: 270, 272, found 271, 273 [M+H]$^+$.

Step 4: Synthesis of 2-bromo-5-(4-methoxy-1-(oxetan-3-yl)piperidin-4-yl)pyridine

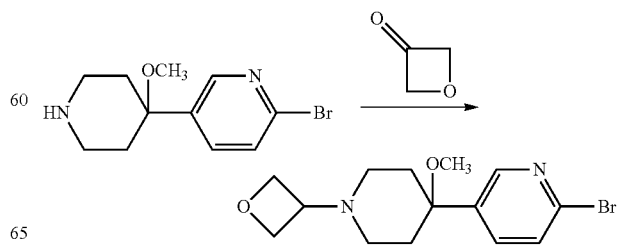

To a solution of 2-bromo-5-(4-methoxypiperidin-4-yl)pyridine hydrochloride (400 mg, 1.30 mmol) and oxetan-3-one (468 mg, 6.50 mmol) in 10 mL of DCM and 10 mL of MeOH was added NaCNBH$_3$ (410 mg, 6.5 mmol) and drops of AcOH. The resulting solution was stirred at RT overnight. The reaction was quenched by addition of water and extracted with EtOAc. The organic phase was dried over Na$_2$SO$_4$ and concentrated in vacuo to afford crude product which was used in the next step without purification. MS (ES+) C$_{14}$H$_{19}$BrN$_2$O$_2$ requires: 326, 328, found 327, 329 [M+H]$^+$.

AA. Synthesis of (S)-tert-butyl 3-(6-bromopyridin-3-yl)-3-ethoxypiperidine-1-carboxylate and (R)-tert-butyl 3-(6-bromopyridin-3-yl)-3-ethoxypiperidine-1-carboxylate Step 1: Synthesis of tert-butyl 3-(6-bromopyridin-3-yl)-3-hydroxypiperidine-1-carboxylate

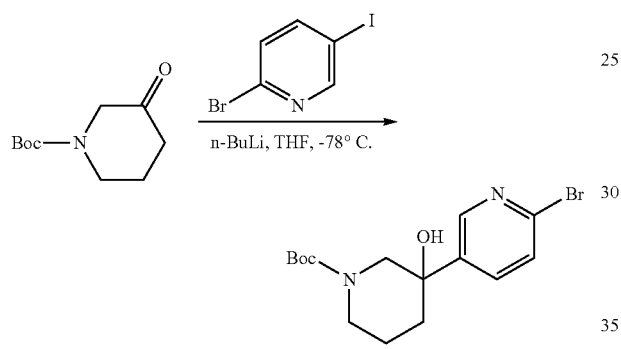

To a solution of 2-bromo-5-iodopyridine (15 g, 52.8 mmol) in dry THF (300 mL) at −78° C. was added n-BuLi (2.5 M, 21 mL), and stirred at −78° C. for 1 hrs, followed by addition of tert-butyl 3-oxopiperidine-1-carboxylate (10.5 g, 52.8 mmol) in THF. The reaction mixture was stirred at −78° C.~−60° C. for 2 hrs, quenched by NH$_4$Cl/H$_2$O and extracted by EA. The organic was dried to give a residue, which was purified by flash chromatography to afford the title compound (8.4 g, 45%). MS (ES+) C$_{15}$H$_{21}$BrN$_2$O$_3$ requires: 356, found: 357 [M+H]$^+$.

Step 2: Synthesis of 6-bromo-4-(piperazin-1-yl)pyrrolo[1,2-b]pyridazine

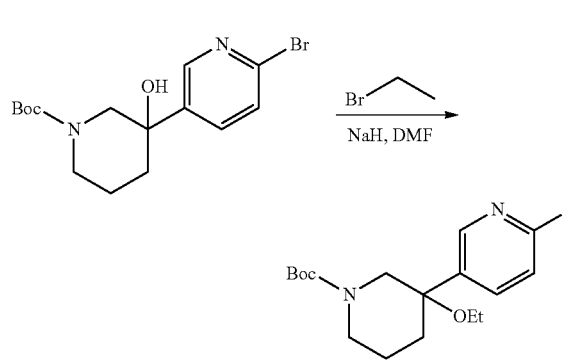

To a solution of tert-butyl 3-(6-bromopyridin-3-yl)-3-hydroxypiperidine-1-carboxylate (6.5 g, 18.1 mmol) in DMF (150 mL) at 0° C. was added 60% NaH (3.00 g, 125 mmol), and stirred at 25° C. for 2 hrs, followed by addition of bromoethane (7.88 g, 72.4 mmol). The mixture was stirred at 25° C. for another 5 hrs. Quenched by water and extracted with EA. Concentrated and purified by flash chromatography to give the title compound (5.7 g, 97%). MS (ES+) C$_{17}$H$_{25}$BrN$_2$O$_3$ requires: 385, found: 386[M+H]$^+$.

Step 3: Chiral separation of 6-bromo-4-(piperazin-1-yl)pyrrolo[1,2-b]pyridazine

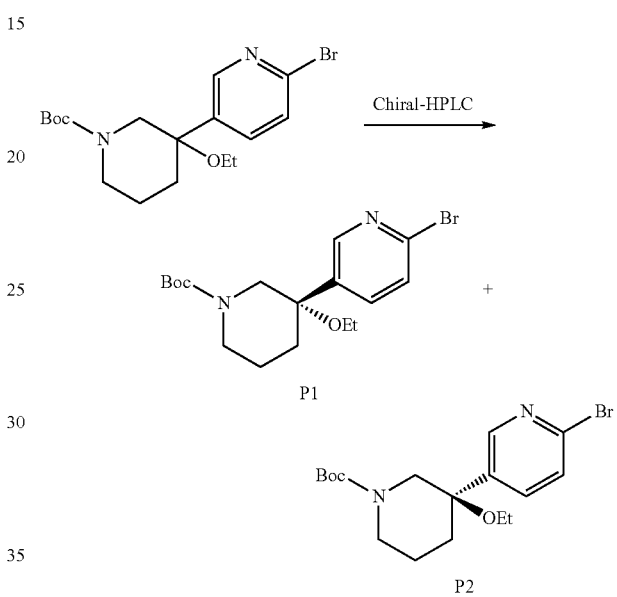

Absolute Configuration of P1 and P2 Unknown.

The title compound (5.7 g) was separated by Chiral-HPLC (Chiral conditions: Co-Solvent: PA (0.1% DEA); Column: Cellulose-SC 4.6*100 mm 5 um; Column Temperature: 39.2; CO$_2$ Flow Rate: 3.6; Co-Solvent Flow Rate: 0.4) to give P1 (1.8 g) and P2 (1.8 g).

BB. Synthesis of 3-(trimethylsilyloxy)oxetane-3-carbonitrile

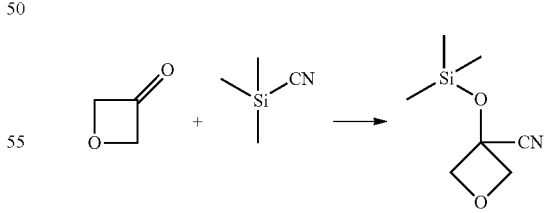

To a mixture of oxetan-3-one (500 mg, 6.93 mmol) and triethylamine (1.39 g, 13.8 mmol) in DCM (5 mL) was added trimethylsilanecarbonitrile (1.71 g, 17.3 mmol). The mixture was stirred at RT for 16 h, then diluted with DCM, washed with saturated Na$_2$CO$_3$ solution and dried with Na$_2$SO$_4$ anhydrous. The organic layer was separated and concentrated in vacuo to afford the title compound (800 mg, yield 67%) as a brown oil.

CC. Synthesis of 3-cyanooxetan-3-yl 1H-imidazole-1-carboxylate

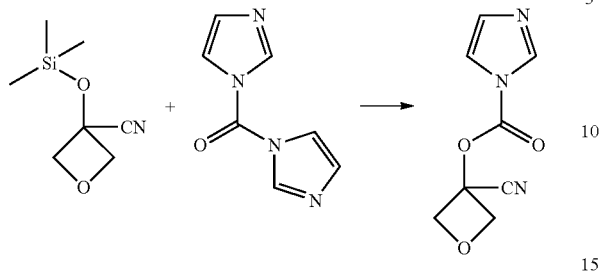

To a mixture of 3-((trimethylsilyl)oxy)oxetane-3-carbonitrile (50 mg, 291 μmol) in DCM (2 mL) was added CDI (51.8 mg, 320 mop. The mixture was stirred at rt for 4 hrs, which was added directly into the next reaction solution. MS (ES+) $C_8H_7N_3O_3$ requires: 193, found: 194 $[M+H]^+$.

DD. Synthesis of (3S,4S)-3-(4-bromophenyl)-4-(difluoromethoxy)-1-isopropylpiperidine

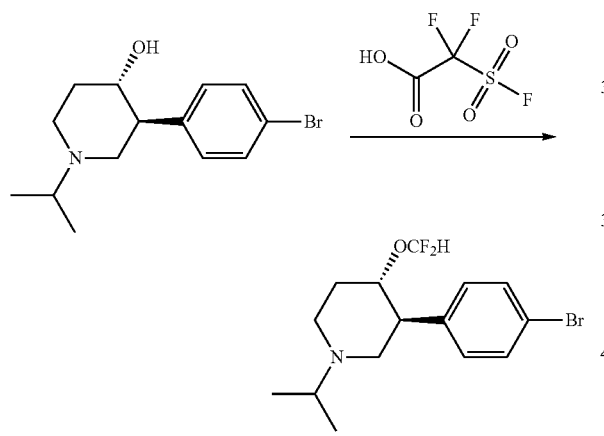

To a mixture of (3S,4S)-3-(4-bromophenyl)-1-isopropylpiperidin-4-ol (900 mg, 3.01 mmol) and CuI (571 mg, 3.01 mmol) in dry $CH_3CN$ (10 mL) was dropwise added a solution of 2,2-difluoro-2-(fluorosulfonyl)acetic acid (2.67 g, 15.00 mmol) in dry $CH_3CN$ (5 mL) at 45° C. After that, the solution was stirred at 45° C. for 2 hrs. The reaction was quenched with water (1.0 mL) and extracted. The combined organic layers were washed with water, dried over $Na_2SO_4$, filtered and concentrated. The residue was purified by silica gel column chromatography (petroleum ether/ethyl acetate/$NH_3$.MeOH=10/10/1) to afford the title compound (500 mg, 48%) as a yellow oil. MS (ES+) $C_{15}H_{20}BrF_2NO$ requires: 347, 349, found: 348, 350 $[M+H]^+$.

Example 25. Synthesis of other Exemplary Compounds

Table 1 indicates which Synthetic Protocol 1, 2, 3, or 4 described in the disclosure was used to synthesize various compounds described herein. Blank values indicate that a synthetic scheme other than one of Synthetic Protocols 1-4 was used and that the synthetic scheme for such compound is set forth in the Examples.

TABLE 1

Synthetic Protocols used for Exemplary Compounds

| Compound | Synthetic Scheme |
|---|---|
| 100 | 2 |
| 101 | 2 |
| 102 | 2 |
| 103 | 1 |
| 104 | 1 |
| 105 | 2 |
| 106 | 2 |
| 107 | 2 |
| 108 | 2 |
| 109 | 2 |
| 110 | 1 |
| 111 | Ex. 18 |
| 112 | 1 |
| 113 | 2 |
| 114 | 1 |
| 115 | 4 |
| 116 | 2 |
| 117 | 1 |
| 118 | 1 |
| 119 | 2 |
| 120 | 2 |
| 121 | Ex. 19 |
| 122 | 2 |
| 123 | 2 |
| 124 | 2 |
| 125 | 2 |
| 126 | 2 |
| 127 | 1 |
| 128 | 2 |
| 129 | 2 |
| 130 | 1 |
| 131 | 1 |
| 132 | 4 |
| 133 | 2 |
| 134 | 2 |
| 135 | 1 |
| 136 | 1 |
| 137 | 2 |
| 138 | 1 |
| 139 | 2 |
| 140 | 2 |
| 141 | 4 |
| 142 | 4 |
| 143 | 2 |
| 144 | 2 |
| 145 | 2 |
| 146 | 2 |
| 147 | 2 |
| 148 | 1 |
| 149 | 1 |
| 150 | 4 |
| 151 | 2 |
| 152 | 1 |
| 153 | 1 |
| 154 | 1 |
| 155 | 2 |
| 156 | 2 |
| 157 | Ex. 16 |
| 158 | 2 |
| 159 | 2 |
| 160 | 2 |
| 161 | 1 |
| 162 | 1 |
| 163 | 1 |
| 164 | 2 |
| 165 | 2 |
| 166 | 2 |
| 167 | 2 |
| 168 | 2 |
| 169 | 2 |
| 170 | 1 |
| 171 | 1 |
| 172 | 2 |
| 173 | 1 |
| 174 | 2 |

TABLE 1-continued

Synthetic Protocols used for Exemplary Compounds

| Compound | Synthetic Scheme |
|---|---|
| 175 | 1 |
| 176 | 1 |
| 177 | 2 |
| 178 | 2 |
| 179 | 2 |
| 180 | 2 |
| 181 | 2 |
| 182 | 4 |
| 183 | 2 |
| 184 | 1 |
| 185 | 1 |
| 186 | 1 |
| 187 | 2 |
| 188 | 2 |
| 189 | 2 |
| 190 | 2 |
| 191 | 2 |
| 192 | 2 |
| 193 | 2 |
| 194 | 1 |
| 195 | 4 |
| 196 | 2 |
| 197 | 4 |
| 198 | 2 |
| 199 | 1 |
| 200 | 2 |
| 201 | 1 |
| 202 | 2 |
| 203 | 1 |
| 204 | 1 |
| 205 | 3 |
| 206 | 2 |
| 207 | 2 |
| 208 | 4 |
| 209 | 2 |
| 210 | 2 |
| 211 | 2 |
| 212 | 1 |
| 213 | 1 |
| 214 | 2 |
| 215 | 3 |
| 216 | 2 |
| 217 | 2 |
| 218 | 2 |
| 219 | 2 |
| 220 | 2 |
| 221 | 1 |
| 222 | 2 |
| 223 | 3 |
| 224 | 4 |
| 225 | 4 |
| 226 | 3 |
| 227 | 3 |
| 228 | 2 |
| 229 | 1 |
| 230 | 3 |
| 231 | 2 |
| 232 | 4 |
| 233 | 2 |
| 234 | 3 |
| 235 | 2 |
| 236 | 2 |
| 237 | 4 |
| 238 | 2 |
| 239 | 2 |
| 240 | 4 |
| 241 | 1 |
| 242 | 2 |
| 243 | 2 |
| 244 | 3 |
| 245 | 2 |
| 246 | 2 |
| 247 | 2 |
| 248 | 2 |
| 249 | 2 |
| 250 | 3 |
| 251 | 4 |
| 252 | 2 |
| 253 | 2 |
| 254 | 2 |
| 255 | 2 |
| 256 | 2 |
| 257 | 2 |
| 258 | 2 |
| 259 | 1 |
| 260 | Ex. 15 |
| 261 | 1 |
| 262 | 1 |
| 263 | 1 |
| 264 | 1 |
| 265 | 2 |
| 266 | 2 |
| 267 | 2 |
| 268 | 2 |
| 269 | 2 |
| 270 | 2 |
| 271 | 2 |
| 272 | 1 |
| 273 | 1 |
| 274 | 1 |
| 275 | 4 |
| 276 | 2 |
| 277 | 4 |
| 278 | 1 |
| 279 | 1 |
| 280 | 1 |
| 281 | 3 |
| 282 | 2 |
| 283 | 2 |
| 284 | 2 |
| 285 | 2 |
| 286 | 4 |
| 287 | 2 |
| 288 | 2 |
| 289 | 2 |
| 290 | 2 |
| 291 | 3 |
| 292 | 1 |
| 293 | 3 |
| 294 | 3 |
| 295 | 2 |
| 296 | 1 |
| 297 | 2 |
| 298 | 4 |
| 299 | 4 |
| 300 | 4 |
| 301 | 3 |
| 302 | 3 |
| 303 | 1 |
| 304 | 1 |
| 305 | 2 |
| 306 | 1 |
| 307 | 2 |
| 308 | 1 |
| 309 | 1 |
| 310 | 1 |
| 311 | 4 |
| 312 | 2 |
| 313 | 2 |
| 314 | 1 |
| 315 | 2 |
| 316 | 2 |
| 317 | 4 |
| 318 | 1 |
| 319 | 1 |
| 320 | 2 |
| 321 | 1 |
| 322 | 2 |
| 323 | 2 |
| 324 | 4 |

TABLE 1-continued

Synthetic Protocols used for Exemplary Compounds

| Compound | Synthetic Scheme |
|---|---|
| 325 | 2 |
| 326 | 2 |
| 327 | 1 |
| 328 | 4 |
| 329 | 1 |
| 330 | 1 |
| 331 | 1 |
| 332 | 3 |
| 333 | 2 |
| 334 | 1 |
| 335 | 1 |
| 336 | 3 |
| 337 | 4 |
| 338 | 4 |
| 339 | 2 |
| 340 | 4 |
| 341 | 4 |
| 342 | 4 |
| 343 | 2 |
| 344 | 1 |
| 345 | 2 |
| 346 | 4 |
| 347 | 4 |
| 348 | 4 |
| 349 | 2 |
| 350 | 1 |
| 351 | 2 |
| 352 | 2 |
| 353 | 4 |
| 354 | 2 |
| 355 | 1 |
| 356 | 4 |
| 357 | 2 |
| 358 | 4 |
| 359 | 1 |
| 360 | 2 |
| 361 | 3 |
| 362 | 2 |
| 363 | 1 |
| 364 | 4 |
| 365 | 4 |
| 366 | 4 |
| 367 | 1 |
| 368 | 3 |
| 369 | 4 |
| 370 | 4 |
| 371 | 2 |
| 372 | 4 |
| 373 | 2 |
| 374 | 2 |
| 375 | 2 |
| 376 | 1 |
| 377 | 4 |
| 378 | 2 |
| 379 | 4 |
| 380 | 4 |
| 381 | 4 |
| 382 | 4 |
| 383 | 4 |
| 384 | 4 |
| 385 | 4 |
| 386 | 4 |
| 387 | 4 |
| 388 | 2 |
| 389 | 2 |
| 390 | 1 |
| 391 | 2 |
| 392 | 4 |
| 393 | 4 |
| 394 | 4 |
| 395 | 4 |
| 396 | 4 |
| 397 | 2 |
| 398 | 4 |
| 399 | 2 |
| 400 | 2 |
| 401 | 4 |
| 402 | 1 |
| 403 | Ex. 17 |
| 404 | 4 |
| 405 | 4 |
| 406 | 4 |
| 407 | 2 |
| 408 | 4 |
| 409 | 4 |
| 410 | 4 |
| 411 | 4 |
| 412 | 4 |
| 413 | 4 |
| 414 | 4 |
| 415 | 4 |
| 416 | 4 |
| 417 | 2 |
| 418 | 2 |
| 419 | 1 |
| 420 | 4 |
| 421 | 4 |
| 422 | 3 |
| 423 | 4 |
| 424 | 4 |
| 425 | 2 |
| 426 | 4 |
| 427 | 1 |
| 428 | 4 |
| 429 | 3 |
| 430 | 4 |
| 431 | 4 |
| 432 | 4 |
| 433 | 3 |
| 434 | 4 |
| 435 | 4 |
| 436 | 2 |
| 437 | 2 |
| 438 | 1 |
| 439 | 3 |
| 440 | 3 |
| 441 | 4 |
| 442 | 4 |
| 443 | 1 |
| 444 | 4 |
| 445 | 4 |
| 446 | 4 |
| 447 | 3 |
| 448 | 4 |
| 449 | 2 |
| 450 | 2 |
| 451 | 2 |
| 452 | 5 |
| 453 | 2 |
| 454 | 2 |
| 455 | 2 |
| 456 | 2 |
| 457 | 2 |
| 458 | 2 |
| 459 | 1 |
| 460 | 1 |
| 461 | 2 |
| 462 | 2 |
| 463 | 2 |
| 464 | 2 |
| 465 | 5 |
| 466 | 5 |
| 467 | 5 |
| 468 | 2 |
| 469 | 2 |
| 470 | 2 |
| 471 | 2 |
| 472 | 2 |
| 473 | 2 |
| 474 | 2 |

TABLE 1-continued

Synthetic Protocols used for Exemplary Compounds

| Compound | Synthetic Scheme |
|---|---|
| 475 | 2 |
| 476 | 5 |
| 477 | 5 |
| 478 | 2 |
| 479 | 2 |
| 480 | 2 |
| 481 | 2 |
| 482 | 2 |
| 483 | 2 |
| 484 | 2 |
| 485 | 2 |
| 486 | 2 |
| 487 | 2 |
| 488 | 2 |
| 489 | 2 |
| 490 | 2 |
| 491 | 2 |
| 492 | 2 |
| 493 | 2 |
| 494 | 2 |
| 495 | 2 |
| 496 | 2 |
| 497 | 2 |
| 498 | 2 |
| 499 | 5 |
| 500 | 2 |
| 501 | 2 |
| 502 | 2 |
| 503 | 2 |
| 504 | 2 |
| 505 | 2 |
| 506 | 2 |
| 507 | 2 |
| 508 | 2 |
| 509 | 4 |
| 510 | 4 |
| 511 | 4 |
| 512 | 2 |
| 513 | 2 |
| 514 | 4 |
| 515 | 2 |
| 516 | 2 |
| 517 | 2 |
| 518 | 2 |
| 519 | 2 |
| 520 | 2 |
| 521 | 2 |
| 522 | 1 |
| 523 | 1 |
| 524 | 2 |
| 525 | 4 |
| 526 | 4 |
| 527 | 4 |
| 528 | 2 |
| 529 | 4 |
| 530 | 4 |
| 531 | 2 |
| 532 | 4 |
| 533 | 2 |
| 534 | 4 |
| 535 | 4 |
| 536 | 4 |
| 537 | 2 |
| 538 | 2 |
| 539 | 2 |
| 540 | 2 |
| 541 | 2 |
| 542 | 2 |
| 543 | 2 |
| 544 | 2 |
| 545 | 2 |
| 546 | 2 |
| 547 | 4 |
| 548 | 2 |
| 549 | 2 |
| 550 | 4 |
| 551 | 4 |
| 552 | 4 |
| 553 | 2 |
| 554 | 4 |
| 555 | 2 |
| 556 | 2 |
| 557 | 2 |
| 558 | 2 |
| 559 | 2 |
| 560 | 2 |
| 561 | 2 |
| 562 | 2 |
| 563 | 2 |
| 564 | 2 |
| 565 | 2 |
| 566 | 2 |
| 567 | 2 |
| 568 | 2 |
| 569 | 2 |
| 570 | 2 |
| 571 | 5 |
| 572 | 4 |
| 573 | 4 |
| 574 | 4 |
| 575 | 2 |
| 576 | 2 |
| 577 | 2 |
| 578 | 2 |
| 579 | 4 |
| 580 | 4 |
| 581 | 5 |
| 582 | 5 |
| 583 | 2 |
| 584 | 5 |
| 585 | 2 |
| 586 | 2 |
| 587 | 2 |
| 588 | 2 |
| 589 | 2 |
| 590 | 4 |
| 591 | 2 |
| 592 | 2 |
| 593 | 2 |
| 594 | 2 |
| 595 | 4 |
| 596 | 4 |
| 597 | 2 |
| 598 | 2 |
| 599 | 2 |
| 600 | 2 |
| 601 | 2 |
| 602 | 5 |
| 603 | 4 |
| 604 | 4 |
| 605 | 2 |
| 606 | 2 |
| 607 | 4 |
| 608 | 4 |
| 609 | 2 |
| 610 | 2 |
| 611 | 2 |
| 612 | 5 |
| 613 | 2 |
| 614 | 2 |
| 615 | 2 |
| 616 | 2 |
| 617 | 4 |
| 618 | 4 |
| 619 | 2 |
| 620 | 2 |
| 621 | 4 |
| 622 | 2 |
| 623 | 4 |
| 624 | 2 |

TABLE 1-continued

Synthetic Protocols used for Exemplary Compounds

| Compound | Synthetic Scheme |
|---|---|
| 625 | 2 |
| 626 | 2 |
| 627 | 4 |
| 628 | 2 |
| 629 | 4 |
| 630 | 2 |
| 631 | 2 |
| 632 | 4 |
| 633 | 2 |
| 634 | 2 |
| 635 | 2 |
| 636 | 2 |
| 637 | 4 |
| 638 | 4 |
| 639 | 2 |
| 640 | 2 |
| 641 | 2 |
| 642 | 2 |
| 643 | 2 |
| 644 | 2 |
| 645 | 2 |
| 646 | 2 |
| 647 | 2 |
| 648 | 5 |
| 649 | 5 |
| 650 | 5 |
| 651 | 2 |
| 652 | 4 |
| 653 | 2 |
| 654 | 2 |
| 655 | 2 |
| 656 | 2 |
| 657 | 2 |
| 658 | 2 |
| 659 | 2 |
| 660 | 2 |
| 661 | 4 |
| 662 | 2 |
| 663 | 4 |
| 664 | 4 |
| 665 | 3 |
| 666 | 4 |
| 667 | 4 |
| 668 | 2 |
| 669 | 2 |
| 670 | 4 |
| 671 | 2 |
| 672 | 2 |
| 673 | 2 |
| 674 | 2 |
| 675 | 2 |
| 676 | 4 |
| 677 | 4 |
| 678 | 2 |
| 679 | 2 |
| 680 | 2 |
| 681 | 4 |
| 682 | 2 |
| 683 | 2 |
| 684 | 2 |
| 685 | 2 |
| 686 | 2 |
| 687 | 2 |
| 688 | 2 |
| 689 | 2 |
| 690 | 2 |
| 691 | 2 |
| 692 | 2 |
| 693 | 2 |
| 694 | 5 |
| 695 | 2 |
| 696 | 2 |
| 697 | 2 |
| 698 | 2 |
| 699 | 2 |
| 700 | 2 |
| 701 | 5 |
| 702 | 4 |
| 703 | 4 |
| 704 | 4 |
| 705 | 4 |
| 706 | 2 |
| 707 | 2 |
| 708 | 4 |
| 709 | 4 |
| 710 | 2 |
| 711 | 2 |
| 712 | 2 |
| 713 | 2 |
| 714 | 2 |
| 715 | 2 |
| 716 | 2 |
| 717 | 2 |
| 718 | 2 |
| 719 | 2 |
| 720 | 2 |
| 721 | 2 |
| 722 | 2 |
| 723 | 2 |
| 724 | 2 |
| 725 | 2 |
| 726 | 2 |
| 727 | 2 |
| 728 | 4 |
| 729 | 2 |
| 730 | 2 |
| 731 | 2 |
| 732 | 2 |
| 733 | 2 |
| 734 | 2 |
| 735 | 2 |
| 736 | 2 |
| 737 | 5 |
| 738 | 2 |
| 739 | 2 |
| 740 | 2 |
| 741 | 2 |
| 742 | 4 |
| 743 | 2 |
| 744 | 2 |
| 745 | 2 |
| 746 | 2 |
| 747 | 2 |
| 748 | 2 |
| 749 | 2 |
| 750 | 2 |
| 751 | 2 |
| 752 | 2 |
| 753 | 2 |
| 754 | 2 |
| 755 | 2 |
| 756 | 2 |
| 757 | 2 |
| 758 | 2 |
| 759 | 2 |
| 760 | 2 |
| 761 | 2 |
| 762 | 2 |
| 763 | 2 |
| 764 | 2 |
| 765 | 2 |
| 766 | 2 |
| 767 | 2 |
| 768 | 2 |
| 769 | 2 |
| 770 | 2 |
| 771 | 2 |
| 772 | 2 |
| 773 | 2 |
| 774 | 2 |

TABLE 1-continued

Synthetic Protocols used for Exemplary Compounds

| Compound | Synthetic Scheme |
|---|---|
| 775 | 2 |
| 776 | 2 |
| 777 | 2 |
| 778 | 2 |
| 779 | 2 |
| 780 | 2 |
| 781 | 2 |
| 782 | 2 |
| 783 | 2 |
| 784 | 2 |
| 785 | 2 |
| 786 | 2 |
| 787 | 2 |
| 788 | 2 |
| 789 | 3 |
| 790 | 3 |
| 791 | 2 |
| 792 | 2 |
| 793 | 3 |
| 794 | 3 |
| 795 | 3 |
| 796 | 2 |
| 797 | 2 |
| 798 | 2 |
| 799 | 2 |
| 800 | 2 |
| 801 | 2 |
| 802 | 2 |
| 803 | 3 |
| 804 | 2 |
| 805 | 2 |
| 806 | 2 |
| 807 | 2 |
| 808 | 2 |
| 809 | 3 |
| 810 | 3 |
| 811 | 2 |
| 812 | 3 |
| 813 | 2 |
| 814 | 3 |
| 815 | 2 |
| 816 | 2 |
| 817 | 2 |
| 818 | 2 |
| 819 | 2 |
| 820 | 2 |
| 821 | 2 |
| 822 | 3 |
| 823 | 2 |
| 824 | 2 |
| 825 | 3 |
| 826 | 3 |
| 827 | 3 |
| 828 | 3 |
| 829 | 3 |
| 830 | 2 |
| 831 | 2 |
| 832 | 3 |
| 833 | 2 |
| 834 | 2 |
| 835 | 2 |
| 836 | 3 |
| 837 | 3 |
| 838 | 3 |
| 839 | 2 |
| 840 | 3 |
| 841 | 3 |
| 842 | 3 |
| 843 | 2 |
| 844 | 2 |
| 845 | 2 |
| 846 | 2 |
| 847 | 3 |
| 848 | 2 |
| 849 | 2 |
| 850 | 2 |
| 851 | 3 |
| 852 | 2 |
| 853 | 3 |
| 854 | 3 |
| 855 | 2 |
| 856 | 2 |
| 857 | 2 |
| 858 | 2 |
| 859 | 2 |
| 860 | 2 |
| 861 | 2 |
| 862 | 2 |
| 863 | 2 |
| 864 | 3 |
| 865 | 3 |
| 866 | 3 |
| 867 | 3 |
| 868 | 2 |
| 869 | 2 |
| 870 | 3 |
| 871 | 3 |
| 872 | 3 |
| 873 | 2 |
| 874 | 2 |
| 875 | 2 |
| 876 | 3 |
| 877 | 3 |
| 878 | 3 |
| 879 | 3 |
| 880 | 2 |
| 881 | 2 |
| 882 | 2 |
| 883 | 2 |
| 884 | 2 |
| 885 | 2 |
| 886 | 2 |
| 887 | 2 |
| 888 | 2 |
| 889 | 2 |
| 890 | 3 |
| 891 | 2 |
| 892 | 2 |
| 893 | 2 |
| 894 | 2 |
| 895 | 2 |
| 896 | 2 |
| 897 | 2 |
| 898 | 2 |
| 899 | 2 |

Example 26. ALK Binding Assays

Binding assays were conducted using the LANTHASCREEN® technology (ThermoFisher Scientific). LANTHASCREEN® is a competitive binding, displacement assay where the assumed steady state occupancy of the binding site is measured using a time-resolved, fluorescence energy transfer (TR-FRET) readout between a fluorescent tracer and Europium (Eu)-tagged antibody specific for the kinase or expression tag (e.g. GST) of interest. Displacement of the tracer by a compound of the disclosure reduces, and is directly proportional to, the TR-FRET between the tracer and the antibody. Tracer was used at a concentration equal to or near to its $K_d$ for the kinase. The Eu-tagged antibody was typically used in excess to ensure sampling of all competent protein capable of binding the tracer.

For these assays a mutant ALK2 was used that was N-terminally tagged with GST (ALK2 R206H Carna Bioscience (09-148) or ALK2 R206H ThermoFisher (PV6232)); a Eu-tagged anti-GST antibody (ThermoFisher) and Kinase Tracer 178 (ThermoFisher). In all cases, the kinase (2-5 nM) was mixed with Eu-tagged antibody (10 nM) mix and tracer (50 nM) were incubated with test compound titrations prepared in 100% DMSO (1% DMSO final) for 30 minutes at room temperature. All reagents and compounds were dissolved in Kinase Buffer A (Thermo-Fisher) to achieve the final concentration. The plates were read on a PerkinElmer EnVision® multilabel plate reader or a BioTek Synergy Neo plate reader, and the assay signal was represented as a ratio of the TR-FRET emission ($\lambda_{ex}$ 330 nm, $\lambda^{em}$ 662 nm and $\lambda^{em}$ 665 nm). This readout was normalized to 0% and 100% inhibited control wells, plotted against inhibitor concentration, and fitted to a 4-parameter log dose response curve.

The results of this assay are shown in Table 2 in the column labelled "Binding Assay" wherein "A" represents an $IC_{50}$ of less than or equal to 10 nM; "B" represents an $IC_{50}$ of greater than 10 nM and less than or equal to 50 nM; and "C" represents an $IC_{50}$ of greater than 50 nM. Blank values in the table indicate that the particular compound was not tested in this assay.

Example 27. Cell-Based ALK2-R206H Cell Activity Assay

A. Cell Line HEK293-ALK2-R206H

A HEK293 (ATCC, Cat# CRL1573) based stable cell line expressing human ALK2 R206H cDNA (synthesized by GeneScript, Piscataway, N.J.) and a FLAG tag at the C-terminus was generated by lentivirus transduction and subsequent blasticidin (Life Technologies, Cat#-A1113902) selection at 10 µg/ml for >2 wks. This cell line was named HEK293-ALK2-R206H.

B. Measurement of Smad1-Ser463/Ser465 Phosphorylation by AlphaLISA

HEK293-ALK2-R206H cells were grown, harvested and then resuspended in serum-free, phenol red-free DMEM high glucose media (Life Technologies, Cat#-31053). The media also contained 50 units/ml penicillin and 50 µg/ml streptomycin (Life Technologies, Cat#-15070-063). HEK293-ALK2-R206H cells were then plated in white opaque 384-wells microplates ($2\times10^4$/well) (OptiPlate-384, PerkinElmer, Waltham, Mass., Cat#6007299) overnight (>16 h) at 37° C., 5% $CO_2$ for use in the assay.

Test compounds were first diluted to 4 mM or 0.4 mM and then serially diluted 3-fold into 10 different concentrations using DMSO. Each concentration of compound was further diluted 40-fold with phenol red-free DMEM (Life Technologies, Cat#-31053). Two µl of the diluted compounds were then dispensed into the HEK293-ALK2-R206H cell-containing wells of the microplates in duplicates. In this way, each compound was tested in 10 doses (3-fold serial dilution with the top concentration being 10 µM or 1 µM). Liquid handling was achieved using a Bravo Automated Liquid Handling Platform (Agilent Technologies). DMSO without compound was used as a negative control. The positive control was 1 µM LDN193189, a known bone morphogenetic protein (BMP inhibitor).

After 2-3 hours of incubation with test compound or control, the cells were lysed and signal was developed using ALPHASCREEN® SUREFIRE® SMAD1 (p-Ser463/465) cellular kinase assay kit (PerkinElmer, Cat# TGRSM1S10K) following the manufacturer's recommended protocol. The microplates were read using Perkin Elmer ENVISION® plate reader (emission 520-620 nM). The signal reflected the level of phospho-Ser/463/465-Smad1 in the lysate. The raw data were plotted using the DMSO negative and LDN193189 positive controls as the 0% and 100% inhibition, respectively. The 10-point dose response curve was used to calculate the IC50 values.

The results of this assay are shown in Table 2 in the column labelled "Cell Assay" wherein "A" represents an $IC_{50}$ of less than or equal to 100 nM; "B" an $IC_{50}$ of greater than 100 nM and less than or equal to 500 nM; "C" an $IC_{50}$ of greater than 500 nM. Blank values in the table indicate that the particular compound was not tested in this assay.

In Table 2, the following designations are used:

For "Binding Assay" data: ≤10 nM=A; ≥10-50 nM=B; >50 nM=C; and a blank value in the table indicates that the particular compound was not tested in this assay.

For "Cell Line" data: ≤100 nM=A; ≥100-500 nM=B; >500 nM=C; and a blank value in the table indicates that the particular compound was not tested in this assay.

TABLE 2

ALK2 Inhibitory Activity of Exemplary Compounds of the Disclosure

| Compound | Binding Assay | Cell Line |
| --- | --- | --- |
| 100 | A | B |
| 101 | C | |
| 102 | A | B |
| 103 | B | C |
| 104 | A | B |
| 105 | B | |
| 106 | C | |
| 107 | A | A |
| 108 | B | |
| 109 | A | A |
| 110 | B | B |
| 111 | A | B |
| 112 | A | B |
| 113 | A | A |
| 114 | A | C |
| 115 | A | B |
| 116 | A | A |
| 117 | A | B |
| 118 | A | B |
| 119 | C | |
| 120 | A | B |
| 121 | A | |
| 122 | A | A |
| 123 | A | B |
| 124 | A | A |
| 125 | A | A |
| 126 | B | |
| 127 | A | A |
| 128 | B | B |
| 129 | A | A |
| 130 | A | B |
| 131 | A | B |
| 132 | A | A |
| 133 | A | A |
| 134 | A | B |
| 135 | B | B |
| 136 | B | |
| 137 | A | A |
| 138 | B | |
| 139 | A | |
| 140 | A | A |
| 141 | B | |
| 142 | A | B |
| 143 | A | A |
| 144 | A | B |
| 145 | A | A |
| 146 | A | B |
| 147 | A | A |
| 148 | A | A |
| 149 | A | A |

TABLE 2-continued

ALK2 Inhibitory Activity of Exemplary Compounds of the Disclosure

| Compound | Binding Assay | Cell Line |
|---|---|---|
| 150 | A | A |
| 151 | C | |
| 152 | A | A |
| 153 | A | B |
| 154 | A | B |
| 155 | A | B |
| 156 | A | A |
| 157 | C | |
| 158 | A | B |
| 159 | A | A |
| 160 | A | B |
| 161 | A | A |
| 162 | A | A |
| 163 | A | A |
| 164 | A | B |
| 165 | B | |
| 166 | A | |
| 167 | A | A |
| 168 | B | |
| 169 | A | B |
| 170 | B | B |
| 171 | B | |
| 172 | A | B |
| 173 | B | C |
| 174 | A | B |
| 175 | B | |
| 176 | B | |
| 177 | A | A |
| 178 | A | A |
| 179 | A | A |
| 180 | A | A |
| 181 | A | A |
| 182 | A | A |
| 183 | B | |
| 184 | A | A |
| 185 | A | A |
| 186 | A | B |
| 187 | A | A |
| 188 | A | A |
| 189 | A | A |
| 190 | A | |
| 191 | A | A |
| 192 | A | A |
| 193 | A | A |
| 194 | B | B |
| 195 | A | A |
| 196 | A | B |
| 197 | B | B |
| 198 | A | |
| 199 | A | A |
| 200 | A | A |
| 201 | A | A |
| 202 | A | A |
| 203 | A | A |
| 204 | A | A |
| 205 | B | B |
| 206 | A | |
| 207 | A | A |
| 208 | A | A |
| 209 | A | A |
| 210 | A | A |
| 211 | A | A |
| 212 | A | B |
| 213 | A | A |
| 214 | B | B |
| 215 | B | |
| 216 | A | A |
| 217 | A | B |
| 218 | B | |
| 219 | A | A |
| 220 | A | |
| 221 | A | B |
| 222 | A | A |
| 223 | B | B |
| 224 | A | A |
| 225 | A | A |
| 226 | A | A |
| 227 | A | A |
| 228 | A | A |
| 229 | A | A |
| 230 | A | A |
| 231 | A | A |
| 232 | A | B |
| 233 | B | B |
| 234 | A | A |
| 235 | A | B |
| 236 | A | B |
| 237 | A | A |
| 238 | A | B |
| 239 | A | |
| 240 | A | A |
| 241 | A | A |
| 242 | A | B |
| 243 | A | A |
| 244 | A | |
| 245 | B | B |
| 246 | A | A |
| 247 | A | A |
| 248 | A | A |
| 249 | A | A |
| 250 | A | A |
| 251 | A | A |
| 252 | A | B |
| 253 | A | B |
| 254 | A | A |
| 255 | A | B |
| 256 | A | B |
| 257 | A | A |
| 258 | A | A |
| 259 | B | C |
| 260 | A | B |
| 261 | A | A |
| 262 | A | B |
| 263 | A | B |
| 264 | A | B |
| 265 | A | A |
| 266 | A | A |
| 267 | A | A |
| 268 | B | B |
| 269 | A | A |
| 270 | A | A |
| 271 | A | B |
| 272 | B | B |
| 273 | B | |
| 274 | A | B |
| 275 | A | A |
| 276 | A | A |
| 277 | A | A |
| 278 | A | A |
| 279 | B | B |
| 280 | B | B |
| 281 | A | A |
| 282 | A | A |
| 283 | A | B |
| 284 | A | A |
| 285 | A | A |
| 286 | A | B |
| 287 | A | A |
| 288 | A | A |
| 289 | A | A |
| 290 | A | A |
| 291 | B | |
| 292 | A | A |
| 293 | A | A |
| 294 | B | |
| 295 | A | A |
| 296 | A | B |
| 297 | A | A |

TABLE 2-continued

ALK2 Inhibitory Activity of Exemplary Compounds of the Disclosure

| Compound | Binding Assay | Cell Line |
|---|---|---|
| 298 | A | A |
| 299 | A | A |
| 300 | A | A |
| 301 | A | B |
| 302 | A | A |
| 303 | A | A |
| 304 | A | A |
| 305 | A | A |
| 306 | B | |
| 307 | A | B |
| 308 | A | A |
| 309 | A | B |
| 310 | A | B |
| 311 | C | |
| 312 | A | A |
| 313 | A | A |
| 314 | B | C |
| 315 | B | B |
| 316 | A | B |
| 317 | A | B |
| 318 | A | B |
| 319 | C | |
| 320 | A | A |
| 321 | A | A |
| 322 | A | A |
| 323 | A | A |
| 324 | A | A |
| 325 | A | A |
| 326 | A | A |
| 327 | B | B |
| 328 | A | B |
| 329 | A | B |
| 330 | A | B |
| 331 | B | |
| 332 | A | A |
| 333 | A | A |
| 334 | B | B |
| 335 | C | C |
| 336 | A | A |
| 337 | A | A |
| 338 | A | B |
| 339 | A | A |
| 340 | A | A |
| 341 | A | A |
| 342 | B | |
| 343 | A | B |
| 344 | B | B |
| 345 | A | A |
| 348 | A | A |
| 349 | A | A |
| 350 | A | A |
| 351 | A | A |
| 352 | A | B |
| 353 | A | B |
| 354 | A | A |
| 355 | B | C |
| 356 | B | |
| 357 | A | A |
| 359 | A | C |
| 360 | A | B |
| 361 | A | B |
| 362 | B | |
| 363 | A | B |
| 364 | A | A |
| 365 | A | A |
| 366 | A | A |
| 367 | A | A |
| 368 | A | A |
| 369 | A | A |
| 370 | A | A |
| 371 | A | A |
| 372 | A | |
| 373 | B | C |
| 374 | B | |
| 375 | A | A |
| 376 | A | A |
| 377 | A | B |
| 378 | A | |
| 379 | A | B |
| 380 | A | A |
| 381 | A | A |
| 382 | A | A |
| 383 | A | A |
| 384 | A | A |
| 385 | A | A |
| 386 | A | B |
| 387 | A | A |
| 388 | A | A |
| 390 | B | B |
| 391 | A | A |
| 392 | B | |
| 393 | A | B |
| 397 | B | |
| 399 | A | A |
| 400 | A | A |
| 401 | A | B |
| 402 | A | B |
| 403 | C | |
| 404 | A | B |
| 405 | A | |
| 406 | A | A |
| 407 | A | A |
| 408 | A | A |
| 409 | A | A |
| 410 | C | |
| 411 | A | B |
| 412 | A | A |
| 413 | A | A |
| 414 | B | |
| 415 | A | A |
| 417 | B | |
| 418 | A | A |
| 419 | A | A |
| 420 | A | A |
| 421 | A | A |
| 422 | A | A |
| 423 | A | B |
| 425 | C | |
| 426 | A | A |
| 427 | A | B |
| 428 | A | B |
| 429 | A | A |
| 430 | A | A |
| 431 | A | B |
| 432 | A | A |
| 433 | C | |
| 434 | A | A |
| 435 | A | A |
| 436 | A | A |
| 437 | A | A |
| 438 | B | |
| 439 | B | |
| 440 | C | |
| 441 | A | A |
| 442 | A | A |
| 443 | B | |
| 444 | B | |
| 445 | A | A |
| 446 | A | |
| 447 | B | C |
| 448 | A | B |
| 449 | A | |
| 450 | A | B |
| 451 | A | A |
| 452 | A | A |
| 453 | A | A |
| 454 | A | B |
| 455 | A | A |

TABLE 2-continued

ALK2 Inhibitory Activity of Exemplary Compounds of the Disclosure

| Compound | Binding Assay | Cell Line |
|---|---|---|
| 456 | A | B |
| 457 | A | B |
| 458 | A | |
| 459 | A | A |
| 460 | A | A |
| 461 | A | |
| 462 | A | B |
| 463 | A | A |
| 464 | A | A |
| 465 | A | B |
| 466 | A | A |
| 467 | A | B |
| 468 | A | A |
| 469 | A | A |
| 470 | A | A |
| 471 | C | |
| 472 | A | |
| 473 | A | A |
| 474 | A | B |
| 475 | A | A |
| 476 | A | A |
| 477 | A | A |
| 478 | A | A |
| 479 | A | A |
| 480 | A | A |
| 481 | A | A |
| 482 | A | A |
| 483 | A | A |
| 484 | A | A |
| 485 | A | A |
| 486 | A | A |
| 487 | A | A |
| 488 | A | A |
| 489 | A | A |
| 490 | A | A |
| 491 | A | A |
| 492 | A | A |
| 493 | A | A |
| 494 | A | A |
| 495 | A | A |
| 496 | A | A |
| 497 | A | A |
| 498 | A | A |
| 499 | A | B |
| 500 | A | B |
| 501 | A | B |
| 502 | A | A |
| 503 | A | B |
| 504 | A | B |
| 505 | A | A |
| 506 | B | |
| 507 | A | A |
| 508 | A | B |
| 509 | A | A |
| 510 | A | A |
| 511 | A | A |
| 512 | A | A |
| 513 | A | A |
| 514 | A | A |
| 515 | A | A |
| 516 | A | A |
| 517 | A | A |
| 518 | A | A |
| 519 | A | A |
| 520 | A | A |
| 521 | A | A |
| 522 | A | A |
| 523 | A | A |
| 524 | A | A |
| 525 | A | |
| 526 | A | A |
| 527 | A | A |
| 528 | B | |
| 529 | A | |
| 530 | A | A |
| 531 | A | A |
| 532 | A | A |
| 533 | A | A |
| 534 | A | A |
| 535 | A | |
| 536 | A | |
| 537 | A | A |
| 538 | A | A |
| 539 | A | A |
| 540 | A | A |
| 541 | A | A |
| 542 | A | A |
| 543 | A | A |
| 544 | A | A |
| 545 | A | A |
| 546 | A | A |
| 547 | A | |
| 548 | A | C |
| 549 | A | A |
| 550 | A | A |
| 551 | A | A |
| 552 | A | |
| 553 | B | |
| 554 | A | B |
| 555 | A | |
| 556 | A | A |
| 557 | A | A |
| 558 | A | A |
| 559 | A | A |
| 560 | A | A |
| 561 | A | A |
| 562 | A | A |
| 563 | A | A |
| 564 | A | A |
| 565 | A | A |
| 566 | A | A |
| 567 | A | A |
| 568 | A | A |
| 569 | A | |
| 570 | A | A |
| 571 | A | |
| 572 | A | A |
| 573 | A | A |
| 574 | A | |
| 575 | A | B |
| 576 | A | A |
| 577 | A | A |
| 578 | A | A |
| 579 | A | A |
| 580 | A | A |
| 581 | A | A |
| 582 | A | A |
| 583 | A | A |
| 584 | A | |
| 585 | A | A |
| 586 | A | B |
| 587 | A | A |
| 588 | A | A |
| 589 | A | A |
| 590 | A | |
| 591 | A | A |
| 592 | A | A |
| 593 | A | A |
| 594 | A | A |
| 595 | A | |
| 596 | A | B |
| 597 | A | A |
| 598 | A | A |
| 599 | A | A |
| 600 | A | A |
| 601 | A | A |
| 602 | A | |
| 603 | A | A |

TABLE 2-continued

ALK2 Inhibitory Activity of Exemplary Compounds of the Disclosure

| Compound | Binding Assay | Cell Line |
|---|---|---|
| 604 | A | A |
| 605 | A | A |
| 606 | A | A |
| 607 | A |   |
| 608 | A | B |
| 609 | A | A |
| 610 | A | A |
| 611 | A | A |
| 612 | A |   |
| 613 | A | A |
| 614 | A | A |
| 615 | A | A |
| 616 | A | A |
| 617 | A | B |
| 618 | A | A |
| 619 | A | A |
| 620 | A | A |
| 621 | A | B |
| 622 | A | C |
| 623 | A | B |
| 624 | A | A |
| 625 | A | A |
| 626 | A | A |
| 627 | A | A |
| 628 | A | A |
| 629 | A | A |
| 630 | A | A |
| 631 | A | A |
| 632 | A | B |
| 633 | A | A |
| 634 | A | A |
| 635 | A | A |
| 636 | A | A |
| 637 | A | A |
| 638 | A | A |
| 639 | A |   |
| 640 | A |   |
| 641 | A | A |
| 642 | A | A |
| 643 | A | A |
| 644 | A | A |
| 645 | A | A |
| 646 | A | A |
| 647 | A | A |
| 648 | A | A |
| 649 | A | A |
| 650 | A | A |
| 651 | A | A |
| 652 | A | A |
| 653 | A | A |
| 654 | A | A |
| 655 | A | A |
| 656 | A | A |
| 657 | A | A |
| 658 | A | A |
| 659 | A | A |
| 660 | A | A |
| 661 | A | B |
| 662 | A | A |
| 663 | A | A |
| 664 | A | B |
| 665 | A | A |
| 666 | A | A |
| 667 | A | A |
| 668 | A | B |
| 669 | A | A |
| 670 | A |   |
| 671 | A | A |
| 672 | A | A |
| 673 | A | A |
| 674 | A | A |
| 675 | A | A |
| 676 | A | A |
| 677 | A | A |
| 678 | A | A |
| 679 | A | A |
| 680 | A | A |
| 681 | A | A |
| 682 | A | A |
| 683 | A | A |
| 684 | A | A |
| 685 | A | A |
| 686 | A | A |
| 687 | A | A |
| 688 | A | A |
| 689 | A | B |
| 690 | A | A |
| 691 | A | A |
| 692 | A | A |
| 693 | A | A |
| 694 | A | A |
| 695 | A | A |
| 696 | A | A |
| 697 | A | A |
| 698 | A | A |
| 699 | A | A |
| 700 | A |   |
| 701 | A | A |
| 702 | A | A |
| 703 | A | A |
| 704 | A | A |
| 705 | A | A |
| 706 | A | A |
| 707 | A |   |
| 708 | A | A |
| 709 | A | B |
| 710 | A | A |
| 711 | A | A |
| 712 | A | A |
| 713 | A | A |
| 714 | A | A |
| 715 | A | A |
| 716 | A | A |
| 717 | A |   |
| 718 | A | A |
| 719 | A | A |
| 720 | A | A |
| 721 | A | A |
| 722 | A | A |
| 723 | A | A |
| 724 | A | A |
| 725 | A | A |
| 726 | A | B |
| 727 | A | A |
| 728 | A | A |
| 729 | A | A |
| 730 | A |   |
| 731 | A | A |
| 732 | A | B |
| 733 | A | A |
| 734 | A | A |
| 735 | A | A |
| 736 | A | A |
| 737 | A | A |
| 738 | A | A |
| 739 | A | A |
| 740 | A | A |
| 741 | A | A |
| 742 | A |   |
| 743 | A | A |
| 744 | A | A |
| 745 | A | A |
| 746 | A | A |
| 747 | A | A |
| 748 | A | A |
| 749 | A | A |
| 750 | A | A |
| 751 | A |   |

TABLE 2-continued

ALK2 Inhibitory Activity of Exemplary Compounds of the Disclosure

| Compound | Binding Assay | Cell Line |
|---|---|---|
| 752 | A | B |
| 753 | A | A |
| 754 | A | A |
| 755 | A | B |
| 756 | A | |
| 757 | A | |
| 758 | A | |
| 759 | A | |
| 760 | A | B |
| 761 | A | A |
| 762 | A | B |
| 763 | A | A |
| 764 | A | A |
| 765 | A | |
| 766 | A | B |
| 767 | A | |
| 768 | A | A |
| 769 | A | |
| 770 | A | A |
| 771 | A | A |
| 772 | A | |
| 773 | A | B |
| 774 | A | A |
| 775 | A | A |
| 776 | A | A |
| 777 | A | A |
| 778 | A | A |
| 779 | A | A |
| 780 | A | A |
| 781 | B | |
| 782 | A | A |
| 783 | A | A |
| 784 | A | A |
| 785 | A | B |
| 786 | A | A |
| 787 | A | A |
| 788 | A | A |
| 789 | A | C |
| 790 | A | C |
| 791 | A | A |
| 792 | A | A |
| 793 | A | A |
| 794 | A | A |
| 795 | A | A |
| 796 | A | A |
| 797 | A | A |
| 798 | A | A |
| 799 | A | A |
| 800 | A | A |
| 801 | A | A |
| 802 | A | A |
| 803 | A | |
| 804 | A | A |
| 805 | A | A |
| 806 | A | |
| 807 | A | |
| 808 | A | A |
| 809 | A | A |
| 810 | A | A |
| 811 | A | A |
| 812 | A | B |
| 813 | A | A |
| 814 | A | A |
| 815 | A | A |
| 816 | A | A |
| 817 | A | A |
| 818 | A | A |
| 819 | A | A |
| 820 | A | A |
| 821 | A | A |
| 822 | B | |
| 823 | A | A |
| 824 | A | A |
| 825 | A | B |
| 826 | A | A |
| 827 | A | B |
| 828 | A | B |
| 829 | A | A |
| 830 | A | B |
| 831 | A | A |
| 832 | A | A |
| 833 | A | A |
| 834 | A | A |
| 835 | A | A |
| 836 | A | B |
| 837 | A | B |
| 838 | A | B |
| 839 | A | A |
| 840 | A | B |
| 841 | B | |
| 842 | B | |
| 843 | A | A |
| 844 | A | A |
| 845 | A | A |
| 846 | A | A |
| 847 | A | C |
| 848 | A | A |
| 849 | A | A |
| 850 | A | A |
| 851 | A | B |
| 852 | A | A |
| 853 | A | B |
| 854 | A | A |
| 855 | A | A |
| 856 | A | A |
| 857 | A | A |
| 858 | A | A |
| 859 | A | A |
| 860 | A | A |
| 861 | A | A |
| 862 | A | |
| 863 | A | A |
| 864 | A | A |
| 865 | A | A |
| 866 | A | |
| 867 | A | A |
| 868 | A | A |
| 869 | A | A |
| 870 | A | A |
| 871 | A | A |
| 872 | A | A |
| 873 | A | A |
| 874 | A | B |
| 875 | A | A |
| 876 | A | A |
| 877 | A | A |
| 878 | A | A |
| 879 | A | A |
| 880 | A | A |
| 881 | A | |
| 882 | A | A |
| 883 | A | A |
| 884 | A | A |
| 885 | A | A |
| 886 | A | A |
| 887 | A | A |
| 888 | A | A |
| 889 | A | A |
| 890 | A | A |
| 891 | A | A |
| 892 | A | A |
| 893 | A | A |
| 894 | A | A |
| 895 | A | B |
| 896 | A | A |
| 897 | A | A |

TABLE 2-continued

ALK2 Inhibitory Activity of Exemplary
Compounds of the Disclosure

| Compound | Binding Assay | Cell Line |
|---|---|---|
| 898 | A | A |
| 899 | A | A |

INCORPORATION BY REFERENCE

All publications and patents mentioned herein are hereby incorporated by reference in their entirety as if each individual publication or patent was specifically and individually indicated to be incorporated by reference.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize, or be able to ascertain using no more than routine experimentation, many equivalents to the specific embodiments of the disclosure described and claimed herein. Such equivalents are intended to be encompassed by the following claims.

The invention claimed is:
1. A compound that is 6-halo-pyrrolo[1,2-b]pyridazin-4-ol, wherein halo is selected from Cl, Br, and I, or a pharmaceutically acceptable salt thereof.
2. A compound, wherein the compounds is 6-bromopyrrolo[1,2-b]pyridazin-4-ol, or a pharmaceutically acceptable salt thereof.
3. A method of synthesizing 6-halo-pyrrolo[1,2-b]pyridazin-4-ol, comprising the step of
combining a compound of Formula C-1:

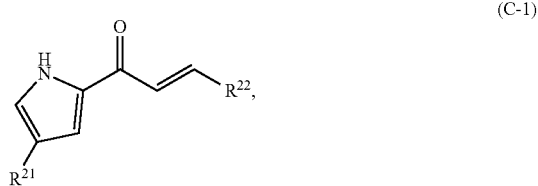

with a compound of Formula D-1:

$$R^{23}-O-NH_2 \quad (D-1),$$

wherein:
$R^{21}$ is selected from chloro, bromo, and iodo;
$R^{22}$ is a leaving group; and
$R^{23}$ is an electron withdrawing group.
4. The method of claim 3, wherein $R^{21}$ is bromo.
5. The method of claim 3, wherein $R^{22}$ is selected from $-N(R^{24})(R^{25})$ and $-OR^{24}$, wherein each of $R^{24}$ and $R^{25}$ is an independently selected $C_1$-$C_4$ alkyl.
6. The method of claim 3, wherein $R^{22}$ is $-N(CH_3)_2$.
7. The method of claim 3, wherein $R^{23}$ is selected from methylcarbonyl, t-butylcarbonyl, 4-nitrophenylcarbonyl, 4-cyanophenylcarbonyl, 4-trifluoromethylphenylcarbonyl, 4-fluorophenylcarbonyl, 4-trifluoromethylcarbonylphenylcarbonyl, 4-ethoxycarbonylphenylcarbonyl, 4-trifluoromethylsulfonylphenylcarbonyl, 2,4,6-trimethylphenylcarbonyl, 2,4,6-trimethyl-3,5-dinitrophenylcarbonyl, 2-trifluoromethyl-4-nitrophenyl, 2,4-dinitrophenyl, and diphenylphosphinyl.
8. The method of claim 3, wherein $R^{23}$ is 4-nitrophenylcarbonyl.
9. The method of claim 3, wherein the compound of Formula C-1 and the compound of Formula D-1 are dissolved in a polar solvent.
10. The method of claim 9, wherein the polar solvent is selected from N-methyl-2-pyrrolidine ("NMP"), N,N-dimethylacetamide ("DMAC"), dimethylformamide ("DMF"), tetrahydrofuran ("THF"), methyl-tetrahydrofuran ("MeTHF"), dimethyl sulfoxide ("DMSO"), and cyclopentylmethyl ether ("CPME").
11. The method of claim 9, wherein the polar solvent is NMP or DMAC.
12. The method of claim 3, wherein the compound of Formula C-1 is treated with a base.
13. The method of claim 12, wherein the base is selected from $KOC(CH_3)_3$, $NaOC(CH_3)_3$, $LiOC(CH_3)_3$, $LiC(CH_3)_3$, $Li(CH_2)_3CH_3$, $LiN(C_3H_7)_2$, $NaOCH_3$, $NaOCH_2CH_3$, $KOCH_3$, $LiOCH_3$, $LiOCH_2CH_3$, and $KOCH_2CH_3$.
14. The method of claim 12, wherein the base is $KOC(CH_3)_3$.
15. The method of claim 3, wherein the method further comprises adding a protonating agent.
16. The method of claim 15, wherein the protonating agent is selected from $NH_4Cl$, $NaHCO_3$, $KHCO_3$, $LiHCO_3$, acetic acid, HCl, HBr, and $H_2SO_4$.

17. The method of claim 15, wherein the protonating agent is $NH_4Cl$.

\* \* \* \* \*